US012403137B2

(12) United States Patent
Cottrell et al.

(10) Patent No.: US 12,403,137 B2
(45) Date of Patent: Sep. 2, 2025

(54) COMPOUNDS AND METHODS OF USE

(71) Applicant: Tango Therapeutics, Inc., Boston, MA (US)

(72) Inventors: Kevin M. Cottrell, Arlington, MA (US); John P. Maxwell, Hingham, MA (US); Douglas A. Whittington, West Newton, MA (US)

(73) Assignee: Tango Therapeutics, Inc., Boston, MA (US)

( * ) Notice: Subject to any disclaimer, the term of this patent is extended or adjusted under 35 U.S.C. 154(b) by 583 days.

(21) Appl. No.: 17/772,465

(22) PCT Filed: Oct. 28, 2020

(86) PCT No.: PCT/US2020/057601
§ 371 (c)(1),
(2) Date: Apr. 27, 2022

(87) PCT Pub. No.: WO2021/086879
PCT Pub. Date: May 6, 2021

(65) Prior Publication Data
US 2023/0054084 A1 Feb. 23, 2023

Related U.S. Application Data

(60) Provisional application No. 62/926,801, filed on Oct. 28, 2019.

(51) Int. Cl.
*A61K 31/4725* (2006.01)
*A61K 31/496* (2006.01)
(Continued)

(52) U.S. Cl.
CPC ........ *A61K 31/4725* (2013.01); *A61K 31/496* (2013.01); *A61K 31/506* (2013.01);
(Continued)

(58) Field of Classification Search
CPC .............. A61K 31/4725; A61K 31/496; A61K 31/506; A61K 31/5377; A61K 31/5386;
(Continued)

(56) References Cited

U.S. PATENT DOCUMENTS

| 5,814,631 A | 9/1998 | Fukami et al. |
| 10,278,955 B1 | 5/2019 | Yao et al. |

(Continued)

FOREIGN PATENT DOCUMENTS

| CN | 116462676 A | 7/2023 |
| CN | 116462677 A | 7/2023 |

(Continued)

OTHER PUBLICATIONS

International Search Report and Written Opinion for International Patent Application No. PCT/US20/57601 mailed on Apr. 1, 2021, 14 pages.

(Continued)

*Primary Examiner* — Clinton A Brooks
*Assistant Examiner* — Kendall Nicole Heitmeier
(74) *Attorney, Agent, or Firm* — GOODWIN PROCTER LLP

(57) ABSTRACT

Compounds are provided according to Formula (I): and pharmaceutically acceptable salts thereof, and pharmaceutical compositions thereof: wherein $X^1$, $X^2$, $X^3$, $X^4$, $X^5$, A, (Continued)

L, $R^1$, $R^2$, $R^5$, m and n are as defined herein. Compounds of the present invention are contemplated useful for the prevention and treatment of a variety of conditions.

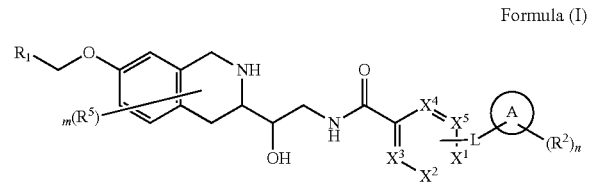

Formula (I)

24 Claims, 1 Drawing Sheet

Specification includes a Sequence Listing.

(51) Int. Cl.
| A61K 31/506 | (2006.01) |
| --- | --- |
| A61K 31/5377 | (2006.01) |
| A61K 31/5386 | (2006.01) |
| A61K 45/06 | (2006.01) |
| C07D 401/12 | (2006.01) |
| C07D 401/14 | (2006.01) |
| C07D 413/12 | (2006.01) |
| C07D 413/14 | (2006.01) |
| C07D 471/08 | (2006.01) |
| C07D 498/08 | (2006.01) |

(52) U.S. Cl.
CPC ...... A61K 31/5377 (2013.01); A61K 31/5386 (2013.01); C07D 401/14 (2013.01); C07D 413/12 (2013.01); C07D 413/14 (2013.01); C07D 471/08 (2013.01); C07D 498/08 (2013.01)

(58) Field of Classification Search
CPC .. C07D 401/14; C07D 413/12; C07D 413/14; C07D 471/08; C07D 498/08
See application file for complete search history.

(56) References Cited

U.S. PATENT DOCUMENTS

| 11,077,101 | B1 | 8/2021 | Cottrell et al. | |
| --- | --- | --- | --- | --- |
| 2017/0027935 | A1 | 2/2017 | Duncan et al. | |
| 2017/0210751 | A1 | 7/2017 | Duncan et al. | |
| 2019/0071425 | A1* | 3/2019 | Bergman | C07D 401/14 |
| 2019/0083482 | A1 | 3/2019 | Duncan et al. | |
| 2019/0175526 | A1 | 6/2019 | Yao et al. | |
| 2019/0175553 | A1 | 6/2019 | Yao et al. | |

FOREIGN PATENT DOCUMENTS

| WO | WO-2004096774 A1 * | 11/2004 | .......... C07D 209/44 |
| --- | --- | --- | --- |
| WO | 2014100719 A2 | 6/2014 | |
| WO | WO-2014100716 A1 | 6/2014 | |
| WO | 2016038550 A1 | 3/2016 | |
| WO | 2016044585 A1 | 3/2016 | |
| WO | 2016089883 A1 | 6/2016 | |
| WO | WO-2017153513 A1 * | 9/2017 | .............. A61P 35/00 |
| WO | 2018039972 A1 | 3/2018 | |
| WO | 2019032859 A1 | 2/2019 | |
| WO | 2019084470 A1 | 5/2019 | |
| WO | 2019094311 A1 | 5/2019 | |
| WO | 2019094312 A1 | 5/2019 | |
| WO | 2019102494 A1 | 5/2019 | |
| WO | 2019110734 A1 | 6/2019 | |
| WO | 2019112719 A1 | 6/2019 | |
| WO | 2019116302 A1 | 6/2019 | |
| WO | 2019165189 A1 | 8/2019 | |
| WO | 2019173804 A1 | 9/2019 | |
| WO | 2019180628 A1 | 9/2019 | |
| WO | 2019180631 A1 | 9/2019 | |
| WO | 2019219805 A1 | 11/2019 | |
| WO | 2019229614 A1 | 12/2019 | |
| WO | 2020094712 A1 | 5/2020 | |
| WO | 2020139991 A1 | 7/2020 | |
| WO | 2020168125 A1 | 8/2020 | |
| WO | 2020182018 A1 | 9/2020 | |
| WO | 2020198323 A1 | 10/2020 | |
| WO | 2020198601 A1 | 10/2020 | |
| WO | 2020205660 A1 | 10/2020 | |
| WO | 2020205867 A1 | 10/2020 | |
| WO | 2020206289 A1 | 10/2020 | |
| WO | 2020206299 A1 | 10/2020 | |
| WO | 2020206308 A1 | 10/2020 | |
| WO | 2020217070 A1 | 10/2020 | |
| WO | WO-2021004547 A1 | 1/2021 | |
| WO | 2021126731 A1 | 6/2021 | |
| WO | 2021126999 A1 | 6/2021 | |
| WO | 2021140427 A1 | 7/2021 | |
| WO | 2021163344 A1 | 8/2021 | |
| WO | WO-2022026892 A1 | 2/2022 | |
| WO | WO-2022115377 A1 | 6/2022 | |
| WO | WO-2022132914 A1 | 6/2022 | |
| WO | WO-2022256806 A1 | 12/2022 | |
| WO | WO-2023098439 A1 | 6/2023 | |

OTHER PUBLICATIONS

Bertino et al., "Targeting tumors that lack methylthioadenosine phosphorylase (MTAP) activity", Cancer Biology & Therapy, vol. 11, No. 7, pp. 627-632, Apr. 1, 2011.
Bogolubsky et al., "2,2,2-Trifluoroethyl Chlorooxoacetate-Universal Reagent for One-Pot Parallel Synthesis of N1-Aryl-N2-alkyl-Substituted Oxamides", ACS Combinational Science, vol. 17, No. 10, Oct. 12, 2015.
Wu et al., "Protein arginine methylation: from enigmatic functions to therapeutic targeting", Nature Reviews Drug Discovery, Nature Publishing Group, GB, vol. 20, No. 7, Mar. 19, 2021, pp. 509-530.
Chan-Penebre "A selective inhibitor of PRMT5 with in vivo and in vitro potency in MCL models," Nature: Chemical Biology, vol. 11 p. 432, 2015, DOI: 10.1038/NCHEMBIO.1810.
Duncan, et al., "Structure and Property Guided Design in the Identification of PRMT5 Tool Compound EPZ015666," ACS Med. Chem. Lett. Vol. 7, pp. 162-166, 2015, DOI: 10.1021/acsmedchemlett.5b00380.
Mavrakis, et al., Disordered methionine metabolism in MTAP/CDKN2A-deleted cancers leads to dependence on PRMT5, Science vol. 351, Issue 6278, 2016.

* cited by examiner

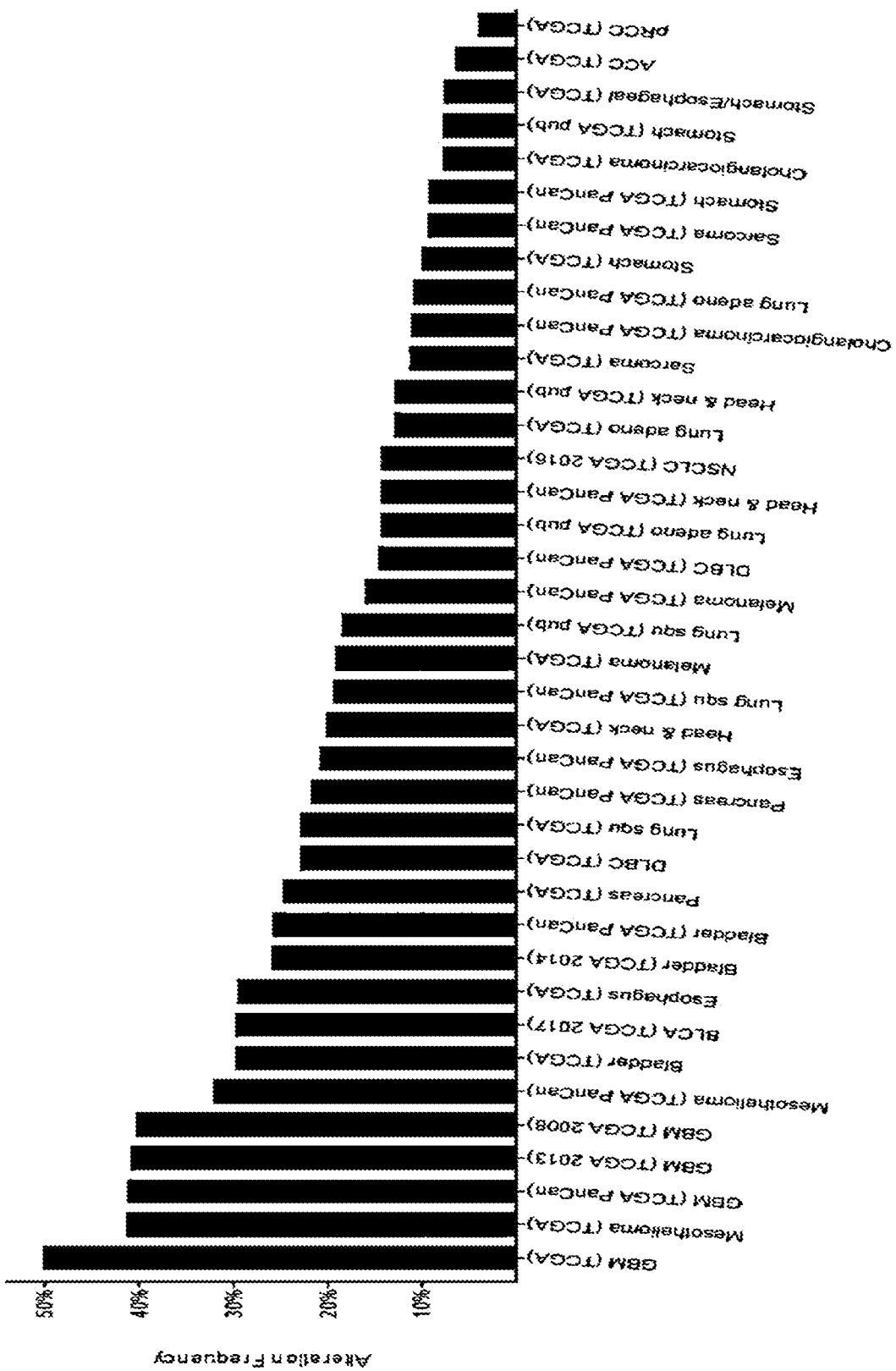

SEQUENCE LISTING

```
<160> NUMBER OF SEQ ID NOS: 2

<210> SEQ ID NO 1
<211> LENGTH: 22
<212> TYPE: PRT
<213> ORGANISM: Artificial Sequence
<220> FEATURE:
<223> OTHER INFORMATION: Synthetic Construct
<220> FEATURE:
<221> NAME/KEY: q2
<222> LOCATION: (1)..(1)
<223> OTHER INFORMATION: The amino acid at position 1 is attached to an
      (Ac) group
<220> FEATURE:
<221> NAME/KEY: q3
<222> LOCATION: (22)..(22)
<223> OTHER INFORMATION: The amino acid at position 22 is attached to an
      (NH2) group
<220> FEATURE:
<221> NAME/KEY: q4
<222> LOCATION: (22)..(22)
<223> OTHER INFORMATION: The amino acid at position 22 is attached to
      5-TAMRA (5-Carboxytetramethylrhodamine)

<400> SEQUENCE: 1

Ser Gly Arg Gly Lys Gly Gly Lys Gly Leu Gly Lys Gly Gly Ala Lys
1               5                   10                  15

Arg His Arg Lys Val Lys
            20

<210> SEQ ID NO 2
<211> LENGTH: 22
<212> TYPE: PRT
<213> ORGANISM: Artificial Sequence
<220> FEATURE:
<223> OTHER INFORMATION: Synthetic Construct
<220> FEATURE:
<221> NAME/KEY: q7
<222> LOCATION: (1)..(1)
<223> OTHER INFORMATION: The amino acid at position 1 is attached to an
      (Ac) group
<220> FEATURE:
<221> NAME/KEY: q8
<222> LOCATION: (3)..(3)
<223> OTHER INFORMATION: The amino acid at position 3 is dimethylated in
      a symmetrical manner
<220> FEATURE:
<221> NAME/KEY: q9
<222> LOCATION: (22)..(22)
<223> OTHER INFORMATION: The amino acid at position 22 is attached to an
      (NH2) group
<220> FEATURE:
<221> NAME/KEY: q10
<222> LOCATION: (22)..(22)
<223> OTHER INFORMATION: The amino acid at position 22 is attached to
      5-TAMRA (5-Carboxytetramethylrhodamine)

<400> SEQUENCE: 2

Ser Gly Arg Gly Lys Gly Gly Lys Gly Leu Gly Lys Gly Gly Ala Lys
1               5                   10                  15

Arg His Arg Lys Val Lys
            20
```

COMPOUNDS AND METHODS OF USE

CROSS-REFERENCE TO RELATED APPLICATIONS

This application is a national phase filing under 35 U.S.C. § 371 claiming the benefit of and priority to International Patent Application No. PCT/US2020/057601, filed Oct. 28, 2022, which claims the benefit of and priority to U.S. Provisional Patent Application No. 62/926,801, filed Oct. 28, 2019. The entire disclosures of these applications are incorporated by reference herein in their entireties for all purposes.

The instant application contains a Sequence Listing which has been submitted electronically in TXT format and is hereby incorporated by reference in its entirety. Said TXT file copy, created on May 22, 2025, is named 2025-05-22 TGO-005WOUS_ST25.txt and is 1,755 bytes in size.

BACKGROUND OF THE INVENTION

Cancer therapeutics can be broadly classified into two categories, cytotoxic and targeted therapies. While cytotoxic therapies are associated with widespread toxicities, targeted therapies have the advantage of selectively targeting the tumor cells that rely on the activity of their substrates. The clinical efficacy of targeted therapies has been demonstrated with BCR/ABL and EGFR inhibitors for the treatment of CML and non-small cell lung cancer, respectively. The success of these programs has furthered development of other therapies that specifically target amplified or mutation-activated oncogenes. The greater challenge is to develop selective therapies that target those tumors with loss-of-function mutations or deletion of tumor suppressor genes, the loss of which obviate traditional strategies for molecular targeted therapeutics.

Efforts to characterize the cancer genome, led by groups like the Cancer Genome Atlas (TCGA), have made tremendous strides in elucidating the size and frequency of the deletion events that promote tumor growth by causing the loss of tumor suppressor genes. However, these events are often regional and cause the co-deletion of genes proximal to their intended targets. Though these passenger events are not known to cause a fitness advantage, they may cause collateral vulnerabilities that can be therapeutically leveraged. One example is the collateral vulnerability to PRMT5 inhibition conferred by loss of methylthioadenosine phosphorylase (MTAP), which is frequently co-deleted with the well-described tumor suppressor gene, CDKN2A (Kruykov et al., 2016; Marjon et al., 2016 and Markarov et al., 2016).

Loss of CDKN2A occurs in ~15% of all human cancers and with frequency in histologies such as malignant peripheral nerve sheath tumors, glioblastoma, mesothelioma, bladder urothelial carcinoma, esophageal squamous cell carcinoma, pancreatic adenocarcinoma, melanoma, non-small cell lung cancer, head and neck cancer and cholangiosarcoma (Gao et al. *Sci. Signal.* 2013 & Cerami et al. *Cancer Discov.* 2012). Because of its proximity to CDKN2A on chromosome 9p21, MTAP is frequently included in the deletion. MTAP is a critical enzyme in the methionine salvage pathway, a six-step process that recycles methionine from the product of polyamine synthesis, methylthioadenosine (MTA). Loss of MTAP causes the accumulation of its substrate, MTA, which has been demonstrated by multiple groups to function as a SAM-competitive PRMT5 inhibitor (Kruykov et al., 2016; Marjon et al., 2016 and Markarov et al., 2016).

PRMT5 is a type II arginine methyltransferase that regulates essential cellular functions, including the regulation of cell cycle progression, apoptosis and the DNA-damage response, by symmetrically dimethylating proteins involved in transcription and signaling (insert reference). However, data from genome-wide genetic perturbation screens using shRNA has revealed a selective requirement for PRMT5 activity in MTAP-deleted cancer cell lines (Kruykov et al., 2016; Marjon et al., 2016 and Markarov et al., 2016). The accumulation of MTA caused by MTAP-deletion in these cell lines partially inhibits PRMT5, rendering those cells selectively sensitive to additional PRMT5 inhibition.

PRMT5 inhibitors have been developed, yet they do not demonstrate selectivity for MTAP-deleted cancer cell lines. This lack of selectivity can be explained by the mechanisms of action of the inhibitors, as they are either SAM-uncompetitive or SAM-competitive inhibitors and therefore, MTAP-agnostic (Kruykov et al., 2016; Marjon et al., 2016 and Markarov et al., 2016) However, if a PRMT5 inhibitor were developed that leverages the accumulation of MTA by binding in an MTA-uncompetitive manner, it could demonstrate selectivity for MTAP-deleted tumor cells.

SUMMARY OF THE INVENTION

In one aspect, the invention provides a compound or a pharmaceutically acceptable salt thereof wherein the compound is of Formula (I)

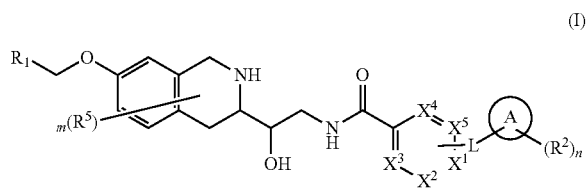

wherein:
- $X^1$, $X^2$, $X^3$, $X^4$ and $X^5$ are each independently N or $CR^x$;
- L is a bond, —C(=O)—, —NH— or —O—;
- Ring A is a carbocycle, heterocycle or a 5-6 membered monocyclic heteroaryl;
- $R^1$ is a 5-6 membered heteroaryl substituted with 0-3 instances of $R^4$;
- each $R^2$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, heteroarylalkyl, arylalkyl, cycloalkylalkyl, —$OR^3$, —$N(R^3)_2$, —C(=O)$R^3$, —C(=O)$OR^3$, —$NR^3$C(=O)$R^3$, —$NR^3$C(=O)$OR^3$, —C(=O)N($R^3$)$_2$, —OC(=O)N($R^3$)$_2$, —S(=O)$R^3$, —S(=O)$_2$$R^3$, —$SR^3$, —S(=O)(=$NR^3$)$R^3$, —$NR^3$S(=O)$_2$$R^3$ and —S(=O)$_2$N($R^3$)$_2$;
- each $R^3$ is independently selected from H, $C_1$-$C_6$ alkyl, —$C_1$-$C_6$ heteroalkyl, $C_3$-$C_9$ carbocyclyl, 3-7 membered heterocyclyl, cycloalkylalkyl, heterocyclylalkyl, aryl, 5-6 membered heteroaryl, arylalkyl and heteroarylalkyl wherein each alkyl, carbocyclyl, heterocyclyl, cycloalkylalkyl, heterocyclylalkyl, aryl, heteroaryl, arylalkyl and heteroarylalkyl is optionally substituted;
- each $R^4$ is independently selected from =O, halo, —CN, —$C_1$-$C_6$ alkyl, —$C_1$-$C_6$ heteroalkyl, —$C_1$-$C_6$ haloalkyl, —C₃-C₉ carbocyclyl, 3-10 membered heterocyclyl, heterocyclylalkyl, cycloalkylalkyl, —OR³, —N(R³)₂, —C(=O)R³, —C(=O)OR³, —NR³C(=O)R³, —NR³C(=O)OR³, —C(=O)N(R³)₂, —OC(=O)N(R³)₂, —S(=O)R³, —S(=O)₂R³, —SR³, —S(=O)(=NR³)R³, —NR³S(=O)₂R³ and —S(=O)₂N(R³)₂; each R$^x$ is independently selected from hydrogen, halo, —CN, —C₁-C₆ alkyl, —C₁-C₆ heteroalkyl, —C₁-C₆ haloalkyl, —C₃-C₉ carbocyclyl, 3-10 membered heterocyclyl, heterocyclylalkyl, cycloalkylalkyl, —OR³, —N(R³)₂, —C(=O)R³, —C(=O)OR³, —NR³C(=O)R³, —NR³C(=O)OR³, —C(=O)N(R³)₂, —OC(=O)N(R³)₂, —S(=O)R³, —S(=O)₂R³, —SR³, —S(=O)(=NR³)R³, —NR³S(=O)₂R³ and —S(=O)₂N(R³)₂ wherein each alkyl, carbocyclyl, heterocyclyl, heterocyclylalkyl, cycloalkylalkyl is optionally substituted;

each R⁵ is independently selected from =O, halo, —CN, —C₁-C₆ alkyl, —C₁-C₆ heteroalkyl, —C₁-C₆ haloalkyl, —C₃-C₉ carbocyclyl, 3-10 membered heterocyclyl, C₆-C₁₀ aryl, 5-10 membered heteroaryl, cycloalkylalkyl, heterocyclylalkyl, arylalkyl, heteroarylalkyl, —OR³, —N(R³)₂, —C(=O)R³, —C(=O)OR³, —NR³C(=O)R³, —NR³C(=O)OR³, —C(=O)N(R³)₂, —OC(=O)N(R³)₂, —S(=O)R³, —S(=O)₂R³, —SR³, —S(=O)(=NR³)R³, —NR³S(=O)₂R³, —S(=O)₂N(R³)₂, or two R⁵ can be taken together with the atoms to which they are attached to form a —C₃-C₉ carbocyclyl or a 3-10 membered heterocyclyl;

m is 0, 1, 2 or 3; and
n is 0, 1, 2 or 3.

In certain embodiments, the compound has structure (Ia)

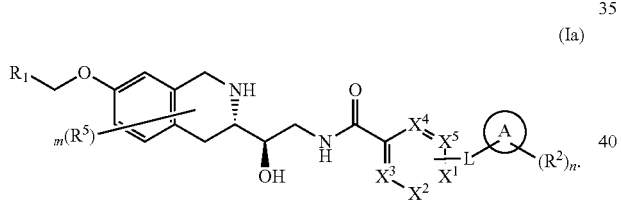

(Ia)

In certain embodiments, the compound has structure (II)

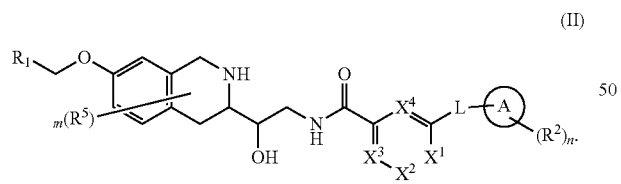

(II)

In a further embodiment, the compound has structure (IIa):

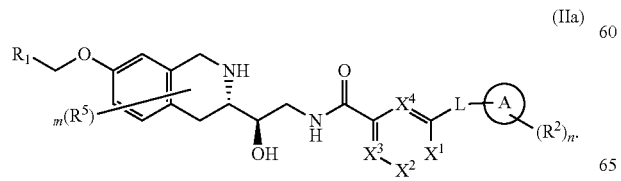

(IIa)

In one aspect, the invention provides a compound or pharmaceutically acceptable salt thereof wherein the compound is of Formula (VI)

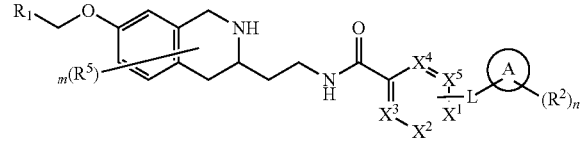

(VI)

wherein:
X¹, X², X³, X⁴ and X⁵ are each independently N or CR$^x$;
L is a bond, —C(=O)—, —NH— or —O—;
Ring A is a carbocycle, heterocycle or a 5-6 membered monocyclic heteroaryl;
R¹ is a 5-6 membered heteroaryl substituted with 0-3 instances of R⁴;
each R² is independently selected from =O, halo, —CN, —C₁-C₆ alkyl, —C₁-C₆ heteroalkyl, —C₁-C₆ haloalkyl, —C₃-C₉ carbocyclyl, 3-10 membered heterocyclyl, heterocyclylalkyl, heteroarylalkyl, arylalkyl, cycloalkylalkyl, —OR³, —N(R³)₂, —C(=O)R³, —C(=O)OR³, —NR³C(=O)R³, —NR³C(=O)OR³, —C(=O)N(R³)₂, —OC(=O)N(R³)₂, —S(=O)R³, —S(=O)₂R³, —SR³, —S(=O)(=NR³)R³, —NR³S(=O)₂R³ and —S(=O)₂N(R³)₂;
each R³ is independently selected from H, C₁-C₆ alkyl, —C₁-C₆ heteroalkyl, C₃-C₉ carbocyclyl, 3-7 membered heterocyclyl, cycloalkylalkyl, heterocyclylalkyl, aryl, 5-6 membered heteroaryl, arylalkyl and heteroarylalkyl wherein each alkyl, carbocyclyl, heterocyclyl, cycloalkylalkyl, heterocyclylalkyl, aryl, heteroaryl, arylalkyl and heteroarylalkyl is optionally substituted;
each R⁴ is independently selected from =O, halo, —CN, —C₁-C₆ alkyl, —C₁-C₆ heteroalkyl, —C₁-C₆ haloalkyl, —C₃-C₉ carbocyclyl, 3-10 membered heterocyclyl, heterocyclylalkyl, cycloalkylalkyl, —OR³, —N(R³)₂, —C(=O)R³, —C(=O)OR³, —NR³C(=O)R³, —NR³C(=O)OR³, —C(=O)N(R³)₂, —OC(=O)N(R³)₂, —S(=O)R³, —S(=O)₂R³, —SR³, —S(=O)(=NR³)R³, —NR³S(=O)₂R³ and —S(=O)₂N(R³)₂;
each R$^x$ is independently selected from hydrogen, halo, —CN, —C₁-C₆ alkyl, —C₁-C₆ heteroalkyl, —C₁-C₆ haloalkyl, —C₃-C₉ carbocyclyl, 3-10 membered heterocyclyl, heterocyclylalkyl, cycloalkylalkyl, —OR³, —N(R³)₂, —C(=O)R³, —C(=O)OR³, —NR³C(=O)R³, —NR³C(=O)OR³, —C(=O)N(R³)₂, —OC(=O)N(R³)₂, —S(=O)R³, —S(=O)₂R³, —SR³, —S(=O)(=NR³)R³, —NR³S(=O)₂R³ and —S(=O)₂N(R³)₂ wherein each alkyl, carbocyclyl, heterocyclyl, heterocyclylalkyl, cycloalkylalkyl is optionally substituted;
each R⁵ is independently selected from =O, halo, —CN, —C₁-C₆ alkyl, —C₁-C₆ heteroalkyl, —C₁-C₆ haloalkyl, —C₃-C₉ carbocyclyl, 3-10 membered heterocyclyl, C₆-C₁₀ aryl, 5-10 membered heteroaryl, cycloalkylalkyl, heterocyclylalkyl, arylalkyl, heteroarylalkyl, —OR³, —N(R³)₂, —C(=O)R³, —C(=O)OR³, —NR³C(=O)R³, —NR³C(=O)OR³, —C(=O)N(R³)₂, —OC(=O)N(R³)₂, —S(=O)R³, —S(=O)₂R³, —SR³, —S(=O)(=NR³)R³, —NR³S(=O)₂R³, —S(=O)₂N(R³)₂, or two R⁵ can be taken together with the atoms to which they are attached to form a —C₃-C₉ carbocyclyl or a 3-10 membered heterocyclyl;
m is 0, 1, 2 or 3; and
n is 0, 1, 2 or 3.

In one embodiment, the compound is of Formula (VIa):

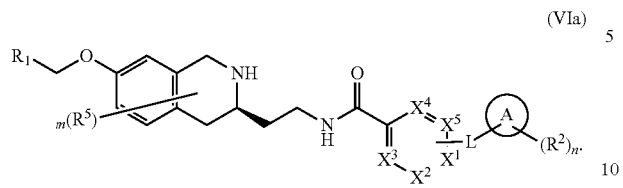
(VIa)

In another embodiment, the compound is of Formula (VIb):

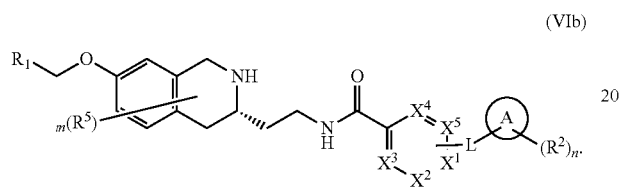
(VIb)

In some embodiments, the compound is of Formula (VII):

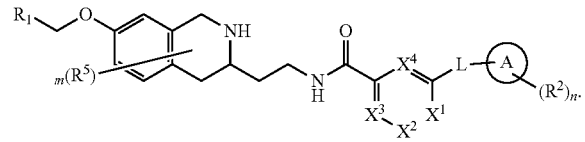
(VII)

In certain embodiments, the compound is of Formula (VIIa):

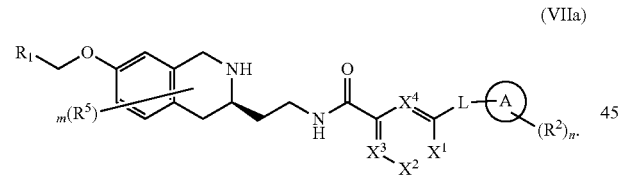
(VIIa)

In some embodiments, the compound is of Formula (VIIb):

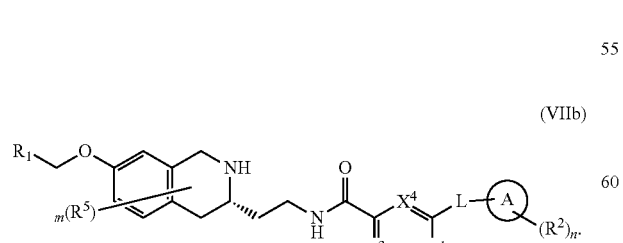
(VIIb)

In some embodiments of the invention, $X^1$ is N and $X^2$, $X^3$ and $X^4$ are $CR^x$.

In further embodiments, the compound has structure (IIa1):

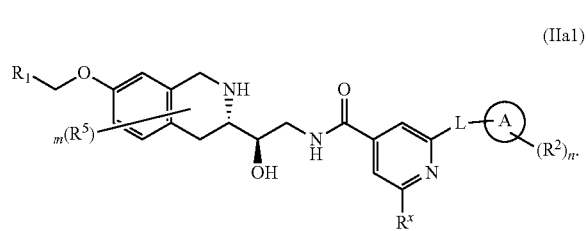
(IIa1)

In some embodiments of the invention, $X^1$ and $X^3$ are N and $X^2$ and $X^4$ are $CR^x$.

In further embodiments, the compound has structure (IIa2):

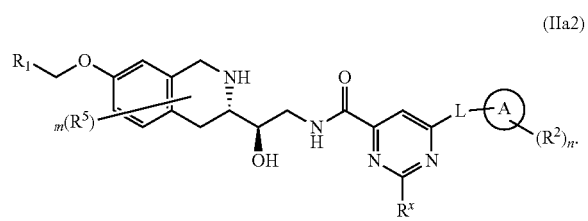
(IIa2)

In some embodiments of the invention, $X^1$, $X^2$, $X^3$ and $X^4$ are $CR^x$.

In some embodiments, the compound is of Formula (VIIa1):

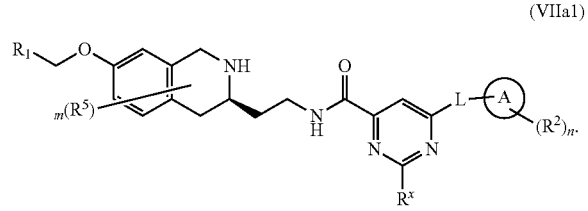
(VIIa1)

In some embodiments, the compound is of Formula (VIIb1):

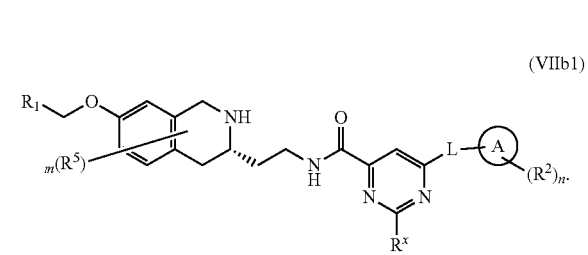
(VIIb1)

In further embodiments, the compound is of Formula (IIa3):

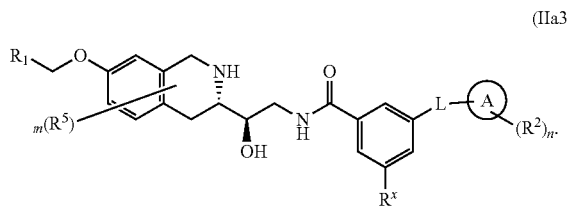

(IIa3)

In some embodiments of the invention $X^3$ is N and $X^1$, $X^2$ and $X^4$ are $CR^x$.

In further embodiments the compound is of Formula (IIa4)

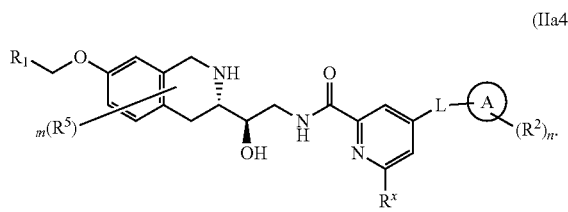

(IIa4)

In alternative embodiments, the compound has structure (III)

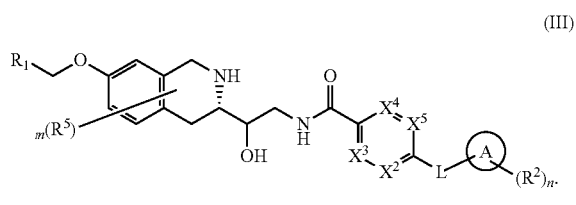

(III)

In further embodiments, the compound has structure (IIIa).

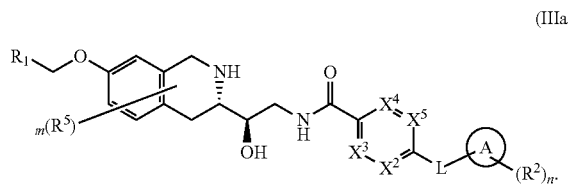

(IIIa)

In certain embodiments, $X^2$ is N, and $X^3$, $X^4$, and $X^5$ are $CR^x$.

In further embodiments, the compound has structure (IIIa1):

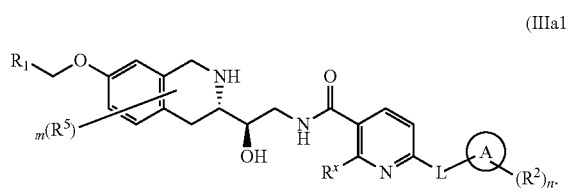

(IIIa1)

In other embodiments, $X^2$, $X^3$, $X^4$ and $X^5$ are $CR^x$.

In further embodiments, the compound has structure (IIIa2)

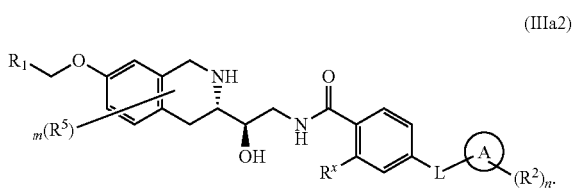

(IIIa2)

In some embodiments of the invention, L is —NH—.

In further embodiments, the compound is of Formula (IIa1i):

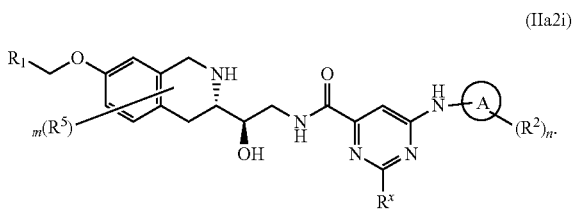

(IIa1i)

In an alternate embodiment, the compound is of Formula (IIa2i):

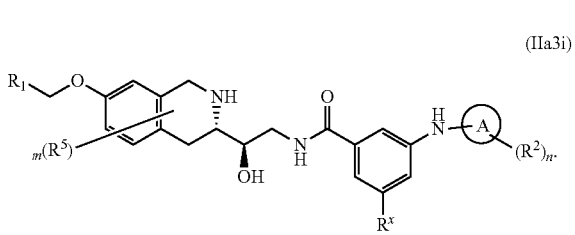

(IIa2i)

In yet another embodiment, the compound is of Formula (IIa3i):

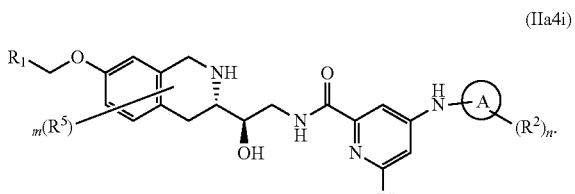

(IIa3i)

In another embodiment the compound is of Formula (IIa4i)

(IIa4i)

In some embodiments, the compound is of Formula (VIIa1i):

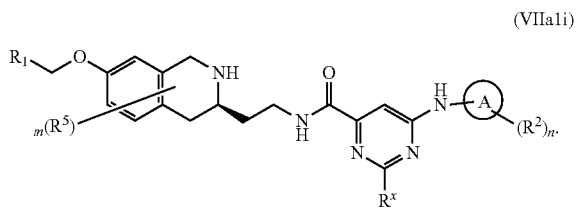
(VIIa1i)

In other embodiments the compound is of Formula (VIIb1i):

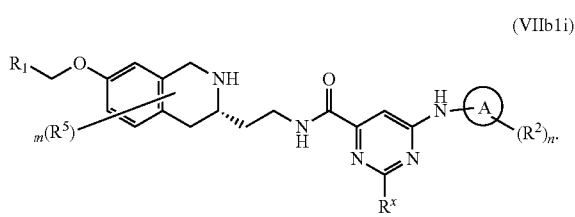
(VIIb1i)

In some embodiments of the invention L is a bond.
In certain embodiments the compound is of Formula (IIa3ii):

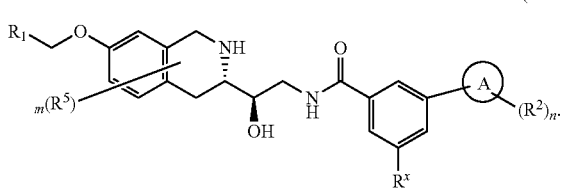
(IIa3ii)

In alternate embodiments the compound is of Formula (IIIa1i):

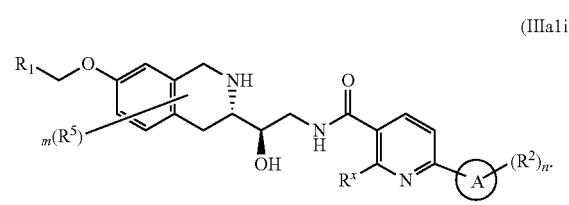
(IIIa1i)

In certain embodiments of the invention L is —O—.
In further embodiments the compound is of Formula (IIIa2i):

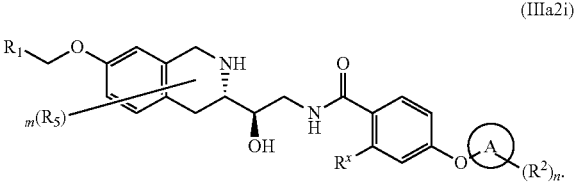
(IIIa2i)

In certain embodiments of the invention L is —C(=O)—.

In further embodiments the compound is of Formula (IIIa2ii):

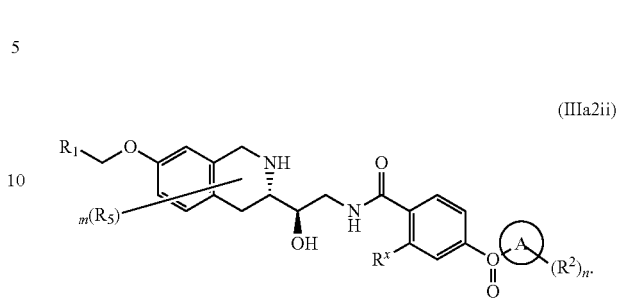
(IIIa2ii)

In certain embodiments of the invention $R^x$ is H, $N(R^3)_2$, $NHR^3$, $N(CH_3)R^3$, $OR^3$, alkyl, optionally substituted —$C_3$-$C_9$ carbocyclyl or optionally substituted -3-10-membered heterocyclyl.

In some embodiments $R^x$ is —$C_3$-$C_9$ carbocyclyl or 3-10 membered heterocyclyl substituted with 0-1 instances of $R^7$, wherein $R^7$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, $C_6$-$C_{10}$ aryl, 5-10 membered heteroaryl, cycloalkylalkyl, heterocyclylalkyl, arylalkyl, heteroarylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$ or —$S(=O)_2N(R^3)_2$.

In further embodiments, $R^7$ is —$C_1$-$C_6$ alkyl or —C(=O)$R^3$.

In some embodiments $R^x$ is a 4-7 membered monocyclic heterocyclyl or 7-10 membered bridged bicyclic heterocyclyl.

In further embodiments $R^x$ is a 7-8 membered bridged bicyclic heterocyclyl or 6 membered monocyclic heterocyclyl; wherein the 7-8 membered bridged bicyclic heterocyclyl or 6 membered monocyclic heterocyclyl contains 1 or 2 heteroatoms independently selected from O and N.

In certain embodiments $R^x$ is selected from piperidinyl, piperazinyl, morpholinyl, 2-azabicyclo[2.2.1]heptanyl, 3-azabicyclo[3.1.1]heptanyl, and 3-azabicyclo[3.2.1]octanyl.

In alternate embodiments $R^x$ is H.

In some embodiments of the invention ring A is a 4-6 membered monocyclic heterocyclyl, containing 1 or 2 heteroatoms independently selected from O and N.

In a preferred embodiment ring A is piperidinyl, piperazinyl, pyrrolidinyl, oxetanyl, tetrahydrofuranyl, azetidinyl, tetrahydropyranyl, 1,4-dioxan-2-yl or morpholinyl.

In some embodiments ring A is piperidinyl.

In some embodiments ring A is oxetanyl.

In some embodiments ring A is tetrahydropyranyl.

In some embodiments ring A is morpholinyl.

In some embodiments ring A is a 7-12 membered bicyclic heterocyclyl.

In some embodiments ring A is a 7-9 membered bridged bicyclic or spirocyclic heterocyclyl containing one or two heteroatoms independently selected from O and N.

In a preferred embodiment ring A is selected from:

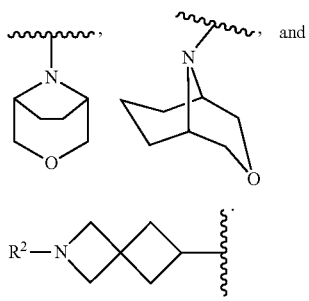

In an alternate embodiment ring A is a 5-6 membered monocyclic heteroaryl.

In a preferred embodiment ring A is pyridinyl (e.g., 3-pyridinyl).

In another embodiment ring A is a 3-8 membered carbocycle.

In one embodiment ring A is a 6-8 membered spirocarbocycle.

In certain embodiments ring A is cyclopropyl, cyclobutyl, cyclopentyl, cyclohexyl, cycloheptyl, spiro[2.3]hexyl or spiro[3.3]heptyl.

In one embodiment ring A is cyclobutyl.

In one aspect of the invention provided is a compound of Formula (IV):

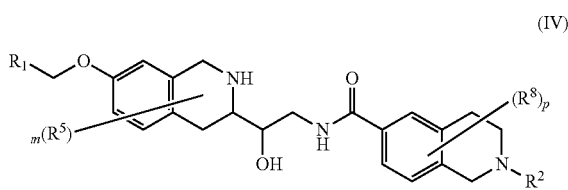

or a pharmaceutically acceptable salt thereof,
wherein:
$R^1$ is a 5-6 membered heteroaryl substituted with 0-3 instances of $R^4$;
each $R^2$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, cycloalkylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$ and —$S(=O)_2N(R^3)_2$;
each $R^3$ is independently selected from H, $C_1$-$C_6$ alkyl, $C_3$-$C_9$ carbocyclyl, 3-10 membered heterocyclyl, cycloalkylalkyl, heterocyclylalkyl, aryl, 5-6 membered heteroaryl, arylalkyl and heteroarylalkyl wherein each alkyl, carbocyclyl, heterocyclyl, cycloalkylalkyl, heterocyclylalkyl, aryl, heteroaryl, arylalkyl and heteroarylalkyl is optionally substituted;
each $R^4$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, cycloalkylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$ and —$S(=O)_2N(R^3)_2$;
each $R^5$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, $C_6$-$C_{10}$ aryl, 5-10 membered heteroaryl, cycloalkylalkyl, heterocyclylalkyl, arylalkyl, heteroarylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$, —$S(=O)_2N(R^3)_2$, or two $R^5$ can be taken together with the atoms to which they are attached to form a —$C_3$-$C_9$ carbocyclyl or a 3-10 membered heterocyclyl;
each $R^8$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, $C_6$-$C_{10}$ aryl, 5-10 membered heteroaryl, cycloalkylalkyl, heterocyclylalkyl, arylalkyl, heteroarylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$, —$S(=O)_2N(R^3)_2$, or two $R^5$ can be taken together with the atoms to which they are attached to form a —$C_3$-$C_9$ carbocyclyl or a 3-10 membered heterocyclyl;
m is 0, 1, 2 or 3; and
p is 0, 1, 2 or 3.
In one embodiment the compound of Formula (IV) is of Formula (IVa):

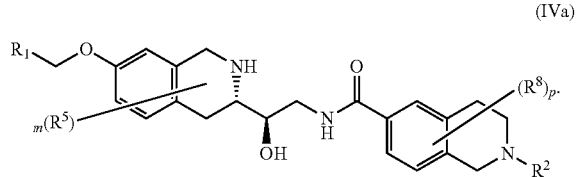

In one aspect of the invention provided is a compound of Formula (V)

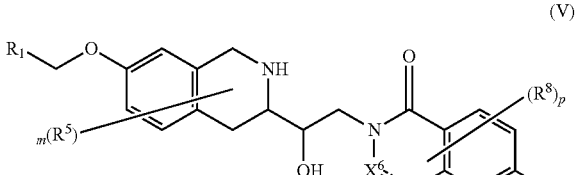

or a pharmaceutically acceptable salt thereof,
wherein:
$X^6$ is N, NH, $CHR^x$ or $CR^x$;
$R^1$ is a 5-6 membered heteroaryl substituted with 0-3 instances of $R^4$;
each $R^2$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, heteroaryl alkyl, cycloalkylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$ and —$S(=O)_2N(R^3)_2$;
each $R^3$ is independently selected from H, $C_1$-$C_6$ alkyl, —$C_1$-$C_6$ heteroalkyl, $C_3$-$C_9$ carbocyclyl, 3-10 membered heterocyclyl, cycloalkylalkyl, heterocyclylalkyl, aryl, 5-6 membered heteroaryl, arylalkyl and heteroarylalkyl wherein each alkyl, carbocyclyl, heterocyclyl, cycloalkylalkyl, heterocyclylalkyl, aryl, heteroaryl, arylalkyl and heteroarylalkyl is optionally substituted;

each $R^4$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, cycloalkylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$ and —$S(=O)_2N(R^3)_2$;

each $R^x$ is independently selected from hydrogen, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, cycloalkylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$ and —$S(=O)_2N(R^3)_2$ wherein each alkyl, carbocyclyl, heterocyclyl, heterocyclylalkyl, cycloalkylalkyl is optionally substituted;

each $R^5$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, $C_6$-$C_{10}$ aryl, 5-10 membered, cycloalkylalkyl, heterocyclylalkyl, arylalkyl, heteroarylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$, —$S(=O)_2N(R^3)_2$, or two $R^5$ can be taken together with the atoms to which they are attached to form a —$C_3$-$C_9$ carbocyclyl or a 3-10 membered heterocyclyl;

each $R^8$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, $C_6$-$C_{10}$ aryl, 5-10 membered heteroaryl, cycloalkylalkyl, heterocyclylalkyl, arylalkyl, heteroarylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$, —$S(=O)_2N(R^3)_2$, or two $R^5$ can be taken together with the atoms to which they are attached to form a —$C_3$-$C_9$ carbocyclyl or a 3-10 membered heterocyclyl;

m is 0, 1, 2 or 3; and p is 0, 1, 2 or 3.

In one embodiment the compound of Formula (V) is of Formula (Va)

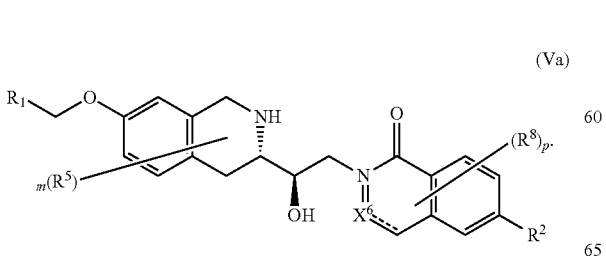

(Va)

In a further embodiment the compound is of Formula (Va1)

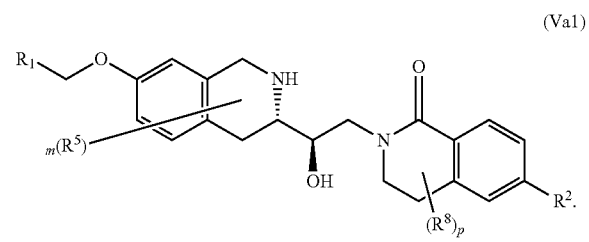

(Va1)

In one embodiment the compound is of Formula (Va2):

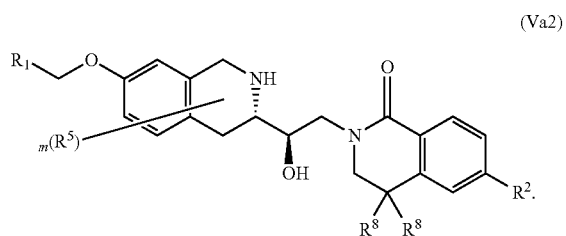

(Va2)

In another embodiment the compound is of Formula (Va3):

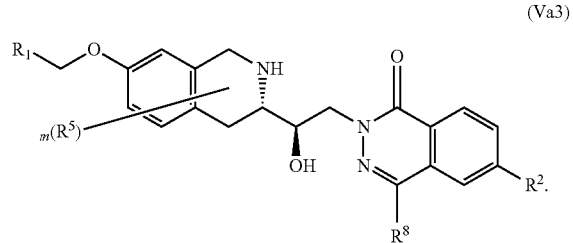

(Va3)

In certain embodiments of the invention $R^1$ is a 5-membered heteroaryl substituted with 0-3 instances of $R^4$.

In some embodiments $R^1$ is selected from:

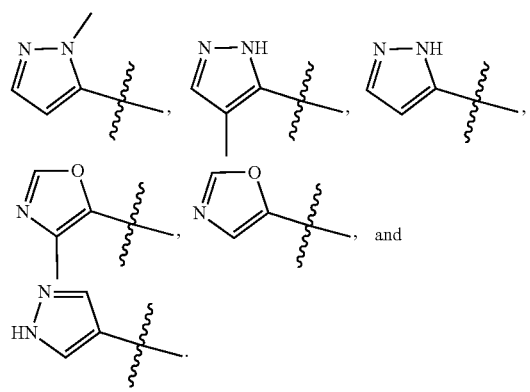

In further embodiments R¹ is:

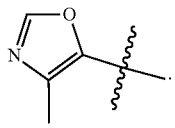

In other embodiments R¹ is a 6-membered heteroaryl (e.g., pyridyl) substituted with 0-3 instances of R⁴.
In certain embodiments R¹ is:

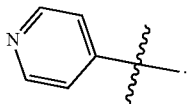

In some embodiments of the invention R⁴ is $C_1$-$C_6$ alkyl.
In certain embodiments R⁴ is methyl.
In some embodiments of the invention n is 0.
In other embodiments n is 1.
In some embodiments of the invention R² is arylalkyl or heteroarylalkyl.
In certain embodiments R² is benzyl or pyridinylmethyl (e.g., pyridin-4-ylmethyl).
In other embodiments R² is —C(=O)OR³ or —C(O)R³.
In certain embodiments R² is —C(O)CH₃, —C(O)cyclopropyl, —C(O)cyclobutyl, —C(O)$^t$Bu, —C(O)$^i$Pr, —C(O)Pr, —C(O)$^i$Bu, or —C(=O)OMe.
In some embodiments R³ is $C_3$-$C_7$ carbocyclyl, $C_1$-$C_6$ alkyl or $C_1$-$C_6$ heteroalkyl.
In further embodiments R³ is $C_1$-$C_3$ alkyl, $C_1$-$C_6$ heteroalkyl (e.g., —(CH₂)₂OCH₃) or $C_3$-$C_7$cycloalkyl.
In some embodiments of the invention R² is —C(=O)R³.
In some further embodiments R³ is optionally substituted aryl.
In certain embodiments R³ is phenyl substituted with 0-2 instances of —OMe or halo.
In other embodiments R³ is $C_3$-$C_9$ carbocyclyl or 3-10 membered heterocyclyl wherein each carbocyclyl and heterocyclyl is optionally substituted.
In certain embodiments R³ is $C_3$-$C_9$ carbocyclyl or 3-10 membered heterocyclyl wherein each carbocyclyl and heterocyclyl is optionally substituted with 0-2 instances of R⁷, wherein each R⁷ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, $C_6$-$C_{10}$ aryl, 5-10 membered heteroaryl, cycloalkylalkyl, heterocyclylalkyl, arylalkyl, heteroarylalkyl, —OR³, —N(R³)₂, —C(=O)R³, —C(=O)OR³, —NR³C(=O)R³, —NR³C(=O)OR³, —C(=O)N(R³)₂, —OC(=O)N(R³)₂, —S(=O)R³, —S(=O)₂R³, —SR³, —S(=O)(=NR³)R³, —NR³S(=O)₂R³ or —S(=O)₂N(R³)₂.
In further embodiments R³ is a monocyclic or bicyclic 3-10 membered heterocyclyl (e.g., morpholine, piperidine, piperazine, azepane, 8-azabicyclo[3.2.1]octane, 3-oxa-8-azabicyclo[3.2.1]octane) substituted with one instance of methyl, ethyl, hydroxy or methoxy.
In some embodiments of the invention m is 0.
In alternate embodiments m is 1 and each R⁵ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, —OR³, —N(R³)₂, —CO(R³), —NR³(CO)R³, —(CO)N(R³)₂.

In some embodiments of the invention p is 0.
In other embodiments p is 1 and each R⁸ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, —OR³, —N(R³)₂, —CO(R³), —NR³(CO)R³, —(CO)N(R³)₂.
In yet other embodiments p is 2 and each R⁸ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, —OR³, —N(R³)₂, —CO(R³), —NR³(CO)R³, —(CO)N(R³)₂.
In certain embodiments R⁸ is $C_1$-$C_6$ alkyl (e.g., methyl, ethyl, propyl, isopropyl)
In one embodiment of the invention, the compound is selected from Table 1.
In one aspect, the invention provides a pharmaceutical composition comprising a compound of the invention and a pharmaceutically acceptable carrier. In one embodiment, the composition further comprises a second therapeutic agent.
In one aspect, the invention provides a method of treating an MTAP-deficient and/or an MTA-accumulating disease in a subject in need thereof by administering to the subject a therapeutically effective amount of a compound of the invention as described herein or a pharmaceutically acceptable composition comprising compounds of the invention.
In one embodiment, the compound or composition is administered in combination with a second therapeutic agent.
In one aspect, the invention provides a method of treating an MTAP-deficient and/or an MTA-accumulating disease in a subject in need thereof by administering to the subject a therapeutically effective amount of a pharmaceutically acceptable composition comprising a compound of the invention as described herein and a second therapeutic agent.
In one embodiment, the disease is a proliferating disease.
In one embodiment, the disease is an MTAP-deficient and/or MTA-accumulating cancer. In some embodiments, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.
In one aspect, the invention provides a method of treating a cancer in a subject in need thereof comprising the steps of:
a) assessing the level of MTAP and/or MTA in a test sample obtained from said subject, wherein the MTA level can be assessed directly (e.g., by ELISA or LC-MS/MS or indirectly (e.g., by SDMA-modified protein ELISA or IHC, or by RNA splicing);
b) comparing the test sample with a reference, wherein MTAP deficiency and/or MTA accumulation in said test sample compared to the reference indicates the cancer in said subject will respond to therapeutic treatment with a PRMT5 inhibitor; and
c) administering a therapeutically effective amount of a compound or composition of the invention as described herein to the subject identified in step b).

Other objects and advantages will become apparent to those skilled in the art from a consideration of the ensuing Detailed Description, Examples, and Claims.

BRIEF DESCRIPTION OF THE DRAWINGS

FIG. 1. Frequency of MTAP homozygous deletion in cell lines representing exemplary cancers according to The Cancer Genome Atlas (TCGA).

DEFINITIONS

MTAP

"MTAP" as used herein refers to methylthioadenosine phosphorylase, an enzyme in the methionine salvage pathway, also known as S-methyl-5'-thioadenosine phosphorylase; also known as BDMF; DMSFH; DMSMFH; LGMBF; MSAP; and c86fus. External IDs:

OMIM: 156540 MGI: 1914152 HomoloGene:1838 chEMBL: 4941 GeneCards: MTAP Gene; Entrez 4507; RefSeq (mRNA): NM_002451; location: Chr 9: 21.8-21.93 Mb. By "wild-type" MTAP is meant that encoded by NM_002451 or having the same amino acid sequence (NP_002442). (Schmid et al. *Oncogene* 2000, 19, pp 5747-54).

As used herein, the term "MTAP-deficient", "MTAP-deficiency", "MTAP-null" and the like refer to cells (including, but not limited to, cancer cells, cell lines, tissues, tissue types, tumors, etc.) that have a significant reduction in post-translational modification, production, expression, level, stability and/or activity of MTAP relative to that in a control, e.g., reference or normal or non-cancerous cells. The reduction can be at least about 20%, 30%, 40%, 50%, 60%, 70%, 80% or 90%. In some embodiments, the reduction is at least 20%. In some embodiments, the reduction is at least 50%. The terms "MTAP-deficient and/or MTA accumulating", "MTAP-deficient and/or MTA-accumulating", MTAP deficient and/or MTA upregulated" and the like, regarding a cell or cells, etc., indicate that the cell or cells, etc., either are deficient in MTAP and/or overproduce or accumulate MTA. MTAP-deficient cells include those wherein the MTAP gene has been mutated, deleted, or transcriptionally silenced. As a non-limiting example, MTAP-deficient cells can have a homozygous deletion. MTAP knockdown is not lethal. In some embodiments, the MTAP-deficient cells are also CDKN2A-deficient. The MTAP deficiency can be detected using any reagent or technique known in the art, for example: immunohistochemistry utilizing an antibody to MTAP, and/or genomic sequencing, and/or nucleic acid hybridization and/or amplification utilizing at least one probe or primer comprising a sequence of at least 12 contiguous nucleotides (nt) of the sequence of MTAP, wherein the primer is no longer than about 30 nt.

An "MTAP-deficiency-related" or "MTAP-deficiency" or "MTAP deficient" disease (for example, a proliferating disease, e.g., a cancer) or a disease (for example, a proliferating disease, e.g., a cancer) "associated with MTAP deficiency" or a disease (for example, a proliferating disease, e.g., a cancer) "characterized by MTAP deficiency" and the like refer to an ailment (for example, a proliferating disease, e.g., a cancer) wherein a significant number of cells are MTAP-deficient. For example, in a MTAP-deficiency-related disease, one or more disease cells can have a significantly reduced post-translational modification, production, expression, level, stability and/or activity of MTAP. Examples of MTAP-deficiency-related diseases include, but are not limited to, cancers, including but not limited to: glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma (See FIG. 1). In a patient afflicted with a MTAP-deficiency-related disease, it is possible that some disease cells (e.g., cancer cells) can be MTAP-deficient while others are not. Similarly, some disease cells may be MTA-accumulating while others are not.

Thus, the present disclosure encompasses methods of treatment involving diseases of these tissues, or any other tissues, wherein the proliferation of MTAP-deficient and/or MTA-accumulating cells can be inhibited by administration of a PRMT5 inhibitor.

Some cancer cells which are MTAP-deficient are also deficient in CDKN2A; the post-translational modification, production, expression, level, stability and/or activity of the CDKN2A gene or its product are decreased in these cells. The genes for MTAP and CDKN2A are in close proximity on chromosome 9p21; MTAP is located approximately 100 kb telomeric to CDKN2A. Many cancer cell types harbor CDKN2A/MTAP loss (loss of both genes). Thus, in some embodiments, a MTAP-deficient cell is also deficient in CDKN2A.

MTA and MTA Accumulation

By "MTA" is meant the PRMT5 inhibitor also known as methyl-thioadenosine, S-methyl-5'-thioadenosine, [5'deoxy-5'-(methylthio)-fl-D-ribofuranosyl] adenine, 5'-methyl-thio-adenosine, 5'-deoxy, 5'-methyl thioadenosine, and the like. MTA selectively inhibits PRMT5 methyltransferase activity. MTA is the sole known catabolic substrate for MTAP. The terms "MTA accumulating", "MTA overproducing", "MTA upregulated" and the like refer to cells (including, but not limited to, cancer cells, cell lines, tissues, tissue types, tumors, etc.) that have a significantly increased production, level and/or stability of MTA. MTA-accumulating cells include those wherein the cells comprise at least about 20%, 30%, 40%, 50%, 60%, 70%, 80%, 90%, 100%, or greater than 100%, higher production, level and/or stability of MTA than that in normal or non-cancerous cells. In some embodiments, MTA-accumulating cells include those wherein the cells comprise at least 20% higher production, level and/or stability of MTA than that in normal or non-cancerous cells. In some embodiments, MTA-accumulating cells include those wherein the cells comprise at least 50% higher production, level and/or stability of MTA than that in normal or non-cancerous cells. Determination of MTA accumulation in test samples (e.g., cells such as cancer cells being tested for MTA accumulation) and reference samples, and other cells, tissues, samples, etc., can be performed using any method known in the art. Such methods for detecting MTA include, as a non-limiting example, liquid chromatography-electrospray ionization-tandem mass spectrometry (LC-ESI-MS/MS), as described in Stevens et al. *J Chromatogr. A.* 2010, 1217, pp 3282-3288; and Kirovski et al. *Am. J Pathol.* 2011, 178, pp 1145-1152; and references cited therein. Loss of MTAP is associated with accumulation of MTA (Williams- Ashman et al. *Biochem. Pharm.* 1982, 31, pp 277-288; and Limm et al. *Eur. J. Cancer.* 2013, 49, Issue 6.

An "MTA-accumulation-related", "MTA-accumulation", "MTA-accumulating", "MTA overproducing", "MTA upregulated" disease (for example, a proliferating disease, e.g., a cancer) or a disease (for example, a proliferating disease, e.g., a cancer) "associated with MTA accumulation" or a disease (for example, a proliferating disease, e.g., a cancer) "characterized by MTA accumulation" and the like refer to an ailment (for example, a proliferating disease, e.g., a cancer) wherein a significant number of cells are MTA accumulating. Examples of MTA-accumulating diseases include, but are not limited to, cancers, including but not limited to: glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma (See FIG. 1). In a patient afflicted with a MTAP-deficiency-related disease, it is possible that some disease cells (e.g., cancer cells) can be MTAP-deficient while others are not.

In a patient having or having been diagnosed with an MTA-accumulating disease, some cells may be MTA-accumulating while others are not.

An increase in therapeutic window between normal cells and MTAP-deleted/MTA accumulating cells could be achieved by using an inhibitor that binds PRMT5 uncompetitively with MTA. As used herein, "uncompetitive binding" and "uncompetitive inhibition" and "cooperative binding" and "cooperative inhibition" (e.g., MTA-uncompetitive binding, MTA-uncompetitive inhibition, MTA-cooperative binding, MTA-cooperative inhibition) refers to binding of an inhibitor to a protein (e.g., PRMT5) that is increased in the presence of a co-factor (e.g., MTA) over the binding of the same inhibitor in the absence of the co-factor. The PRMT5 inhibitors known in the art are generally either SAM (S-adenosylmethionine) uncompetitive or SAM competitive. As the concentration of SAM in wild-type and MTAP-null cells is similar, these inhibitors are expected to bind with similar potency to both cell types. By contrast, an MTA-cooperative (and either SAM competitive or showing enhanced cooperativity with MTA relative to SAM) inhibitor would bind with apparent greater potency in the presence of high concentrations of MTA and would therefore result in preferential inhibition of PRMT5 in MTA-accumulating cells relative to normal cells.

As described further herein, a cancer cell, a cancer type, or a subject with cancer, is "PRMT5 inhibitor sensitive," sensitive to treatment with PRMT5 inhibitors," sensitive to PRMT5 therapeutic inhibition," or described in similar terms if it is amenable to treatment with a PRMT5 inhibitor, e.g., due to its MTAP deficiency and/or MTA accumulation character.

PRMT5

"PRMT5" as used herein is the gene or protein Protein Arginine Methyltransferase 5, also known as HRMT1L5; IBP72; JBP1; SKB1; or SKB1Hs External IDs: OMIM: 604045, MGI: 1351645, HomoloGene: 4454, ChEMBL: 1795116, GeneCards: PRMT5 Gene; EC number 2.1.1.125. Ensembl ENSG00000100462; UniProt O14744; Entrez Gene ID: 10419; RefSeq (mRNA): NM_001039619. The mouse homolog is NM_013768.

Methyltransferases such as PRMT5 catalyze the transfer of one to three methyl groups from the co-factor S-adenosylmethionine (also known as SAM or AdoMet) to lysine or arginine residues of histone proteins. Arginine methylation is carried out by 9 different protein arginine methyltransferases (PRMT) in humans. Three types of methylarginine species exist: (1) Monomethylarginine (MMA); (2) Asymmetric dimethyl arginine (ADMA), which is produced by Type I methyl transferases (PRMT1, PRMT2, PRMT3, CARM1, PRMT6 and PRMT8); and (3) Symmetrical dimethylarginine (SDMA), which is produced by Type II methyl transferases (PRMT5 and PRMT7). PRMT1 and PRMT5 are the major asymmetric and symmetric arginine methyltransferases, respectively. PRMT5 promotes symmetric dimethylation on histones at H3R8 and H4R3 (H4R3me2). Symmetric methylation of H4R3 is associated with transcriptional repression and can act as a binding site for DNMT3A. Loss of PRMT5 results in reduced DNMT3A binding and gene activation. Tumor suppressor gene ST7 and chemokines RNATES, IP10, CXCL11 are targeted and silenced by PRMT5. WO 2011/079236.

Additional substrates include E2F1, p53, EGFR and CRAF. PRMT5 is part of a multi-protein complex comprising the co-regulatory factor WDR77 (also known as MEP50, a CDK4 substrate) during G1/S transition. Phosphorylation increases PRMT5/WDR77 activity. WDR77 is the non-catalytic component of the complex and mediates interactions with binding partners and substrates. PRMT5 can also interact with pICln or RioK1 adaptor proteins in a mutually exclusive fashion to modulate complex composition and substrate specificity.

PRMT5 has either a positive or negative effect on its substrates by arginine methylation when interacting with a number of complexes and is involved in a variety of cellular processes, including RNA processing, signal transduction, transcriptional regulation, and germ cell development. PRMT5 is a major pro-survival factor regulating eIF4E expression and p53 translation. PRMT5 triggers p53-dependent apoptosis and sensitized various cancer cells to Tumor necrosis factor (TNF)-related apoptosis-inducing ligand (TRAIL) without affecting TRAIL resistance in non-transformed cells.

The term "PRMT5 inhibitor" refers to any compound capable of inhibiting the production, level, activity, expression or presence of PRMT5. These include, as non-limiting examples, any compound inhibiting the transcription of the gene, the maturation of RNA, the translation of mRNA, the posttranslational modification of the protein, the enzymatic activity of the protein, the interaction of same with a substrate, etc. The term also refers to any agent that inhibits the cellular function of the PRMT5 protein, either by ATP-competitive inhibition of the active site, allosteric modulation of the protein structure, disruption of protein-protein interactions, or by inhibiting the transcription, translation, post-translational modification, or stability of PRMT5 protein.

In some embodiments, a PRMT5 inhibitor competes with another compound, protein or other molecule which interacts with PRMT5 and is necessary for PRMT5 function.

As a non-limiting example, a PRMT5 inhibitor can compete with the co-factor S-adenosylmethionine (also known as SAM or AdoMet).

In some embodiments, the PRMT5 inhibitor is uncompetitive with MTA. In further embodiments, the PRMT5 inhibitor is uncompetitive with MTA and competitive with SAM.

In some embodiments, the PRMT5 inhibitor is uncompetitive with MTA and uncompetitive with SAM but binds with a higher degree of potency for the MTA complex relative to the SAM complex.

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high-pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

The "enantiomeric excess" ("e.e.") or "% enantiomeric excess" ("% e.e.") of a composition as used herein refers to an excess of one enantiomer relative to the other enantiomer present in the composition. For example, a composition can contain 90% of one enantiomer, e.g., the S enantiomer, and 10% of the other enantiomer, i.e., the R enantiomer.

$$e.e.=(90-10)/100=80\%.$$

Thus, a composition containing 90% of one enantiomer and 10% of the other enantiomer is said to have an enantiomeric excess of 80%.

The "diastereomeric excess" ("d.e.") or "% diastereomeric excess" ("% d.e.") of a composition as used herein refers to an excess of one diastereomer relative to one or more different diastereomers present in the composition. For example, a composition can contain 90% of one diastereomer, and 10% of one or more different diastereomers.

$$d.e.=(90-10)/100=80\%.$$

Thus, a composition containing 90% of one diastereomers and 10% of one or more different diastereomers is said to have a diastereomeric excess of 80%.

In an alternative embodiment, compounds described herein may also comprise one or more isotopic substitutions. For example, hydrogen may be $^2$H (D or deuterium) or $^3$H (T or tritium); carbon may be, for example, $^{13}$C or $^{14}$C; oxygen may be, for example, $^{18}$O; nitrogen may be, for example, $^{15}$N, and the like. In other embodiments, a particular isotope (e.g., $^3$H, $^{13}$C, $^{14}$C, $^{18}$O, or $^{15}$N) can represent at least 1%, at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, at least 99%, or at least 99.9% of the total isotopic abundance of an element that occupies a specific site of the compound.

In a formula, ⁓ is a single bond where the stereochemistry of the moieties immediately attached thereto is not specified.

When a range of values is listed, it is intended to encompass each value and sub-range within the range. For example, "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention. When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

The term "azido" refers to the radical —N$_3$.

"Aliphatic" refers to an alkyl, alkenyl, alkynyl, or carbocyclyl group, as defined herein.

"Cycloalkylalkyl" refers to an alkyl radical in which the alkyl group is substituted with a cycloalkyl group. Typical cycloalkylalkyl groups include, but are not limited to, cyclopropylmethyl, cyclobutylmethyl, cyclopentylmethyl, cyclohexylmethyl, cycloheptylmethyl, cyclooctylmethyl, cyclopropylethyl, cyclobutylethyl, cyclopentylethyl, cyclohexylethyl, cycloheptylethyl, and cyclooctylethyl, and the like.

"Heterocyclylalkyl" refers to an alkyl radical in which the alkyl group is substituted with a heterocyclyl group. Typical heterocyclylalkyl groups include, but are not limited to, pyrrolidinylmethyl, piperidinylmethyl, piperazinylmethyl, morpholinylmethyl, pyrrolidinylethyl, piperidinylethyl, piperazinylethyl, morpholinylethyl, and the like.

"Aralkyl" or "arylalkyl" is a subset of alkyl and aryl, as defined herein, and refers to an optionally substituted alkyl group substituted by an optionally substituted aryl group.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$ alkyl. Common alkyl abbreviations include Me (—$CH_3$), Et (—$CH_2CH_3$), $^iPr$ (—$CH(CH_3)_2$), $^nPr$ (—$CH_2CH_2CH_3$), $^nBu$ (—$CH_2CH_2CH_2CH_3$), or $^tBu$ (—$CH_2CH(CH_3)_2$).

"Alkylene" refers to an alkyl group wherein two hydrogens are removed to provide a divalent radical, and which may be substituted or unsubstituted. Unsubstituted alkylene groups include, but are not limited to, methylene (—$CH_2$—), ethylene (—$CH_2CH_2$—), propylene (—$CH_2CH_2CH_2$—), butylene (—$CH_2CH_2CH_2CH_2$—), pentylene (—$CH_2CH_2CH_2CH_2CH_2$—), hexylene (—$CH_2CH_2CH_2CH_2CH_2CH_2$—), and the like. Exemplary substituted alkylene groups, e.g., substituted with one or more alkyl (methyl) groups, include but are not limited to, substituted methylene (—$CH(CH_3)$—, —$C(CH_3)_2$—), substituted ethylene (—$CH(CH_3)CH_2$—, —$CH_2CH(CH_3)$—, —$C(CH_3)_2CH_2$—, —$CH_2C(CH_3)_2$—), substituted propylene (—$CH(CH_3)CH_2CH_2$—, —$CH_2CH(CH_3)CH_2$—, —$CH_2CH_2CH(CH_3)$—, —$C(CH_3)_2CH_2CH_2$—, —$CH_2C(CH_3)_2CH_2$—, —$CH_2CH_2C(CH_3)_2$—), and the like. When a range or number of carbons is provided for a particular alkylene group, it is understood that the range or number refers to the range or number of carbons in the linear carbon divalent chain. Alkylene groups may be substituted or unsubstituted with one or more substituents as described herein.

"Alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted C$_{2-10}$ alkynyl. In certain embodiments, the alkynyl group is substituted C$_{2-10}$ alkynyl.

The term "heteroalkyl," as used herein, refers to an alkyl group, as defined herein, which further comprises 1 or more (e.g., 1, 2, 3, or 4) heteroatoms (e.g., oxygen, sulfur, nitrogen, boron, silicon, phosphorus) within the parent chain, wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkyl group refers to a saturated group having from 1 to 10 carbon atoms and 1, 2, 3, or 4 heteroatoms ("heteroC$_{1-10}$ alkyl"). In some embodiments, a heteroalkyl group is a saturated group having 1 to 9 carbon atoms and 1, 2, 3, or 4 heteroatoms ("heteroC$_{1-9}$ alkyl"). In some embodiments, a heteroalkyl group is a saturated group having 1 to 8 carbon atoms and 1, 2, 3, or 4 heteroatoms ("heteroC$_{1-8}$ alkyl"). In some embodiments, a heteroalkyl group is a saturated group having 1 to 7 carbon atoms and 1, 2, 3, or 4 heteroatoms ("heteroC$_{1-7}$ alkyl"). In some embodiments, a heteroalkyl group is a group having 1 to 6 carbon atoms and 1, 2, or 3 heteroatoms ("heteroC$_{1-6}$ alkyl"). In some embodiments, a heteroalkyl group is a saturated group having 1 to 5 carbon atoms and 1 or 2 heteroatoms ("heteroC$_{1-5}$ alkyl"). In some embodiments, a heteroalkyl group is a saturated group having 1 to 4 carbon atoms and 1 or 2 heteroatoms ("heteroC$_{1-4}$ alkyl"). In some embodiments, a heteroalkyl group is a saturated group having 1 to 3 carbon atoms and 1 heteroatom ("heteroC$_{1-3}$ alkyl"). In some embodiments, a heteroalkyl group is a saturated group having 1 to 2 carbon atoms and 1 heteroatom ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl. Exemplary heteroalkyl groups include: —CH$_2$OH, —CH$_2$OCH$_3$, —CH$_2$NH$_2$, —CH$_2$NH(CH$_3$), —CH$_2$N(CH$_3$)$_2$, —CH$_2$CH$_2$OH, —CH$_2$CH$_2$OCH$_3$, —CH$_2$CH$_2$NH$_2$, —CH$_2$CH$_2$NH(CH$_3$), —CH$_2$CH$_2$N(CH$_3$)$_2$.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("C$_{6-14}$ aryl"). In some embodiments, an aryl group has six ring carbon atoms ("C$_6$ aryl"; e.g., phenyl). In some embodiments, an aryl group has ten ring carbon atoms ("C$_{10}$ aryl"; e.g., naphthyl such as 1-naphthyl and 2-naphthyl). In some embodiments, an aryl group has fourteen ring carbon atoms ("C$_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted C$_{6-14}$ aryl. In certain embodiments, the aryl group is substituted C$_{6-14}$ aryl.

In certain embodiments, an aryl group is substituted with one or more of groups selected from halo, C$_1$-C$_8$ alkyl, C$_1$-C$_8$ haloalkyl, cyano, hydroxy, C$_1$-C$_8$ alkoxy, and amino.

Examples of representative substituted aryls include the following

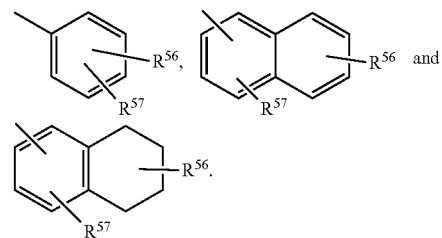

wherein one of R$^{56}$ and R$^{57}$ may be hydrogen and at least one of R$^{56}$ and R$^{57}$ is each independently selected from C$_1$-C$_8$ alkyl, C$_1$-C$_8$ haloalkyl, 4-10 membered heterocyclyl, alkanoyl, C$_1$-C$_8$ alkoxy, heteroaryloxy, alkylamino, arylamino, heteroarylamino, NR$^{58}$COR$^{59}$, NR$^{58}$SOR$^{59}$NR$^{58}$SO$_2$R$^{59}$, COOalkyl, COOaryl, CONR$^{58}$R$^{59}$, CONR$^{58}$OR$^{59}$, NR$^{58}$R$^{59}$, SO$_2$NR$^{58}$R$^{59}$, S-alkyl, SOalkyl, SO$_2$alkyl, Saryl, SOaryl, SO$_2$aryl; or R$^{56}$ and R$^{57}$ may be joined to form a cyclic ring (saturated or unsaturated) from 5 to 8 atoms, optionally containing one or more heteroatoms selected from the group N, O, or S. R$^{60}$ and R$^{61}$ are independently hydrogen, C$_1$-C$_8$ alkyl, C$_1$-C$_4$ haloalkyl, C$_3$-C$_{10}$ cycloalkyl, 4-10 membered heterocyclyl, C$_6$-C$_{10}$ aryl, substituted C$_6$-C$_{10}$ aryl, 5-10 membered heteroaryl, or substituted 5-10 membered heteroaryl.

"Fused aryl" refers to an aryl having two of its ring carbons in common with a second aryl or heteroaryl ring or with a carbocyclyl or heterocyclyl ring.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl. In some embodiments, a heteroaryl group is a bicyclic 8-12 membered aromatic ring system having ring carbon atoms and 1-6 ring heteroatoms provided in the aromatic ring system, wherein each heteroatom is independently selected from nitrogen, oxygen, and sulfur ("8-12 membered bicyclic heteroaryl"). In some embodiments, a heteroaryl group is an 8-10 membered bicyclic aromatic ring system having ring carbon atoms and 1-6 ring heteroatoms provided in the aromatic ring system, wherein each heteroatom is independently selected from nitrogen, oxygen, and sulfur ("8-10 membered bicyclic heteroaryl"). In some embodiments, a heteroaryl group is a 9-10 membered bicyclic aromatic ring system having ring carbon atoms and 1-6 ring heteroatoms provided in the aromatic ring system, wherein each heteroatom is independently selected from nitrogen, oxygen, and sulfur ("9-10 membered bicyclic heteroaryl"). Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

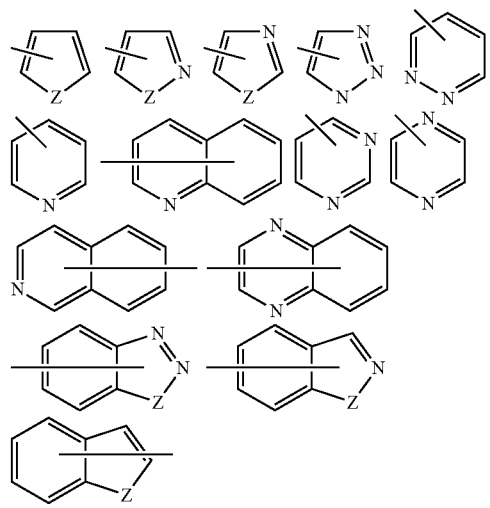

wherein each Z is selected from carbonyl, N, NR$^{65}$, O, and S; and R$^{65}$ is independently hydrogen, C$_1$-C$_8$ alkyl, C$_3$-C$_{10}$ cycloalkyl, 4-10 membered heterocyclyl, C$_6$-C$_{10}$ aryl, and 5-10 membered heteroaryl.

In the structures described herein, a substituent attached to a polycyclic (e.g., bicyclic or tricyclic) cycloalkyl, heterocycloalkyl, aryl or heteroaryl with a bond that spans two or more rings is understood to mean that the substituent can be attached at any position in each of the rings.

"Heteroaralkyl" or "heteroarylalkyl" is a subset of "alkyl" and refers to an alkyl group substituted by a heteroaryl group, wherein the point of attachment is on the alkyl moiety.

The term "carbocyclyl" or "carbocyclic" refers to a radical of a non-aromatic monocyclic, bicyclic, or tricyclic or polycyclic hydrocarbon ring system having from 3 to 14 ring carbon atoms ("C$_{3-14}$ carbocyclyl") and zero heteroatoms in the non-aromatic ring system. Carbocyclyl groups include fully saturated ring systems (e.g., cycloalkyls), and partially saturated ring systems. In some embodiments, a carbocyclyl group has 3 to 10 ring carbon atoms ("C$_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like.

As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

The term "cycloalkyl" as employed herein includes saturated cyclic, bicyclic, tricyclic, or polycyclic hydrocarbon groups having 3 to 14 carbons containing the indicated number of rings and carbon atoms (for example a $C_3$-$C_{14}$ monocyclic, $C_4$-$C_{14}$ bicyclic, $C_5$-$C_{14}$ tricyclic, or $C_6$-$C_{14}$ polycyclic cycloalkyl). In some embodiments "cycloalkyl" is a monocyclic cycloalkyl. In some embodiments, a monocyclic cycloalkyl has 3-14 ring carbon atoms. ("$C_{3-14}$ monocyclic cycloalkyl"). In some embodiments, a monocyclic cycloalkyl group has 3 to 10 ring carbon atoms ("$C_{3-10}$ monocyclic cycloalkyl"). In some embodiments, a monocyclic cycloalkyl group has 3 to 8 ring carbon atoms ("$C_{3-8}$ monocyclic cycloalkyl"). In some embodiments, a monocyclic cycloalkyl group has 3 to 6 ring carbon atoms ("$C_{3-6}$ monocyclic cycloalkyl"). In some embodiments, a monocyclic cycloalkyl group has 4 to 6 ring carbon atoms ("$C_{4-6}$ monocyclic cycloalkyl"). In some embodiments, a monocyclic cycloalkyl group has 5 to 6 ring carbon atoms ("$C_{5-6}$ monocyclic cycloalkyl"). In some embodiments, a monocyclic cycloalkyl group has 5 to 10 ring carbon atoms ("$C_{5-10}$ monocyclic cycloalkyl"). Examples of monocyclic $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$).

In some embodiments "cycloalkyl" is a bicyclic cycloalkyl. In some embodiments, a bicyclic cycloalkyl has 4-14 ring carbon atoms. ("$C_{4-14}$ bicyclic cycloalkyl"). In some embodiments, a bicyclic cycloalkyl group has 4 to 12 ring carbon atoms ("$C_{4-12}$ bicyclic cycloalkyl"). In some embodiments, a bicyclic cycloalkyl group has 4 to 10 ring carbon atoms ("$C_{4-10}$ bicyclic cycloalkyl"). In some embodiments, a bicyclic cycloalkyl group has 5 to 10 ring carbon atoms ("$C_{5-10}$ bicyclic cycloalkyl"). In some embodiments, a bicyclic cycloalkyl group has 6 to 10 ring carbon atoms ("$C_{6-10}$ bicyclic cycloalkyl"). In some embodiments, a bicyclic cycloalkyl group has 8 to 10 ring carbon atoms ("$C_{8-10}$ bicyclic cycloalkyl"). In some embodiments, a bicyclic cycloalkyl group has 7 to 9 ring carbon atoms ("$C_7$-9 bicyclic cycloalkyl"). Examples of bicyclic cycloalkyls include bicyclo[1.1.0]butane ($C_4$), bicyclo[1.1.1]pentane ($C_5$), spiro[2.2] pentane ($C_5$), bicyclo[2.1.0]pentane ($C_5$), bicyclo[2.1.1]hexane ($C_6$), bicyclo[3.1.0]hexane ($C_6$), spiro [2.3] hexane ($C_6$), bicyclo[2.2.1]heptane (norbornane) ($C_7$), bicyclo[3.2.0]heptane ($C_7$), bicyclo[3.1.1]heptane ($C_7$), bicyclo[3.1.1]heptane ($C_7$), bicyclo[4.1.0]heptane ($C_7$), spiro[2.4] heptane ($C_7$), spiro[3.3] heptane ($C_7$), bicyclo [2.2.2]octane ($C_8$), bicyclo[4.1.1]octane ($C_8$)octahydropentalene ($C_8$), bicyclo[3.2.1]octane ($C_8$), bicyclo[4.2.0]octane ($C_8$), spiro[2.5]octane ($C_8$), spiro[3.4]octane ($C_8$), bicyclo [3.3.1]nonane ($C_9$), octahydro-1H-indene ($C_9$), bicyclo [4.2.1]nonane ($C_9$), spiro[3.5]nonane ($C_9$), spiro[4.4]nonane ($C_9$), bicyclo[3.3.2]decane ($C_{10}$), bicyclo[4.3.1]decane ($C_{10}$), spiro[4.5]decane ($C_{10}$), bicyclo[3.3.3]undecane ($C_{11}$), decahydronaphthalene ($C_{10}$), bicyclo[4.3.2]undecane ($C_{11}$), spiro[5.5]undecane ($C_{11}$) and bicyclo[4.3.3]dodecane ($C_{12}$).

In some embodiments "cycloalkyl" is a tricyclic cycloalkyl. In some embodiments, a tricyclic cycloalkyl has 6-14 ring carbon atoms. ("$C_{6-14}$ tricyclic cycloalkyl"). In some embodiments, a tricyclic cycloalkyl group has 8 to 12 ring carbon atoms ("$C_{8-12}$ tricyclic cycloalkyl"). In some embodiments, a tricyclic cycloalkyl group has 10 to 12 ring carbon atoms ("$C_{10-12}$ tricyclic cycloalkyl. Examples of tricyclic cycloalkyls include adamantine ($C_{12}$).

Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl "Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, aziridinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetra-hydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[2,3-b]pyridinyl, 4,5,6,7-tetrahydro-thieno[3,2-b]pyridinyl, 1,2,3,4-tetrahydro-1,6-naphthyridinyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Nitrogen-containing heterocyclyl" group means a 4- to 7-membered non-aromatic cyclic group containing at least one nitrogen atom, for example, but without limitation, morpholine, piperidine (e.g., 2-piperidinyl, 3-piperidinyl and 4-piperidinyl), pyrrolidine (e.g., 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g., heteroaryl, cycloalkenyl, e.g., cycloheteroalkenyl, and the like having from 1 to 5, and particularly from 1 to 3 heteroatoms.

"Acyl" refers to a radical —C(=O)$R^{20}$, where $R^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. "Alkanoyl" is an acyl group wherein $R^{20}$ is a group other than hydrogen. Representative acyl groups include, but are not limited to, formyl (—CHO), acetyl (—C(=O)CH$_3$), cyclohexylcarbonyl, cyclohexylmethylcarbonyl, benzoyl (—C(=O)Ph), benzylcarbonyl (—C(=O)CH$_2$Ph), —C(=O)—$C_1$-$C_8$ alkyl, —C(=O)—(CH$_2$)$_t$($C_6$-$C_{10}$ aryl), —C(=O)—(CH$_2$)$_t$(5-10 membered heteroaryl), —C(=O)—(CH$_2$)$_t$($C_3$-$C_{10}$ cycloalkyl), and —C(=O)—(CH$_2$)$_t$(4-10 membered heterocyclyl), wherein t is an integer from 0 to 4. In certain embodiments, $R^{21}$ is $C_1$-$C_8$ alkyl, substituted with halo or hydroxy; or $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

The term aminoalkyl refers to a substituted alkyl group wherein one or more of the hydrogen atoms are independently replaced by an —NH$_2$ group.

The term hydroxyalkyl refers to a substituted alkyl group wherein one or more of the hydrogen atoms are independently replaced by an —OH group.

The terms "alkylamino" and "dialkylamino" refer to —NH(alkyl) and —N(alkyl)$_2$ radicals respectively. In some embodiments the alkylamino is a —NH($C_1$-$C_4$ alkyl). In some embodiments the alkylamino is methylamino, ethylamino, propylamino, isopropylamino, n-butylamino, isobutylamino, sec-butylamino or tert-butylamino. In some embodiments the dialkylamino is —N($C_1$-$C_6$ alkyl)$_2$. In some embodiments the dialkylamino is a dimethylamino, a methylethylamino, a diethylamino, a methylpropylamino, a methylisopropylamino, a methylbutylamino, a methylisobutylamino or a methyltertbutylamino.

The term "aryloxy" refers to an —O-aryl radical. In some embodiments the aryloxy group is phenoxy.

The term "haloalkoxy" refers to alkoxy structures that are substituted with one or more halo groups or with combinations thereof. For example, the term "fluoroalkoxy" includes haloalkoxy groups, in which the halo is fluorine. In some embodiments haloalkoxy groups are difluoromethoxy and trifluoromethoxy.

"Alkoxy" refers to the group —OR$^{29}$ where R$^{29}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

In certain embodiments, R$^{29}$ is a group that has 1 or more substituents, for instance from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocyclyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups include, but are not limited to, —O—(CH$_2$)$_t$($C_6$-$C_{10}$ aryl), —O—(CH$_2$)$_t$(5-10 membered heteroaryl), —O—(CH$_2$)$_t$($C_3$-$C_{10}$ cycloalkyl), and —O—(CH$_2$)$_t$(4-10 membered heterocyclyl), wherein t is an integer from 0 to 4 and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are —OCF$_3$, —OCH$_2$CF$_3$, —OCH$_2$Ph, —OCH$_2$-cyclopropyl, —OCH$_2$CH$_2$OH, and —OCH$_2$CH$_2$NMe$_2$.

"Amino" refers to the radical —NH$_2$.

"Oxo group" refers to —C(=O)—.

"Substituted amino" refers to an amino group of the formula —N(R$^{38}$)$_2$ wherein R$^{38}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of R$^{38}$ is not a hydrogen. In certain embodiments, each R$^{38}$ is independently selected from hydrogen, $C_1$-$C_8$ alkyl, $C_3$-$C_8$ alkenyl, $C_3$-$C_8$ alkynyl, $C_6$-$C_{10}$ aryl, 5-10 membered heteroaryl, 4-10 membered heterocyclyl, or $C_3$-$C_{10}$ cycloalkyl; or $C_1$-$C_8$ alkyl, substituted with halo or hydroxy; $C_3$-$C_8$ alkenyl, substituted with halo or hydroxy; $C_3$-$C_8$ alkynyl, substituted with halo or hydroxy, or —(CH$_2$)$_t$($C_6$-$C_{10}$ aryl), —(CH$_2$)$_t$(5-10 membered heteroaryl), —(CH$_2$)$_t$($C_3$-$C_{10}$ cycloalkyl), or —(CH$_2$)$_t$(4-10 membered heterocyclyl), wherein t is an integer between 0 and 8, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; or both R$^{38}$ groups are joined to form an alkylene group.

Exemplary "substituted amino" groups include, but are not limited to, —NR$^{39}$—$C_1$-$C_8$ alkyl, —NR$^{39}$—(CH$_2$)$_t$($C_6$-$C_{10}$ aryl), —NR$^{39}$—(CH$_2$)$_t$(5-10 membered heteroaryl), —NR$^{39}$—(CH$_2$)$_t$($C_3$-$C_{10}$ cycloalkyl), and —NR$^{39}$—(CH$_2$)$_t$(4-10 membered heterocyclyl), wherein t is an integer from 0 to 4, for instance 1 or 2, each R$^{39}$ independently represents H or $C_1$-$C_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

In certain embodiments, the substituent present on the nitrogen atom is a nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, C(=S)N(R$^{cc}$)$_2$, —C(=O)SR$^{cc}$, —C(=S)SR$^{cc}$, —$C_{1-10}$ alkyl (e.g., aralkyl, heteroaralkyl), —$C_{2-10}$ alkenyl, —$C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in Protecting Groups in Organic Synthesis, T. W. Greene and P. G. M. Wuts, 3rd edition, John Wiley & Sons, 1999, incorporated herein by reference.

each instance of R$^{aa}$ is, independently, selected from —$C_{1-10}$ alkyl, —$C_{1-10}$ perhaloalkyl, —$C_{2-10}$ alkenyl, —$C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, —$C_{1-10}$ alkyl, —$C_{1-10}$ perhaloalkyl, —$C_{2-10}$ alkenyl, —$C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion.

each instance of $R^{cc}$ is, independently, selected from hydrogen, —$C_{1-10}$ alkyl, —$C_{1-10}$ perhaloalkyl, —$C_{2-10}$ alkenyl, —$C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —$NO_2$, —$N_3$, —$SO_2H$, —$SO_3H$, —OH, —$OR^{ee}$, —$ON(R^{ff})_2$, —$N(R^{ff})_2$, —$N(R^{ff})_3^+X^-$, —$N(OR^{ee})R^{ff}$, —SH, —$SR^{ee}$, —$SSR^{ee}$, —$C(=O)R^{ee}$, —$CO_2H$, —$CO_2R^{ee}$, —$OC(=O)R^{ee}$, —$OCO_2R^{ee}$, —$C(=O)N(R^{ff})_2$, —$OC(=O)N(R^{ff})_2$, —$NR^{ff}C(=O)R^{ee}$, —$NR^{ff}CO_2R^{ee}$, —$NR^{ff}C(=O)N(R^{ff})_2$, —$C(=NR^{ff})OR^{ee}$, —$OC(=NR^{ff})R^{ee}$, —$OC(=NR^{ff})OR^{ee}$, —$C(=NR^{ff})N(R^{ff})_2$, —$OC(=NR^{ff})N(R^{ff})_2$, —$NR^{ff}C(=NR^{ff})N(R^{ff})_2$, —$NR^{ff}SO_2R^{ee}$, —$SO_2N(R^{ee})_2$, —$SO_2R^{ee}$, —$SO_2OR^{ee}$, —$OSO_2R^{ee}$, —$S(=O)R^{ee}$, —$Si(R^{ee})_3$, —$OSi(R^{ee})_3$—$C(=S)N(R^{ee})_2$, —$C(=O)SR^{ee}$, —$C(=S)SR^{ee}$, —$SC(=S)SR^{ee}$, —$P(=O)(OR^{ee})_2$—$P(=O)(R^{ee})_2$, —$OP(=O)(R^{ee})_2$, —$OP(=O)(OR^{ee})_2$, —$C_{1-6}$ alkyl, —$C_{1-6}$ perhaloalkyl, —$C_{2-6}$ alkenyl, —$C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein X is a counterion;

each instance of $R^{ee}$ is, independently, selected from —$C_{1-6}$ alkyl, —$C_{1-6}$ perhaloalkyl, —$C_{2-6}$ alkenyl, —$C_{2-6}$ alkynyl, hetero$C_{1-6}$ alkyl, hetero$C_{2-6}$alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, —$C_{1-6}$ alkyl, —$C_{1-6}$ perhaloalkyl, —$C_{2-6}$ alkenyl, —$C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —$ON(C_{1-6}$ alkyl$)_2$, —$N(C_{1-6}$ alkyl$)_2$, —$N(C_{1-6}$ alkyl$)_3^+X^-$, —$NH(C_{1-6}$ alkyl$)_2^+X^-$, —$NH_2(C_{1-6}$ alkyl$)_3^+X^-$, —$NH_3^+X^-$, —$N(OC_{1-6}$ alkyl$)(C_{1-6}$ alkyl), —$N(OH)(C_{1-6}$ alkyl), —NH(OH), —SH, —$SC_{1-6}$ alkyl, —$SS(C_{1-6}$ alkyl), —$C(=O)(C_{1-6}$ alkyl), —$CO_2H$, —$CO_2(C_{1-6}$ alkyl), —$OC(=O)(C_{1-6}$ alkyl), —$OCO_2(C_{1-6}$ alkyl), —$C(=O)NH_2$, —$C(=O)N(C_{1-6}$ alkyl$)_2$, —$OC(=O)NH(C_{1-6}$ alkyl), —$NHC(=O)(C_{1-6}$ alkyl), —$N(C-6$ alkyl$)C(=O)(C_{1-6}$ alkyl), —$NHCO_2(C_{1-6}$ alkyl), —$NHC(=O)N(C_{1-6}$ alkyl$)_2$, —$NHC(=O)NH(C_{1-6}$ alkyl), —$NHC(=O)NH_2$, —$C(=NH)O(C_{1-6}$ alkyl), —$OC(=NH)(C_{1-6}$ alkyl), —$OC(=NH)OC_{1-6}$ alkyl, —$C(=NH)N(C_{1-6}$ alkyl$)_2$, —$C(=NH)NH(C_{1-6}$ alkyl), —$C(=NH)NH_2$, —$OC(=NH)N(C_{1-6}$ alkyl$)_2$, —$OC(NH)NH(C_{1-6}$ alkyl), —$OC(NH)NH_2$, —$NHC(NH)N(C_{1-6}$ alkyl$)_2$, —$NHC(=NH)NH_2$, —$NHSO_2(C_{1-6}$ alkyl), —$SO_2N(C_{1-6}$ alkyl$)_2$, —$SO_2NH(C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —$Si(C_{1-6}$ alkyl$)_3$, —$OSi(C_{1-6}$ alkyl$)_3$, —$C(=S)N(C_{1-6}$ alkyl$)_2$, —$C(=S)NH(C_{1-6}$ alkyl), —$C(=S)NH_2$, —$C(=O)S(C_{1-6}$ alkyl), —$C(=S)SC_{1-6}$ alkyl, —$SC(=S)SC_{1-6}$ alkyl, —$P(=O)(OC_{1-6}$ alkyl$)_2$, —$P(=O)(C_{1-6}$ alkyl$)_2$, —$OP(=O)(C_{1-6}$ alkyl$)_2$, —$OP(=O)(OC_{1-6}$ alkyl$)_2$, —$C_{1-6}$ alkyl, —$C_{1-6}$ perhaloalkyl, —$C_{2-6}$ alkenyl, —$C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

For example, nitrogen protecting groups such as amide groups (e.g., —$C(=O)R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —$C(=O)OR^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N (R$^{bb}$)$_2$, —C(=NR$^{bb}$)R$^{aa}$, —C(=NR$^{bb}$)OR$^{aa}$, —C(=NR$^{bb}$) N(R$^{bb}$)$_2$, —S(=O)R$^{aa}$, SO$_2$R$^{aa}$, —Si(R$^{aa}$)$_3$, —P(R$^{cc}$)$_2$, —P(R$^{cc}$)$_3$X$^-$, —P(OR$^{cc}$)$_2$, —P(OR$^{cc}$)$_3$X$^-$, —P(=O)(R$^{aa}$)$_2$, —P(=O)(OR$^{cc}$)$_2$, and —P(=O)(N(R$^{bb}$)$_2$)$_2$, wherein R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxymethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthtyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3{}^+X^-$, —$P(OR^{cc})_2$, —$P(OR^{cc})_3{}^+X^-$, —$P(=O)(R^{aa})_2$, —$P(=O)(OR^{cc})_2$, and —$P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

The term "leaving group" is given its ordinary meaning in the art of synthetic organic chemistry and refers to an atom or a group capable of being displaced by a nucleophile. Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In certain embodiments, the leaving group is halogen, alkanesulfonyloxy, arenesulfonyloxy, diazonium, alkyl diazenes, aryl diazenes, alkyl triazenes, aryl triazenes, nitro, alkyl nitrate, aryl nitrate, alkyl phosphate, aryl phosphate, alkyl carbonyl oxy, aryl carbonyl oxy, alkoxcarbonyl oxy, aryoxcarbonyl oxy ammonia, alkyl amines, aryl amines, hydroxyl group, alkyloxy group, or aryloxy. In some cases, the leaving group is a sulfonic acid ester, such as toluenesulfonate (tosylate, —OTs), methanesulfonate (mesylate, —OMs), p-bromobenzenesulfonyloxy (brosylate, —OBs), —$OS(=O)_2(CF_2)_3CF_3$ (nonaflate, —ONf), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

"Carboxy" refers to the radical —C(=O)OH.

"Cyano" refers to the radical —CN.

"Halo" or "halogen" refers to fluoro (F), chloro (Cl), bromo (Br), and iodo (I). In certain embodiments, the halo group is either fluoro or chloro.

"Haloalkyl" refers to an alkyl radical in which the alkyl group is substituted with one or more halogens. Typical haloalkyl groups include, but are not limited to, trifluoromethyl (—$CF_3$), difluoromethyl (—$CHF_2$), fluoromethyl (—$CH_2F$), chloromethyl (—$CH_2Cl$), dichloromethyl (—$CHCl_2$), tribromomethyl (—$CH_2Br$), and the like.

"Hydroxy" refers to the radical —OH.

"Nitro" refers to the radical —$NO_2$.

"Thioketo" refers to the group =S.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —$NO_2$, —$N_3$, —$SO_2H$, —$SO_3H$, —OH, —$OR^{aa}$, —$ON(R^{bb})_2$, —$N(R^b)_2$, —$N(R^{bb})_3{}^+X^-$, —$N(OR^{cc})R^{bb}$, —SH, —$SR^{aa}$, —$SSR^{cc}$, —$C(=O)R^{aa}$, —$CO_2H$, —CHO, —$C(OR^{cc})_2$, —$CO_2R^{aa}$, —$OC(=O)R^{aa}$, —$OCO_2R^{aa}$, —$C(=O)N(R^{bb})_2$, —$OC(=O)N(R^{bb})_2$, —$NR^{bb}C(=O)R^{aa}$, —$NR^{bb}CO_2R^{aa}$, —$NR^{bb}C(=O)N(R^{bb})_2$, —$C(=NR^{bb})R^{aa}$, —$C(=NR^{bb})OR^{aa}$, —$OC(=NR^{bb})R^{aa}$, —$OC(=NR^{bb})OR^{aa}$, —$C(=NR^{bb})N(R^{bb})_2$, —$OC(=NR^{bb})N(R^{bb})_2$, —$NR^{bb}C$ =NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$R$^{aa}$, —OSO$_2$R$^{aa}$, —S(=O)R$^{aa}$, —S(=O), =NR$^{bb}$)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$), —OP(=O)(R$^{ee}$), —OP(=O)(OR$^{ee}$)$_2$, C$_{1-6}$ alkyl, C$_{1-6}$ haloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ haloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ haloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$, —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ haloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, SO$_4$$^{-2}$ sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$), —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$), —SO$_2$N(R$^{cc}$)$_2$, —SO$_2$R$^{cc}$, —SO$_2$OR$^{cc}$, —SOR$^{aa}$, —C(=S)N(R$^{cc}$), —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$), C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

These and other exemplary substituents are described in more detail in the Detailed Description, Examples, and Claims. The invention is not intended to be limited in any manner by the above exemplary listing of substituents.

Other Definitions

As used herein, the term "salt" refers to any and all salts and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or a non-human animal, e.g., a mammal such as primates (e.g., cynomolgous monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

DETAILED DESCRIPTION OF CERTAIN EMBODIMENTS OF THE INVENTION

As generally described herein, the present invention provides compounds (e.g., compounds of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or compounds of Table 1, or pharmaceutically acceptable salts thereof) that are MTA-uncompetitive PRMT5 inhibitors useful for treating proliferating disorders (e.g., cancers) associated with MTAP deficiencies and/or MTA accumulation.

Compounds

In one aspect, provided herein are compounds or pharmaceutically acceptable salts thereof according to Formula (I)

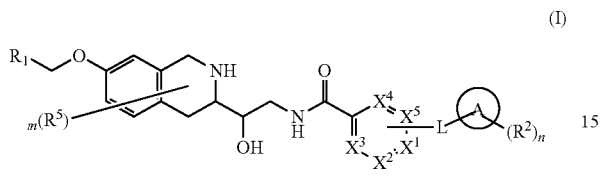

(I)

wherein $X^1$, $X^2$, $X^3$, $X^4$ and $X^5$ are each independently N or $CR^x$;

L is a bond, —C(=O)—, —NH— or —O—;

Ring A is a carbocycle, heterocycle or a 5-6 membered monocyclic heteroaryl;

$R^1$ is a 5-6 membered heteroaryl substituted with 0-3 instances of $R^4$;

each $R^2$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, heteroarylalkyl, arylalkyl, cycloalkylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$ and —$S(=O)_2N(R^3)_2$;

each $R^3$ is independently selected from H, $C_1$-$C_6$ alkyl, —$C_1$-$C_6$ heteroalkyl, $C_3$-$C_9$ carbocyclyl, 3-7 membered heterocyclyl, cycloalkylalkyl, heterocyclylalkyl, aryl, 5-6 membered heteroaryl, arylalkyl and heteroarylalkyl wherein each alkyl, carbocyclyl, heterocyclyl, cycloalkylalkyl, heterocyclylalkyl, aryl, heteroaryl, arylalkyl and heteroarylalkyl is optionally substituted;

each $R^4$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, cycloalkylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$ and —$S(=O)_2N(R^3)_2$;

each $R^x$ is independently selected from hydrogen, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, cycloalkylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$ and —$S(=O)_2N(R^3)_2$ wherein each alkyl, carbocyclyl, heterocyclyl, heterocyclylalkyl, cycloalkylalkyl is optionally substituted;

each $R^5$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, $C_6$-$C_{10}$ aryl, 5-10 membered heteroaryl, cycloalkylalkyl, heterocyclylalkyl, arylalkyl, heteroarylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$, —$S(=O)_2N(R^3)_2$, or two $R^5$ can be taken together with the atoms to which they are attached to form a —$C_3$-$C_9$ carbocyclyl or a 3-10 membered heterocyclyl;

m is 0, 1, 2 or 3; and n is 0, 1, 2 or 3.

In certain embodiments the invention provides a compound of Formula (Ia) or a pharmaceutically acceptable salt thereof, wherein:

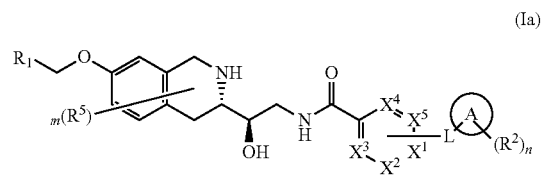

(Ia)

and each instance of $X^1$, $X^2$, $X^3$, $X^4$, $X^5$ A, L, $R^1$, $R^2$, $R^5$, m and n are as defined herein.

In certain embodiments the invention provides a compound of Formula (II) or a pharmaceutically acceptable salt thereof, wherein:

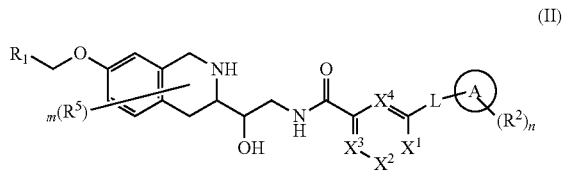

(II)

and each instance of $X^1$, $X^2$, $X^3$, $X^4$, A, L, $R^1$, $R^2$, $R^5$, m and n are as defined herein.

In certain embodiments the invention provides a compound of Formula (IIa) or a pharmaceutically acceptable salt thereof, wherein:

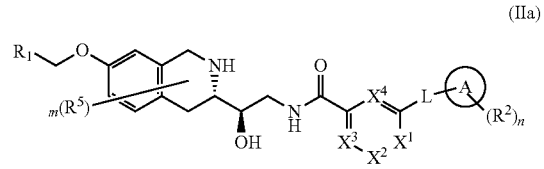

(IIa)

and each instance of $X^1$, $X^2$, $X^3$, $X^4$, A, L, $R^1$, $R^2$, $R^5$, m and n are as defined herein.

In certain embodiments the invention provides a compound of Formula (III) or a pharmaceutically acceptable salt thereof, wherein:

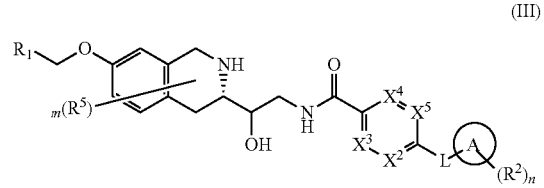

(III)

and each instance of $X^2$, $X^3$, $X^4$, $X^5$, A, L, $R^1$, $R^2$, $R^5$, m and n are as defined herein.

In certain embodiments the invention provides a compound of Formula (IIIa) or a pharmaceutically acceptable salt thereof, wherein:

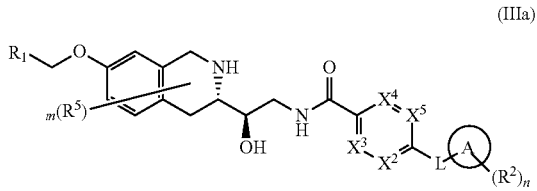

(IIIa)

and each instance of $X^2$, $X^3$, $X^4$, $X^5$, A, L, $R^1$, $R^2$, $R^5$, m and n are as defined herein.

As generally defined herein, $X^1$, $X^2$, $X^3$, $X^4$ and $X^5$ are each independently N or $CR^x$, wherein each $R^x$ is independently selected from hydrogen, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, cycloalkylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$ and —$S(=O)_2N(R^3)_2$ wherein each alkyl, carbocyclyl, heterocyclyl, heterocyclylalkyl, cycloalkylalkyl is optionally substituted. In certain embodiments each alkyl, carbocyclyl, heterocyclyl, heterocyclylalkyl, cycloalkylalkyl of $R^x$ is substituted with 0-3 instances of $R^7$. In certain embodiments each alkyl, carbocyclyl, heterocyclyl, heterocyclylalkyl, cycloalkylalkyl is substituted with 0-2 instances of $R^7$. In some embodiments each alkyl, carbocyclyl, heterocyclyl, heterocyclylalkyl, cycloalkylalkyl is substituted with 0-1 instances of $R^7$.

In certain embodiments, $R^x$ is H, $N(R^3)_2$, $NHR^3$, $N(CH_3)R^3$, $OR^3$, $C_1$-$C_6$ alkyl, optionally substituted —$C_3$-$C_9$ carbocyclyl or optionally substituted 3-10 membered heterocyclyl. In further embodiments, $R^x$ is —$C_3$-$C_9$ carbocyclyl or 3-10 membered heterocyclyl substituted with 0-1 instances of $R^7$, wherein $R^7$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, $C_6$-$C_{10}$ aryl, 5-10 membered heteroaryl, cycloalkylalkyl, heterocyclylalkyl, arylalkyl, heteroarylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$ or —$S(=O)_2N(R^3)_2$.

In certain embodiments, $R^x$ is hydrogen.

In certain embodiments, $R^x$ is halo (e.g., fluoro, chloro, bromo, iodo). In further embodiments, $R^x$ is chloro. In some embodiments, $R^x$ is fluoro. In some embodiments, $R^x$ is bromo. In some embodiments, $R^x$ is iodo.

In some embodiments, $R^x$ is —CN.

In certain embodiments, $R^x$ is optionally substituted —$C_1$-$C_6$ alkyl. In certain embodiments, $R^x$ is unsubstituted alkyl. In further embodiments, $R^x$ is methyl. In some embodiments, $R^x$ is ethyl. In some embodiments $R^x$ is propyl or isopropyl. In certain embodiments, $R^x$ is alkyl substituted with 1-2 instances of $R^7$.

In some embodiments, $R^x$ is —$C_1$-$C_6$ heteroalkyl. In further embodiments, $R^x$ is methoxymethyl (—$CH_2OCH_3$). In some embodiments, $R^x$ is aminomethyl (e.g., —$CH_2NH_2$, —$CH_2NHCH_3$, —$CH_2N(CH_3)_2$, —$CH_2CH_2N(CH_3)_2$. In certain embodiments, $R^x$ is heteroalkyl further substituted with 1-2 instances of $R^7$.

In some embodiments, $R^x$ is —$C_1$-$C_6$ haloalkyl. In further embodiments, $R^x$ is trifluoromethyl (—$CF_3$).

In some embodiments, $R^x$ is optionally substituted —$C_3$-$C_9$ carbocyclyl (e.g., cyclopropyl, cyclobutyl, cyclopentyl, cyclohexyl). In some embodiments, $R^x$ is cyclopropyl. In some embodiments $R^x$ is cyclobutyl. In some embodiments, $R^x$ is cyclopentyl. In some embodiments, $R^x$ is cyclohexyl. In certain embodiments, $R^x$ is —$C_3$-$C_9$ carbocyclyl (e.g., cyclopropyl, cyclobutyl, cyclopentyl, cyclohexyl) substituted with 1-2 instances of $R^7$. In further embodiments, the $R^7$ substituent is selected from $C_1$-$C_6$ alkyl (e.g., methyl, ethyl, propyl, isopropyl) and —$C(=O)R^3$ (e.g., —$C(=O)Me$, —$C(=O)Et$, —$C(=O)Pr$, —$C(=O)^iPr$, —$C(=O)Ph$, —$C(=O)cyclopropyl$, $C(=O)heteroalkyl$).

In some embodiments, $R^x$ is optionally substituted 3-10 membered heterocyclyl. In further embodiments, $R^x$ is a 3-10 membered heterocyclyl substituted with 0-2 instances of $R^7$. In some embodiments, $R^x$ is a 4-7 membered monocyclic heterocyclyl (e.g., oxetanyl, tetrahydropyranyl, tetrahydrofuranyl, azetidinyl, pyrrolidinyl, piperidinyl, piperazinyl, morpholinyl, azepanyl) or a 7-10 membered bicyclic heterocyclyl (e.g., a 7-10 membered bridged bicyclic heterocyclyl, e.g., 8-oxa-3-azabicyclo[3.2.1]octanyl, 2-azabicyclo[2.2.1]heptanyl, 3-azabicyclo[3.1.1]heptanyl, and 3-azabicyclo[3.2.1]octanyl) substituted with 0-2 instances of $R^7$. In certain embodiments $R^x$ is a 6 membered monocyclic heterocyclyl or a 7-8 membered bridged bicyclic heterocyclyl substituted with 0-2 instances of $R^7$, wherein the bridged bicyclic heterocyclyl or the monocyclic heterocyclyl contains 1 or 2 heteroatoms independently selected from O and N. In some embodiments $R^x$ is selected from piperidinyl, piperazinyl, morpholinyl, 2-azabicyclo[2.2.1]heptanyl, 3-azabicyclo[3.1.1]heptanyl, 8-oxa-3-azabicyclo[3.2.1]octanyl and 3-azabicyclo[3.2.1]octanyl substituted with 0-2 instances of $R^7$. In exemplary embodiments, the $R^7$ substituent is selected from $C_1$-$C_6$ alkyl (e.g., methyl, ethyl, propyl, isopropyl) and —$C(=O)R^3$ (e.g., —$C(=O)Me$, —$C(=O)Et$, —$C(=O)Pr$, —$C(=O)^iPr$, —$C(=O)Ph$, —$C(=O)cyclopropyl$, $C(=O)heteroalkyl$).

In some embodiments, $R^x$ is oxetanyl, optionally substituted with 0-2 instances of $R^7$. In some embodiments, $R^x$ is tetrahydropyranyl, optionally substituted with 0-2 instances of $R^7$. In some embodiments, $R^x$ is tetrahydrofuranyl, optionally substituted with 0-2 instances of $R^7$. In some embodiments, $R^x$ is azetidinyl, optionally substituted with 0-2 instances of $R^7$. In some embodiments, $R^x$ is pyrrolidinyl, optionally substituted with 0-2 instances of $R^7$. In some embodiments, $R^x$ is piperidinyl, optionally substituted with 0-2 instances of $R^7$. In some embodiments, $R^x$ is piperazinyl, optionally substituted with 0-2 instances of $R^7$ (e.g., N-acetyl piperazinyl, N-methyl piperazinyl, N-ethyl piperazinyl). In some embodiments, $R^x$ is morpholinyl, optionally substituted with 0-2 instances of $R^7$. In some embodiments, $R^x$ is azepanyl optionally substituted with 0-2 instances of $R^7$. In some embodiments, $R^x$ is 8-oxa-3-azabicyclo[3.2.1]octanyl (e.g., 8-oxa-3-azabicyclo[3.2.1]octan-3-yl), optionally substituted with 0-2 instances of $R^7$. In some embodiments $R^x$ is 2-azabicyclo[2.2.1]heptanyl substituted with 0-2 instances of $R^7$. In some embodiments, $R^x$ is 3-azabicyclo[3.1.1]heptanyl substituted with 0-2 instances of $R^7$. In some embodiments, $R^x$ is 3-azabicyclo[3.2.1]octanyl substituted with 0-2 instances of $R^7$.

In some embodiments $R^x$ is optionally substituted cycloalkylalkyl (e.g., cyclopropylmethyl, cyclobutylmethyl, cyclopentylmethyl, cyclohexylmethyl, cycloheptylmethyl). In some embodiments, $R^x$ is cycloalkylalkyl optionally substituted with 0-2 instances of $R^7$. In some embodiments, $R^x$ is optionally substituted heterocyclylalkyl (e.g., oxetanylmethyl, aziridinylmethyl, tetrahydrofuranylmethyl, pyrolidinylmethyl, tetrahydropyranylmethyl, piperidinylmethyl, piperazinylmethyl, morpholinylmethyl, azepanylmethyl). In some embodiments, $R^x$ is heterocyclylalkyl optionally substituted with 0-2 instances of $R^7$.

In some embodiments, $R^x$ is —$OR^3$ (e.g., methoxy, fluoromethoxy (—$OCHF_2$), trifluoromethoxy (—$OCF_3$), ethoxy, propoxy, isopropoxy, cyclopropyloxy, cyclobutyloxy). In some embodiments, $R^x$ is methoxy. In some embodiments, $R^x$ is ethoxy. In some embodiments, $R^x$ is propoxy. In some embodiments, $R^x$ is isopropoxy. In some embodiments $R^x$ is fluoromethoxy (—$OCHF_2$). In some embodiments, $R^x$ is trifluoromethoxy (—$OCF_3$).

In some embodiments, $R^x$ is —$N(R^3)_2$ (e.g., —$NH_2$, —$NHR^3$, —$N(CH_3)R_3$). In some embodiments, $R^x$ is —$NH_2$. In some embodiments, $R^x$ is —$NHR^3$ (e.g., —NHMe, —NHEt, —NHPr, —$NH^iPr$, —NHcyclopropyl, —NHcyclobutyl). In some embodiments, $R^x$ is —$N(CH_3)R^3$ (e.g., —$NMe_2$, —$N(CH_3)Et$, —$N(CH_3)Pr$, —$N(CH_3)^iPr$, —$N(CH_3)$cyclopropyl, —$N(CH_3)$cyclobutyl).

In some embodiments, $R^x$ is —$C(=O)R^3$. In some embodiments, $R^x$ is —C(=O)alkyl. In some embodiments, $R^x$ is acetyl (—C(=O)Me). In some embodiments, $R^x$ is —C(=O)cycloalkyl (e.g. —C(=O)cyclopropyl).

In some embodiments, $R^x$ is —$C(=O)OR^3$. In some embodiments, $R^x$ is —COOH. In some embodiments, $R^x$ is COOMe.

In some embodiments, $R^x$ is —$NR^3C(=O)R^3$. In certain embodiments, $R^x$ is —$NHC(=O)R^3$ (e.g., NHC(=O)Me, NHC(=O)Et, NHC(=O)Pr, NHC(=O)$^iPr$, NHC(=O)Bu, NHC(=O)$^tBu$, NHC(=O)Cyclopropyl, NHC(=O)Cyclobutyl). In some embodiments, $R^x$ is —$N(CH_3)C(=O)R^3$ (e.g., $N(CH_3)C(=O)Me$, $N(CH_3)C(=O)Et$, $N(CH_3)C(=O)Pr$, $N(CH_3)C(=O)^iPr$, $N(CH_3)C(=O)Bu$, $N(CH_3)C(=O)^tBu$, $N(CH_3)C(=O)Cyclopropyl$, $N(CH_3)C(=O)Cyclobutyl$).

In some embodiments, $R^x$ is —$NR^3C(=O)OR^3$. In certain embodiments, $R^x$ is —$NHC(=O)OR^3$ (e.g., NHC(=O)OMe, NHC(=O)OEt, NHC(=O)OPr, NHC(=O)O$^iPr$, NHC(=O)OBu, NHC(=O)O$^tBu$, NHC(=O)OCyclopropyl, NHC(=O)OCyclobutyl). In some embodiments, $R^x$ is —$N(CH_3)C(=O)OR^3$ (e.g., $N(CH_3)C(=O)OMe$, $N(CH_3)C(=O)OEt$, $N(CH_3)C(=O)OPr$, $N(CH_3)C(=O)O^iPr$, $N(CH_3)C(=O)OBu$, $N(CH_3)C(=O)O^tBu$, $N(CH_3)C(=O)OCyclopropyl$, $N(CH_3)C(=O)OCyclobutyl$).

In some embodiments, $R^x$ is —$C(=O)N(R^3)_2$ (e.g., —$C(=O)NH_2$, —$C(=O)NHR^3$, —$C(=O)N(CH_3)R_3$). In some embodiments, $R^x$ is —$C(=O)NH_2$. In certain embodiments, $R^x$ is —$C(=O)NHR^3$ (e.g., —C(=O)NHMe, —C(=O)NHEt, —C(=O)NHPr, —$C(=O)NH^iPr$, —C(=O)NHBu, —C(=O)NHrBu, —C(=O)NHCyclopropyl, —C(=O)NHCyclobutyl). In certain embodiments, $R^x$ is —$C(=O)N(CH_3)R^3$ (e.g., —$C(=O)NMe_2$, —$C(=O)N(CH_3)Et$, —$C(=O)N(CH_3)Pr$, —$C(=O)N(CH_3)^iPr$, —$C(=O)N(CH_3)Bu$, —$C(=O)N(CH_3)Bu$, —$C(=O)N(CH_3)Cyclopropyl$, —$C(=O)N(CH_3)Cyclobutyl$).

In some embodiments, $R^x$ is —$OC(=O)N(R^3)_2$. In certain embodiments, $R^x$ is —$OC(=O)NHR^3$ (e.g., —OC(=O)NHMe, —OC(=O)NHEt, —OC(=O)NHPr, —OC(=O)NH$^iPr$, —OC(=O)NHBu, —OC(=O)NH$^tBu$, —OC(=O)NHCyclopropyl, —OC(=O)NHCyclobutyl). In certain embodiments, $R^x$ is —$OC(=O)N(CH_3)R^3$ (e.g., —$OC(=O)NMe_2$, —$OC(=O)N(CH_3)Et$, —$OC(=O)N(CH_3)Pr$, —$OC(=O)N(CH_3)^iPr$, —$OC(=O)N(CH_3)Bu$, —$OC(=O)N(CH_3)Bu$, —$OC(=O)N(CH_3)Cyclopropyl$, —$OC(=O)N(CH_3)Cyclobutyl$).

In some embodiments, $R^x$ is —$S(=O)R^3$. In certain embodiments, $R^x$ is —S(=O)alkyl (e.g., —S(=O)Me, —S(=O)Et, —S(=O)Pr, —$S(=O)^iPr$). In certain embodiments, $R^x$ is —S(=O)cycloalkyl (e.g., —S(=O)cyclopropyl, —S(=O)cyclobutyl, —S(=O)cyclopentyl, —S(=O)cyclohexyl).

In some embodiments, $R^x$ is —$S(=O)_2R^3$. In certain embodiments, $R^x$ is —$S(=O)_2$alkyl (e.g., —$S(=O)_2Me$, —$S(=O)_2Et$, —$S(=O)_2Pr$, —$S(=O)_2^iPr$). In certain embodiments, $R^x$ is —$S(=O)_2$cycloalkyl (e.g., —$S(=O)_2$cyclopropyl, —$S(=O)_2$cyclobutyl, —$S(=O)_2$cyclopentyl, —$S(=O)_2$cyclohexyl). In some embodiments, $R^x$ is $S(=O)_2$ aryl (e.g., $S(=O)_2$phenyl).

In some embodiments, $R^x$ is —$SR^3$. In certain embodiments, $R^x$ is —Salkyl (e.g., —SMe, —SEt, —SPr, —$S^iPr$). In certain embodiments, $R^x$ is —Scycloalkyl (e.g., —Scyclopropyl, —Scyclobutyl, —Scyclopentyl, —Scyclohexyl). In certain embodiments, R is —Saryl (e.g., Sphenyl).

In some embodiments, $R^x$ is —$S(=O)(=NR^3)R^3$. In certain embodiments, $R^x$ is —$S(=O)(=NH)R^3$ (e.g., —S(=O)(=NH)Me, —S(=O)(=NH)Et, —S(=O)(=NH)Pr, —$S(=O)(=NH)^iPr$, —S(=O)(=NH)Bu, —$S(=O)(=NH)^tBu$, —S(=O)(=NH)Cyclopropyl, —S(=O)(=NH)Cyclobutyl). In some embodiments, $R^x$ is —$S(=O)(=NCH_3)R^3$ (e.g., —$S(=O)(=NCH_3)Me$, —$S(=O)(=NCH_3)Et$, —$S(=O)(=NCH_3)Pr$, —$S(=O)(=NCH_3)^iPr$, —$S(=O)(=NCH_3)Bu$, —$S(=O)(=NCH_3)^tBu$, —$S(=O)(=NCH_3)Cyclopropyl$, —$S(=O)(=NCH_3)Cyclobutyl$).

In some embodiments, $R^x$ is —$NR^3S(=O)_2R^3$. In certain embodiments, R is —$NHS(=O)_2$alkyl (e.g., —$NHS(=O)_2Me$, —$NHS(=O)_2Et$, —$NHS(=O)_2Pr$, —$NHS(=O)_2^iPr$). In certain embodiments, $R^x$ is —$NHS(=O)_2$cycloalkyl (e.g., —$NHS(=O)_2$cyclopropyl, —$NHS(=O)_2$cyclobutyl, —$NHS(=O)_2$cyclopentyl, —$NHS(=O)_2$cyclohexyl). In certain embodiments, $R^x$ is —$N(CH_3)S(=O)_2$alkyl (e.g., —$N(CH_3)S(=O)_2Me$, —$N(CH_3)S(=O)_2Et$, —$N(CH_3)S(=O)_2Pr$, —$N(CH_3)S(=O)_2^iPr$). In certain embodiments, $R^x$ is —$N(CH_3)S(=O)_2$cycloalkyl (e.g., —$N(CH_3)S(=O)_2$cyclopropyl, —$N(CH_3)S(=O)_2$cyclobutyl, —$N(CH_3)S(=O)_2$cyclopentyl, —$N(CH_3)S(=O)_2$cyclohexyl).

In some embodiments, $R^x$ is —$S(=O)_2N(R^3)_2$. (e.g., —$S(=O)_2NH_2$, —$S(=O)_2NHR^3$, —$S(=O)_2N(CH_3)R_3$). In some embodiments, $R^x$ is —$S(=O)_2NH_2$. In some embodiments, $R^x$ is —$S(=O)_2NHR^3$ (e.g., —$S(=O)_2NHMe$, —$S(=O)_2NHEt$, —$S(=O)_2NHPr$, —$S(=O)_2NH^iPr$, —$S(=O)_2NHcyclopropyl$, —$S(=O)_2NHcyclobutyl$). In certain embodiments, $R^x$ is —$S(=O)_2N(CH_3)R^3$ (e.g., —$S(=O)_2NMe_2$, —$S(=O)_2N(CH_3)Et$, —$S(=O)_2N(CH_3)Pr$, —$S(=O)_2N(CH_3)^iPr$, —$S(=O)_2N(CH_3)$cyclopropyl, —$S(=O)_2N(CH_3)$cyclobutyl).

In certain embodiments, $X^1$ is N and $X^2$, $X^3$, $X^4$ and $X^5$ are $CR^x$. In a further embodiment, $X^1$ is N and $X^2$, $X^3$, $X^4$ and $X^5$ are CH. In other embodiments, $X^2$ is N and $X^1$, $X^3$, $X^4$ and $X^5$ are $CR^x$. In a further embodiment, $X^2$ is N and $X^1$, $X^3$, $X^4$ and $X^5$ are CH. In other embodiments, $X^3$ is N and $X^1$, $X^2$, $X^4$ and $X^5$ are $CR^x$. In a further embodiment, $X^3$ is N and $X^1$, $X^2$, $X^4$ and $X^5$ are CH. In other embodiments, $X^4$ is N and $X^1$, $X^2$, $X^3$ and $X^5$ are $CR^x$. In a further embodiment, $X^4$ is N a $X^1$, $X^2$, $X^3$ and $X^5$ are CH.

In certain embodiments, $X^1$ and $X^2$ are N and $X^3$, $X^4$ and $X^5$ are $CR^x$. In further embodiments, $X^1$ and $X^2$ are N and $X^3$, $X^4$ and $X^5$ are CH. In certain embodiments, $X^1$ and $X^3$ are N and $X^2$, $X^4$ and $X^5$ are $CR^x$. In further embodiments, $X^1$ and $X^3$ are N and $X^2$, $X^4$ and $X^5$ are CH. In certain embodiments, $X^1$ and $X^4$ are N and $X^2$, $X^3$ and $X^5$ are $CR^x$. In further embodiments, $X^1$ and $X^4$ are N and $X^2$, $X^3$ and $X^5$ are CH. In certain embodiments, $X^2$ and $X^3$ are N and $X^1$, $X^4$ and $X^5$ are $CR^x$. In further embodiments, $X^2$ and $X^3$ are N and $X^1$, $X^4$ and $X^5$ are CH. In certain embodiments, $X^2$ and $X^4$ are N and $X^1$, $X^3$ and $X^5$ are $CR^x$. In further embodiments, $X^2$ and $X^4$ are N and $X^1$, $X^3$ and $X^5$ are CH. In certain embodiments, $X^3$ and $X^4$ are N and $X^1$, $X^2$ and $X^5$ are $CR^x$. In further embodiments, $X^3$ and $X^4$ are N and $X^1$, $X^2$ and $X^5$ are CH. In some embodiments, $X^1$, $X^2$, $X^3$, $X^4$ and $X^5$ are all $CR^x$. In some embodiments, $X^1$, $X^2$, $X^3$, $X^4$ and $X^5$ are all CH.

In some embodiments the invention provides a compound of Formula (IIa1) or a pharmaceutically acceptable salt thereof wherein:

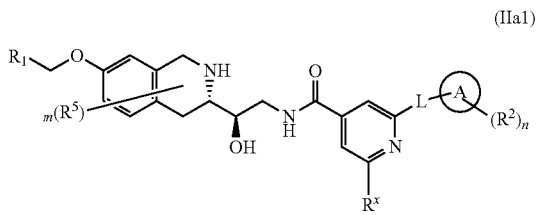

(IIa1)

and each instance of L, $R^1$, $R^2$, $R^5$, $R^x$, A, m and n is as described herein.

In some embodiments the invention provides a compound of Formula (IIa2) or a pharmaceutically acceptable salt thereof wherein:

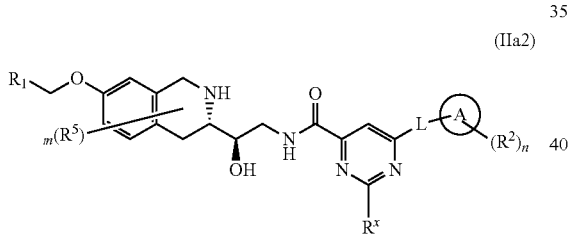

(IIa2)

and each instance of L, $R^1$, $R^2$, $R^5$, $R^x$, A, m and n is as described herein.

In some embodiments the invention provides a compound of Formula (IIa3) or a pharmaceutically acceptable salt thereof wherein:

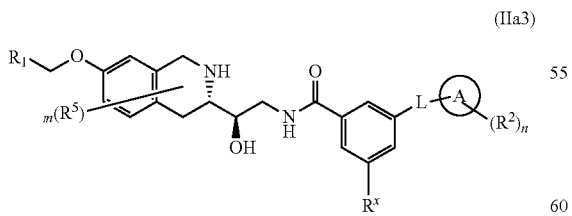

(IIa3)

and each instance of L, $R^1$, $R^2$, $R^5$, $R^x$, A, m and n is as described herein.

In some embodiments the invention provides a compound of Formula (IIa4) or a pharmaceutically acceptable salt thereof wherein:

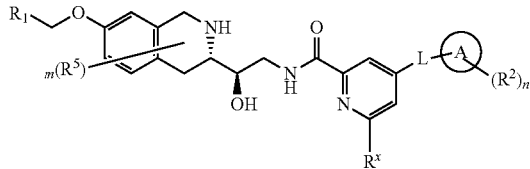

(IIa4)

and each instance of L, $R^1$, $R^2$, $R^5$, $R^x$, A, m and n is as described herein In some embodiments the invention provides a compound of Formula (VIIa1) or a pharmaceutically acceptable salt thereof wherein:

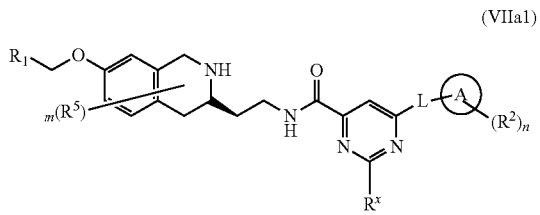

(VIIa1)

and each instance of L, $R^1$, $R^2$, $R^5$, $R^x$, A, m and n is as described herein.

In some embodiments the invention provides a compound of Formula (VIIb1) or a pharmaceutically acceptable salt thereof wherein

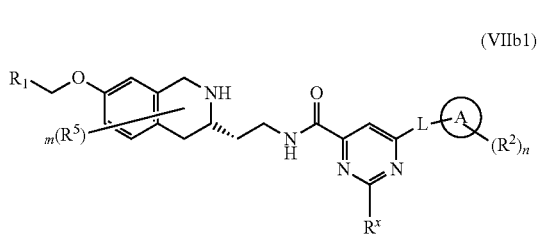

(VIIb1)

and each instance of L, $R^1$, $R^2$, $R^5$, $R^x$, A, m and n is as described herein.

In some embodiments the invention provides a compound of Formula (IIIa1) or a pharmaceutically acceptable salt thereof wherein:

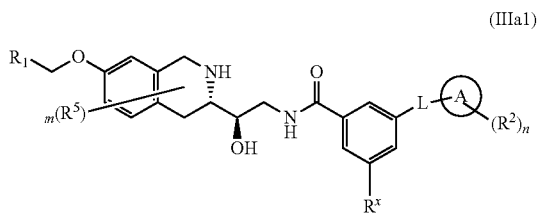

(IIIa1)

and each instance of L, $R^1$, $R^2$, $R^5$, $R^x$, A, m and n is as described herein.

In some embodiments the invention provides a compound of Formula (IIIa2) or a pharmaceutically acceptable salt thereof wherein:

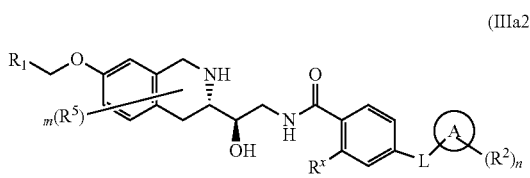
(IIIa2)

and each instance of L, $R^1$, $R^2$, $R^5$, $R^x$, A, m and n is as described herein.

As generally described herein, L is a bond, —C(=O)—, —NH— or —O—.

In certain embodiments of the invention, L is —NH—.

In some embodiments the invention provides a compound or pharmaceutically acceptable salt thereof, wherein the compound is of Formula (IIa1i) wherein:

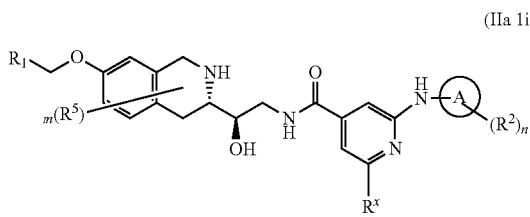
(IIa1i)

and each instance of $R^1$, $R^2$, $R^5$, $R^x$, A, m and n is as described herein.

In some embodiments the invention provides a compound or pharmaceutically acceptable salt thereof, wherein the compound is of Formula (IIa2i) wherein:

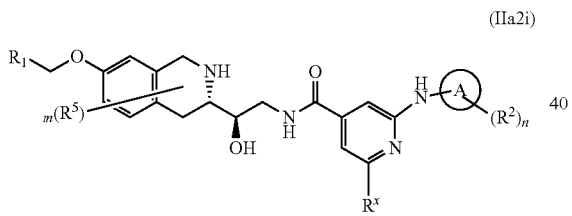
(IIa2i)

and each instance of $R^1$, $R^2$, $R^5$, $R^x$, A, m and n is as described herein.

In some embodiments the invention provides a compound or pharmaceutically acceptable salt thereof, wherein the compound is of Formula (IIa3i) wherein:

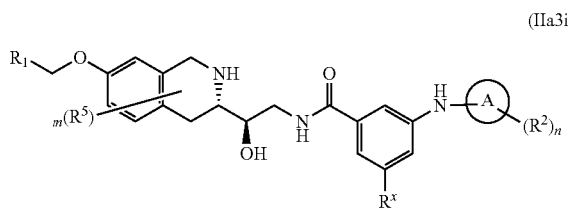
(IIa3i)

and each instance of $R^1$, $R^2$, $R^5$, $R^x$, A, m and n is as described herein.

In some embodiments the invention provides a compound or pharmaceutically acceptable salt thereof, wherein the compound is of Formula (IIa4i) wherein:

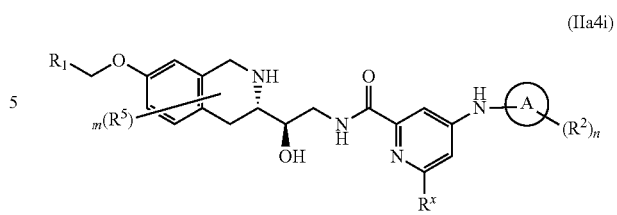
(IIa4i)

and each instance of $R^1$, $R^2$, $R^5$, $R^x$, A, m and n is as described herein.

In some embodiments the invention provides a compound or pharmaceutically acceptable salt thereof, wherein the compound is of Formula (VIIa1i) wherein:

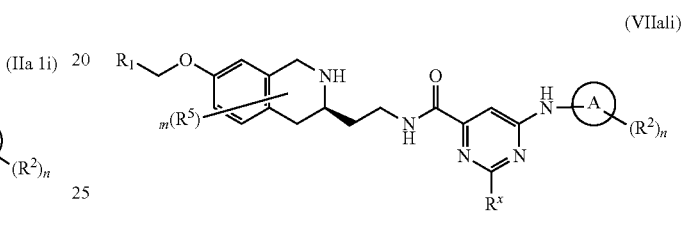
(VIIa1i)

and each instance of $R^1$, $R^2$, $R^5$, $R^x$, A, m and n is as described herein.

In some embodiments the invention provides a compound or pharmaceutically acceptable salt thereof, wherein the compound is of Formula (VIIb1i) wherein:

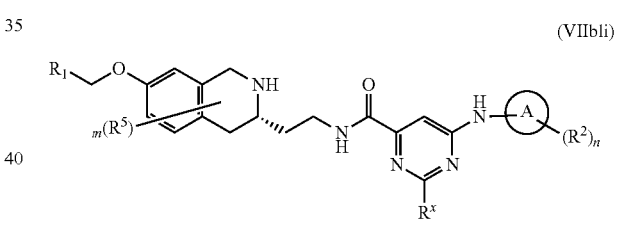
(VIIb1i)

and each instance of $R^1$, $R^2$, $R^5$, $R^x$, A, m and n is as described herein.

In some embodiments, $L^2$ is a bond.

In some embodiments the invention provides a compound or pharmaceutically acceptable salt thereof, wherein the compound is of Formula (IIa3ii) wherein:

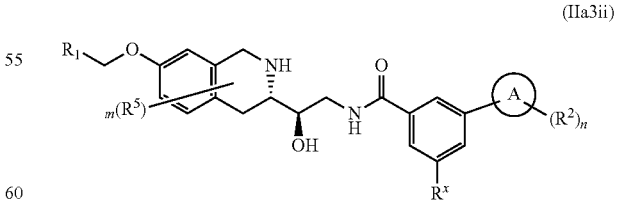
(IIa3ii)

and each instance of $R^1$, $R^2$, $R^5$, $R^x$, A, m and n is as described herein.

In some embodiments the invention provides a compound or pharmaceutically acceptable salt thereof, wherein the compound is of Formula (IIIa1i) wherein:

(IIIa1i)

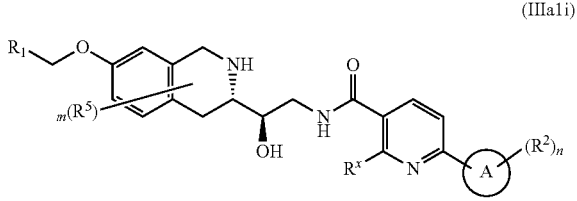

and each instance of $R^1$, $R^2$, $R^5$, $R^x$, A, m and n is as described herein.

In some embodiments, L is —O—.

In some embodiments the invention provides a compound or pharmaceutically acceptable salt thereof, wherein the compound is of Formula (IIIa2i) wherein:

(IIIa2i)

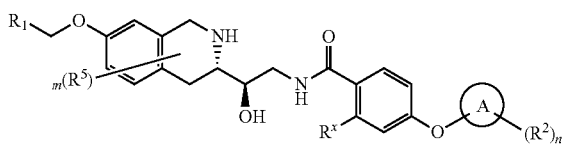

and each $R^1$, $R^2$, $R^5$, $R^x$, A, m and n is as described herein.

In certain embodiments, L is —C(=O)—.

In some embodiments the invention provides a compound or pharmaceutically acceptable salt thereof, wherein the compound is of Formula (IIIa2ii) wherein:

(IIIa2ii)

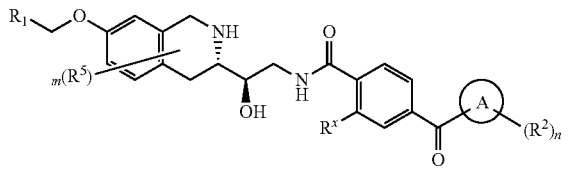

and each instance of $R^1$, $R^2$, $R^5$, $R^x$, A, m and n is as described herein.

As generally described herein, ring A is selected from a carbocycle (e.g., a $C_3$-$C_{12}$ monocyclic or bicyclic carbocycle), a heterocycle (e.g., a 3-12 member monocyclic or bicyclic heterocycle containing 1-2 heteroatoms independently selected from O and N) and a 5-6 member monocyclic heteroaryl.

In certain embodiments of the invention, ring A is a 4-7 membered monocyclic heterocycle containing 1 or 2 heteroatoms independently selected from O and N. In certain embodiments of the invention, ring A is a 4-6 membered monocyclic heterocycle containing 1 or 2 heteroatoms independently selected from O and N. In some embodiments, ring A is selected from piperidinyl, piperazinyl, pyrrolidinyl, oxetanyl, tetrahydrofuranyl, azetidinyl, tetrahydropyranyl, 1,4-dioxan-2-yl or morpholinyl In some embodiments, ring A is piperidinyl. In some embodiments ring A is piperazinyl. In some embodiments, ring A is oxetanyl. In some embodiments, ring A is tetrahydropyranyl. In some embodiments, ring A is morpholinyl.

In some embodiments ring A is a 7-12 membered bicyclic heterocyclyl containing one or two heteroatoms independently selected from O and N. In further embodiments, A is a 7-9 membered bridged bicyclic or spirocyclic heterocyclyl containing one or two heteroatoms independently selected from O and N. In some embodiments ring A is selected from:

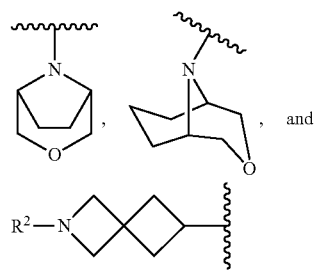

In certain embodiments, ring A is a 5-6 membered monocyclic heteroaryl. In an exemplary embodiment, Ring A is pyridinyl (e.g., 3-pyridinyl).

In certain embodiments of the invention, ring A is a 3-8 membered carbocycle. In some embodiments, ring A is selected from cyclopropyl, cyclobutyl, cyclopentyl, cyclohexyl cycloheptyl, spiro[2.3]hexyl and spiro[3.3]heptyl.

In some embodiments, ring A is cyclopropyl. In some embodiments, ring A is cyclobutyl. In some embodiments, ring A is cyclopentyl. In some embodiments, ring A is cyclohexyl. In some embodiments, ring A is cycloheptyl.

In some embodiments, ring A is a 6-8 membered spirocarbocycle. In exemplary embodiments, A is spiro[2.3]hexyl or spiro[3.3]heptyl.

In one aspect the invention provides a compound of Formula (IV) or a pharmaceutically acceptable salt thereof wherein:

(IV)

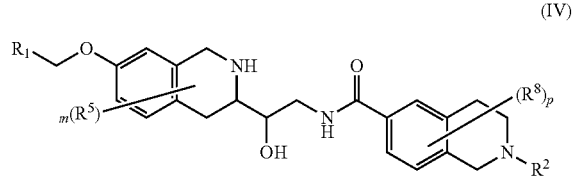

wherein:

$R^1$ is a 5-6 membered heteroaryl substituted with 0-3 instances of $R^4$;

each $R^2$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, cycloalkylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$ and —$S(=O)_2N(R^3)_2$;

each $R^3$ is independently selected from H, $C_1$-$C_6$ alkyl, $C_3$-$C_9$ carbocyclyl, $C_3$-$C_7$ heterocyclyl, cycloalkylalkyl, heterocyclylalkyl, aryl, 5-6 membered heteroaryl, arylalkyl and heteroarylalkyl wherein each alkyl, carbocyclyl, heterocyclyl, cycloalkylalkyl, heterocyclylalkyl, aryl, heteroaryl, arylalkyl and heteroarylalkyl is optionally substituted;

each $R^4$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, cycloalkylalkyl, —$OR^3$, —$N(R^3)_2$, —$C(=O)R^3$, —$C(=O)OR^3$, —$NR^3C(=O)$ R³, —NR³C(=O)OR³, —C(=O)N(R³)₂, —OC(=O)N(R³)₂, —S(=O)R³, —S(=O)₂R³, —SR³, —S(=O)(=NR³)R³, —NR³S(=O)₂R³ and —S(=O)₂N(R³)₂;

each R⁵ is independently selected from =O, halo, —CN, —C₁-C₆ alkyl, —C₁-C₆ heteroalkyl, —C₁-C₆ haloalkyl, —C₃-C₉ carbocyclyl, 3-10 membered heterocyclyl, C₆-C₁₀ aryl, 5-10 membered heteroaryl, cycloalkylalkyl, heterocyclylalkyl, arylalkyl, heteroarylalkyl, —OR³, —N(R³)₂, —C(=O)R³, —C(=O)OR³, —NR³C(=O)R³, —NR³C(=O)OR³, —C(=O)N(R³)₂, —OC(=O)N(R³)₂, —S(=O)R³, —S(=O)₂R³, —SR³, —S(=O)(=NR³)R³, —NR³S(=O)₂R³, —S(=O)₂N(R³)₂, or two R⁵ can be taken together with the atoms to which they are attached to form a —C₃-C₉ carbocyclyl or a 3-10 membered heterocyclyl;

each R⁸ is independently selected from =O, halo, —CN, —C₁-C₆ alkyl, —C₁-C₆ heteroalkyl, —C₁-C₆ haloalkyl, —C₃-C₉ carbocyclyl, 3-10 membered heterocyclyl, C₆-C₁₀ aryl, 5-10 membered heteroaryl, cycloalkylalkyl, heterocyclylalkyl, arylalkyl, heteroarylalkyl, —OR³, —N(R³)₂, —C(=O)R³, —C(=O)OR³, —NR³C(=O)R³, —NR³C(=O)OR³, —C(=O)N(R³)₂, —OC(=O)N(R³)₂, —S(=O)R³, —S(=O)₂R³, —SR³, —S(=O)(=NR³)R³, —NR³S(=O)₂R³, —S(=O)₂N(R³)₂, or two R⁵ can be taken together with the atoms to which they are attached to form a —C₃-C₉ carbocyclyl or a 3-10 membered heterocyclyl;

m is 0, 1, 2 or 3; and
p is 0, 1, 2 or 3.

In certain embodiments the invention provides a compound of Formula (IVa) or a pharmaceutically acceptable salt thereof, wherein:

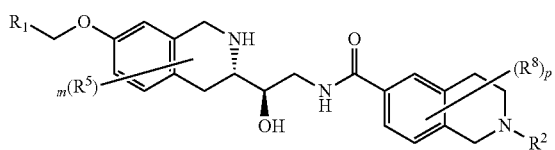

(IVa)

and each instance of R¹, R², R⁵, R⁸, m and p is as defined herein.

In one aspect the invention provides a compound of Formula (V) or a pharmaceutically acceptable salt thereof, wherein:

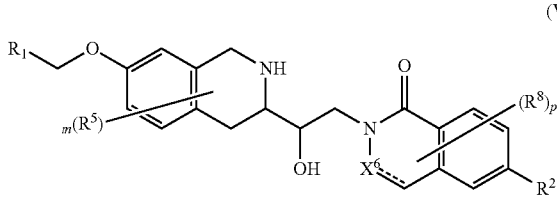

(V)

X⁶ is N, NH, CHR or CR^x;
R¹ is a 5-6 membered heteroaryl substituted with 0-3 instances of R⁴;
each R² is independently selected from =O, halo, —CN, —C₁-C₆ alkyl, —C₁-C₆ heteroalkyl, —C₁-C₆ haloalkyl, —C₃-C₉ carbocyclyl, 3-10 membered heterocyclyl, heterocyclylalkyl, heteroaryl alkyl, cycloalkylalkyl, —OR³, —N(R³)₂, —C(=O)R³, —C(=O)OR³, —NR³C(=O)R³, —NR³C(=O)OR³, —C(=O)N(R³)₂, —OC(=O)N(R³)₂, —S(=O)R³, —S(=O)₂R³, —SR³, —S(=O)(=NR³)R³, —NR³S(=O)₂R³ and —S(=O)₂N(R³)₂;

each R³ is independently selected from H, C₁-C₆ alkyl, —C₁-C₆ heteroalkyl, C₃-C₉ carbocyclyl, C₃-C₇ heterocyclyl, cycloalkylalkyl, heterocyclylalkyl, aryl, 5-6 membered heteroaryl, arylalkyl and heteroarylalkyl wherein each alkyl, carbocyclyl, heterocyclyl, cycloalkylalkyl, heterocyclylalkyl, aryl, heteroaryl, arylalkyl and heteroarylalkyl is optionally substituted;

each R⁴ is independently selected from =O, halo, —CN, —C₁-C₆ alkyl, —C₁-C₆ heteroalkyl, —C₁-C₆ haloalkyl, —C₃-C₉ carbocyclyl, 3-10 membered heterocyclyl, heterocyclylalkyl, cycloalkylalkyl, —OR³, —N(R³)₂, —C(=O)R³, —C(=O)OR³, —NR³C(=O)R³, —NR³C(=O)OR³, —C(=O)N(R³)₂, —OC(=O)N(R³)₂, —S(=O)R³, —S(=O)₂R³, —SR³, —S(=O)(=NR³)R³, —NR³S(=O)₂R³ and —S(=O)₂N(R³)₂;

each R^x is independently selected from hydrogen, halo, —CN, —C₁-C₆ alkyl, —C₁-C₆ heteroalkyl, —C₁-C₆ haloalkyl, —C₃-C₉ carbocyclyl, 3-10 membered heterocyclyl, heterocyclylalkyl, cycloalkylalkyl, —OR³, —N(R³)₂, —C(=O)R³, —C(=O)OR³, —NR³C(=O)R³, —NR³C(=O)OR³, —C(=O)N(R³)₂, —OC(=O)N(R³)₂, —S(=O)R³, —S(=O)₂R³, —SR³, —S(=O)(=NR³)R³, —NR³S(=O)₂R³ and —S(=O)₂N(R³)₂ wherein each alkyl, carbocyclyl, heterocyclyl, heterocyclylalkyl, cycloalkylalkyl is optionally substituted;

each R⁵ is independently selected from =O, halo, —CN, —C₁-C₆ alkyl, —C₁-C₆ heteroalkyl, —C₁-C₆ haloalkyl, —C₃-C₉ carbocyclyl, 3-10 membered heterocyclyl, C₆—C₁₀ aryl, 5-10 membered, cycloalkylalkyl, heterocyclylalkyl, arylalkyl, heteroarylalkyl, —OR³, —N(R³)₂, —C(=O)R³, —C(=O)OR³, —NR³C(=O)R³, —NR³C(=O)OR³, —C(=O)N(R³)₂, —OC(=O)N(R³)₂, —S(=O)R³, —S(=O)₂R³, —SR³, —S(=O)(=NR³)R³, —NR³S(=O)₂R³, —S(=O)₂N(R³)₂, or two R⁵ can be taken together with the atoms to which they are attached to form a —C₃-C₉ carbocyclyl or a 3-10 membered heterocyclyl;

each R⁸ is independently selected from =O, halo, —CN, —C₁-C₆ alkyl, —C₁-C₆ heteroalkyl, —C₁-C₆ haloalkyl, —C₃-C₉ carbocyclyl, 3-10 membered heterocyclyl, C₆-C₁₀ aryl, 5-10 membered heteroaryl, cycloalkylalkyl, heterocyclylalkyl, arylalkyl, heteroarylalkyl, —OR³, —N(R³)₂, —C(=O)R³, —C(=O)OR³, —NR³C(=O)R³, —NR³C(=O)OR³, —C(=O)N(R³)₂, —OC(=O)N(R³)₂, —S(=O)R³, —S(=O)₂R³, —SR³, —S(=O)(=NR³)R³, —NR³S(=O)₂R³, —S(=O)₂N(R³)₂, or two R⁵ can be taken together with the atoms to which they are attached to form a —C₃-C₉ carbocyclyl or a 3-10 membered heterocyclyl;

m is 0, 1, 2 or 3; and
p is 0, 1, 2 or 3.

In some embodiments the invention provides a compound of Formula (Va) or a pharmaceutically acceptable salt thereof, wherein:

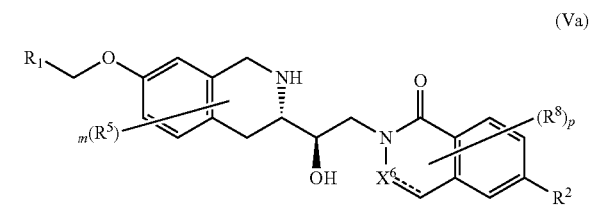

(Va)

and each instance of $R^1$, $R^2$, $R^5$, $R^8$, $X^6$, m and p are as defined herein.

In some embodiments, $X^6$ is N. In some embodiments, $X^6$ is NH. In some embodiments $X^6$ is $CHR^x$. In some embodiments $X_6$ is $CH_2$. In some embodiments $X_6$ is CH. In some embodiments $X^6$ is $CR^x$.

In some embodiments the invention provides a compound of Formula (Va1) or a pharmaceutically acceptable salt thereof, wherein:

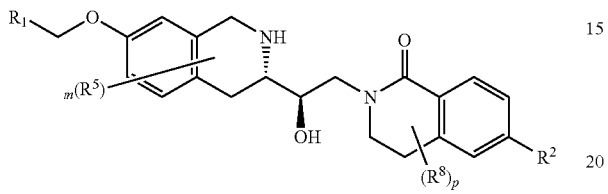

(Va1)

and each instance of $R^1$, $R^2$, $R^5$, $R^8$ m and p is as defined herein.

In some embodiments the invention provides a compound of Formula (Va2) or a pharmaceutically acceptable salt thereof, wherein:

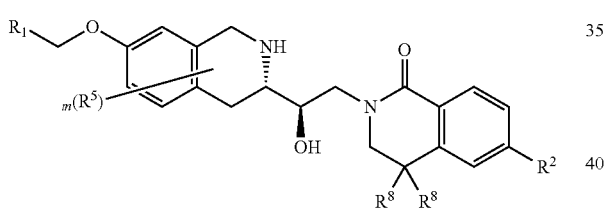

(Va2)

and each instance of $R^1$, $R^2$, $R^5$, $R^8$ and m is as defined herein. 5.

In some embodiments the invention provides a compound of Formula (Va3) or a pharmaceutically acceptable salt thereof, wherein:

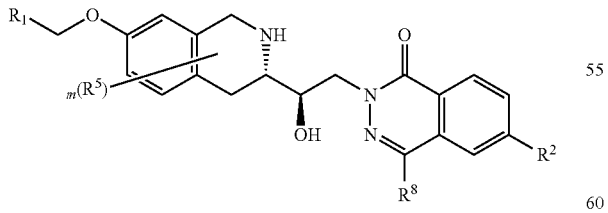

(Va3)

and each instance of $R^1$, $R^2$, $R^5$, $R^8$ and m is as defined herein.

In one aspect, the invention provides a compound or pharmaceutically acceptable salt thereof wherein the compound is of Formula (VI)

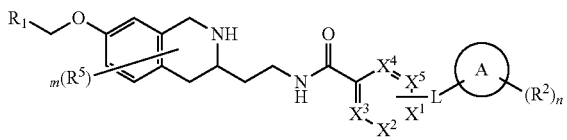

(VI)

wherein:
$X^1$, $X^2$, $X^3$, $X^4$ and $X^5$ are each independently N or $CR^x$;
L is a bond, —C(=O)—, —NH— or —O—;
Ring A is a carbocycle, heterocycle or a 5-6 membered monocyclic heteroaryl;
$R^1$ is a 5-6 membered heteroaryl substituted with 0-3 instances of $R^4$;
each $R^2$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, heteroarylalkyl, arylalkyl, cycloalkylalkyl, —$OR^3$, —$N(R^3)_2$, —C(=O)$R^3$, —C(=O)$OR^3$, —$NR^3$C(=O)$R^3$, —$NR^3$C(=O)$OR^3$, —C(=O)N($R^3$)$_2$, —OC(=O)N($R^3$)$_2$, —S(=O)$R^3$, —S(=O)$_2R^3$, —$SR^3$, —S(=O)(=$NR^3$)$R^3$, —$NR^3$S(=O)$_2R^3$ and —S(=O)$_2$N($R^3$)$_2$;
each $R^3$ is independently selected from H, $C_1$-$C_6$ alkyl, —$C_1$-$C_6$ heteroalkyl, $C_3$-$C_9$ carbocyclyl, 3-7 membered heterocyclyl, cycloalkylalkyl, heterocyclylalkyl, aryl, 5-6 membered heteroaryl, arylalkyl and heteroarylalkyl wherein each alkyl, carbocyclyl, heterocyclyl, cycloalkylalkyl, heterocyclylalkyl, aryl, heteroaryl, arylalkyl and heteroarylalkyl is optionally substituted;
each $R^4$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, cycloalkylalkyl, —$OR^3$, —$N(R^3)_2$, —C(=O)$R^3$, —C(=O)$OR^3$, —$NR^3$C(=O)$R^3$, —$NR^3$C(=O)$OR^3$, —C(=O)N($R^3$)$_2$, —OC(=O)N($R^3$)$_2$, —S(=O)$R^3$, —S(=O)$_2R^3$, —$SR^3$, —S(=O)(=$NR^3$)$R^3$, —$NR^3$S(=O)$_2R^3$ and —S(=O)$_2$N($R^3$)$_2$;
each $R^x$ is independently selected from hydrogen, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, cycloalkylalkyl, —$OR^3$, —$N(R^3)_2$, —C(=O)$R^3$, —C(=O)$OR^3$, —$NR^3$C(=O)$R^3$, —$NR^3$C(=O)$OR^3$, —C(=O)N($R^3$)$_2$, —OC(=O)N($R^3$)$_2$, —S(=O)$R^3$, —S(=O)$_2R^3$, —$SR^3$, —S(=O)(=$NR^3$)$R^3$, —$NR^3$S(=O)$_2R^3$ and —S(=O)$_2$N($R^3$)$_2$ wherein each alkyl, carbocyclyl, heterocyclyl, heterocyclylalkyl, cycloalkylalkyl is optionally substituted;
each $R^5$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, $C_6$-$C_{10}$ aryl, 5-10 membered heteroaryl, cycloalkylalkyl, heterocyclylalkyl, arylalkyl, heteroarylalkyl, —$OR^3$, —$N(R^3)_2$, —C(=O)$R^3$, —C(=O)$OR^3$, —$NR^3$C(=O)$R^3$, —$NR^3$C(=O)$OR^3$, —C(=O)N($R^3$)$_2$, —OC(=O)N($R^3$)$_2$, —S(=O)$R^3$, —S(=O)$_2R^3$, —$SR^3$, —S(=O)(=$NR^3$)$R^3$, —$NR^3$S(=O)$_2R^3$, —S(=O)$_2$N($R^3$)$_2$, or two $R^5$ can be taken together with the atoms to which they are attached to form a —$C_3$-$C_9$ carbocyclyl or a 3-10 membered heterocyclyl;
m is 0, 1, 2 or 3; and
n is 0, 1, 2 or 3.

In some embodiments the invention provides a compound of Formula (VIa) or a pharmaceutically acceptable salt thereof, wherein:

(VIa)

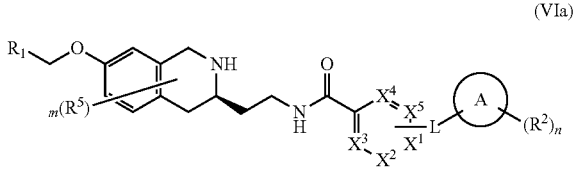

and each instance of $X^1$, $X^2$, $X^3$, $X^4$, $X^5$, A, L, $R^1$, $R^2$, $R^5$, m and n are as defined herein.

In some embodiments the invention provides a compound of Formula (VIb) or a pharmaceutically acceptable salt thereof, wherein:

(VIb)

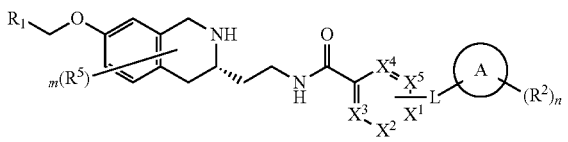

and each instance of $X^1$, $X^2$, $X^3$, $X^4$, $X^5$, A, L, $R^1$, $R^2$, $R^5$, m and n are as defined herein.

In some embodiments the invention provides a compound of Formula (VII) or a pharmaceutically acceptable salt thereof, wherein:

(VII)

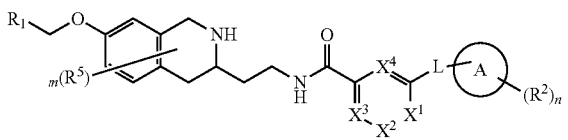

and each instance of $X^1$, $X^2$, $X^3$, $X^4$, A, L, $R^1$, $R^2$, $R^5$, m and n are as defined herein.

In certain embodiments, the compound is of Formula (VIIa):

(VIIa)

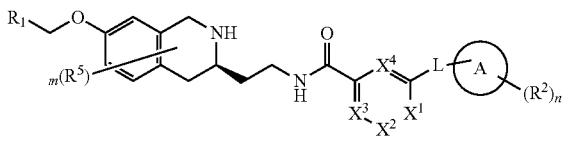

and each instance of $X^1$, $X^2$, $X^3$, $X^4$, A, L, $R^1$, $R^2$, $R^5$, m and n are as defined herein.

In some embodiments, the compound is of Formula (VIIb):

(VIIb)

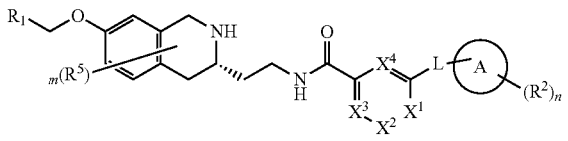

and each instance of $X^1$, $X^2$, $X^3$, $X^4$, A, L, $R^1$, $R^2$, $R^5$, m and n are as defined herein.

As generally described herein, $R^1$ is a 5-6 membered heteroaryl substituted with 0-3 instances of $R^4$ (e.g., 0, 1, 2 or 3 instances of $R^4$), wherein each $R^4$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, cycloalkylalkyl, —$OR^3$, —$N(R^3)_2$, —C(=O)$R^3$, —C(=O)$OR^3$, —$NR^3$C(=O)$R^3$, —$NR^3$C(=O)$OR^3$, —C(=O)$N(R^3)_2$, —OC(=O)$N(R^3)_2$, —S(=O)$R^3$, —S(=O)$_2R^3$, —$SR^3$, —S(=O)(=$NR^3$)$R^3$, —$NR^3$S(=O)$_2R^3$ and —S(=O)$_2N(R^3)_2$. In certain embodiments, $R^4$ is selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, cycloalkylalkyl, —$OR^3$, —$NHR^3$, $N(CH_3)R^3$, —C(=O)$R^3$, —C(=O)$OR^3$, —NHC(=O)$R^3$, —N($CH_3$)C(=O)$R^3$, —NHC(=O)$OR^3$, —N($CH_3$)C(=O)$OR^3$, —C(=O)NH$R^3$, —C(=O)N($CH_3$)($R^3$), —OC(=O)NH$R^3$, —OC(=O)N($CH_3$)$R^3$—S(=O)$R^3$, —S(=O)$_2R^3$, —$SR^3$, —S(=O)(=NH)$R^3$, —S(=O)(=$NCH_3$)$R^3$, —NHS(=O)$_2R^3$, —N($CH_3$)S(=O)$_2R^3$, —S(=O)$_2$NH$R^3$ and —S(=O)$_2$N($CH^3$)$R^3$.

In some embodiments, $R^4$ is =O.

In certain embodiments, $R^4$ is halo (e.g., fluoro, chloro, bromo, iodo). In further embodiments, $R^4$ is chloro. In some embodiments, $R^4$ is fluoro. In some embodiments, $R^4$ is bromo. In some embodiments, $R^4$ is iodo.

In some embodiments, $R^4$ is —CN.

In certain embodiments, $R^4$ is —$C_1$-$C_6$ alkyl. In further embodiments, $R^4$ is methyl. In some embodiments, $R^4$ is ethyl. In some embodiments $R^4$ is propyl or isopropyl.

In some embodiments, $R^4$ is —$C_1$-$C_6$ heteroalkyl. In further embodiments, $R^4$ is methoxymethyl (—$CH_2OCH_3$). In some embodiments, $R^4$ is aminomethyl (e.g., —$CH_2NH_2$, —$CH_2NHCH_3$, —$CH_2N(CH_3)_2$.

In some embodiments, $R^4$ is —$C_1$-$C_6$ haloalkyl. In further embodiments, $R^4$ is trifluoromethyl (—$CF_3$).

In some embodiments, $R^4$ is —$C_3$-$C_9$ carbocyclyl (e.g., cyclopropyl, cyclobutyl, cyclopentyl, cyclohexyl). In some embodiments, $R^4$ is cyclopropyl. In some embodiments $R^4$ is cyclobutyl. In some embodiments, $R^4$ is cyclopentyl. In some embodiments, $R^4$ is cyclohexyl, In some embodiments, $R^4$ is 3-10 membered heterocyclyl (e.g., oxetanyl, tetrahydropyranyl, tetrahydrofuranyl, azetidinyl, pyrrolidinyl, piperidinyl, piperazinyl, morpholinyl, azepanyl). In some embodiments, $R^4$ is oxetanyl. In some embodiments, $R^4$ is tetrahydropyranyl. In some embodiments, $R^4$ is tetrahydrofuranyl. In some embodiments, $R^4$ is azetidinyl. In some embodiments, $R^4$ is pyrrolidinyl. In some embodiments, $R^4$ is piperidinyl. In some embodiments, $R^4$ is piperazinyl. In some embodiments, $R^4$ is morpholinyl. In some embodiments, $R^4$ is azepanyl.

In some embodiments $R^4$ is cycloalkylalkyl (e.g., cyclopropylmethyl, cyclobutylmethyl, cyclopentylmethyl, cyclohexylmethyl, cycloheptylmethyl). In some embodiments, $R^4$ is heterocyclylalkyl (e.g., oxetanylmethyl, aziridinylmethyl, tetrahydrofuranylmethyl, pyrolidinylmethyl, tetrahydropyranylmethyl, piperidinylmethyl, piperazinylmethyl, morpholinylmethyl, azepanylmethyl).

In some embodiments, $R^4$ is —$OR^3$ (e.g., methoxy, fluoromethoxy (—$OCHF_2$), trifluoromethoxy (—$OCF_3$), ethoxy, propoxy, isopropoxy, cyclopropyloxy, cyclobutyloxy). In some embodiments, $R^4$ is methoxy. In some embodiments, $R^4$ is ethoxy. In some embodiments, $R^4$ is propoxy. In some embodiments, $R^4$ is isopropoxy. In some embodiments $R^4$ is fluoromethoxy. (—OCHF$_2$). In some embodiments, $R^4$ is trifluoromethoxy (—OCF$_3$).

In some embodiments, $R^4$ is —N(R$^3$)$_2$ (e.g., —NH$_2$, —NHR$^3$, —N(CH$_3$)R$_3$). In some embodiments, $R^4$ is —NH$_2$. In some embodiments, $R^4$ is —NHR$^3$ (e.g., —NHMe, —NHEt, —NHPr, —NH$^i$Pr, —NHcyclopropyl, —NHcyclobutyl). In some embodiments, $R^4$ is —N(CH$_3$)R$^3$ (e.g., —NMe$_2$, —N(CH$_3$)Et, —N(CH$_3$)Pr, —N(CH$_3$)$^i$Pr, —N(CH$_3$)cyclopropyl, —N(CH$_3$)cyclobutyl).

In some embodiments, $R^4$ is —C(=O)R$^3$. In some embodiments, $R^4$ is —C(=O)alkyl. In some embodiments, $R^4$ is acetyl (—C(=O)Me). In some embodiments, $R^4$ is —C(=O)cycloalkyl (e.g. —C(=O)cyclopropyl).

In some embodiments, $R^4$ is —C(=O)OR$^3$. In some embodiments, $R^4$ is —COOH. In some embodiments, $R^4$ is COOMe.

In some embodiments, $R^4$ is —NR$^3$C(=O)R$^3$. In certain embodiments, $R^4$ is —NHC(=O)R$^3$ (e.g., NHC(=O)Me, NHC(=O)Et, NHC(=O)Pr, NHC(=O)$^i$Pr, NHC(=O)Bu, NHC(=O)$^t$Bu, NHC(=O)Cyclopropyl, NHC(=O)Cyclobutyl). In some embodiments, $R^4$ is —N(CH$_3$)C(=O)R$^3$ (e.g., N(CH$_3$)C(=O)Me, N(CH$_3$)C(=O)Et, N(CH$_3$)C(=O)Pr, N(CH$_3$)C(=O)$^i$Pr, N(CH$_3$)C(=O)Bu, N(CH$_3$)C(=O)$^t$Bu, N(CH$_3$)C(=O)Cyclopropyl, N(CH$_3$)C(=O)Cyclobutyl).

In some embodiments, $R^4$ is —NR$^3$C(=O)OR$^3$. In certain embodiments, $R^4$ is —NHC(=O)OR$^3$ (e.g., NHC(=O)OMe, NHC(=O)OEt, NHC(=O)OPr, NHC(=O)O$^i$Pr, NHC(=O)OBu, NHC(=O)O$^t$Bu, NHC(=O)OCyclopropyl, NHC(=O)OCyclobutyl). In some embodiments, $R^4$ is —N(CH$_3$)C(=O)OR$^3$ (e.g., N(CH$_3$)C(=O)OMe, N(CH$_3$)C(=O)OEt, N(CH$_3$)C(=O)OPr, N(CH$_3$)C(=O)O$^i$Pr, N(CH$_3$)C(=O)OBu, N(CH$_3$)C(=O)O$^t$Bu, N(CH$_3$)C(=O)OCyclopropyl, N(CH$_3$)C(=O)OCyclobutyl).

In some embodiments, $R^4$ is —C(=O)N(R$^3$)$_2$ (e.g., —C(=O)NH$_2$, —C(=O)NHR$^3$, —C(=O)N(CH$_3$)R$_3$). In some embodiments, $R^4$ is —C(=O)NH$_2$. In certain embodiments, $R^4$ is —C(=O)NHR$^3$ (e.g., —C(=O)NHMe, —C(=O)NHEt, —C(=O)NHPr, —C(=O)NH$^i$Pr, —C(=O)NHBu, —C(=O)NHrBu, —C(=O)NHCyclopropyl, —C(=O)NHCyclobutyl). In certain embodiments, $R^4$ is —C(=O)N(CH$_3$)R$^3$ (e.g., —C(=O)NMe$_2$, —C(=O)N(CH$_3$)Et, —C(=O)N(CH$_3$)Pr, —C(=O)N(CH$_3$)$^i$Pr, —C(=O)N(CH$_3$)Bu, —C(=O)N(CH$_3$)Bu, —C(=O)N(CH$_3$)Cyclopropyl, —C(=O)N(CH$_3$)Cyclobutyl).

In some embodiments, $R^4$ is —OC(=O)N(R$^3$)$_2$. In certain embodiments, $R^4$ is —OC(=O)NHR$^3$ (e.g., —OC(=O)NHMe, —OC(=O)NHEt, —OC(=O)NHPr, —OC(=O)NH$^i$Pr, —OC(=O)NHBu, —OC(=O)NH$^t$Bu, —OC(=O)NHCyclopropyl, —OC(=O)NHCyclobutyl). In certain embodiments, $R^4$ is —OC(=O)N(CH$_3$)R$^3$ (e.g., —OC(=O)NMe$_2$, —OC(=O)N(CH$_3$)Et, —OC(=O)N(CH$_3$)Pr, —OC(=O)N(CH$_3$)$^i$Pr, —OC(=O)N(CH$_3$)Bu, —OC(=O)N(CH$_3$)Bu, —OC(=O)N(CH$_3$)Cyclopropyl, —OC(=O)N(CH$_3$)Cyclobutyl).

In some embodiments, $R^4$ is —S(=O)R$^3$. In certain embodiments, $R^4$ is —S(=O)alkyl (e.g., —S(=O)Me, —S(=O)Et, —S(=O)Pr, —S(=O)$^i$Pr). In certain embodiments, $R^4$ is —S(=O)cycloalkyl (e.g., —S(=O)cyclopropyl, —S(=O)cyclobutyl, —S(=O)cyclopentyl, —S(=O)cyclohexyl).

In some embodiments, $R^4$ is —S(=O)$_2$R$^3$. In certain embodiments, $R^4$ is —S(=O)$_2$alkyl (e.g., —S(=O)$_2$Me, —S(=O)$_2$Et, —S(=O)$_2$Pr, —S(=O)$_2$$^i$Pr). In certain embodiments, $R^4$ is —S(=O)$_2$cycloalkyl (e.g., —S(=O)$_2$cyclopropyl, —S(=O)$_2$cyclobutyl, —S(=O)$_2$cyclopentyl, —S(=O)$_2$cyclohexyl).

In some embodiments, $R^4$ is S(=O)$_2$aryl (e.g., S(=O)$_2$phenyl).

In some embodiments, $R^4$ is —SR$^3$. In certain embodiments, $R^4$ is —Salkyl (e.g., —SMe, —SEt, —SPr, —S$^i$Pr). In certain embodiments, $R^4$ is —Scycloalkyl (e.g., —Scyclopropyl, —Scyclobutyl, —Scyclopentyl, —Scyclohexyl). In certain embodiments, $R^4$ is —Saryl (e.g., Sphenyl).

In some embodiments, $R^4$ is —S(=O)(=NR$^3$)R$^3$. In certain embodiments, $R^4$ is —S(=O)(=NH)R$^3$ (e.g., —S(=O)(=NH)Me, —S(=O)(=NH)Et, —S(=O)(=NH)Pr, —S(=O)(=NH)$^i$Pr, —S(=O)(=NH)Bu, —S(=O)(=NH)$^t$Bu, —S(=O)(=NH)Cyclopropyl, —S(=O)(=NH)Cyclobutyl). In some embodiments, $R^4$ is —S(=O)(=NCH$_3$)R$^3$ (e.g., —S(=O)(=NCH$_3$)Me, —S(=O)(=NCH$_3$)Et, —S(=O)(=NCH$_3$)Pr, —S(=O)(=NCH$_3$)$^i$Pr, —S(=O)(=NCH$_3$)Bu, —S(=O)(=NCH$_3$)$^t$Bu, —S(=O)(=NCH$_3$)Cyclopropyl, —S(=O)(=NCH$_3$)Cyclobutyl).

In some embodiments, $R^4$ is —NR$^3$S(=O)$_2$R$^3$. In certain embodiments, $R^4$ is —NHS(=O)$_2$alkyl (e.g., —NHS(=O)$_2$Me, —NHS(=O)$_2$Et, —NHS(=O)$_2$Pr, —NHS(=O)$_2$$^i$Pr). In certain embodiments, $R^4$ is —NHS(=O)$_2$cycloalkyl (e.g., —NHS(=O)$_2$cyclopropyl, —NHS(=O)$_2$cyclobutyl, —NHS(=O)$_2$cyclopentyl, —NHS(=O)$_2$cyclohexyl). In certain embodiments, $R^4$ is —N(CH$_3$)S(=O)$_2$alkyl (e.g., —N(CH$_3$)S(=O)$_2$Me, —N(CH$_3$)S(=O)$_2$Et, —N(CH$_3$)S(=O)$_2$Pr, —N(CH$_3$)S(=O)$_2$$^i$Pr). In certain embodiments, $R^4$ is —N(CH$_3$)S(=O)$_2$cycloalkyl (e.g., —N(CH$_3$)S(=O)$_2$cyclopropyl, —N(CH$_3$)S(=O)$_2$cyclobutyl, —N(CH$_3$)S(=O)$_2$cyclopentyl, —N(CH$_3$)S(=O)$_2$cyclohexyl).

In some embodiments, $R^4$ is —S(=O)$_2$N(R$^3$)$_2$. (e.g., —S(=O)$_2$NH$_2$, —S(=O)$_2$NHR$^3$, —S(=O)$_2$N(CH$_3$)R$_3$). In some embodiments, $R^4$ is —S(=O)$_2$NH$_2$. In some embodiments, $R^4$ is —S(=O)$_2$NHR$^3$ (e.g., —S(=O)$_2$NHMe, —S(=O)$_2$NHEt, —S(=O)$_2$NHPr, —S(=O)$_2$NH$^i$Pr, —S(=O)$_2$NHcyclopropyl, —S(=O)$_2$NHcyclobutyl). In some embodiments, $R^4$ is —S(=O)$_2$N(CH$_3$)R$^3$ (e.g., —S(=O)$_2$NMe$_2$, —S(=O)$_2$N(CH$_3$)Et, —S(=O)$_2$N(CH$_3$)Pr, —S(=O)$_2$N(CH$_3$)$^i$Pr, —S(=O)$_2$N(CH$_3$)cyclopropyl, —S(=O)$_2$N(CH$_3$)cyclobutyl).

As generally defined herein, each $R^3$ is independently selected from H, C$_1$-C$_6$ alkyl, —C$_1$-C$_6$ heteroalkyl, C$_3$-C$_9$ carbocyclyl, 3-7 membered heterocyclyl, cycloalkylalkyl, heterocyclylalkyl, aryl, 5-6 membered heteroaryl, arylalkyl and heteroarylalkyl wherein each alkyl, carbocyclyl, heterocyclyl, cycloalkylalkyl, heterocyclylalkyl, aryl, heteroaryl, arylalkyl and heteroarylalkyl is optionally substituted (e.g., substituted with 0-2 instances of $R^7$). In some embodiments, each $R^3$ is independently selected from H, C$_1$-C$_6$ alkyl (e.g., methyl, ethyl, propyl, iso-propyl, butyl, iso-butyl, sec-butyl and tert-butyl), C$_3$-C$_7$ carbocyclyl (e.g., cyclopropyl, cyclobutyl, cyclopentyl, cyclohexyl, cycloheptyl), and C$_1$-C$_6$ heteroalkyl. In some embodiments, each $R^3$ is independently selected from C$_1$-C$_3$ alkyl, C$_1$-C$_6$ heteroalkyl (e.g., —(CH$_2$)$_2$OCH$_3$) or C$_3$-C$_7$ cycloalkyl.

In some embodiments, each $R^3$ is independently selected from H, C$_1$-C$_6$ alkyl (e.g., methyl, ethyl, propyl, iso-propyl, butyl, iso-butyl, sec-butyl and tert-butyl), C$_3$-C$_7$ carbocyclyl (e.g., cyclopropyl, cyclobutyl, cyclopentyl, cyclohexyl, cycloheptyl), and 3-10 membered heterocyclyl (e.g., oxetanyl, aziridinyl, tetrahydrofuranyl, pyrolidinyl, tetrahydropyranyl, piperidinyl, piperazinyl, morpholinyl, azepanyl). In some embodiments, each $R^3$ is independently selected from H and C$_1$-C$_6$ alkyl. In some embodiments, $R^3$ is selected from H, methyl, ethyl, propyl, iso-propyl, butyl, iso-butyl, sec-butyl and tert-butyl. In some embodiments, $R^3$ is selected from H and methyl.

In some embodiments, each $R^3$ is independently selected from H, $C_1$-$C_6$ alkyl (e.g., methyl, ethyl, propyl, iso-propyl, butyl, iso-butyl, sec-butyl and tert-butyl), $C_1$-$C_6$ heteroalkyl (e.g., —$(CH_2)_2N(CH_3)_2$, —$(CH_2)_2OCH_3$), $C_3$-$C_7$ carbocyclyl (e.g., cyclopropyl, cyclobutyl, cyclopentyl, cyclohexyl, cycloheptyl), and 3-10 membered heterocyclyl (e.g., oxetanyl, aziridinyl, tetrahydrofuranyl, pyrolidinyl, tetrahydropyranyl, piperidinyl, piperazinyl, morpholinyl, azepanyl).

In some embodiments $R^3$ is $C_3$-$C_7$ carbocyclyl, $C_1$-$C_6$ alkyl or $C_1$-$C_6$ heteroalkyl. In further embodiments $R^3$ is $C_1$-$C_3$ alkyl, $C_1$-$C_6$ heteroalkyl (e.g., —$(CH_2)_2OCH_3$) or —$(CH_2)_2N(CH_3)_2$) or $C_3$-$C_7$ cycloalkyl In some embodiments $R^3$ is $C_3$-$C_9$ carbocyclyl or 3-10 membered heterocyclyl wherein each carbocyclyl and heterocyclyl is optionally substituted (e.g., substituted with 0-2 instances of $R^7$). In certain embodiments each $R^7$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, $C_6$-$C_{10}$ aryl, 5-10 membered heteroaryl, cycloalkylalkyl, heterocyclylalkyl, arylalkyl, heteroarylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$ or —$S(=O)_2N(R^3)_2$.

In some embodiments $R^3$ is a monocyclic or bicyclic 3-10 membered heterocyclyl (e.g., morpholine, piperidine, piperazine, azepane, 8-azabicyclo[3.2.1]octane, 3-oxa-8-azabicyclo[3.2.1]octane) substituted with one instance of methyl, ethyl, hydroxy or methoxy.

In some embodiments $R^3$ is optionally substituted aryl (e.g., phenyl). In some embodiments $R_3$ is aryl substituted with 0-2 instances of OMe or halo.

In some embodiments, $R^3$ is $C_1$-$C_6$ heteroalkyl. In certain embodiments, $R^3$ is —$(CH_2)_2N(CH_3)_2$ or —$(CH_2)_2OCH_3$.

In some embodiments, $R^3$ is 5-6 membered heteroaryl (e.g., pyridinyl, pyrimidinyl, pyridazinyl, pyrazinyl, furanyl, thiophenyl, pyrrolyl, pyrazolyl, imidazolyl, thiazolyl, oxazolyl, isoxazolyl, isothiazolyl, triazolyl, oxadiazolyl, thiadiazolyl, tetrazolyl). In some embodiments, $R^3$ is arylalkyl (e.g., benzyl). In some embodiments, $R^3$ is heteroarylalkyl (e.g., pyridinylmethyl, pyrimidinylmethyl, pyridazinylmethyl, pyrazinylmethyl, furanylmethyl, thiophenylmethyl, pyrrolylmethyl, pyrazolylmethyl, imidazolylmethyl, thiazolylmethyl, oxazolylmethyl, isoxazolylmethyl, isothiazolylmethyl, triazolylmethyl, oxadiazolylmethyl, thiadiazolylmethyl, tetrazolylmethyl). In some embodiments $R^3$ is cycloalkylalkyl (e.g., cyclopropylmethyl, cyclobutylmethyl, cyclopentylmethyl, cyclohexylmethyl, cycloheptylmethyl). In some embodiments, $R^3$ is heterocyclylalkyl (e.g., oxetanylmethyl, aziridinylmethyl, tetrahydrofuranylmethyl, pyrolidinylmethyl, tetrahydropyranylmethyl, piperidinylmethyl, piperazinylmethyl, morpholinylmethyl, azepanylmethyl).

In some embodiments of the invention, $R^1$ is a 5-6 membered heteroaryl substituted with 0-3 instances of $R^4$ (e.g., 0, 1, 2 or 3 instances of $R^4$). In some embodiments, the heteroaryl is a 6-membered nitrogen containing heteroaryl (e.g., pyridinyl, pyrimidinyl, pyridazinyl, pyrazinyl, triazinyl), substituted with 0-3 instances of $R^4$ (e.g., 0, 1, 2 or 3 instances of $R^4$). In some embodiments $R^1$ is:

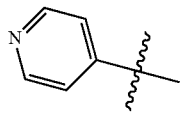 [SMILES: *c1ccncc1]

In certain embodiments, the heteroaryl is a 5-membered heteroaryl. In further embodiments, the heteroaryl is a 5-membered nitrogen containing heteroaryl (e.g., pyrrolyl, pyrazolyl, imidazolyl, thiazolyl, oxazolyl, isoxazolyl, isothiazolyl, triazolyl, oxadiazolyl, thiadiazolyl, tetrazolyl). In some embodiments, the heteroaryl is selected from pyrazolyl, triazolyl, oxazolyl, isoxazolyl, oxadiazolyl, thiazolyl, and thiadiazolyl.

In some embodiments of the invention, $R^1$ is a 5-membered heteroaryl (e.g., a 5-membered nitrogen containing heteroaryl (e.g., pyrrolyl, pyrazolyl, imidazolyl, thiazolyl, oxazolyl, isoxazolyl, isothiazolyl, triazolyl, oxadiazolyl, thiadiazolyl, tetrazolyl))substituted with 0-3 instances of $R^4$ (e.g., 0, 1, 2 or 3 instances of $R^4$). In some embodiments of the invention, $R^1$ is a 5-membered heteroaryl (e.g., a 5-membered nitrogen containing heteroaryl (e.g., pyrrolyl, pyrazolyl, imidazolyl, thiazolyl, oxazolyl, isoxazolyl, isothiazolyl, triazolyl, oxadiazolyl, thiadiazolyl, tetrazolyl)) substituted with one instance of $C_1$-$C_6$ alkyl (e.g., methyl, ethyl, propyl, isopropyl). In some embodiments of the invention, $R^1$ is a 5-membered heteroaryl (e.g., a 5-membered nitrogen containing heteroaryl (e.g., pyrrolyl, pyrazolyl, imidazolyl, thiazolyl, oxazolyl, isoxazolyl, isothiazolyl, triazolyl, oxadiazolyl, thiadiazolyl, tetrazolyl)) substituted with methyl. In some embodiments of the invention, $R^1$ is a 5-membered heteroaryl (e.g., a 5-membered nitrogen containing heteroaryl (e.g., pyrrolyl, pyrazolyl, imidazolyl, thiazolyl, oxazolyl, isoxazolyl, isothiazolyl, triazolyl, oxadiazolyl, thiadiazolyl, tetrazolyl)) substituted with two instances of $C_1$-$C_6$ alkyl (e.g., methyl, ethyl, propyl, isopropyl). In some embodiments of the invention, $R^1$ is a 5-membered heteroaryl (e.g., 5-membered nitrogen containing heteroaryl (e.g., pyrrolyl, pyrazolyl, imidazolyl, thiazolyl, oxazolyl, isoxazolyl, isothiazolyl, triazolyl, oxadiazolyl, thiadiazolyl, tetrazolyl)) substituted with two instances of methyl.

In certain embodiments of the invention, $R^1$ is selected from:

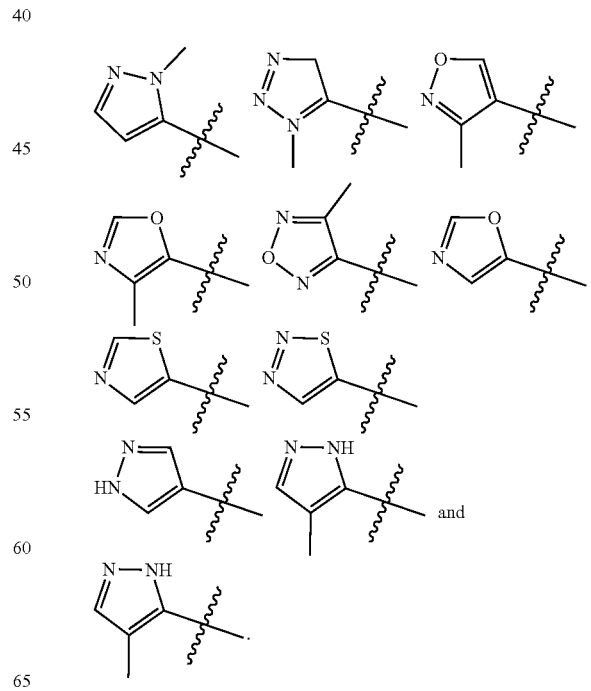

In further embodiments, $R^1$ is selected from:

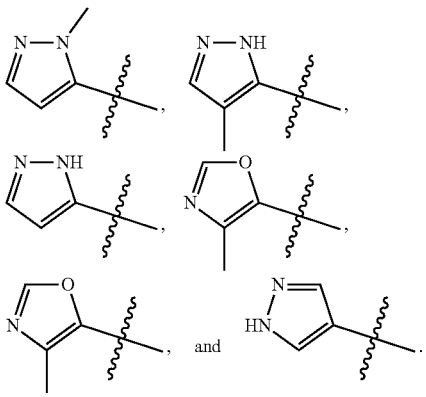

In a preferred embodiment, $R^1$ is

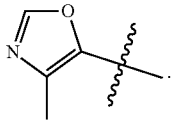 [SMILES: *c1ocnc1C]

As generally defined herein, each $R^8$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, $C_6$-$C_{10}$ aryl, 5-10 membered heteroaryl, cycloalkylalkyl, heterocyclylalkyl, arylalkyl, heteroarylalkyl, —$OR^3$, —$N(R^3)_2$, —C(=O)$R^3$, —C(=O)$OR^3$, —$NR^3$C(=O)$R^3$, —$NR^3$C(=O)$OR^3$, —C(=O)N($R^3$)$_2$, —OC(=O)N($R^3$)$_2$, —S(=O)$R^3$, —S(=O)$_2R^3$, —$SR^3$, —S(=O)(=$NR^3$)$R^3$, —$NR^3$S(=O)$_2R^3$, —S(=O)$_2$N($R^3$)$_2$, or two $R^8$ can be taken together with the atoms to which they are attached to form a —$C_3$-$C_9$ carbocyclyl or a 3-10 membered heterocyclyl;

In some embodiments, $R^8$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, —$OR^3$, —$N(R^3)_2$, —CO($R^3$), —$NR^3$(CO)$R^3$, —(CO)N($R^3$)$_2$. In certain embodiments $R^8$ is $C_1$-$C_6$ alkyl (e.g., methyl, ethyl, propyl, isopropyl). In certain embodiments $R^8$ is methyl.

As generally defined herein, p is 0, 1, 2 or 3. In some embodiments p is 0. In other embodiments p is 1. In yet other embodiments p is 2. In some embodiments p is 3.

As generally defined herein, $R^2$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, heteroarylalkyl, arylalkyl, cycloalkylalkyl, —$OR^3$, —$N(R^3)_2$, —C(=O)$R^3$, —C(=O)$OR^3$, —$NR^3$C(=O)$R^3$, —$NR^3$C(=O)$OR^3$, —C(=O)N($R^3$)$_2$, —OC(=O)N($R^3$)$_2$, —S(=O)$R^3$, —S(=O)$_2R^3$, —$SR^3$, —S(=O)(=$NR^3$)$R^3$, —$NR^3$S(=O)$_2R^3$ and —S(=O)$_2$N($R^3$)$_2$.

In some embodiments, $R^2$ is selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, cycloalkylalkyl, —$OR^3$, —$N(R^3)_2$, —C(=O)$R^3$, —C(=O)$OR^3$, —$NR^3$C(=O)$R^3$, —$NR^3$C(=O)$OR^3$, —C(=O)N($R^3$)$_2$, —OC(=O)N($R^3$)$_2$, —S(=O)$R^3$, —S(=O)$_2R^3$, —$SR^3$, —S(=O)(=$NR^3$)$R^3$, —$NR^3$S(=O)$_2R^3$ and —S(=O)$_2$N($R^3$)$_2$.

In certain embodiments, $R^2$ is selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, heteroarylalkyl, cycloalkylalkyl, —$OR^3$, —$NHR^3$, $N(CH_3)R^3$, —C(=O)$R^3$, —C(=O)$OR^3$, —NHC(=O)$R^3$, —N($CH_3$)C(=O)$R^3$, —NHC(=O)$OR^3$, —N($CH_3$)C(=O)$OR^3$, —C(=O)NH($R^3$), —C(=O)N($CH_3$)($R^3$), —OC(=O)$NHR^3$, —OC(=O)N($CH_3$)$R^3$—S(=O)$R^3$, —S(=O)$_2R^3$, —$SR^3$, —S(=O)(=NH)$R^3$, —S(=O)(=$NCH_3$)$R^3$, —NHS(=O)$_2R^3$, —N($CH_3$)S(=O)$_2R^3$, —S(=O)$_2NHR^3$ and —S(=O)$_2$N($CH_3$)$R^3$.

In certain embodiments, $R^2$ is =O.

In certain embodiments, $R^2$ is halo (e.g., fluoro, chloro, bromo, iodo). In further embodiments, $R^2$ is chloro. In some embodiments, $R^2$ is fluoro. In some embodiments, $R^2$ is bromo. In some embodiments, $R^2$ is iodo.

In some embodiments, $R^2$ is —CN.

In certain embodiments, $R^2$ is —$C_1$-$C_6$ alkyl. In further embodiments, $R^2$ is methyl. In some embodiments, $R^2$ is ethyl. In some embodiments $R^2$ is propyl or isopropyl.

In some embodiments, $R^2$ is —$C_1$-$C_6$ heteroalkyl. In further embodiments, $R^2$ is methoxymethyl (—$CH_2OCH_3$). In some embodiments, $R^2$ is aminomethyl (e.g., —$CH_2NH_2$, —$CH_2NHCH_3$, —$CH_2N(CH_3)_2$).

In some embodiments, $R^2$ is —$C_1$-$C_6$ haloalkyl. In further embodiments, $R^2$ is trifluoromethyl (—$CF_3$).

In some embodiments, $R^2$ is —$C_3$-$C_9$ carbocyclyl (e.g., cyclopropyl, cyclobutyl, cyclopentyl, cyclohexyl). In some embodiments, $R^2$ is cyclopropyl. In some embodiments $R^2$ is cyclobutyl. In some embodiments, $R^2$ is cyclopentyl. In some embodiments, $R^2$ is cyclohexyl, In some embodiments, $R^2$ is 3-10 membered heterocyclyl (e.g., oxetanyl, tetrahydropyranyl, tetrahydrofuranyl, azetidinyl, pyrrolidinyl, piperidinyl, piperazinyl, morpholinyl, azepanyl). In some embodiments, $R^2$ is oxetanyl. In some embodiments, $R^2$ is tetrahydropyranyl. In some embodiments, $R^2$ is tetrahydrofuranyl. In some embodiments, $R^2$ is azetidinyl. In some embodiments, $R^2$ is pyrrolidinyl. In some embodiments, $R^2$ is piperidinyl. In some embodiments, $R^2$ is piperazinyl. In some embodiments, $R^2$ is morpholinyl. In some embodiments, $R^2$ is azepanyl.

In some embodiments $R^2$ is cycloalkylalkyl (e.g., cyclopropylmethyl, cyclobutylmethyl, cyclopentylmethyl, cyclohexylmethyl, cycloheptylmethyl). In some embodiments, $R^2$ is heterocyclylalkyl (e.g., oxetanylmethyl, aziridinylmethyl, tetrahydrofuranylmethyl, pyrolidinylmethyl, tetrahydropyranylmethyl, piperidinylmethyl, piperazinylmethyl, morpholinylmethyl, azepanylmethyl).

In some embodiments, $R^2$ is arylalkyl. In some embodiments, $R^2$ is benzyl.

In some embodiments, $R^2$ is heteroarylalkyl. In some embodiments, $R^2$ is pyridinylmethyl (e.g., pyridinyl-4-methyl).

In some embodiments, $R^2$ is —$OR^3$ (e.g., methoxy, fluoromethoxy (—$OCHF_2$), trifluoromethoxy (—$OCF_3$), ethoxy, propoxy, isopropoxy, cyclopropyloxy, cyclobutyloxy). In some embodiments, $R^2$ is methoxy. In some embodiments, $R^2$ is ethoxy. In some embodiments, $R^2$ is propoxy. In some embodiments, $R^2$ is isopropoxy. In some embodiments $R^2$ is fluoromethoxy. (—$OCHF_2$). In some embodiments, $R^2$ is trifluoromethoxy (—$OCF_3$).

In some embodiments, $R^2$ is —$N(R^3)_2$ (e.g., —$NH_2$, —$NHR^3$, —$N(CH_3)R_3$). In some embodiments, $R^2$ is —$NH_2$. In some embodiments, $R^2$ is —$NHR^3$ (e.g., —NHMe, —NHEt, —NHPr, —$NH^iPr$, —NHcyclopropyl, —NHcyclobutyl). In some embodiments, $R^2$ is —N(CH$_3$)R$^3$ (e.g., —NMe$_2$, —N(CH$_3$)Et, —N(CH$_3$)Pr, —N(CH$_3$)$^i$Pr, —N(CH$_3$)cyclopropyl, —N(CH$_3$)cyclobutyl).

In some embodiments, $R^2$ is —C(=O)R$^3$ or —C(=O)OR$^3$. In some embodiments, $R^2$ is —C(=O)R$^3$ wherein $R^3$ is as described herein. In some embodiments, $R^2$ is —C(=O)R$^3$ wherein $R^3$ is C$_1$-C$_6$ alkyl, C$_3$-C$_9$ carbocyclyl or 3-10 membered heterocyclyl, wherein each carbocyclyl and heterocyclyl is optionally substituted (e.g., substituted with 0-2 instances of $R^7$, wherein each $R^7$ is as described herein, (e.g., each $R^7$ is independently selected from =O, halo, —CN, —C$_1$-C$_6$ alkyl, —C$_1$-C$_6$ heteroalkyl, —C$_1$-C$_6$ haloalkyl, —C$_3$-C$_9$ carbocyclyl, 3-10 membered heterocyclyl, C$_6$-C$_{10}$ aryl, 5-10 membered heteroaryl, cycloalkylalkyl, heterocyclylalkyl, arylalkyl, heteroarylalkyl, —OR$^3$, —N(R$^3$)$_2$, —C(=O)R$^3$, —C(=O)OR$^3$, —NR$^3$C(=O)R$^3$, —NR$^3$C(=O)OR$^3$, —C(=O)N(R$^3$)$_2$, —OC(=O)N(R$^3$)$_2$, —S(=O)R$^3$, —S(=O)$_2$R$^3$, —SR$^3$, —S(=O)(=NR$^3$)R$^3$, —NR$^3$S(=O)$_2$R$^3$ or —S(=O)$_2$N(R$^3$)$_2$)). In certain embodiments, $R^2$ is —C(=O)R$^3$ wherein $R^3$ is a monocyclic or bicyclic 3-10 membered heterocyclyl (e.g., morpholine, piperidine, piperazine, azepane, 8-azabicyclo[3.2.1]octane, 3-oxa-8-azabicyclo[3.2.1]octane) substituted with one instance of methyl, ethyl, hydroxy or methoxy or optionally substituted aryl (e.g., aryl substituted with 0-2 instances of $R^7$).

In some embodiments $R^2$ is —C(=O)R$^3$ wherein $R^3$ is optionally substituted aryl (e.g., optionally substituted phenyl, e.g., phenyl substituted with 0-2 instances of OMe or halo).

In some embodiments, $R^2$ is —C(=O)alkyl. In some embodiments, $R^2$ is —C(O)CH$_3$, —C(O)cyclopropyl, —C(O)cyclobutyl, —C(O)$^t$Bu, —C(O)$^i$Pr, —C(O)Pr, —C(O)$^t$Bu, or —C(=O)OMe. In some embodiments, $R^2$ is acetyl (—C(=O)Me). In some embodiments, $R^2$ is —C(=O)cycloalkyl (e.g. —C(=O)cyclopropyl). In some embodiments, $R^2$ is C(=O)aryl wherein the aryl is optionally substituted with 0-2 instances of $R^7$. In some embodiments $R^2$ is C(=O)phenyl, wherein the phenyl is optionally substituted with 0-2 instances of halo (e.g., bromo) or alkoxy (e.g., methoxy).

In some embodiments, $R^2$ is —C(=O)OR$^3$. In some embodiments, $R^2$ is —COOH. In some embodiments, $R^2$ is COOMe.

In some embodiments, $R^2$ is —NR$^3$C(=O)R$^3$. In certain embodiments, $R^2$ is —NHC(=O)R$^3$ (e.g., NHC(=O)Me, NHC(=O)Et, NHC(=O)Pr, NHC(=O)$^i$Pr, NHC(=O)Bu, NHC(=O)$^t$Bu, NHC(=O)Cyclopropyl, NHC(=O)Cyclobutyl). In some embodiments, $R^2$ is —N(CH$_3$)C(=O)R$^3$ (e.g., N(CH$_3$)C(=O)Me, N(CH$_3$)C(=O)Et, N(CH$_3$)C(=O)Pr, N(CH$_3$)C(=O)$^i$Pr, N(CH$_3$)C(=O)Bu, N(CH$_3$)C(=O)$^t$Bu, N(CH$_3$)C(=O)Cyclopropyl, N(CH$_3$)C(=O)Cyclobutyl).

In some embodiments, $R^2$ is —NR$^3$C(=O)OR$^3$. In certain embodiments, $R^2$ is —NHC(=O)OR$^3$ (e.g., NHC(=O)OMe, NHC(=O)OEt, NHC(=O)OPr, NHC(=O)O$^i$Pr, NHC(=O)OBu, NHC(=O)O$^t$Bu, NHC(=O)OCyclopropyl, NHC(=O)OCyclobutyl). In some embodiments, $R^2$ is —N(CH$_3$)C(=O)OR$^3$ (e.g., N(CH$_3$)C(=O)OMe, N(CH$_3$)C(=O)OEt, N(CH$_3$)C(=O)OPr, N(CH$_3$)C(=O)O$^i$Pr, N(CH$_3$)C(=O)OBu, N(CH$_3$)C(=O)O$^t$Bu, N(CH$_3$)C(=O)OCyclopropyl, N(CH$_3$)C(=O)OCyclobutyl).

In some embodiments, $R^2$ is —C(=O)N(R$^3$)$_2$ (e.g., —C(=O)NH$_2$, —C(=O)NHR$^3$, —C(=O)N(CH$_3$)R$_3$). In some embodiments, $R^2$ is —C(=O)NH$_2$. In certain embodiments, $R^2$ is —C(=O)NHR$^3$ (e.g., —C(=O)NHMe, —C(=O)NHEt, —C(=O)NHPr, —C(=O)NH$^i$Pr, —C(=O)NHBu, —C(=O)NH$^t$Bu, —C(=O)NHCyclopropyl, —C(=O)NHCyclobutyl). In certain embodiments, $R^2$ is —C(=O)N(CH$_3$)R$^3$ (e.g., —C(=O)NMe$_2$, —C(=O)N(CH$_3$)Et, —C(=O)N(CH$_3$)Pr, —C(=O)N(CH$_3$)$^i$Pr, —C(=O)N(CH$_3$)Bu, —C(=O)N(CH$_3$)$^t$Bu, —C(=O)N(CH$_3$)Cyclopropyl, —C(=O)N(CH$_3$)Cyclobutyl).

In some embodiments, $R^2$ is —OC(=O)N(R$^3$)$_2$. In certain embodiments, $R^2$ is —OC(=O)NHR$^3$ (e.g., —OC(=O)NHMe, —OC(=O)NHEt, —OC(=O)NHPr, —OC(=O)NH$^i$Pr, —OC(=O)NHBu, —OC(=O)NH$^t$Bu, —OC(=O)NHCyclopropyl, —OC(=O)NHCyclobutyl). In certain embodiments, $R^2$ is —OC(=O)N(CH$_3$)R$^3$ (e.g., —OC(=O)NMe$_2$, —OC(=O)N(CH$_3$)Et, —OC(=O)N(CH$_3$)Pr, —OC(=O)N(CH$_3$)$^i$Pr, —OC(=O)N(CH$_3$)Bu, —OC(=O)N(CH$_3$)Bu, —OC(=O)N(CH$_3$)Cyclopropyl, —OC(=O)N(CH$_3$)Cyclobutyl).

In some embodiments, $R^2$ is —S(=O)R$^3$. In certain embodiments, $R^2$ is —S(=O)alkyl (e.g., —S(=O)Me, —S(=O)Et, —S(=O)Pr, —S(=O)$^i$Pr). In certain embodiments, $R^2$ is —S(=O)cycloalkyl (e.g., —S(=O)cyclopropyl, —S(=O)cyclobutyl, —S(=O)cyclopentyl, —S(=O)cyclohexyl).

In some embodiments, $R^2$ is —S(=O)$_2$R$^3$. In certain embodiments, $R^2$ is —S(=O)$_2$alkyl (e.g., —S(=O)$_2$Me, —S(=O)$_2$Et, —S(=O)$_2$Pr, —S(=O)$_2$$^i$Pr). In certain embodiments, $R^2$ is —S(=O)$_2$cycloalkyl (e.g., —S(=O)$_2$cyclopropyl, —S(=O)$_2$cyclobutyl, —S(=O)$_2$cyclopentyl, —S(=O)$_2$cyclohexyl). In some embodiments, $R^2$ is S(=O)$_2$ aryl (e.g., S(=O)$_2$phenyl).

In some embodiments, $R^2$ is —SR$^3$. In certain embodiments, $R^2$ is —Salkyl (e.g., —SMe, —SEt, —SPr, —S$^i$Pr). In certain embodiments, $R^2$ is —Scycloalkyl (e.g., —Scyclopropyl, —Scyclobutyl, —Scyclopentyl, —Scyclohexyl). In certain embodiments, $R^2$ is —Saryl (e.g., Sphenyl).

In some embodiments, $R^2$ is —S(=O)(=NR$^3$)R$^3$. In certain embodiments, $R^2$ is —S(=O)(=NH)R$^3$ (e.g., —S(=O)(=NH)Me, —S(=O)(=NH)Et, —S(=O)(=NH)Pr, —S(=O)(=NH)$^i$Pr, —S(=O)(=NH)Bu, —S(=O)(=NH)$^t$Bu, —S(=O)(=NH)Cyclopropyl, —S(=O)(=NH)Cyclobutyl). In some embodiments, $R^2$ is —S(=O)(=NCH$_3$)R$^3$ (e.g., —S(=O)(=NCH$_3$)Me, —S(=O)(=NCH$_3$)Et, —S(=O)(=NCH$_3$)Pr, —S(=O)(=NCH$_3$)$^i$Pr, —S(=O)(=NCH$_3$)Bu, —S(=O)(=NCH$_3$)$^t$Bu, —S(=O)(=NCH$_3$)Cyclopropyl, —S(=O)(=NCH$_3$)Cyclobutyl).

In some embodiments, $R^2$ is —NR$^3$S(=O)$_2$R$^3$. In certain embodiments, $R^2$ is —NHS(=O)$_2$alkyl (e.g., —NHS(=O)$_2$Me, —NHS(=O)$_2$Et, —NHS(=O)$_2$Pr, —NHS(=O)$_2$$^i$Pr). In certain embodiments, $R^2$ is —NHS(=O)$_2$cycloalkyl (e.g., —NHS(=O)$_2$cyclopropyl, —NHS(=O)$_2$cyclobutyl, —NHS(=O)$_2$cyclopentyl, —NHS(=O)$_2$cyclohexyl). In certain embodiments, $R^2$ is —N(CH$_3$)S(=O)$_2$alkyl (e.g., —N(CH$_3$)S(=O)$_2$Me, —N(CH$_3$)S(=O)$_2$Et, —N(CH$_3$)S(=O)$_2$Pr, —N(CH$_3$)S(=O)$_2$$^i$Pr). In certain embodiments, $R^2$ is —N(CH$_3$)S(=O)$_2$cycloalkyl (e.g., —N(CH$_3$)S(=O)$_2$cyclopropyl, —N(CH$_3$)S(=O)$_2$cyclobutyl, —N(CH$_3$)S(=O)$_2$cyclopentyl, —N(CH$_3$)S(=O)$_2$cyclohexyl).

In some embodiments, $R^2$ is —S(=O)$_2$N(R$^3$)$_2$. (e.g., —S(=O)$_2$NH$_2$, —S(=O)$_2$NHR$^3$, —S(=O)$_2$N(CH$_3$)R$_3$). In some embodiments, $R^2$ is —S(=O)$_2$NH$_2$. In some embodiments, $R^2$ is —S(=O)$_2$NHR$^3$ (e.g., —S(=O)$_2$NHMe, —S(=O)$_2$NHEt, —S(=O)$_2$NHPr, —S(=O)$_2$NH$^i$Pr, —S(=O)$_2$NHcyclopropyl, —S(=O)$_2$NHcyclobutyl). In some embodiments, $R^2$ is —S(=O)$_2$N(CH$_3$)R$^3$ (e.g., —S(=O)$_2$NMe$_2$, —S(=O)$_2$N(CH$_3$)Et, —S(=O)$_2$N(CH$_3$)Pr, —S(=O)$_2$N(CH$_3$)$^i$Pr, —S(=O)$_2$N(CH$_3$)cyclopropyl, —S(=O)$_2$N(CH$_3$)cyclobutyl).

As generally defined herein, n is 0, 1, 2 or 3.

In certain embodiments, n is 0. In some embodiments, ring A is a 3-8 membered carbocycle (e.g., cyclopropyl, cyclobutyl, cyclopentyl, cyclohexyl, cycloheptyl) and n is 0. In a further embodiment, ring A is cyclobutyl and n is 0. In some embodiments, ring A is a 6-8 membered spirocarbocycle (e.g., spiro[2.3]hexyl, spiro[3.3]heptyl) and n is 0.

In an exemplary embodiment, ring A is a 4-7 membered monocyclic heterocycle (e.g., piperidinyl, pyrrolidinyl, oxetanyl, tetrahydrofuranyl, azetidinyl, tetrahydropyranyl, 1,4-dioxan-2-yl and morpholinyl) and n is 0.

In certain embodiments, n is 1. In an exemplary embodiment, ring A is a cycloalkyl (e.g., cyclopropyl, cyclobutyl, cyclopentyl, cyclohexyl, cycloheptyl) and n is 1. In an exemplary embodiment, ring A is a cycloalkyl (e.g., cyclopropyl, cyclobutyl, cyclopentyl, cyclohexyl, cycloheptyl), $R^2$ is selected from =O, halo (e.g., chloro, fluoro, bromo, iodo), $C_1$-$C_4$ alkyl (e.g., methyl, ethyl, propyl, isopropyl) and —OH and n is 1. In an exemplary embodiment, ring A is a 4-7 membered monocyclic heterocycle (e.g., piperidinyl, pyrrolidinyl, oxetanyl, tetrahydrofuranyl, azetidinyl, tetrahydropyranyl, 1,4-dioxan-2-yl and morpholinyl) and n is 1. In some embodiments, ring A is selected from piperidinyl, pyrrolidinyl, oxetanyl, tetrahydrofuranyl, azetidinyl, tetrahydropyranyl, 1,4-dioxan-2-yl and morpholinyl, n is 1 and $R^2$ is selected from —C(=O)$R^3$, =O, halo (e.g., chloro, fluoro, bromo, iodo), $C_1$-$C_4$ alkyl (e.g., methyl, ethyl, propyl, isopropyl) and —OH. In one exemplary embodiment, A is piperidinyl, n is 1 and $R^2$ is —C(=O)$R^3$. For example, A is piperidinyl, n is 1 and $R^2$ is —C(=O)$CH_3$.

In certain embodiments, n is 2. In an exemplary embodiment, ring A is a cycloalkyl (e.g., cyclopropyl, cyclobutyl, cyclopentyl, cyclohexyl, cycloheptyl) and n is 2. In an exemplary embodiment, ring A is a cycloalkyl (e.g., cyclopropyl, cyclobutyl, cyclopentyl, cyclohexyl, cycloheptyl), each $R^2$ is independently selected from =O, halo (e.g., chloro, fluoro, bromo, iodo), $C_1$-$C_4$ alkyl (e.g., methyl, ethyl, propyl, isopropyl) and —OH and n is 2. In an exemplary embodiment, ring A is a 4-7 membered monocyclic heterocycle (e.g., piperidinyl, pyrrolidinyl, oxetanyl, tetrahydrofuranyl, azetidinyl, tetrahydropyranyl, 1,4-dioxan-2-yl and morpholinyl) and n is 2. In some embodiments, ring A is selected from piperidinyl, pyrrolidinyl, oxetanyl, tetrahydrofuranyl, azetidinyl, tetrahydropyranyl, 1,4-dioxan-2-yl and morpholinyl, n is 2 and each $R^2$ is independently selected from —C(=O)$R^3$, =0, halo (e.g., chloro, fluoro, bromo, iodo), $C_1$-$C_4$ alkyl (e.g., methyl, ethyl, propyl, isopropyl) and —OH.

In certain embodiments, n is 3.

As generally described herein, each $R^5$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, $C_6$-$C_{10}$ aryl, 5-10 membered heteroaryl, cycloalkylalkyl, heterocyclylalkyl, arylalkyl, heteroarylalkyl, —O$R^3$, —N($R^3$)$_2$, —C(=O)$R^3$, —C(=O)O$R^3$, —N$R^3$C(=O)$R^3$, —N$R^3$C(=O)O$R^3$, —C(=O)N($R^3$)$_2$, —OC(=O)N($R^3$)$_2$, —S(=O)$R^3$, —S(=O)$_2R^3$, —S$R^3$, —S(=O)(=N$R^3$)$R^3$, —N$R^3$S(=O)$_2R^3$, —S(=O)$_2$N($R^3$)$_2$, or two $R^5$ can be taken together with the atoms to which they are attached to form a —$C_3$-$C_9$ carbocyclyl or a 3-10 membered heterocyclyl;

Each instance of $R^5$ can be independently attached to any available position on either the phenyl or the tetrahydropyridine ring of the isoquinoline moiety.

In certain embodiments, $R^5$ is selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, —O$R^3$, —NH$R^3$, N(CH$_3$)$R^3$, —C(=O)$R^3$, —C(=O)O$R^3$, —NHC(=O)$R^3$, —N(CH$_3$)C(=O)$R^3$, —NHC(=O)O$R^3$, —N(CH$_3$)C(=O)O$R^3$, —C(=O)NH($R^3$), —C(=O)N(CH$_3$)($R^3$), —OC(=O)NH$R^3$, —OC(=O)N(CH$_3$)$R^3$, —S(=O)$R^3$, —S(=O)$_2R^3$, —S$R^3$, —S(=O)(=NH)$R^3$, —S(=O)(=NCH$_3$)$R^3$, —NHS(=O)$_2R^3$, —N(CH$_3$)S(=O)$_2R^3$, —S(=O)$_2$NH$R^3$ and —S(=O)$_2$N(CH$^3$)$R^3$.

In some embodiments, each $R^5$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, —O$R^3$, —N($R^3$)$_2$, —CO($R^3$), —N$R^3$(CO)$R^3$, —(CO)N($R^3$)$_2$.

In certain embodiments, each $R^5$ is independently selected from halo, —CN and —$C_1$-$C_6$ alkyl.

In certain embodiments, $R^5$ is =O.

In certain embodiments, $R^5$ is halo (e.g., fluoro, chloro, bromo, iodo). In further embodiments, $R^5$ is chloro. In some embodiments, $R^5$ is fluoro. In some embodiments, $R^5$ is bromo. In some embodiments, $R^5$ is iodo.

In some embodiments, $R^5$ is —CN.

In certain embodiments, $R^5$ is —$C_1$-$C_6$ alkyl. In further embodiments, $R^5$ is methyl. In some embodiments, $R^5$ is ethyl. In some embodiments $R^5$ is propyl or isopropyl.

In some embodiments, $R^5$ is —$C_1$-$C_6$ heteroalkyl. In further embodiments, $R^5$ is methoxymethyl (—CH$_2$OCH$_3$). In some embodiments, $R^5$ is aminomethyl (e.g., —CH$_2$NH$_2$, —CH$_2$NHCH$_3$, —CH$_2$N(CH$_3$)$_2$.

In some embodiments, $R^5$ is —$C_1$-$C_6$ haloalkyl. In further embodiments, $R^5$ is trifluoromethyl (—CF$_3$).

In some embodiments, $R^5$ is —$C_3$-$C_9$ carbocyclyl (e.g., cyclopropyl, cyclobutyl, cyclopentyl, cyclohexyl). In some embodiments, $R^5$ is cyclopropyl. In some embodiments $R^5$ is cyclobutyl. In some embodiments, $R^5$ is cyclopentyl. In some embodiments, $R^5$ is cyclohexyl, In some embodiments, $R^5$ is 3-10 membered heterocyclyl (e.g., oxetanyl, tetrahydropyranyl, tetrahydrofuranyl, azetidinyl, pyrrolidinyl, piperidinyl, piperazinyl, morpholinyl, azepanyl). In some embodiments, $R^5$ is oxetanyl. In some embodiments, $R^5$ is tetrahydropyranyl. In some embodiments, $R^5$ is tetrahydrofuranyl. In some embodiments, $R^5$ is azetidinyl. In some embodiments, $R^5$ is pyrrolidinyl. In some embodiments, $R^5$ is piperidinyl. In some embodiments, $R^5$ is piperazinyl. In some embodiments, $R^5$ is morpholinyl. In some embodiments, $R^5$ is azepanyl.

In some embodiments, $R^5$ is phenyl. In some embodiments, $R^5$ is 5-6 membered heteroaryl (e.g., pyridinyl, pyrimidinyl, pyridazinyl, pyrazinyl, furanyl, thiophenyl, pyrrolyl, pyrazolyl, imidazolyl, thiazolyl, oxazolyl, isoxazolyl, isothiazolyl, triazolyl, oxadiazolyl, thiadiazolyl, tetrazolyl). In some embodiments, $R^5$ is arylalkyl (e.g., benzyl). In some embodiments, $R^5$ is heteroarylalkyl (e.g., pyridinylmethyl, pyrimidinylmethyl, pyridazinylmethyl, pyrazinylmethyl, furanylmethyl, thiophenylmethyl, pyrrolylmethyl, pyrazolylmethyl, imidazolylmethyl, thiazolylmethyl, oxazolylmethyl, isoxazolylmethyl, isothiazolylmethyl, triazolylmethyl, oxadiazolylmethyl, thiadiazolylmethyl, tetrazolylmethyl). In some embodiments $R^5$ is cycloalkylalkyl (e.g., cyclopropylmethyl, cyclobutylmethyl, cyclopentylmethyl, cyclohexylmethyl, cycloheptylmethyl). In some embodiments, $R^5$ is heterocyclylalkyl (e.g., oxetanylmethyl, aziridinylmethyl, tetrahydrofuranylmethyl, pyrolidinylmethyl, tetrahydropyranylmethyl, piperidinylmethyl, piperazinylmethyl, morpholinylmethyl, azepanylmethyl).

In some embodiments, $R^5$ is —O$R^3$ (e.g., methoxy, fluoromethoxy (—OCHF$_2$), trifluoromethoxy (—OCF$_3$), ethoxy, propoxy, isopropoxy, cyclopropyloxy, cyclobutyloxy). In some embodiments, $R^5$ is methoxy. In some embodiments, $R^5$ is ethoxy. In some embodiments, $R^5$ is propoxy. In some embodiments, $R^5$ is isopropoxy. In some embodiments $R^5$ is fluoromethoxy. (—OCHF$_2$). In some embodiments, $R^5$ is trifluoromethoxy (—OCF$_3$).

In some embodiments, $R^5$ is —N(R$^3$)$_2$ (e.g., —NH$_2$, —NHR$^3$, —N(CH$_3$)R$_3$). In some embodiments, $R^5$ is —NH$_2$. In some embodiments, $R^5$ is —NHR$^3$ (e.g., —NHMe, —NHEt, —NHPr, —NH$^i$Pr, —NHcyclopropyl, —NHcyclobutyl). In some embodiments, $R^5$ is —N(CH$_3$)R$^3$ (e.g., —NMe$_2$, —N(CH$_3$)Et, —N(CH$_3$)Pr, —N(CH$_3$)$^i$Pr, —N(CH$_3$)cyclopropyl, —N(CH$_3$)cyclobutyl).

In some embodiments, $R^5$ is —C(=O)R$^3$. In some embodiments, $R^5$ is —C(=O)alkyl. In some embodiments, $R^5$ is acetyl (—C(=O)Me). In some embodiments, $R^5$ is —C(=O)cycloalkyl (e.g. —C(=O)cyclopropyl).

In some embodiments, $R^5$ is —C(=O)OR$^3$. In some embodiments, $R^5$ is —COOH. In some embodiments, $R^5$ is COOMe.

In some embodiments, $R^5$ is —NR$^3$C(=O)R$^3$. In certain embodiments, $R^5$ is —NHC(=O)R$^3$ (e.g., NHC(=O)Me, NHC(=O)Et, NHC(=O)Pr, NHC(=O)$^i$Pr, NHC(=O)Bu, NHC(=O)$^t$Bu, NHC(=O)Cyclopropyl, NHC(=O)Cyclobutyl). In some embodiments, $R^5$ is —N(CH$_3$)C(=O)R$^3$ (e.g., N(CH$_3$)C(=O)Me, N(CH$_3$)C(=O)Et, N(CH$_3$)C(=O)Pr, N(CH$_3$)C(=O)$^i$Pr, N(CH$_3$)C(=O)Bu, N(CH$_3$)C(=O)$^t$Bu, N(CH$_3$)C(=O)Cyclopropyl, N(CH$_3$)C(=O)Cyclobutyl).

In some embodiments, $R^5$ is —NR$^3$C(=O)OR$^3$. In certain embodiments, $R^5$ is —NHC(=O)OR$^3$ (e.g., NHC(=O)OMe, NHC(=O)OEt, NHC(=O)OPr, NHC(=O)O$^i$Pr, NHC(=O)OBu, NHC(=O)O$^t$Bu, NHC(=O)OCyclopropyl, NHC(=O)OCyclobutyl). In some embodiments, $R^5$ is —N(CH$_3$)C(=O)OR$^3$ (e.g., N(CH$_3$)C(=O)OMe, N(CH$_3$)C(=O)OEt, N(CH$_3$)C(=O)OPr, N(CH$_3$)C(=O)O$^i$Pr, N(CH$_3$)C(=O)OBu, N(CH$_3$)C(=O)O$^t$Bu, N(CH$_3$)C(=O)OCyclopropyl, N(CH$_3$)C(=O)OCyclobutyl).

In some embodiments, $R^5$ is —C(=O)N(R$^3$)$_2$ (e.g., —C(=O)NH$_2$, —C(=O)NHR$^3$, —C(=O)N(CH$_3$)R$_3$). In some embodiments, $R^5$ is —C(=O)NH$_2$. In certain embodiments, $R^5$ is —C(=O)NHR$^3$ (e.g., —C(=O)NHMe, —C(=O)NHEt, —C(=O)NHPr, —C(=O)NH$^i$Pr, —C(=O)NHBu, —C(=O)NHrBu, —C(=O)NHCyclopropyl, —C(=O)NHCyclobutyl). In certain embodiments, $R^5$ is —C(=O)N(CH$_3$)R$^3$ (e.g., —C(=O)NMe$_2$, —C(=O)N(CH$_3$)Et, —C(=O)N(CH$_3$)Pr, —C(=O)N(CH$_3$)$^i$Pr, —C(=O)N(CH$_3$)Bu, —C(=O)N(CH$_3$)$^t$Bu, —C(=O)N(CH$_3$)Cyclopropyl, —C(=O)N(CH$_3$)Cyclobutyl).

In some embodiments, $R^5$ is —OC(=O)N(R$^3$)$_2$. In certain embodiments, $R^5$ is —OC(=O)NHR$^3$ (e.g., —OC(=O)NHMe, —OC(=O)NHEt, —OC(=O)NHPr, —OC(=O)NH$^i$Pr, —OC(=O)NHBu, —OC(=O)NHrBu, —OC(=O)NHCyclopropyl, —OC(=O)NHCyclobutyl). In certain embodiments, $R^5$ is —OC(=O)N(CH$_3$)R$^3$ (e.g., —OC(=O)NMe$_2$, —OC(=O)N(CH$_3$)Et, —OC(=O)N(CH$_3$)Pr, —OC(=O)N(CH$_3$)$^i$Pr, —OC(=O)N(CH$_3$)Bu, —OC(=O)N(CH$_3$)Bu, —OC(=O)N(CH$_3$)Cyclopropyl, —OC(=O)N(CH$_3$)Cyclobutyl).

In some embodiments, $R^5$ is —S(=O)R$^3$. In certain embodiments, $R^5$ is —S(=O)alkyl (e.g., —S(=O)Me, —S(=O)Et, —S(=O)Pr, —S(=O)$^i$Pr). In certain embodiments, $R^5$ is —S(=O)cycloalkyl (e.g., —S(=O)cyclopropyl, —S(=O)cyclobutyl, —S(=O)cyclopentyl, —S(=O)cyclohexyl).

In some embodiments, $R^5$ is —S(=O)$_2$R$^3$. In certain embodiments, $R^5$ is —S(=O)$_2$alkyl (e.g., —S(=O)$_2$Me, —S(=O)$_2$Et, —S(=O)$_2$Pr, —S(=O)$_2$$^i$Pr). In certain embodiments, $R^5$ is —S(=O)$_2$cycloalkyl (e.g., —S(=O)$_2$cyclopropyl, —S(=O)$_2$cyclobutyl, —S(=O)$_2$cyclopentyl, —S(=O)$_2$cyclohexyl). In some embodiments, $R^5$ is S(=O)$_2$ aryl (e.g., S(=O)$_2$phenyl).

In some embodiments, $R^5$ is —SR$^3$. In certain embodiments, $R^5$ is —Salkyl (e.g., —SMe, —SEt, —SPr, —S$^i$Pr). In certain embodiments, $R^5$ is —Scycloalkyl (e.g., —Scyclopropyl, —Scyclobutyl, —Scyclopentyl, —Scyclohexyl). In certain embodiments, $R^5$ is —Saryl (e.g., Sphenyl).

In some embodiments, $R^5$ is —S(=O)(=NR$^3$)R$^3$. In certain embodiments, $R^5$ is —S(=O)(=NH)R$^3$ (e.g., —S(=O)(=NH)Me, —S(=O)(=NH)Et, —S(=O)(=NH)Pr, —S(=O)(=NH)$^i$Pr, —S(=O)(=NH)Bu, —S(=O)(=NH)$^t$Bu, —S(=O)(=NH)Cyclopropyl, —S(=O)(=NH)Cyclobutyl). In some embodiments, $R^5$ is —S(=O)(=NCH$_3$)R$^3$ (e.g., —S(=O)(=NCH$_3$)Me, —S(=O)(=NCH$_3$)Et, —S(=O)(=NCH$_3$)Pr, —S(=O)(=NCH$_3$)$^i$Pr, —S(=O)(=NCH$_3$)Bu, —S(=O)(=NCH$_3$)$^t$Bu, —S(=O)(=NCH$_3$)Cyclopropyl, —S(=O)(=NCH$_3$)Cyclobutyl).

In some embodiments, $R^5$ is —NR$^3$S(=O)$_2$R$^3$. In certain embodiments, $R^5$ is —NHS(=O)$_2$alkyl (e.g., —NHS(=O)$_2$Me, —NHS(=O)$_2$Et, —NHS(=O)$_2$Pr, —NHS(=O)$_2$$^i$Pr). In certain embodiments, $R^5$ is —NHS(=O)$_2$cycloalkyl (e.g., —NHS(=O)$_2$cyclopropyl, —NHS(=O)$_2$cyclobutyl, —NHS(=O)$_2$cyclopentyl, —NHS(=O)$_2$cyclohexyl). In certain embodiments, $R^5$ is —N(CH$_3$)S(=O)$_2$alkyl (e.g., —N(CH$_3$)S(=O)$_2$Me, —N(CH$_3$)S(=O)$_2$Et, —N(CH$_3$)S(=O)$_2$Pr, —N(CH$_3$)S(=O)$_2$$^i$Pr). In certain embodiments, $R^5$ is —N(CH$_3$)S(=O)$_2$cycloalkyl (e.g., —N(CH$_3$)S(=O)$_2$cyclopropyl, —N(CH$_3$)S(=O)$_2$cyclobutyl, —N(CH$_3$)S(=O)$_2$cyclopentyl, —N(CH$_3$)S(=O)$_2$cyclohexyl).

In some embodiments, $R^5$ is —S(=O)$_2$N(R$^3$)$_2$. (e.g., —S(=O)$_2$NH$_2$, —S(=O)$_2$NHR$^3$, —S(=O)$_2$N(CH$_3$)R$_3$). In some embodiments, $R^5$ is —S(=O)$_2$NH$_2$. In some embodiments, $R^5$ is —S(=O)$_2$NHR$^3$ (e.g., —S(=O)$_2$NHMe, —S(=O)$_2$NHEt, —S(=O)$_2$NHPr, —S(=O)$_2$NH$^i$Pr, —S(=O)$_2$NHcyclopropyl, —S(=O)$_2$NHcyclobutyl). In some embodiments, $R^5$ is —S(=O)$_2$N(CH$_3$)R$^3$ (e.g., —S(=O)$_2$NMe$_2$, —S(=O)$_2$N(CH$_3$)Et, —S(=O)$_2$N(CH$_3$)Pr, —S(=O)$_2$N(CH$_3$)$^i$Pr, —S(=O)$_2$N(CH$_3$)cyclopropyl, —S(=O)$_2$N(CH$_3$)cyclobutyl).

In some embodiments of the invention, two $R^5$ can be taken together with the atoms to which they are attached to form a $C_3$-$C_9$ carbocycle (e.g., cyclopropyl, cyclobutyl, cyclopentyl, cyclohexyl) or a 3-10 membered heterocycle (e.g., oxetanyl, azetidinyl, tetrahydropyranyl, tetrahydrofuranyl, pyrrolidinyl, piperidinyl, piperazinyl, morpholinyl, azepanyl). In some embodiments, the two $R^5$ are taken together with the atom to which they are attached to form a cyclopropyl. In some embodiments, the two $R^5$ are taken together with the atom to which they are attached to form a cyclobutyl. In some embodiments, the two $R^5$ are taken together with the atom to which they are attached to form a cyclopentyl. In some embodiments, the two $R^5$ are taken together with the atom to which they are attached to form a cyclohexyl. In some embodiments, the two $R^5$ are taken together with the atom to which they are attached to form an oxetanyl. In some embodiments, the two $R^5$ are taken together with the atom to which they are attached to form a tetrahydrofuranyl. In some embodiments, the two $R^5$ are taken together with the atom to which they are attached to form a tetrahydropyranyl.

As generally described herein, each $R^7$ is independently selected from =O, halo, —CN, —C$_1$-C$_6$ alkyl, —C$_1$-C$_6$ heteroalkyl, —C$_1$-C$_6$ haloalkyl, —C$_3$-C$_9$ carbocyclyl, 3-10 membered heterocyclyl, C$_6$-C$_{10}$ aryl, 5-10 membered heteroaryl, cycloalkylalkyl, heterocyclylalkyl, arylalkyl, heteroarylalkyl, —OR³, —N(R³)₂, —C(=O)R³, —C(=O)OR³, —NR³C(=O)R³, —NR³C(=O)OR³, —C(=O)N(R³)₂, —OC(=O)N(R³)₂, —S(=O)R³, —S(=O)₂R³, —SR³, —S(=O)(=NR³)R³, —NR³S(=O)₂R³ or —S(=O)₂N(R³)₂.

Each instance of R⁷ can be independently attached to any available position of the underlying moiety.

In certain embodiments, R⁷ is selected from =O, halo, —CN, —C₁-C₆ alkyl, —C₁-C₆ heteroalkyl, —C₁-C₆ haloalkyl, —C₃-C₉ carbocyclyl, 3-10 membered heterocyclyl, —OR³, —NHR³, N(CH₃)R³, —C(=O)R³, —C(=O)OR³, —NHC(=O)R³, —N(CH₃)C(=O)R³, —NHC(=O)OR³, —N(CH₃)C(=O)OR³, —C(=O)NH(R³), —C(=O)N(CH₃)(R³), —OC(=O)NHR³, —OC(=O)N(CH₃)R³, —S(=O)R³, —S(=O)₂R³, —SR³, —S(=O)(=NH)R³, —S(=O)(=NCH₃)R³, —NHS(=O)₂R³, —N(CH₃)S(=O)₂R³, —S(=O)₂NHR³ and —S(=O)₂N(CH³)R³.

In some embodiments, each R⁷ is independently selected from =O, halo, —CN, —C₁-C₆ alkyl, —C₁-C₆ heteroalkyl, —C₁-C₆ haloalkyl, —C₃-C₉ carbocyclyl, 3-10 membered heterocyclyl, —OR³, —N(R³)₂, —CO(R³), —NR³(CO)R³, —(CO)N(R³)₂, optionally wherein R³ is C₁-C₆ alkyl.

In certain embodiments, each R⁷ is independently selected from halo, —CN and —C₁-C₆ alkyl.

In some embodiments each R⁷ is independently selected from C₁-C₆ alkyl or —C(=O)R³ (optionally wherein R³ is —C₁-C₆ alkyl (e.g., —C(=O)CH₃)).

In certain embodiments, R⁷ is =O.

In certain embodiments, R⁷ is halo (e.g., fluoro, chloro, bromo, iodo). In further embodiments, R⁷ is chloro. In some embodiments, R⁷ is fluoro. In some embodiments, R⁷ is bromo. In some embodiments, R⁷ is iodo.

In some embodiments, R⁷ is —CN.

In certain embodiments, R⁷ is —C₁-C₆ alkyl. In further embodiments, R⁷ is methyl. In some embodiments, R⁷ is ethyl. In some embodiments R⁷ is propyl or isopropyl.

In some embodiments, R⁷ is —C₁-C₆ heteroalkyl. In further embodiments, R⁷ is methoxymethyl (—CH₂OCH₃). In some embodiments, R⁷ is aminomethyl (e.g., —CH₂NH₂, —CH₂NHCH₃, —CH₂N(CH₃)₂, —CH₂CH₂N(CH₃)₂.

In some embodiments, R⁷ is —C₁-C₆ haloalkyl. In further embodiments, R⁷ is trifluoromethyl (—CF₃).

In some embodiments, R⁷ is —C₃-C₉ carbocyclyl (e.g., cyclopropyl, cyclobutyl, cyclopentyl, cyclohexyl). In some embodiments, R⁷ is cyclopropyl. In some embodiments R⁷ is cyclobutyl. In some embodiments, R⁷ is cyclopentyl. In some embodiments, R⁷ is cyclohexyl, In some embodiments, R⁷ is 3-10 membered heterocyclyl (e.g., oxetanyl, tetrahydropyranyl, tetrahydrofuranyl, azetidinyl, pyrrolidinyl, piperidinyl, piperazinyl, morpholinyl, azepanyl). In some embodiments, R⁷ is oxetanyl. In some embodiments, R⁷ is tetrahydropyranyl. In some embodiments, R⁷ is tetrahydrofuranyl. In some embodiments, R⁷ is azetidinyl. In some embodiments, R⁷ is pyrrolidinyl. In some embodiments, R⁷ is piperidinyl. In some embodiments, R⁷ is piperazinyl. In some embodiments, R⁷ is morpholinyl. In some embodiments, R⁷ is azepanyl.

In some embodiments, R⁷ is phenyl. In some embodiments, R⁷ is 5-6 membered heteroaryl (e.g., pyridinyl, pyrimidinyl, pyridazinyl, pyrazinyl, furanyl, thiophenyl, pyrrolyl, pyrazolyl, imidazolyl, thiazolyl, oxazolyl, isoxazolyl, isothiazolyl, triazolyl, oxadiazolyl, thiadiazolyl, tetrazolyl). In some embodiments, R⁷ is arylalkyl (e.g., benzyl). In some embodiments, R⁷ is heteroarylalkyl (e.g., pyridinylmethyl, pyrimidinylmethyl, pyridazinylmethyl, pyrazinylmethyl, furanylmethyl, thiophenylmethyl, pyrrolylmethyl, pyrazolylmethyl, imidazolylmethyl, thiazolylmethyl, oxazolylmethyl, isoxazolylmethyl, isothiazolylmethyl, triazolylmethyl, oxadiazolylmethyl, thiadiazolylmethyl, tetrazolylmethyl). In some embodiments R⁷ is cycloalkylalkyl (e.g., cyclopropylmethyl, cyclobutylmethyl, cyclopentylmethyl, cyclohexylmethyl, cycloheptylmethyl). In some embodiments, R⁷ is heterocyclylalkyl (e.g., oxetanylmethyl, aziridinylmethyl, tetrahydrofuranylmethyl, pyrrolidinylmethyl, tetrahydropyranylmethyl, piperidinylmethyl, piperazinylmethyl, morpholinylmethyl, azepanylmethyl).

In some embodiments, R⁷ is —OR³ (e.g., methoxy, fluoromethoxy (—OCHF₂), trifluoromethoxy (—OCF₃), ethoxy, propoxy, isopropoxy, cyclopropyloxy, cyclobutyloxy). In some embodiments, R⁷ is methoxy. In some embodiments, R⁷ is ethoxy. In some embodiments, R⁷ is propoxy. In some embodiments, R⁷ is isopropoxy. In some embodiments R⁷ is fluoromethoxy. (—OCHF₂). In some embodiments, R⁷ is trifluoromethoxy (—OCF₃).

In some embodiments, R⁷ is —N(R³)₂ (e.g., —NH₂, —NHR³, —N(CH₃)R₃). In some embodiments, R⁷ is —NH₂. In some embodiments, R⁷ is —NHR³ (e.g., —NHMe, —NHEt, —NHPr, —NHⁱPr, —NHcyclopropyl, —NHcyclobutyl). In some embodiments, R⁷ is —N(CH₃)R³ (e.g., —NMe₂, —N(CH₃)Et, —N(CH₃)Pr, —N(CH₃)ⁱPr, —N(CH₃)cyclopropyl, —N(CH₃)cyclobutyl).

In some embodiments, R⁷ is —C(=O)R³. In some embodiments, R⁷ is —C(=O)alkyl. In some embodiments, R⁷ is acetyl (—C(=O)Me). In some embodiments, R⁷ is —C(=O)(C₃-C₇)cycloalkyl (e.g., —C(=O)cyclopropyl). In some embodiments, R⁷ is —C(=O)heteroalkyl.

In some embodiments, R⁷ is —C(=O)OR³. In some embodiments, R⁷ is —COOH. In some embodiments, R⁷ is COOMe.

In some embodiments, R⁷ is —NR³C(=O)R³. In certain embodiments, R⁷ is —NHC(=O)R³ (e.g., NHC(=O)Me, NHC(=O)Et, NHC(=O)Pr, NHC(=O)ⁱPr, NHC(=O)Bu, NHC(=O)ᵗBu, NHC(=O)Cyclopropyl, NHC(=O)Cyclobutyl). In some embodiments, R⁷ is —N(CH₃)C(=O)R³ (e.g., N(CH₃)C(=O)Me, N(CH₃)C(=O)Et, N(CH₃)C(=O)Pr, N(CH₃)C(=O)ⁱPr, N(CH₃)C(=O)Bu, N(CH₃)C(=O)ᵗBu, N(CH₃)C(=O)Cyclopropyl, N(CH₃)C(=O)Cyclobutyl).

In some embodiments, R⁷ is —NR³C(=O)OR³. In certain embodiments, R⁷ is —NHC(=O)OR³ (e.g., NHC(=O)OMe, NHC(=O)OEt, NHC(=O)OPr, NHC(=O)OⁱPr, NHC(=O)OBu, NHC(=O)OᵗBu, NHC(=O)OCyclopropyl, NHC(=O)OCyclobutyl). In some embodiments, R⁷ is —N(CH₃)C(=O)OR³ (e.g., N(CH₃)C(=O)OMe, N(CH₃)C(=O)OEt, N(CH₃)C(=O)OPr, N(CH₃)C(=O)OⁱPr, N(CH₃)C(=O)OBu, N(CH₃)C(=O)OᵗBu, N(CH₃)C(=O)OCyclopropyl, N(CH₃)C(=O)OCyclobutyl).

In some embodiments, R⁷ is —C(=O)N(R³)₂ (e.g., —C(=O)NH₂, —C(=O)NHR³, —C(=O)N(CH₃)R₃). In some embodiments, R⁷ is —C(=O)NH₂. In certain embodiments, R⁷ is —C(=O)NHR³ (e.g., —C(=O)NHMe, —C(=O)NHEt, —C(=O)NHPr, —C(=O)NHⁱPr, —C(=O)NHBu, —C(=O)NHrBu, —C(=O)NHCyclopropyl, —C(=O)NHCyclobutyl). In certain embodiments, R⁷ is —C(=O)N(CH₃)R³ (e.g., —C(=O)NMe₂, —C(=O)N(CH₃)Et, —C(=O)N(CH₃)Pr, —C(=O)N(CH₃)ⁱPr, —C(=O)N(CH₃)Bu, —C(=O)N(CH₃)ᵗBu, —C(=O)N(CH₃)Cyclopropyl, —C(=O)N(CH₃)Cyclobutyl).

In some embodiments, R⁷ is —OC(=O)N(R³)₂. In certain embodiments, R⁷ is —OC(=O)NHR³ (e.g., —OC(=O)NHMe, —OC(=O)NHEt, —OC(=O)NHPr, —OC(=O)NHⁱPr, —OC(=O)NHBu, —OC(=O)NHrBu, —OC (=O)NHCyclopropyl, —OC(=O)NHCyclobutyl). In certain embodiments, R$^7$ is —OC(=O)N(CH$_3$)R$^3$ (e.g., —OC(=O)NMe$_2$, —OC(=O)N(CH$_3$)Et, —OC(=O)N(CH$_3$)Pr, —OC(=O)N(CH$_3$)$^i$Pr, —OC(=O)N(CH$_3$)Bu, —OC(=O)N(CH$_3$)$^i$Bu, —OC(=O)N(CH$_3$)Cyclopropyl, —OC(=O)N(CH$_3$)Cyclobutyl).

In some embodiments, R$^7$ is —S(=O)R$^3$. In certain embodiments, R$^7$ is —S(=O)alkyl (e.g., —S(=O)Me, —S(=O)Et, —S(=O)Pr, —S(=O)$^i$Pr). In certain embodiments, R$^7$ is —S(=O)cycloalkyl (e.g., —S(=O)cyclopropyl, —S(=O)cyclobutyl, —S(=O)cyclopentyl, —S(=O)cyclohexyl).

In some embodiments, R$^7$ is —S(=O)$_2$R$^3$. In certain embodiments, R$^7$ is —S(=O)$_2$alkyl (e.g., —S(=O)$_2$Me, —S(=O)$_2$Et, —S(=O)$_2$Pr, —S(=O)$_2$$^i$Pr). In certain embodiments, R$^7$ is —S(=O)$_2$cycloalkyl (e.g., —S(=O)$_2$cyclopropyl, —S(=O)$_2$cyclobutyl, —S(=O)$_2$cyclopentyl, —S(=O)$_2$cyclohexyl). In some embodiments, R$^7$ is S(=O)$_2$ aryl (e.g., S(=O)$_2$phenyl).

In some embodiments, R$^7$ is —SR$^3$. In certain embodiments, R$^7$ is —Salkyl (e.g., —SMe, —SEt, —SPr, —S$^i$Pr). In certain embodiments, R$^7$ is —Scycloalkyl (e.g., —Scyclopropyl, —Scyclobutyl, —Scyclopentyl, —Scyclohexyl). In certain embodiments, R$^7$ is —Saryl (e.g., Sphenyl).

In some embodiments, R$^7$ is —S(=O)(=NR$^3$)R$^3$. In certain embodiments, R$^7$ is —S(=O)(=NH)R$^3$ (e.g., —S(=O)(=NH)Me, —S(=O)(=NH)Et, —S(=O)(=NH)Pr, —S(=O)(=NH)$^i$Pr, —S(=O)(=NH)Bu, —S(=O)(=NH)$^i$Bu, —S(=O)(=NH)Cyclopropyl, —S(=O)(=NH)Cyclobutyl). In some embodiments, R$^7$ is —S(=O)(=NCH$_3$)R$^3$ (e.g., —S(=O)(=NCH$_3$)Me, —S(=O)(=NCH$_3$)Et, —S(=O)(=NCH$_3$)Pr, —S(=O)(=NCH$_3$)$^i$Pr, —S(=O)(=NCH$_3$)Bu, —S(=O)(=NCH$_3$)$^i$Bu, —S(=O)(=NCH$_3$)Cyclopropyl, —S(=O)(=NCH$_3$)Cyclobutyl).

In some embodiments, R$^7$ is —NR$^3$S(=O)$_2$R$^3$. In certain embodiments, R$^7$ is —NHS(=O)$_2$alkyl (e.g., —NHS(=O)$_2$e, —NHS(=O)$_2$Et, —NHS(=O)$_2$Pr, —NHS(=O)$_2$$^i$Pr). In certain embodiments, R$^7$ is —NHS(=O)$_2$cycloalkyl (e.g., —NHS(=O)$_2$cyclopropyl, —NHS(=O)$_2$cyclobutyl, —NHS(=O)$_2$cyclopentyl, —NHS(=O)$_2$cyclohexyl). In certain embodiments, R$^7$ is —N(CH$_3$)S(=O)$_2$alkyl (e.g., —N(CH$_3$)S(=O)$_2$Me, —N(CH$_3$)S(=O)$_2$Et, —N(CH$_3$)S(=O)$_2$Pr, —N(CH$_3$)S(=O)$_2$$^i$Pr). In certain embodiments, R$^7$ is —N(CH$_3$)S(=O)$_2$cycloalkyl (e.g., —N(CH$_3$)S(=O)$_2$cyclopropyl, —N(CH$_3$)S(=O)$_2$cyclobutyl, —N(CH$_3$)S(=O)$_2$cyclopentyl, —N(CH$_3$)S(=O)$_2$cyclohexyl).

In some embodiments, R$^7$ is —S(=O)$_2$N(R$^3$)$_2$. (e.g., —S(=O)$_2$NH$_2$, —S(=O)$_2$NHR$^3$, —S(=O)$_2$N(CH$_3$R$_3$). In some embodiments, R$^7$ is —S(=O)$_2$NH$_2$. In some embodiments, R$^7$ is —S(=O)$_2$NHR$^3$ (e.g., —S(=O)$_2$NHMe, —S(=O)$_2$NHEt, —S(=O)$_2$NHPr, —S(=O)$_2$H$^i$Pr, —S(=O)$_2$NHcyclopropyl, —S(=O)$_2$NHcyclobutyl). In some embodiments, R$^7$ is —S(=O)$_2$N(CH$_3$)R$^3$ (e.g., —S(=O)$_2$NMe$_2$, —S(=O)$_2$N(CH$_3$)Et, —S(=O)$_2$N(CH$_3$)Pr, —S(=O)$_2$N(CH$_3$)$^i$Pr, —S(=O)$_2$N(CH$_3$)cyclopropyl, —S(=O)$_2$N(CH$_3$)cyclobutyl).

As generally described herein, m is 0, 1, 2 or 3. In certain embodiments, m is 0. In certain embodiments m is 1. In some embodiments m is 2. In some embodiments m is 3. In one embodiment m is 1 and each R$^5$ is independently selected from =O, halo, —CN, —C$_1$-C$_6$ alkyl, —C$_1$-C$_6$ heteroalkyl, —C$_1$-C$_6$ haloalkyl, —C$_3$-C$_9$ carbocyclyl, 3-10 membered heterocyclyl, —OR$^3$, —N(R$^3$)$_2$, —CO(R$^3$), —NR$^3$(CO)R$^3$, —(CO)N(R$^3$)$_2$.

As generally described herein, m is 0, 1, 2 or 3. In certain embodiments, m is 0. In certain embodiments m is 1. In some embodiments m is 2. In some embodiments m is 3. In one embodiment m is 1 and each R$^5$ is independently selected from =O, halo, —CN, —C$_1$-C$_6$ alkyl, —C$_1$-C$_6$ heteroalkyl, —C$_1$-C$_6$ haloalkyl, —C$_3$-C$_9$ carbocyclyl, 3-10 membered heterocyclyl, —OR$^3$, —N(R$^3$)$_2$, —CO(R$^3$), —NR$^3$(CO)R$^3$, —(CO)N(R$^3$)$_2$.

In one embodiment, the invention provides a compound selected from the compounds of Table 1, or pharmaceutically acceptable salts thereof.

Compounds described herein (e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) are useful as inhibitors of PRMT5 (e.g., MTA uncompetitive PRMT5 inhibitors).

Table 1 indicates IC$_{50}$ values (μM) against PRMT5 for exemplary compounds in the presence of SAM as cofactor, with no cofactor and with MTA as cofactor, respectively (columns 3-5). For Table 1, "a" "aa" and "aaa" indicates an IC$_{50}$ less than 50 nM in the assays with SAM, no cofactor and MTA respectively; "b", "bb" and "bbb" indicates an IC$_{50}$ of 50 nM to less than 500 nM in the assays with SAM, no cofactor and MTA, respectively; "c", "cc" and "ccc" indicates an IC$_{50}$ of greater than or equal to 500 nM to less than 5 μM in the assays with SAM, no cofactor and MTA, respectively; "d", "dd" and "ddd" indicates an IC$_{50}$ of greater than or equal to 5 μM in the assays with SAM, no cofactor and MTA, respectively. The Ki values can be calculated from the IC$_{50}$ values as described in the Examples section. As detailed in the Examples section, for the assay performed in the presence of SAM, IC$_{50}$=Ki×1.5 (Ki=IC$_{50}$/1.5). For the assay performed in the presence of MTA, IC$_{50}$=Ki×13.5 (Ki=IC$_{50}$/13.5). Column 6 indicates the ratio between the Ki of compounds in the presence of SAM and the Ki of compounds in the presence of MTA In column 6, "A" indicates a Ki ratio greater than or equal to 10 fold between the Ki in the presence of SAM and the Ki in the presence of MTA; "B" indicates a Ki ratio greater than or equal to 3 fold but lower than 10 fold between the Ki in the presence of SAM and the Ki in the presence of MTA; "C" indicates a Ki ratio of less than 3 fold between the IC$_{50}$ in the presence of SAM and the IC$_{50}$ in the presence of MTA; Compounds with a SAM/MTA ratio of more than 1 show greater cooperativity with MTA than with SAM.

Table 1 also indicates IC$_{50}$ values in an MTAP-isogenic cell line pair for exemplary compounds in an SDMA in-cell western assay (columns 7-8). HAP1 MTAP-intact is a cell line in which endogenous levels of MTAP are expressed, and HAP1 MTAP-deleted is an MTAP-null cell line. For Table 1, "a*" and "aa*" indicates an IC$_{50}$ of <1 μM, "b*" and "bb*" indicates an IC$_{50}$ equal to or greater than 1 μM but less than 10 μM, and "c*" and "cc*" indicates an IC$_{50}$ of greater than or equal to 10 μM in the HAP1 MTAP-intact and the HAP1 MTAP-deleted assays, respectively. In column 9, "A*" indicates an IC$_{50}$ ratio greater than or equal to 10 fold between the IC$_{50}$ in the HAP1 MTAP-intact cell line and the HAP1 MTAP-deleted cell line; "B*" indicates an IC$_{50}$ ratio greater than or equal to 3 fold but lower than 10 fold between the IC$_{50}$ in the HAP1 MTAP-intact cell line and the HAP1 MTAP-deleted cell line; "C*" indicates an IC$_{50}$ ratio of less than 3 fold between the IC$_{50}$ in the HAP1 MTAP-intact cell line and the HAP1 MTAP-deleted cell line. Compounds with a ratio in the SDMA in-cell western assay of equal to or greater than 3 fold are considered MTAP-selective.

Unless otherwise indicated, the absolute stereochemistry of all chiral atoms is as depicted. For compounds marked with (**), the configuration at the secondary alcohol stereocenter was arbitrarily assigned based on chiral SFC elution as described in detail in the Examples section.

TABLE 1
Exemplary compounds of the invention and biological data
| Structure | Nr. | SAM IC50 | No Co-factor IC50 | MTA IC50 | SAM/MTA Ratio | HAP1 MTAP Intact $IC_{50}$ | HAP1 MTAP Deleted $IC_{50}$ | MTAP Intact/Deleted Ratio |
|---|---|---|---|---|---|---|---|---|
| 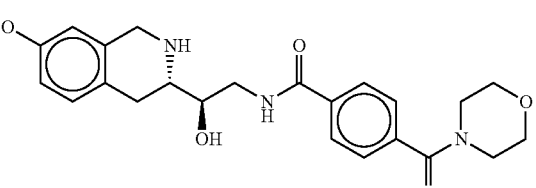 | 1 | b | dd | bbb | A | c* | cc* | C* |
| 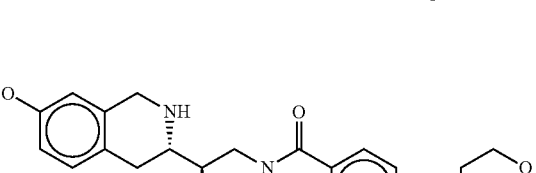 | 2 | b | cc | bbb | A | c* | cc* | C* |
| 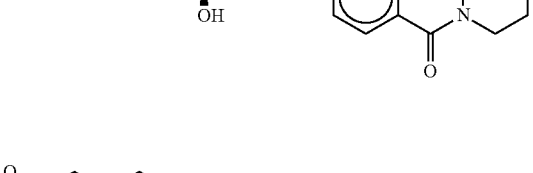 | 3 | b | cc | bbb | A | c* | bb* | C* |
| 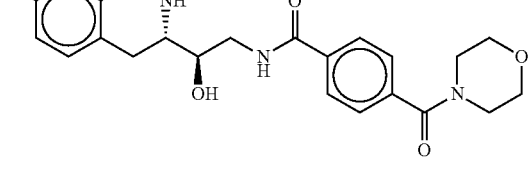 | 4 | b | bb | bbb | A | c* | bb* | C* |
| 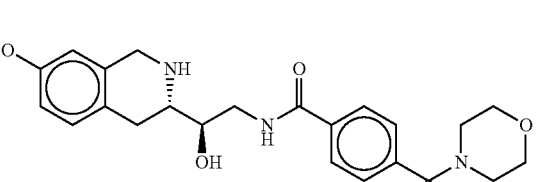 | 5 | b | cc | bbb | A | a* | aa* | C* |
| 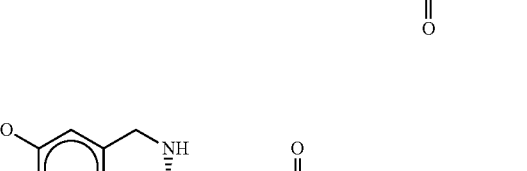 | 6 | b | cc | bbb | A | a* | aa* | C* |

TABLE 1-continued
Exemplary compounds of the invention and biological data
| Structure | Nr. | SAM IC50 | No Cofactor IC50 | MTA IC50 | SAM/ MTA Ratio | HAP1 MTAP Intact IC$_{50}$ | HAP1 MTAP Deleted IC$_{50}$ | MTAP Intact/ Deleted Ratio |
|---|---|---|---|---|---|---|---|---|
| 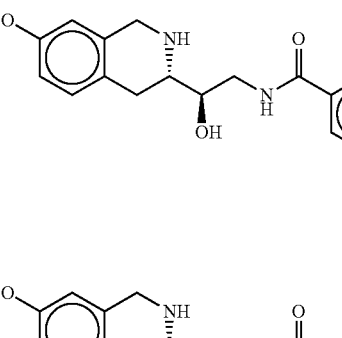 | 7 | b | cc | bbb | A | c* | bb* | B* |
| 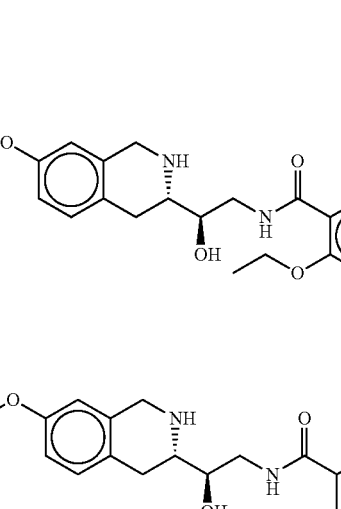 | 8 | b | bb | bbb | A | b* | aa* | A* |
| 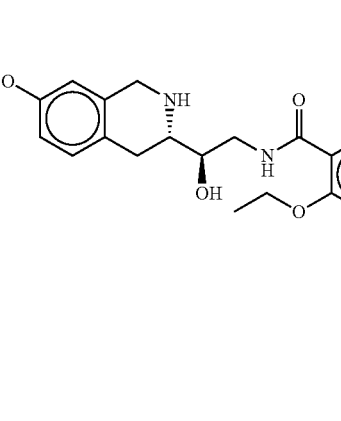 | 9 | b | cc | bbb | A | c* | bb* | B* |
| 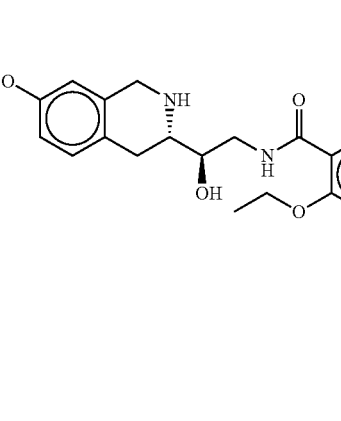 | 10 | b | bb | aaa | A | b* | aa* | A* |
| 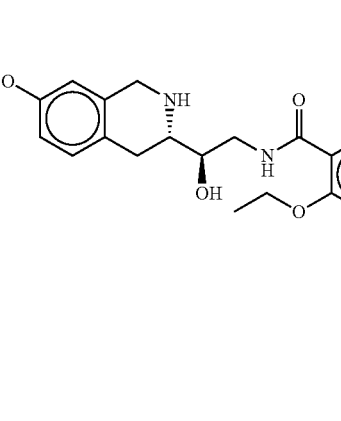 | 11 | b | cc | bbb | A | b* | aa* | B* |
| 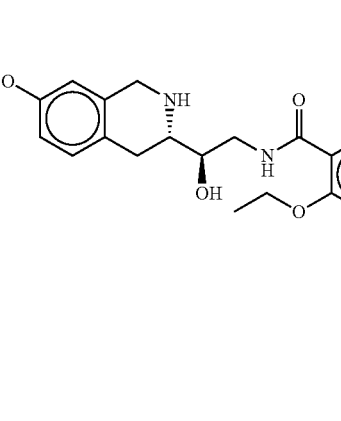 | 12 | b | cc | bbb | A | a* | aa* | B* |

TABLE 1-continued

Exemplary compounds of the invention and biological data

| Structure | Nr. | SAM IC50 | No Co-factor IC50 | MTA IC50 | SAM/ MTA Ratio | HAP1 MTAP Intact $IC_{50}$ | HAP1 MTAP Deleted $IC_{50}$ | MTAP Intact/ Deleted Ratio |
|---|---|---|---|---|---|---|---|---|
| 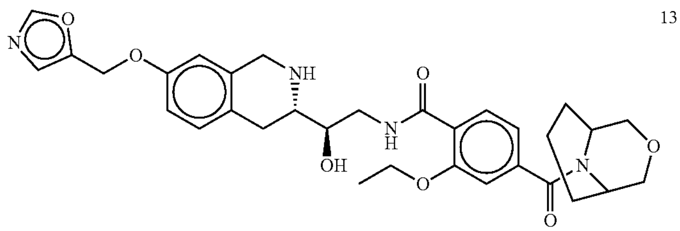 | 13 | b | cc | bbb | A | b* | aa* | A* |
| 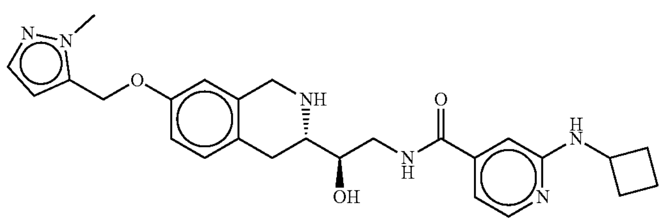 | 14 | b | cc | bbb | A | c* | aa* | A* |
| 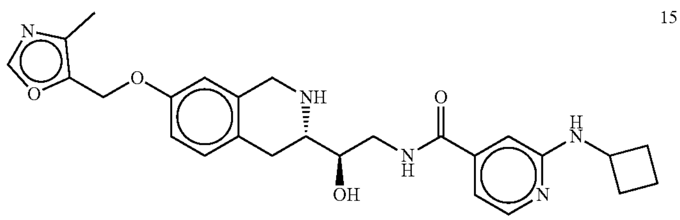 | 15 | b | bb | aaa | A | c* | aa* | A* |
| 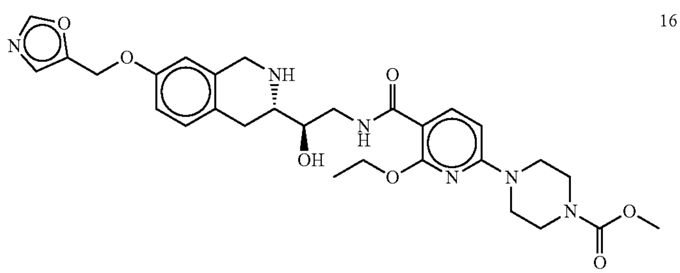 | 16 | b | bb | aaa | A | b* | aa* | B* |
| 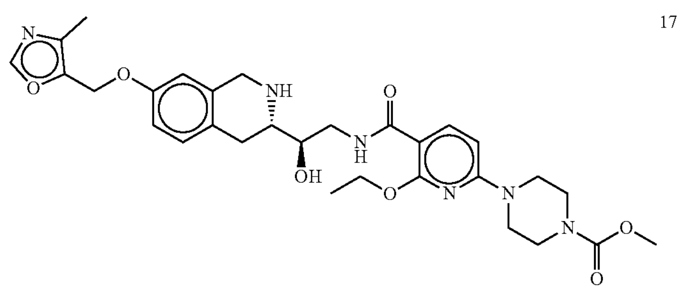 | 17 | b | bb | aaa | A | b* | aa* | A* |

TABLE 1-continued

Exemplary compounds of the invention and biological data

| Structure | Nr. | SAM IC50 | No Co-factor IC50 | MTA IC50 | SAM/MTA Ratio | HAP1 MTAP Intact IC$_{50}$ | HAP1 MTAP Deleted IC$_{50}$ | MTAP Intact/Deleted Ratio |
|---|---|---|---|---|---|---|---|---|
| | 18 | b | cc | aaa | A | c* | aa* | A* |
| | 19 | b | cc | bbb | A | c* | bb* | B* |
| | 20 | b | bb | aaa | A | b* | aa* | A* |
| | 21 | b | bb | aaa | A | b* | aa* | A* |
| | 22 | b | aa | aaa | A | b* | aa* | A* |
| | 23 | b | bb | aaa | A | a* | aa* | B* |

TABLE 1-continued

Exemplary compounds of the invention and biological data

| Structure | Nr. | SAM IC50 | No Co-factor IC50 | MTA IC50 | SAM/ MTA Ratio | HAP1 MTAP Intact IC$_{50}$ | HAP1 MTAP Deleted IC$_{50}$ | MTAP Intact/ Deleted Ratio |
|---|---|---|---|---|---|---|---|---|
| (structure) | 24 | b | bb | bbb | A | c* | aa* | A* |
| (structure) | 25 | b | dd | bbb | A | c* | bb* | C* |
| (structure) | 26 | b | bb | aaa | A | a* | aa* | C* |
| (structure) | 27 | b | cc | bbb | A | b* | aa* | A* |
| (structure) | 28 | b | bb | aaa | A | b* | aa* | A* |

TABLE 1-continued
Exemplary compounds of the invention and biological data
| Structure | Nr. | SAM IC50 | No Co-factor IC50 | MTA IC50 | SAM/MTA Ratio | HAP1 MTAP Intact IC$_{50}$ | HAP1 MTAP Deleted IC$_{50}$ | MTAP Intact/Deleted Ratio |
|---|---|---|---|---|---|---|---|---|
| 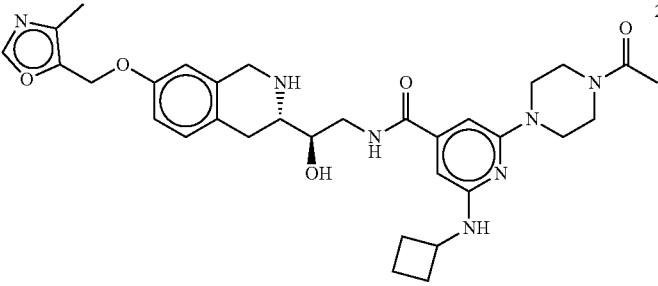 | 29 | b | bb | aaa | A | b* | aa* | A* |
| 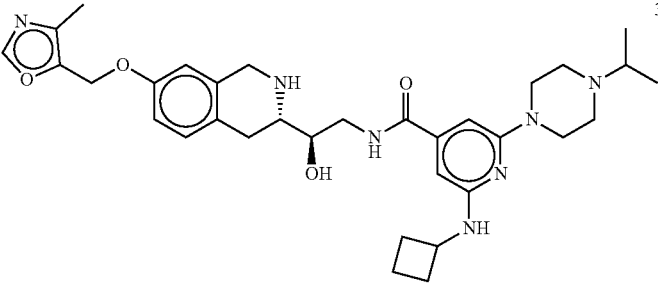 | 30 | b | bb | aaa | A | c* | cc* | C* |
| 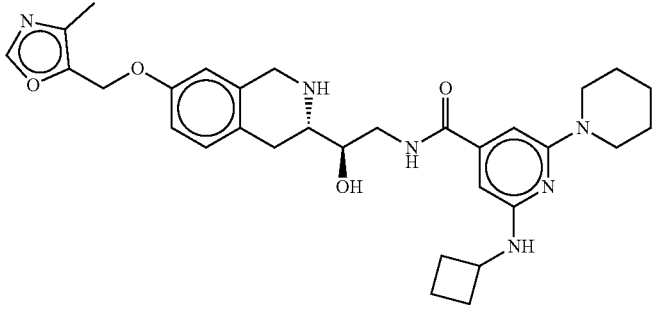 | 31 | b | bb | bbb | A | a* | aa* | C* |
| 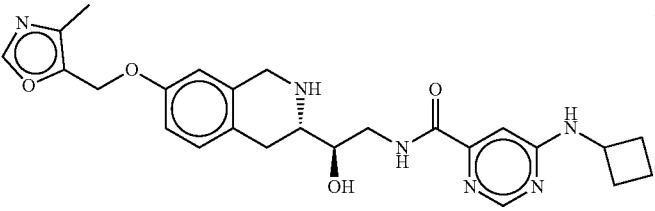 | 32 | b | cc | aaa | A | b* | aa* | B* |
| 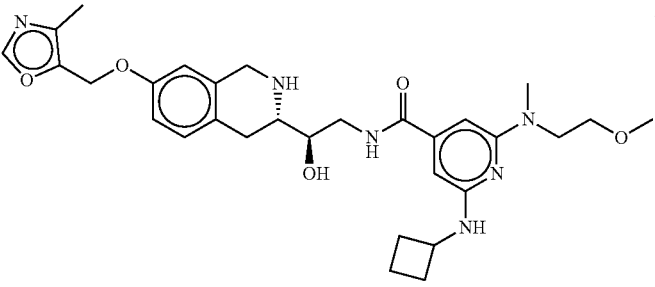 | 33 | b | bb | bbb | A | b* | aa* | B* |

TABLE 1-continued
Exemplary compounds of the invention and biological data
| Structure | Nr. | SAM IC50 | No Co-factor IC50 | MTA IC50 | SAM/ MTA Ratio | HAP1 MTAP Intact $IC_{50}$ | HAP1 MTAP Deleted $IC_{50}$ | MTAP Intact/ Deleted Ratio |
|---|---|---|---|---|---|---|---|---|
| 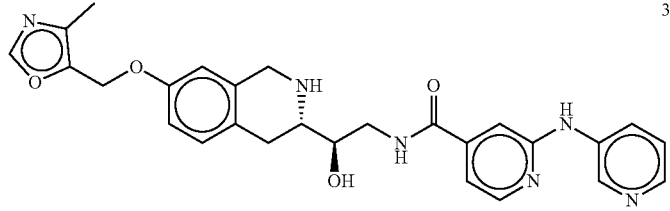 | 34 | b | bb | aaa | A | c* | bb* | B* |
| 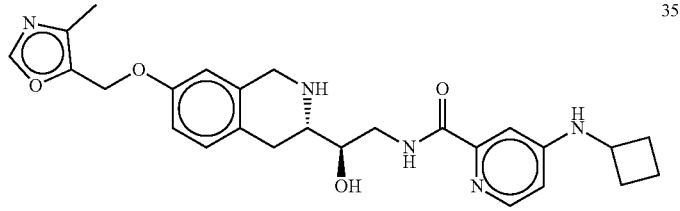 | 35 | b | cc | aaa | A | b* | aa* | A* |
| 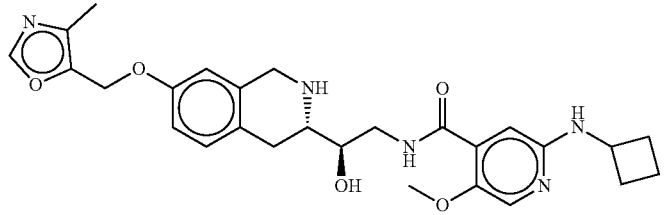 | 36 | b | cc | aaa | A | b* | aa* | B* |
| 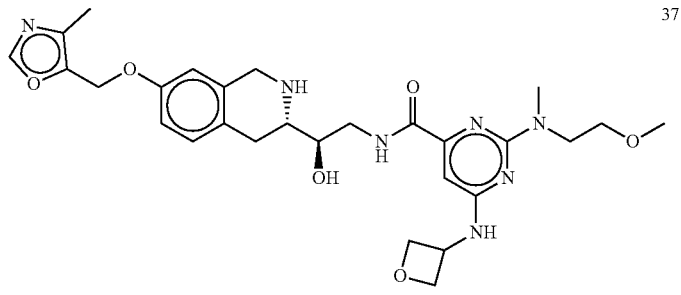 | 37 | c | dd | ccc | A | | | |
| 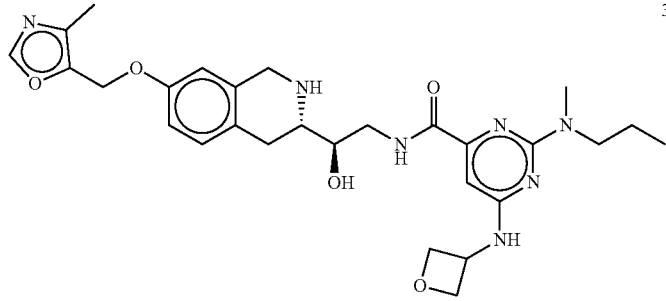 | 38 | c | dd | ccc | A | | | |

TABLE 1-continued

Exemplary compounds of the invention and biological data

| Structure | Nr. | SAM IC50 | No Co-factor IC50 | MTA IC50 | SAM/ MTA Ratio | HAP1 MTAP Intact IC$_{50}$ | HAP1 MTAP Deleted IC$_{50}$ | MTAP Intact/ Deleted Ratio |
|---|---|---|---|---|---|---|---|---|
| | 39 | b | bb | aaa | A | b* | aa* | A* |
| | 40 | b | bb | aaa | A | b* | aa* | A* |
| | 41 | b | cc | aaa | A | c* | bb* | B* |
| | 42 | b | bb | bbb | A | a* | aa* | A* |
| | 43 | b | bb | aaa | A | b* | aa* | A* |

TABLE 1-continued

Exemplary compounds of the invention and biological data

| Structure | Nr. | SAM IC50 | No Co-factor IC50 | MTA IC50 | SAM/ MTA Ratio | HAP1 MTAP Intact $IC_{50}$ | HAP1 MTAP Deleted $IC_{50}$ | MTAP Intact/ Deleted Ratio |
|---|---|---|---|---|---|---|---|---|
| 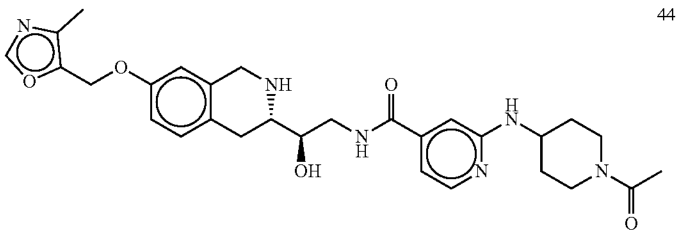 | 44 | b | bb | aaa | A | c* | bb* | B* |
| 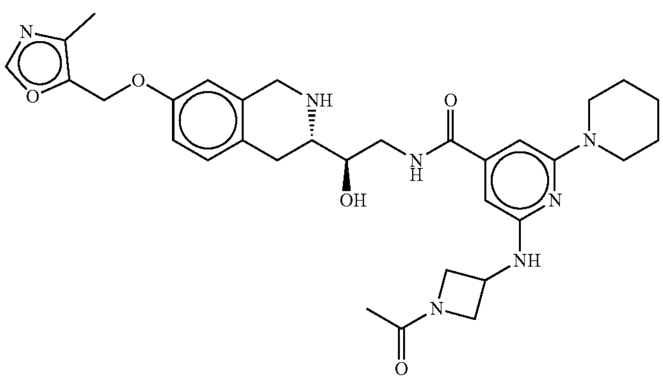 | 45 | b | bb | aaa | A | c* | aa* | A* |
| 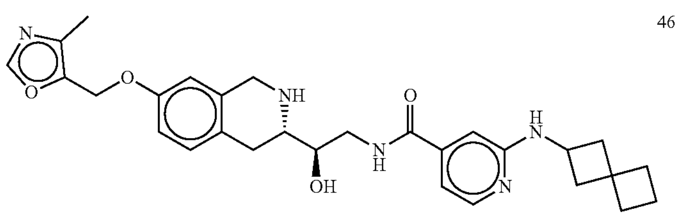 | 46 | b | bb | aaa | A | a* | aa* | B* |
| 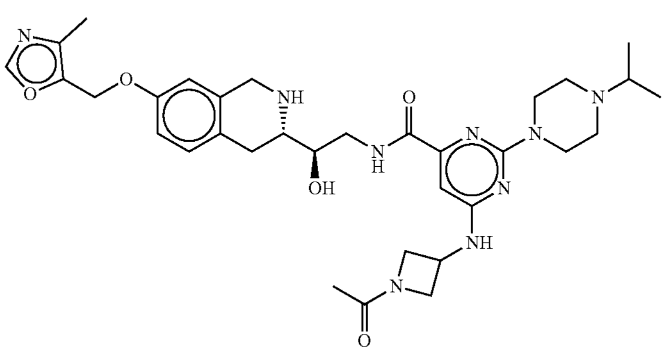 | 47 | b | bb | aaa | A | c* | bb* | C* |

TABLE 1-continued

Exemplary compounds of the invention and biological data

| Structure | Nr. | SAM IC50 | No Co-factor IC50 | MTA IC50 | SAM/ MTA Ratio | HAP1 MTAP Intact IC$_{50}$ | HAP1 MTAP Deleted IC$_{50}$ | MTAP Intact/ Deleted Ratio |
|---|---|---|---|---|---|---|---|---|
| 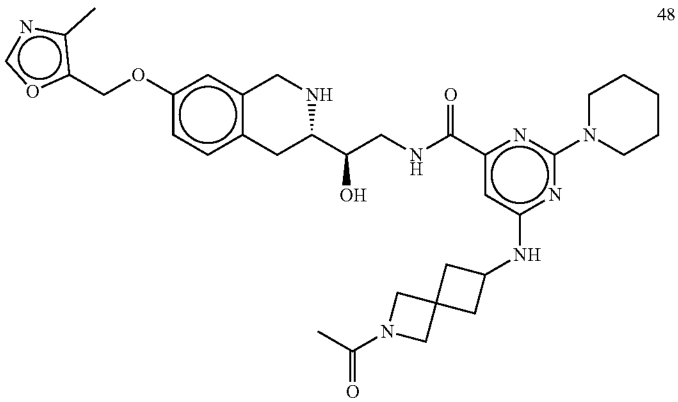 | 48 | b | aa | aaa | A | a* | aa* | A* |
| 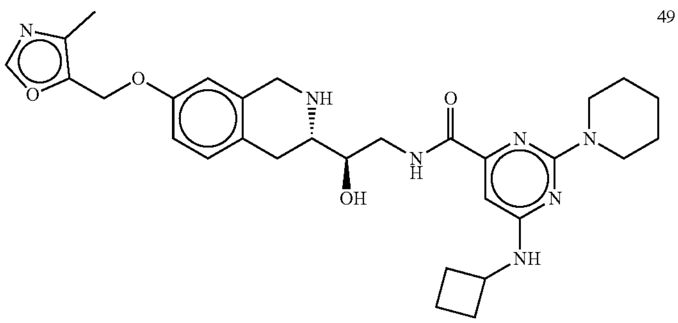 | 49 | b | bb | aaa | A | b* | aa* | A* |
| 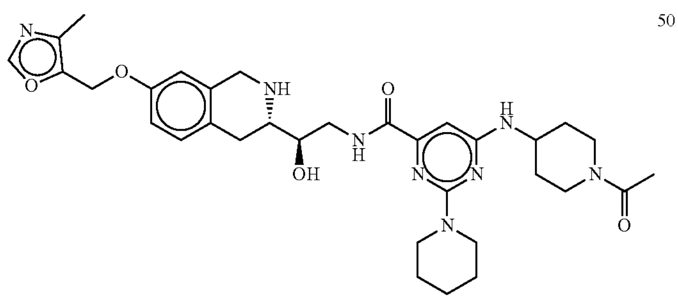 | 50 | b | bb | aaa | A | a* | aa* | A* |
| 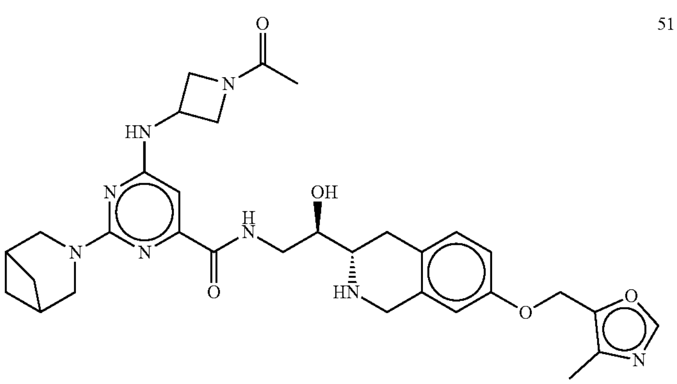 | 51 | b | bb | aaa | A | b* | aa* | A* |

TABLE 1-continued
Exemplary compounds of the invention and biological data
| Structure | Nr. | SAM IC50 | No Co-factor IC50 | MTA IC50 | SAM/ MTA Ratio | HAP1 MTAP Intact IC$_{50}$ | HAP1 MTAP Deleted IC$_{50}$ | MTAP Intact/ Deleted Ratio |
|---|---|---|---|---|---|---|---|---|
| 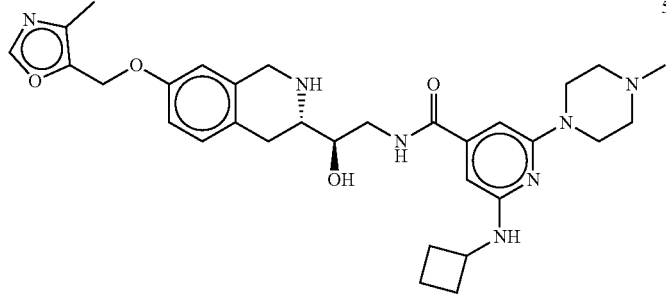 | 52 | b | bb | aaa | A | a* | aa* | A* |
| 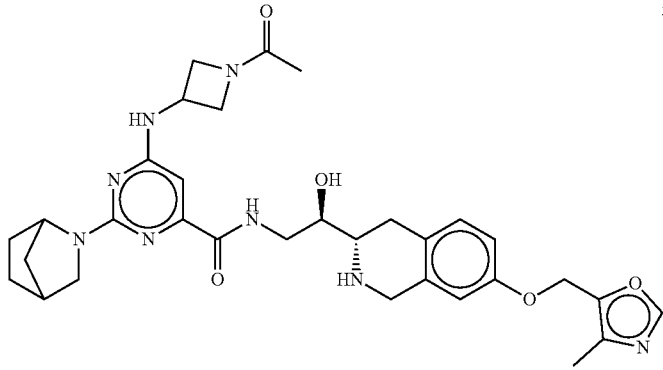 | 53 | b | bb | aaa | A | b* | aa* | A* |
| 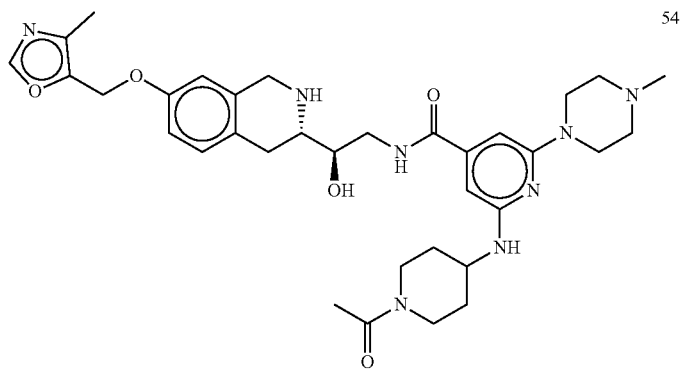 | 54 | b | bb | aaa | A | c* | bb* | C* |
| 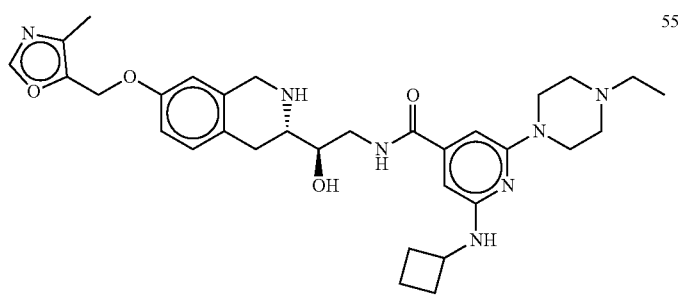 | 55 | b | bb | aaa | A | a* | aa* | B* |

TABLE 1-continued

Exemplary compounds of the invention and biological data

| Structure | Nr. | SAM IC50 | No Co-factor IC50 | MTA IC50 | SAM/ MTA Ratio | HAP1 MTAP Intact IC$_{50}$ | HAP1 MTAP Deleted IC$_{50}$ | MTAP Intact/ Deleted Ratio |
|---|---|---|---|---|---|---|---|---|
| 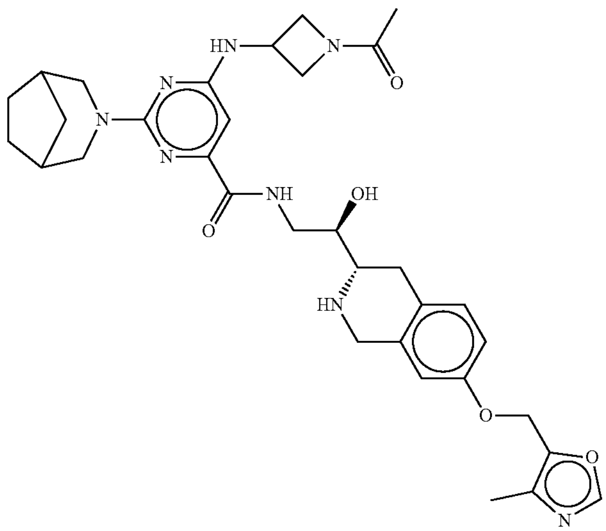 | 56 | b | bb | aaa | A | b* | aa* | A* |
| 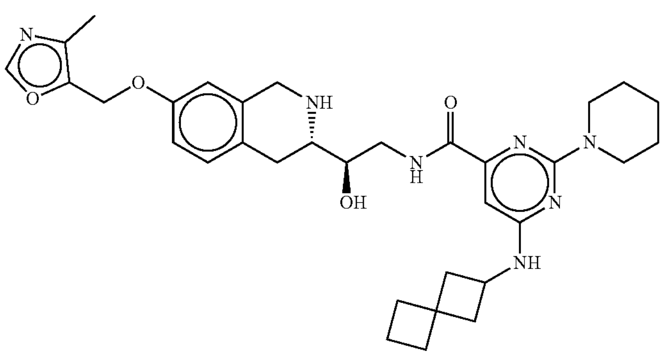 | 57 | b | bb | bbb | A | b* | aa* | A* |
| 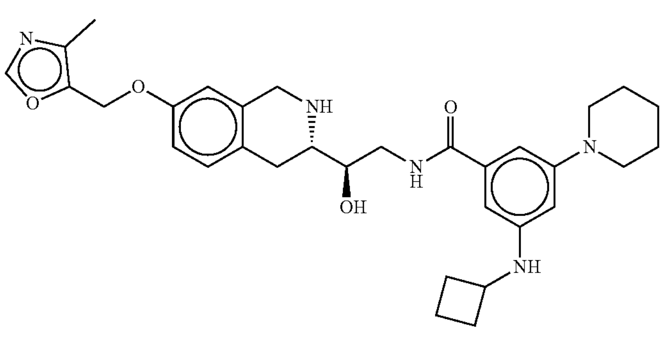 | 58 | b | bb | aaa | A | b* | aa* | A* |

TABLE 1-continued

Exemplary compounds of the invention and biological data

| Structure | Nr. | SAM IC50 | No Co-factor IC50 | MTA IC50 | SAM/ MTA Ratio | HAP1 MTAP Intact $IC_{50}$ | HAP1 MTAP Deleted $IC_{50}$ | MTAP Intact/ Deleted Ratio |
|---|---|---|---|---|---|---|---|---|
| 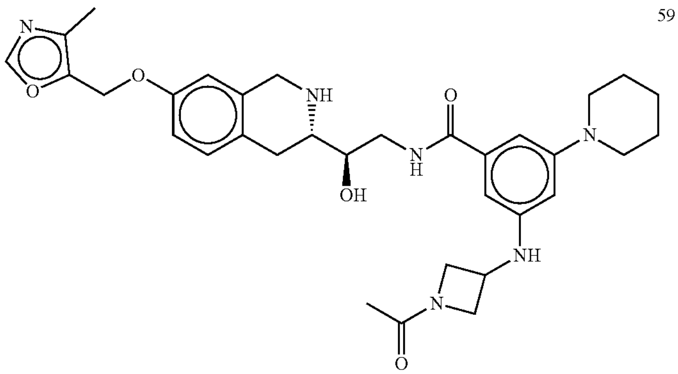 | 59 | b | bb | bbb | A | c* | cc* | C* |
| 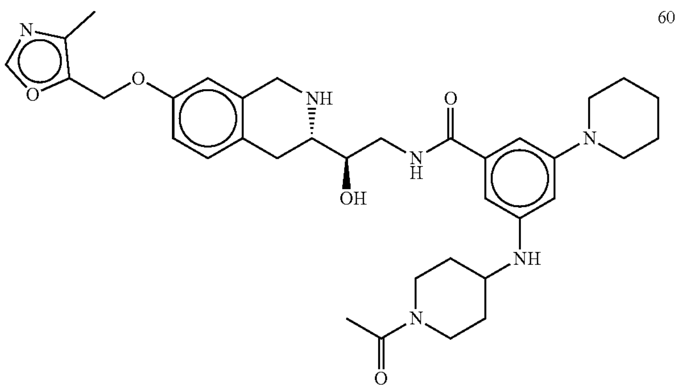 | 60 | b | bb | aaa | A | c* | bb* | C* |
| 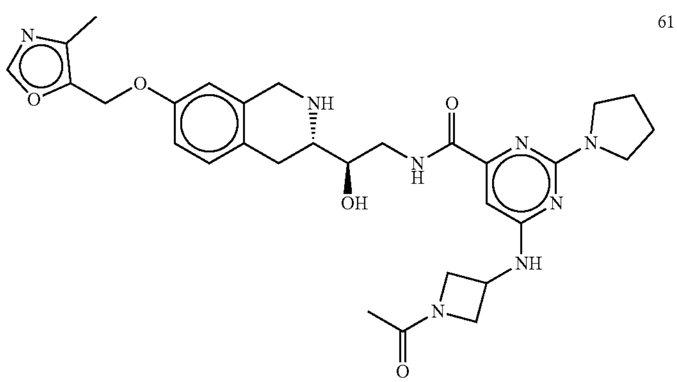 | 61 | b | bb | aaa | A | c* | aa* | A* |
| 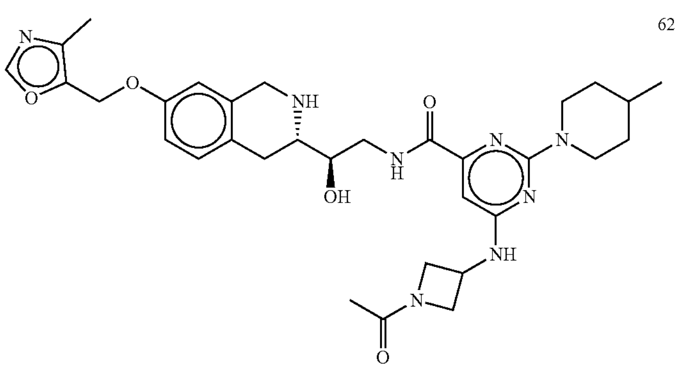 | 62 | b | bb | aaa | A | b* | aa* | A* |

TABLE 1-continued

Exemplary compounds of the invention and biological data

| Structure | Nr. | SAM IC50 | No Co-factor IC50 | MTA IC50 | SAM/ MTA Ratio | HAP1 MTAP Intact IC$_{50}$ | HAP1 MTAP Deleted IC$_{50}$ | MTAP Intact/ Deleted Ratio |
|---|---|---|---|---|---|---|---|---|
| 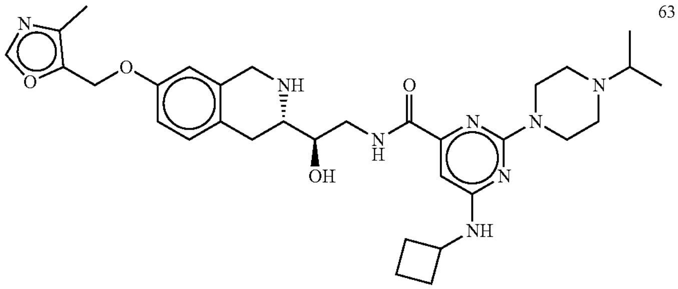 | 63 | b | bb | aaa | A | a* | aa* | C* |
| 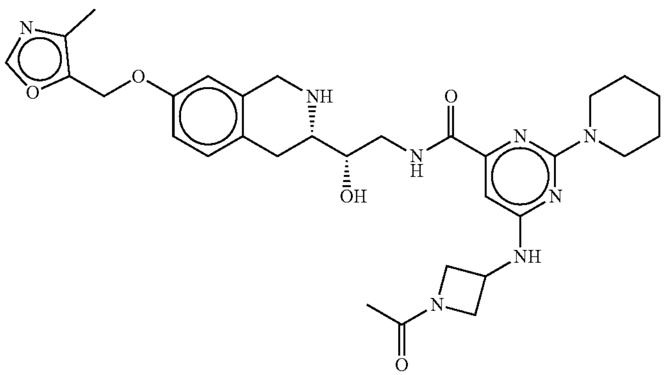 | 64 | b | cc | bbb | A | | bb* | |
| 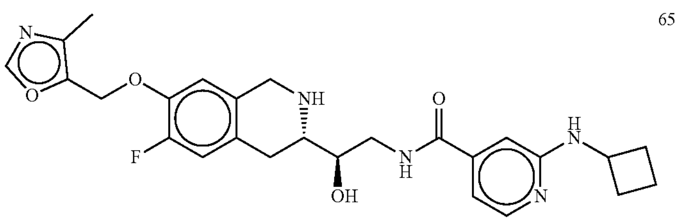 | 65 | | cc | aaa | | c* | aa* | A* |
| 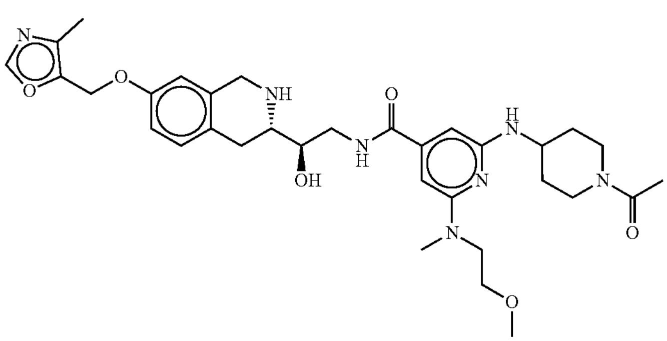 | 66 | | bb | aaa | | c* | aa* | A* |

TABLE 1-continued
Exemplary compounds of the invention and biological data
| Structure | Nr. | SAM IC50 | No Co-factor IC50 | MTA IC50 | SAM/MTA Ratio | HAP1 MTAP Intact IC$_{50}$ | HAP1 MTAP Deleted IC$_{50}$ | MTAP Intact/Deleted Ratio |
|---|---|---|---|---|---|---|---|---|
| 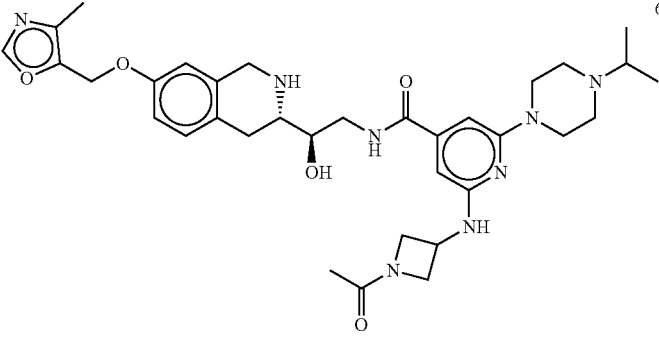 | 67 | bb | aaa | | | c* | bb* | C* |
| 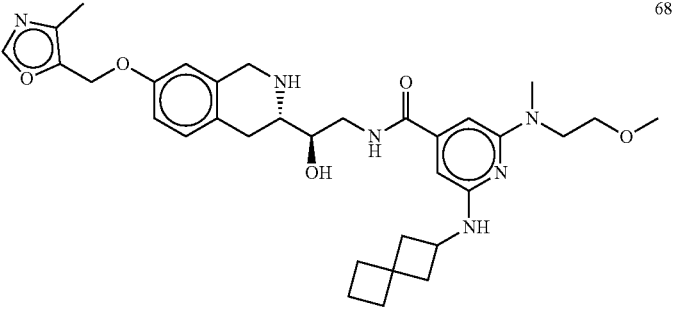 | 68 | bb | aaa | | | b* | aa* | A* |
| 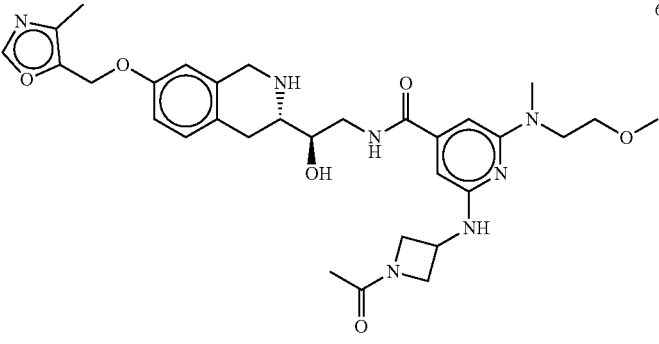 | 69 | bb | aaa | | | c* | bb* | C* |
| 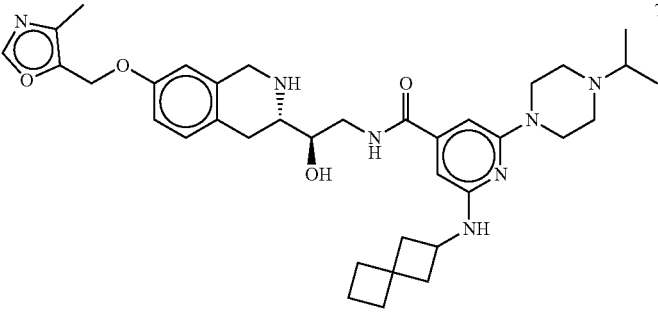 | 70 | aa | aaa | | | a* | aa* | B* |

TABLE 1-continued

Exemplary compounds of the invention and biological data

| Structure | Nr. | SAM IC50 | No Co-factor IC50 | MTA IC50 | SAM/MTA Ratio | HAP1 MTAP Intact IC$_{50}$ | HAP1 MTAP Deleted IC$_{50}$ | MTAP Intact/Deleted Ratio |
|---|---|---|---|---|---|---|---|---|
| 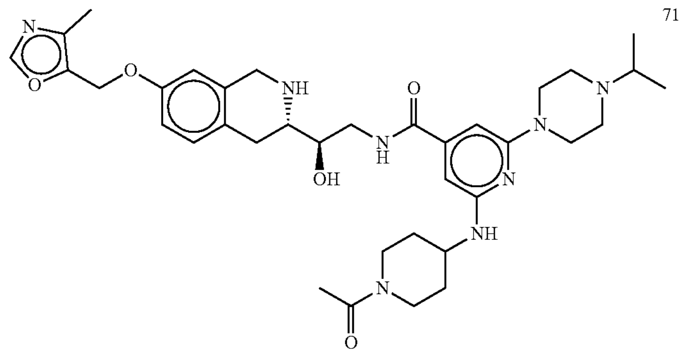 | 71 | aa | aaa | | | c* | bb* | B* |
| 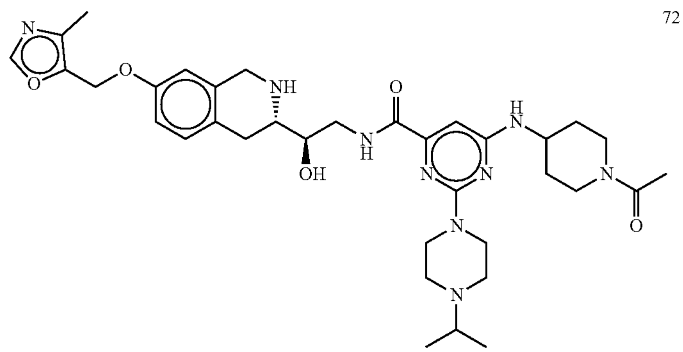 | 72 | bb | aaa | | | B* | aa* | A* |
| 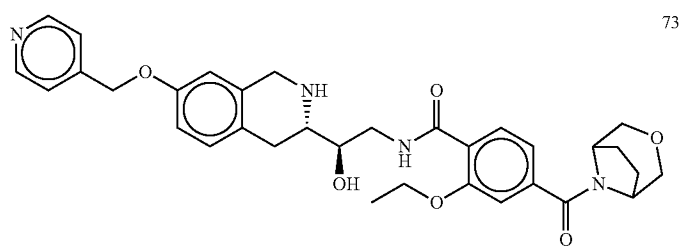 | 73 | dd | bbb | | | | bb* | |
| 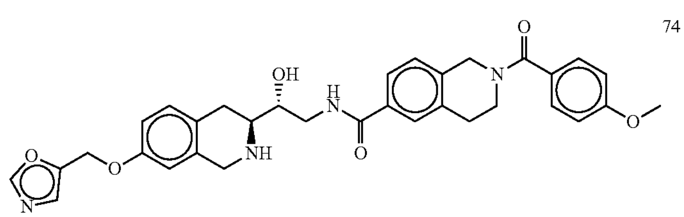 | 74 | bb | aaa | | | | aa* | |
| 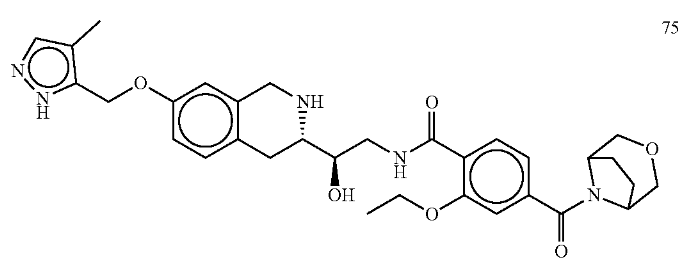 | 75 | | | | | | | |

TABLE 1-continued

Exemplary compounds of the invention and biological data

| Structure | Nr. | SAM IC50 | No Co-factor IC50 | MTA IC50 | SAM/ MTA Ratio | HAP1 MTAP Intact IC$_{50}$ | HAP1 MTAP Deleted IC$_{50}$ | MTAP Intact/ Deleted Ratio |
|---|---|---|---|---|---|---|---|---|
| 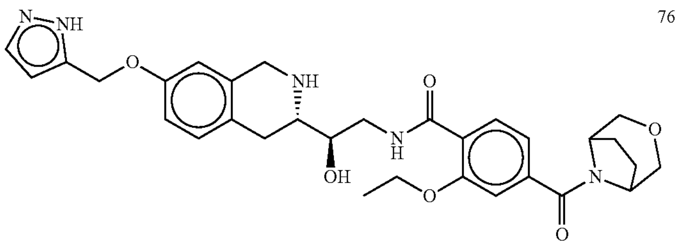 | 76 | cc | bbb | | c* | | | |
| 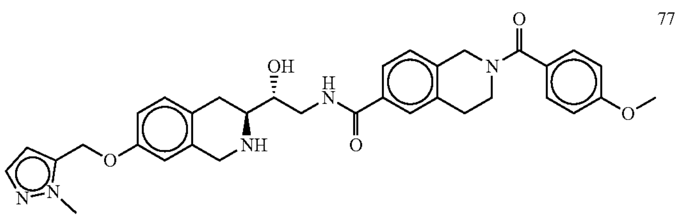 | 77 | cc | aaa | | b* | | | |
| 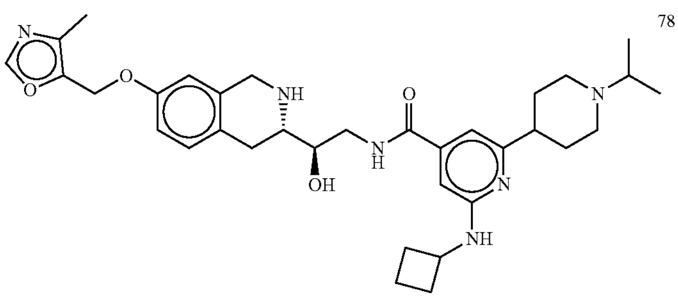 | 78 | bb | aaa | | b* | aa* | A* | |
| 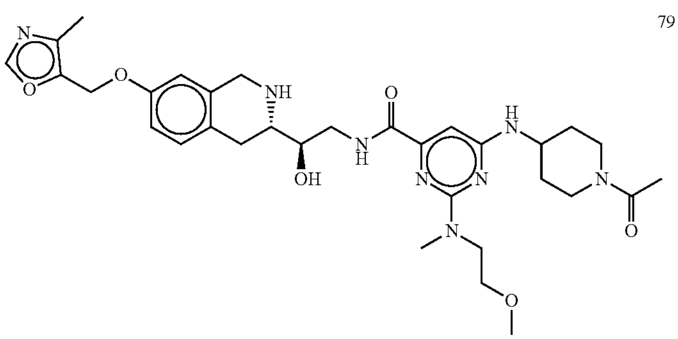 | 79 | bb | aaa | | b* | aa* | A* | |
| 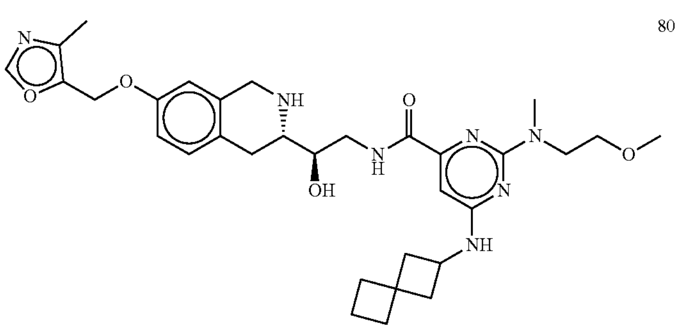 | 80 | bb | aaa | | b* | aa* | A* | |

TABLE 1-continued
Exemplary compounds of the invention and biological data
| Structure | Nr. | No Co-factor IC50 | SAM IC50 | MTA IC50 | SAM/ MTA Ratio | HAP1 MTAP Intact $IC_{50}$ | HAP1 MTAP Deleted $IC_{50}$ | MTAP Intact/ Deleted Ratio |
|---|---|---|---|---|---|---|---|---|
| 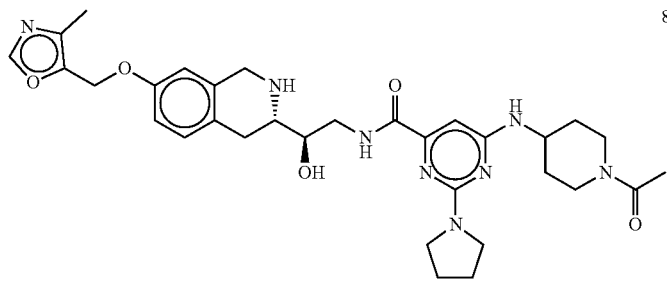 | 81 | | bb | aaa | | b* | aa* | A* |
| 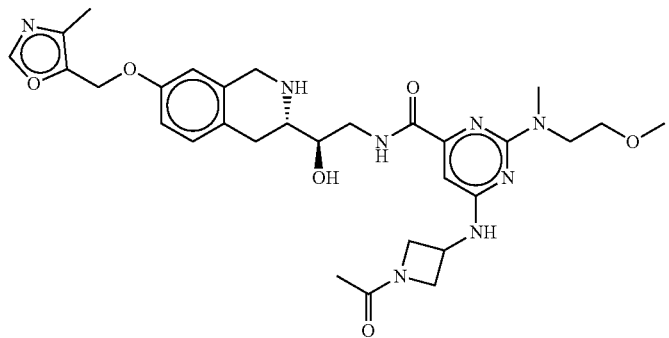 | 82 | | bb | aaa | | c* | aa* | A* |
| 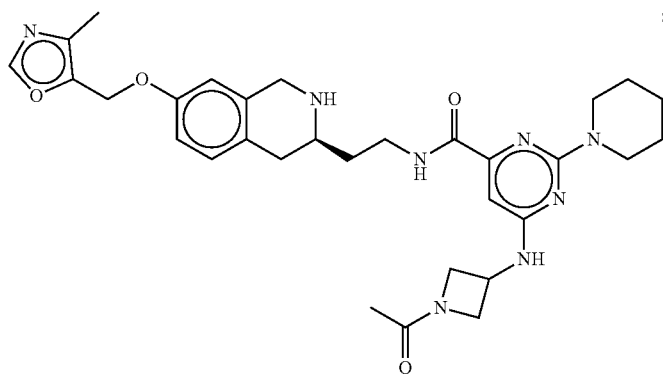 | 83** | | bb | aaa | | | | |
| 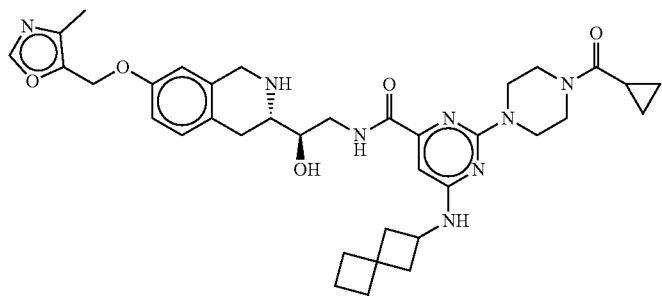 | 84 | | aa | aaa | | | | |

TABLE 1-continued

Exemplary compounds of the invention and biological data

| Structure | Nr. | SAM IC50 | No Co-factor IC50 | MTA IC50 | SAM/ MTA Ratio | HAP1 MTAP Intact IC$_{50}$ | HAP1 MTAP Deleted IC$_{50}$ | MTAP Intact/ Deleted Ratio |
|---|---|---|---|---|---|---|---|---|
| 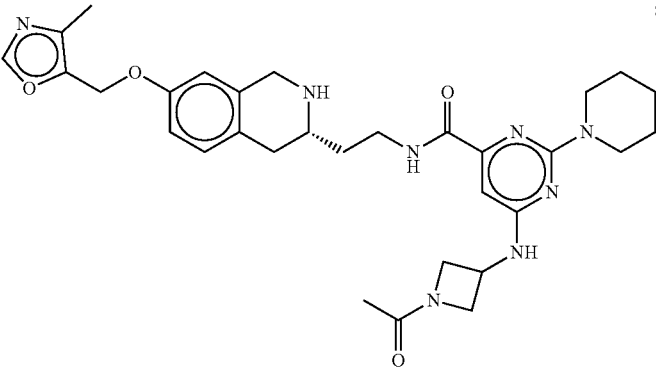 | 85** | cc | | bbb | | | | |
| 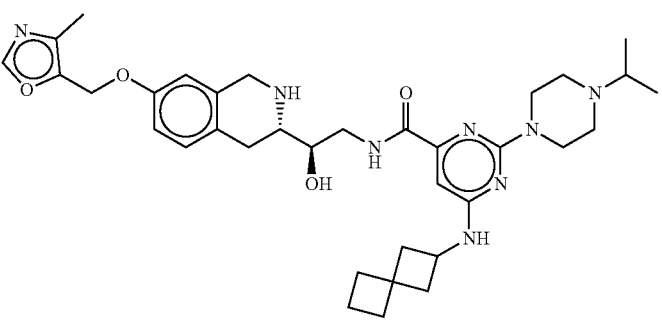 | 86 | aa | | aaa | | | | |

In some embodiments, compounds of Formula (I) and (Ia) described herein can be prepared using methods illustrated in Scheme 1.

As used herein, LG$^1$ is a leaving group as defined herein. In some embodiments LG$^1$ is halogen (e.g., fluoro, chloro, bromo, iodo). As used herein, PG$^1$ and PG$^3$ are nitrogen protecting groups as defined herein (e.g., Boc); PG$^2$ is an oxygen protecting group as defined herein (e.g., methoxymethylene (MOM), $^t$Bu, Me). G is an oxygen protective group as defined herein (e.g., $^t$Bu, Me)

Protected isoquinoline A or Aa reacts with a suitable carboxylic acid or carboxylate B to give intermediates of formula C or Ca, which can be deprotected (e.g., by simultaneous removal of PG$^1$ and PG$^2$) under acidic conditions (e.g., TFA, HCl (e.g., 4M HCl) in a suitable solvent (e.g., methanol, dichloromethane, dioxane, diethylether) to provide the isoquinoline intermediate D or Da. In certain embodiments, the reaction of A and B takes place under basic conditions (e.g., a carbonate base (Cs$_2$CO$_3$, NaHCO$_3$, Na$_2$CO$_3$), an amine base (e.g., DIPEA, TEA, DBU)) in an appropriate solvent (e.g., DMF, MTBE, DCM). In certain embodiments, the reaction additionally takes place in the presence of an amide coupling agent (e.g., HATU, HOBT, HBTU, PyBop). Intermediates D and Da can be re-protected by treatment with a suitable protecting agent (e.g., Boc$_2$O) in the presence of a base (e.g., a carbonate base (CsCO$_3$, NaHCO$_3$, Na$_2$CO$_3$), an amine base (e.g., DIPEA, TEA, DBU)) in an acceptable solvent (e.g., THF, H$_2$O, DCM), to provide intermediates E and Ea.

Intermediates E and Ea can react with R$^1$—CH$_2$-LG$^1$ (Intermediate J) to provide structures F and Fa, respectively. In certain embodiments, (e.g., when LG$^1$ is a halogen such as fluoro, bromo or iodo) the reaction takes place under basic conditions (e.g., a carbonate base (CsCO$_3$, NaHCO$_3$, Na$_2$CO$_3$), an amine base (e.g., DIPEA, TEA, DBU)) in an appropriate solvent (e.g., DMF, MTBE, DCM). In certain embodiments an iodide salt (e.g., sodium iodide) is also added.

Intermediates of formula F or Fa can be deprotected under acidic conditions (e.g., TFA, HCl (e.g., 4M HCl) in a suitable solvent (e.g., methanol, dichloromethane, dioxane, diethylether) to provide the final products I or Ia, respectively.

Scheme 1.
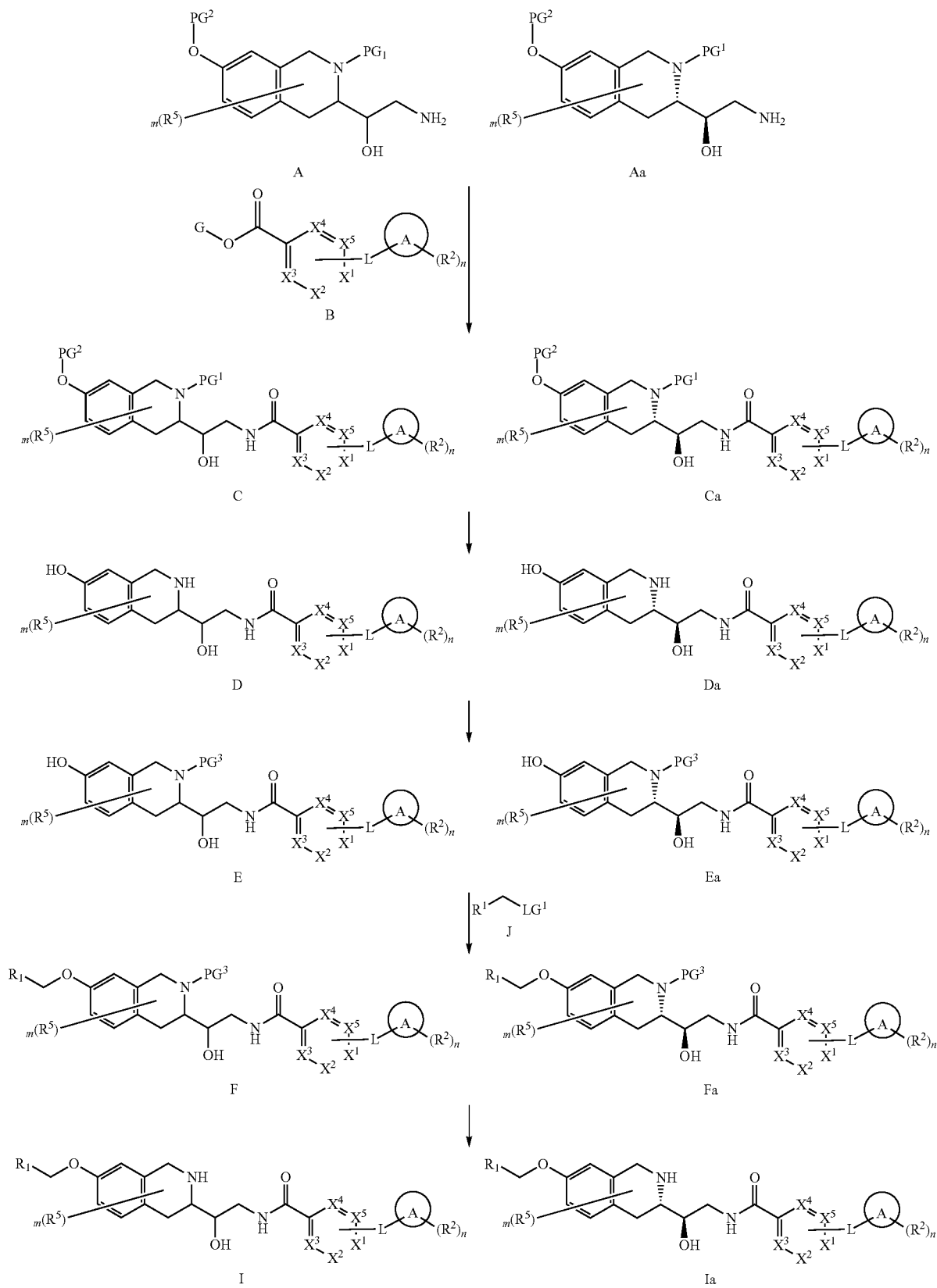

Further, intermediates of Formula Aa can be prepared as shown in Scheme 2.

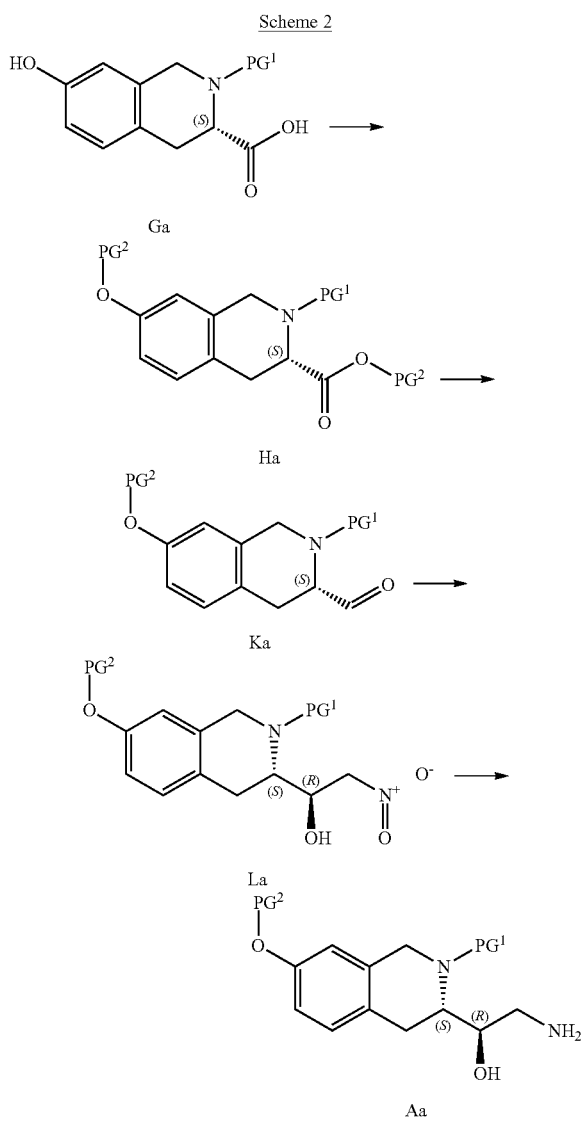

The isoquinoline carboxylic acid Ga can be protected by treatment with a suitable protecting group precursor (e.g., MOMCl). The reaction can be carried out in a suitable solvent (e.g., DMF, DCM, THF). Optionally, the reaction can be carried out in the presence of a base (e.g., a carbonate base ($CsCO_3$, $NaHCO_3$, $Na_2CO_3$) or an amine base (e.g., DIPEA, TEA, DBU)). The carboxylate moiety of Ha can be reduced to a carbonyl group using a reducing agent (e.g., $NaBH_4$, $NaBH(OAc)_3$, DIBAL-H) in a suitable solvent or combination of solvents (e.g., an alcohol solvent such as MeOH, EtOH, $^i$PrOH, an aprotic solvent such as DCM, $Et_2O$, DCE, or a combination thereof). Aldehyde Ka can be treated with $MeNO_2$ in a suitable solvent (e.g., EtOH, MTBE, $Et_2O$ or a combination thereof) in the presence of a chiral amine (e.g., (1R,2R)—$N^1$,$N^2$-bis(4-chlorobenzyl)cyclohexane-1,2-diamine)) and a metal salt (e.g., $Cu(OAc)_2$) to provide compound La, which can be reduced to intermediate Aa, for example under catalytic hydrogenation conditions in a suitable solvent (e.g., MeOH, EtOAc). The catalytic hydrogenation conditions can utilize a metal catalyst (e.g., a Pd catalyst, e.g., Pd/C) in the presence of hydrogen gas.

Alternative Embodiments

In an alternative embodiment, compounds described herein may also comprise one or more isotopic substitutions. For example, hydrogen may be $^2H$ (D or deuterium) or $^3H$ (T or tritium); carbon may be, for example, $^{13}C$ or $^{14}C$; oxygen may be, for example, $^{18}O$; nitrogen may be, for example, $^{15}N$, and the like. In other embodiments, a particular isotope (e.g., $^3H$, $^{13}C$, $^{14}C$, $^{18}O$, or $^{15}N$) can represent at least 1%, at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, at least 99%, or at least 99.9% of the total isotopic abundance of an element that occupies a specific site of the compound.

Pharmaceutical Compositions

In another aspect, the invention provides a pharmaceutical composition comprising a pharmaceutically acceptable carrier and an effective amount of a compound described herein (e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1), or a pharmaceutically acceptable salt thereof.

The term "pharmaceutically acceptable carrier or adjuvant" refers to a carrier or adjuvant that may be administered to a patient, together with a compound provided herewith, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions provided herewith include, but are not limited to, ion exchangers, alumina, aluminum stearate, lecithin, self emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose based substances, polyethylene glycol, sodium carboxymethylcellulose, polyacrylates, waxes, polyethylene polyoxypropylene block polymers, polyethylene glycol and wool fat. Cyclodextrins such as α-, β-, and γ-cyclodextrin, or chemically modified derivatives such as hydroxyalkylcyclodextrins, including 2 and 3 hydroxypropyl-o-cyclodextrins, or other solubilized derivatives may also be advantageously used to enhance delivery of compounds of the formulae described herein.

When employed as pharmaceuticals, the compounds provided herein are typically administered in the form of a pharmaceutical composition. Such compositions can be prepared in a manner well known in the pharmaceutical art and comprise at least one active compound.

In one embodiment, with respect to the pharmaceutical composition, the carrier is a parenteral carrier, oral or topical carrier.

The present invention also relates to a compound described herein (e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) (or pharmaceutical composition thereof) for use as a pharmaceutical or a medicament (e.g., a medicament for the treatment of an MTAP-deficient and/or an MTA-accumulating disease in a subject in need thereof). In one embodiment, the disease is a proliferating disease. In a further embodiment, the disease is an MTAP-deficient and/or MTA-accumulating cancer. In one embodiment, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

The present invention also relates to a compound described herein (e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) (or pharmaceutical composition thereof) for use in the treatment of an MTAP-deficient and/or an MTA-accumulating disease in a subject in need thereof. In one embodiment, the disease is a proliferating disease. In a further embodiment, the disease is an MTAP-deficient and/or MTA-accumulating cancer. In one embodiment, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

The present invention also relates to a compound described herein (e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) (or pharmaceutical composition thereof) for use in the manufacturing of a medicament (e.g., a medicament for the treatment of an MTAP-deficient and/or an MTA-accumulating disease in a subject in need thereof). In one embodiment, the disease is a proliferating disease. In a further embodiment, the disease is an MTAP-deficient and/or MTA-accumulating cancer. In one embodiment, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

Generally, the compounds provided herein are administered in a therapeutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions provided herewith may be administered orally, parenterally, by inhalation spray, topically, rectally, nasally, buccally, vaginally or via an implanted reservoir, preferably by oral administration or administration by injection. The pharmaceutical compositions provided herewith may contain any conventional non-toxic pharmaceutically acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like. The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

Transdermal compositions are typically formulated as a topical ointment or cream containing the active ingredient (s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The pharmaceutical compositions provided herewith may also be administered in the form of suppositories for rectal administration. These compositions can be prepared by mixing a compound provided herewith with a suitable non irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions provided herewith may be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The above-described components for orally administrable, injectable or topically administrable, rectally administrable and nasally administrable compositions are merely representative. Other materials as well as processing techniques and the like are set forth in Part 8 of *Remington's Pharmaceutical Sciences,* 17th edition, 1985, Mack Publishing Company, Easton, Pennsylvania, which is incorporated herein by reference.

The compounds of this invention can also be administered in sustained release forms or from sustained release drug delivery systems. A description of representative sustained release materials can be found in *Remington's Pharmaceutical Sciences.*

When the compositions provided herewith comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds provided herewith. Alternatively, those agents may be part of a single dosage form, mixed together with the compounds provided herewith in a single composition.

The present invention also relates to the pharmaceutically acceptable acid addition salt of a compound described herein (e.g., compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1).

The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions provided herewith will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination provided herewith may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long term basis upon any recurrence of disease symptoms.

Methods of Treatment and Use

Treatment of MTAP-Deficient and/or MTA-Accumulating Proliferation Disorders

In one embodiment, the present invention provides methods of treating human or animal subjects having or having been diagnosed with an MTAP-deficiency-related and/or MTA-accumulating proliferative disorder (e.g., cancer) comprising administering to the subject in need thereof a therapeutically effective amount of a compound of the present invention (e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1) or a pharmaceutically acceptable salt thereof.

In one embodiment, the present invention provides methods of an MTAP-deficiency-related and/or MTA-accumulating proliferative disorder (e.g., cancer) in a subject in need thereof comprising administering to the subject a therapeutically effective amount of a compound of the present invention (e.g., compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1) or a pharmaceutically acceptable salt thereof.

In one embodiment, the present invention provides methods of treating human or animal subjects having or having been diagnosed with an MTAP-deficiency-related and/or MTA-accumulating proliferative disorder (e.g., cancer) comprising administering to the subject in need thereof a therapeutically effective amount of pharmaceutical composition of the present invention (e.g., a composition comprising a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof and a pharmaceutically acceptable carrier). In one embodiment, the compound or composition is administered in combination with a second therapeutic agent.

In one embodiment, the present invention provides methods of treating an MTAP-deficiency-related and/or MTA-accumulating proliferative disorder (e.g., cancer) in a subject in need thereof comprising administering to the subject a therapeutically effective amount of pharmaceutical composition of the present invention (e.g., a composition comprising a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof and a pharmaceutically acceptable carrier). In one embodiment, the compound or composition is administered in combination with a second therapeutic agent.

In certain embodiments, the disease is an MTAP-deficient and/or MTA-accumulating cancer.

In one embodiment, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

In one embodiment, the cancer is an MTAP-deficient and/or MTA-accumulating glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

The PRMT5 inhibitors (e.g., an MTA-uncompetitive PRMT5 inhibitor, e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) described herein can be used in a method of inhibiting proliferation of MTAP-deficient cells in a subject in need thereof, the method comprising the step of administering to the subject, a PRMT5 inhibitor (e.g., an MTA-uncompetitive PRMT5 inhibitor, e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) in an amount that is effective to inhibit proliferation of the MTAP-deficient cells. In one embodiment, the subject in need thereof suffers from a cancer selected from glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

The PRMT5 inhibitors (e.g., an MTA-uncompetitive PRMT5 inhibitor, e.g., a compound of Formula (I), (Ia), (II), (IIa), (IIa1), (IIa1i), (IIa2), (IIa2i), (IIa3), (IIa3i), (IIa3ii) (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) described herein can be used in a method of inhibiting proliferation of MTA-accumulating cells in a subject in need thereof, the method comprising the step of administering to the subject, a PRMT5 inhibitor (e.g., an MTA-uncompetitive PRMT5 inhibitor, e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) in an amount that is effective to inhibit proliferation of the MTA-accumulating cells. In one embodiment, the subject in need thereof suffers from a cancer selected from glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

The PRMT5 inhibitors (e.g., an MTA-uncompetitive PRMT5 inhibitor, e.g., a compound of Formula (I), (Ia), (II), (IIa), (IIa1), (IIa1i), (IIa2), (IIa2i), (IIa3), (IIa3i), (IIa3ii) (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) described herein can be used in a method of inhibiting proliferation of MTAP deficient and/or MTA-accumulating cells in a subject in need thereof, the method comprising the step of administering to the subject, a PRMT5 inhibitor (e.g., an MTA-uncompetitive PRMT5 inhibitor, e.g., a compound of Formula (I), (Ia), (II), (IIa), (IIa1), (IIa1i), (IIa2), (IIa2i), (IIa3), (IIa3i), (IIa3ii) (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) in an amount that is effective to inhibit proliferation of the MTAP deficient and/or MTA-accumulating cells. In one embodiment, the subject in need thereof suffers from a cancer selected from glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

Combination Therapies

The present invention provides methods of treatment of MTAP-deficient and/or MTA accumulating proliferative disorders (e.g., cancers) with a PRMT5 inhibitor (e.g., an MTA-uncompetitive PRMT5 inhibitor, e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) in combination with a second therapeutic agent.

The term "Combination" refers to either a fixed combination in one dosage unit form, or a combined administration where a compound of the present invention (e.g., a compound of Formula (I), (Ia), (II), (IIa), (Ial), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) and a combination partner (e.g., another drug as explained below, also referred to as "therapeutic agent" or "co-agent") may be administered independently at the same time or separately within time intervals, especially where these time intervals allow that the combination partners show a cooperative, e.g., synergistic effect. The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one therapeutic agent and includes both fixed and non-fixed combinations of the therapeutic agents. The term "fixed combination" means that the therapeutic agents, e.g., a compound of the present invention (e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) and a combination partner, are both administered to a patient simultaneously in the form of a single entity or dosage. The term "non-fixed combination" means that the therapeutic agents, e.g., a compound of the present invention (e.g., a compound of Formula (I), (Ia), (II), (IIa), (IIIa1), (IIIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more therapeutic agent.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., tablets, capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times.

In certain embodiments, compounds of the present invention are combined with other therapeutic agents, including, but not limited to, other anti-cancer agents, anti-allergic agents, anti-nausea agents (or anti-emetics), pain relievers, cytoprotective agents, and combinations thereof.

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N₄-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), nab-paclitaxel (Abraxane®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Further compounds of particular interest for combinations with the compounds of the present invention include: EGFR-inhibitors, such as cetuximab, panitumimab, erlotinib, gefitinib and EGFRi NOS; MAPK-pathway inhibitors, such as BRAFi, panRAFi, MEKi, ERKi; PI3K-mTOR pathway inhibitors, such as alpha-specific PI3Ki, pan-class I PI3Ki and mTOR/PI3Ki, particularly everolimus and analogues thereof.

Specific compounds and classes of compounds acting via specific mechanisms can be particularly effective in conjunction with PRMT5 inhibitors (e.g., MTA-uncompetitive PRMT5 inhibitors, e.g., compounds of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or compounds of Table 1, or pharmaceutically acceptable salts thereof). For example, PRMT5 is known to associate with SWI/SNF chromatin remodeling complexes along with other co-repressor molecules like HDAC2. PRMT5 activity on target H4R3 and H3R8 is enhanced when lysine residues become deacetylated by HDAC enzymes. Thus, HDAC inhibitors can be effective (e.g., synergistic) when used in conjunction with PRMT5 inhibitors (WO 011/079236).

Thus, PRMT5 inhibitors of the present disclosure can be used in combination with other compounds, for example: HDAC inhibitor or DNA methyltransferase inhibitor. In some embodiments, the HDAC inhibitor is Trichostatin A. In some embodiments, the DNA methyltransferase inhibitor is 5-azacytidine.

A PRMT5 inhibitor (e.g., MTA-uncompetitive PRMT5 inhibitors e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) can also be administered or co-administered in any order with a MAT2A inhibitor.

A PRMT5 inhibitor (e.g., MTA-uncompetitive PRMT5 inhibitors e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) can also be administered or co-administered in any order with an inhibitor of a protein which interacts with or is required for PRMT5 function, including, but not limited to, pICIN, WDR77 or RIOK1.

A PRMT5 inhibitor (e.g., MTA-uncompetitive PRMT5 inhibitors, e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) can be administered in combination with a HDM2 inhibitor and/or with 5-FU. The loss has been observed of wild-type p53 as a consequence of HDM2 activation resulting from CDKN2A deletion. This relates to the inability of MTAP deleted cells to salvage ATP and methionine from endogenous methyl-thioadenosine (MTA). As a consequence, tumor cells become differentially sensitive towards 5-FU and other purine analogues (e.g., 6-thioguanine, 6-mercaptopurine).

Given that CDKN2A/MTAP loss also leads to deregulation of p16/CDK4/6 pathway, PRMT5 inhibitor (e.g., MTA-uncompetitive PRMT5 inhibitors, e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) can be administered in combination with a CDK4 inhibitor, including, but not limited to, LEE011 or a CDK 4/6 inhibitor (e.g., palbociclib (Ibrance®), ribociclib (Kisqali®), and abemaciclib (Verzenio®).

A PRMT5 inhibitor (e.g., MTA-uncompetitive PRMT5 inhibitors, e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) can be administered in combination with targeted treatments contingent on the dependency of individual target tumors on relevant pathways as determined by suitable predictive markers, including but not limited to: inhibitors of HDM2i, PI3K/mTOR-I, MAPKi, RTKi (EGFRi, FGFRi, METi, IGFiRi, JAKi, and WNTi.

A PRMT5 inhibitor (e.g., MTA-uncompetitive PRMT5 inhibitors, e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) can be administered in combination with immunotherapy.

In some embodiments, the compounds described herein are used with a cancer immunotherapy (e.g., a checkpoint blocking antibody) to treat a subject (e.g., a human subject), e.g., having a disease or disorder described herein (e.g., a cancer described herein)).

In some embodiments, the immunotherapeutic agent is an anti-CTLA-4 antibody (e.g., ipilimumab, tremelimumab).

In some embodiments, the immunotherapeutic agent is an anti-PD-1 ligand (e.g., PD-L1 (e.g., B7-HI or CD274); or PD-L2 (e.g., B7-DC or CD273)). In some embodiments, the immunotherapeutic agent is an anti-PD-1 antibody (e.g., anti-PD-1 or anti-PD-L1, e.g., nivolumab (i.e., MDX-1106, BMS-936558, ONO-4538); CT-011; AMP-224; pembrolizumab; pidilizumab; or MK-3475). In some embodiments, the immunotherapeutic agent is an anti-PD-L1 antibody (e.g., BMS936559 (i.e., MDX-1105); MEDI4736; MSB0010718C (avelumab); or MPDL-3280A).

In some embodiments, the immunotherapeutic agent is a checkpoint blocking antibody (e.g., anti-TIM3, anti-LAG3, anti-TIGIT including IMP321 and MGA271).

In some embodiments, the immunotherapeutic agent is a cell-based therapy. In some embodiments, the cell-based therapy is a CAR-T therapy.

In some embodiments, the immunotherapeutic agent is a co-stimulatory antibody (e.g., anti-4-1BB, anti-OX40, anti-GITR, anti-CD27, anti-CD40).

In some embodiments, the immunotherapeutic agent is a cancer vaccine such as a neoantigen. These vaccines can be developed using peptides or RNA, e.g., In some embodiments, the immunotherapeutic agent is an oncolytic virus.

In some embodiments, the immunotherapeutic agent is a STING pathway agonist. Exemplary STING agonists include MK-1454 and ADU-S100.

A PRMT5 inhibitor (e.g., MTA-uncompetitive PRMT5 inhibitors, e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) can be administered in combination with disease-specific huMABs (e.g., an anti-HER3 huMAB)

A PRMT5 inhibitor (e.g., MTA-uncompetitive PRMT5 inhibitors e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) can be administered in combination with ADCs/ADCCs contingent on the expression of relevant surface targets on target tumors of interest.

Some patients may experience allergic reactions to the compounds of the present invention and/or other anti-cancer agent(s) during or after administration; therefore, anti-allergic agents are often administered to minimize the risk of an allergic reaction. Suitable anti-allergic agents include corticosteroids, including, but not limited to, dexamethasone (e.g., Decadron®), beclomethasone (e.g., Beclovent®), hydrocortisone (also known as cortisone, hydrocortisone sodium succinate, hydrocortisone sodium phosphate, and sold under the tradenames Ala-Cort®, hydrocortisone phosphate, Solu-Cortef®, Hydrocort Acetate® and Lanacort®), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-methylprednisolone, methylprednisolone acetate, methylprednisolone sodium succinate, sold under the tradenames Duralone®, Medralone®, Medrol®, M-Prednisol® and Solu-Medrol®); antihistamines, such as diphenhydramine (e.g., Benadryl®), hydroxyzine, and cyproheptadine; and bronchodilators, such as the beta-adrenergic receptor agonists, albuterol (e.g., Proventil®), and terbutaline (Brethine®).

Some patients may experience nausea during and after administration of the compound of the present invention and/or other anti-cancer agent(s); therefore, anti-emetics are used in preventing nausea (upper stomach) and vomiting. Suitable anti-emetics include aprepitant (Emend®), ondansetron (Zofran®), granisetron HCl (Kytril®), lorazepam (Ativan®, dexamethasone (Decadron®), prochlorperazine (Compazine®), casopitant (Rezonic® and Zunrisa®), and combinations thereof.

Medication to alleviate the pain experienced during the treatment period is often prescribed to make the patient more comfortable. Common over-the-counter analgesics, such Tylenol®, are often used. However, opioid analgesic drugs including, but not limited to, hydrocodone/paracetamol or hydrocodone/acetaminophen (e.g., Vicodin®), morphine (e.g., Astramorph® or Avinza®), oxycodone (e.g., OxyContin® or Percocet®), oxymorphone hydrochloride (Opana®), and fentanyl (e.g., Duragesic®) are also useful for moderate or severe pain.

In an effort to protect normal cells from treatment toxicity and to limit organ toxicities, cytoprotective agents (such as neuroprotectants, free-radical scavengers, cardioprotectors, anthracycline extravasation neutralizers, nutrients and the like) may be used as an adjunct therapy. Suitable cytoprotective agents include Amifostine (Ethyol®), glutamine, dimesna (Tavocept®), mesna (Mesnex®), dexrazoxane (Zinecard® or Totect®), xaliproden (Xaprila®), and leucovorin (also known as calcium leucovorin, citrovorum factor and folinic acid).

The structure of the active compounds identified by code numbers, generic or trade names may be taken from the actual edition of the standard compendium "The Merck Index" or from databases, e.g., Patents International (e.g., IMS World Publications).

The above-mentioned compounds, which can be used in combination with a compound of the present invention, can be prepared and administered as described in the art, including, but not limited to, in the documents cited above.

In one embodiment, the present invention provides pharmaceutical compositions comprising at least one compound of the present invention (e.g., a PRMT5 inhibitor, e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1) or a pharmaceutically acceptable salt thereof together with a pharmaceutically acceptable carrier suitable for administration to a human or animal subject, either alone or together with other anti-cancer agents.

In one embodiment, the present invention provides methods of treating human or animal subjects having or having been diagnosed with an MTAP-deficient and/or MTA accumulating proliferative disorder (e.g., cancer) comprising administering to the subject in need thereof a therapeutically effective amount of a compound of the present invention (e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1) or a pharmaceutically acceptable salt thereof in combination with a second therapeutic agent.

In one embodiment, the present invention provides methods of an MTAP-deficient and/or MTA accumulating proliferative disorder (e.g., cancer) in a subject in need thereof comprising administering to the subject a therapeutically effective amount of a compound of the present invention (e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1) or a pharmaceutically acceptable salt thereof in combination with a second therapeutic agent.

In particular, compositions will either be formulated together as a combination therapeutic or administered separately.

In combination therapy, the compound of the present invention and other anti-cancer agent(s) may be administered either simultaneously, concurrently or sequentially with no specific time limits, wherein such administration provides therapeutically effective levels of the two compounds in the body of the patient.

In a preferred embodiment, the compound of the present invention (e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) and the other anti-cancer agent(s) is generally administered sequentially in any order by infusion or orally. The dosing regimen may vary depending upon the stage of the disease, physical fitness of the patient, safety profiles of the individual drugs, and tolerance of the individual drugs, as well as other criteria well-known to the attending physician and medical practitioner(s) administering the combination. The compound of the present invention and other anti-cancer agent(s) may be administered within minutes of each other, hours, days, or even weeks apart depending upon the particular cycle being used for treatment. In addition, the cycle could include administration of one drug more often than the other during the treatment cycle and at different doses per administration of the drug.

In another aspect of the present invention, kits that include one or more compound of the present invention (e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) and a second therapeutic agent as disclosed herein are provided. Representative kits include (a) a compound of the present invention or a pharmaceutically acceptable salt thereof (e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof), (b) at least one other therapeutic agent, e.g., as indicated above, whereby such kit may comprise a package insert or other labeling including directions for administration.

A compound of the present invention (e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) may also be used in combination with known therapeutic processes, for example, the administration of hormones or especially radiation. A compound of the present invention may in particular be used as a radiosensitizer, especially for the treatment of tumors which exhibit poor sensitivity to radiotherapy.

In certain instances, compounds of the present invention are combined with other therapeutic agents, including, but not limited to, other anti-cancer agents, anti-allergic agents, anti-nausea agents (or anti-emetics), pain relievers, cytoprotective agents, and combinations thereof.

Patient Selection and Monitoring

In one aspect, the present invention provides a method of determining if a subject having or having been diagnosed with a cancer (e.g., a cancer patient) will respond to therapeutic treatment with a PRMT5 inhibitor (e.g., an MTA-uncompetitive PRMT5 inhibitor, e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof), comprising the steps of:
a) contacting a test sample obtained from said subject with a reagent capable of detecting human cancer cells that have MTAP deficiency and/or MTA accumulation; and b) comparing the test sample with a reference (e.g., a reference sample taken from a non-cancerous or normal control subject), wherein the presence of MTAP deficiency and/or MTA accumulation in said test sample indicates that the subject will respond to therapeutic treatment with a PRMT5 inhibitor (e.g., an MTA-uncompetitive PRMT5 inhibitor, e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof).

In one aspect, the present invention provides a method of determining if a cancer will respond to therapeutic treatment with a PRMT5 inhibitor (e.g., an MTA-uncompetitive PRMT5 inhibitor, e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof), comprising the steps of:
a) contacting a test sample obtained from a subject having or having been diagnosed with said cancer with a reagent capable of detecting human cancer cells that have MTAP deficiency and/or MTA accumulation; and
b) comparing the test sample with a reference (e.g., a reference sample taken from a non-cancerous or normal control subject), wherein the presence of MTAP deficiency and/or MTA accumulation in said test sample indicates that the cancer will respond to therapeutic treatment with a PRMT5 inhibitor (e.g., an MTA-uncompetitive PRMT5 inhibitor, e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof). In some embodiments, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma. In some embodiments, the method further comprises the step of determining the level of PRMT5 in the cancer cells. The level of expression of PRMT5 can be considered when determining the therapeutically effective dosage of a PRMT5 inhibitor.

In one aspect, the present invention provides a method of determining the sensitivity of a cancer cell to PRMT5 inhibition (e.g., inhibition with an MTA-uncompetitive PRMT5 inhibitor, e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof), comprising the steps of:
a) assaying the production, level, activity, expression or presence of MTAP), in said cancer cell;
b) comparing the production, level, activity, expression or presence of MTAP in the cancer cell with the production, level, activity, expression or presence of MTAP, respectively, in a non-cancerous or normal control cell, wherein a decreased level, activity or expression in the cancer cell indicates MTAP deficiency and wherein MTAP deficiency indicates that said cancer cell is sensitive to the PRMT5 inhibitor. In some embodiments, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

In one embodiment, the present invention provides a method of determining the sensitivity of a cancer cell to a PRMT5 inhibitor (e.g., an MTA-uncompetitive PRMT5 inhibitor, e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof), comprising the steps of: a) assaying for level, activity or expression of the MTAP gene or its gene product in both the cancer cell and a normal control cell, wherein a decreased level, activity or expression in the cancer cell indicates MTAP deficiency; b) assaying for PRMT5 expression in said cancer cell; c) comparing the PRMT5 expression with PRMT5 expression in the cancer cell and a normal control cell; wherein the similarity in PRMT5 expression, and the presence of said MTAP deficiency in said cancer cell, indicates said cell is sensitive to a PRMT5 inhibitor.

In some embodiments, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

In one aspect the present invention provides a therapeutic method of treating a subject having or having been diagnosed with a cancer (e.g., a cancer associated with MTAP deficiency and/or MTA accumulation) comprising the steps of:
  a) assessing the level of MTAP and/or MTA in a test sample obtained from said subject (e.g., by contacting the sample with a reagent capable of detecting human MTAP-deficient and/or MTA-accumulating cancer cells in a test sample obtained from said subject), wherein the MTA level can be assessed directly (e.g., by ELISA or LC-MS/MS) or indirectly (e.g., by SDMA-modified protein ELISA or IHC, or by RNA splicing);
  b) comparing the test sample with a reference (e.g., a reference sample taken from a non-cancerous or normal control subject), wherein MTAP deficiency and/or MTA accumulation in said test sample indicates said subject will respond to therapeutic treatment with a PRMT5 inhibitor; and
  c) administering a therapeutically effective amount of PRMT5 inhibitor (e.g., an MTA-uncompetitive PRMT5 inhibitor, e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) to the subject identified in step b).

In one aspect the present invention provides a therapeutic method of treating a cancer (e.g., a cancer associated with MTAP deficiency and/or MTA accumulation) in a subject in need thereof comprising the steps of:
  a) assessing the level of MTAP and/or MTA in a test sample obtained from said subject (e.g., by contacting the sample with a reagent capable of detecting human MTAP-deficient and/or MTA-accumulating cancer cells), wherein the MTA level can be assessed directly (e.g., by ELISA or LC-MS/MS) or indirectly (e.g., by SDMA-modified protein ELISA or IHC, or by RNA splicing);
  b) comparing the test sample with a reference (e.g., a reference sample taken from a non-cancerous or normal control subject), wherein MTAP deficiency and/or MTA accumulation in said test sample indicates said cancer will respond to therapeutic treatment with a PRMT5 inhibitor (e.g., an MTA-uncompetitive PRMT5 inhibitor); and
  c) administering a therapeutically effective amount of PRMT5 inhibitor (e.g., an MTA-uncompetitive PRMT5 inhibitor, e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) to the subject identified in step b).

In some embodiments, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

In some embodiments, the method further comprises the step of determining the level of PRMT5 in the cancer cells.

In one aspect the present invention provides a therapeutic method of treating a subject having or having been diagnosed with a cancer associated with MTAP deficiency and/or MTA accumulation comprising the steps of:
  a) assessing the level of MTAP and/or MTA in a test sample obtained from said subject (e.g., by contacting the sample with a reagent capable of detecting human MTAP-deficient and/or MTA-accumulating cancer cells), wherein the MTA level can be assessed directly (e.g., by ELISA or LC-MS/MS) or indirectly (e.g., by SDMA-modified protein ELISA or IHC, or by RNA splicing);
  b) comparing the test sample with a reference sample (e.g., a reference sample taken from a non-cancerous or normal control subject), wherein MTAP deficiency and/or MTA accumulation in said test sample indicates said cancer will respond to therapeutic treatment with a PRMT5 inhibitor (e.g., an MTA-uncompetitive PRMT5 inhibitor); and
  c) administering a therapeutically effective amount of a composition comprising a PRMT5 inhibitor (e.g., an MTA-uncompetitive PRMT5 inhibitor e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) to the subject identified in step b).

In one aspect the present invention provides a therapeutic method of treating cancer associated with MTAP deficiency and/or MTA accumulation in a subject in need thereof comprising the steps of:
  a) assessing the level of MTAP and/or MTA in a test sample obtained from said subject (e.g., by contacting the sample with a reagent capable of detecting human MTAP-deficient and/or MTA-accumulating cancer cells), wherein the MTA level can be assessed directly (e.g., by ELISA or LC-MS/MS) or indirectly (e.g., by SDMA-modified protein ELISA or IHC, or by RNA splicing);
  b) comparing the test sample with a reference sample (e.g., a reference sample taken from a non-cancerous or normal control subject), wherein MTAP deficiency and/or MTA accumulation in said test sample indicates said cancer will respond to therapeutic treatment with a PRMT5 inhibitor (e.g., an MTA-uncompetitive PRMT5 inhibitor); and
  c) administering a therapeutically effective amount of a composition comprising a PRMT5 inhibitor (e.g., an MTA-uncompetitive PRMT5 inhibitor e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) to the subject identified in step b).

In some embodiments, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

In some embodiments, the method further comprises the step of determining the level of PRMT5 in the cancer cells.

In one aspect the present invention provides a method of determining if a subject having or having been diagnosed with a cancer associated with MTAP deficiency and/or MTA accumulation will respond to treatment with a PRMT5 inhibitor (e.g., an MTA-uncompetitive PRMT5 inhibitor, e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) comprising the steps of:
a) assessing the level of MTAP and/or MTA in a test sample obtained from said subject (e.g., by contacting the sample with a reagent capable of detecting human MTAP-deficient and/or MTA-accumulating cancer cells), wherein the MTA level can be assessed directly (e.g., by ELISA or LC-MS/MS) or indirectly (e.g., by SDMA-modified protein ELISA or IHC, or by RNA splicing);
b) comparing the test sample with a reference (e.g., a reference sample taken from a non-cancerous or normal control subject), wherein MTAP deficiency and/or MTA accumulation in said test sample indicates said subject will respond to therapeutic treatment with a PRMT5 inhibitor (e.g., an MTA-uncompetitive PRMT5 inhibitor).

In one aspect the present invention provides a method of determining if a cancer associated with MTAP deficiency and/or MTA accumulation will respond to treatment with a PRMT5 inhibitor (e.g., an MTA-uncompetitive PRMT5 inhibitor, e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) comprising the steps of:
a) assessing the level of MTAP and/or MTA in a test sample obtained from a subject having or having been diagnosed with said cancer (e.g., by contacting the sample with a reagent capable of detecting human MTAP-deficient and/or MTA-accumulating cancer cells), wherein the MTA level can be assessed directly (e.g., by ELISA or LC-MS/MS) or indirectly (e.g., by SDMA-modified protein ELISA or IHC, or by RNA splicing);
b) comparing the test sample with a reference (e.g., a reference sample taken from a non-cancerous or normal control subject), wherein MTAP deficiency and/or MTA accumulation in said test sample indicates said cancer will respond to therapeutic treatment with a PRMT5 inhibitor (e.g., an MTA-uncompetitive PRMT5 inhibitor).

In some embodiments, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

In some embodiments, the method further comprises the step of determining the level of PRMT5 in the cancer cells.

Sample Preparation

The invention further provides assays for the detection of MTAP deficiency and/or MTA accumulation. They can include detecting a mutation related to MTAP deficiency and/or MTA accumulation, e.g., in a body fluid such as blood (e.g., serum or plasma) bone marrow, cerebral spinal fluid, peritoneal/pleural fluid, lymph fluid, ascites, serous fluid, sputum, lacrimal fluid, stool, and urine, or in a tissue such as a tumor tissue. The tumor tissue can be fresh tissue or preserved tissue (e.g., formalin fixed tissue, e.g., paraffin-embedded tissue).

Body fluid samples can be obtained from a subject using any of the methods known in the art. Methods for extracting cellular DNA from body fluid samples are well known in the art. Typically, cells are lysed with detergents. After cell lysis, proteins are removed from DNA using various proteases. DNA is then extracted with phenol, precipitated in alcohol, and dissolved in an aqueous solution. Methods for extracting acellular DNA from body fluid samples are also known in the art. Commonly, a cellular DNA in a body fluid sample is separated from cells, precipitated in alcohol, and dissolved in an aqueous solution.

Detection of PRMT5 Selectivity

Samples, once prepared, can be tested for MTAP deficiency and/or MTA accumulation, either or both of which indicates that the sample is sensitive to treatment with a PRMT5 inhibitor. Cells can be determined to be MTA accumulating by techniques known in the art; methods for detecting MTA include, as a non-limiting example, liquid chromatography-electrospray ionization-tandem mass spectrometry (LC-ESI-MS/MS), as described in Stevens et al. 2010. J. Chromatogr. A. 1217: 3282-3288; and Kirovski et al. 2011 Am. J. Pathol. 178: 1145-1152; and references cited therein. The detection of MTAP deficiency can be done by any number of ways, for example: DNA sequencing, PCR based methods, including RT-PCR, microarray analysis, Southern blotting, Northern blotting, Next Generation Sequencing, and dip stick analysis. In some embodiments, MTAP deficiency is evaluated by any technique known in the art, for example, immunohistochemistry utilizing an anti-MTAP antibody or derivative thereof, and/or genomic sequencing, or nucleic acid hybridization, or amplification utilizing at least one probe or primer comprising a sequence of at least 12 contiguous nucleotides (nt) of the sequence of MTAP wherein the primer is no longer than about 30 nt.

The polymerase chain reaction (PCR) can be used to amplify and identify MTAP deficiency from either genomic DNA or RNA extracted from tumor tissue. PCR is well known in the art and is described in detail in Saiki et al., Science 1988, 239:487.

Methods of detecting MTAP deficiency by hybridization are provided. The method comprises identifying MTAP deficiency in a sample by its inability to hybridize to MTAP nucleic acid. The nucleic acid probe is detectably labeled with a label such as a radioisotope, a fluorescent agent or a chromogenic agent. Radioisotopes can include without limitation; 3H, 32P, 33P and 35S etc. Fluorescent agents can include without limitation: FITC, texas red, rhodamine, etc.

The probe used in detection that is capable of hybridizing to MTAP nucleic acid can be from about 8 nucleotides to about 100 nucleotides, from about 10 nucleotides to about 75 nucleotides, from about 15 nucleotides to about 50 nucleotides, or about 20 to about 30 nucleotides. The kit can also provide instructions for analysis of patient cancer samples, wherein the presence or absence of MTAP deficiency indicates if the subject is sensitive or insensitive to treatment with a PRMT5 inhibitor.

Single stranded conformational polymorphism (SSCP) can also be used to detect MTAP deficiency. This technique is well described in Orita et al., PNAS 1989, 86:2766-2770.

Measurement of Gene Expression

Evaluation of MTAP deficiency and measurement of MTAP gene expression, and measurement of PRMT5 gene expression can be performed using any method or reagent known in the art.

Detection of gene expression can be by any appropriate method, including for example, detecting the quantity of mRNA transcribed from the gene or the quantity of cDNA produced from the reverse transcription of the mRNA transcribed from the gene or the quantity of the polypeptide or protein encoded by the gene. These methods can be performed on a sample by sample basis or modified for high throughput analysis. For example, using Affymetrix™ U133 microarray chips.

In one aspect, gene expression is detected and quantitated by hybridization to a probe that specifically hybridizes to the appropriate probe for that biomarker. The probes also can be attached to a solid support for use in high throughput screening assays using methods known in the art.

In one aspect, the expression level of a gene is determined through exposure of a nucleic acid sample to the probe-modified chip. Extracted nucleic acid is labeled, for example, with a fluorescent tag, preferably during an amplification step.

Hybridization of the labeled sample is performed at an appropriate stringency level. The degree of probe-nucleic acid hybridization is quantitatively measured using a detection device.

Alternatively, any one of gene copy number, transcription, or translation can be determined using known techniques. For example, an amplification method such as PCR may be useful. General procedures for PCR are taught in MacPherson et al., PCR: A Practical Approach, (IRL Press at Oxford University Press (1991)). However, PCR conditions used for each application reaction are empirically determined. A number of parameters influence the success of a reaction. Among them are annealing temperature and time, extension time, Mg 2+ and/or ATP concentration, pH, and the relative concentration of primers, templates, and deoxyribonucleotides. After amplification, the resulting DNA fragments can be detected by agarose gel electrophoresis followed by visualization with ethidium bromide staining and ultraviolet illumination. In one embodiment, the hybridized nucleic acids are detected by detecting one or more labels attached to the sample nucleic acids. The labels can be incorporated by any of a number of means well known to those of skill in the art. However, in one aspect, the label is simultaneously incorporated during the amplification step in the preparation of the sample nucleic acid. Thus, for example, polymerase chain reaction (PCR) with labeled primers or labeled nucleotides will provide a labeled amplification product. In a separate embodiment, transcription amplification, as described above, using a labeled nucleotide (e.g., fluorescein-labeled UTP and/or CTP) incorporates a label in to the transcribed nucleic acids.

Alternatively, a label may be added directly to the original nucleic acid sample (e.g., mRNA, polyA, mRNA, cDNA, etc.) or to the amplification product after the amplification is completed. Means of attaching labels to nucleic acids are well known to those of skill in the art and include, for example nick translation or end-labeling (e.g., with a labeled RNA) by kinasing of the nucleic acid and subsequent attachment (ligation) of a nucleic acid linker joining the sample nucleic acid to a label (e.g., a fluorophore).

In one example, the gene expression can be measured through an in-situ hybridization protocol that can detect RNA molecules on a slide containing tissue sections or cells (e.g., through RNAscope®).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., 3H, 125I, 35S, 14C, or 32P) enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads.

Detection of labels is well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label. The detectable label may be added to the target (sample) nucleic acid(s) prior to, or after the hybridization, such as described in WO 97/10365. These detectable labels are directly attached to or incorporated into the target (sample) nucleic acid prior to hybridization. In contrast, "indirect labels" are joined to the hybrid duplex after hybridization. Generally, the indirect label is attached to a binding moiety that has been attached to the target nucleic acid prior to the hybridization. For example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids see Laboratory Techniques in Biochemistry and Molecular Biology, Vol. 24: Hybridization with Nucleic Acid Probes, P. Tijssen, ed. Elsevier, N.Y. (1993).

Detection of Polypeptides

Protein levels of MTAP can be determined by examining protein expression or the protein product. Determining the protein level involves measuring the amount of any immunospecific binding that occurs between an antibody that selectively recognizes and binds to the polypeptide of the biomarker in a sample obtained from a subject and comparing this to the amount of immunospecific binding of at least one biomarker in a control sample.

A variety of techniques are available in the art for protein analysis. They include but are not limited to radioimmunoassays, ELISA (enzyme linked immunosorbent assays), "sandwich" immunoassays, immunoradiometric assays, in situ immunoassays (using e.g., colloidal gold, enzyme or radioisotope labels), Western blot analysis, immunoprecipitation assays, immunofluorescent assays, flow cytometry, immunohistochemistry, HPLC, mass spectrometry, confocal microscopy, enzymatic assays, surface plasmon resonance and PAGE-SDS.

Adjacent Biomarkers

Near or adjacent to MTAP on chromosome 9 are several other biomarkers. CDKN2A is often, if not usually, deleted along with MTAP. Additional genes or pseudogenes in this region include: C9orf53, ERVFRD-3, TUBB8P1, KHSRPP1, MIR31, and MIR31HG.

In some embodiments of the methods, the cell that is MTAP-deficient is also deficient in CDKN2A. In some embodiments, the cell that is MTAP-deficient is also deficient in one or more of: CDKN2A, C9orf53, ERVFRD-3, TUBB8P1, KHSRPP1, MIR31, and MIR31HG.

Thus, in various methods involving a step of evaluating a cell for MTAP deficiency or determining if a cell is MTAP-deficient, this step can comprise the step of determining if the cell is deficient for one or more of these markers: CDKN2A, C9orf53, ERVFRD-3, TUBB8P1, KHSRPP1, MIR31, and MIR31HG.

Thus, in some embodiments, the disclosure encompasses: A method of determining if a subject having or having been diagnosed with a cancer will respond to therapeutic treatment with a PRMT5 inhibitor (e.g., an MTA-uncompetitive PRMT5 inhibitor), comprising the steps of:
  a) evaluating a test sample obtained from said subject for MTAP deficiency, and evaluating a reference sample from a non-cancerous or normal control subject for MTAP deficiency, wherein MTAP deficiency in the test sample relative to the reference sample indicates that the subject will respond to therapeutic treatment with a PRMT5 inhibitor (e.g., an MTA-uncompetitive PRMT5 inhibitor, e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof); wherein MTAP deficiency is evaluated by evaluating the deficiency of one or more of the following biomarkers: CDKN2A, C9orf53, ERVFRD-3, TUBB8P1, KHSRPP1, MIR31, and MIR31HG, and wherein the method can further comprise the following steps:
  b) determining the level of MTAP in the subject, wherein steps a) and b) can be performed in any order;
  c) administering a therapeutically effective amount of a PRMT5 inhibitor (e.g., an MTA-uncompetitive PRMT5 inhibitor, e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) to the subject; and
  d) determining the level of PRMT5 activity in the subject following step c), wherein a decrease in the level of PRMT5 activity is correlated with the inhibition of the proliferation of the cancer, and wherein steps c) and d) are performed after steps a) and b).

In some embodiments, the disclosure encompasses: A method of determining if a cancer will respond to therapeutic treatment with a PRMT5 inhibitor (e.g., an MTA-uncompetitive PRMT5 inhibitor), comprising the steps of:
  a) evaluating a test sample obtained from a subject having or having been diagnosed with said cancer for MTAP deficiency, and evaluating a reference sample from a non-cancerous or normal control subject for MTAP deficiency, wherein MTAP deficiency in the test sample relative to the reference sample indicates that the cancer will respond to therapeutic treatment with a PRMT5 inhibitor (e.g., an MTA-uncompetitive PRMT5 inhibitor, e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof); wherein MTAP deficiency is evaluated by evaluating the deficiency of one or more of the following biomarkers: CDKN2A, C9orf53, ERVFRD-3, TUBB8P1, KHSRPP1, MIR31, and MIR31HG, and wherein the method can further comprise the following steps:
  b) determining the level of MTAP in the subject, wherein steps a) and b) can be performed in any order;
  c) administering a therapeutically effective amount of a PRMT5 inhibitor (e.g., an MTA-uncompetitive PRMT5 inhibitor, e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) to the subject; and
  d) determining the level of PRMT5 activity in the subject following step c), wherein a decrease in the level of PRMT5 activity is correlated with the inhibition of the proliferation of the cancer, and wherein steps c) and d) are performed after steps a) and b).

Assaying for Biomarkers and PRMT5 Inhibitor Treatment

A number of patient stratification strategies could be employed to find patients likely to be sensitive to PRMT5 inhibition with an MTA-uncompetitive PRMT5 inhibitor (e.g., a PRMT5 inhibitor of the present invention, e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof), including but not limited to, testing for MTAP deficiency and/or MTA accumulation.

Once a patient has been assayed for MTAP deficiency and/or MTA accumulation and predicted to be sensitive to treatment with a PRMT5 inhibitor, administration of any PRMT5 inhibitor (e.g., an MTA-uncompetitive PRMT5 inhibitor, e.g., a compound of Formula (I), (Ia), (II), (IIa), (IIa1), (IIa1i), (IIa2), (IIa2i), (IIa3), (IIa3i), (IIa3ii), (IIa3), (IIa4), (IIa4i), (III), (IIIa), (IIIa1), (IIIa1i), (IIIa2), (IIIa2i), (IIIa2ii), (IV), (IVa), (V), (Va), (Va1), (Va2), (Va3), (VI), (VIa), (VIb), (VII), (VIIa), (VIIa1), (VIIa1i), (VIIb), (VIIb1), (VIIb1i) or a compound of Table 1, or pharmaceutically acceptable salts thereof) to a patient can be effected in one dose, continuously or intermittently throughout the course of treatment. Methods of determining the most effective means and dosage of administration are well known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents may be empirically adjusted.

Kits

In some embodiments kits related to methods of the invention are provided.

In one embodiment, a for predicting the sensitivity of a subject having or having been diagnosed with an MTAP-deficiency-related cancer for treatment with a PRMT5 inhibitor is provided. The kit comprises: i) reagents capable of detecting human MTAP-deficient and/or MTA-accumulating cancer cells; and ii) instructions for how to use said kit.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope. In the synthetic examples below, the descriptions of experimental procedures within a reaction sequence are listed in numerical order.

Abbreviations

General
  ADDP 1,1'-(azodicarbonyl)dipiperidine
  anhy. anhydrous
  aq. aqueous
  satd. saturated
  min(s) minute(s)
  hr(s) hour(s)
  mL milliliter
  mmol millimole(s)
  mol mole(s)
  MS mass spectrometry
  NMR nuclear magnetic resonance
  TLC thin layer chromatography
  HPLC high-performance liquid chromatography
  Me methyl
  i-Pr iso-propyl
  t-Bu tert-butyl
  ᵗBuXPhos 2-di-tert-butylphosphino-2',4',6'-triisopropylbiphenyl
  Ph phenyl
  Et ethyl
  Bz benzoyl
  RuPhos 2-dicyclohexylphosphino-2',6'-diisopropoxybiphenyl
Spectrum
  Hz hertz
  δ chemical shift
  J coupling constant
  s singlet
  d doublet
  t triplet
  q quartet
  m multiplet
  br broad
  qd quartet of doublets
  dquin doublet of quintets
  dd doublet of doublets
  dt doublet of triplets
Solvents and Reagents
  DAST Diethylaminosulfurtrifluoride
  $CHCl_3$ chloroform
  DCM dichloromethane
  DMF dimethylformamide
  $Et_2O$ diethyl ether
  EtOH ethyl alcohol
  EtOAc ethyl acetate
  MeOH methyl alcohol
  MeCN acetonitrile
  PE petroleum ether
  THF tetrahydrofuran
  DMSO dimethyl sulfoxide
  t-BuOK potassium tert-butoxide
  9-BBN 9-borabicyclo[3.3.1]nonane
  AcOH acetic acid
  HCl hydrochloric acid
  $H_2SO_4$ sulfuric acid
  $NH_4C_1$ ammonium chloride
  KOH potassium hydroxide
  NaOH sodium hydroxide
  $K_2CO_3$ potassium carbonate
  $Na_2CO_3$ sodium carbonate
  TFA trifluoroacetic acid
  $Na_2SO_4$ sodium sulfate
  $NaBH_4$ sodium borohydride
  $NaHCO_3$ sodium bicarbonate
  LiHMDS lithium hexamethyldisilylamide
  $NaBH_4$ sodium borohydride
  $Et_3N$ triethylamine
  Py pyridine
  PCC pyridinium chlorochromate
  DMAP 4-(dimethylamino)pyridine
  DIPEA N,N-diisopropylethylamine
  BINAP 2,2'-bis(diphenylphosphanyl)-1,1'-binaphthyl
  dppf 1,1'-bis(diphenylphosphino)ferrocene
  PEP Phospho(enol)pyruvic acid
  LDH Lactate Dehydrogenase
  DTT DL-Dithiothreitol
  BSA Bovine Serum Albumin
  NADH β-Nicotinamide adenine dinucleotide, reduced
  $Pd(t-Bu_3P)_2$ bis(tri-tert-butylphosphine)palladium(0)
  AcCl acetyl chloride
  i-PrMgCl Isopropylmagnesium chloride
  TBSCl tert-Butyl(chloro)dimethylsilane
  $(i-PrO)_4Ti$ titanium tetraisopropoxide
  BHT 2,6-di-t-butyl-4-methylphenoxide
  BzCl benzoyl chloride
  CsF cesium fluoride
  DCC dicyclohexylcarbodiimide
  DMP Dess-Martin periodinane
  EtMgBr ethylmagnesium bromide
  EtOAc ethyl acetate
  TEA triethylamine
  AlaOH alanine
  TBAF tetra-n-butylammonium fluoride
  TBS t-butyldimethylsilyl
  TMS trimethylsilyl
  $TMSCF_3$ (Trifluoromethyl)trimethylsilane
  Ts p-toluenesulfonyl Bu butyl
Ti(O$^i$Pr)$_4$ tetraisopropoxytitanium
LAH Lithium Aluminium Hydride
LDA lithium diisopropylamide
LiOH·H$_2$O lithium hydroxide hydrates
MAD methyl aluminum bis(2,6-di-t-butyl-4-methylphenoxide)
NBS N-bromosuccinimide
Na$_2$SO$_4$ sodium sulfate
Na$_2$S$_2$O$_3$ sodium thiosulfate
PE petroleum ether
MeCN acetonitrile
Boc t-butoxycarbonyl
MTBE methyl tert-butyl ether
DIAD diisopropyl azodicarboxylate General Experimental Notes:

In the following examples, the chemical reagents were purchased from commercial sources (such as Alfa, Acros, Sigma Aldrich, TCI and Shanghai Chemical Reagent Company), and used without further purification.

In some examples, purification of intermediates and final compounds was performed using HPLC (H$_2$O-MeOH; Agilent 1260 Infinity systems equipped with DAD and mass-detectors. Waters Sunfire C18 OBD Prep Column, 100A, 5 µm, 19 mm×100 mm with SunFire C18 Prep Guard Cartridge, 100A, 10 µm, 19 mm×10 mm) The material was dissolved in 0.7 mL DMSO. Flow: 30 mL/min. Purity of the obtained fractions was checked via the analytical LCMS. Spectra were recorded for each fraction as it was obtained straight after chromatography in the solution form. The solvent was evaporated under the N$_2$ flow upon heating to 80° C. On the basis of post-chromatography LCMS analysis fractions were united. Solid fractions were dissolved in 0.5 mL MeOH and transferred into pre-weighted marked vials. Obtained solutions were again evaporated under the N$_2$ flow upon heating to 80° C. After drying, products were subjected to lyophilization using acetonitrile-water mixtures and finally characterized by LCMS and $^1$H NMR.

Nuclear magnetic resonance (NMR) spectra were recorded using Brucker AVANCE DRX 500, Bruker 400 spectrometer or Varian UNITYplus 400. Chemical shifts for protons were reported as parts per million in δ scale using solvent residual peak (CHCl$_3$: 7.27 ppm) (methanol-d$_4$: 3.31 ppm) (DMSO-d$_6$: 2.50 ppm) or tetramethylsilane (0.00 ppm) as internal standards. Chemical shifts of $^{13}$C NMR spectra were reported in ppm from the central peak of CDCl$_3$ (77.00 ppm) (methanol-d$_4$: 49.15 ppm) (DMSO-d$_6$: 39.51 ppm) on the δ scale. Data are represented as follows: chemical shift, multiplicity (s=singlet, d=doublet, t=triplet, q=quartet, qn=quintuplet, sx=sextet, sp=septuplet, m=multiplet, br=broad), coupling constant (J, Hz) and integration.

In certain examples, mass spectra were recorded on an Agilent 1100 Series LC/MSD system with DAD†LSD and Agilent LC†MSD VL (G1956A), SL (G1956B) mass-spectrometer or an Agilent 1200 Series LC/MSD system with DAD†ELSD and Agilent LC†MSD SL (G6130A), SL (G6140A) mass-spectrometer. All the LC/MS data were obtained using positive/negative mode switching.

Column Zorbax SB-C18 1.8 µm 4.6×15 mm Rapid Resolution cartridge (PN 821975-932)
Mobile phase A—acetonitrile, 0.1% formic acid
B—water (0.1% formic acid)
Flow rate 3 ml/min
Gradient 0 min—100% B
0.01 min—100% B
1.5 min—0% B
1.8 min—0% B
1.81 min—100% B
Injection volume 1 µl
Ionization mode atmospheric pressure chemical ionization (APCI)
Scan range m/z 80-1000.

Other Exemplary Analytical LC/MS Instruments and Conditions are Described Below:

Instrument: Agilent LC1100-MS6100 series G1956B; Column: Xbridge Shield RP-18, 50*2.1 mm*5 m; Mobile Phase A: H$_2$O with 0.05% NH$_3$—H$_2$O (v %); Mobile Phase B: MeCN; Flow rate: 1.0 mL/min; Wavelength: UV 220 nm, 254 nm; Column temperature: 30° C.; MS ionization: ESI.

0-30CD: Gradient: B from 0%~30% over 2 minutes and holding at 30% for 0.48 minutes;
0-60CD: Gradient: B from 0%~60% over 2 minutes and holding at 60% for 0.48 minutes;
10-80CD: Gradient: B from 10%~80% over 2 minutes and holding at 80% for 0.48 minutes;
30-90CD: Gradient: B from 30%~90% over 2 minutes and holding at 90% for 0.48 minutes;
50-100CD: Gradient: B from 50%~100% over 2 minutes and holding at 100% for 0.48 minutes.

Instrument: Agilent LC1100-MS6100 series G1956B; Column: Xtimate C18, 30*2.1 mm*3 m; Mobile Phase A: H$_2$O with 0.0375% TFA (v %); Mobile Phase B: MeCN with 0.01875% TFA (v %): Flow rate: 0.8 mL/min; Wavelength: UV 220 nm, 254 nm; Column temperature: 50° C.; MS ionization: ESI.

0-30AB: Gradient: B from 0%~30% over 3 minutes and holding at 30% for 0.5 minutes;
0-60AB: Gradient: B from 0%~60% over 3 minutes and holding at 30% for 0.5 minutes;
10-80AB: Gradient: B from 10%~80% over 3 minutes and holding at 30% for 0.5 minutes;
30-90AB: Gradient: B from 0%~30% over 3 minutes and holding at 30% for 0.5 minutes;
50-100AB: Gradient: B from 50%~100% over 3 minutes and holding at 100% for 0.5 minutes.

Instrument: Shimadzu LC20-MS2010; Column: Agilent Pursuit 5 C18 20*2.0 mm; Mobile Phase A: H$_2$O with 0.0375% of TFA (v %); Mobile Phase B: MeCN with 0.01875% of TFA (v %); Gradient: B from 5~95% over 0.7 minutes and holding at 95% for 0.4 minutes; Flow Rate: 1.5 mL/min; Wavelength: UV 220 nm, 254 nm, 215 nm; Column temperature: 50° C.; MS ionization: ESI.

Instrument: Shimadzu LC20-MS2020; Column: Agilent Pursuit 5 C18 20*2.0 mm; Mobile Phase A: H$_2$O with 0.0375% of TFA (v %); Mobile Phase B: MeCN with 0.01875% of TFA (v %); Gradient: B from 5~95% over 0.7 minutes and holding at 95% for 0.4 minutes; Flow Rate: 1.5 mL/min; Wavelength: UV 220 nm, 254 nm; Column temperature: 50° C.; MS ionization: ESI.

Exemplary HPLC Instruments and Conditions

Instrument: Shimadzu LC20; Column: YMC-Pack ODS-A 150*4.6 mm; Mobile Phase A: H$_2$O with 0.06875% TFA (v %); Mobile Phase B: MeCN with 0.0625% TFA (v %); Flow rate: 1.5 mL/min; Wavelength: UV 220 nm, 215 nm, 254 nm; Column temperature: 40° C.

0-30: Gradient: B from 0~30% over 10 minutes and holding at 30% for 5 minutes;
0~60: Gradient: B from 0~60% over 10 minutes and holding at 60% for 5 minutes;
0-95: Gradient: B from 0~95% over 10 minutes and holding at 95% for 5 minutes;
10-80: Gradient: B from 10~80% over 10 minutes and holding at 80% for 5 minutes;

30-90: Gradient: B from 30~90% over 10 minutes and holding at 90% for 5 minutes;

50-100: Gradient: B from 50~100% over 10 minutes and holding at 100% for 5 minutes.

Instrument: Shimadzu LC20; Column: Xbridge Shield RP-18 50*2.1 mm, 5 µm; Mobile Phase A: $H_2O$ with 0.01% $NH_3$—$H_2O$; Mobile Phase B: MeCN; Flow Rate: 1.2 mL/min; Wavelength: UV 220 nm, 215 nm, 254 nm; Column temperature: 40° C.

0-30CD: Gradient: B from 0~30% over 6 minutes and holding at 30% for 2 minutes;

0-60CD: Gradient: B from 0~60% over 6 minutes and holding at 60% for 2 minutes;

10-80CD: Gradient: B from 10~80% over 6 minutes and holding at 80% for 2 minutes;

30-90CD: Gradient: B from 30~90% over 6 minutes and holding at 90% for 2 minutes;

50-100CD: Gradient: B from 10~80% over 6 minutes and holding at 100% for 2 minutes.

Instrument: Shimadzu LC20; Column: Ultimate C18 50*3 mm, 3 m; Mobile Phase A: $H_2O$ with 0.06875% TFA (v %); Mobile Phase B: MeCN with 0.0625% TFA (v %); Flow Rate: 1.2 mL/min; Wavelength: UV 220 nm, 215 nm, 254 nm; Column temperature: 40° C.

0-30AB: Gradient: B from 0~30% over 2.5 minutes and holding at 30% for 0.75 minutes;

0-60AB: Gradient: B from 0~60% over 2.5 minutes and holding at 60% for 0.75 minutes;

5-95AB: Gradient: B from 5~95% over 2.5 minutes and holding at 95% for 0.75 minutes.

Instrument: Shimadzu LC20; Column: Ultimate C18 50*3 mm, 3 m; Mobile Phase A: $H_2O$ with 0.06875% TFA (v %); Mobile Phase B: MeCN with 0.0625% TFA (v %); Flow Rate: 1.2 mL/min; Wavelength: UV 220 nm, 215 nm, 254 nm; Column temperature: 40° C.

10-80AB: Gradient: B from 10~80% over 4 minutes and holding at 80% for 2 minutes.

Exemplary TLC, Concentration and Normal Phase Chromatography.

Analytical thin layer chromatography (TLC) was performed with silica gel 60 F254 aluminum plates. Visualization was done under a UV lamp (254 nm) and by iodine or immersion in ethanolic phosphomolybdic acid (PMA) or potassium permanganate ($KMnO_4$), followed by heating using a heat gun. Organic solutions were concentrated by rotary evaporation at 20~40° C. Purification of reaction products were generally done by flash column chromatography with 230-400 mesh silica gel or Agela flash silica column.

Exemplary Chiral SFC Analytical Methods

Column: Chiralpak AD-3 150×4.6 mm I.D., 3 m; Mobile phase: A: supercritical $CO_2$; Mobile phase B: EtOH (0.05% DEA); Gradient: from 5% to 40% of B in 5 min and hold 40% for 2.5 min, then 5% of B for 2.5 min; Flow rate: 2.5 mL/min; Column temperature: 35° C.; ABPR: 1500 psi.

Column: Chiralpak AD-3 100×4.6 mm I.D., 3 m; Mobile phase: A: supercritical $CO_2$ Mobile phase B: EtOH (0.1% ethanolamine); Gradient: from 5% to 40% of B in 4.5 min and hold 40% for 2.5 min, then 5% of B for 1 min; Flow rate: 2.8 mL/min; Column temperature: 40° C.

Exemplary Preparative HPLC Separation Methods

Basic condition ($NH_3$—$H_2O$): Instrument: Gilson GX-281 Liquid Handler, Gilson 322 Pump, Gilson 156 UV Detector; Column: Waters Xbridge 150×25 mm×5 µm; Mobile phase A: $H_2O$ with 0.05% $NH_3$—$H_2O$ (v %); Mobile phase B: MeCN; Gradient: B from 22% to 52% in 9.5 min, hold 100% B for 1 min; Flow Rate: 25 mL/min; Column Temperature: 30° C.; Wavelength: 220 nm, 254 nm.

Acid condition (HCOOH): Instrument: Gilson GX-281 Liquid Handler, Gilson 322 Pump, Gilson 156 UV Detector; Column: Agela Durashell C18 150*25 mm 5 µm; Mobile phase A: $H_2O$ (0.0225% HCOOH); Mobile phase B: MeCN; Gradient: B from 7% to 37% in 9 min, hold 100% B for 0 min; Flow Rate: 25 mL/min; Column Temperature: 30° C.; Wavelength: 220 nm, 254 nm.

Acid condition (HCl): Gilson GX-281 Liquid Handler, Gilson 322 Pump, Gilson 156 UV Detector; Column: Xtimate C18 150*25 mm*5 m; Mobile phase A: $H_2O$ with 0.05% HCl (v %); Mobile phase B: MeCN; Gradient: B from 0% to 30% in 6.5 min, hold 100% B for 2.5 min; Flow Rate: 25 mL/min; Column Temperature: 30° C.; Wavelength: 220 nm, 254 nm).

Neutral condition ($NH_4HCO_3$): (Instrument: Gilson GX-281 Liquid Handler, Gilson 322 Pump, Gilson 156 UV Detector; Column: Waters Xbridge 150×25 mm×5 m; Mobile phase A: $H_2O$ with 10 mmol $NH_4HCO_3$; Mobile phase B: MeCN; Gradient: B from 39% to 69% in 10 min, hold 100% B for 2.5 min; Flow Rate: 25 mL/min; Column Temperature: 30° C.; Wavelength: 220 nm, 254 nm).

Exemplary Large-Scale Separation

Basic condition: Instrument: Shimadzu LC-8A Pumps, Shimadzu SCL-10A VP System Controller, Shimadzu SPD-20AV UV/VIS Detector; Column: Phenomenex Gemini C18 250*50 mm*10 m; Mobile phase A: water (0.04% $NH_3$—$H_2O$+10 mM $NH_4HCO_3$); Mobile phase B: MeCN; Gradient: B from 65% to 95% in 26 min, hold 100% B for 3 min; Flow Rate: 110 mL/min; Column Temperature: 30° C.; Wavelength: 220 nm, 254 nm.

Acid condition (TFA): Instrument: Shimadzu LC-20AP Pumps, Shimadzu CBM-20A System Controller Shimadzu SPD-20AV UV/VIS Detector; Column: Phenomenex luna C18 250×50 mm×10 m; Mobile phase A: $H_2O$ with 0.1% TFA (v %); Mobile phase B: MeCN; Gradient: B from 0% to 25% in 15 min, hold 100% B for 4 min; Flow Rate: 120 mL/min; Column Temperature: 30° C.; Wavelength: 220 nm, 254 nm.

Exemplary Preparative Chiral SFC Method:

Exemplary chiral columns available for use in the separation/purification of the enantiomers/diastereomers provided herein include, but are not limited to, CHIRALPAK® AD-10, CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK.

In certain examples, the chiral separation was performed under the following conditions: Instrument: Thar 80; Column: Daicel Chiralpak AD. 250×30 mm I.D. m; Mobile phase: supercritical $CO_2$/MeOH (0.1% $NH_3$—$H_2O$, v %)=60/40; Flow Rate: 70 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm.

Materials and Methods

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography, HPLC, or supercritical fluid chromatography (SFC). The following schemes are presented with details as to the preparation of representative pyrazoles that have been listed herein. The compounds provided herein may be prepared from known or commercially available starting materials and reagents by one skilled in the art of organic synthesis.

Exemplary general method for preparative HPLC: Column: Waters RBridge prep 10 m C18, 19*250 mm. Mobile phase:acetonitrile, water ($NH_4HCO_3$) (30 L water, 24 g $NH_4HCO_3$, 30 mL $NH_3 \cdot H_2O$). Flow rate: 25 mL/min Exemplary general method for analytical HPLC: Mobile phase: A: water (10 mM $NH_4HCO_3$), B: acetonitrile Gradient: 5%-95% B in 1.6 or 2 min Flow rate: 1.8 or 2 mL/min; Column: XBridge C18, 4.6*50 mm, 3.5 μm at 45° C.

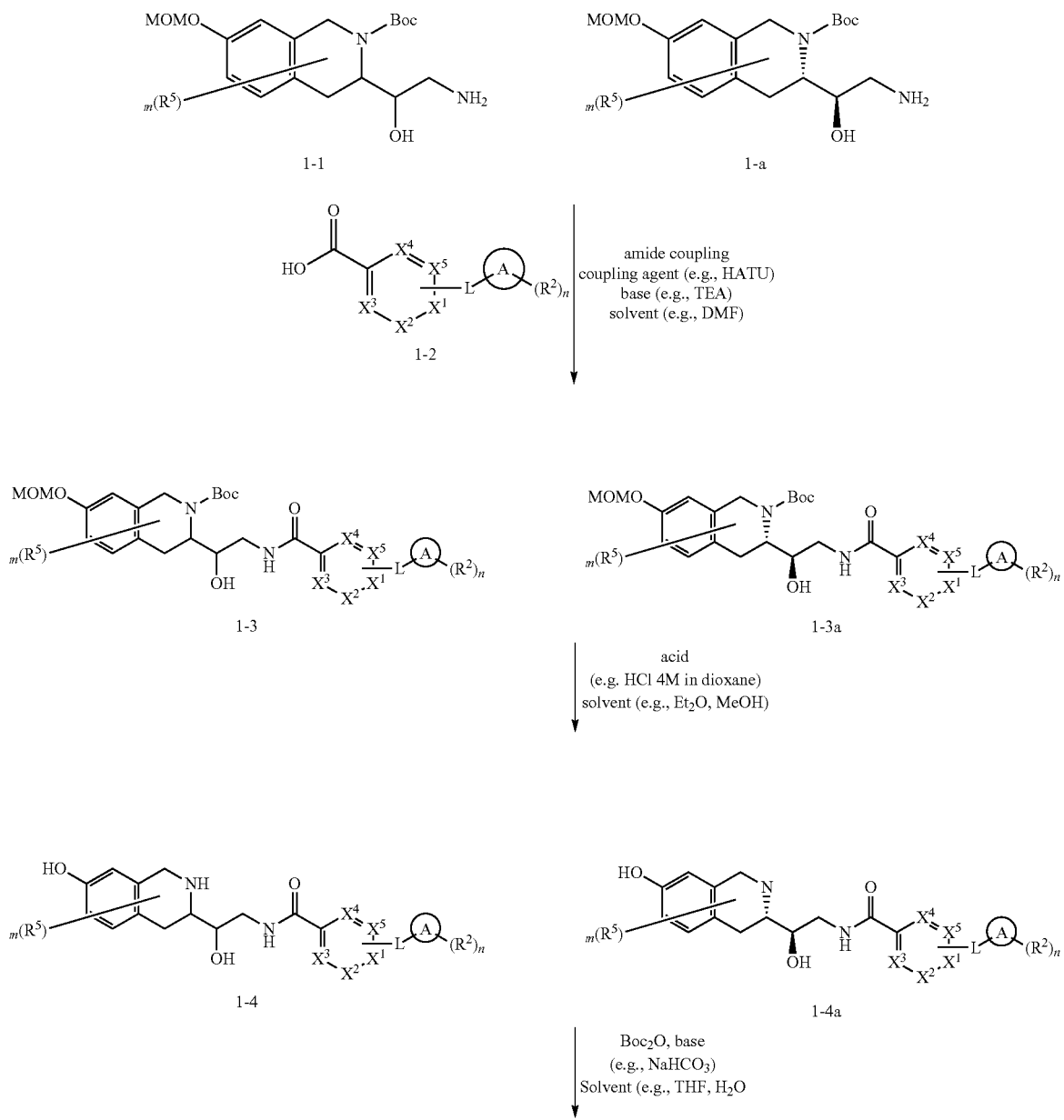

-continued

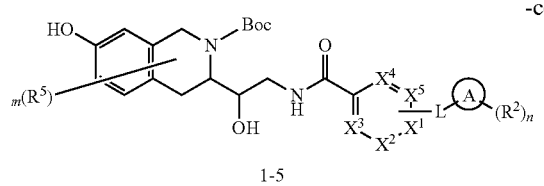
1-5

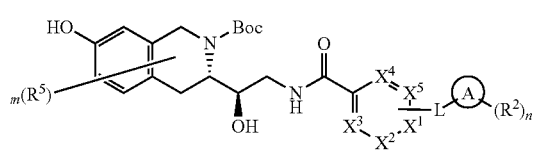
1-5a $R^1\diagdown X$ (X=halo (e.g., Cl, Br, I))
base (e.g., Cs₂CO₃)
solvent (e.g., DMF)
1-6

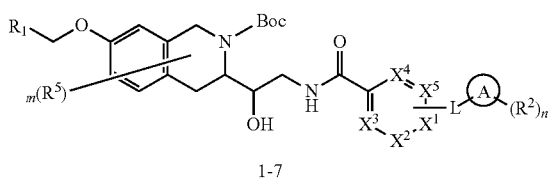
1-7

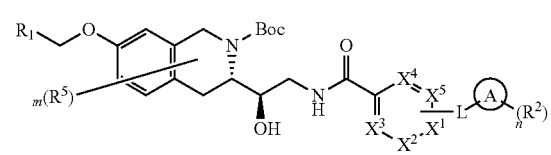
1-7a acid
(e.g. HCl 4M in dioxane)
solvent (e.g., Et₂O, MeOH)

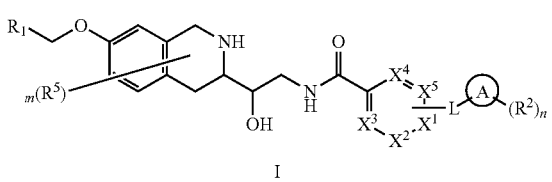
I

Ia

As shown in Scheme A, compounds of Formula (I) and (Ia) can be prepared from compounds of formula 1-1 and 1-1a, respectively. Compounds of formula 1-1 and 1-1a can be subjected to an amide coupling with compounds of formula 1-2 to form compounds of formula 1-3 and 1-3a, respectively. Examples of conditions known to generate compounds of formula 1-3 from compounds of formula 1-1 and formula 1-2 include but are not limited to adding a coupling agent such as CDI, HATU, HOBT, HBTU or PyBOP, a base such as a hydride base e.g., NaH, or KH, an amine base such as DBU, NEt₃, and NEt($^i$Pr)₂ or a carbonate base e.g., Na₂CO₃, K₂CO₃, or Cs₂CO₃, and in one embodiment stirring the reaction at 0° C. to room temperature or another embodiment at a temperature of 70° C. or higher, for example at a temperature in a range of 70° C. to 110° C., or in a range of 70° C. to 80° C., or at 80° C. The reaction may be carried out in solvents such as but not limited to DMF, and MTBE.

Compounds of formula 1-3 and 1-3a can undergo MoM and Boc deprotection using conditions known to one of skill in the art to give compounds of formula 1-4 and 1-4a. For example, Boc deprotection may comprise treatment with an acid. Exemplary acids include TFA, and HCl, and exemplary solvents include protic solvents such as methanol, halogenated solvents such as DCM and hexafluoroisopropanol or ether solvents such as dioxane and dimethylether. Compounds of formula 1-4 and 1-4a may be isolated as a salt or converted to the free base.

Compounds of formula 1-4 and 1-4a can be Boc protected using Boc anhydride (Boc₂O) in a solvent such as DMF, THF, H₂O, MeOH, DCM or a mixture thereof, optionally in the presence of a base. Exemplary bases include carbonate bases such as K₂CO₃, Cs₂CO₃, and amine bases such as DBU, NEt₃, and NEt($^i$Pr)₂.

Compounds of formula 1-5 and 1-5a can be coupled with alkyl chlorides of formula 1-6 under N-alkylation conditions to yield compounds of formula 1-7 and 1-7a, respectively. Examples of conditions known to generate compounds of formula 1-7 and 1-7a from a mixture of compounds of formula 1-5 and an alkyl chloride of formula 1-6 include but are not limited to adding one or more bases with or without an iodide salt. Exemplary iodide salts include such as NaI, KI and tetra-n-butylammonium iodide. Exemplary bases include carbonate bases such as K₂CO₃, Cs₂CO₃, and amine bases such as DBU, NEt₃, and NEt($^i$Pr)₂. The reaction may be carried out in solvents such as but not limited to DMF, acetonitrile and ethanol. The reaction may be heated at a temperature such as the reflux temperature of the solvent, or at a temperature in a range of 70° C. to 100° C., or in a range of 85° C. to 95° C., or at 90° C., or at 75° C.

Compounds of formula 1-7 and 1-7a can undergo Boc deprotection using conditions known to one of skill in the art to give compounds of formula I and Ia, respectively. For example, Boc deprotection may comprise treatment with an acid. Exemplary acids include TFA, and HCl, and exemplary solvents include protic solvents such as methanol, halogenated solvents such as DCM and hexafluoroisopropanol or ether solvents such as dioxane and dimethylether. Compounds of formula I and Ia may be isolated as a salt or converted to the free base.

SYNTHESIS OF INTERMEDIATE ACIDS

Synthesis of Acids of Formula Acid-IIa2i

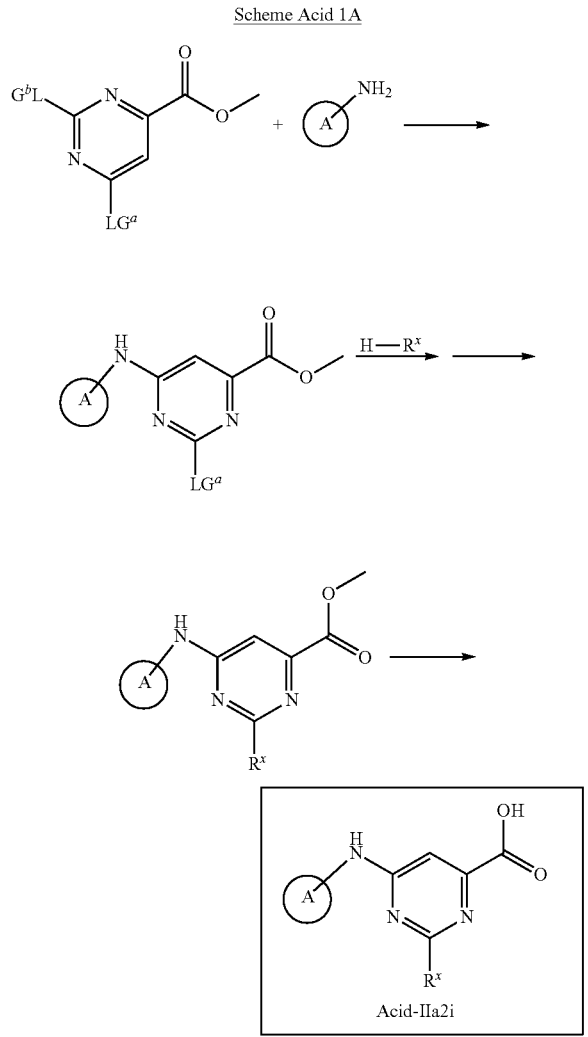

Scheme Acid 1A

Acid-IIa2i wherein A and R$^x$ are as described herein and LG$^a$ and LG$^b$ are leaving groups as described herein.

In certain embodiments LG$^a$ and LG$^b$ are halo (e.g., fluoro, chloro, bromo, iodo). One of the leaving groups, for example LG$^b$ can be displaced by the A-NH$_2$ moiety under conditions known to one of skill in the art (e.g., in a suitable solvent such as DCM, in the presence of a base such as a carbonate base (e.g., NaHCO$_3$, Na$_2$CO$_3$, Cs$_2$CO$_3$) or amine base (e.g., DBU, Et$_3$N, DIPEA). The other leaving group, for example LG$^a$ can be displaced by the R$^x$ moiety under conditions known to one of skill in the art (e.g., in a suitable solvent such as DCM, in the presence of a base such as a carbonate base (e.g., NaHCO$_3$, Na$_2$CO$_3$, Cs$_2$CO$_3$) or amine base (e.g., DBU, Et$_3$N, DIPEA). Finally, the ester group can be hydrolyzed to the corresponding carboxylic acid, for example under basic conditions (e.g., in the presence of a hydroxide base such as NaOH, LiOH) in a suitable solvent (e.g., THF, H$_2$O or a mixture thereof).

2-((2-methoxyethyl)(methyl)amino)-6-(oxetan-3-ylamino)pyrimidine-4-carboxylic acid

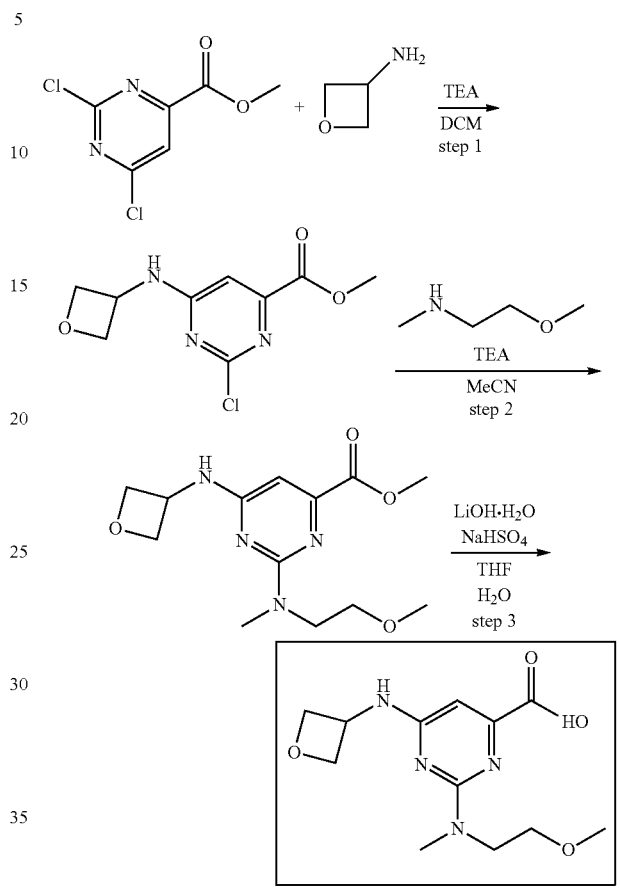

methyl 2-((2-methoxyethyl)(methyl)amino)-6-(oxetan-3-ylamino)pyrimidine-4-carboxylate. To a solution of methyl 2-chloro-6-(oxetan-3-ylamino)pyrimidine-4-carboxylate (0.7 g, 2.87 mmol) in ACN (30 mL), Triethylamine (581.44 mg, 5.75 mmol, 800.88 µL) and 2-methoxy-N-methyl-ethanamine (281.70 mg, 3.16 mmol, 339.39 µL) were added. The resulting mixture was heated in sealed tube at 80° C. for 48 hr and the solvent was removed in vacuo. The residue was taken up with water (80 mL) and extracted with DCM (3*50 mL). The combined organic extract was washed with brine (3*50 mL), dried over Na$_2$SO$_4$ and evaporated in vacuo to afford methyl 2-[2-methoxyethyl(methyl)amino]-6-(oxetan-3-ylamino)pyrimidine-4-carboxylate (0.78 g, 2.63 mmol, 91.62% yield). $^1$H NMR (400 MHz, DMSO-d$_6$) δ (ppm) 3.05 (s, 3H), 3.24 (s, 3H), 3.47 (m, 2H), 3.67 (m, 2H), 3.78 (s, 3H), 4.46 (m, 2H), 4.78 (m, 2H), 4.90 (m, 1H), 6.36 (s, 1H), 8.02 (bds, 1H). LCMS (ESI): [M+H]+ m/z: calc'd 296.3; found 297.2; Rt=0.851 min.

2-((2-methoxyethyl)(methyl)amino)-6-(oxetan-3-ylamino)pyrimidine-4-carboxylic acid. To a solution of methyl 2-[2-methoxyethyl(methyl)amino]-6-(oxetan-3-ylamino)pyrimidine-4-carboxylate (0.78 g, 2.63 mmol) in THF (30 mL), a solution of lithium hydroxide, monohydrate (243.01 mg, 5.79 mmol, 160.93 µL) in water (15 mL) was added in one portion. The resulting mixture was stirred at 25° C. for 2 hr and the organic solvents were evaporated in vacuo. To this solution, a solution of sodium bisulfate (695.27 mg, 5.79 mmol) in water (10 mL) was added and evaporated to dryness. The residue was diluted with THF (50 mL), the precipitate was filtered, filtercake was washed with THF (3*50 mL) and discarded. The solvent was evaporated in vacuo to obtain 2-[2-methoxyethyl(methyl)amino]-6-(oxetan-3-ylamino)pyrimidine-4-carboxylic acid (0.51 g, 1.81 mmol, 68.63% yield). LCMS (ESI): [M+H]+ m/z: calc'd 282.3; found 283.2; Rt=0.814 min.

6-(oxetan-3-ylamino)-2-(piperidin-1-yl)pyrimidine-4-carboxylic acid

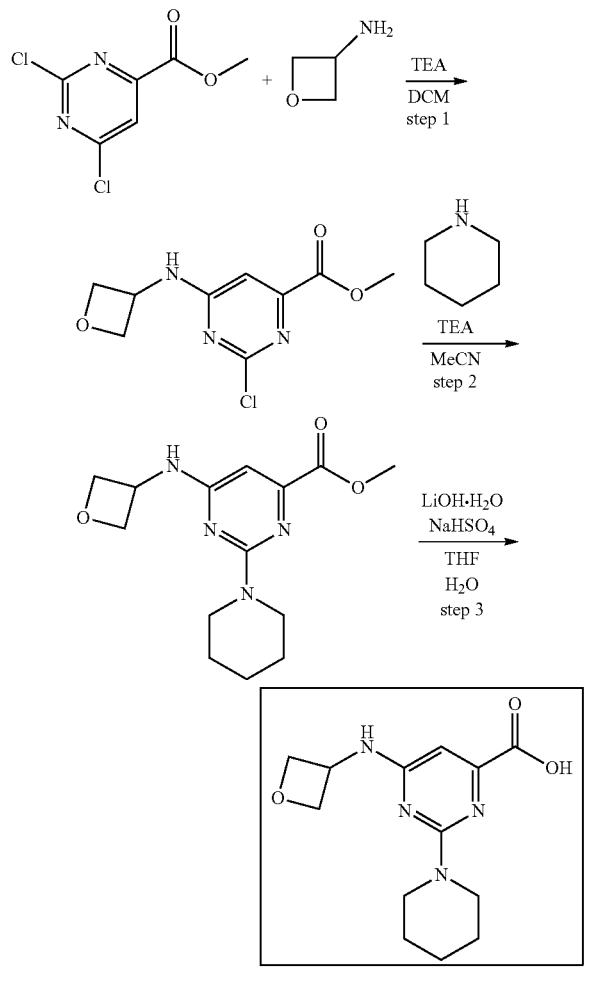

methyl 6-(oxetan-3-ylamino)-2-(piperidin-1-yl)pyrimidine-4-carboxylate. To a solution of methyl 2-chloro-6-(oxetan-3-ylamino)pyrimidine-4-carboxylate (0.7 g, 2.87 mmol) in ACN (30 mL), triethylamine (581.44 mg, 5.75 mmol, 800.88 μL) and piperidine (269.09 mg, 3.16 mmol, 312.17 μL) were added. The resulting mixture was heated at 80° C. for 48 hr and the solvent was removed in vacuo. The residue was taken up with water (80 mL) and extracted with DCM (3*50 mL). The combined organic extract was washed with brine (3*50 mL), dried over Na₂SO₄ and evaporated in vacuo to afford methyl 6-(oxetan-3-ylamino)-2-(1-piperidyl)pyrimidine-4-carboxylate (0.8 g, 2.74 mmol, 95.25% yield). ¹H NMR (400 MHz, DMSO-d₆) δ (ppm) 1.47 (m, 4H), 1.58 (m, 2H), 3.66 (m, 4H), 3.78 (s, 3H), 4.45 (m, 2H), 4.78 (m, 2H), 4.92 (m, 1H), 6.34 (s, 1H), 8.01 (bds, 1H)LCMS (ESI): [M+H]+ m/z: calc'd 292.3; found 293.2; Rt=0.841 min.

6-(oxetan-3-ylamino)-2-(piperidin-1-yl)pyrimidine-4-carboxylic acid. To a solution of methyl 6-(oxetan-3-ylamino)-2-(1-piperidyl)pyrimidine-4-carboxylate (0.8 g, 2.74 mmol) in THF (15 mL) and MeOH (15 mL), a solution of lithium hydroxide, monohydrate (252.62 mg, 6.02 mmol, 167.30 μL) in water (15 mL) was added in one portion. The resulting mixture was stirred at 25° C. for 24 hr and the organic solvents were evaporated in vacuo. To this solution, a solution of sodium hydrogen sulfate (722.83 mg, 6.02 mmol) in water (10 mL) was added and evaporated to dryness. The residue was diluted with THF (50 mL), the precipitate was filtered, filtercake was washed with THF (3*50 mL) and discarded. The solvent was evaporated in vacuo to obtain 6-(oxetan-3-ylamino)-2-(1-piperidyl)pyrimidine-4-carboxylic acid (0.7 g, 2.52 mmol, 91.91% yield). ¹H NMR (400 MHz, DMSO-d₆) δ (ppm) 1.45 (m, 4H), 1.57 (m, 2H), 3.64 (m, 5H), 4.46 (m, 2H), 4.76 (m, 2H), 4.78 (m, 1H), 6.30 (s, 1H), 7.97 (bds, 1H)LCMS (ESI): [M+H]+ m/z: calc'd 278.3; found 279.0; Rt=0.920 min.

2-(methyl(propyl)amino)-6-(oxetan-3-ylamino)pyrimidine-4-carboxylic acid

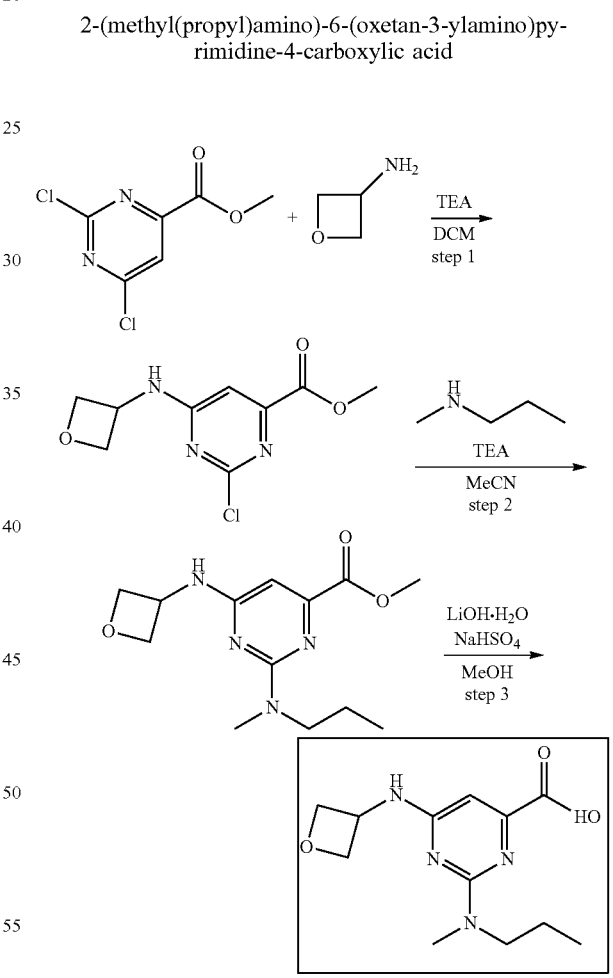

methyl 2-(methyl(propyl)amino)-6-(oxetan-3-ylamino)pyrimidine-4-carboxylate. To a solution of methyl 2-chloro-6-(oxetan-3-ylamino)pyrimidine-4-carboxylate (0.7 g, 2.87 mmol) in ACN (30 mL), triethylamine (581.44 mg, 5.75 mmol, 800.88 μL) and N-methylpropan-1-amine (231.13 mg, 3.16 mmol, 324.17 μL) were added. The resulting mixture was heated at 80° C. for 48 hr and the solvent was removed in vacuo. The residue was taken up with water (80 mL) and extracted with DCM (3*50 mL). The combined organic extract was washed with brine (3*50 mL), dried over Na$_2$SO$_4$ and evaporated in vacuo to afford methyl 2-[methyl(propyl)amino]-6-(oxetan-3-ylamino)pyrimidine-4-carboxylate (0.8 g, 2.85 mmol, 99.33% yield). $^1$H NMR (400 MHz, DMSO-d$_6$) δ (ppm) 0.83 (t, 3H), 1.52 (m, 2H), 3.01 (s, 3H), 3.46 (m, 2H), 3.78 (s, 3H), 4.46 (m, 2H), 4.78 (m, 2H), 4.88 (m, 1H), 6.33 (s, 1H), 7.97 (bds, 1H)LCMS (ESI): [M+H]+ m/z: calc'd 280.3; found 281.2; Rt=0.696 min.

2-(methyl(propyl)amino)-6-(oxetan-3-ylamino)pyrimidine-4-carboxylic acid. To a solution of methyl 2-[methyl(propyl)amino]-6-(oxetan-3-ylamino)pyrimidine-4-carboxylate (0.8 g, 2.85 mmol) in THF (15 mL) and MeOH (15 mL), a solution of lithium hydroxide, monohydrate (263.45 mg, 6.28 mmol, 174.47 μL) in water (15 mL) was added in one portion. The resulting mixture was stirred at 25° C. for 24 hr and the organic solvents were evaporated in vacuo. To this solution, a solution of sodium hydrogen sulfate (753.80 mg, 6.28 mmol) in water (10 mL) was added and evaporated to dryness. The residue was diluted with THF (50 mL), the precipitate was filtered, filtercake was washed with THF (3*50 mL) and discarded. The solvent was evaporated in vacuo to obtain 2-[methyl(propyl)amino]-6-(oxetan-3-ylamino)pyrimidine-4-carboxylic acid (0.59 g, 2.22 mmol, 77.63% yield). $^1$H NMR (400 MHz, DMSO-d$_6$) δ (ppm) 0.84 (t, 3H), 1.51 (m, 2H), 3.01 (s, 3H), 3.49 (m, 2H), 4.47 (m, 2H), 4.78 (m, 2H), 4.89 (m, 1H), 6.35 (s, 1H), 8.13 (bds, 1H)LCMS (ESI): [M+H]+ m/z: calc'd 266.3; found 267.2; Rt=0.804 min.

2-morpholino-6-(oxetan-3-ylamino)pyrimidine-4-carboxylic acid

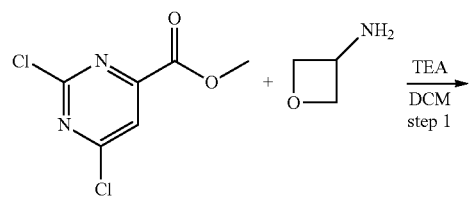

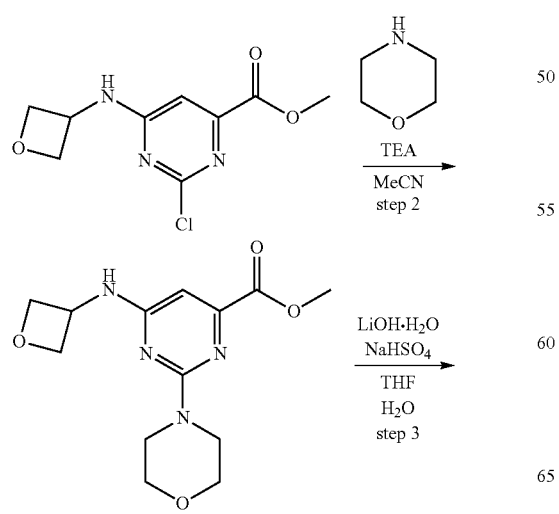

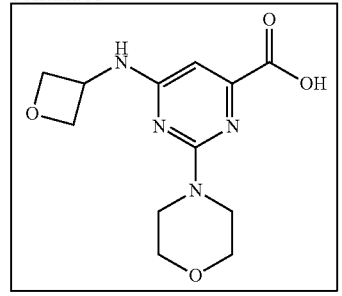

methyl 2-morpholino-6-(oxetan-3-ylamino)pyrimidine-4-carboxylate. To a solution of methyl 2-chloro-6-(oxetan-3-ylamino)pyrimidine-4-carboxylate (1 g, 4.10 mmol) in ACN (20 mL) at r.t. was added TEA (415.31 mg, 4.10 mmol, 572.06 μL) followed by morpholine (357.57 mg, 4.10 mmol, 359.00 μL) and the resulting reaction mixture was stirred at 80° C. for 48 hr and cooled down. The precipitate formed was collected by filtration, washed with ACN and dried in vacuo to give methyl 2-morpholino-6-(oxetan-3-ylamino)pyrimidine-4-carboxylate (0.95 g, 3.23 mmol, 78.65% yield). $^1$H NMR (400 MHz, DMSO-d$_6$) δ (ppm) 3.32 (t, 4H), 3.62 (t, 4H), 3.79 (s, 3H), 4.46 (m, 2H), 4.95 (m, 2H), 4.96 (m, 1H), 6.44 (s, 1H), 8.14 (bds, 1H)LCMS (ESI): [M+H]+ m/z: calc'd 294.3; found 295.2; Rt=0.888 min.

2-morpholino-6-(oxetan-3-ylamino)pyrimidine-4-carboxylic acid. A mixture of methyl 2-morpholino-6-(oxetan-3-ylamino)pyrimidine-4-carboxylate (0.95 g, 3.23 mmol) and lithium hydroxide, hydrate (297.98 mg, 7.10 mmol, 197.34 μL) in THF (15 mL)—methanol (15 mL)—water (15 mL) was stirred at r.t. for 12 hr. Then, volatile organic solvents were rotoevaporated, the aqueous phase was acidified (NaHSO$_4$, monohydrate) to pH 5 and the mixture was concentrated in vacuo. The residue was suspended in hot ethanol (100 mL) and filtered. The filtercake was washed with hot ethanol (2×50 mL) and discarded. The filtrate was evaporated in vacuo to leave the residue 2-morpholino-6-(oxetan-3-ylamino)pyrimidine-4-carboxylic acid (0.83 g, 2.96 mmol, 91.74% yield). $^1$H NMR (400 MHz, DMSO-d$_6$) δ (ppm) 3.63 (m, 8H), 4.45 (m, 2H), 4.78 (m, 2H), 4.94 (m, 1H), 6.41 (s, 1H), 8.13 (bds, 1H). LCMS (ESI): [M+H]+ m/z: calc'd 280.3; found 281.2; Rt=0.647 min.

6-((1-acetylazetidin-3-yl)amino)-2-(piperidin-1-yl)pyrimidine-4-carboxylic acid

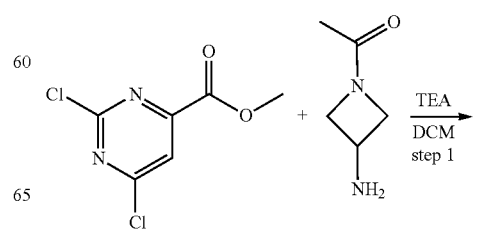

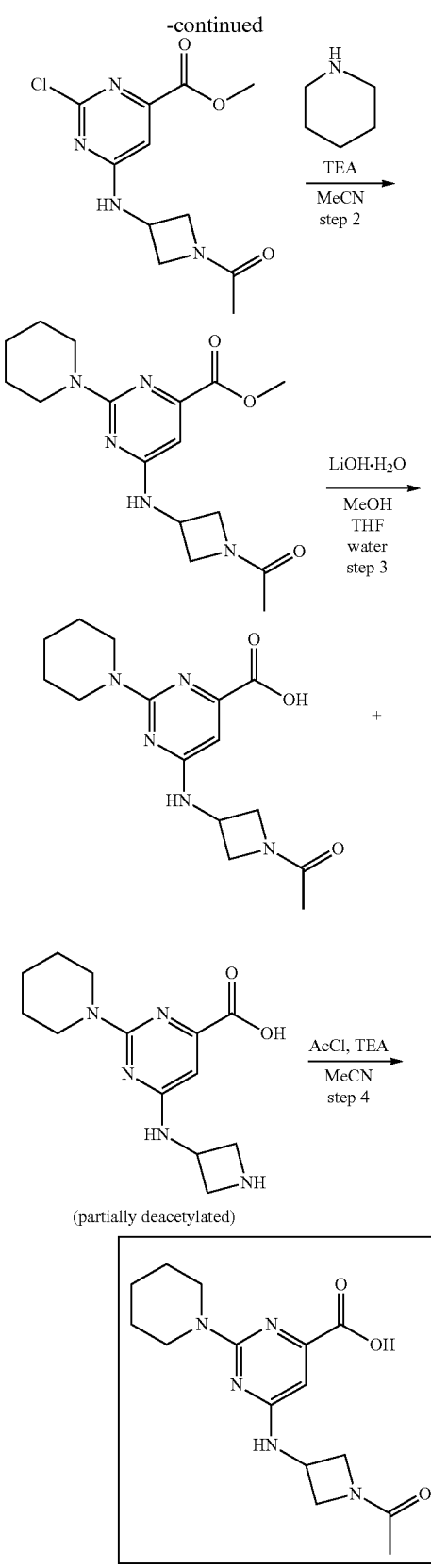

methyl 6-((1-acetylazetidin-3-yl)amino)-2-chloropyrimidine-4-carboxylate. To a solution of methyl 2,6-dichloropyrimidine-4-carboxylate (3 g, 14.49 mmol) in DCM (50 mL) at 0° C. was added TEA (2.93 g, 28.98 mmol, 4.04 mL) followed by 1-(3-aminoazetidin-1-yl)ethanone (3.31 g, 14.49 mmol, $CF_3CO_2H$) and the resulting reaction mixture was stirred at 0° C. for 30 min. and allowed to warm to room temperature. After 12 hr the reaction mixture was triturated with water (30 mL). The layers were separated, and the aqueous layer was extracted with DCM (30 mL). The combined organic layers were washed with water (25 mL) and brine, dried over $Na_2SO_4$ and concentrated in vacuo to give methyl 6-[(1-acetylazetidin-3-yl)amino]-2-chloro-pyrimidine-4-carboxylate (2.95 g, crude). $^1$H NMR (500 MHz, DMSO-$d_6$) δ (ppm) 1.75 (s, 3H), 3.85 (s, 3H), 3.93 (m, 2H), 4.17 (m, 1H), 4.56 (m, 2H), 7.07 (s, 1H), 8.97 (bds, 1H) LCMS (ESI): [M+H]+ m/z: calc'd 284.7; found 286.0; Rt=0.817 min methyl 6-((1-acetylazetidin-3-yl)amino)-2-(piperidin-1-yl)pyrimidine-4-carboxylate. To a solution of methyl 6-[(1-acetylazetidin-3-yl)amino]-2-chloro-pyrimidine-4-carboxylate (1.5 g, 5.27 mmol) in ACN (20 mL) at r.t. was added TEA (586.46 mg, 5.80 mmol, 807.79 μL) followed by piperidine (493.48 mg, 5.80 mmol, 572.48 μL) and the resulting reaction mixture was stirred at 80° C. for 32 hr, then it was diluted with water (40 mL). The aqueous layer was extracted with DCM (40 mL×2). The combined organic layers were washed with water (15 mL) and brine, dried over $Na_2SO_4$ and concentrated in vacuo to give methyl 6-[(1-acetylazetidin-3-yl)amino]-2-(1-piperidyl)pyrimidine-4-carboxylate (1.1 g, crude). $^1$H NMR (500 MHz, DMSO-$d_6$) δ (ppm) 1.49 (m, 6H), 1.75 (s, 3H), 3.58 (m, 3H), 3.68 (m, 5H), 3.95 (m, 1H), 4.12 (m, 1H), 4.39 (m, 1H), 4.53 (m, 1H), 6.53 (s, 1H), 8.31 (bds, 1H). LCMS (ESI): [M+H]+ m/z: calc'd 333.4; found 334.2; Rt=0.951 min.

6-(azetidin-3-ylamino)-2-(piperidin-1-yl)pyrimidine-4-carboxylic acid as a crude mixture with deacylated byproduct. A mixture of methyl 6-[(1-acetylazetidin-3-yl)amino]-2-(1-piperidyl)pyrimidine-4-carboxylate (1.1 g, 3.30 mmol) and lithium hydroxide, hydrate (304.58 mg, 7.26 mmol, 201.71 μL) in THF (10 mL)—methanol (10 mL)—water (15 mL) was stirred at r.t. for 12 hr. Then, volatile organic solvents were rotoevaporated. The aqueous phase was washed with DCM (10 mL), then acidified ($NaHSO_4$, monohydrate) to pH 5 and the mixture was concentrated in vacuo. The residue was suspended in hot ethanol (100 mL) and filtered. The filtercake was washed with hot ethanol (2×50 mL) and discarded. The filtrate was evaporated in vacuo to leave the residue 6-(azetidin-3-ylamino)-2-(piperidin-1-yl)pyrimidine-4-carboxylic acid (1 g, crude, contains 37% of deacylated byproduct). $^1$H NMR (400 MHz, DMSO-$d_6$) δ (ppm) 1.60 (m, 6H), 3.69 (m, 4H), 4.18 (m, 2H), 4.39 (m, 1H), 4.53 (m, 1H), 4.78 (m, 1H), 6.32 (s, 1H), 8.02 (bds, 1H), 8.73 (bds, 1H), 10.45 (bds, 1H). LCMS (ESI): [M+H]+ m/z: calc'd 277.3; found 278.2; Rt=0.644 min.

6-((1-acetylazetidin-3-yl)amino)-2-(piperidin-1-yl)pyrimidine-4-carboxylic acid. To a solution of the crude material from previous step which contain 6-(azetidin-3-ylamino)-2-(1-piperidyl)pyrimidine-4-carboxylic acid (1 g, 1.33 mmol) as impurity (37% by LCMS) and TEA (54.00 mg, 533.68 μmol, 74.38 μL) in ACN (25 mL) was added acetyl chloride (41.89 mg, 533.68 μmol, 32.47 μL) dropwise at 0° C. The reaction mixture was then stirred at r.t. with LCMS control. After 24 hr 70% conversion was observed. TEA (54.00 mg, 533.68 μmol, 74.38 μL) and acetyl chloride (41.89 mg, 533.68 μmol, 32.47 μL) was added again and the reaction mixture was then stirred at 35° C. another 24 hr. After full consumption of the starting material (according to LCMS) the reaction mixture was concentrated in vacuo. Then $Na_2CO_3$ (15 mL, 5% aqueous solution) was added and the aqueous phase was washed with DCM (2×10 mL), then it was acidified (NaHSO₄, monohydrate) to pH 5 and the mixture was concentrated in vacuo. The residue was suspended in hot ethanol (100 mL) and filtered. The filtercake was washed with hot ethanol (2×50 mL) and discarded. The filtrate was evaporated in vacuo to provide the product 6-[(1-acetylazetidin-3-yl)amino]-2-(1-piperidyl)pyrimidine-4-carboxylic acid (0.68 g, crude). ¹H NMR (400 MHz, DMSO-d₆) δ (ppm) 1.47 (m, 4H), 1.56 (m, 2H), 1.75 (s, 3H), 3.62 (m, 4H), 3.74 (m, 1H), 3.97 (m, 1H), 4.10 (m, 1H), 4.38 (m, 1H), 4.51 (m, 1H), 6.32 (s, 1H), 7.85 (bds, 1H), 11.45 (bds, 1H). LCMS (ESI): [M-Boc]⁺ m/z: calc'd 319.4; found 320.2; Rt=0.866 min.

6-(cyclobutylamino)-2-(piperidin-1-yl)pyrimidine-4-carboxylic acid

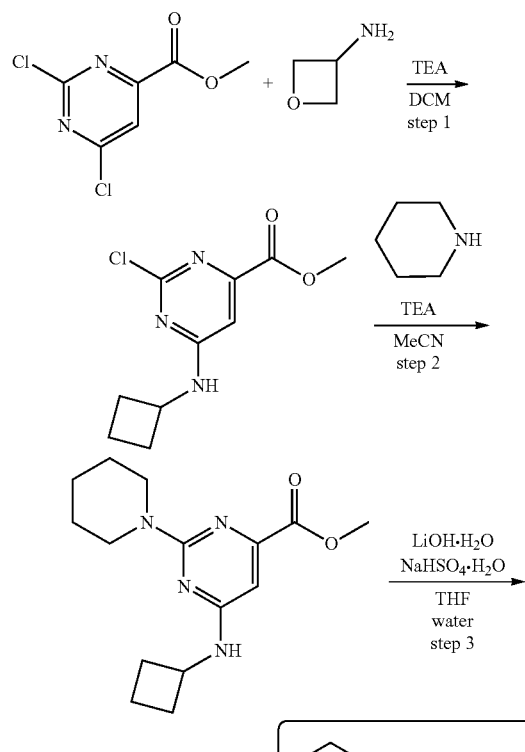

Methyl 2-chloro-6-(cyclobutylamino)pyrimidine-4-carboxylate To a solution of methyl 2,6-dichloropyrimidine-4-carboxylate (5 g, 24.15 mmol) in DCM (150 mL) at 0° C. was added triethylamine (2.69 g, 26.57 mmol, 3.70 mL) followed by cyclobutanamine (1.72 g, 24.15 mmol, 2.06 mL) and the resulting reaction mixture was stirred at 0° C. for 30 min and allowed to warm to room temperature and stirred for 12 hr. The resulting solution was taken up with water (150 mL). The organic layer was separated, washed with brine (3*50 mL), dried over Na₂SO₄ and evaporated in vacuo to obtain crude product (6 g). This compound was purified by gradient chromatography (hexane-EtOAc tubes 20-34 contain the title compound) to give methyl 2-chloro-6-(cyclobutylamino)pyrimidine-4-carboxylate (3.5 g, 14.48 mmol, 59.96% yield). ¹H NMR (500 MHz, DMSO-d₆) δ (ppm) 1.70 (m, 2H), 1.91 (m, 2H), 2.27 (m, 2H), 3.83 (s, 3H), 4.36 (m, 1H), 7.00 (s, 1H), 8.59 (d, 1H). LCMS (ESI): [M+H]+ m/z: calc'd 241.7; found 242.2; Rt=1.229 min.

Methyl 6-(cyclobutylamino)-2-(piperidin-1-yl)pyrimidine-4-carboxylate To a solution of methyl 2-chloro-6-(cyclobutylamino)pyrimidine-4-carboxylate (2 g, 8.28 mmol) and piperidine (739.88 mg, 8.69 mmol, 858.33 µL) in ACN (80 mL), triethylamine (1.67 g, 16.55 mmol, 2.31 mL) was added. The resulting mixture was stirred at 80° C. for 48 hr and evaporated. The residue was taken up with water (100 mL) and extracted with DCM (3*50 mL). The combined organic layer was washed with brine (2*70 mL), dried over Na₂SO₄ and evaporated in vacuo to give methyl 6-(cyclobutylamino)-2-(1-piperidyl)pyrimidine-4-carboxylate (2.3 g, 7.92 mmol, 95.72% yield). ¹H NMR (500 MHz, DMSO-d₆) δ (ppm) 1.46 (m, 4H), 1.63 (m, 4H), 1.88 (m, 2H), 2.25 (m, 2H), 3.67 (m, 4H), 3.77 (s, 3H), 4.36 (m, 1H), 6.28 (s, 1H), 7.58 (d, 1H). LCMS (ESI): [M+H]+ m/z: calc'd 290.4; found 291.2; Rt=1.065 min.

6-(cyclobutylamino)-2-(piperidin-1-yl)pyrimidine-4-carboxylic acid To a solution of methyl 6-(cyclobutylamino)-2-(1-piperidyl)pyrimidine-4-carboxylate (2.3 g, 7.92 mmol) in THF (50 mL) was added a solution of Lithium hydroxide, monohydrate (731.28 mg, 17.43 mmol, 484.29 µL) in water (50 mL). The resulting mixture was stirred at 25° C. for 3 hr and THF was evaporated in vacuo. pH was adjusted to 6 with solution of sodium bisulfate monohydrate (2.52 g, 18.22 mmol) in water (20 mL). The formed precipitate was filtered, washed with cold water (10 mL), MTBE (10 mL) and dried to obtain 6-(cyclobutylamino)-2-(1-piperidyl)pyrimidine-4-carboxylic acid (1.6 g, 5.79 mmol, 73.10% yield). ¹H NMR (500 MHz, DMSO-d₆) δ (ppm) 1.47 (m, 4H), 1.58 (m, 2H), 1.68 (m, 2H), 1.89 (m, 2H), 2.25 (m, 2H), 3.69 (m, 4H), 4.36 (m, 1H), 6.27 (s, 1H), 7.68 (d, 1H). LCMS (ESI): [M+H]+ m/z: calc'd 276.3; found 277.2; Rt=1.059 min.

6-((1-acetylpiperidin-4-yl)amino)-2-(piperidin-1-yl)pyrimidine-4-carboxylic acid

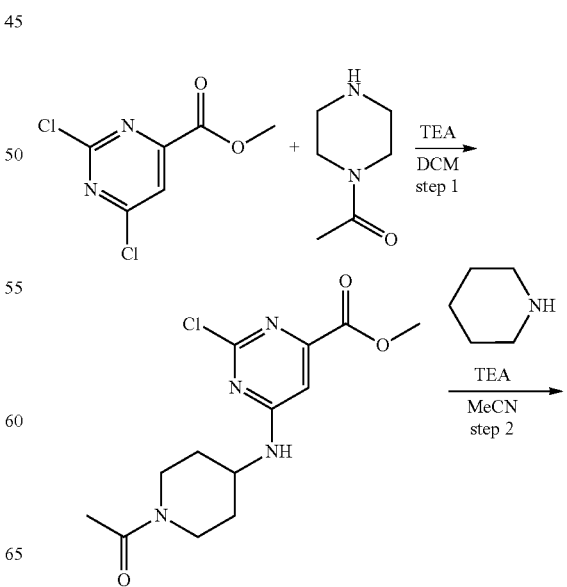

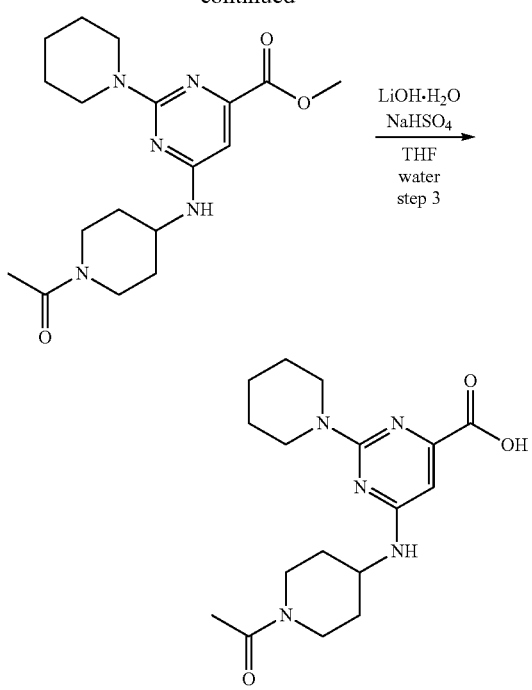

Methyl 6-((1-acetylpiperidin-4-yl)amino)-2-chloropyrimidine-4-carboxylate To a solution of methyl 2,6-dichloropyrimidine-4-carboxylate (6 g, 28.98 mmol) in DCM (100 mL) at 0° C. was added TEA (3.08 g, 30.43 mmol, 4.24 mL) followed by 1-(4-amino-1-piperidyl)ethanone (4.12 g, 28.98 mmol) and the resulting reaction mixture was stirred at 0° C. for 30 min and allowed to warm to room temperature. After 14 hr the reaction mixture was evaporated. The residue was purified by column chromatography to give methyl 6-[(1-acetyl-4-piperidyl)amino]-2-chloro-pyrimidine-4-carboxylate (2.3 g, 7.35 mmol, 25.37% yield). $^1$H NMR (500 MHz, DMSO-$d_6$) δ (ppm) 1.26 (m, 1H), 1.38 (m, 1H), 1.88 (m, 1H), 2.00 (s, 3H), 2.82 (m, 1H), 3.19 (m, 1H), 3.31 (m, 1H), 3.80 (m, 1H), 3.84 (s, 3H), 4.03 (m, 1H), 4.20 (m, 1H), 7.06 (s, 1H), 8.31 (d, 1H). LCMS (ESI): [M+H]+ m/z: calc'd 312.7; found 313.2; Rt=1.032 min.

Methyl 6-((1-acetylpiperidin-4-yl)amino)-2-(piperidin-1-yl)pyrimidine-4-carboxylate To a solution of methyl 6-[(1-acetyl-4-piperidyl)amino]-2-chloro-pyrimidine-4-carboxylate (2.3 g, 7.35 mmol) in ACN (40 mL) at r.t. was added TEA (1.12 g, 11.03 mmol, 1.54 mL) followed by piperidine (688.80 mg, 8.09 mmol, 799.07 μL) and the resulting reaction mixture was stirred at 80° C. for 10 hr, then it was diluted with water (50 mL). The aqueous layer was extracted with DCM (50 mL). The combined organic layers were washed with water (25 mL) and brine, dried over $Na_2SO_4$ and concentrated in vacuo to give methyl 6-[(1-acetyl-4-piperidyl)amino]-2-(1-piperidyl)pyrimidine-4-carboxylate (2.2 g, 6.09 mmol, 82.77% yield) which was used in the next step without further purification. $^1$H NMR (500 MHz, DMSO-$d_6$) δ (ppm) 1.16 (m, 1H), 1.28 (m, 1H), 1.31 (m, 1H), 1.48 (m, 3H), 1.59 (m, 2H), 1.85 (m, 2H), 1.98 (s, 3H), 2.64 (m, 1H), 3.17 (m, 1H), 3.31 (m, 1H), 3.57 (m, 2H), 3.67 (m, 2H), 3.77 (s, 3H), 4.03 (m, 1H), 4.17 (m, 1H), 6.34 (s, 1H), 7.31 (d, 1H). LCMS (ESI): [M+H]+ m/z: calc'd 361.4; found 362.2; Rt=0.978 min.

6-((1-acetylpiperidin-4-yl)amino)-2-(piperidin-1-yl)pyrimidine-4-carboxylic acid To the solution of methyl 6-[(1-acetyl-4-piperidyl)amino]-2-(1-piperidyl)pyrimidine-4-carboxylate (2.2 g, 6.09 mmol) in THF (15 mL)/water (15 mL) lithium hydroxide monohydrate, 98% (536.39 mg, 12.78 mmol, 355.23 μL) was added and the reaction mixture was stirred at 25° C. for 3 hr. Mixture was evaporated to dryness. The residue (water solution) was acidified with sodium bisulfate to slightly acidic pH. Product was extracted with DCM (3*25 mL), dried over $Na_2SO_4$. DCM was evaporated to give 2 g of crude product which was purified by reverse phase HPLC to give 2 fractions: 1st: needed product: 0.5 g, 2nd: regioisomer: 0.4 g. $^1$H NMR (400 MHz, DMSO-$d_6$) δ (ppm) 1.25 (m, 2H), 1.37 (m, 4H), 1.59 (m, 2H), 1.85 (m, 2H), 1.99 (s, 3H), 2.83 (m, 1H), 3.15 (m, 1H), 3.69 (m, 5H), 4.02 (m, 1H), 4.17 (m, 1H), 6.34 (s, 1H), 7.39 (d, 1H). LCMS (ESI): [M+H]+ m/z: calc'd 347.4; found 348.2; Rt=2.045 min.

Scheme Acid 1B

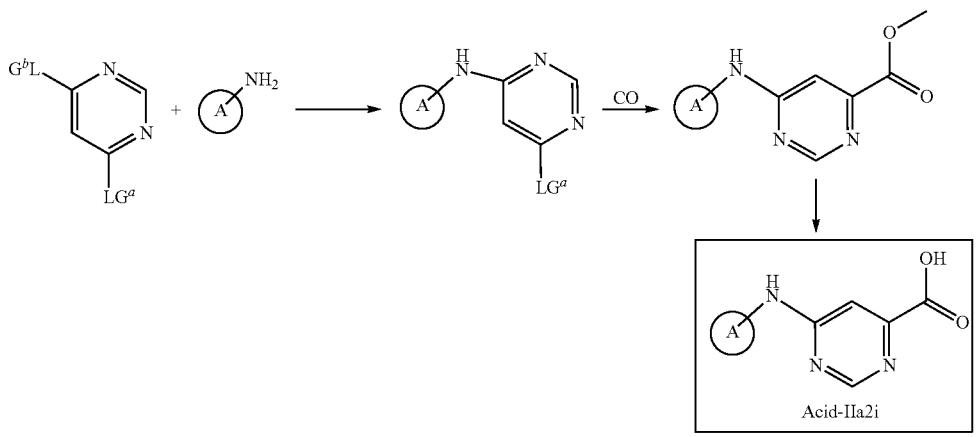

wherein A and $R^x$ are as described herein and $LG^a$ and $LG^b$ are leaving groups as described herein.

In certain embodiments $LG^a$ and $LG^b$ are halo (e.g., fluoro, chloro, bromo, iodo). One of the leaving groups, for example $LG^b$ can be displaced by the $A-NH_2$ moiety under conditions known to one of skill in the art (e.g., in a suitable solvent such as DCM, in the presence of a base such as a carbonate base (e.g., $NaHCO_3$, $Na_2CO_3$, $Cs_2CO_3$) or amine base (e.g., DBU, Et₃N, DIPEA). The other leaving group, for example LG$^a$ can be converted to a carboxylate moiety under conditions known to one of skill in the art through a palladium mediated carbonylation with CO and MeOH (e.g., in a suitable solvent such as MeOH, in the presence of a base such as a carbonate base (e.g., NaHCO₃, Na₂CO₃, Cs₂CO₃) or amine base (e.g., DBU, Et₃N, DIPEA), a palladium catalyst (e.g., Pd(dppf)Cl₂ DCM complex). Finally, the ester group can be hydrolyzed to the corresponding carboxylic acid, for example under basic conditions (e.g., in the presence of a hydroxide base such as NaOH, LiOH) in a suitable solvent (e.g., THF, H₂O or a mixture thereof).

6-(cyclobutylamino)pyrimidine-4-carboxylic acid

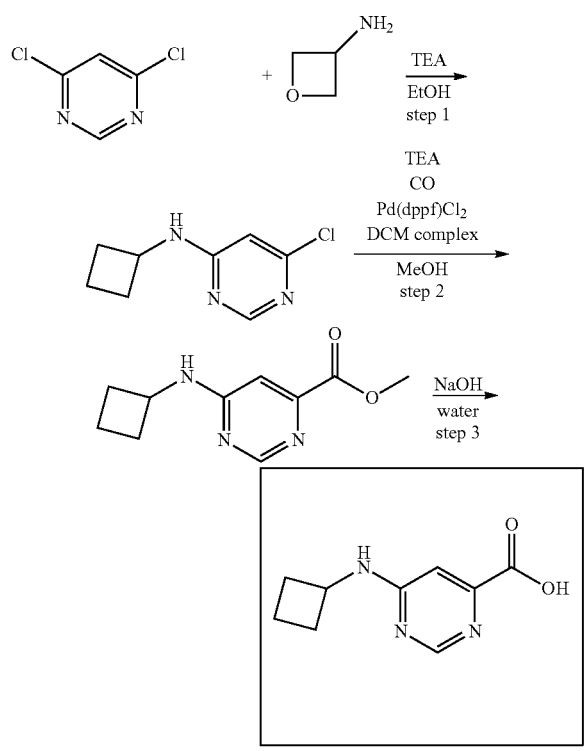

6-chloro-N-cyclobutylpyrimidin-4-amine. 4,6-Dichloropyrimidine (50 g, 335.62 mmol), TEA (50.94 g, 503.43 mmol, 70.17 mL) were dissolved in EtOH (500 mL) and cyclobutanamine (26.26 g, 369.18 mmol, 31.52 mL) was added. The mixture was stirred for 30 min (spontaneous heating was observed) and then for 3 hr at 80° C. The reaction mixture was cooled to r.t. and evaporated in vacuo at 50° C. The residue was triturated with H₂O (0.5 L). The precipitate was filtered, washed with H₂O (3*300 mL) and dried at 40° C. to give 6-chloro-N-cyclobutyl-pyrimidin-4-amine (56 g, 304.95 mmol, 90.86% yield). ¹H NMR (400 MHz, DMSO-d₆) δ (ppm) 1.68 (m, 2H), 1.89 (m, 2H), 2.25 (m, 2H), 4.40 (m, 1H), 6.43 (s, 1H), 7.98 (bds, 1H), 8.23 (s, 1H). LCMS (ESI): [M+H]+ m/z: calc'd 183.6; found 184.2; Rt=1.161 min.

methyl 6-(cyclobutylamino)pyrimidine-4-carboxylate. 6-Chloro-N-cyclobutyl-pyrimidin-4-amine (5 g, 27.23 mmol), TEA (8.27 g, 81.68 mmol, 11.38 mL), [1,1'-bis(diphenylphosphino)ferrocene]dichloropalladium(II), complex with dichloromethane (222.34 mg, 272.28 µmol) were dissolved in methanol (250 mL). The mixture was stirred in autoclave at 115° C. in atmosphere of CO (872.42 mg, 27.23 mmol) (40 atm) for 40 hr. Then the reaction mixture was cooled to r.t. and the solvent was evaporated in vacuo at 40° C. EtOAc (200 mL) was added and the mixture was extracted with H₂O (3*50 mL). The organic phase was separated, dried with Na₂SO₄ and evaporated in vacuo to give methyl 6-(cyclobutylamino)pyrimidine-4-carboxylate (4.55 g, 21.96 mmol, 80.64% yield). ¹H NMR (400 MHz, DMSO-d₆) δ (ppm) 1.70 (m, 2H), 1.90 (m, 2H), 2.28 (m, 2H), 3.83 (s, 3H), 4.42 (m, 1H), 7.03 (s, 1H), 8.07 (bds, 1H), 8.48 (s, 1H). LCMS (ESI): [M+H]+ m/z: calc'd 207.2; found 208.2; Rt=0.797 min.

6-(cyclobutylamino)pyrimidine-4-carboxylic acid. Methyl 6-(cyclobutylamino)pyrimidine-4-carboxylate (1 g, 4.83 mmol) was added to the solution of sodium hydroxide (212.31 mg, 5.31 mmol, 99.68 µL) in H₂O (5 mL). The mixture was stirred at 50° C. for 1 hr. Then the mixture was cooled to r.t. The insoluble materials were filtered off The filtrate was acidified to pH=3. The solid formed was filtered, washed with H₂O (3*5 mL) and dried in vacuo at 45° C. to give 6-(cyclobutylamino)pyrimidine-4-carboxylic acid (0.7 g, 3.05 mmol, 63.16% yield, HCl). ¹H NMR (500 MHz, DMSO-d₆) δ (ppm) 1.72 (m, 2H), 1.94 (m, 2H), 2.28 (m, 2H), 4.46 (m, 1H), 6.99 (s, 1H), 8.49 (m, 2H), 12.12 (bds, 1H). LCMS (ESI): [M+H]+ m/z: calc'd 193.2; found 194.2; Rt=0.790 min.

6-((1-acetylpiperidin-4-yl)amino)pyrimidine-4-carboxylic acid

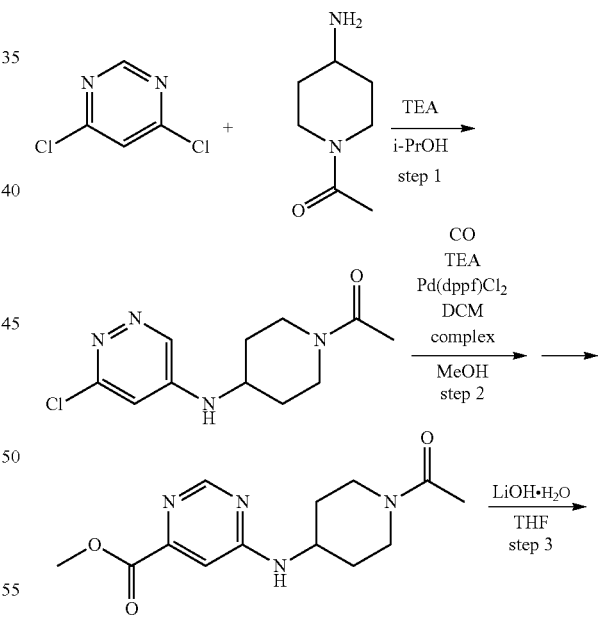

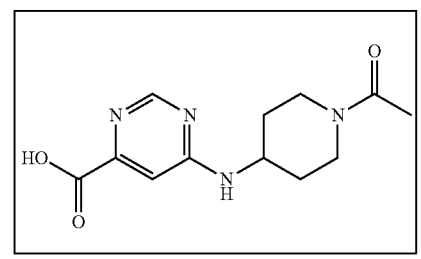

1-(4-((6-chloropyrimidin-4-yl)amino)piperidin-1-yl)ethenone. 4,6-Dichloropyrimidine (26.2 g, 175.86 mmol), 1-(4-amino-1-piperidyl)ethanone (25.01 g, 175.86 mmol), triethylamine (21.35 g, 211.04 mmol, 29.41 mL) were mixed in isopropanol (300 mL) and refluxed for 10 hr. Then the mixture was cooled to r.t. and evaporated in vacuo. EtOAc (300 mL) was added to the residue and the mixture was extracted with aqueous NaCl (5*100 mL). The organic phase was separated, dried with $Na_2SO_4$ and evaporated in vacuo at 45° C. to give 1-[4-[(6-chloropyrimidin-4-yl)amino]-1-piperidyl]ethanone (41.3 g, 162.14 mmol, 92.20% yield). $^1$H NMR (500 MHz, $CDCl_3$) δ 1.42 (m, 2H), 2.03 (m, 1H), 2.12 (m, 4H), 2.83 (m, 1H), 3.23 (m, 1H), 3.82 (m, 1H), 4.01 (bds, 1H), 4.55 (m, 1H), 5.26 (m, 1H), 6.37 (s, 1H), 8.35 (s, 1H). LCMS (ESI): [M+H]+ m/z: calc'd 254.7; found 255.2; Rt=0.924 min.

methyl 6-((1-acetylpiperidin-4-yl)amino)pyrimidine-4-carboxylate. 1-[4-[(6-Chloropyrimidin-4-yl)amino]-1-piperidyl]ethanone (41 g, 160.96 mmol), triethylamine (48.86 g, 482.89 mmol, 67.31 mL), [1,1'-bis(diphenylphosphino)ferrocene]dichloropalladium(II), complex with dichloromethane (6.57 g, 8.05 mmol) were dissolved in methanol (500 mL). The mixture was stirred in autoclave at 110° C. in atmosphere of carbon monoxide (40 atm) for 20 hr. Then the reaction mixture was cooled to r.t. and the solvent was evaporated in vacuo at 40° C. to give the mixture of methyl 6-[(1-acetyl-4-piperidyl)amino]pyrimidine-4-carboxylate and triethylamine hydrochloride, which was purified by column chromatography to give methyl 6-[(1-acetyl-4-piperidyl)amino]pyrimidine-4-carboxylate (18.7 g, 67.19 mmol, 41.74% yield). $^1$H NMR (500 MHz, $CDCl_3$) δ 1.43 (m, 2H), 2.03 (m, 1H), 2.11 (s, 3H), 2.17 (m, 1H), 2.82 (t, 1H), 3.24 (t, 1H), 3.85 (m, 1H), 3.96 (s, 3H), 4.12 (bds, 1H), 4.57 (m, 1H), 5.47 (m, 1H), 7.08 (s, 1H), 8.65 (s, 1H). LCMS (ESI): [M+H]+ m/z: calc'd 278.3; found 279.2; Rt=0.788 min.

6-((1-acetylpiperidin-4-yl)amino)pyrimidine-4-carboxylic acid. Methyl 6-[(1-acetyl-4-piperidyl)amino]pyrimidine-4-carboxylate (18.7 g, 67.19 mmol) was dissolved in THF (200 mL). The solution was cooled to 0° C. and lithium hydroxide, monohydrate (2.82 g, 67.19 mmol, 1.87 mL) was added. The mixture was warmed to 20° C. and stirred for 2 hr. The mixture was cooled to 0° C. and conc. HCl was added to pH 2-3. The solvents were evaporated in vacuo at 45° C. The residue was triturated with MeCN (100 mL). The solid formed was filtered, washed with MeCN (100 mL) and dried in vacuo at 45° C. to give 6-[(1-acetyl-4-piperidyl)amino]pyrimidine-4-carboxylic acid (16.5 g, 62.43 mmol, 92.92% yield). $^1$H NMR (500 MHz, DMSO-$d_6$) δ 1.28 (m, 1H), 1.42 (m, 1H), 1.87 (m, 2H), 2.00 (s, 3H), 2.79 (t, 1H), 3.17 (t, 1H), 3.80 (m, 1H), 4.12 (m, 1H), 4.20 (m, 1H), 7.09 (s, 1H), 8.40 (bds, 1H), 8.49 (s, 1H). LCMS (ESI): [M+H]+ m/z: calc'd 264.3; found 265.0; Rt=0.574 min.

Synthesis of Acids of Formula Acid-IIa1i

Scheme Acid 2A

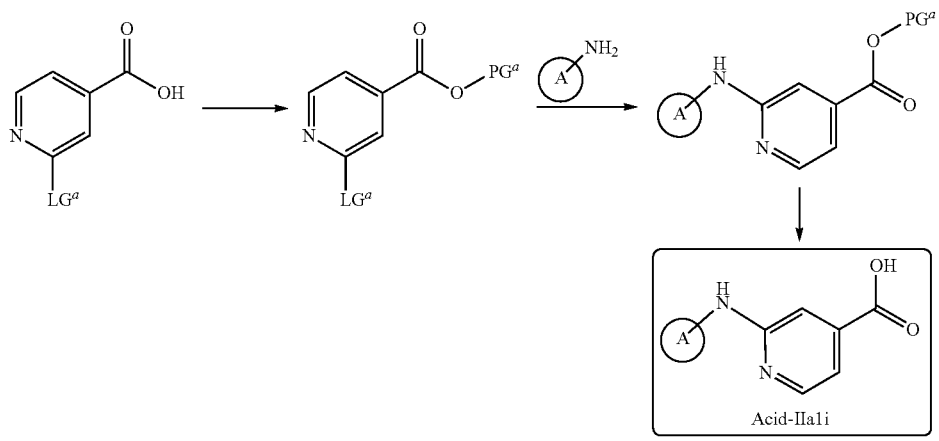

wherein A and $R^x$ are as described herein, $PG^a$ is a carboxylate protective group as described herein (e.g., a $^t$Bu group) and $LG^a$ is a leaving group as described herein.

In certain embodiments $LG^a$ is halo (e.g., fluoro, chloro, bromo, iodo). The carboxylic acid can be protected with a suitable protecting group (e.g., $^t$Bu) by treatment with a protecting agent (e.g., $Boc_2O$) in the presence of a coupling agent (e.g., DMAP) in a suitable solvent (e.g., THF). The leaving group $LG^a$ can be displaced by the A-$NH_2$ moiety under conditions known to one of skill in the art (e.g., in a suitable solvent such as DCM, THF, DMF or a combination thereof) in the presence of a base such as a carbonate base (e.g., $NaHCO_3$, $Na_2CO_3$, $K_2CO_3$, $Cs_2CO_3$) or amine base (e.g., DBU, $Et_3N$, DIPEA). In some embodiments the displacement is a palladium-catalyzed aryl coupling (e.g., in the presence of a palladium source such as $Pd_2(dba)_3$, a base such as NaOEt or sodium 2-methyl propanolate and a ligand such as XantPhos) in a suitable solvent (e.g., toluene). Finally, the protective group can be removed to provide the corresponding carboxylic acid, for example under acidic conditions (e.g., in the presence of HCl) in a suitable solvent (e.g., EtOAc).

2-(cyclobutylamino)isonicotinic acid

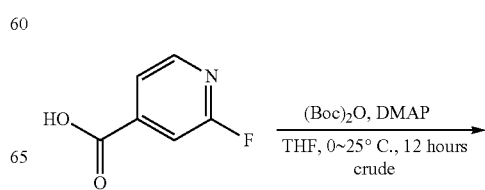

-continued

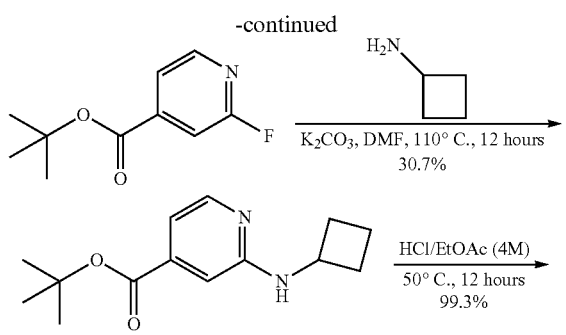

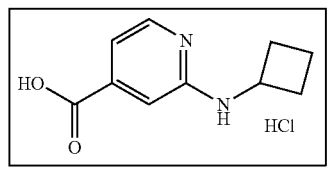

tert-Butyl 2-fluoropyridine-4-carboxylate. To a solution of 2-fluoropyridine-4-carboxylic acid (20 g, 141.74 mmol, 1 eq) and DMAP (3.46 g, 28.35 mmol, 0.2 eq) in THF (150 mL) was added (Boc)$_2$O (68.0 g, 311.57 mmol, 2.2 eq) at 0° C. The mixture was stirred at 25° C. for 12 hours. The resulting mixture was quenched by addition of NaHCO$_3$ (20 mL) and extracted with EtOAc (150 mL*3). The combined organic layer was dried over anhydrous Na$_2$SO$_4$, filtered and concentrated under reduced pressure to afford tert-butyl 2-fluoropyridine-4-carboxylate (37 g, crude) which was used in next step without further purification. $^1$H NMR (400 MHz, chloroform-d) δ ppm 8.30 (d, J=5.0 Hz, 1H), 7.67 (dt, J=5.0, 1.5 Hz, 1H), 7.40 (d, J=1.0 Hz, 1H), 1.58 (s, 9H); LCMS (M+H$^+$) m/z: calc'd 198.1; found 198.1. tert-butyl 2-(cyclobutylamino) pyridine-4-carboxylate. To a mixture of tert-butyl 2-fluoropyridine-4-carboxylate (70.87 mmol, crude product, 1 eq), cyclobutanamine (15 mL, 175.05 mmol, 2.5 eq) in DMF (150 mL) was added K$_2$CO$_3$ (29.38 g, 212.61 mmol, 3 eq). The mixture was stirred at 110° C. for 12 hours (2 batches in parallel). The resulting mixture was filtered and diluted with EtOAc (100 mL*3). The organic layers were washed with brine (150 mL*3), dried over anhydrous Na$_2$SO$_4$, filtered and concentrated under reduced pressure. The residue was purified by column chromatography (silica, petroleum ether/EtOAc=30:1 to 10:1) to afford tert-butyl 2-(cyclobutylamino) pyridine-4-carboxylate (12 g, 30.7% for two steps) as yellow oil. $^1$H NMR (400 MHz, chloroform-d) δ ppm 8.15 (d, J=5.0 Hz, 1H), 7.03 (dd, J=5.3, 1.3 Hz, 1H), 6.84 (s, 1H), 4.85 (d, J=6.0 Hz, 1H), 4.10-4.23 (m, 1H), 2.41-2.51 (m, 2H), 1.69-1.94 (m, 4H), 1.59 (s, 9H); LCMS (M+H$^+$) m/z: calc'd 249.2; found 249.0.

2-(cyclobutylamino) pyridine-4-carboxylic acid. A solution of tert-butyl 2-(cyclobutylamino) pyridine-4-carboxylate (12 g, 43.49 mmol, 1 eq) in HCl/EtOAc (250 mL, 4M) was stirred at 50° C. for 12 hours. The precipitate was collected by filtration, washed with EtOAc (30 mL*3) and dried over under high vacuum to afford 2-(cyclobutylamino) pyridine-4-carboxylic acid (9.9 g, HCl salt, 99.3% yield) as yellow solid. $^1$H NMR (400 MHz, DMSO-d$_6$) δ ppm 9.27 (br s, 1H), 7.99 (d, J=6.3 Hz, 1H), 7.41 (s, 1H), 7.06 (dd, J=6.5, 1.3 Hz, 1H), 4.29 (t, J=7.5 Hz, 1H), 2.37-2.46 (m, 2H), 1.94-2.07 (m, 2H), 1.65-1.85 (m, 2H); LCMS (M+H$^+$) m/z: calc'd 193.1; found 193.4.

2-[(1-acetyl-4-piperidyl)amino]pyridine-4-carboxylic acid

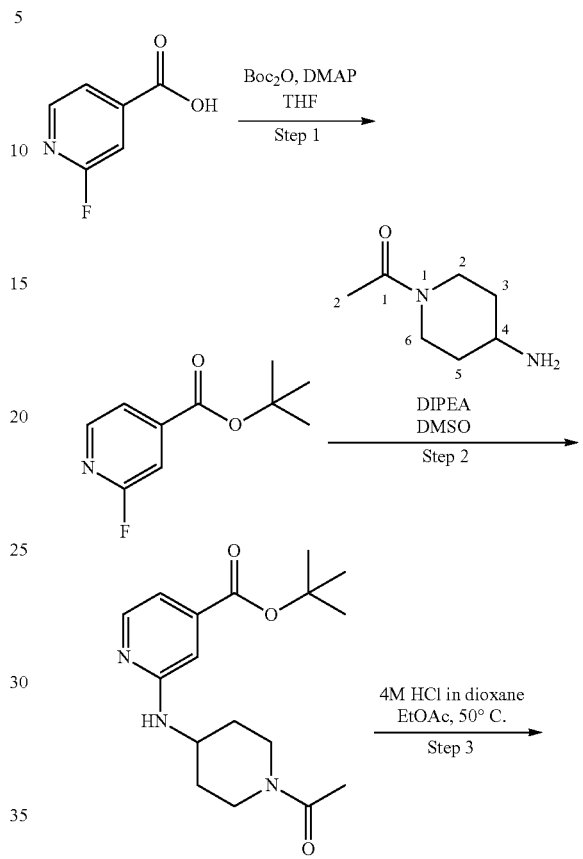

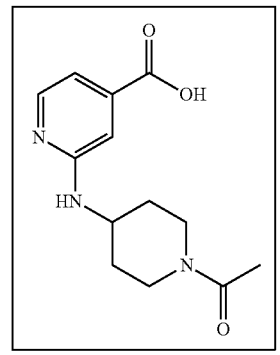

tert-butyl 2-fluoropyridine-4-carboxylate. To a solution of 2-fluoropyridine-4-carboxylic acid (10 g, 70.8 mmol) in THF (80 mL) was added DMAP (17 g, 0.139 mol). A solution of di-tert-butyl dicarbonate (24 mL, 0.105 mol) in THF (40 mL) was added drop-wise and the mixture was stirred at 25° C. for 12 hours. The resulting mixture was quenched by addition of water (100 mL) and extracted with EtOAc (100 mL*3). The combined organic layer was washed with saturated NH$_4$Cl aqueous solution (100 mL*2), brine (100 mL), dried over anhydrous Na$_2$SO$_4$, filtered and concentrated under reduced pressure. The residue was purified by flash chromatography (ISCO®; 80 g AgelaFlash® Silica Flash Column, petroleum ether/EtOAc with EtOAc from 0-10%, Flow Rate: 30 mL/min) to afford tert-butyl 2-fluoropyridine-4-carboxylate (11 g, 78.7% yield) as colorless liquid. ¹H NMR (400 MHz, methanol-d₄) δ ppm 8.35 (d, J=5.0 Hz, 1H), 7.67-7.81 (m, 1H), 7.39-7.55 (m, 1H), 1.61 (s, 9H).

tert-butyl 2-[(1-acetyl-4-piperidyl)amino]pyridine-4-carboxylate. To a mixture of tert-butyl 2-fluoropyridine-4-carboxylate (3.0 g, 15.2 mmol) and 1-(4-amino-1-piperidyl)ethanone (3.0 g, 21.1 mmol) in DMSO (30 mL) was added DIPEA (7.5 mL, 43.1 mmol) and the mixture was stirred for 12 hours at 90° C. under nitrogen. The resulting mixture was quenched by addition of water (50 mL) and extracted with EtOAc (50 mL*3). The combined organic layer was washed with saturated NH₄Cl aqueous solution (100 mL*2), brine (100 mL), dried over anhydrous Na₂SO₄, filtered and concentrated under reduced pressure. The residue was purified by flash chromatography (ISCO®; 40 g AgelaFlash® Silica Flash Column, DCM/MeOH with MeOH from 0~5.3%, Flow Rate: 30 mL/min) to afford tert-butyl 2-[(1-acetyl-4-piperidyl)amino]pyridine-4-carboxylate (1.84 g, crude) as yellow solid. LCMS (ESI) [M+H]⁺ calc'd 320.2, found 320.1.

2-[(1-acetyl-4-piperidyl)amino]pyridine-4-carboxylic acid. A mixture of tert-butyl 2-[(1-acetyl-4-piperidyl)amino]pyridine-4-carboxylate (1.84 g, 5.76 mmol) in 4M HCl/EtOAc (40 mL) was stirred for 12 hours at 50° C. under nitrogen. The precipitate was collected by filtration and dried to afford 2-[(1-acetyl-4-piperidyl)amino]pyridine-4-carboxylic acid (1.1 g, crude) as white solid.

2-(pyridin-3-ylamino)isonicotinic acid

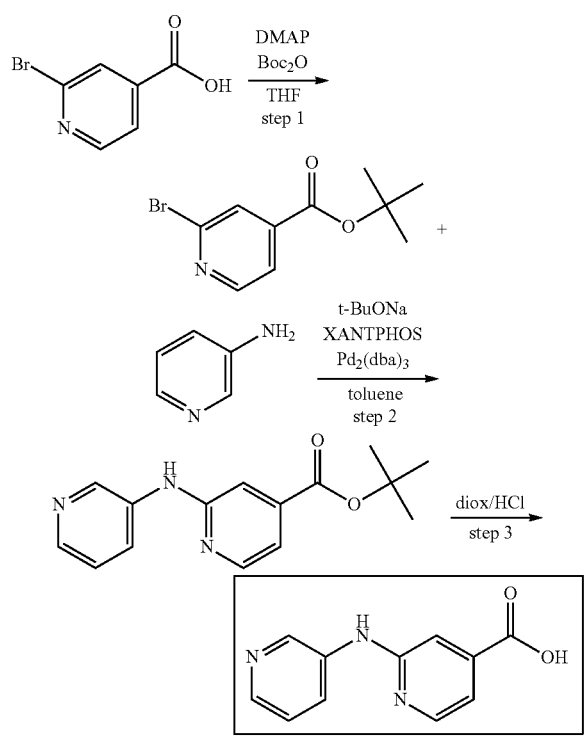

tert-butyl 2-bromoisonicotinate. tert-Butoxycarbonyl tert-butyl carbonate (9.51 g, 43.56 mmol, 10.00 mL) was added dropwise to the solution of 2-bromopyridine-4-carboxylic acid (8 g, 39.60 mmol) and 4-dimethylaminopyridine (2.42 g, 19.80 mmol) in THF (150 mL) at 0° C. The resulting mixture was left to warm slowly to r.t. and stirred for 17 hr. After consumption of the starting material (H-NMR control) the reaction mixture was evaporated. The residue was subjected to column chromatography (Companion Combiflash; 220 g SiO₂; petroleum ether/MtBE with MtBE from 0 to 15%, flow rate=85 ml/min, Rv=5 cv). To obtain tert-butyl 2-bromopyridine-4-carboxylate (7.81 g, 30.26 mmol, 76.40% yield) tert-butyl 2-bromopyridine-4-carboxylate (7.81 g, 30.26 mmol, 76.40% yield). ¹H NMR (400 MHz, DMSO) δ (ppm) 1.57 (s, 9H), 7.79 (d, 1H), 7.88 (s, 1H), 8.55 (d, 1H). LCMS (ESI): [M+H]+ m/z: calc'd 201.0; found 202.0; Rt=1.543 min.

tert-butyl 2-(pyridin-3-ylamino)isonicotinate. tert-Butyl 2-bromopyridine-4-carboxylate (8.3 g, 32.16 mmol) and sodium tert-butoxide (4.64 g, 48.24 mmol) sodium tert-butoxide (4.64 g, 48.24 mmol) were mixed together in toluene (100 mL). The resulting mixture was evacuated and then backfilled with argon, this operation was repeated three times, then pyridin-3-amine (3.03 g, 32.16 mmol), 4,5-bis(diphenylphosphino)-9,9-dimethylxanthene (930.32 mg, 1.61 mmol) and tris(dibenzylideneacetone)dipalladium (0) (736.16 mg, 803.92 μmol) were added under argon. The resulting mixture was stirred under argon at 90° C. for 12 hr. The reaction was controlled by LCMS and HNMR. After consumption of the starting material the reaction mixture was cooled to r.t. and diluted with water. The resulting mixture was extracted twice with 20 mL EtOAc. The combined organic extracts were dried over sodium sulfate and evaporated. The residue was subjected to column chromatography (Ok. Companion Combiflash; 120 g SiO₂; MtBE/methanol with methanol from 0 to 1%, flow rate=85 ml/min, Rv=8 cv) to obtain tert-butyl 2-(3-pyridylamino)pyridine-4-carboxylate (3.87 g, 14.26 mmol, 44.36% yield). ¹H NMR (500 MHz, DMSO) δ (ppm) 1.54 (s, 9H), 7.08 (m, 1H), 7.20 (m, 1H), 7.28 (m, 1H), 8.04 (m, 1H), 8.21 (m, 1H), 8.24 (m, 1H), 8.73 (m, 1H), 9.40 (m, 1H). LCMS (ESI): [M+H]+ m/z: calc'd 271.3; found 272.2; Rt=1.116 min.

2-(pyridin-3-ylamino)isonicotinic acid. The solution of tert-butyl 2-(3-pyridylamino)pyridine-4-carboxylate (3.87 g, 14.26 mmol) in dioxane/HCl (50 mL) with 5 drops of water was stirred at 20° C. for 24 hr. The resulting mixture was evaporated to dryness to obtain 2-(3-pyridylamino)pyridine-4-carboxylic acid (2.7 g, 10.73 mmol, 75.21% yield, HCl). ¹H NMR (500 MHz, DMSO) δ (ppm) 7.37 (m, 1H), 7.57 (m, 1H), 7.98 (m, 1H), 8.45 (m, 2H), 8.63 (m, 1H), 9.52 (m, 1H), 10.84 (m, 1H). LCMS (ESI): [M+H]+ m/z: calc'd 215.3; found 216.2; Rt=0.720 min.

4-(cyclobutylamino)picolinic acid

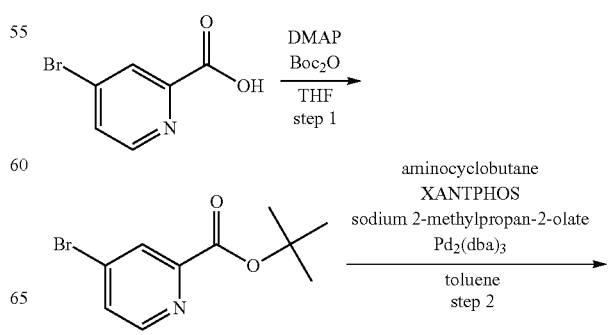

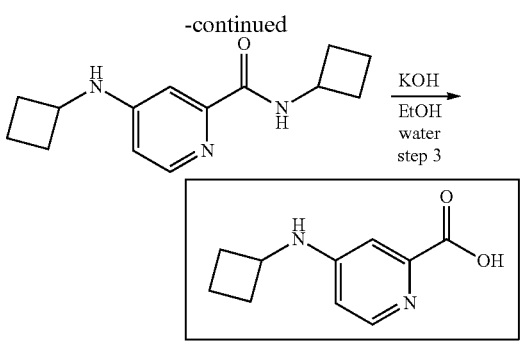

tert-butyl 4-bromopicolinate. 4-Bromopyridine-2-carboxylic acid (6.26 g, 31.01 mmol) and 4-dimethylaminopyridine (1.89 g, 15.50 mmol) were dissolved in THF (120 mL). Di-tert-butyl dicarbonate (8.80 g, 40.31 mmol, 9.25 mL) was added dropwise over 10 minutes. Solution was stirred at 20° C. for 16 hr. After that, excess of Boc$_2$O was destroyed with few ml of water. When CO$_2$ evolution ceased, the solvent was distilled off under reduced pressure. Residue was dissolved in MTBE (150 mL) and washed successively with 5-% NaHSO$_4$ (100 mL), water (100 mL), 5-% NaHCO$_3$ (50 mL) and brine. Then it was dried over Na$_2$SO$_4$ end evaporated in vacuo affording tert-butyl 4-bromopyridine-2-carboxylate (7.78 g, 30.16 mmol, 97.25% yield). $^1$H NMR (500 MHz, DMSO-d$_6$) δ (ppm) 1.64 (s, 9H), 7.61 (d, 1H), 8.20 (s, 1H), 8.56 (d, 1H). GCMS: [M]: calc'd 258.1; found 258.0; Rt=8.149 min.

N-cyclobutyl-4-(cyclobutylamino)picolinamide. tert-Butyl 4-bromopyridine-2-carboxylate (6.78 g, 26.27 mmol) and sodium tert-butoxide (3.79 g, 39.40 mmol) was dissolved in toluene (120 mL). Reaction flask was evacuated and refilled with argon 3 times. Then, cyclobutylamine (5.60 g, 78.80 mmol, 6.73 mL) and tris(dibenzylideneacetone)dipalladium(0) (601.34 mg, 656.69 μmol) with 4,5-bis(diphenylphosphino)-9,9-dimethylxanthene (759.95 mg, 1.31 mmol) were added under stream of argon. Obtained mixture was stirred at 110° C. for 72 hr. After that, reaction mixture was diluted with benzene (150 mL) and washed with water (150 mL). Then, dioxane-HCl was added dropwise, until strongly acidic media formed. When gummy precipitate settled down, supernatant solution was decanted, and residue was rinsed with benzene. Obtained crude hydrochloride was dissolved in water (150 mL) and filtered through pad of cotton wool. Then, solution was basified with solid potassium carbonate to pH—9 and extracted with DCM(2×50 mL). After drying over Na$_2$SO$_4$, it was evaporated in vacuo affording N-cyclobutyl-4-(cyclobutylamino)pyridine-2-carboxamide (3.56 g, crude). $^1$H NMR (400 MHz, CDCl$_3$) δ (ppm) 1.82 (m, 6H), 2.01 (m, 2H), 2.40 (m, 4H), 3.98 (m, 1H), 4.55 (m, 2H), 6.40 (m, 1H), 7.28 (s, 1H), 8.07 (d, 1H), 8.14 (m, 1H). LCMS (ESI): [M+H]+ m/z: calc'd 245.3; found 246.2; Rt=0.927 min.

4-(cyclobutylamino)picolinic acid. N-cyclobutyl-4-(cyclobutylamino)pyridine-2-carboxamide (3.56 g, 14.51 mmol) was dissolved in ethanol (30 mL) and solution of potassium hydroxide (12.21 g, 217.68 mmol, 5.99 mL) in water (20 mL) was added. The mixture was stirred at 90° C. during 120 hr. Most of ethanol was distilled off under reduced pressure. Residue was diluted with water (100 mL) and all insoluble stuff was filtered off. Then 6N hydrochloric acid was added dropwise until pH become 2-3. Solution was evaporated to dryness under reduced pressure and washed out from inorganic salt by hot isopropyl alcohol (100 mL). Solvent was removed in vacuo and residue was subjected to column chromatography affording 4-(cyclobutylamino)pyridine-2-carboxylic acid (1.1 g, 5.72 mmol, 39.44% yield) as a mixture of freebase and hydrochloride. $^1$H NMR (400 MHz, DMSO-d$_6$) δ (ppm) 1.78 (m, 2H), 2.03 (m, 2H), 2.37 (m, 2H), 4.19 (m, 1H), 6.82 (d, 1H), 7.53 (s, 1H), 8.12 (m, 1H), 9.65 (d, 1H), 13.34 (bds, 1H). LCMS (ESI): [M+H]+ m/z: calc'd 192.2; found 193.2; Rt=0.729 min.

2-(cyclobutylamino)-5-fluoroisonicotinic acid

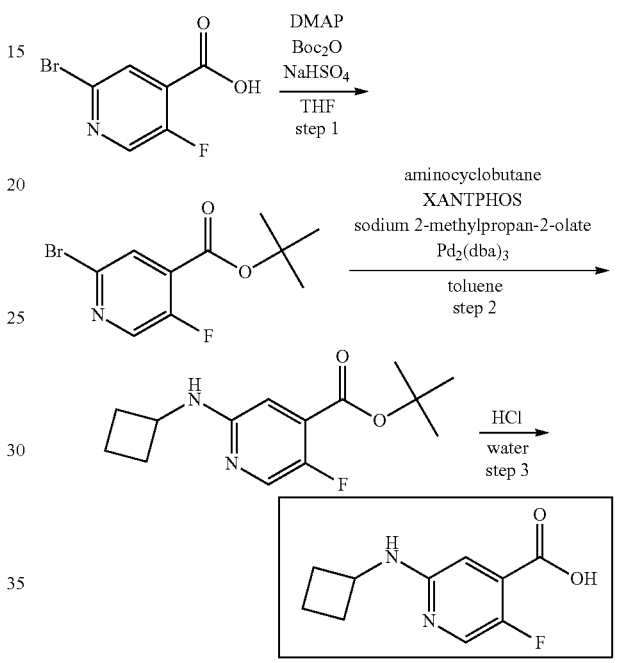

tert-butyl 2-bromo-5-fluoroisonicotinate. Di-tert-butyl dicarbonate (8.10 g, 37.09 mmol, 8.51 mL) was added to a stirred mixture of 2-bromo-5-fluoro-pyridine-4-carboxylic acid (6.8 g, 30.91 mmol) and N,N-dimethylpyridin-4-amine (1.89 g, 15.45 mmol) in THF (100 mL) at 25° C. The reaction mixture was stirred at 40° C. for 1 hr and evaporated in vacuo. The residue was dissolved in dichloromethane (100 mL) and washed successively with aqueous sodium hydrogen sulphate (2.60 g, 21.64 mmol) solution (40 mL) and water (50 mL). The organic layer was separated, dried over sodium sulphate and evaporated in vacuo to afford tert-butyl 2-bromo-5-fluoro-pyridine-4-carboxylate (8.2 g, 29.70 mmol, 96.08% yield) as light-brown solid. $^1$H NMR (500 MHz, CDCl$_3$) δ (ppm) 1.61 (s, 9H), 7.85 (s, 1H), 8.35 (s, 1H). LCMS (ESI): [M+H]+ m/z: calc'd 219.0; found 221.2; Rt=1.559 min.

tert-butyl 2-(cyclobutylamino)-5-fluoroisonicotinate. tert-Butyl 2-bromo-5-fluoro-pyridine-4-carboxylate (3.74 g, 13.56 mmol) and sodium 2-methylpropan-2-olate (1.95 g, 20.34 mmol) were mixed together in toluene (50 mL). The resulting mixture was evacuated and then backfilled with argon, this operation was repeated three times, then cyclobutanamine (1.93 g, 27.12 mmol, 2.32 mL), [5-(diphenylphosphanyl)-9,9-dimethyl-9H-xanthen-4-yl]diphenylphosphane (392.31 mg, 678.00 μmol) and tris(1,5-diphenylpenta-1,4-dien-3-one) dipalladium (310.43 mg, 339.00 μmol) were added under argon. The reaction mixture was stirred under argon at 70° C. for 12 hr, then cooled and evaporated in vacuo to leave 5.4 g of the crude product (67.9% purity by LCMS), which was purified by column chromatography on silica gel using hexane/ethyl acetate gradient (5-100% ethyl acetate) to afford tert-butyl 2-(cyclobutylamino)-5-fluoropyridine-4-carboxylate (1.1 g, 4.13 mmol, 30.46% yield) as yellow oil. $^1$H NMR (500 MHz, CDCl$_3$) δ (ppm) 1.80 (s, 9H), 1.86 (m, 4H), 2.45 (m, 2H), 4.12 (m, 1H), 4.73 (m, 1H), 6.66 (s, 1H), 8.01 (s, 1H). LCMS (ESI): [M+H]+ m/z: calc'd 266.3; found 267.2; Rt=1.430 min.

2-(cyclobutylamino)-5-fluoroisonicotinic acid. tert-Butyl 2-(cyclobutylamino)-5-fluoro-pyridine-4-carboxylate (1.1 g, 4.13 mmol) was diluted with a mixture of hydrochloric acid, 36% w/w aq. soln. (5 g, 137.13 mmol, 4.24 mL) and water (10 mL). The suspension of hydrochloride salt of the ester formed immediately. It was stirred at 70° C. for 0.5 hr, then cooled and the resulting solution was decanted from the oily residue, evaporated and dried in vacuo to afford 2-(cyclobutylamino)-5-fluoro-pyridine-4-carboxylic acid (0.8 g, 3.24 mmol, 78.52% yield, HCl) as yellow solid. $^1$H NMR (500 MHz, DMSO-d$_6$) δ (ppm) 1.76 (m, 2H), 1.96 (m, 2H), 2.35 (m, 2H), 4.28 (m, 1H), 7.11 (s, 1H), 8.06 (s, 1H). LCMS (ESI): [M+H]+ m/z: calc'd 210.2; found 211.2; Rt=0.618 min.

2-(cyclobutylamino)-5-methoxyisonicotinic acid

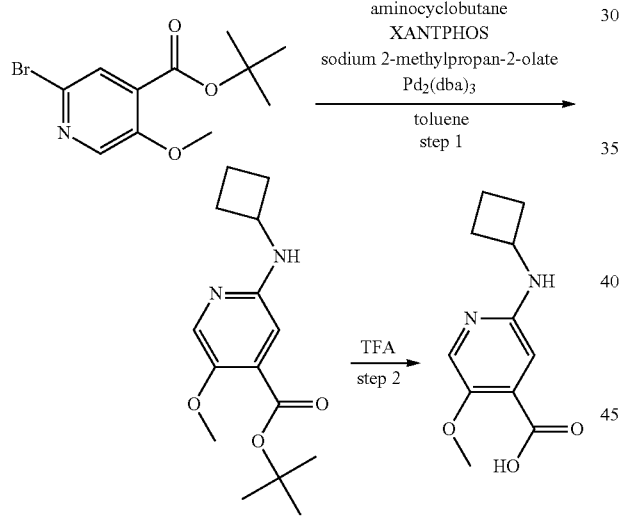

tert-butyl 2-(cyclobutylamino)-5-methoxyisonicotinate. tert-Butyl 2-bromo-5-methoxy-pyridine-4-carboxylate (2.6 g, 9.02 mmol) and sodium 2-methylpropan-2-olate (1.30 g, 13.54 mmol) were mixed together in toluene (50 mL). The resulting mixture was evacuated and then backfilled with argon, this operation was repeated three times, then cyclobutanamine (1.28 g, 18.05 mtmol, 1.54 mL), [5-(diphenylphosphanyl)-9,9-dimethyl-9H-xanthen-4-yl]diphenylphosphane (261.06 mg, 451.17 μmol) and tris(1,5-diphenylpenta-1,4-dien-3-one) dipalladium (206.57 mg, 225.59 μmol) were added under argon. The reaction mixture was stirred under argon at 75° C. for 18 hr, then cooled, evaporated in vacuo, and the residue was purified by column chromatography on silica gel using hexane/ethyl acetate gradient (5-100% ethyl acetate) to afford tert-butyl 2-(cyclobutylamino)-5-methoxypyridine-4-carboxylate (0.9 g, 3.23 mmol, 35.83% yield) as light-yellow gum. $^1$H NMR (400 MHz, CDCl$_3$) δ (ppm) 1.59 (s, 9H), 1.81 (m, 4H), 2.43 (m, 2H), 3.85 (s, 3H), 4.11 (m, 1H), 4.54 (m, 1H), 6.56 (s, 1H), 7.89 (s, 1H). LCMS (ESI): [M+H]+ m/z: calc'd 278.3; found 279.2; Rt=1.122 min.

2-(cyclobutylamino)-5-methoxyisonicotinic acid tert-Butyl 2-(cyclobutylamino)-5-methoxy-pyridine-4-carboxylate (0.9 g, 3.23 mmol) was dissolved in trifluoroacetic acid (18.43 g, 161.67 mmol, 12.46 mL). The resulting solution was stirred at 25° C. for 1 hr, and then evaporated in vacuo. The residue was triturated with MTBE/hexane mixture (1/1, 30 mL). The precipitate was filtered, washed with hexane (2*10 mL) and dried in vacuo to afford 2-(cyclobutylamino)-5-methoxy-pyridine-4-carboxylic acid (0.65 g, 1.93 mmol, 59.78% yield, CF$_3$COOH) as light-yellow solid. $^1$H NMR (500 MHz, DMSO-d$_6$) δ (ppm) 1.74 (m, 2H), 1.88 (m, 2H), 2.34 (m, 2H), 3.76 (s, 3H), 4.17 (m, 2H), 6.89 (s, 1H), 7.68 (s, 1H). LCMS (ESI): [M+H]+ m/z: calc'd 222.2; found 223.2; Rt=0.602 min.

Scheme Acid 2B

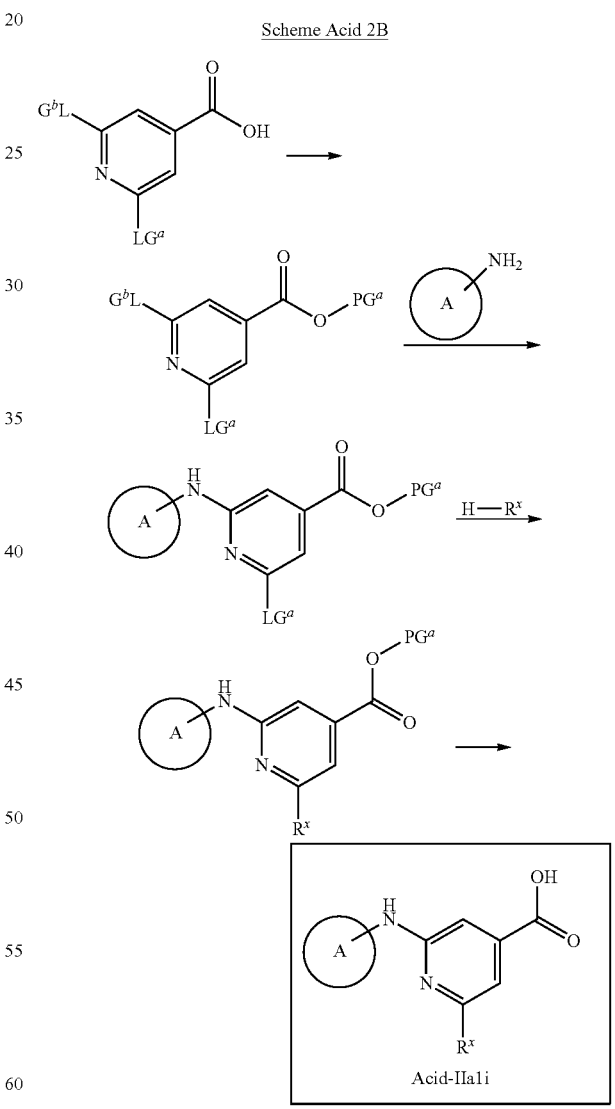

wherein A and R$^x$ are as described herein, PG$^a$ is a carboxylate protective group as described herein (e.g., a Bu group) and LG$^a$ and LG$^b$ are leaving groups as described herein.

In certain embodiments LG$^a$ and LG$^b$ are halo (e.g., fluoro, chloro, bromo, iodo). The carboxylic acid can be protected with a suitable protecting group (e.g., ′Bu) by treatment with a protecting agent (e.g., Boc$_2$O) in the presence of a coupling agent (e.g., DMAP) in a suitable solvent (e.g., THF). The leaving group LG$^a$ can be displaced by the A-NH$_2$ moiety under conditions known to one of skill in the art (e.g., in a suitable solvent such as DCM, THF, DMF, MeCN or a combination thereof), optionally in the presence of a base such as a carbonate base (e.g., NaHCO$_3$, Na$_2$CO$_3$, K$_2$CO$_3$, Cs$_2$CO$_3$) or amine base (e.g., DBU, Et$_3$N, DIPEA). The other leaving group, for example LG$^a$ can be displaced by the R$^x$ moiety under conditions known to one of skill in the art. In one embodiment, the displacement is an aromatic substitution reaction (e.g., in a suitable solvent such as DCM, H$_2$O), optionally in the presence of a base such as a carbonate base (e.g., NaHCO$_3$, Na$_2$CO$_3$, Cs$_2$CO$_3$) or amine base (e.g., DBU, Et$_3$N, DIPEA). In some embodiments, the displacement is a copper catalyzed displacement (e.g., in the presence of CuI). In some embodiments the displacement is a palladium-catalyzed aryl coupling (e.g., in the presence of a palladium source such as Pd$_2$(dba)$_3$, a base such as NaOEt or sodium 2-methyl propanolate and a ligand such as XantPhos) in a suitable solvent (e.g., toluene). Finally, the protective group can be removed to provide the corresponding carboxylic acid, for example under acidic conditions (e.g., in the presence of HCl or TFA) in a suitable solvent (e.g., EtOAc).

2-(cyclobutylamino)-6-(piperidin-1-yl)isonicotinic acid

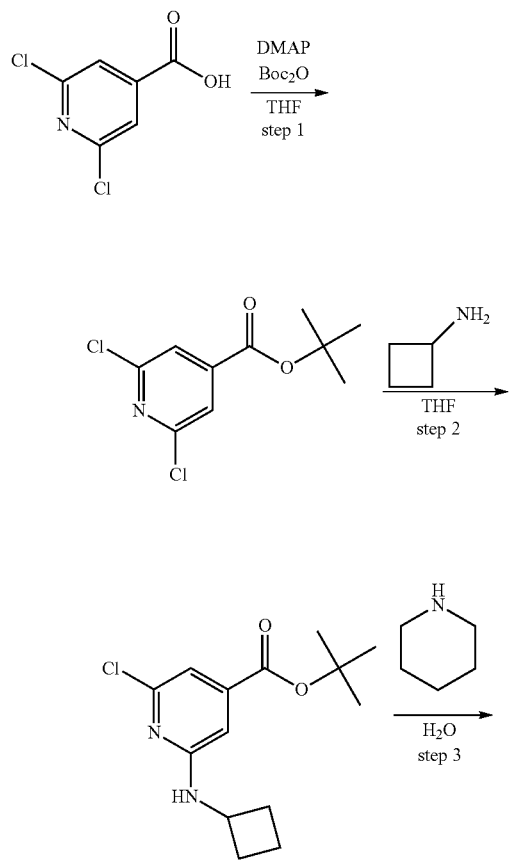

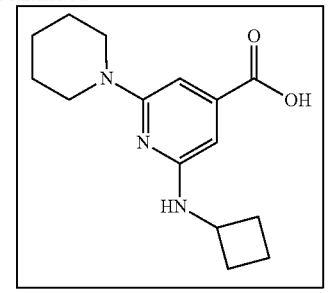

2-(cyclobutylamino)-6-(piperidin-1-yl)isonicotinic acid. tert-Butyl 2-chloro-6-(cyclobutylamino)pyridine-4-carboxylate (1 g, 3.54 mmol), and piperidine (4.52 g, 53.05 mmol, 5.24 mL) in H$_2$O (10 mL). The resulting reaction mixture was stirred at 120° C. for 48 h. The reaction mixture was concentrated, and the residue was purified to prep-HPLC (column: Waters SunFire C18 100.19 mm, 5 u; mobile phase: water-ACN; B %: 20-40%, 4 min) to obtain a 2-(cyclobutylamino)-6-(1-piperidyl)pyridine-4-carboxylic acid (0.272 g, 987.85 μmol, 27.93% yield). $^1$H NMR (400 MHz, DMSO-d$_6$) δ (ppm) 1.61 (m, 8H), 1.86 (m, 2H), 2.23 (m, 2H), 2.92 (m, 4H), 4.18 (m, 1H), 6.14 (s, 1H), 6.25 (bds, 1H), 6.34 (s, 1H). LCMS (ESI): [M+H]+ m/z: calc'd 275.4; found 276.2; Rt=1.080 min.

2-(cyclobutylamino)-6-(4-ethylpiperazin-1-yl)isonicotinic acid

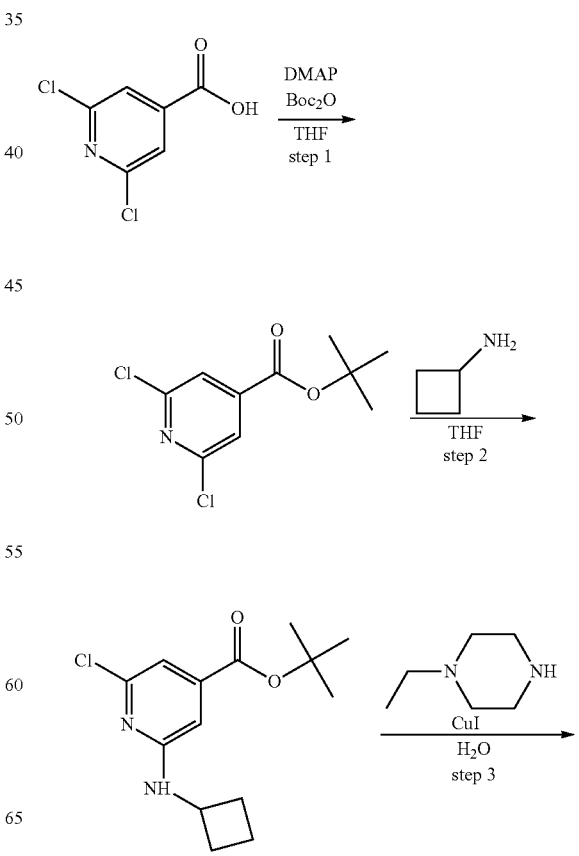

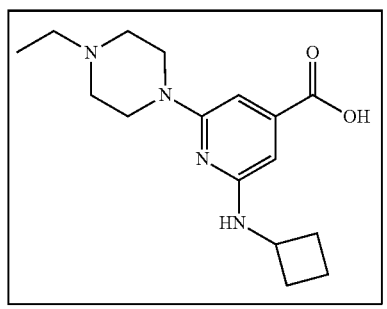

2-(cyclobutylamino)-6-(4-ethylpiperazin-1-yl)isonicotinic acid tert-Butyl 2-chloro-6-(cyclobutylamino)pyridine-4-carboxylate (1 g, 3.54 mmol), 1-ethylpiperazine (2.02 g, 17.68 mmol, 2.25 mL) and copper(I) iodide (67.35 mg, 353.65 μmol, 11.98 μL) in H$_2$O (10 mL). The resulting reaction mixture was stirred at 120° C. for 48 h. The reaction mixture was concentrated, and the residue was purified to prep-HPLC (column: Waters SunFire C18 100.19 mm, 5 u; mobile phase: water-ACN; B %: 20-40%, 4 min) to obtain 2-(cyclobutylamino)-6-(4-ethylpiperazin-1-yl)pyridine-4-carboxylic acid. $^1$H NMR (400 MHz, DMSO-d$_6$) δ (ppm) 1.24 (t, 3H), 1.68 (m, 2H), 1.85 (m, 2H), 2.24 (m, 2H), 3.32 (m, 6H), 3.55 (d, 2H), 4.18 (m, 1H), 4.38 (d, 2H), 6.32 (s, 1H), 6.36 (s, 1H), 9.71 (bds, 1H), 12.82 (bds, 1H). LCMS (ESI): [M+H]+ m/z: calc'd 304.4; found 305.2; Rt=0.840 min.

2-(cyclobutylamino)-6-(4-propionylpiperazin-1-yl)isonicotinic acid

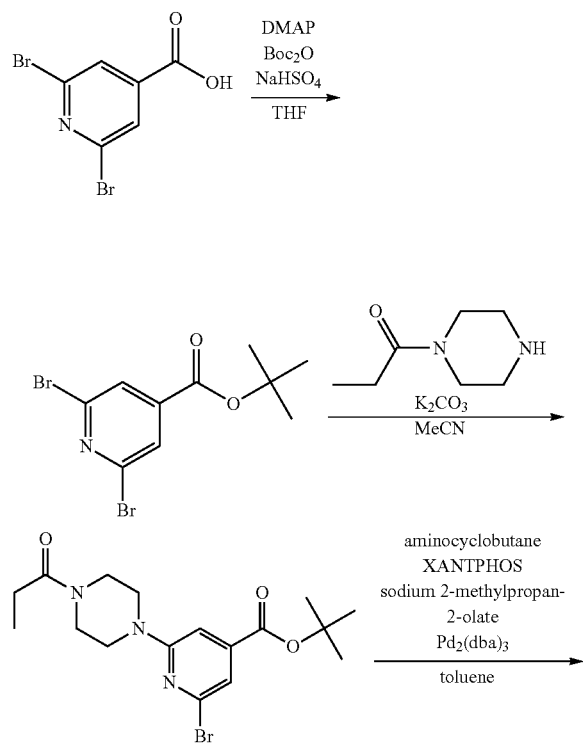

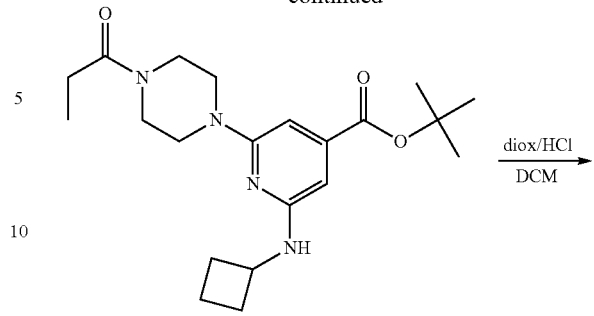

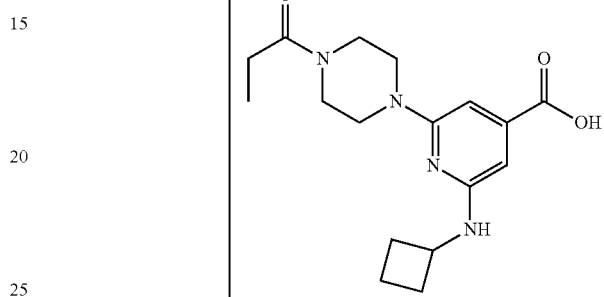

tert-butyl 2,6-dibromoisonicotinate. Di-tert-butyl dicarbonate (20.20 g, 92.56 mmol, 21.24 mL) was added to a stirred mixture of 2,6-dibromopyridine-4-carboxylic acid (20 g, 71.20 mmol) and N,N-dimethylpyridin-4-amine (4.35 g, 35.60 mmol) in THF (300 mL) at 25° C. The reaction mixture was stirred at 25° C. for 12 hr and evaporated in vacuo. The residue was dissolved in dichloromethane (400 mL) and washed successively with aqueous sodium hydrogen sulphate (5.98 g, 49.84 mmol) solution (120 mL), and water (100 mL). The organic layer was separated, dried over sodium sulphate, filtered through short pad of silica gel and evaporated in vacuo to afford tert-butyl 2,6-dibromopyridine-4-carboxylate (21 g, 62.31 mmol, 87.52% yield) as white solid. $^1$H NMR (400 MHz, CDCl$_3$) δ (ppm) 1.60 (s, 9H), 7.92 (s, 2H). LCMS (ESI): [M+H]+ m/z: calc'd 337.0; found 338.2; Rt=1.700 min.

tert-butyl 2-bromo-6-(4-propionylpiperazin-1-yl)isonicotinate. 1-Piperazin-1-ylpropan-1-one (2.23 g, 10.39 mmol, 1.47 mL, 2HCl) was added to a stirred mixture of tert-butyl 2,6-dibromopyridine-4-carboxylate (2.5 g, 7.42 mmol) and potassium carbonate, anhydrous, 99% (5.13 g, 37.09 mmol, 2.24 mL) in acetonitrile (50 mL). The resulting mixture was stirred at 80° C. for 96 hr (the reaction progress was monitored by HNMR of the aliquots), then cooled and filtered. The filtercake was washed with acetonitrile (2*20 mL) and discarded. The filtrate was evaporated in vacuo, the residue was dissolved in dichloromethane, dried over sodium sulphate and filtered through a pad of silica gel (50 g). The silica gel pad was additionally washed with THF (3*50 mL). The combined CH$_2$Cl$_2$-THF filtrate was evaporated in vacuo to afford tert-butyl 2-bromo-6-(4-propanoylpiperazin-1-yl)pyridine-4-carboxylate (2.7 g, 6.78 mmol, 91.38% yield) as light-yellow solid. $^1$H NMR (500 MHz, CDCl$_3$) δ (ppm) 1.18 (t, 3H), 1.58 (s, 9H), 2.41 (m, 2H), 3.57 (m, 4H), 3.67 (m, 2H), 3.76 (m, 2H), 7.08 (s, 1H), 7.23 (s, 1H). LCMS (ESI): [M+H]+ m/z: calc'd 398.3; found 400.2; Rt=1.585 min.

tert-butyl 2-(cyclobutylamino)-6-(4-propionylpiperazin-1-yl)isonicotinate. tert-Butyl 2-bromo-6-(4-propanoylpiperazin-1-yl)pyridine-4-carboxylate (2.7 g, 6.78 mmol) and sodium 2-methylpropan-2-olate (977.18 mg, 10.17 mmol) were mixed together in toluene (50 mL). The resulting mixture was evacuated and then backfilled with argon, this operation was repeated three times, then cyclobutanamine (964.24 mg, 13.56 mmol, 1.16 mL), [5-(diphenylphosphanyl)-9,9-dimethyl-9H-xanthen-4-yl]diphenylphosphane (196.12 mg, 338.95 μmol) and tris(1,5-diphenylpenta-1,4-dien-3-one) dipalladium (155.19 mg, 169.47 μmol) were added under argon. The reaction mixture was stirred under argon at 70° C. for 18 hr, then cooled, filtered and the filtrate was evaporated in vacuo to leave 2.6 g of the crude product (78.99% purity by LCMS, 13.08% of corresponding acid by LCMS (ester cleavage)) tert-butyl 2-(cyclobutylamino)-6-(4-propanoylpiperazin-1-yl)pyridine-4-carboxylate (2.6 g, 6.69 mmol, 98.72% yield) as red solid, which was directly used in the next step. $^1$H NMR (500 MHz, CDCl$_3$) δ (ppm) 1.18 (t, 3H), 1.58 (s, 9H), 1.80 (m, 2H), 1.89 (m, 2H), 2.41 (m, 4H), 3.51 (m, 2H), 3.57 (m, 4H), 3.74 (m, 2H), 4.18 (m, 1H), 6.24 (s, 1H), 6.45 (s, 1H), 7.18 (bds, 1H). LCMS (ESI): [M+H]+ m/z: calc'd 388.5; found 389.2; Rt=1.532 min.

2-(cyclobutylamino)-6-(4-propionylpiperazin-1-yl)isonicotinic acid. Hydrogen chloride solution 4.0M in dioxane (52.66 g, 200.77 mmol, 50.16 mL, 13.9% purity) was added to a solution of tert-butyl 2-(cyclobutylamino)-6-(4-propanoylpiperazin-1-yl)pyridine-4-carboxylate (2.6 g, 6.69 mmol) (crude from previous step) in dichloromethane (30 mL). The reaction mixture was stirred at 25° C. for 72 hr, then filtered from tarry solid, and the filtrate was evaporated to dryness in vacuo to afford crude 2-(cyclobutylamino)-6-(4-propanoylpiperazin-1-yl)pyridine-4-carboxylic acid (1.65 g, 4.47 mmol, 66.84% yield, HCl) as yellow solid, which was used in the next step without further purification. $^1$H NMR (400 MHz, DMSO-d$_6$) δ (ppm) 1.01 (t, 3H), 1.72 (m, 3H), 1.91 (m, 2H), 2.35 (m, 4H), 3.64 (m, 9H), 4.16 (m, 1H), 6.25 (s, 1H), 6.42.

2-(cyclobutylamino)-6-(4-isopropylpiperazin-1-yl) isonicotinic acid

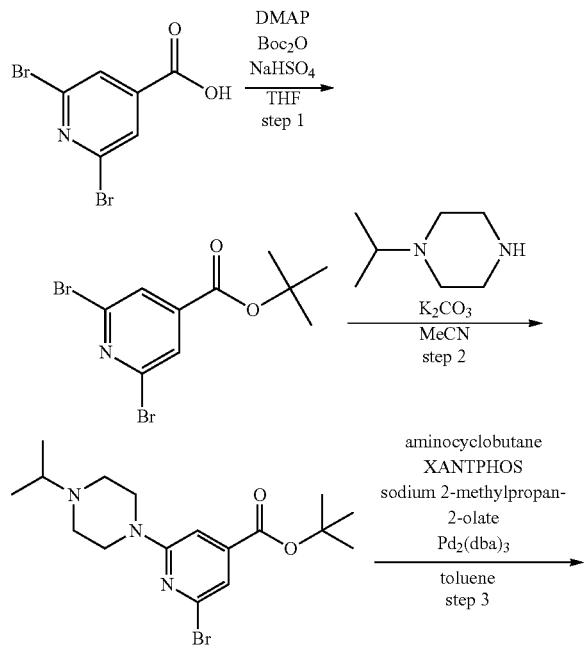

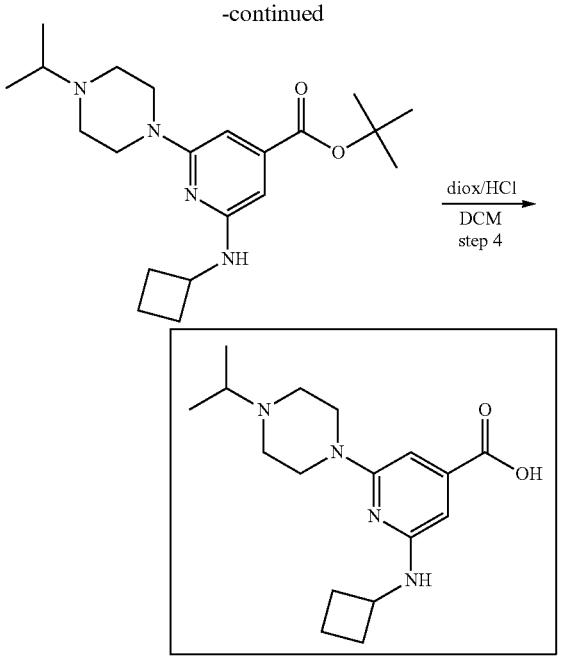

tert-butyl 2-bromo-6-(4-isopropylpiperazin-1-yl)isonicotinate. 1-Isopropylpiperazine (1.60 g, 12.46 mmol, 1.78 mL) was added to a stirred mixture of tert-butyl 2,6-dibromopyridine-4-carboxylate (3 g, 8.90 mmol) and potassium carbonate, anhydrous, 99% (2.46 g, 17.80 mmol, 1.07 mL) in acetonitrile (50 mL). The resulting mixture was stirred at 80° C. for 72 hr (the reaction progress was monitored by H-NMR of the aliquots), then cooled and filtered. The filtercake was washed with acetonitrile (2*20 mL) and discarded. The filtrate was evaporated in vacuo, the residue was dissolved in dichloromethane, dried over sodium sulphate and filtered through a pad of silica gel (50 g). The silica gel pad was additionally washed with THF (3*50 mL). The combined CH$_2$Cl$_2$-THF filtrate was evaporated in vacuo to afford tert-butyl 2-bromo-6-(4-isopropylpiperazin-1-yl) pyridine-4-carboxylate (3.1 g, 8.07 mmol, 90.61% yield) as yellow gum. $^1$H NMR (500 MHz, CDCl$_3$) δ (ppm) 1.08 (d, 6H), 1.58 (s, 9H), 2.60 (t, 4H), 2.75 (m, 1H), 3.60 (t, 4H), 7.06 (s, 1H), 7.16 (s, 1H). LCMS (ESI): [M+H]+ m/z: calc'd 384.3; found 386.2; Rt=1.229 min.

tert-butyl 2-(cyclobutylamino)-6-(4-isopropylpiperazin-1-yl)isonicotinate. tert-Butyl 2-bromo-6-(4-isopropylpiperazin-1-yl)pyridine-4-carboxylate (3.1 g, 8.07 mmol) and sodium 2-methylpropan-2-olate (1.16 g, 12.10 mmol) were mixed together in toluene (50 mL). The resulting mixture was evacuated and then backfilled with argon, this operation was repeated three times, then cyclobutanamine (1.15 g, 16.13 mmol, 1.38 mL), [5-(diphenylphosphanyl)-9,9-dimethyl-9H-xanthen-4-yl]diphenylphosphane (233.37 mg, 403.32 μmol) and tris(1,5-diphenylpenta-1,4-dien-3-one) dipalladium (184.66 mg, 201.66 μmol) were added under argon. The reaction mixture was stirred under argon at 70° C. for 18 hr, then cooled, filtered and the filtrate was evaporated in vacuo to leave 3.7 g of the crude product (80.48% purity by LCMS, 19.52% of corresponding acid by LCMS (ester cleavage), and 90% by HNMR, approximately 3 g of the target compound), tert-butyl 2-(cyclobutylamino)-6-(4-isopropylpiperazin-1-yl)pyridine-4-carboxylate (3 g, 8.01 mmol, 99.30% yield) as red gum, which was directly used in the next step. $^1$H NMR (500 MHz, CDCl$_3$) δ (ppm)

1.08 (d, 6H), 1.58 (s, 9H), 1.87 (m, 5H), 2.42 (m, 2H), 2.58 (t, 4H), 2.72 (m, 1H), 3.54 (t, 4H), 4.17 (m, 1H), 6.19 (s, 1H), 6.46 (s, 1H). LCMS (ESI): [M+H]+ m/z: calc'd 374.5; found 375.4; Rt=1.161 min.

2-(cyclobutylamino)-6-(4-isopropylpiperazin-1-yl)isonicotinic acid. Hydrogen chloride solution 4.0M in dioxane (77.74 g, 296.38 mmol, 74.04 mL, 13.9% purity) was added to a solution of tert-butyl 2-(cyclobutylamino)-6-(4-isopropylpiperazin-1-yl)pyridine-4-carboxylate (3.7 g, 9.88 mmol) (crude from previous step) in dichloromethane (50 mL). The reaction mixture was stirred at 25° C. for 72 hr, then evaporated to dryness in vacuo. The residue was triturated with dichloromethane (30 mL), stirred for 0.1 hr and the precipitate was filtered, washed with dichloromethane (2*20 mL) and dried in vacuo to afford crude 2-(cyclobutylamino)-6-(4-isopropylpiperazin-1-yl)pyridine-4-carboxylic acid (3 g, 7.67 mmol, 77.60% yield, 2HCl) as yellow solid, which was used in the next step without further purification. ¹H NMR (400 MHz, DMSO-d₆) δ (ppm) 1.30 (d, 6H), 1.66 (m, 2H), 1.88 (m, 2H), 2.28 (m, 2H), 3.05 (m, 2H), 3.45 (m, 5H), 4.17 (m, 1H), 4.39 (m, 2H), 6.33 (s, 1H), 6.42 (s, 1H), 11.44 (bds, 2H). LCMS (ESI): [M+H]+ m/z: calc'd 318.4; found 319.2; Rt=0.893 min.

2-(cyclobutylamino)-6-(ethyl(methyl)amino)isonicotinic acid

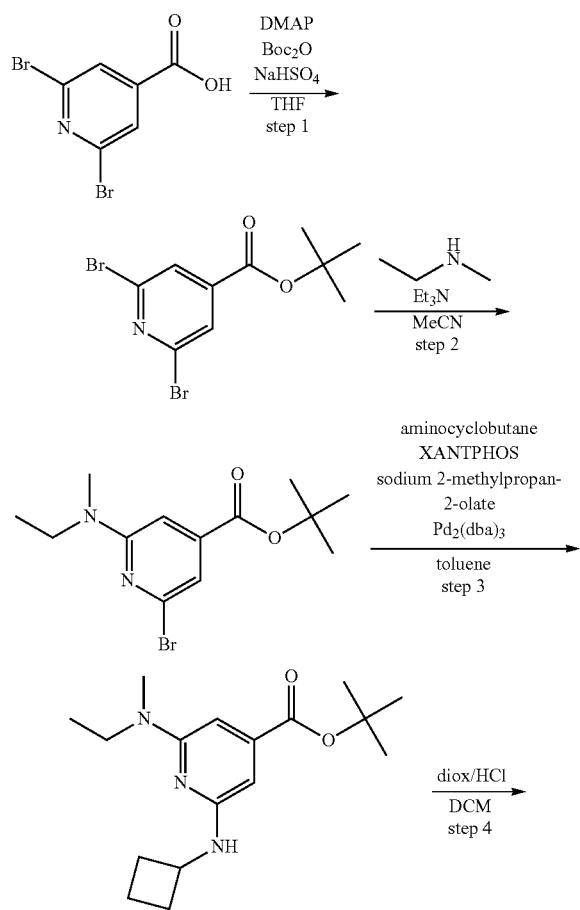

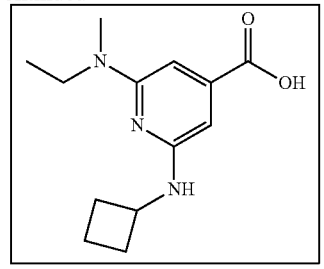

tert-butyl 2-bromo-6-(ethyl(methyl)amino)isonicotinate. To a solution of tert-butyl 2,6-dibromopyridine-4-carboxylate (2.5 g, 7.42 mmol) and N-methylethanamine (526.19 mg, 8.90 mmol, 764.82 µL) in ACN (35 mL), triethylamine (1.13 g, 11.13 mmol, 1.55 mL) was added. The resulting mixture was stirred at 80° C. for 72 hr and evaporated in vacuo. The residue was diluted with water (70 mL) and extracted with DCM (3*50 mL). The combined organic layer was washed with brine (2*50 mL), dried over Na₂SO₄ and evaporated in vacuo to give tert-butyl 2-bromo-6-[ethyl(methyl)amino]pyridine-4-carboxylate (2.1 g, 6.66 mmol, 89.81% yield). ¹H NMR (400 MHz, CDCl₃) δ (ppm) 1.13 (t, 3H), 1.55 (s, 9H), 3.02 (s, 3H), 3.56 (m, 2H), 6.90 (s, 1H), 7.06 (s, 1H). LCMS (ESI): [M+H]+ m/z: calc'd 315.2; found 315.0; Rt=1.736 min.

tert-butyl 2-(cyclobutylamino)-6-(ethyl(methyl)amino) isonicotinate. To a solution of tert-butyl 2-bromo-6-[ethyl(methyl)amino]pyridine-4-carboxylate (2.1 g, 6.66 mmol), cyclobutanamine (947.66 mg, 13.32 mmol, 1.14 mL) and sodium tert-butoxide (960.37 mg, 9.99 mmol) in toluene (50 mL), 4,5-bis(diphenylphosphino)-9,9-dimethylxanthene (192.75 mg, 333.12 µmol) and tris(dibenzylideneacetone)dipalladium(0) (152.52 mg, 166.56 µmol) were added under Ar atmosphere. The resulting mixture was heated at 70° C. for 18 hr, cooled and filtered through a thin layer of silica gel. Silica gel was washed with MTBE (50 mL). The solvent was evaporated in vacuo to obtain tert-butyl 2-(cyclobutylamino)-6-[ethyl(methyl)amino]pyridine-4-carboxylate (2.0 g, crude). The product was used for the next step without purification. ¹H NMR (500 MHz, CDCl₃) δ (ppm) 1.10 (t, 3H), 1.55 (s, 9H), 1.76 (m, 2H), 1.85 (m, 2H), 2.40 (m, 2H), 2.97 (s, 3H), 3.53 (m, 2H), 4.15 (m, 1H), 4.51 (m, 1H), 6.07 (s, 1H), 6.31 (s, 1H). LCMS (ESI): [M+H]+ m/z: calc'd 305.4; found 306.2; Rt=1.401 min.

2-(cyclobutylamino)-6-(ethyl(methyl)amino)isonicotinic acid. To a solution of tert-butyl 2-(cyclobutylamino)-6-[ethyl(methyl)amino]pyridine-4-carboxylate (2 g, 5.89 mmol) in DCM (30 mL), hydrogen chloride solution, 4.0 M in dioxane (50 g, 5.89 mmol) was added. The resulting mixture was stirred at 25° C. for 72 hr and evaporated in vacuo to dryness. The residue was triturated with MTBE (100 mL) and the precipitate was filtered, washed with MTBE (30 mL) and dried to obtain 2-(cyclobutylamino)-6-[ethyl(methyl)amino]pyridine-4-carboxylic acid (1.5 g, 5.25 mmol, 89.06% yield, HCl). ¹H NMR (500 MHz, DMSO-d₆) δ (ppm) 1.09 (t, 3H), 1.76 (m, 2H), 1.90 (m, 2H), 2.34 (m, 2H), 3.12 (s, 3H), 3.64 (m, 2H), 4.06 (m, 1H), 6.09 (s, 1H), 6.35 (s, 1H), 9.30 (bds, 1H), 12.85 (bds, 1H). LCMS (ESI): [M+H]+ m/z: calc'd 249.3; found 250.2; Rt=0.942 min.

2-(cyclobutylamino)-6-((2-methoxyethyl)(methyl)amino)isonicotinic acid

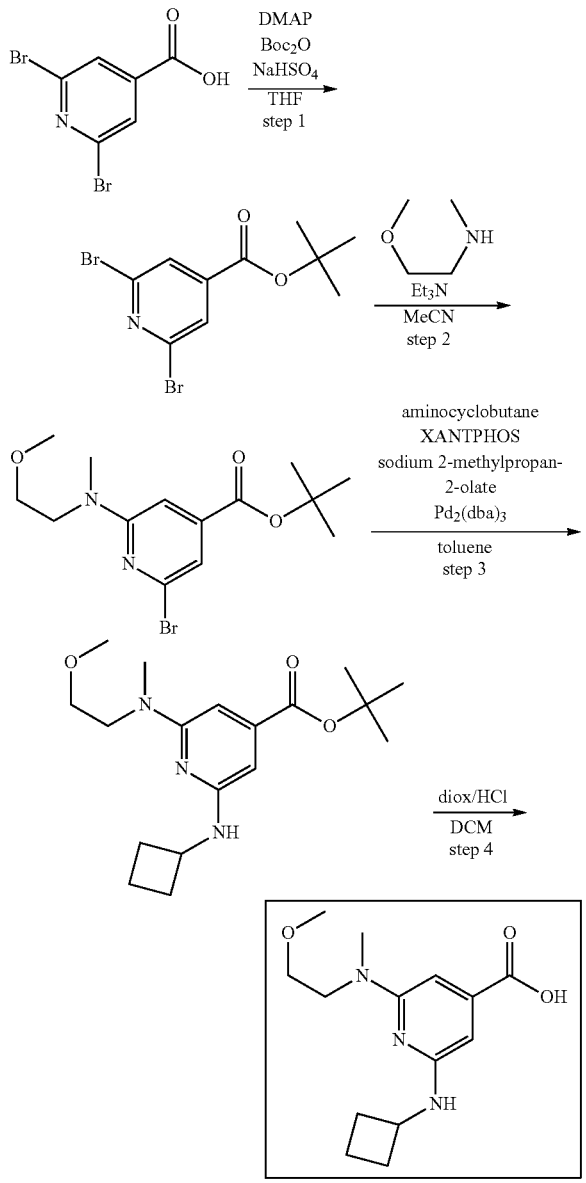

tert-butyl 2-bromo-6-((2-methoxyethyl)(methyl)amino)isonicotinate. tert-Butyl 2,6-dibromopyridine-4-carboxylate (2.4 g, 7.12 mmol), 2-methoxy-N-methylethanamine (825.22 mg, 9.26 mmol, 994.24 µL) and triethylamine (936.81 mg, 9.26 mmol, 1.29 mL) were mixed together in acetonitrile (30 mL). The flask was sealed, and the reaction mixture was stirred at 80° C. for 72 hr (the reaction progress was monitored by HNMR of the aliquots, more amines can be added if necessary), then cooled and evaporated in vacuo. The residue was diluted with water (20 mL) and extracted with dichloromethane (2*30 mL). The combined organic extracts were dried over sodium sulphate and evaporated in vacuo to afford tert-butyl 2-bromo-6-[2-methoxyethyl(methyl)amino]pyridine-4-carboxylate (2.2 g, 6.37 mmol, 89.48% yield) as yellow gum. $^1$H NMR (500 MHz, CDCl$_3$) δ (ppm) 1.58 (s, 9H), 3.12 (s, 3H), 3.35 (s, 3H), 3.58 (t, 2H), 3.75 (t, 2H), 6.96 (s, 1H), 7.12 (s, 1H). LCMS (ESI): [M+H]+ m/z: calc'd 345.2; found 347.0; Rt=1.586 min.

tert-butyl 2-(cyclobutylamino)-6-((2-methoxyethyl)(methyl)amino)isonicotinate. tert-Butyl 2-bromo-6-[2-methoxyethyl(methyl)amino]pyridine-4-carboxylate (1.5 g, 4.34 mmol) and sodium 2-methylpropan-2-olate (626.32 mg, 6.52 mmol) were mixed together in toluene (50 mL). The resulting mixture was evacuated and then backfilled with argon, this operation was repeated three times, then cyclobutanamine (618.03 mg, 8.69 mmol, 741.93 µL), [5-(diphenylphosphanyl)-9,9-dimethyl-9H-xanthen-4-yl]diphenylphosphane (125.70 mg, 217.25 µmol) and tris(1,5-diphenylpenta-1,4-dien-3-one) dipalladium (99.47 mg, 108.62 µmol) were added under argon. The reaction mixture was stirred under argon at 70° C. for 18 hr, then cooled, filtered and the filtrate was evaporated in vacuo to leave 1.9 g of the crude product (76.89% purity by LCMS, 15.02% of corresponding acid by LCMS (ester cleavage), and 90% by HNMR, approximately 1.4 g of the target compound), tert-butyl 2-(cyclobutylamino)-6-[2-methoxyethyl(methyl)amino]pyridine-4-carboxylate (1.4 g, 4.17 mmol, 96.06% yield) as red gum, which was directly used in the next step. $^1$H NMR (500 MHz, CDCl$_3$) δ (ppm) 1.61 (s, 9H), 1.76 (m, 2H), 1.88 (m, 2H), 2.41 (m, 2H), 3.06 (s, 3H), 3.36 (s, 3H), 3.57 (t, 2H), 3.72 (t, 2H), 4.19 (m, 1H), 6.12 (s, 1H), 6.34 (s, 1H), 7.19 (bds, 1H). LCMS (ESI): [M+H]+ m/z: calc'd 335.4; found 336.2; Rt=1.327 min.

2-(cyclobutylamino)-6-((2-methoxyethyl)(methyl)amino) isonicotinic acid. Hydrogen chloride solution 4.0M in dioxane (44.57 g, 169.93 mmol, 42.45 mL, 13.9% purity) was added to a solution of tert-butyl 2-(cyclobutylamino)-6-[2-methoxyethyl(methyl)amino]pyridine-4-carboxylate (1.9 g, 5.66 mmol) (crude from previous step) in dichloromethane (30 mL). The reaction mixture was stirred at 25° C. for 72 hr, then evaporated to dryness in vacuo. The residue was reevaporated with MTBE (30 mL) and dried in vacuo to afford crude 2-(cyclobutylamino)-6-[2-methoxyethyl(methyl)amino]pyridine-4-carboxylic acid (1.58 g, 5.00 mmol, 88.33% yield, HCl) as brown solid, which was used in the next step without further purification. $^1$H NMR (400 MHz, DMSO-d$_6$) δ (ppm) 1.82 (m, 2H), 1.98 (m, 2H), 2.28 (m, 2H), 3.06 (m, 2H), 3.22 (s, 3H), 3.42 (s, 3H), 3.89 (t, 2H), 4.02 (t, 2H), 4.19 (m, 1H), 6.13 (s, 1H), 6.34 (s, 1H). LCMS (ESI): [M+H]+ m/z: calc'd 279.3; found 280.2; Rt=0.934 min.

2-(cyclobutylamino)-6-(4-methylpiperazin-1-yl) isonicotinic acid

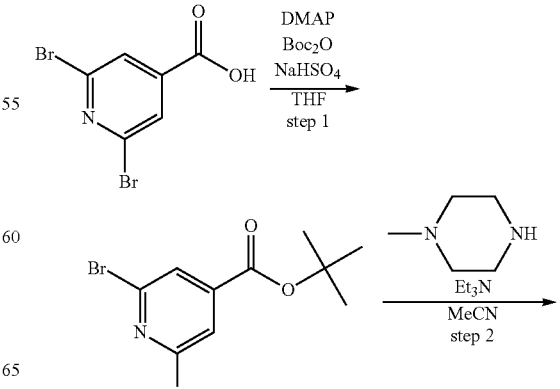

-continued

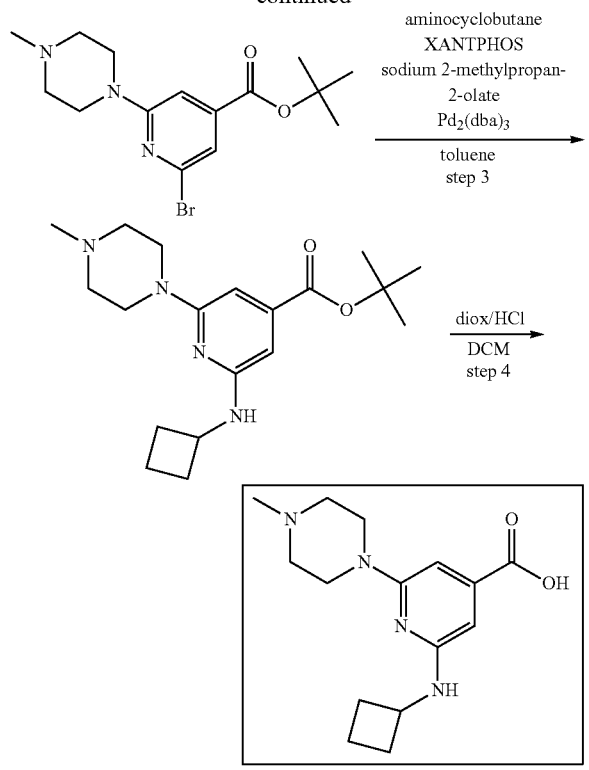

tert-butyl 2-bromo-6-(4-methylpiperazin-1-yl)isonicotinate. To a solution of tert-butyl 2,6-dibromopyridine-4-carboxylate (2.5 g, 7.42 mmol) and 1-methylpiperazine (817.33 mg, 8.16 mmol, 905.12 µL) in ACN (35 mL), triethylamine (1.13 g, 11.13 mmol, 1.55 mL) was added. The resulting mixture was stirred at 80° C. for 72 hr and evaporated in vacuo. The residue was diluted with water (70 mL) and extracted with DCM (3*50 mL). The combined organic layer was washed with brine (2*50 mL), dried over Na₂SO₄ and evaporated in vacuo to give tert-butyl 2-bromo-6-(4-methylpiperazin-1-yl)pyridine-4-carboxylate (2.55 g, 7.16 mmol, 96.49% yield). ¹H NMR (500 MHz, CDCl₃) δ (ppm) 1.58 (s, 9H), 2.35 (s, 3H), 2.50 (t, 4H), 3.62 (t, 4H), 7.07 (s, 1H), 7.18 (s, 1H). LCMS (ESI): [M+H]+ m/z: calc'd 356.2; found 357.2; Rt=1.188 min.

tert-butyl 2-(cyclobutylamino)-6-(4-methylpiperazin-1-yl)isonicotinate. To a solution of tert-butyl 2-bromo-6-(4-methylpiperazin-1-yl)pyridine-4-carboxylate (2.55 g, 7.16 mmol), cyclobutanamine (1.02 g, 14.32 mmol, 1.22 mL) and sodium tert-butoxide (1.03 g, 10.74 mmol) in toluene (50 mL), 4,5-bis(diphenylphosphino)-9,9-dimethylxanthene (207.08 mg, 357.89 µmol) and tris(dibenzylideneacetone)dipalladium(0) (163.86 mg, 178.94 µmol) were added under Ar atmosphere. The resulting mixture was heated at 70° C. for 18 hr, cooled and filtered through a thin layer of silica gel. Silica gel was washed with MTBE (50 mL). The solvent was evaporated in vacuo to obtain tert-butyl 2-(cyclobutylamino)-6-(4-methylpiperazin-1-yl)pyridine-4-carboxylate (3.0 g, crude). The product was used for the next step without purification. ¹H NMR (500 MHz, CDCl₃) δ (ppm) 1.57 (s, 9H), 1.78 (m, 2H), 1.87 (m, 2H), 2.35 (s, 3H), 2.41 (m, 2H), 2.52 (t, 4H), 3.55 (t, 4H), 4.15 (m, 1H), 4.60 (m, 1H), 6.20 (s, 1H), 6.46 (s, 1H). LCMS (ESI): [M+H]+ m/z: calc'd 346.5; found 347.2; Rt=1.194 min.

2-(cyclobutylamino)-6-(4-methylpiperazin-1-yl)isonicotinic acid. To a solution of tert-butyl 2-(cyclobutylamino)-6-(4-methylpiperazin-1-yl)pyridine-4-carboxylate (3 g, 7.79 mmol) in DCM (30 mL), hydrogen chloride solution, 4.0 M in dioxane (50 g, 7.79 mmol) was added. The resulting mixture was stirred at 25° C. for 72 hr. The formed precipitate was filtered, washed with DCM (50 mL) and MTBE (30 mL) to give 2-(cyclobutylamino)-6-(4-methylpiperazin-1-yl)pyridine-4-carboxylic acid (1.9 g, 5.23 mmol, 67.11% yield, 2HCl). The product was obtained as a mixture of salt forms. ¹H NMR (400 MHz, DMSO-d₆) δ (ppm) 1.68 (m, 2H), 1.86 (m, 2H), 2.25 (m, 2H), 2.75 (s, 3H), 3.09 (m, 2H), 3.26 (m, 2H), 3.76 (m, 2H), 4.20 (m, 2H), 4.31 (m, 2H), 6.24 (s, 1H), 6.38 (s, 1H), 11.41 (bds, 1H). LCMS (ESI): [M+H]+ m/z: calc'd 290.4; found 291.2; Rt=0.851 min.

2-(4-acetylpiperazin-1-yl)-6-(cyclobutylamino)isonicotinic acid

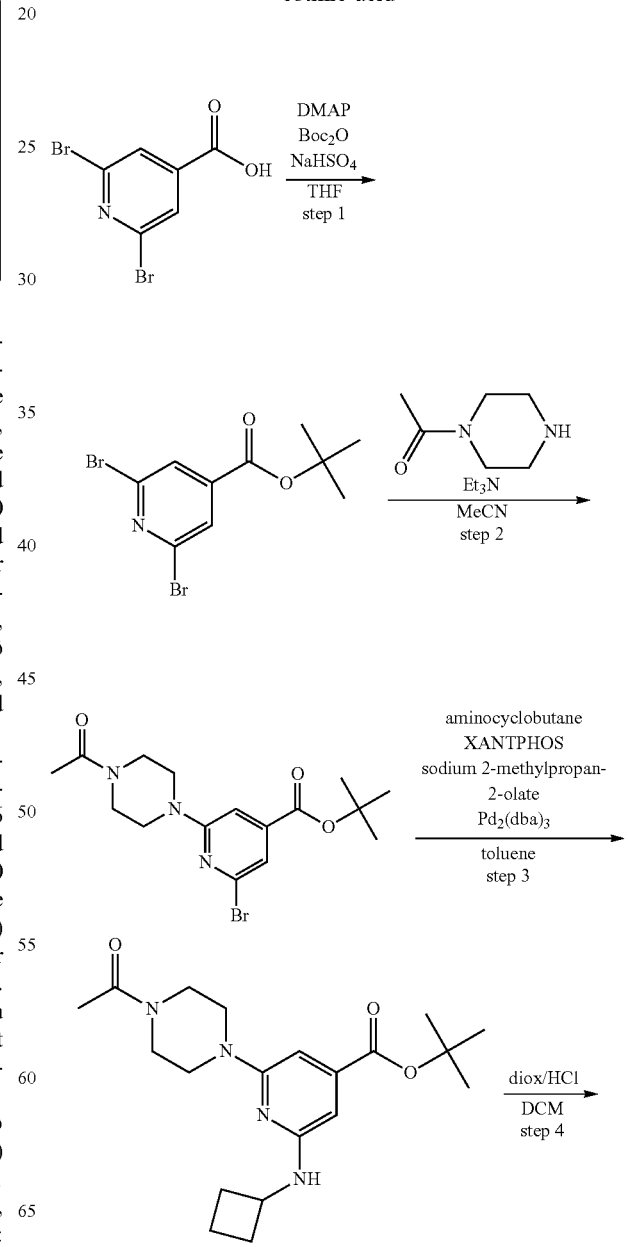

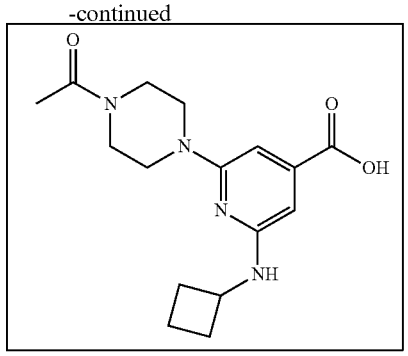

tert-butyl 2-(4-acetylpiperazin-1-yl)-6-bromoisonicotinate. 1-Piperazin-1-ylethanone (2.51 g, 12.46 mmol, 2.16 mL, 2HCl) was added to a stirred mixture of tert-butyl 2,6-dibromopyridine-4-carboxylate (3 g, 8.90 mmol) and potassium carbonate, anhydrous, 99% (6.15 g, 44.51 mmol, 2.69 mL) in acetonitrile (50 mL). The resulting mixture was stirred at 80° C. for 96 hr (the reaction progress was monitored by H-NMR of the aliquots), then cooled and filtered. The filtercake was washed with acetonitrile (2*20 mL) and discarded. The filtrate was evaporated in vacuo, the residue was dissolved in dichloromethane, dried over sodium sulphate and filtered through a pad of silica gel (50 g). The silica gel pad was additionally washed with THF (4*50 mL). The combined $CH_2Cl_2$-THF filtrate was evaporated in vacuo to afford tert-butyl 2-(4-acetylpiperazin-1-yl)-6-bromo-pyridine-4-carboxylate (2.6 g, 6.77 mmol, 76.01% yield) as light-yellow solid. $^1$H NMR (500 MHz, $CDCl_3$) δ (ppm) 1.59 (s, 9H), 2.15 (s, 3H), 3.58 (t, 4H), 3.69 (t, 2H), 3.74 (t, 2H), 7.08 (s, 1H), 7.24 (s, 1H). LCMS (ESI): [M+H]+ m/z: calc'd 384.3; found 386.2; Rt=1.449 min.

tert-butyl 2-(4-acetylpiperazin-1-yl)-6-(cyclobutylamino)isonicotinate. tert-Butyl 2-(4-acetylpiperazin-1-yl)-6-bromo-pyridine-4-carboxylate (2.60 g, 6.78 mmol) and sodium 2-methylpropan-2-olate (977.18 mg, 10.17 mmol) were mixed together in toluene (50 mL). The resulting mixture was evacuated and then backfilled with argon, this operation was repeated three times, then cyclobutanamine (964.24 mg, 13.56 mmol, 1.16 mL), [5-(diphenylphosphanyl)-9,9-dimethyl-9H-xanthen-4-yl]diphenylphosphane (196.12 mg, 338.95 µmol) and tris(1,5-diphenylpenta-1,4-dien-3-one) dipalladium (155.19 mg, 169.47 µmol) were added under argon. The reaction mixture was stirred under argon at 70° C. for 18 hr, then cooled, filtered and the filtrate was evaporated in vacuo to leave the crude product tert-butyl 2-(4-acetylpiperazin-1-yl)-6-(cyclobutylamino)pyridine-4-carboxylate (2.3 g, 6.14 mmol, 90.60% yield) as red solid, which was directly used in the next step. $^1$H NMR (500 MHz, $CDCl_3$) δ (ppm) 1.56 (s, 9H), 1.78 (m, 2H), 1.87 (m, 2H), 2.13 (s, 3H), 2.41 (m, 2H), 3.48 (t, 2H), 3.56 (t, 4H), 3.71 (t, 2H), 4.16 (m, 1H), 6.23 (s, 1H), 6.44 (s, 1H), 7.12 (bds, 1H). LCMS (ESI): [M+H]+ m/z: calc'd 374.5; found 375.2; Rt=1.374 min.

2-(4-acetylpiperazin-1-yl)-6-(cyclobutylamino)isonicotinic acid. tert-Butyl 2-(4-acetylpiperazin-1-yl)-6-(cyclobutylamino)pyridine-4-carboxylate (2.3 g, 6.14 mmol) was dissolved in trifluoroacetic acid (21.01 g, 184.26 mmol, 14.20 mL). The resulting mixture was stirred at 25° C. for 1 hr, then evaporated in vacuo and the residue was triturated with MTBE (40 mL). The precipitate was filtered, washed with MTBE(2*10 mL) and dried in vacuo to afford 2-(4-acetylpiperazin-1-yl)-6-(cyclobutylamino)pyridine-4-carboxylic acid (1 g, 2.31 mmol, 37.65% yield, $CF_3COOH$) as light-brown solid, which was used in the next step without further purification. $^1$H NMR (400 MHz, DMSO-$d_6$) δ (ppm) 1.52 (m, 2H), 1.81 (m, 2H), 1.92 (m, 2H), 2.03 (s, 3H), 2.25 (m, 2H), 3.05 (m, 1H), 3.41 (m, 7H), 4.22 (m, 1H), 6.24 (s, 1H), 6.29 (s, 1H). LCMS (ESI): [M+H]+ m/z: calc'd 318.4; found 319.2; Rt=0.979 min.

2-((1-acetylpiperidin-4-yl)amino)-6-(piperidin-1-yl)isonicotinic acid

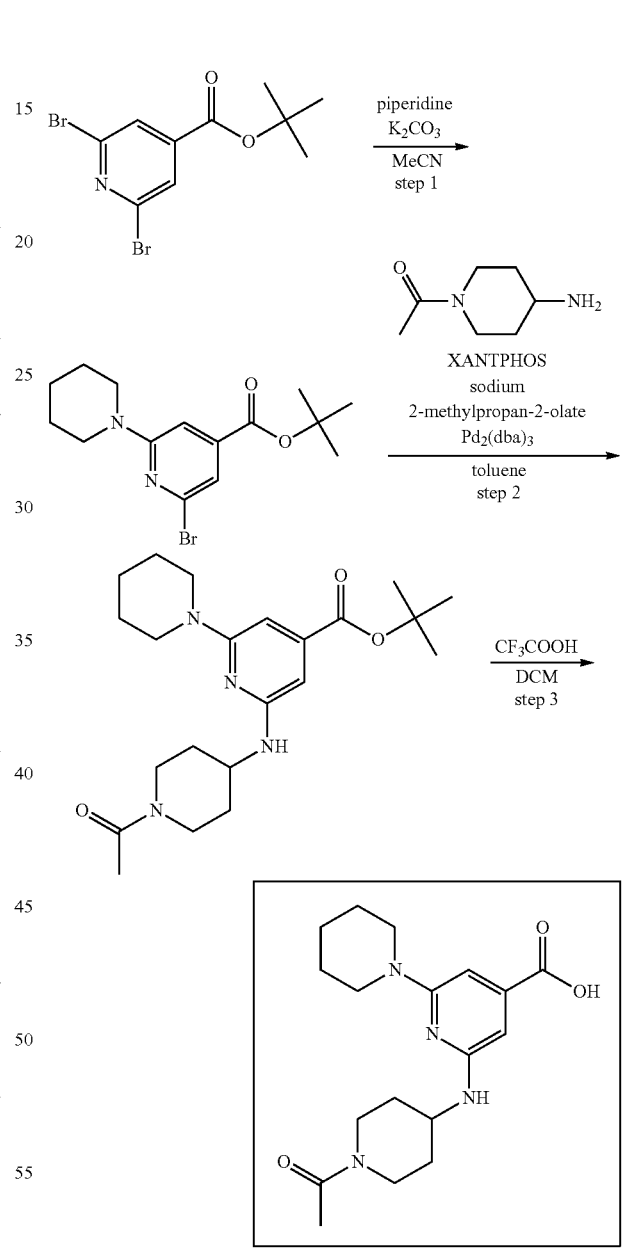

tert-butyl 2-bromo-6-(piperidin-1-yl)isonicotinate. Piperidine (947.46 mg, 11.13 mmol, 1.10 mL) was added to a stirred mixture of tert-butyl 2,6-dibromopyridine-4-carboxylate (2.5 g, 7.42 mmol) and potassium carbonate, anhydrous, 99% (2.05 g, 14.84 mmol, 895.44 µL) in acetonitrile (50 mL). The resulting mixture was stirred at 80° C. for 72 hr (the reaction progress was monitored by H-NMR of the aliquots), then cooled and filtered. The filtercake was washed with acetonitrile (2*20 mL) and discarded. The filtrate was evaporated in vacuo, the residue was diluted with water (30 mL) and extracted with dichloromethane (2*30 mL). The combined organic extracts were dried over sodium sulphate and evaporated in vacuo to afford tert-butyl 2-bromo-6-(1-piperidyl)pyridine-4-carboxylate (2.1 g, 6.15 mmol, 82.96% yield) as yellow gum. $^1$H NMR (500 MHz, CDCl$_3$) δ (ppm) 1.58 (s, 9H), 1.65 (m, 6H), 3.58 (m, 4H), 7.07 (s, 1H), 7.10 (s, 1H). LCMS (ESI): [M+H]+ m/z: calc'd 341.2; found 343.0; Rt=1.734 min.

tert-butyl 2-((1-acetylpiperidin-4-yl)amino)-6-(piperidin-1-yl)isonicotinate. tert-Butyl 2-bromo-6-(1-piperidyl)pyridine-4-carboxylate (2.1 g, 6.15 mmol), 1-(4-amino-1-piperidyl)ethanone (1.05 g, 7.38 mmol) and sodium 2-methylpropan-2-olate (887.10 mg, 9.23 mmol) were mixed together in toluene (40 mL). The resulting mixture was evacuated and then backfilled with argon, this operation was repeated three times, then [5-(diphenylphosphanyl)-9,9-dimethyl-9H-xanthen-4-yl]diphenylphosphane (178.04 mg, 307.70 μmol) and tris(1,5-diphenylpenta-1,4-dien-3-one) dipalladium (140.88 mg, 153.85 μmol) were added under argon. The reaction mixture was stirred under argon at 75° C. for 18 hr, then cooled and evaporated in vacuo. The residue was purified by column chromatography on silica gel using hexane-ethyl acetate gradient (5-100% ethyl acetate) to afford tert-butyl 2-[(1-acetyl-4-piperidyl)amino]-6-(1-piperidyl)pyridine-4-carboxylate (1.5 g, 3.73 mmol, 60.55% yield) as yellow solid. $^1$H NMR (500 MHz, CDCl$_3$) δ (ppm) 1.38 (m, 2H), 1.58 (s, 9H), 1.62 (m, 6H), 2.02 (m, 2H), 2.12 (s, 3H), 2.82 (m, 1H), 3.24 (m, 1H), 3.50 (m, 4H), 3.85 (m, 2H), 4.24 (m, 1H), 4.49 (m, 1H), 6.20 (s, 1H), 6.47 (s, 1H). LCMS (ESI): [M+H]+ m/z: calc'd 402.5; found 403.2; Rt=1.494 min.

2-((1-acetylpiperidin-4-yl)amino)-6-(piperidin-1-yl)isonicotinic acid. tert-Butyl 2-[(1-acetyl-4-piperidyl)amino]-6-(1-piperidyl)pyridine-4-carboxylate (1.5 g, 3.73 mmol) was dissolved in trifluoroacetic acid (21.24 g, 186.32 mmol, 14.35 mL). The reaction mixture was stirred at 25° C. for 1 hr, and then evaporated in vacuo. The residue was triturated with hexane/MTBE mixture (2/1, 70 mL), stirred for 0.1 hr and the precipitate was filtered, washed with hexane (2*10 mL) and dried in vacuo to afford 2-[(1-acetyl-4-piperidyl)amino]-6-(1-piperidyl)pyridine-4-carboxylic acid (1 g, 2.17 mmol, 58.28% yield, CF$_3$COOH) as yellow solid, which was used directly in the next step. $^1$H NMR (400 MHz, DMSO-d$_6$) δ (ppm) 1.28 (m, 1H), 1.42 (m, 1H), 1.53 (m, 6H), 1.82 (m, 1H), 1.89 (m, 1H), 1.99 (s, 3H), 2.82 (m, 1H), 3.15 (m, 1H), 3.46 (m, 4H), 3.76 (m, 1H), 3.85 (m, 1H), 4.17 (m, 1H), 6.29 (s, 1H), 6.33 (s, 1H). LCMS (ESI): [M+H]+ m/z: calc'd 346.4; found 347.2; Rt=0.996 min.

2-(cyclobutylamino)-6-methoxyisonicotinic acid

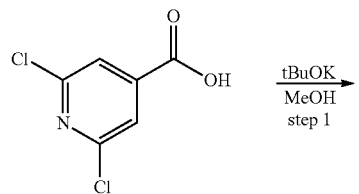

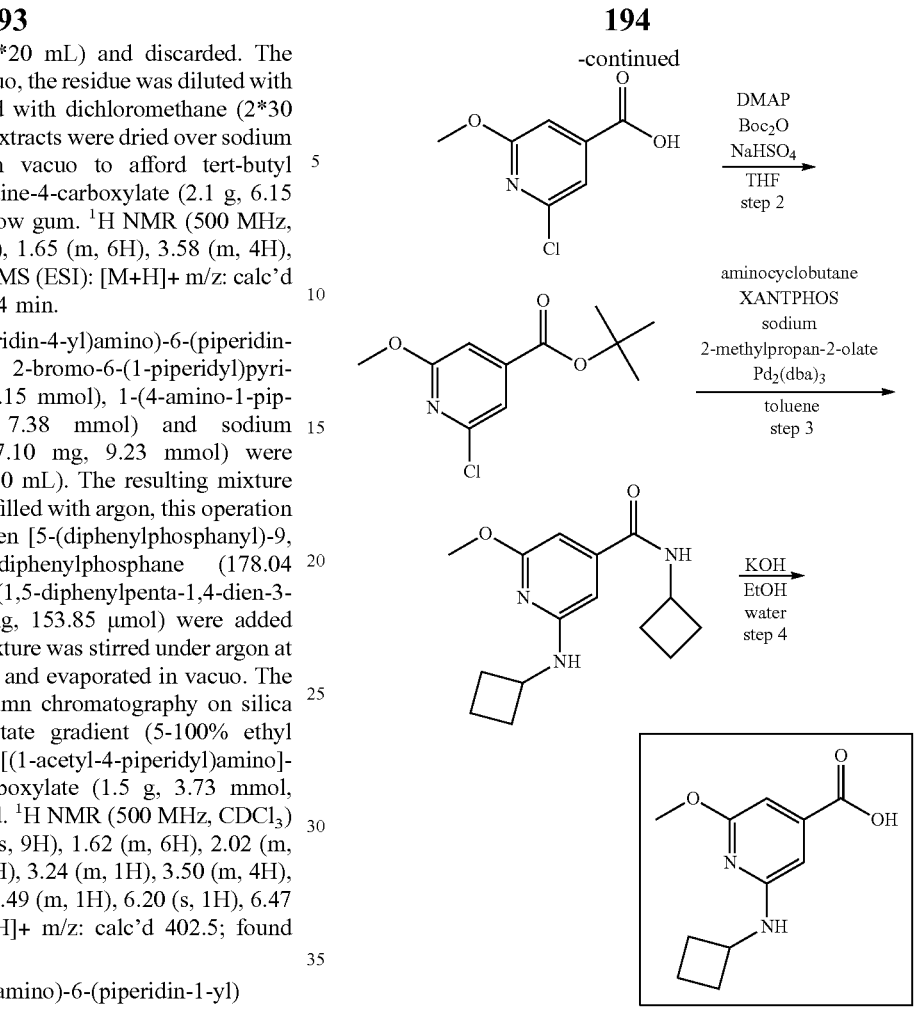

2-chloro-6-methoxyisonicotinic acid. 2,6-Dichloropyridine-4-carboxylic acid (5 g, 26.04 mmol) was added to solution of potassium 2-methylpropan-2-olate (9.64 g, 85.94 mmol) in methanol (100 mL). The resulting mixture was stirred with a reflux condenser at 65° C. for 24 hr, then cooled down and evaporated in vacuo. The residue was dissolved in water (50 mL) and acidified with concentrated hydrochloric acid to pH 5. The resulting precipitate was filtered, washed with water (2*10 mL) and dried in vacuo to afford 2-chloro-6-methoxy-pyridine-4-carboxylic acid (4.6 g, 24.52 mmol, 94.17% yield) as white solid. $^1$H NMR (400 MHz, DMSO-d$_6$) δ (ppm) 3.89 (s, 3H), 7.17 (s, 1H), 7.39 (s, 1H), 13.92 (bds, 1H). LCMS (ESI): [M+H]+ m/z: calc'd 187.6; found 188.2; Rt=1.097 min.

tert-butyl 2-chloro-6-methoxyisonicotinate. Di-tert-butyl dicarbonate (6.42 g, 29.43 mmol, 6.75 mL) was added to a stirred mixture of 2-chloro-6-methoxy-pyridine-4-carboxylic acid (4.6 g, 24.52 mmol) and N,N-dimethylpyridin-4-amine (1.50 g, 12.26 mmol) in THF (50 mL) at 25° C. The reaction mixture was stirred at 25° C. for 12 hr and evaporated in vacuo. The residue was dissolved in dichloromethane (100 mL) and washed with aqueous sodium hydrogen sulphate (2.06 g, 17.17 mmol) solution (40 mL). The organic layer was separated, dried over sodium sulphate and evaporated in vacuo to afford tert-butyl 2-chloro-6-methoxy-pyridine-4-carboxylate (5.5 g, 22.57 mmol, 92.04% yield) as white solid. $^1$H NMR (400 MHz, CDCl$_3$) δ (ppm) 1.59 (s, 9H), 3.97 (s, 3H), 7.17 (s, 1H), 7.38 (s, 1H). LCMS (ESI): [M-$^t$Bu]+ m/z: calc'd 187.2; found 188.2; Rt=1.673 min.

N-cyclobutyl-2-(cyclobutylamino)-6-methoxyisonicotinamide. tert-Butyl 2-chloro-6-methoxy-pyridine-4-carboxylate (1 g, 4.10 mmol) and sodium 2-methylpropan-2-olate (591.54 mg, 6.16 mmol) were mixed together in toluene (50 mL). The resulting mixture was evacuated and then backfilled with argon, this operation was repeated three times, then cyclobutanamine (875.56 mg, 12.31 mmol, 1.05 mL), [5-(diphenylphosphanyl)-9,9-dimethyl-9H-xanthen-4-yl]diphenylphosphane (118.72 mg, 205.18 μmol) and tris(1,5-diphenylpenta-1,4-dien-3-one) dipalladium (93.94 mg, 102.59 μmol) were added under argon. The flask was sealed, and the reaction mixture was stirred under argon at 110° C. for 48 hr, then cooled, filtered through short pad of silica gel and the filtrate was evaporated in vacuo to leave 1.4 g of the crude product (63.9% purity by LCMS, 0.89 g of the target compound)N-cyclobutyl-2-(cyclobutylamino)-6-methoxy-pyridine-4-carboxamide (0.89 g, 3.23 mmol, 78.77% yield) as brown gum, which was used in the next step without further purification. $^1$H NMR (400 MHz, CDCl$_3$) δ (ppm) 1.72 (m, 5H), 1.91 (m, 5H), 2.40 (m, 4H), 3.83 (s, 3H), 4.14 (m, 1H), 4.54 (m, 1H), 6.16 (s, 1H), 6.19 (s, 1H). LCMS (ESI): [M+H]+ m/z: calc'd 275.3; found 276.2; Rt=1.339 min.

2-(cyclobutylamino)-6-methoxyisonicotinic acid. N-Cyclobutyl-2-(cyclobutylamino)-6-methoxy-pyridine-4-carboxamide (1.4 g, 5.08 mmol) was dissolved in a solution of potassium hydroxide (855.88 mg, 15.25 mmol, 419.55 μL) in a mixture of water (5 mL) and ethanol (11 mL). The resulting mixture was stirred with reflux condenser at 90° C. for 48 hr, then cooled and evaporated in vacuo. The residue was diluted with water (20 mL), stirred for 0.25 hr and filtered. The filtercake was washed with water (2*5 mL) and discarded. The filtrate was acidified to pH 5 with concentrated hydrochloric acid. The precipitate was filtered, washed successively with water (2*5 mL) and MTBE (2*10 mL), and dried in vacuo to afford 2-(cyclobutylamino)-6-methoxy-pyridine-4-carboxylic acid (0.44 g, 1.98 mmol, 38.94% yield) as brown solid. $^1$H NMR (400 MHz, DMSO-d$_6$) δ (ppm) 1.67 (m, 2H), 1.88 (m, 2H), 2.26 (m, 2H), 3.77 (s, 3H), 4.20 (m, 1H), 6.22 (s, 1H), 6.44 (s, 1H), 7.08 (bds, 1H), 13.01 (bds, 1H). LCMS (ESI): [M+H]+ m/z: calc'd 222.2; found 223.1; Rt=1.222 min.

2-((1-acetylazetidin-3-yl)amino)-6-(piperidin-1-yl) isonicotinic acid

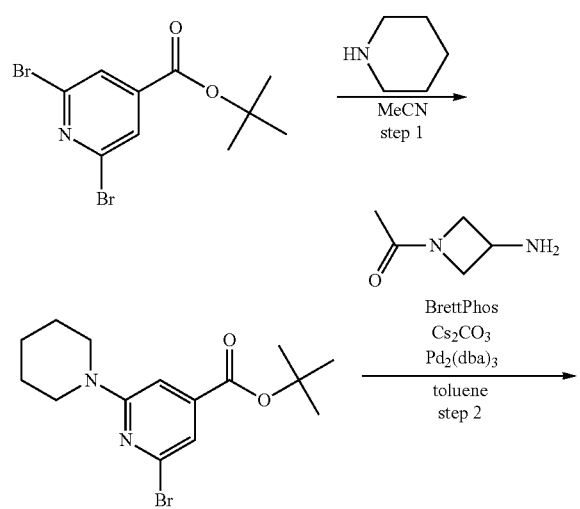

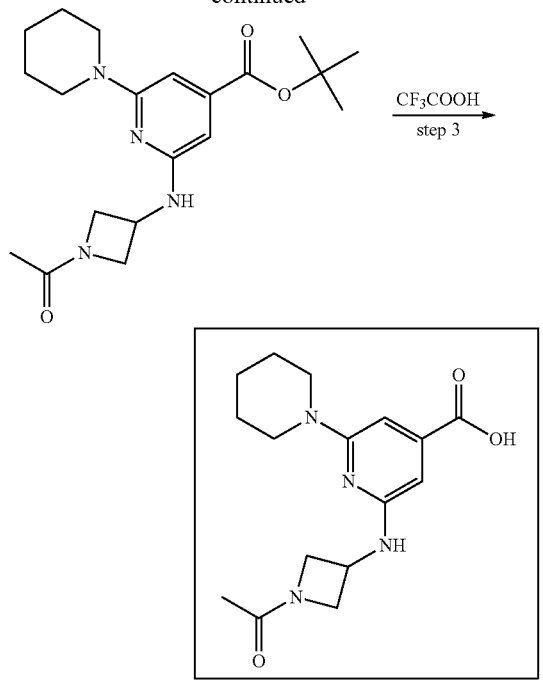

tert-butyl 2-bromo-6-(piperidin-1-yl)isonicotinate. Piperidine (7.58 g, 89.02 mmol, 8.79 mL) was added to a stirred mixture of tert-butyl 2,6-dibromopyridine-4-carboxylate (6 g, 17.80 mmol) in acetonitrile (100 mL). The resulting mixture was stirred at 80° C. for 7 hr (the reaction progress was monitored by HNMR of the aliquots), then cooled and evaporated in vacuo, the residue was diluted with water (100 mL) and extracted with dichloromethane (2*75 mL). The combined organic extracts were dried over sodium sulphate and evaporated in vacuo to afford tert-butyl 2-bromo-6-(1-piperidyl)pyridine-4-carboxylate (6 g, 17.58 mmol, 98.76% yield) as light-brown solid. $^1$H NMR (400 MHz, DMSO-d$_6$) δ (ppm) 1.56 (m, 15H), 3.54 (m, 4H), 6.95 (s, 1H), 7.08 (s, 1H). LCMS (ESI): [M+H]+ m/z: calc'd 341.2; found 342.2; Rt=1.865 min.

tert-butyl 2-((1-acetylazetidin-3-yl)amino)-6-(piperidin-1-yl)isonicotinate. tert-Butyl 2-bromo-6-(1-piperidyl)pyridine-4-carboxylate (5.2 g, 15.24 mmol), 1-(3-aminoazetidin-1-yl)ethanone (4.17 g, 18.29 mmol, CF$_3$CO$_2$H) and cesium carbonate (14.89 g, 45.72 mmol) were mixed together in toluene (150 mL). The resulting mixture was evacuated and then backfilled with argon, this operation was repeated three times, then tris(1,5-diphenylpenta-1,4-dien-3-one) dipalladium (348.85 mg, 380.96 μmol) and 2-(dicyclohexylphosphino)$_{3,6}$-dimethoxy-2',4',6'-triisopropyl-1,1'-biphenyl (817.95 mg, 1.52 mmol) were added under argon. The reaction mixture was stirred under argon at 100° C. for 120 hr, then it was diluted with water (150 mL). The layers were separated, and the organic layer was washed with brine, dried over Na$_2$SO$_4$ and concentrated in vacuo. The residue was triturated with hexane (60 mL). The precipitate was filtered, washed with hexane (2×20 mL) and dried in vacuo to afford tert-butyl 2-[(1-acetylazetidin-3-yl)amino]-6-(1-piperidyl)pyridine-4-carboxylate (5.7 g, 15.22 mmol, 99.89% yield). $^1$H NMR (500 MHz, DMSO-d$_6$) δ (ppm) 1.13 (m, 1H), 1.56 (m, 12H), 1.75 (m, 4H), 3.44 (m, 5H), 3.49 (m, 1H), 3.89 (m, 1H), 4.08 (m, 1H), 4.36 (m, 1H), 4.43 (m, 1H), 6.18 (s, 1H), 6.29 (s, 1H), 7.13 (m, 1H). LCMS (ESI): [M+H]+ m/z: calc'd 374.5; found 375.2; Rt=1.505 min.

2-((1-acetylazetidin-3-yl)amino)-6-(piperidin-1-yl)isonicotinic acid. tert-Butyl 2-[(1-acetylazetidin-3-yl)amino]-6-(1-piperidyl)pyridine-4-carboxylate (5.7 g, 15.22 mmol) was dissolved in TFA (173.55 g, 1.52 mol, 117.27 mL). The resulting solution was stirred at 20° C. for 3 hr, and then evaporated in vacuo. The residue was triturated with MTBE/hexane mixture (1/1, 100 mL). The precipitate was filtered, washed with hexane (2*30 mL) and dried in vacuo to afford 2-[(1-acetylazetidin-3-yl)amino]-6-(1-piperidyl)pyridine-4-carboxylic acid (6 g, 13.88 mmol, 91.16% yield, $CF_3CO_2H$) as yellow solid. $^1H$ NMR (400 MHz, DMSO-$d_6$) δ (ppm) 1.58 (m, 9H), 3.45 (m, 4H), 3.70 (m, 1H), 3.91 (m, 1H), 4.09 (m, 1H), 4.40 (m, 2H), 6.23 (s, 1H), 6.36 (s, 1H), 7.28 (m, 2H). LCMS (ESI): [M+H]+ m/z: calc'd 318.4; found 319.2; Rt=1.025.

2-(4-(cyclopropanecarbonyl)piperazin-1-yl)-6-(spiro[3.3]heptan-2-ylamino)isonicotinic acid

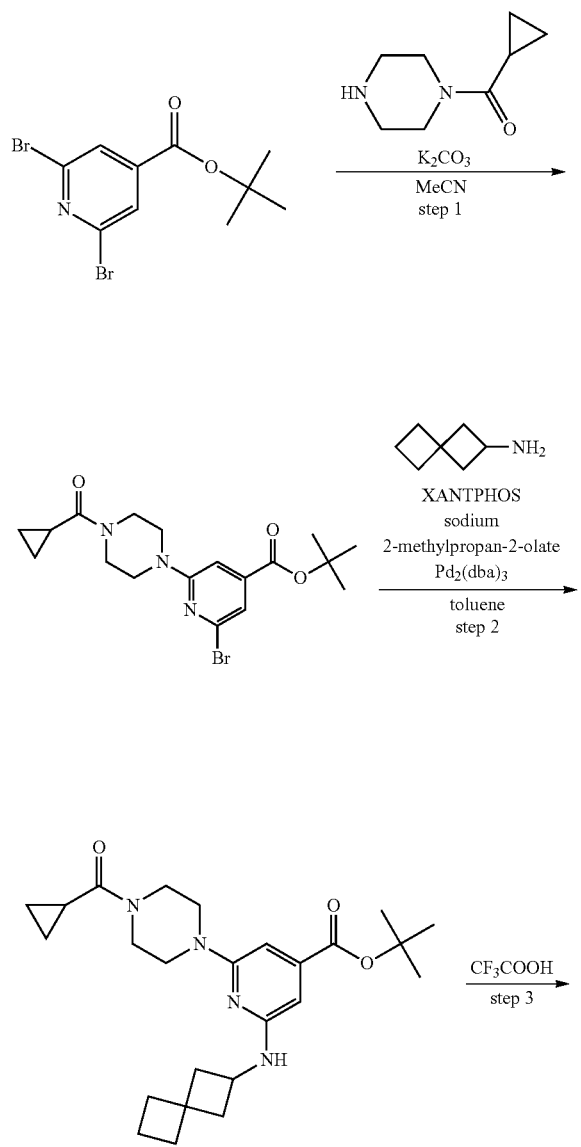

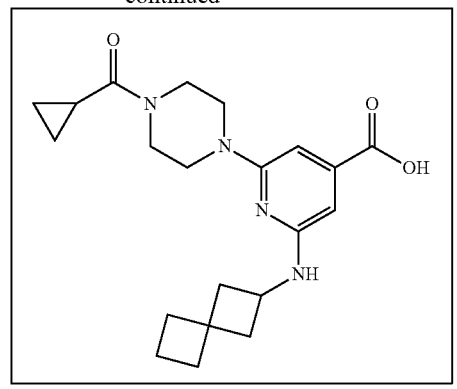

tert-butyl 2-bromo-6-(4-(cyclopropanecarbonyl)piperazin-1-yl)isonicotinate Cyclopropyl(piperazin-1-yl)methanone (7.58 g, 33.38 mmol, 6.96 mL, 2HCl) was added to a stirred mixture of tert-butyl 2,6-dibromopyridine-4-carboxylate (7.5 g, 22.25 mmol) and potassium carbonate, anhydrous, 99% (12.30 g, 89.02 mmol, 5.37 mL) in acetonitrile (150 mL). The resulting mixture was stirred at 80° C. for 72 hr (the reaction progress was monitored by HNMR of the aliquots), then cooled and filtered. The filtercake was washed with acetonitrile (2*20 mL) and discarded. The filtrate was evaporated in vacuo to leave 11 g of the residue, which was purified by column chromatography on silica gel (80 g pre-column, 80 g column) using hexane/ethyl acetate gradient (5-100% ethyl acetate) to afford tert-butyl 2-bromo-6-[4-(cyclopropanecarbonyl)piperazin-1-yl]pyridine-4-carboxylate (5.2 g, 12.67 mmol, 56.95% yield) as light-yellow solid. $^1H$ NMR (400 MHz, $CDCl_3$) δ (ppm) 0.82 (m, 2H), 1.02 (m, 2H), 1.58 (m, 9H), 1.77 (m, 1H), 3.58 (m, 2H), 3.77 (m, 6H), 7.08 (s, 1H), 7.25 (s, 1H). LCMS (ESI): [M+H]+ m/z: calc'd 410.3; found 411.2; Rt=1.585 min.

tert-butyl 2-(4-(cyclopropanecarbonyl)piperazin-1-yl)-6-(spiro[3.3]heptan-2-ylamino)isonicotinate tert-Butyl 2-bromo-6-[4-(cyclopropanecarbonyl)piperazin-1-yl]pyridine-4-carboxylate (2.6 g, 6.34 mmol) and sodium 2-methylpropan-2-olate (1.58 g, 16.48 mmol) were mixed together in toluene (50 mL). The resulting mixture was evacuated and then backfilled with argon, this operation was repeated three times, then spiro[3.3]heptan-2-amine (1.12 g, 7.60 mmol, HCl), [5-(diphenylphosphanyl)-9,9-dimethyl-9H-xanthen-4-yl]diphenylphosphane (183.33 mg, 316.84 μmol) and tris(1,5-diphenylpenta-1,4-dien-3-one) dipalladium (145.07 mg, 158.42 μmol) were added under argon. The reaction mixture was stirred under argon at 70° C. for 2 hr, then cooled and evaporated in vacuo. The residue was purified by column chromatography on silica gel (40 g pre-column, 40 g column, 5th peak was collected, tubes 41-62)) using hexane/ethyl acetate gradient (0-100% ethyl acetate) to afford tert-butyl 2-[4-(cyclopropanecarbonyl) piperazin-1-yl]-6-(spiro[3.3]heptan-2-ylamino)pyridine-4-carboxylate (1.6 g, 3.63 mmol, 57.31% yield) as yellow solid, which was used directly in the next step. $^1H$ NMR (500 MHz, $CDCl_3$) δ (ppm) 0.78 (m, 2H), 1.01 (m, 2H), 1.58 (m, 9H), 1.78 (m, 5H), 1.96 (m, 2H), 2.08 (m, 2H), 2.52 (m, 2H), 3.62 (m, 4H), 3.75 (m, 4H), 3.98 (m, 1H), 4.56 (m, 1H), 6.22 (s, 1H), 6.45 (s, 1H). LCMS (ESI): [M+H]+ m/z: calc'd 440.6; found 441.2; Rt=1.647 min.

2-(4-(cyclopropanecarbonyl)piperazin-1-yl)-6-(spiro[3.3]heptan-2-ylamino)isonicotinic acid tert-Butyl 2-[4-(cyclopropanecarbonyl)piperazin-1-yl]-6-(spiro[3.3]heptan-2-ylamino)pyridine-4-carboxylate (1.6 g, 3.63 mmol) was dissolved in trifluoroacetic acid (20.70 g, 181.58 mmol, 13.99 mL). The reaction mixture was stirred at 25° C. for 1 hr, and then evaporated in vacuo. The residue was triturated with hexane/MTBE mixture (4/1, 60 mL), stirred for 0.1 hr and the precipitate was filtered, washed with hexane (2*10 mL) and dried in vacuo to afford 2-[4-(cyclopropanecarbonyl)piperazin-1-yl]-6-(spiro[3.3]heptan-2-ylamino)pyridine-4-carboxylic acid (1.51 g, 3.04 mmol, 83.58% yield, TFA) as yellow solid, which was used directly in the next step. $^1$H NMR (400 MHz, DMSO-$d_6$) δ (ppm) 0.73 (m, 4H), 1.88 (m, 5H), 2.03 (m, 3H), 2.40 (m, 2H), 3.50 (m, 6H), 3.77 (m, 2H), 4.02 (m, 2H), 6.23 (s, 1H), 6.32 (s, 1H). LCMS (ESI): [M+H]+ m/z: calc'd 384.5; found 385.2; Rt=1.294 min.

Synthesis of Acids of Formula Acid-IIa3i

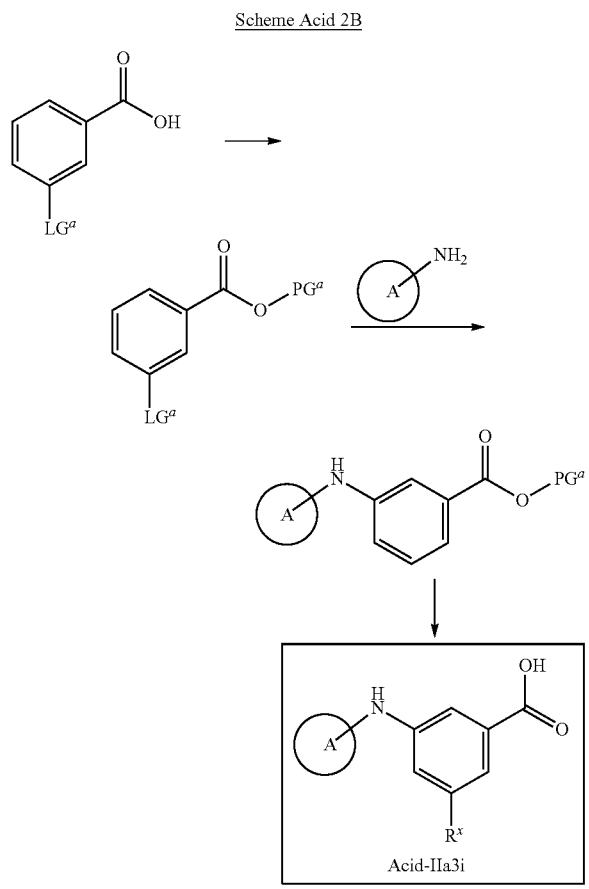

Scheme Acid 2B

Acid-IIa3i wherein A and $R^x$ are as described herein, $PG^a$ is a carboxylate protective group as described herein (e.g., a $^t$Bu group) and $LG^a$ is a leaving as described herein.

In certain embodiments $LG^a$ is halo (e.g., fluoro, chloro, bromo, iodo). The carboxylic acid can be protected with a suitable protecting group (e.g., $^t$Bu) by treatment with a protecting agent (e.g., Boc$_2$O) in the presence of a coupling agent (e.g., DMAP) in a suitable solvent (e.g., THF). The leaving group $LG^a$ can be displaced by the A-NH$_2$ moiety under conditions known to one of skill in the art. In some embodiments the displacement is a palladium-catalyzed aryl coupling (e.g., in the presence of a palladium source such as Pd$_2$(dba)$_3$, a base such as NaOEt or sodium 2-methyl propanolate and a ligand such as XantPhos) in a suitable solvent (e.g., toluene). Finally, the protective group can be removed to provide the corresponding carboxylic acid, for example under acidic conditions (e.g., in the presence of HCl or TFA) in a suitable solvent (e.g., EtOAc) or basic conditions (e.g., in the presence of LiOH, KOH or NaOH in a suitable solvent such as H$_2$O, MeOH or EtOH).

3-(cyclobutylamino)benzoic acid

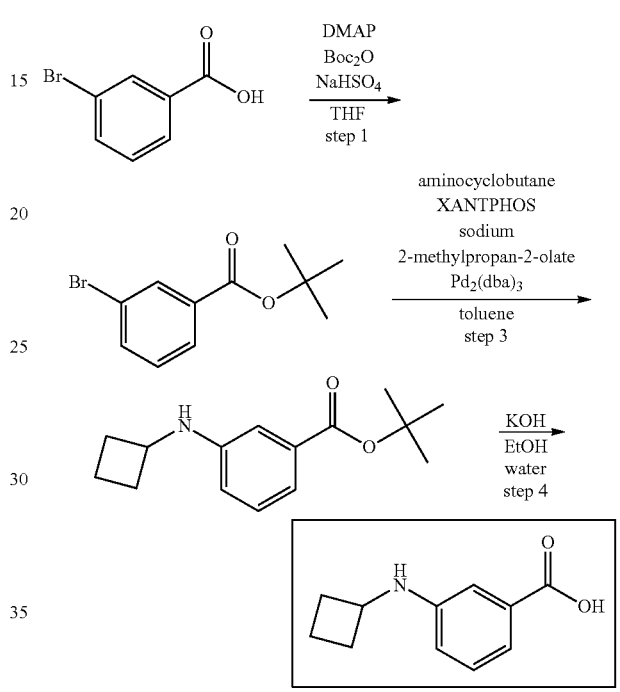

tert-butyl 3-(cyclobutylamino)benzoate. To a solution of tert-butyl 3-bromobenzoate (5 g, 19.45 mmol), cyclobutanamine (5.53 g, 77.78 mmol, 6.64 mL) and sodium tert-butoxide (5.61 g, 58.34 mmol) in toluene (150 mL), 4,5-bis (diphenylphosphino)-9,9-dimethylxanthene (562.59 mg, 972.30 μmol) and tris(dibenzylideneacetone)dipalladium (0) (445.17 mg, 486.15 μmol) were added under Ar atmosphere. The resulting mixture was heated at 90° C. for 72 hr and evaporated to dryness to obtain tert-butyl 3-(cyclobutylamino)benzoate (10 g, crude), which was used for the next step without purification. $^1$H NMR (500 MHz, DMSO-$d_6$) δ (ppm) 1.15 (s, 9H), 1.50 (m, 1H), 1.69 (m, 3H), 1.80 (m, 2H), 3.81 (m, 1H), 6.47 (d, 1H), 6.96 (t, 1H), 7.14 (m, 2H), 7.23 (m, 1H). LCMS (ESI): [M-$^t$Bu]+ m/z: calc'd 191.2; found 192.2; Rt=1.129 min.

3-(cyclobutylamino)benzoic acid. To a solution of tert-butyl 3-(cyclobutylamino)benzoate (10 g, 20.22 mmol) in EtOH (70 mL), a solution of potassium hydroxide (3.40 g, 60.65 mmol, 1.67 mL) in water (30 mL) was added. The resulting mixture was heated at 90° C. for 12 hr and evaporated in vacuo. The residue was taken up with water (50 mL) and extracted with DCM (3*50 mL). The pH of aqueous layer was adjusted to 7 with NaHSO$_4$ and extracted with DCM (3*50 mL). The combined organic layer was washed with brine (50 mL), dried over Na$_2$SO$_4$ and evaporated in vacuo to obtain crude product (1.7 g). The crude product was purified by gradient chromatography using MTBE—DCM as eluent to obtain 3-(cyclobutylamino)benzoic acid (0.62 g, 3.24 mmol, 16.04% yield). $^1$H NMR (500 MHz, DMSO-d$_6$) δ (ppm) 1.83 (m, 4H), 2.34 (m, 2H), 3.84 (m, 1H), 6.00 (bds, 1H), 6.67 (d, 1H), 7.10 (m, 3H), 12.44 (bds, 1H). LCMS (ESI): [M+H]+ m/z: calc'd 191.2; found 192.2; Rt=1.152 min.

Synthesis of Acids of Formula Acid-IIIa2i

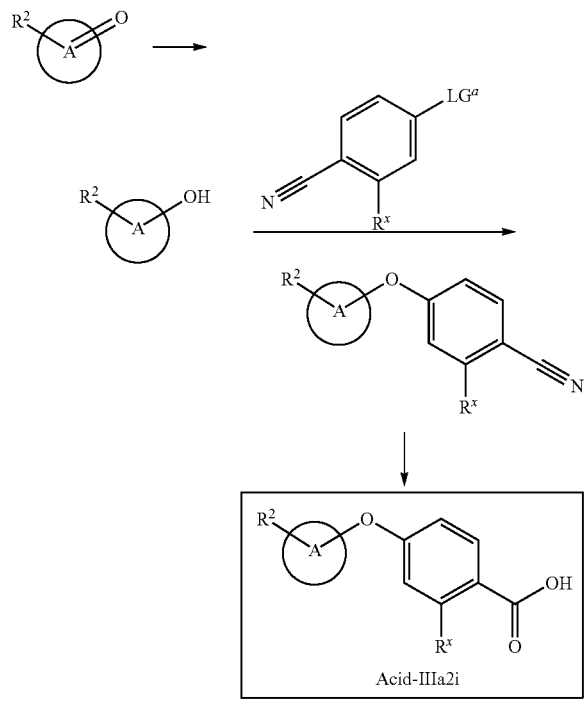

wherein A, R$^x$ and R$^2$ are as described herein and LG$^a$ is a leaving group as described herein.

In certain embodiments LG$^a$ is halo (e.g., fluoro, chloro, bromo, iodo). The leaving group LG$^a$ can be displaced by the A-OH moiety under conditions known to one of skill in the art. In some embodiments the displacement takes place under basic conditions, for example using a hydride base such as NaH in a suitable solvent (e.g., DMF). The nitrile group can be hydrolyzed to provide the corresponding carboxylic acid, for example under basic conditions (e.g., in the presence of LiOH, KOH or NaOH in a suitable solvent such as H$_2$O, MeOH or EtOH or a mixture thereof). The A-OH moiety can be prepared from the corresponding ketone using reductive conditions (e.g., using a borohydride reducing agent such as NaBH$_4$ in a suitable solvent such as water, ethanol or a mixture thereof.

4-((1-(pyridin-4-ylmethyl)piperidin-4-yl)oxy)benzoic acid

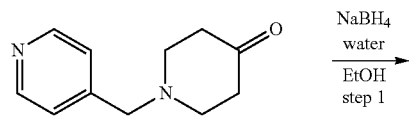

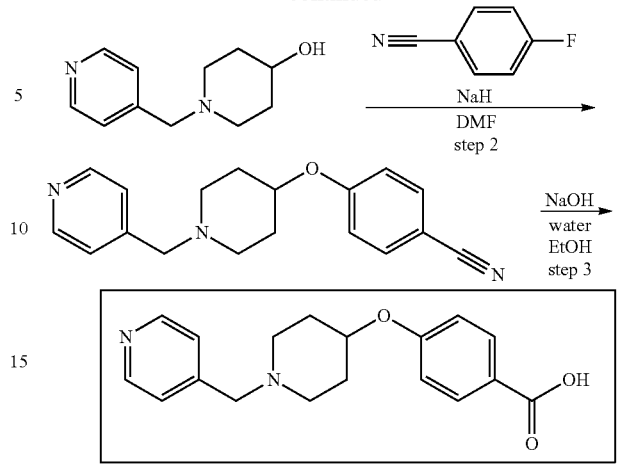

1-(pyridin-4-ylmethyl)piperidin-4-ol. 1-(4-Pyridylmethyl)piperidin-4-one (1 g, 5.26 mmol) was dissolved in ethanol (30 mL). The mixture was cooled to 0° C. and was added sodium borohydride (198.85 mg, 5.26 mmol, 185.84 µL). The mixture was stirred for 10 hr at 20° C. water (3.79 g, 210.26 mmol, 3.79 mL) was added. The mixture was stirred for 30 min at 20° C. The mixture was evaporated in vacuo at 35° C. DCM (50 mL) was added. The organic phase was dried with Na$_2$SO$_4$ and evaporated in vacuo at 35° C. to obtain 1-(4-pyridylmethyl)piperidin-4-ol (0.82 g, 4.27 mmol, 81.14% yield). $^1$H NMR (500 MHz, CDCl$_3$) δ (ppm) 1.62 (m, 2H), 1.75 (m, 1H), 1.90 (m, 2H), 2.19 (m, 2H), 2.74 (m, 2H), 3.50 (s, 2H), 3.74 (m, 1H), 7.28 (d, 2H), 8.54 (d, 2H). LCMS (ESI): [M+H]+ m/z: calc'd 192.3; found 193.2; Rt=0.159 min.

4-((1-(pyridin-4-ylmethyl)piperidin-4-yl)oxy)benzonitrile. 1-(4-Pyridylmethyl)piperidin-4-ol (0.57 g, 2.96 mmol) was dissolved in DMF (2 mL). Sodium hydride (in oil dispersion) 60% dispersion in mineral oil (85.20 mg, 3.71 mmol) was added. The mixture was stirred for 30 min at 20° C. 4-Fluorobenzonitrile (359.07 mg, 2.96 mmol) was added. The mixture was stirred for 10 hr at 20° C. Aqueous NaCl (50 mL) was added. The mixture was extracted with EtOAc (3*30 mL). The organic layer was extracted with aqueous NaCl (5*10 mL). The organic phase was dried with Na$_2$SO$_4$ and evaporated in vacuo at 35° C. The residue was purified by HPLC to obtain 4-[[1-(4-pyridylmethyl)-4-piperidyl]oxy]benzonitrile (297 mg, 1.01 mmol, 34.15% yield). $^1$H NMR (400 MHz, CDCl$_3$) δ (ppm) 1.85 (m, 2H), 1.98 (m, 2H), 2.32 (m, 2H), 2.67 (m, 2H), 3.50 (s, 2H), 4.40 (m, 1H), 6.91 (d, 2H), 7.24 (d, 2H), 7.53 (d, 2H), 8.51 (d, 2H). LCMS (ESI): [M+H]+ m/z: calc'd 293.4; found 294.2; Rt=0.763 min.

4-((1-(pyridin-4-ylmethyl)piperidin-4-yl)oxy)benzoic acid. Solution of sodium hydroxide (121.48 mg, 3.04 mmol, 57.03 µL) in H$_2$O (1 mL) was added to the solution of 4-[[1-(4-pyridylmethyl)-4-piperidyl]oxy]benzonitrile (297 mg, 1.01 mmol) in ethanol (1.5 mL). The mixture was stirred for 10 hr at 80° C. HCl (1 mL, 18%) was added. The mixture was evaporated in vacuo at 50° C. to obtain 4-[[1-(4-pyridylmethyl)-4-piperidyl]oxy]benzoic acid (385 mg, 999.26 µmol, 98.70% yield, 2HCl). $^1$H NMR (400 MHz, D$_2$O) δ (ppm) 2.12 (m, 4H), 3.33 (m, 2H), 3.47 (m, 2H), 4.58 (s, 2H), 4.82 (m, 1H), 7.02 (d, 2H), 7.91 (d, 2H), 8.08 (d, 2H), 8.80 (d, 2H). LCMS (ESI): [M+H]+ m/z: calc'd 312.4; found 313.0; Rt=0.749 min.

4-((1-benzylpiperidin-4-yl)oxy)benzoic acid

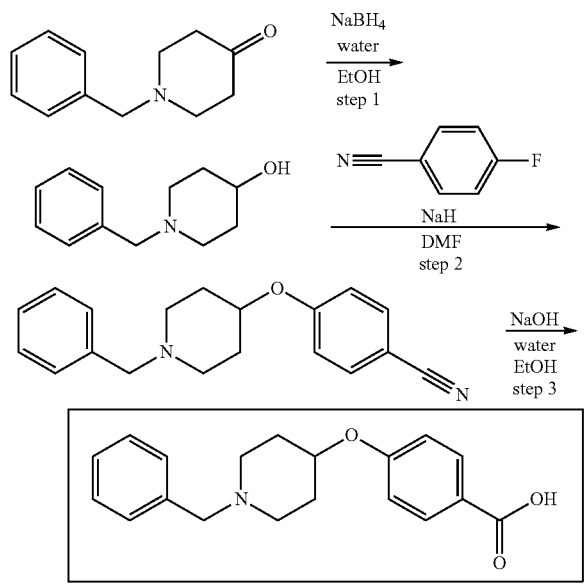

1-benzylpiperidin-4-ol. 1-Benzylpiperidin-4-one (1 g, 5.28 mmol, 943.40 μL) was dissolved in ethanol (30 mL). The mixture was cooled to 0° C. and was added sodium borohydride (199.89 mg, 5.28 mmol, 186.81 μL). The mixture was stirred for 10 hr at 20° C. water (3.81 g, 211.36 mmol, 3.81 mL) was added. The mixture was stirred for 30 min at 20° C. The mixture was evaporated in vacuo at 35° C. DCM (50 mL) was added. The organic phase was dried with $Na_2SO_4$ and evaporated in vacuo at 35° C. to obtain 1-benzylpiperidin-4-ol (0.98 g, 5.12 mmol, 96.97% yield). $^1$H NMR (500 MHz, $CDCl_3$) δ (ppm) 1.43 (m, 1H), 1.61 (m, 2H), 1.89 (m, 2H), 2.16 (m, 2H), 2.75 (m, 2H), 3.51 (s, 2H), 3.71 (m, 1H), 7.27 (m, 2H), 7.32 (m, 3H). LCMS (ESI): [M+H]+ m/z: calc'd 191.3; found 192.2; Rt=0.606 min.

4-((1-benzylpiperidin-4-yl)oxy)benzonitrile. 1-Benzylpiperidin-4-ol (0.25 g, 1.31 mmol) was dissolved in DMF (2 mL). Sodium hydride (in oil dispersion) 60% dispersion in mineral oil (37.56 mg, 1.63 mmol) was added. The mixture was stirred for 30 min at 20° C. 4-Fluorobenzonitrile (158.30 mg, 1.31 mmol) was added. The mixture was stirred for 10 hr at 20° C. Aqueous NaCl (50 mL) was added. The mixture was extracted with EtOAc (3*30 mL). The organic layer was extracted with aqueous NaCl (5*10 mL). The organic phase was dried with $Na_2SO_4$ and evaporated in vacuo at 35° C. The residue was purified by HPLC to obtain 4-[(1-benzyl-4-piperidyl)oxy]benzonitrile (131.6 mg, 450.11 μmol, 34.44% yield). $^1$H NMR (400 MHz, DMSO) δ (ppm) 1.64 (m, 2H), 1.93 (m, 2H), 2.23 (m, 2H), 2.65 (m, 2H), 3.48 (s, 2H), 4.52 (m, 1H), 7.11 (d, 2H), 7.31 (m, 5H), 7.74 (d, 2H). LCMS (ESI): [M+H]+ m/z: calc'd 292.4; found 293.2; Rt=0.908 min.

4-((1-benzylpiperidin-4-yl)oxy)benzoic acid. Solution of sodium hydroxide (54.17 mg, 1.35 mmol, 25.43 μL) in $H_2O$ (1 mL) was added to the solution of 4-[(1-benzyl-4-piperidyl)oxy]benzonitrile (132 mg, 451.48 μmol) in ethanol (1.5 mL). The mixture was stirred for 10 hr at 80° C. HCl (0.5 mL, 185) was added. The mixture was evaporated in vacuo at 50° C. to obtain 4-[(1-benzyl-4-piperidyl)oxy] benzoic acid (150 mg, 431.24 μmol, 95.52% yield, HCl. $^1$H NMR (400 MHz, $D_2O$) δ (ppm) 1.76 (m, 1H), 1.97 (m, 1H), 2.17 (m, 1H), 2.33 (m, 1H), 3.11 (m, 1H), 3.29 (m, 3H), 3.51 (m, 1H), 4.25 (s, 2H), 4.82 (bds, 1H), 7.00 (d, 2H), 7.41 (m, 5H), 7.72 (m, 1H), 7.89 (m, 1H). LCMS (ESI): [M+H]+ m/z: calc'd 311.4; found 312.2; Rt=0.905 min.

Synthesis of Acids of Formula Acid IIIa2ii

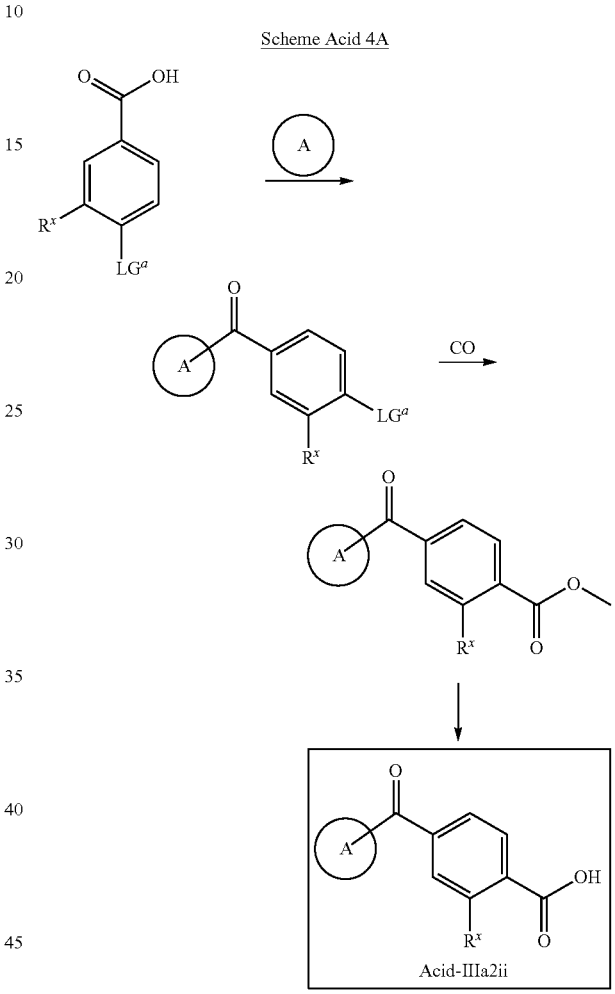

Scheme Acid 4A wherein A and $R^x$ are as described herein and $LG^a$ is a leaving group as described herein.

In certain embodiments A is a nitrogen containing heterocycle, wherein at least one of the N atoms of the heterocycle is present as an NH group. The NH group can react with the benzoic acid under standard acid coupling conditions (e.g., by converting the acid to the corresponding acid chloride using oxalyl chloride in DMF/DCM followed by treatment of the acid chloride with the NH containing ring A under basic conditions such as TEA in a suitable solvent such as DCM). In certain embodiments $LG^a$ is halo (e.g., fluoro, chloro, bromo, iodo). $LG^a$ can be converted to a carboxylate moiety under conditions known to one of skill in the art through a palladium mediated carbonylation with CO and MeOH (e.g., in a suitable solvent such as MeOH, in the presence of a base such as a carbonate base (e.g., $NaHCO_3$, $Na_2CO_3$, $Cs_2CO_3$) or amine base (e.g., DBU, $Et_3N$, DIPEA) and a palladium catalyst (e.g., Pd(dppf)$Cl_2$ DCM complex). Finally, the ester group can be hydrolyzed to the corresponding carboxylic acid, for example under basic conditions (e.g., in the presence of a hydroxide base such as NaOH, LiOH) in a suitable solvent (e.g., THF, H₂O or a mixture thereof).

4-(3-oxa-9-azabicyclo[3.3.1]nonane-9-carbonyl)-2-ethoxybenzoic acid

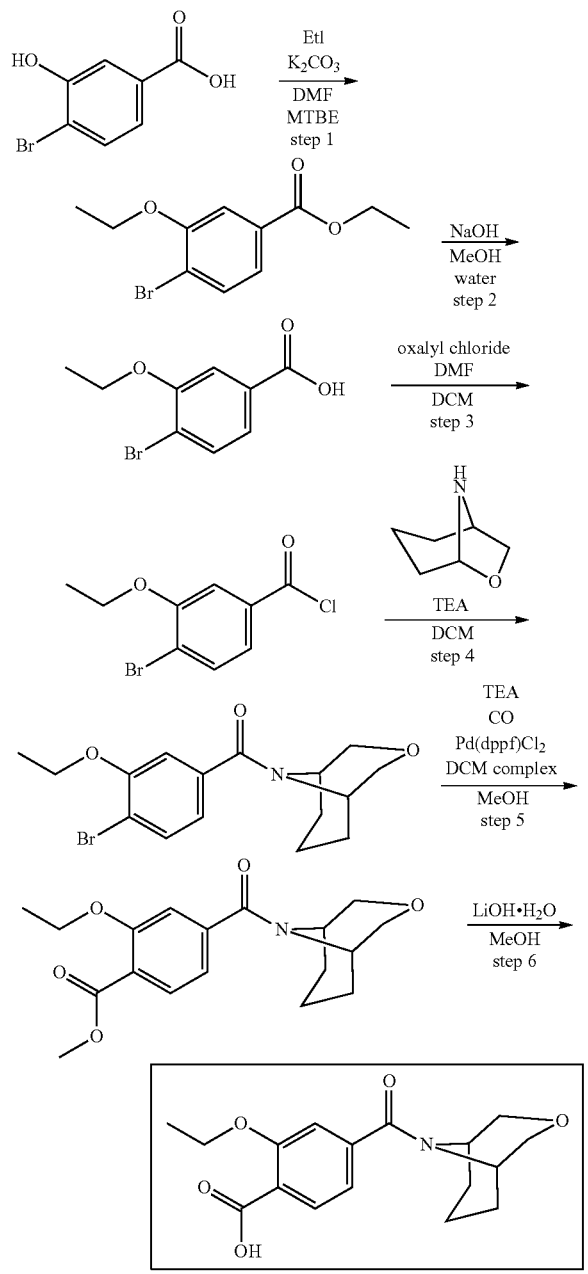

Synthesis of ethyl-4-bromo-3-ethoxybenzoate 4-Bromo-3-hydroxy-benzoic acid (10 g, 46.08 mmol) was dissolved in DMF (100 mL) and potassium carbonate (19.11 g, 138.24 mmol, 8.34 mL) was added. Ethyl iodide (28.75 g, 184.32 mmol, 14.82 mL) was added and the mixture was stirred for 10 hr at 60° C. Then the mixture was cooled to r.t. and MTBE (1500 mL) was added. The mixture was extracted with aqueous NaCl (5*300 mL). The organic phase was separated, dried with Na₂SO₄ and evaporated in vacuo at 40° C. to give ethyl 4-bromo-3-ethoxy-benzoate (11 g, 40.27 mmol, 87.40% yield). ¹H NMR (500 MHz, CDCl₃) δ (ppm) 1.39 (t, 3H), 1.49 (t, 3H), 4.18 (m, 2H), 4.37 (m, 2H), 7.49 (d, 1H), 7.53 (s, 1H), 7.59 (d, 1H). GCMS: [M]: calc'd 273.1; found 274.0; Rt=9.270 min.

Synthesis of 4-bromo-3-ethoxybenzoic acid Ethyl 4-bromo-3-ethoxy-benzoate (15 g, 54.92 mmol) was dissolved in methanol (50 mL) and sodium hydroxide (2.64 g, 65.90 mmol, 1.24 mL) solution in H₂O (50 mL) was added. The mixture was stirred at 20° C. for 10 hr. Then the mixture was evaporated in vacuo at 45° C. to remove methanol and 100 mL of H₂O was added. The mixture was treated with activated charcoal and filtered. The filtrate was acidified to pH=1 with aqueous HCl. The precipitate was filtered and washed with H₂O (3*50 mL) to give 4-bromo-3-ethoxy-benzoic acid (10 g, 40.80 mmol, 74.30% yield). ¹H NMR (500 MHz, DMSO-d₆) δ (ppm) 1.37 (t, 3H), 4.16 (m, 2H), 7.43 (d, 1H), 7.51 (s, 1H), 7.70 (d, 1H), 13.17 (bds, 1H). LCMS (ESI): [M+H]+ m/z: calc'd 245.1; found 245.2; Rt=1.276 min.

Synthesis of 4-bromo-3-ethoxybenzoyl chloride 4-Bromo-3-ethoxy-benzoic acid (10 g, 40.80 mmol) and oxalyl chloride (7.77 g, 61.21 mmol, 5.32 mL) were mixed in DCM (100 mL) and DMF (149.13 mg, 2.04 mmol, 157.98 μL) was added. The mixture was stirred at 20° C. for 5 hr. Then the mixture was evaporated in vacuo at 40° C., re-dissolved in DCM (100 mL) and evaporated again to give 4-bromo-3-ethoxy-benzoyl chloride (10.7 g, 40.60 mmol, 99.51% yield). ¹H NMR (400 MHz, CDCl₃) δ (ppm) 1.52 (t, 3H), 4.17 (m, 2H), 7.52 (s, 1H), 7.62 (d, 1H), 7.69 (d, 1H).

Synthesis of 3-oxa-9-azabicyclo[3.3.1]nonan-9-yl(4-bromo-3-ethoxyphenyl)methanone The solution of 4-bromo-3-ethoxy-benzoyl chloride (4.39 g, 16.67 mmol) in 30 mL of DCM was added dropwise to the mixture of 3-oxa-9-azabicyclo[3.3.1]nonane (3 g, 18.33 mmol, HCl) and TEA (5.06 g, 50.00 mmol, 6.97 mL) in DCM (100 mL) at 0° C. The resulting mixture was stirred for 3 hr at r.t. Then the mixture was extracted with H₂O (2*50 mL) and aqueous HCl (2*50 mL). The organic phase was separated, dried with Na₂SO₄ and evaporated in vacuo at 35° C. to give (4-bromo-3-ethoxy-phenyl)-(3-oxa-9-azabicyclo[3.3.1]nonan-9-yl) methanone (5.8 g, 16.37 mmol, 98.24% yield). ¹H NMR (500 MHz, CDCl₃) δ (ppm) 1.48 (t, 3H), 1.68 (m, 1H), 1.79 (m, 2H), 1.94 (m, 1H), 2.02 (m, 1H), 2.58 (m, 1H), 3.64 (m, 1H), 3.74 (m, 1H), 3.85 (m, 2H), 3.98 (m, 1H), 4.12 (m, 2H), 4.57 (m, 1H), 6.83 (d, 1H), 6.95 (s, 1H), 7.56 (d, 1H). LCMS (ESI): [M+H]+ m/z: calc'd 354.2; found 356.0; Rt=1.425 min.

Synthesis of methyl 4-(3-oxa-9-azabicyclo[3.3.1]nonane-9-carbonyl)-2-ethoxybenzoate (4-Bromo-3-ethoxy-phenyl)-(3-oxa-9-azabicyclo[3.3.1]nonan-9-yl)methanone (6.1 g, 17.22 mmol), [1,1'-bis(diphenylphosphino)ferrocene]dichloropalladium(II), complex with dichloromethane (703.09 mg, 861.00 μmol), TEA (5.23 g, 51.66 mmol, 7.20 mL) were dissolved in methanol (250 mL). The mixture was stirred in autoclave at 130° C. in atmosphere of carbon monoxide (17.22 mmol) (40 atm) for 30 hr. Then the reaction mixture was cooled to r.t. and the solvent was evaporated in vacuo at 40° C. The residue was mixed in EtOAc (200 mL) and the mixture was extracted with H₂O (3*50 mL). The organic phase was separated, dried with Na₂SO₄ and evaporated in vacuo to give methyl 2-ethoxy-4-(3-oxa-9-azabicyclo[3.3.1] nonane-9-carbonyl)benzoate (5.3 g, 15.90 mmol, 92.32% yield). ¹H NMR (400 MHz, CDCl₃) δ (ppm) 1.47 (t, 3H), 1.70 (m, 1H), 1.79 (m, 2H), 1.94 (m, 1H), 2.01 (m, 1H), 2.59 (m, 1H), 3.56 (m, 1H), 3.71 (m, 1H), 3.82 (m, 2H), 3.90 (s, 3H), 3.99 (m, 1H), 4.13 (m, 2H), 4.60 (m, 1H), 6.95 (d, 1H), 7.01 (s, 1H), 7.77 (d, 1H). LCMS (ESI): [M+H]+ m/z: calc'd 333.4; found 334.2; Rt=1.179 min.

Synthesis of 4-(3-oxa-9-azabicyclo[3.3.1]nonane-9-carbonyl)-2-ethoxybenzoic acid Methyl 2-ethoxy-4-(3-oxa-9-azabicyclo[3.3.1]nonane-9-carbonyl)benzoate (5 g, 15.00 mmol) was dissolved in methanol (50 mL) and lithium hydroxide, monohydrate (1.26 g, 30.00 mmol, 833.60 µL) was added. The mixture was stirred at 20° C. for 10 hr. The solvent was evaporated in vacuo at 30° C. The residue was dissolved in H$_2$O (30 mL), treated with activated charcoal and filtered. The filtrate was cooled to 5° C. and acidified with aq. HCl to pH=3-4. The precipitate was filtered, washed with H$_2$O (3*10 mL) and dried in vacuo at 35° C. to give 2-ethoxy-4-(3-oxa-9-azabicyclo[3.3.1]nonane-9-carbonyl)benzoic acid (4.5 g, 14.09 mmol, 93.95% yield). $^1$H NMR (400 MHz, CDCl$_3$) δ (ppm) 1.58 (t, 3H), 1.72 (m, 1H), 1.83 (m, 2H), 2.03 (m, 2H), 2.59 (m, 1H), 3.57 (m, 1H), 3.72 (m, 1H), 3.87 (m, 2H), 4.00 (m, 1H), 4.35 (m, 2H), 4.59 (m, 1H), 7.10 (m, 2H), 8.21 (d, 1H), 10.84 (bds, 1H). LCMS (ESI): [M+H]+ m/z: calc'd 319.6; found 320.2; Rt=1.014 min.

4-(3-oxa-9-azabicyclo[3.3.1]nonane-9-carbonyl)benzoic acid

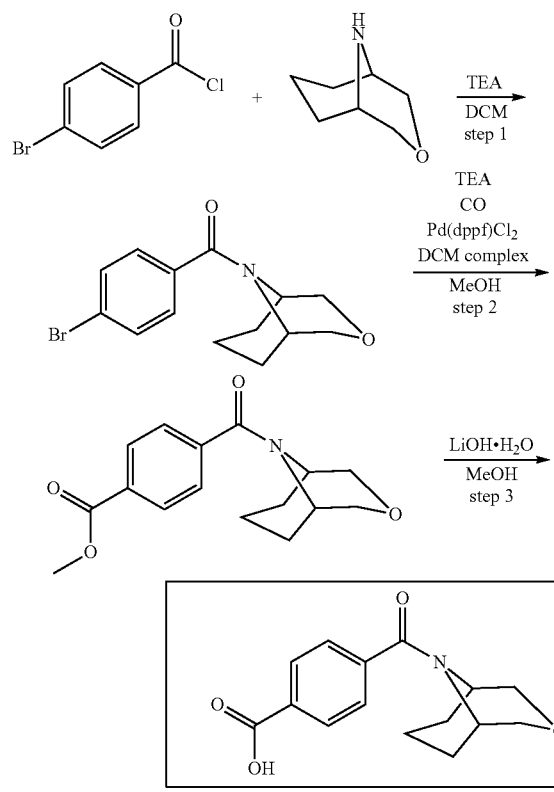

(1R,5S)-3-oxa-9-azabicyclo[3.3.1]nonan-9-yl(4-bromophenyl)methanone The solution of 4-bromobenzoyl chloride (0.2 g, 911.32 µmol) in 3 mL of DCM was added dropwise to the mixture of 3-oxa-9-azabicyclo[3.3.1]nonane (164.05 mg, 1.00 mmol, HCl) and TEA (276.65 mg, 2.73 mmol, 381.06 µL) in DCM (5 mL) at 0° C. The resulting mixture was stirred for 24 hr at r.t. Then the mixture was extracted with H$_2$O (2*10 mL) and aqueous HCl (2*10 mL). The organic phase was separated, dried with Na$_2$SO$_4$ and evaporated in vacuo at 35° C. to give (4-bromophenyl)-(3-oxa-9-azabicyclo[3.3.1]nonan-9-yl)methanone (0.220 g, 709.25 µmol, 77.83% yield) which was used in further steps without purification. $^1$H NMR (400 MHz, CDCl$_3$) δ (ppm) 1.66 (m, 1H), 1.77 (m, 2H), 1.99 (m, 2H), 2.55 (m, 1H), 3.57 (m, 1H), 3.73 (m, 1H), 3.84 (m, 2H), 3.97 (m, 1H), 4.46 (m, 1H), 7.27 (d, 2H), 7.53 (d, 2H). LCMS (ESI): [M+H]+ m/z: calc'd 310.2; found 311.2; Rt=1.212 min.

Methyl 4-((1R,5S)-3-oxa-9-azabicyclo[3.3.1]nonane-9-carbonyl)benzoate (4-Bromophenyl)-(3-oxa-9-azabicyclo[3.3.1]nonan-9-yl)methanone (0.22 g, 709.25 µmol), 1,1'-bis(diphenylphosphino)ferrocene-palladium(II) dichloride dichloromethane complex (11.58 mg, 14.19 µmol) and TEA (86.12 mg, 851.10 µmol, 118.63 µL) was dissolved in methanol (10 mL) and stirred overnight at 130° C. in atmosphere carbon monoxide (40 atm). Reaction mixture was cooled to RT, filtered and evaporated in vacuo at 40° C. The mixture was dissolved in 10 mL of DCM and washed with water. Organic phase was dried over Na$_2$SO$_4$, filtered and evaporated in vacuo at 35° C. to give methyl 4-(3-oxa-9-azabicyclo[3.3.1]nonane-9-carbonyl)benzoate (0.180 g, 622.14 µmol, 87.72% yield) which was used in further steps without purification. $^1$H NMR (500 MHz, CDCl$_3$) δ (ppm) 1.69 (m, 1H), 1.80 (m, 2H), 1.95 (m, 1H), 2.04 (m, 1H), 2.57 (m, 1H), 3.53 (m, 1H), 3.76 (m, 1H), 3.85 (m, 1H), 3.92 (m, 1H), 3.94 (s, 3H), 4.00 (m, 1H), 4.63 (m, 1H), 7.48 (d, 2H), 8.09 (d, 2H). LCMS (ESI): [M+H]+ m/z: calc'd 289.3; found 290.2; Rt=1.225 min.

4-(3-oxa-9-azabicyclo[3.3.1]nonane-9-carbonyl)benzoic acid Methyl 4-(3-oxa-9-azabicyclo[3.3.1]nonane-9-carbonyl)benzoate (0.18 g, 622.14 µmol) was dissolved in methanol (2 mL) and lithium hydroxide monohydrate, 98% (52.21 mg, 1.24 mmol, 34.58 µL) in water (1 mL) was added. The mixture was stirred overnight at RT. Methanol was evaporated in vacuo at 40° C. water was acidified with 1M water solution of HCl and extracted with DCM. Organic phase was dried over Na$_2$SO$_4$, filtered and evaporated at 35° C. to give 4-(3-oxa-9-azabicyclo[3.3.1]nonane-9-carbonyl)benzoic acid (0.12 g, 435.89 µmol, 70.06% yield). $^1$H NMR (500 MHz, CDCl$_3$) δ (ppm) 1.71 (m, 1H), 1.79 (m, 2H), 1.95 (m, 1H), 2.04 (m, 1H), 2.56 (m, 1H), 3.53 (m, 1H), 3.83 (m, 1H), 3.90 (m, 2H), 4.03 (m, 1H), 4.62 (m, 1H), 7.49 (d, 2H), 8.13 (d, 2H), 10.56 (bds, 1H). LCMS (ESI): [M+H]+ m/z: calc'd 275.3; found 276.0; Rt=1.048 min.

4-(3-oxa-8-azabicyclo[3.2.1]octane-8-carbonyl)-2-ethoxybenzoic acid

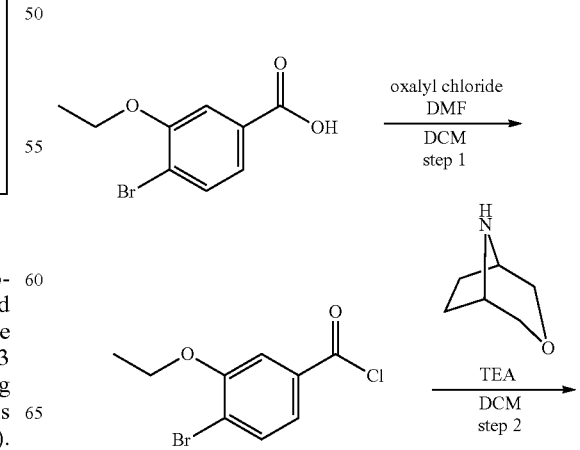

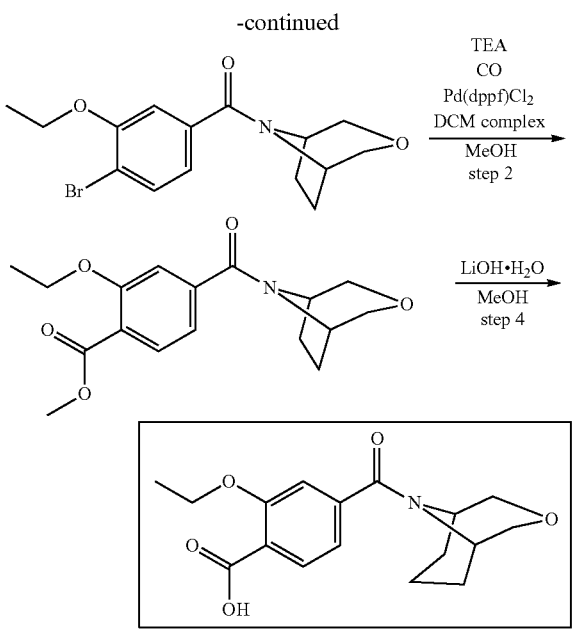

oxa-8-azabicyclo[3.2.1]octan-8-yl(4-bromo-3-ethoxyphenyl)methanone The solution of 4-bromo-3-ethoxy-benzoyl chloride (see synthesis above) (5.28 g, 20.05 mmol) in 30 mL of DCM was added dropwise to the mixture of 3-oxa-8-azabicyclo[3.2.1]octane (3 g, 20.05 mmol, HCl) and TEA (6.09 g, 60.15 mmol, 8.38 mL) in DCM (100 mL) at 0° C. The resulting mixture was stirred for 3 hr at r.t. Then the mixture was extracted with $H_2O$ (2*50 mL) and aqueous HCl (2*50 mL). The organic phase was separated, dried with $Na_2SO_4$ and evaporated in vacuo at 35° C. to give (4-bromo-3-ethoxy-phenyl)-(3-oxa-8-azabicyclo[3.2.1]octan-8-yl) methanone (6.3 g, 18.52 mmol, 92.35% yield). $^1$H NMR (500 MHz, $CDCl_3$) δ (ppm) 1.47 (t, 3H), 1.93 (m, 1H), 2.05 (m, 3H), 3.60 (m, 1H), 3.68 (m, 2H), 3.85 (m, 1H), 3.99 (m, 1H), 4.14 (m, 2H), 4.70 (m, 1H), 6.89 (d, 1H), 7.04 (s, 1H), 7.55 (d, 1H). LCMS (ESI): [M+H]+ m/z: calc'd 340.2; found 341.0; Rt=1.370 min.

Methyl 4-(3-oxa-8-azabicyclo[3.2.1]octane-8-carbonyl)-2-ethoxybenzoate (4-Bromo-3-ethoxy-phenyl)-(3-oxa-8-azabicyclo[3.2.1]octan-8-yl)methanone (4.3 g, 12.64 mmol), [1,1'-bis(diphenylphosphino)ferrocene]dichloropalladium(II), complex with dichloromethane (516.06 mg, 631.96 μmol), TEA (3.84 g, 37.92 mmol, 5.28 mL) were dissolved in methanol (250 mL). The mixture was stirred in autoclave at 130° C. in atmosphere of carbon monoxide (40 atm) for 30 hr. Then the reaction mixture was cooled to r.t. and the solvent was evaporated in vacuo at 40° C. The residue was mixed in EtOAc (200 mL) and the mixture was extracted with $H_2O$ (3*50 mL). The organic phase was separated, dried with $Na_2SO_4$ and evaporated in vacuo to give methyl 2-ethoxy-4-(3-oxa-8-azabicyclo[3.2.1]octane-8-carbonyl)benzoate (3.5 g, 10.96 mmol, 86.71% yield). $^1$H NMR (400 MHz, $CDCl_3$) δ (ppm) 1.46 (t, 3H), 1.93 (m, 1H), 2.01 (m, 3H), 3.56 (m, 1H), 3.69 (m, 2H), 3.85 (m, 2H), 3.90 (s, 3H), 4.13 (m, 2H), 4.71 (m, 1H), 7.00 (d, 1H), 7.09 (s, 1H), 7.79 (d, 1H). LCMS (ESI): [M+H]+ m/z: calc'd 319.4; found 320.2; Rt=1.169 min.

4-(3-oxa-8-azabicyclo[3.2.1]octane-8-carbonyl)-2-ethoxybenzoic acid Methyl 2-ethoxy-4-(3-oxa-8-azabicyclo[3.2.1]octane-8-carbonyl)benzoate (3 g, 9.39 mmol) was dissolved in methanol (50 mL) and lithium hydroxide, monohydrate (788.42 mg, 18.79 mmol, 522.13 μL) was added. The mixture was stirred at 20° C. for 10 hr. The solvent was evaporated in vacuo at 30° C. The residue was dissolved in $H_2O$ (30 mL), treated with activated charcoal and filtered. The filtrate was cooled to 5° C. and acidified with aq. HCl to pH=3-4. The precipitate was filtered, washed with $H_2O$ (3*10 mL) and dried in vacuo at 35° C. to give 2-ethoxy-4-(3-oxa-8-azabicyclo[3.2.1]octane-8-carbonyl) benzoic acid (2.8 g, 9.17 mmol, 97.62% yield). $^1$H NMR (500 MHz, $CDCl_3$) δ (ppm) 1.58 (t, 3H), 1.95 (m, 1H), 2.08 (m, 3H), 3.61 (m, 1H), 3.70 (m, 2H), 3.90 (m, 2H), 4.37 (m, 2H), 4.72 (m, 1H), 7.15 (d, 1H), 7.23 (s, 1H), 8.21 (d, 1H), 10.86 (bds, 1H). LCMS (ESI): [M+H]+ m/z: calc'd 305.3; found 306.2; Rt=0.921 min.

2-(4-methoxybenzoyl)-1,2,3,4-tetrahydroisoquinoline-6-carboxylic acid

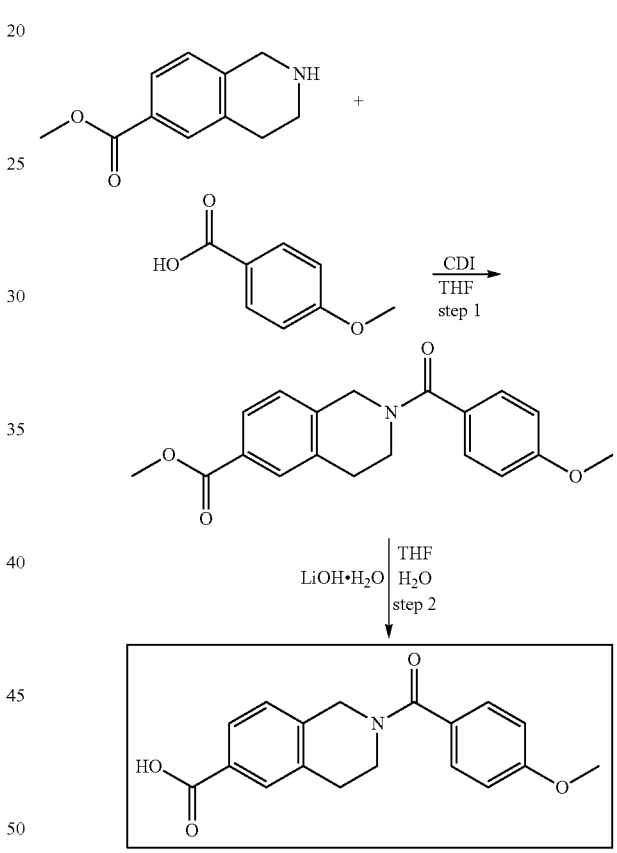

methyl 2-(4-methoxybenzoyl)-1,2,3,4-tetrahydroisoquinoline-6-carboxylate. CDI (1.51 g, 9.32 mmol) was added in one portion to a solution of 4-methoxybenzoic acid (1.35 g, 8.87 mmol, 971.22 μL) in THF (50 mL). The resulting solution was warmed to 55° C. and stirred until carbon dioxide evolution was completed, then methyl 1,2,3,4-tetrahydroisoquinoline-6-carboxylate (1.70 g, 8.87 mmol) was added and the reaction mixture was stirred at 55° C. for 2 hr, then cooled and evaporated in vacuo. The residue was diluted with 5% aqueous sodium hydrogen sulphate solution (50 mL) and the oily product was extracted with dichloromethane (2*40 mL). The combined organic extracts were washed with water (40 mL), dried over sodium sulphate and evaporated in vacuo to afford methyl 2-(4-methoxybenzoyl)-3,4-dihydro-1H-isoquinoline-6-carboxylate (2.6 g, 7.99 mmol, 90.06% yield) as yellow gum, which slowly crystallized into yellow solid. ¹H NMR (400 MHz, DMSO) δ (ppm) 2.92 (m, 2H), 3.68 (m, 2H), 3.80 (s, 3H), 3.83 (s, 3H), 4.76 (m, 2H), 7.01 (d, 2H), 7.42 (m, 3H), 7.77 (d, 2H). LCMS (ESI): [M+H]+ m/z: calc'd 325.4; found 326.2; Rt=1.315 min.

2-(4-methoxybenzoyl)-1,2,3,4-tetrahydroisoquinoline-6-carboxylic acid. Lithium hydroxide, monohydrate (1.01 g, 23.97 mmol, 666.24 μL) was added in one portion to a stirred solution of methyl 2-(4-methoxybenzoyl)-3,4-dihydro-1H-isoquinoline-6-carboxylate (2.6 g, 7.99 mmol) in a mixture of water (10 mL) and THF (30 mL). The resulting mixture was stirred at 25° C. for 12 hr, and then evaporated in vacuo. The residue was diluted with water (30 mL) and acidified with concentrated aqueous hydrochloric acid to pH 4. The oily product was extracted with dichloromethane (2*40 mL). The combined organic extracts were dried over sodium sulphate and evaporated in vacuo to afford 2-(4-methoxybenzoyl)-3,4-dihydro-1H-isoquinoline-6-carboxylic acid (2.05 g, 6.58 mmol, 82.40% yield) as light-yellow solid. ¹H NMR (400 MHz, DMSO) δ (ppm) 2.92 (m, 2H), 3.69 (m, 2H), 3.80 (s, 3H), 4.75 (m, 2H), 7.01 (d, 2H), 7.29 (m, 1H), 7.30 (m, 2H), 7.75 (m, 2H), 12.83 (bds, 1H). LCMS (ESI): [M+H]+ m/z: calc'd 311.3; found 312.2; Rt=1.114 mi.

2-(4-bromobenzoyl)-1,2,3,4-tetrahydroisoquinoline-6-carboxylic acid

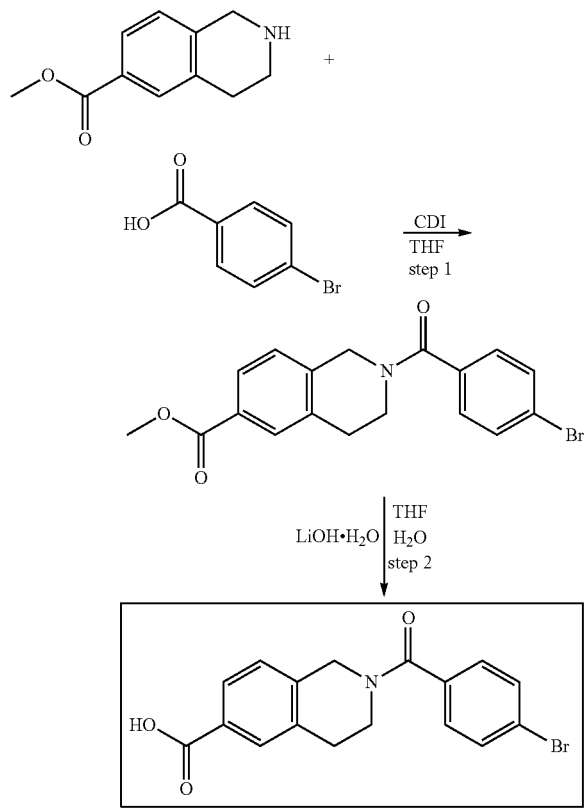

methyl 2-(4-bromobenzoyl)-1,2,3,4-tetrahydroisoquinoline-6-carboxylate. CDI (1.19 g, 7.31 mmol) was added in one portion to a solution of 4-bromobenzoic acid (1.4 g, 6.96 mmol, 359.71 μL) in THF (50 mL). The resulting solution was warmed to 55° C. and stirred until carbon dioxide evolution was completed, then methyl 1,2,3,4-tetrahydroisoquinoline-6-carboxylate (1.33 g, 6.96 mmol) was added and the reaction mixture was stirred at 55° C. for 2 hr, then cooled and evaporated in vacuo. The residue was diluted water (50 mL), the precipitate was filtered, washed with water (2*20 mL) and air dried to afford methyl 2-(4-bromobenzoyl)-3,4-dihydro-1H-isoquinoline-6-carboxylate (2.4 g, 6.41 mmol, 92.08% yield) as light-yellow solid. ¹H NMR (400 MHz, DMSO) δ (ppm) 2.92 (m, 2H), 3.56 (m, 1H), 3.80 (m, 1H), 3.83 (s, 3H), 4.82 (m, 2H), 7.20 (m, 3H), 7.67 (m, 2H), 7.78 (m, 2H). LCMS (ESI): [M+H]+ m/z: calc'd 374.2; found 376.0; Rt=1.425 min.

2-(4-bromobenzoyl)-1,2,3,4-tetrahydroisoquinoline-6-carboxylic acid. Lithium hydroxide, monohydrate (807.29 mg, 19.24 mmol, 534.63 μL) was added in one portion to a stirred solution of methyl 2-(4-bromobenzoyl)-3,4-dihydro-1H-isoquinoline-6-carboxylate (2.4 g, 6.41 mmol) in a mixture of water (10 mL) and THF (30 mL). The resulting mixture was stirred at 25° C. for 12 hr, and then evaporated in vacuo. The residue was diluted with water (50 mL) and acidified with concentrated aqueous hydrochloric acid to pH 4. The precipitate was filtered, washed with water (2*20 mL) and dried in vacuo to afford 2-(4-bromobenzoyl)-3,4-dihydro-1H-isoquinoline-6-carboxylic acid (1.95 g, 5.41 mmol, 84.41% yield) as light-yellow solid. ¹H NMR (400 MHz, DMSO) δ (ppm) 2.91 (m, 2H), 3.83 (m, 2H), 4.81 (m, 2H), 7.42 (m, 3H), 7.75 (m, 4H), 12.88 (bds, 1H). LCMS (ESI): [M+H]+ m/z: calc'd 360.2; found 361.0; Rt=1.228 min.

Synthesis of Tetrahydroisoquinoline Intermediates (S)-tert-butyl 3-((R)-2-amino-1-hydroxyethyl)-7-(methoxymethoxy)-3,4-dihydroisoquinoline-2(1H)-carboxylate

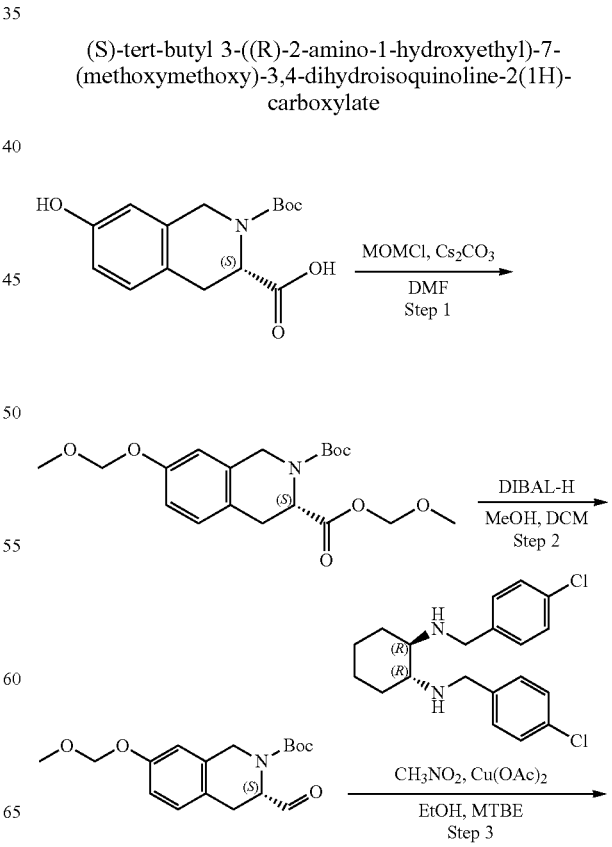

-continued

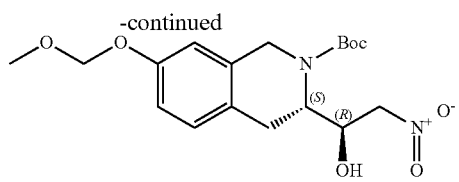

↓ 10%-Pd/C
MeOH
Step 4

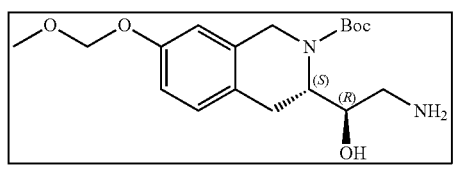

(S)-2-tert-butyl 3-(methoxymethyl) 7-(methoxymethoxy)-3,4-dihydroisoquinoline-2,3(1H)-dicarboxylate (3S)-2-tert-Butoxycarbonyl-7-hydroxy-3,4-dihydro-1H-isoquinoline-3-carboxylic acid (25 g, 85.23 mmol) and cesium carbonate (83.31 g, 255.70 mmol) were mixed in DMF (250 mL). Then, methoxymethyl chloride (20.59 g, 255.70 mmol) was added dropwise while stirring. The mixture was stirred at 20° C. for 10 h. After the completion of the reaction, MTBE (1 L) was added and the mixture was extracted with $H_2O$ (5*300 mL). The organic phase was separated, dried with $Na_2SO_4$ and evaporated in vacuo at 35° C. to give (S)-2-tert-butyl 3-(methoxymethyl) 7-(methoxymethoxy)-3,4-dihydroisoquinoline-2,3(1H)-dicarboxylate (31 g, 81.28 mmol, 95.36% yield) which was used without further purification on the next step. $^1$H NMR (500 MHz, CDCl$_3$) δ (ppm) 1.47 (s, 9H), 3.20 (s, 2H), 3.24 (d, 2H), 3.38 (t, 1H), 3.45 (s, 3H), 3.51 (s, 3H), 5.12 (s, 2H), 5.27 (s, 2H), 6.79 (s, 1H), 6.84 (d, 1H), 7.05 (d, 1H). LCMS (ESI): [M-Boc]$^+$ m/z: calc'd 281.4; found 282.2; Rt=1.48 min.

(S)-tert-butyl 3-formyl-7-(methoxymethoxy)-3,4-dihydroisoquinoline-2(1H)-carboxylate (S)-2-tert-butyl 3-(Methoxymethyl) 7-(methoxymethoxy)-3,4-dihydroisoquinoline-2,3(1H)-dicarboxylate (31 g, 81.28 mmol) was dissolved in DCM (1000 mL) and cooled to -78° C. Then, DIBAL-H (23.12 g, 162.55 mmol, 32.98 mL) was added dropwise at the same temperature while stirring. The mixture was stirred at -78° C. for 1 h followed by the dropwise addition of the solution of methanol (26.04 g, 812.75 mmol, 32.92 mL) in DCM (100 mL). The mixture was warmed to r.t. and carefully poured into solution of citric acid in $H_2O$ while vigorous stirring. After 15 min of vigorous stirring the organic layer was separated, dried with $Na_2SO_4$ and evaporated in vacuo at 35° C. to give crude tert-butyl (3S)-3-formyl-7-(methoxymethoxy)-3,4-dihydro-1H-isoquinoline-2-carboxylate (26 g, 80.90 mmol, 99.54% yield) which was used as is on the next step. $^1$H NMR (500 MHz, CDCl$_3$) δ (ppm) 1.46 (m, 9H), 3.03 (m, 2H), 3.48 (s, 3H), 4.82 (m, 3H), 5.13 (s, 2H), 6.79 (m, 2H), 7.07 (d, 1H), 9.49 (d, 1H). LCMS (ESI): [M-Boc]$^+$ m/z: calc'd 221.4; found 222.2; Rt=1.38 min.

(S)-tert-butyl 3-((R)-1-hydroxy-2-nitroethyl)-7-(methoxymethoxy)-3,4-dihydroisoquinoline-2(1H)-carboxylate (1R,2R)—$N^1,N^2$-Bis[(4-chlorophenyl)methyl]cyclohexane-1,2-diamine (3.66 g, 10.08 mmol) and copper(II) acetate hydrate (1.68 g, 8.40 mmol, 892.22 μL) were mixed together in ethanol (150 mL) and stirred for 15 min at 20° C. Then, the mixture was cooled to 0° C. and solution of tert-butyl (3S)-3-formyl-7-(methoxymethoxy)-3,4-dihydro-1H-isoquinoline-2-carboxylate (27 g, 84.02 mmol) in ethanol (150 mL) was added. After that, nitromethane (102.57 g, 1.68 mol, 90.77 mL) was added in one portion. The mixture was stirred at 20° C. for 10 h. Then, the solvent was evaporated in vacuo at 35° C. The residue was dissolved in MTBE (500 mL) and the mixture was extracted with aqueous $NH_3$ (3*100 mL) and aqueous citric acid (3*100 mL). The organic phase was separated, dried over $Na_2SO_4$ and evaporated in vacuo at 35° C. The crude product was purified by column chromatography (Interchim, 330 g SiO$_2$, petroleum ether/MTBE with MTBE from 0-30%, flow rate=127 mL/min, Rt=35 min) to give tert-butyl (3S)-3-[(1R)-1-hydroxy-2-nitro-ethyl]-7-(methoxymethoxy)-3,4-dihydro-1H-isoquinoline-2-carboxylate (10 g, 26.15 mmol, 31.13% yield). $^1$H NMR (400 MHz, CDCl$_3$) δ (ppm) 1.50 (s, 9H), 2.92 (d, 1H), 3.15 (m, 1H), 3.26 (m, 1H), 3.48 (s, 3H), 4.08 (m, 1H), 4.26 (m, 2H), 4.44 (m, 2H), 4.82 (m, 1H), 5.16 (s, 2H), 6.83 (s, 1H), 6.91 (d, 1H), 7.09 (d, 1H). LCMS (ESI): [M-Boc]+ m/z: calc'd 282.4; found 283.2; Rt=1.38 min.

(S)-tert-butyl 3-((R)-2-amino-1-hydroxyethyl)-7-(methoxymethoxy)-3,4-dihydroisoquinoline-2(1H)-carboxylate tert-Butyl (3S)-3-[(1R)-1-hydroxy-2-nitro-ethyl]-7-(methoxymethoxy)-3,4-dihydro-1H-isoquinoline-2-carboxylate (9 g, 23.54 mmol) was dissolved in methanol (500 mL) and palladium, 10% on carbon (1 g, 2.09 mmol) was added. The mixture was hydrogenated in autoclave at 50° C., 50 atm (H$_2$) for 10 h. The catalyst was filtered off and the solvent was removed in vacuo at 35° C. to give tert-butyl (3S)-3-[(1R)-2-amino-1-hydroxy-ethyl]-7-(methoxymethoxy)-3,4-dihydro-1H-isoquinoline-2-carboxylate (8.2 g, 23.27 mmol, 98.86% yield). $^1$H NMR (400 MHz, DMSO-d$_6$) δ (ppm) 1.42 (s, 9H), 2.39 (m, 1H), 2.71 (m, 1H), 3.03 (m, 1H), 3.16 (m, 2H), 3.36 (s, 3H), 4.09 (m, 2H), 4.70 (m, 1H), 5.14 (s, 2H), 6.82 (m, 2H), 7.06 (d, 1H), OH and NH$_2$ are not observed. LCMS (ESI): [M+H]$^+$ m/z: calc'd 352.4; found 353.2; Rt=1.07 min.

Example 1—Synthesis of Compounds of Formula (IIIa2ii)

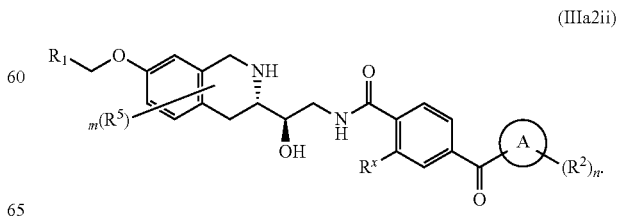

(IIIa2ii)

wherein $R^1$, $R^2$, $R^5$, $R^x$, m, n and A are as defined herein
Scheme 1A
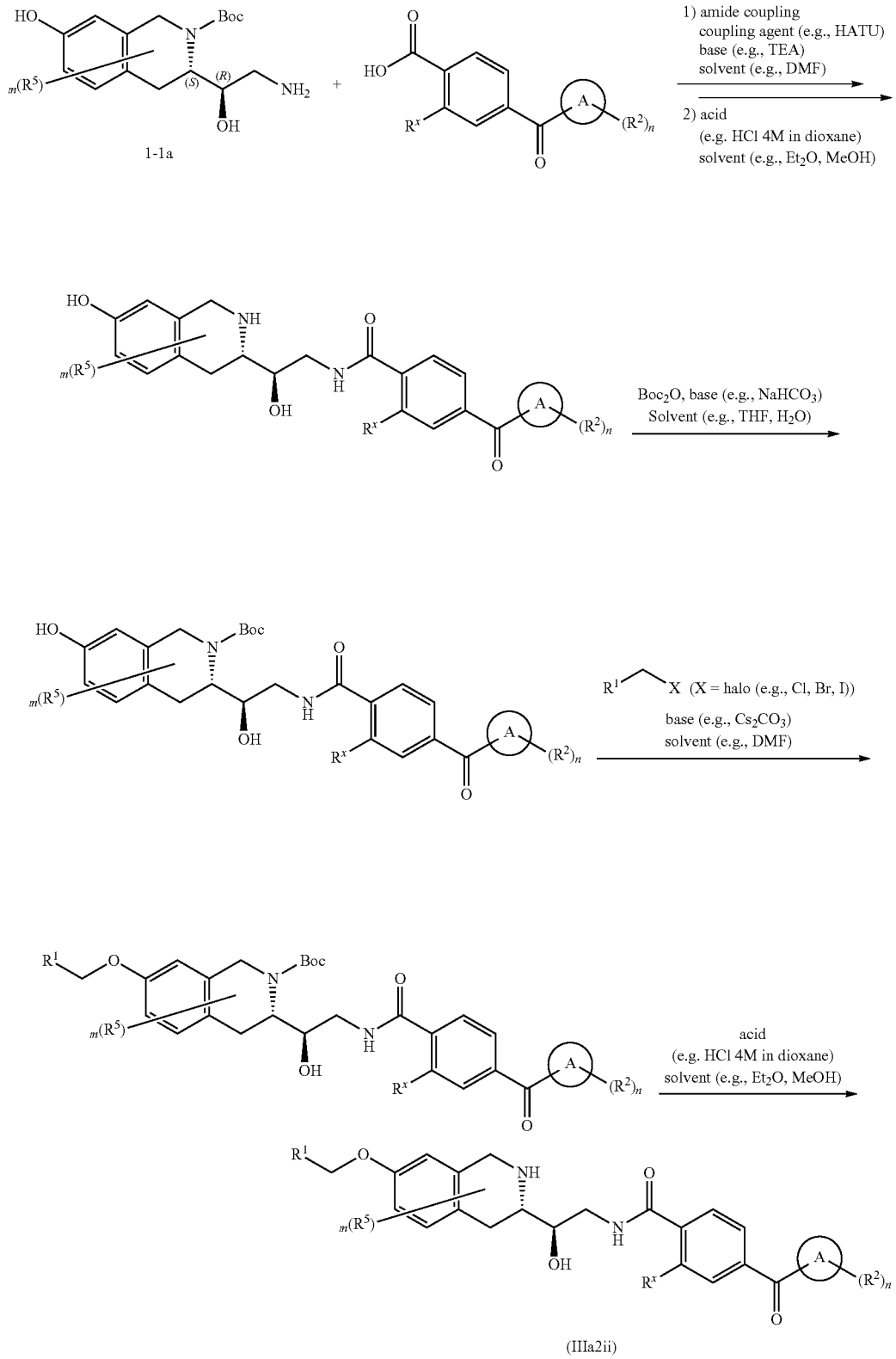
(IIIa2ii)

wherein X is a leaving group. In some embodiments, X is selected from Cl, Br, and I. In some embodiments X is Cl or Br.
Example 1A1. Synthesis of 4-((1R,5S)-3-oxa-9-azabicyclo[3.3.1]nonane-9-carbonyl)-2-ethoxy-N—((R)-2-hydroxy-2-((S)-7-(oxazol-5-ylmethoxy)-1,2,3,4-tetrahydroisoquinolin-3-yl)ethyl)benzamide (Compound 13)
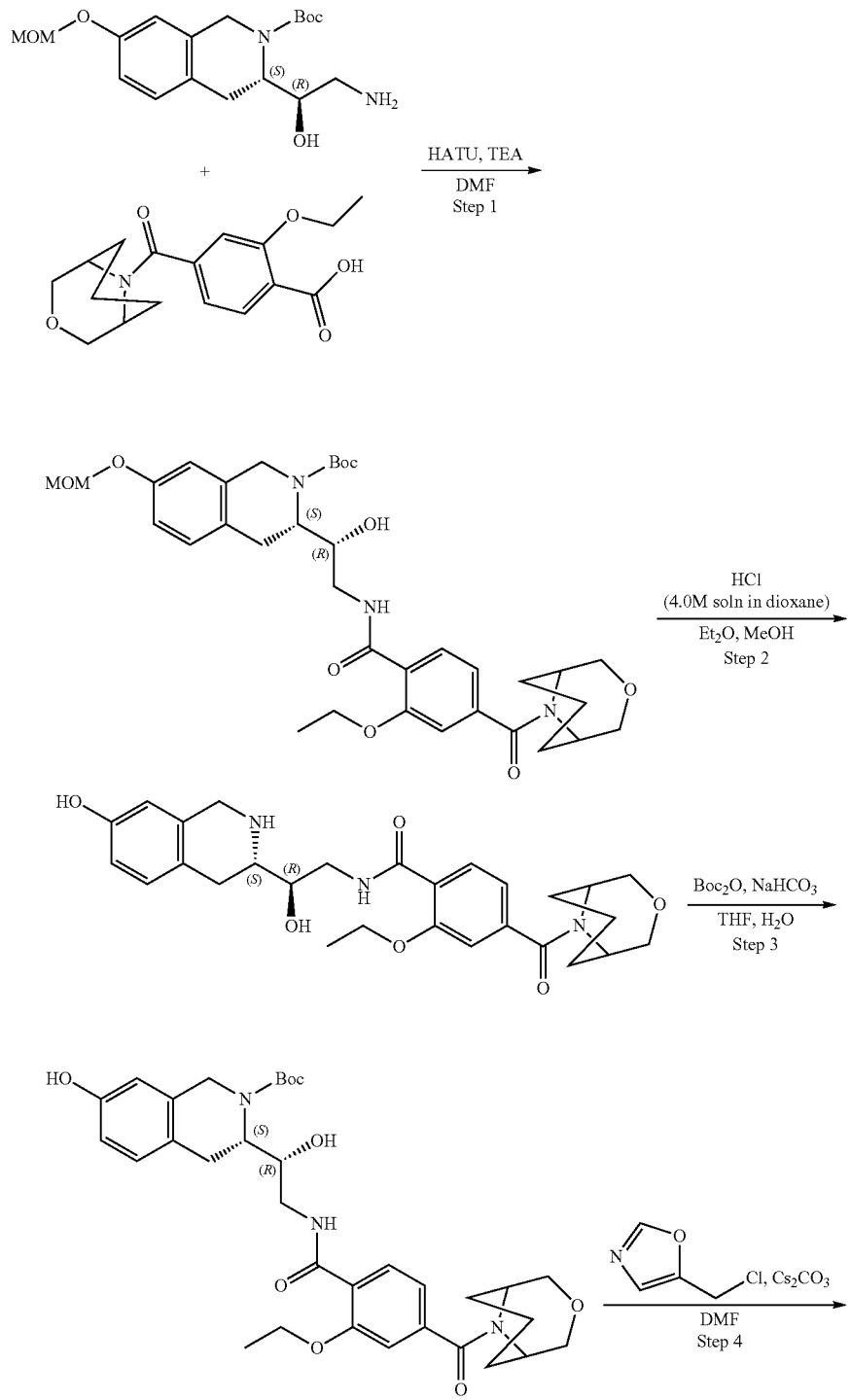

-continued

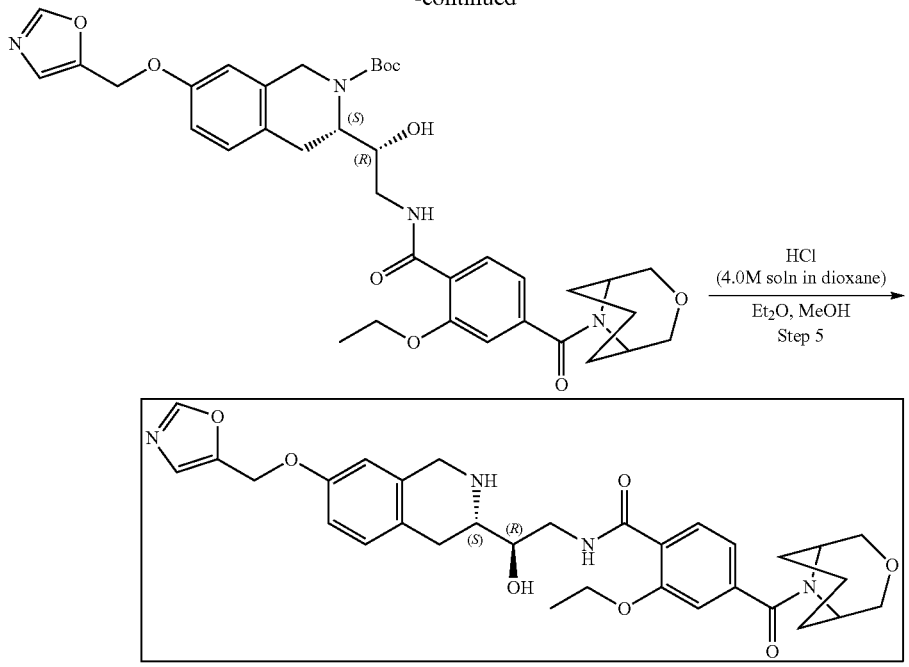

Step 1: Synthesis of (S)-tert-butyl 3-((R)-2-(4-((1R,5S)-3-oxa-9-azabicyclo[3.3.1]nonane-9-carbonyl)-2-ethoxybenzamido)-1-hydroxyethyl)-7-(methoxymethoxy)-3,4-dihydroisoquinoline-2(1H)-carboxylate 2-Ethoxy-4-(3-oxa-9-azabicyclo[3.3.1]nonane-9-carbonyl)benzoic acid (453.08 mg, 1.42 mmol) and TEA (1.44 g, 14.19 mmol, 1.98 mL) were dissolved in DMF (10 mL) and cooled to 0° C. Then, HATU (809.17 mg, 2.13 mmol) was added and the mixture was stirred for 15 min at 0° C. followed by the addition of tert-butyl (3S)-3-[(1R)-2-amino-1-hydroxy-ethyl]-7-(methoxymethoxy)-3,4-dihydro-1H-isoquinoline-2-carboxylate (0.5 g, 1.42 mmol). The resulting mixture was warmed to r.t. and stirred overnight. After LCMS showed no starting material, 50 mL of ethyl acetate was added, and the organic phase was washed with brine three times. The organic layer was dried over Na$_2$SO$_4$, filtered and concentrated in vacuo at 45° C. to give crude product which was purified by HPLC (40-55% water-acetonitrile, 2-10 min, flow: 30 mL/min (loading pump 4 mL/min acetonitrile) column: SunFire C18 100×19 mm) to give tert-butyl (3S)-3-[(1R)-2-[[2-ethoxy-4-(3-oxa-9-azabicyclo[3.3.1]nonane-9-carbonyl)benzoyl]amino]-1-hydroxy-ethyl]-7-(methoxymethoxy)-3,4-dihydro-1H-isoquinoline-2-carboxylate (0.58 g, 887.18 µmol, 62.53% yield). $^1$H NMR (400 MHz, DMSO-d$_6$) δ (ppm) 1.32 (m, 12H), 1.43 (m, 1H), 1.58 (m, 2H), 1.71 (m, 2H), 2.40 (m, 1H), 3.22 (m, 1H), 3.35 (s, 3H), 3.75 (m, 6H), 4.09 (m, 1H), 4.18 (m, 4H), 4.38 (m, 1H), 4.75 (m, 1H), 5.14 (s, 3H), 6.83 (s, 2H), 7.08 (m, 3H), 7.90 (m, 1H), 8.36 (m, 1H), OH and NH are not observed. LCMS (ESI): [M+H]+ m/z: calc'd 653.7; found 654.4; Rt=1.41 min.

Step 2: Synthesis of 4-((1R,5S)-3-oxa-9-azabicyclo[3.3.1]nonane-9-carbonyl)-2-ethoxy-N—((R)-2-hydroxy-2-((S)-7-hydroxy-1,2,3,4-tetrahydroisoquinolin-3-yl)ethyl)benzamide tert-Butyl (3S)-3-[(1R)-2-[[2-ethoxy-4-(3-oxa-9-azabicyclo[3.3.1]nonane-9-carbonyl)benzoyl]-amino]-1-hydroxy-ethyl]-7-(methoxymethoxy)-3,4-dihydro-1H-isoquinoline-2-carboxylate (0.58 g, 887.18 µmol) was dissolved in the mixture of Et$_2$O (8 mL) and MeOH (4 mL). Hydrogen chloride solution 4.0M in dioxane (2.43 g, 66.54 mmol, 3.03 mL) was added. The resulting mixture was stirred for 24 h at 25° C. After the completion of the reaction, monitored by LCMS, the formed solid was filtered on, washed with Et$_2$O (8 mL) and dried in vacuo at 35° C. to give 2-ethoxy-N-[(2R)-2-hydroxy-2-[(3S)-7-hydroxy-1,2,3,4-tetrahydroisoquinolin-3-yl]ethyl]-4-(3-oxa-9-azabicyclo[3.3.1]nonane-9-carbonyl)benzamide (0.435 g, 853.62 µmol, 96.22% yield) which was used in further steps without purification. $^1$H NMR (400 MHz, DMSO-d$_6$) δ (ppm) 1.31 (m, 3H), 1.57 (m, 2H), 1.86 (s, 2H), 2.41 (m, 1H), 2.95 (m, 3H), 3.52 (m, 3H), 3.68 (m, 2H), 3.75 (m, 4H), 3.95 (m, 1H), 4.15 (m, 4H), 4.37 (s, 1H), 6.60 (s, 1H), 6.68 (d, 1H), 7.01 (m, 2H), 7.08 (s, 1H), 7.77 (d, 1H), 8.36 (m, 1H), 8.95 (m, 1H), 9.64 (m, 1H). LCMS (ESI): [M+H]+ m/z: calc'd 509.6; found 510.2; Rt=0.88 min.

Step 3: Synthesis of (S)-tert-butyl 3-((R)-2-(4-((1R,5S)-3-oxa-9-azabicyclo[3.3.1]nonane-9-carbonyl)-2-ethoxybenzamido)-1-hydroxyethyl)-7-hydroxy-3,4-dihydroisoquinoline-2(1H)-carboxylate Sodium hydrogen carbonate, 99% (200.77 mg, 2.39 mmol, 92.95 µL) was added in one portion to the solution of 2-ethoxy-N-[(2R)-2-hydroxy-2-[(3S)-7-hydroxy-1,2,3,4-tetrahydroisoquinolin-3-yl]ethyl]-4-(3-oxa-9-azabicyclo[3.3.1]nonane-9-carbonyl)benzamide (0.435 g, 796.63 µmol, HCl) in water (8 mL). The resulting mixture was stirred for 5 min followed by the dropwise addition of the solution of di-tert-butyl dicarbonate (191.25 mg, 876.29 µmol, 201.10 µL) in THF (2 mL). The reaction mixture was stirred overnight at room temperature. After NMR showed no starting material, ethyl acetate (15 mL) was added to the reaction mixture, organic phase was separated, and the aqueous phase was extracted with ethyl acetate (2*15 mL). The organic phase was washed with brine, dried over Na$_2$SO$_4$, filtered and evaporated in vacuo at 40° C. to give tert-butyl (3S)-3-[(1R)-2-[[2-ethoxy-4-(3-oxa-9-azabicyclo[3.3.1]nonane-9-carbonyl)benzoyl]amino]-1-hydroxy-ethyl]-7-hydroxy-3,4-dihydro-TH-isoquinoline-2-carboxylate (0.445 g, 729.86 μmol, 91.62% yield). $^1$H NMR (400 MHz, DMSO-d$_6$) δ (ppm) 1.32 (m, 3H), 1.38 (m, 9H), 1.71 (m, 2H), 1.86 (m, 2H), 2.41 (m, 1H), 2.70 (m, 1H), 3.00 (m, 1H), 3.20 (m, 1H), 3.47 (m, 2H), 3.74 (m, 3H), 4.01 (m, 2H), 4.19 (m, 4H), 4.36 (m, 1H), 4.70 (m, 1H), 5.19 (m, 1H), 6.52 (s, 1H), 6.59 (d, 1H), 6.93 (d, 1H), 7.04 (d, 1H), 7.11 (s, 1H), 7.91 (m, 1H), 8.36 (m, 1H), 9.17 (s, 1H). LCMS (ESI): [M-Boc]$^+$ m/z: calc'd 509.7; found 510.2; Rt=1.32 min.

Step 4: Synthesis of (S)-tert-butyl 3-((R)-2-(4-((1R,5S)-3-oxa-9-azabicyclo[3.3.1]nonane-9-carbonyl)-2-ethoxybenzamido)-1-hydroxyethyl)-7-(oxazol-5-ylmethoxy)-3,4-dihydroisoquinoline-2(1H)-carboxylate tert-Butyl (3S)-3-[(1R)-2-[[2-ethoxy-4-(3-oxa-9-azabicyclo[3.3.1]nonane-9-carbonyl)benzoyl]-amino]-1-hydroxy-ethyl]-7-hydroxy-3,4-dihydro-1H-isoquinoline-2-carboxylate (0.1 g, 164.01 μmol), 5-(chloromethyl)oxazole (32.83 mg, 213.22 μmol, HCl) and cesium carbonate (160.32 mg, 492.04 μmol) were dissolved in DMF (3 mL) and stirred at 50° C. overnight. The reaction mixture was diluted with water and extracted three times with EtOAc, then EtOAc-layer was washed three times with brine. The organic phase was dried over Na$_2$SO$_4$, filtered off and concentrated at 40° C. to give tert-butyl (3S)-3-[(1R)-2-[[2-ethoxy-4-(3-oxa-9-azabicyclo[3.3.1]nonane-9-carbonyl)benzoyl]amino]-1-hydroxy-ethyl]-7-(oxazol-5-ylmethoxy)-3,4-dihydro-1H-isoquinoline-2-carboxylate (0.097 g, 140.42 μmol, 85.62% yield) which was used in the next step without further purification. $^1$H NMR (500 MHz, DMSO-d$_6$) δ (ppm) 1.37 (m, 13H), 1.43 (m, 1H), 1.70 (m, 2H), 1.86 (m, 2H), 2.41 (m, 1H), 2.97 (m, 3H), 3.50 (m, 3H), 3.69 (m, 4H), 4.19 (m, 1H), 4.19 (m, 3H), 4.38 (m, 1H), 4.72 (m, 1H), 5.12 (m, 3H), 6.88 (m, 1H), 7.11 (m, 3H), 7.30 (s, 1H), 7.93 (m, 1H), 8.32 (m, 2H). LCMS (ESI): [M+H]$^+$ m/z: calc'd 690.8; found 691.2; Rt=1.47 min.

Step 5: Synthesis of 4-((1R,5S)-3-oxa-9-azabicyclo[3.3.1]nonane-9-carbonyl)-2-ethoxy-N—((R)-2-hydroxy-2-((S)-7-(oxazol-5-ylmethoxy)-1,2,3,4-tetrahydroisoquinolin-3-yl)ethyl)benzamide (Compound 13) tert-Butyl (3S)-3-[(1R)-2-[[2-ethoxy-4-(3-oxa-9-azabicyclo[3.3.1]nonane-9-carbonyl)benzoyl]amino]-1-hydroxy-ethyl]-7-(oxazol-5-ylmethoxy)-3,4-dihydro-1H-isoquinoline-2-carboxylate (0.097 g, 140.42 μmol) was dissolved in the mixture of Et$_2$O (1 mL) and MeOH (0.5 mL). then, hydrogen chloride solution 4.0M in dioxane (383.99 mg, 10.53 mmol, 479.99 μL) was added. The reaction mixture was stirred for 24 h at 20° C. The formed solid was filtered on, washed with Et$_2$O (1 mL) and dried in vacuo at 35° C. to give crude product which was purified by HPLC (20-40% water-acetonitrile+NH$_3$, 2-10 min, flow 30 mL/min (loading pump 4 mL/min acetonitrile), column: SunFire C18 100*20 mm to give 2-ethoxy-N-[(2R)-2-hydroxy-2-[(3S)-7-(oxazol-5-ylmethoxy)-1,2,3,4-tetrahydroisoquinolin-3-yl]ethyl]-4-(3-oxa-9-azabicyclo-[3.3.1]nonane-9-carbonyl)benzamide (0.0216 g, 36.57 μmol, 26.04% yield). $^1$H NMR (Chloroform-d, 400 MHz): δ (ppm) 1.51 (t, 3H), 1.68 (m, 2H), 1.78 (m, 2H), 1.91 (m, 2H), 2.59 (m, 1H), 2.77 (m, 2H), 2.99 (m, 1H), 3.59 (m, 2H), 3.73 (m, 1H), 3.84 (m, 5H), 3.99 (m, 3H), 4.22 (q, 2H), 4.57 (m, 1H), 5.02 (s, 2H), 6.60 (s, 1H), 6.77 (dd, 1H), 7.03 (m, 3H), 7.12 (s, 1H), 7.88 (s, 1H), 8.20 (d, 1H), 8.44 (t, 1H). LCMS (ESI): [M+H]$^+$ m/z: calc'd 590.7; found 591.2; Rt=1.00 min.

Example 1A2. Synthesis of 4-((1R,5S)-3-oxa-9-azabicyclo[3.3.1]nonane-9-carbonyl)-2-ethoxy-N—((R)-2-hydroxy-2-((S)-7-((4-methyloxazol-5-yl)methoxy)-1,2,3,4-tetrahydroisoquinolin-3-yl)ethyl)benzamide (Compound 10)

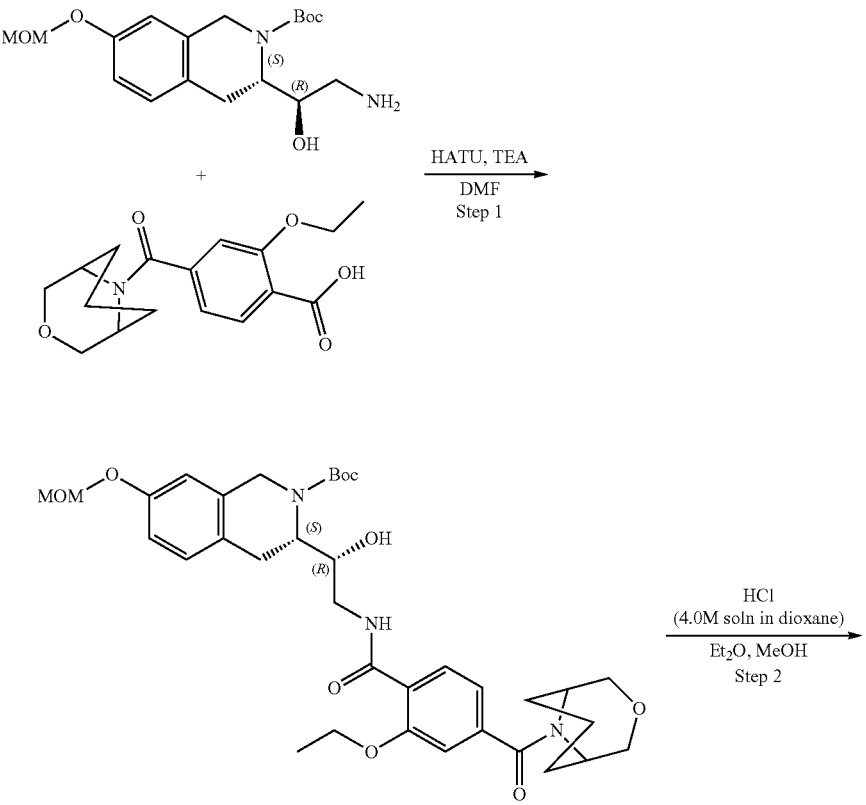

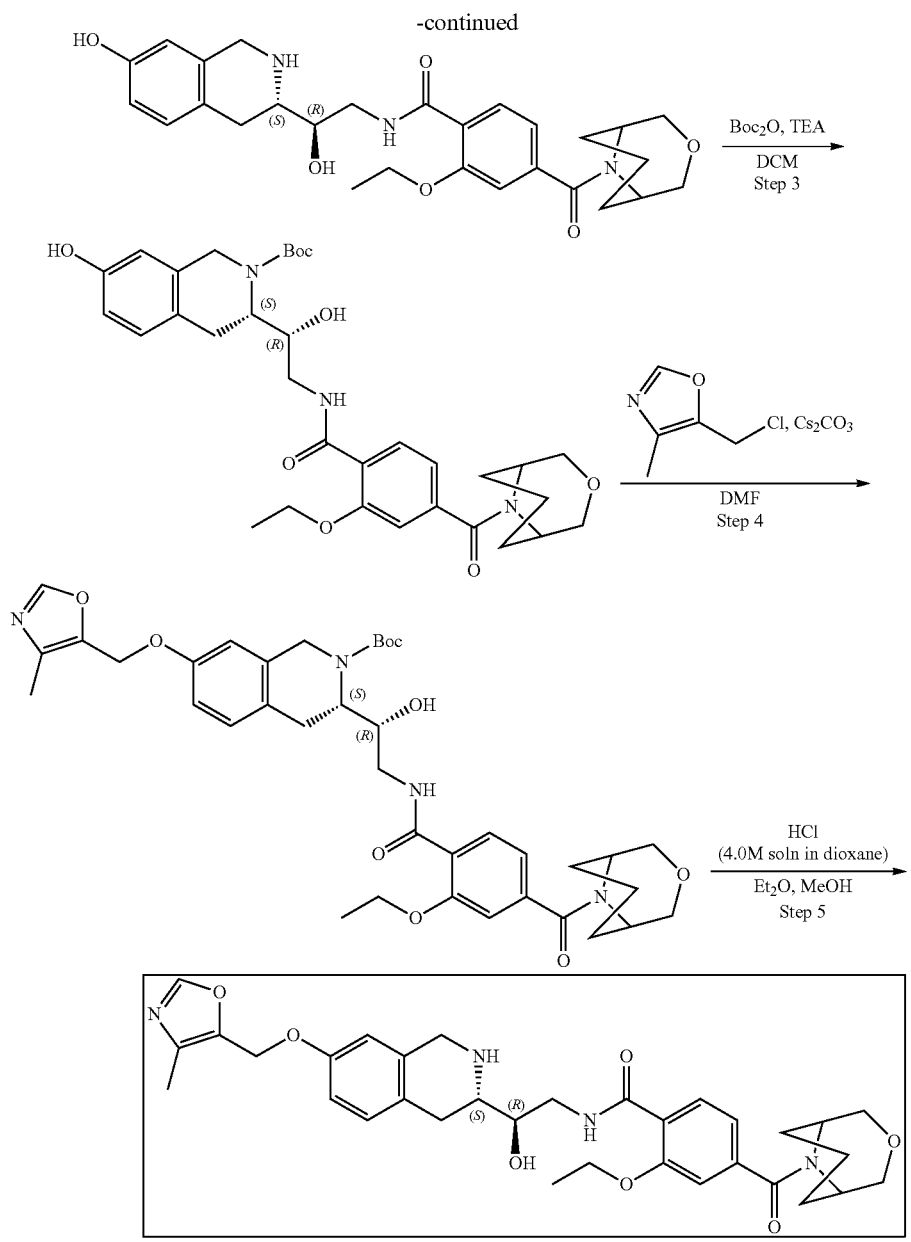

Steps 1-3 are described in example 1A1

Step 4: Synthesis of (S)-tert-butyl 3-((R)-2-(4-((1R,5S)-3-oxa-9-azabicyclo[3.3.1]nonane-9-carbonyl)-2-ethoxybenzamido)-1-hydroxyethyl)-7-((4-methyloxazol-5-yl)methoxy)-3,4-dihydroisoquinoline-2(1H)-carboxylate tert-Butyl (3S)-3-[(1R)-2-[[2-ethoxy-4-(3-oxa-9-azabicyclo[3.3.1]nonane-9-carbonyl)benzoyl]amino]-1-hydroxyethyl]-7-hydroxy-3,4-dihydro-1H-isoquinoline-2-carboxylate (0.1 g, 164.01 µmol), 5-(chloromethyl)-4-methyl-oxazole (35.82 mg, 213.22 µmol, HCl) and cesium carbonate (160.32 mg, 492.04 µmol) were mixed together in DMF (3 mL). The resulting mixture was stirred at 50° C. overnight. After LCMS showed no starting material, the reaction mixture was diluted with water and extracted three times with EtOAc, then EtOAc layer was extracted three times with brine. The organic phase was dried over $Na_2SO_4$, filtered off and evaporated at 40° C. to give tert-butyl (3S)-3-[(1R)-2-[[2-ethoxy-4-(3-oxa-9-azabicyclo[3.3.1] nonane-9-carbonyl)benzoyl]amino]-1-hydroxy-ethyl]-7-[(4-methyloxazol-5-yl)-methoxy]-3,4-dihydro-1H-isoquinoline-2-carboxylate (0.1 g, 141.88 µmol, 86.51% yield) which was used in the next step without further purification. $^1$H NMR (500 MHz, DMSO-$d_6$) δ (ppm) 1.38 (m, 5H), 1.59 (m, 1H), 1.71 (m, 2H), 1.87 (m, 2H), 2.14 (s, 3H), 2.86 (m, 4H), 3.49 (m, 3H), 3.72 (m, 4H), 3.94 (m, 1H), 4.20 (m, 4H), 4.37 (m, 1H), 4.79 (m, 1H), 5.08 (m, 3H), 6.82 (s, 1H), 6.84 (s, 1H), 7.02 (d, 1H), 7.10 (m, 2H), 7.91 (m, 1H), 8.34 (m, 1H). LCMS (ESI): [M+H]$^+$ m/z: calc'd 704.8; found 705.4; Rt=1.46 min Step 5: Synthesis of 4-((1R,5S)-3-oxa-9-azabicyclo[3.3.1]nonane-9-carbonyl)-2-ethoxy-N—((R)-2-hydroxy-2-((S)-7-((4-methyloxazol-5-yl)methoxy)-1,2,3,4-tetrahydroisoquinolin-3-yl)ethyl)benzamide (Compound 10) Hydrogen chloride solution 4.0M in dioxane (387.99 mg, 10.64 mmol, 484.99 µL) was added to the solution of tert-butyl (3S)-3-[(1R)-2-[[2-ethoxy-4-(3-oxa-9-azabicyclo[3.3.1]

[3.3.1]nonane-9-carbonyl)benzoyl]amino]-1-hydroxy-ethyl]-7-[(4-methyloxazol-5-yl)methoxy]-3,4-dihydro-1H-isoquinoline-2-carboxylate (0.1 g, 141.88 μmol) in the mixture of Et$_2$O (1 mL) and MeOH (0.5 mL). The resulting mixture was stirred for 24 h at 20° C. The formed solid was filtered on, washed with Et$_2$O (1 mL) and dried in vacuo at 35° C. to give crude product which was purified by HPLC (20-40% water-acetonitrile+NH$_3$, 2-10 min, flow: 30 mL/min (loading pump 4 mL/min acetonitrile), column: SunFire C18 100*20 mm to give 2-ethoxy-N-[(2R)-2-hydroxy-2-[(3S)-7-[(4-methyloxazol-5-yl)methoxy]-1,2,3,4-tetrahydroisoquinolin-3-yl]ethyl]-4-(3-oxa-9-azabicyclo[3.3.1]nonane-9-carbonyl)benzamide (33.60 mg, 55.57 μmol, 39.16% yield). $^1$H NMR (Chloroform-d, 400 MHz): δ (ppm) 1.52 (t, 3H), 1.68 (m, 2H), 1.78 (m, 2H), 1.97 (m, 3H), 2.20 (s, 3H), 2.53 (m, 1H), 2.78 (m, 2H), 2.98 (m, 1H), 3.58 (m, 2H), 3.71 (d, 1H), 3.83 (m, 4H), 3.99 (m, 3H), 4.22 (q, 2H), 4.58 (m, 1H), 4.95 (s, 2H), 6.61 (d, 1H), 6.77 (dd, 1H), 7.03 (m, 3H), 7.79 (s, 1H), 8.20 (d, 1H), 8.44 (t, 1H). LCMS (ESI): [M+H]+ m/z: calc'd 604.7; found 605.4; Rt=0.98 min.

Example 1A3. Synthesis of 4-((1R,5S)-3-oxa-9-azabicyclo[3.3.1]nonane-9-carbonyl)-2-ethoxy-N—((R)-2-hydroxy-2-((S)-7-((1-methyl-1H-pyrazol-5-yl)methoxy)-1,2,3,4-tetrahydroisoquinolin-3-yl)ethyl)benzamide (Compound 6)

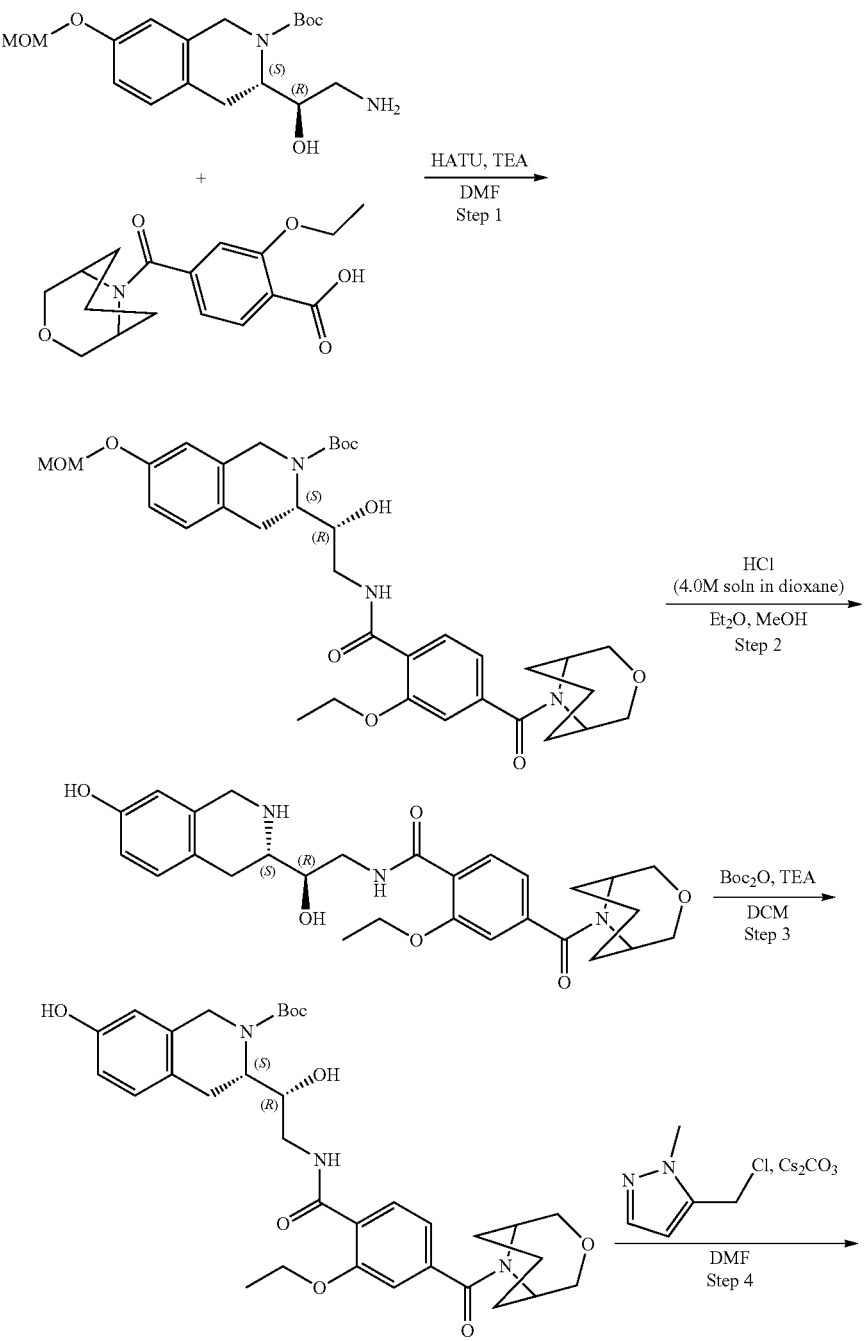

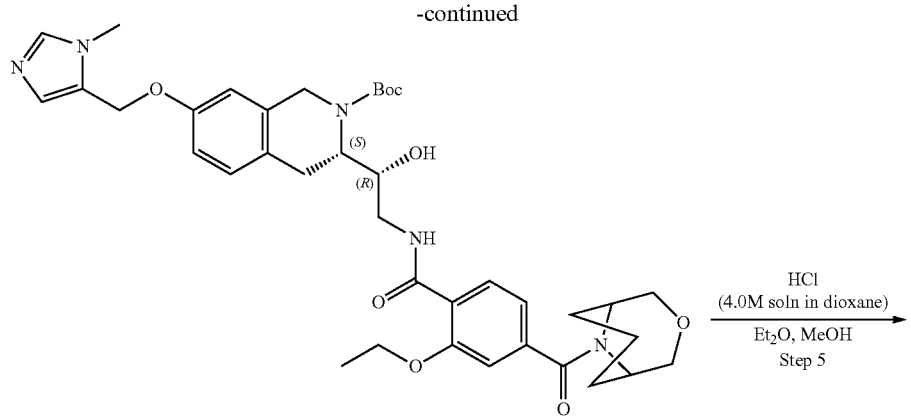

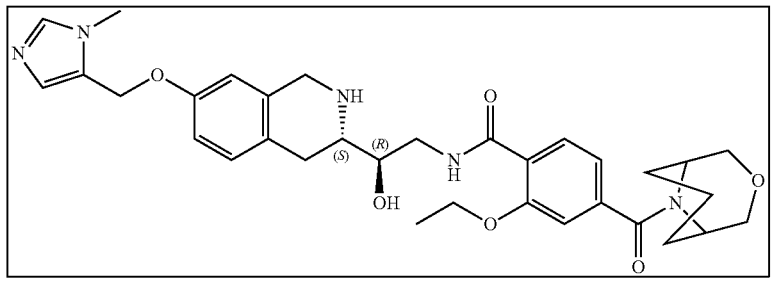

Steps 1-3 are described in Example 1A1.

Step 4: Synthesis of (S)-tert-butyl 3-((R)-2-(4-((1R,5R)-3-oxa-9-azabicyclo[3.3.1]nonane-9-carbonyl)-2-ethoxybenzamido)-1-hydroxyethyl)-7-((1-methyl-1H-pyrazol-5-yl)methoxy)-3,4-dihydroisoquinoline-2(1H)-carboxylate Cesium carbonate (48.09 mg, 147.61 µmol) was added in one portion to the mixture of tert-butyl (3S)-3-[(1R)-2-[[2-ethoxy-4-(3-oxa-9-azabicyclo[3.3.1]nonane-9-carbonyl)benzoyl]amino]-1-hydroxy-ethyl]-7-hydroxy-3,4-dihydro-1H-isoquinoline-2-carboxylate (0.03 g, 49.20 µmol) and 5-(chloromethyl)-1-methyl-pyrazole (9.04 mg, 54.12 µmol, HCl) in DMF (2 mL). The resulting mixture was stirred at 50° C. for 24 h. After LCMS showed no starting material, the resulting mixture was diluted with water end extracted three times with EtOAc. The organic phase was washed three times with brine, dried over $Na_2SO_4$, filtered off and concentrated at 40° C. to give tert-butyl (3S)-3-[(1R)-2-[[2-ethoxy-4-(3-oxa-9-azabicyclo[3.3.1]nonane-9-carbonyl)benzoyl]amino]-1-hydroxy-ethyl]-7-[(2-methylpyrazol-3-yl)methoxy]-3,4-dihydro-1H-isoquinoline-2-carboxylate (0.013 g, 18.47 µmol, 37.54% yield) which was used in the next step without further purification. $^1$H NMR (400 MHz, DMSO-$d_6$) δ (ppm) 1.38 (m, 11H), 1.48 (m, 1H), 1.57 (m, 1H), 1.70 (m, 1H), 3.44 (m, 5H), 3.65 (m, 5H), 3.80 (m, 4H), 3.94 (m, 2H), 4.18 (m, 4H), 4.38 (m, 2H), 5.15 (m, 3H), 6.35 (m, 1H), 6.89 (m, 1H), 7.03 (m, 1H), 7.11 (m, 2H), 7.36 (m, 2H), 7.94 (m, 1H), 8.36 (m, 1H). LCMS (ESI): [M+H]$^+$ m/z: calc'd 703.8; found 704.4; Rt=1.35 min.

Step 5: Synthesis of 4-((1R,5S)-3-oxa-9-azabicyclo[3.3.1]nonane-9-carbonyl)-2-ethoxy-N—((R)-2-hydroxy-2-((S)-7-((1-methyl-1H-pyrazol-5-yl)methoxy)-1,2,3,4-tetrahydroisoquinolin-3-yl)ethyl)benzamide (Compound 6)

Hydrogen chloride solution 4.0M in dioxane (310.82 mg, 8.52 mmol, 388.52 µL) was added to the solution of tert-butyl (3S)-3-[(1R)-2-[[2-ethoxy-4-(3-oxa-9-azabicyclo[3.3.1]nonane-9-carbonyl)benzoyl]amino]-1-hydroxy-ethyl]-7-[(2-methylpyrazol-3-yl)methoxy]-3,4-dihydro-1H-isoquino-line-2-carboxylate (0.08 g, 113.67 µmol) in the mixture of $Et_2O$ (2 mL) and MeOH (1 mL). The resulting mixture was stirred for 24 h at 25° C. The formed solid was filtered on, washed with $Et_2O$ (2 mL) and dried in vacuo at 35° C. to give crude product which was purified by HPLC (30-40% water-acetonitrile, 10 min, flow: 30 mL/min (loading pump 4 mL/min acetonitrile) column: SunFire C18 100*19 mm) to give 2-ethoxy-N-[(2R)-2-hydroxy-2-[(3S)-7-[(2-methylpyrazol-3-yl)methoxy]-1,2,3,4-tetrahydroisoquinolin-3-yl]ethyl]-4-(3-oxa-9-azabicyclo[3.3.1]-nonane-9-carbonyl)benzamide (0.01 g, 14.78 µmol, 13.00% yield, 2HCl). $^1$H NMR (DMSO-$d_6$, 500 MHz): δ (ppm) 1.44 (t, 3H), 1.64 (m, 1H), 1.76 (m, 2H), 1.93 (m, 2H), 3.11 (m, 1H), 3.42 (m, 2H), 3.53 (m, 1H), 3.69 (m, 2H), 3.78 (m, 2H), 3.85 (s, 3H), 3.94 (m, 1H), 4.24 (m, 5H), 4.41 (s, 1H), 5.09 (s, 2H), 5.87 (m, 1H), 6.30 (m, 1H), 6.89 (m, 2H), 6.97 (d, 1H), 7.04 (s, 1H), 7.13 (m, 1H), 7.26 (m, 1H), 7.88 (d, 1H), 8.40 (s, 1H), 9.24 (s, 1H), 10.25 (s, 1H) LCMS (ESI): [M+H]$^+$ m/z: calc'd 603.3; found 604.4; Rt=1.02 min.

Example 1A4. Synthesis of 4-((1R,5S)-3-oxa-9-azabicyclo[3.3.1]nonane-9-carbonyl)-N—((R)-2-hydroxy-2-((S)-7-(oxazol-5-ylmethoxy)-1,2,3,4-tetrahydroisoquinolin-3-yl)ethyl)benzamide (Compound 7)
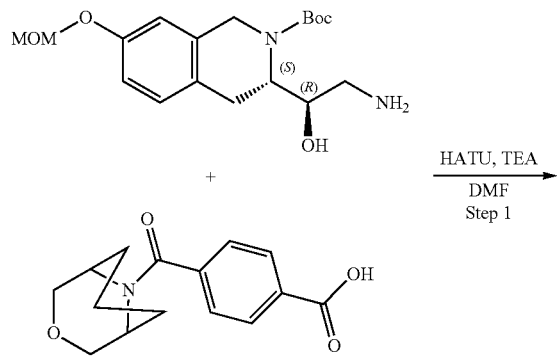
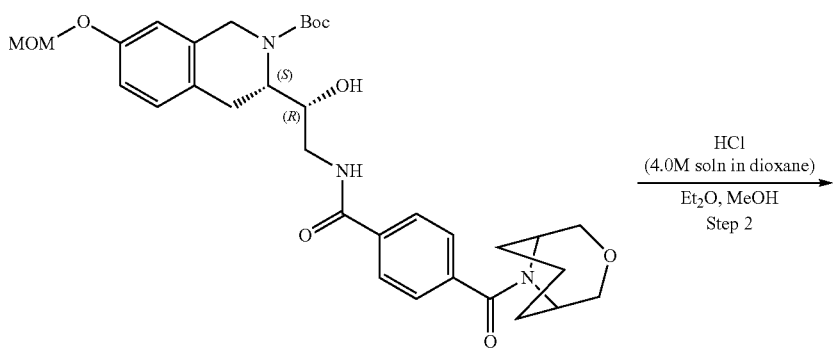
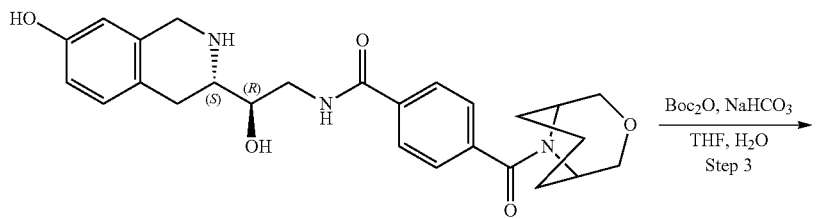
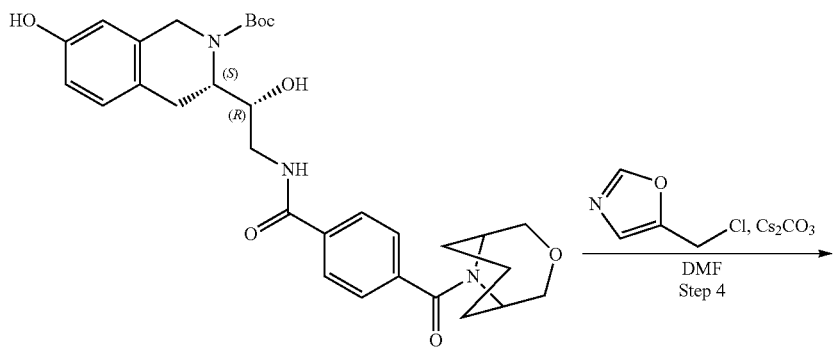

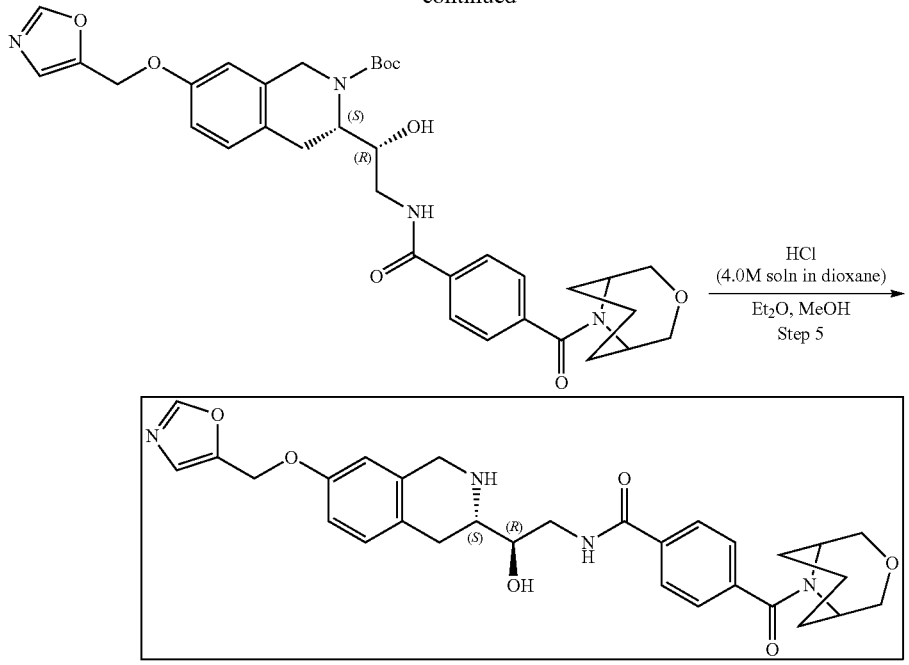

Step 1: Synthesis of (S)-tert-butyl 3-((R)-2-(4-((1R,5S)-3-oxa-9-azabicyclo[3.3.1]nonane-9-carbonyl)benzamido)-1-hydroxyethyl)-7-(methoxymethoxy)-3,4-dihydroisoquinoline-2(1H)-carboxylate. HATU (218.48 mg, 574.59 µmol, 131.87 µL) was added to the cooled to 0° C. solution of 4-(3-oxa-9-azabicyclo[3.3.1]nonane-9-carbonyl)benzoic acid (105.46 mg, 383.06 µmol) and TEA (387.62 mg, 3.83 mmol, 533.91 µL) in DMF (2 mL). The resulting mixture was stirred for 15 min at 0° C. followed by the addition of tert-butyl (3S)-3-[(1R)-2-amino-1-hydroxy-ethyl]-7-(methoxymethoxy)-3,4-dihydro-1H-isoquinoline-2-carboxylate (0.135 g, 383.06 µmol). The reaction mixture was warmed to r.t. and stirred overnight at room temperature. After LCMS showed full conversion of the starting material, 10 mL of ethyl acetate was added, and the organic solution was washed with brine three times. Then, the organic phase was dried over $Na_2SO_4$, filtered off and concentrated in vacuo at 45° C. to give crude product. The obtained residue was purified by HPLC (40-55% water-acetonitrile, 10 min, flow: 40 mL/min (loading pump 5 mL/min acetonitrile) column: SunFire C18 100*19 mm) to give tert-butyl (3S)-7-tert-butoxycarbonyloxy-3-[(1R)-2-[[2-ethoxy-4-(3-oxa-9-azabicyclo[3.3.1]nonane-9-carbonyl)benzoyl]amino]-1-hydroxy-ethyl]-3,4-dihydro-1H-isoquinoline-2-carboxylate (0.099 g, 162.37 µmol, 42.39% yield). $^1$H NMR (400 MHz, DMSO-$d_6$) δ (ppm) 1.40 (s, 9H), 1.57 (m, 1H), 1.70 (m, 1H), 1.86 (m, 2H), 2.07 (s, 4H), 2.42 (m, 1H), 2.75 (m, 1H), 3.36 (m, 2H), 3.41 (m, 2H), 3.49 (m, 2H), 3.68 (m, 3H), 3.92 (m, 1H), 4.25 (m, 1H), 4.38 (m, 1H), 4.78 (t, 1H), 5.15 (s, 3H), 6.82 (d, 1H), 6.83 (s, 1H), 7.08 (d, 1H), 7.46 (m, 2H), 7.88 (m, 2H), 8.43 (m, 1H). LCMS (ESI): [M-Boc]$^+$ m/z: calc'd 509.7; found 510.1; Rt=1.41 min.

Step 2: Synthesis of 4-((1R,5S)-3-oxa-9-azabicyclo[3.3.1]nonane-9-carbonyl)-N—((R)-2-hydroxy-2-((S)-7-hydroxy-1,2,3,4-tetrahydroisoquinolin-3-yl)ethyl)benzamide. Hydrogen chloride solution 4.0M in dioxane (444.01 mg, 12.18 mmol, 555.01 µL) was added to the solution of tert-butyl (3S)-3-[(1R)-1-hydroxy-2-[[4-(3-oxa-9-azabicyclo[3.3.1]nonane-9-carbonyl)benzoyl]amino]ethyl]-7-(methoxymethoxy)-3,4-dihydro-1H-isoquinoline-2-carboxylate (0.099 g, 162.37 µmol) in the mixture of $Et_2O$ (1 mL) and MeOH (0.5 mL). The resulting mixture was stirred for 24 h at 25° C. The formed solid was filtered on, washed with $Et_2O$ (1 mL) and dried in vacuo at 35° C. to give N-[(2R)-2-hydroxy-2-[(3S)-7-hydroxy-1,2,3,4-tetrahydroisoquinolin-3-yl]ethyl]-4-(3-oxa-9-azabicyclo[3.3.1]-nonane-9-carbonyl)benzamide (0.063 g, 125.50 µmol, 77.29% yield, HCl) which was used in the next step without further purification. $^1$H NMR (500 MHz, CDCl$_3$) δ (ppm) 1.70 (m, 1H), 1.83 (m, 2H), 2.00 (m, 2H), 3.13 (m, 1H), 3.57 (m, 5H), 3.78 (m, 1H), 3.86 (m, 3H), 4.02 (m, 1H), 4.24 (m, 2H), 4.39 (m, 1H), 4.53 (m, 1H), 6.62 (s, 1H), 6.75 (d, 1H), 7.11 (s, 1H), 7.54 (m, 2H), 7.96 (m, 2H), OH and NH are not observed. LCMS (ESI): [M+H]$^+$ m/z: calc'd 465.2; found 466.2; Rt=0.92 min.

Step 3: Synthesis of (S)-tert-butyl 3-((R)-2-(4-((1R,5S)-3-oxa-9-azabicyclo[3.3.1]nonane-9-carbonyl)benzamido)-1-hydroxyethyl)-7-hydroxy-3,4-dihydroisoquinoline-2(1H)-carboxylate. Sodium hydrogen carbonate, 99% (31.63 mg, 376.49 µmol, 14.64 µL) was added in one portion to the solution of N-[(2R)-2-hydroxy-2-[(3S)-7-hydroxy-1,2,3,4-tetrahydroisoquinolin-3-yl]ethyl]-4-(3-oxa-9-azabicyclo[3.3.1]nonane-9-carbonyl)benzamide (0.063 g, 125.50 µmol, HCl) in water (7 mL). The resulting mixture was stirred for 5 min followed by the dropwise addition of the solution of di-tert-butyl dicarbonate (30.13 mg, 138.05 µmol, 31.68 µL). The reaction mixture was stirred overnight at room temperature. After the completion of the reaction, monitored by LCMS, ethyl acetate (15 mL) was added to the reaction mixture. The organic phase was separated, and the aqueous phase was extracted with ethyl acetate (2*15 mL). The organic phase was washed with brine, dried over $Na_2SO_4$, filtered off and evaporated in vacuo at 40° C. to give tert-butyl (3S)-7-hydroxy-3-[(1R)-1-hydroxy-2-[[4-(3-oxa-9-azabicyclo[3.3.1]nonane-9-carbonyl)-benzoyl]amino]ethyl]-3,4-dihydro-1H-isoquinoline-2-carboxylate (0.065 g, 114.91 μmol, 91.56% yield) which was used in the next step without further purification. $^1$H NMR (500 MHz, DMSO-$d_6$) δ (ppm) 1.35 (m 9H), 1.43 (m, 1H), 1.59 (m, 2H), 1.87 (m, 2H), 2.38 (m, 1H), 2.70 (m, 1H), 2.99 (m, 1H), 3.12 (m, 1H), 3.41 (m, 3H), 3.69 (m, 3H), 3.94 (m, 1H), 4.19 (m, 2H), 4.38 (d, 1H), 4.68 (m, 1H), 5.05 (m, 1H), 6.56 (m, 2H), 6.94 (d, 1H), 7.45 (m, 2H), 7.88 (m, 2H), 8.39 (m, 1H), 9.16 (s, 1H). LCMS (ESI): [M+H]+ m/z: calc'd 465.7; found 466.4; Rt=1.30 min.

Step 4: Synthesis of (S)-tert-butyl 3-((R)-2-(4-((1R,5S)-3-oxa-9-azabicyclo[3.3.1]nonane-9-carbonyl)benzamido)-1-hydroxyethyl)-7-(oxazol-5-ylmethoxy)-3,4-dihydroisoquinoline-2(1H)-carboxylate tert-Butyl (3S)-7-hydroxy-3-[(1R)-1-hydroxy-2-[[4-(3-oxa-9-azabicyclo[3.3.1]nonane-9-carbonyl)-benzoyl]amino]ethyl]-3,4-dihydro-1H-isoquinoline-2-carboxylate (0.1 g, 176.79 μmol), 5-(chloromethyl)oxazole (27.01 mg, 229.82 μmol, HCl) and cesium carbonate (172.80 mg, 530.36 μmol) were dissolved in DMF (2 mL) and stirred at 50° C. overnight. After LCMS showed no starting material, the reaction mixture was diluted with water end extracted three times with EtOAc. The organic phase was washed with brine, dried over Na$_2$SO$_4$, filtered off and concentrated at 40° C. to give tert-butyl (3S)-3-[(1R)-1-hydroxy-2-[[4-(3-oxa-9-azabicyclo[3.3.1]nonane-9-carbonyl)benzoyl]amino]ethyl]-7-(oxazol-5-ylmethoxy)-3,4-dihydro-1H-isoquinoline-2-carboxylate (0.08 g, 123.70 μmol, 69.97% yield) which was used in the next step without further purification. $^1$H NMR (400 MHz, DMSO-$d_6$) δ (ppm) 1.42 (m, 9H), 1.56 (m, 1H), 1.71 (m, 2H), 1.86 (m, 2H), 2.77 (m, 1H), 3.05 (m, 2H), 3.47 (m, 2H), 3.72 (m, 3H), 3.79 (m, 4H), 4.38 (m, 1H), 4.68 (m, 2H), 5.13 (s, 2H), 6.85 (d, 1H), 6.87 (s, 1H), 7.07 (d, 1H), 7.32 (s, 1H), 7.47 (m, 2H), 7.87 (m, 2H), 8.42 (s, 1H). LCMS (ESI): [M-Boc]+ m/z: calc'd 546.3; found 547.2; Rt=1.25 min.

Step 5: Synthesis of 4-((1R,5S)-3-oxa-9-azabicyclo[3.3.1]nonane-9-carbonyl)-N—((R)-2-hydroxy-2-((S)-7-(oxazol-5-ylmethoxy)-1,2,3,4-tetrahydroisoquinolin-3-yl)ethyl)benzamide (Compound 7). Hydrogen chloride solution 4.0M in dioxane (338.26 mg, 9.28 mmol, 422.83 μL) was added to the solution of tert-butyl (3S)-3-[(1R)-1-hydroxy-2-[[4-(3-oxa-9-azabicyclo[3.3.1]nonane-9-carbonyl)benzoyl]-amino]ethyl]-7-(oxazol-5-ylmethoxy)-3,4-dihydro-1H-isoquinoline-2-carboxylate (0.08 g, 123.70 μmol) in the mixture of Et$_2$O (2 mL) and MeOH (0.5 mL). The resulting mixture was stirred for 24 h at 20° C. The formed solid was filtered on, washed with Et$_2$O (2 mL) and dried in vacuo at 35° C. to give crude product which was purified by HPLC (15-40% water-acetonitrile+NH$_3$, 10 min, flow: 30 mL/min (loading pump 4 mL/min acetonitrile), column: SunFire C18 100*29 mm to give N-[(2R)-2-hydroxy-2-[(3S)-7-(oxazol-5-ylmethoxy)-1,2,3,4-tetrahydroisoquinolin-3-yl]ethyl]-4-(3-oxa-9-azabicyclo[3.3.1]nonane-9-carbonyl)-benzamide (0.0288 g, 52.69 μmol, 42.59% yield). $^1$H NMR (Chloroform-d, 400 MHz): δ (ppm) 1.71 (m, 2H), 1.77 (m, 2H), 1.90 (m, 1H), 2.04 (m, 1H), 2.53 (m, 1H), 2.73 (m, 1H), 2.80 (m, 1H), 3.04 (m, 1H), 3.54 (m, 2H), 3.72 (m, 1H), 3.85 (m, 4H), 3.99 (m, 3H), 4.59 (m, 1H), 5.02 (s, 2H), 6.61 (s, 1H), 6.78 (dd, 1H), 7.04 (d, 1H), 7.12 (s, 1H), 7.16 (t, 1H), 7.45 (d, 2H), 7.82 (d, 2H), 7.88 (s, 1H). LCMS (ESI): [M+H]+ m/z: calc'd 546.6; found 547.2; Rt=0.99 min.

Example 1A5. Synthesis of 4-((1R,5S)-3-oxa-9-azabicyclo[3.3.1]nonane-9-carbonyl)-N—((R)-2-hydroxy-2-((S)-7-((4-methyloxazol-5-yl)methoxy)-1,2,3,4-tetrahydroisoquinolin-3-yl)ethyl)benzamide (Compound 8)

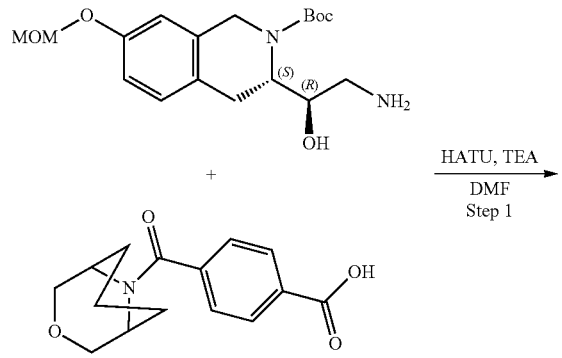

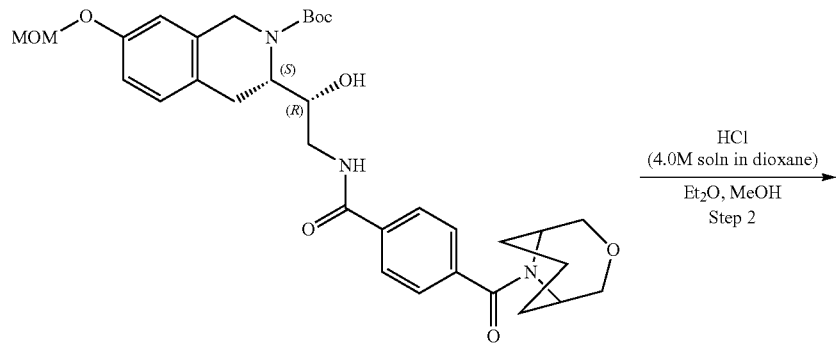

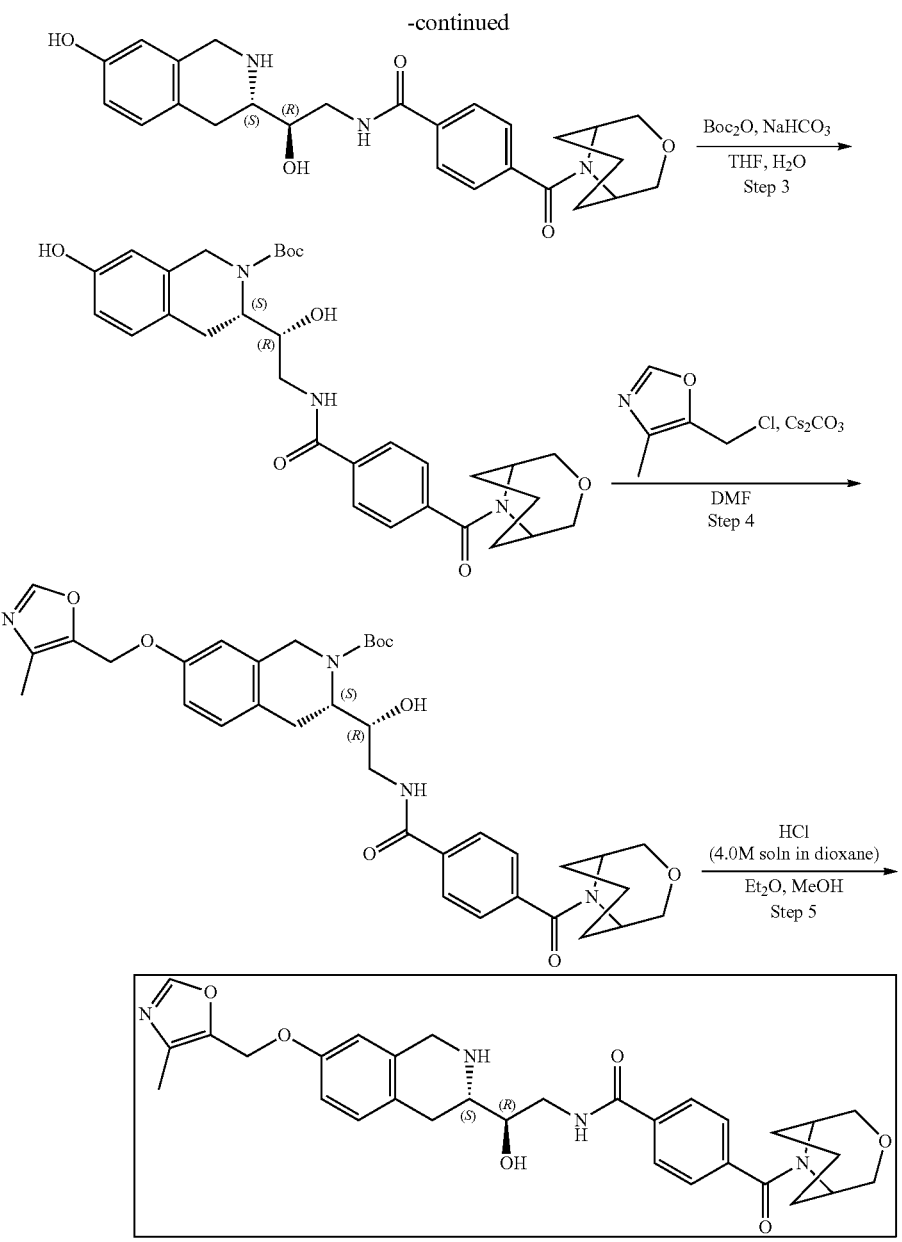

Steps 1-3 are the same as for Example 1A4.

Step 4: Synthesis of (S)-tert-butyl 3-((R)-2-(4-((1R,5S)-3-oxa-9-azabicyclo[3.3.1]nonane-9-carbonyl)benzamido)-1-hydroxyethyl)-7-((4-methyloxazol-5-yl)methoxy)-3,4-dihydroisoquinoline-2(1H)-carboxylate (tert-Butyl (3S)-7-hydroxy-3-[(1R)-1-hydroxy-2-[[4-(3-oxa-9-azabicyclo[3.3.1]nonane-9-carbonyl)-benzoyl]amino]ethyl]-3,4-dihydro-1H-isoquinoline-2-carboxylate (0.1 g, 176.79 μmol), 5-(chloromethyl)-4-methyl-oxazole (30.24 mg, 229.82 μmol, HCl) and cesium carbonate (201.60 mg, 618.75 μmol) were mixed together in DMF (3 mL). The reaction mixture was stirred at 50° C. overnight. The reaction mixture was diluted with water end extracted three times with EtOAc. The organic phase was washed with brine, dried over Na₂SO₄, filtered off and evaporated at 40° C. to give tert-butyl (3S)-3-[(1R)-1-hydroxy-2-[[4-(3-oxa-9-azabicyclo[3.3.1]nonane-9-carbonyl)benzoyl]amino]ethyl]-7-[(4-methyloxazol-5-yl)methoxy]-3,4-dihydro-1H-isoquinoline-2-carboxylate (0.08 g, 121.07 μmol, 68.49% yield) which was used in the next step without further purification. ¹H NMR (500 MHz, DMSO-d₆) δ (ppm) 1.39 (m, 9H), 1.58 (m, 1H), 1.70 (m, 2H), 1.86 (m, 2H), 2.87 (m, 5H), 3.48 (m, 4H), 3.67 (m, 4H), 3.95 (m, 3H), 4.38 (m, 3H), 5.08 (m, 2H), 6.53 (d, 1H), 6.91 (m, 3H), 7.47 (m, 2H), 7.89 (m, 2H), 8.38 (m, 1H). LCMS (ESI): [M-Boc]⁺ m/z: calc'd 560.7; found 561.2; Rt=1.43 min.

Step 5: Synthesis of 4-((1R,5S)-3-oxa-9-azabicyclo[3.3.1]nonane-9-carbonyl)-N—((R)-2-hydroxy-2-((S)-7-((4-methyloxazol-5-yl)methoxy)-1,2,3,4-tetrahydroisoquinolin-3-yl)ethyl)benzamide (Compound 8) Hydrogen chloride solution 4.0M in dioxane (331.08 mg, 9.08 mmol, 413.86 μL) was added to the solution of tert-butyl (3S)-3-[(1R)-1-hydroxy-2-[[4-(3-oxa-9-azabicyclo[3.3.1]nonane-9-carbonyl)benzoyl]-amino]ethyl]-7-[(4-methyloxazol-5-yl)methoxy]-3,4-dihydro-1H-isoquinoline-2-carboxylate (0.08 g, 121.07 μmol) in the mixture of Et₂O (2 mL) and MeOH (0.5 mL). The resulting mixture was stirred for 24 h at 20° C. The formed solid was filtered on, washed with Et₂O (2 mL) and dried in vacuo at 35° C. to give crude product which was purified by HPLC (30-40% water-acetonitrile+NH₃, 10 min, flow: 30 mL/min (loading pump 4 mL/min acetonitrile), column: SunFire C18 100*19 mm to give N-[(2R)-2-hydroxy-2-[(3S)-7-[(4-methyloxazol-5-yl)methoxy]-1,2,3,4-tetrahydroisoquinolin-3-yl]ethyl]-4-(3-oxa-9-azabicyclo[3.3.1]nonane-9-carbonyl)benzamide (0.021 g, 37.46 μmol, 30.94% yield). ¹H NMR (Chloroform-d, 400 MHz): δ (ppm) 1.66 (m, 3H), 1.77 (m, 3H), 1.93 (m, 3H), 2.21 (s, 3H), 2.79 (m, 2H), 3.04 (m, 1H), 3.53 (m, 2H), 3.85 (m, 4H), 4.00 (m, 3H), 4.59 (m, 1H), 4.96 (s, 2H), 6.62 (m, 1H), 6.78 (m, 1H), 7.05 (d, 1H), 7.15 (s, 1H), 7.46 (d, 2H), 7.82 (m, 3H). LCMS (ESI): [M+H]+ m/z: calc'd 560.6; found 561.2; Rt=0.98 min.

Example 1A6. Synthesis of 4-((1R,5S)-3-oxa-9-azabicyclo[3.3.1]nonane-9-carbonyl)-N—((R)-2-hydroxy-2-((S)-7-((1-methyl-1H-pyrazol-5-yl)methoxy)-1,2,3,4-tetrahydroisoquinolin-3-yl)ethyl)benzamide (Compound 9)

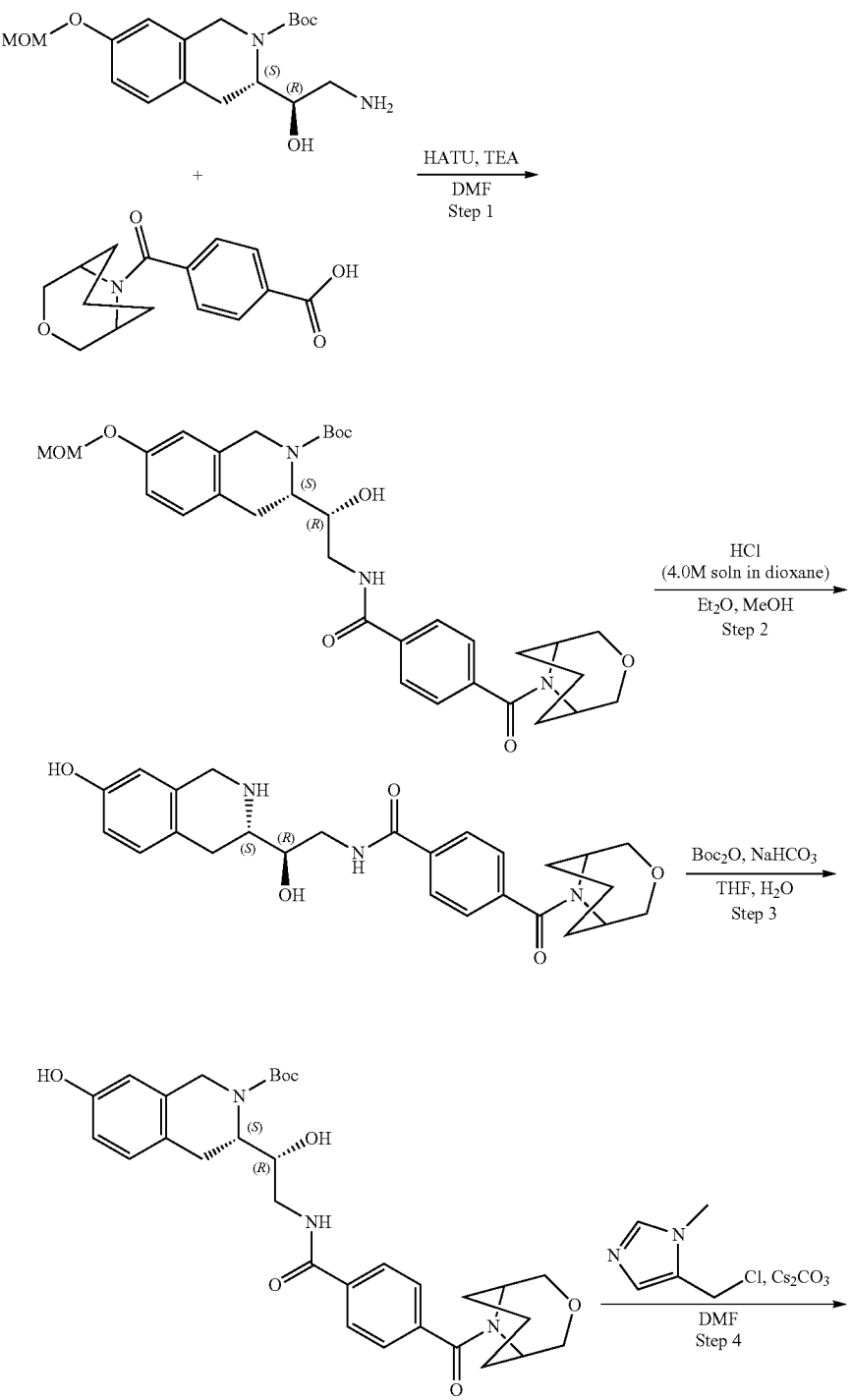

-continued

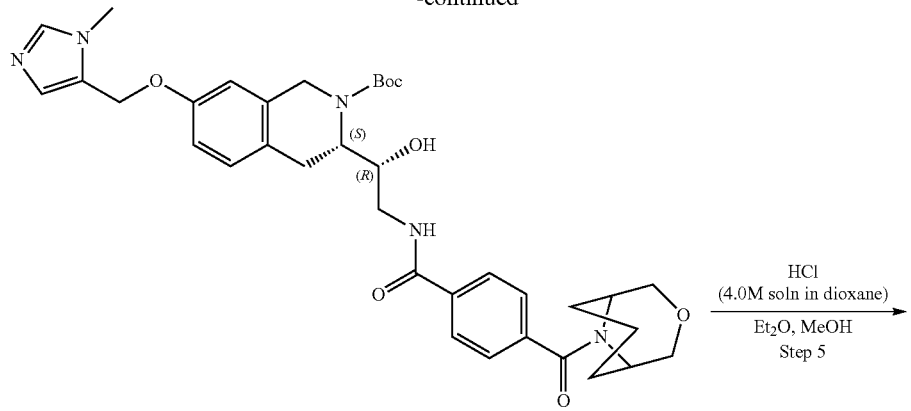

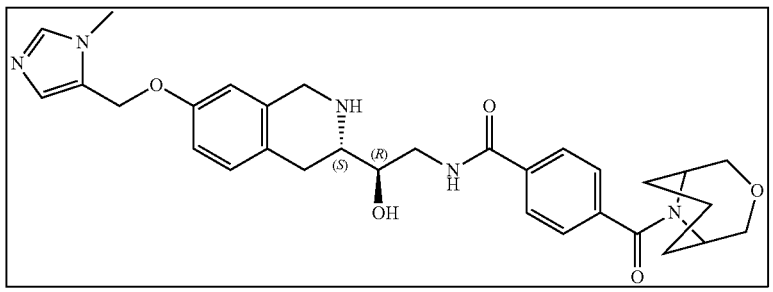

Steps 1-3 are the same as for Example 1A4.

Step 4: Synthesis of (S)-tert-butyl 3-((R)-2-(4-((1R,5S)-3-oxa-9-azabicyclo[3.3.1]nonane-9-carbonyl)benzamido)-1-hydroxyethyl)-7-((1-methyl-1H-pyrazol-5-yl)methoxy)-3,4-dihydroisoquinoline-2(1H)-carboxylate tert-Butyl (3S)-7-hydroxy-3-[(1R)-1-hydroxy-2-[[4-(3-oxa-9-azabicyclo[3.3.1]nonane-9-carbonyl)-benzoyl]amino]ethyl]-3,4-dihydro-1H-isoquinoline-2-carboxylate (0.1 g, 176.79 μmol), 5-(chloromethyl)-1-methyl-pyrazole (38.39 mg, 229.82 μmol, HCl) and cesium carbonate (201.60 mg, 618.75 μmol) were mixed together in DMF (3 mL) and stirred at 50° C. overnight. After LCMS showed no starting material, the reaction mixture was diluted with water end extracted three times with EtOAc. The organic phase was washed three times with brine, dried over Na$_2$SO$_4$, filtered off and evaporated at 40° C. to give tert-butyl (3S)-3-[(1R)-1-hydroxy-2-[[4-(3-oxa-9-azabicyclo[3.3.1]nonane-9-carbonyl)benzoyl]amino]ethyl]-7-[(2-methylpyrazol-3-yl)methoxy]-3,4-dihydro-1H-isoquinoline-2-carboxylate (0.09 g, 136.41 μmol, 77.16% yield) which was used in the next step without further purification. $^1$H NMR (500 MHz, DMSO-d$_6$) δ (ppm) 1.44 (m, 6H), 1.58 (m, 1H), 1.71 (m, 2H), 1.86 (m, 2H), 3.45 (m, 3H), 3.76 (m, 4H), 3.81 (m, 4H), 3.95 (m, 2H), 4.05 (m, 2H), 4.39 (m, 2H), 4.74 (m, 2H), 5.12 (m, 3H), 6.36 (d, 1H), 6.91 (m, 2H), 7.12 (d, 1H), 7.35 (s, 1H), 7.51 (d, 1H), 7.86 (d, 1H), 7.89 (d, 1H), NH and OH are not observed. LCMS (ESI): [M+H]$^+$ m/z: calc'd 659.3; found 660.1; Rt=1.42 min.

Step 5: Synthesis of 4-((1R,5S)-3-oxa-9-azabicyclo[3.3.1]nonane-9-carbonyl)-N—((R)-2-hydroxy-2-((S)-7-((1-methyl-1H-pyrazol-5-yl)methoxy)-1,2,3,4-tetrahydroisoquinolin-3-yl)ethyl)benzamide (Compound 9) Hydrogen chloride solution 4.0M in dioxane (373.03 mg, 10.23 mmol, 466.28 μL) was added to the solution of tert-butyl (3S)-3-[(1R)-1-hydroxy-2-[[4-(3-oxa-9-azabicyclo[3.3.1]nonane-9-carbonyl)-benzoyl]amino]ethyl]-7-[(2-methylpyrazol-3-yl)methoxy]-3,4-dihydro-1H-isoquinoline-2-carboxylate (0.09 g, 136.41 μmol) in the mixture of Et$_2$O (2 mL) and MeOH (0.5 mL). The resulting mixture was stirred for 24 h at 20° C. The formed solid was filtered on, washed with Et$_2$O (2 mL) and dried in vacuo at 35° C. to give crude product which was purified by HPLC (15-40% water-acetonitrile+NH$_3$, 10 min, flow: 30 mL/min (loading pump 4 mL/min acetonitrile), column: SunFire C18 100*20 mm to give N-[(2R)-2-hydroxy-2-[(3S)-7-[(2-methylpyrazol-3-yl)methoxy]-1,2,3,4-tetrahydroisoquinolin-3-yl]ethyl]-4-(3-oxa-9-azabicyclo-[3.3.1]nonane-9-carbonyl)benzamide (0.03 g, 53.60 μmol, 39.30% yield). $^1$H NMR (Chloroform-d, 400 MHz): δ (ppm) 1.68 (m, 1H), 1.78 (m, 3H), 1.98 (m, 3H), 2.59 (m, 2H), 2.78 (m, 2H), 3.04 (m, 1H), 3.54 (m, 2H), 3.70 (m, 1H), 3.85 (m, 7H), 3.99 (m, 3H), 4.58 (s, 1H), 4.98 (s, 2H), 6.27 (d, 1H), 6.61 (m, 1H), 6.78 (d, 1H), 7.04 (d, 1H), 7.18 (m, 1H), 7.44 (m, 3H), 7.82 (d, 2H). LCMS (ESI): [M+H]+ m/z: calc'd 559.6; found 560.2; Rt=0.99 min.

Example 1A7. Synthesis of 4-(3-oxa-8-azabicyclo[3.2.1]octane-8-carbonyl)-2-ethoxy-N—((R)-2-hydroxy-2-((S)-7-(oxazol-5-ylmethoxy)-1,2,3,4-tetrahydroisoquinolin-3-yl)ethyl)benzamide (Compound 11)
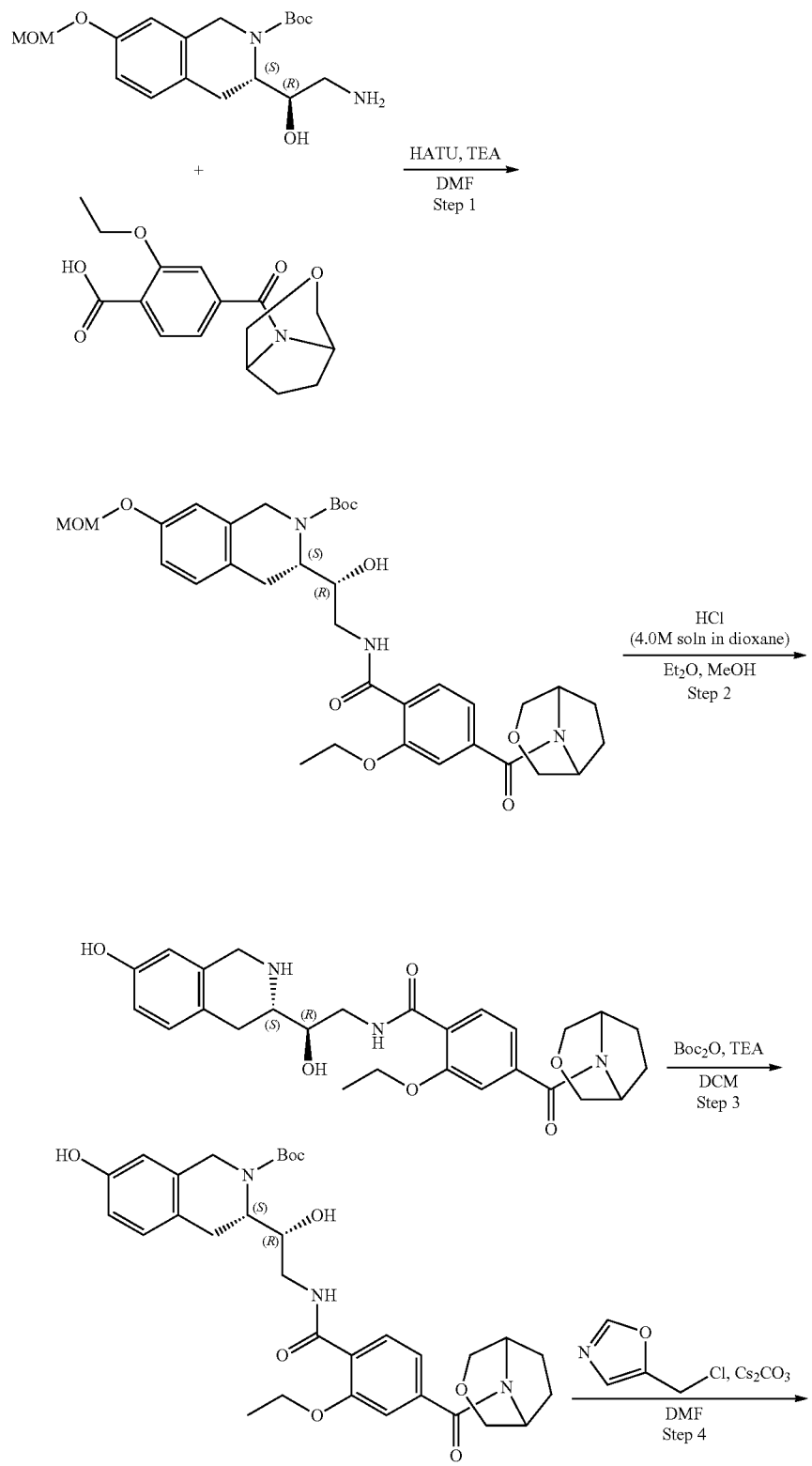

-continued

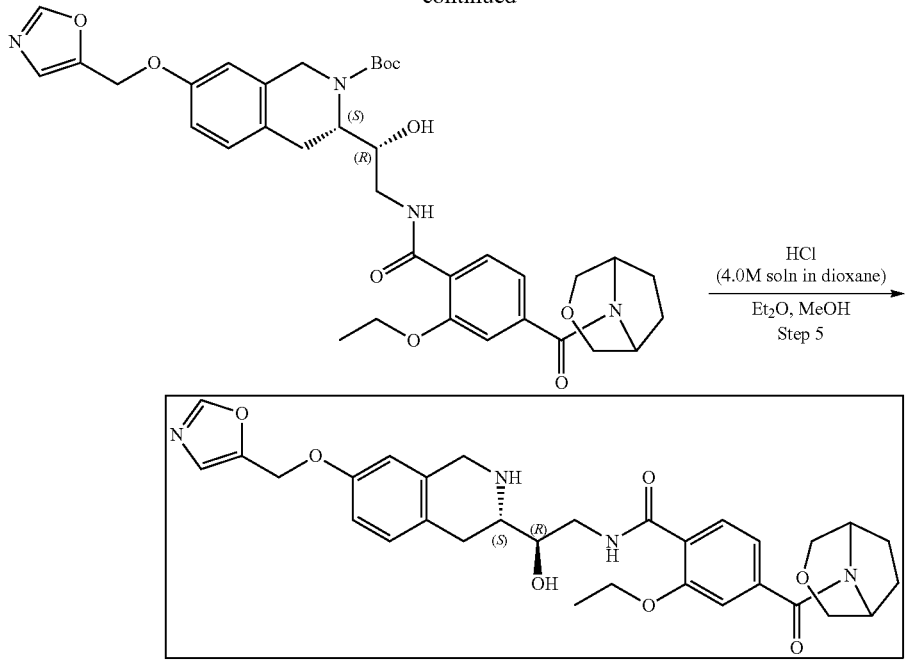

Step 1: Synthesis of (3S)-tert-butyl 3-((1R)-2-(4-(3-oxa-8-azabicyclo[3.2.1]octane-8-carbonyl)-2-ethoxybenzamido)-1-hydroxyethyl)-7-(methoxymethoxy)-3,4-dihydroisoquinoline-2(1H)-carboxylate 2-Ethoxy-4-(3-oxa-8-azabicyclo[3.2.1]octane-8-carbonyl)benzoic acid (86.64 mg, 283.75 μmol) and TEA (287.13 mg, 2.84 mmol, 395.50 μL) were mixed together in DMF (2 mL) and cooled to 0° C. Then, HATU (161.83 mg, 425.62 μmol) was added and the mixture was stirred for 15 min at 0° C. followed by the addition of the tert-butyl (3S)-3-[(1R)-2-amino-1-hydroxyethyl]-7-(methoxymethoxy)-3,4-dihydro-1H-isoquinoline-2-carboxylate (0.1 g, 283.75 μmol). The resulting mixture was allowed to warm to room temperature and stirred overnight. After LCMS showed no starting material, 10 mL of ethyl acetate was added, and the organic phase was washed with brine three times. The organic layer was dried over Na₂SO₄, filtered off and concentrated in vacuo at 45° C. to give tert-butyl (3S)-3-[(1R)-2-[[2-ethoxy-4-(3-oxa-8-azabicyclo[3.2.1]octane-8-carbonyl)benzoyl]amino]-1-hydroxy-ethyl]-7-(methoxymethoxy)-3,4-dihydro-1H-isoquinoline-2-carboxylate (0.144 g, 225.09 μmol, 79.33% yield) which was used in further steps without purification. $^1$H NMR (500 MHz, CDCl₃) δ (ppm) 1.53 (m, 12H), 1.94 (m, 1H), 2.06 (m, 3H), 2.87 (m, 1H), 3.05 (m, 1H), 3.15 (m, 4H), 3.58 (s, 2H), 3.71 (m, 2H), 3.87 (m, 2H), 3.95 (m, 2H), 4.11 (m, 4H), 4.30 (m, 2H), 5.16 (s, 2H), 6.81 (s, 1H), 6.90 (d, 1H), 7.13 (m, 3H), 8.23 (d, 1H), 8.78 (m, 1H). LCMS (ESI): [M+H]⁺ m/z: calc'd 639.7; found 640.4; Rt=1.36 min.

Step 2: Synthesis of 4-(3-oxa-8-azabicyclo[3.2.1]octane-8-carbonyl)-2-ethoxy-N—((R)-2-hydroxy-2-((S)-7-hydroxy-1,2,3,4-tetrahydroisoquinolin-3-yl)ethyl)benzamide Hydrogen chloride solution 4.0M in dioxane (618.30 mg, 16.96 mmol, 772.87 μL) was added to the solution of tert-butyl (3S)-3-[(1R)-2-[[2-ethoxy-4-(3-oxa-8-azabicyclo[3.2.1]octane-8-carbonyl)-benzoyl]amino]-1-hydroxy-ethyl]-7-(methoxymethoxy)-3,4-dihydro-1H-isoquinoline-2-carboxylate (144.65 mg, 226.11 μmol) in the mixture of Et₂O (1 mL) and MeOH (0.5 mL). The reaction mixture was stirred for 24 h at 25° C. The formed solid was filtered on, washed with Et₂O (1 mL) and dried in vacuo at 35° C. to give 2-ethoxy-N-[(2R)-2-hydroxy-2-[(3S)-7-hydroxy-1,2,3,4-tetrahydroisoquinolin-3-yl]ethyl]-4-(3-oxa-8-aza-bicyclo[3.2.1]octane-8-carbonyl)benzamide (0.06 g, 112.78 μmol, 49.88% yield, HCl). $^1$H NMR (400 MHz, MeOD) δ (ppm) 1.40 (q, 3H), 2.01 (m, 4H), 3.10 (m, 3H), 3.62 (m, 6H), 3.79 (m, 2H), 3.94 (m, 1H), 4.30 (m, 5H), 4.62 (m, 1H), 6.60 (s, 1H), 6.72 (d, 1H), 7.06 (d, 1H), 7.13 (d, 1H), 7.20 (s, 1H), 7.95 (d, 1H), NH and OH are not observed. LCMS (ESI): [M+H]⁺ m/z: calc'd 495.2; found 496.2; Rt=0.94 min.

Step 3: Synthesis of (3S)-tert-butyl 3-((1R)-2-(4-(3-oxa-8-azabicyclo[3.2.1]octane-8-carbonyl)-2-ethoxybenzamido)-1-hydroxyethyl)-7-hydroxy-3,4-dihydroisoquinoline-2(1H)-carboxylate Di-tert-butyl dicarbonate (29.52 mg, 135.25 μmol, 31.04 μL) was added dropwise to the mixture of 2-ethoxy-N-[(2R)-2-hydroxy-2-[(3S)-7-hydroxy-1,2,3,4-tetrahydroisoquinolin-3-yl]ethyl]-4-(3-oxa-8-aza-bicyclo[3.2.1]octane-8-carbonyl)benzamide (60.93 mg, 122.96 μmol, HCl) and triethylamine (31.11 mg, 307.39 μmol, 42.84 μL) in DCM (4 mL) and this mixture was stirred overnight at rt. Then, the mixture was extracted with saturated water solution of Na₂CO₃ and 1M aqueous solution of HCl. The organic phase was separated, dried over Na₂SO₄, filtered off and evaporated in vacuo at 35° C. to give tert-butyl (3S)-3-[(1R)-2-[[2-ethoxy-4-(3-oxa-8-azabicyclo[3.2.1]octane-8-carbonyl)benzoyl]amino]-1-hydroxy-ethyl]-7-hydroxy-3,4-dihydro-1H-isoquinoline-2-carboxylate (0.05 g, 83.94 μmol, 68.27% yield) which was used in the next step without further purification. $^1$H NMR (500 MHz, CDCl₃) δ (ppm) 1.52 (m, 12H), 2.02 (m, 4H), 2.87 (m, 1H), 3.08 (m, 2H), 3.58 (m, 5H), 3.71 (m, 2H), 4.09 (m, 1H), 4.17 (m, 2H), 4.37 (m, 3H), 4.60 (d, 1H), 4.72 (s, 1H), 6.57 (s, 1H), 6.67 (d, 1H), 7.01 (d, 1H), 7.09 (d, 1H), 7.14 (s, 1H), 8.19 (d, 1H), 8.77 (s, 1H). LCMS (ESI): [M+H]⁺ m/z: calc'd 595.3; found 596.2; Rt=1.23 min.

Step 4: Synthesis of (3S)-tert-butyl 3-((1R)-2-(4-(3-oxa-8-azabicyclo[3.2.1]octane-8-carbonyl)-2-ethoxybenzamido)-1-hydroxyethyl)-7-(oxazol-5-ylmethoxy)-3,4-dihydroisoquinoline-2(1H)-carboxylate tert-Butyl (3S)-3-[(1R)-2-[[2-ethoxy-4-(3-oxa-8-azabicyclo[3.2.1]octane-8-carbonyl)benzoyl]-amino]-1-hydroxy-ethyl]-7-hydroxy-3,4-dihydro-1H-isoquinoline-2-carboxylate (0.1 g, 167.87 µmol), 5-(chloromethyl)oxazole (31.02 mg, 201.45 µmol, HCl) and cesium carbonate (164.09 mg, 503.62 µmol) were mixed together in DMF (3 mL) and heated at 50° C. overnight. Then, the reaction mixture was diluted with water end extracted three times with EtOAc. The organic phase was washed with brine, dried over Na$_2$SO$_4$, filtered off and evaporated at 40° C. to give tert-butyl (3S)-3-[(1R)-2-[[2-ethoxy-4-(3-oxa-8-azabicyclo-[3.2.1]octane-8-carbonyl)benzoyl]amino]-1-hydroxy-ethyl]-7-(oxazol-5-ylmethoxy)-3,4-dihydro-1H-isoquinoline-2-carboxylate (0.09 g, 132.99 µmol, 79.22% yield) which was used in the next step without further purification. $^1$H NMR (400 MHz, DMSO-d$_6$) δ (ppm) 1.35 (m, 12H), 1.86 (m, 4H), 2.74 (m, 1H), 3.01 (m, 2H), 3.48 (m, 3H), 3.63 (m, 4H), 3.81 (m, 2H), 4.20 (m, 3H), 4.50 (m, 1H), 4.79 (m, 1H), 5.13 (s, 2H), 6.88 (m, 2H), 7.07 (d, 1H), 7.16 (s, 1H), 7.31 (m, 1H), 7.90 (m, 1H), 8.36 (m, 1H). LCMS (ESI): [M+H]$^+$ m/z: calc'd 676.3; found 677.2; Rt=1.38 min.

Step 5: Synthesis of 4-(3-oxa-8-azabicyclo[3.2.1]octane-8-carbonyl)-2-ethoxy-N—((R)-2-hydroxy-2-((S)-7-(oxazol-5-ylmethoxy)-1,2,3,4-tetrahydroisoquinolin-3-yl)ethyl)benzamide (Compound 11) Hydrogen chloride solution 4.0M in dioxane (363.66 mg, 9.97 mmol, 454.58 µL) was added to the solution of tert-butyl (3S)-3-[(1R)-2-[[2-ethoxy-4-(3-oxa-8-azabicyclo[3.2.1]octane-8-carbonyl)-benzoyl]amino]-1-hydroxy-ethyl]-7-(oxazol-5-ylmethoxy)-3,4-dihydro-1H-isoquinoline-2-carboxylate (0.09 g, 132.99 µmol) in the mixture of Et$_2$O (2 mL) and MeOH (1 mL). The resulting mixture was stirred for 24 h at 25° C. The formed solid was filtered on, washed with Et$_2$O (2 mL) and dried in vacuo at 35° C. to give crude product which was purified by HPLC (20-35% water-acetonitrile, 10 min, flow: 30 mL/min (loading pump 4 mL/min acetonitrile), column: SunFire C18 100*20 mm to give 2-ethoxy-N-[(2R)-2-hydroxy-2-[(3S)-7-(oxazol-5-ylmethoxy)-1,2,3,4-tetrahydroisoquinolin-3-yl]ethyl]-4-(3-oxa-8-azabicyclo[3.2.1]octane-8-carbonyl)benzamide (0.0298 g, 45.88 µmol, 34.50% yield, 2HCl). $^1$H NMR (Chloroform-d, 400 MHz): δ (ppm) 1.51 (t, 3H), 1.91 (m, 1H), 2.02 (m, 3H), 2.74 (m, 2H), 2.97 (m, 1H), 3.45 (s, 3H), 3.57 (m, 2H), 3.67 (m, 2H), 3.82 (m, 3H), 3.92 (m, 1H), 3.99 (m, 2H), 4.21 (q, 2H), 4.69 (m, 1H), 5.01 (s, 2H), 6.60 (s, 1H), 6.75 (d, 1H), 7.03 (d, 1H), 7.08 (d, 1H), 7.12 (s, 2H), 7.87 (s, 1H), 8.19 (d, 1H), 8.46 (t, 1H). LCMS (ESI): [M+H]+ m/z: calc'd 576.2; found 574.4; Rt=0.97 min.

Example 1A8. Synthesis of 4-(3-oxa-8-azabicyclo[3.2.1]octane-8-carbonyl)-2-ethoxy-N—((R)-2-hydroxy-2-((S)-7-((1-methyl-1H-pyrazol-5-yl)methoxy)-1,2,3,4-tetrahydroisoquinolin-3-yl)ethyl)benzamide (Compound 5)

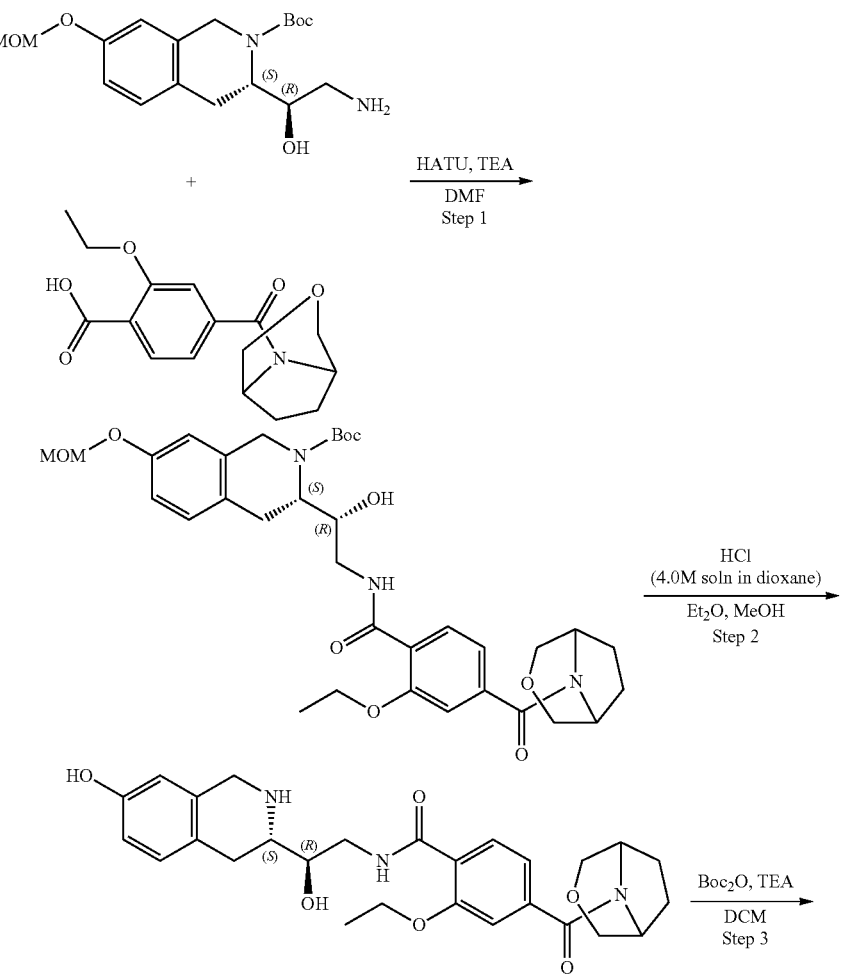

-continued

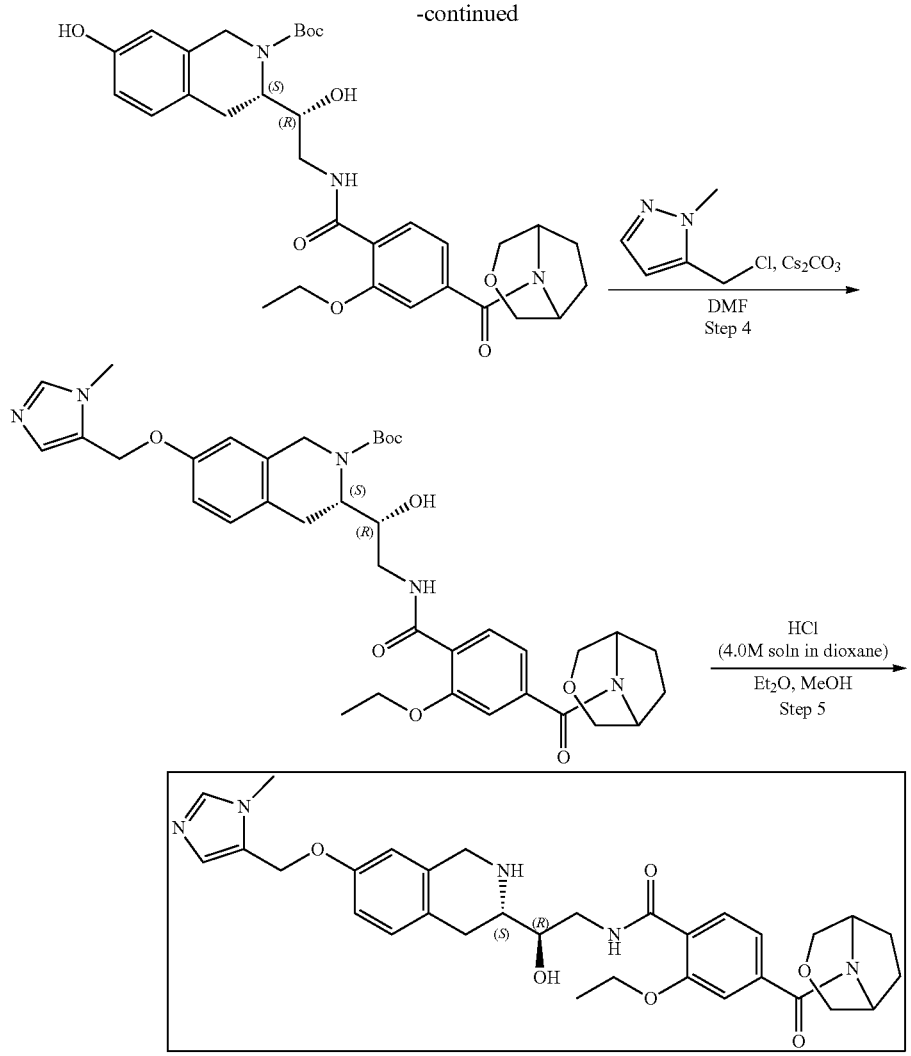

Steps 1-3 are the same as for Example 1A7

Step 4: Synthesis of (3S)-tert-butyl 3-((1R)-2-(4-(3-oxa-8-azabicyclo[3.2.1]octane-8-carbonyl)-2-ethoxybenzamido)-1-hydroxyethyl)-7-((1-methyl-1H-pyrazol-5-yl)methoxy)-3,4-dihydroisoquinoline-2(1H)-carboxylate tert-Butyl (3S)-3-[(1R)-2-[[2-ethoxy-4-(3-oxa-8-azabicyclo[3.2.1]octane-8-carbonyl)benzoyl]-amino]-1-hydroxyethyl]-7-hydroxy-3,4-dihydro-1H-isoquinoline-2-carboxylate (53.99 mg, 90.64 μmol), 5-(chloromethyl)-1-methyl-pyrazole (16.65 mg, 99.70 μmol, HCl) and cesium carbonate (88.60 mg, 271.92 μmol) were mixed together in DMF (10 mL) and stirred at 50° C. overnight. The reaction mixture was diluted with water end extracted three times with EtOAc. The organic phase was washed three times with EtOAc, dried over $Na_2SO_4$, filtered and evaporated at 40° C. to give tert-butyl (3S)-3-[(1R)-2-[[2-ethoxy-4-(3-oxa-8-azabicyclo[3.2.1]octane-8-carbonyl)benzoyl]amino]-1-hydroxy-ethyl]-7-[(2-methylpyrazol-3-yl)-methoxy]-3,4-dihydro-1H-isoquinoline-2-carboxylate (0.035 g, 50.74 μmol, 55.98% yield) which was used in the next step without further purification $^1$H NMR (400 MHz, $CDCl_3$) δ (ppm) 1.24 (q, 3H), 1.48 (m, 2H), 1.54 (s, 9H), 2.02 (m, 5H), 2.85 (m, 3H), 3.11 (m, 4H), 3.54 (m, 4H), 3.67 (m, 2H), 3.89 (m, 3H), 4.71 (m, 2H), 4.99 (s, 2H), 6.28 (s, 1H), 6.69 (d, 1H), 6.82 (d, 1H), 7.14 (m, 2H), 7.42 (d, 1H), 8.17 (m, 1H), 8.77 (m, 1H). LCMS (ESI): $[M+H]^+$ m/z: calc'd 689.3; found 690.4; Rt=1.40 min.

Step 5: Synthesis of 4-(3-oxa-8-azabicyclo[3.2.1]octane-8-carbonyl)-2-ethoxy-N—((R)-2-hydroxy-2-((S)-7-((1-methyl-1H-pyrazol-5-yl)methoxy)-1,2,3,4-tetrahydroisoquinolin-3-yl)ethyl)benzamide (Compound 5) Hydrogen chloride solution 4.0M in dioxane (158.57 mg, 4.35 mmol, 198.21 μL) was added to the solution of tert-butyl (3S)-3-[(1R)-2-[[2-ethoxy-4-(3-oxa-8-azabicyclo[3.2.1]octane-8-carbonyl)benzoyl]-amino]-1-hydroxy-ethyl]-7-[(2-methylpyrazol-3-yl)methoxy]-3,4-dihydro-1H-isoquinoline-2-carboxylate (0.04 g, 57.99 μmol) in the mixture of $Et_2O$ (1 mL) and methanol (0.5 mL). The resulting mixture was stirred for 24 h at 25° C. The formed solid was filtered on, washed with $Et_2O$ (1 mL) and dried in vacuo at 35° C. to give crude product which was purification by HPLC (55-70% water-acetonitrile, 2-10 min, flow: 30 mL/min (loading pump 4 mL/min acetonitrile) column: SunFire C18 100*19 mm) to give 2-ethoxy-N-[(2R)-2-hydroxy-2-[(3S)-7-[(2-methylpyrazol-3-yl)methoxy]-1,2,3,4-tetrahydroisoquinolin-3-yl]ethyl]-4-(3-oxa-8-azabicyclo[3.2.1]octane-8-carbonyl)benzamide (0.0169 g, 25.51 μmol, 43.98% yield, 2HCl). $^1$H NMR (DMSO-$d_6$, 400 MHz): δ (ppm) 1.28 (t, 3H), 1.85

(m, 4H), 2.35 (m, 2H), 2.63 (m, 1H), 3.16 (s, 2H), 3.61 (m, 5H), 3.80 (s, 3H), 4.20 (m, 5H), 5.14 (s, 2H), 5.92 (s, 1H), 6.38 (s, 1H), 6.96 (m, 2H), 7.08 (d, 1H), 7.16 (m, 2H), 7.36 (s, 1H), 7.76 (d, 1H), 8.41 (m, 1H), 9.00 (m, 1H), 9.65 (m, 1H). LCMS (ESI): [M+H]+ m/z: calc'd 589.3; found 590.4; Rt=0.92 min.
Example 1A9 Synthesis of 4-(3-oxa-8-azabicyclo [3.2.1]octane-8-carbonyl)-2-ethoxy-N—((R)-2-hydroxy-2-((S)-7-((4-methyloxazol-5-yl)methoxy)-1,2,3,4-tetrahydroisoquinolin-3-yl)ethyl)benzamide (Compound 12)
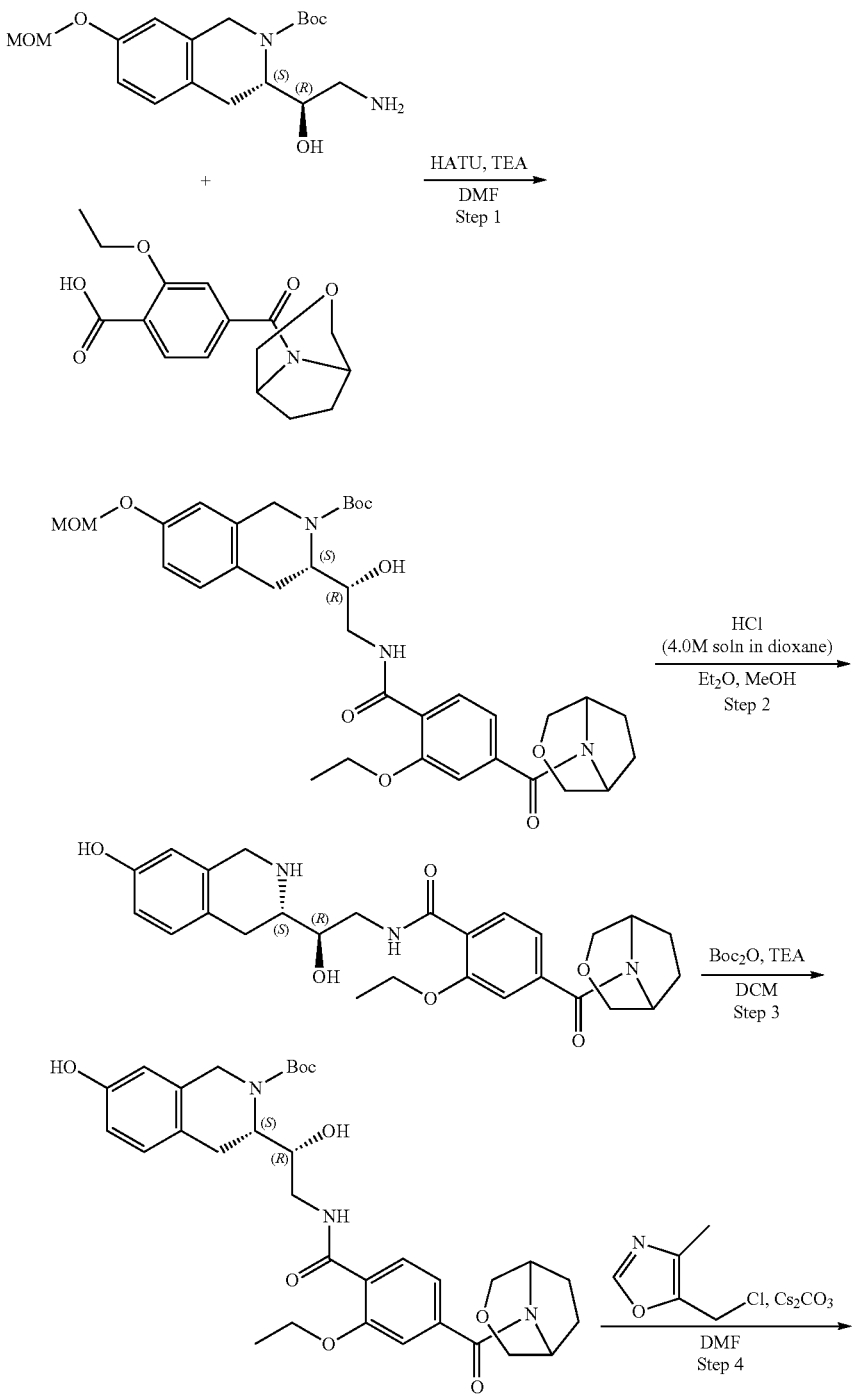

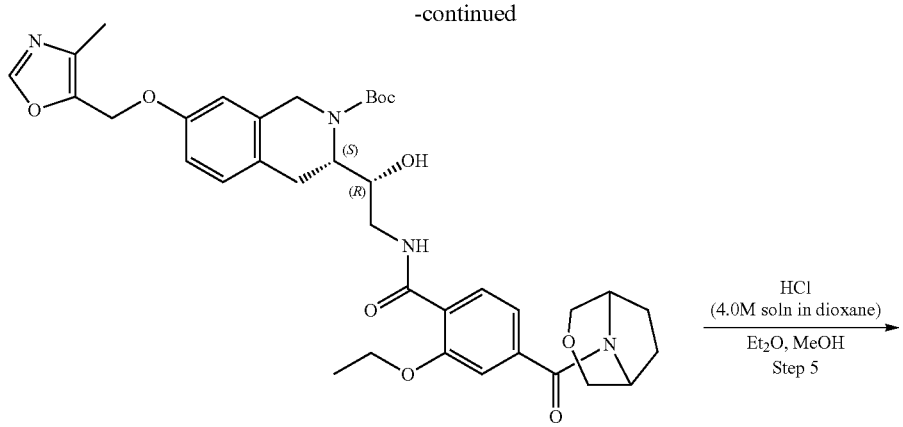

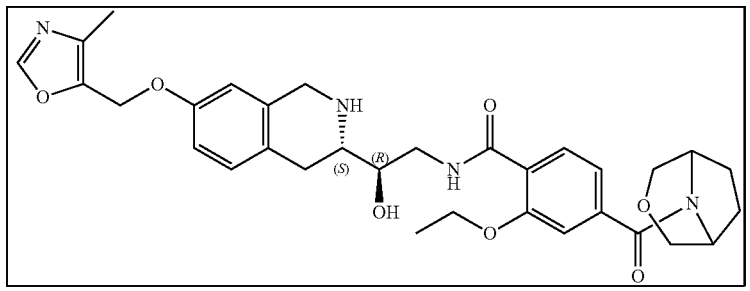

Steps 1-3 are the same as for Example 1A7.

Step 4: Synthesis of (3S)-tert-butyl 3-((1R)-2-(4-(3-oxa-8-azabicyclo[3.2.1]octane-8-carbonyl)-2-ethoxybenzamido)-1-hydroxyethyl)-7-((4-methyloxazol-5-yl)methoxy)-3,4-dihydroisoquinoline-2(1H)-carboxylate tert-Butyl (3S)-3-[(1R)-2-[[2-ethoxy-4-(3-oxa-8-azabicyclo[3.2.1]octane-8-carbonyl)benzoyl]-amino]-1-hydroxyethyl]-7-hydroxy-3,4-dihydro-1H-isoquinoline-2-carboxylate (0.07 g, 117.51 μmol), 5-(chloromethyl)-4-methyl-oxazole (21.72 mg, 129.26 μmol, HCl) and cesium carbonate (114.86 mg, 352.54 μmol) were mixed together in DMF (2 mL) and stirred at 50° C. overnight. Then, the reaction mixture was diluted with water end extracted three times with EtOAc. The organic phase was washed three times with EtOAc and dried over Na$_2$SO$_4$, filtered off and evaporated at 40° C. to give tert-butyl (3S)-3-[(1R)-2-[[2-ethoxy-4-(3-oxa-8-azabicyclo[3.2.1]octane-8-carbonyl)benzoyl]amino]-1-hydroxy-ethyl]-7-[(4-methyl-oxazol-5-yl)methoxy]-3,4-dihydro-1H-isoquinoline-2-carboxylate (0.07 g, 101.33 μmol, 86.23% yield) which was used in the next step without further purification. $^1$H NMR (500 MHz, DMSO-d$_6$) δ (ppm) 1.33 (m, 5H), 1.42 (s, 9H), 1.85 (m, 4H), 2.14 (s, 3H), 2.76 (m, 1H), 2.99 (m, 2H), 3.19 (m, 1H), 3.50 (m, 3H), 3.61 (m, 4H), 3.81 (m, 1H), 4.19 (m, 3H), 4.51 (m, 1H), 5.08 (s, 2H), 7.08 (m, 4H), 7.91 (d, 1H), 8.27 (m, 1H), 8.36 (m, 1H). LCMS (ESI): [M+H]$^+$ m/z: calc'd 690.3; found 691.2; Rt=1.31 min.

Step 5: Synthesis of 4-(3-oxa-8-azabicyclo[3.2.1]octane-8-carbonyl)-2-ethoxy-N—((R)-2-hydroxy-2-((S)-7-((4-methyloxazol-5-yl)methoxy)-1,2,3,4-tetrahydroisoquinolin-3-yl)ethyl)benzamide (Compound 12) Hydrogen chloride solution 4.0M in dioxane (277.11 mg, 7.60 mmol, 346.38 μL) was added to the solution of tert-butyl (3S)-3-[(1R)-2-[[2-ethoxy-4-(3-oxa-8-azabicyclo[3.2.1]octane-8-carbonyl)benzoyl]-amino]-1-hydroxy-ethyl]-7-[(4-methyloxazol-5-yl)methoxy]-3,4-dihydro-1H-isoquinoline-2-carboxylate (0.07 g, 101.33 μmol) in the mixture of Et$_2$O (2 mL) and MeOH (1 mL). The resulting mixture was stirred for 24 h at 25° C. The formed solid was filtered on, washed with Et$_2$O (2 mL) and dried in vacuo at 35° C. to give crude product which was purified by HPLC (20-35% water-acetonitrile, 10 min, flow 30 mL/min (loading pump 4 mL/min acetonitrile), column: SunFire C18 100*20 mm to give 2-ethoxy-N-[(2R)-2-hydroxy-2-[(3S)-7-[(4-methyloxazol-5-yl)methoxy]-1,2,3,4-tetrahydroisoquinolin-3-yl]ethyl]-4-(3-oxa-8-azabicyclo[3.2.1]octane-8-carbonyl)benzamide (0.0156 g, 23.51 μmol, 23.20% yield, 2HCl). $^1$H NMR (Chloroform-d, 400 MHz): δ (ppm) 1.51 (t, 3H), 1.97 (m, 5H), 2.20 (s, 3H), 2.78 (m, 2H), 2.98 (m, 1H), 3.62 (m, 5H), 3.82 (m, 3H), 3.93 (m, 1H), 4.00 (m, 2H), 4.21 (q, 2H), 4.69 (m, 1H), 4.95 (s, 2H), 6.60 (m, 1H), 6.75 (d, 1H), 7.03 (d, 1H), 7.07 (d, 1H), 7.12 (s, 1H), 7.78 (s, 1H), 8.20 (d, 1H), 8.46 (t, 1H). LCMS (ESI): [M+H]$^+$ m/z: calc'd 590.3; found 591.2; Rt=0.99 min.

Example 1A10. Synthesis of N—((R)-2-hydroxy-2-((S)-7-((4-methyloxazol-5-yl)methoxy)-1,2,3,4-tetrahydroisoquinolin-3-yl)ethyl)-4-(morpholine-4-carbonyl)benzamide (Compound 3) and N—((R)-2-hydroxy-2-((S)-7-hydroxy-1,2,3,4-tetrahydroisoquinolin-3-yl)ethyl)-4-(morpholine-4-carbonyl)benzamide
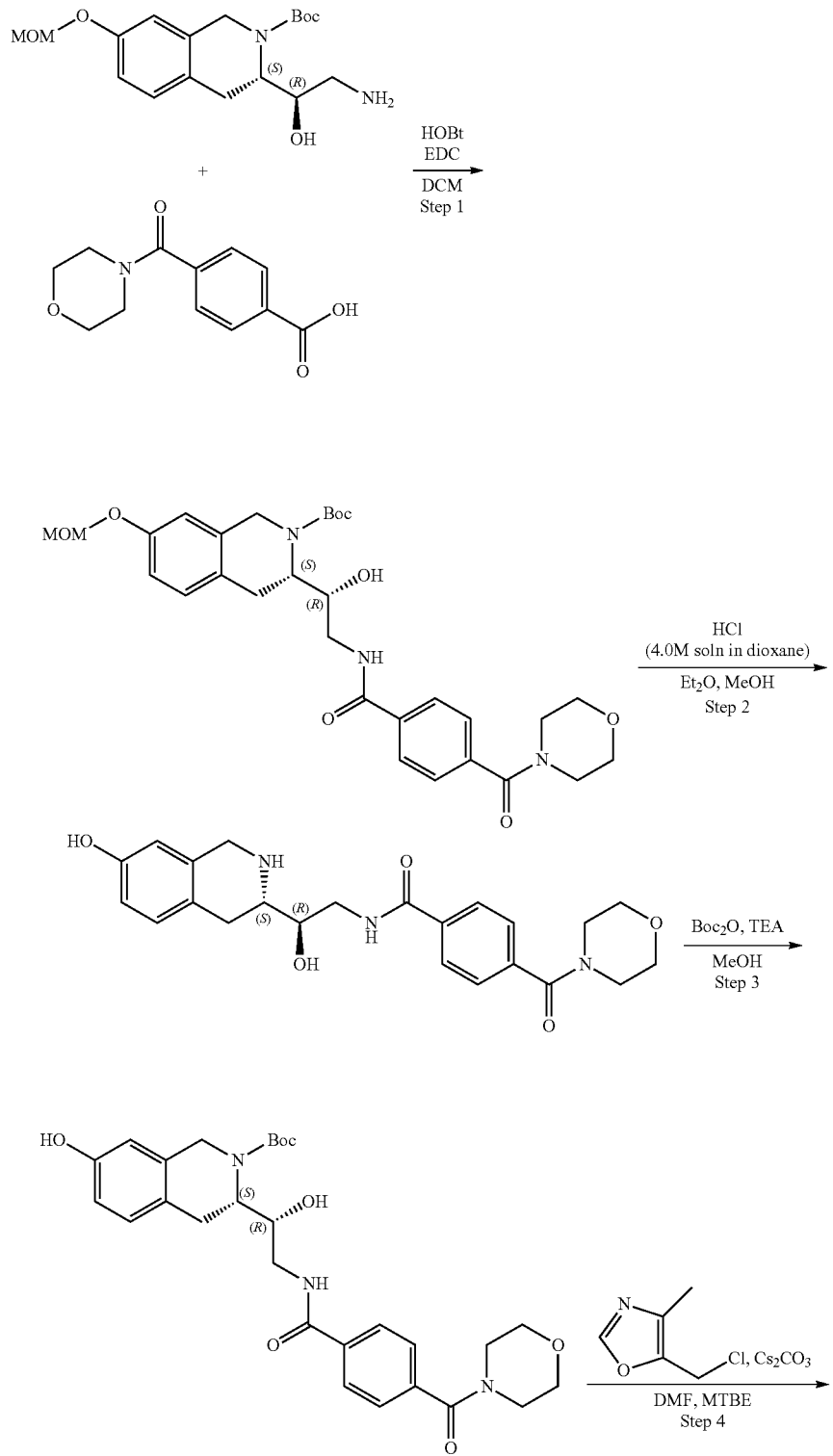

-continued

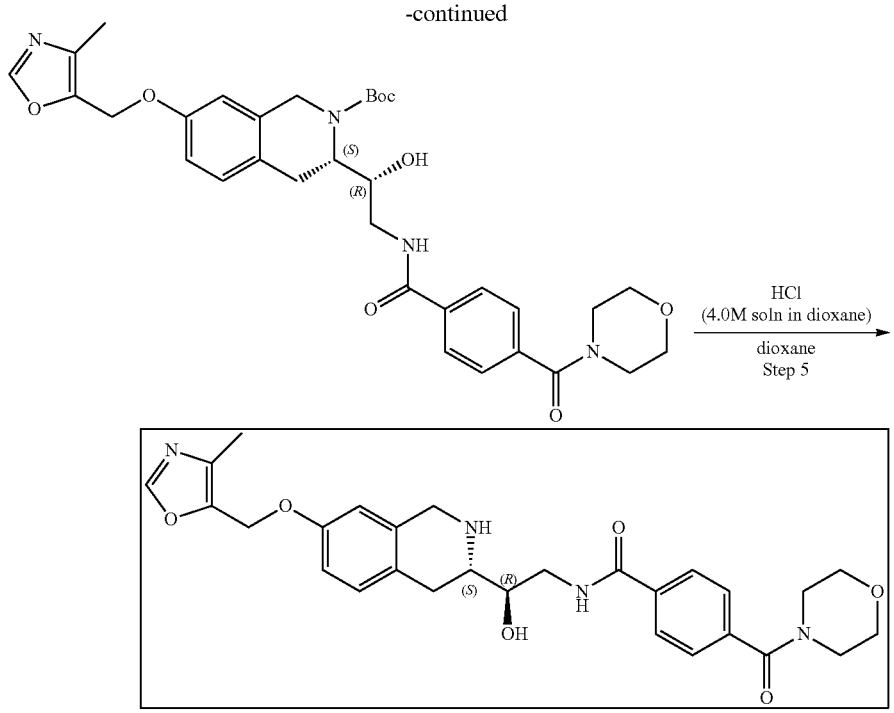

Step 1: Synthesis of (S)-tert-butyl 3-((R)-1-hydroxy-2-(4-(morpholine-4-carbonyl)benzamido)ethyl)-7-(methoxymethoxy)-3,4-dihydroisoquinoline-2(1H)-carboxylate. 1-Hydroxybenzotriazole (2.11 g, 15.61 mmol) and N-(3-dimethylaminopropyl)-N'-ethylcarbodiimide hydrochloride (2.99 g, 15.61 mmol) were dissolved in DCM (100 mL). The mixture was cooled to 0° C. and 4-(morpholine-4-carbonyl)benzoic acid (3.67 g, 15.61 mmol) was added. The mixture was stirred for 15 min at the same temperature. The resulting mixture was dropwise added to the solution of tert-butyl (3S)-3-[(1R)-2-amino-1-hydroxy-ethyl]-7-(methoxymethoxy)-3,4-dihydro-1H-isoquinoline-2-carboxylate (5.50 g, 15.61 mmol) in DCM (100 mL) at 0° C. while stirring. The mixture was stirred at r.t. for 10 h and then extracted with aq. NaHSO$_4$ (3*50 mL) and aq. NaHCO$_3$ (3*50 mL). The organic phase was separated, dried with Na$_2$SO$_4$ and evaporated in vacuo at 35° C. to give tert-butyl (3S)-3-[(1R)-1-hydroxy-2-[[4-(morpholine-4-carbonyl)benzoyl]amino]ethyl]-7-(methoxymethoxy)-3,4-dihydro-1H-isoquinoline-2-carboxylate (8.3 g, 14.57 mmol, 93.36% yield). $^1$H NMR (500 MHz, CDCl$_3$) δ (ppm) 1.54 (s, 9H), 1.67 (m, 2H), 2.89 (m, 2H), 3.18 (m, 1H), 3.41 (m, 2H), 3.48 (s, 3H), 3.63 (m, 2H), 3.78 (m, 4H), 4.22 (m, 2H), 4.38 (m, 1H), 4.69 (m, 1H), 5.15 (s, 2H), 6.79 (s, 1H), 6.88 (d, 1H), 7.10 (d, 1H), 7.50 (m, 2H), 7.96 (m, 2H), 8.05 (s, 1H). LCMS (ESI): [M-Boc]$^+$ m/z: calc'd 469.3; found 470.2; Rt=1.36 min.

Step 2: Synthesis of N—((R)-2-hydroxy-2-((S)-7-hydroxy-1,2,3,4-tetrahydroisoquinolin-3-yl)ethyl)-4-(morpholine-4-carbonyl)benzamide Hydrogen chloride, 4M in 1,4-dioxane, 99% (40.00 g, 1.10 mol, 50 mL) was added to the solution of tert-butyl (3S)-3-[(1R)-1-hydroxy-2-[[4-(morpholine-4-carbonyl)benzoyl]amino]ethyl]-7-(methoxymethoxy)-3,4-dihydro-1H-isoquinoline-2-carboxylate (8.30 g, 14.57 mmol) in the mixture of Et$_2$O (50 mL) and MeOH (30 mL). The mixture was stirred for 10 h at 25° C. The formed solid was filtered, washed with Et$_2$O (50 mL) and dried in vacuo at 35° C. to give the crude N-[(2R)-2-hydroxy-2-[(3S)-7-hydroxy-1,2,3,4-tetrahydroisoquinolin-3-yl]ethyl]-4-(morpholine-4-carbonyl)benzamide (6 g, 14.10 mmol, 96.78% yield). 20 mg of the crude product was dissolved in 5 mL of H$_2$O and the solution was evaporated in vacuo at 50° C. to give pure compound without impurities of the solvents. $^1$H NMR (400 MHz, D$_2$O) δ (ppm) 3.14 (m, 2H), 3.50 (m, 2H), 3.69 (m, 6H), 3.85 (m, 4H), 4.42 (m, 3H), 6.74 (s, 1H), 6.89 (d, 1H), 7.21 (d, 1H), 7.58 (m, 2H), 7.89 (m, 2H). LCMS (ESI): [M+H]$^+$ m/z: calc'd 425.2; found 426.2; Rt=0.81 min.

Step 3: Synthesis of (S)-tert-butyl 7-hydroxy-3-((R)-1-hydroxy-2-(4-(morpholine-4-carbonyl)benzamido)ethyl)-3,4-dihydroisoquinoline-2(1H)-carboxylate. N-[(2R)-2-Hydroxy-2-[(3S)-7-hydroxy-1,2,3,4-tetrahydroisoquinolin-3-yl]ethyl]-4-(morpholine-4-carbonyl)benzamide (3 g, 7.05 mmol, HCl), triethylamine (713.48 mg, 7.05 mmol, 982.76 μL) were mixed in methanol (100 mL) and cooled to 0° C. Then, di-tert-butyl dicarbonate (1.54 g, 7.05 mmol, 1.62 mL) was added and the mixture was stirred at 0° C. for 1 h and then at r.t. for 10 h. After all starting material was consumed as was shown by LCMS, EtOAc (500 mL) was added and the mixture was extracted with aq. NaHSO$_4$ (3*200 mL). The organic phase was separated, dried with Na$_2$SO$_4$ and evaporated in vacuo at 35° C. to give tert-butyl (3S)-7-hydroxy-3-[(1R)-1-hydroxy-2-[[4-(morpholine-4-carbonyl)benzoyl]amino]ethyl]-3,4-dihydro-1H-isoquinoline-2-carboxylate (3.4 g, 6.47 mmol, 91.75% yield). $^1$H NMR (500 MHz, DMSO-d$_6$) δ (ppm) 1.43 (s, 9H), 2.72 (m, 1H), 3.03 (m, 2H), 3.27 (m, 1H), 3.59 (m, 8H), 4.15 (m, 2H), 4.71 (m, 1H), 5.14 (m, 1H), 6.57 (m, 2H), 6.93 (d, 1H), 7.46 (m, 2H), 7.87 (m, 2H), 8.45 (m, 1H), 9.18 (m, 1H). LCMS (ESI): [M-Boc]+ m/z: calc'd 425.2; found 426.2; Rt=1.08 min.

Step 4: Synthesis of (S)-tert-butyl 3-((R)-1-hydroxy-2-(4-(morpholine-4-carbonyl)benzamido)ethyl)-7-((4-methyloxazol-5-yl)methoxy)-3,4-dihydroisoquinoline-2(1H)-carboxylate. tert-Butyl (3S)-7-hydroxy-3-[(1R)-1-hydroxy-2-[[4-(morpholine-4-carbonyl)benzoyl]amino]ethyl]-3,4-dihydro-1H-isoquinoline-2-carboxylate (0.391 g, 743.92 μmol), $C_5H_6NOCl$ · HCl (117.44 mg, 698.99 μmol, HCl), cesium carbonate (242.38 mg, 743.92 μmol) were mixed in DMF (5 mL) and the mixture was stirred for 10 h at 80° C. Then, the mixture was cooled to r.t. and MTBE (100 mL) was added. The reaction mixture was extracted with aqueous NaCl (5*10 mL). The organic phase was separated, dried with $Na_2SO_4$ and evaporated in vacuo at 35° C. The residue was purified by HPLC (Waters SunFire C18 19*100 5 mkm column and $H_2O$-MeOH as an eluent mixture, RunTime=5 min) to give pure product (90 mg, 145.00 μmol, 19.49% yield). $^1H$ NMR (400 MHz, $CDCl_3$) δ (ppm) 1.52 (s, 9H), 2.21 (s, 3H), 2.58 (s, 1H), 2.88 (m, 2H), 3.14 (m, 1H), 3.60 (m, 9H), 4.18 (m, 2H), 4.36 (m, 1H), 4.66 (m, 1H), 4.96 (s, 2H), 6.68 (s, 1H), 6.82 (d, 1H), 7.11 (d, 1H), 7.47 (m, 2H), 7.80 (s, 1H), 7.92 (m, 2H), 8.02 (m, 1H). LCMS (ESI): [M-Boc]+ m/z: calc'd 520.3; found 521.4; Rt=1.34 min.

Step 5: Synthesis of N—((R)-2-hydroxy-2-((S)-7-((4-methyloxazol-5-yl)methoxy)-1,2,3,4-tetrahydroisoquinolin-3-yl)ethyl)-4-(morpholine-4-carbonyl)benzamide (Compound 3) Hydrogen chloride solution 4.0M in dioxane (4.00 g, 109.71 mmol, 5 mL) was added to the solution of tert-butyl (3S)-3-[(1R)-1-hydroxy-2-[[4-(morpholine-4-carbonyl)benzoyl]amino]ethyl]-7-[(4-methyloxazol-5-yl)methoxy]-3,4-dihydro-1H-isoquinoline-2-carboxylate (90 mg, 145.00 μmol) was dissolved in dioxane (5 mL). The resulting mixture was stirred at 20° C. for 3 h. Then, the solvent was evaporated in vacuo at 35° C. The residue was dissolved in a minimum volume of methanol (less than 0.5 mL) and poured into diethyl ether (5 mL). The formed solid was filtered, washed with diethyl ether (3.10 mL) and dried in vacuo at 35° C. to give N-[(2R)-2-hydroxy-2-[(3S)-7-[(4-methyloxazol-5-yl)methoxy]-1,2,3,4-tetrahydroisoquinolin-3-yl]ethyl]-4-(morpholine-4-carbonyl)benzamide (75 mg, 126.37 μmol, 87.15% yield, 2HCl). $^1H$ NMR, δ 2.05 (s, 3H), 3.03 (m, 2H), 3.37 (t, 2H), 3.48 (m, 1H), 3.58 (m, 5H), 3.68 (m, 2H), 3.74 (m, 2H), 4.23 (m, 1H), 4.36 (m, 2H), 4.59 (m, 3H), 5.06 (s, 2H), 6.78 (s, 1H), 6.89 (d, 1H), 7.17 (d, 1H), 7.43 (d, 2H), 7.75 (d, 2H), 8.11 (s, 1H). LCMS (ESI): [M+H]+ m/z: calc'd 520.3; found 521.2; Rt=0.85 min.

Example 1A11. Synthesis of N—((R)-2-hydroxy-2-((S)-7-((1-methyl-1H-pyrazol-5-yl)methoxy)-1,2,3,4-tetrahydroisoquinolin-3-yl)ethyl)-4-(morpholine-4-carbonyl)benzamide (Compound 2)

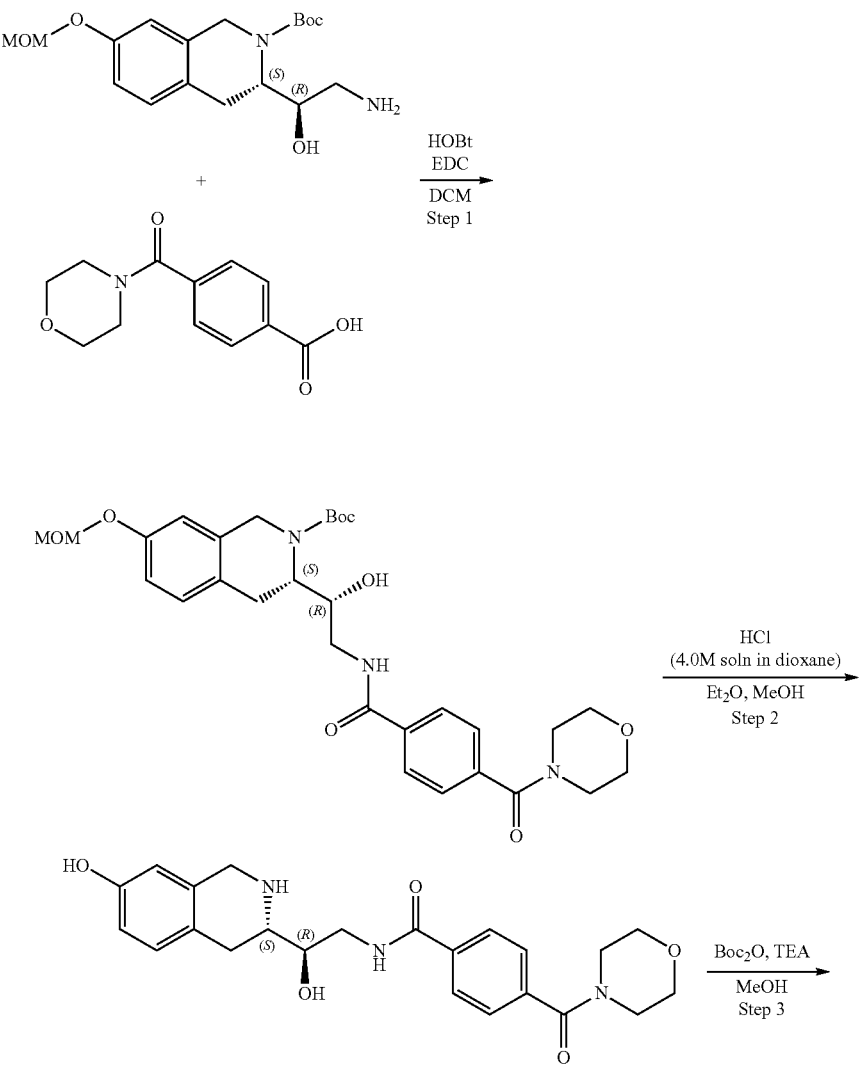

-continued

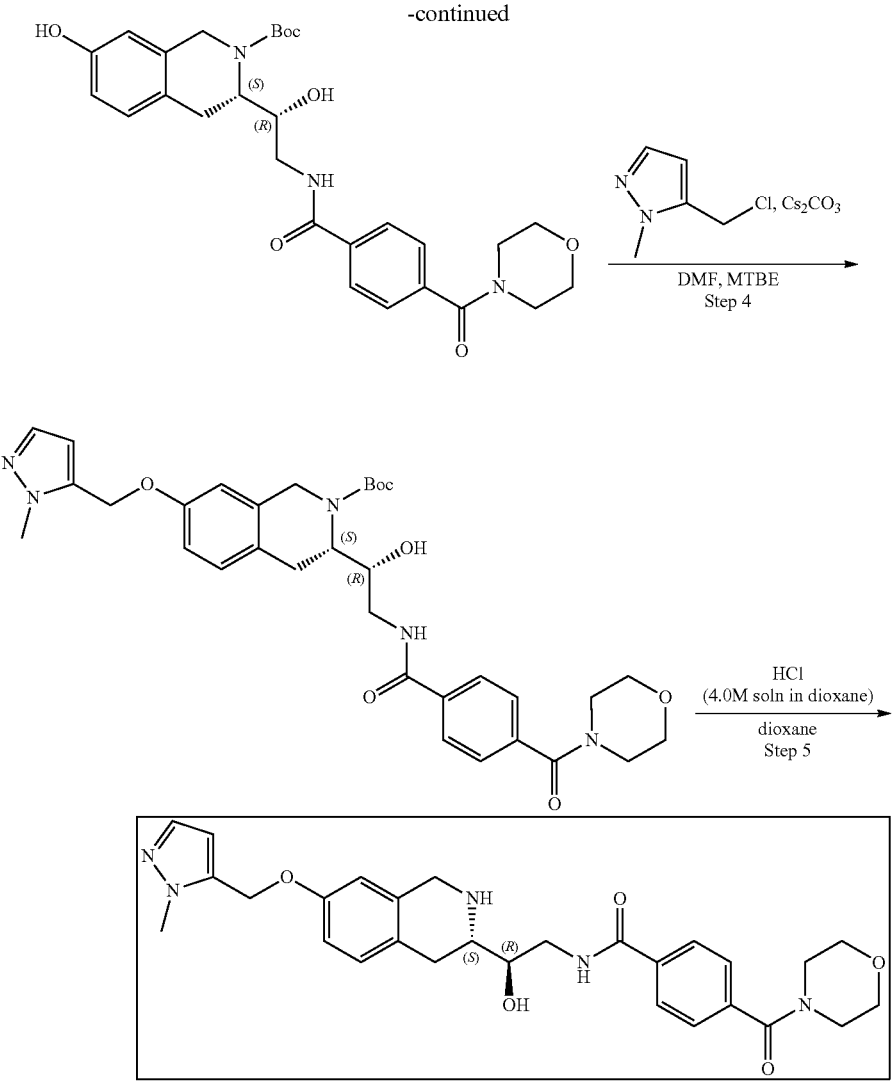

Steps 1-3 are the same as for Example 1A10.

Step 4: Synthesis of (S)-tert-butyl 3-((R)-1-hydroxy-2-(4-(morpholine-4-carbonyl)benzamido)ethyl)-7-((1-methyl-1H-pyrazol-5-yl)methoxy)-3,4-dihydroisoquinoline-2(1H)-carboxylate tert-butyl (3S)-7-hydroxy-3-[(1R)-1-hydroxy-2-[[4-(morpholine-4-carbonyl)benzoyl]amino]ethyl]-3,4-dihydro-1H-isoquinoline-2-carboxylate (500.00 mg, 951.31 μmol), 5-(chloromethyl)-1-methyl-pyrazole (149.06 mg, 1.14 mmol), Cesium carbonate (774.89 mg, 2.38 mmol) were mixed in DMF (5 mL) and the mixture was stirred for 10 hr at 80° C. Then the mixture was cooled to r.t. and MTBE (100 mL) was added. The mixture was extracted with aqueous NaCl (5*10 mL). The organic phase was separated, dried with Na$_2$SO$_4$ and evaporated in vacuo at 35° C. The residue was purified by HPLC to give tert-butyl (3S)-3-[(1R)-1-hydroxy-2-[[4-(morpholine-4-carbonyl)benzoyl]amino]ethyl]-7-[(2-methylpyrazol-3-yl)methoxy]-3,4-dihydro-1H-isoquinoline-2-carboxylate (210 mg, 338.87 μmol, 35.62% yield) $^1$H NMR (400 MHz, DMSO-d$_6$) δ (ppm) 1.40 (s, 9H), 2.90 (m, 2H), 3.20 (d, 1H), 3.25-3.50 (m, 2H), 3.60 (m, 2H), 3.80 (m, 4H), 3.91 (m, 3H), 4.20 (d, 2H), 4.38 (br s, 1H), 4.68 (d, 1H), 5.02 (s, 3H), 6.73 (s, 2H), 6.30 (d, 1H), 6.85 (s, 1H), 6.71 (s, 1H), 6.83 (d, 1H), 7.13 (d, 1H), 7.44 (s, 1H), 7.49 (d, 1H), 7.95 (d, 1H), 8.04 (br s, 1H) LCMS (ESI): [M+H]$^+$ m/z: calc'd 619.3; found 620.0; Rt=1.28 min.

Step 5: Synthesis of N—((R)-2-hydroxy-2-((S)-7-((1-methyl-1H-pyrazol-5-yl)methoxy)-1,2,3,4-tetrahydroisoquinolin-3-yl)ethyl)-4-(morpholine-4-carbonyl)benzamide (Compound 2) tert-butyl (3S)-3-[(1R)-1-hydroxy-2-[[4-(morpholine-4-carbonyl)benzoyl]amino]ethyl]-7-[(2-methylpyrazol-3-yl)methoxy]-3,4-dihydro-1H-isoquinoline-2-carboxylate (0.2 g, 322.73 μmol) was dissolved in methanol (1 mL) and Hydrogen chloride solution 4.0M in dioxane (4.00 g, 109.71 mmol, 5 mL) was added. The mixture was stirred at 20° C. for 10 hr. Then the solvents were evaporated in vacuo at 40° C. and the residue was purified by HPLC to give N-[(2R)-2-hydroxy-2-[(3S)-7-[(2-methylpyrazol-3-yl)methoxy]-1,2,3,4-tetrahydroisoquinolin-3-yl]ethyl]-4-(morpholine-4-carbonyl)benzamide (70 mg, 118.14 μmol, 36.61% yield, 2HCl)$^1$H NMR (400 MHz, DMSO-d$_6$) δ (ppm) 3.05 (m, 2H), 3.30 (m, 2H), 3.43 (t, 2H), 3.53 (m, 8H), 3.81 (s, 3H), 4.15 (d, 1H), 4.23 (m, 1H), 4.33 (m, 1H), 5.15 (s, 2H), 5.97 (s, 1H), 6.37 (s, 1H), 6.94 (s, 1H), 6.97 (d, 1H), 7.20 (d, 1H), 7.36 (s, 1H), 7.48 (d, 2H), 7.95 (d, 2H), 8.87 (t, 1H), 8.98 (d, 1H), 9.76 (d, 1H). LCMS (ESI): [M+H]$^+$ m/z: calc'd 519.2; found 520.2; Rt=2.27 min.

Example 1A12. Synthesis of N—((R)-2-hydroxy-2-((S)-7-((1-methyl-1H-pyrazol-5-yl)methoxy)-1,2,3,4-tetrahydroisoquinolin-3-yl)ethyl)-4-(morpholine-4-carbonyl)benzamide (Compound 1)
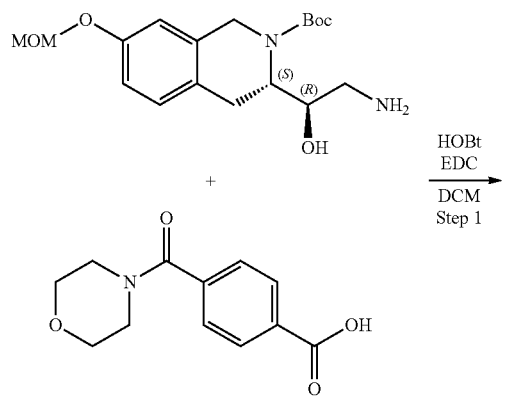
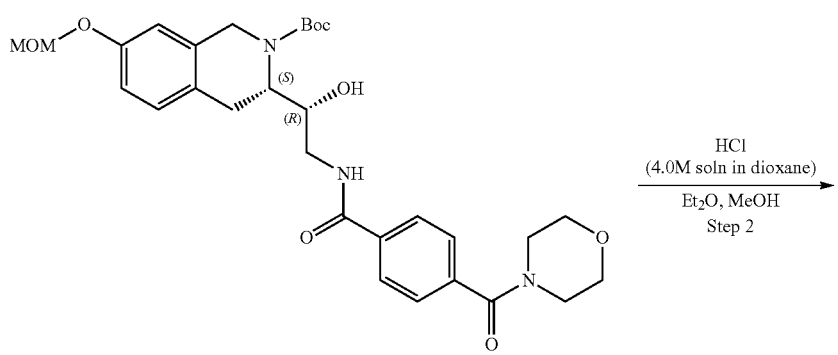
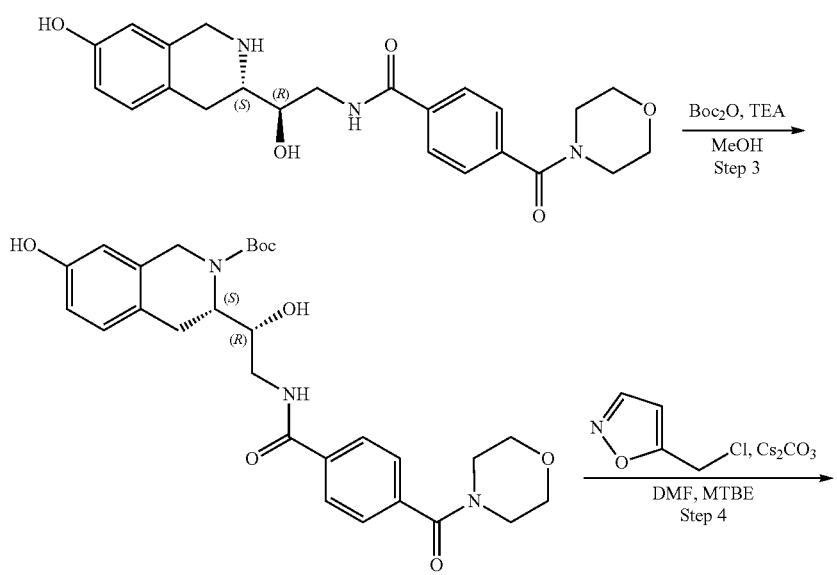

-continued

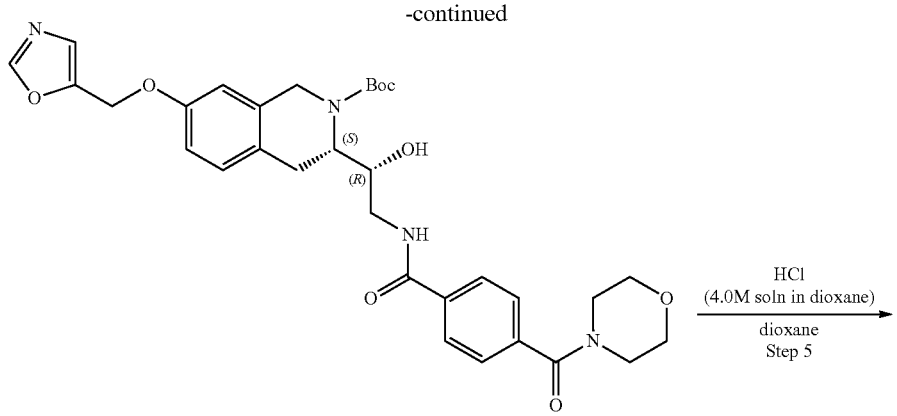

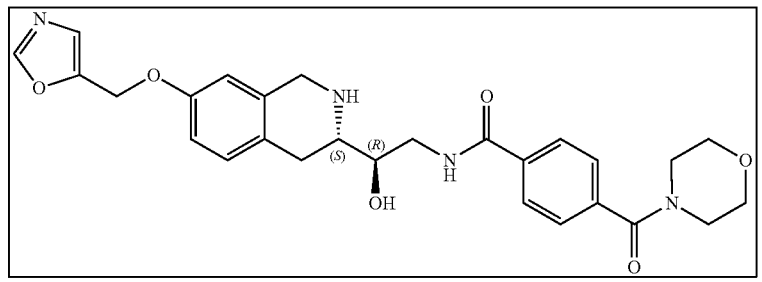

Steps 1-3 are the same as for Example 1A10.

Step 4: Synthesis of (S)-tert-butyl 3-((R)-1-hydroxy-2-(4-(morpholine-4-carbonyl)benzamido)ethyl)-7-(oxazol-5-yl-methoxy)-3,4-dihydroisoquinoline-2(1H)-carboxylate N-[(2R)-2-hydroxy-2-[(3S)-7-hydroxy-1,2,3,4-tetrahydroisoquinolin-3-yl]ethyl]-4-(morpholine-4-carbonyl)benzamide (1.00 g, 2.35 mmol), Triethylamine (237.83 mg, 2.35 mmol, 327.59 µL) were mixed in Methanol (10 mL) and cooled to 0° C. Di-tert-butyl dicarbonate (512.95 mg, 2.35 mmol, 539.38 µL) was added and the mixture was stirred at 0° C. for 1 h and then at r.t. for 10 hr. EtOAc (100 mL) was added and the mixture was extracted with aq. NaHSO$_4$ (3*20 mL). The organic phase was separated, dried with Na$_2$SO$_4$ and evaporated in vacuo at 35° C. to give tert-butyl (3S)-7-hydroxy-3-[(1R)-1-hydroxy-2-[[4-(morpholine-4-carbonyl)benzoyl]amino]ethyl]-3,4-dihydro-1H-isoquinoline-2-carboxylate (0.52 g, 989.36 µmol, 42.09% yield). $^1$H NMR (400 MHz, DMSO-d$_6$) δ (ppm) 1.46 (m, 9H), 2.71 (m, 2H), 3.03 (m, 5H), 3.50-3.59 (m, 5H), 4.10-4.26 (m, 2H), 4.75 (m, 1H), 4.21-4.25 (m, 2H), 4.70 (m, 1H), 5.14 (m, 3H), 6.82 (d, 1H), 6.90 (s, 1H), 7.07 (d, 1H), 7.31 (s, 1H), 7.46 (d, 1H), 7.86 (d, 1H), 8.38 (s, 1H), 8.45 (m, 1H) LCMS (ESI): [M-Boc]+ m/z: calc'd 506.3; found 506.2; Rt=1.30 min.

Step 5: Synthesis of N—((R)-2-hydroxy-2-((S)-7-(oxazol-5-ylmethoxy)-1,2,3,4-tetrahydroisoquinolin-3-yl)ethyl)-4-(morpholine-4-carbonyl)benzamide (Compound 1) tert-butyl (3S)-3-[(1R)-1-hydroxy-2-[[4-(morpholine-4-carbonyl)benzoyl]amino]ethyl]-7-(oxazol-5-ylmethoxy)-3,4-dihydro-1H-isoquinoline-2-carboxylate (0.2 g, 329.67 µmol) was dissolved in Dioxane (5 mL) and Hydrogen chloride solution 4.0M in dioxane (12.02 mg, 329.67 µmol, 15.02 µL) was added. The mixture was stirred at 20° C. for 10 hr. Then the solvent was evaporated in vacuo at 35° C. The residue was dissolved in a minimum volume of methanol (less than 0.5 mL) and poured into diethyl ether (5 mL). The solid formed was filtered, washed with diethyl ether (3*10 mL) and dried in vacuo at 35° C. to give N-[(2R)-2-hydroxy-2-[(3S)-7-(oxazol-5-ylmethoxy)-1,2,3,4-tetrahydroisoquinolin-3-yl]ethyl]-4-(morpholine-4-carbonyl)benzamide (0.1 g, 172.57 µmol, 52.35% yield, 2HCl). $^1$H NMR (400 MHz, DMSO) δ 3.05 (m, 3H), 3.27 (m, 3H), 3.40 (m, 7H), 4.17 (m, 2H), 4.32 (m, 1H), 5.15 (s, 2H), 6.92 (m, 1H), 6.96 (dd, 1H), 7.19 (d, 1H), 7.33 (s, 1H), 7.48 (d, 2H), 7.93 (d, 2H), 8.39 (s, 1H), 8.83 (t, 1H), 8.94 (m, 1H), 9.62 (m, 1H). LCMS (ESI): [M+H]$^+$ m/z: calc'd 519.2; found 520.2; Rt=2.27 min. LCMS (ESI): [M+H]$^+$ m/z: calc'd 506.2; found 507.2; Rt=0.905 min.

Example 1A13. Synthesis of 2-ethoxy-N-[(2R)-2-hydroxy-2-[(3S)-7-[(4-methyl-1H-pyrazol-5-yl)methoxy]-1,2,3,4-tetrahydroisoquinolin-3-yl]ethyl]-4-(3-oxa-8-azabicyclo[3.2.1]octane-8-carbonyl)benzamide (Compound 75)
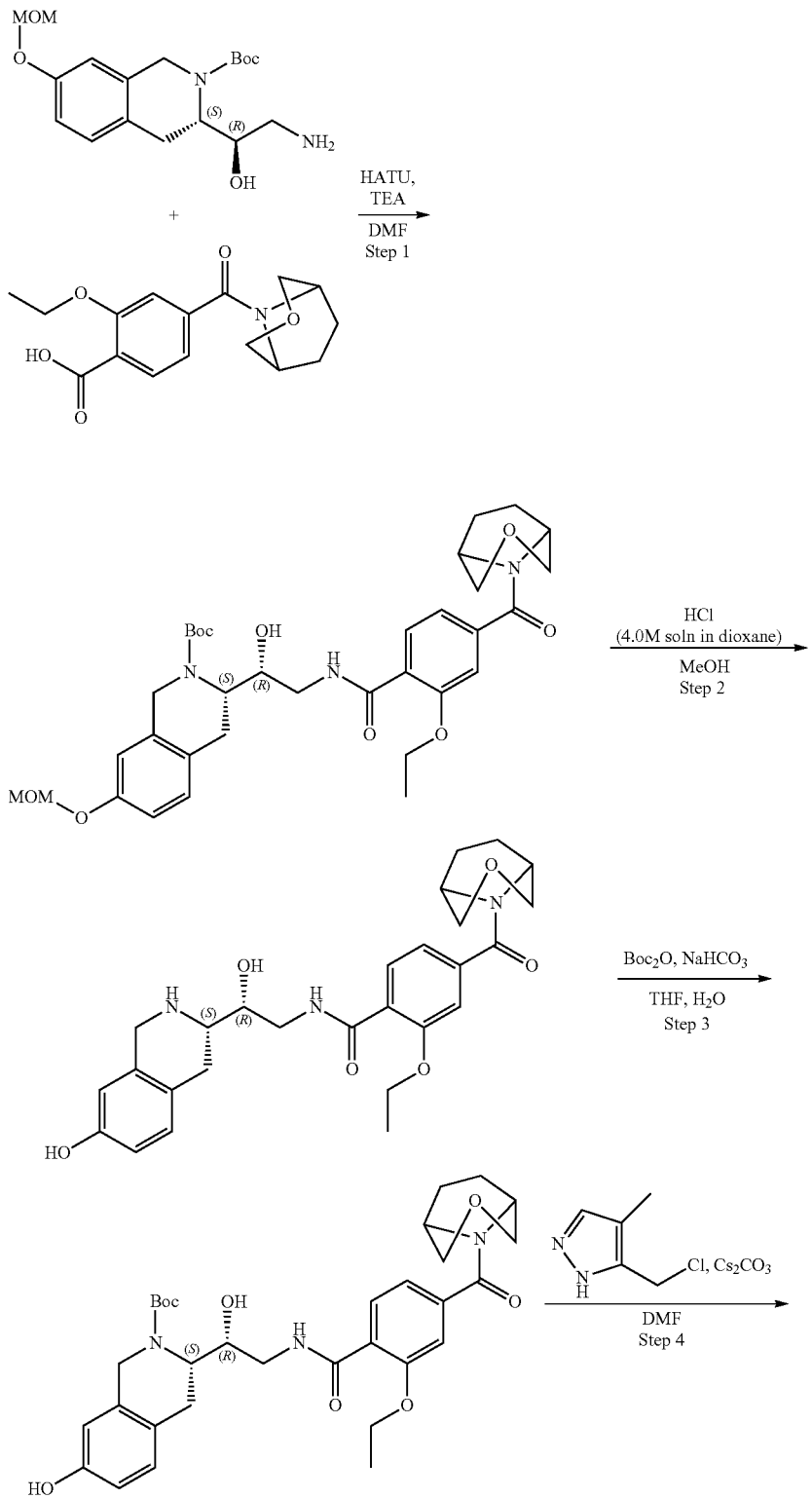

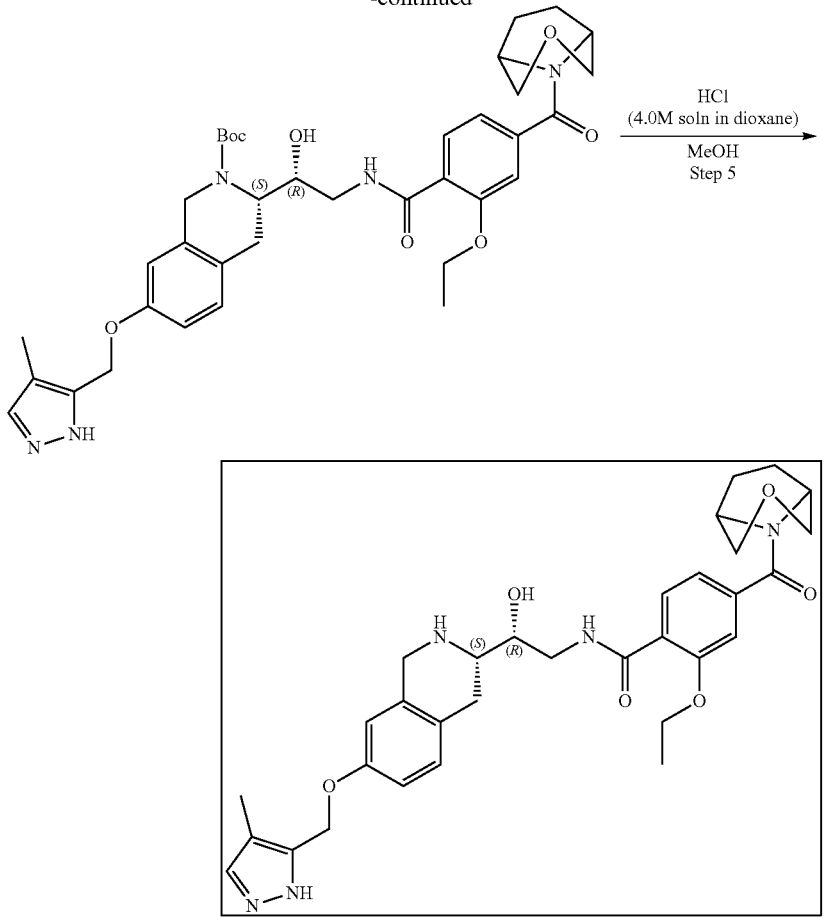

Step 1: Synthesis of tert-butyl (3S)-3-[(1R)-2-[[2-ethoxy-4-(3-oxa-8-azabicyclo[3.2.1]octane-8-carbonyl)benzoyl]amino]-1-hydroxy-ethyl]-7-(methoxymethoxy)-3,4-dihydro-1H-isoquinoline-2-carboxylate tert-Butyl (3S)-3-[(1R)-2-amino-1-hydroxy-ethyl]-7-(methoxymethoxy)-3,4-dihydro-1H-isoquinoline-2-carboxylate (0.4 g, 1.13 mmol), 2-ethoxy-4-(3-oxa-8-azabicyclo[3.2.1]octane-8-carbonyl)benzoic acid (346.54 mg, 1.13 mmol) and HATU (647.34 mg, 1.70 mmol) were dissolved in DMF (10 mL) and heated at 20° C. for 3 hr. The reaction mixture was diluted with water end extracted three times with EtOAc, then EtOAc was extracted three times with brine. The organic phase was dried over Na$_2$SO$_4$, filtered off and evaporated at 40° C. to give crude product which was purified by HPLC (40-55% water-methanol, 10 min, flow 30 mL/min (loading pump 4 mL/min methanol) column: SunFire C18 100*19 mm) to afford tert-butyl (3S)-3-[(1R)-2-[[2-ethoxy-4-(3-oxa-8-azabicyclo[3.2.1]octane-8-carbonyl)benzoyl]amino]-1-hydroxy-ethyl]-7-(methoxymethoxy)-3,4-dihydro-1H-isoquinoline-2-carboxylate (0.5 g, 781.57 µmol, 68.86% yield) which was used in the next step without further purification. LCMS (ESI): [M+H]$^+$ m/z: calc'd 639.7; found 640.2; Rt=1.36 min.

Step 2: Synthesis of 2-ethoxy-N-[(2R)-2-hydroxy-2-[(3S)-7-hydroxy-1,2,3,4-tetrahydroisoquinolin-3-yl]ethyl]-4-(3-oxa-8-azabicyclo[3.2.1]octane-8-carbonyl)benzamide tert-Butyl (3S)-3-[(1R)-2-[[2-ethoxy-4-(3-oxa-8-azabicyclo[3.2.1]octane-8-carbonyl)benzoyl]amino]-1-hydroxy-ethyl]-7-(methoxymethoxy)-3,4-dihydro-1H-isoquinoline-2-carboxylate (0.5 g, 781.57 µmol) was dissolved in MeOH (5 mL). Then hydrogen chloride solution 4.0M in dioxane (2.14 g, 58.62 mmol, 2.67 mL) was added. The resulting mixture was stirred for 3 hr at 25° C. After the completion of the reaction, the solvent was removed in vacuo at 35° C. to give 2-ethoxy-N-[(2R)-2-hydroxy-2-[(3S)-7-hydroxy-1,2,3,4-tetrahydroisoquinolin-3-yl]ethyl]-4-(3-oxa-8-azabicyclo[3.2.1]octane-8-carbonyl)benzamide (0.415 g, 780.04 µmol, 99.80% yield, HCl) which was used in the next step without further purification. LCMS (ESI): [M+H]$^+$ m/z: calc'd 495.5; found 496.2; Rt=2.47 min.

Step 3: Synthesis of tert-butyl (3S)-3-[(1R)-2-[[2-ethoxy-4-(3-oxa-8-azabicyclo[3.2.1]octane-8-carbonyl)benzoyl]amino]-1-hydroxy-ethyl]-7-hydroxy-3,4-dihydro-1H-isoquinoline-2-carboxylate 2-Ethoxy-N-[(2R)-2-hydroxy-2-[(3S)-7-hydroxy-1,2,3,4-tetrahydroisoquinolin-3-yl]ethyl]-4-(3-oxa-8-azabicyclo[3.2.1]octane-8-carbonyl)benzamide (0.415 g, 780.04 µmol, HCl) was dissolved in the mixture of water (4 mL) and THF (4 mL) then sodium hydrogen carbonate, 99% (196.58 mg, 2.34 mmol, 91.01 µL) was added in one portion. The resulting mixture was stirred for 5 min at room temperature followed by the dropwise addition of the solution of di-tert-butyl dicarbonate (170.24 mg, 780.04 µmol, 179.01 µL) in THF (0.4 mL). The reaction mixture was stirred for 4 hr at room temperature. After the completion of the reaction, ethyl acetate (15 mL) was added, the organic phase was separated, and the aqueous phase was extracted with ethyl acetate (2*15 mL). The organic phase was washed with brine, dried over Na$_2$SO$_4$, filtered off and evaporated in vacuo at 40° C. to give tert-butyl (3S)-3-[(1R)-2-[[2-ethoxy-4-(3-oxa-8-azabicyclo[3.2.1]octane-8-carbonyl)benzoyl]amino]-1-hydroxy-ethyl]-7-hydroxy-3,4-dihydro-1H-isoquinoline-2-carboxylate (0.41 g, 688.29 µmol, 88.24% yield) which was used in the next step without purification. LCMS (ESI): [M+H]⁺ m/z: calc'd 595.7; found 597.4; Rt=3.25 min.

Step 4: Synthesis of tert-butyl (3S)-3-[(1R)-2-[[2-ethoxy-4-(3-oxa-8-azabicyclo[3.2.1]octane-8-carbonyl)benzoyl]amino]-1-hydroxy-ethyl]-7-[(4-methyl-1H-pyrazol-5-yl)methoxy]-3,4-dihydro-1H-isoquinoline-2-carboxylate tert-Butyl (3S)-3-[(1R)-2-[[2-ethoxy-4-(3-oxa-8-azabicyclo[3.2.1]octane-8-carbonyl)benzoyl]-amino]-1-hydroxy-ethyl]-7-hydroxy-3,4-dihydro-1H-isoquinoline-2-carboxylate (0.135 g, 226.63 µmol), 5-(chloromethyl)-4-methyl-1H-pyrazole (41.43 mg, 317.28 µmol, HCl) and cesium carbonate (295.36 mg, 906.52 µmol) were dissolved in DMF (3 mL) and heated at 50° C. overnight. The reaction mixture was filtered off and washed with DMF (2 mL). The filtrate was concentrated on vacuo at 60° C. to give tert-butyl (3S)-3-[(1R)-2-[[2-ethoxy-4-(3-oxa-8-azabicyclo[3.2.1]octane-8-carbonyl)benzoyl]amino]-1-hydroxy-ethyl]-7-[(4-methyl-1H-pyrazol-5-yl)methoxy]-3,4-dihydro-1H-isoquinoline-2-carboxylate (0.14 g, 202.96 µmol, 89.55% yield) which was used in the next step without further purification. ¹H NMR (CDCl₃, 400 MHz): δ 1.48 (s, 9H), 1.92 (m, 8H), 1.62 (m, 6H), 3.53 (m, 4H), 3.67 (m, 2H), 3.91 (m, 4H), 4.29 (m, 2H), 4.57 (m, 2H), 6.66 (m, 2H), 7.10 (m, 3H), 8.18 (s, 1H). LCMS (ESI): [M+H]⁺ m/z: calc'd 689.8; found 690.4; Rt=3.36 min.

Step 5: Synthesis of 2-ethoxy-N-[(2R)-2-hydroxy-2-[(3S)-7-[(4-methyl-1H-pyrazol-5-yl)methoxy]-1,2,3,4-tetrahydroisoquinolin-3-yl]ethyl]-4-(3-oxa-8-azabicyclo[3.2.1]octane-8-carbonyl)benzamide (Compound 75) tert-Butyl (3S)-3-[(1R)-2-[[2-ethoxy-4-(3-oxa-8-azabicyclo[3.2.1]octane-8-carbonyl)benzoyl]-amino]-1-hydroxy-ethyl]-7-[(4-methyl-1H-pyrazol-5-yl)methoxy]-3,4-dihydro-1H-isoquinoline-2-carboxylate (0.14 g, 202.96 µmol) was dissolved in MeOH (3 mL). Then, hydrogen chloride solution 4.0M in dioxane (555.00 mg, 15.22 mmol, 693.75 µL) was added. The resulting mixture was stirred for 4 hr at 20° C. After the completion of the reaction, the solvent was removed in vacuo at 45° C. The obtained residue was dissolved in 5 mL of methanol and 12 mg of scavenger (SiliaMetS© Dimercaptotriazine(DMT) was added. The resulting suspension was stirred at room temperature for 12 h. The obtained suspension was filtered off, the filtrate was evaporated under reduced pressure and the residue was purified by HPLC (60-100% water+NH₃-methanol+NH₃, 2-7 min, flow 30 mL/min (loading pump 4 mL/min methanol+NH₃), column: YMC-Actus Triart C18 100*20 mm) to give 2-ethoxy-N-[(2R)-2-hydroxy-2-[(3S)-7-[(4-methyl-1H-pyrazol-5-yl)methoxy]-1,2,3,4-tetrahydroisoquinolin-3-yl]ethyl]-4-(3-oxa-8-azabicyclo[3.2.1]octane-8-carbonyl)benzamide (0.0072 g, 12.21 µmol, 6.02% yield)¹H NMR (400 MHz, CDCl₃) δ 1.51 (t, 3H), 1.91 (m, 2H), 2.02 (m, 4H), 2.08 (s, 3H), 2.75 (m, 2H), 2.96 (m, 1H), 3.56 (m, 2H), 3.67 (m, 2H), 3.84 (m, 3H), 3.96 (m, 3H), 4.20 (q, 2H), 4.69 (m, 1H), 4.97 (s, 2H), 6.58 (m, 1H), 6.77 (dd, 1H), 6.99 (d, 1H), 7.07 (d, 1H), 7.12 (s, 1H), 7.32 (s, 1H), 8.20 (d, 1H), 8.48 (t, 1H). LCMS (ESI): [M+2H]⁺ m/z: calc'd 589.7; found 591.4; Rt=2.52 min.

Example 1A14. Synthesis of 2-ethoxy-N-[(2R)-2-hydroxy-2-[(3S)-7-(1H-pyrazol-5-ylmethoxy)-1,2,3,4-tetrahydroisoquinolin-3-yl]ethyl]-4-(3-oxa-8-azabicyclo[3.2.1](octane-8-carbonyl)benzamide (Compound 76)

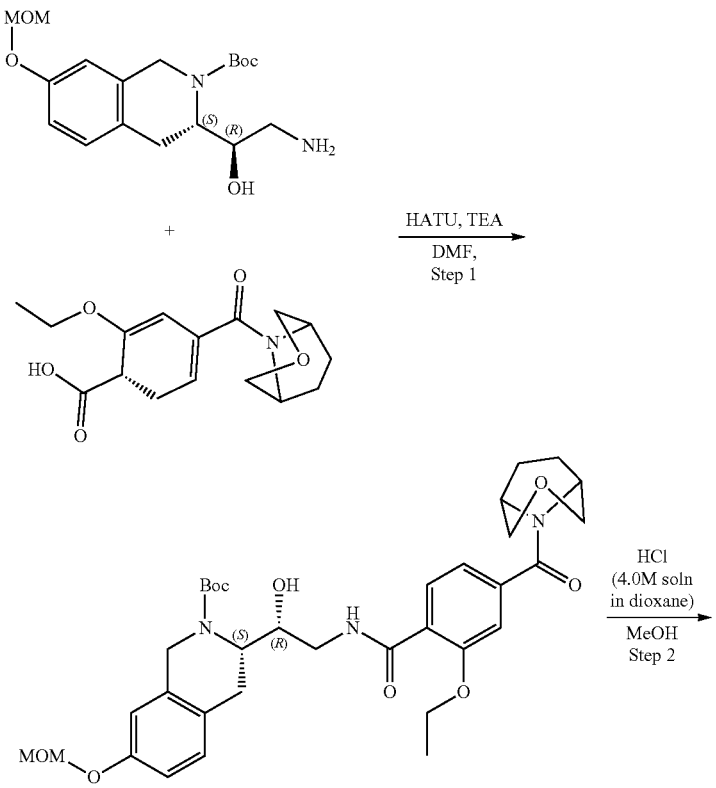

-continued

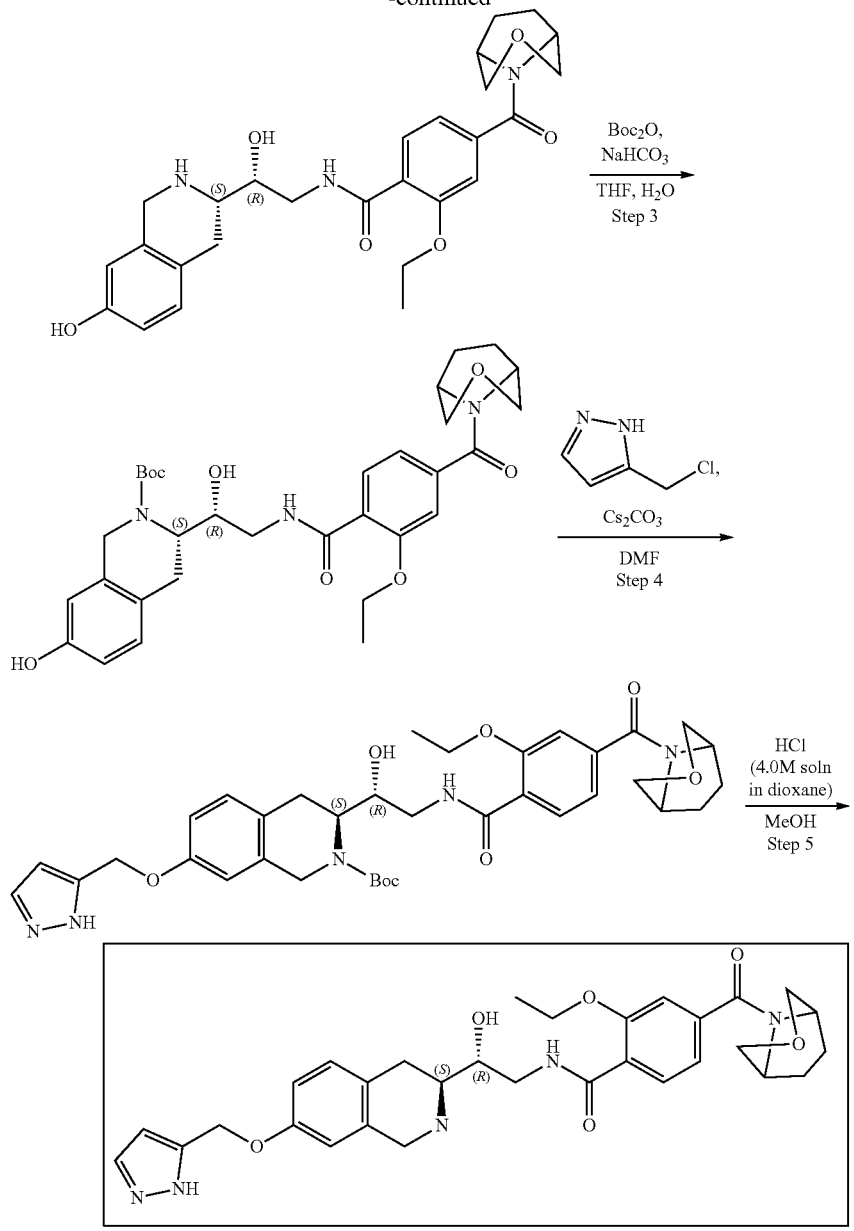

Steps 1-3 are the same as for Example 1A14.

Step 4: Synthesis of tert-butyl (3S)-3-[(1R)-2-[[2-ethoxy-4-(3-oxa-8-azabicyclo[3.2.1]octane-8-carbonyl)benzoyl]amino]-1-hydroxy-ethyl]-7-(1H-pyrazol-5-ylmethoxy)-3,4-dihydro-1H-isoquinoline-2-carboxylate tert-Butyl (3S)-3-[(1R)-2-[[2-ethoxy-4-(3-oxa-8-azabicyclo[3.2.1]octane-8-carbonyl)benzoyl]-amino]-1-hydroxy-ethyl]-7-hydroxy-3,4-dihydro-1H-isoquinoline-2-carboxylate (0.135 g, 226.63 µmol), 5-(chloromethyl)-1H-pyrazole (48.55 mg, 317.28 µmol, HCl) and cesium carbonate (295.36 mg, 906.52 µmol) were dissolved in DMF (2 mL) and stirred at 50° C. overnight. The resulting mixture was filtered off and washed with DMF (2 mL). The obtained filtrate was concentrated in vacuo at 60° C. to give tert-butyl (3S)-3-[(1R)-2-[[2-ethoxy-4-(3-oxa-8-azabicyclo[3.2.1]octane-8-carbonyl)benzoyl]amino]-1-hydroxy-ethyl]-7-(1H-pyrazol-5-ylmethoxy)-3,4-dihydro-1H-isoquinoline-2-carboxylate (0.137 g, 202.73 µmol, 89.45% yield) which was used in the next step without further purification. $^1$H NMR (CDCl$_3$, 400 MHz): δ 1.48 (s, 9H), 2.01 (m, 6H), 3.52 (m, 6H), 3.66 (m, 4H), 4.03 (m, 2H), 4.34 (m, 4H), 4.74 (m, 2H), 5.07 (m, 2H), 6.39 (s, 1H), 6.57 (d, 1H), 6.65 (s, 1H), 6.97 (d, 1H), 7.03 (d, 1H), 7.11 (d, 1H), 8.11 (d, 1H). LCMS (ESI): [M+H]$^+$ m/z: calc'd 675.3; found 676.2; Rt=3.56 min.

Step 5: Synthesis of 2-ethoxy-N-[(2R)-2-hydroxy-2-[(3S)-7-(1H-pyrazol-5-ylmethoxy)-1,2,3,4-tetrahydroisoquinolin-3-yl]ethyl]-4-(3-oxa-8-azabicyclo[3.2.1]octane-8-carbonyl)benzamide (Compound 76) tert-Butyl (3S)-3-[(1R)-2-[[2-ethoxy-4-(3-oxa-8-azabicyclo[3.2.1]octane-8-carbonyl)benzoyl]-amino]-1-hydroxy-ethyl]-7-(1H-pyrazol-5-ylmethoxy)-3,4-dihydro-1H-isoquinoline-2-carboxylate (0.137 g, 202.73 µmol) was dissolved in MeOH (3 mL). Then, hydrogen chloride solution 4.0M in dioxane (554.38 mg, 15.20 mmol, 692.98 µL) was added. The resulting mixture was stirred for 4 hr at 20° C. After the completion of the reaction, solvent was removed in vacuo at 45° C. The residue was dissolved in 5 mL of methanol and 12 mg of scavenger (SiliaMetS© Dimercaptotriazine(DMT) was added. The resulting suspension was stirred for 12 h. The obtained suspension was filtered off, the filtrate was evaporated under reduced pressure, and the residue was purified by HPLC (60-100% water+NH$_3$-methanol+NH$_3$, 2-7 min, flow 30 mL/min (loading pump 4 mL/min methanol+NH$_3$), column: YMC-Actus Triart C18 100*20 mm) to give 2-ethoxy-N-[(2R)-2-hydroxy-2-[(3S)-7-(1H-pyrazol-5-ylmethoxy)-1,2,3,4-tetrahydroisoquinolin-3-yl]ethyl]-4-(3-oxa-8-azabicyclo[3.2.1]octane-8-carbonyl)benzamide (0.0179 g, 31.10 μmol, 15.34% yield). $^1$H NMR (400 MHz, CDCl$_3$) δ 1.50 (t, 3H), 1.92 (m, 2H), 2.02 (m, 3H), 2.75 (m, 2H), 2.98 (m, 1H), 3.57 (m, 3H), 3.69 (m, 2H), 3.83 (m, 4H), 3.93 (m, 1H), 3.98 (m, 2H), 4.22 (q, 2H), 4.70 (m, 1H), 5.06 (s, 2H), 6.37 (m, 1H), 6.61 (m, 1H), 6.78 (m, 1H), 7.01 (d, 1H), 7.08 (d, 1H), 7.13 (s, 1H), 7.54 (d, 1H), 8.21 (d, 1H), 8.48 (t, 1H). LCMS (ESI): [M+H]+ m/z: calc'd 575.3; found 576.4; Rt=0.93 min.

Example 1A15. Synthesis of 2-ethoxy-N-[(2R)-2-hydroxy-2-[(3S)-7-(4-pyridylmethoxy)-1,2,3,4-tetrahydroisoquinolin-3-yl]ethyl]-4-(3-oxa-8-azabicyclo[3.2.1]octane-8-carbonyl)benzamide (Compound 73)

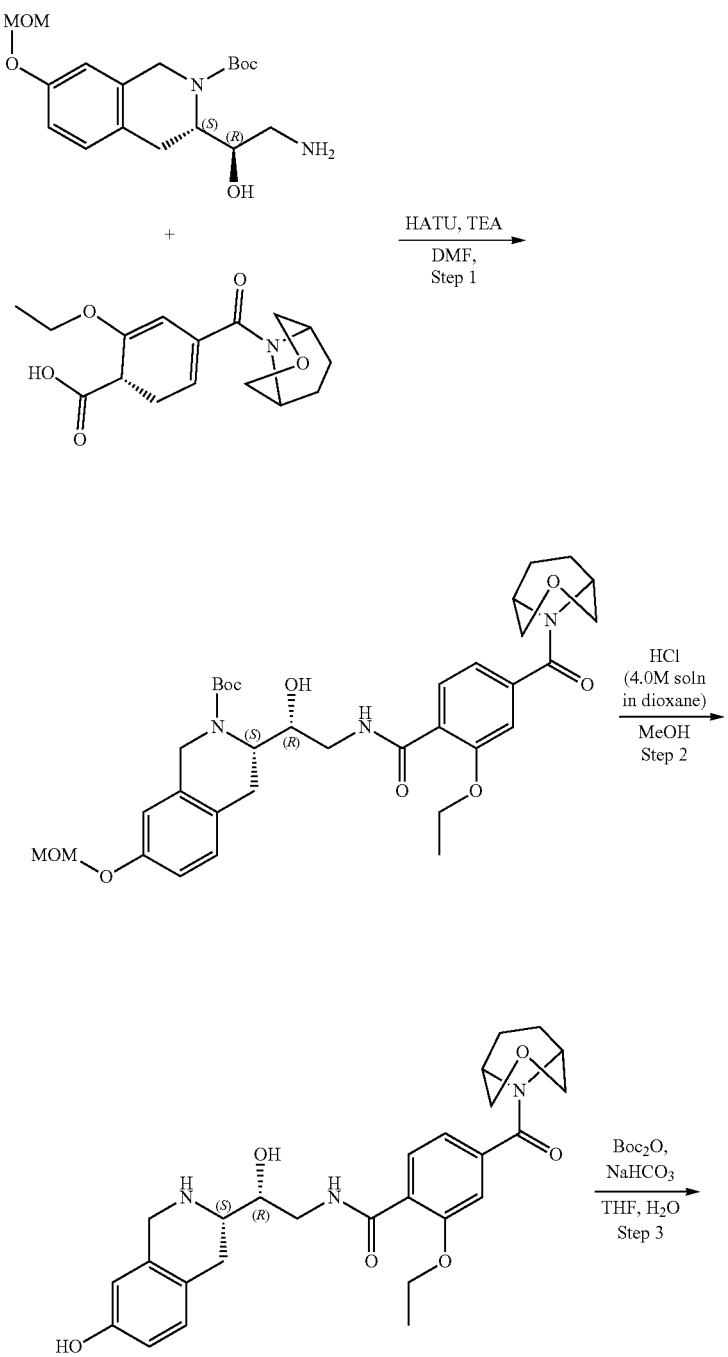

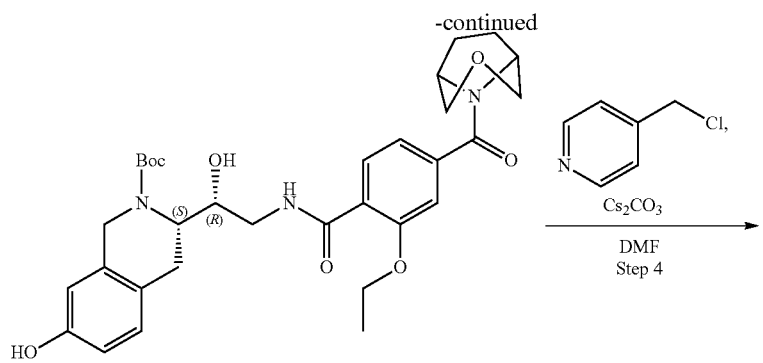

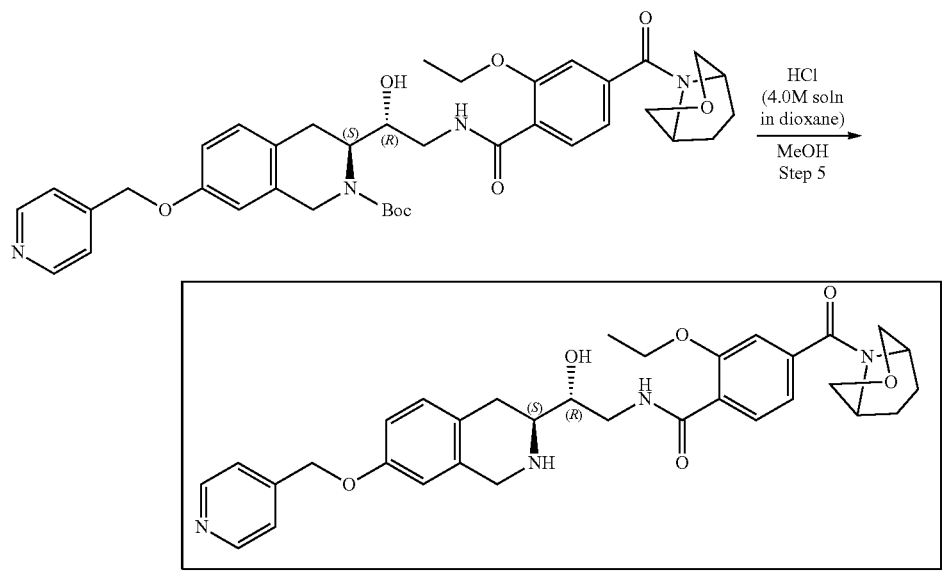

Steps 1-3 are the same as for Example 1A14.

Step 4: Synthesis of tert-butyl (3S)-3-[(1R)-2-[[2-ethoxy-4-(3-oxa-8-azabicyclo[3.2.1]octane-8-carbonyl)benzoyl]amino]-1-hydroxy-ethyl]-7-(4-pyridylmethoxy)-3,4-dihydro-1H-isoquinoline-2-carboxylate tert-Butyl (3S)-3-[(1R)-2-[[2-ethoxy-4-(3-oxa-8-azabicyclo[3.2.1]octane-8-carbonyl)benzoyl]-amino]-1-hydroxy-ethyl]-7-hydroxy-3,4-dihydro-1H-isoquinoline-2-carboxylate (0.135 g, 226.63 μmol), 4-(chloromethyl)pyridine (52.04 mg, 317.28 μmol, HCl) and cesium carbonate (295.36 mg, 906.52 μmol) were dissolved in DMF (3 mL) and stirred at 50° C. overnight. The reaction mixture was filtered off and washed with DMF (2 mL). The filtrate was concentrated in vacuo at 60° C. to give tert-butyl (3S)-3-[(1R)-2-[[2-ethoxy-4-(3-oxa-8-azabicyclo[3.2.1]octane-8-carbonyl)benzoyl]amino]-1-hydroxy-ethyl]-7-(4-pyridyl-methoxy)-3,4-dihydro-1H-isoquinoline-2-carboxylate (0.151 g, 219.86 μmol, 97.01% yield) which was used in the next step without further purification. $^1$H NMR (CDCl$_3$, 400 MHz): δ 1.48 (s, 9H), 2.01 (m, 6H), 3.07 (m, 2H), 3.54 (m, 4H), 3.70 (m, 4H), 4.25 (m, 5H), 4.67 (m, 2H), 5.04 (m, 2H), 6.78 (m, 2H), 6.80 (m, 4H), 7.33 (m, 2H), 8.57 (m, 2H). LCMS (ESI): [M+H]$^+$ m/z: calc'd 686.3; found 687.2; Rt=3.22 min.

Step 5: Synthesis of 2-ethoxy-N-[(2R)-2-hydroxy-2-[(3S)-7-(4-pyridylmethoxy)-1,2,3,4-tetrahydroisoquinolin-3-yl]ethyl]-4-(3-oxa-8-azabicyclo[3.2.1]octane-8-carbonyl)benzamide (Compound 73) tert-Butyl (3S)-3-[(1R)-2-[[2-ethoxy-4-(3-oxa-8-azabicyclo[3.2.1]octane-8-carbonyl)benzoyl]-amino]-1-hydroxy-ethyl]-7-(4-pyridylmethoxy)-3,4-dihydro-1H-isoquinoline-2-carboxylate (0.151 g, 219.86 μmol) was dissolved in MeOH (3 mL). Then hydrogen chloride solution 4.0M in dioxane (601.23 mg, 16.49 mmol, 751.54 μL) was added. The resulting mixture was stirred for 4 hr at 20° C. After the completion of the reaction, solvent was removed in vacuo at 45° C. The residue was dissolved in 5 mL of methanol and 12 mg of scavenger (SiliaMetS© Dimercaptotriazine(DMT) was added. The resulting suspension was stirred for 12 h. The suspension was filtered off, the filtrate was evaporated under reduced pressure, and the residue was purified by HPLC (60-100% water+NH$_3$-methanol+NH$_3$, 2-7 min, flow 30 mL/min (loading pump 4 mL/min methanol+NH$_3$), column: YMC-Actus Triart C18 100*20 mm) to give 2-ethoxy-N-[(2R)-2-hydroxy-2-[(3S)-7-(4-pyridylmethoxy)-1,2,3,4-tetrahydroisoquinolin-3-yl]ethyl]-4-(3-oxa-8-azabicyclo[3.2.1]octane-8-carbonyl)benzamide (15.30 mg, 26.08 μmol, 11.86% yield). $^1$H NMR (DMSO-d$_6$, 500 MHz): δ 1.48 (t, 3H), 1.93 (m, 4H), 2.62 (m, 1H), 2.76 (m, 2H), 3.38 (m, 1H), 3.50 (m, 2H), 3.65 (m, 4H), 3.72 (m, 1H), 3.92 (m, 3H), 4.23 (q, 2H), 4.53 (m, 1H), 4.91 (m, 1H), 5.08 (s, 2H), 6.62 (s, 1H), 6.70 (d, 1H), 6.98 (d, 1H), 7.06 (d, 1H), 7.12 (s, 1H), 7.36 (d, 2H), 7.97 (d, 1H), 8.35 (t, 1H), 8.50 (m, 2H). LCMS (ESI): [M+2H]$^+$ m/z: calc'd 586.3; found 588.2; Rt=0.84 min.

Example 2—Synthesis of Compounds of Formula (IIa1i)
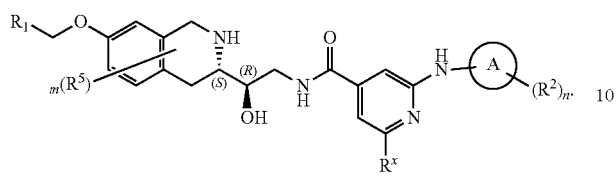
wherein $R^1$, $R^2$, $R^5$, $R^x$, m, n and A are as defined herein
Scheme 2A
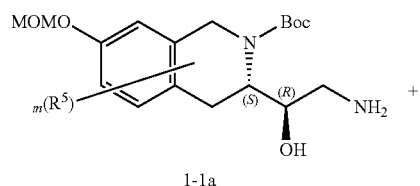
1-1a
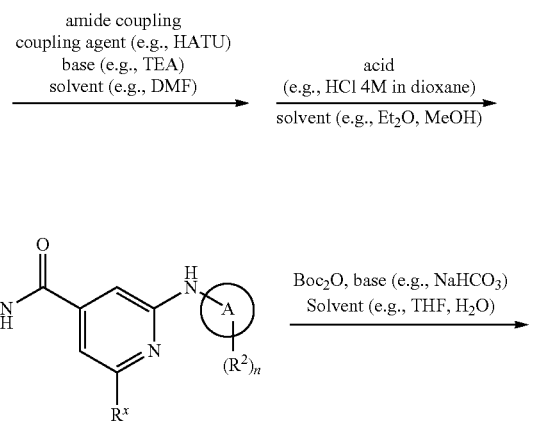
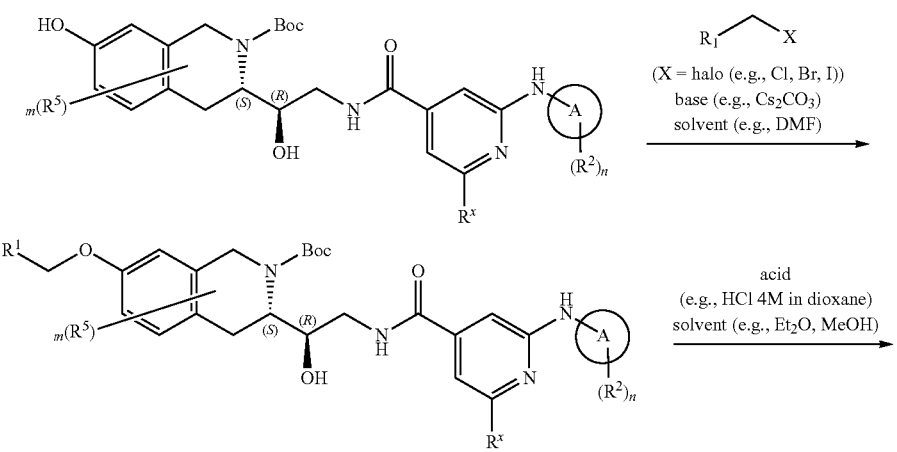

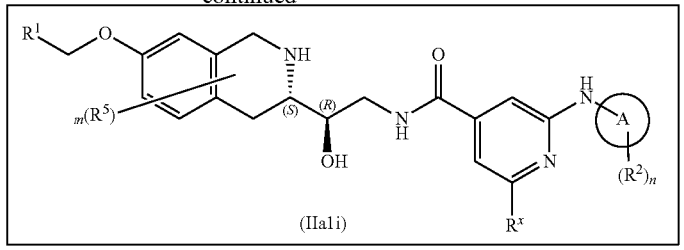
wherein X is a leaving group. In some embodiments, X is selected from Cl, Br, and I. In some embodiments X is Cl or Br.
Example 2A1. Synthesis of 2-(cyclobutylamino)-N—((R)-2-hydroxy-2-((S)-7-(oxazol-5-ylmethoxy)-1,2,3,4-tetrahydroisoquinolin-3-yl)ethyl)isonicotinamide (Compound 19)
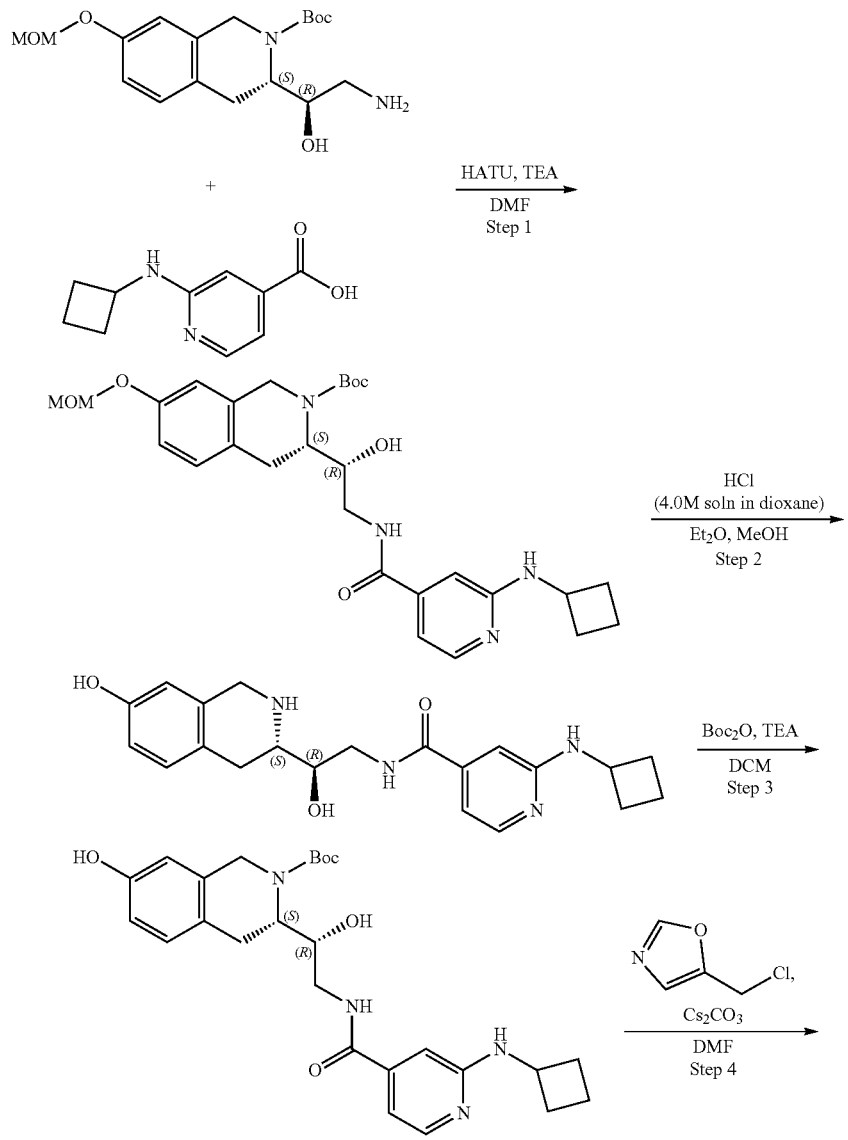

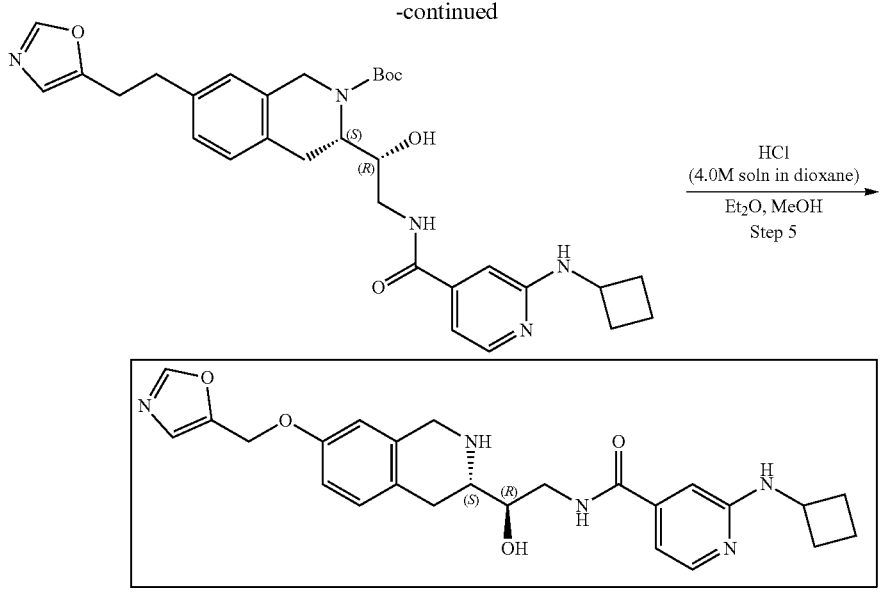

Step 1: Synthesis of (S)-tert-butyl 3-((R)-2-(2-(cyclobutylamino)isonicotinamido)-1-hydroxyethyl)-7-(methoxymethoxy)-3,4-dihydroisoquinoline-2(1H)-carboxylate 2-(Cyclobutylamino)pyridine-4-carboxylic acid (272.70 mg, 1.42 mmol) and TEA (1.44 g, 14.19 mmol, 1.98 mL) were mixed together in DMF (10 mL) and cooled to 0° C. Then, HATU (809.17 mg, 2.13 mmol) was added and the mixture was stirred for 15 min at 0° C. followed by the addition of the tert-butyl (3S)-3-[(1R)-2-amino-1-hydroxyethyl]-7-(methoxymethoxy)-3,4-dihydro-1H-isoquinoline-2-carboxylate (0.5 g, 1.42 mmol). The resulting mixture was warmed to r.t. and stirred overnight. After all starting material was consumed, as was shown by LCMS, 10 mL of ethyl acetate was added, and the organic phase was washed with brine three times. The organic layer was dried over $Na_2SO_4$, filtered off and concentrated in vacuo at 45° C. to give crude product which was purified by HPLC (40-55% water-acetonitrile, 2-10 min, flow: 30 mL/min (loading pump 4 mL/min acetonitrile) column: SunFire C18 100*19 mm) to give tert-butyl (3S)-3-[(1R)-2-[[2-(cyclobutylamino)pyridine-4-carbonyl]amino]-1-hydroxy-ethyl]-7-(methoxymethoxy)-3,4-dihydro-TH-isoquinoline-2-carboxylate (0.406 g, 770.95 μmol, 54.34% yield). $^1$H NMR (400 MHz, DMSO-$d_6$) δ (ppm) 1.40 (s, 9H), 1.44 (m, 2H), 1.66 (m, 2H), 2.25 (m, 2H), 2.77 (m, 1H), 3.02 (m, 2H), 3.32 (s, 3H), 3.46 (m, 1H), 3.60 (m, 1H), 4.16 (m, 3H), 4.77 (m, 1H), 5.15 (m, 3H), 6.73 (s, 1H), 6.80 (d, 1H), 6.85 (m, 2H), 6.91 (d, 1H), 7.08 (d, 1H), 7.99 (m, 1H), 8.36 (m, 1H). LCMS (ESI): [M+H]$^+$ m/z: calc'd 526.6; found 527.4; Rt=1.21 min.

Step 2: Synthesis of 2-(cyclobutylamino)-N—((R)-2-hydroxy-2-((S)-7-hydroxy-1,2,3,4-tetrahydroisoquinolin-3-yl)ethyl)isonicotinamide Hydrogen chloride solution 4.0M in dioxane (2.11 g, 57.82 mmol, 2.64 mL) was added to the solution of the tert-butyl (3S)-3-[(1R)-2-[[2-(cyclobutylamino)pyridine-4-carbonyl]amino]-1-hydroxy-ethyl]-7-(methoxymethoxy)-3,4-dihydro-TH-isoquinoline-2-carboxylate (0.406 g, 770.95 μmol) in the mixture of $Et_2O$ (4 mL) and MeOH (2 mL). The resulting mixture was stirred for 24 h at 20° C. The formed solid was filtered on, washed with $Et_2O$ (4 mL) and dried in vacuo at 35° C. to give 2-(cyclobutylamino)-N-[(2R)-2-hydroxy-2-[(3S)-7-hydroxy-1,2,3,4-tetrahydroisoquinolin-3-yl]ethyl]pyridine-4-carboxamide (0.302 g, 663.19 μmol, 86.02% yield, 2HCl). $^1$H NMR (500 MHz, DMSO-$d_6$) δ (ppm) 1.75 (m, 3H), 1.99 (m, 2H), 2.41 (m, 2H), 2.97 (m, 2H), 3.39 (m, 2H), 4.12 (m, 4H), 6.59 (m, 1H), 6.70 (s, 1H), 6.72 (d, 1H), 7.19 (m, 3H), 8.01 (d, 1H), 8.88 (m, 1H), 9.14 (m, 1H), 6.42 (m, 1H), 9.61 (m, 1H). LCMS (ESI): [M+H]$^+$ m/z: calc'd 382.2; found 383.2; Rt=0.67 min.

Step 3: Synthesis of (S)-tert-butyl 3-((R)-2-(2-(cyclobutylamino)isonicotinamido)-1-hydroxyethyl)-7-hydroxy-3,4-dihydroisoquinoline-2(1H)-carboxylate Sodium hydrogen carbonate, 99% (169.35 mg, 2.02 mmol, 78.40 μL) was added in one portion to the solution of the 2-(cyclobutylamino)-N-[(2R)-2-hydroxy-2-[(3S)-7-hydroxy-1,2,3,4-tetrahydroisoquinolin-3-yl]ethyl]pyridine-4-carboxamide (0.306 g, 671.97 μmol, 2HCl) in the mixture of water (8 mL) and THF (8 mL). The resulting mixture was stirred for 5 min at room temperature followed by the dropwise addition of the solution of di-tert-butyl dicarbonate (146.66 mg, 671.97 μmol, 154.21 μL) in THF (2 mL). The reaction mixture was stirred overnight at room temperature. After the completion of the reaction, ethyl acetate (15 mL) was added to the reaction mixture. The organic phase was separated and washed with brine, dried over $Na_2SO_4$, filtered off and evaporated in vacuo at 40° C. to give tert-butyl (3S)-3-[(1R)-2-[[2-(cyclobutylamino)pyridine-4-carbonyl]amino]-1-hydroxy-ethyl]-7-hydroxy-3,4-dihydro-1H-isoquinoline-2-carboxylate (0.27 g, 559.50 μmol, 83.26% yield) which was used in the next step without purification. $^1$H NMR (500 MHz, DMSO-$d_6$) δ (ppm) 1.46 (m, 12H), 1.51 (m, 2H), 1.69 (m, 2H), 2.27 (m, 2H), 2.72 (m, 1H), 2.98 (m, 2H), 3.49 (m, 2H), 4.14 (m, 2H), 4.72 (m, 1H), 5.09 (m, 1H), 6.56 (m, 1H), 6.61 (s, 1H), 6.76 (d, 1H), 6.80 (d, 1H), 6.96 (d, 1H), 8.02 (s, 1H), 8.32 (m, 1H), 9.15 (s, 1H). LCMS (ESI): [M+H]$^+$ m/z: calc'd 482.6; found 483.4; Rt=1.03 min.

Step 4: Synthesis of (S)-tert-butyl 3-((R)-2-(2-(cyclobutylamino)isonicotinamido)-1-hydroxyethyl)-7-(oxazol-5-ylmethoxy)-3,4-dihydroisoquinoline-2(1H)-carboxylate tert-Butyl (3S)-3-[(1R)-2-[[2-(cyclobutylamino)pyridine-4-carbonyl]amino]-1-hydroxy-ethyl]-7-hydroxy-3,4-dihydro-1H-isoquinoline-2-carboxylate (0.06 g, 124.33 μmol), 5-(chloromethyl)oxazole (21.06 mg, 136.77 μmol, HCl) and cesium carbonate (121.53 mg, 373.00 µmol) were mixed together in DMF (2 mL) and stirred at 50° C. overnight. The reaction mixture was diluted with water end extracted three times with EtOAc. The organic phase was washed three times with brine, dried over Na$_2$SO$_4$, filtered off and evaporated at 40° C. to give tert-butyl (3S)-3-[(1R)-2-[[2-(cyclobutylamino)pyridine-4-carbonyl]amino]-1-hydroxyethyl]-7-(oxazol-5-ylmethoxy)-3,4-dihydro-1H-isoquinoline-2-carboxylate (0.052 g, 92.26 µmol, 74.20% yield) which was used in the next step without further purification. $^1$H NMR (400 MHz, DMSO-d$_6$) δ (ppm) 1.41 (m, 9H), 1.67 (m, 3H), 1.87 (m, 2H), 2.25 (m, 3H), 3.04 (m, 2H), 3.51 (m, 2H), 4.13 (m, 4H), 5.13 (s, 2H), 6.73 (s, 1H), 6.84 (m, 4H), 7.32 (s, 1H), 7.99 (d, 1H), 8.40 (m, 1H). LCMS (ESI): [M+H]$^+$ m/z: calc'd 563.6; found 564.4; Rt=2.86 min.

Step 5: Synthesis of 2-(cyclobutylamino)-N—((R)-2-hydroxy-2-((S)-7-(oxazol-5-ylmethoxy)-1, 2, 3,4-tetrahydroisoquinolin-3-yl)ethyl)isonicotinamide (Compound 19) Hydrogen chloride solution 4.0M in dioxane (252.28 mg, 6.92 mmol, 315.35 µL) was added to the solution of the tert-butyl (3S)-3-[(1R)-2-[[2-(cyclobutylamino)pyridine-4-carbonyl]amino]-1-hydroxy-ethyl]-7-(oxazol-5-ylmethoxy)-3,4-dihydro-1H-isoquinoline-2-carboxylate (0.052 g, 92.26 µmol) in the mixture of Et$_2$O (1 mL) and MeOH (0.5 mL). The resulting mixture was stirred for 24 h at 20° C. The formed solid was filtered on, washed with Et$_2$O (1 mL) and dried in vacuo at 35° C. to give crude product which was purified by HPLC (40-55% water-acetonitrile+NH$_3$, 10 min, flow: 30 mL/min (loading pump 4 mL/min acetonitrile), column: YMC-Actus Triart C18 to give 2-(cyclobutylamino)-N-[(2R)-2-hydroxy-2-[(3S)-7-(oxazol-5-ylmethoxy)-1,2,3,4-tetrahydroisoquinolin-3-yl]ethyl]pyridine-4-carboxamide (13.30 mg, 28.69 µmol, 31.10% yield). $^1$H NMR (400 MHz, DMSO-d$_6$) δ 1.67 (m, 2H), 1.86 (m, 2H), 2.26 (m, 2H), 2.43 (m, 1H), 2.59 (m, 2H), 2.69 (m, 2H), 3.26 (m, 1H), 3.52 (m, 1H), 3.64 (m, 1H), 3.88 (AB-system, 2H), 4.27 (m, 1H), 4.94 (d, 1H), 5.11 (s, 2H), 6.70 (s, 1H), 6.76 (s, 1H), 6.80 (d, 1H), 6.96 (d, 1H), 7.01 (d, 1H), 7.30 (s, 1H), 8.02 (d, 1H), 8.39 (s, 1H), 8.51 (t, 1H). LCMS (ESI): [M+H]$^+$ m/z: calc'd 463.2; found 464.2; Rt=0.77 min.

Example 2A2. Synthesis of 2-(cyclobutylamino)-N—((R)-2-hydroxy-2-((S)-7-((1-methyl-1H-pyrazol-5-yl)methoxy)-1,2,3,4-tetrahydroisoquinolin-3-yl)ethyl)isonicotinamide (Compound 14)

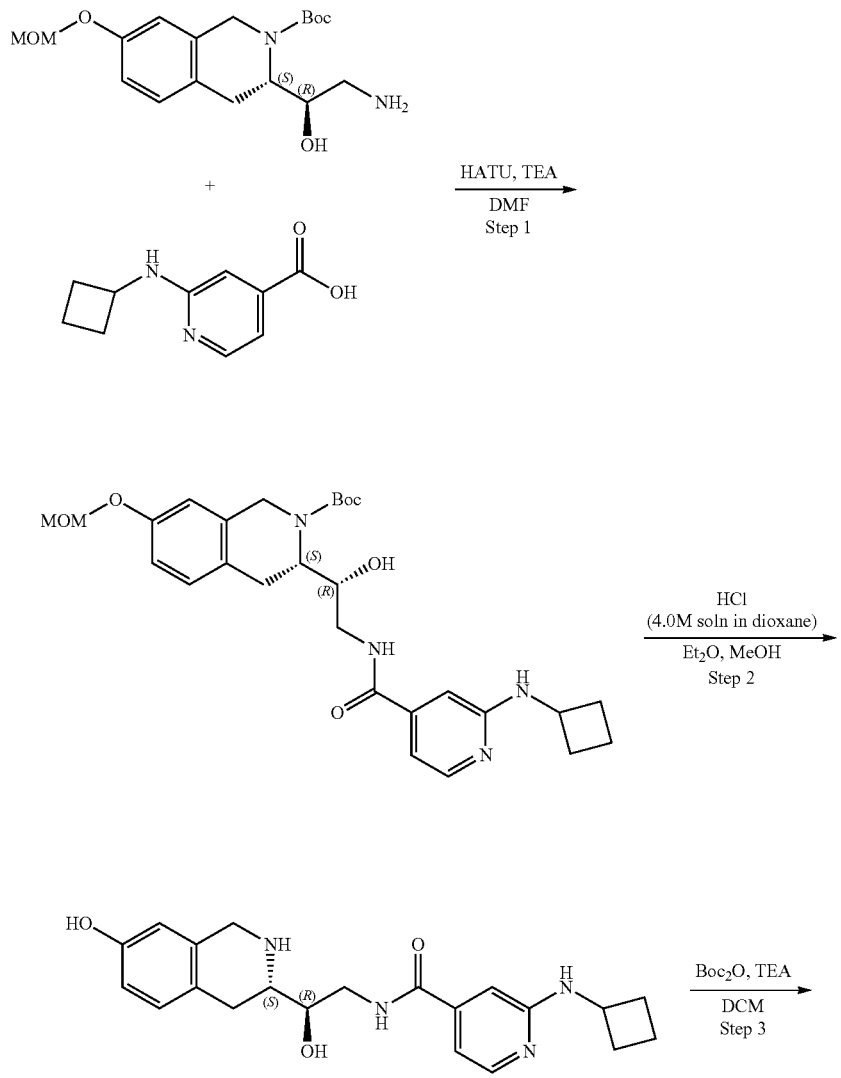

-continued

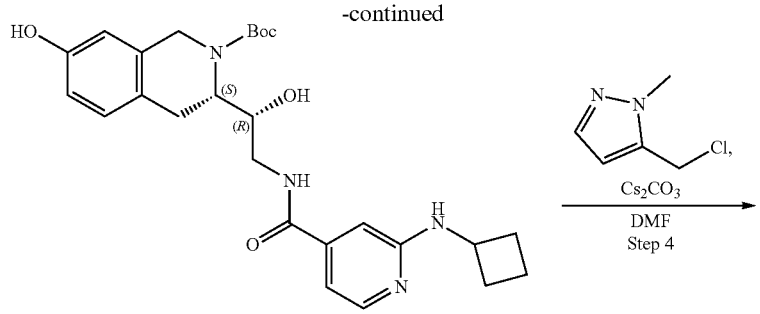

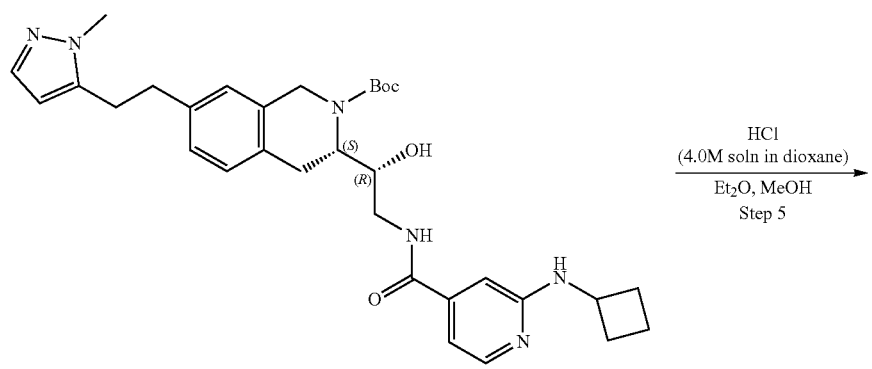

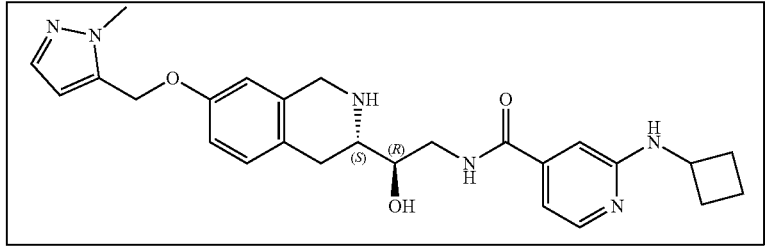

Steps 1-3 are the same as for Example 2A1.

Step 4: Synthesis of (S)-tert-butyl 3-((R)-2-(2-(cyclobutylamino)isonicotinamido)-1-hydroxyethyl)-7-((1-methyl-1H-pyrazol-5-yl)methoxy)-3,4-dihydroisoquinoline-2(1H)-carboxylate (S)-tert-Butyl 3-((R)-2-(2-(cyclobutylamino)isonicotinamido)-1-hydroxyethyl)-7-hydroxy-3,4-dihydroisoquinoline-2(1H)-carboxylate (103.61 μmol), 5-(chloromethyl)-1-methyl-1H-pyrazole (19.04 mg, 113.97 μmol, HCl) and cesium carbonate (101.28 mg, 310.84 μmol) were mixed together in DMF (2 mL) and stirred at 50° C. overnight. The reaction mixture was diluted with water end extracted three times with EtOAc. The organic phase was washed with brine, dried over $Na_2SO_4$, filtered on and evaporated at 40° C. to give product (0.048 g, 83.23 μmol, 80.33% yield) which was used in the next step without further purification. $^1$H NMR (400 MHz, DMSO-$d_6$) δ (ppm) 1.40 (m, 9H), 1.65 (m, 4H), 1.84 (m, 2H), 2.24 (m, 2H), 2.77 (m, 2H), 3.46 (m, 2H), 3.81 (s, 3H), 4.03 (m, 1H), 4.23 (m, 2H), 4.81 (m, 1H), 5.11 (m, 3H), 6.36 (s, 1H), 6.72 (d, 1H), 6.88 (m, 2H), 7.07 (d, 1H), 7.34 (s, 1H), 7.99 (d, 1H), 8.33 (m, 1H). LCMS (ESI): [M+H]$^+$ m/z: calc'd 576.3; found 577.2; Rt=1.19 min.

Step 5: Synthesis of 2-(cyclobutylamino)-N—((R)-2-hydroxy-2-((S)-7-((1-methyl-1H-pyrazol-5-yl)methoxy)-1,2,3,4-tetrahydroisoquinolin-3-yl)ethyl)isonicotinamide (Compound 14) Hydrogen chloride solution 4.0M in dioxane (227.61 mg, 6.24 mmol, 284.51 μL) was added to the solution of the tert-butyl (3S)-3-[(1R)-2-[[2-(cyclobutylamino)pyridine-4-carbonyl]amino]-1-hydroxy-ethyl]-7-[(2-methylpyrazol-3-yl)methoxy]-3,4-dihydro-1H-isoquinoline-2-carboxylate (0.048 g, 83.23 μmol) in the mixture of $Et_2O$ (1 mL) and MeOH (0.5 mL). The resulting mixture was stirred for 24 h at 20° C. The formed solid was filtered, washed with $Et_2O$ (1 mL) and dried in vacuo at 35° C. to give crude product which was purified by HPLC (15-40% water-acetonitrile+$NH_3$, 10 min, flow: 30 mL/min (loading pump 4 mL/min acetonitrile), column: SunFire C18 100*19 mm to give 2-(cyclobutylamino)-N-[(2R)-2-hydroxy-2-[(3S)-7-[(2-methylpyrazol-3-yl)methoxy]-1,2,3,4-tetrahydroisoquinolin-3-yl]ethyl]pyridine-4-carboxamide (0.0166 g, 34.83 μmol, 41.85% yield). $^1$H NMR (Chloroform-d, 400 MHz): δ (ppm) 1.83 (m, 7H), 2.44 (m, 2H), 2.80 (m, 2H), 3.04 (m, 2H), 3.89 (s, 3H), 4.02 (s, 2H), 4.17 (m, 2H), 4.88 (m, 1H), 4.98 (s, 2H), 6.28 (s, 1H), 6.61 (d, 1H), 6.69 (s, 1H), 6.74 (t, 2H), 7.06 (m, 2H), 7.42 (s, 1H), 8.11 (d, 1H). LCMS (ESI): [M+2H]$^+$ m/z: calc'd 476.2; found 478.2; Rt=0.85 min.

Example 2A3. Synthesis of 2-(cyclobutylamino)-N—((R)-2-hydroxy-2-((S)-7-((4-methyloxazol-5-yl)methoxy)-1,2,3,4-tetrahydroisoquinolin-3-yl)ethyl)isonicotinamide (Compound 15)
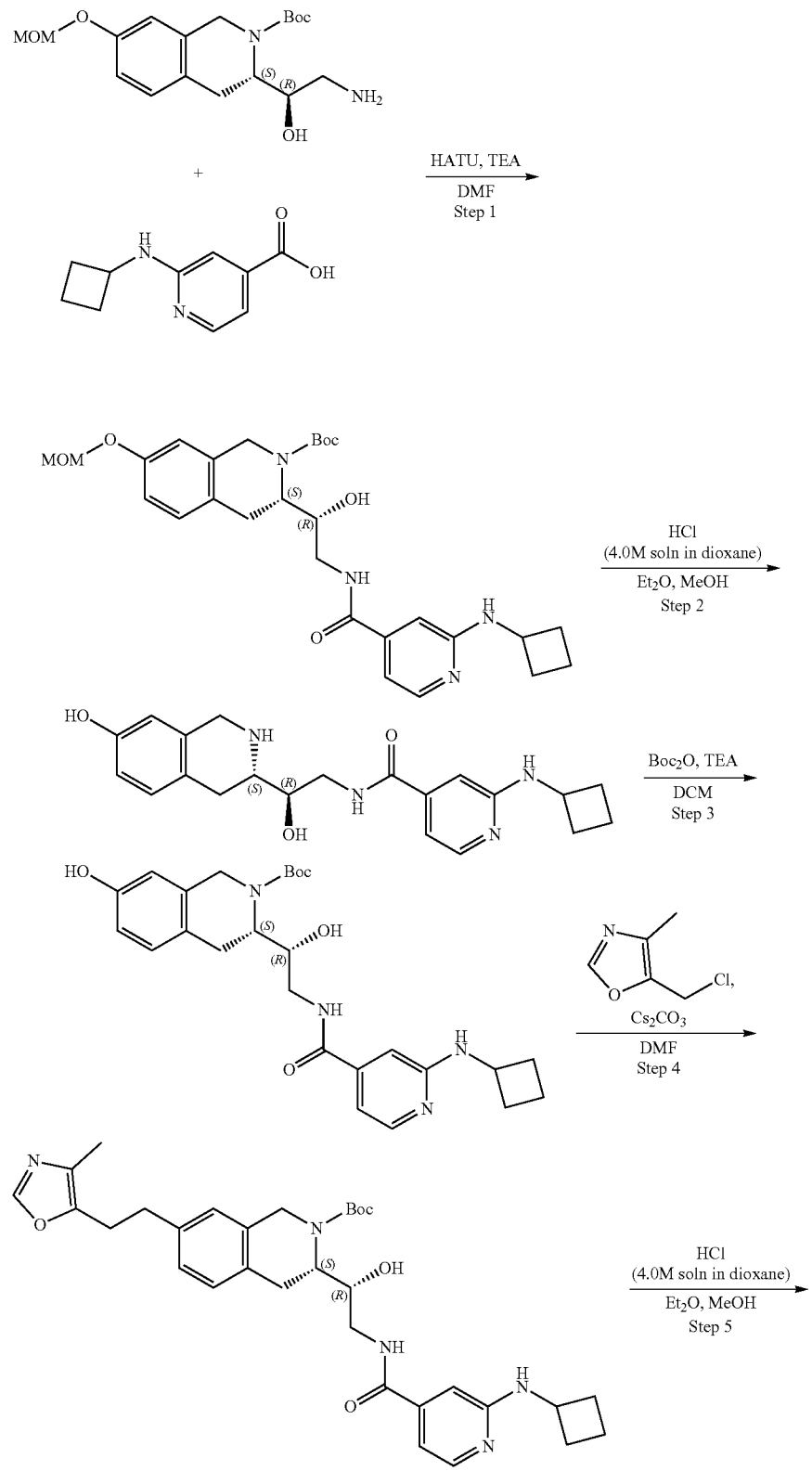

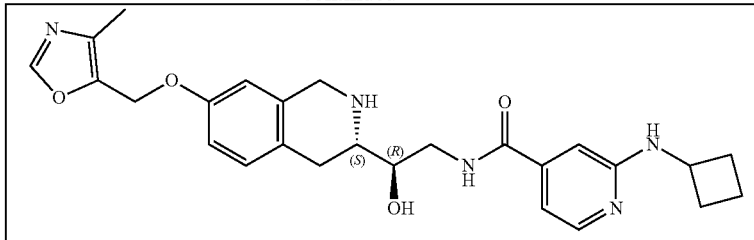

Steps 1-3 are the same as for Example 2A1.

Step 4: Synthesis of (S)-tert-butyl 3-((R)-2-(2-(cyclobutylamino)isonicotinamido)-1-hydroxyethyl)-7-((4-methyloxazol-5-yl)methoxy)-3,4-dihydroisoquinoline-2(1H)-carboxylate tert-Butyl (3S)-3-[(1R)-2-[[2-(cyclobutylamino)pyridine-4-carbonyl]amino]-1-hydroxy-ethyl]-7-hydroxy-3,4-dihydro-1H-isoquinoline-2-carboxylate (0.06 g, 124.33 μmol), 5-(chloromethyl)-4-methyl-oxazole (22.98 mg, 136.77 μmol, HCl) and cesium carbonate (121.53 mg, 373.00 μmol) were mixed together in DMF (2 mL) and stirred at 50° C. overnight. The reaction mixture was diluted with water and extracted three times with EtOAc. The organic phase was washed with brine, dried over Na$_2$SO$_4$, filtered and evaporated at 40° C. to give tert-butyl (3S)-3-[(1R)-2-[[2-(cyclobutylamino)pyridine-4-carbonyl]amino]-1-hydroxy-ethyl]-7-[(4-methyloxazol-5-yl)methoxy]-3,4-dihydro-1H-isoquinoline-2-carboxylate (0.045 g, 77.90 μmol, 62.65% yield) which was used in the next step without further purification. $^1$H NMR (400 MHz, DMSO-d$_6$) δ (ppm) 1.41 (m, 9H), 1.66 (m, 2H), 1.84 (m, 2H), 2.15 (s, 3H), 2.86 (m, 2H), 3.02 (m, 2H), 4.08 (m, 4H), 4.76 (m, 1H), 5.08 (m, 2H), 6.73 (s, 1H), 6.78 (m, 2H), 6.88 (m, 2H), 7.06 (d, 1H), 7.99 (m, 1H). LCMS (ESI): [M+H]$^+$ m/z: calc'd 577.6; found 578.4; Rt=3.15 min.

Step 5: Synthesis of 2-(cyclobutylamino)-N—((R)-2-hydroxy-2-((S)-7-((4-methyloxazol-5-yl)methoxy)-1,2,3,4-tetrahydroisoquinolin-3-yl)ethyl)isonicotinamide (Compound 15) Hydrogen chloride solution 4.0M in dioxane (213.02 mg, 5.84 mmol, 266.28 μL) was added to the solution of the tert-butyl (3S)-3-[(1R)-2-[[2-(cyclobutylamino)pyridine-4-carbonyl]amino]-1-hydroxy-ethyl]-7-[(4-methyloxazol-5-yl)methoxy]-3,4-dihydro-1H-isoquinoline-2-carboxylate (0.045 g, 77.90 μmol) in the mixture of Et$_2$O (1 mL) and MeOH (0.5 mL). The resulting mixture was stirred for 24 h at 20° C. The formed solid was filtered on, washed with Et$_2$O (1 mL) and dried in vacuo at 35° C. to give crude product which was purified by HPLC (50-70% water-methanol+NH$_3$, 10 min, flow: 30 mL/min (loading pump 5 mL/min methanol+NH$_3$), column: YMC Actus Triart C18 100*20 mm to give 2-(cyclobutylamino)-N-[(2R)-2-hydroxy-2-[(3S)-7-[(4-methyloxazol-5-yl)methoxy]-1,2,3,4-tetrahydroisoquinolin-3-yl]ethyl]-pyridine-4-carboxamide (0.0179 g, 37.48 μmol, 48.12% yield).

Example 2A4. Synthesis of 2-(cyclobutylamino)-N—((R)-2-hydroxy-2-((S)-7-((4-methyloxazol-5-yl)methoxy)-1,2,3,4-tetrahydroisoquinolin-3-yl)ethyl)-6-(piperidin-1-yl)isonicotinamide (Compound 31)

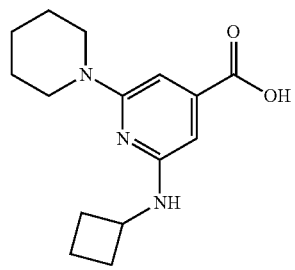

+

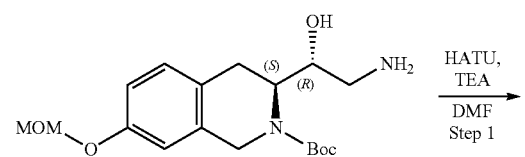

-continued
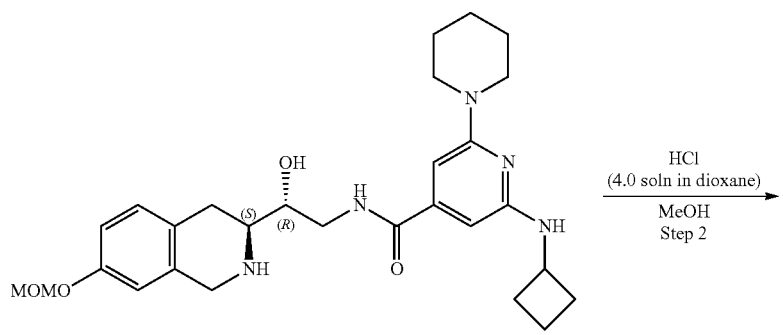
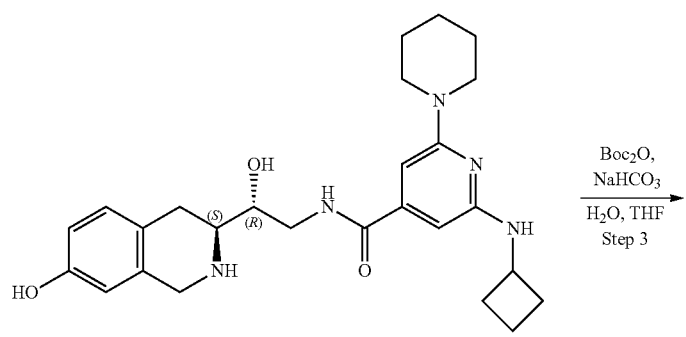
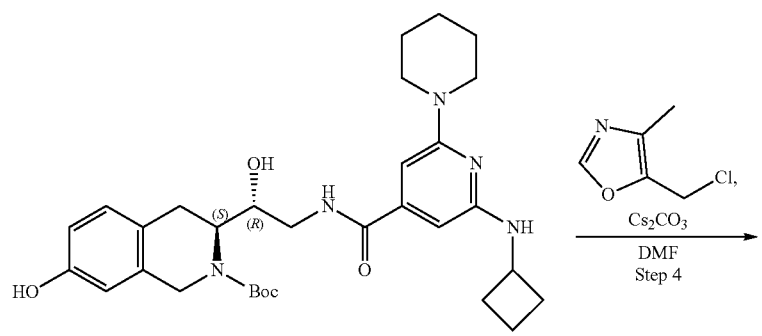
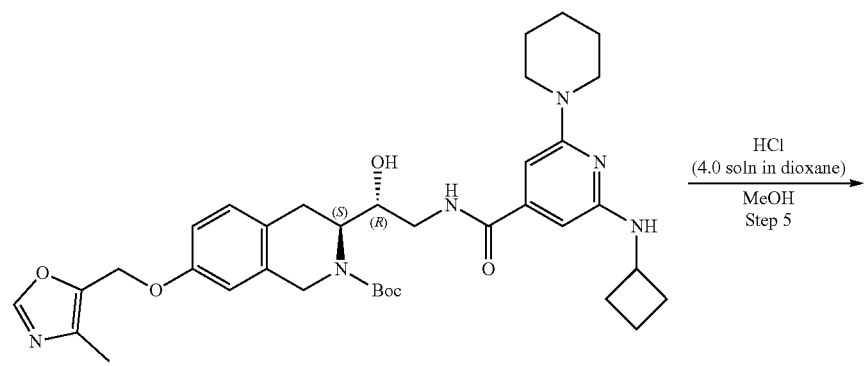

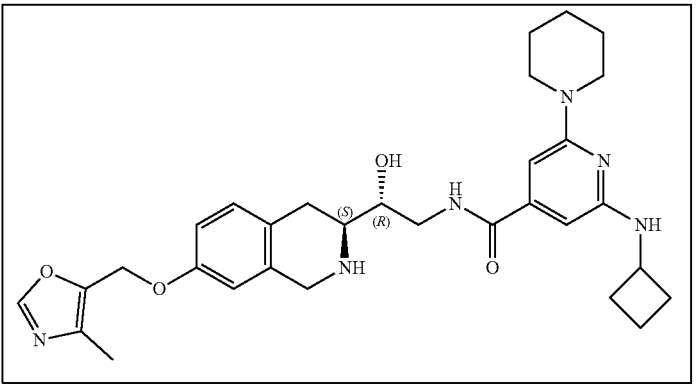

Step 1: Synthesis of (S)-tert-butyl 3-((R)-2-(2-(cyclobutylamino)-6-(piperidin-1-yl)isonicotinamido)-1-hydroxyethyl)-7-(methoxymethoxy)-3,4-dihydroisoquinoline-2(1H)-carboxylate 2-(Cyclobutylamino)-6-(1-piperidyl)pyridine-4-carboxylic acid (117.19 mg, 425.62 µmol), tert-butyl (3S)-3-[(1R)-2-amino-1-hydroxy-ethyl]-7-(methoxymethoxy)-3,4-dihydro-1H-isoquinoline-2-carboxylate (150 mg, 425.62 µmol), HATU (1.62 g, 4.26 mmol, 2.23 mL) were mixed in DMF (3 mL) and then triethylamine (64.60 mg, 638.44 µmol, 88.99 µL) was added. The resulting mixture were stirred at 25° C. for 12 hr. The mixture was evaporated under reduce pressure and purified with HPLC (50-75% water-acetonitrile, 10 min, flow: 30 mL/min) to obtain tert-butyl (3S)-3-[(1R)-2-[[2-[ethyl(methyl)amino]-6-(oxetan-3-ylamino)pyrimidine-4-carbonyl]amino]-1-hydroxy-ethyl]-7-(methoxymethoxy)-3,4-dihydro-1H-isoquinoline-2-carboxylate (47.6 mg, 78.06 µmol, 18.34% yield) $^1$H NMR (DMSO-d$_6$, 400 MHz) δ: 1.44 (m, 9H), 1.59 (m, 8H), 1.84 (m, 2H), 2.07 (m, 2H), 2.54 (s, 3H), 2.89 (m, 3H), 3.37 (s, 3H), 3.45 (m, 5H), 4.14 (m, 3H), 4.74 (m, 1H), 5.15 (s, 2H), 5.99 (s, 1H), 6.22 (s, 1H), 6.46 (d, 1H), 6.83 (m, 2H), 7.06 (d, 1H), 8.22 (m, 1H). LCMS (ESI): [M+H]$^+$ m/z: calc'd 609.5; found 610.4; Rt=1.52 min.

Step 2: Synthesis of 2-(cyclobutylamino)-N—((R)-2-hydroxy-2-((S)-7-hydroxy-1,2,3,4-tetrahydroisoquinolin-3-yl)ethyl)-6-(piperidin-1-yl)isonicotinamide The solution of tert-butyl (3S)-3-[(1R)-2-[[2-(cyclobutylamino)-6-(1-piperidyl)pyridine-carbonyl]amino]-1-hydroxy-ethyl]-7-(methoxymethoxy)-3,4-dihydro-1H-isoquinoline-2-carboxylate (47.6 mg, 78.06 µmol) in dioxane/HCl (2 mL) and methanol (2 mL) was stirred for 12 hr at 25° C. Then, the solution was evaporated to obtain 2-(cyclobutylamino)-N-[(2R)-2-hydroxy-2-[(3S)-7-hydroxy-1,2,3,4-tetrahydroisoquinolin-3-yl]ethyl]-6-(1-piperidyl)pyridine-4-carboxamide (30 mg, 55.71 µmol, 71.36% yield, 2HCl). $^1$H NMR (CDCl$_3$, 500 MHz) δ:1.76 (m, 6H), 2.03 (m, 4H), 2.52 (m, 3H), 3.09 (m, 3H), 3.38 (s, 3H), 3.62 (m, 6H), 4.29 (m, 4H), 5.17 (m, 1H), 6.28 (s, 1H), 6.64 (s, 1H), 6.74 (d, 1H), 7.12 (d, 1H), 7.98 (m, 1H). LCMS (ESI): [M+2H]$^+$ m/z: calc'd 465.3; found 467.2; Rt=0.95 min.

Step 3: Synthesis of (S)-tert-butyl 3-((R)-2-(2-(cyclobutylamino)-6-(piperidin-1-yl)isonicotinamido)-1-hydroxyethyl)-7-hydroxy-3,4-dihydroisoquinoline-2(1H)-carboxylate To a stirred solution of sodium hydrogen carbonate (13.15 mg, 156.53 µmol, 6.09 µL) in water (1 mL) 2-(cyclobutylamino)-N-[(2R)-2-hydroxy-2-[(3S)-7-hydroxy-1,2,3,4-tetrahydroisoquinolin-3-yl]ethyl]-6-(1-piperidyl)pyridine-4-carboxamide (30 mg, 52.18 µmol, 3HCl) was added in THF (1 mL) followed by di-tert-butyl dicarbonate (11.39 mg, 52.18 µmol, 11.97 µL) in THF (1 mL). The resulting mixture was stirred at 25° C. for 12 hr. EtOAc (10 mL) was added and organic phase was separated and washed with brine (2×5 mL). Then, the solvent was dried over sodium sulfate, filtered and evaporated to obtain tert-butyl (3S)-3-[(1R)-2-[[2-(cyclobutylamino)-6-(1-piperidyl)pyridine-4-carbonyl]amino]-1-hydroxy-ethyl]-7-hydroxy-3,4-dihydro-1H-isoquinoline-2-carboxylate (28 mg, crude). $^1$H NMR (CD$_3$OD, 400 MHz) δ:1.52 (m, 9H), 1.65 (m, 7H), 1.86 (m, 6H), 2.35 (m, 2H), 2.85 (m, 3H), 3.51 (m, 4H), 3.72 (m, 4H), 4.23 (m, 2H), 6.06 (s, 1H), 6.25 (s, 1H), 6.58 (m, 2H), 6.97 (d, 1H). LCMS (ESI): [M+H]$^+$ m/z: calc'd 565.2; found 566.2; Rt=1.27 min.

Step 4: Synthesis of (S)-tert-butyl 3-((R)-2-(2-(cyclobutylamino)-6-(piperidin-1-yl)isonicotinamido)-1-hydroxyethyl)-7-((4-methyloxazol-5-yl)methoxy)-3,4-dihydroisoquinoline-2(1H)-carboxylate To the solution of tert-butyl (3S)-3-[(1R)-2-[[2-(cyclobutylamino)-6-(1-piperidyl)pyridine-4-carbonyl]amino]-1-hydroxy-ethyl]-7-hydroxy-3,4-dihydro-1H-isoquinoline-2-carboxylate (28 mg, 49.50 µmol), cesium carbonate (48.38 mg, 148.49 µmol) in DMF (2 mL) was added 5-(chloromethyl)-4-methyl-oxazole (9.98 mg, 59.40 µmol, HCl). Resulting mixture was heated at 50° C. for 12 hr. The mixture was filtered and evaporated to obtain tert-butyl (3S)-3-[(1R)-2-[[2-(cyclobutylamino)-6-(1-piperidyl)pyridine-4-carbonyl]amino]-1-hydroxy-ethyl]-7-[(4-methyloxazol-5-yl)methoxy]-3,4-dihydro-1H-isoquinoline-2-carboxylate (50 mg, crude) that was used without further purification. $^1$H NMR (CD$_3$OD, 500 MHz) δ: 1.48 (m, 9H), 1.62 (m, 7H), 1.82 (m, 3H), 2.18 (m, 3H), 2.36 (m, 1H), 2.73 (m, 4H), 3.12 (s, 3H), 3.51 (m, 4H), 4.31 (m, 4H), 5.07 (s, 2H), 6.07 (s, 1H), 6.25 (s, 1H), 6.81 (s, 1H), 7.10 (m, 1H), 8.11 (m, 1H). LCMS (ESI): [M+H]$^+$ m/z: calc'd 660.8; found 661.4; Rt=1.48 min.

Step 5: Synthesis of 2-(cyclobutylamino)-N—((R)-2-hydroxy-2-((S)-7-((4-methyloxazol-5-yl)methoxy)-1,2,3,4-tetrahydroisoquinolin-3-yl)ethyl)-6-(piperidin-1-yl)isonicotinamide (Compound 31) The solution of tert-butyl (3S)-3-[(1R)-2-[[2-(cyclobutylamino)-6-(1-piperidyl)pyridine-4-carbonyl]amino]-1-hydroxy-ethyl]-7-[(4-methyloxazol-5-yl)methoxy]-3,4-dihydro-1H-isoquinoline-2-carboxylate (50 mg, 75.67 µmol) in dioxane/HCl (2.0 mL) and methanol (2.0 mL) was stirred for 12 h at 25° C. Then, the resulting solution was evaporated and the crude product was purified by HPLC (25-60% water-methanol, 10 min, flow: 30 mL/min) to obtain 2-(cyclobutylamino)-N-[(2R)-2-hydroxy-2-[(3S)-7-[(4-methyloxazol-5-yl)methoxy]-1,2,3,4-tetrahydroisoquinolin-3-yl]ethyl]-6-(1-piperidyl)pyridine-4-carboxamide (7.8 mg, 11.64 µmol, 15.38% yield, 3HCl). $^1$H NMR (CD₃OD, 400 MHz) δ: 1.63 (m, 6H), 1.86 (m, 4H), 2.23 (m, 3H), 2.43 (m, 2H), 2.75 (m, 2H), 3.12 (m, 2H), 3.45 (m, 1H), 3.63 (m, 6H), 4.28 (m, 4H), 5.14 (s, 2H), 6.58 (s, 1H), 6.83 (m, 2H), 6.95 (d, 1H), 7.32 (d, 1H), 8.23 (s, 1H). LCMS (ESI): [M+H]⁺ m/z: calc'd 560.1; found 561.4; Rt=2.48 min.
Example 2A5. Synthesis of 2-(cyclobutylamino)-N—((R)-2-hydroxy-2-((S)-7-((4-methyloxazol-5-yl)methoxy)-1,2,3,4-tetrahydroisoquinolin-3-yl)ethyl)-6-(4-isopropylpiperazin-1-yl)isonicotinamide (Compound 30)
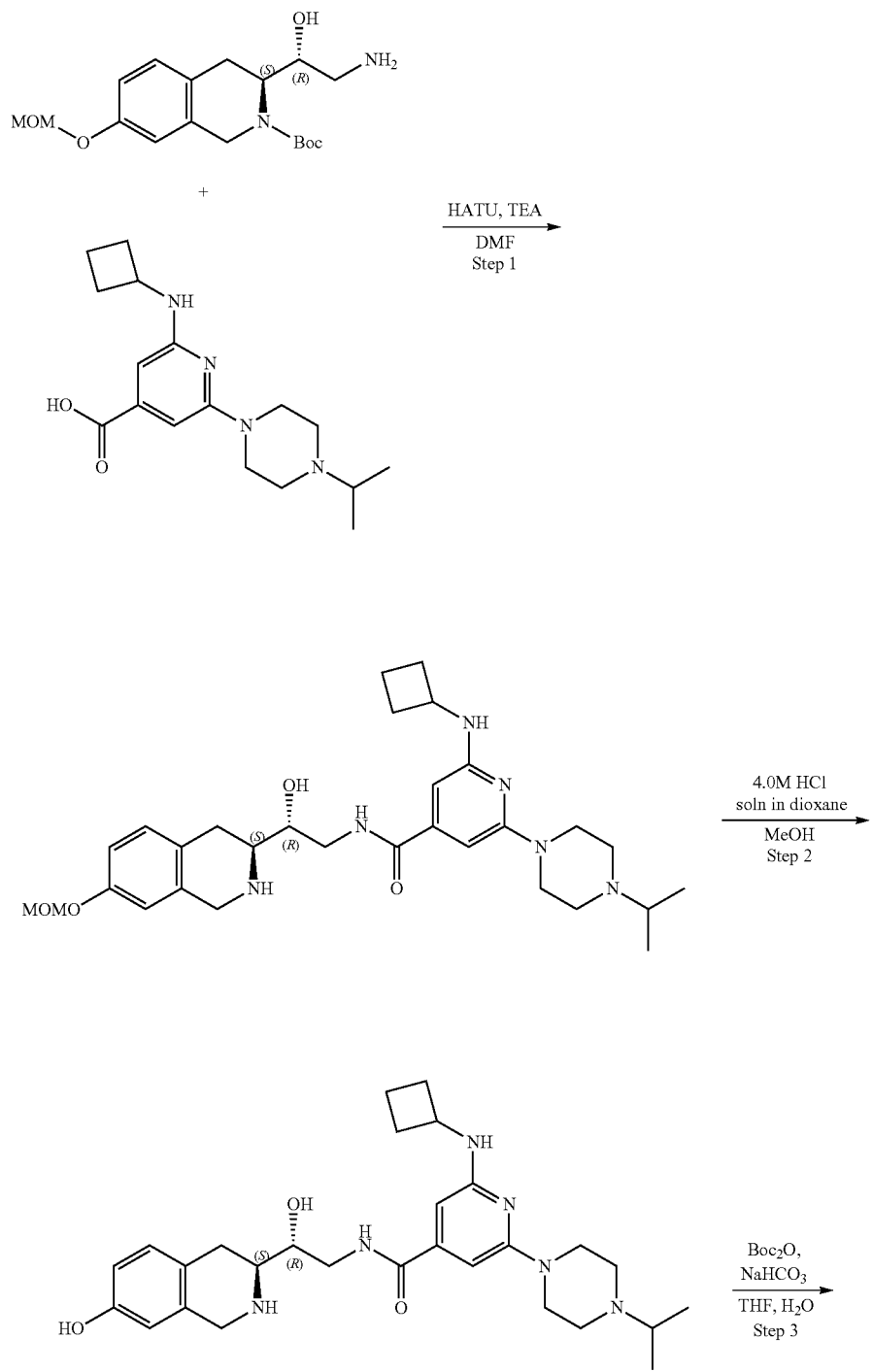

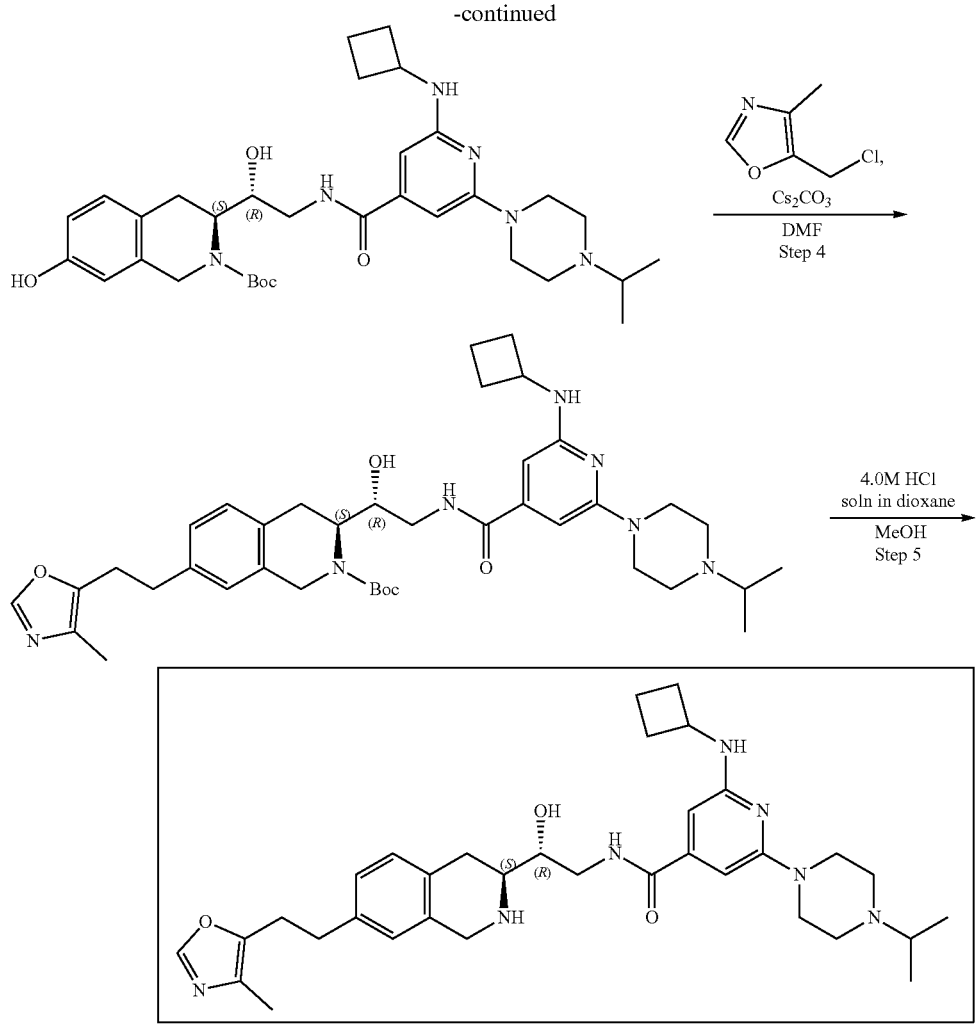

Step 1: Synthesis of (S)-tert-butyl 3-((R)-2-(2-(cyclobutylamino)-6-(4-isopropylpiperazin-1-yl)isonicotinamido)-1-hydroxyethyl)-7-(methoxymethoxy)-3,4-dihydroisoquinoline-2(1H)-carboxylate 2-(Cyclobutylamino)-6-(4-isopropylpiperazin-1-yl)pyridine-4-carboxylic acid (199.87 mg, 510.75 μmol, 2HCl) and TEA (430.69 mg, 4.26 mmol, 593.23 μL) were dissolved in DMF (3 mL) and cooled to 0° C., HATU (242.75 mg, 638.44 μmol) was added and the mixture was stirred for 15 min at 0° C. tert-Butyl (3S)-3-[(1R)-2-amino-1-hydroxy-ethyl]-7-(methoxymethoxy)-3,4-dihydro-1H-isoquinoline-2-carboxylate (0.15 g, 425.62 μmol) was added and the mixture was warmed to r.t. and stirred overnight. 10 ml of ethyl acetate was added, and organic phase was washed with brine three times. Organic phase was dried over Na$_2$SO$_4$, filtered and concentrated in vacuo at 45° C. to give crude product which was purified by HPLC (35-45% water-acetonitrile, 2-10 min, flow: 30 mL/min (loading pump 4 mL/min acetonitrile) column: SunFire C18 100×19 mm) to give tert-butyl (3S)-3-[(1R)-2-[[2-(cyclobutylamino)-6-(4-isopropylpiperazin-1-yl)pyridine-4-carbonyl]amino]-1-hydroxy-ethyl]-7-(methoxymethoxy)-3,4-dihydro-1H-isoquinoline-2-carboxylate (0.116 g, 177.69 μmol, 41.75% yield). $^1$H NMR (DMSO-d$_6$, 400 MHz) δ: 1.26 (m, 6H), 1.44 (s, 9H), 1.86 (m, 4H), 2.26 (m, 2H), 2.76 (m, 1H), 3.02 (m, 6H), 3.36 (m, 3H), 3.49 (m, 6H), 4.19 (m, 4H), 4.77 (m, 1H), 5.16 (s, 2H), 6.17 (s, 1H), 6.32 (s, 1H), 6.73 (d, 1H), 7.07 (m, 2H), 7.11 (d, 1H), 8.25 (m, 1H), 9.22 (t, 1H). LCMS (ESI): [M+H]$^+$ m/z: calc'd 652.3; found 653.4; Rt=1.31 min.

Step 2: Synthesis of 2-(cyclobutylamino)-N—((R)-2-hydroxy-2-((S)-7-hydroxy-1,2,3,4-tetrahydroisoquinolin-3-yl)ethyl)-6-(4-isopropylpiperazin-1-yl)isonicotinamide tert-Butyl (3S)-3-[(1R)-2-[[2-(cyclobutylamino)-6-(4-isopropylpiperazin-1-yl)pyridine-4-carbonyl]-amino]-1-hydroxy-ethyl]-7-(methoxymethoxy)-3,4-dihydro-1H-isoquinolin-2-carboxylate (0.116 g, 177.69 μmol) was dissolved in the mixture of MeOH (2 mL). Hydrogen chloride solution 4.0M in dioxane (485.91 mg, 13.33 mmol, 607.38 μL) was added. The mixture was stirred for 12 h at 20° C. Solvent was removed in vacuo at 35° C. to give 2-(cyclobutylamino)-N-[(2R)-2-hydroxy-2-[(3S)-7-hydroxy-1,2,3,4-tetrahydroisoquinolin-3-yl]ethyl]-6-(4-isopropylpiperazin-1-yl)pyridine-4-carboxamide (63 mg, 101.94 μmol, 57.37% yield, 3HCl). $^1$H NMR (CD$_3$OD, 400 MHz) δ: 1.40 (m, 6H), 1.77 (m, 2H), 1.94 (m, 2H), 2.38 (m, 2H), 3.18 (m, 6H), 3.58 (m, 8H), 4.38 (m, 4H), 5.15 (m, 2H), 6.60 (s, 1H), 6.73 (d, 1H), 7.11 (m, 3H). LCMS (ESI): [M+H]$^+$ m/z: calc'd 508.3; found 509.4; Rt=2.70 min.

Step 3: Synthesis of (S)-tert-butyl 3-((R)-2-(2-(cyclobutylamino)-6-(4-isopropylpiperazin-1-yl)isonicotinamido)-1- hydroxyethyl)-7-hydroxy-3,4-dihydroisoquinoline-2(1H)-carboxylate 2-(Cyclobutylamino)-N-[(2R)-2-hydroxy-2-[(3S)-7-hydroxy-1,2,3,4-tetrahydroisoquinolin-3-yl]-ethyl]-6-(4-isopropylpiperazin-1-yl)pyridine-4-carboxamide (63 mg, 101.94 µmol, 3HCl) was dissolved in the mixture of water (1 mL) and THF (1 mL), then sodium hydrogen carbonate, 99% (34.25 mg, 407.74 µmol, 15.86 µL) was added in one portion, after that solution of di-tert-butyl dicarbonate (22.25 mg, 101.94 µmol, 23.39 µL) in THF (0.2 mL) was added dropwise. The reaction mixture was stirred overnight at room temperature. Ethyl acetate (15 mL) was added to the reaction mixture, organic phase was separated, and the aqueous phase was extracted with ethyl acetate (2×15 mL). Organic phase was washed with brine, dried over Na$_2$SO$_4$, filtered and evaporated in vacuo at 40° C. to give tert-butyl (3S)-3-[(1R)-2-[[2-(cyclobutylamino)-6-(4-isopropylpiperazin-1-yl)pyridine-4-carbonyl]amino]-1-hydroxy-ethyl]-7-hydroxy-3,4-dihydro-1H-iso-quinoline-2-carboxylate (0.06 g, 98.56 µmol, 96.69% yield) which was used in the next step without purification. $^1$H NMR (CD$_3$OD, 500 MHz) δ: 1.14 (m, 6H), 1.52 (s, 11H), 1.75 (m, 3H), 1.90 (m, 2H), 2.37 (m, 2H), 2.82 (m, 6H), 3.08 (m, 2H), 3.58 (m, 5H), 4.30 (m, 3H), 6.13 (d, 1H), 6.31 (s, 1H), 6.60 (m, 2H), 7.00 (s, 1H). LCMS (ESI): [M+H]$^+$ m/z: calc'd 608.3; found 609.4; Rt=3.04 min.

Step 4: Synthesis of (S)-tert-butyl 3-((R)-2-(2-(cyclobutylamino)-6-(4-isopropylpiperazin-1-yl)isonicotinamido)-1-hydroxyethyl)-7-((4-methyloxazol-5-yl)methoxy)-3,4-dihydroisoquinoline-2(1H)-carboxylate tert-Butyl (3S)-3-[(1R)-2-[[2-(cyclobutylamino)-6-(4-isopropylpiperazin-1-yl)pyridine-4-carbonyl]-amino]-1-hydroxy-ethyl]-7-hydroxy-3,4-dihydro-1H-isoquinoline-2-carboxylate (0.06 g, 98.56 µmol), 5-(chloromethyl)-4-methyl-oxazole (19.87 mg, 118.27 µmol, HCl) and cesium carbonate (96.34 mg, 295.68 µmol) was dissolved in DMF (2 mL) and heated at 50° C. overnight. Reaction mixture was diluted with water end extracted three times with EA, then EA was extracted three times with brine. Organic phase was dried over Na$_2$SO$_4$, filtered and evaporated at 40° C. to give tert-butyl (3S)-3-[(1R)-2-[[2-(cyclobutylamino)-6-(4-isopropylpiperazin-1-yl)pyridine-4-carbonyl]amino]-1-hydroxy-ethyl]-7-[(4-methyloxazol-5-yl)-methoxy]-3,4-dihydro-1H-isoquinoline-2-carboxylate (0.063 g, 89.51 µmol, 90.81% yield) which was used in the next step without further purification. $^1$H NMR (CD$_3$OD, 500 MHz) δ:1.13 (d, 6H), 1.53 (m, 14H), 1.74 (m, 2H), 1.90 (m, 2H), 2.20 (m, 4H), 2.36 (m, 2H), 2.70 (m, 5H), 3.54 (m, 5H), 4.30 (m, 3H), 5.07 (s, 1H), 6.12 (d, 1H), 6.24 (d, 1H), 6.82 (s, 1H), 6.96 (s, 1H), 7.15 (m, 1H), 8.13 (m, 1H). LCMS (ESI): [M+2H]$^+$ m/z: calc'd 703.4; found 705.4; Rt=3.36 min.

Step 5: Synthesis of 2-(cyclobutylamino)-N—((R)-2-hydroxy-2-((S)-7-((4-methyloxazol-5-yl)methoxy)-1,2,3,4-tetrahydroisoquinolin-3-yl)ethyl)-6-(4-isopropylpiperazin-1-yl)isonicotinamide Compound 30) tert-Butyl (3S)-3-[(1R)-2-[[2-(cyclobutylamino)-6-(4-isopropylpiperazin-1-yl)pyridine-4-carbonyl]-amino]-1-hydroxy-ethyl]-7-[(4-methyloxazol-5-yl)methoxy]-3,4-dihydro-1H-isoquinoline-2-carboxylate (0.063 g, 89.51 µmol) was dissolved in the mixture of Methanol (1.5 mL). Hydrogen chloride solution 4.0M in dioxane (3.26 mg, 89.51 µmol, 4.08 µL) was added. The mixture was stirred for 20 hr at RT. Solvent was removed on vacuo at 45° C. The residue was dissolved in 5 ml of methanol and 12 mg of scavenger (SiliaMetS© Dimercaptotriazine(DMT) was added thereto and the resulting suspension was stirred for 12 h. The suspension was filtered, the filtrate was evaporated under reduced pressure and the residue was purified by HPLC (10-45% water-methanol, 10 min, flow: 30 mL/min (loading pump 4 mL/min methanol), column: SunFire C18 100*19 mm to give 2-(cyclobutylamino)-N-[(2R)-2-hydroxy-2-[(3S)-7-[(4-methyloxazol-5-yl)methoxy]-1,2,3,4-tetrahydroisoquinolin-3-yl]ethyl]-6-(4-isopropylpiperazin-1-yl)pyridine-4-carboxamide (0.0193 g, 25.75 µmol, 28.77% yield, 4HCl). $^1$H NMR, δ 1.39 (d, 6H), 1.74 (m, 2H), 1.90 (m, 2H), 2.19 (s, 3H), 2.34 (m, 2H), 2.65 (m, 1H), 3.17 (m, 6H), 3.58 (m, 6H), 4.27 (m, 3H), 4.47 (m, 2H), 5.08 (s, 2H), 6.24 (s, 1H), 6.41 (s, 1H), 6.87 (s, 1H), 6.96 (d, 1H), 7.21 (d, 1H), 8.13 (s, 1H), NH, NH, NH, OH, HCl are not observed. LCMS (ESI): [M+H]$^+$ m/z: calc'd 603.3; found 604.2; Rt=0.86 min.

Example 2A6. Synthesis of N—((R)-2-hydroxy-2-((S)-7-((4-methyloxazol-5-yl)methoxy)-1,2,3,4-tetrahydroisoquinolin-3-yl)ethyl)-2-(pyridin-3-ylamino)isonicotinamide (Compound 34)

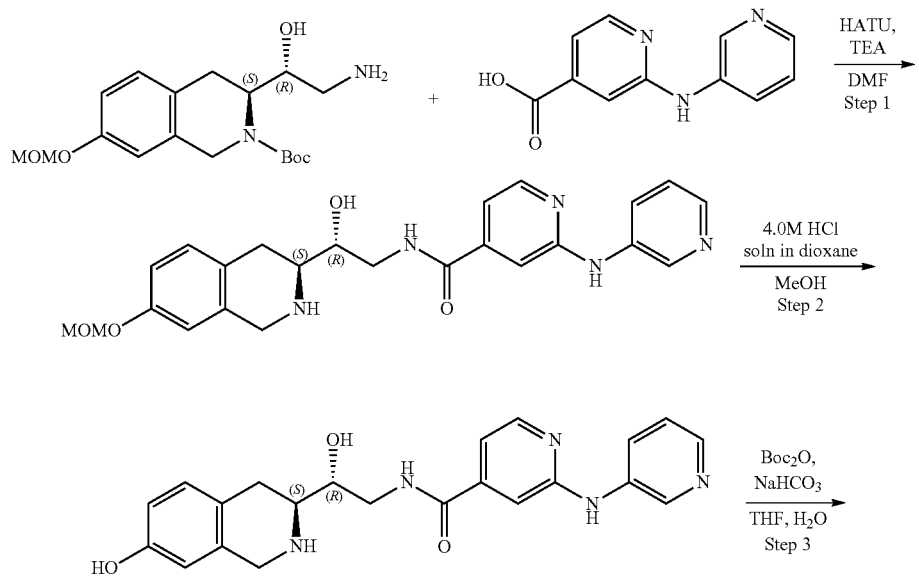

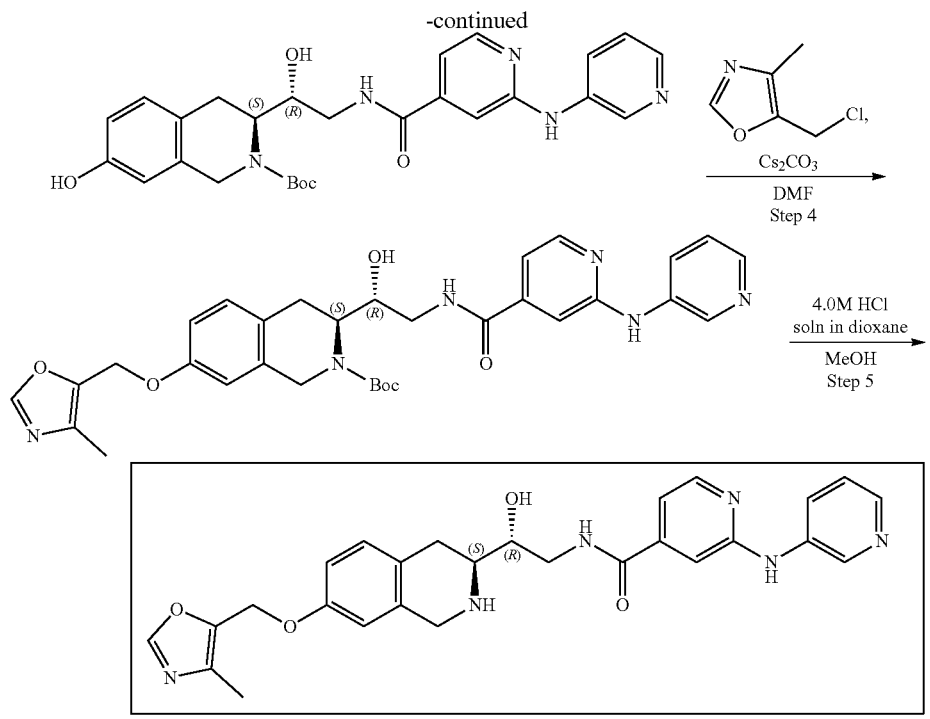

Step 1: Synthesis of (S)-tert-butyl 3-((R)-1-hydroxy-2-(2-(pyridin-3-ylamino)isonicotinamido)ethyl)-7-(methoxymethoxy)-3,4-dihydroisoquinoline-2(1H)-carboxylate 2-(3-Pyridylamino)pyridine-4-carboxylic acid (107.12 mg, 425.62 μmol, HCl), tert-butyl (3S)-3-[(1R)-2-amino-1-hydroxy-ethyl]-7-(methoxymethoxy)-3,4-dihydro-1H-isoquinoline-2-carboxylate (150.00 mg, 425.62 μmol), triethylamine (430.69 mg, 4.26 mmol, 593.23 μL) were mixed in DMF (4 mL) and then HATU (242.75 mg, 638.44 μmol) were added. Resulting mixture were stirred at 25° C. for 12 h. The mixture was evaporated under reduce pressure and purified with HPLC (50-65% water-acetonitrile, 2-10 min, Flow: 30 mL/min) to obtain tert-butyl (3S)-3-[(1R)-1-hydroxy-2-[[2-(3-pyridylamino)pyridine-4-carbonyl]amino]ethyl]-7-(methoxymethoxy)-3,4-dihydro-1H-isoquinoline-2-carboxylate (64.6 mg, 117.54 μmol, 27.62% yield). $^1$H NMR (CDCl$_3$, 400 MHz) δ:1.50 (s, 9H), 2.89 (m, 2H), 3.16 (m, 2H), 3.46 (m, 5H), 4.16 (m, 2H), 4.39 (m, 1H), 4.65 (m, 1H), 5.13 (s, 2H), 6.77 (s, 1H), 6.85 (d, 1H), 7.09 (m, 2H), 7.35 (m, 3H), 8.16 (m, 2H), 8.25 (d, 1H), 8.59 (m, 1H). LCMS (ESI): [M+H]$^+$ m/z: calc'd 549.2; found 550.2; Rt=1.15 min.

Step 2: Synthesis of N—((R)-2-hydroxy-2-((S)-7-hydroxy-1,2,3,4-tetrahydroisoquinolin-3-yl)ethyl)-2-(pyridin-3-ylamino)isonicotinamide A solution of tert-butyl (3S)-3-[(1R)-1-hydroxy-2-[[2-(3-pyridylamino)pyridine-4-carbonyl]amino]ethyl]-7-(methoxymethoxy)-1H-isoquinoline-2-carboxylate (64.6 mg, 117.54 μmol) in dioxane/HCl (2 mL) and methanol (2 mL) was stirred for 12 h at 25° C. Then, the solution was evaporated to obtain N-[(2R)-2-hydroxy-2-[(3S)-7-hydroxy-1,2,3,4-tetrahydroisoquinolin-3-yl]ethyl]-2-(3-pyridylamino)pyridine-4-carboxamide (53 mg, 110.79 μmol, 94.26% yield, 2HCl). $^1$H NMR (CD$_3$OD, 500 MHz) δ: 3.36 (m, 4H), 3.62 (m, 4H), 4.35 (m, 3H), 6.63 (s, 1H), 6.75 (d, 1H), 7.12 (d, 1H), 7.36 (d, 1H), 7.37 (s, 1H), 7.95 (td, 1H), 8.35 (d, 1H), 8.44 (d, 1H), 8.54 (d, 1H), 9.80 (t, 1H), OH isn't observed. LCMS (ESI): [M+H]+ m/z: calc'd 405.2; found 406.2; Rt=0.71 min.

Step 3: Synthesis of (S)-tert-butyl 7-hydroxy-3-((R)-1-hydroxy-2-(2-(pyridin-3-ylamino)isonicotinamido)ethyl)-3,4-dihydroisoquinoline-2(1H)-carboxylate To a stirred solution of sodium hydrogen carbonate, 99% (27.92 mg, 332.38 μmol, 12.93 μL) in water (1 mL), N-[(2R)-2-hydroxy-2-[(3S)-7-hydroxy-1,2,3,4-tetrahydroisoquinolin-3-yl]ethyl]-2-(3-pyridylamino)pyridine-4-carboxamide (53 mg, 110.79 μmol, 2HCl) was added in THF (1 mL) followed by di-tert-butyl dicarbonate (24.18 mg, 110.79 μmol, 25.43 μL) in THF (1 mL). The resulting mixture was stirred at 25° C. for 12 h. EtOAc (10 mL) was added and organic phase was separated and washed with brine (2×5 mL). Then solvent was dried over sodium sulfate, filtered and evaporated to obtain tert-butyl (3S)-7-hydroxy-3-[(1R)-1-hydroxy-2-[[2-(3-pyridylamino)pyridine-4-carbonyl]amino]ethyl]-3,4-dihydro-1H-isoquinoline-2-carboxylate (52 mg, crude). $^1$H NMR (CD$_3$OD, 500 MHz) δ: 1.52 (s, 9H), 1.88 (m, 4H), 3.02 (m, 2H), 3.62 (m, 1H), 3.72 (m, 4H) 4.34 (m, 2H), 6.59 (m, 1H), 6.99 (td, 1H), 7.17 (m, 2H), 7.33 (d, 1H), 8.09 (d, 1H), 8.25 (m, 2H), 8.80 (t, 1H). LCMS (ESI): [M+H]$^+$ m/z: calc'd 505.2; found 506.2; Rt=1.03 min.

Step 4: Synthesis of (S)-tert-butyl 3-((R)-1-hydroxy-2-(2-(pyridin-3-ylamino)isonicotinamido)ethyl)-7-((4-methyloxazol-5-yl)methoxy)-3,4-dihydroisoquinoline-2(1H)-carboxylate To the solution of tert-butyl (3S)-7-hydroxy-3-[(1R)-1-hydroxy-2-[[2-(3-pyridylamino)pyridine-4-carbonyl]amino]ethyl]-3,4-dihydro-1H-isoquinoline-2-carboxylate (53 mg, 104.83 μmol), cesium carbonate (102.47 mg, 314.50 μmol) in DMF (2 mL) was added 5-(chloromethyl)-4-methyl-oxazole (21.14 mg, 125.80 μmol, HCl). Resulting mixture was heated at 50° C. for 12 hr. The mixture was filtered and evaporated to obtain tert-butyl (3S)-3-[(1R)-1-hydroxy-2-[[2-(3-pyridylamino)pyridine-4-carbonyl]amino]ethyl]-7-[(4-methyloxazol-5-yl)

methoxy]-3,4-dihydro-TH-isoquinoline-2-carboxylate (60 mg, crude) that was used without further purification. ¹H NMR (CD₃OD, 500 MHz) δ: 1.48 (s, 9H), 2.20 (m, 3H), 3.12 (m, 2H), 3.62 (m, 4H), 4.44 (m, 5H), 5.08 (s, 2H), 6.87 (m, 2H), 7.10 (m, 2H), 7.23 (m, 2H), 8.14 (m, 2H), 8.29 (m, 1H), 8.82 (m, 1H). LCMS (ESI): [M+H]⁺ m/z: calc'd 600.3; found 601.4; Rt=1.04 min.

Step 5: Synthesis of N—((R)-2-hydroxy-2-((S)-7-((4-methyloxazol-5-yl)methoxy)-1,2,3,4-tetrahydroisoquinolin-3-yl)ethyl)-2-(pyridin-3-ylamino)isonicotinamide (Compound 34) A solution of tert-butyl (3S)-3-[(1R)-1-hydroxy-2-[[2-(3-pyridylamino)pyridine-4-carbonyl]amino]ethyl]-7-[(4-methyloxazol-5-yl)methoxy]-3,4-dihydro-TH-isoquinoline-2-carboxylate (60 mg, 99.89 μmol) in dioxane/HCl (1 mL) and methanol (1 mL) was stirred for 12 h at 25° C. Then, the solution was evaporated and resulting crude product was purified by HPLC (10-40% water-methanol, 10 min, flow: 30 mL/min) to obtain N-[(2R)-2-hydroxy-2-[(3S)-7-[(4-methyloxazol-5-yl)methoxy]-1,2,3,4-tetrahydroisoquinolin-3-yl]ethyl]-2-(3-pyridylamino)pyridine-4-carboxamide (12 mg, 20.93 μmol, 20.95% yield, 2HCl). ¹H NMR (Methanol-d₄, 400 MHz): δ (ppm) 2.23 (s, 3H), 3.19 (m, 2H), 3.56 (m, 1H), 3.66 (m, 2H), 4.31 (m, 2H), 4.48 (m, 1H), 5.12 (s, 2H), 6.88 (s, 1H), 6.97 (d, 1H), 7.24 (d, 1H), 7.38 (d, 1H), 7.44 (s, 1H), 7.96 (dd, 1H), 8.37 (d, 1H), 8.39 (s, 1H), 8.42 (d, 1H), 8.57 (d, 1H), 9.74 (s, 1H). LCMS (ESI): [M+2H]⁺ m/z: calc'd 500.2; found 502.2; Rt=0.83 min.

Example 2A7. Synthesis of 2-(cyclobutylamino)-N—((R)-2-hydroxy-2-((S)-7-((4-methyloxazol-5-yl)methoxy)-1,2,3,4-tetrahydroisoquinolin-3-yl)ethyl)-6-(4-propionylpiperazin-1-yl)isonicotinamide (Compound 39)

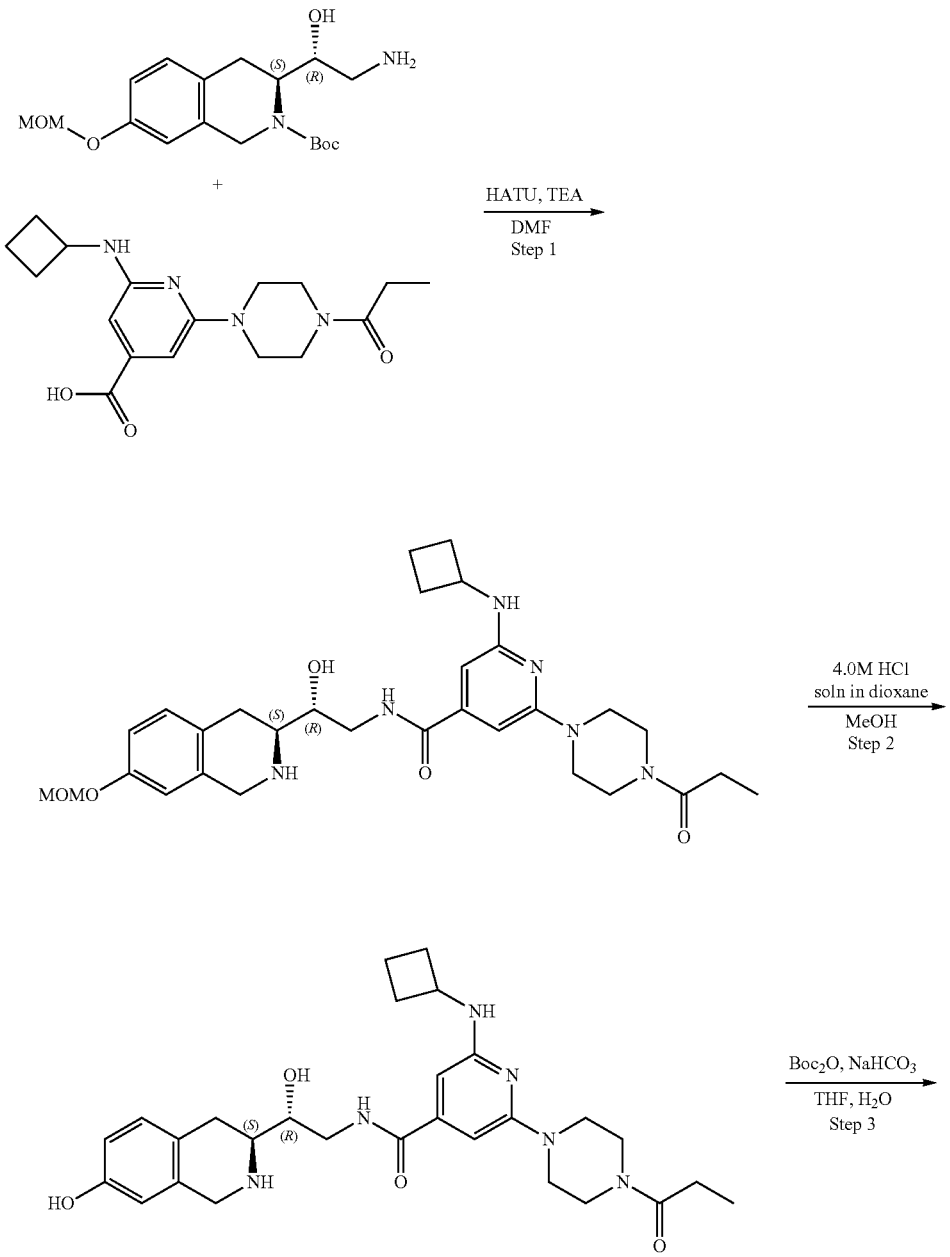

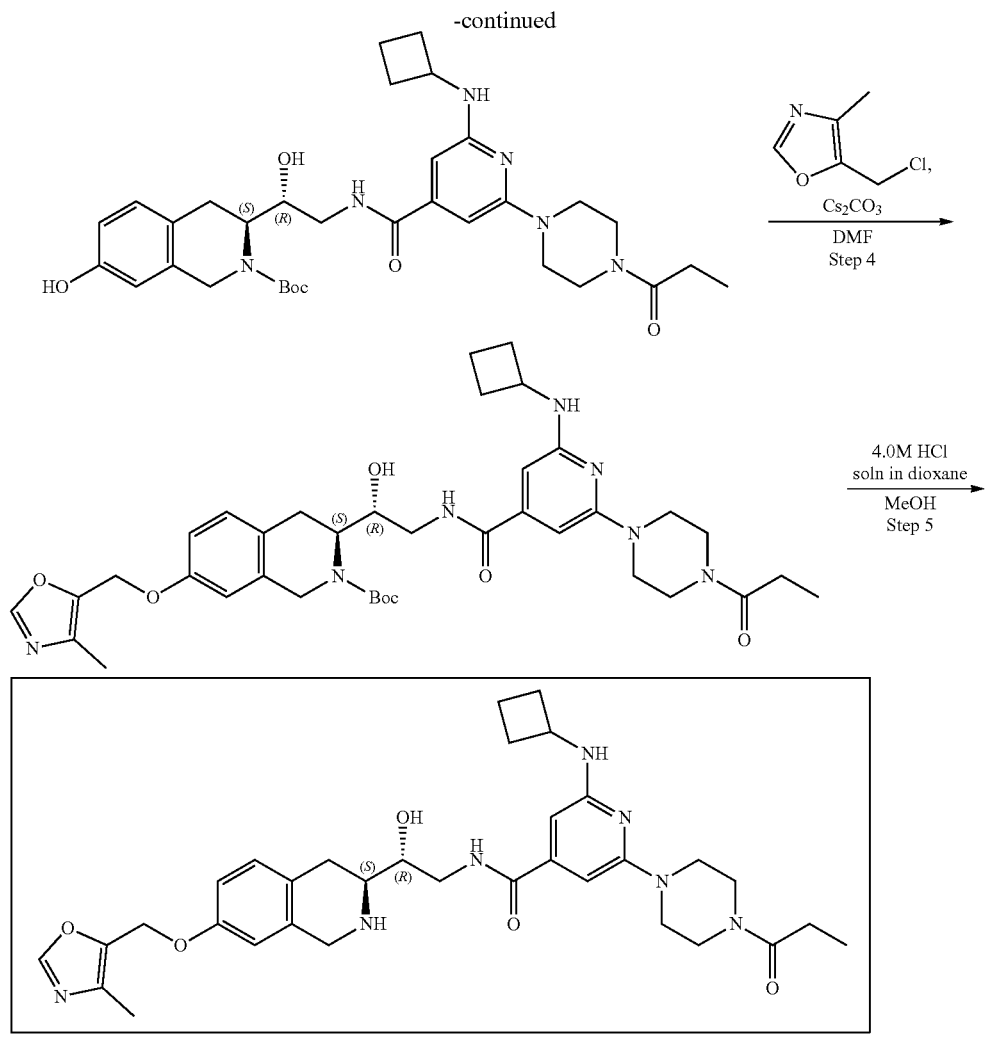

Step 1: Synthesis of (S)-tert-butyl 3-((R)-2-(2-(cyclobutylamino)-6-(4-propionylpiperazin-1-yl)isonicotinamido)-1-hydroxyethyl)-7-(methoxymethoxy)-3,4-dihydroisoquinoline-2(1H)-carboxylate 2-(Cyclobutylamino)-6-(4-propanoylpiperazin-1-yl)pyridine-4-carboxylic acid (156.99 mg, 425.62 μmol, HCl), tert-butyl (3S)-3-[(1R)-2-amino-1-hydroxy-ethyl]-7-(methoxymethoxy)-3,4-dihydro-1H-isoquinoline-2-carboxylate (150 mg, 425.62 μmol), triethylamine (430.69 mg, 4.26 mmol, 593.23 μL) were mixed in DMF (3 mL) and then HATU (242.75 mg, 638.44 μmol) was added. The resulting mixture were stirred at RT for 12 h. The mixture was evaporated under reduce pressure and purified with HPLC (50-65% water-acetonitrile, 2-10 min, Flow: 30 mL/min) to obtain tert-butyl (3S)-3-[(1R)-2-[[2-(cyclobutylamino)-6-(4-propanoylpiperazin-1-yl)pyridine-4-carbonyl]amino]-1-hydroxy-ethyl]-7-(methoxy-methoxy)-3,4-dihydro-1H-isoquinoline-2-carboxylate (71.7 mg, 107.53 μmol, 25.26% yield). $^1$H NMR (DMSO-$d_6$, 400 MHz) δ: 0.97 (t, 3H), 1.41 (m, 10H), 1.76 (m, 4H), 2.07 (s, 3H), 2.32 (q, 2H), 3.03 (m, 4H), 3.49 (m, 10H), 4.24 (m, 3H), 4.75 (m, 1H), 5.15 (m, 3H), 6.08 (s, 1H), 6.25 (s, 1H), 6.60 (d, 1H), 6.86 (m, 2H), 7.06 (d, 1H), 8.23 (m, 1H). LCMS (ESI): [M+H]$^+$ m/z: calc'd 666.3; found 667.4; Rt=1.48 min.

Step 2: Synthesis of 2-(cyclobutylamino)-N—((R)-2-hydroxy-2-((S)-7-hydroxy-1,2,3,4-tetrahydroisoquinolin-3-yl)ethyl)-6-(4-propionylpiperazin-1-yl)isonicotinamide A solution of tert-butyl (3S)-3-[(1R)-2-[[2-(cyclobutylamino)-6-(4-propanoylpiperazin-1-yl)pyridine-4-carbonyl]amino]-1-hydroxy-ethyl]-7-(methoxymethoxy)-3,4-dihydro-1H-isoquinoline-2-carboxylate (71.7 mg, 107.53 μmol) in dioxane/HCl (2 mL) and methanol (2 mL) was stirred for 12 h at 25° C. Then the solution was evaporated to obtain 2-(cyclobutylamino)-N-[(2R)-2-hydroxy-2-[(3S)-7-hydroxy-1,2,3,4-tetrahydroisoquinolin-3-yl]ethyl]-6-(4-propanoylpiperazin-1-yl)pyridine-4-carboxamide (67 mg, crude, 3HCl). $^1$H NMR (CD$_3$OD, 500 MHz) δ: 1.15 (t, 3H), 2.03 (m, 5H), 2.47 (m, 4H), 3.38 (m, 3H), 3.53 (m, 2H), 3.67 (m, 8H), 3.77 (m, 4H), 4.23 (m, 4H), 6.63 (s, 1H), 6.77 (d, 1H), 7.13 (d, 1H), 8.12 (s, 1H). LCMS (ESI): [M+H]$^+$ m/z: calc'd 522.3; found 523.2; Rt=0.98 min.

Step 3: Synthesis of (S)-tert-butyl 3-((R)-2-(2-(cyclobutylamino)-6-(4-propionylpiperazin-1-yl)isonicotinamido)-1-hydroxyethyl)-7-hydroxy-3,4-dihydroisoquinoline-2(1H)-carboxylate To a stirred solution of sodium hydrogen carbonate (26.72 mg, 318.03 μmol, 12.37 μL) in water (1 mL) 2-(cyclobutylamino)-N—[(2R)-2-hydroxy-2-[(3S)-7-hydroxy-1,2,3,4-tetrahydroisoquinolin-3-yl]ethyl]-6-(4-propanoylpiperazin-1-yl)pyridine-4-carboxamide (67 mg, 106.01 μmol, 3HCl) was added in THF (1 mL) followed by di-tert-butyl dicarbonate (23.14 mg, 106.01 μmol, 24.33 μL)

in THF (1 mL). Resulting mixture was stirred at 25° C. for 12 h. EtOAc (10 mL) was added and organic phase was separated and washed with brine (2×5 mL). Then solvent was dried over sodium sulfate, filtered and evaporated to obtain tert-butyl (3S)-3-[(1R)-2-[[2-(cyclobutylamino)-6-(4-propanoylpiperazin-1-yl)pyridine-4-carbonyl]amino]-1-hydroxy-ethyl]-7-hydroxy-3,4-dihydro-1H-isoquinoline-2-carboxylate (64 mg, crude). $^1$H NMR (CD$_3$OD, 400 MHz) δ: 1.11 (t, 3H), 1.52 (m, 9H), 1.78 (m, 2H), 1.88 (m, 4H), 2.38 (m, 4H), 3.05 (m, 5H), 3.63 (m, 10H), 4.23 (m, 2H), 6.13 (s, 1H), 6.31 (d, 1H), 6.55 (m, 2H), 6.98 (m, 1H). LCMS (ESI): [M+H]$^+$ m/z: calc'd 622.3; found 623.4; Rt=1.36 min.

Step 4: Synthesis of (S)-tert-butyl 3-((R)-2-(2-(cyclobutylamino)-6-(4-propionylpiperazin-1-yl)isonicotinamido)-1-hydroxyethyl)-7-((4-methyloxazol-5-yl)methoxy)-3,4-dihydroisoquinoline-2(1H)-carboxylate To the solution of tert-butyl (3S)-3-[(1R)-2-[[2-(cyclobutylamino)-6-(4-propanoylpiperazin-1-yl)pyridine-4-carbonyl]amino]-1-hydroxy-ethyl]-7-hydroxy-3,4-dihydro-1H-isoquinoline-2-carboxylate (64 mg, 102.77 μmol), Cesium carbonate (100.45 mg, 308.31 μmol) in DMF (2 mL) was added 5-(chloromethyl)-4-methyl-oxazole (20.72 mg, 123.32 μmol, HCl). Resulting mixture was heated at 50° C. for 12 h. The mixture was filtered and evaporated to obtain tert-butyl (3S)-3-[(1R)-2-[[2-(cyclobutylamino)-6-(4-propanoylpiperazin-1-yl)pyridine-4-carbonyl]amino]-1-hydroxy-ethyl]-7-[(4-methyloxazol-5-yl)-methoxy]-3,4-dihydro-1H-isoquinoline-2-carboxylate (70 mg, crude) that was used without further purification. $^1$H NMR (CD$_3$OD, 500 MHz) δ: 1.14 (m, 3H), 1.51 (m, 13H), 1.85 (m, 4H), 2.18 (m, 5H), 2.38 (m, 3H), 3.63 (m, 10H), 4.23 (m, 2H), 5.08 (s, 2H), 6.13 (s, 1H), 6.31 (d, 1H), 6.82 (s, 1H), 7.12 (d, 1H), 7.98 (s, 1H), 8.13 (d, 1H). LCMS (ESI): [M+H]$^+$ m/z: calc'd 717.3; found 718.4; Rt=1.46 min.

Step 5: Synthesis of 2-(cyclobutylamino)-N—((R)-2-hydroxy-2-((S)-7-((4-methyloxazol-5-yl)methoxy)-1,2,3,4-tetrahydroisoquinolin-3-yl)ethyl)-6-(4-propionylpiperazin-1-yl)isonicotinamide (Compound 39) A solution of tert-butyl (3S)-3-[(1R)-2-[[2-(cyclobutylamino)-6-(4-propanoylpiperazin-1-yl)pyridine-4-carbonyl]amino]-1-hydroxy-ethyl]-7-[(4-methyloxazol-5-yl)methoxy]-3,4-dihydro-1H-isoquinoline-2-carboxylate (70 mg, 97.51 μmol) in dioxane/HCl (2 mL) and methanol (2 mL) was stirred for 12 h at 25° C. Then the solution was evaporated and resulting crude product was purified by HPLC with 10-40% water-methanol, 10 min, flow: 30 mL/min and then with 0.1% FA-ACN 5-95% ACN 6 min. Zorbax Eclipse-plus to obtain ma 2-(cyclobutylamino)-N-[(2R)-2-hydroxy-2-[(3S)-7-[(4-methyloxazol-5-yl)methoxy]-1,2,3,4-tetrahydroisoquinolin-3-yl]ethyl]-6-(4-propanoylpiperazin-1-yl)pyridine-4-carboxamide (3.1 mg, 4.26 μmol, 4.37% yield, 3HCl). $^1$H NMR (500 MHz, CDCl$_3$) δ 1.19 (m, 4H), 1.26 (m, 2H), 2.24 (s, 3H), 2.40 (m, 5H), 2.89 (m, 2H), 3.18 (m, 1H), 3.50 (m, 3H), 3.55 (m, 6H), 3.70 (m, 2H), 3.83 (m, 1H), 4.02 (m, 1H), 4.11 (m, 3H), 4.67 (m, 1H), 4.99 (s, 2H), 5.98 (s, 1H), 6.25 (s, 1H), 6.63 (s, 1H), 6.84 (m, 1H), 7.09 (m, 1H), 7.15 (m, 1H), 7.82 (s, 1H). LCMS (ESI): [M+H]$^+$ m/z: calc'd 617.3; found 618.4; Rt=1.06 min.

Example 2A8. Synthesis of 2-(cyclobutylamino)-N—((R)-2-hydroxy-2-((S)-7-((4-methyloxazol-5-yl)methoxy)-1,2,3,4-tetrahydroisoquinolin-3-yl)ethyl)-6-((2-methoxyethyl)(methyl)amino)isonicotinamide (Compound 33)

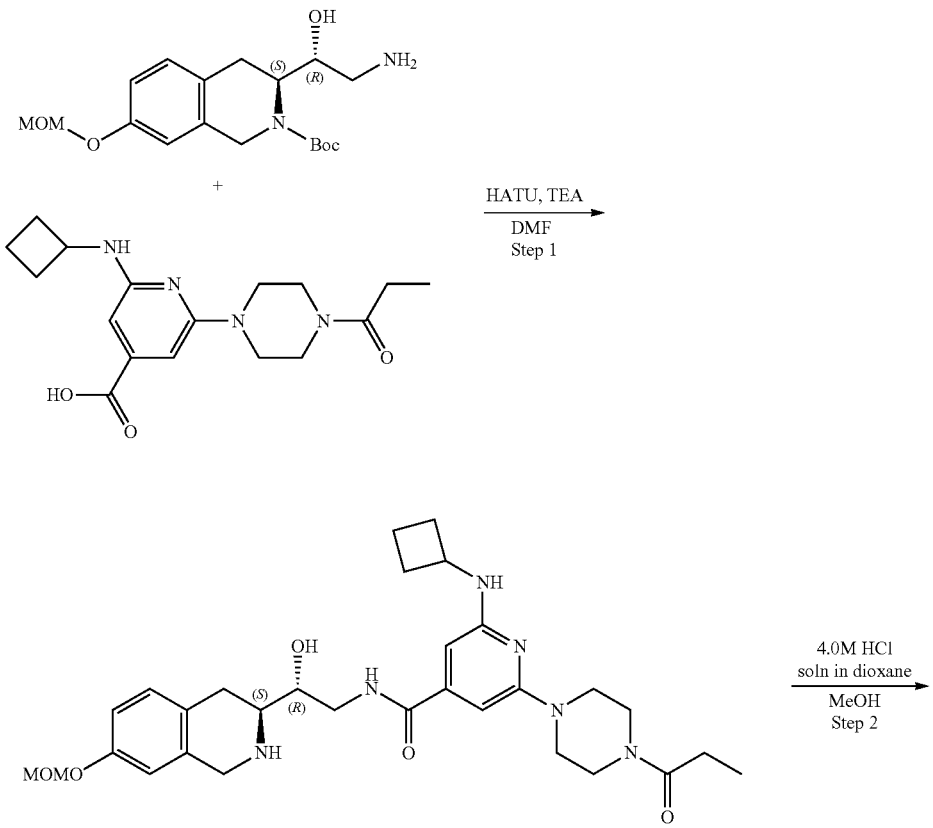

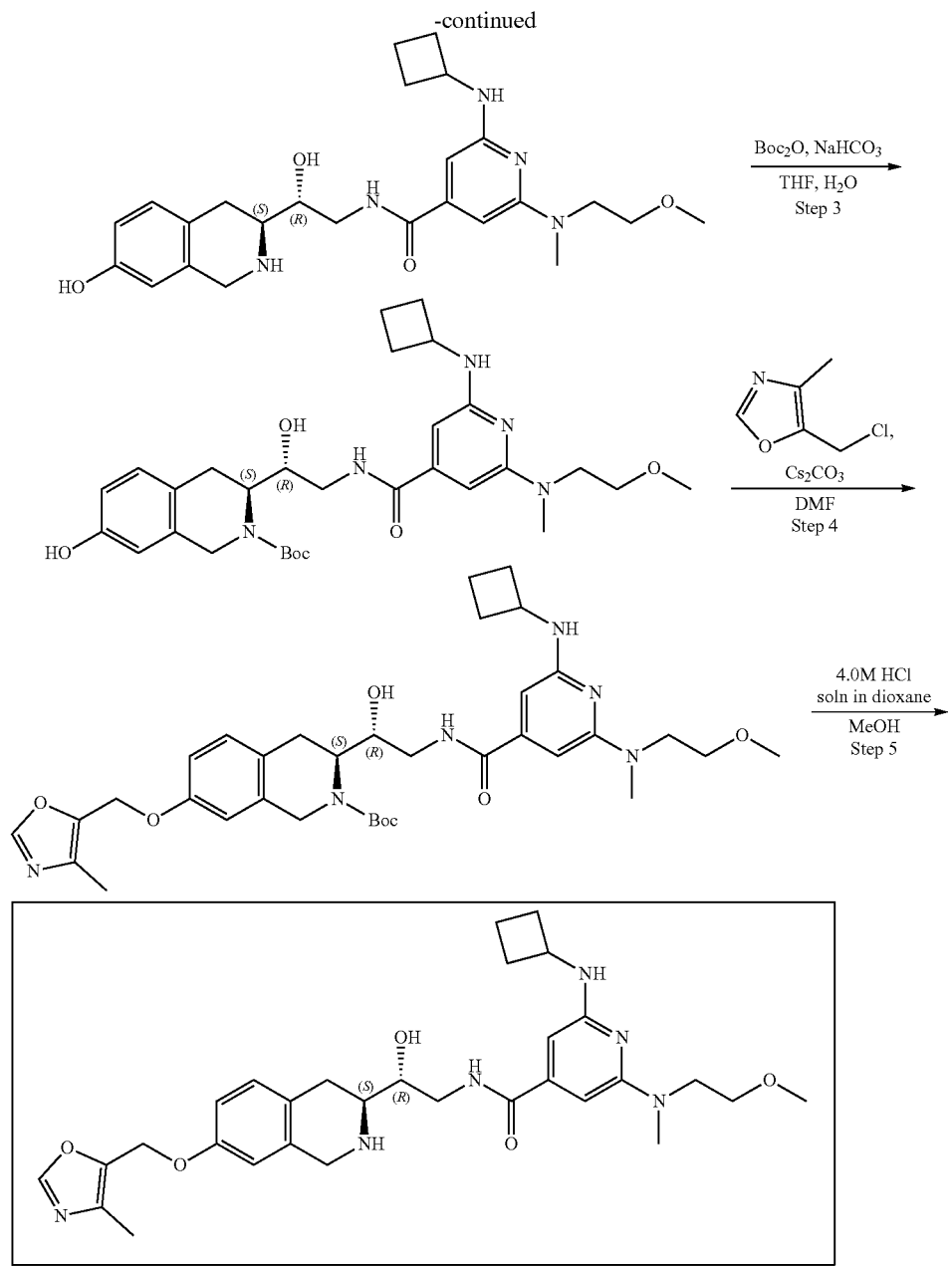

Step 1: Synthesis of (S)-tert-butyl 3-((R)-2-(2-(cyclobutylamino)-6-((2-methoxyethyl)(methyl)amino)isonicotinamido)-1-hydroxyethyl)-7-(methoxymethoxy)-3,4-dihydroisoquinoline-2(1H)-carboxylate 2-(Cyclobutylamino)-6-[2-methoxyethyl(methyl)amino]pyridine-4-carboxylic acid (134.41 mg, 425.62 μmol, HCl), tert-butyl (3S)-3-[(1R)-2-amino-1-hydroxy-ethyl]-7-(methoxymethoxy)-3,4-dihydro-1H-isoquinoline-2-carboxylate (150 mg, 425.62 μmol), triethylamine (430.69 mg, 4.26 mmol, 593.23 μL) were mixed in DMF (3 mL) and HATU (242.75 mg, 638.44 μmol) was added. The resulting mixture was stirred at RT for 12 h. The mixture was evaporated under reduce pressure and purified with HPLC (50-65% water-acetonitrile, 2-10 min, Flow: 30 mL/min) to obtain tert-butyl (3S)-3-[(1R)-2-[[2-(cyclobutylamino)-6-[2-methoxyethyl(methyl)amino]pyridine-4-carbonyl]amino]-1-hydroxy-ethyl]-7-(methoxymethoxy)-3,4-dihydro-1H-isoquinoline-2-carboxylate (57.8 mg, 94.18 μmol, 22.13% yield). $^1$H NMR (DMSO-$d_6$, 400 MHz) δ: 1.42 (m, 9H), 1.63 (m, 2H), 1.84 (m, 2H), 2.21 (m, 2H), 2.95 (m, 5H), 3.23 (s, 2H), 3.34 (m, 5H), 3.46 (M, 3H), 3.63 (m, 3H), 4.18 (m, 3H), 4.78 (m, 1H), 5.15 (m, 3H), 5.97 (s, 1H), 6.02 (s, 1H), 6.44 (d, 1H), 6.85 (m, 2H), 7.08 (d, 1H), 8.16 (m, 1H). LCMS (ESI): [M+H]$^+$ m/z: calc'd 613.3; found 614.4; Rt=1.38 min.

Step 2: Synthesis of 2-(cyclobutylamino)-N—((R)-2-hydroxy-2-((S)-7-hydroxy-1,2,3,4-tetrahydroisoquinolin-3-yl)ethyl)-6-((2-methoxyethyl)(methyl)amino)isonicotinamide A solution of tert-butyl (3S)-3-[(1R)-2-[[2-(cyclobutylamino)-6-[2-methoxyethyl-(methyl)amino]pyridine-4-carbonyl]amino]-1-hydroxy-ethyl]-7-(methoxymethoxy)-3,4-dihydro-1H-iso-quinoline-2-carboxylate (57.8 mg, 94.18 μmol) in Dioxane/HCl (2 mL) and methanol (2 mL) was stirred for 12 h at 25° C. Then, the solution was evaporated to obtain 2-(cyclobutylamino)-N-[(2R)-2-hydroxy-2-[(3S)-

7-hydroxy-1,2,3,4-tetrahydroisoquinolin-3-yl]ethyl]-6-[2-methoxyethyl(methyl)amino]pyridine-4-carboxamide (53 mg, crude, 3HCl). $^1$H NMR (CD$_3$OD, 500 MHz) δ:1.96 (m, 5H), 2.51 (m, 2H), 3.09 (m, 2H), 3.22 (m, 4H), 3.43 (m, 4H), 3.45 (m, 2H), 3.76 (m, 4H), 4.26 (m, 4H), 6.35 (m, 1H), 6.37 (m, 1H), 6.63 (d, 1H), 6.75 (d, 1H), 7.10 (d, 1H), 8.07 (m, 1H). LCMS (ESI): [M+H]$^+$ m/z: calc'd 469.2; found 470.2; Rt=0.88 min.

Step 3: Synthesis of (S)-tert-butyl 3-((R)-2-(2-(cyclobutylamino)-6-((2-methoxyethyl)(methyl)amino)isonicotinamido)-1-hydroxyethyl)-7-hydroxy-3,4-dihydroisoquinoline-2(1H)-carboxylate To a stirred solution of di-tert-butyl dicarbonate (19.98 mg, 91.54 μmol, 21.01 μL) sodium hydrogen carbonate, 99% (23.07 mg, 274.63 μmol, 10.68 μL) in water (1 mL), 2-(cyclobutylamino)-N-[(2R)-2-hydroxy-2-[(3S)-7-hydroxy-1,2,3,4-tetrahydroisoquinolin-3-yl]ethyl]-6-[2-methoxyethyl(methyl)amino]-pyridine-4-carboxamide (53 mg, 91.54 μmol, 3HCl) were added in THF (1 mL) followed by sodium hydrogen carbonate, 99% (23.07 mg, 274.63 μmol, 10.68 μL) solution in THF (1 mL). The resulting mixture was stirred at 25° C. for 12 h. EtOAc (10 mL) was added and the organic phase was separated and washed with brine (2×5 mL). Then, the solvent was dried over sodium sulfate, filtered and evaporated to obtain tert-butyl (3S)-3-[(1R)-2-[[2-(cyclobutylamino)-6-[2-methoxyethyl(methyl)amino]pyridine-4-carbonyl]amino]-1-hydroxy-ethyl]-7-hydroxy-3,4-dihydro-1H-isoquinoline-2-carboxylate (50 mg, crude). $^1$H NMR (CD$_3$OD, 400 MHz) δ: 1.51 (m, 9H), 1.71 (m, 2H), 1.86 (m, 3H), 2.32 (m, 2H), 2.82 (m, 1H), 3.02 (m, 5H), 3.32 (m, 3H), 3.57 (m, 3H), 3.70 (m, 4H), 4.26 (m, 3H), 6.02 (s, 1H), 6.04 (d, 1H), 6.57 (m, 1H), 6.59 (d, 1H), 6.97 (m, 1H). LCMS (ESI): [M+H]$^+$ m/z: calc'd 569.3; found 570.2; Rt=1.17 min.

Step 4: Synthesis of (S)-tert-butyl 3-((R)-2-(2-(cyclobutylamino)-6-((2-methoxyethyl)(methyl)amino)isonicotinamido)-1-hydroxyethyl)-7-((4-methyloxazol-5-yl)methoxy)-3,4-dihydroisoquinoline-2(1H)-carboxylate To the solution of tert-butyl (3S)-3-[(1R)-2-[[2-(cyclobutylamino)-6-[2-methoxyethyl(methyl)-amino]pyridine-4-carbonyl]amino]-1-hydroxy-ethyl]-7-hydroxy-3,4-dihydro-1H-isoquinoline-2-carboxylate (50 mg, 87.77 μmol), cesium carbonate (85.79 mg, 263.30 μmol) in DMF (2 mL) and 5-(chloromethyl)-4-methyl-oxazole (17.70 mg, 105.32 μmol, HCl) were added. The resulting mixture was heated at 50° C. for 12 h. The mixture was filtered off and evaporated to obtain tert-butyl (3S)-3-[(1R)-2-[[2-(cyclobutylamino)-6-[2-methoxyethyl (methyl)amino]pyridine-4-carbonyl]amino]-1-hydroxy-ethyl]-7-[(4-methyloxazol-5-yl)methoxy]-3,4-dihydro-1H-isoquinoline-2-carboxylate (55 mg, crude). The obtained crude product was used in the next step without further purification. $^1$H NMR (CD$_3$OD, 500 MHz) δ:1.51 (m, 9H), 1.83 (m, 5H), 2.19 (m, 6H), 2.32 (m, 2H), 2.86 (s, 3H), 3.18 (m, 4H), 3.32 (m, 3H), 3.67 (m, 4H), 4.31 (m, 1H), 5.07 (m, 3H), 6.82 (s, 1H), 7.07 (d, 1H), 8.04 (m, 2H), 8.07 (s, 1H), 8.10 (m, 1H). LCMS (ESI): [M+H]$^+$ m/z: calc'd 664.3; found 665.4; Rt=1.36 min.

Step 5: Synthesis of 2-(cyclobutylamino)-N—((R)-2-hydroxy-2-((S)-7-((4-methyloxazol-5-yl)methoxy)-1,2,3,4-tetrahydroisoquinolin-3-yl)ethyl)-6-((2-methoxyethyl)(methyl)amino)isonicotinamide (Compound 33) A solution of tert-butyl (3S)-3-[(1R)-2-[[2-(cyclobutylamino)-6-[2-methoxyethyl-(methyl)amino]pyridine-4-carbonyl]amino]-1-hydroxy-ethyl]-7-[(4-methyloxazol-5-yl)methoxy]-3,4-dihydro-1H-isoquinoline-2-carboxylate (55 mg, 82.73 μmol) in Dioxane/HCl (2 mL) and methanol (2 mL) was stirred for 12 h at 25° C. Then, the solution was evaporated and resulting crude product was purified by HPLC (25-60% water-methanol, 10 min, flow: 30 mL/min) to obtain 2-(cyclobutylamino)-N-[(2R)-2-hydroxy-2-[(3S)-7-[(4-methyl-oxazol-5-yl)methoxy]-1,2,3,4-tetrahydroisoquinolin-3-yl] ethyl]-6-[2-methoxy-ethyl(methyl)amino]pyridine-4-carboxamide (13.3 mg, crude, 3HCl). $^1$H NMR (Methanol-d$_4$, 400 MHz): δ (ppm) 1.87 (m, 2H), 2.03 (m, 2H), 2.21 (s, 3H), 2.49 (m, 2H), 3.16 (m, 2H), 3.23 (s, 3H), 3.39 (s, 3H), 3.51 (m, 1H), 3.65 (m, 4H), 3.77 (m, 2H), 4.12 (m, 1H), 4.32 (m, 2H), 4.47 (d, 1H), 5.11 (s, 2H), 6.30 (s, 2H), 6.88 (s, 1H), 6.96 (d, 1H), 7.23 (d, 1H), 8.30 (s, 1H). LCMS (ESI): [M+H]$^+$ m/z: calc'd 564.3; found 566.4; Rt=0.98 min.

Example 2A9. Synthesis of 2-(cyclobutylamino)-5-fluoro-N—((R)-2-hydroxy-2-((S)-7-((4-methyloxazol-5-yl)methoxy)-1,2,3,4-tetrahydroisoquinolin-3-yl)ethyl)isonicotinamide (Compound 27)

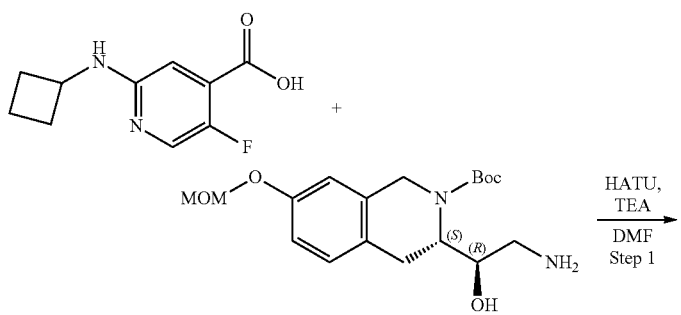

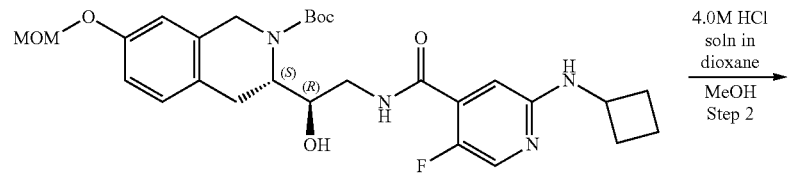

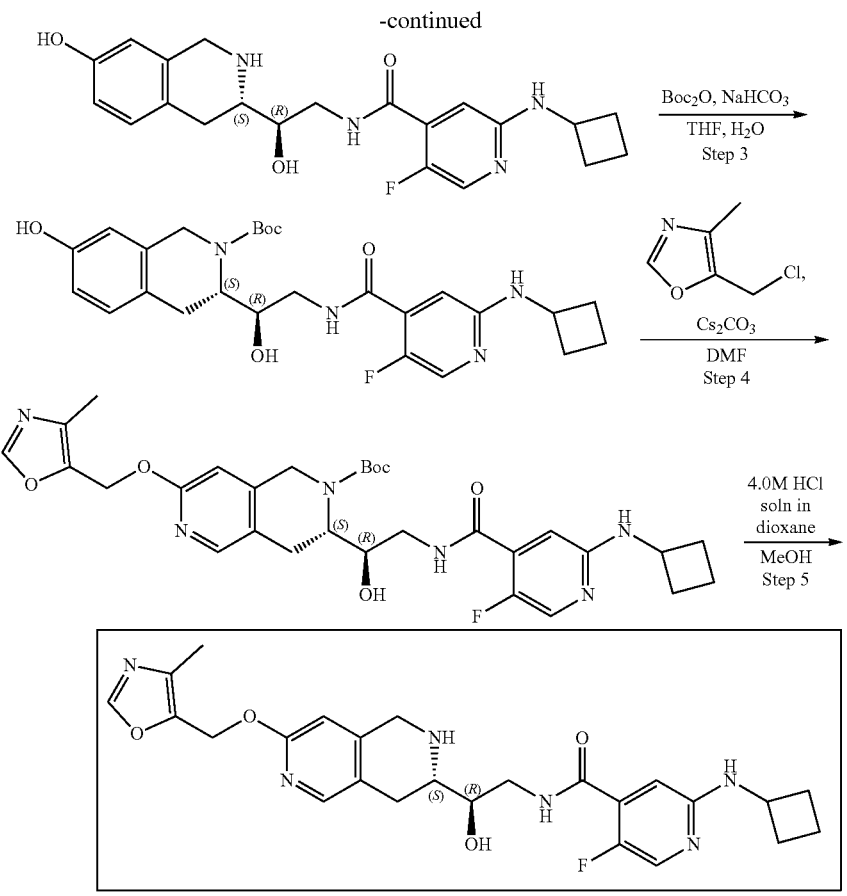

Step 1: Synthesis of (S)-tert-butyl 3-((R)-2-(2-(cyclobutylamino)-5-fluoroisonicotinamido)-1-hydroxyethyl)-7-(methoxymethoxy)-3,4-dihydroisoquinoline-2(1H)-carboxylate 2-(Cyclobutylamino)-5-fluoro-pyridine-4-carboxylic acid (104.99 mg, 425.62 μmol, HCl), tert-butyl (3S)-3-[(1R)-2-amino-1-hydroxy-ethyl]-7-(methoxymethoxy)-3,4-dihydro-1H-isoquinoline-2-carboxylate (150 mg, 425.62 μmol), triethylamine (430.69 mg, 4.26 mmol, 593.23 μL) were mixed in DMF (3 mL) and then HATU (242.75 mg, 638.44 μmol) was added. The resulting mixture was stirred at 25° C. for 12 h. The mixture was evaporated under reduce pressure and purified with HPLC (50-75% water-acetonitrile, 10 min, flow: 30 mL/min) to obtain tert-butyl (3S)-3-[(1R)-2-[[2-(cyclobutylamino)-5-fluoro-pyridine-4-carbonyl]amino]-1-hydroxy-ethyl]-7-(methoxymethoxy)-3,4-dihydro-1H-isoquinoline-2-carboxylate (59.1 mg, 108.52 μmol, 25.50% yield). $^1$H NMR (DMSO-d$_6$, 400 MHz) δ:1.42 (m, 9H), 1.70 (m, 2H), 1.74 (m, 2H), 2.07 (s, 3H), 2.24 (m, 2H), 2.54 (m, 1H), 2.89 (m, 2H), 3.36 (m, 2H), 3.52 (m, 1H), 4.15 (m, 2H), 4.75 (m, 1H), 5.15 (m, 3H), 6.57 (d, 1H), 6.85 (m, 2H), 6.91 (d, 1H), 7.07 (d, 1H), 7.97 (s, 1H), 8.20 (m, 1H). LCMS (ESI): [M+H]$^+$ m/z: calc'd 544.3; found 545.2; Rt=1.48 min.

Step 2: Synthesis of 2-(cyclobutylamino)-5-fluoro-N—((R)-2-hydroxy-2-((S)-7-hydroxy-1,2,3,4-tetrahydroisoquinolin-3-yl)ethyl)isonicotinamide A solution of tert-butyl (3S)-3-[(1R)-2-[[2-(cyclobutylamino)-5-fluoro-pyridine-4-carbonyl]amino]-1-hydroxy-ethyl]-7-(methoxymethoxy)-3,4-dihydro-1H-isoquinoline-2-carboxylate (59.1 mg, 108.52 μmol) in dioxane/HCl (2 mL) and methanol (2 mL) was stirred for 12 h at 25° C. Then, the solution was evaporated to obtain 2-(cyclobutylamino)-5-fluoro-N-[(2R)-2-hydroxy-2-[(3S)-7-hydroxy-1,2,3,4-tetrahydroisoquinolin-3-yl]ethyl]pyridine-4-carboxamide (50 mg, 105.63 μmol, 97.34% yield, 2HCl). $^1$H NMR (CD$_3$OD, 500 MHz) δ:1.99 (m, 4H), 2.52 (m, 2H), 3.10 (m, 3H), 3.48 (m, 2H), 3.59 (m, 5H), 4.28 (m, 4H), 6.61 (s, 1H), 6.75 (d, 1H), 7.11 (m, 1H), 7.26 (m, 1H), 8.01 (m, 1H). LCMS (ESI): [M+H]$^+$ m/z: calc'd 400.2; found 401.2; Rt=0.85 min.

Step 3: Synthesis of (S)-tert-butyl 3-((R)-2-(2-(cyclobutylamino)-5-fluoroisonicotinamido)-1-hydroxyethyl)-7-hydroxy-3,4-dihydroisoquinoline-2(1H)-carboxylate To a stirred solution of sodium hydrogen carbonate (26.62 mg, 316.88 μmol, 12.32 μL) in water (1 mL) 2-(cyclobutylamino)-5-fluoro-N-[(2R)-2-hydroxy-2-[(3S)-7-hydroxy-1,2,3,4-tetrahydroisoquinolin-3-yl]ethyl]pyridine-4-carboxamide (50 mg, 105.63 μmol, 2HCl) was added in THF (1 mL) followed by di-tert-butyl dicarbonate (23.05 mg, 105.63 μmol, 24.24 μL) in THF (1 mL). The resulting mixture was stirred at 25° C. for 12 h. EtOAc (10 mL) was added and organic phase was separated and washed with brine (2×5 mL). Then, the solvent was dried over sodium sulfate, filtered off and evaporated to obtain tert-butyl (3S)-3-[(1R)-2-[[2-(cyclobutylamino)-5-fluoro-pyridine-4-carbonyl]amino]-1-hydroxy-ethyl]-7-hydroxy-3,4-dihydro-1H-isoquinoline-2-carboxylate (50 mg, crude). $^1$H NMR (CD$_3$OD, 400 MHz) δ:1.49 (m, 9H), 1.86 (m, 7H), 2.35 (m, 2H), 2.96 (m, 3H), 3.66 (m, 5H), 4.19 (m, 2H), 6.56 (s, 1H), 6.61 (d, 1H), 6.69 (s, 1H), 6.97 (d, 1H), 7.88 (m, 1H). LCMS (ESI): [M+H]$^+$ m/z: calc'd 500.2; found 501.0; Rt=1.25 min.

Step 4: Synthesis of (S)-tert-butyl 3-((R)-2-(2-(cyclobutylamino)-5-fluoroisonicotinamido)-1-hydroxyethyl)-7-((4- methyloxazol-5-yl)methoxy)-3,4-dihydroisoquinoline-2 (1H)-carboxylate To the solution of tert-butyl (3S)-3-[(1R)-2-[[2-(cyclobutylamino)-5-fluoro-pyridine-4-carbonyl]-amino]-1-hydroxy-ethyl]-7-hydroxy-3,4-dihydro-1H-isoquinoline-2-carboxylate (50 mg, 99.89 µmol), cesium carbonate (97.64 mg, 299.66 µmol) in DMF (2 mL) was added 5-(chloromethyl)-4-methyl-oxazole (20.14 mg, 119.87 µmol, HCl). Resulting mixture was heated at 50° C. for 12 h. The mixture was filtered off and evaporated to obtain tert-butyl (3S)-3-[(1R)-2-[[2-(cyclobutylamino)-5-fluoro-pyridine-4-carbonyl]-amino]-1-hydroxy-ethyl]-7-[(4-methyloxazol-5-yl)methoxy]-3,4-dihydro-1H-isoquinoline-2-carboxylate (70 mg, crude) that was used without further purification. $^1$H NMR (CD$_3$OD, 500 MHz) δ: 1.51 (m, 9H), 1.80 (m, 4H), 2.20 (m, 6H), 2.36 (m, 2H), 3.66 (m, 2H), 4.22 (m, 2H), 4.56 (m, 2H), 5.07 (s, 2H), 6.81 (d, 1H), 7.10 (s, 1H), 7.90 (d, 1H), 8.01 (m, 2H), 8.11 (m, 1H). LCMS (ESI): [M-Boc]$^+$ m/z: calc'd 495.3; found 496.2; Rt=1.38 min.

Step 5: Synthesis of 2-(cyclobutylamino)-5-fluoro-N—((R)-2-hydroxy-2-((S)-7-((4-methyloxazol-5-yl)methoxy)-1,2,3,4-tetrahydroisoquinolin-3-yl)ethyl)isonicotinamide (Compound 27) A solution of tert-butyl (3S)-3-[(1R)-2-[[2-(cyclobutylamino)-5-fluoro-pyridine-4-carbonyl]amino]-1-hydroxy-ethyl]-7-[(4-methyloxazol-5-yl)methoxy]-3,4-dihydro-1H-isoquinoline-2-carboxylate (70 mg, 117.52 µmol) in dioxane/HCl (2 mL) and methanol (2 mL) was stirred for 12 h at 25° C. Then, the solution was evaporated and resulting crude product was purified by HPLC (35-70%, 0-5 min, water (0.0034% HCl)-methanol) to obtain 2-(cyclobutylamino)-5-fluoro-N-[(2R)-2-hydroxy-2-[(3S)-7-[(4-methyloxazol-5-yl)methoxy]-1,2,3,4-tetrahydroisoquinolin-3-yl]ethyl]pyridine-4-carboxamide (10.9 mg, 22.00 µmol, 18.72% yield). $^1$H NMR, δ 1.87 (m, 2H), 2.09 (m, 2H), 2.19 (s, 3H), 2.49 (m, 2H), 3.10 (dd, 1H), 3.22 (m, 1H), 3.54 (dd, 1H), 3.65 (dd, 2H), 4.17 (p, 1H), 4.31 (m, 2H), 4.48 (m, 1H), 5.09 (s, 2H), 6.88 (d, 1H), 6.96 (dd, 1H), 7.22 (m, 2H), 7.98 (d, 1H), 8.13 (s, 1H), NH, NH, NH, OH are not observed. LCMS (ESI): [M+H]$^+$ m/z: calc'd 495.2; found 496.2; Rt=0.98 min.

Example 2A10. Synthesis of 2-(cyclobutylamino)-N—((R)-2-hydroxy-2-((S)-7-((4-methyloxazol-5-yl)methoxy)-1,2,3,4-tetrahydroisoquinolin-3-yl)ethyl)-6-methoxyisonicotinamide (Compound 26)

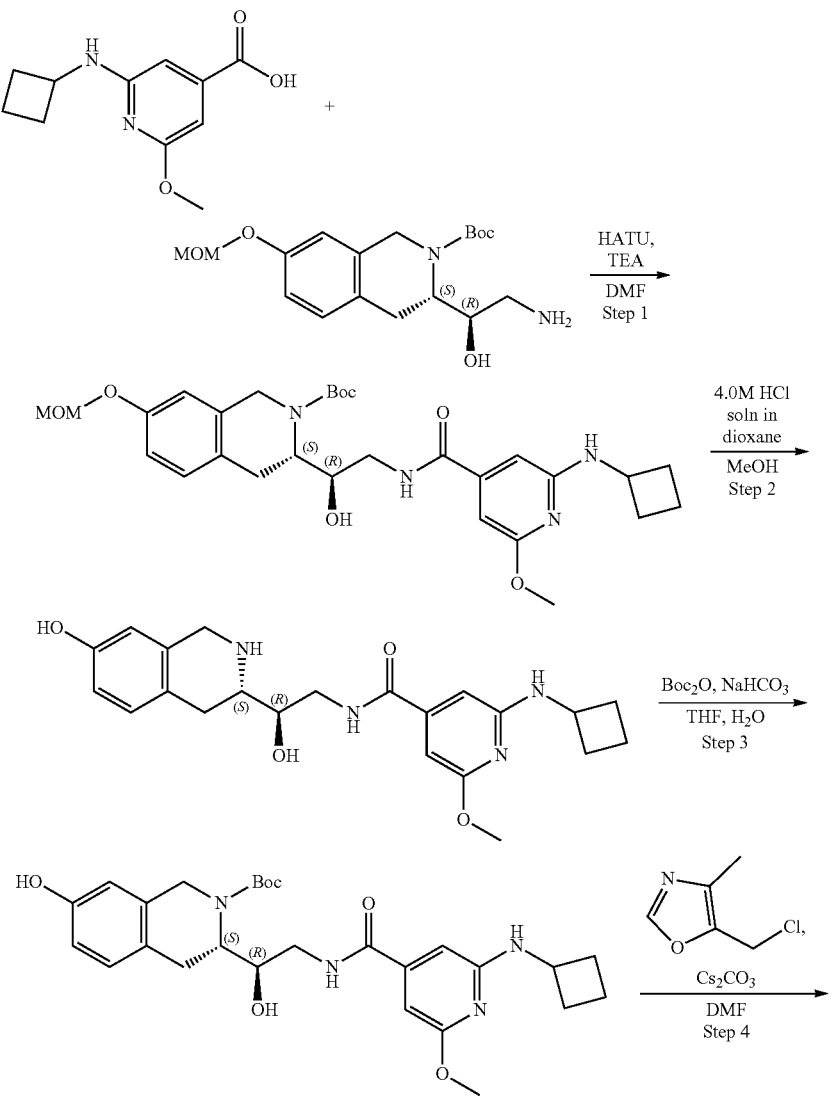

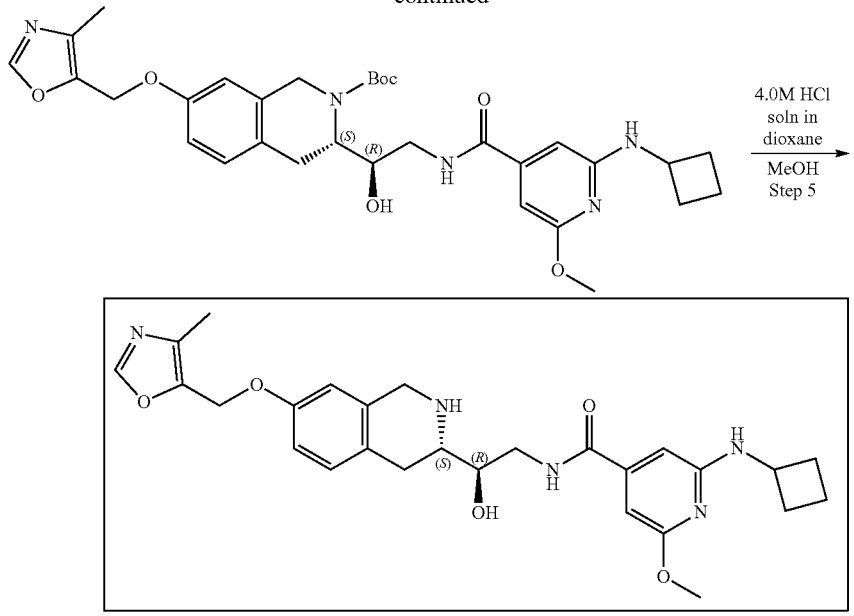

Step 1: Synthesis of (S)-tert-butyl 3-((R)-2-(2-(cyclobutylamino)-6-methoxyisonicotinamido)-1-hydroxyethyl)-7-(methoxymethoxy)-3,4-dihydroisoquinoline-2(1H)-carboxylate 2-(Cyclobutylamino)-6-methoxy-pyridine-4-carboxylic acid (94.59 mg, 425.62 μmol), tert-butyl (3S)-3-[(1R)-2-amino-1-hydroxy-ethyl]-7-(methoxymethoxy)-3,4-dihydro-1H-isoquinoline-2-carboxylate (150 mg, 425.62 μmol) and triethylamine (430.69 mg, 4.26 mmol, 593.23 μL) were mixed in DMF (3 mL) and then HATU (242.75 mg, 638.44 μmol) was added. The resulting mixture were stirred at 25° C. for 12 h. The mixture was evaporated under reduce pressure and purified by HPLC (50-75% water-acetonitrile, 10 min, flow: 30 mL/min) to obtain tert-butyl (3S)-3-[(1R)-2-[[2-(cyclobutylamino)-6-methoxy-pyridine-4-carbonyl]amino]-1-hydroxy-ethyl]-7-(methoxymethoxy)-3,4-dihydro-1H-isoquinoline-2-carboxylate (82.1 mg, 147.49 μmol, 34.65% yield). $^1$H NMR (DMSO-$d_6$, 400 MHz) δ:1.40 (m, 9H), 1.77 (m, 4H), 2.07 (s, 2H), 2.27 (m, 2H), 2.53 (m, 4H), 2.87 (m, 2H), 3.36 (s, 2H), 3.51 (m, 1H), 3.75 (s, 3H), 4.11 (m, 2H), 4.71 (m, 1H), 5.15 (m, 2H), 6.21 (s, 1H), 6.29 (s, 1H), 6.89 (m, 2H), 7.08 (d, 1H), 8.26 (m, 1H). LCMS (ESI): [M+H]$^+$ m/z: calc'd 556.6; found 557.2; Rt=1.58 min.

Step 2: Synthesis of 2-(cyclobutylamino)-N-[(2R)-2-hydroxy-2-[(3S)-7-hydroxy-1,2,3,4-tetrahydroisoquinolin-3-yl]ethyl]-6-methoxy-pyridine-4-carboxamide) A solution of tert-butyl (3S)-3-[(1R)-2-[[2-(cyclobutylamino)-6-methoxy-pyridine-4-carbonyl]amino]-1-hydroxy-ethyl]-7-(methoxymethoxy)-3,4-dihydro-1H-isoquinoline-2-carboxylate (82.1 mg, 147.49 μmol) in dioxane/HCl (2 mL) and methanol (2 mL) was stirred for 12 h at 25° C. Then, the solution was evaporated to obtain 2-(cyclobutylamino)-N-[(2R)-2-hydroxy-2-[(3S)-7-hydroxy-1,2,3,4-tetrahydroisoquinolin-3-yl]ethyl]-6-methoxy-pyridine-4-carboxamide (70 mg, 144.21 μmol, 97.78% yield, 2HCl). $^1$H NMR (CD$_3$OD, 500 MHz) δ:1.88 (m, 2H), 2.08 (m, 2H), 2.49 (m, 2H), 2.54 (s, 2H), 3.15 (m, 2H), 3.56 (m, 4H), 4.09 (s, 3H), 4.26 (m, 3H), 4.42 (m, 1H), 6.62 (m, 2H), 6.74 (d, 1H), 6.87 (s, 1H), 7.11 (d, 1H). LCMS (ESI): [M+H]$^+$ m/z: calc'd 412.5; found 413.2; Rt=1.00 min.

Step 3: Synthesis of (S)-tert-butyl 3-((R)-2-(2-(cyclobutylamino)-6-methoxyisonicotinamido)-1-hydroxyethyl)-7-hydroxy-3,4-dihydroisoquinoline-2(1H)-carboxylate To a stirred solution of sodium hydrogen carbonate (36.34 mg, 432.63 μmol, 16.83 μL) in water (1 mL) 2-(cyclobutylamino)-N-[(2R)-2-hydroxy-2-[(3S)-7-hydroxy-1,2,3,4-tetrahydroisoquinolin-3-yl]ethyl]-6-methoxy-pyridine-4-carboxamide (70 mg, 144.21 μmol, 2HCl) was added in THF (1 mL) followed by di-tert-butyl dicarbonate (31.47 mg, 144.21 μmol, 33.10 μL) in THF (1 mL). The resulting mixture was stirred at 25° C. for 12 h. EtOAc (10 mL) was added and the organic phase was separated and washed with brine (2*5 mL). Then, the solvent was dried over sodium sulfate, filtered and evaporated to obtain tert-butyl (3S)-3-[(1R)-2-[[2-(cyclobutylamino)-6-methoxy-pyridine-4-carbonyl]amino]-1-hydroxy-ethyl]-7-hydroxy-3,4-dihydro-1H-isoquinoline-2-carboxylate (70 mg, crude). $^1$H NMR (CD$_3$OD, 400 MHz) δ:1.51 (m, 9H), 1.84 (m, 6H), 2.38 (m, 2H), 3.02 (m, 3H), 3.72 (m, 4H), 3.82 (m, 3H), 4.27 (m, 3H), 4.72 (m, 1H), 6.28 (m, 2H), 6.56 (s, 1H), 6.59 (d, 1H), 6.98 (d, 1H). LCMS (ESI): [M+H]$^+$ m/z: calc'd 512.3; found 513.0; Rt=1.36 min.

Step 4: Synthesis of (S)-tert-butyl 3-((R)-2-(2-(cyclobutylamino)-6-methoxyisonicotinamido)-1-hydroxyethyl)-7-((4-methyloxazol-5-yl)methoxy)-3,4-dihydroisoquinoline-2(1H)-carboxylate) To the solution of tert-butyl (3S)-3-[(1R)-2-[[2-(cyclobutylamino)-6-methoxy-pyridine-4-carbonyl]amino]-1-hydroxy-ethyl]-7-hydroxy-3,4-dihydro-1H-isoquinoline-2-carboxylate (70 mg, 136.56 μmol), cesium carbonate (133.48 mg, 409.68 μmol) in DMF (2 mL) was added 5-(chloromethyl)-4-methyl-oxazole (27.53 mg, 163.87 μmol, HCl). The resulting mixture was heated at 50° C. for 12 h. The mixture was filtered off and evaporated to obtain tert-butyl (3S)-3-[(1R)-2-[[2-(cyclobutylamino)-6-methoxy-pyridine-4-carbonyl]amino]-1-hydroxy-ethyl]-7-[(4-methyloxazol-5-yl)methoxy]-3,4-dihydro-1H-isoquinoline-2-carboxylate (100 mg, crude) which was used without further purification. $^1$H NMR (CD$_3$OD, 500 MHz) δ: 1.51 (m, 9H), 1.87 (m, 4H), 2.19 (m, 6H), 2.38 (m, 2H), 3.12 (m, 1H), 3.83 (m, 3H), 4.34 (m, 2H), 4.56 (m, 1H), 5.07 (s, 2H), 6.24 (m, 1H), 6.83 (m, 2H), 7.11 (d, 1H), 8.04 (s, 1H), 8.07 (s, 1H). LCMS (ESI): [M+H]⁺ m/z: calc'd 607.3; found 608.4; Rt=1.54 min.

Step 5: Synthesis of 2-(cyclobutylamino)-N—((R)-2-hydroxy-2-((S)-7-((4-methyloxazol-5-yl)methoxy)-1,2,3,4-tetrahydroisoquinolin-3-yl)ethyl)-6-methoxyisonicotinamide (Compound 26) A solution of tert-butyl (3S)-3-[(1R)-2-[[2-(cyclobutylamino)-6-methoxy-pyridine-4-carbonyl]amino]-1-hydroxy-ethyl]-7-[(4-methyloxazol-5-yl)methoxy]-3,4-dihydro-1H-isoquinoline-2-carboxylate (100 mg, 164.56 µmol) in dioxane/HCl (2 mL) and methanol (2 mL) was stirred for 12 h at 25° C. Then, the solution was evaporated and resulting crude product was purified by HPLC (10-40% water-methanol, 10 min, flow: 30 mL/min) to obtain 2-(cyclobutylamino)-N-[(2R)-2-hydroxy-2-[(3S)-7-[(4-methyloxazol-5-yl)methoxy]-1,2,3,4-tetrahydroisoquinolin-3-yl]ethyl]-6-methoxy-pyridine-4-carboxamide (15.8 mg, 27.22 µmol, 16.54% yield, 2HCl). ¹H NMR, δ 1.85 (m, 2H), 2.10 (m, 2H), 2.23 (s, 3H), 2.48 (m, 2H), 3.20 (m, 2H), 3.54 (m, 1H), 3.67 (m, 2H), 4.10 (s, 3H), 4.25 (m, 1H), 4.32 (m, 2H), 4.46 (m, 1H), 5.12 (s, 2H), 6.89 (s, 1H), 6.94 (s, 1H), 6.98 (d, 1H), 7.25 (d, 1H), 8.44 (s, 2H), NH, NH, NH, OH, HCl are not observed. LCMS (ESI): [M+H]⁺ m/z: calc'd 507.2; found 508.2; Rt=1.09 min.

Example 2A11. Synthesis of 2-(cyclobutylamino)-6-(ethyl(methyl)amino)-N—((R)-2-hydroxy-2-((S)-7-((4-methyloxazol-5-yl)methoxy)-1,2,3,4-tetrahydroisoquinolin-3-yl)ethyl)isonicotinamide (Compound 24)

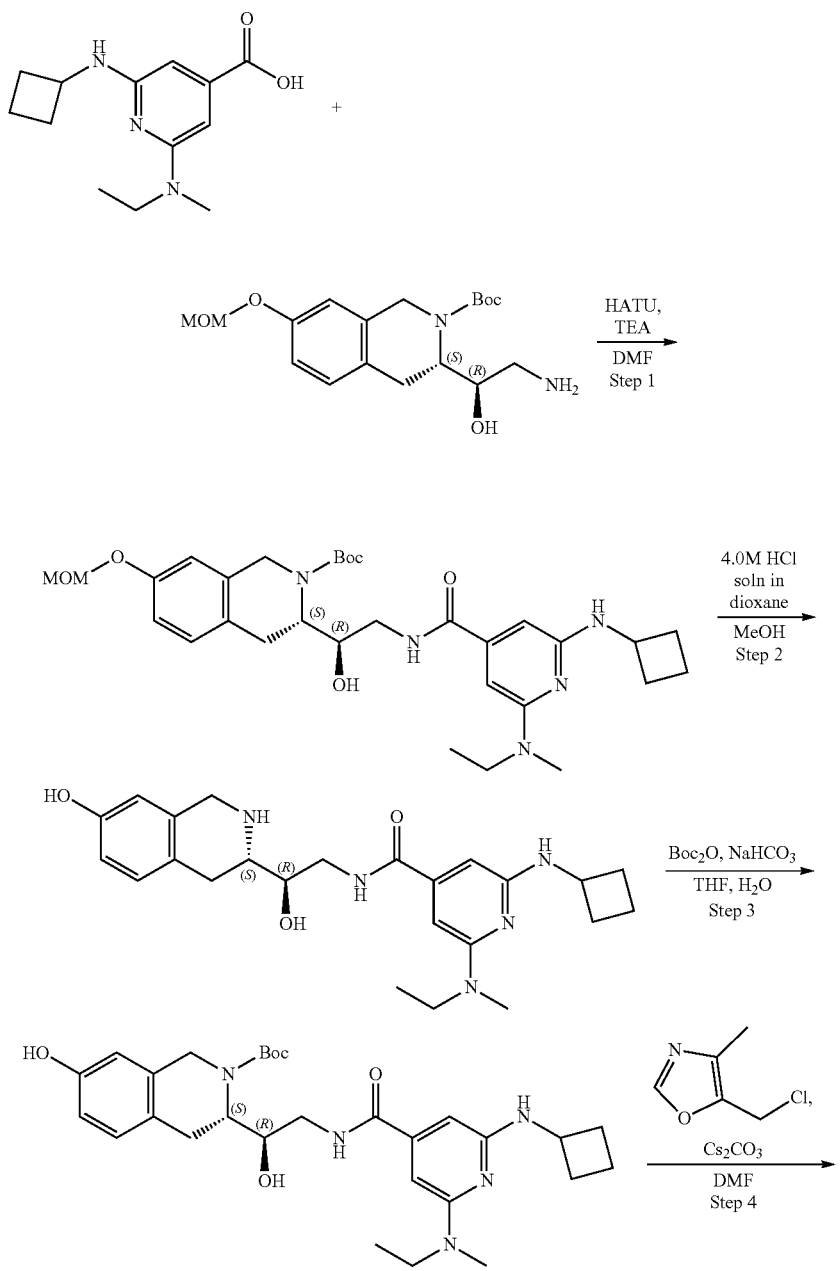

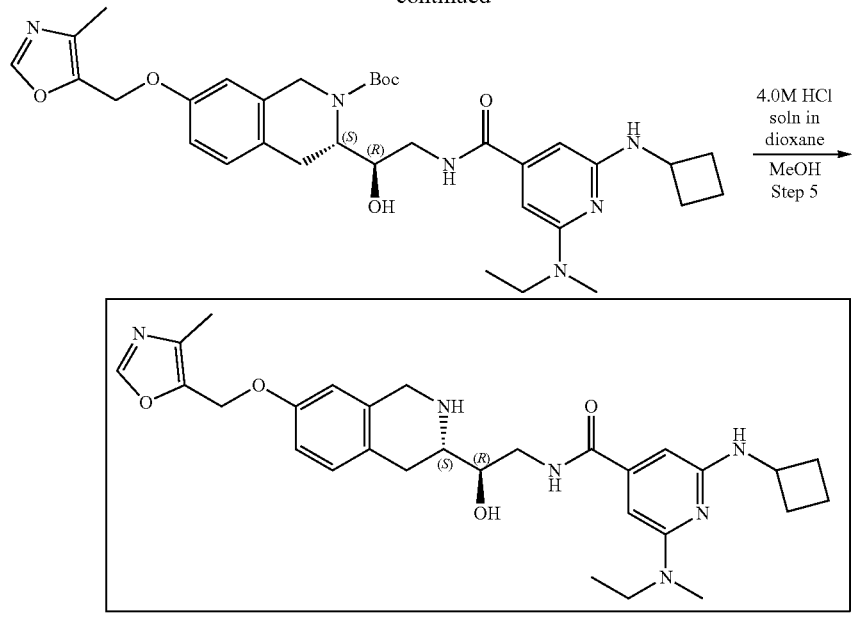

Step 1: Synthesis of (S)-tert-butyl 3-((R)-2-(2-(cyclobutylamino)-6-(ethyl(methyl)amino)isonicotinamido)-1-hydroxyethyl)-7-(methoxymethoxy)-3,4-dihydroisoquinoline-2(1H)-carboxylate 2-(Cyclobutylamino)-6-[ethyl(methyl)amino]pyridine-4-carboxylic acid (106.11 mg, 425.62 µmol) and TEA (430.69 mg, 4.26 mmol, 593.23 µL) were dissolved in DMF (3 mL) and cooled to 0° C., HATU (242.75 mg, 638.44 µmol) was added and the mixture was stirred for 15 min at 0° C. tert-Butyl (3S)-3-[(1R)-2-amino-1-hydroxyethyl]-7-(methoxymethoxy)-3,4-dihydro-1H-isoquinoline-2-carboxylate (0.15 g, 425.62 µmol) was added and the mixture was allowed to warm to r.t. and stirred overnight. Then, 10 mL of ethyl acetate was added, and the organic phase was washed with brine three times. Organic phase was dried over Na₂SO₄, filtered off and concentrated in vacuo at 45° C. to give crude product which was purified by HPLC (15-40% water-acetonitrile, 2-10 min, flow: 30 mL/min (loading pump 4 mL/min acetonitrile) column: SunFire C18 100×19 mm) to give tert-butyl (3S)-3-[(1R)-2-[[2-(cyclobutylamino)-6-[ethyl(methyl)amino]pyridine-4-carbonyl]amino]-1-hydroxy-ethyl]-7-(methoxymethoxy)-3,4-dihydro-1H-isoquinoline-2-carboxylate (0.052 g, 89.08 µmol, 20.93% yield). ¹H NMR (DMSO-d₆, 400 MHz) δ:1.03 (t, 3H), 1.44 (m, 9H), 1.65 (m, 2H), 1.83 (m, 2H), 2.23 (m, 2H), 2.76 (m, 1H), 2.91 (m, 5H), 3.36 (m, 4H), 3.48 (m, 4H), 4.17 (m, 3H), 4.77 (m, 1H), 5.15 (s, 2H), 5.99 (s, 1H), 6.01 (s, 1H), 6.41 (m, 1H), 6.85 (m, 2H), 7.08 (d, 1H), 8.17 (m, 1H). LCMS (ESI): [M+H]⁺ m/z: calc'd 583.3; found 584.3; Rt=1.38 min.

Step 2: Synthesis of 2-(cyclobutylamino)-6-(ethyl(methyl)amino)-N—((R)-2-hydroxy-2-((S)-7-hydroxy-1,2,3,4-tetrahydroisoquinolin-3-yl)ethyl)isonicotinamide tert-Butyl (3S)-3-[(1R)-2-[[2-(cyclobutylamino)-6-[ethyl(methyl)amino]pyridine-4-carbonyl]amino]-1-hydroxyethyl]-7-(methoxymethoxy)-3,4-dihydro-1H-isoquinoline-2-carboxylate (0.052 g, 89.08 µmol) was dissolved in MeOH (2 mL). Hydrogen chloride solution 4.0M in dioxane (243.61 mg, 6.68 mmol, 304.51 µL) was added. The resulting mixture was stirred for 12 h at 20° C. After the completion of the reaction, the solvent was removed on vacuo at 35° C. to give 2-(cyclobutylamino)-6-[ethyl(methyl)amino]-N-[(2R)-2-hydroxy-2-[(3S)-7-hydroxy-1,2,3,4-tetrahydroisoquinolin-3-yl]ethyl]pyridine-4-carboxamide (24 mg, 46.83 µmol, 52.57% yield, 2HCl). ¹H NMR (CD₃OD, 400 MHz) δ:1.25 (t, 3H), 1.90 (m, 4H), 2.48 (m, 2H), 3.09 (m, 2H), 3.18 (m, 4H), 3.61 (m, 5H), 4.23 (m, 2H), 6.18 (m, 2H), 6.61 (s, 1H), 6.73 (d, 1H), 7.09 (d, 1H), NH and OH aren't observed. LCMS (ESI): [M+H]⁺ m/z: calc'd 439.2; found 440.2; Rt=2.84 min.

Step 3: Synthesis of (S)-tert-butyl 3-((R)-2-(2-(cyclobutylamino)-6-(ethyl(methyl)amino)isonicotinamido)-1-hydroxyethyl)-7-hydroxy-3,4-dihydroisoquinoline-2(1H)-carboxylate 2-(Cyclobutylamino)-6-[ethyl(methyl)amino]-N-[(2R)-2-hydroxy-2-[(3S)-7-hydroxy-1,2,3,4-tetrahydroisoquinolin-3-yl]ethyl]pyridine-4-carboxamide (24 mg, 46.83 µmol, 2HCl) was dissolved in the mixture of water (1 mL) and THF (1 mL) then sodium hydrogen carbonate, 99% (11.80 mg, 140.50 µmol, 5.46 µL) was added in one portion. The resulting mixture was stirred for 5 min solution of di-tert-butyl dicarbonate (10.22 mg, 46.83 µmol, 10.75 µL) in THF (0.2 mL) was added dropwise. The reaction mixture was stirred overnight at room temperature. After the completion of the reaction, ethyl acetate (15 mL) was added to the reaction mixture, organic phase was separated, and the aqueous phase was extracted with ethyl acetate (2*15 mL). The organic phase was washed with brine, dried over Na₂SO₄, filtered off and evaporated in vacuo at 40° C. to give tert-butyl (3S)-3-[(1R)-2-[[2-(cyclobutylamino)-6-[ethyl(methyl)amino]pyridine-4-carbonyl]amino]-1-hydroxy-ethyl]-7-hydroxy-3,4-dihydro-1H-isoquinoline-2-carboxylate (0.024 g, 44.47 µmol, 94.96% yield) which was used in the next step without purification. ¹H NMR (CD₃OD, 500 MHz) δ: 1.12 (t, 3H), 1.54 (m, 9H), 1.76 (m, 3H), 1.89 (m, 3H), 2.36 (m, 2H), 2.85 (m, 2H), 2.99 (m, 4H), 3.09 (m, 2H), 3.58 (m, 4H), 4.25 (m, 3H), 5.99 (s, 1H), 6.10 (s, 1H), 6.57 (s, 1H), 6.64 (d, 1H), 6.98 (d, 1H), 7.91 (m, 1H). LCMS (ESI): [M+H]⁺ m/z: calc'd 539.3; found 540.2; Rt=3.22 min.

Step 4: Synthesis of (S)-tert-butyl 3-((R)-2-(2-(cyclobutylamino)-6-(ethyl(methyl)amino)isonicotinamido)-1-hydroxyethyl)-7-((4-methyloxazol-5-yl)methoxy)-3,4-dihydroisoquinoline-2(1H)-carboxylate tert-Butyl (3S)-3-[(1R)-2-[[2-(cyclobutylamino)-6-[ethyl(methyl)amino]pyridine-4-carbonyl]amino]-1-hydroxy-ethyl]-7-hydroxy-3,4-dihydro-1H-isoquinoline-2-carboxylate (0.024 g, 44.47 µmol), 5-(chloromethyl)-4-methyl-oxazole (8.97 mg, 53.37 µmol, HCl) and cesium carbonate (43.47 mg, 133.42 µmol) were dissolved in DMF (2 mL) and stirred at 50° C. overnight. The reaction mixture was diluted with water end extracted three times with EA, then EA was extracted three times with brine. The organic phase was dried over $Na_2SO_4$, filtered off and evaporated at 40° C. to give tert-butyl (3S)-3-[(1R)-2-[[2-(cyclobutylamino)-6-[ethyl(methyl)amino]pyridine-4-carbonyl]amino]-1-hydroxy-ethyl]-7-[(4-methyl-oxazol-5-yl)methoxy]-3,4-dihydro-1H-isoquinoline-2-carboxylate (0.027 g, 42.54 µmol, 95.65% yield) which was used in the next step without further purification. $^1$H NMR ($CD_3OD$, 500 MHz) δ: 1.11 (m, 4H), 1.54 (m, 9H), 1.74 (m, 3H), 1.91 (m, 3H), 2.20 (m, 4H), 2.37 (m, 3H), 3.56 (m, 4H), 4.31 (m, 3H), 5.08 (s, 2H), 6.05 (m, 2H), 6.57 (d, 1H), 6.83 (m, 2H), 7.12 (d, 1H), 7.98 (m, 1H), 8.14 (m, 1H). LCMS (ESI): $[M+H]^+$ m/z: calc'd 634.3; found 635.4; Rt=3.86 min.

Step 5: Synthesis of 2-(cyclobutylamino)-6-(ethyl(methyl)amino)-N—((R)-2-hydroxy-2-((S)-7-((4-methyl-oxazol-5-yl)methoxy)-1,2,3,4-tetrahydroisoquinolin-3-yl)ethyl)isonicotinamide (Compound 24) tert-Butyl (3S)-3-[(1R)-2-[[2-(cyclobutylamino)-6-[ethyl(methyl)amino]pyridine-4-carbonyl]amino]-1-hydroxy-ethyl]-7-[(4-methyloxazol-5-yl)methoxy]-3,4-dihydro-1H-isoquinoline-2-carboxylate (0.027 g, 42.54 µmol) was dissolved in methanol (1.5 mL). Hydrogen chloride solution 4.0M in dioxane (116.32 mg, 3.19 mmol, 145.40 µL) was added. The mixture was stirred at 20° C. for 4 h. Then, the solvent was removed in vacuo at 45° C. The residue was dissolved in 5 mL of methanol and 10 mg of scavenger (SiliaMetS© dimercaptotriazine (DMT) was added thereto. The resulting suspension was stirred for 12 h. The suspension was filtered off, the filtrate was evaporated under reduced pressure and the residue was purified by HPLC (40-100% methanol 0-10 min methanol/$H_2O$(0.0034%) (loading pump 4 mL/min methanol), column: SunFire C18 100*19 mm to give 2-(cyclobutylamino)-6-[ethyl(methyl)amino]-N-[(2R)-2-hydroxy-2-[(3S)-7-[(4-methyloxazol-5-yl)methoxy]-1,2,3,4-tetrahydroisoquinolin-3-yl]ethyl]pyridine-4-carboxamide (0.0154 g, 23.91 µmol, 56.22% yield, 3HCl). $^1$H NMR, δ 1.12 (m, 3H), 1.76 (m, 2H), 1.88 (m, 2H), 2.19 (s, 3H), 2.36 (m, 2H), 2.65 (s, 0.75H), 2.69 (s, 0.25H), 3.00 (s, 3H), 3.17 (m, 2H), 3.56 (m, 4H), 4.24 (m, 2H), 4.38 (AB-system, 2H), 5.08 (s, 2H), 6.02 (s, 0.75H), 6.15 (s, 0.25H), 6.87 (s, 1H), 6.94 (d, 1H), 7.23 (d, 1H), 8.13 (s, 1H), NH, NH, NH, HCl are not observed. LCMS (ESI): $[M+H]^+$ m/z: calc'd 534.3; found 536.2; Rt=0.91 min.

Example 2A12. Synthesis of 2-(4-acetylpiperazin-1-yl)-6-(cyclobutylamino)-N—((R)-2-hydroxy-2-((S)-7-((4-methyloxazol-5-yl)methoxy)-1,2,3,4-tetrahydroisoquinolin-3-yl)ethyl)isonicotinamide
(Compound 29)

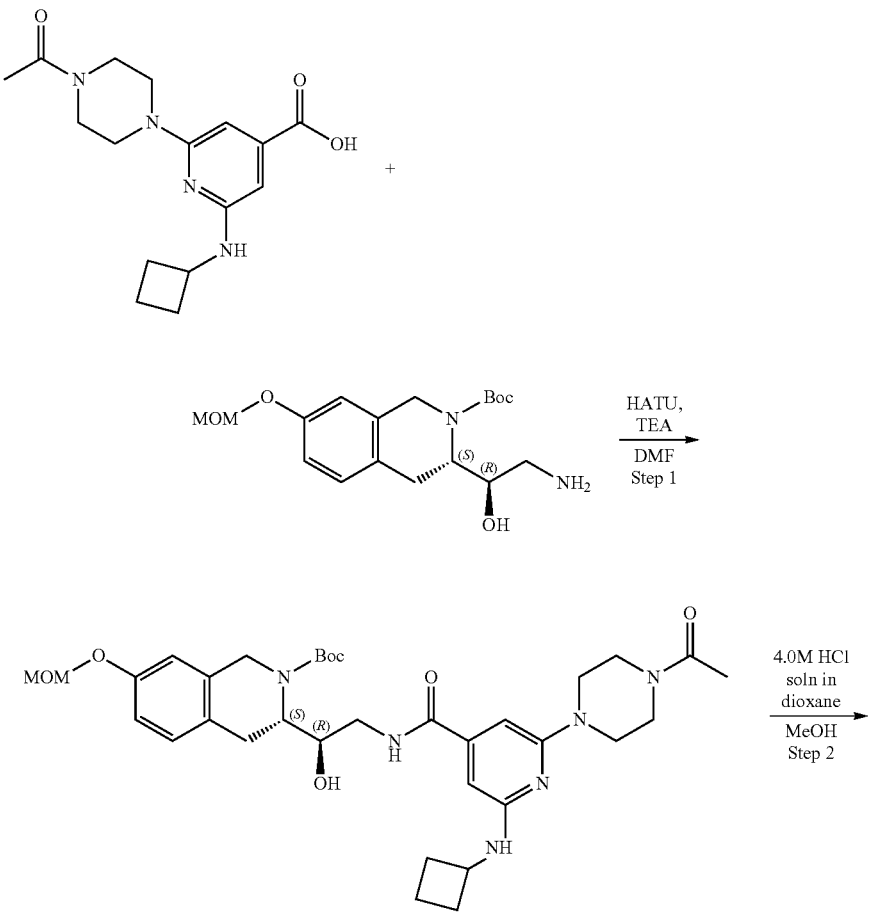

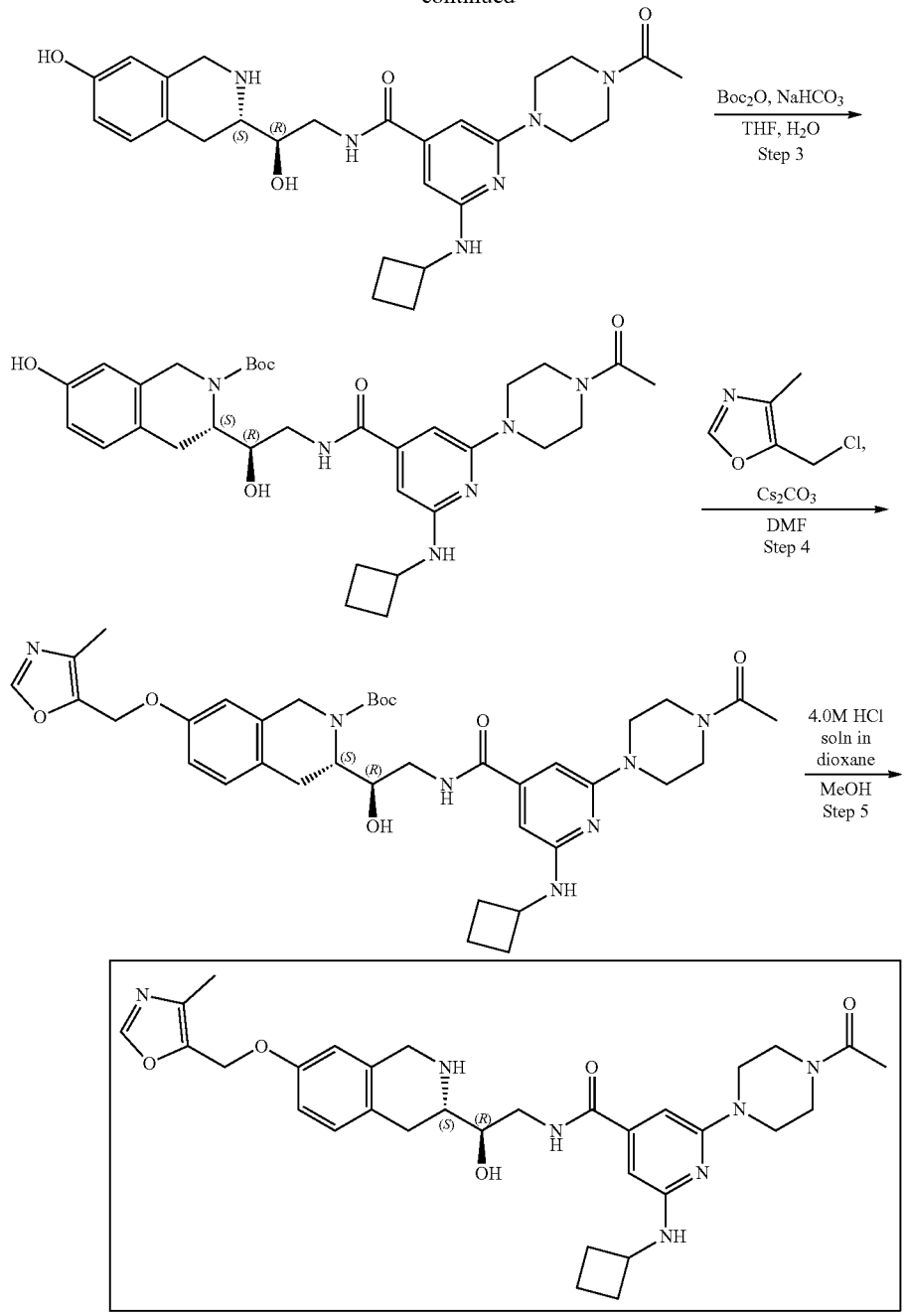

Step 1: Synthesis of (S)-tert-butyl 3-((R)-2-(2-(4-acetylpiperazin-1-yl)-6-(cyclobutylamino)isonicotinamido)-1-hydroxyethyl)-7-(methoxymethoxy)-3,4-dihydroisoquinoline-2(1H)-carboxylate 2-(4-Acetylpiperazin-1-yl)-6-(cyclobutylamino)pyridine-4-carboxylic acid (184.04 mg, 425.62 μmol, CF₃COOH), tert-butyl (3S)-3-[(1R)-2-amino-1-hydroxy-ethyl]-7-(methoxymethoxy)-3,4-dihydro-1H-isoquinoline-2-carboxylate (150 mg, 425.62 μmol), triethylamine (430.69 mg, 4.26 mmol, 593.23 μL) were mixed in DMF (3 mL) and then HATU (242.75 mg, 638.44 μmol) was added. The resulting mixture was stirred at 25° C. for 12 h. The mixture was evaporated under reduce pressure and purified with HPLC (50-75% water-acetonitrile, 10 min, flow: 30 mL/min) to obtain tert-butyl (3S)-3-[(1R)-2-[[2-(4-acetylpiperazin-1-yl)-6-(cyclobutylamino)pyridine-4-carbonyl]amino]-1-hydroxy-ethyl]-7-(methoxymethoxy)-3,4-dihydro-1H-isoquinoline-2-carboxylate (77.8 mg, 119.18 μmol, 28.00% yield). ¹H NMR (DMSO-d₆, 400 MHz) δ:1.44 (m, 9H), 1.76 (m, 4H), 2.04 (m, 7H), 2.24 (m, 2H), 2.54 (s, 2H), 2.89 (m, 4H), 3.40 (m, 3H), 3.49 (m, 2H), 4.16 (m, 3H), 4.76 (m, 1H), 5.15 (s, 2H), 6.08 (s, 1H), 6.24 (s, 1H), 6.59 (d, 1H), 6.85 (m, 2H), 7.06 (d, 1H), 8.22 (m, 1H). LCMS (ESI): [M+H]⁺ m/z: calc'd 652.3; found 653.4; Rt=1.43 min.

Step 2: Synthesis of 2-(4-acetylpiperazin-1-yl)-6-(cyclobutylamino)-N—((R)-2-hydroxy-2-((S)-7-hydroxy-1,2,3,4-tetrahydroisoquinolin-3-yl)ethyl)isonicotinamide A solution of tert-butyl (3S)-3-[(1R)-2-[[2-(4-acetylpiperazin- 1-yl)-6-(cyclobutylamino)pyridine-4-carbonyl]amino]-1-hydroxy-ethyl]-7-(methoxymethoxy)-3,4-dihydro-1H-isoquinoline-2-carboxylate (77.8 mg, 119.18 μmol) in dioxane/HCl (2 mL) and methanol (2 mL) was stirred for 12 h at 25° C. Then, the solution was evaporated to obtain 2-(4-acetylpiperazin-1-yl)-6-(cyclobutylamino)-N-[(2R)-2-hydroxy-2-[(3S)-7-hydroxy-1,2,3,4-tetrahydroisoquinolin-3-yl]ethyl]pyridine-4-carboxamide (70 mg, crude, 3HCl) $^1$H NMR (CD$_3$OD, 500 MHz) δ:1.89 (m, 2H), 2.08 (m, 2H), 2.14 (m, 2H), 2.51 (m, 2H), 3.15 (m, 3H), 3.52 (m, 8H), 3.80 (m, 6H), 4.31 (m, 4H), 6.43 (m, 2H), 6.63 (s, 1H), 6.75 (d, 1H), 7.11 (d, 1H), 7.98 (m, 1H). LCMS (ESI): [M+H]$^+$ m/z: calc'd 508.3; found 509.2; Rt=0.95 min.

Step 3: Synthesis of (S)-tert-butyl 3-((R)-2-(2-(4-acetylpiperazin-1-yl)-6-(cyclobutylamino)isonicotinamido)-1-hydroxyethyl)-7-hydroxy-3,4-dihydroisoquinoline-2(1H)-carboxylate) To a stirred solution of sodium hydrogen carbonate (28.55 mg, 339.81 μmol, 13.22 μL) in water (1 mL) the solution of 2-(4-acetylpiperazin-1-yl)-6-(cyclobutylamino)-N-[(2R)-2-hydroxy-2-[(3S)-7-hydroxy-1,2,3,4-tetrahydroisoquinolin-3-yl]ethyl]pyridine-4-carboxamide (70 mg, 113.27 μmol, 3HCl) in THF (1 mL) was added followed by di-tert-butyl dicarbonate (24.72 mg, 113.27 μmol, 25.99 μL) in THF (1 mL). The resulting mixture was stirred at 25° C. for 12 h. Then, EtOAc (10 mL) was added and the organic phase was separated and washed with brine (2*5 mL). Then, the solvent was dried over sodium sulfate, filtered off and evaporated to obtain tert-butyl (3S)-3-[(1R)-2-[[2-(4-acetylpiperazin-1-yl)-6-(cyclobutylamino)pyridine-4-carbonyl]amino]-1-hydroxy-ethyl]-7-hydroxy-3,4-dihydro-1H-isoquinoline-2-carboxylate (65 mg, crude). $^1$H NMR (CD$_3$OD, 400 MHz) δ: 1.49 (m, 9H), 1.74 (m, 2H), 1.89 (m, 4H), 2.12 (s, 2H), 2.37 (m, 2H), 2.93 (m, 3H), 3.48 (m, 4H), 3.59 (m, 4H), 3.73 (m, 3H), 4.24 (m, 2H), 6.07 (s, 1H), 6.31 (s, 1H), 6.54 (s, 1H), 6.56 (d, 1H), 6.96 (d, 1H). LCMS (ESI): [M+H]$^+$ m/z: calc'd 608.3; found 609.4; Rt=1.30 min.

Step 4: Synthesis of (S)-tert-butyl 3-((R)-2-(2-(4-acetylpiperazin-1-yl)-6-(cyclobutylamino)isonicotinamido)-1-hydroxyethyl)-7-((4-methyloxazol-5-yl)methoxy)-3,4-dihydroisoquinoline-2(1H)-carboxylate To the solution of tert-butyl (3S)-3-[(1R)-2-[[2-(4-acetylpiperazin-1-yl)-6-(cyclobutyl-amino)pyridine-4-carbonyl]amino]-1-hydroxy-ethyl]-7-hydroxy-3,4-dihydro-1H-isoquinoline-2-carboxylate (65 mg, 106.78 μmol), the mixture of cesium carbonate (104.37 mg, 320.34 μmol) in DMF (2 mL) was added 5-(chloromethyl)-4-methyl-oxazole (21.53 mg, 128.14 μmol, HCl). The resulting mixture was heated at 50° C. for 12 h. The reaction mixture was filtered off and evaporated to obtain tert-butyl (3S)-3-[(1R)-2-[[2-(4-acetylpiperazin-1-yl)-6-(cyclobutylamino)pyridine-4-carbonyl]amino]-1-hydroxy-ethyl]-7-[(4-methyloxazol-5-yl)methoxy]-3,4-dihydro-1H-isoquinoline-2-carboxylate (90 mg, crude) which was used without further purification. $^1$H NMR (CD$_3$OD, 500 MHz) δ:1.53 (m, 9H), 1.88 (m, 6H), 2.15 (m, 6H), 2.43 (m, 6H), 3.26 (m, 3H), 3.45 (s, 3H), 4.24 (m, 1H), 4.55 (m, 2H), 5.07 (s, 2H), 6.63 (m, 2H), 6.81 (m, 3H), 7.11 (m, 1H), 8.10 (m, 1H). LCMS (ESI): [M+H]$^+$ m/z: calc'd 703.3; found 704.4; Rt=1.41 min.

Step 5: Synthesis of 2-(4-acetylpiperazin-1-yl)-6-(cyclobutylamino)-N—((R)-2-hydroxy-2-((S)-7-((4-methyloxazol-5-yl)methoxy)-1,2,3,4-tetrahydroisoquinolin-3-yl)ethyl)isonicotinamide (Compound 29) A solution of tert-butyl (3S)-3-[(1R)-2-[[2-(4-acetylpiperazin-1-yl)-6-(cyclobutylamino)pyridine-4-carbonyl]amino]-1-hydroxy-ethyl]-7-[(4-methyloxazol-5-yl)methoxy]-3,4-dihydro-1H-isoquinoline-2-carboxylate (90 mg, 127.87 μmol) in dioxane/HCl (2 mL) and methanol (2 mL) was stirred for 12 h at 25° C. Then, the solution was evaporated and the resulting crude product was purified by HPLC (35-70%, 0-5 min, water(0.0034% HCl)-methanol) to obtain 2-(4-acetylpiperazin-1-yl)-6-(cyclobutylamino)-N-[(2R)-2-hydroxy-2-[(3S)-7-[(4-methyloxazol-5-yl)methoxy]-1,2,3,4-tetrahydroisoquinolin-3-yl]ethyl]pyridine-4-carboxamide (11.5 mg, 17.00 μmol, 13.29% yield, 2HCl). $^1$H NMR, δ 1.88 (m, 2H), 2.05 (m, 2H), 2.15 (s, 3H), 2.20 (s, 3H), 2.49 (m, 2H), 3.17 (m, 2H), 3.50 (dd, 1H), 3.66 (m, 4H), 3.76 (m, 8H), 4.18 (q, 1H), 4.31 (m, 2H), 4.49 (m, 1H), 5.10 (s, 2H), 6.87 (d, 1H), 6.97 (dd, 1H), 7.22 (d, 1H), 8.22 (s, 1H), NH, NH, NH, OH, HCl are not observed. LCMS (ESI): [M+H]$^+$ m/z: calc'd 603.3; found 604.4; Rt=1.01 min.

Example 2A13. Synthesis of 2-(cyclobutylamino)-N—((R)-2-hydroxy-2-((S)-7-((4-methyloxazol-5-yl)methoxy)-1,2,3,4-tetrahydroisoquinolin-3-yl)ethyl)-5-methoxyisonicotinamide (Compound 36)

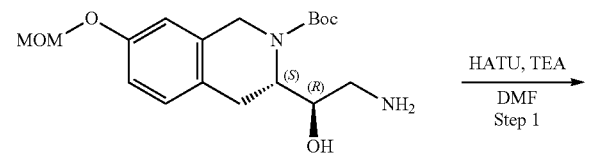

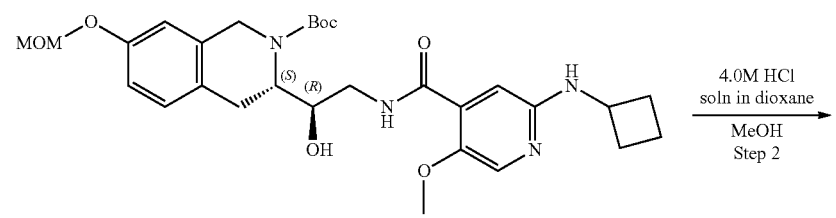

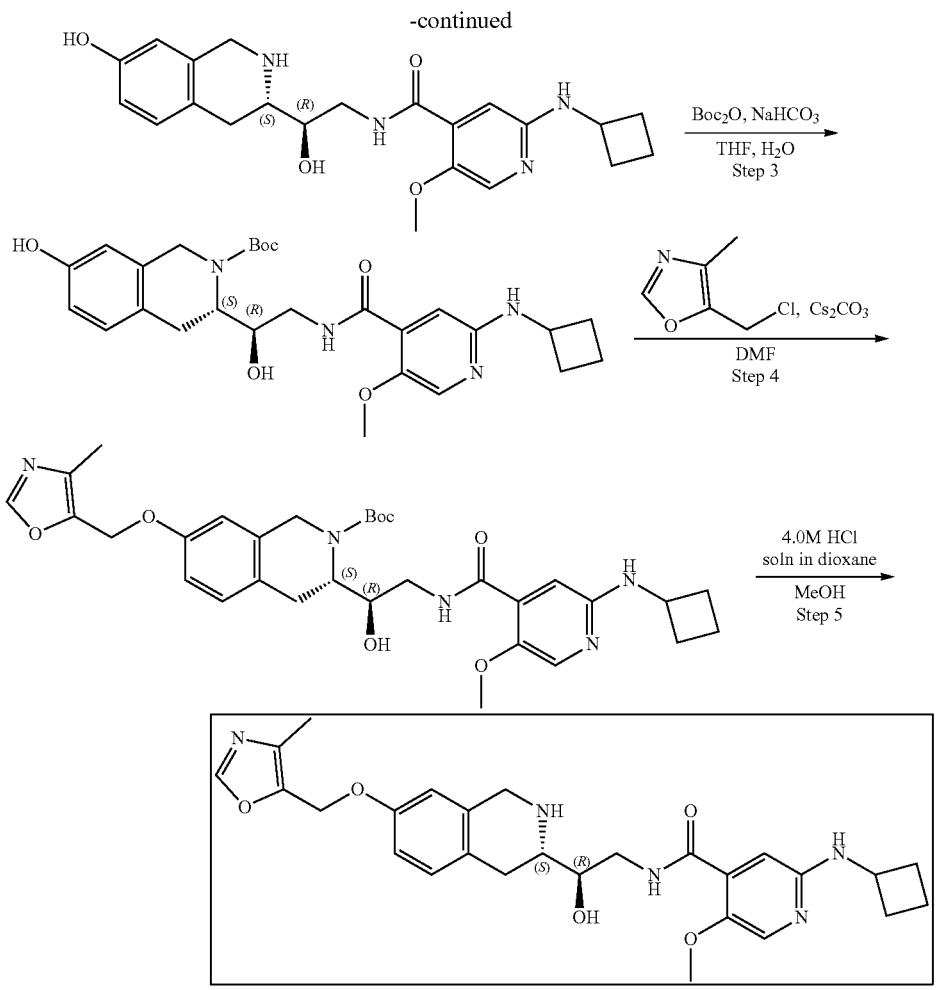

Step 1: Synthesis of (S)-tert-butyl 3-((R)-2-(2-(cyclobutylamino)-5-methoxyisonicotinamido)-1-hydroxyethyl)-7-(methoxymethoxy)-3,4-dihydroisoquinoline-2(1H)-carboxylate 2-(Cyclobutylamino)-5-methoxy-pyridine-4-carboxylic acid (143.12 mg, 425.62 µmol, CF₃COOH), tert-butyl (3S)-3-[(1R)-2-amino-1-hydroxy-ethyl]-7-(methoxymethoxy)-3,4-dihydro-1H-isoquinoline-2-carboxylate (150 mg, 425.62 µmol) and triethylamine (430.69 mg, 4.26 mmol, 593.23 µL) were mixed in DMF (4 mL) and HATU (242.75 mg, 638.44 µmol) was added. The resulting mixture were stirred at 25° C. for 12 h. After the completion of the reaction, the solvent was evaporated under reduce pressure and the residue was purified with HPLC (50-75% water-acetonitrile, 10 min, flow: 30 mL/min) to obtain tert-butyl (3S)-3-[(1R)-2-[[2-(cyclobutylamino)-5-methoxy-pyridine-4-carbonyl]amino]-1-hydroxy-ethyl]-7-(methoxymethoxy)-3,4-dihydro-1H-isoquinoline-2-carboxylate (90.8 mg, 163.12 µmol, 38.32% yield). ¹H NMR (CDCl₃, 400 MHz) δ: 1.51 (s, 9H), 1.82 (m, 5H), 2.43 (m, 2H), 3.02 (m, 3H), 3.25 (m, 3H), 3.92 (m, 1H), 3.99 (s, 2H), 4.08 (m, 2H), 4.23 (m, 1H), 4.37 (m, 1H), 4.66 (m, 2H), 5.13 (s, 2H), 6.77 (s, 1H), 6.89 (d, 1H), 7.07 (m, 2H), 7.87 (s, 1H), 9.01 (m, 1H). LCMS (ESI): [M+H]⁺ m/z: calc'd 556.3; found 557.2; Rt=1.25 min.

Step 2: Synthesis of 2-(cyclobutylamino)-N—((R)-2-hydroxy-2-((S)-7-hydroxy-1,2,3,4-tetrahydroisoquinolin-3-yl)ethyl)-5-methoxyisonicotinamide A solution of tert-butyl (3S)-3-[(1R)-2-[[2-(cyclobutylamino)-5-methoxy-pyridine-4-carbonyl]-amino]-1-hydroxy-ethyl]-7-(methoxymethoxy)-3,4-dihydro-1H-isoquinoline-2-carboxylate (90.8 mg, 163.12 µmol) in dioxane/HCl (2 mL) and methanol (2 mL) was stirred for 12 h at 25° C. Then, the solution was evaporated to obtain 2-(cyclobutylamino)-N-[(2R)-2-hydroxy-2-[(3S)-7-hydroxy-1,2,3,4-tetrahydro-isoquinolin-3-yl]ethyl]-5-methoxy-pyridine-4-carboxamide (75 mg, 154.51 µmol, 94.72% yield, 2HCl). ¹H NMR (CD₃OD, 500 MHz) δ: 2.01 (m, 4H), 2.53 (m, 2H), 3.10 (m, 2H), 3.36 (s, 3H), 3.60 (m, 4H), 3.85 (s, 3H), 4.28 (m, 4H), 6.63 (s, 1H), 6.77 (d, 1H), 7.11 (d, 1H), 7.30 (s, 1H), 7.48 (s, 1H). LCMS (ESI): [M+H]⁺ m/z: calc'd 412.2; found 413.2; Rt=0.75 min.

Step 3: Synthesis of (S)-tert-butyl 3-((R)-2-(2-(cyclobutylamino)-5-methoxyisonicotinamido)-1-hydroxyethyl)-7-hydroxy-3,4-dihydroisoquinoline-2(1H)-carboxylate To a stirred solution of sodium hydrogen carbonate, 99% (38.94 mg, 463.53 µmol, 18.03 µL) in water (1 mL), the solution of 2-(cyclobutylamino)-N-[(2R)-2-hydroxy-2-[(3S)-7-hydroxy-1,2,3,4-tetrahydroisoquinolin-3-yl]ethyl]-5-methoxy-pyridine-4-carboxamide (75 mg, 154.51 µmol, 2HCl) was added in THF (1 mL) followed by di-tert-butyl dicarbonate (33.72 mg, 154.51 µmol, 35.46 µL) in THF (1 mL). The resulting mixture was stirred at 25° C. for 12 h. EtOAc (10 mL) was added and the organic phase was separated and washed with brine (2*5 mL). Then, the solvent was dried over sodium sulfate, filtered off and evaporated to obtain tert-butyl (3S)-3-[(1R)-2-[[2-(cyclobutylamino)-5-methoxy-pyridine-4-carbonyl]-amino]-1-hydroxy-ethyl]-7-hydroxy-3,4-dihydro-1H-isoquinoline-2-carboxylate (73 mg, crude). $^1$H NMR (CD$_3$OD, 500 MHz) δ:1.23 (m, 1H), 1.52 (m, 9H), 1.88 (m, 2H), 1.93 (m, 3H), 2.37 (m, 2H), 2.85 (m, 1H), 3.10 (m, 2H), 3.77 (m, 3H), 3.93 (m, 2H), 4.17 (m, 2H), 4.33 (m, 2H), 6.57 (s, 1H), 6.60 (d, 1H), 6.97 (m, 2H), 7.81 (s, 1H). LCMS (ESI): [M+H]$^+$ m/z: calc'd 512.2; found 513.2; Rt=1.12 min.

Step 4: Synthesis of (S)-tert-butyl 3-((R)-2-(2-(cyclobutylamino)-5-methoxyisonicotinamido)-1-hydroxyethyl)-7-((4-methyloxazol-5-yl)methoxy)-3,4-dihydroisoquinoline-2(1H)-carboxylate To the solution of tert-butyl (3S)-3-[(1R)-2-[[2-(cyclobutylamino)-5-methoxy-pyridine-4-carbonyl]-amino]-1-hydroxy-ethyl]-7-hydroxy-3,4-dihydro-1H-isoquinoline-2-carboxylate (73 mg, 142.41 μmol), cesium carbonate (139.20 mg, 427.24 μmol) in DMF (2 mL) was added 5-(chloromethyl)-4-methyl-oxazole (28.71 mg, 170.89 μmol, HCl). The resulting mixture was heated at 50° C. for 12 h. The mixture was filtered off and evaporated to obtain tert-butyl (3S)-3-[(1R)-2-[[2-(cyclobutylamino)-5-methoxy-pyridine-4-carbonyl]amino]-1-hydroxy-ethyl]-7-[(4-methyloxazol-5-yl)methoxy]-3,4-dihydro-1H-isoquinoline-2-carboxylate (80 mg, crude) that was used in the next step without further purification. $^1$H NMR (CD$_3$OD, 500 MHz) δ:1.49 (m, 9H), 1.81 (m, 4H), 2.20 (m, 4H), 2.40 (m, 2H), 3.12 (m, 2H), 3.93 (m, 4H), 4.26 (m, 6H), 5.07 (s, 2H), 6.84 (m, 2H), 6.98 (s, 1H), 7.11 (d, 1H), 7.79 (s, 1H), 8.12 (m, 1H). LCMS (ESI): [M+H]$^+$ m/z: calc'd 607.3; found 608.4; Rt=1.25 min.

Step 5: Synthesis of 2-(cyclobutylamino)-N—((R)-2-hydroxy-2-((S)-7-((4-methyloxazol-5-yl)methoxy)-1,2,3,4-tetrahydroisoquinolin-3-yl)ethyl)-5-methoxyisonicotinamide (Compound 36) A solution of tert-butyl (3S)-3-[(1R)-2-[[2-(cyclobutylamino)-5-methoxy-pyridine-4-carbonyl]-amino]-1-hydroxy-ethyl]-7-[(4-methyloxazol-5-yl)methoxy]-3,4-dihydro-1H-isoquinoline-2-carboxylate (80 mg, 131.64 μmol) in dioxane/HCl (1 mL) and methanol (1 mL) was stirred for 12 h at 25° C. Then, the solution was evaporated and the resulting crude product was purified by HPLC (5-50% water-R1, 10 min, flow: 30 mL/min) to obtain 2-(cyclobutylamino)-N-[(2R)-2-hydroxy-2-[(3S)-7-[(4-methyloxazol-5-yl)-methoxy]-1,2,3,4-tetrahydroisoquinolin-3-yl]ethyl]-5-methoxy-pyridine-4-carboxamide (18.4 mg, 31.70 μmol, 24.08% yield, 2HCl)$^1$H NMR (Methanol-d$_4$, 400 MHz): δ (ppm) 1.89 (m, 2H), 2.09 (m, 2H), 2.24 (s, 3H), 2.52 (m, 2H), 3.17 (m, 3H), 3.54 (m, 1H), 3.68 (m, 2H), 3.83 (s, 3H), 4.16 (m, 1H), 4.34 (m, 2H), 4.50 (m, 1H), 5.13 (s, 2H), 6.90 (s, 1H), 6.96 (d, 1H), 7.23 (d, 1H), 7.32 (s, 1H), 7.48 (s, 1H), 8.44 (s, 1H). LCMS (ESI): [M+H]$^+$ m/z: calc'd 507.2; found 508.2; Rt=0.88 min.

Example 2A14. Synthesis of 2-[(1-acetyl-4-piperidyl)amino]-N-[(2R)-2-hydroxy-2-[(3S)-7-[(4-methyloxazol-5-yl)methoxy]-1,2,3,4-tetrahydroisoquinolin-3-yl]ethyl]-6-(1-piperidyl)pyridine-4-carboxamide (Compound 40)

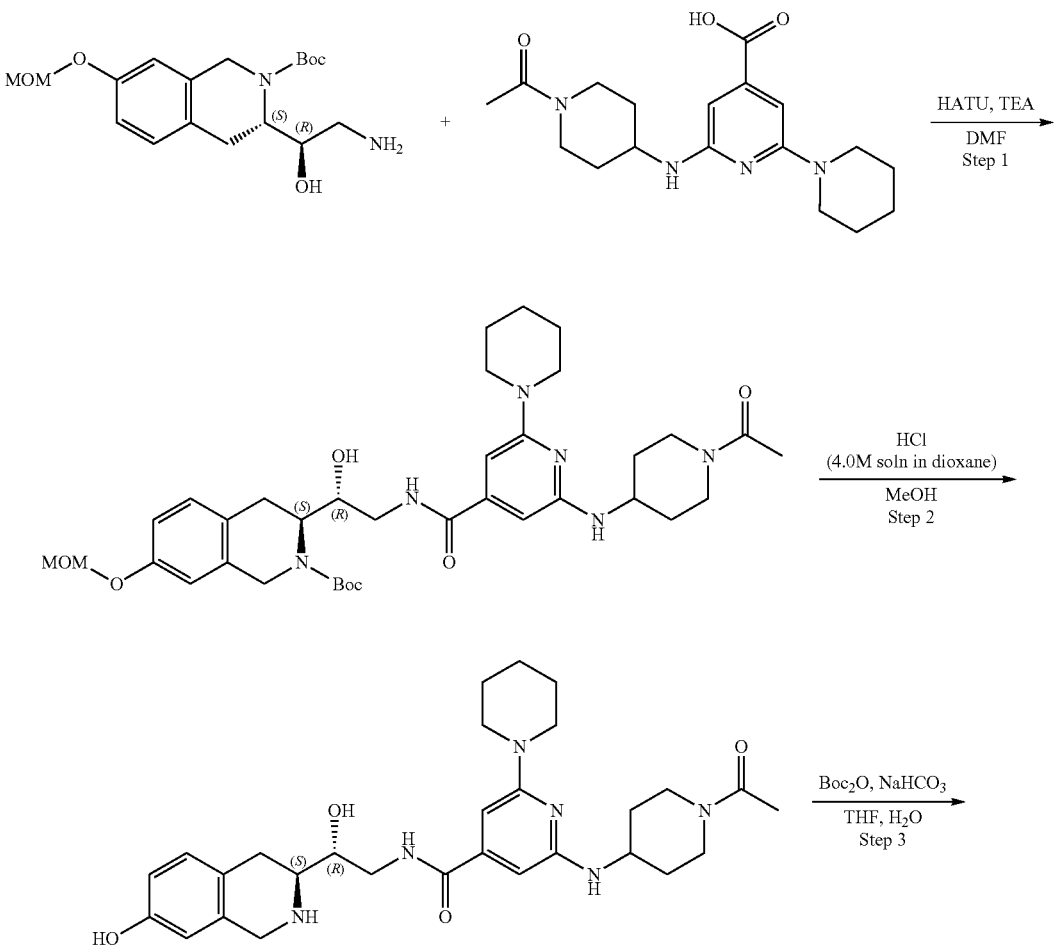

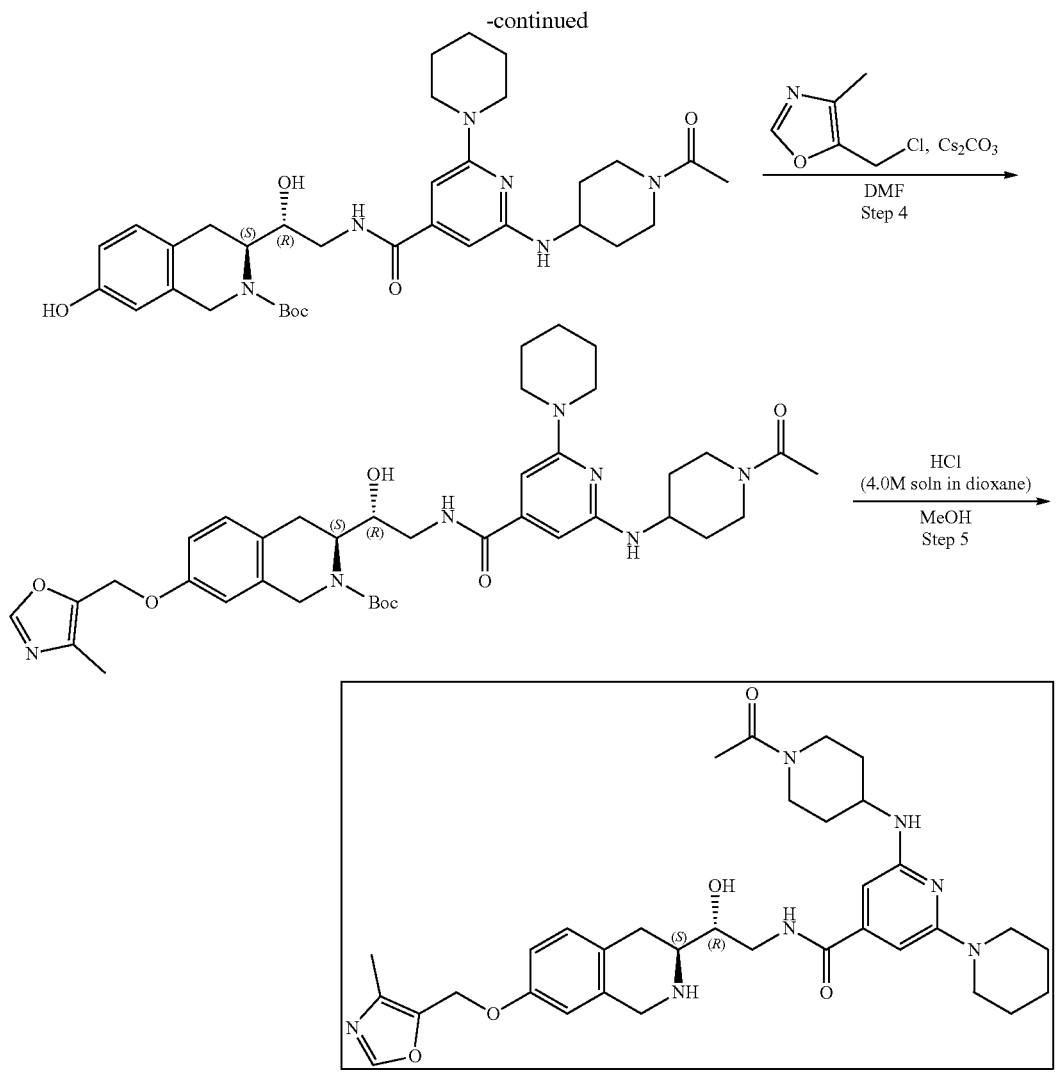

Step 1: Synthesis of tert-butyl (3S)-3-[(1R)-2-[[2-[(1-acetyl-4-piperidyl)amino]-6-(1-piperidyl)pyridine-4-carbonyl]amino]-1-hydroxy-ethyl]-7-(methoxymethoxy)-3,4-dihydro-1H-isoquinoline-2-carboxylate 2-[(1-acetyl-4-piperidyl)amino]-6-(1-piperidyl)pyridine-4-carboxylic acid (391.95 mg, 851.25 μmol, CF$_3$COOH) and TEA (861.38 mg, 8.51 mmol, 1.19 mL) were dissolved in DMF (10 mL) and cooled to 0° C. After that, HATU (485.50 mg, 1.28 mmol) was added and the mixture was stirred for 15 min at 0° C. followed by the addition of tert-butyl (3S)-3-[(1R)-2-amino-1-hydroxy-ethyl]-7-(methoxymethoxy)-3,4-dihydro-1H-isoquinoline-2-carboxylate (0.3 g, 851.25 μmol). The reaction mixture was warmed to r.t. and stirred for 3 h. After the completion of the reaction, 10 mL of ethyl acetate was added, and organic phase was washed with brine three times. The organic phase was dried over Na$_2$SO$_4$, filtered off and concentrated in vacuo at 45° C. to give crude product which was purified by HPLC (30-40% water-acetonitrile, 10 min, flow 30 mL/min (loading pump 4 mL/min ACN) column: SunFire C18 100×19 mm) to give tert-butyl (3S)-3-[(1R)-2-[[2-[(1-acetyl-4-piperidyl)amino]-6-(1-piperidyl)pyridine-4-carbonyl]amino]-1-hydroxy-ethyl]-7-(methoxymethoxy)-3,4-dihydro-1H-isoquinoline-2-carboxylate (0.199 g, 292.29 μmol, 34.34% yield). $^1$H NMR (DMSO-d$_6$, 400 MHz): δ 1.39 (m, 2H), 1.50 (s, 9H), 1.62 (m, 6H), 2.01 (m, 2H), 2.92 (m, 2H), 3.03 (m, 1H), 3.47 (s, 3H), 3.54 (m, 5H), 3.71 (m, 3H), 4.30 (m, 3H), 5.14 (s, 2H), 6.14 (s, 1H), 6.30 (s, 1H), 6.83 (s, 1H), 6.84 (d, 1H), 7.09 (d, 1H). LCMS (ESI): [M+H]$^+$ m/z: calc'd 680.4; found 681.1; Rt=1.31 min.

Step 2: Synthesis of 2-[(1-acetyl-4-piperidyl)amino]-N-[(2R)-2-hydroxy-2-[(3S)-7-hydroxy-1,2,3,4-tetrahydroisoquinolin-3-yl]ethyl]-6-(1-piperidyl)pyridine-4-carboxamide tert-Butyl (3S)-3-[(1R)-2-[[2-[(1-acetyl-4-piperidyl)amino]-6-(1-piperidyl)pyridine-4-carbonyl]-amino]-1-hydroxy-ethyl]-7-(methoxymethoxy)-3,4-dihydro-1H-isoquinoline-2-carboxylate (0.199 g, 292.29 μmol) was dissolved in MeOH (3 mL). Hydrogen chloride solution 4.0M in dioxane (799.29 mg, 21.92 mmol, 999.11 μL) was added. The reaction mixture was stirred for 12 h at 20° C. After the completion of the reaction, the solvent was removed in vacuo at 35° C. to give 2-[(1-acetyl-4-piperidyl)amino]-N-[(2R)-2-hydroxy-2-[(3S)-7-hydroxy-1,2,3,4-tetrahydroisoquinolin-3-yl]ethyl]-6-(1-piperidyl)pyridine-4-carboxamide (0.173 g, 283.80 μmol, 97.10% yield, 2HCl) which was used in the next step without further purification. $^1$H NMR (DMSO-d$_6$, 400 MHz): δ 1.75 (m, 6H), 2.13 (m, 5H), 3.10 (m, 3H), 3.53 (m, 2H), 3.62 (m, 12H), 4.28 (m, 2H), 4.40 (m, 4H), 6.62 (s, 1H), 6.75 (m, 2H), 7.12 (m, 2H). LCMS (ESI): [M+H]⁺ m/z: calc'd 536.3; found 537.4; Rt=2.19 min.

Step 3: Synthesis of tert-butyl (3S)-3-[(1R)-2-[[2-[(1-acetyl-4-piperidyl)amino]-6-(1-piperidyl)pyridine-4-carbonyl]amino]-1-hydroxy-ethyl]-7-hydroxy-3,4-dihydro-1H-isoquinoline-2-carboxylate) 2-[(1-Acetyl-4-piperidyl)amino]-N-[(2R)-2-hydroxy-2-[(3S)-7-hydroxy-1,2,3,4-tetrahydroiso-quinolin-3-yl]ethyl]-6-(1-piperidyl)pyridine-4-carboxamide (0.173 g, 283.80 μmol, 2HCl) was dissolved in the mixture of water (2 mL) and THF (2 mL) and sodium hydrogen carbonate, 99% (71.52 mg, 851.40 μmol, 33.11 μL) was added in one portion. The resulting mixture was stirred for 5 min at room temperature and the solution of di-tert-butyl dicarbonate (61.94 mg, 283.80 μmol, 65.13 μL) in THF (0.5 mL) was added dropwise. The reaction mixture was stirred for 12 h at room temperature. After the completion of the reaction, ethyl acetate (15 mL) was added to the reaction mixture, the organic phase was separated, and the aqueous phase was extracted with ethyl acetate (2*15 mL). The organic phase was washed with brine, dried over Na₂SO₄, filtered off and evaporated in vacuo at 40° C. to give tert-butyl (3S)-3-[(1R)-2-[[2-[(1-acetyl-4-piperidyl)amino]-6-(1-piperidyl)pyridine-4-carbonyl]amino]-1-hydroxy-ethyl]-7-hydroxy-3,4-dihydro-1H-isoquinoline-2-carboxylate (0.163 g, 255.98 μmol, 90.20% yield) which was used in the next step without purification. ¹H NMR (CDCl₃, 400 MHz): δ 1.53 (m, 11H), 1.61 (m, 6H), 1.98 (m, 2H), 2.11 (s, 3H), 2.89 (m, 3H), 3.08 (m, 1H), 3.51 (m, 6H), 3.91 (m, 3H), 4.32 (m, 4H), 6.12 (s, 1H), 6.30 (s, 1H), 6.54 (s, 1H), 6.61 (d, 1H), 6.98 (d, 1H). LCMS (ESI): [M+H]⁺ m/z: calc'd 636.3; found 637.4; Rt=2.94 min.

Step 4: Synthesis of tert-butyl (3S)-3-[(1R)-2-[[2-[(1-acetyl-4-piperidyl)amino]-6-(1-piperidyl)pyridine-4-carbonyl]amino]-1-hydroxy-ethyl]-7-[(4-methyloxazol-5-yl)methoxy]-3,4-dihydro-1H-isoquinoline-2-carboxylate tert-Butyl (3S)-3-[(1R)-2-[[2-[(1-acetyl-4-piperidyl)amino]-6-(1-piperidyl)pyridine-4-carbonyl]-amino]-1-hydroxy-ethyl]-7-hydroxy-3,4-dihydro-1H-isoquinoline-2-carboxylate (0.163 g, 255.98 μmol), 5-(chloromethyl)-4-methyl-oxazole (60.21 mg, 358.37 μmol, HCl) and cesium carbonate (333.61 mg, 1.02 mmol) were dissolved in DMF (3 mL) and heated at 60° C. overnight. The reaction mixture was filtered off, the residue was washed with DMF (2 mL), filtrate was concentrated on vacuo at 60° C. to give tert-butyl (3S)-3-[(1R)-2-[[2-[(1-acetyl-4-piperidyl)amino]-6-(1-piperidyl)pyridine-4-carbonyl]amino]-1-hydroxy-ethyl]-7-[(4-methyloxazol-5-yl)methoxy]-3,4-dihydro-1H-isoquinoline-2-carboxylate (0.177 g, 241.84 μmol, 94.48% yield) which was used in the next step without further purification. ¹H NMR (CD₃OD, 400 MHz): δ 1.50 (s, 9H), 1.58 (m, 6H), 2.00 (m, 2H), 2.08 (s, 4H), 2.18 (s, 3H), 3.50 (m, 4H), 3.64 (m, 10H), 3.89 (m, 2H), 4.32 (m, 2H), 5.05 (s, 2H), 6.10 (s, 1H), 6.29 (s, 1H), 6.78 (m, 3H), 7.12 (d, 1H). LCMS (ESI): [M+H]⁺ m/z: calc'd 731.4; found 732.4; Rt=3.67 min.

Step 5: Synthesis of 2-[(1-acetyl-4-piperidyl)amino]-N-[(2R)-2-hydroxy-2-[(3S)-7-[(4-methyloxazol-5-yl)methoxy]-1,2,3,4-tetrahydroisoquinolin-3-yl]ethyl]-6-(1-piperidyl)pyridine-4-carboxamide (Compound 40) tert-Butyl (3S)-3-[(1R)-2-[[2-[(1-acetyl-4-piperidyl)amino]-6-(1-piperidyl)pyridine-4-carbonyl]-amino]-1-hydroxy-ethyl]-7-[(4-methyloxazol-5-yl)methoxy]-3,4-dihydro-1H-isoquinoline-2-carboxylate (0.177 g, 241.84 μmol) was dissolved in Methanol (2 mL). Hydrogen chloride solution 4.0M in dioxane (661.34 mg, 18.14 mmol, 826.67 μL) was added. The reaction mixture was stirred for 20 hrs at RT. After the completion of the reaction, the solvent was removed on vacuo at 45° C. The residue was dissolved in 5 mL of methanol and 10 mg of scavenger (SiliaMetS© Dimercaptotriazine(DMT)) was added thereto. The resulting suspension was stirred for 12 h. The obtained mixture was filtered off, the filtrate was evaporated under reduced pressure and the residue was purified by HPLC (10-50% water+HCl-methanol, 0-10 min, flow 30 mL/min methanol (loading pump 4 mL/min methanol), column: SunFire C18 100*19 mm to give 2-[(1-acetyl-4-piperidyl)amino]-N-[(2R)-2-hydroxy-2-[(3S)-7-[(4-methyloxazol-5-yl)methoxy]-1,2,3,4-tetrahydroisoquinolin-3-yl]ethyl]-6-(1-piperidyl)pyridine-4-carboxamide (0.029 g, 39.13 μmol, 16.18% yield, 3HCl). ¹H NMR (DMSO-d₆, 400 MHz): δ (ppm) 1.28 (m, 1H), 1.42 (m, 1H), 1.59 (m, 6H), 1.90 (m, 2H), 2.01 (s, 3H), 2.15 (s, 3H), 3.03 (m, 3H), 3.30 (m, 3H), 3.48 (m, 4H), 3.73 (m, 5H), 3.87 (m, 2H), 4.05 (m, 1H), 4.17 (m, 2H), 4.35 (m, 1H), 5.11 (s, 2H), 6.46 (s, 1H), 6.56 (s, 1H), 6.94 (ds, 2H), 7.19 (d, 1H), 8.29 (s, 1H), 8.99 (s, 1H), 9.12 (s, 1H), 9.69 (s, 1H). LCMS (ESI): [M+H]⁺ m/z: calc'd 631.3; found 632.2; Rt=0.99 min.

Example 2A15. Synthesis of 2-[(1-acetylazetidin-3-yl)amino]-N-[(2R)-2-hydroxy-2-[(3S)-7-[(4-methyloxazol-5-yl)methoxy]-1,2,3,4-tetrahydroisoquinolin-3-yl]ethyl]-6-(1-piperidyl)pyridine-4-carboxamide (Compound 45)

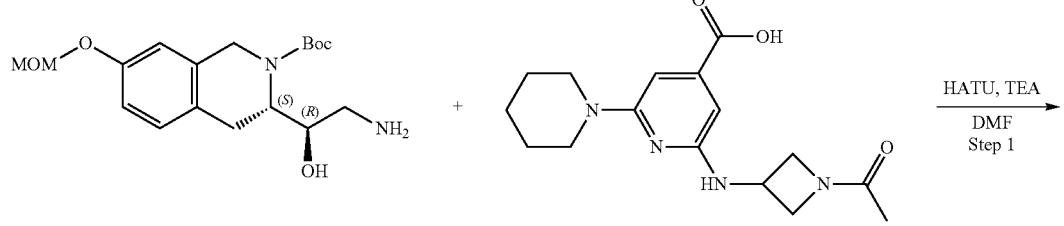

-continued
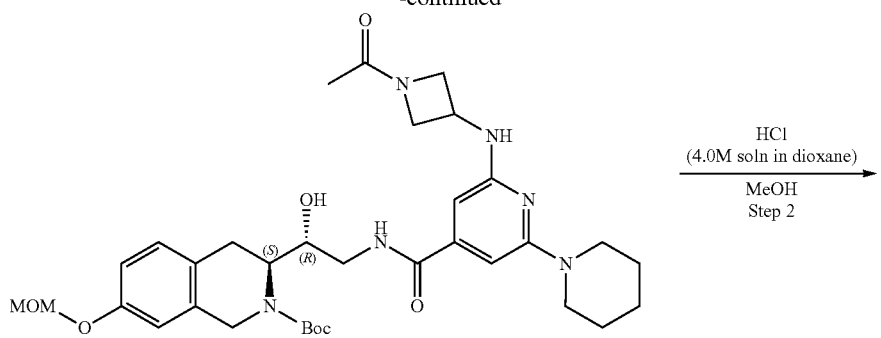
HCl
(4.0M soln in dioxane)
MeOH
Step 2
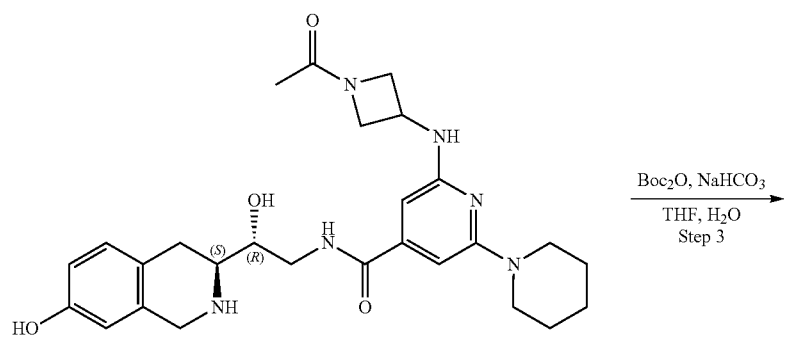
Boc₂O, NaHCO₃
THF, H₂O
Step 3
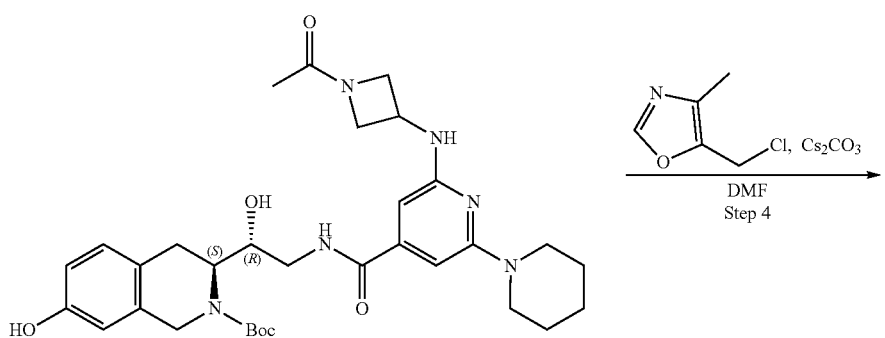
Cl, Cs₂CO₃
DMF
Step 4
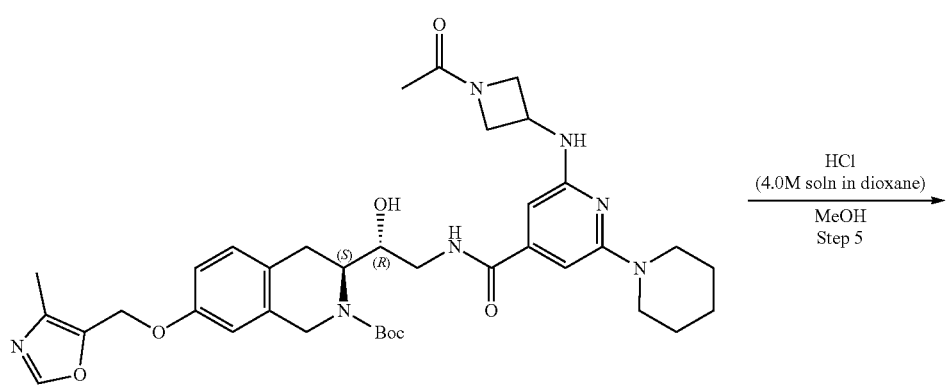
HCl
(4.0M soln in dioxane)
MeOH
Step 5

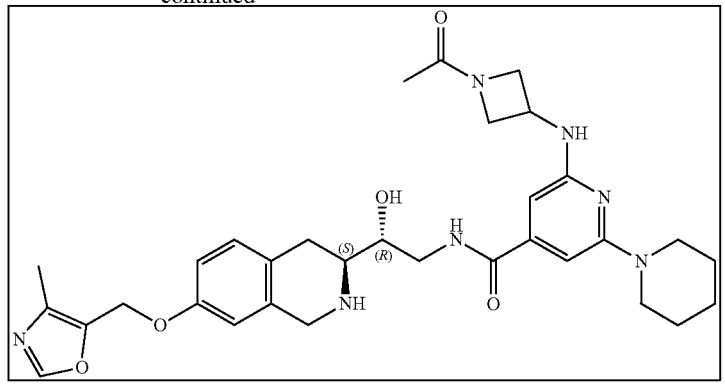

Step 1: Synthesis of tert-butyl (3S)-3-[(1R)-2-[[2-[(1-acetylazetidin-3-yl)amino]-6-(1-piperidyl)pyridine-4-carbonyl]amino]-1-hydroxy-ethyl]-7-(methoxymethoxy)-3,4-dihydro-1H-isoquinoline-2-carboxylate 2-[(1-Acetylazetidin-3-yl)amino]-6-(1-piperidyl)pyridine-4-carboxylic acid (0.271 g, 851.25 µmol) and TEA (861.34 mg, 8.51 mmol, 1.19 mL) were dissolved in DMF (10 mL) and cooled to 0° C. and HATU (485.48 mg, 1.28 mmol) was added. The resulting mixture was stirred for 15 min at 0° C. followed by the addition of tert-butyl (3S)-3-[(1R)-2-amino-1-hydroxy-ethyl]-7-(methoxymethoxy)-3,4-dihydro-1H-isoquinoline-2-carboxylate (0.3 g, 851.25 µmol). The reaction mixture was warmed to r.t. and stirred for 3 h. After the completion of the reaction, 10 mL of ethyl acetate was added, and the organic phase was washed with brine three times. The organic phase was dried over Na$_2$SO$_4$, filtered off and concentrated in vacuo at 45° C. to give crude product which was purified by HPLC (25-40% water-acetonitrile, 10 min, flow 30 mL/min (loading pump 4 mL/min acetonitrile) column: SunFire C18 100*19 mm) to give tert-butyl (3S)-3-[(1R)-2-[[2-[(1-acetylazetidin-3-yl)amino]-6-(1-piperidyl)pyridine-4-carbonyl]amino]-1-hydroxy-ethyl]-7-(methoxymethoxy)-3,4-dihydro-1H-isoquinoline-2-carboxylate (0.17 g, 260.43 µmol, 30.59% yield). $^1$H NMR (CDCl$_3$, 400 MHz): δ 1.51 (s, 9H), 1.60 (m, 4H), 1.85 (s, 3H), 1.98 (s, 5H), 2.87 (m, 2H), 3.14 (m, 1H), 3.46 (m, 4H), 3.53 (m, 3H), 3.88 (m, 1H), 3.96 (m, 1H), 4.15 (m, 2H), 4.34 (m, 2H), 4.43 (m, 1H), 4.56 (m, 1H), 4.68 (m, 1H), 4.83 (m, 1H), 5.13 (s, 2H), 6.11 (s, 1H), 6.50 (s, 1H), 6.77 (s, 1H), 6.85 (d, 1H), 7.10 (d, 1H), 7.96 (m, 1H). LCMS (ESI): [M+H]$^+$ m/z: calc'd 652.3; found 653.4; Rt=1.45 min.

Step 2: Synthesis of 2-[(1-acetylazetidin-3-yl)amino]-N-[(2R)-2-hydroxy-2-[(3S)-7-hydroxy-1,2,3,4-tetrahydroisoquinolin-3-yl]ethyl]-6-(1-piperidyl)pyridine-4-carboxamide tert-Butyl (3S)-3-[(1R)-2-[[2-[(1-acetylazetidin-3-yl)amino]-6-(1-piperidyl)pyridine-4-carbonyl]-amino]-1-hydroxy-ethyl]-7-(methoxymethoxy)-3,4-dihydro-1H-isoquinoline-2-carboxylate (0.17 g, 260.43 µmol) was dissolved in MeOH (3 mL) and hydrogen chloride solution 4.0M in dioxane (712.15 mg, 19.53 mmol, 890.19 µL) was added. The resulting mixture was stirred for 12 h at 20° C. After LCMS showed full conversion of starting material, the solvent was removed in vacuo at 35° C. to give 2-[(1-acetylazetidin-3-yl)amino]-N-[(2R)-2-hydroxy-2-[(3S)-7-hydroxy-1,2,3,4-tetrahydroisoquinolin-3-yl]ethyl]-6-(1-piperidyl)-pyridine-4-carboxamide (0.149 g, 256.22 µmol, 98.39% yield, 2HCl) which was used in the next step without further purification. $^1$H NMR (CD$_3$OD, 500 MHz): δ 1.79 (m, 6H), 1.91 (s, 3H), 3.09 (m, 2H), 3.18 (m, 1H), 3.52 (m, 6H), 3.64 (m, 1H), 3.90 (m, 2H), 4.12 (m, 2H), 4.39 (m, 2H), 4.56 (m, 1H), 6.62 (s, 1H), 6.75 (m, 2H), 7.11 (m, 2H). LCMS (ESI): [M+H]$^+$ m/z: calc'd 508.3; found 509.2; Rt=2.15 min.

Step 3: Synthesis of tert-butyl (3S)-3-[(1R)-2-[[2-[(1-acetylazetidin-3-yl)amino]-6-(1-piperidyl)pyridine-4-carbonyl]amino]-1-hydroxy-ethyl]-7-hydroxy-3,4-dihydro-1H-isoquinoline-2-carboxylate 2-[(1-Acetylazetidin-3-yl)amino]-N-[(2R)-2-hydroxy-2-[(3S)-7-hydroxy-1,2,3,4-tetrahydroiso-quinolin-3-yl]ethyl]-6-(1-piperidyl)pyridine-4-carboxamide (0.149 g, 292.95 µmol) was dissolved in the mixture of water (1 mL) and THF (1 mL) then sodium hydrogen carbonate, 99% (73.83 mg, 878.86 µmol, 34.18 µL) was added in one portion, after that the solution of di-tert-butyl dicarbonate (63.94 mg, 292.95 µmol, 67.23 µL) in THF (0.2 mL) was added dropwise. The reaction mixture was stirred for 12 h at room temperature. After the completion of the reaction, ethyl acetate (15 mL) was added to the reaction mixture, organic phase was separated, and the aqueous phase was extracted with ethyl acetate (2*15 mL). The organic phase was washed with brine, dried over Na$_2$SO$_4$, filtered off and evaporated in vacuo at 40° C. to give tert-butyl (3S)-3-[(1R)-2-[[2-[(1-acetylazetidin-3-yl)amino]-6-(1-piperidyl)pyridine-4-carbonyl]amino]-1-hydroxy-ethyl]-7-hydroxy-3,4-dihydro-1H-isoquinoline-2-carboxylate (0.142 g, 233.27 µmol, 79.63% yield) which was used in the next step without purification. $^1$H NMR (DMSO-d$_6$, 400 MHz): δ 1.57 (s, 9H), 1.85 (m, 6H), 2.11 (m, 4H), 3.78 (m, 6H), 3.91 (s, 2H), 4.05 (m, 2H), 4.49 (m, 4H), 4.79 (m, 2H), 6.32 (s, 1H), 6.57 (s, 1H), 6.81 (s, 1H), 6.86 (d, 1H), 7.24 (d, 1H). LCMS (ESI): [M+H]$^+$ m/z: calc'd 608.3; found 609.4; Rt=3.11 min.

Step 4: Synthesis of tert-butyl (3S)-3-[(1R)-2-[[2-[(1-acetylazetidin-3-yl)amino]-6-(1-piperidyl)pyridine-4-carbonyl]amino]-1-hydroxy-ethyl]-7-[(4-methyloxazol-5-yl)methoxy]-3,4-dihydro-1H-isoquinoline-2-carboxylate tert-Butyl (3S)-3-[(1R)-2-[[2-[(1-acetylazetidin-3-yl)amino]-6-(1-piperidyl)pyridine-4-carbonyl]-amino]-1-hydroxy-ethyl]-7-hydroxy-3,4-dihydro-1H-isoquinoline-2-carboxylate (0.142 g, 233.27 µmol), 5-(chloromethyl)-4-methyl-oxazole (50.95 mg, 303.26 µmol, HCl) and cesium carbonate (304.02 mg, 933.10 µmol) were dissolved in DMF (3 mL) and heated at 60° C. overnight. After the completion of the reaction, the reaction mixture was filtered off, the residue was washed with DMF (2 mL), and filtrate was concentrated in vacuo at 60° C. to give tert-butyl (3S)-3-[(1R)-2-[[2-[(1-acetylazetidin-3-yl)amino]-6-(1-piperidyl) pyridine-4-carbonyl]amino]-1-hydroxy-ethyl]-7-[(4-methyloxazol-5-yl)methoxy]-3,4-dihydro-TH-isoquinoline-2- carboxylate (0.143 g, 203.18 μmol, 87.10% yield) which was used in the next step without further purification. ¹H NMR (CD₃OD, 500 MHz): δ 1.45 (m, 11H), 1.60 (m, 6H), 1.90 (s, 2H), 2.21 (m, 4H), 3.54 (m, 6H), 3.81 (m, 3H), 3.90 (m, 1H), 4.08 (m, 2H), 4.21 (m, 1H), 4.39 (m, 2H), 5.08 (m, 2H), 6.13 (s, 1H), 6.33 (s, 1H), 6.79 (s, 1H), 6.80 (d, 1H), 7.07 (d, 1H), 8.14 (s, 1H). LCMS (ESI): [M+H]⁺ m/z: calc'd 703.3; found 704.4; Rt=3.90 min.

Step 5: Synthesis of 2-[1-acetylazetidin-3-yl)amino]-N-[(2R)-2-hydroxy-2-[(3S)-7-[(4-methyloxazol-5-yl)methoxy]-1,2,3,4-tetrahydroisoquinolin-3-yl]ethyl]-6-(1-piperidyl)pyridine-4-carboxamide (Compound 45) tert-Butyl (3S)-3-[(1R)-2-[[2-[(1-acetylazetidin-3-yl)amino]-6-(1-piperidyl)pyridine-4-carbonyl]-amino]-1-hydroxy-ethyl]-7-[(4-methyloxazol-5-yl)methoxy]-3,4-dihydro-TH-isoquinoline-2-carboxylate (0.143 g, 203.18 μmol) was dissolved in the mixture of MeOH (3 mL) and hydrogen chloride solution 4.0M in dioxane (555.60 mg, 15.24 mmol, 694.50 μL) was added. The resulting mixture was stirred for 4 h at 20° C. After the completion of the reaction, the solvent was removed on vacuo at 45° C. The residue was dissolved in 5 mL of methanol and 12 mg of scavenger (SiliaMetS© Dimercaptotriazine(DMT) was added thereto and the resulting suspension was stirred for 12 h. The obtained mixture was filtered off, the filtrate was evaporated under reduced pressure and the residue was purified by HPLC (35% water-methanol+NH₃, 10 min, flow 30 mL/min (loading pump 4 mL/min methanol+NH₃), column: SunFire C18 100*19 mm to give 2-[(1-acetylazetidin-3-yl)amino]-N-[(2R)-2-hydroxy-2-[(3S)-7-[(4-methyloxazol-5-yl)methoxy]-1,2,3,4-tetrahydroisoquinolin-3-yl]ethyl]-6-(1-piperidyl)pyridine-4-carboxamide (0.0074 g, 12.26 μmol, 6.03% yield). ¹H NMR (400 MHz, CDCl₃) δ 1.22 (m, 4H), 1.61 (m, 4H), 1.86 (s, 3H), 2.23 (s, 3H), 2.77 (m, 2H), 3.00 (m, 1H), 3.50 (m, 4H), 3.77 (m, 1H), 3.86 (m, 2H), 3.94 (m, 1H), 4.00 (m, 2H), 4.05 (m, 1H), 4.31 (t, 1H), 4.41 (t, 1H), 4.55 (m, 1H), 4.98 (s, 2H), 5.08 (m, 1H), 6.03 (s, 1H), 6.30 (s, 1H), 6.62 (s, 1H), 6.79 (d, 1H), 7.05 (d, 1H), 7.33 (m, 1H), 7.82 (s, 1H). LCMS (ESI): [M+H]⁺ m/z: calc'd 603.3; found 604.4; Rt=0.97 min.

Example 2A16. Synthesis of 2-[(1-acetyl-4-piperidyl)amino]-N-[(2R)-2-hydroxy-2-[(3S)-7-[(4-methyloxazol-5-yl)methoxy]-1,2,3,4-tetrahydroisoquinolin-3-yl]ethyl]pyridine-4-carboxamide Compound 44)

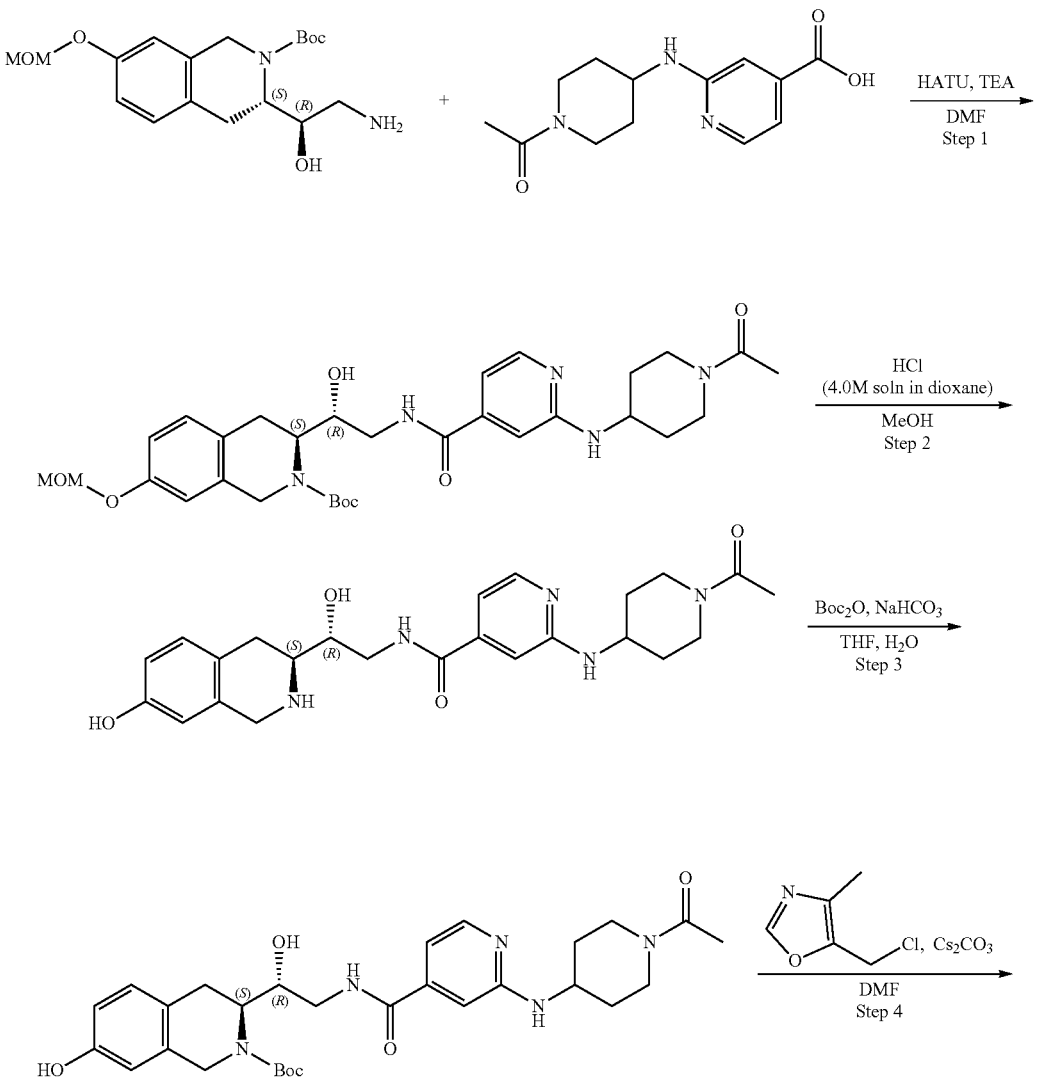

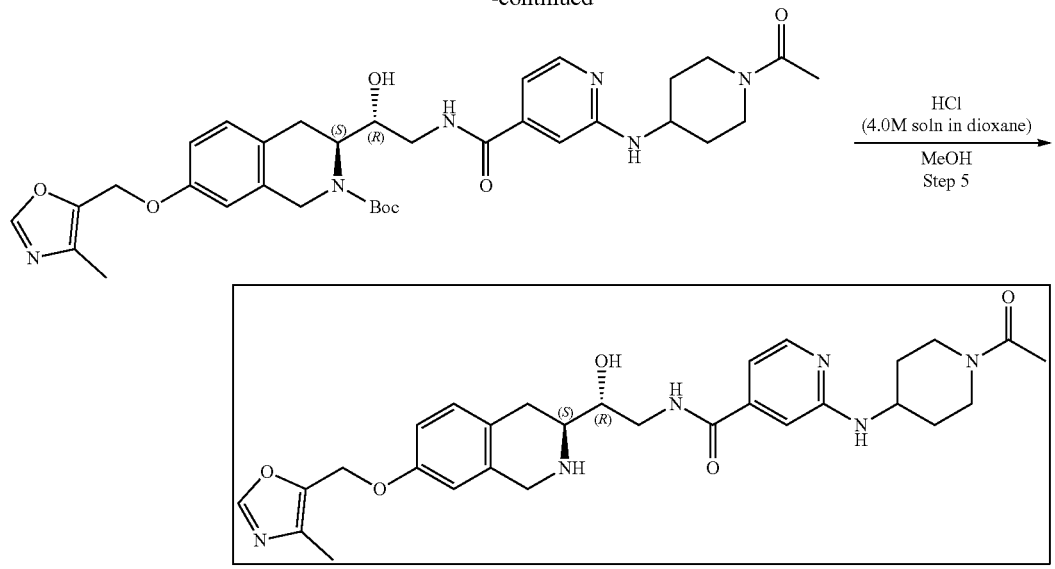

Step 1: Synthesis of tert-butyl (3S)-3-[(1R)-2-[[2-[(1-acetyl-4-piperidyl)amino]pyridine-4-carbonyl]amino]-1-hydroxy-ethyl]-7-(methoxymethoxy)-3,4-dihydro-1H-isoquinoline-2-carboxylate 2-[(1-Acetyl-4-piperidyl)amino]pyridine-4-carboxylic acid (224.13 mg, 851.25 μmol) and TEA (861.38 mg, 8.51 mmol, 1.19 mL) were dissolved in DMF (10 mL) and cooled to 0° C., then HATU (485.50 mg, 1.28 mmol) was added. The mixture was stirred for 15 min at 0° C. followed by the addition of tert-butyl (3S)-3-[(1R)-2-amino-1-hydroxy-ethyl]-7-(methoxymethoxy)-3,4-dihydro-1H-isoquinoline-2-carboxylate (0.3 g, 851.25 μmol). The reaction mixture was warmed to r.t. and stirred for 3 h. After the completion of the reaction, 10 mL of ethyl acetate was added, and organic phase was washed with brine three times. The organic phase was dried over Na$_2$SO$_4$, filtered off and concentrated in vacuo at 45° C. to give crude product which was purified by HPLC (15-45% water-acetonitrile, 10 min, flow 30 mL/min (loading pump 4 mL/min acetonitrile) column: SunFire C18 100*19 mm) to give tert-butyl (3S)-3-[(1R)-2-[[2-[(1-acetyl-4-piperidyl)amino]pyridine-4-carbonyl]amino]-1-hydroxy-ethyl]-7-(methoxymethoxy)-3,4-dihydro-TH-isoquinoline-2-carboxylate (0.15 g, 250.96 μmol, 29.48% yield). $^1$H NMR (CDCl$_3$, 400 MHz): δ 1.38 (m, 2H), 1.50 (s, 9H), 1.76 (m, 1H), 1.98 (m, 4H), 2.12 (m, 3H), 2.84 (m, 2H), 3.17 (m, 2H), 3.46 (m, 4H), 3.79 (m, 1H), 3.94 (m, 1H), 4.13 (m, 2H), 4.18 (m, 1H), 4.34 (m, 1H), 4.67 (m, 2H), 5.13 (s, 2H), 6.78 (s, 1H), 6.87 (s, 1H), 6.92 (d, 1H), 7.08 (d, 1H), 8.02 (m, 1H), 8.14 (m, 1H). LCMS (ESI): [M+H]$^+$ m/z: calc'd 597.3; found 598.3; Rt=1.06 min.

Step 2: Synthesis of 2-[(1-acetyl-4-piperidyl)amino]-N-[(2R)-2-hydroxy-2-[(3S)-7-hydroxy-1,2,3,4-tetrahydroisoquinolin-3-yl]ethyl]pyridine-4-carboxamide tert-Butyl (3S)-3-[(1R)-2-[[2-[(1-acetyl-4-piperidyl)amino]pyridine-4-carbonyl]amino]-1-hydroxy-ethyl]-7-(methoxymethoxy)-3,4-dihydro-1H-isoquinoline-2-carboxylate (0.15 g, 250.96 μmol) was dissolved in MeOH (3 mL) and hydrogen chloride solution 4.0M in dioxane (686.27 mg, 18.82 mmol, 857.84 μL) was added. The resulting mixture was stirred for 12 h at 20° C. After the completion of the reaction, the solvent was removed in vacuo at 40° C. to give 2-[(1-acetyl-4-piperidyl)amino]-N-[(2R)-2-hydroxy-2-[(3S)-7-hydroxy-1,2,3,4-tetrahydroisoquinolin-3-yl]ethyl]pyridine-4-carboxamide (0.13 g, 246.93 μmol, 98.40% yield, 2HCl) which was used in the next step without further purification. $^1$H NMR (CD$_3$OD, 500 MHz): δ 1.60 (m, 2H), 2.18 (m, 4H), 2.92 (m, 1H), 3.11 (m, 1H), 3.20 (m, 1H), 3.36 (m, 6H), 3.54 (m, 1H), 3.63 (m, 3H), 3.99 (m, 2H), 4.29 (m, 2H), 4.45 (m, 1H), 4.53 (m, 1H), 6.62 (s, 1H), 6.76 (d, 1H), 7.13 (d, 1H), 7.24 (d, 1H), 7.51 (s, 1H), 7.95 (d, 1H). LCMS (ESI): [M+H]$^+$ m/z: calc'd 453.2; found 454.2; Rt=1.41 min.

Step 3: Synthesis of tert-butyl (3S)-3-[(1R)-2-[[2-[(1-acetyl-4-piperidyl)amino]pyridine-4-carbonyl]amino]-1-hydroxy-ethyl]-7-hydroxy-3,4-dihydro-1H-isoquinoline-2-carboxylate 2-[(1-Acetyl-4-piperidyl)amino]-N-[(2R)-2-hydroxy-2-[(3S)-7-hydroxy-1,2,3,4-tetrahydroiso-quinolin-3-yl]ethyl]pyridine-4-carboxamide (0.13 g, 246.93 μmol, 2HCl) was dissolved in the mixture of water (1 mL) and THF (1 mL) then sodium hydrogen carbonate, 99% (62.23 mg, 740.80 μmol, 28.81 μL) was added in one portion. The resulting mixture was stirred for 5 min at room temperature followed by the dropwise addition of the solution of di-tert-butyl dicarbonate (53.89 mg, 246.93 μmol, 56.67 μL) in THF (0.2 mL). The reaction mixture was stirred for 12 h at room temperature. After the completion of the reaction, ethyl acetate (15 mL) was added to the reaction mixture, the organic phase was separated, and the aqueous phase was extracted with ethyl acetate (2*15 mL). The organic phase was washed with brine, dried over Na$_2$SO$_4$, filtered off and evaporated in vacuo at 40° C. to give tert-butyl (3S)-3-[(1R)-2-[[2-[(1-acetyl-4-piperidyl)amino]pyridine-4-carbonyl]amino]-1-hydroxy-ethyl]-7-hydroxy-3,4-dihydro-1H-isoquinoline-2-carboxylate (0.088 g, 158.95 μmol, 64.37% yield) which was used in the next step without purification. $^1$H NMR (DMSO-d$_6$, 400 MHz): δ 1.62 (m, 2H), 1.79 (s, 9H), 2.35 (m, 6H), 3.14 (m, 2H), 3.32 (m, 2H), 4.17 (m, 4H), 4.52 (m, 4H), 6.81 (s, 1H), 6.82 (d, 1H), 6.88 (m, 2H), 7.23 (d, 1H), 8.28 (m, 1H). LCMS (ESI): [M+H]$^+$ m/z: calc'd 553.3; found 554.4; Rt=2.31 min.

Step 4: Synthesis of tert-butyl (3S)-3-[(1R)-2-[[2-[(1-acetyl-4-piperidyl)amino]pyridine-4-carbonyl]amino]-1-hydroxy-ethyl]-7-[(4-methyloxazol-5-yl)methoxy]-3,4-dihydro-1H-isoquinoline-2-carboxylate tert-Butyl (3S)-3-[(1R)-2-[[2-[(1-acetyl-4-piperidyl)amino]pyridine-4-carbonyl]amino]-1-hydroxy-ethyl]-7-hydroxy-3,4-dihydro- 1H-isoquinoline-2-carboxylate (0.088 g, 158.95 µmol), 5-(chloromethyl)-4-methyl-oxazole (34.72 mg, 206.63 µmol, HCl) and cesium carbonate (207.15 mg, 635.78 µmol) were dissolved in DMF (2 mL) and heated at 60° C. overnight. The reaction mixture was filtered off, the residue was washed with DMF (2 mL), filtrate was concentrated on vacuo at 60° C. to give tert-butyl (3S)-3-[(1R)-2-[[2-[(1-acetyl-4-piperidyl)amino]pyridine-4-carbonyl]amino]-1-hydroxy-ethyl]-7-[(4-methyloxazol-5-yl)methoxy]-3,4-dihydro-1H-isoquinoline-2-carboxylate (0.096 g, 147.98 µmol, 93.10% yield) which was used in the next step without further purification. $^1$H NMR (CD$_3$OD, 500 MHz): δ 1.52 (m, 11H), 2.02 (m, 6H), 2.20 (m, 4H), 3.52 (m, 4H), 3.93 (m, 4H), 4.40 (m, 2H), 5.07 (m, 3H), 6.82 (m, 4H), 7.14 (m, 2H), 8.13 (m, 2H). LCMS (ESI): [M+H]$^+$ m/z: calc'd 648.3; found 649.2; Rt=2.96 min.

Step 5: Synthesis of 2-[(1-acetyl-4-piperidyl)amino]-N-[(2R)-2-hydroxy-2-[(3S)-7-[(4-methyloxazol-5-yl)methoxy]-1,2,3,4-tetrahydroisoquinolin-3-yl]ethyl]pyridine-4-carboxamide (Compound 44) tert-Butyl (3S)-3-[(1R)-2-[[2-[(1-acetyl-4-piperidyl)amino]pyridine-4-carbonyl]amino]-1-hydroxy-ethyl]-7-[(4-methyloxazol-5-yl)methoxy]-3,4-dihydro-1H-isoquinoline-2-carboxylate (0.096 g, 147.98 µmol) was dissolved in MeOH (3 mL) and hydrogen chloride solution 4.0M in dioxane (404.65 mg, 11.10 mmol, 505.82 µL) was added. The resulting mixture was stirred for 4 h at RT. After the completion of the reaction, the solvent was removed in vacuo at 45° C. The residue was dissolved in 5 mL of methanol and 10 mg of scavenger (SiliaMetS© Dimercaptotriazine(DMT) was added thereto and the resulting suspension was stirred for 12 h at room temperature. The obtained suspension was filtered off, the filtrate was evaporated under reduced pressure and the residue was purified by HPLC (0-50% water+HCl-methanol, 2-10 min, flow 30 mL/min (loading pump 4 mL/min methanol), column: SunFire C18 100*19 mm to give 2-[(1-acetyl-4-piperidyl)amino]-N-[(2R)-2-hydroxy-2-[(3S)-7-[(4-methyloxazol-5-yl)methoxy]-1,2,3,4-tetrahydroisoquinolin-3-yl]ethyl]pyridine-4-carboxamide (0.033 g, 50.15 µmol, 33.89% yield, 3HCl). $^1$H NMR (400 MHz, CD$_3$OD) δ 1.57 (m, 2H), 2.05 (m, 2H), 2.14 (s, 3H), 2.22 (s, 3H), 2.92 (m, 1H), 3.13 (m, 1H), 3.21 (m, 2H), 3.35 (m, 1H), 3.53 (m, 1H), 3.66 (m, 2H), 4.00 (m, 2H), 4.33 (m, 2H), 4.47 (m, 2H), 5.11 (s, 2H), 6.88 (s, 1H), 6.97 (d, 1H), 7.23 (m, 2H), 7.52 (s, 1H), 7.95 (d, 1H), 8.34 (s, 1H). LCMS (ESI): [M+H]$^+$ m/z: calc'd 548.2; found 549.2; Rt=0.76 min.

Example 2A17. Synthesis of N-[(2R)-2-hydroxy-2-[(3S)-7-[(4-methyloxazol-5-yl)methoxy]-1,2,3,4-tetrahydroisoquinolin-3-yl]ethyl]-2-(spiro[3.3]heptan-2-ylamino)pyridine-4-carboxamide (Compound 46)

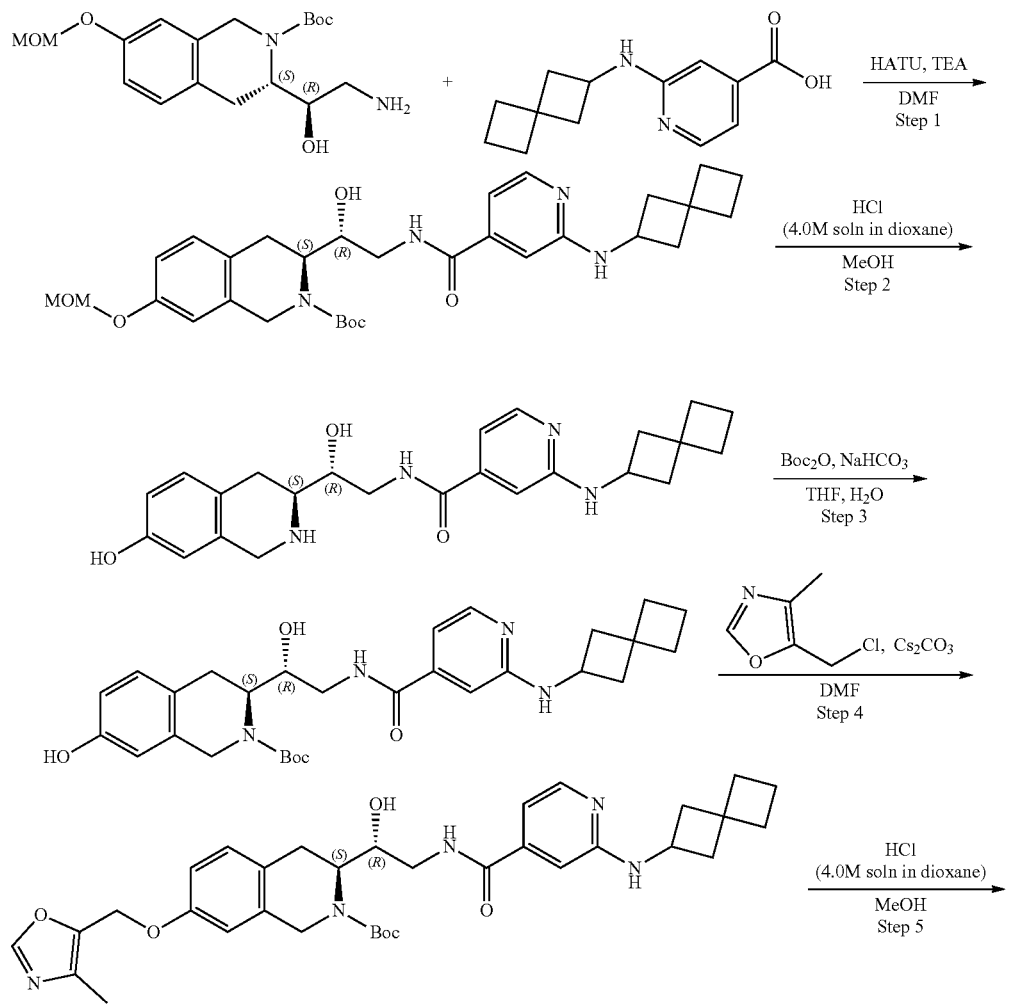

-continued

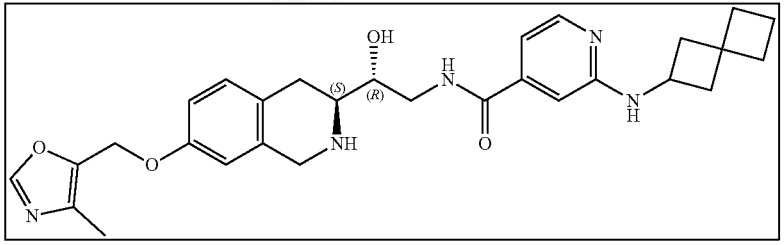

Step 1: Synthesis of tert-butyl (3S)-3-[(1R)-1-hydroxy-2-[[2-(spiro[3.3]heptan-2-ylamino)pyridine-4-carbonyl]amino]ethyl]-7-(methoxymethoxy)-3,4-dihydro-1H-isoquinoline-2-carboxylate 2-(Spiro[3.3]heptan-2-ylamino)pyridine-4-carboxylic acid (148.29 mg, 638.44 μmol), tert-butyl (3S)-3-[(1R)-2-amino-1-hydroxy-ethyl]-7-(methoxymethoxy)-3,4-dihydro-1H-isoquinoline-2-carboxylate (225 mg, 638.44 μmol), triethylamine (646.03 mg, 6.38 mmol, 889.85 μL) were mixed in DMF (6 mL) and then HATU (364.13 mg, 957.65 μmol) was added. The reaction mixture was stirred at 25° C. for 12 h. After the completion of the reaction, the resulting mixture was evaporated under reduce pressure and purified with HPLC (60-75% water-acetonitrile, 10 min, flow: 30 mL/min) to obtain tert-butyl (3S)-3-[(1R)-1-hydroxy-2-[[2-(spiro[3.3]heptan-2-ylamino)pyridine-4-carbonyl]amino]ethyl]-7-(methoxymethoxy)-3,4-dihydro-1H-isoquinoline-2-carboxylate (108.9 mg, 192.17 μmol, 30.10% yield). $^1$H NMR (DMSO-$d_6$, 400 MHz): δ 1.40 (m, 9H), 1.79 (m, 4H), 1.95 (m, 4H), 2.02 (s, 2H), 2.37 (m, 2H), 2.93 (m, 2H), 3.36 (m, 4H), 3.51 (m, 2H), 4.18 (m, 2H), 4.77 (m, 1H), 5.20 (s, 2H), 6.71 (s, 1H), 6.77 (d, 1H), 6.85 (m, 3H), 7.06 (d, 1H), 7.98 (d, 1H), 8.34 (m, 1H). LCMS (ESI): [M+H]$^+$ m/z: calc'd 566.3; found 567.4; Rt=1.25 min.

Step 2: Synthesis of N-[(2R)-2-hydroxy-2-[(3S)-7-hydroxy-1, 2, 3,4-tetrahydroisoquinolin-3-yl]ethyl]-2-(spiro[3.3]heptan-2-ylamino)pyridine-4-carboxamide A solution of tert-butyl (3S)-3-[(1R)-1-hydroxy-2-[[2-(spiro[3.3]heptan-2-ylamino)pyridine-4-carbonyl]amino]ethyl]-7-(methoxymethoxy)-3,4-dihydro-1H-isoquinoline-2-carboxylate (108.9 mg, 192.17 μmol) in Dioxane/HCl (2 mL) and Methanol (2 mL) was stirred for 12 h at 25° C. Then the solution was evaporated and the resulting crude product was purified by HPLC (5-50% water-MeOH, 10 min, flow 30 mL/min) to obtain N-[(2R)-2-hydroxy-2-[(3S)-7-hydroxy-1,2,3,4-tetrahydroisoquinolin-3-yl]ethyl]-2-(spiro[3.3]heptan-2-ylamino)pyridine-4-carboxamide (92 mg, crude, 2HCl). $^1$H NMR (CD$_3$OD, 500 MHz): δ 2.04 (m, 8H), 2.64 (m, 2H), 3.12 (m, 3H), 3.50 (m, 2H), 4.27 (m, 4H), 6.61 (s, 1H), 6.76 (d, 1H), 7.13 (d, 1H), 7.15 (d, 1H), 7.40 (s, 1H), 7.89 (m, 1H). LCMS (ESI): [M+H]$^+$ m/z: calc'd 422.2; found 423.2; Rt=0.86 min.

Step 3: Synthesis of tert-butyl (3S)-7-hydroxy-3-[(1R)-1-hydroxy-2-[[2-(spiro[3.3]heptan-2-ylamino)pyridine-4-carbonyl]amino]ethyl]-3,4-dihydro-1H-isoquinoline-2-carboxylate To a stirred solution of sodium hydrogen carbonate (78.00 mg, 928.47 μmol, 36.11 μL) in water (1 mL) the solution of N-[(2R)-2-hydroxy-2-[(3S)-7-hydroxy-1,2,3,4-tetrahydroisoquinolin-3-yl]ethyl]-2-(spiro[3.3]heptan-2-ylamino)pyridine-4-carboxamide (92 mg, 185.69 μmol, 2HCl) in THF (1 mL) was added followed by the solution of di-tert-butyl dicarbonate (40.53 mg, 185.69 μmol, 42.61 μL) in THF (1 mL). The resulting mixture was stirred at 25° C. for 12 h. After the completion of the reaction, EtOAc (10 mL) was added and the organic phase was separated and washed with brine (2*5 mL). Then the solvent was dried over sodium sulfate, filtered off and evaporated to obtain tert-butyl (3S)-7-hydroxy-3-[(1R)-1-hydroxy-2-[[2-(spiro[3.3]heptan-2-ylamino)pyridine-4-carbonyl]amino]ethyl]-3,4-dihydro-1H-isoquinoline-2-carboxylate (96 mg, crude). $^1$H NMR (CD$_3$OD, 400 MHz): δ 1.47 (m, 9H), 1.85 (m, 4H), 2.02 (m, 4H), 2.47 (m, 2H), 2.91 (m, 3H), 3.70 (m, 4H), 4.22 (m, 4H), 6.54 (s, 1H), 6.56 (d, 1H), 6.78 (m, 2H), 6.96 (d, 1H), 7.94 (m, 1H). LCMS (ESI): [M+H]$^+$ m/z: calc'd 522.2; found 523.2; Rt=1.12 min.

Step 4: Synthesis of tert-butyl (3S)-3-[(1R)-1-hydroxy-2-[[2-(spiro[3.3]heptan-2-ylamino)pyridine-4-carbonyl]amino]ethyl]-7-[(4-methyloxazol-5-yl)methoxy]-3,4-dihydro-1H-isoquinoline-2-carboxylate To the mixture of tert-butyl (3S)-7-hydroxy-3-[(1R)-1-hydroxy-2-[[2-(spiro[3.3]heptan-2-ylamino)pyridine-4-carbonyl]amino]ethyl]-3,4-dihydro-1H-isoquinoline-2-carboxylate (96 mg, 183.68 μmol), cesium carbonate (179.54 mg, 551.05 μmol) in DMF (2 mL) was added 5-(chloromethyl)-4-methyl-oxazole (37.04 mg, 220.42 μmol, HCl). The reaction mixture was heated at 50° C. for 12 h. After the completion of the reaction, the resulting mixture was filtered off and evaporated to obtain tert-butyl (3S)-3-[(1R)-1-hydroxy-2-[[2-(spiro[3.3]heptan-2-ylamino)pyridine-4-carbonyl]amino]ethyl]-7-[(4-methyloxazol-5-yl)methoxy]-3,4-dihydro-1H-isoquinoline-2-carboxylate (105 mg, 169.98 μmol, 92.54% yield). The obtained product was used without further purification.

Step 5: Synthesis of N-[(2R)-2-hydroxy-2-[(3S)-7-[(4-methyloxazol-5-yl)methoxy]-1,2,3,4-tetrahydroisoquinolin-3-yl]ethyl]-2-(spiro[3.3]heptan-2-ylamino)pyridine-4-carboxamide (Compound 46) A solution of tert-butyl (3S)-3-[(1R)-1-hydroxy-2-[[2-(spiro[3.3]heptan-2-ylamino)pyridine-4-carbonyl]amino]ethyl]-7-[(4-methyloxazol-5-yl)methoxy]-3,4-dihydro-1H-isoquinoline-2-carboxylate (105 mg, 169.98 μmol) in Dioxane/HCl (2 mL) and Methanol (2 mL) was stirred for 12 h at 25° C. After the completion of the reaction, the resulting mixture was stirred with SiliaMetS DMT (30 mg) in methanol (1 mL) for 12 h at room temperature. The obtained suspension was filtered off, evaporated and purified by HPLC (10-30%, 0-5 min, water (HCl)—MeCN,) to obtain N-[(2R)-2-hydroxy-2-[(3S)-7-[(4-methyloxazol-5-yl)methoxy]-1,2,3,4-tetrahydroisoquinolin-3-yl]ethyl]-2-(spiro[3.3]heptan-2-ylamino)pyridine-4-carboxamide (45.1 mg, 76.37 μmol, 44.93% yield, 2HCl). $^1$H NMR (400 MHz, CD$_3$OD) δ 1.90 (m, 2H), 2.03 (m, 4H), 2.16 (m, 3H), 2.19 (s, 3H), 2.61 (m, 2H), 3.11 (m, 2H), 3.53 (m, 1H), 3.63 (m, 2H), 4.05 (m, 1H), 4.31 (m, 2H), 4.45 (m, 1H), 5.09 (s, 2H), 6.87 (s, 1H), 6.97 (d, 1H), 7.16 (d, 1H), 7.23 (d, 1H), 7.38 (s, 1H), 7.89 (d, 1H), 8.13 (s, 1H). LCMS (ESI): [M+2H]$^+$ m/z: calc'd 517.2; found 519.2; Rt=0.92 min.

Example 2A18. Synthesis of 2-(cyclobutylamino)-N-[(2R)-2-hydroxy-2-[(3S)-7-[(4-methyloxazol-5-yl)methoxy]-1,2,3,4-tetrahydroisoquinolin-3-yl]ethyl]-6-(4-methylpiperazin-1-yl)pyridine-4-carboxamide (Compound 52)
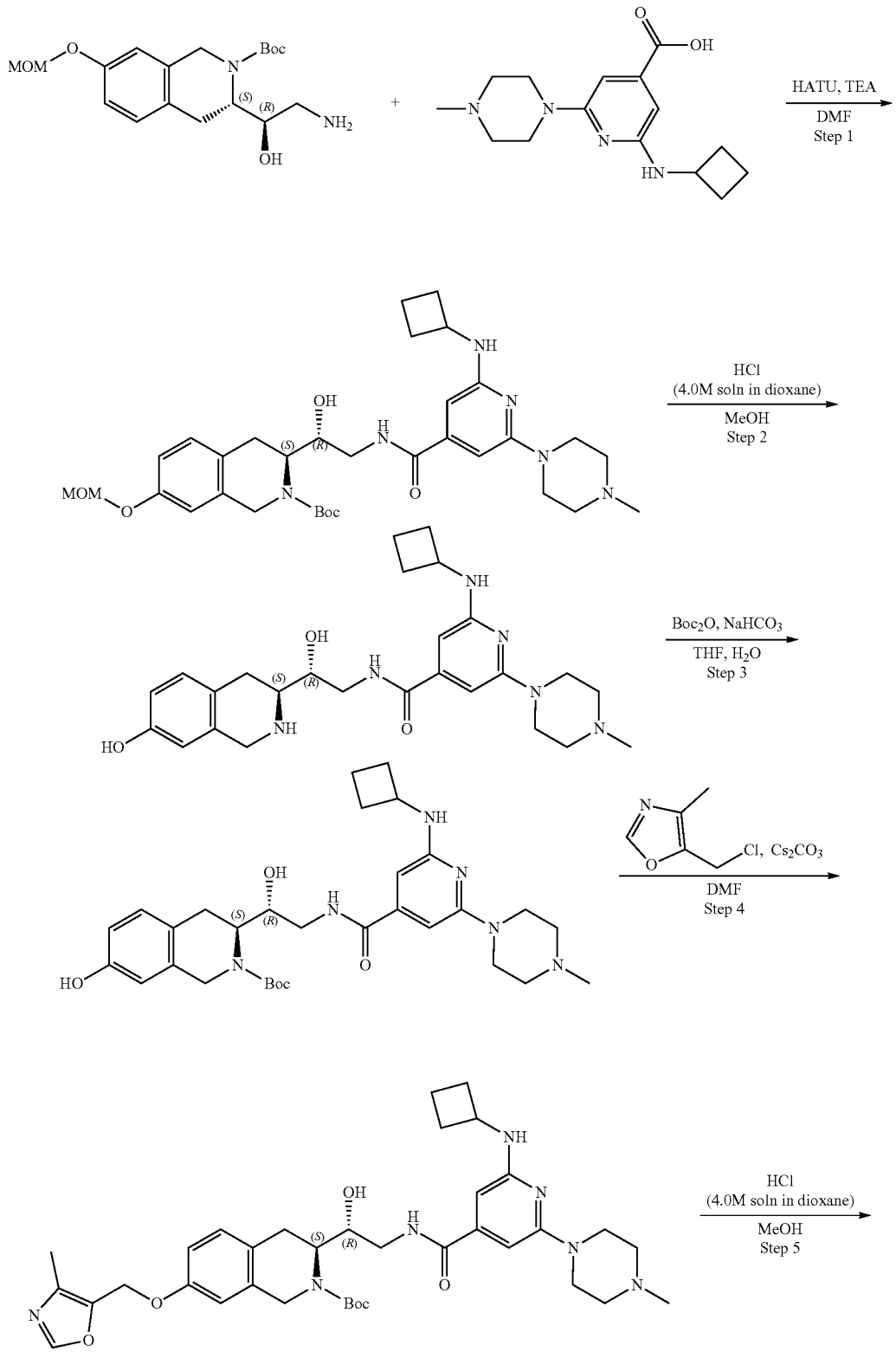

-continued

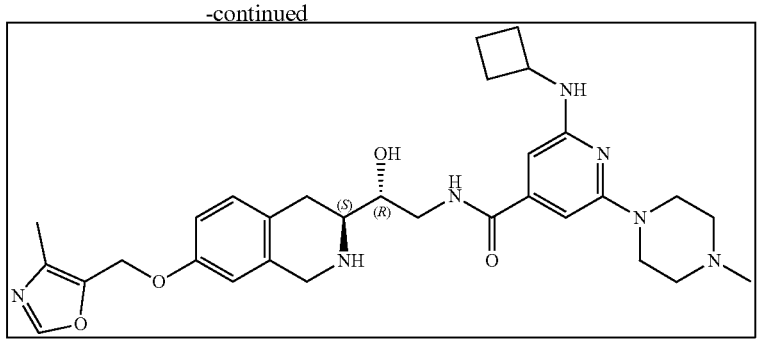

Step 1: Synthesis of tert-butyl (3S)-3-[(1R)-2-[[2-(cyclobutylamino)-6-(4-methylpiperazin-1-yl)pyridine-4-carbonyl]amino]-1-hydroxy-ethyl]-7-(methoxymethoxy)-3,4-dihydro-1H-isoquinoline-2-carboxylate tert-Butyl (3S)-3-[(1R)-2-amino-1-hydroxy-ethyl]-7-(methoxymethoxy)-3,4-dihydro-1H-iso-quinoline-2-carboxylate (0.2 g, 567.50 μmol), 2-(cyclobutylamino)-6-(4-methylpiperazin-1-yl)pyridine-4-carboxylic acid (206.16 mg, 567.50 μmol, 2HCl) and triethylamine (574.25 mg, 5.67 mmol, 790.98 μL) were mixed together in DMF (4 mL) and HATU (323.67 mg, 851.25 μmol) was added thereto. The reaction mixture was stirred at room temperature for 18 h. After the completion of the reaction, the reaction mixture was poured into water (25 mL) and the resulting mixture was extracted with EtOAc (2*25 mL). The combined organic layers were washed with water (3*25 mL), brine, dried over $Na_2SO_4$, filtered off and evaporated. The residue was purified by HPLC (Column: SunFire C18 100*19 mm, 5 μm 15-40% $H_2O$-MeCN, 2-10 min, flow: 30 mL/min (Loading pump 4 mL/min MeCN)) to obtain tert-butyl (3S)-3-[(1R)-2-[[2-(cyclobutylamino)-6-(4-methylpiperazin-1-yl)pyridine-4-carbonyl]amino]-1-hydroxy-ethyl]-7-(methoxymethoxy)-3,4-dihydro-1H-isoquinoline-2-carboxylate (0.1707 g, 273.22 μmol, 48.14% yield). $^1$H NMR (DMSO-$d_6$, 400 MHz): δ 1.44 (m, 9H), 1.64 (m, 2H), 1.84 (m, 2H), 2.19 (s, 3H), 2.23 (m, 2H), 2.35 (s, 3H), 2.76 (m, 3H), 3.02 (m, 2H), 3.36 (m, 3H), 3.42 (m, 4H), 4.20 (m, 3H), 4.77 (m, 1H), 5.15 (m, 3H), 6.05 (s, 1H), 6.23 (s, 1H), 6.51 (d, 1H), 6.85 (m, 2H), 7.07 (d, 1H), 8.20 (m, 1H). LCMS (ESI): [M+H]$^+$ m/z: calc'd 624.3; found 625.4; Rt=1.23 min.

Step 2: Synthesis of 2-(cyclobutylamino)-N-[(2R)-2-hydroxy-2-[(3S)-7-hydroxy-1,2,3,4-tetrahydroisoquinolin-3-yl]ethyl]-6-(4-methylpiperazin-1-yl)pyridine-4-carboxamide) tert-Butyl (3S)-3-[(1R)-2-[[2-(cyclobutylamino)-6-(4-methylpiperazin-1-yl)pyridine-4-carbonyl]-amino]-1-hydroxy-ethyl]-7-(methoxymethoxy)-3,4-dihydro-1H-isoquinoline-2-carboxylate (0.1707 g, 273.22 μmol) was dissolved in MeOH (3 mL) and hydrogen chloride solution 4.0M in dioxane (119.54 mg, 3.28 mmol, 149.43 μL) was added. The reaction mixture was stirred for 3 h. After the completion of the reaction, the reaction mixture was evaporated to dryness to obtain 2-(cyclobutylamino)-N-[(2R)-2-hydroxy-2-[(3S)-7-hydroxy-1,2,3,4-tetrahydroisoquinolin-3-yl]ethyl]-6-(4-methylpiperazin-1-yl)pyridine-4-carboxamide (0.16 g, 255.41 μmol, 93.48% yield, 4HCl). $^1$H NMR (DMSO-$d_6$, 400 MHz): δ 1.67 (m, 2H), 1.84 (m, 2H), 2.24 (m, 3H), 2.77 (s, 3H), 2.99 (m, 5H), 3.16 (m, 3H), 4.20 (m, 7H), 6.20 (s, 1H), 6.43 (s, 1H), 6.59 (s, 1H), 6.69 (d, 1H), 7.03 (d, 1H), 8.67 (m, 1H), 8.87 (m, 1H), 9.45 (m, 1H), 10.64 (m, 1H). LCMS (ESI): [M+2H]$^+$ m/z: calc'd 480.3; found 482.2; Rt=0.75 min.

Step 3: Synthesis of tert-butyl (3S)-3-[(1R)-2-[[2-(cyclobutylamino)-6-(4-methylpiperazin-1-yl)pyridine-4-carbonyl]amino]-1-hydroxy-ethyl]-7-hydroxy-3,4-dihydro-1H-isoquinoline-2-carboxylate tetrahydroisoquinolin-3-yl]ethyl]-6-(4-methylpiperazin-1-yl)pyridine-4-carboxamide (0.16 g, 255.41 μmol, 4HCl) was dissolved in water (2 mL) and sodium bicarbonate (128.74 mg, 1.53 mmol, 59.60 μL) was added. The resulting mixture was diluted with THF (2 mL) and di-tert-butyl dicarbonate (55.74 mg, 255.41 μmol, 58.61 μL) was added. The reaction mixture was stirred for 17 h. After that, the reaction mixture was diluted with EtOAc (15 mL) and an organic layer was separated. An aqueous layer was washed with EtOAc (2*10 mL) and the combined organic layers were washed with brine, dried over $Na_2SO_4$, filtered and evaporated to obtain tert-butyl (3S)-3-[(1R)-2-[[2-(cyclobutylamino)-6-(4-methylpiperazin-1-yl)pyridine-4-carbonyl]amino]-1-hydroxy-ethyl]-7-hydroxy-3,4-dihydro-1H-isoquinoline-2-carboxylate (123.40 mg, 212.50 μmol, 83.20% yield). $^1$H NMR (DMSO-$d_6$, 400 MHz): δ 1.40 (m, 9H), 1.64 (m, 2H), 1.83 (m, 2H), 2.18 (m, 6H), 2.35 (m, 5H), 2.67 (m, 2H), 2.99 (m, 2H), 4.12 (m, 4H), 4.68 (m, 1H), 5.14 (m, 1H), 6.04 (s, 1H), 6.21 (s, 1H), 6.53 (m, 3H), 6.92 (d, 1H), 8.15 (m, 1H), 9.20 (m, 1H). LCMS (ESI): [M+H]$^+$ m/z: calc'd 580.3; found 581.2; Rt=1.15 min.

Step 4: Synthesis of tert-butyl (3S)-3-[(1R)-2-[[2-(cyclobutylamino)-6-(4-methylpiperazin-1-yl)pyridine-4-carbonyl]amino]-1-hydroxy-ethyl]-7-[(4-methyloxazol-5-yl)methoxy]-3,4-dihydro-1H-isoquinoline-2-carboxylate tert-Butyl (3S)-3-[(1R)-2-[[2-(cyclobutylamino)-6-(4-methylpiperazin-1-yl)pyridine-4-carbonyl]-amino]-1-hydroxy-ethyl]-7-hydroxy-3,4-dihydro-1H-isoquinoline-2-carboxylate (123.40 mg, 212.50 μmol), 5-(chloromethyl)-4-methyl-oxazole (49.99 mg, 297.49 μmol, HCl) and cesium carbonate (276.94 mg, 849.98 μmol) were mixed together in DMF (2 mL) and the resulting mixture was heated at 60° C. for 18 h.

Then the reaction mixture was cooled to room temperature and diluted with water (10 mL). The resulting mixture was extracted with EtOAc (2*15 mL) and the combined organic layers were washed with water (4*5 mL) and brine, dried over $Na_2SO_4$, filtered off and evaporated in vacuo. Due to low reaction conversion the residue was dissolved in DMF (2 mL) and an additional portion of 5-(chloromethyl)-4-methyl-oxazole (49.99 mg, 297.49 μmol, HCl) was added and the resulting mixture was heated at 60° C. for additional 18 h. The reaction mixture was cooled to room temperature and diluted with water (10 mL). The resulting mixture was extracted with EtOAc (2*15 mL) and the combined organic layers were washed with water (4*5 mL), brine, dried over $Na_2SO_4$, filtered off and evaporated to obtain tert-butyl (3S)-3-[(1R)-2-[[2-(cyclobutylamino)-6-(4-methylpiperazin-1-yl)pyridine-4-carbonyl]amino]-1-hydroxy-ethyl]-7-[(4-methyl-oxazol-5-yl)methoxy]-3,4-dihydro-1H-isoquinoline-2-carboxylate (82.70 mg, 122.37 μmol, 57.59% yield). $^1$H NMR (DMSO-$d_6$, 400 MHz): δ 1.43 (m, 9H), 1.64 (m, 2H), 1.85 (m, 2H), 2.15 (m, 4H), 2.19 (m, 4H), 2.36 (m, 4H), 2.72 (m, 2H), 2.87 (m, 2H), 3.41 (m, 5H), 4.15 (m, 4H), 5.08 (m, 3H), 6.05 (s, 1H), 6.22 (s, 1H), 6.51 (s, 1H), 6.80 (d, 1H), 6.88 (s, 1H), 7.06 (d, 1H), 8.27 (s, 1H). LCMS (ESI): [M+H]$^+$ m/z: calc'd 675.3; found 676.4; Rt=1.18 min.

Step 5: Synthesis of 2-(cyclobutylamino)-N-[(2R)-2-hydroxy-2-[(3S)-7-[(4-methyloxazol-5-yl)methoxy]-1,2,3,4-tetrahydroisoquinolin-3-yl]ethyl]-6-(4-methylpiperazin-1-yl)pyridine-4-carboxamide (Compound 52) tert-Butyl (3S)-3-[(1R)-2-[[2-(cyclobutylamino)-6-(4-methylpiperazin-1-yl)pyridine-4-carbonyl]-amino]-1-hydroxy-ethyl]-7-[(4-methyloxazol-5-yl)methoxy]-3,4-dihydro-1H-isoquinoline-2-carboxylate (82.70 mg, 122.37 μmol) was dissolved in MeOH (2 mL) and hydrogen chloride solution 4.0M in dioxane (26.77 mg, 734.22 μmol, 33.46 μL) was added. The reaction mixture was stirred for 2 h and then evaporated to dryness. After the completion of the reaction, the residue was dissolved in 3 mL of MeOH and 10 mg of scavenger (SiliaMetS Dimercaptotriazine(DMT)) was added and the resulting suspension was stirred for 12 h. The suspension was filtered off, the filtrate was evaporated under reduced pressure. The residue was purified by HPLC(30-40% water+HCl-methanol, 10 min, flow 30 mL/min (loading pump 4 mL/min acetonitrile)) to obtain 2-(cyclobutylamino)-N-[(2R)-2-hydroxy-2-[(3S)-7-[(4-methyloxazol-5-yl)methoxy]-1,2,3,4-tetrahydroisoquinolin-3-yl]ethyl]-6-(4-methylpiperazin-1-yl)pyridine-4-carboxamide (7.10 mg, 9.37 μmol, 7.65% yield, 5HCl). $^1$H NMR (400 MHz, CD$_3$OD) δ 1.86 (m, 2H), 2.07 (m, 2H), 2.21 (s, 3H), 2.49 (m, 2H), 2.97 (s, 3H), 3.20 (m, 3H), 3.33 (m, 1H), 3.54 (m, 3H), 3.66 (m, 4H), 4.21 (m, 1H), 4.35 (m, 4H), 4.47 (m, 1H), 5.10 (s, 2H), 6.87 (s, 1H), 6.96 (d, 1H), 7.23 (d, 1H), 8.24 (s, 1H). LCMS (ESI): [M+H]$^+$ m/z: calc'd 575.3; found 576.4; Rt=1.97 min.

Example 2A19. Synthesis of 2-(cyclobutylamino)-6-(4-ethylpiperazin-1-yl)-N-[(2R)-2-hydroxy-2-[(3S)-7-[(4-methyloxazol-5-yl)methoxy]-1,2,3,4-tetrahydroisoquinolin-3-yl]ethyl]pyridine-4-carboxamide (Compound 55)

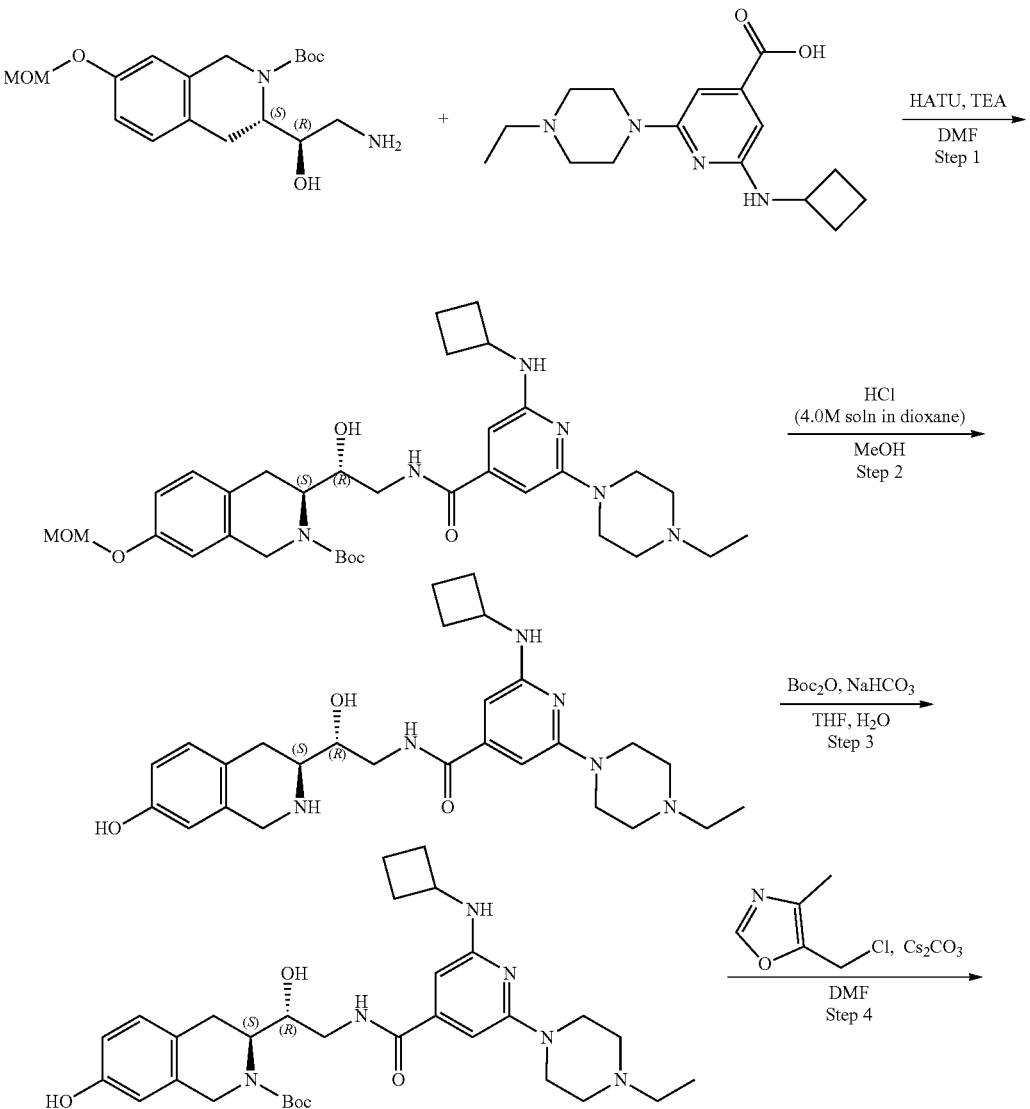

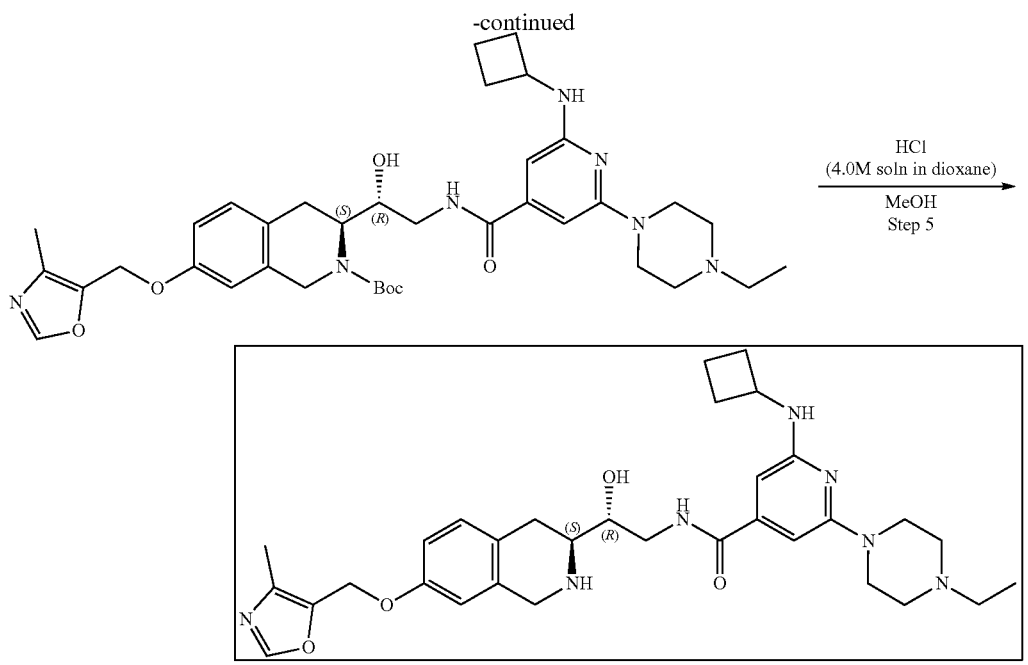

Step 1: Synthesis of tert-butyl (3S)-3-[(1R)-2-[[2-(cyclobutylamino)-6-(4-ethylpiperazin-1-yl)pyridine-4-carbonyl]amino]-1-hydroxy-ethyl]-7-(methoxymethoxy)-3,4-dihydro-1H-isoquinoline-2-carboxylate tert-Butyl (3S)-3-[(1R)-2-amino-1-hydroxy-ethyl]-7-(methoxymethoxy)-3,4-dihydro-1H-iso-quinoline-2-carboxylate (73.11 mg, 207.45 μmol), 2-(cyclobutylamino)-6-(4-ethylpiperazin-1-yl)pyridine-4-carboxylic acid (0.0868 g, 207.45 μmol, $CF_3COOH$) and triethylamine (209.92 mg, 2.07 mmol, 289.15 μL) were mixed together in DMF (2 mL) and HATU (118.32 mg, 311.18 μmol) was added. The reaction mixture was stirred at room temperature for 18 h. Then the reaction mixture was poured into water (20 mL) and extracted with EtOAc (2*25 mL). The combined organic layers were washed with water (3*15 mL), brine, dried over $Na_2SO_4$, filtered off and evaporated. The residue was purified by HPLC (Column: SunFire C18 100*19 mm, 5 μm, 15-40% $H_2O$-MeOH, 2-10 min, Flow: 30 mL/min (Loading pump 4 mL/min MeOH)) to obtain tert-butyl (3S)-3-[(1R)-2-[[2-(cyclobutylamino)-6-(4-ethylpiperazin-1-yl)pyridine-4-carbonyl]amino]-1-hydroxy-ethyl]-7-(methoxymethoxy)-3,4-dihydro-1H-isoquinoline-2-carboxylate (0.0562 g, 87.98 μmol, 42.41% yield). $^1$H NMR (DMSO-$d_6$, 400 MHz): δ 1.02 (t, 3H), 1.42 (m, 9H), 1.66 (m, 2H), 1.85 (m, 2H), 2.33 (m, 8H), 3.03 (m, 3H), 3.36 (m, 3H), 3.42 (m, 5H), 4.14 (m, 2H), 4.77 (m, 1H), 5.15 (m, 3H), 6.05 (s, 1H), 6.21 (s, 1H), 6.52 (d, 1H), 6.85 (m, 2H), 7.06 (d, 1H), 8.20 (m 1H). LCMS (ESI): [M+H]$^+$ m/z: calc'd 638.3; found 639.4; Rt=1.24 min.

Step 2: Synthesis of 2-(cyclobutylamino)-6-(4-ethylpiperazin-1-yl)-N-[(2R)-2-hydroxy-2-[(3S)-7-hydroxy-1, 2,3,4-tetrahydroisoquinolin-3-yl]ethyl]pyridine-4-carboxamide tert-Butyl (3S)-3-[(1R)-2-[[2-(cyclobutylamino)-6-(4-ethylpiperazin-1-yl)pyridine-4-carbonyl]-amino]-1-hydroxy-ethyl]-7-(methoxymethoxy)-3,4-dihydro-1H-isoquinoline-2-carboxylate (0.0562 g, 87.98 μmol) was dissolved in MeOH (2 mL) and hydrogen chloride solution 4.0M in dioxane (38.49 mg, 1.06 mmol, 48.12 μL) was added. The reaction mixture was stirred for 3 h. After the completion of the reaction, the reaction mixture was evaporated to dryness to obtain 2-(cyclobutylamino)-6-(4-ethylpiperazin-1-yl)-N-[(2R)-2-hydroxy-2-[(3S)-7-hydroxy-1, 2,3,4-tetrahydroisoquinolin-3-yl]ethyl]pyridine-4-carboxamide (0.05 g, 78.07 μmol, 88.74% yield, 4HCl). $^1$H NMR (DMSO-$d_6$, 400 MHz): δ 1.25 (t, 3H), 1.67 (m, 2H), 1.85 (m, 2H), 2.26 (m, 2H), 2.99 (m, 4H), 3.14 (m, 6H), 4.20 (m, 6H), 6.19 (s, 1H), 6.38 (s, 1H), 6.58 (s, 1H), 6.68 (d, 1H), 7.02 (d, 1H), 8.62 (m, 1H), 8.82 (m, 1H), 9.40 (m, 1H), 1.17 (m, 1H). LCMS (ESI): [M+2H]$^+$ m/z: calc'd 494.3; found 496.4; Rt=0.76 min.

Step 3: Synthesis of tert-butyl (3S)-3-[(1R)-2-[[2-(cyclobutylamino)-6-(4-ethylpiperazin-1-yl)pyridine-4-carbonyl]amino]-1-hydroxy-ethyl]-7-hydroxy-3,4-dihydro-1H-isoquinoline-2-carboxylate 2-(Cyclobutylamino)-6-(4-ethylpiperazin-1-yl)-N-[(2R)-2-hydroxy-2-[(3S)-7-hydroxy-1,2,3,4-tetrahydroisoquinolin-3-yl]ethyl]pyridine-4-carboxamide (0.05 g, 78.07 μmol, 4HCl) was dissolved in water (1.5 mL) and sodium bicarbonate (39.35 mg, 468.40 μmol, 18.22 μL) was added. The resulting mixture was diluted with THF (1.5 mL) and di-tert-butyl dicarbonate (17.04 mg, 78.07 μmol, 17.92 μL) was added. The reaction mixture was stirred for 17 h. After the completion of the reaction (monitored by LCMS), the resulting mixture was diluted with EtOAc (15 mL) and an organic layer was separated. An aqueous layer was washed with EtOAc (2-10 mL) and combined organic layers were washed with brine, dried over $Na_2SO_4$, filtered off and evaporated to obtain tert-butyl (3S)-3-[(1R)-2-[[2-(cyclobutylamino)-6-(4-ethylpiperazin-1-yl)pyridine-4-carbonyl]amino]-1-hydroxyethyl]-7-hydroxy-3,4-dihydro-1H-isoquinoline-2-carboxylate (0.044 g, 73.98 μmol, 94.77% yield). $^1$H NMR (DMSO-$d_6$, 400 MHz): δ 1.01 (t, 3H), 1.40 (m, 9H), 1.64 (m, 2H), 1.80 (m, 2H), 2.23 (m, 2H), 2.39 (m, 6H), 2.95 (m, 2H), 3.16 (m, 3H), 4.13 (m, 4H), 4.68 (m, 2H), 5.10 (m, 2H), 6.03 (s, 1H), 6.21 (s, 1H), 6.58 (m, 2H), 6.91 (d, 1H), 8.17 (m, 1H), 9.20 (m, 1H). LCMS (ESI): [M+H]$^+$ m/z: calc'd 595.3; found 595.4; Rt=1.17 min.

Step 4: Synthesis of tert-butyl (3S)-3-[(1R)-2-[[2-(cyclobutylamino)-6-(4-ethylpiperazin-1-yl)pyridine-4-carbonyl]amino]-1-hydroxy-ethyl]-7-[(4-methyloxazol-5-yl)methoxy]-3,4-dihydro-1H-isoquinoline-2-carboxylate tert-Butyl (3S)-3-[(1R)-2-[[2-(cyclobutylamino)-6-(4-ethylpiperazin-1-yl)pyridine-4-carbonyl]-amino]-1-hydroxy-ethyl]-7-hydroxy-3,4-dihydro-1H-isoquinoline-2-carboxylate (0.044 g, 73.98 µmol), 5-(chloromethyl)-4-methyl-oxazole (17.40 mg, 103.57 µmol, HCl) and cesium carbonate (96.42 mg, 295.93 µmol) were mixed together in DMF (1 mL) and the resulting mixture was heated at 60° C. for 18 h. After that, the reaction mixture was cooled to room temperature and diluted with water (10 mL). The resulting mixture was extracted with EtOAc (2*15 mL) and the combined organic layers were washed with water (4*5 mL), brine, dried over $Na_2SO_4$, filtered off and evaporated to obtain tert-butyl (3S)-3-[(1R)-2-[[2-(cyclobutylamino)-6-(4-ethylpiperazin-1-yl)pyridine-4-carbonyl]amino]-1-hydroxy-ethyl]-7-[(4-methyloxazol-5-yl)methoxy]-3,4-dihydro-1H-isoquinoline-2-carboxylate (0.0471 g, 68.28 µmol, 92.29% yield). $^1$H NMR (DMSO-$d_6$, 400 MHz): δ 1.02 (t, 3H), 1.42 (m, 9H), 1.48 (m, 2H), 1.69 (m, 2H), 1.87 (s, 3H), 2.24 (m, 3H), 2.40 (m, 6H), 4.17 (m, 8H), 5.08 (m, 4H), 6.04 (s, 1H), 6.23 (s, 1H), 6.52 (s, 1H), 6.82 (s, 1H), 6.89 (d, 1H), 7.09 (d, 1H), 8.08 (m, 1H). LCMS (ESI): [M+H]$^+$ m/z: calc'd 689.4; found 690.4; Rt=1.25 min.

Step 5: Synthesis of 2-(cyclobutylamino)-6-(4-ethylpiperazin-1-yl)-N-[(2R)-2-hydroxy-2-[(3S)-7-[(4-methyloxazol-5-yl)methoxy]-1,2,3,4-tetrahydroisoquinolin-3-yl]ethyl]pyridine-4-carboxamide (Compound 55) tert-Butyl (3S)-3-[(1R)-2-[[2-(cyclobutylamino)-6-(4-ethylpiperazin-1-yl)pyridine-4-carbonyl]-amino]-1-hydroxy-ethyl]-7-[(4-methyloxazol-5-yl)methoxy]-3,4-dihydro-1H-isoquinoline-2-carboxylate (0.0471 g, 68.28 µmol) was dissolved in MeOH (2 mL) and hydrogen chloride solution 4.0M in dioxane (14.94 mg, 409.66 µmol, 18.67 µL) was added. The reaction mixture was stirred for 2 h and then evaporated to dryness. After the completion of the reaction, the residue was dissolved in 3 mL of MeOH and 10 mg of scavenger (SiliaMetS Dimercaptotriazine(DMT)) was added thereto and the resulting suspension was stirred for 12 h. The suspension was filtered off, the filtrate was evaporated under reduced pressure. The residue was purified by HPLC(5-35% water-MeOH+HCl, 10 min, flow 30 mL/min (loading pump 4 mL/min MeOH)) to obtain 2-(cyclobutylamino)-6-(4-ethylpiperazin-1-yl)-N-[(2R)-2-hydroxy-2-[(3S)-7-[(4-methyloxazol-5-yl)methoxy]-1,2,3,4-tetrahydroisoquinolin-3-yl]ethyl]pyridine-4-carboxamide (0.0128 g, 16.58 µmol, 24.28% yield, 5HCl). $^1$H NMR (400 MHz, CD$_3$OD) δ 1.40 (t, 3H), 1.87 (m, 2H), 2.07 (m, 2H), 2.21 (s, 3H), 2.49 (m, 2H), 3.20 (m, 6H), 3.54 (m, 3H), 3.68 (m, 4H), 4.21 (m, 1H), 4.34 (m, 3H), 4.41 (m, 1H), 4.48 (m, 1H), 5.10 (s, 2H), 6.88 (s, 1H), 6.96 (d, 1H), 7.23 (d, 1H), 8.25 (s, 1H). LCMS (ESI): [M+H]$^+$ m/z: calc'd 589.3; found 590.2; Rt=0.92 min.

Example 2A20. Synthesis of 2-[(1-acetyl-4-piperidyl)amino]-N-[(2R)-2-hydroxy-2-[(3S)-7-[(4-methyloxazol-5-yl)methoxy]-1,2,3,4-tetrahydroisoquinolin-3-yl]ethyl]-6-(4-methylpiperazin-1-yl)pyridine-4-carboxamide (Compound 54)

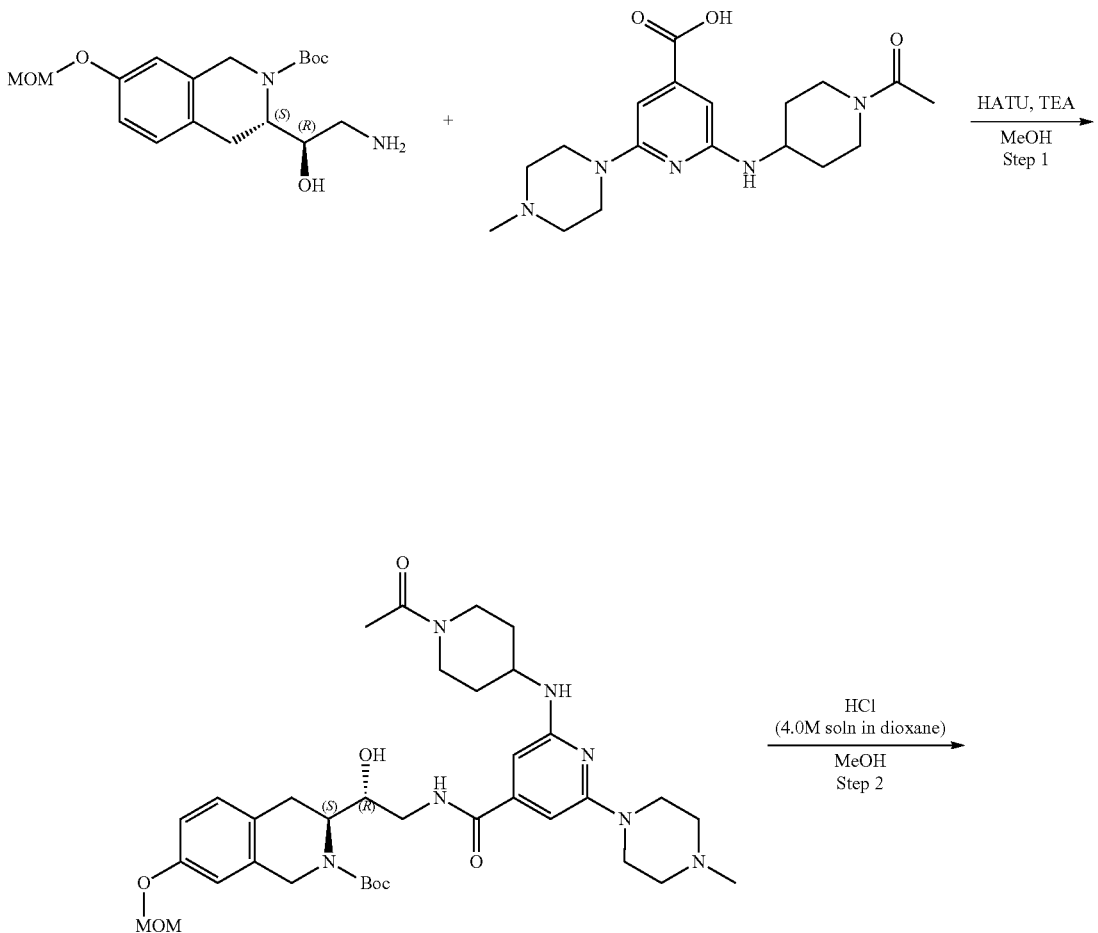

-continued
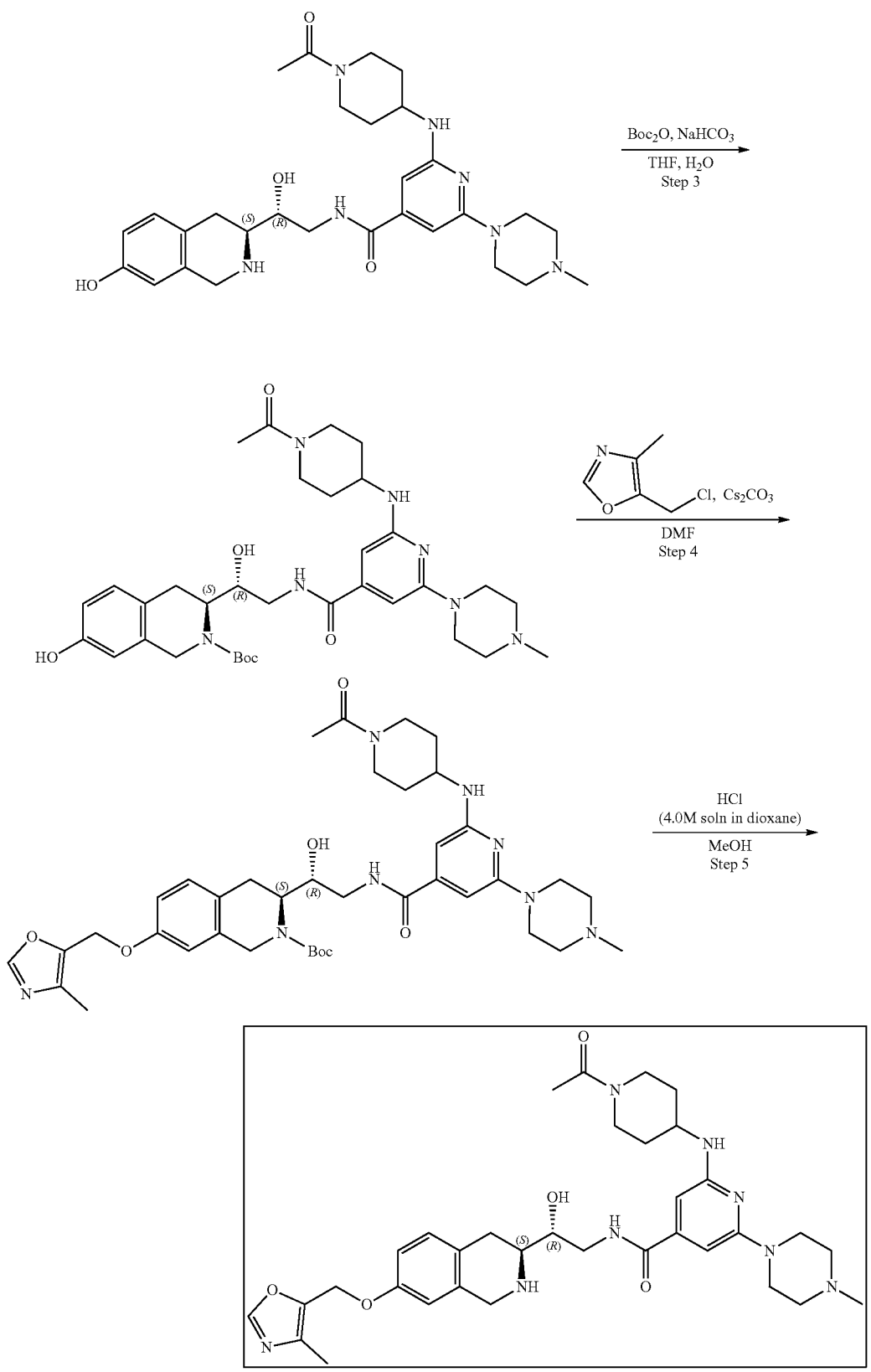

Step 1: Synthesis of tert-butyl (3S)-3-[(1R)-2-[[2-[(1-acetyl-4-piperidyl)amino]-6-(4-methylpiperazin-1-yl)pyridine-4-carbonyl]amino]-1-hydroxy-ethyl]-7-(methoxymethoxy)-3,4-dihydro-1H-isoquinoline-2-carboxylate tert-Butyl (3S)-3-[(1R)-2-amino-1-hydroxy-ethyl]-7-(methoxymethoxy)-3,4-dihydro-1H-iso-quinoline-2-carboxylate (0.2 g, 567.50 μmol), 2-[(1-acetyl-4-piperidyl)amino]-6-(4-methylpiperazin-1-yl)pyridine-4-carboxylic acid (334.53 mg, 567.50 μmol, 2CF$_3$COOH) and triethylamine (574.25 mg, 5.67 mmol, 790.98 μL) were mixed together in DMF (4 mL) and HATU (323.67 mg, 851.25 μmol) was added. The reaction mixture was stirred at room temperature for 18 h. Then the reaction mixture was poured into water (25 mL) and the resulting mixture was extracted with EtOAc (2*25 mL). The combined organic layer was washed with water (3*25 mL), brine, dried over Na$_2$SO$_4$, filtered and evaporated. The residue was purified by HPLC (Column: SunFire C18 100*19 mm, 5 μm 15-40% H$_2$O-MeCN, 2-10 min, flow: 30 mL/min (Loading pump 4 mL/min MeCN)) to obtain tert-butyl (3S)-3-[(1R)-2-[[2-[(1-acetyl-4-piperidyl)amino]-6-(4-methylpiperazin-1-yl)pyridine-4-carbonyl]amino]-1-hydroxy-ethyl]-7-(methoxymethoxy)-3,4-dihydro-1H-isoquinoline-2-carboxylate (0.1172 g, 168.43 μmol, 29.68% yield). $^1$H NMR (DMSO-d$_6$, 400 MHz): δ 1.41 (m, 9H), 1.89 (m, 2H), 2.07 (s, 3H), 2.19 (s, 3H), 2.35 (m, 4H), 2.78 (m, 2H), 3.36 (m, 3H), 3.41 (m, 8H), 3.78 (m, 2H), 4.20 (m, 3H), 4.76 (m, 1H), 5.10 (m, 3H), 6.13 (s, 1H), 6.22 (s, 1H), 6.29 (d, 1H), 6.85 (m, 2H), 7.08 (d, 1H), 8.20 (m, 1H). LCMS (ESI): [M+H]$^+$ m/z: calc'd 695.4; found 969.2; Rt=1.17 min.

Step 2: Synthesis of 2-[(1-acetyl-4-piperidyl)amino]-N-[(2R)-2-hydroxy-2-[(3S)-7-hydroxy-1,2,3,4-tetrahydroisoquinolin-3-yl]ethyl]-6-(4-methylpiperazin-1-yl)pyridine-4-carboxamide tert-Butyl (3S)-3-[(1R)-2-[[2-[(1-acetyl-4-piperidyl)amino]-6-(4-methylpiperazin-1-yl)pyridine-4-carbonyl]amino]-1-hydroxy-ethyl]-7-(methoxymethoxy)-3,4-dihydro-TH-isoquinoline-2-carboxylate (0.1172 g, 168.43 μmol) was dissolved in MeOH (2 mL) and hydrogen chloride solution 4.0M in dioxane (73.69 mg, 2.02 mmol, 92.12 μL) was added. The resulting mixture was stirred for 3 h. After the completion of the reaction, the resulting mixture was evaporated to dryness to obtain 2-[(1-acetyl-4-piperidyl)amino]-N-[(2R)-2-hydroxy-2-[(3S)-7-hydroxy-1,2,3,4-tetrahydroisoquinolin-3-yl]ethyl]-6-(4-methylpiperazin-1-yl)pyridine-4-carboxamide (0.11748 g, 168.42 μmol, 100.00% yield, 4HCl). $^1$H NMR (DMSO-d$_6$, 400 MHz): δ 1.88 (m, 2H), 1.99 (s, 3H), 2.78 (m, 4H), 2.97 (m, 5H), 3.16 (m, 7H), 3.84 (m, 3H), 4.29 (m, 6H), 6.28 (s, 1H), 6.40 (s, 1H), 6.59 (s, 1H), 6.67 (d, 1H), 7.02 (d, 1H), 8.65 (m, 1H), 8.86 (m, 1H), 9.40 (m, 1H), 10.56 (m, 1H). LCMS (ESI): [M+2H]$^+$ m/z: calc'd 551.3; found 553.2; Rt=0.67 min.

Step 3: Synthesis of tert-butyl (3S)-3-[(1R)-2-[[2-[(1-acetyl-4-piperidyl)amino]-6-(4-methylpiperazin-1-yl)pyridine-4-carbonyl]amino]-1-hydroxy-ethyl]-7-hydroxy-3,4-dihydro-1H-isoquinoline-2-carboxylate 2-[(1-Acetyl-4-piperidyl)amino]-N-[(2R)-2-hydroxy-2-[(3S)-7-hydroxy-1,2,3,4-tetrahydro-isoquinolin-3-yl]ethyl]-6-(4-methylpiperazin-1-yl)pyridine-4-carboxamide (0.1175 g, 168.45 μmol, 4HCl) was dissolved in water (1 mL) and sodium bicarbonate (84.91 mg, 1.01 mmol, 39.31 μL) was added. The resulting mixture was diluted with THF (1 mL) and di-tert-butyl dicarbonate (36.76 mg, 168.45 μmol, 38.66 μL) was added. The reaction mixture was stirred for 17 h. Then, the reaction mixture was diluted with EtOAc (15 mL) and an organic layer was separated. An aqueous layer was washed with EtOAc (2*10 mL) and the combined organic layer was washed with brine, dried over Na$_2$SO$_4$, filtered off and evaporated to obtain tert-butyl (3S)-3-[(1R)-2-[[2-[(1-acetyl-4-piperidyl)amino]-6-(4-methylpiperazin-1-yl)pyridine-4-carbonyl]amino]-1-hydroxy-ethyl]-7-hydroxy-3,4-dihydro-1H-isoquinoline-2-carboxylate (0.0762 g, 116.91 μmol, 69.40% yield). $^1$H NMR (DMSO-d$_6$, 400 MHz): δ 1.40 (m, 9H), 1.91 (m, 2H), 1.98 (s, 3H), 2.19 (s, 3H), 2.34 (m, 4H), 2.94 (m, 4H), 3.75 (m, 3H), 4.04 (m, 3H), 4.18 (m, 4H), 4.71 (m, 1H), 5.10 (m, 1H), 6.12 (s, 1H), 6.21 (s, 1H), 6.27 (d, 1H), 6.58 (m, 2H), 6.92 (d, 1H), 8.15 (m, 1H), 9.20 (m, 1H). LCMS (ESI): [M+H]$^+$ m/z: calc'd 651.3; found 652.4; Rt=0.95 min.

Step 4: Synthesis of tert-butyl (3S)-3-[(1R)-2-[[2-[(1-acetyl-4-piperidyl)amino]-6-(4-methylpiperazin-1-yl)pyridine-4-carbonyl]amino]-1-hydroxy-ethyl]-7-[(4-methyloxazol-5-yl)methoxy]-3,4-dihydro-1H-isoquinoline-2-carboxylate tert-Butyl (3S)-3-[(1R)-2-[[2-[(1-acetyl-4-piperidyl)amino]-6-(4-methylpiperazin-1-yl)pyridine-4-carbonyl]amino]-1-hydroxy-ethyl]-7-hydroxy-3,4-dihydro-1H-isoquinoline-2-carboxylate (0.0762 g, 116.91 μmol), 5-(chloromethyl)-4-methyl-oxazole (25.54 mg, 151.98 μmol, HCl), and cesium carbonate (152.36 mg, 467.63 μmol) were mixed together in DMF (1.5 mL) and the resulting mixture was heated at 60° C. for 18 h. After the completion of the reaction, the reaction mixture was cooled to room temperature and diluted with water (10 mL). The resulting mixture was extracted with EtOAc (2*15 mL) and the combined organic layer was washed with water (4*5 mL), brine, dried over Na$_2$SO$_4$, filtered off and evaporated to obtain tert-butyl (3S)-3-[(1R)-2-[[2-[(1-acetyl-4-piperidyl)amino]-6-(4-methylpiperazin-1-yl)pyridine-4-carbonyl]-amino]-1-hydroxy-ethyl]-7-[(4-methyloxazol-5-yl)methoxy]-3,4-dihydro-1H-isoquinoline-2-carboxylate (54.20 mg, 72.57 μmol, 62.07% yield). $^1$H NMR (DMSO-d$_6$, 500 MHz): δ 1.44 (m, 9H), 1.98 (s, 3H), 2.17 (m, 7H), 2.35 (m, 6H), 2.89 (m, 6H), 3.41 (m, 4H), 3.78 (m, 4H), 4.15 (m, 6H), 5.09 (m, 3H), 6.13 (s, 1H), 6.25 (m, 2H), 6.85 (m, 2H), 7.08 (d, 1H), 8.29 (m, 1H). LCMS (ESI): [M+2H]$^+$ m/z: calc'd 745.4; found 747.2; Rt=1.13 min.

Step 5: Synthesis of 2-[(1-acetyl-4-piperidyl)amino]-N-[(2R)-2-hydroxy-2-[(3S)-7-[(4-methyloxazol-5-yl)methoxy]-1,2,3,4-tetrahydroisoquinolin-3-yl]ethyl]-6-(4-methylpiperazin-1-yl)pyridine-4-carboxamide (Compound 54) tert-Butyl (3S)-3-[(1R)-2-[[2-[(1-acetyl-4-piperidyl)amino]-6-(4-methylpiperazin-1-yl)pyridine-4-carbonyl]amino]-1-hydroxy-ethyl]-7-[(4-methyloxazol-5-yl)methoxy]-3,4-dihydro-1H-isoquinoline-2-carboxylate (54.20 mg, 72.57 μmol) was dissolved in MeOH (2 mL) and hydrogen chloride solution 4.0M in dioxane (15.88 mg, 435.40 μmol, 19.84 μL) was added. The reaction mixture was stirred for 2 h and then evaporated to dryness. Then the residue was dissolved in 3 mL of MeOH and 10 mg of scavenger (SiliaMetS Dimercaptotriazine(DMT)) was added thereto and the resulting suspension was stirred for 12 h. The suspension was filtered off, the filtrate was evaporated under reduced pressure. The residue was purified by HPLC (5-35% water-MeOH+HCl, 10 min, flow 30 mL/min (loading pump 4 mL/min MeOH)) to obtain 2-[(1-acetyl-4-piperidyl)amino]-N-[(2R)-2-hydroxy-2-[(3S)-7-[(4-methyl-oxazol-5-yl)methoxy]-1,2,3,4-tetrahydroisoquinolin-3-yl]ethyl]-6-(4-methylpiperazin-1-yl)pyridine-4-carboxamide (0.0155 g, 18.70 μmol, 25.76% yield, 5HCl). $^1$H NMR (400 MHz, CD$_3$OD) δ 1.53 (m, 1H), 1.62 (m, 1H), 2.08 (m, 2H), 2.15 (s, 3H), 2.23 (s, 3H), 2.97 (s, 3H), 3.16 (m, 4H), 3.42 (m, 1H), 3.54 (m, 4H), 3.66 (m, 4H), 3.93 (m, 1H), 4.02 (m, 1H), 4.32 (m, 3H), 4.42 (m, 3H), 5.11 (s, 2H), 6.88 (s, 1H), 6.96 (d, 1H), 7.23 (d, 1H), 8.37 (s, 1H). LCMS (ESI): [M+H]$^+$ m/z: calc'd 646.3; found 647.4; Rt=0.84 min.

Example 2A21. Synthesis of 2-[4-(cyclopropanecarbonyl)piperazin-1-yl]-N-[(2R)-2-hydroxy-2-[(3S)-7-[(4-methyloxazol-5-yl)methoxy]-1,2,3,4-tetrahydroisoquinolin-3-yl]ethyl]-6-(spiro[3.3]heptan-2-ylamino)pyridine-4-carboxamide (Compound 42)
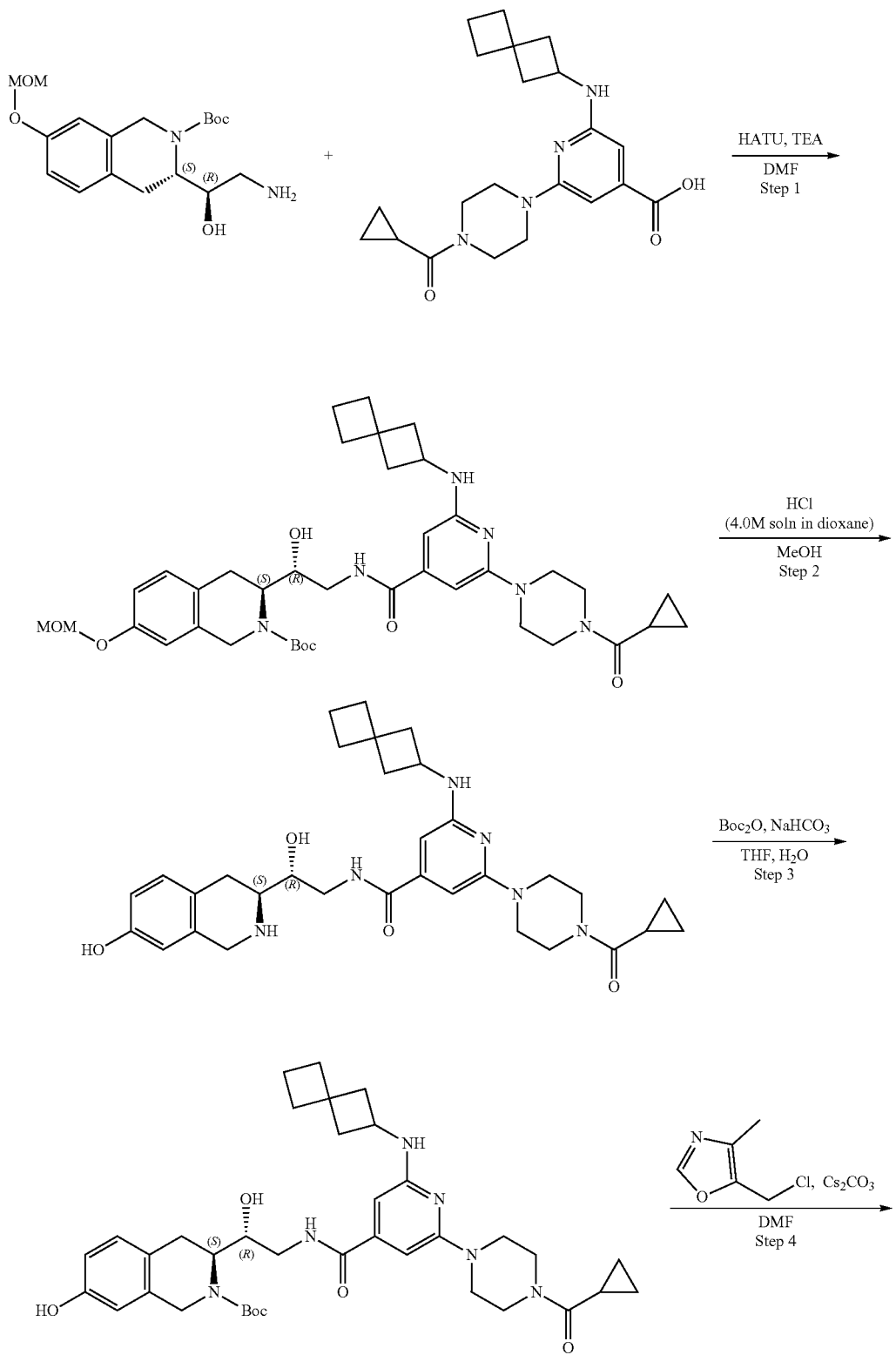

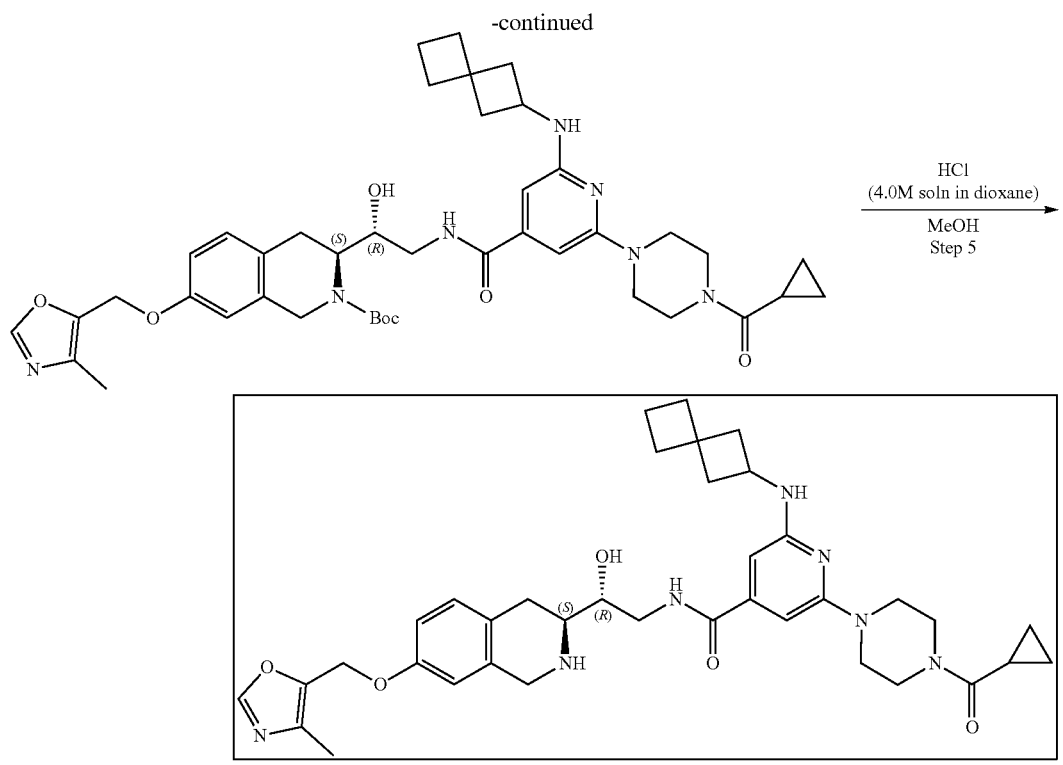

Step 1: Synthesis of tert-butyl (3S)-3-[(1R)-2-[[2-[4-(cyclopropanecarbonyl)piperazin-1-yl]-6-(spiro[3.3]heptan-2-ylamino)pyridine-4-carbonyl]amino]-1-hydroxy-ethyl]-7-(methoxymethoxy)-3,4-dihydro-1H-isoquinoline-2-carboxylate 2-[4-(Cyclopropanecarbonyl)piperazin-1-yl]-6-(spiro[3.3]heptan-2-ylamino)pyridine-4-carboxylic acid (247.53 mg, 496.56 μmol, CF₃COOH), tert-butyl (3S)-3-[(1R)-2-amino-1-hydroxy-ethyl]-7-(methoxymethoxy)-3,4-dihydro-1H-isoquinoline-2-carboxylate (250 mg, 496.56 μmol), and triethylamine (502.47 mg, 4.97 mmol, 692.11 μL) were mixed in DMF (10 mL). The resulting mixture was stirred for 5 min at room temperature followed by the addition of HATU (283.21 mg, 744.84 μmol). The resulting mixture were stirred at 25° C. for 12 hr. After the completion of the reaction, the mixture was evaporated under reduce pressure and purified with HPLC (60-75% water-acetonitrile, 10 min, flow 30 mL/min) to obtain tert-butyl (3S)-3-[(1R)-2-[[2-[4-(cyclopropanecarbonyl)piperazin-1-yl]-6-(spiro[3.3]heptan-2-ylamino)pyridine-4-carbonyl]amino]-1-hydroxy-ethyl]-7-(methoxymethoxy)-3,4-dihydro-1H-isoquinoline-2-carboxylate (164.3 mg, 228.55 μmol, 46.03% yield). $^1$H NMR (CDCl₃, 400 MHz): δ 0.75 (m, 2H), 0.99 (m, 2H), 1.51 (s, 9H), 1.81 (m, 3H), 1.92 (m, 2H), 1.98 (m, 4H), 2.01 (m, 2H), 2.52 (m, 2H), 2.83 (m, 2H), 3.17 (m, 1H), 3.30 (m, 1H), 3.46 (m, 5H), 3.94 (m, 6H), 4.17 (m, 1H), 4.37 (m, 2H), 4.64 (m, 2H), 5.13 (s, 2H), 6.10 (s, 1H), 6.44 (s, 1H), 6.77 (s, 1H), 6.85 (d, 1H), 7.11 (d, 1H), 8.02 (m, 1H). LCMS (ESI): [M+H]⁺ m/z: calc'd 718.4; found 719.4; Rt=1.56 min.

Step 2: Synthesis of 2-[4-(cyclopropanecarbonyl)piperazin-1-yl]-N-[(2R)-2-hydroxy-2-[(3S)-7-hydroxy-1, 2, 3,4-tetrahydroisoquinolin-3-yl]ethyl]-6-(spiro[3.3]heptan-2-ylamino)pyridine-4-carboxamide The solution of tert-butyl (3S)-3-[(1R)-2-[[2-[4-(cyclopropanecarbonyl)piperazin-1-yl]-6-(spiro-[3.3]heptan-2-ylamino)pyridine-4-carbonyl]amino]-1-hydroxy-ethyl]-7-(methoxymethoxy)-3,4-dihydro-1H-isoquinoline-2-carboxylate (164.3 mg, 228.55 μmol) in TFA (3 mL) and DCM (3 mL) was stirred for 12 hr at 25° C. Then the solution was evaporated to obtain 2-[4-(cyclopropanecarbonyl)piperazin-1-yl]-N-[(2R)-2-hydroxy-2-[(3S)-7-hydroxy-1,2,3,4-tetrahydroisoquinolin-3-yl]ethyl]-6-(spiro[3.3]heptan-2-ylamino)-pyridine-4-carboxamide (201 mg, crude, 3CF₃COOH). LCMS (ESI): [M+H]⁺ m/z: calc'd 574.3; found 575.2; Rt=1.08 min.

Step 3: Synthesis of tert-butyl (3S)-3-[(1R)-2-[[2-[4-(cyclopropanecarbonyl)piperazin-1-yl]-6-(spiro[3.3]heptan-2-ylamino)pyridine-4-carbonyl]amino]-1-hydroxy-ethyl]-7-hydroxy-3,4-dihydro-1H-isoquinoline-2-carboxylate To a stirred solution of sodium hydrogen carbonate (92.09 mg, 1.10 mmol, 42.63 μL) in water (1.5 mL), the solution of 2-[4-(cyclopropanecarbonyl)piperazin-1-yl]-N-[(2R)-2-hydroxy-2-[(3S)-7-hydroxy-1,2,3,4-tetrahydroisoquinolin-3-yl]ethyl]-6-(spiro[3.3]heptan-2-ylamino)pyridine-4-carboxamide (201 mg, 219.25 μmol, 3CF₃COOH) in THF (1.5 mL) was added. The resulting mixture was stirred for 5 min at room temperature followed by the addition of the solution of di-tert-butyl dicarbonate (47.85 mg, 219.25 μmol, 50.32 μL) in THF (1.5 mL). The resulting mixture was stirred at 25° C. for 12 hr. After the completion of the reaction mixture, EtOAc (10 mL) was added and the organic phase was separated and washed with brine (2*5 mL). Then the solvent was dried over sodium sulfate, filtered off and evaporated to obtain tert-butyl (3S)-3-[(1R)-2-[[2-[4-(cyclopropanecarbonyl)piperazin-1-yl]-6-(spiro[3.3]heptan-2-ylamino)pyridine-4-carbonyl]amino]-1-hydroxy-ethyl]-7-hydroxy-3,4-dihydro-1H-isoquinoline-2-carboxylate (138 mg, crude). LCMS (ESI): [M+H]⁺ m/z: calc'd 674.4; found 675.4; Rt=1.45 min.

Step 4: Synthesis of tert-butyl (3S)-3-[(1R)-2-[[2-[4-(cyclopropanecarbonyl)piperazin-1-yl]-6-(spiro[3.3]heptan-2- ylamino)pyridine-4-carbonyl]amino]-1-hydroxy-ethyl]-7-[(4-methyloxazol-5-yl)methoxy]-3,4-dihydro-1H-isoquinoline-2-carboxylate To the solution of tert-butyl (3S)-3-[(1R)-2-[[2-[4-(cyclopropanecarbonyl)piperazin-1-yl]-6-(spiro-[3.3]heptan-2-ylamino)pyridine-4-carbonyl]amino]-1-hydroxy-ethyl]-7-hydroxy-3,4-dihydro-1H-isoquinoline-2-carboxylate (138 mg, 204.50 µmol), cesium carbonate (199.89 mg, 613.49 µmol) in DMF (3 mL), 5-(chloromethyl)-4-methyl-oxazole (41.23 mg, 245.40 µmol, HCl) was added. The resulting mixture was heated at 50° C. for 12 hr. After the completion of the reaction, the mixture was filtered off and evaporated to obtain tert-butyl (3S)-3-[(1R)-2-[[2-[4-(cyclopropanecarbonyl)piperazin-1-yl]-6-(spiro[3.3]heptan-2-ylamino)pyridine-4-carbonyl]amino]-1-hydroxy-ethyl]-7-[(4-methyloxazol-5-yl)methoxy]-3,4-dihydro-1H-isoquinoline-2-carboxylate (143 mg, crude) that was used without further purification. LCMS (ESI): [M+H]+ m/z: calc'd 769.4; found 770.4; Rt=1.58 min.

Step 5: Synthesis of 2-[4-(cyclopropanecarbonyl)piperazin-1-yl]-N-[(2R)-2-hydroxy-2-[(3S)-7-[(4-methyloxazol-5-yl)methoxy]-1,2,3,4-tetrahydroisoquinolin-3-yl]ethyl]-6-(spiro[3.3]heptan-2-ylamino)pyridine-4-carboxamide (Compound 42) The solution of tert-butyl (3S)-3-[(1R)-2-[[2-[4-(cyclopropanecarbonyl)piperazin-1-yl]-6-(spiro-[3.3]heptan-2-ylamino)pyridine-4-carbonyl]amino]-1-hydroxy-ethyl]-7-[(4-methyloxazol-5-yl)methoxy]-3,4-dihydro-1H-isoquinoline-2-carboxylate (143 mg, 185.73 µmol) in TFA (2 mL) and DCM (2 mL) was stirred for 12 hr at 25° C. Then the solution was evaporated and the resulting crude product was purified by HPLC (55-70% water-methanol+NH3, 10 min, flow 30 mL/min) to obtain 2-[4-(cyclopropanecarbonyl)-piperazin-1-yl]-N-[(2R)-2-hydroxy-2-[(3S)-7-[(4-methyloxazol-5-yl)methoxy]-1,2,3,4-tetrahydro-isoquinolin-3-yl]ethyl]-6-(spiro[3.3]heptan-2-ylamino)pyridine-4-carboxamide (10.5 mg, 15.68 µmol, 8.44% yield). 1H NMR (DMSO-d6, 400 MHz): δ 0.83 (d, 2H), 0.88 (m, 2H), 1.83 (m, 4H), 1.95 (m, 3H), 2.07 (t, 2H), 2.18 (s, 3H), 2.44 (m, 2H), 2.82 (m, 3H), 2.94 (m, 1H), 3.50 (m, 3H), 3.62 (m, 6H), 3.85 (m, 4H), 4.05 (m, 3H), 5.03 (s, 2H), 6.09 (s, 1H), 6.27 (s, 1H), 6.70 (d, 1H), 6.79 (dd, 1H), 7.06 (d, 1H), 8.11 (s, 1H), OH is not observed. LCMS (ESI): [M+H]+ m/z: calc'd 669.3; found 670.4; Rt=1.21 min.

Scheme 2B

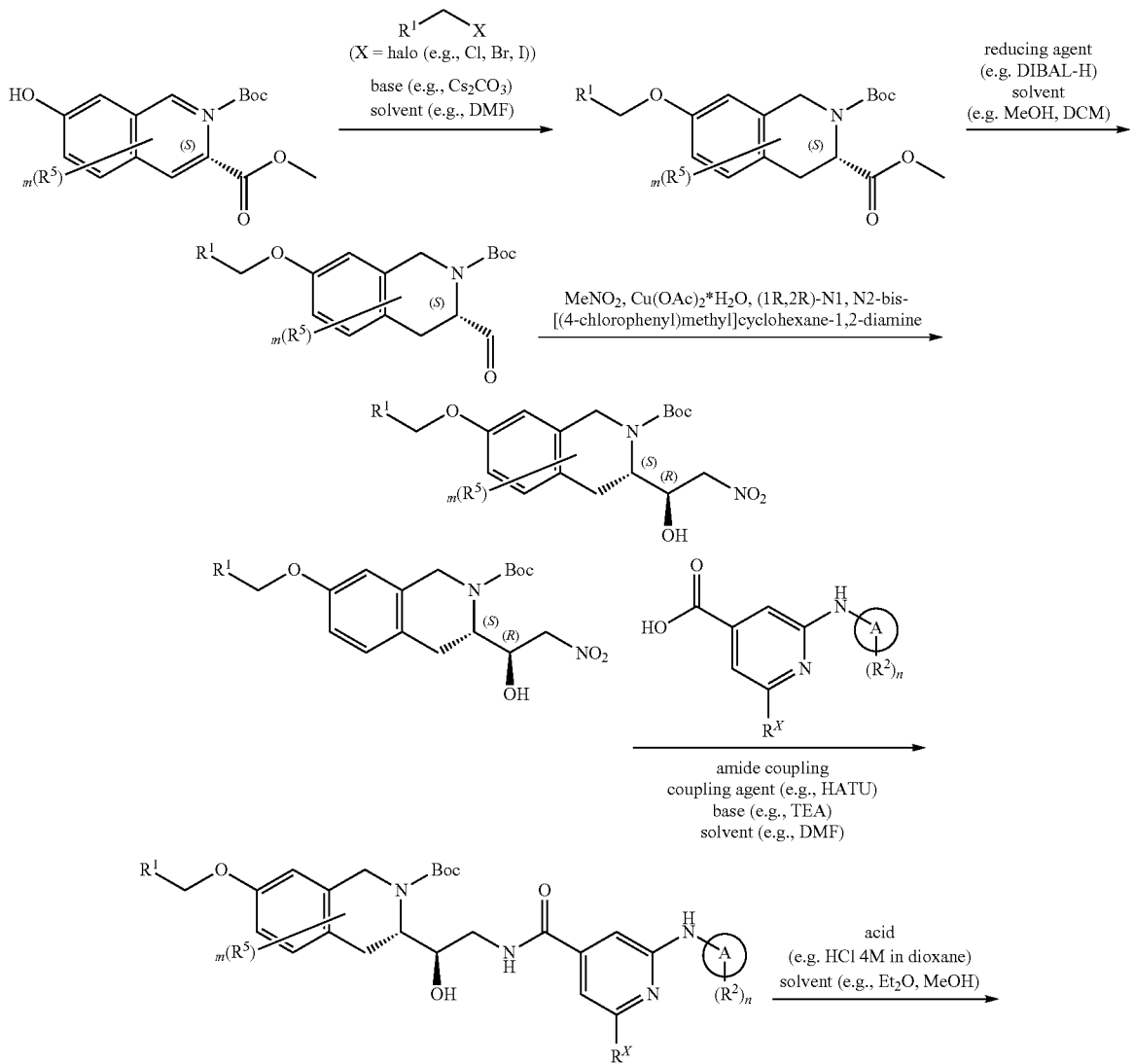

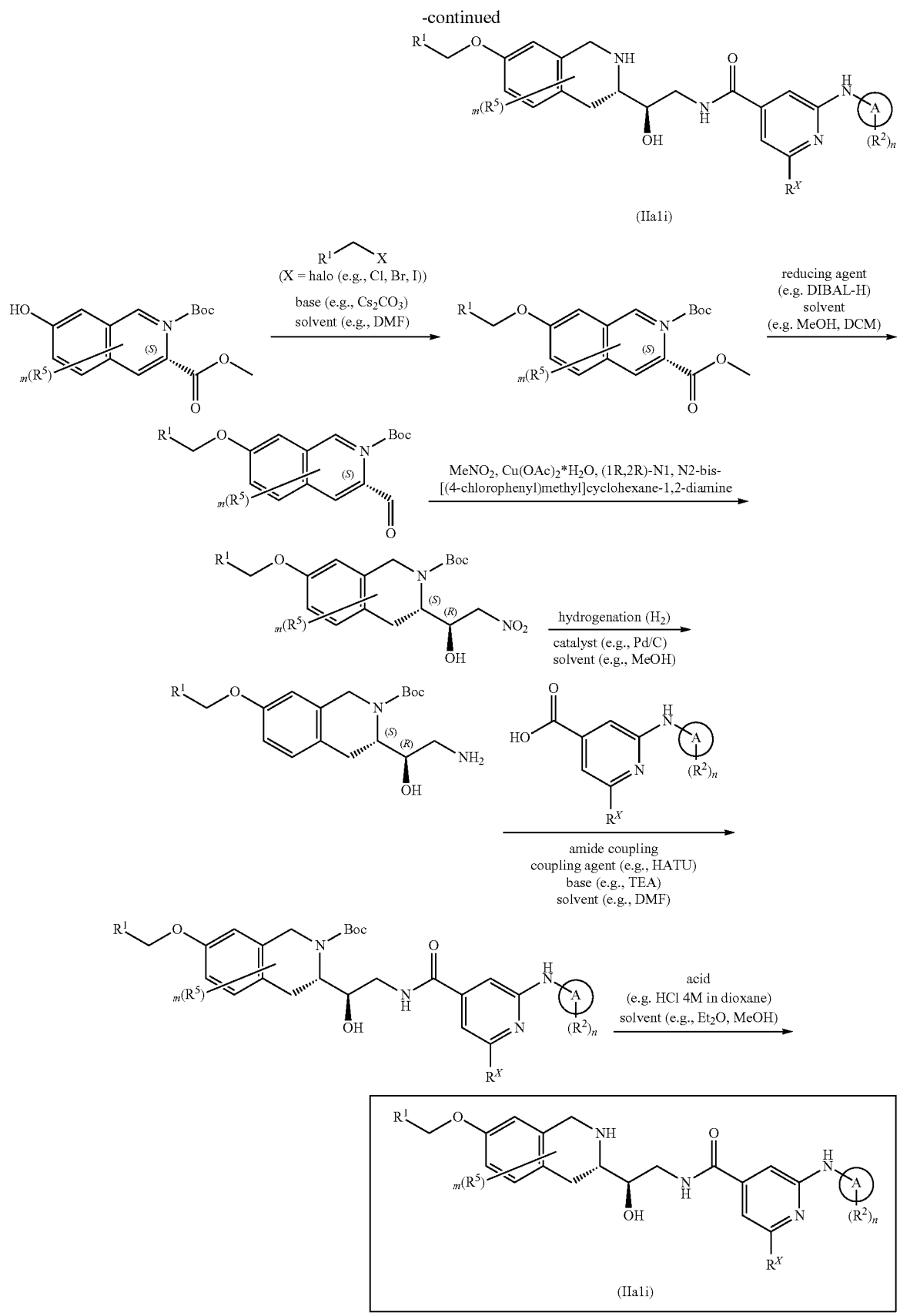

wherein X is a leaving group. In some embodiments, X is selected from Cl, Br, and I. In some embodiments X is Cl or Br.
Example 2B1. Synthesis of 2-(cyclobutylamino)-N-[(2R)-2-[(3S)-6-fluoro-7-[(4-methyloxazol-5-yl)methoxy]-1,2,3,4-tetrahydroisoquinolin-3-yl]-2-hydroxy-ethyl]pyridine-4-carboxamide (Compound 65)
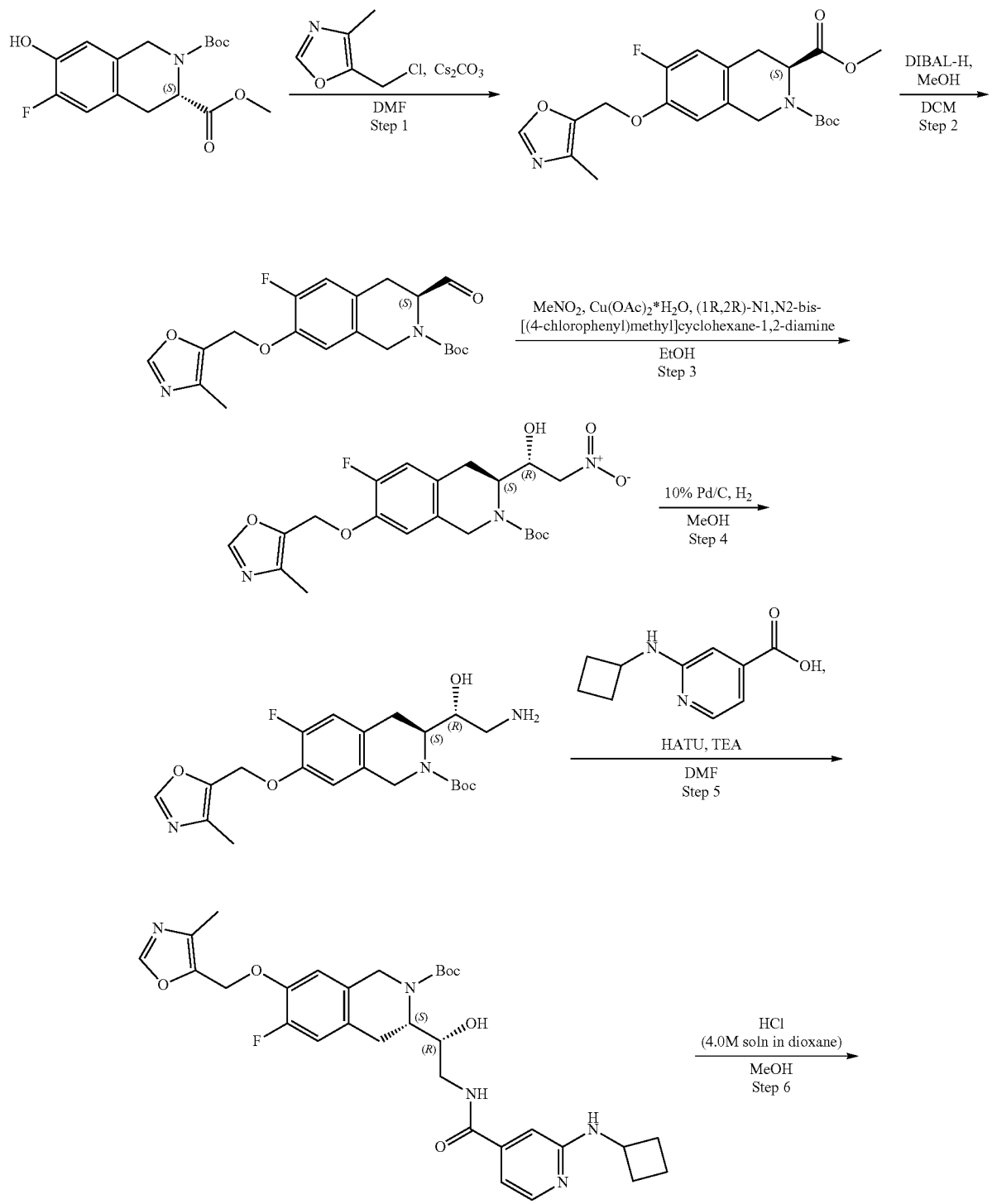

-continued

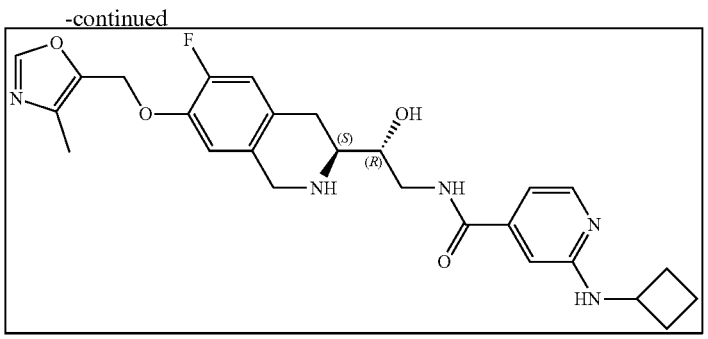

Step 1: Synthesis of 2-(tert-butyl) 3-methyl (S)-6-fluoro-7-((4-methyloxazol-5-yl)methoxy)-3,4-dihydroisoquinoline-2,3(1H)-dicarboxylate 2-(tert-butyl) 3-methyl (S)-6-fluoro-7-hydroxy-3,4-dihydroisoquinoline-2,3(1H)-dicarboxylate (2.3 g, 7.07 mmol) was dissolved in DMF (30 mL) and cesium carbonate (6.91 g, 21.21 mmol) was added followed by the addition of 5-(chloromethyl)-4-methyl-oxazole (1.43 g, 8.48 mmol, HCl). The resulting mixture was heated and stirred at 60° C. for 18 hr. After the completion of the reaction, the reaction mixture was cooled and poured into water (100 mL). The resulting mixture was extracted with MTBE (2*100 mL). The combined organic layers were washed with water (3*50 mL), brine, dried over $Na_2SO_4$, filtered off and evaporated to obtain 2-(tert-butyl) 3-methyl (S)-6-fluoro-7-((4-methyloxazol-5-yl)methoxy)-3,4-dihydroisoquinoline-2,3(1H)-dicarboxylate (2.88 g, 6.85 mmol, 96.89% yield). $^1$H NMR (DMSO-$d_6$, 500 MHz): δ 1.40 (m, 9H), 2.12 (s, 3H), 3.11 (m, 3H), 3.55 (m, 2H), 4.47 (m, 2H), 4.94 (m, 1H), 5.16 (m, 2H), 7.11 (m, 1H), 7.19 (m, 1H), 8.30 (m, 1H). LCMS (ESI): [M-Boc]$^+$ m/z: calc'd 320.2; found 321.2; Rt=1.37 min.

Step 2: Synthesis of tert-butyl (3S)-6-fluoro-3-formyl-7-[(4-methyloxazol-5-yl)methoxy]-3,4-dihydro-1H-isoquinoline-2-carboxylate 2-(tert-butyl) 3-methyl (S)-6-fluoro-7-((4-methyloxazol-5-yl)methoxy)-3,4-dihydroisoquinoline-2,3(1H)-dicarboxylate (2.88 g, 6.85 mmol) was dissolved in DCM (120 mL) and the resulting mixture was cooled to −78° C. under an argon atmosphere. DIBAL-H (1.95 g, 13.70 mmol, 2.44 mL) was added dropwise at −78° C. and the reaction mixture was stirred at −78° C. for 1 hr. The solution of methanol (2.19 g, 68.50 mmol, 2.77 mL) in DCM (12 mL) was carefully added dropwise at −78° C. and the resulting mixture was allowed to warm to room temperature. The reaction mixture was carefully poured into citric acid aqueous solution and the resulting mixture was stirred for 30 min. The organic layer was separated, and the aqueous layer was washed with DCM (100 mL). The combined organic layers were washed with solution of citric acid, dried over $Na_2SO_4$, filtered off and evaporated to obtain tert-butyl (3S)-6-fluoro-3-formyl-7-[(4-methyloxazol-5-yl)methoxy]-3,4-dihydro-1H-isoquinoline-2-carboxylate (2.67 g, crude). $^1$H NMR (DMSO-$d_6$, 500 MHz): δ 1.46 (m, 9H), 2.12 (s, 3H), 3.07 (m, 2H), 3.56 (m, 1H), 4.62 (m, 3H), 5.15 (s, 2H), 7.11 (m, 1H), 7.20 (m, 1H), 8.29 (s, 1H), 9.44 (m, 1H). LCMS (ESI): [M-Boc]$^+$ m/z: calc'd 390.2; found 291.0; Rt=1.44 min.

Step 3: Synthesis of tert-butyl (3S)-6-fluoro-3-[(1R)-1-hydroxy-2-nitro-ethyl]-7-[(4-methyloxazol-5-yl)methoxy]-3,4-dihydro-1H-isoquinoline-2-carboxylate (1R,2R)—$N_1$,$N_2$-bis[(4-chlorophenyl)methyl]cyclohexane-1,2-diamine (298.17 mg, 820.69 µmol) and copper(II) acetate monohydrate (136.54 mg, 683.91 µmol, 72.63 µL) were mixed together in EtOH (5 mL) at 0° C. and the resulting mixture was stirred for 15 min. The solution of tert-butyl (3S)-6-fluoro-3-formyl-7-[(4-methyloxazol-5-yl)methoxy]-3,4-dihydro-1H-isoquinoline-2-carboxylate (2.67 g, 6.84 mmol) in EtOH (15 mL) was added thereto followed by addition of nitromethane, 98+% (8.35 g, 136.78 mmol, 7.39 mL). The reaction mixture was allowed to warm to room temperature and stirred for 18 hr. After the completion of the reaction, the reaction mixture was concentrated in vacuo and the residue was dissolved in MTBE (100 mL). The resulting mixture was washed with ammonia solution (3*500 mL), citric acid solution (3*500 mL), water (150 mL), dried over $Na_2SO_4$, filtered off and evaporated. The residue was purified by HPLC (Waters SunFire C18 19*100 5 mkm column and $H_2O$-MeOH as a mobile phase) to obtain tert-butyl (3S)-6-fluoro-3-[(1R)-1-hydroxy-2-nitro-ethyl]-7-[(4-methyloxazol-5-yl)methoxy]-3,4-dihydro-1H-isoquinoline-2-carboxylate (0.637 g, 1.41 mmol, 20.63% yield). $^1$H NMR (CDCl$_3$, 400 MHz): δ 1.48 (s, 9H), 2.15 (s, 3H), 2.86 (m, 2H), 4.09 (m, 2H), 4.30 (m, 3H), 4.57 (m, 1H), 5.04 (s, 2H), 6.78 (d, 1H), 6.90 (d, 1H), 7.79 (s, 1H). LCMS (ESI): [M-Boc]$^+$ m/z: calc'd 351.2; found 352.2; Rt=3.44 min.

Step 4: Synthesis of tert-butyl (3S)-3-[(1R)-2-amino-1-hydroxy-ethyl]-6-fluoro-7-[(4-methyloxazol-5-yl)methoxy]-3,4-dihydro-1H-isoquinoline-2-carboxylate tert-Butyl (3S)-6-fluoro-3-[(1R)-1-hydroxy-2-nitro-ethyl]-7-[(4-methyloxazol-5-yl)methoxy]-3,4-dihydro-1H-isoquinoline-2-carboxylate (0.637 g, 1.41 mmol) was dissolved in MeOH (40 mL) and Palladium, 10% on carbon, Type 487, dry (75.08 mg, 705.51 µmol) was added. The resulting mixture was hydrogenated at 50 atm at 50° C. for 18 hr. After the completion of the reaction, the catalyst was filtered off and the filtrate was evaporated to obtain tert-butyl (3S)-3-[(1R)-2-amino-1-hydroxy-ethyl]-6-fluoro-7-[(4-methyloxazol-5-yl)methoxy]-3,4-dihydro-1H-isoquinoline-2-carboxylate (0.472 g, 1.12 mmol, 79.37% yield). $^1$H NMR (CDCl$_3$, 400 MHz): δ 1.48 (s, 9H), 1.94 (m, 2H), 2.17 (s, 3H), 2.60 (m, 2H), 2.84 (m, 1H), 2.96 (m, 2H), 4.02 (m, 1H), 4.23 (m, 2H), 4.63 (m, 1H), 5.02 (s, 2H), 6.73 (d, 1H), 6.89 (d, 1H), 7.79 (s, 1H). LCMS (ESI): [M+H]$^+$ m/z: calc'd 421.2; found 422.2; Rt=0.97 min.

Step 5: Synthesis of tert-butyl (3S)-3-[(1R)-2-[[2-(cyclobutylamino)pyridine-4-carbonyl]amino]-1-hydroxyethyl]-6-fluoro-7-[(4-methyloxazol-5-yl)methoxy]-3,4-dihydro-1H-isoquinoline-2-carboxylate tert-Butyl (3S)-3-[(1R)-2-amino-1-hydroxy-ethyl]-6-fluoro-7-[(4-methyloxazol-5-yl)methoxy]-3,4-dihydro-1H-isoquinoline-2-carboxylate (0.15 g, 355.90 µmol), 2-(cyclobutylamino)pyridine-4-carboxylic acid (108.99 mg, 355.90 µmol, CF$_3$COOH) and TEA (360.14 mg, 3.56 mmol, 496.06 µL)

were mixed together in DMF (2 mL) and HATU (202.99 mg, 533.86 µmol) was added. The resulting mixture was stirred for 18 hr. After the completion of the reaction, the reaction mixture was poured into water (15 mL) and the resulting mixture was extracted with EtOAc (2*15 mL). The combined organic layers were washed with water (4*10 mL), brine, dried over $Na_2SO_4$, filtered off and evaporated to obtain tert-butyl (3S)-3-[(1R)-2-[[2-(cyclobutylamino)pyridine-4-carbonyl]amino]-1-hydroxy-ethyl]-6-fluoro-7-[(4-methyloxazol-5-yl)methoxy]-3,4-dihydro-1H-isoquinoline-2-carboxylate (0.2366 g, crude). $^1$H NMR (DMSO-$d_6$, 500 MHz): δ 1.42 (m, 9H), 1.66 (m, 3H), 1.85 (m, 3H), 2.14 (s, 3H), 2.26 (m, 3H), 2.90 (m, 2H), 3.55 (m, 2H), 4.23 (m, 2H), 4.80 (m, 1H), 5.17 (s, 2H), 6.73 (m, 1H), 6.80 (m, 1H), 6.91 (m, 1H), 7.01 (m, 1H), 7.13 (m, 1H), 7.18 (m, 1H), 8.00 (m, 1H), 8.29 (m, 1H). LCMS (ESI): [M+H]$^+$ m/z: calc'd 595.3; found 596.2; Rt=1.16 min.

Step 6: Synthesis of 2-(cyclobutylamino)-N-[(2R)-2-[(3S)-6-fluoro-7-[(4-methyloxazol-5-yl)methoxy]-1,2,3,4-tetrahydroisoquinolin-3-yl]-2-hydroxy-ethyl]pyridine-4-carboxamide Compound 65) tert-Butyl (3S)-3-[(1R)-2-[[2-(cyclobutylamino)pyridine-4-carbonyl]amino]-1-hydroxy-ethyl]-6-fluoro-7-[(4-methyloxazol-5-yl)methoxy]-3,4-dihydro-1H-isoquinoline-2-carboxylate (0.2366 g, 397.21 µmol) was dissolved in MeOH (4 mL) and hydrogen chloride solution 4.0M in dioxane (86.90 mg, 2.38 mmol, 108.62 µL) was added. The resulting mixture was stirred for 3 hr and evaporated. The residue was dissolved in 10 mL of MeOH and 50 mg of scavenger (SiliaMetS© Dimercaptotriazine(DMT)) was added and the resulting suspension was stirred for 12 h. The suspension was filtered off, the filtrate was evaporated under reduced pressure. The residue was purified by HPLC (30-40% water-methanol+NH$_3$, 10 min, flow 30 mL/min (loading pump 4 mL/min R1+NH$_3$)) to obtain 2-(cyclobutylamino)-N-[(2R)-2-[(3S)-6-fluoro-7-[(4-methyloxazol-5-yl)methoxy]-1,2,3,4-tetrahydroisoquinolin-3-yl]-2-hydroxy-ethyl]pyridine-4-carboxamide (0.0158 g, 31.88 µmol, 8.03% yield). $^1$H NMR (400 MHz, CDCl$_3$) δ 1.82 (m, 6H), 2.17 (s, 3H), 2.41 (m, 2H), 2.73 (m, 2H), 2.96 (m, 1H), 3.51 (m, 1H), 3.79 (m, 2H), 3.93 (m, 2H), 4.13 (m, 1H), 4.98 (m, 1H), 5.01 (s, 2H), 6.64 (m, 1H), 6.67 (s, 1H), 6.72 (m, 1H), 6.82 (d, 1H), 7.14 (m, 1H), 7.78 (s, 1H), 8.09 (d, 1H). LCMS (ESI): [M+H]$^+$ m/z: calc'd 495.2; found 496.2; Rt=0.81 min.

Example 3—Synthesis of Compounds of Formula (IIIa1i)

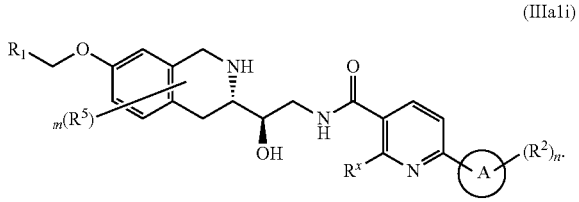

wherein $R^1$, $R^2$, $R^5$, $R^x$, m, n and A are as defined herein

Scheme 3A

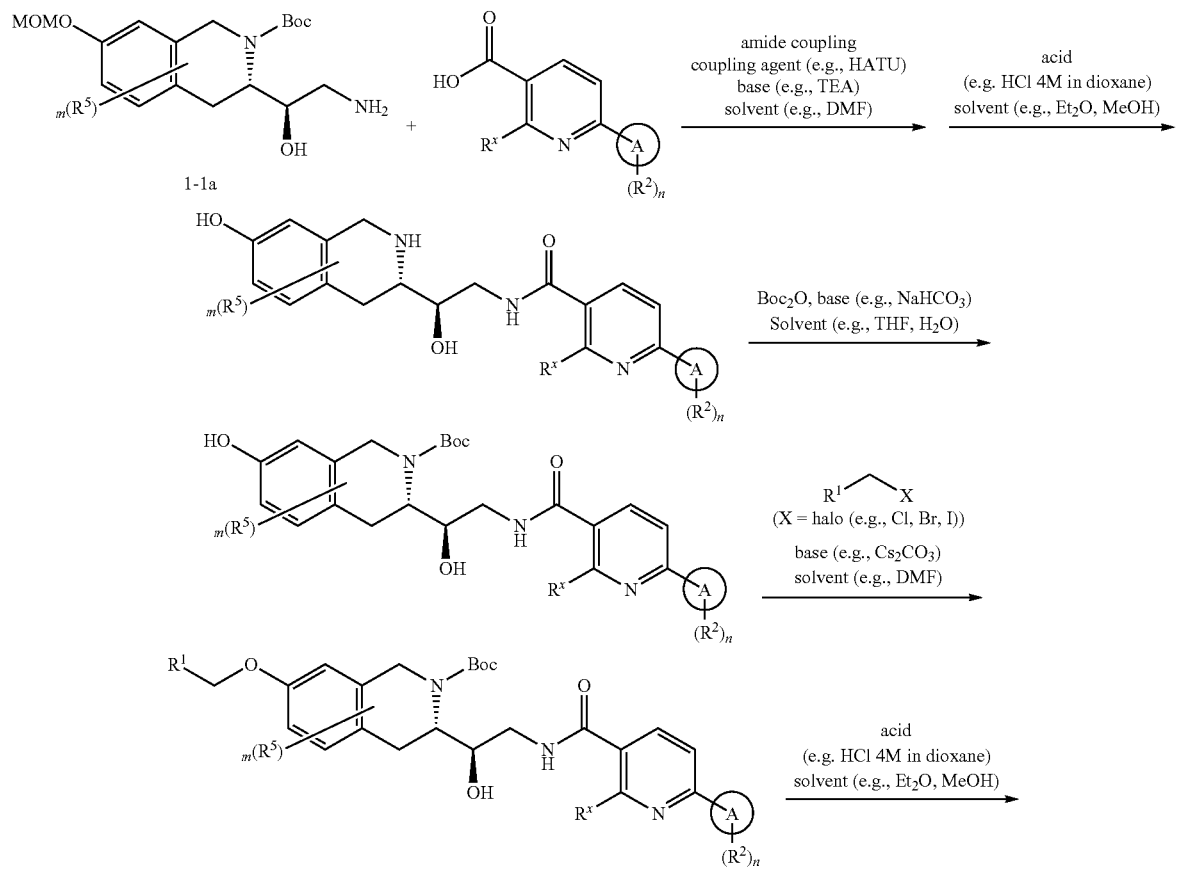

-continued
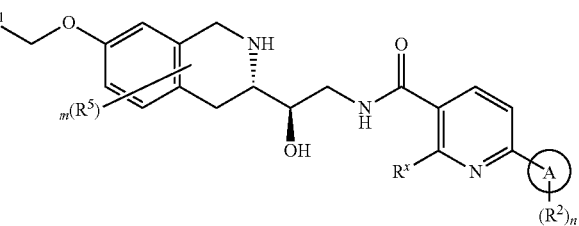
(IIIa1i)
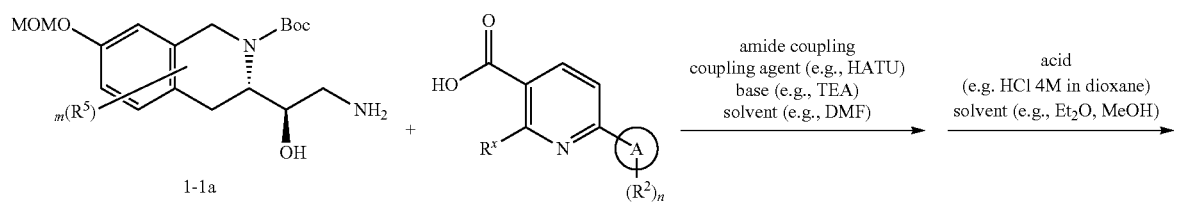
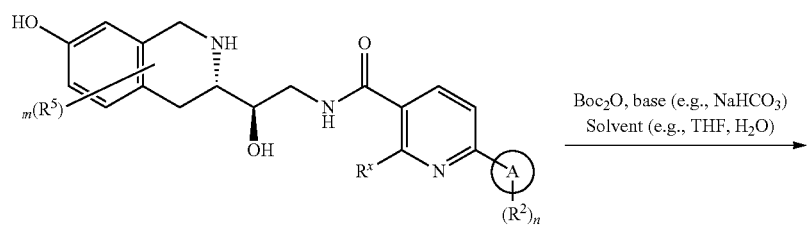
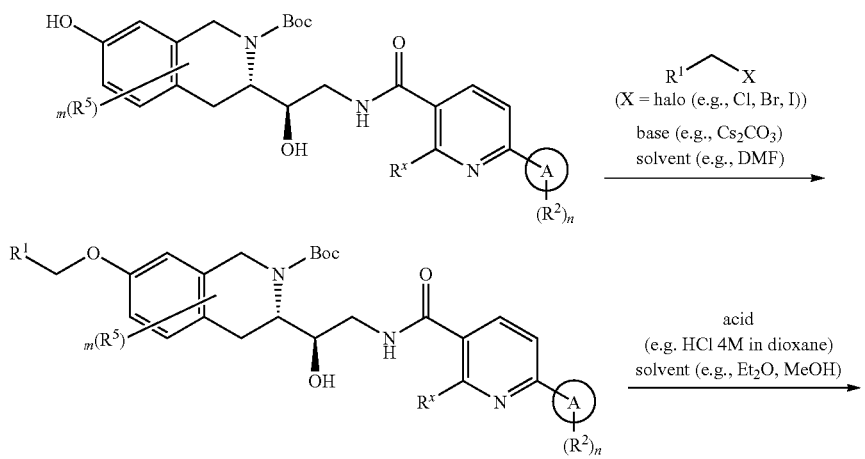
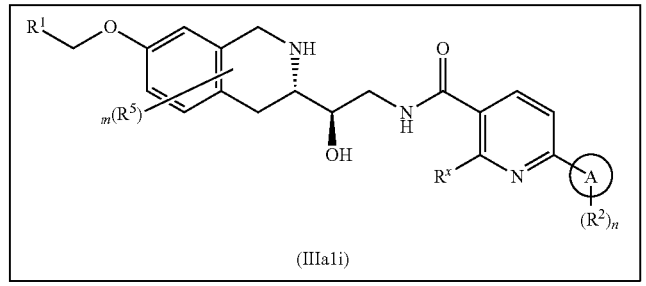
(IIIa1i)

Example 3A1. Synthesis of methyl 4-(6-ethoxy-5-(((R)-2-hydroxy-2-((S)-7-(oxazol-5-ylmethoxy)-1,2,3,4-tetrahydroisoquinolin-3-yl)ethyl)carbamoyl)pyridin-2-yl)piperazine-1-carboxylate (Compound 16)
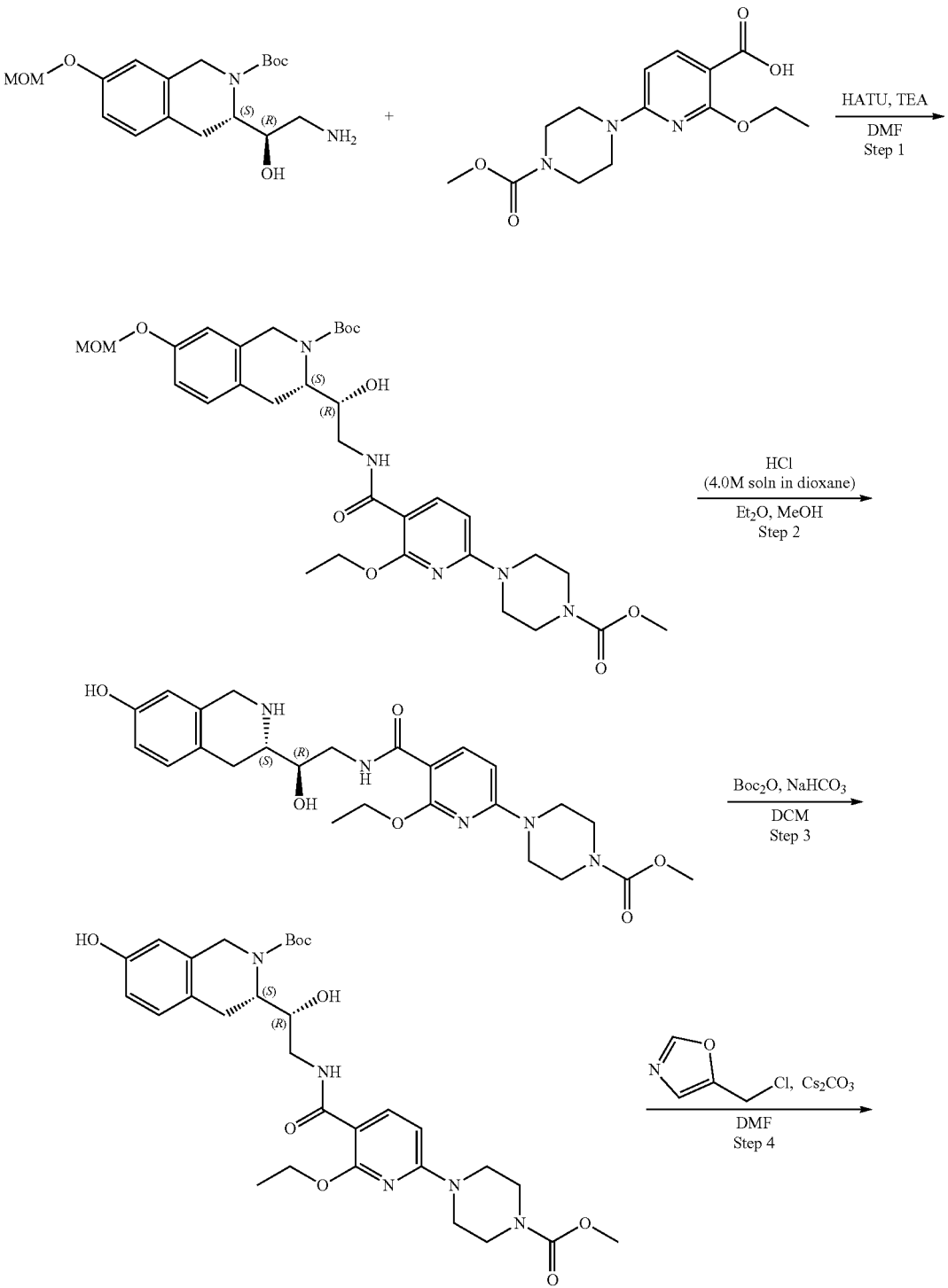

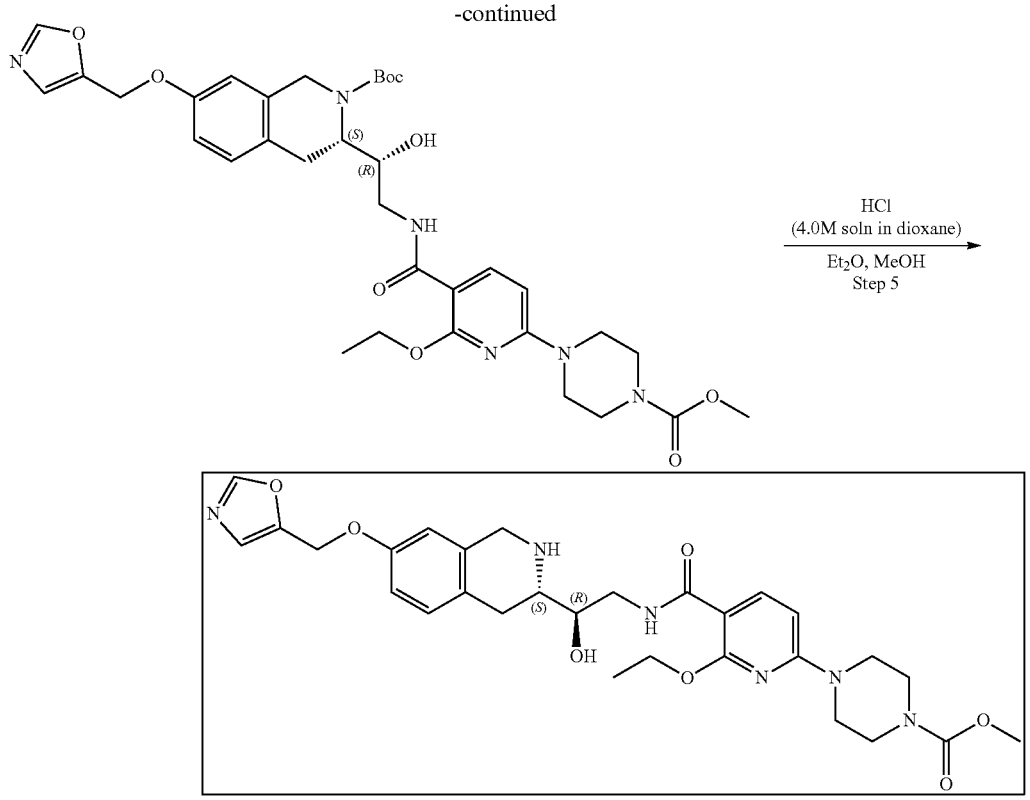

Step 1: Synthesis of (S)-tert-butyl 3-((R)-2-(2-ethoxy-6-(4-(methoxycarbonyl)piperazin-1-yl)nicotinamido)-1-hydroxyethyl)-7-(methoxymethoxy)-3,4-dihydroisoquinoline-2(1H)-carboxylate (2-Ethoxy-6-(4-methoxycarbonylpiperazin-1-yl)pyridine-3-carboxylic acid (351.07 mg, 1.13 mmol) and TEA (1.15 g, 11.35 mmol, 1.58 mL) were dissolved in DMF (8 mL) and cooled to 0° C. Then, HATU (647.34 mg, 1.70 mmol) was added and the mixture was stirred for 15 min at 0° C. followed by the addition of tert-butyl (3S)-3-[(1R)-2-amino-1-hydroxyethyl]-7-(methoxymethoxy)-3,4-dihydro-1H-isoquinoline-2-carboxylate (0.4 g, 1.13 mmol). The reaction mixture was warmed to r.t. and stirred overnight. After LCMS showed full conversion of the starting material, 10 mL of ethyl acetate was added, and organic phase was washed with brine three times. The organic layer was dried over Na₂SO₄, filtered off and concentrated in vacuo at 45° C. The obtained residue was purified by HPLC (40-55% water-acetonitrile, 10 min, flow: 40 mL/min (loading pump 5 mL/min acetonitrile) column: SunFire C18 100*19 mm) to give tert-butyl (3S)-3-[(1R)-2-[[2-ethoxy-6-(4-methoxycarbonylpiperazin-1-yl)pyridine-3-carbonyl]amino]-1-hydroxy-ethyl]-7-(methoxymethoxy)-3,4-dihydro-1H-isoquinoline-2-carboxylate (0.396 g, 615.17 μmol, 54.20% yield). $^1$H NMR (400 MHz, DMSO-d₆) δ (ppm) 1.40 (m, 12H), 2.75 (m, 1H), 3.03 (m, 2H), 3.35 (s, 3H), 3.45 (m, 5H), 3.59 (m, 8H), 4.19 (m, 2H), 4.41 (m, 2H), 4.73 (m, 1H), 5.14 (s, 2H), 5.31 (m, 1H), 6.46 (d, 1H), 6.83 (m, 2H), 7.06 (d, 1H), 8.04 (m, 1H), 8.12 (m, 1H). LCMS (ESI): [M+H]⁺ m/z: calc'd 643.7; found 644.4; Rt=1.44 min.

Step 2: Synthesis of methyl 4-(6-ethoxy-5-(((R)-2-hydroxy-2-((S)-7-hydroxy-1,2,3,4-tetrahydroisoquinolin-3-yl)ethyl)carbamoyl)pyridin-2-yl)piperazine-1-carboxylate Hydrogen chloride solution 4.0M in dioxane (1.68 g, 46.14 mmol, 2.10 mL) was added to the solution of tert-butyl (3S)-3-[(1R)-2-[[2-ethoxy-6-(4-methoxycarbonylpiperazin-1-yl)pyridine-3-carbonyl]-amino]-1-hydroxy-ethyl]-7-(methoxymethoxy)-3,4-dihydro-1H-isoquinoline-2-carboxylate (0.396 g, 615.17 μmol) in the mixture of Et₂O (3 mL) and MeOH (1.5 mL). The resulting mixture was stirred for 24 h at 20° C. The formed solid was filtered on, washed with Et₂O (3 mL) and dried in vacuo at 35° C. to give methyl 4-[6-ethoxy-5-[[(2R)-2-hydroxy-2-[(3S)-7-hydroxy-1,2,3,4-tetrahydroisoquinolin-3-yl]ethyl]carbamoyl]-2-pyridyl]piperazine-1-carboxylate (0.33 g, 576.44 μmol, 93.70% yield, 2HCl). $^1$H NMR (500 MHz, DMSO-d₆) δ (ppm) 1.32 (t, 3H), 2.96 (m, 2H), 3.46 (m, 7H), 3.62 (m, 5H), 4.12 (m, 4H), 4.28 (m, 1H), 4.41 (m, 2H), 6.45 (d, 1H), 6.59 (s, 1H), 6.68 (d, 1H), 7.02 (d, 1H), 8.07 (m, 2H), 8.87 (m, 1H), 9.29 (m, 1H), 9.37 (m, 1H). LCMS (ESI): [M+H]+ m/z: calc'd 499.2; found 500.2; Rt=1.07 min.

Step 3: Synthesis of (S)-tert-butyl 3-((R)-2-(2-ethoxy-6-(4-(methoxycarbonyl)piperazin-1-yl)nicotinamido)-1-hydroxyethyl)-7-hydroxy-3,4-dihydroisoquinoline-2(1H)-carboxylate. Sodium hydrogen carbonate, 99% (101.69 mg, 1.21 mmol, 47.08 μL) was added in one portion to the solution of methyl 4-[6-ethoxy-5-[[(2R)-2-hydroxy-2-[(3S)-7-hydroxy-1,2,3,4-tetrahydroisoquinolin-3-yl]ethyl]carbamoyl]-2-pyridyl]piperazine-1-carboxylate (0.33 g, 576.44 μmol, 2HCl) in the mixture of water (8 mL) and THF (8 mL). Then, the solution of di-tert-butyl dicarbonate (125.81 mg, 576.44 μmol, 132.29 μL) in THF (2 mL) was added dropwise to the reaction mixture and stirred overnight at room temperature overnight. After the completion of the reaction, ethyl acetate (15 mL) was added to the reaction mixture. The organic phase was separated, and the aqueous phase was extracted with ethyl acetate (2*15 mL). The organic phase was washed with brine, dried over Na₂SO₄, filtered and evaporated in vacuo at 40° C. to give crude product which was purified by HPLC (45-55% water-acetonitrile, 10 min, flow: 30 mL/min (loading pump 4 mL/min acetonitrile), column: SunFire C18 100*19 mm to give tert-butyl (3S)-3-[(1R)-2-[[2-ethoxy-6-(4-methoxycarbonylpiperazin-1-yl)pyridine-3-carbonyl]amino]-1-hydroxy-ethyl]-7-hydroxy-3,4-dihydro-1H-isoquinoline-2-carboxylate (0.14 g, 233.46 µmol, 40.50% yield). $^1$H NMR (400 MHz, DMSO-$d_6$) δ (ppm) 1.35 (t, 3H), 1.43 (s, 9H), 2.96 (m, 2H), 2.97 (m, 2H), 3.46 (m, 5H), 3.59 (m, 4H), 3.62 (s, 3H), 4.13 (m, 2H), 4.37 (m, 2H), 4.69 (m, 1H), 5.17 (m, 1H), 6.44 (d, 1H), 6.51 (s, 1H), 6.59 (d, 1H), 6.95 (d, 1H), 8.09 (m, 2H), 9.18 (s, 1H). LCMS (ESI): [M+H]$^+$ m/z: calc'd 599.3; found 600.1; Rt=1.41 min.

Step 4: Synthesis of (S)-tert-butyl 3-((R)-2-(2-ethoxy-6-(4-(methoxycarbonyl)piperazin-1-yl)nicotinamido)-1-hydroxyethyl)-7-(oxazol-5-ylmethoxy)-3,4-dihydroisoquinoline-2(1H)-carboxylate tert-Butyl (3S)-3-[(1R)-2-[[2-ethoxy-6-(4-methoxycarbonylpiperazin-1-yl)pyridine-3-carbonyl]-amino]-1-hydroxy-ethyl]-7-hydroxy-3,4-dihydro-1H-isoquinoline-2-carboxylate (0.046 g, 76.71 µmol), 5-(chloromethyl)oxazole (12.99 mg, 84.38 µmol, HCl) and cesium carbonate (74.98 mg, 230.13 µmol) were mixed together in DMF (2 mL) and heated at 50° C. overnight. The reaction mixture was diluted with water end extracted three times with EtOAc. The organic phase was washed with brine, dried over Na$_2$SO$_4$, filtered off and evaporated at 40° C. to give tert-butyl (3S)-3-[(1R)-2-[[2-ethoxy-6-(4-methoxycarbonylpiperazin-1-yl)pyridine-3-carbonyl]amino]-1-hydroxy-ethyl]-7-(oxazol-5-ylmethoxy)-3,4-dihydro-1H-isoquinoline-2-carboxylate (0.05 g, 73.45 µmol, 95.75% yield) which was used in the next step without further purification. $^1$H NMR (400 MHz, DMSO-$d_6$) δ (ppm) 1.35 (t, 3H), 1.43 (s, 9H), 1.46 (m, 4H), 3.45 (m, 5H), 3.59 (m, 4H), 4.15 (m, 3H), 4.07 (m, 4H), 4.40 (m, 2H), 5.12 (s, 2H), 5.29 (m, 1H), 6.43 (d, 1H), 6.45 (s, 1H), 6.88 (m, 2H), 7.06 (d, 1H), 8.05 (m, 2H). LCMS (ESI): [M+H]$^+$ m/z: calc'd 680.3; found 681.2; Rt=3.96 min.

Step 5: Synthesis of methyl 4-(6-ethoxy-5-(((R)-2-hydroxy-2-((S)-7-(oxazol-5-ylmethoxy)-1,2,3,4-tetrahydroisoquinolin-3-yl)ethyl)carbamoyl)pyridin-2-yl)piperazine-1-carboxylate (Compound 16) Hydrogen chloride solution 4.0M in dioxane (200.85 mg, 5.51 mmol, 251.06 µL) was added to the solution of tert-butyl (3S)-3-[(1R)-2-[[2-ethoxy-6-(4-methoxycarbonylpiperazin-1-yl)pyridine-3-carbonyl]-amino]-1-hydroxy-ethyl]-7-(oxazol-5-yl-methoxy)-3,4-dihydro-1H-isoquinoline-2-carboxylate (0.05 g, 73.45 µmol) in the mixture of Et$_2$O (1 mL) and MeOH (0.5 mL). The resulting mixture was stirred for 24 h at 20° C. The formed solid was filtered on, washed with Et$_2$O (1 mL) and dried in vacuo at 35° C. to give crude product which was purified by HPLC (50-65% water-methanol+NH$_3$, 2-10 min, flow: 30 mL/min (loading pump 4 mL/min methanol+NH$_3$), column: SunFire C18 100*19 mm to give methyl 4-[6-ethoxy-5-[[(2R)-2-hydroxy-2-[(3S)-7-(oxazol-5-ylmethoxy)-1,2,3,4-tetrahydroisoquinolin-3-yl]ethyl]carbamoyl]-2-pyridyl]piperazine-1-carboxylate (12.20 mg, 21.01 µmol, 28.61% yield). $^1$H NMR (400 MHz, CD$_3$OD) δ 1.43 (t, 3H), 2.86 (m, 3H), 3.49 (m, 1H), 3.55 (m, 4H), 3.66 (m, 4H), 3.71 (s, 3H), 3.78 (m, 2H), 3.95 (AB-system, 2H), 4.48 (q, 2H), 5.08 (s, 2H), 6.41 (d, 1H), 6.70 (s, 1H), 6.78 (d, 1H), 7.04 (d, 1H), 7.20 (s, 1H), 8.14 (d, 1H), 8.21 (s, 1H), NH, NH, OH are not observed. LCMS (ESI): [M+H]$^+$ m/z: calc'd 580.3; found 581.2; Rt=1.11 min.

Example 3A2. Synthesis of methyl 4-(6-ethoxy-5-(((R)-2-hydroxy-2-((S)-7-((1-methyl-1H-pyrazol-5-yl)methoxy)-1,2,3,4-tetrahydroisoquinolin-3-yl)ethyl)carbamoyl)pyridin-2-yl)piperazine-1-carboxylate (Compound 18)

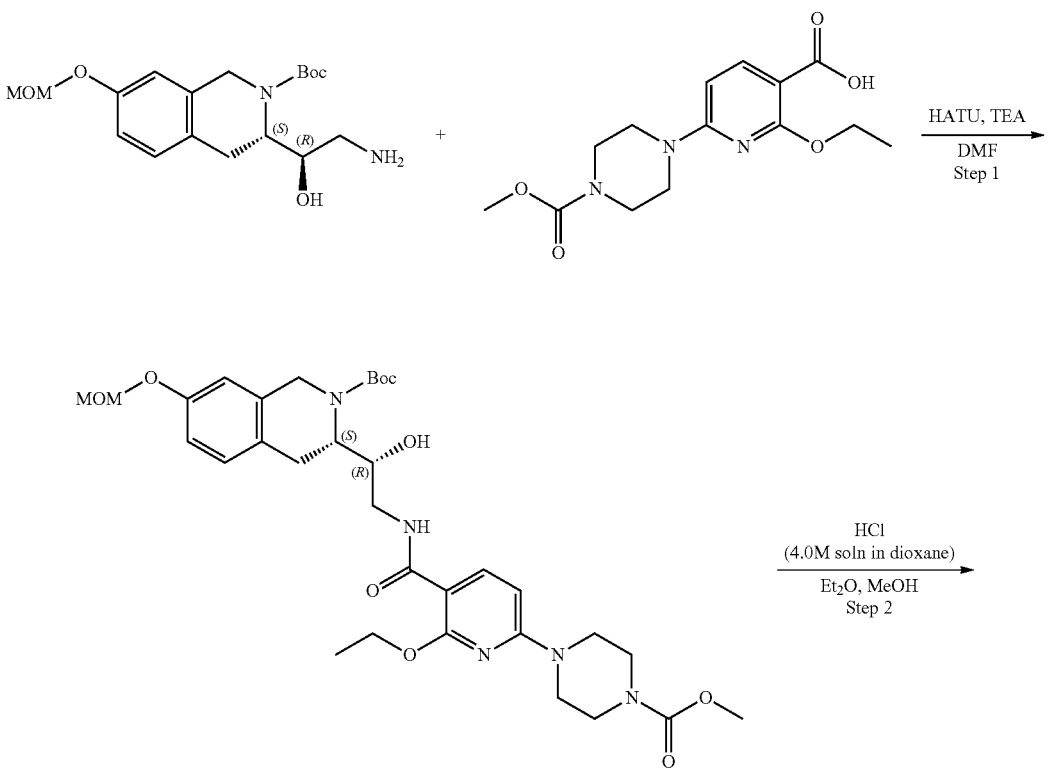

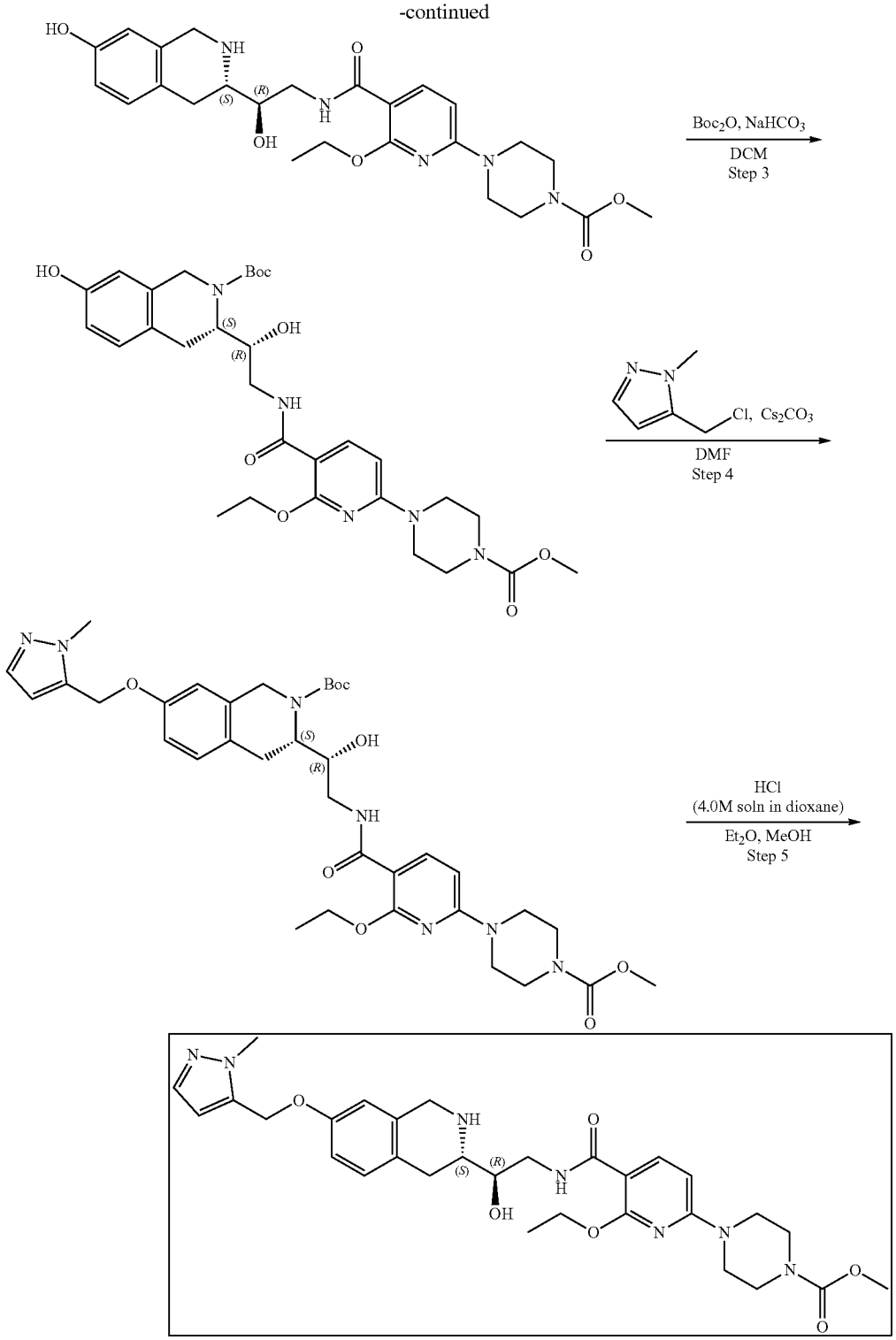

Steps 1-3 are the same as for Example 3A1.

Step 4: Synthesis of (S)-tert-butyl 3-((R)-2-(2-ethoxy-6-(4-(methoxycarbonyl)piperazin-1-yl)nicotinamido)-1-hydroxyethyl)-7-((1-methyl-1H-pyrazol-5-yl)methoxy)-3,4-dihydroisoquinoline-2(1H)-carboxylate tert-Butyl (3S)-3-[(1R)-2-[[2-ethoxy-6-(4-methoxycarbonylpiperazin-1-yl)pyridine-3-carbonyl]-amino]-1-hydroxy-ethyl]-7-hydroxy-3,4-dihydro-1H-isoquinoline-2-carboxylate (0.046 g, 76.71 μmol), 5-(chloromethyl)-1-methyl-pyrazole (14.09 mg, 84.38 μmol, HCl) and cesium carbonate (24.99 mg, 76.71 μmol) were mixed together in DMF (2 mL) and heated at 50° C. overnight. Then, the reaction mixture was diluted with water end extracted three times with EtOAc. The organic phase was dried over Na₂SO₄, filtered off and evaporated at 40° C. to give tert-butyl (3S)-3-[(1R)-2-[[2-ethoxy-6-(4-methoxycarbonylpiperazin-1-yl)pyridine-3-carbonyl]amino]-1-hydroxy-ethyl]-7-[(2-methylpyrazol-3-yl)methoxy]-3,4-dihydro-1H-isoquinoline-2-carboxylate (0.051 g, 73.51 μmol, 95.83% yield) which was used in the next step without further purification. $^1$H NMR (400 MHz, DMSO-$d_6$) δ (ppm) 1.34 (s, 9H), 1.44 (m, 5H), 3.46 (m, 6H), 3.59 (m, 7H), 3.80 (s, 3H), 4.10 (m, 3H), 4.40 (m, 2H), 5.11 (m, 3H), 6.33 (m, 1H), 6.45 (d, 1H), 6.88 (m, 2H), 7.09 (d, 1H), 7.34 (m, 1H), 8.03 (m, 1H), 8.10 (m, 1H). LCMS (ESI): [M+H]$^+$ m/z: calc'd 693.3; found 694.4; Rt=3.96 min.

Step 5: Synthesis of methyl 4-(6-ethoxy-5-(((R)-2-hydroxy-2-((S)-7-(((1-methyl-1H-pyrazol-5-yl)methoxy)-1,2,3,4-tetrahydroisoquinolin-3-yl)ethyl)carbamoyl)pyridin-2-yl)piperazine-1-carboxylate (Compound 18) Hydrogen chloride solution 4.0M in dioxane (201.02 mg, 5.51 mmol, 251.27 μL) was added to the solution of tert-butyl (3S)-3-[(1R)-2-[[2-ethoxy-6-(4-methoxycarbonylpiperazin-1-yl)pyridine-3-carbonyl]amino]-1-hydroxy-ethyl]-7-[(2-methylpyrazol-3-yl)methoxy]-3,4-dihydro-1H-isoquinoline-2-carboxylate (0.051 g, 73.51 μmol) in the mixture of Et$_2$O (1 mL) and MeOH (0.5 mL). The resulting mixture was stirred for 24 h at 20° C. The formed solid was filtered on, washed with Et$_2$O (1 mL) and dried in vacuo at 35° C. to give crude product which was purified by HPLC (30-40% water-methanol+NH$_3$, 10 min, flow: 30 mL/min (loading pump 4 mL/min methanol+NH$_3$), column: YMC-Actus Triart C18 to give methyl 4-[6-ethoxy-5-[[(2R)-2-hydroxy-2-[(3S)-7-[(2-methylpyrazol-3-yl)methoxy]-1,2,3,4-tetrahydroisoquinolin-3-yl]ethyl]carbamoyl]-2-pyridyl]piperazine-1-carboxylate (0.0127 g, 21.39 μmol, 29.10% yield). $^1$H NMR (400 MHz, CD$_3$OD) δ 1.43 (t, 3H), 2.79 (m, 2H), 2.85 (m, 1H), 3.49 (m, 1H), 3.55 (m, 4H), 3.66 (m, 4H), 3.71 (s, 3H), 3.76 (m, 2H), 3.86 (s, 3H), 3.98 (AB-system, 2H), 4.48 (q, 2H), 5.08 (s, 2H), 6.34 (s, 1H), 6.41 (d, 1H), 6.72 (s, 1H), 6.80 (d, 1H), 7.04 (d, 1H), 7.39 (s, 1H), 8.14 (d, 1H), NH, NH, OH are not observed. LCMS (ESI): [M+H]$^+$ m/z: calc'd 593.3; found 594.3; Rt=1.09 min.

Example 3A3. Synthesis of methyl 4-(6-ethoxy-5-(((R)-2-hydroxy-2-((S)-7-((4-methyloxazol-5-yl)methoxy)-1,2,3,4-tetrahydroisoquinolin-3-yl)ethyl)carbamoyl)pyridin-2-yl)piperazine-1-carboxylate (Compound 17)

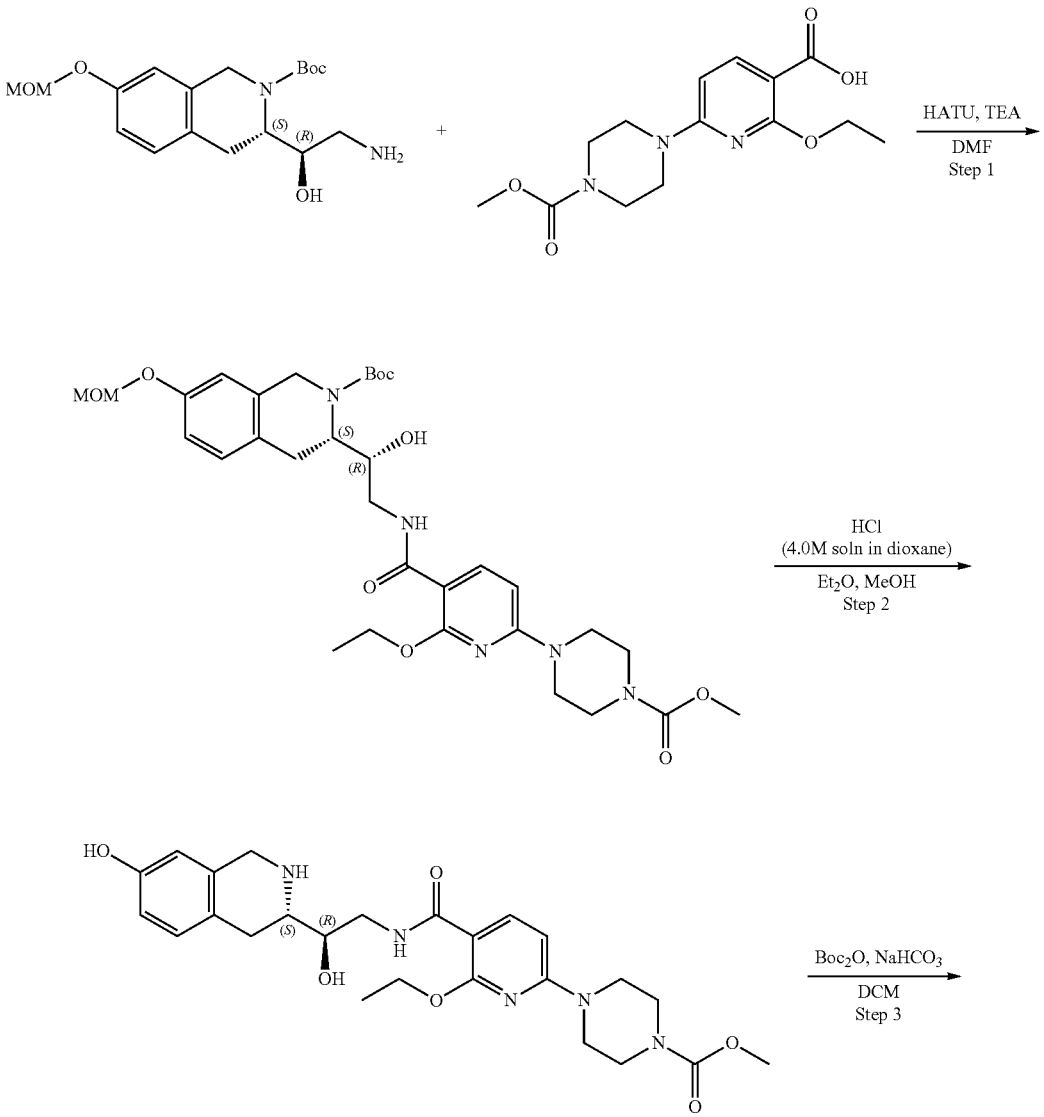

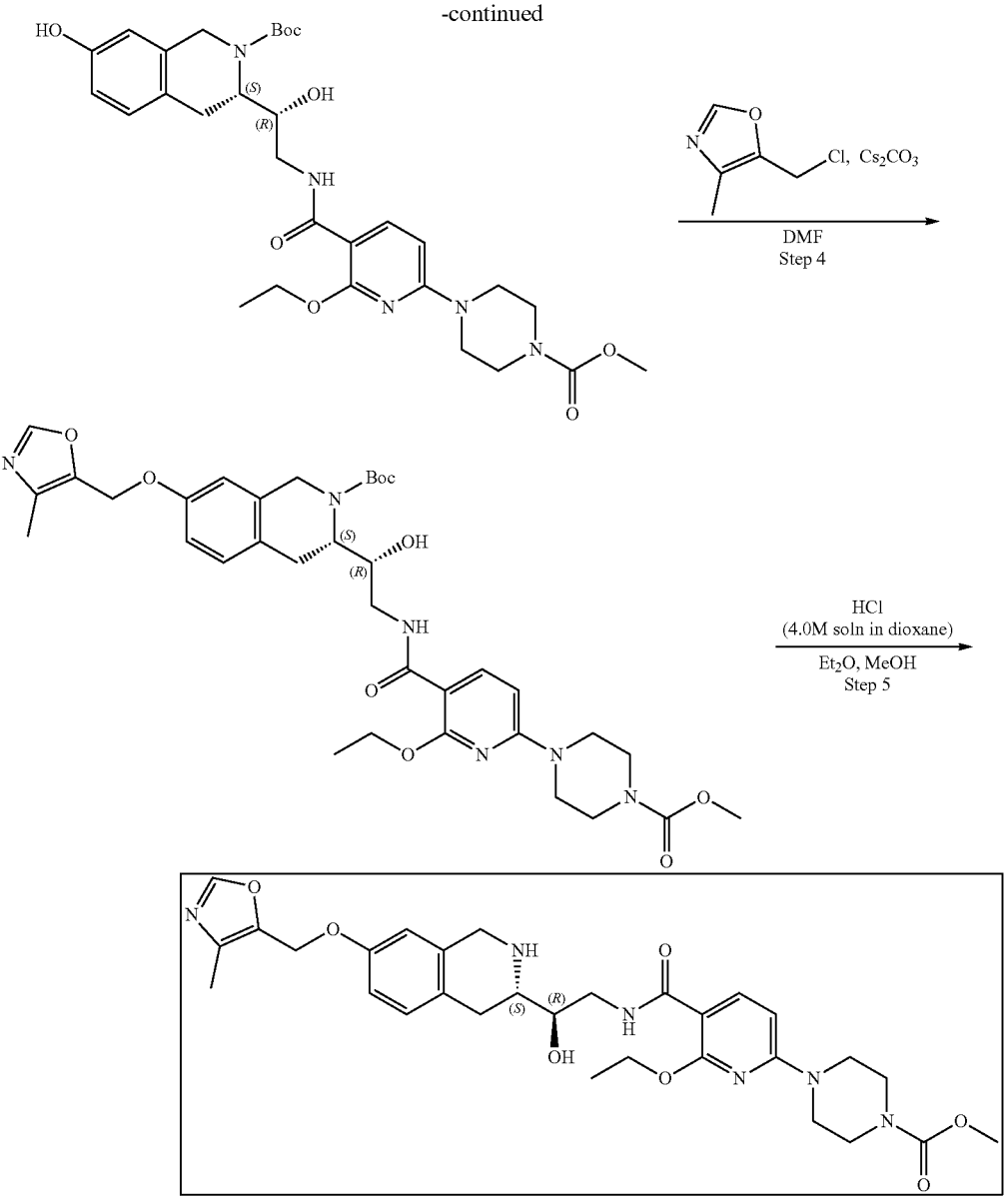

Steps 1-3 are the same as for Example 3A1.

Step 4: Synthesis of (S)-tert-butyl 3-((R)-2-(2-ethoxy-6-(4-(methoxycarbonyl)piperazin-1-yl)nicotinamido)-1-hydroxyethyl)-7-((4-methyloxazol-5-yl)methoxy)-3,4-dihydroisoquinoline-2(1H)-carboxylate tert-Butyl (3S)-3-[(1R)-2-[[2-ethoxy-6-(4-methoxycarbonylpiperazin-1-yl)pyridine-3-carbonyl]-amino]-1-hydroxy-ethyl]-7-hydroxy-3,4-dihydro-1H-isoquinoline-2-carboxylate (0.054 g, 90.05 μmol), 5-(chloromethyl)-4-methyl-oxazole (16.64 mg, 99.05 μmol, HCl) and cesium carbonate (88.02 mg, 270.15 μmol) were mixed together in DMF (2 mL) and heated at 50° C. overnight. The reaction mixture was diluted with water end extracted three times with EtOAc. The organic phase was washed with brine, dried over Na$_2$SO$_4$, filtered off and evaporated at 40° C. to give tert-butyl (3S)-3-[(1R)-2-[[2-ethoxy-6-(4-methoxycarbonylpiperazin-1-yl)pyridine-3-carbonyl]amino]-1-hydroxy-ethyl]-7-[(4-methyloxazol-5-yl)-methoxy]-3,4-dihydro-1H-isoquinoline-2-carboxylate (0.05 g, 71.97 μmol, 79.92% yield) which was used in the next step without further purification. $^1$H NMR (400 MHz, DMSO-d$_6$) δ (ppm) 1.30 (t, 3H), 1.36 (s, 9H), 1.44 (m, 5H), 2.14 (s, 3H), 3.45 (m, 6H), 3.59 (m, 3H), 3.62 (s, 3H), 4.20 (m, 4H), 4.75 (m, 1H), 5.07 (s, 2H), 5.30 (m, 1H), 6.46 (d, 1H), 6.80 (d, 1H), 6.86 (s, 1H), 7.06 (d, 1H), 8.07 (m, 2H). LCMS (ESI): [M+H]$^+$ m/z: calc'd 694.2; found 965.2; Rt=4.26 min.

Step 5: Synthesis of methyl 4-(6-ethoxy-5-(((R)-2-hydroxy-2-((S)-7-((4-methyloxazol-5-yl)methoxy)-1,2,3,4-tetrahydroisoquinolin-3-yl)ethyl)carbamoyl)pyridin-2-yl)piperazine-1-carboxylate (Compound 17) Hydrogen chloride solution 4.0M in dioxane (196.80 mg, 5.40 mmol, 245.99 μL) was added to the solution of tert-butyl (3S)-3-[(1R)-2-[[2-ethoxy-6-(4-methoxycarbonylpiperazin-1-yl)pyridine-3-carbonyl]amino]-1-hydroxy-ethyl]-7-[(4-methyloxazol-5-yl)methoxy]-3,4-dihydro-1H-isoquinoline-2-carboxylate (0.05 g, 71.97 μmol) in the mixture of Et$_2$O (1 mL) and MeOH (0.5 mL). The resulting mixture was stirred for 24 h at 20° C. The formed solid was filtered on, washed with Et$_2$O (1 mL) and dried in vacuo at 35° C. to give crude product which was purified by HPLC (50-70% water-methanol+NH$_3$, 10 min, flow 30 mL/min (loading pump 5 mL/min methanol+NH$_3$), column: YMC Actus Triart C18 100*20 mm to give methyl 4-[6-ethoxy-5-[[(2R)-2-hydroxy-2-[(3S)-7-[(4-methyloxazol-5-yl)methoxy]-1,2,3,4-tetrahydroisoquinolin-3-yl]ethyl]carbamoyl]-2-pyridyl]piperazine-1-carboxylate (0.021 g, 35.31 μmol, 49.07% yield). $^1$H NMR (400 MHz, CDCl$_3$) δ 1.42 (s, 3H), 2.19 (t, 3H), 2.70 (dd, 1H), 2.82 (dd, 1H), 2.94 (m, 1H), 3.57 (m, 8H), 3.71 (s, 3H), 3.77 (m, 1H), 3.99 (s, 4H), 4.31 (br.s, 2H), 4.46 (q, 2H), 4.94 (s, 2H), 6.22 (d, 1H), 6.59 (d, 1H), 6.74 (dd, 1H), 7.03 (s, 1H), 7.78 (d, 1H), 8.24 (m, 2H). LCMS (ESI): [M+H]$^+$ m/z: calc'd 594.3; found 595.1; Rt=1.13 min.

Example 3A4. Synthesis of N—((R)-2-((S)-7-((1H-pyrazol-4-yl)methoxy)-1,2,3,4-tetrahydroisoquinolin-3-yl)-2-hydroxyethyl)-4-(morpholine-4-carbonyl)benzamide (Compound 4)

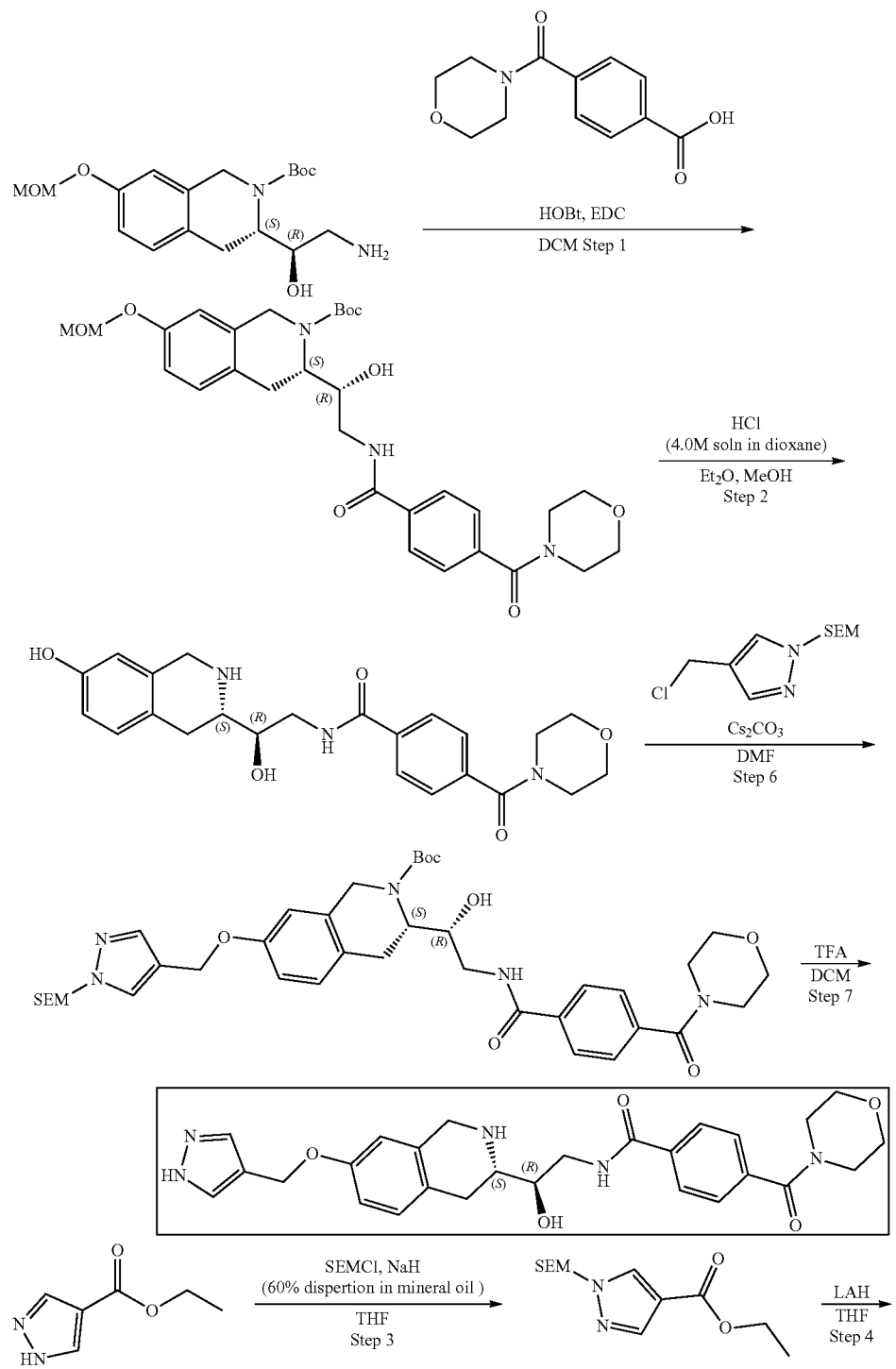

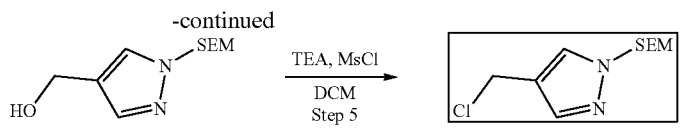

Steps 1-2 are the same as for Example 3A1.

Step 3: Synthesis of ethyl 1-((2-(trimethylsilyl)ethoxy)methyl)-1H-pyrazole-4-carboxylate. To a suspension of sodium hydride (in oil dispersion) 60% dispersion in mineral oil (2.62 g, 114.17 mmol) in dry THF (15 mL), at 0° C., was added the solution of ethyl 1H-pyrazole-4-carboxylate (10 g, 71.36 mmol) in dry THF (5 mL). The resulting purple suspension was stirred at 20° C. for 3 h followed by the dropwise addition of the solution of 2-(chloromethoxy)ethyl-trimethyl-silane (14.28 g, 85.63 mmol, 15.16 mL) in dry THF (5 mL) at 0° C. The resulting solution was allowed to warm up to rt and stirred for 3 h. After the completion of the reaction, monitored by LCMS, water was added, and the aqueous phase was extracted 4 times with EtOAc. The combined organic layers were dried over anhydrous $Na_2SO_4$, filtered and concentrated in vacuo to give a yellow oil. The residue was purified by CC to obtain ethyl 1-(2-trimethylsilylethoxymethyl)pyrazole-4-carboxylate (16 g, 59.17 mmol, 82.92% yield). $^1$H NMR (400 MHz, $CDCl_3$) δ (ppm) −0.04 (m, 9H), 0.89 (m, 2H), 1.32 (m, 3H), 3.57 (m, 2H), 4.28 (m, 2H), 5.41 (s, 2H), 7.91 (s, 1H), 8.04 (s, 1H). LCMS (ESI): $[M+H]^+$ m/z: calc'd 270.1; found 271.0; Rt=1.49 min.

Step 4: Synthesis of (1-((2-(trimethylsilyl)ethoxy)methyl)-1H-pyrazol-4-yl)methanol Lithium alumanuide (2.25 g, 59.17 mmol) was added to ethyl 1-(2-trimethylsilylethoxymethyl)pyrazole-4-carboxylate (16 g, 59.17 mmol) in THF (4 mL) at 0° C., and the mixture was stirred at r.t. for 1 h. After LCMS showed full conversion of starting material, water (106 μL) was added, followed by NaOH (15 percent aq, 314 μL) and water (106 μL). The mixture was stirred at r.t. for 1 h, filtered, the solids washed with EtOAc, and the filtrate evaporated in vacuo to give [1-(2-trimethylsilylethoxymethyl)pyrazol-4-yl]methanol (13.1 g, 57.36 mmol, 96.95% yield). $^1$H NMR (500 MHz, $CDCl_3$) δ (ppm) −0.02 (m, 9H), 0.91 (t, 2H), 3.56 (t, 2H), 4.61 (s, 2H), 5.39 (s, 2H), 7.53 (s, 1H), 7.57 (s, 1H). LCMS (ESI): $[M+H]^+$ m/z: calc'd 228.1; found 229.2; Rt=1.21 min.

Step 5: Synthesis of 4-(chloromethyl)-1-((2-(trimethylsilyl)ethoxy)methyl)-1H-pyrazole. To a solution of [1-(2-trimethylsilylethoxymethyl)pyrazol-4-yl]methanol (0.5 g, 2.19 mmol) and triethylamine (443.11 mg, 4.38 mmol, 610.35 μL) in DCM (5 mL), methanesulfonyl chloride (300.97 mg, 2.63 mmol, 203.36 μL) was added at 0° C. The resulting mixture was stirred for 1 h at 20° C. After the completion of the reaction, saturated ammonium chloride solution was added, and the mixture was extracted with EtOAc (3*20 mL). The organic phase was dried over $Na_2SO_4$ and evaporated in vacuo at 35° C. to obtain 2-[[4-(chloromethyl)pyrazol-1-yl]methoxy]ethyl-trimethyl-silane (0.38 g, 1.54 mmol, 70.32% yield). $^1$H NMR (400 MHz, $CDCl_3$) δ (ppm) −0.04 (s, 9H), 0.88 (t, 2H), 3.54 (t, 2H), 4.53 (s, 2H), 5.41 (s, 2H), 7.54 (s, 1H), 7.58 (s, 1H). LCMS (ESI): $[M+H]^+$ m/z: calc'd 246.1; found 247.1; Rt=1.23 min.

Step 6: Synthesis of (S)-tert-butyl 3-((R)-1-hydroxy-2-(4-(morpholine-4-carbonyl)benzamido)ethyl)-7-((1-((2-(trimethylsilyl)ethoxy)methyl)-1H-pyrazol-4-yl)methoxy)-3,4-dihydroisoquinoline-2(1H)-carboxylate The solution of 2-[[4-(chloromethyl)pyrazol-1-yl]methoxy]ethyl-trimethyl-silane (51.65 mg, 209.29 μmol), tert-butyl (3S)-7-hydroxy-3-[(1R)-1-hydroxy-2-[[4-(morpholine-4-carbonyl)benzoyl]amino]ethyl]-3,4-di-hydro-1H-isoquinoline-2-carboxylate (0.1 g, 190.26 μmol) and cesium carbonate (185.97 mg, 570.78 μmol) in N,N-dimethylformamide (10 mL) was heated at 50° C. for 10 h. The resulting mixture was diluted with $H_2O$ (20 mL) and extracted with EtOAc (2*10 mL). The organic phase was washed with water (3*10 mL), dried over $Na_2SO_4$, evaporated in vacuo at 35° C. to obtain tert-butyl (3S)-3-[(1R)-1-hydroxy-2-[[4-(morpholine-4-carbonyl)benzoyl]amino]ethyl]-7-[[1-(2-trimethylsilylethoxymethyl)pyrazol-4-yl]methoxy]-3,4-dihydro-1H-isoquinoline-2-carboxylate (120 mg, 163.06 μmol, 85.70% yield) that was used on the next step without further purification. $^1$H NMR (500 MHz, $CDCl_3$) δ (ppm) 0.08 (m, 9H), 1.55 (s, 9H), 1.58 (m, 4H), 3.15 (m, 1H), 3.42 (m, 3H), 3.59 (m, 3H), 3.65 (m, 4H), 3.81 (m, 4H), 4.23 (m, 2H), 4.40 (m, 1H), 4.66 (m, 1H), 4.96 (m, 2H), 5.42 (s, 2H), 6.71 (s, 1H), 6.83 (d, 1H), 7.12 (d, 1H), 7.50 (m, 2H), 7.60 (s, 1H), 7.64 (s, 1H), 7.96 (d, 1H), 8.03 (m, 3H), 8.56 (t, 1H). LCMS (ESI): $[M+H]^+$ m/z: calc'd; 735.3 found 736.4; Rt=1.55 min.

Step 7: Synthesis of N—((R)-2-((S)-7-((1H-pyrazol-4-yl)methoxy)-1,2,3,4-tetrahydroisoquinolin-3-yl)-2-hydroxyethyl)-4-(morpholine-4-carbonyl)benzamide (Compound 4) To a solution of tert-butyl (3S)-3-[(1R)-1-hydroxy-2-[[4-(morpholine-4-carbonyl)benzoyl]-amino]ethyl]-7-[[1-(2-trimethylsilylethoxymethyl)pyrazol-4-yl]methoxy]-3,4-dihydro-1H-isoquinoline-2-carboxylate (0.120 g, 163.06 μmol) in $CH_2Cl_2$ (0.5 mL) was added trifluoroacetic acid (740.00 mg, 6.49 mmol, 0.5 mL). The reaction mixture was stirred at rt for 2 h. The mixture was evaporated and purified by HPLC (ACN-$H_2O$+$NH_3$-10-40%) to provide N-[(2R)-2-hydroxy-2-[(3S)-7-(1H-pyrazol-4-ylmethoxy)-1,2,3,4-tetrahydroisoquinolin-3-yl]ethyl]-4-(morpholine-4-carbonyl)benzamide (0.0125 g, 24.72 μmol, 15.16% yield). $^1$H NMR (400 MHz, DMSO-$d_6$) δ 2.20 (m, 1H), 2.57 (m, 2H), 2.71 (m, 2H), 3.38 (m, 1H), 3.61 (m, 9H), 3.82 (m, 1H), 3.90 (m, 1H), 4.91 (s, 2H), 4.94 (d, 1H), 6.65 (m, 1H), 6.73 (dd, 1H), 6.99 (d, 1H), 7.48 (d, 2H), 7.57 (m, 1H), 7.88 (m, 1H), 7.90 (d, 2H), 8.59 (t, 1H), 12.79 (m, 1H). LCMS (ESI): $[M+H]^+$ m/z: calc'd 505.2; found 506.2; Rt=0.81 min.

Example 4—Synthesis of Compounds of Formula (IIa2i)

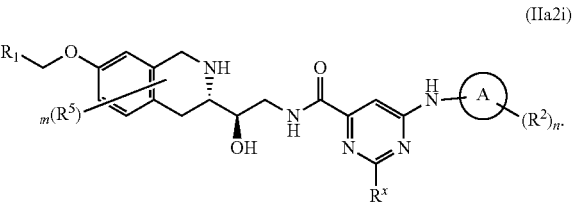

wherein $R^1$, $R^2$, $R^5$, $R^x$, m, n and A are as defined herein
Scheme 4A
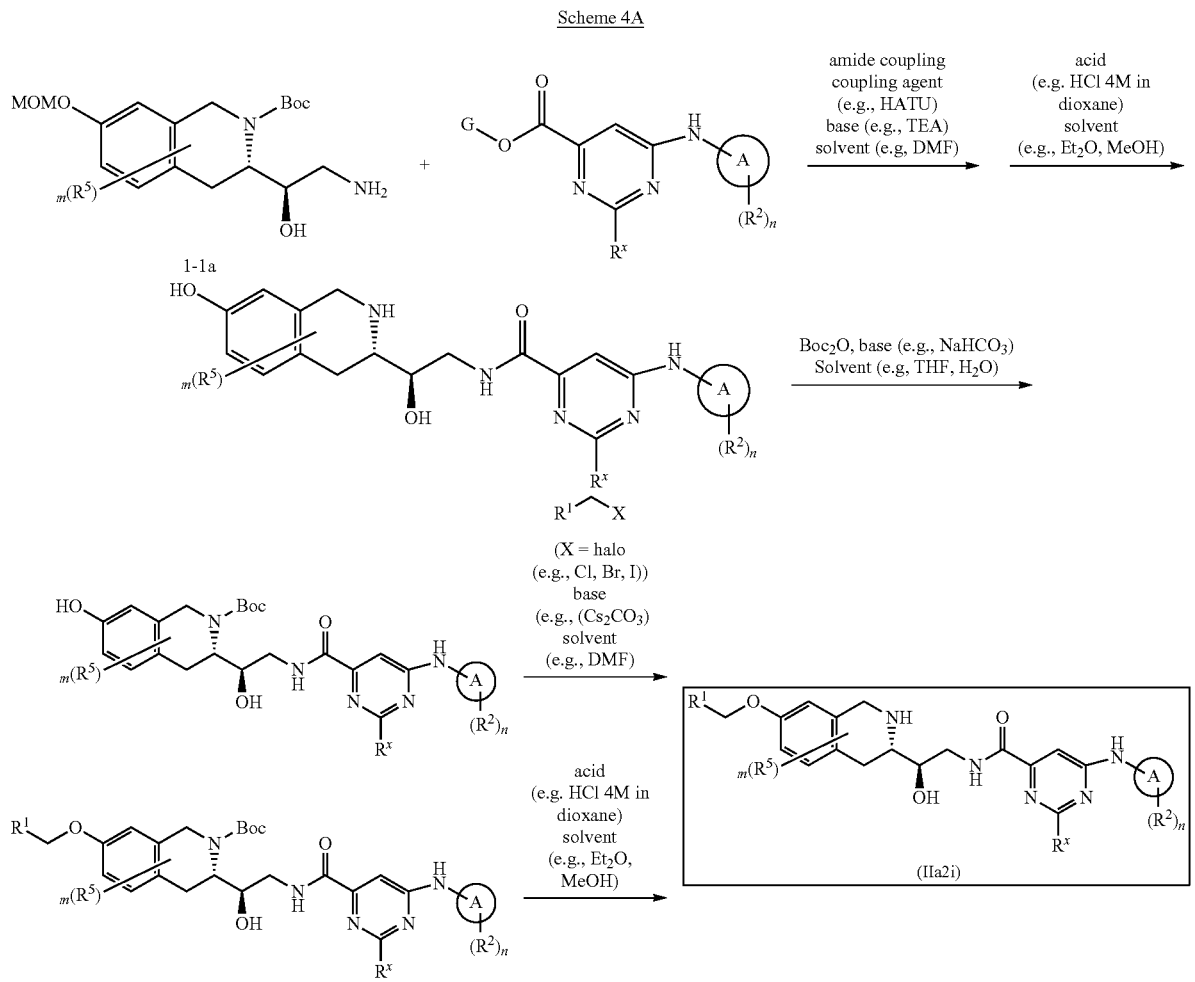
Wherein G is Me or H. X is a leaving group. In some embodiments, X is selected from Cl, Br, and I. In some embodiments X is Cl or Br.
Example 4A1. Synthesis of 6-((1-acetylazetidin-3-yl)amino)-N—((R)-2-hydroxy-2-((S)-7-((4-methyl-oxazol-5-yl)methoxy)-1,2,3,4-tetrahydroisoquinolin-3-yl)ethyl)-2-(piperidin-1-yl)pyrimidine-4-carboxamide (Compound 22)
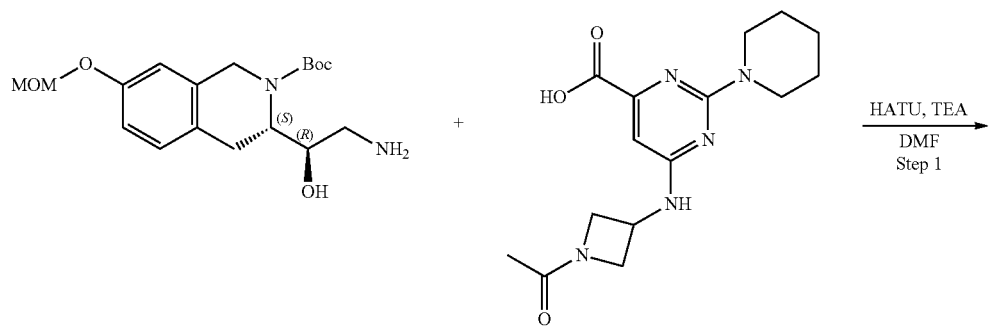

-continued
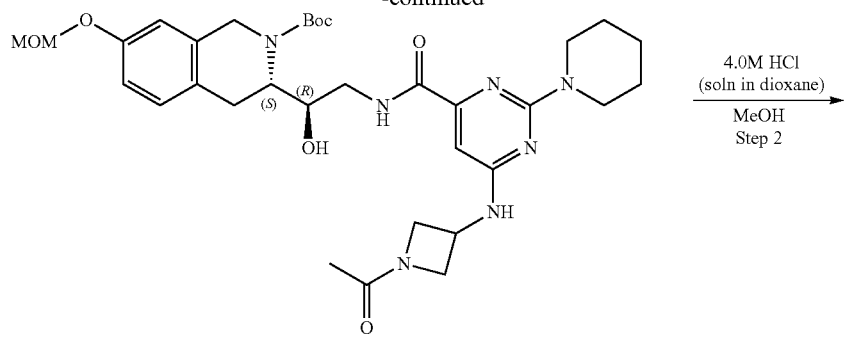
4.0M HCl
(soln in dioxane)
―――――――――
MeOH
Step 2
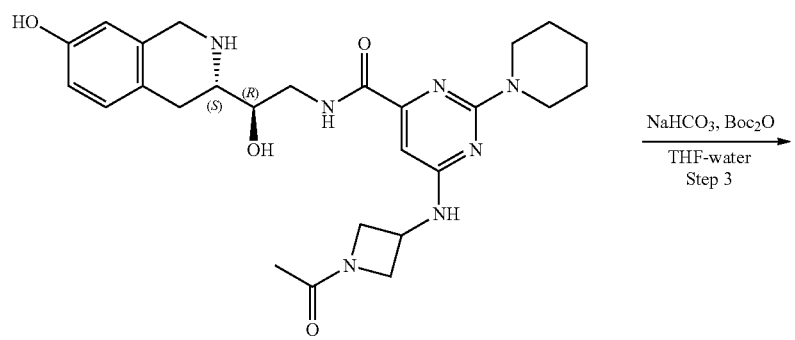
NaHCO₃, Boc₂O
―――――――――
THF-water
Step 3
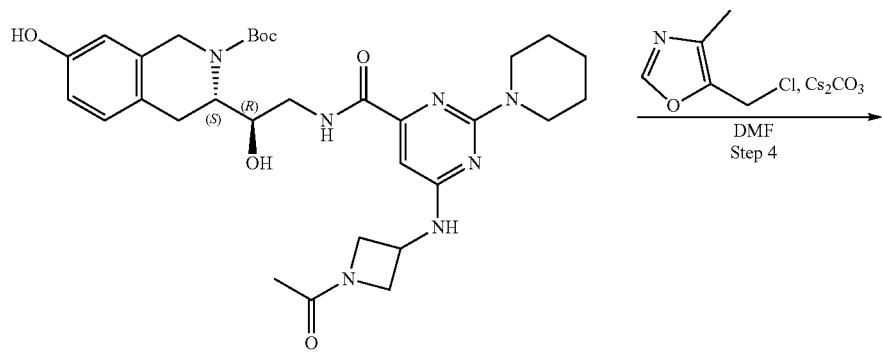
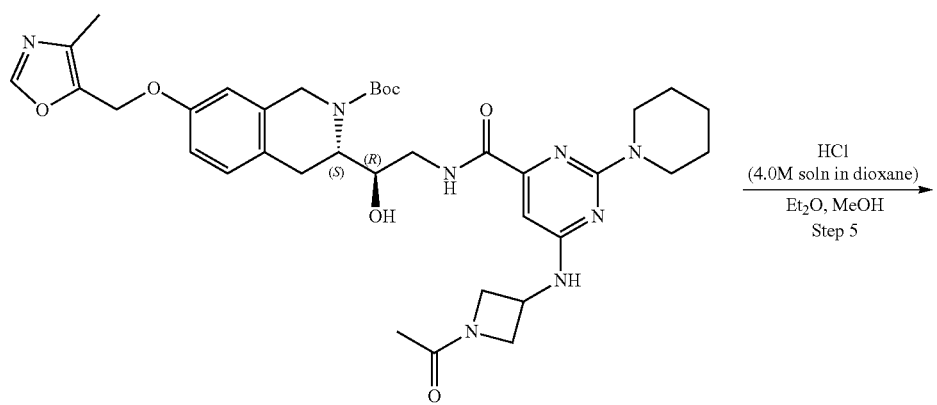
HCl
(4.0M soln in dioxane)
―――――――――
Et₂O, MeOH
Step 5

-continued

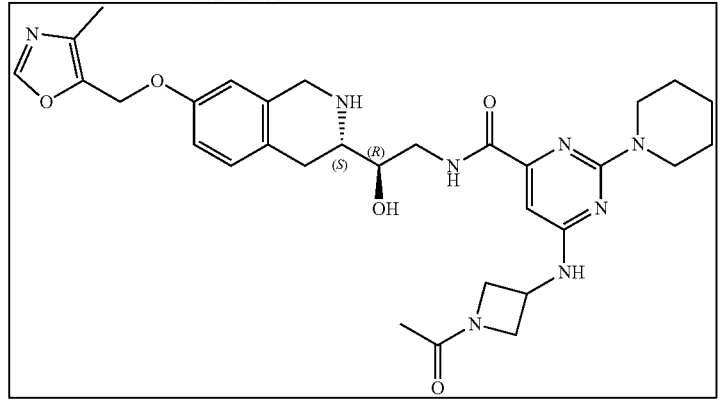

Step 1: Synthesis of (S)-tert-butyl 3-((R)-2-(6-((1-acetylazetidin-3-yl)amino)-2-(piperidin-1-yl)pyrimidine-4-carboxamido)-1-hydroxyethyl)-7-(methoxymethoxy)-3,4-dihydroisoquinoline-2(1H)-carboxylate 6-[(1-Acetylazetidin-3-yl)amino]-2-(1-piperidyl)pyrimidine-4-carboxylic acid (151.45 mg, 425.62 μmol, HCl) and TEA (430.69 mg, 4.26 mmol, 593.23 μL) were dissolved in DMF (3 mL) and cooled to 0° C., HATU (242.75 mg, 638.44 μmol) was added and the mixture was stirred for 15 min at 0° C. tert-butyl (3S)-3-[(1R)-2-amino-1-hydroxy-ethyl]-7-(methoxymethoxy)-3,4-dihydro-1H-isoquinoline-2-carboxylate (0.15 g, 425.62 μmol) was added and the mixture was warmed to r.t. and stirred overnight. 10 ml of ethyl acetate was added, and organic phase was washed with brine three times. Organic phase was dried over Na₂SO₄, filtered and concentrated in vacuo at 45° C. to give crude product which was purified by HPLC (45-60% water-acetonitrile, 2-10 min, flow: 30 mL/min (loading pump 4 mL/min acetonitrile) column: SunFire C18 100×19 mm) to give tert-butyl (3S)-3-[(1R)-2-[[6-[(1-acetylazetidin-3-yl)amino]-2-(1-piperidyl)pyrimidine-4-carbonyl]amino]-1-hydroxy-ethyl]-7-(methoxymethoxy)-3,4-dihydro-1H-isoquinoline-2-carboxylate (0.048 g, 73.42 μmol, 17.25% yield). ¹H NMR (CDCl₃, 400 MHz) δ: 1.49 (m, 11H), 1.62 (m, 3H), 1.69 (s, 3H), 2.83 (m, 1H), 2.96 (m, 1H), 3.11 (m, 1H), 3.43 (s, 3H), 3.69 (m, 2H), 3.79 (m, 4H), 3.99 (m, 3H), 4.21 (m, 1H), 4.31 (m, 4H), 4.65 (m, 2H), 5.10 (s, 2H), 5.84 (m, 1H), 6.46 (s, 1H), 6.76 (s, 1H), 6.85 (d, 1H), 7.06 (d, 1H), 9.12 (m, 1H). LCMS (ESI): [M+H]⁺ m/z: calc'd 653.3; found 654.4; Rt=1.46 min.

Step 2: Synthesis of 6-((1-acetylazetidin-3-yl)amino)-N—((R)-2-hydroxy-2-((S)-7-hydroxy-1,2,3,4-tetrahydroisoquinolin-3-yl)ethyl)-2-(piperidin-1-yl)pyrimidine-4-carboxamide tert-Butyl (3S)-3-[(1R)-2-[[6-[(1-acetylazetidin-3-yl)amino]-2-(1-piperidyl)pyrimidine-4-carbonyl]amino]-1-hydroxy-ethyl]-7-(methoxymethoxy)-3,4-dihydro-1H-isoquinoline-2-carboxylate (0.048 g, 73.42 μmol) was dissolved in the mixture of MeOH (2 mL). Hydrogen chloride solution 4.0M in dioxane (200.77 mg, 5.51 mmol, 250.97 μL) was added. The mixture was stirred for 12 hr at 20° C. Solvent was removed in vacuo at 35° C. to give 6-[(1-acetylazetidin-3-yl)amino]-N-[(2R)-2-hydroxy-2-[(3S)-7-hydroxy-1,2,3,4-tetrahydroisoquinolin-3-yl]ethyl]-2-(1-piperidyl)pyrimidine-4-carboxamide (0.032 g, 54.93 μmol, 74.82% yield, 2HCl) which was used in the next step without further purification. ¹H NMR (CDCl₃, 500 MHz) δ: 1.73 (m, 6H), 1.90 (s, 3H), 3.10 (m, 2H), 3.18 (m, 1H), 3.51 (m, 3H), 3.67 (m, 4H), 3.79 (m, 4H), 4.00 (m, 1H), 4.27 (m, 2H), 4.60 (m, 1H), 4.78 (m, 1H), 6.63 (s, 1H), 6.68 (s, 1H), 6.75 (d, 1H), 7.12 (d, 1H), OH and NH isn't observed. LCMS (ESI): [M+H]⁺ m/z: calc'd 509.2; found 508.2; Rt=2.47 min.

Step 3: Synthesis of (S)-tert-butyl 3-((R)-2-(6-((1-acetylazetidin-3-yl)amino)-2-(piperidin-1-yl)pyrimidine-4-carboxamido)-1-hydroxyethyl)-7-hydroxy-3,4-dihydroisoquinoline-2(1H)-carboxylate 6-[(1-acetylazetidin-3-yl)amino]-N-[(2R)-2-hydroxy-2-[(3S)-7-hydroxy-1,2,3,4-tetrahydroisoquinolin-3-yl]ethyl]-2-(1-piperidyl)pyrimidine-4-carboxamide (0.032 g, 54.93 μmol, 2HCl) was dissolved in the mixture of water (1 mL) and THF (1 mL) then Sodium hydrogen carbonate, 99% (13.84 mg, 164.80 μmol, 6.41 μL) was added in one portion, after that solution of Di-tert-butyl dicarbonate (11.99 mg, 54.93 μmol, 12.61 μL) in THF (0.2 mL) was added dropwise. The reaction mixture was stirred overnight at room temperature. Ethyl acetate (15 mL) was added to the reaction mixture, organic phase was separated, and the aqueous phase was extracted with ethyl acetate (2×15 mL). Organic phase was washed with brine, dried over Na₂SO₄, filtered and evaporated in vacuo at 40° C. to give tert-butyl (3S)-3-[(1R)-2-[[6-[(1-acetylazetidin-3-yl)amino]-2-(1-piperidyl)pyrimidine-4-carbonyl]amino]-1-hydroxy-ethyl]-7-hydroxy-3,4-dihydro-1H-isoquinoline-2-carboxylate (0.03 g, 49.20 μmol, 89.57% yield) which was used in the next step without purification. ¹H NMR (CDCl₃, 500 MHz) δ: 1.45 (m, 10H), 1.67 (m, 6H), 1.88 (s, 3H), 2.82 (m, 3H), 3.76 (m, 6H), 3.83 (m, 2H), 4.13 (m, 2H), 4.27 (m, 2H), 4.52 (m, 1H), 4.65 (m, 1H), 6.41 (s, 1H), 6.56 (s, 1H), 6.64 (d, 1H), 6.98 (d, 1H), OH and NH isn't observed. LCMS (ESI): [M+H]⁺ m/z: calc'd 609.3; found 610.4; Rt=1.38 min.

Step 4: Synthesis of (S)-tert-butyl 3-((R)-2-(6-((1-acetylazetidin-3-yl)amino)-2-(piperidin-1-yl)pyrimidine-4-carboxamido)-1-hydroxyethyl)-7-((4-methyloxazol-5-yl)methoxy)-3,4-dihydroisoquinoline-2(1H)-carboxylate tert-Butyl (3S)-3-[(1R)-2-[[6-[(1-acetylazetidin-3-yl)amino]-2-(1-piperidyl)pyrimidine-4-carbonyl]amino]-1-hydroxy-ethyl]-7-hydroxy-3,4-dihydro-1H-isoquinoline-2-carboxylate (0.03 g, 49.20 μmol), 5-(chloromethyl)-4-methyl-oxazole (9.92 mg, 59.04 μmol, HCl) and Cesium carbonate (48.09 mg, 147.61 μmol) was dissolved in DMF (2 mL) and heated at 50° C. overnight. The reaction mixture was filtered, solid was washed with DMF (2 mL), filtrate was concentrated on vacuo at 60° C. to give tert-butyl (3S)-3-[(1R)-2-[[6-[(1-acetylazetidin-3-yl)amino]-2-(1-piperidyl)pyrimidine-4-carbonyl]amino]-1-hydroxy-ethyl]-7-[(4-methyloxazol-5-yl)methoxy]-3,4-dihydro-1H-isoquinoline-2-carboxylate (0.034 g, 48.24 μmol, 98.04% yield) which was used in the next step without further purification. ¹H NMR (CDCl₃, 400 MHz) δ:1.50 (m, 19H), 1.86 (m, 2H), 2.21 (s, 3H), 3.12 (m, 1H), 3.69 (m, 6H), 4.00 (m, 2H), 4.21 (m, 4H), 4.62 (m, 2H), 4.96 (m, 2H), 6.41 (s, 1H), 6.68 (s, 1H), 6.79 (d, 1H), 7.12 (d, 1H), 7.80 (s, 1H), 8.00 (s, 1H), 9.07 (m, 1H). LCMS (ESI): [M+H]⁺ m/z: calc'd 704.3; found 705.2; Rt=4.29 min.

Step 5: Synthesis of 6-((1-acetylazetidin-3-yl)amino)-N—((R)-2-hydroxy-2-((S)-7-((4-methyloxazol-5-yl)methoxy)-1,2,3,4-tetrahydroisoquinolin-3-yl)ethyl)-2-(piperidin-1-yl)pyrimidine-4-carboxamide (Compound 22) tert-Butyl (3S)-3-[(1R)-2-[[6-[(1-acetylazetidin-3-yl)amino]-2-(1-piperidyl)pyrimidine-4-carbonyl]amino]-1-hydroxyethyl]-7-[(4-methyloxazol-5-yl)methoxy]-3,4-dihydro-1H-isoquinoline-2-carboxylate (0.034 g, 48.24 μmol) was dissolved in the mixture of Et₂O (1 mL) and MeOH (0.2 mL). Hydrogen chloride solution 4.0M in dioxane (131.91 mg, 3.62 mmol, 164.89 μL) was added. Solvent was removed on vacuo at 45° C. The residue was dissolved in 5 ml of methanol and 10 mg of scavenger (SiliaMetS© Dimercaptotriazine(DMT) was added thereto and the resulting suspension was stirred for 12 h. The suspension was filtered, the filtrate was evaporated under reduced pressure and the residue was purified by HPLC (25-60% water-methanol, 10 min, flow: 30 mL/min (loading pump 4 mL/min methanol), column: SunFire C18 100*29 mm to give 6-[(1-acetylazetidin-3-yl)amino]-N-[(2R)-2-hydroxy-2-[(3S)-7-[(4-methyloxazol-5-yl)methoxy]-1,2,3,4-tetrahydroisoquinolin-3-yl]ethyl]-2-(1-piperidyl)pyrimidine-4-carboxamide (10.5 mg, 14.70 μmol, 30.48% yield, 3HCl). ¹H NMR (Methanol-d₄, 400 MHz): δ (ppm) 1.73 (m, 6H), 1.91 (s, 3H), 2.23 (s, 3H), 2.66 (s, 2H), 3.16 (m, 2H), 3.59 (m, 3H), 3.79 (m, 3H), 4.24 (m, 5H), 4.57 (m, 2H), 4.80 (m, 1H), 5.12 (s, 2H), 6.74 (s, 1H), 6.89 (s, 1H), 6.96 (d, 1H), 7.23 (d, 1H), 8.44 (s, 1H). LCMS (ESI): [M+H]⁺ m/z: calc'd 604.3; found 605.3; Rt=1.01 min.

Example 4A2. Synthesis of 6-(cyclobutylamino)-N—((R)-2-hydroxy-2-((S)-7-((4-methyloxazol-5-yl)methoxy)-1,2,3,4-tetrahydroisoquinolin-3-yl)ethyl)pyrimidine-4-carboxamide (Compound 32)

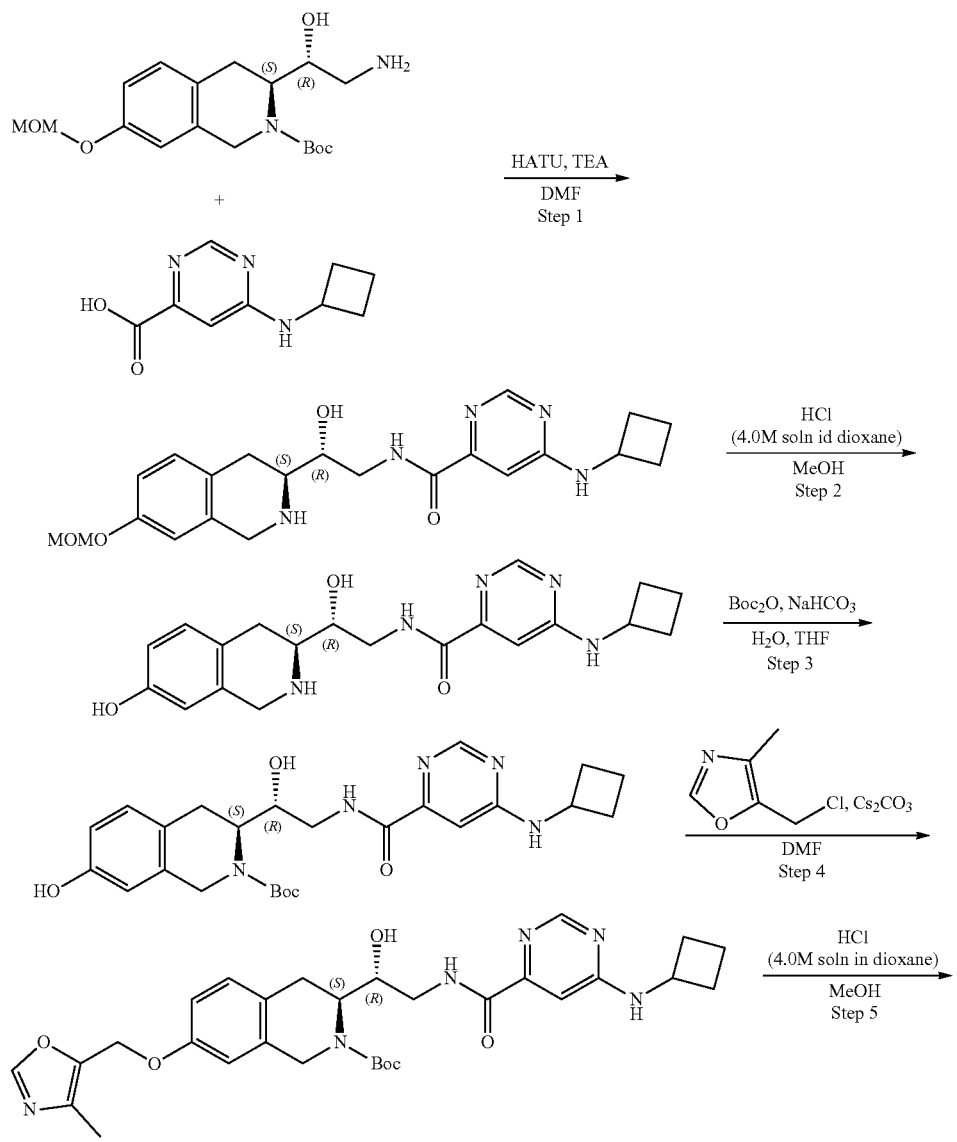

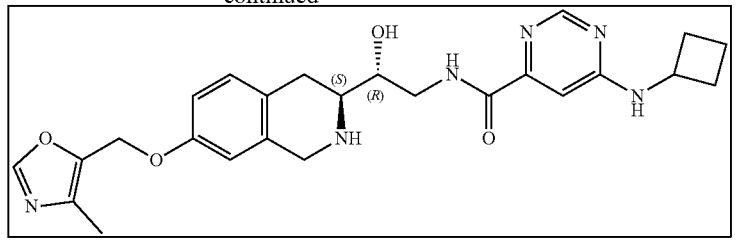

Step 1: Synthesis of (S)-tert-butyl 3-((R)-2-(6-(cyclobutylamino)pyrimidine-4-carboxamido)-1-hydroxyethyl)-7-(methoxymethoxy)-3,4-dihydroisoquinoline-2(1H)-carboxylate 6-(Cyclobutylamino)pyrimidine-4-carboxylic acid (97.75 mg, 425.62 mol, HCl), tert-butyl (3S)-3-[(1R)-2-amino-1-hydroxy-ethyl]-7-(methoxymethoxy)-3,4-dihydro-1H-isoquinoline-2-carboxylate (150 mg, 425.62 µmol) and HATU (242.75 mg, 638.44 µmol) were mixed in DMF (4.0 mL) and then triethylamine (430.69 mg, 4.26 mmol, 593.23 µL) was added. The resulting mixture was stirred for 12 h. The reaction substance was evaporated under reduce pressure and purified with HPLC (50-75% water-acetonitrile, 10 min, flow: 30 mL/min) to obtain tert-butyl (3 S)-3-[1(1R)-2-[[6-(cyclobutylamino)pyrimidine-4-carbonyl]-amino]-1-hydroxy-ethyl]-7-(methoxymethoxy)-3,4-dihydro-1H-isoquinoline-2-carboxylate (29.4 mg, 55.72 µmol, 13.09% yield). $^1$H NMR (CDCl$_3$, 400 MHz) δ: 1.49 (s, 9H), 1.83 (m, 6H), 2.44 (m, 2H), 2.83 (m, 1H), 3.12 (m, 2H), 3.71 (s, 3H), 3.82 (m, 2H), 4.25 (m, 3H), 4.74 (m, 1H), 5.12 (s, 2H), 6.77 (s, 1H), 6.85 (d, 1H), 7.03 (s, 1H), 7.07 (d, 1H), 8.60 (m, 2H). LCMS (ESI): [M+H]$^+$ m/z: calc'd 527.1; found 528.2; Rt=1.43 min.

Step 2: Synthesis of 6-(cyclobutylamino)-N—((R)-2-hydroxy-2-((S)-7-hydroxy-1,2,3,4-tetrahydroisoquinolin-3-yl)ethyl)pyrimidine-4-carboxamide The solution of tert-butyl (3S)-3-[(1R)-2-[[6-(cyclobutylamino)pyrimidine-4-carbonyl]amino]-1-hydroxy-ethyl]-7-(methoxymethoxy)-3,4-dihydro-1H-isoquinoline-2-carboxylate (29.4 mg, 55.72 µmol) in dioxane/HCl (2.0 mL) and methanol (2.0 mL) was stirred for 12 h at 25° C. Then, the solution was evaporated to obtain 6-(cyclobutylamino)-N-[(2R)-2-hydroxy-2-[(3S)-7-hydroxy-1,2,3,4-tetrahydro-isoquinolin-3-yl]ethyl]pyrimidine-4-carboxamide (23 mg, 50.40 µmol, 90.44% yield, 2HCl). $^1$H NMR (CD$_3$OD, 500 MHz) δ: 1.88 (m, 3H), 2.12 (m, 3H), 2.44 (m, 2H), 3.13 (m, 5H), 3.62 (m, 4H), 4.33 (m, 3H), 6.62 (s, 1H), 6.74 (d, 1H), 7.09 (d, 1H), 7.23 (s, 1H), 8.65 (t, 1H). LCMS (ESI): [M+H]$^+$ m/z: calc'd 383.2; found 384.2; Rt=0.87 min.

Step 3: Synthesis of (S)-tert-butyl 3-((R)-2-(6-(cyclobutylamino)pyrimidine-4-carboxamido)-1-hydroxyethyl)-7-hydroxy-3,4-dihydroisoquinoline-2(1H)-carboxylate To a stirred solution of sodium hydrogen carbonate (12.70 mg, 151.19 µmol, 5.88 µL) in water (1.0 mL), the solution of 6-(cyclobutylamino)-N-[(2R)-2-hydroxy-2-[(3S)-7-hydroxy-1,2,3,4-tetrahydroisoquinolin-3-yl]ethyl]-pyrimidine-4-carboxamide (23 mg, 50.40 µmol, 2HCl). The resulting mixture was stirred at 25° C. for 12 h. Then, EtOAc (10 mL) was added and the organic phase was separated and washed with brine (2*5 mL). The solution was dried over sodium sulfate, filtered and evaporated to obtain tert-butyl (3S)-3-[(1R)-2-[[6-(cyclobutylamino)pyrimidine-4-carbonyl]amino]-1-hydroxy-ethyl]-7-hydroxy-3,4-dihydro-1H-isoquinoline-2-carboxylate (23 mg, crude). $^1$H NMR (CD$_3$OD, 500 MHz) δ:1.52 (m, 12H), 1.81 (m, 2H), 1.94 (m, 2H), 2.38 (m, 2H), 2.82 (m, 2H), 3.10 (m, 2H), 3.70 (m, 4H), 6.56 (m, 2H), 7.00 (m, 2H), 8.41 (s, 1H). LCMS (ESI): [M+H]$^+$ m/z: calc'd 483.2; found 484.2; Rt=1.27 min.

Step 4: Synthesis of (S)-tert-butyl 3-((R)-2-(6-(cyclobutylamino)pyrimidine-4-carboxamido)-1-hydroxyethyl)-7-((4-methyloxazol-5-yl)methoxy)-3,4-dihydroisoquinoline-2(1H)-carboxylate To the solution of tert-butyl (3S)-3-[(1R)-2-[[6-(cyclobutylamino)pyrimidine-4-carbonyl]amino]-1-hydroxy-ethyl]-7-hydroxy-3,4-dihydro-1H-isoquinoline-2-carboxylate (23 mg, 47.56 µmol), cesium carbonate (46.49 mg, 142.69 µmol) in DMF (2 mL) was added 5-(chloromethyl)-4-methyl-oxazole (9.59 mg, 57.08 µmol, HCl). The resulting mixture was heated at 50° C. for 12 h. The mixture was filtered and evaporated to obtain tert-butyl (3S)-3-[(1R)-2-[[6-(cyclobutylamino)pyrimidine-4-carbonyl]amino]-1-hydroxy-ethyl]-7-[(4-methyloxazol-5-yl)methoxy]-3,4-dihydro-1H-isoquinoline-2-carboxylate (25 mg, 43.20 µmol, 90.83% yield) that was used without further purification. $^1$H NMR (CD$_3$OD, 500 MHz) δ: 1.52 (m, 9H), 1.87 (m, 5H), 2.19 (m, 4H), 2.39 (m, 2H), 3.10 (m, 2H), 3.62 (m, 3H), 4.24 (m, 2H), 5.08 (m, 2H), 6.79 (m, 2H), 7.04 (m, 2H), 8.07 (m, 2H), 8.13 (s, 1H), 8.41 (m, 1H). LCMS (ESI): [M+H]$^+$ m/z: calc'd 578.3; found 579.4; Rt=1.41 min.

Step 6: Synthesis of 6-(cyclobutylamino)-N—((R)-2-hydroxy-2-((S)-7-((4-methyloxazol-5-yl)methoxy)-1,2,3,4-tetrahydroisoquinolin-3-yl)ethyl)pyrimidine-4-carboxamide (Compound 32) The solution of tert-butyl (3S)-3-[(1R)-2-[[6-(cyclobutylamino)pyrimidine-4-carbonyl]amino]-1-hydroxy-ethyl]-7-[(4-methyloxazol-5-yl)methoxy]-3,4-dihydro-1H-isoquinoline-2-carboxylate (25 mg, 43.20 µmol) in methanol (1 mL) and dioxane/HCl (1 mL) was stirred for 12 h at 25° C. Then, the solution was evaporated and resulting crude product was purified by HPLC (5-50% water-R1, 10 min, flow: 30 mL/min) to obtain 6-(cyclobutylamino)-N-[(2R)-2-hydroxy-2-[(3S)-7-[(4-methyloxazol-5-yl)methoxy]-1,2,3,4-tetrahydroisoquinolin-3-yl]ethyl]pyrimidine-4-carboxamide (10.4 mg, 18.86 µmol, 43.65% yield, 2HCl). $^1$H NMR (Methanol-d$_4$, 400 MHz): δ (ppm) 1.85 (m, 2H), 2.14 (m, 2H), 2.19 (s, 3H), 2.42 (m, 2H), 3.20 (m, 2H), 3.55 (m, 1H), 3.68 (m, 2H), 4.32 (d, 2H), 4.45 (d, 1H), 4.68 (m, 1H), 5.09 (s, 2H), 6.87 (s, 1H), 6.96 (d, 1H), 7.23 (d, 1H), 7.30 (s, 1H), 8.13 (s, 1H), 8.60 (s, 1H). LCMS (ESI): [M+H]$^+$ m/z: calc'd 478.2; found 479.2; Rt=0.99 min.

Example 4A3. Synthesis of N—((R)-2-hydroxy-2-((S)-7-((4-methyloxazol-5-yl)methoxy)-1,2,3,4-tetrahydroisoquinolin-3-yl)ethyl)-2-(methyl(propyl)amino)-6-(oxetan-3-ylamino)pyrimidine-4-carboxamide (Compound 38)
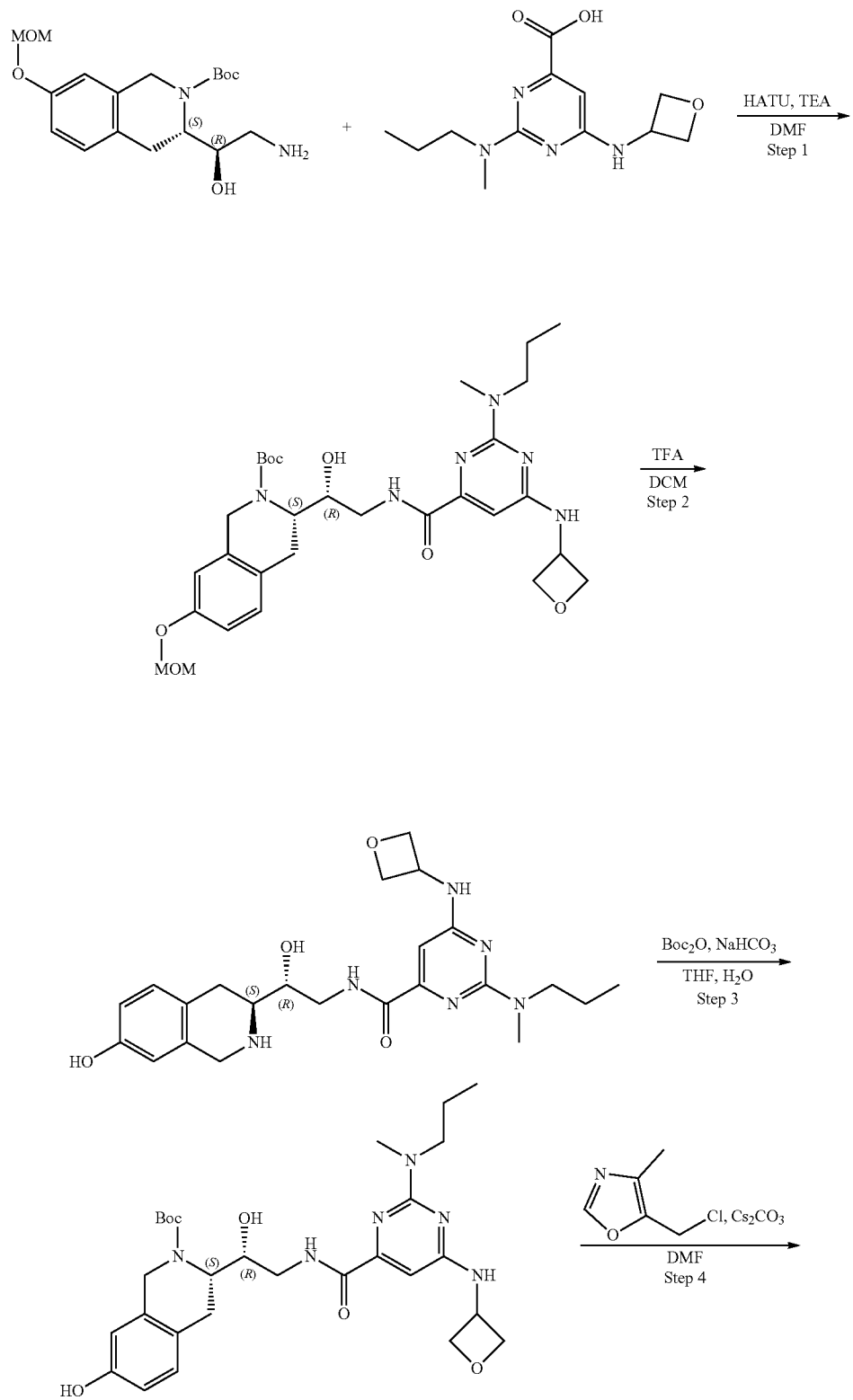

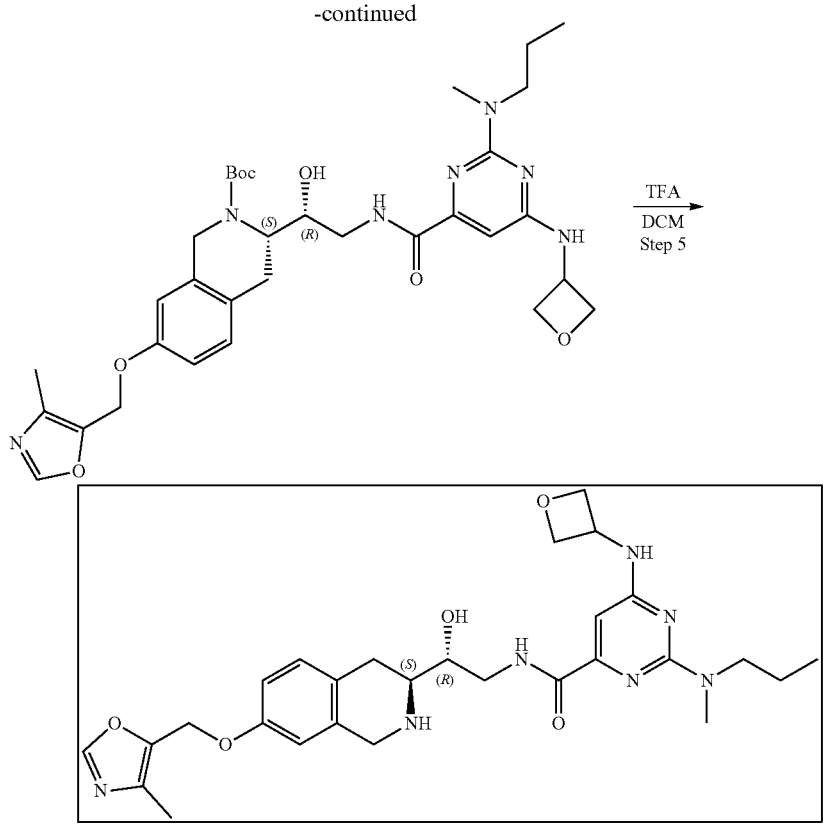

Step 1: Synthesis of (S)-tert-butyl 3-((R)-1-hydroxy-2-(2-(methyl(propyl)amino)-6-(oxetan-3-ylamino)pyrimidine-4-carboxamido)ethyl)-7-(methoxymethoxy)-3,4-dihydroisoquinoline-2(1H)-carboxylate 2-[Methyl(propyl)amino]-6-(oxetan-3-ylamino)pyrimidine-4-carboxylic acid (113.34 mg, 425.62 μmol) and TEA (430.69 mg, 4.26 mmol, 593.23 μL) were dissolved in DMF (2 mL) and cooled to 0° C., HATU (242.75 mg, 638.44 μmol) was added and the mixture was stirred for 15 min at 0° C. tert-Butyl (3S)-3-[(1R)-2-amino-1-hydroxy-ethyl]-7-(methoxymethoxy)-3,4-dihydro-1H-isoquinoline-2-carboxylate (0.15 g, 425.62 μmol) was added and the mixture was warmed to r.t. and stirred for 3 h. 10 mL of Ethyl acetate was added and organic phase was washed with brine three times. The organic phase was dried over Na$_2$SO$_4$, filtered and concentrated in vacuo at 45° C. to give crude product which was purified by HPLC (60-75% water-acetonitrile, 0-5 min, flow: 30 mL/min (loading pump 4 mL/min acetonitrile) column: SunFire C18 100×19 mm) to give tert-butyl (3S)-3-[(1R)-1-hydroxy-2-[[2-[methyl(propyl)amino]-6-(oxetan-3-ylamino)pyrimidine-4-carbonyl]amino]ethyl]-7-(methoxymethoxy)-3,4-dihydro-1H-isoquinoline-2-carboxylate (0.079 g, 131.51 μmol, 30.90% yield). $^1$H NMR (DMSO-d$_6$, 400 MHz) δ: 0.84 (t, 3H), 1.44 (s, 9H), 1.51 (m, 1H), 2.75 (m, 1H), 2.90 (m, 4H), 3.04 (m, 2H), 3.16 (m, 3H), 3.36 (m, 2H), 4.09 (m, 1H), 4.25 (m, 1H), 4.46 (m, 2H), 4.77 (t, 2H), 4.88 (m, 3H), 5.14 (m, 1H), 5.32 (s, 2H), 6.34 (s, 1H), 6.83 (m, 2H), 7.08 (d, 1H), 7.95 (s, 1H), 8.33 (m, 1H), 8.51 (m, 1H). LCMS (ESI): [M+H]$^+$ m/z: calc'd 600.3; found 601.4; Rt=1.46 min.

Step 2: Synthesis of N—((R)-2-hydroxy-2-((S)-7-hydroxy-1,2,3,4-tetrahydroisoquinolin-3-yl)ethyl)-2-(methyl(propyl)amino)-6-(oxetan-3-ylamino)pyrimidine-4-carboxamide tert-Butyl (3S)-3-[(1R)-1-hydroxy-2-[[2-[methyl (propyl)amino]-6-(oxetan-3-ylamino)pyrimidine-4-carbonyl]amino]ethyl]-7-(methoxymethoxy)-3,4-dihydro-1H-isoquinoline-2-carboxylate (0.079 g, 131.51 μmol) was dissolved in DCM (1 mL) and trifluoroacetic acid (1 mL) was added dropwise at cooling with water+ice. The reaction mixture was stirred overnight. Solvent was removed in vacuo at 50° C. to give N-[(2R)-2-hydroxy-2-[(3S)-7-hydroxy-1,2,3,4-tetrahydroisoquinolin-3-yl]ethyl]-2-[methyl(propyl)amino]-6-(oxetan-3-ylamino)pyrimidine-4-carboxamide (0.087 g, 127.08 μmol, 96.63% yield, 2CF$_3$COOH) which was used in the next step without further purification $^1$H NMR (CD$_3$OD, 500 MHz) δ: 0.98 (t, 3H), 1.76 (q, 2H), 3.05 (m, 1H), 3.18 (m, 2H), 3.37 (m, 4H), 3.54 (m, 3H), 3.69 (m, 6H), 4.25 (m, 2H), 4.40 (m, 2H), 4.67 (m, 3H), 6.62 (s, 1H), 6.74 (m, 2H), 7.09 (d, 1H). LCMS (ESI): [M+H]$^+$ m/z: calc'd 456.2; found 457.2; Rt=1.60 min.

Step 3: Synthesis of (S)-tert-butyl 7-hydroxy-3-((R)-1-hydroxy-2-(2-(methyl(propyl)amino)-6-(oxetan-3-ylamino)pyrimidine-4-carboxamido)ethyl)-3,4-dihydroisoquinoline-2(1H)-carboxylate N-[(2R)-2-Hydroxy-2-[(3S)-7-hydroxy-1,2,3,4-tetrahydroisoquinolin-3-yl]ethyl]-2-[methyl (propyl)-amino]-6-(oxetan-3-ylamino)pyrimidine-4-carboxamide (0.087 g, 127.08 μmol, 2CF$_3$COOH) was dissolved in the mixture of water (1 mL) and THF (1 mL) then sodium hydrogen carbonate, 99% (32.03 mg, 381.25 μmol, 14.83 μL) was added in one portion, after that solution of di-tert-butyl dicarbonate (27.74 mg, 127.08 μmol, 29.16 μL) in THF (0.2 mL) was added dropwise. The reaction mixture was stirred for 4 h at room temperature. Ethyl acetate (15 mL) was added to the reaction mixture, organic phase was separated, and the aqueous phase was extracted with ethyl acetate (2*15 mL). The organic phase was washed with brine, dried over Na$_2$SO$_4$, filtered and evaporated in vacuo at 40° C. to give tert-butyl (3S)-7-hydroxy-3-[(1R)-1-hydroxy-2-[[2-[methyl(propyl)amino]-6-(oxetan-3-ylamino)pyrimidine-4-carbonyl]amino]ethyl]-3,4-dihydro-1H-iso-quinoline-2-carboxylate (0.064 g, 114.97 μmol, 90.47% yield) which was used in the next step without purification. LCMS (ESI): [M+H]⁺ m/z: calc'd 556.3; found 557.2; Rt=2.23 min.

Step 4: Synthesis of (S)-tert-butyl 3-((R)-1-hydroxy-2-(2-(methyl(propyl)amino)-6-(oxetan-3-ylamino)pyrimidine-4-carboxamido)ethyl)-7-((4-methyloxazol-5-yl)methoxy)-3,4-dihydroisoquinoline-2(1H)-carboxylate tert-Butyl (3S)-7-hydroxy-3-[(1R)-1-hydroxy-2-[[2-[methyl(propyl)amino]-6-(oxetan-3-ylamino)-pyrimidine-4-carbonyl]amino]ethyl]-3,4-dihydro-1H-isoquinoline-2-carboxylate (0.064 g, 114.97 μmol), 5-(chloromethyl)-4-methyl-oxazole (27.05 mg, 160.96 μmol, HCl) and cesium carbonate (149.84 mg, 459.89 μmol) was dissolved in DMF (2 mL) and heated at 50° C. overnight. The reaction mixture was filtered off, solid was washed with DMF (2 mL), filtrate was concentrated on vacuo at 60° C. to give tert-butyl (3S)-3-[(1R)-1-hydroxy-2-[[2-[methyl(propyl)amino]-6-(oxetan-3-ylamino)pyrimidine-4-carbonyl]amino]ethyl]-7-[(4-methyloxazol-5-yl)methoxy]-3,4-dihydro-1H-isoquinoline-2-carboxylate (0.066 g, 101.27 μmol, 88.08% yield) which was used in the next step without further purification. ¹H NMR (CD₃OD, 400 MHz) δ: 0.93 (t, 3H), 1.28 (m, 3H), 1.41 (m, 9H), 1.70 (q, 2H), 2.15 (m, 4H), 3.08 (m, 3H), 3.60 (m, 2H), 4.06 (m, 2H), 4.22 (m, 2H), 4.34 (m, 3H), 5.02 (s, 2H), 6.49 (s, 1H), 6.75 (m, 2H), 7.04 (d, 1H), 8.09 (m, 2H). LCMS (ESI): [M+H]⁺ m/z: calc'd 651.3; found 652.2; Rt=3.39 min.

Step 5: Synthesis of N—((R)-2-hydroxy-2-((S)-7-((4-methyloxazol-5-yl)methoxy)-1,2,3,4-tetrahydroisoquinolin-3-yl)ethyl)-2-(methyl(propyl)amino)-6-(oxetan-3-ylamino)pyrimidine-4-carboxamide (Compound 38) tert-Butyl (3S)-3-[(1R)-1-hydroxy-2-[[2-[methyl(propyl)amino]-6-(oxetan-3-ylamino)pyrimidine-4-carbonyl]amino]ethyl]-7-[(4-methyloxazol-5-yl)methoxy]-3,4-dihydro-1H-isoquinoline-2-carboxylate (0.066 g, 101.27 μmol) was dissolved in DCM (0.5 mL) and trifluoroacetic acid (0.5 mL) was added dropwise at cooling with water+ice. The reaction mixture was stirred for 1 h. Solvent was removed in vacuo at 50° C. to give crude product. The residue was dissolved in 5 mL of methanol and 10 mg of scavenger (SiliaMetS© Dimercaptotriazine(DMT)) was added thereto and the resulting suspension was stirred for 12 h. The suspension was filtered off, the filtrate was evaporated under reduced pressure and the residue was purified by HPLC (40-80% water-methanol+NH₃, 0-5 min, flow 30 mL/min (loading pump 4 ml/min methanol+NH₃) column: SunFire C18 190*10 mm) to give N-[(2R)-2-hydroxy-2-[(3S)-7-[(4-methyloxazol-5-yl)methoxy]-1,2,3,4-tetrahydroisoquinolin-3-yl]ethyl]-2-[methyl(propyl)amino]-6-(oxetan-3-ylamino)pyrimidine-4-carboxamide (9.7 mg, 17.58 μmol, 17.36% yield). ¹H NMR (500 MHz, CDCl₃) δ 0.96 (m, 3H), 1.69 (m, 2H), 2.24 (m, 3H), 2.80 (m, 2H), 3.02 (m, 1H), 3.05 (s, 3H), 3.33 (m, 3H), 3.58 (m, 2H), 3.65 (m, 1H), 3.79 (m, 1H), 3.90 (m, 1H), 3.96 (m, 2H), 4.03 (m, 2H), 4.10 (m, 1H), 4.18 (m, 1H), 4.32 (m, 1H), 4.98 (s, 2H), 6.62 (m, 2H), 6.80 (d, 1H), 7.07 (m, 1H), 7.82 (s, 1H), 8.10 (m, 1H). LCMS (ESI): [M+2H]⁺ m/z: calc'd 551.3; found 553.2; Rt=0.79 min.

Example 4A4. Synthesis of N—((R)-2-hydroxy-2-((S)-7-((4-methyloxazol-5-yl)methoxy)-1,2,3,4-tetrahydroisoquinolin-3-yl)ethyl)-2-((2-methoxyethyl)(methyl)amino)-6-(oxetan-3-ylamino)pyrimidine-4-carboxamide (Compound 37)

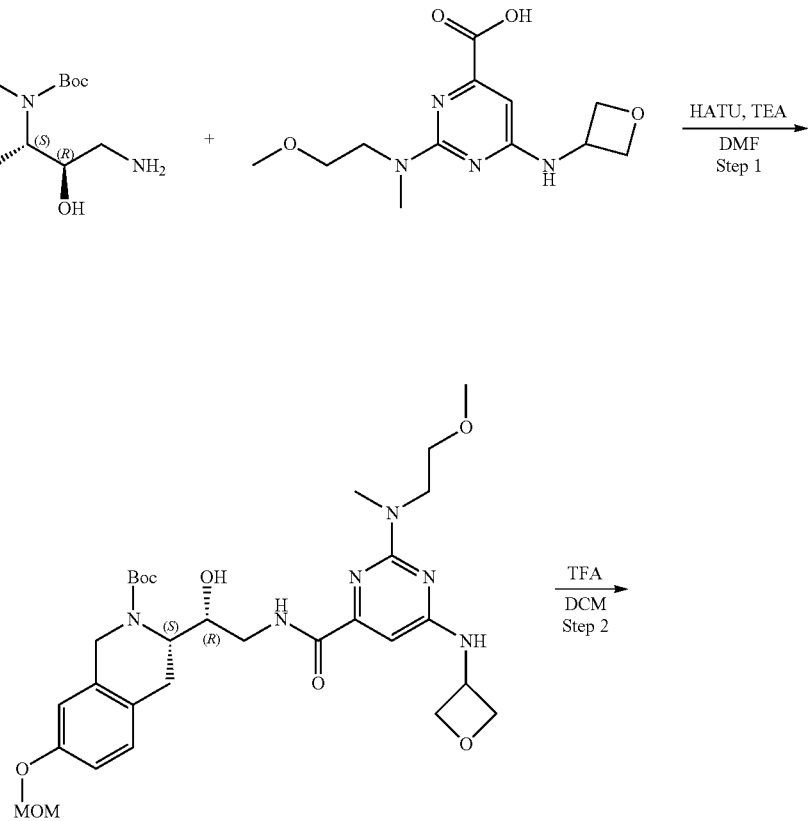

-continued
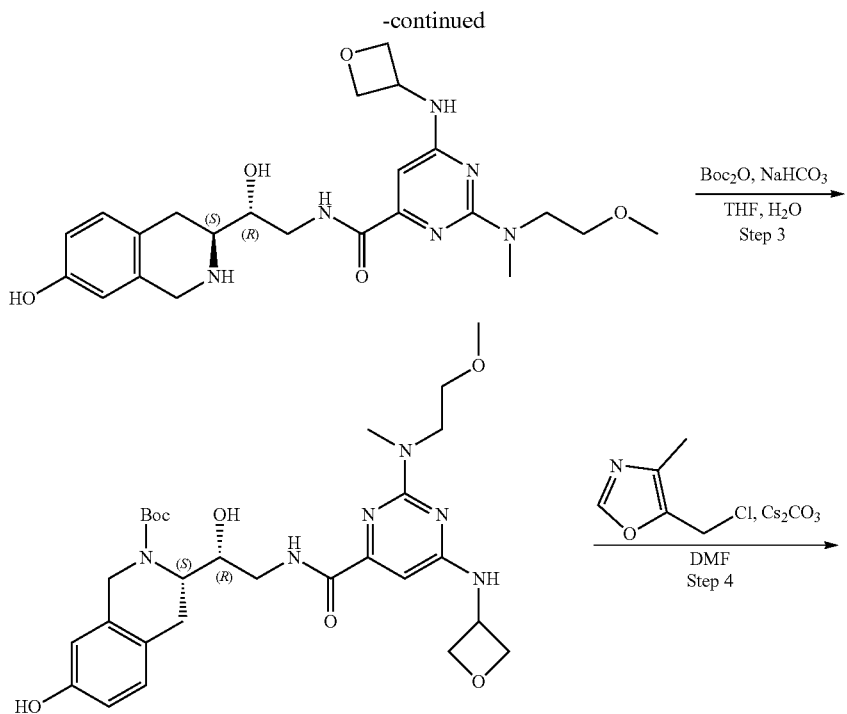
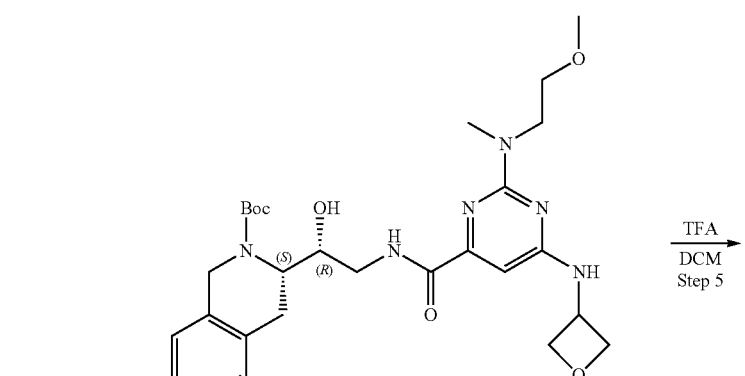
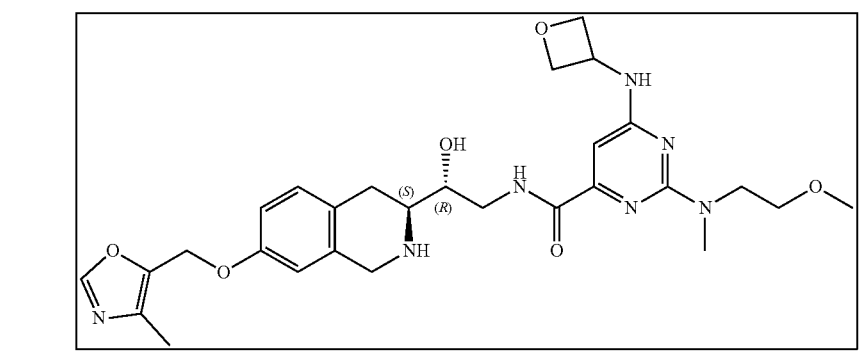

Step 1: Synthesis of (S)-tert-butyl 3-((R)-1-hydroxy-2-(2-((2-methoxyethyl)(methyl)amino)-6-(oxetan-3-ylamino)pyrimidine-4-carboxamido)ethyl)-7-(methoxymethoxy)-3,4-dihydroisoquinoline-2(1H)-carboxylate 2-[2-Methoxyethyl(methyl)amino]-6-(oxetan-3-ylamino)pyrimidine-4-carboxylic acid (120.15 mg, 425.62 µmol) and TEA (430.69 mg, 4.26 mmol, 593.23 µL) were dissolved in DMF (2.0 mL) and cooled to 0° C., HATU (242.75 mg, 638.44 µmol) was added and the mixture was stirred for 15 min at 0° C. tert-Butyl (3S)-3-[(1R)-2-amino-1-hydroxy-ethyl]-7-(methoxymethoxy)-3,4-dihydro-1H-isoquinoline-2-carboxylate (0.15 g, 425.62 µmol) was added and the mixture was warmed to r.t. and stirred overnight. 10 mL of Ethyl acetate was added, and organic phase was washed with brine three times. The organic phase was dried over Na$_2$SO$_4$, filtered off and concentrated in vacuo at 45° C. to give crude product which was purified by HPLC (45-75% water-acetonitrile, 0-5 min, flow: 30 mL/min (loading pump 4 mL/min acetonitrile) column: SunFire C18 100*19 mm) to give tert-butyl (3S)-3-[(1R)-1-hydroxy-2-[[2-[2-methoxyethyl(methyl)amino]-6-(oxetan-3-ylamino)pyrimidine-4-carbonyl]amino]ethyl]-7-(methoxymethoxy)-3,4-dihydro-1H-isoquinoline-2-carboxylate (0.059 g, 95.67 µmol, 22.48% yield). $^1$H NMR (DMSO-d$_6$, 400 MHz) δ: 1.40 (m, 9H), 2.76 (m, 1H), 3.08 (m, 4H), 3.23 (m, 3H), 3.32 (m, 2H), 3.48 (m, 3H), 3.65 (m, 2H), 4.12 (m, 2H), 4.24 (m, 2H), 4.46 (m, 2H), 4.76 (m, 4H), 5.15 (m, 3H), 6.37 (s, 1H), 6.84 (m, 2H), 7.08 (d, 1H), 7.99 (s, 1H), 8.32 (m, 1H), 8.51 (m, 1H). LCMS (ESI): [M+H]$^+$ m/z: calc'd 616.3; found 617.4; Rt=1.32 min.

Step 2: Synthesis of N—((R)-2-hydroxy-2-((S)-7-hydroxy-1,2,3,4-tetrahydroisoquinolin-3-yl)ethyl)-2-((2-methoxyethyl)(methyl)amino)-6-(oxetan-3-ylamino)pyrimidine-4-carboxamide tert-Butyl (3S)-3-[(1R)-1-hydroxy-2-[[2-[2-methoxyethyl(methyl)amino]-6-(oxetan-3-ylamino)-pyrimidine-4-carbonyl]amino]ethyl]-7-(methoxymethoxy)-3,4-dihydro-1H-isoquinoline-2-carboxylate (0.059 g, 95.67 µmol) was dissolved in DCM (1 mL) and trifluoracetic acid (1 mL) was added dropwise at cooling with water+ice. The reaction mixture was stirred overnight. The solvent was removed in vacuo at 50° C. to give N-[(2R)-2-hydroxy-2-[(3S)-7-hydroxy-1,2,3,4-tetrahydroisoquinolin-3-yl]ethyl]-2-[2-methoxy-ethyl(methyl)amino]-6-(oxetan-3-ylamino)pyrimidine-4-carboxamide (0.061 g, 87.07 µmol, 91.01% yield, 2CF$_3$COOH) which was used in the next step without further purification. $^1$H NMR (CD$_3$OD, 500 MHz) δ: 3.05 (m, 2H), 3.19 (m, 2H), 3.42 (m, 2H), 3.55 (m, 4H), 3.67 (m, 1H), 3.74 (m, 3H), 4.00 (m, 2H), 4.29 (m, 2H), 4.37 (m, 2H), 4.56 (m, 1H), 4.67 (m, 2H), 6.62 (s, 1H), 6.75 (d, 1H), 6.81 (s, 1H), 7.11 (d, 1H). LCMS (ESI): [M+H]$^+$ m/z: calc'd 472.2; found 473.2; Rt=1.45 min.

Step 3: Synthesis of (S)-tert-butyl 7-hydroxy-3-((R)-1-hydroxy-2-(2-((2-methoxyethyl)(methyl)amino)-6-(oxetan-3-ylamino)pyrimidine-4-carboxamido)ethyl)-3,4-dihydroisoquinoline-2(1H)-carboxylate N-[(2R)-2-Hydroxy-2-[(3S)-7-hydroxy-1,2,3,4-tetrahydroisoquinolin-3-yl]ethyl]-2-[2-methoxy-ethyl(methyl)amino]-6-(oxetan-3-ylamino)pyrimidine-4-carboxamide (0.061 g, 87.07 µmol, 2CF$_3$COOH) was dissolved in the mixture of water (1 mL) and THF (1 mL) then sodium hydrogen carbonate, 99% (21.94 mg, 261.21 µmol, 10.16 µL) was added in one portion, after that solution of di-tert-butyl dicarbonate (19.00 mg, 87.07 µmol, 19.98 µL) in THF (0.2 mL) was added dropwise. The reaction mixture was stirred overnight at room temperature. Ethyl acetate (15 mL) was added to the reaction mixture, organic phase was separated, and the aqueous phase was extracted with ethyl acetate (2*15 mL). The organic phase was washed with brine, dried over Na$_2$SO$_4$, filtered off and evaporated in vacuo at 40° C. to give tert-butyl (3S)-7-hydroxy-3-[(1R)-1-hydroxy-2-[[2-[2-methoxyethyl(methyl)amino]-6-(oxetan-3-ylamino)pyrimidine-4-carbonyl]amino]ethyl]-3,4-dihydro-1H-isoquinoline-2-carboxylate (0.036 g, 62.87 µmol, 72.20% yield) which was used in the next step without purification. $^1$H NMR (DMSO-d$_6$, 400 MHz) δ: 1.44 (m, 3H), 1.53 (m, 12H), 1.87 (m, 1H), 2.85 (m, 3H), 3.14 (m, 2H), 3.50 (m, 2H), 3.62 (m, 6H), 3.72 (m, 2H), 4.27 (m, 5H), 6.43 (s, 1H), 6.56 (s, 1H), 6.61 (d, 1H), 6.97 (d, 1H). LCMS (ESI): [M+H]$^+$ m/z: calc'd 572.3; found 573.2; Rt=2.67 min.

Step 4: Synthesis of (S)-tert-butyl 3-((R)-1-hydroxy-2-(2-((2-methoxyethyl)(methyl)amino)-6-(oxetan-3-ylamino)pyrimidine-4-carboxamido)ethyl)-7-((4-methyloxazol-5-yl)methoxy)-3,4-dihydroisoquinoline-2(1H)-carboxylate tert-Butyl (3S)-7-hydroxy-3-[(1R)-1-hydroxy-2-[[2-[2-methoxyethyl(methyl)amino]-6-(oxetan-3-ylamino)pyrimidine-4-carbonyl]amino]ethyl]-3,4-dihydro-1H-isoquinoline-2-carboxylate (0.036 g, 62.87 µmol), 5-(chloromethyl)-4-methyl-oxazole (14.79 mg, 88.01 µmol, HCl) and cesium carbonate (81.93 mg, 251.46 µmol) was dissolved in DMF (2 mL) and heated at 50° C. overnight. The reaction mixture was filtered off, solid was washed with DMF (2 mL), filtrate was concentrated on vacuo at 60° C. to give tert-butyl (3S)-3-[(1R)-1-hydroxy-2-[[2-[2-methoxyethyl(methyl)amino]-6-(oxetan-3-ylamino)pyrimidine-4-carbonyl]amino]ethyl]-7-[(4-methyloxazol-5-yl)methoxy]-3,4-dihydro-1H-isoquinoline-2-carboxylate (0.036 g, 53.91 µmol, 85.76% yield) which was used in the next step without further purification. $^1$H NMR (CD$_3$OD, 400 MHz) δ: 1.27 (m, 4H), 1.42 (m, 12H), 2.17 (m, 4H), 3.12 (m, 3H), 3.45 (m, 6H), 3.62 (m, 1H), 4.10 (m, 3H), 5.04 (s, 2H), 6.40 (s, 1H), 6.79 (m, 2H), 7.06 (d, 1H), 8.10 (m, 1H). LCMS (ESI): [M+H]$^+$ m/z: calc'd 667.3; found 668.4; Rt=3.26 min.

Step 5: Synthesis of N—((R)-2-hydroxy-2-((S)-7-((4-methyloxazol-5-yl)methoxy)-1,2,3,4-tetrahydroisoquinolin-3-yl)ethyl)-2-((2-methoxyethyl)(methyl)amino)-6-(oxetan-3-ylamino)pyrimidine-4-carboxamide (Compound 37) tert-Butyl (3S)-3-[(1R)-1-hydroxy-2-[[2-[2-methoxyethyl(methyl)amino]-6-(oxetan-3-ylamino)-pyrimidine-4-carbonyl]amino]ethyl]-7-[(4-methyloxazol-5-yl)methoxy]-3,4-dihydro-1H-isoquinoline-2-carboxylate (0.036 g, 53.91 µmol) was dissolved in DCM (0.5 mL) and trifluoroacetic acid (0.5 mL) was added dropwise at cooling with water+ice. The reaction mixture was stirred for 1 hr. The solvent was removed in vacuo at 50° C. to give crude product. The residue was dissolved in 5 mL of methanol and 10 mg of scavenger (SiliaMetS© Dimercaptotriazine(DMT)) was added thereto and the resulting suspension was stirred for 12 h. The suspension was filtered off, the filtrate was evaporated under reduced pressure and the residue was purified by HPLC (45-75% water-methanol+NH$_3$, 0-5 min, flow 30 mL/min (loading pump 4 ml/min methanol+NH$_3$) column: SunFire C18 190*10 mm) to give N-[(2R)-2-hydroxy-2-[(3S)-7-[(4-methyloxazol-5-yl)methoxy]-1,2,3,4-tetrahydroisoquinolin-3-yl]ethyl]-2-[2-methoxyethyl(methyl)amino]-6-(oxetan-3-ylamino)pyrimidine-4-carboxamide (9.4 mg, 16.56 µmol, 30.72% yield). $^1$H NMR (500 MHz, CDCl$_3$) δ 2.24 (m, 3H), 2.80 (m, 2H), 3.02 (m, 1H), 3.13 (s, 3H), 3.37 (m, 3H), 3.60 (m, 8H), 3.79 (m, 1H), 3.95 (m, 3H), 4.03 (m, 2H), 4.16 (m, 1H), 4.23 (m, 1H), 4.30 (m, 1H), 4.98 (s, 2H), 6.62 (s, 2H), 6.80 (d, 1H), 7.06 (m, 1H), 7.82 (s, 1H), 8.10 (m, 1H). LCMS (ESI): [M+H]$^+$ m/z: calc'd 567.2; found 569.4; Rt=0.76 min.

Example 4A5. Synthesis of 6-[(1-acetyl-4-piperidyl)amino]-N-[(2R)-2-hydroxy-2-[(3S)-7-[(4-methyloxazol-5-yl)methoxy]-1,2,3,4-tetrahydroisoquinolin-3-yl]ethyl]pyrimidine-4-carboxamide (Compound 41)
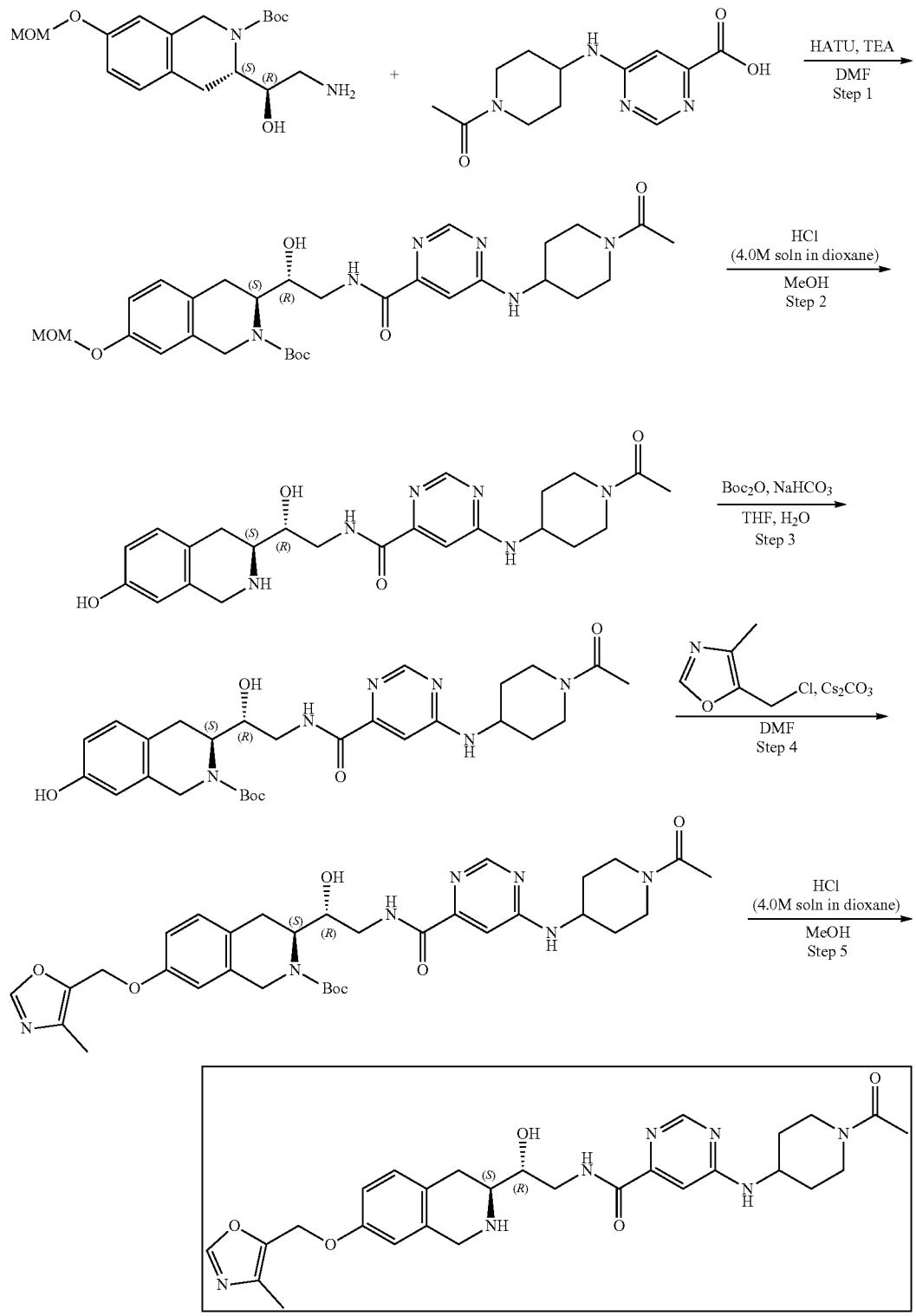

Step 1: Synthesis of tert-butyl (3S)-3-[(1R)-2-[[6-[(1-acetyl-4-piperidyl)amino]pyrimidine-4-carbonyl]amino]-1-hydroxy-ethyl]-7-(methoxymethoxy)-3,4-dihydro-1H-isoquinoline-2-carboxylate 6-[(1-Acetyl-4-piperidyl)amino]pyrimidine-4-carboxylic acid (224.97 mg, 851.25 μmol) and TEA (861.38 mg, 8.51 mmol, 1.19 mL) were mixed together in DMF (10 mL) and cooled to 0° C., HATU (485.50 mg, 1.28 mmol) was added. The resulting mixture was stirred for 15 min at 0° C. followed by the addition of tert-butyl (3S)-3-[(1R)-2-amino-1-hydroxy-ethyl]-7-(methoxymethoxy)-3,4-dihydro-1H-isoquinoline-2-carboxylate (0.3 g, 851.25 μmol). The reaction mixture was warmed to r.t. and stirred for 3 h. After that, 10 mL of ethyl acetate was added, and the organic phase was washed with brine three times. The organic phase was dried over $Na_2SO_4$, filtered off and concentrated in vacuo at 45° C. to give crude product which was purified by HPLC (30-40% water-ACN, 10 min, flow 30 mL/min (loading pump 4 mL/min ACN) column: SunFire C18 100*19 mm) to give tert-butyl (3S)-3-[(1R)-2-[[6-[(1-acetyl-4-piperidyl)amino]pyrimidine-4-carbonyl]amino]-1-hydroxy-ethyl]-7-(methoxymethoxy)-3,4-dihydro-1H-isoquinoline-2-carboxylate (0.09 g, 150.33 μmol, 17.66% yield). $^1$H NMR (DMSO-$d_6$, 500 MHz): δ 1.47 (s, 9H), 2.04 (m, 4H), 2.87 (m, 2H), 3.12 (m, 2H), 3.43 (s, 3H), 3.60 (m, 4H), 3.93 (m, 2H), 4.31 (m, 6H), 5.14 (s, 2H), 6.85 (m, 2H), 7.07 (m, 2H), 8.44 (s, 1H). LCMS (ESI): [M+H]$^+$ m/z: calc'd 598.2; found 599.2; Rt=1.34 min.

Step 2: Synthesis of 6-((1-acetylpiperidin-4-yl)amino)-N—((R)-2-hydroxy-2-((S)-7-hydroxy-1,2,3,4-tetrahydroisoquinolin-3-yl)ethyl)pyrimidine-4-carboxamide tert-Butyl (3S)-3-[(1R)-2-[[6-[(1-acetyl-4-piperidyl)amino]pyrimidine-4-carbonyl]amino]-1-hydroxy-ethyl]-7-(methoxymethoxy)-3,4-dihydro-1H-isoquinoline-2-carboxylate (0.09 g, 150.33 μmol) was dissolved in MeOH (2 mL). Hydrogen chloride solution 4.0M in dioxane (411.08 mg, 11.27 mmol, 513.85 μL) was added. The resulting mixture was stirred for 12 h at 20° C. After the completion of the reaction, the solvent was removed in vacuo at 35° C. to give 6-[(1-acetyl-4-piperidyl)amino]-N-[(2R)-2-hydroxy-2-[(3S)-7-hydroxy-1,2,3,4-tetrahydroisoquinolin-3-yl]ethyl]pyrimidine-4-carboxamide (0.078 g, 147.88 μmol, 98.37% yield, 2HCl) which was used in the next step without further purification. $^1$H NMR (DMSO-$d_6$, 400 MHz): δ 2.14 (m, 6H), 2.87 (m, 1H), 3.14 (m, 1H), 3.43 (s, 3H), 3.97 (m, 2H), 4.28 (m, 3H), 4.44 (m, 4H), 6.62 (s, 1H), 6.76 (d, 1H), 7.10 (d, 1H), 7.32 (s, 1H), 8.67 (s, 1H), LCMS (ESI): [M+H]$^+$ m/z: calc'd 454.2; found 455.2; Rt=1.85 min.

Step 3: Synthesis of tert-butyl (3S)-3-[(1R)-2-[[6-[(1-acetyl-4-piperidyl)amino]pyrimidine-4-carbonyl]amino]-1-hydroxy-ethyl]-7-hydroxy-3,4-dihydro-1H-isoquinoline-2-carboxylate 6-[(1-Acetyl-4-piperidyl)amino]-N-[(2R)-2-hydroxy-2-[(3S)-7-hydroxy-1,2,3,4-tetrahydro-isoquinolin-3-yl]ethyl]pyrimidine-4-carboxamide (0.078 g, 147.88 μmol, 2HCl) was dissolved in the mixture of water (1 mL) and THF (1 mL) following by the addition of sodium hydrogen carbonate, 99% (37.27 mg, 443.65 μmol, 17.25 μL) was added in one portion, after that the solution of di-tert-butyl dicarbonate (32.28 mg, 147.88 μmol, 33.94 μL) in THF (0.2 mL) was added dropwise. The reaction mixture was stirred for 12 h at room temperature. After the completion of the reaction, ethyl acetate (15 mL) was added to the reaction mixture, organic phase was separated, and the aqueous phase was extracted with ethyl acetate (2*15 mL). The organic phase was washed with brine, dried over $Na_2SO_4$, filtered and evaporated in vacuo at 40° C. to give tert-butyl (3S)-3-[(1R)-2-[[6-[(1-acetyl-4-piperidyl)amino]pyrimidine-4-carbonyl]amino]-1-hydroxy-ethyl]-7-hydroxy-3,4-dihydro-1H-isoquinoline-2-carboxylate (0.07 g, 126.21 μmol, 85.34% yield) which was used in the next step without purification. $^1$H NMR (CDCl$_3$, 400 MHz): δ 1.47 (m, 5H), 1.52 (s, 9H), 2.01 (m, 2H), 2.14 (s, 3H), 2.87 (m, 2H), 3.07 (m, 1H), 3.62 (m, 2H), 4.15 (m, 1H), 4.44 (m, 4H), 6.54 (s, 1H), 6.63 (d, 1H), 6.99 (d, 1H), 7.08 (s, 1H), 8.41 (s, 1H). LCMS (ESI): [M+H]$^+$ m/z: calc'd 554.3; found 555.4; Rt=2.69 min.

Step 4: Synthesis of tert-butyl (3S)-3-[(1R)-2-[[6-[(1-acetyl-4-piperidyl)amino]pyrimidine-4-carbonyl]amino]-1-hydroxy-ethyl]-7-[(4-methyloxazol-5-yl)methoxy]-3,4-dihydro-1H-isoquinoline-2-carboxylate tert-Butyl (3S)-3-[(1R)-2-[[6-[(1-acetyl-4-piperidyl)amino]pyrimidine-4-carbonyl]amino]-1-hydroxyethyl]-7-hydroxy-3,4-dihydro-1H-isoquinoline-2-carboxylate (0.07 g, 126.21 μmol), 5-(chloromethyl)-4-methyl-oxazole (29.69 mg, 176.69 μmol, HCl) and cesium carbonate (164.48 mg, 504.84 μmol) were mixed together in DMF (2 mL) and heated at 60° C. overnight. The reaction mixture was filtered off and the obtained solid was washed with DMF (2 mL). The filtrate was concentrated in vacuo at 60° C. to give tert-butyl (3S)-3-[(1R)-2-[[6-[(1-acetyl-4-piperidyl)amino]pyrimidine-4-carbonyl]amino]-1-hydroxy-ethyl]-7-[(4-methyloxazol-5-yl)methoxy]-3,4-dihydro-1H-isoquinoline-2-carboxylate (0.077 g, 118.51 μmol, 93.90% yield) which was used in the next step without further purification. $^1$H NMR (CD$_3$OD, 400 MHz): δ 1.49 (m, 13H), 2.10 (s, 3H), 2.20 (m, 5H), 3.17 (m, 2H), 3.63 (m, 3H), 3.88 (m, 2H), 4.31 (m, 5H), 5.04 (s, 2H), 6.78 (m, 2H), 7.08 (m, 2H), 8.10 (s, 1H). LCMS (ESI): [M+H]$^+$ m/z: calc'd 649.3; found 650.2; Rt=3.37 min.

Step 5: Synthesis of 6-[(1-acetyl-4-piperidyl)amino]-N-[(2R)-2-hydroxy-2-[(3S)-7-[(4-methyloxazol-5-yl)methoxy]-1,2,3,4-tetrahydroisoquinolin-3-yl]ethyl]pyrimidine-4-carboxamide (Compound 41) tert-Butyl (3S)-3-[(1R)-2-[[6-[(1-acetyl-4-piperidyl)amino]pyrimidine-4-carbonyl]amino]-1-hydroxy-ethyl]-7-[(4-methyloxazol-5-yl)methoxy]-3,4-dihydro-1H-isoquinoline-2-carboxylate (0.077 g, 118.51 μmol) was dissolved in the mixture of methanol (2 mL). Hydrogen chloride solution 4.0M in dioxane (324.07 mg, 8.89 mmol, 405.09 μL) was added. The mixture was stirred for 20° C. 4 h at RT. After the completion of the reaction, the solvent was removed in vacuo at 45° C. The residue was dissolved in 5 mL of methanol and 10 mg of scavenger (SiliaMetS© Dimercaptotriazine(DMT) was added thereto and the resulting suspension was stirred for 12 h. The suspension was filtered off, the filtrate was evaporated under reduced pressure and the residue was purified by HPLC (15-40% water+HCl-methanol, 2-10 min, flow 30 mL/min (loading pump 4 mL/min methanol), column: SunFire C18 100*19 mm to give 6-[(1-acetyl-4-piperidyl)amino]-N-[(2R)-2-hydroxy-2-[(3S)-7-[(4-methyloxazol-5-yl)methoxy]-1,2,3,4-tetrahydroisoquinolin-3-yl]ethyl]pyrimidine-4-carboxamide (0.016 g, 24.28 μmol, 20.49% yield, 3HCl). $^1$H NMR (Methanol-$d_4$, 400 MHz): δ (ppm) 1.62 (m, 2H), 2.08 (m, 2H), 2.16 (s, 3H), 2.24 (s, 3H), 2.93 (t, 1H), 3.20 (m, 2H), 3.65 (m, 4H), 4.00 (d, 1H), 4.43 (m, 6H), 5.13 (s, 2H), 6.89 (s, 1H), 6.96 (d, 1H), 7.23 (d, 1H), 7.41 (s, 1H), 8.52 (s, 1H), 8.68 (s, 1H). LCMS (ESI): [M+H]$^+$ m/z: calc'd 549.3; found 550.2; Rt=0.90 min.

Example 4A6. Synthesis of N-[(2R)-2-hydroxy-2-[(3S)-7-[(4-methyloxazol-5-yl)methoxy]-1,2,3,4-tetrahydroisoquinolin-3-yl]ethyl]-6-(spiro[3.3]heptan-2-ylamino)pyrimidine-4-carboxamide (Compound 43)

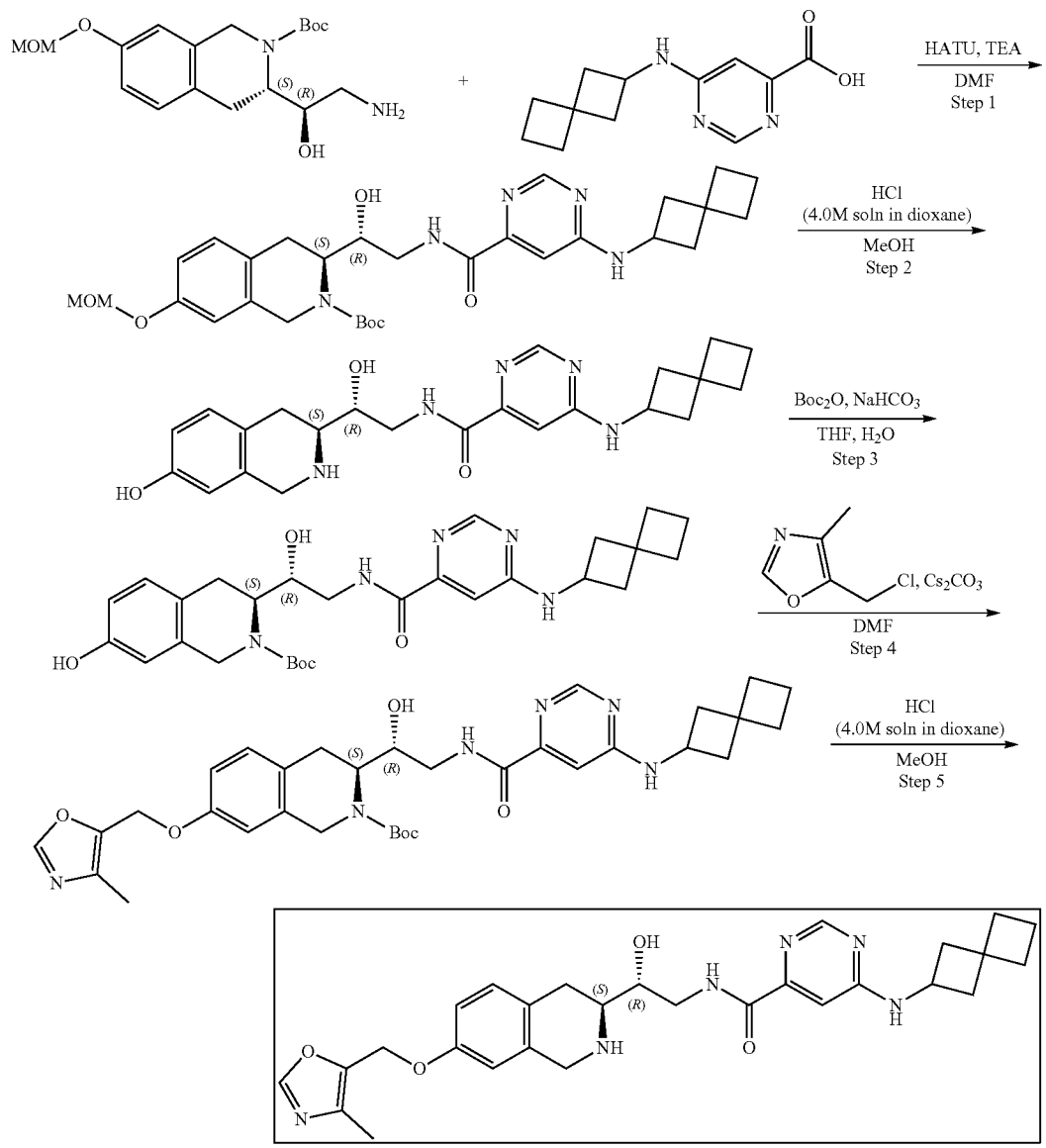

Step 1: Synthesis of tert-butyl (3S)-3-[(1R)-1-hydroxy-2-[[6-(spiro[3.3]heptan-2-ylamino)pyrimidine-4-carbonyl]amino]ethyl]-7-(methoxymethoxy)-3,4-dihydro-1H-isoquinoline-2-carboxylate 6-(Spiro[3.3]heptan-2-ylamino)pyrimidine-4-carboxylic acid (148.93 mg, 638.44 μmol), tert-butyl (3S)-3-[(1R)-2-amino-1-hydroxy-ethyl]-7-(methoxymethoxy)-3,4-dihydro-1H-isoquinoline-2-carboxylate (225 mg, 638.44 μmol), triethylamine (646.03 mg, 6.38 mmol, 889.85 μL) were mixed in DMF (6 mL) and then HATU (364.13 mg, 957.65 μmol) was added. The resulting mixture was stirred at 25° C. for 12 h. After the completion of the reaction, the mixture was evaporated under reduce pressure and purified with HPLC (60-75% water-acetonitrile, 10 min, flow: 30 mL/min) to obtain tert-butyl (3S)-3-[(1R)-1-hydroxy-2-[[6-(spiro[3.3]heptan-2-ylamino)pyrimidine-4-carbonyl]amino]ethyl]-7-(methoxymethoxy)-3,4-dihydro-1H-isoquinoline-2-carboxylate (41.1 mg, 72.40 μmol, 11.34% yield). $^1$H NMR (CDCl$_3$, 400 MHz): δ 1.50 (s, 9H), 1.62 (m, 4H), 2.03 (m, 8H), 2.49 (m, 2H), 3.04 (m, 2H), 3.71 (m, 3H), 5.13 (m, 2H), 5.13 (s, 2H), 6.77 (s, 1H), 6.79 (d, 1H), 7.10 (s, 1H), 7.12 (d, 1H), 8.40 (m, 1H), 8.73 (m, 1H). LCMS (ESI): [M+H]$^+$ m/z: calc'd 567.3; found 568.4; Rt=1.53 min.

Step 2: Synthesis of N-[(2R)-2-hydroxy-2-[(3S)-7-hydroxy-1, 2, 3,4-tetrahydroisoquinolin-3-yl]ethyl]-6-(spiro[3.3]heptan-2-ylamino)pyrimidine-4-carboxamide A solution of tert-butyl (3S)-3-[(1R)-1-hydroxy-2-[[6-(spiro[3.3]heptan-2-ylamino)pyrimidine-4-carbonyl]amino]ethyl]-7-

(methoxymethoxy)-3,4-dihydro-1H-isoquinoline-2-carboxylate (41.1 mg, 72.40 µmol) in dioxane/HCl (2 mL) and methanol (2 mL) was stirred for 12 h at 25° C. Then the solution was evaporated and resulting crude product was purified by HPLC (5-50% water-MeOH, 10 min, flow: 30 mL/min) to obtain N-[(2R)-2-hydroxy-2-[(3S)-7-hydroxy-1,2,3,4-tetrahydroisoquinolin-3-yl]ethyl]-6-(spiro[3.3]heptan-2-ylamino)pyrimidine-4-carboxamide (32 mg, crude, 2HCl). $^1$H NMR (CD$_3$OD, 500 MHz): δ 2.01 (m, 8H), 2.70 (m, 2H), 3.14 (m, 4H), 3.49 (m, 2H), 4.42 (m, 4H), 6.61 (s, 1H), 6.78 (d, 1H), 7.16 (d, 1H), 7.18 (s, 1H), 8.59 (s, 1H). LCMS (ESI): [M+H]+ m/z: calc'd 423.2; found 424.2; Rt=1.07 min.

Step 3: Synthesis of tert-butyl (3S)-7-hydroxy-3-[(1R)-1-hydroxy-2-[[6-(spiro[3.3]heptan-2-ylamino)pyrimidine-4-carbonyl]amino]ethyl]-3,4-dihydro-1H-isoquinoline-2-carboxylate To a stirred solution of sodium hydrogen carbonate (27.08 mg, 322.30 µmol, 12.54 µL) in water (1 mL) the solution of N-[(2R)-2-hydroxy-2-[(3S)-7-hydroxy-1,2,3,4-tetrahydroisoquinolin-3-yl]ethyl]-6-(spiro[3.3]heptan-2-ylamino)pyrimidine-4-carboxamide (32 mg, 64.46 µmol, 2HCl) in THF (1 mL) was added followed by the solution of di-tert-butyl dicarbonate (14.07 mg, 64.46 µmol, 14.79 µL) in THF (1 mL). The resulting mixture was stirred at 25° C. for 12 h. After the completion of the reaction, EtOAc (10 mL) was added and the organic phase was separated and washed with brine (2*5 mL). Then the solvent was dried over sodium sulfate, filtered and evaporated under reduced pressure to obtain tert-butyl (3S)-7-hydroxy-3-[(1R)-1-hydroxy-2-[[6-(spiro[3.3]heptan-2-ylamino)pyrimidine-4-carbonyl]amino]ethyl]-3,4-dihydro-1H-isoquinoline-2-carboxylate (42 mg, crude). $^1$H NMR (CD$_3$OD, 400 MHz): δ 1.17 (m, 4H), 1.49 (m, 4H), 1.98 (m, 6H), 2.45 (m, 2H), 2.92 (m, 4H), 3.94 (m, 4H), 4.17 (m, 2H), 4.53 (m, 2H), 6.57 (m, 1H), 6.59 (m, 1H), 6.96 (m, 1H), 6.98 (m, 1H), 8.35 (m, 1H). LCMS (ESI): [M+H]$^+$ m/z: calc'd 523.3; found 524.4; Rt=1.29 min.

Step 4: Synthesis of tert-butyl (3S)-3-[(1R)-1-hydroxy-2-[[6-(spiro[3.3]heptan-2-ylamino)pyrimidine-4-carbonyl]amino]ethyl]-7-[(4-methyloxazol-5-yl)methoxy]-3,4-dihydro-1H-isoquinoline-2-carboxylate To the mixture of tert-butyl (3S)-7-hydroxy-3-[(1R)-1-hydroxy-2-[[6-(spiro[3.3]heptan-2-ylamino)pyrimidine-4-carbonyl]amino]ethyl]-3,4-dihydro-1H-isoquinoline-2-carboxylate (42 mg, 80.21 µmol), cesium carbonate (78.40 mg, 240.63 µmol) in DMF (2 mL) was added 5-(chloromethyl)-4-methyl-oxazole (16.17 mg, 96.25 µmol, HCl). The reaction mixture was heated at 50° C. for 12 h. After the completion of the reaction (monitored by LCMS), the resulting mixture was filtered off and evaporated to obtain tert-butyl (3S)-3-[(1R)-1-hydroxy-2-[[6-(spiro[3.3]heptan-2-ylamino)pyrimidine-4-carbonyl]amino]-ethyl]-7-[(4-methyloxazol-5-yl)methoxy]-3,4-dihydro-1H-isoquinoline-2-carboxylate (48 mg, 77.58 µmol, 96.72% yield). The obtained product was used without further purification.

Step 5: Synthesis of N-[(2R)-2-hydroxy-2-[(3S)-7-[(4-methyloxazol-5-yl)methoxy]-1,2,3,4-tetrahydroisoquinolin-3-yl]ethyl]-6-(spiro[3.3]heptan-2-ylamino)pyrimidine-4-carboxamide (Compound 43) A solution of tert-butyl (3S)-3-[(1R)-1-hydroxy-2-[[6-(spiro[3.3]heptan-2-ylamino)pyrimidine-4-carbonyl]amino]ethyl]-7-[(4-methyloxazol-5-yl)methoxy]-3,4-dihydro-1H-isoquinoline-2-carboxylate (48 mg, 77.58 µmol) in Dioxane/HCl (2 mL) and Methanol (2 mL) was stirred for 12 h at 25° C. After the completion of the reaction, the resulting mixture was stirred with SiliaMetS DMT (20 mg) in methanol (1 mL) for 12 h. The resulting suspension was filtered off, evaporated and purified by HPLC (10-30%, 0-5 min, water(HCl)—MeCN) to obtain N-[(2R)-2-hydroxy-2-[(3S)-7-[(4-methyloxazol-5-yl)methoxy]-1,2,3,4-tetrahydroisoquinolin-3-yl]ethyl]-6-(spiro[3.3]heptan-2-ylamino)pyrimidine-4-carboxamide (15.6 mg, 26.37 µmol, 33.99% yield, 2HCl). $^1$H NMR (400 MHz, CD$_3$OD) δ 1.87 (m, 2H), 2.00 (m, 2H), 2.11 (m, 3H), 2.19 (s, 3H), 2.51 (m, 1H), 2.65 (s, 6H), 3.14 (m, 1H), 3.54 (m, 1H), 3.67 (m, 2H), 4.32 (m, 2H), 4.48 (m, 2H), 5.09 (s, 2H), 6.87 (s, 1H), 6.96 (d, 1H), 7.23 (d, 1H), 7.39 (m, 1H), 8.16 (s, 1H), 8.56 (m, 1H). LCMS (ESI): [M+H]$^+$ m/z: calc'd 518.2; found 519.2; Rt=1.12 min.

Example 4A7. Synthesis of N-[(2R)-2-hydroxy-2-[(3S)-7-[(4-methyloxazol-5-yl)methoxy]-1,2,3,4-tetrahydroisoquinolin-3-yl]ethyl]-2-(1-piperidyl)-6-(spiro[3.3]heptan-2-ylamino)pyrimidine-4-carboxamide (Compound 57)

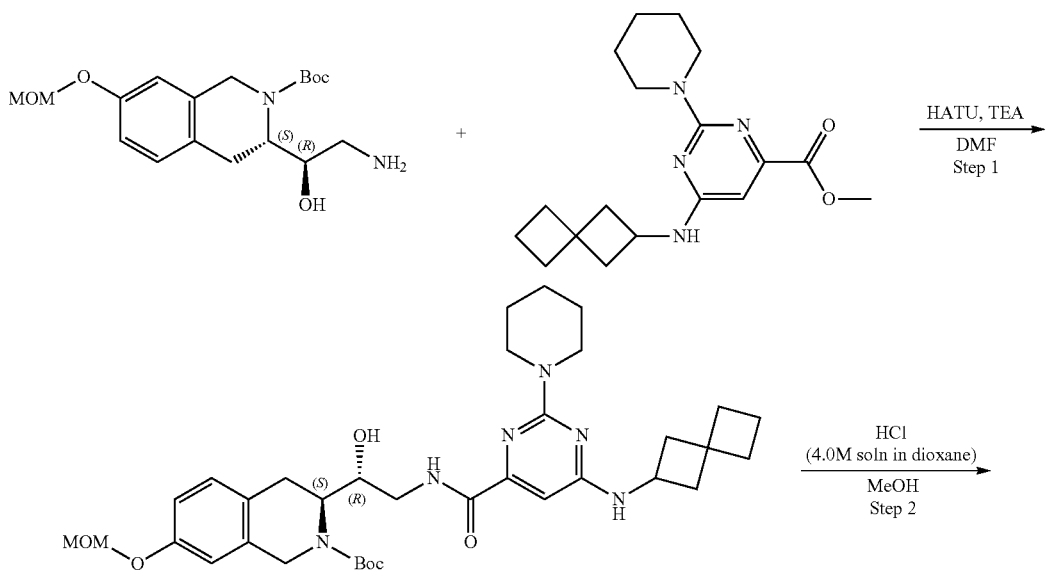

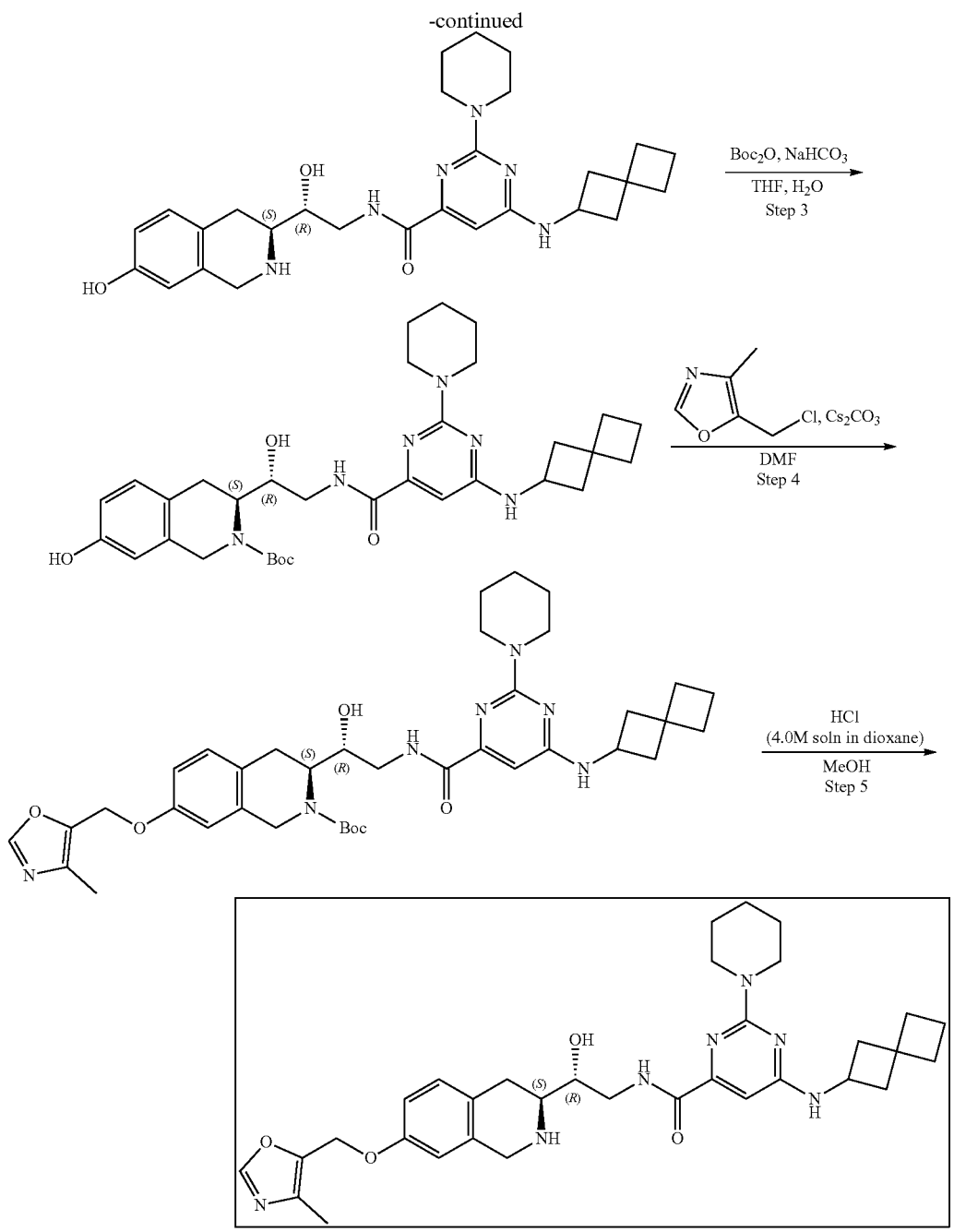

Step 1: Synthesis of tert-butyl (3S)-3-[(1R)-1-hydroxy-2-[[2-(1-piperidyl)-6-(spiro[3.3]heptan-2-ylamino)pyrimidine-4-carbonyl]amino]ethyl]-7-(methoxymethoxy)-3,4-dihydro-1H-isoquinoline-2-carboxylate Methyl 2-(1-piperidyl)-6-(spiro[3.3]heptan-2-ylamino)pyrimidine-4-carboxylate (187.52 mg, 567.50 μmol) and tert-butyl (3S)-3-[(1R)-2-amino-1-hydroxy-ethyl]-7-(methoxymethoxy)-3,4-dihydro-1H-isoquinoline-2-carboxylate (200 mg, 567.50 μmol) were mixed in methanol (2 mL) and heated at 75° C. for 72 h. After the completion of the reaction, the solution was evaporated under reduce pressure. The obtained crude product was purified by HPLC (70-95% water-acetonitrile, 2-10 min, Flow: 30 mL/min) to afford tert-butyl (3S)-3-[(1R)-1-hydroxy-2-[[2-(1-piperidyl)-6-(spiro[3.3]heptan-2-ylamino)pyrimidine-4-carbonyl]amino]ethyl]-7-(methoxymethoxy)-3,4-dihydro-1H-isoquinoline-2-carboxylate (134 mg, 205.90 μmol, 36.28% yield). $^1$H NMR (CDCl$_3$, 400 MHz): δ 1.53 (m, 11H), 1.61 (m, 9H), 1.95 (m, 8H), 2.52 (m, 2H), 3.04 (m, 2H), 3.79 (m, 4H), 4.42 (m, 4H), 4.95 (m, 1H), 5.15 (s, 2H), 6.37 (s, 1H), 6.80 (s, 1H), 6.87 (d, 1H), 7.13 (d, 1H), 9.10 (m, 1H). LCMS (ESI): [M+H]$^+$ m/z: calc'd 650.3; found 651.2; Rt=5.02 min.

Step 2: Synthesis of N-[(2R)-2-hydroxy-2-[(3S)-7-hydroxy-1, 2, 3,4-tetrahydroisoquinolin-3-yl]ethyl]-2-(1-piperidyl)-6-(spiro[3.3]heptan-2-ylamino)pyrimidine-4-carboxamide A solution of tert-butyl (3S)-3-[(1R)-1-hydroxy-2-[[2-(1-piperidyl)-6-(spiro[3.3]heptan-2-ylamino)pyrimidine-4-carbonyl]amino]ethyl]-7-(methoxymethoxy)-

3,4-dihydro-1H-isoquinoline-2-carboxylate (134 mg, 205.90 μmol) and TFA (2 mL) in DCM (2 mL) was stirred for 12 h at 25° C. Then the solution was evaporated to obtain N-[(2R)-2-hydroxy-2-[(3S)-7-hydroxy-1,2,3,4-tetrahydroisoquinolin-3-yl]ethyl]-2-(1-piperidyl)-6-(spiro[3.3]heptan-2-ylamino)pyrimidine-4-carboxamide (120 mg, crude, 3HCl). $^1$H NMR (CD$_3$OD, 400 MHz): δ 1.85 (m, 18H), 2.44 (m, 2H), 3.06 (m, 2H), 3.56 (m, 4H), 3.75 (m, 4H), 4.33 (m, 4H), 6.40 (s, 1H), 6.59 (s, 1H), 6.72 (d, 1H), 7.09 (d, 1H). LCMS (ESI): [M+2H]$^+$ m/z: calc'd 506.3; found 508.4; Rt=1.17 min.

Step 3: Synthesis of tert-butyl (3S)-7-hydroxy-3-[(1R)-1-hydroxy-2-[[2-(1-piperidyl)-6-(spiro[3.3]heptan-2-ylamino)pyrimidine-4-carbonyl]amino]ethyl]-3,4-dihydro-1H-isoquinoline-2-carboxylate To a stirred solution of sodium hydrogen carbonate (68.61 mg, 816.68 μmol, 31.76 μL) in water (2 mL) the solution of N-[(2R)-2-hydroxy-2-[(3S)-7-hydroxy-1,2,3,4-tetrahydroisoquinolin-3-yl]ethyl]-2-(1-piperidyl)-6-(spiro[3.3]heptan-2-ylamino)pyrimidine-4-carboxamide (120 mg, 163.34 μmol, 2CF$_3$COOH) in THF (1.5 mL) was added followed by di-tert-butyl dicarbonate (37.43 mg, 171.50 μmol, 39.36 μL) in THF (1.5 mL). The resulting mixture was stirred at 25° C. for 12 h. After the completion of the reaction, EtOAc (10 mL) was added and the organic phase was separated and washed with brine (2*5 mL). Then the solvent was dried over sodium sulfate, filtered off and evaporated to obtain tert-butyl (3S)-7-hydroxy-3-[(1R)-1-hydroxy-2-[[2-(1-piperidyl)-6-(spiro[3.3]heptan-2-ylamino)pyrimidine-4-carbonyl]amino]ethyl]-3,4-dihydro-1H-isoquinoline-2-carboxylate (85 mg, crude). $^1$H NMR (CDCl$_3$, 400 MHz): δ 1.23 (m, 6H), 1.38 (m, 14H), 1.91 (m, 6H), 3.12 (m, 4H), 3.75 (m, 6H), 4.25 (m, 4H), 6.50 (s, 1H), 6.55 (s, 1H), 6.58 (d, 1H), 6.99 (d, 1H), 9.15 (m, 1H). LCMS (ESI): [M+H]$^+$ m/z: calc'd 606.3; found 607.4; Rt=1.67 min.

Step 4: Synthesis of tert-butyl (3S)-3-[(1R)-1-hydroxy-2-[[2-(1-piperidyl)-6-(spiro[3.3]heptan-2-ylamino)pyrimidine-4-carbonyl]amino]ethyl]-7-[(4-methyloxazol-5-yl)methoxy]-3,4-dihydro-1H-isoquinoline-2-carboxylate To the mixture of tert-butyl (3S)-7-hydroxy-3-[(1R)-1-hydroxy-2-[[2-(1-piperidyl)-6-(spiro[3.3]heptan-2-ylamino)pyrimidine-4-carbonyl]amino]ethyl]-3,4-dihydro-1H-isoquinoline-2-carboxylate (85 mg, 140.09 μmol), cesium carbonate (136.93 mg, 420.27 μmol) in DMF (3 mL) was added 5-(chloromethyl)-4-methyl-oxazole (28.25 mg, 168.11 μmol, HCl). The reaction mixture was heated at 50° C. for 12 h. After the completion of the reaction, the resulting mixture was filtered off and evaporated under reduced pressure to obtain tert-butyl (3S)-3-[(1R)-1-hydroxy-2-[[2-(1-piperidyl)-6-(spiro[3.3]heptan-2-ylamino)pyrimidine-4-carbonyl]amino]ethyl]-7-[(4-methyloxazol-5-yl)methoxy]-3,4-dihydro-1H-isoquinoline-2-carboxylate (90 mg, crude). The obtained product was used without further purification. LCMS (ESI): [M+2H]$^+$ m/z: calc'd 701.4; found 703.4; Rt=1.52 min.

Step 5: Synthesis of N-[(2R)-2-hydroxy-2-[(3S)-7-[(4-methyloxazol-5-yl)methoxy]-1,2,3,4-tetrahydroisoquinolin-3-yl]ethyl]-2-(1-piperidyl)-6-(spiro[3.3]heptan-2-ylamino)pyrimidine-4-carboxamide (Compound 57) The solution of tert-butyl (3S)-3-[(1R)-1-hydroxy-2-[[2-(1-piperidyl)-6-(spiro[3.3]heptan-2-ylamino)pyrimidine-4-carbonyl]amino]ethyl]-7-[(4-methyloxazol-5-yl)methoxy]-3,4-dihydro-1H-isoquinoline-2-carboxylate (90 mg, 128.23 μmol) in dioxane/HCl (2 mL) and Methanol (2 mL) was stirred for 3 h at 25° C. After LCMS showed full conversion of starting material, the resulting mixture was stirred with SiliaMetS DMT (30 mg) in methanol (1 mL) for 12 h. The obtained suspension was filtered off, evaporated in vacuo and purified by HPLC (40-90% 0-5 min, water+NH$_3$-methanol+NH$_3$) to obtain N-[(2R)-2-hydroxy-2-[(3S)-7-[(4-methyloxazol-5-yl)methoxy]-1,2,3,4-tetrahydroisoquinolin-3-yl]ethyl]-2-(1-piperidyl)-6-(spiro[3.3]heptan-2-ylamino)pyrimidine-4-carboxamide (14.9 mg, 24.76 μmol, 19.31% yield). $^1$H NMR (500 MHz, DMSO-d$_6$) δ 1.56 (m, 4H), 1.65 (m, 2H), 1.82 (m, 2H), 1.87 (m, 2H), 1.94 (m, 2H), 2.06 (m, 2H), 2.17 (s, 3H), 2.37 (m, 2H), 2.59 (m, 1H), 2.75 (m, 2H), 2.98 (m, 1H), 3.37 (m, 1H), 3.54 (m, 2H), 3.71 (m, 4H), 3.90 (m, 2H), 4.18 (m, 1H), 4.89 (m, 1H), 4.97 (s, 2H), 6.29 (m, 1H), 6.60 (s, 1H), 6.69 (m, 1H), 6.97 (d, 1H), 7.17 (m, 1H), 8.02 (s, 1H), 8.52 (t, 1H). LCMS (ESI): [M+H]$^+$ m/z: calc'd 601.3; found 603.4; Rt=1.26 min.

Example 4A8. Synthesis of 6-[(2-acetyl-2-azaspiro[3.3]heptan-6-yl)amino]-N-[(2R)-2-hydroxy-2-[(3S)-7-[(4-methyloxazol-5-yl)methoxy]-1,2,3,4-tetrahydroisoquinolin-3-yl]ethyl]-2-(1-piperidyl)pyrimidine-4-carboxamide (Compound 48)

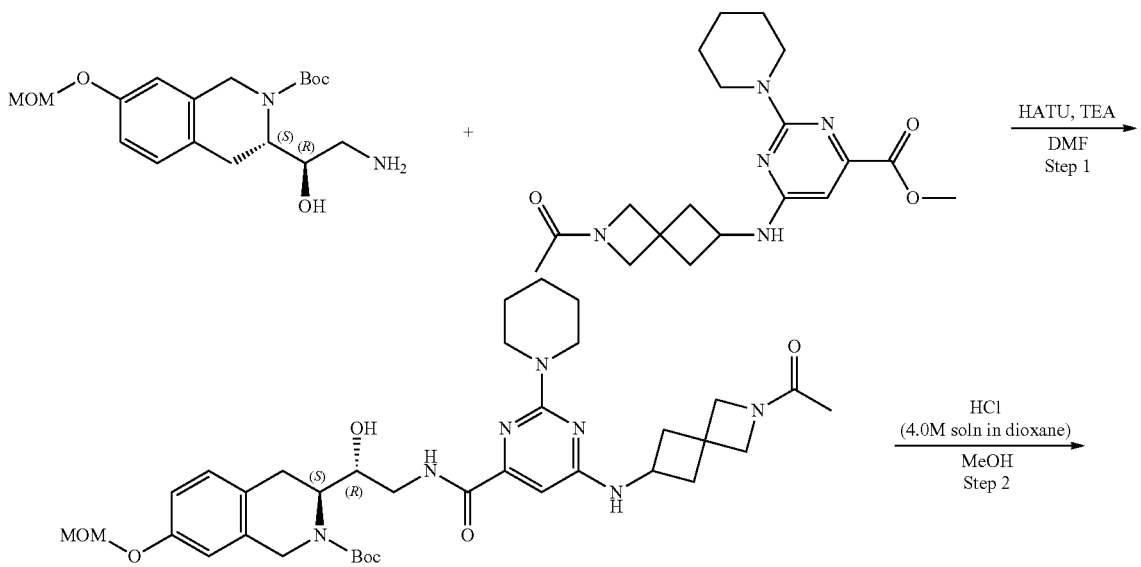

427 428
-continued
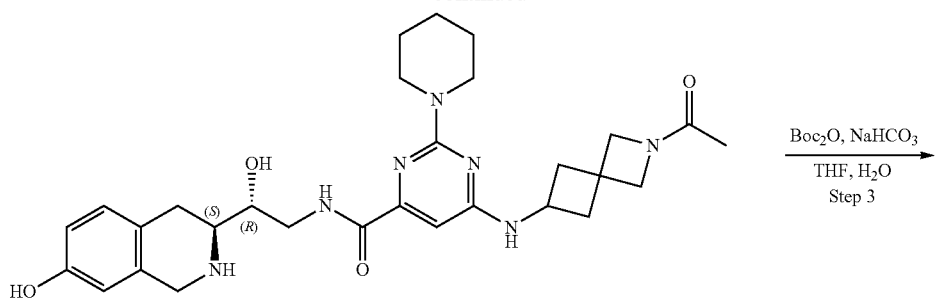
Boc₂O, NaHCO₃
———————→
THF, H₂O
Step 3
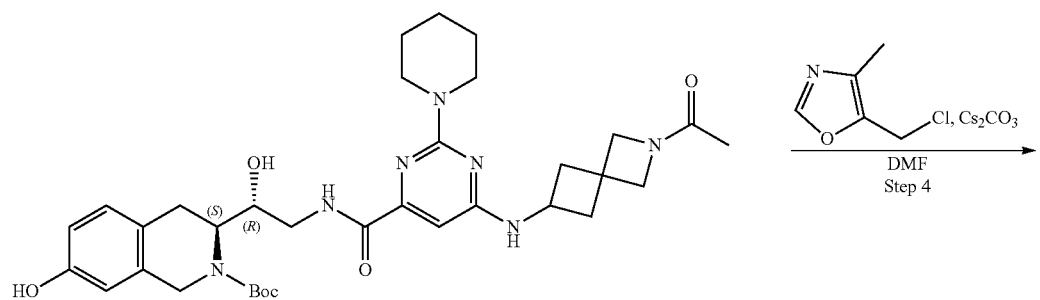
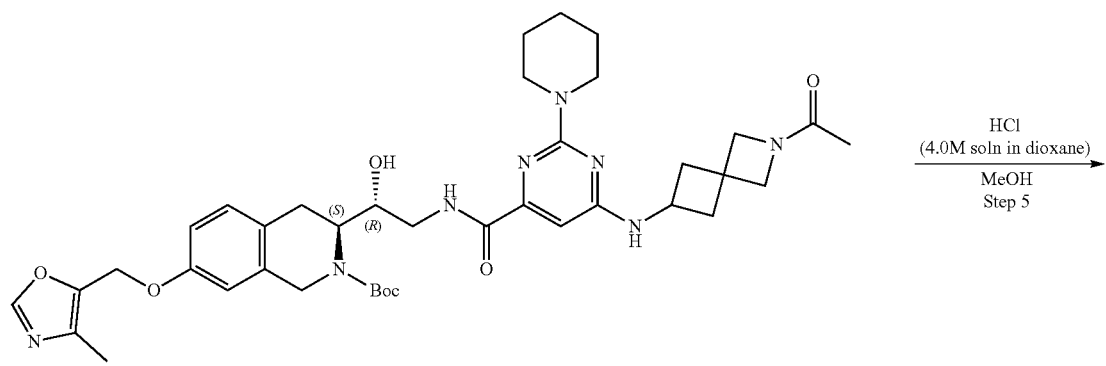
HCl
(4.0M soln in dioxane)
————————→
MeOH
Step 5
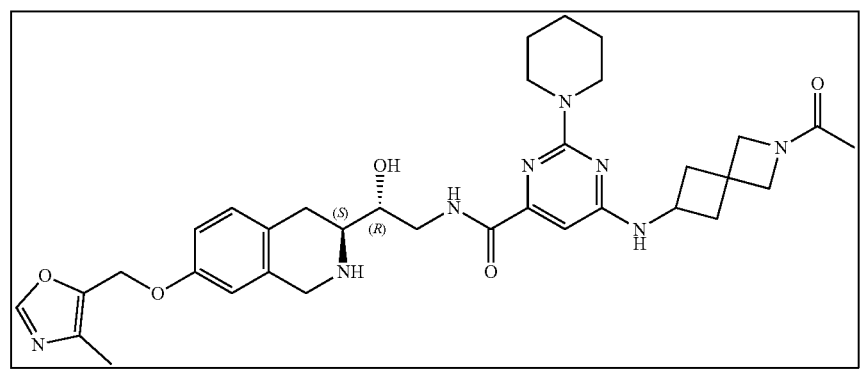

Step 1: Synthesis of tert-butyl (3S)-3-[(1R)-2-[[6-[(2-acetyl-2-azaspiro[3.3]heptan-6-yl)amino]-2-(1-piperidyl)pyrimidine-4-carbonyl]amino]-1-hydroxy-ethyl]-7-(methoxymethoxy)-3,4-dihydro-1H-isoquinoline-2-carboxylate tert-Butyl (3S)-3-[(1R)-2-amino-1-hydroxy-ethyl]-7-(methoxymethoxy)-3,4-dihydro-1H-isoquinoline-2-carboxylate (0.2 g, 567.50 μmol) and methyl 6-[(2-acetyl-2-azaspiro[3.3]heptan-6-yl)amino]-2-(1-piperidyl)pyrimidine-4-carboxylate (211.93 mg, 567.50 μmol) were mixed together in MeOH (3 mL) and the resulting mixture was heated at 75° C. for 65 h. After the completion of the reaction, the resulting mixture was allowed to cool to room temperature and evaporated to dryness. The residue was purified by HPLC (30-40% water-acetonitrile, 10 min, flow: 30 mL/min (loading pump 4 mL/min acetonitrile)) to obtain tert-butyl (3S)-3-[(1R)-2-[[6-[(2-acetyl-2-azaspiro[3.3]heptan-6-yl)amino]-2-(1-piperidyl)pyrimidine-4-carbonyl]amino]-1-hydroxy-ethyl]-7-(methoxymethoxy)-3,4-dihydro-1H-isoquinoline-2-carboxylate (154.70 mg, 222.97 μmol, 39.29% yield). $^1$H NMR (DMSO-$d_6$, 400 MHz): δ 1.39 (m, 15H), 1.45 (m, 2H), 1.72 (m, 3H), 2.10 (m, 2H), 2.87 (m, 4H), 3.36 (m, 4H), 3.73 (m, 6H), 4.10 (m, 6H), 4.70 (m, 1H), 5.14 (m, 3H), 6.83 (m, 2H), 7.08 (d, 1H), 7.51 (m, 1H), 8.49 (m, 1H). LCMS (ESI): [M+H]$^+$ m/z: calc'd 693.3; found 694.4; Rt=1.48 min.

Step 2: Synthesis of 6-[(2-acetyl-2-azaspiro[3.3]heptan-6-yl)amino]-N-[(2R)-2-hydroxy-2-[(3S)-7-hydroxy-1,2,3,4-tetrahydroisoquinolin-3-yl]ethyl]-2-(1-piperidyl)pyrimidine-4-carboxamide tert-Butyl (3S)-3-[(1R)-2-[[6-[(2-acetyl-2-azaspiro[3.3]heptan-6-yl)amino]-2-(1-piperidyl)pyrimidine-4-carbonyl]amino]-1-hydroxy-ethyl]-7-(methoxymethoxy)-3,4-dihydro-1H-isoquinoline-2-carboxylate (154.70 mg, 222.97 μmol) was dissolved in MeOH (4 mL) and hydrogen chloride solution 4.0M in dioxane (97.55 mg, 2.68 mmol, 121.94 μL) was added thereto. The resulting mixture was stirred for 3 h. Then the reaction mixture was evaporated to dryness to obtain 6-[(2-acetyl-2-azaspiro[3.3]heptan-6-yl)amino]-N-[(2R)-2-hydroxy-2-[(3S)-7-hydroxy-1,2,3,4-tetrahydroisoquinolin-3-yl]ethyl]-2-(1-piperidyl)pyrimidine-4-carboxamide (0.155 g, 222.86 μmol, 99.95% yield, 4HCl). $^1$H NMR (DMSO-$d_6$, 400 MHz): δ 1.54 (m, 6H), 1.72 (m, 3H), 2.16 (m, 2H), 2.56 (m, 2H), 2.97 (m, 2H), 3.40 (m, 3H), 3.73 (m, 5H), 4.03 (m, 6H), 6.40 (s, 1H), 6.59 (s, 1H), 6.70 (d, 1H), 7.02 (d, 1H), 8.90 (m, 2H), 9.64 (m, 1H). LCMS (ESI): [M+2H]$^+$ m/z: calc'd 549.3; found 551.2; Rt=0.98 min.

Step 3: Synthesis of tert-butyl (3S)-3-[(1R)-2-[[6-[(2-acetyl-2-azaspiro[3.3]heptan-6-yl)amino]-2-(1-piperidyl)pyrimidine-4-carbonyl]amino]-1-hydroxy-ethyl]-7-hydroxy-3,4-dihydro-1H-isoquinoline-2-carboxylate 6-[(2-Acetyl-2-azaspiro[3.3]heptan-6-yl)amino]-N-[(2R)-2-hydroxy-2-[(3S)-7-hydroxy-1,2,3,4-tetrahydroisoquinolin-3-yl]ethyl]-2-(1-piperidyl)pyrimidine-4-carboxamide (0.155 g, 222.86 μmol, 4HCl) was dissolved in water (2 mL) and sodium bicarbonate (131.05 mg, 1.56 mmol, 60.67 μL) was added thereto. The resulting mixture was diluted with THF (2 mL) and di-tert-butyl dicarbonate (48.64 mg, 222.86 μmol, 51.14 μL) was added. The reaction mixture was stirred for 18 h. After the completion of the reaction, the resulting mixture was extracted with EtOAc (2*15 mL) and combined organic layers were washed with brine, dried over Na$_2$SO$_4$, filtered off, and evaporated to obtain tert-butyl (3S)-3-[(1R)-2-[[6-[(2-acetyl-2-azaspiro[3.3]heptan-6-yl)amino]-2-(1-piperidyl)pyrimidine-4-carbonyl]amino]-1-hydroxy-ethyl]-7-hydroxy-3,4-dihydro-1H-isoquinoline-2-carboxylate (0.0843 g, 129.74 μmol, 58.21% yield). $^1$H NMR (DMSO-$d_6$, 400 MHz): δ 1.38 (m, 10H), 1.58 (m, 4H), 2.09 (m, 4H), 2.69 (m, 2H), 2.94 (m, 2H), 3.69 (m, 6H), 4.10 (m, 6H), 4.63 (m, 1H), 5.02 (m, 1H), 6.25 (s, 1H), 6.51 (s, 1H), 6.56 (d, 1H), 6.93 (d, 1H), 7.47 (m, 1H), 8.47 (m, 1H), 9.17 (m, 1H). LCMS (ESI): [M+H]$^+$ m/z: calc'd 649.3; found 650.4; Rt=1.37 min.

Step 4: Synthesis of tert-butyl (3S)-3-[(1R)-2-[[6-[(2-acetyl-2-azaspiro[3.3]heptan-6-yl)amino]-2-(1-piperidyl)pyrimidine-4-carbonyl]amino]-1-hydroxy-ethyl]-7-[(4-methyloxazol-5-yl)methoxy]-3,4-dihydro-1H-isoquinoline-2-carboxylate tert-Butyl (3S)-3-[(1R)-2-[[6-[(2-acetyl-2-azaspiro[3.3]heptan-6-yl)amino]-2-(1-piperidyl)-pyrimidine-4-carbonyl]amino]-1-hydroxy-ethyl]-7-hydroxy-3,4-dihydro-1H-isoquinoline-2-carboxylate (0.0843 g, 129.74 μmol), 5-(chloromethyl)-4-methyl-oxazole (30.52 mg, 181.63 μmol, HCl) and cesium carbonate (169.08 mg, 518.95 μmol) were mixed together in DMF (2 mL) and the resulting mixture was heated at 60° C. for 18 h. After the completion of the reaction, the resulting mixture was cooled to room temperature and diluted with water (10 mL). The resulting mixture was extracted with EtOAc (2*15 mL) and the combined organic layers were washed with water (4*5 mL) and brine, dried over Na$_2$SO$_4$, filtered off and evaporated to obtain tert-butyl (3S)-3-[(1R)-2-[[6-[(2-acetyl-2-azaspiro[3.3]heptan-6-yl)amino]-2-(1-piperidyl)pyrimidine-4-carbonyl]amino]-1-hydroxy-ethyl]-7-[(4-methyloxazol-5-yl)methoxy]-3,4-dihydro-1H-isoquinoline-2-carboxylate (65.70 mg, 88.20 μmol, 67.99% yield). $^1$H NMR (DMSO-$d_6$, 500 MHz): δ 1.39 (m, 9H), 1.47 (m, 3H), 1.70 (m, 4H), 1.98 (s, 3H), 2.09 (m, 3H), 2.72 (m, 2H), 3.04 (m, 1H), 3.71 (m, 8H), 4.02 (m, 4H), 4.14 (m, 4H), 4.68 (m, 1H), 5.32 (m, 3H), 6.27 (s, 1H), 6.53 (d, 1H), 6.81 (m, 2H), 7.05 (d, 1H), 7.48 (m, 1H), 8.37 (m, 2H). LCMS (ESI): [M+H]$^+$ m/z: calc'd 744.4; found 745.2; Rt=1.37 min.

Step 5: Synthesis of 6-[(2-acetyl-2-azaspiro[3.3]heptan-6-yl)amino]-N-[(2R)-2-hydroxy-2-[(3S)-7-[(4-methyloxazol-5-yl)methoxy]-1,2,3,4-tetrahydroisoquinolin-3-yl]ethyl]-2-(1-piperidyl)pyrimidine-4-carboxamide (Compound 48) tert-Butyl (3S)-3-[(1R)-2-[[6-[(2-acetyl-2-azaspiro[3.3]heptan-6-yl)amino]-2-(1-piperidyl)-pyrimidine-4-carbonyl]amino]-1-hydroxy-ethyl]-7-[(4-methyloxazol-5-yl)methoxy]-3,4-dihydro-1H-isoquinoline-2-carboxylate (65.70 mg, 88.20 μmol) was dissolved in MeOH (2 mL) and hydrogen chloride solution 4.0M in dioxane (19.30 mg, 529.21 μmol, 24.12 μL) was added thereto. The resulting mixture was stirred for 2 h and the evaporated to dryness. The residue was dissolved in 3 mL of MeOH and 15 mg of scavenger (SiliaMetS Dimercaptotriazine(DMT)) was added thereto and the resulting suspension was stirred for 12 h. The suspension was filtered off, the filtrate was evaporated under reduced pressure. The residue was purified by HPLC (40-90% 0-5 min, water+NH$_3$-methanol+NH$_3$, flow 30 mL/min (loading pump 4 mL/min) to obtain 6-[(2-acetyl-2-azaspiro[3.3]heptan-6-yl)amino]-N-[(2R)-2-hydroxy-2-[(3S)-7-[(4-methyloxazol-5-yl)methoxy]-1,2,3,4-tetrahydroisoquinolin-3-yl]ethyl]-2-(1-piperidyl)pyrimidine-4-carboxamide (0.0251 g, 38.93 μmol, 44.14% yield). $^1$H NMR (500 MHz, DMSO-$d_6$) δ 1.56 (m, 4H), 1.65 (m, 2H), 1.72 (m, 3H), 2.01 (m, 1H), 2.17 (m, 5H), 2.57 (m, 3H), 2.75 (m, 2H), 3.38 (m, 1H), 3.55 (m, 2H), 3.72 (m, 4H), 3.79 (m, 1H), 3.90 (m, 3H), 4.05 (m, 1H), 4.17 (m, 1H), 4.23 (m, 1H), 4.88 (d, 1H), 4.97 (s, 2H), 6.30 (s, 1H), 6.60 (s, 1H), 6.69 (d, 1H), 6.96 (d, 1H), 7.31 (m, 1H), 8.02 (s, 1H), 8.54 (m, 1H). LCMS (ESI): [M+H]$^+$ m/z: calc'd 644.3; found 645.4; Rt=1.03 min.

Example 4A9. Synthesis of 6-[(1-acetylazetidin-3-yl)amino]-N-[(2R)-2-hydroxy-2-[(3S)-7-[(4-methyl-oxazol-5-yl)methoxy]-1,2,3,4-tetrahydroisoquinolin-3-yl]ethyl]-2-(4-isopropylpiperazin-1-yl)pyrimidine-4-carboxamide (Compound 47)
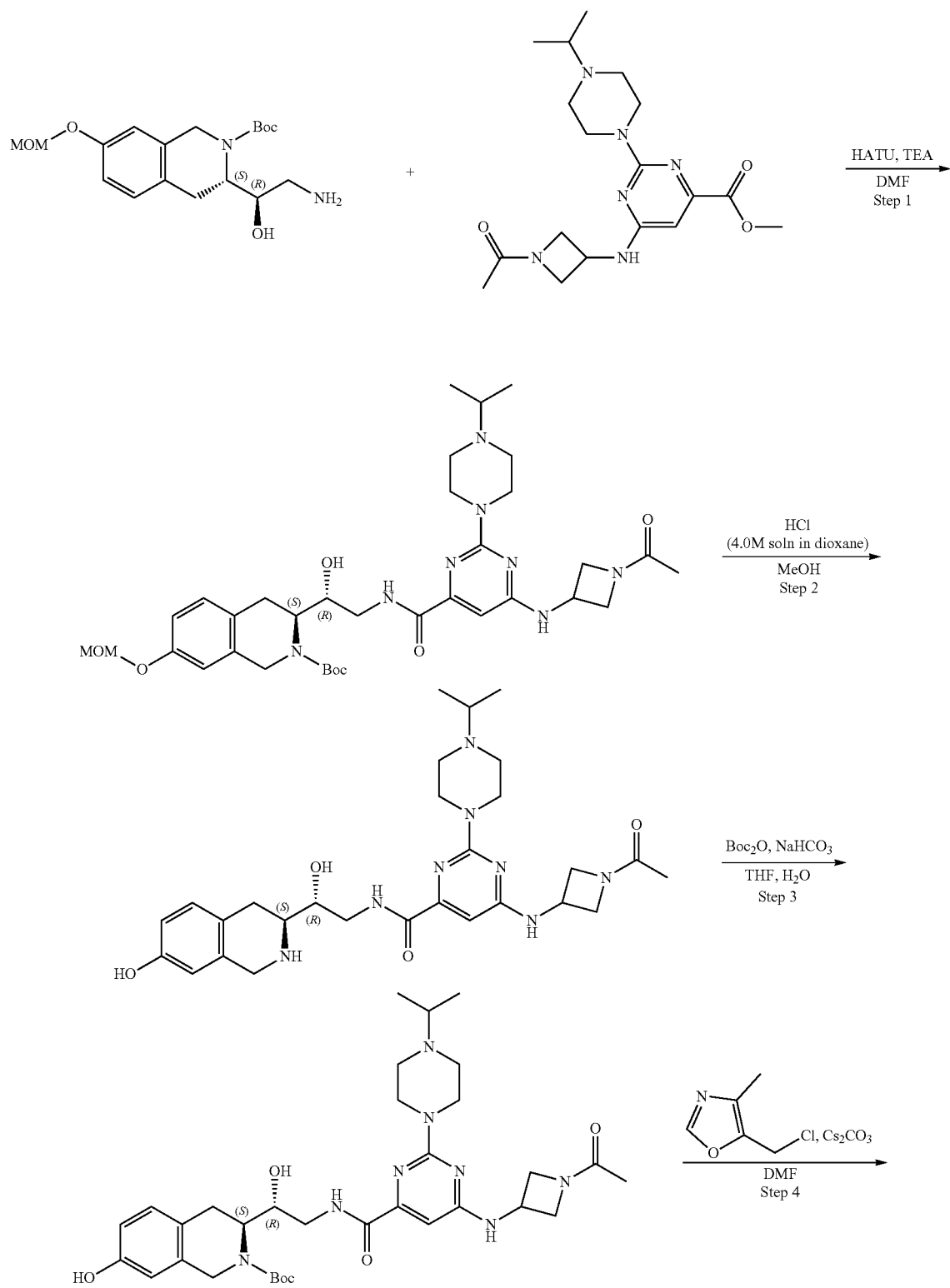

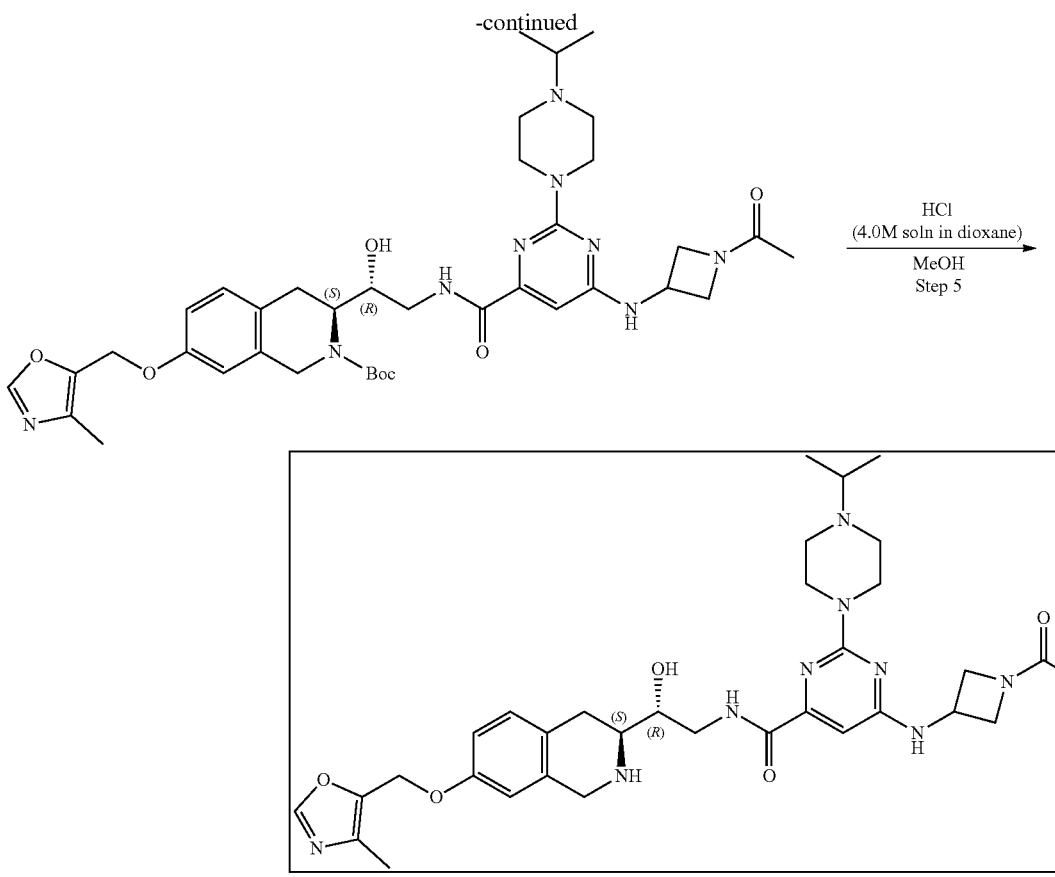

Step 1: Synthesis of tert-butyl (3S)-3-[(1R)-2-[[6-[(1-acetylazetidin-3-yl)amino]-2-(4-isopropylpiperazin-1-yl)pyrimidine-4-carbonyl]amino]-1-hydroxy-ethyl]-7-(methoxymethoxy)-3,4-dihydro-1H-isoquinoline-2-carboxylate tert-Butyl (3S)-3-[(1R)-2-amino-1-hydroxy-ethyl]-7-(methoxymethoxy)-3,4-dihydro-1H-iso-quinoline-2-carboxylate (0.2 g, 567.50 μmol) and methyl 6-[(1-acetylazetidin-3-yl)amino]-2-(4-iso-propylpiperazin-1-yl)pyrimidine-4-carboxylate (213.64 mg, 567.50 μmol) were mixed together in MeOH (3 mL) and the resulting mixture was heated at 75° C. for 65 h. After LCMS showed full conversion of starting material, the reaction mixture was cooled to room temperature and evaporated to dryness. The residue was purified by HPLC (Column: SunFire C18 100*19 mm, 5 μm 15-40% H$_2$O-MeCN, 2-10 min, flow: 30 mL/min) to obtain tert-butyl (3S)-3-[(1R)-2-[[6-[(1-acetylazetidin-3-yl)amino]-2-(4-isopropylpiperazin-1-yl)pyrimidine-4-carbonyl]amino]-1-hydroxy-ethyl]-7-(methoxymethoxy)-3,4-dihydro-1H-isoquinoline-2-carboxylate (122.90 mg, 176.37 μmol, 31.08% yield). $^1$H NMR (DMSO-d$_6$, 400 MHz): δ 0.98 (m, 6H), 1.43 (m, 9H), 1.76 (s, 3H), 2.45 (m, 4H), 2.87 (m, 4H), 3.29 (m, 1H), 3.36 (s, 2H), 3.71 (m, 6H), 3.95 (m, 1H), 4.11 (m, 2H), 4.22 (m, 1H), 4.40 (m, 1H), 4.54 (m, 1H), 4.75 (m, 1H), 5.14 (m, 3H), 6.37 (s, 1H), 6.82 (m, 2H), 7.06 (d, 1H), 7.92 (m, 1H), 8.35 (m, 1H), 8.55 (m, 1H). LCMS (ESI): [M+H]$^+$ m/z: calc'd 696.4; found 697.4; Rt=1.21 min.

Step 2: Synthesis of 6-[(1-acetylazetidin-3-yl)amino]-N-[(2R)-2-hydroxy-2-[(3S)-7-hydroxy-1,2,3,4-tetrahydroiso-quinolin-3-yl]ethyl]-2-(4-isopropylpiperazin-1-yl)pyrimidine-4-carboxamide tert-Butyl (3S)-3-[(1R)-2-[[6-[(1-acetylazetidin-3-yl)amino]-2-(4-isopropylpiperazin-1-yl)-pyrimidine-4-carbonyl]amino]-1-hydroxy-ethyl]-7-(methoxymethoxy)-3,4-dihydro-1H-isoquinoline-2-carboxylate (122.90 mg, 176.37 μmol) was dissolved in MeOH (4 mL) and hydrogen chloride solution 4.0M in dioxane (77.17 mg, 2.12 mmol, 96.46 μL) was added. The resulting mixture was stirred for 3 h. Then the reaction mixture was evaporated to dryness to obtain 6-[(1-acety-lazetidin-3-yl)amino]-N-[(2R)-2-hydroxy-2-[(3S)-7-hy-droxy-1,2,3,4-tetrahydroisoquinolin-3-yl]ethyl]-2-(4-iso-propylpiperazin-1-yl)pyrimidine-4-carboxamide (0.1296 g, 176.33 μmol, 99.98% yield, 5HCl). $^1$H NMR (DMSO-d$_6$, 500 MHz): δ 1.30 (m, 6H), 1.76 (s, 3H), 3.00 (m, 6H), 3.35 (m, 8H), 3.95 (m, 2H), 4.14 (m, 3H), 4.41 (m, 3H), 4.82 (m, 2H), 6.50 (s, 1H), 6.58 (s, 1H), 6.70 (d, 1H), 7.03 (d, 1H), 8.17 (m, 1H), 8.77 (m, 1H), 8.88 (m, 1H), 9.43 (m, 1H), 10.58 (m, 1H). LCMS (ESI): [M+H]$^+$ m/z: calc'd 552.3; found 553.4; Rt=0.71 min.

Step 3: Synthesis of tert-butyl (3S)-3-[(1R)-2-[[6-[(1-acetylazetidin-3-yl)amino]-2-(4-isopropylpiperazin-1-yl)pyrimidine-4-carbonyl]amino]-1-hydroxy-ethyl]-7-hy-droxy-3,4-dihydro-1H-isoquinoline-2-carboxylate 6-[(1-Acetylazetidin-3-yl)amino]-N-[(2R)-2-hydroxy-2-[(3S)-7-hydroxy-1,2,3,4-tetrahydro-isoquinolin-3-yl]ethyl]-2-(4-isopropylpiperazin-1-yl)pyrimidine-4-carboxamide (0.1296 g, 176.33 μmol, 5HCl) was dissolved in water (2 mL) and sodium bicarbonate (103.69 mg, 1.23 mmol, 48.01 μL) was added. The resulting mixture was diluted with THF (2 mL) and di-tert-butyl dicarbonate (38.48 mg, 176.33 μmol, 40.47 μL) was added. The reaction mixture was stirred for 18 h. After the completion of the reaction, the resulting mixture was extracted with EtOAc (2*15 mL) and the combined organic layer was washed with brine, dried over Na$_2$SO$_4$, filtered off and evaporated to obtain tert-butyl (3S)-3-[(1R)-2-[[6-[(1-acetylazetidin-3-yl)amino]-2-(4-isopropylpiperazin-1-yl)pyrimidine-4-carbonyl]amino]-1-hydroxy-ethyl]-7-hydroxy-3,4-dihydro-1H-isoquinoline-2-carboxylate (0.0833 g, 127.61 μmol, 72.37% yield). $^1$H NMR (DMSO-d$_6$, 400 MHz): δ 0.98 (m, 6H), 1.40 (m, 9H), 1.75 (s, 3H), 2.65 (m, 6H), 2.94 (m, 2H), 3.70 (m, 6H), 3.93 (m, 2H), 4.10 (m, 3H), 4.52 (m, 3H), 5.27 (m, 1H), 6.36 (s, 1H), 6.51 (s, 1H), 6.58 (d, 1H), 6.93 (d, 1H), 7.92 (m, 1H), 8.53 (m, 1H), 9.18 (m, 1H). LCMS (ESI): [M+H]$^+$ m/z: calc'd 652.3; found 653.4; Rt=1.06 min.

Step 4: Synthesis of tert-butyl (3S)-3-[(1R)-2-[[6-[(1-acetylazetidin-3-yl)amino]-2-(4-isopropylpiperazin-1-yl)pyrimidine-4-carbonyl]amino]-1-hydroxy-ethyl]-7-[(4-methyloxazol-5-yl)methoxy]-3,4-dihydro-1H-isoquinoline-2-carboxylate tert-Butyl (3S)-3-[(1R)-2-[[6-[(1-acetylazetidin-3-yl)amino]-2-(4-isopropylpiperazin-1-yl)-pyrimidine-4-carbonyl]amino]-1-hydroxy-ethyl]-7-hydroxy-3,4-dihydro-1H-isoquinoline-2-carboxylate (0.0833 g, 127.61 μmol), 5-(chloromethyl)-4-methyl-oxazole (30.02 mg, 178.65 μmol, HCl) and cesium carbonate (166.31 mg, 510.43 μmol) were mixed together in DMF (2 mL) and the resulting mixture was heated at 60° C. for 18 h. After the completion of the reaction, the reaction mixture was cooled to room temperature and diluted with water (10 mL). The resulting mixture was extracted with EtOAc (2*15 mL) and the combined organic layer was washed with water (4*5 mL), brine, dried over Na$_2$SO$_4$, filtered off and evaporated to obtain tert-butyl (3S)-3-[(1R)-2-[[6-[(1-acetylazetidin-3-yl)amino]-2-(4-isopropylpiperazin-1-yl)pyrimidine-4-carbonyl]amino]-1-hydroxy-ethyl]-7-[(4-methyloxazol-5-yl)methoxy]-3,4-dihydro-1H-isoquinoline-2-carboxylate (0.0736 g, 98.41 μmol, 77.12% yield). $^1$H NMR (DMSO-d$_6$, 500 MHz): δ 0.98 (m, 6H), 1.42 (m, 9H), 1.75 (s, 3H), 2.15 (m, 4H), 2.62 (m, 2H), 3.05 (m, 2H), 3.70 (m, 8H), 3.94 (m, 2H), 4.11 (m, 2H), 4.39 (m, 2H), 4.71 (m, 2H), 5.29 (m, 3H), 6.38 (s, 1H), 6.83 (d, 1H), 6.86 (s, 1H), 7.08 (d, 1H), 7.94 (m, 1H), 8.27 (m, 1H). LCMS (ESI): [M+H]$^+$ m/z: calc'd 747.4; found 748.4; Rt=1.07 min.

Step 5: Synthesis of 6-[(1-acetylazetidin-3-yl)amino]-N-[(2R)-2-hydroxy-2-[(3S)-7-[(4-methyloxazol-5-yl)methoxy]-1,2,3,4-tetrahydroisoquinolin-3-yl]ethyl]-2-(4-isopropylpiperazin-1-yl)pyrimidine-4-carboxamide (Compound 47) tert-Butyl (3S)-3-[(1R)-2-[[6-[(1-acetylazetidin-3-yl)amino]-2-(4-isopropylpiperazin-1-yl)-pyrimidine-4-carbonyl]amino]-1-hydroxy-ethyl]-7-[(4-methyloxazol-5-yl)methoxy]-3,4-dihydro-1H-isoquinoline-2-carboxylate (0.0736 g, 98.41 μmol) was dissolved in MeOH (2 mL) and hydrogen chloride solution 4.0M in dioxane (21.53 mg, 590.47 μmol, 26.91 μL) was added. The resulting mixture was stirred for 2 h and then evaporated to dryness. After the completion of the reaction, the residue was dissolved in 3 mL of MeOH and 15 mg of scavenger (SiliaMetS Dimercaptotriazine(DMT)) was added and the resulting suspension was stirred for 12 h. The suspension was filtered off, the filtrate was evaporated under reduced pressure. The residue was purified by HPLC (40-90% 0-5 min, water+NH$_3$-methanol+NH$_3$, flow 30 mL/min (loading pump 4 mL/min)) to obtain 6-[(1-acetylazetidin-3-yl)amino]-N-[(2R)-2-hydroxy-2-[(3S)-7-[(4-methyloxazol-5-yl)methoxy]-1,2,3,4-tetrahydroisoquinolin-3-yl]ethyl]-2-(4-isopropylpiperazin-1-yl)pyrimidine-4-carboxamide (0.0235 g, 36.28 μmol, 36.86% yield). $^1$H NMR (400 MHz, DMSO-d$_6$) δ 0.99 (d, 6H), 1.76 (s, 3H), 2.15 (s, 3H), 2.45 (m, 6H), 2.73 (m, 4H), 3.54 (m, 2H), 3.69 (m, 5H), 3.85 (m, 2H), 3.95 (m, 1H), 4.12 (m, 1H), 4.41 (m, 1H), 4.54 (m, 1H), 5.06 (s, 3H), 6.39 (m, 1H), 6.70 (s, 1H), 6.76 (d, 1H), 7.00 (d, 1H), 7.93 (m, 1H), 8.27 (s, 1H), 8.77 (m, 1H). LCMS (ESI): [M+H]$^+$ m/z: calc'd 647.3; found 649.4; Rt=0.79 min.

Example 4A10. Synthesis of 6-[(1-acetylazetidin-3-yl)amino]-N-[(2R)-2-hydroxy-2-[(3S)-7-[(4-methyloxazol-5-yl)methoxy]-1,2,3,4-tetrahydroisoquinolin-3-yl]ethyl]-2-pyrrolidin-1-yl-pyrimidine-4-carboxamide (Compound 61)

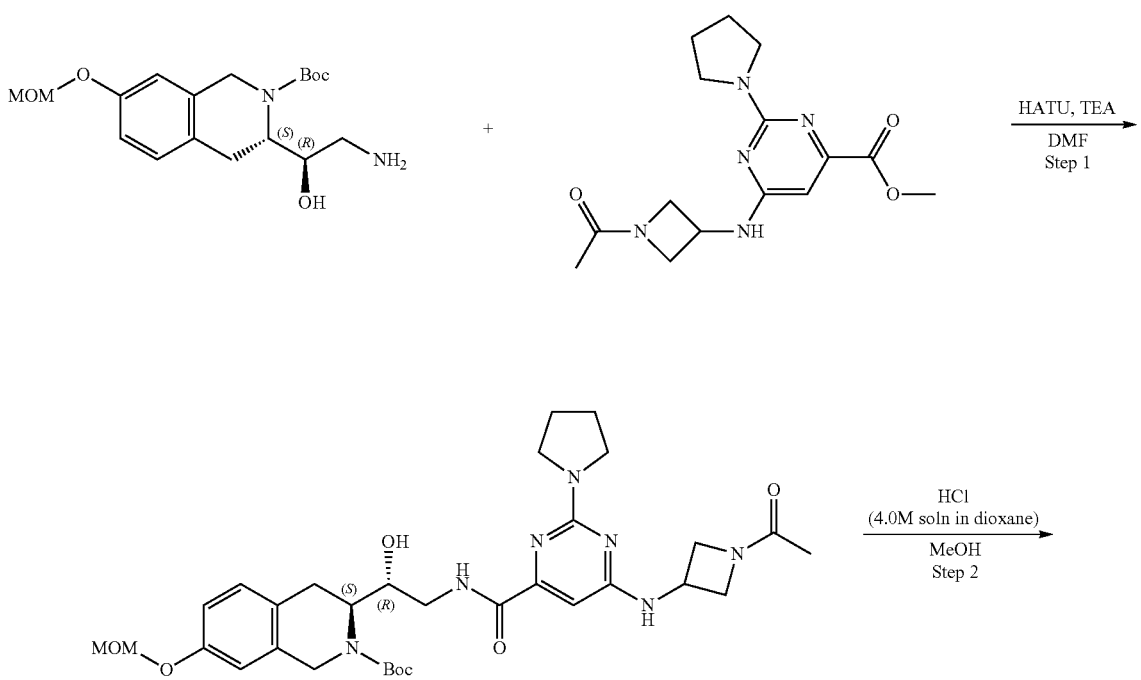

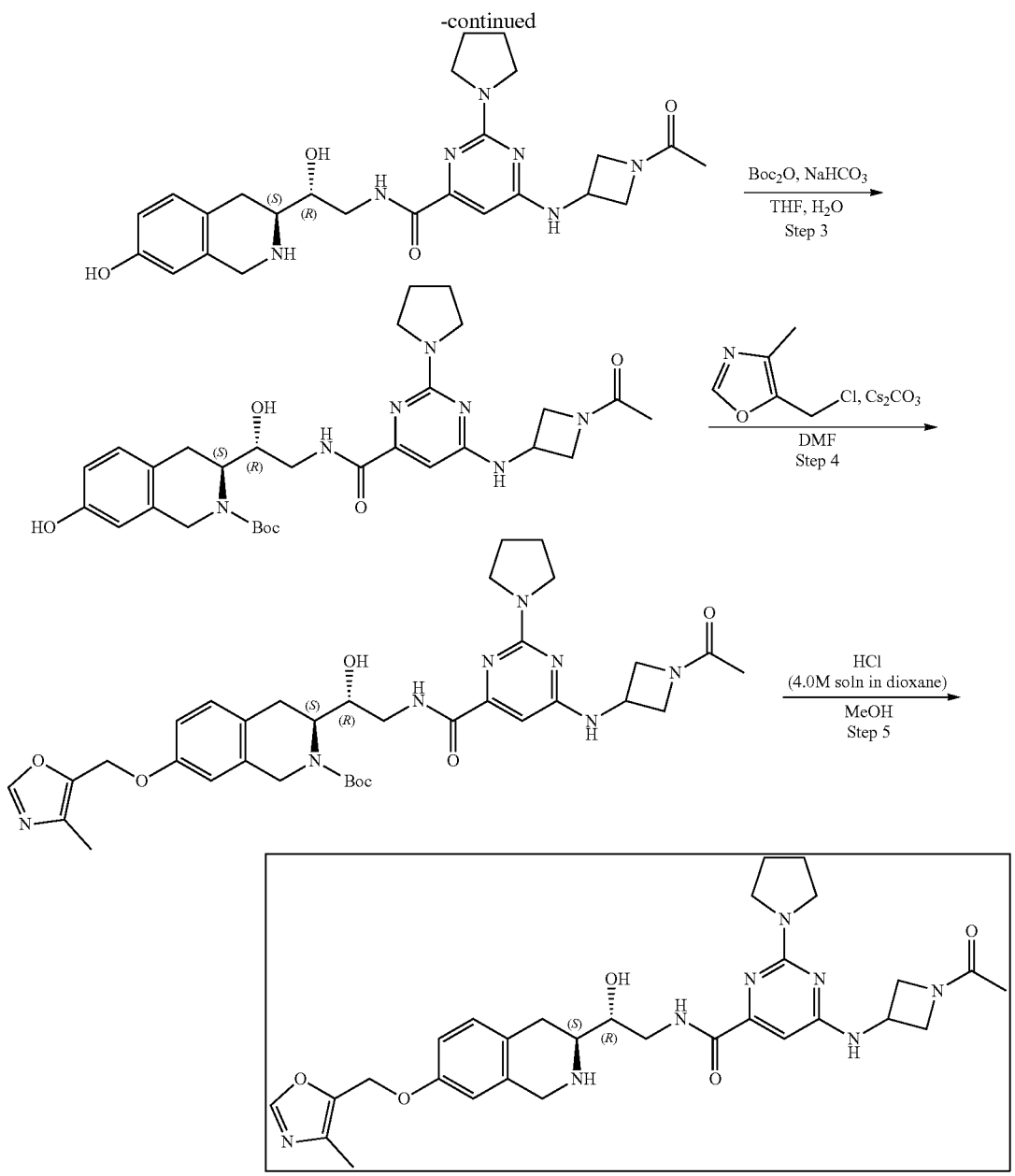

Step 1: Synthesis of tert-butyl (3S)-3-[(1R)-2-[[6-[(1-acetylazetidin-3-yl)amino]-2-pyrrolidin-1-yl-pyrimidine-4-carbonyl]amino]-1-hydroxy-ethyl]-7-(methoxymethoxy)-3,4-dihydro-1H-isoquinoline-2-carboxylate tert-Butyl (3S)-3-[(1R)-2-amino-1-hydroxy-ethyl]-7-(methoxymethoxy)-3,4-dihydro-1H-iso-quinoline-2-carboxylate (0.2 g, 567.50 µmol) and methyl 6-[(1-acetylazetidin-3-yl)amino]-2-pyrrolidin-1-yl-pyrimidine-4-carboxylate (181.24 mg, 567.50 µmol) were dissolved in methanol (3 mL) and heated at 75° C. for 72 hr. After the completion of the reaction, the solvent was evaporated in vacuo at 45° C. to give crude product which was purified by HPLC (30-40% water-acetonitrile, 10 min, flow 30 mL/min (loading pump 4 mL/min acetonitrile) column: SunFire C18 100*19 mm) to give tert-butyl (3S)-3-[(1R)-2-[[6-[(1-acetylazetidin-3-yl)amino]-2-pyrrolidin-1-yl-pyrimidine-4-carbonyl]amino]-1-hydroxy-ethyl]-7-(methoxymethoxy)-3,4-dihydro-1H-isoquinoline-2-carboxylate (0.126 g, 196.95 µmol, 34.71% yield). $^1$H NMR (DMSO-$d_6$, 400 MHz): δ 1.39 (m, 9H), 1.45 (s, 3H), 1.75 (m, 4H), 1.90 (m, 2H), 2.76 (m, 1H), 2.92 (m, 2H), 3.05 (m, 2H), 3.15 (m, 4H), 3.29 (m, 1H), 3.36 (m, 1H), 3.45 (m, 1H), 3.60 (m, 2H), 3.74 (m, 1H), 3.95 (m, 1H), 4.09 (m, 1H), 4.23 (m, 1H), 4.76 (m, 1H), 5.16 (s, 2H), 6.34 (s, 1H), 6.85 (m, 1H), 7.07 (d, 1H), 7.86 (m, 1H), 8.31 (m, 1H), 8.54 (m, 1H). LCMS (ESI): [M+H]$^+$ m/z: calc'd 639.3; found 640.4; Rt=1.34 min.

Step 2: Synthesis of 6-[(1-acetylazetidin-3-yl)amino]-N-[(2R)-2-hydroxy-2-[(3S)-7-hydroxy-1,2,3,4-tetrahydroisoquinolin-3-yl]ethyl]-2-pyrrolidin-1-yl-pyrimidine-4-carboxamide tert-Butyl (3S)-3-[(1R)-2-[[6-[(1-acetylazetidin-3-yl)amino]-2-pyrrolidin-1-yl-pyrimidine-4-carbonyl]amino]-1-hydroxy-ethyl]-7-(methoxymethoxy)-3,4-dihydro-1H-isoquinoline-2-carboxylate (0.126 g, 196.95 µmol) was dissolved in MeOH (4 mL) and hydrogen chloride solution 4.0M in dioxane (538.59 mg, 14.77 mmol, 673.23 μL) was added. The mixture was stirred for 3 hr at 20° C. Then the solvent was removed in vacuo at 35° C. to give 6-[(1-acetylazetidin-3-yl)amino]-N-[(2R)-2-hydroxy-2-[(3S)-7-hydroxy-1,2,3,4-tetrahydroisoquinolin-3-yl]ethyl]-2-pyrrolidin-1-yl-pyrimidine-4-carboxamide (0.114 g, 188.44 μmol, 95.68% yield, 3HCl) which was used in the next step without further purification. $^1$H NMR (DMSO-d$_6$, 500 MHz): δ 1.03 (m, 1H), 1.41 (m, 1H), 1.56 (m, 1H), 1.75 (s, 3H), 1.87 (s, 3H), 2.93 (m, 2H), 3.16 (m, 1H), 3.29 (m, 1H), 3.78 (m, 2H), 3.99 (m, 2H), 4.13 (m, 4H), 4.29 (m, 2H), 4.41 (m, 2H), 4.56 (m, 2H), 6.41 (s, 1H), 6.59 (s, 1H), 6.70 (d, 1H), 7.02 (d, 1H), 8.90 (m, 1H), 9.49 (m, 1H). LCMS (ESI): [M+H]$^+$ m/z: calc'd 495.2; found 497.4; Rt=1.80 min.

Step 3: Synthesis of tert-butyl (3S)-3-[(1R)-2-[[6-[(1-acetylazetidin-3-yl)amino]-2-pyrrolidin-1-yl-pyrimidine-4-carbonyl]amino]-1-hydroxy-ethyl]-7-hydroxy-3,4-dihydro-1H-isoquinoline-2-carboxylate 6-[(1-Acetylazetidin-3-yl)amino]-N-[(2R)-2-hydroxy-2-[(3S)-7-hydroxy-1,2,3,4-tetrahydro-isoquinolin-3-yl]ethyl]-2-pyrrolidin-1-yl-pyrimidine-4-carboxamide (0.114 g, 188.44 μmol, 3HCl) was dissolved in the mixture of water (2 mL) and THF (2 mL) then sodium hydrogen carbonate, 99% (63.32 mg, 753.77 μmol, 29.32 μL) was added in one portion. The resulting solution was stirred for 5 min at room temperature followed by the dropwise addition of the solution of di-tert-butyl dicarbonate (41.13 mg, 188.44 μmol, 43.25 μL) in THF (0.2 mL). The reaction mixture was stirred for 4 hr at room temperature. After that ethyl acetate (15 mL) was added to the reaction mixture, the organic phase was separated, and the aqueous phase was extracted with ethyl acetate (2*15 mL). The organic phase was washed with brine, dried over Na$_2$SO$_4$, filtered off and evaporated in vacuo at 40° C. to give tert-butyl (3S)-3-[(1R)-2-[[6-[(1-acetylazetidin-3-yl)amino]-2-pyrrolidin-1-yl-pyrimidine-4-carbonyl]amino]-1-hydroxy-ethyl]-7-hydroxy-3,4-dihydro-TH-isoquinoline-2-carboxylate (0.111 g, 186.34 μmol, 98.88% yield) which was used in the next step without purification. $^1$H NMR (CDCl$_3$, 400 MHz): δ 1.25 (m, 2H), 1.47 (m, 9H), 1.83 (m, 4H), 1.96 (m, 4H), 2.79 (m, 1H), 2.95 (m, 2H), 3.07 (m, 2H), 3.49 (m, 2H), 3.72 (m, 2H), 3.89 (m, 1H), 4.01 (m, 1H), 4.28 (m, 2H), 4.60 (m, 2H), 5.28 (m, 1H), 5.44 (m, 1H), 6.45 (s, 1H), 6.54 (d, 1H), 6.62 (d, 1H), 6.99 (s, 1H), 9.09 (m, 1H). LCMS (ESI): [M+H]$^+$ m/z: calc'd 595.3; found 596.4; Rt=2.72 min.

Step 4: Synthesis of tert-butyl (3S)-3-[(1R)-2-[[6-[(1-acetylazetidin-3-yl)amino]-2-pyrrolidin-1-yl-pyrimidine-4-carbonyl]amino]-1-hydroxy-ethyl]-7-[(4-methyloxazol-5-yl)methoxy]-3,4-dihydro-1H-isoquinoline-2-carboxylate tert-Butyl (3S)-3-[(1R)-2-[[6-[(1-acetylazetidin-3-yl)amino]-2-pyrrolidin-1-yl-pyrimidine-4-carbonyl]amino]-1-hydroxy-ethyl]-7-hydroxy-3,4-dihydro-1H-isoquinoline-2-carboxylate (0.111 g, 186.34 μmol), 5-(chloromethyl)-4-methyl-oxazole (43.83 mg, 260.87 μmol, HCl) and cesium carbonate (242.85 mg, 745.36 μmol) were dissolved in DMF (3 mL) and stirred at 50° C. overnight. The reaction mixture was filtered off and washed with DMF (2 mL). The obtained filtrate was concentrated in vacuo at 60° C. to give tert-butyl (3S)-3-[(1R)-2-[[6-[(1-acetylazetidin-3-yl)amino]-2-pyrrolidin-1-yl-pyrimidine-4-carbonyl]-amino]-1-hydroxy-ethyl]-7-[(4-methyloxazol-5-yl)methoxy]-3,4-dihydro-1H-isoquinoline-2-carboxylate (0.114 g, 165.03 μmol, 88.56% yield) which was used in the next step without further purification. $^1$H NMR (CDCl$_3$, 400 MHz): δ 1.52 (s, 9H), 1.68 (m, 4H), 1.87 (s, 3H), 1.98 (m, 4H), 2.23 (s, 3H), 3.12 (m, 2H), 3.55 (m, 4H), 3.94 (m, 3H), 4.23 (m, 2H), 4.42 (m, 3H), 4.66 (m, 2H), 5.00 (s, 2H), 6.45 (s, 1H), 6.73 (s, 1H), 6.80 (d, 1H), 7.13 (d, 1H), 7.79 (s, 1H). LCMS (ESI): [M+H]$^+$ m/z: calc'd 690.3; found 691.2; Rt=3.86 min.

Step 5: Synthesis of 6-[(1-acetylazetidin-3-yl)amino]-N-[(2R)-2-hydroxy-2-[(3S)-7-[(4-methyloxazol-5-yl)methoxy]-1,2,3,4-tetrahydroisoquinolin-3-yl]ethyl]-2-pyrrolidin-1-yl-pyrimidine-4-carboxamide (Compound 61) tert-Butyl (3S)-3-[(1R)-2-[[6-[(1-acetylazetidin-3-yl)amino]-2-pyrrolidin-1-yl-pyrimidine-4-carbonyl]amino]-1-hydroxy-ethyl]-7-[(4-methyloxazol-5-yl)methoxy]-3,4-dihydro-1H-isoquinoline-2-carboxylate (0.114 g, 165.03 μmol) was dissolved in MeOH (2 mL) and hydrogen chloride solution 4.0M in dioxane (451.28 mg, 12.38 mmol, 564.10 μL) was added. The resulting mixture was stirred for 4 hr at RT. After that the solvent was removed in vacuo at 45° C. The residue was dissolved in 5 mL of methanol and 10 mg of scavenger (SiliaMetS© Dimercaptotriazine (DMT)) was added. The resulting suspension was stirred for 12 h at room temperature. The suspension was filtered off, the filtrate was evaporated under reduced pressure and the residue was purified by HPLC (10-60% water-methanol+NH$_3$, 0-10 min, flow 30 mL/min (loading pump 4 mL/min methanol+NH$_3$), column: YMC-Actus Triart C18 100*20 mm) to give 6-[(1-acetylazetidin-3-yl)amino]-N-[(2R)-2-hydroxy-2-[(3S)-7-[(4-methyloxazol-5-yl)methoxy]-1,2,3,4-tetrahydroisoquinolin-3-yl]ethyl]-2-pyrrolidin-1-yl-pyrimidine-4-carboxamide (0.0263 g, 44.53 μmol, 26.98% yield). $^1$H NMR (400 MHz, CDCl$_3$) δ 1.86 (s, 3H), 1.94 (m, 5H), 2.20 (s, 3H), 2.70 (m, 1H), 2.82 (m, 1H), 2.97 (m, 1H), 3.50 (m, 4H), 3.61 (m, 1H), 3.68 (m, 1H), 3.80 (m, 1H), 4.00 (m, 5H), 4.35 (m, 1H), 4.45 (m, 1H), 4.68 (m, 1H), 4.95 (s, 2H), 5.90 (m, 1H), 6.53 (s, 1H), 6.60 (d, 1H), 6.75 (dd, 1H), 7.03 (d, 1H), 7.78 (s, 1H), 8.56 (m, 1H). LCMS (ESI): [M+H]$^+$ m/z: calc'd 590.3; found 591.2; Rt=0.91 min.

Example 4A11. Synthesis of 6-(cyclobutylamino)-N-[(2R)-2-hydroxy-2-[(3S)-7-[(4-methyloxazol-5-yl)methoxy]-1,2,3,4-tetrahydroisoquinolin-3-yl]ethyl]-2-(1-piperidyl)pyrimidine-4-carboxamide (Compound 49)

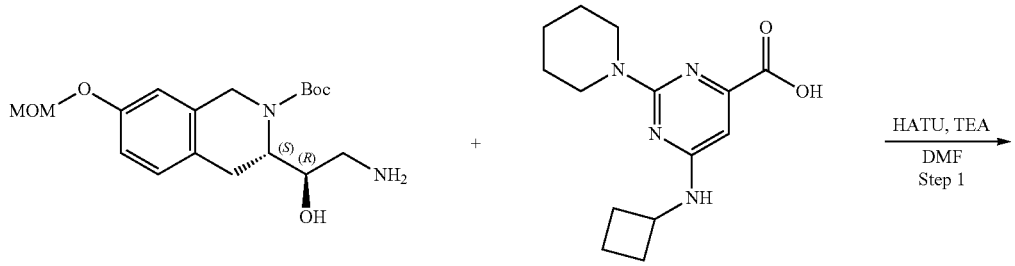

-continued
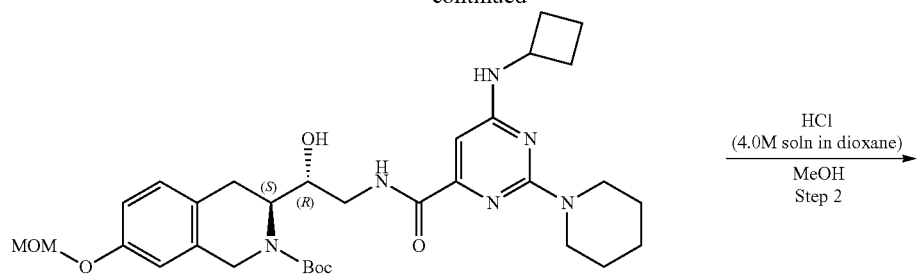
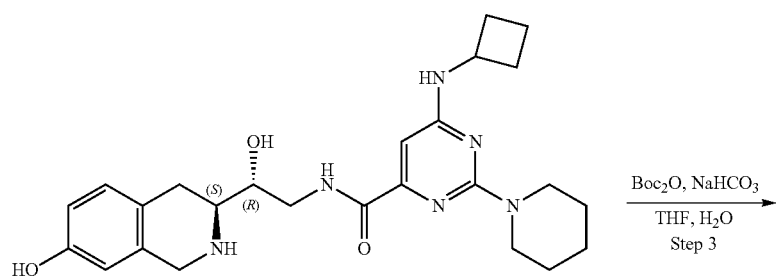
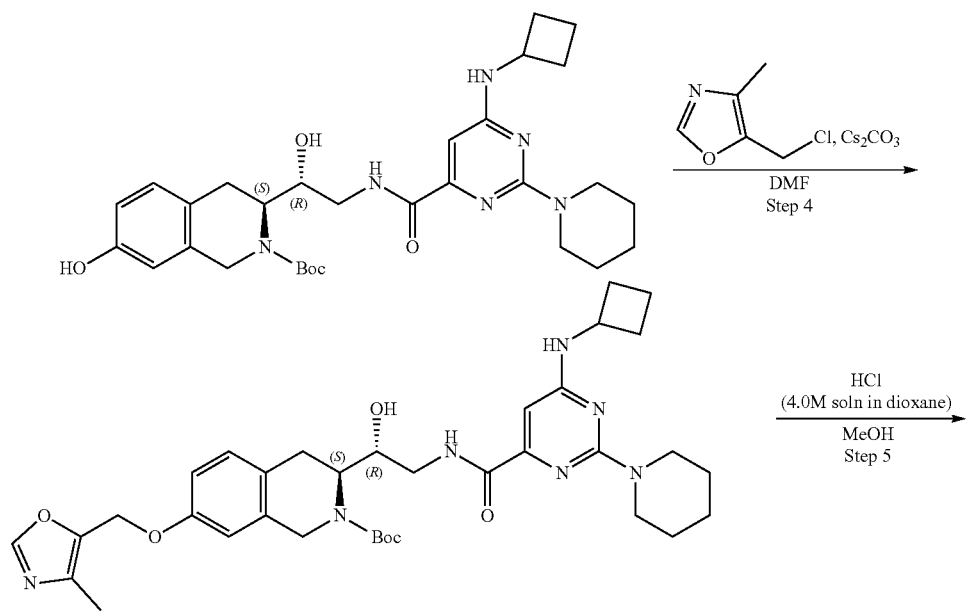
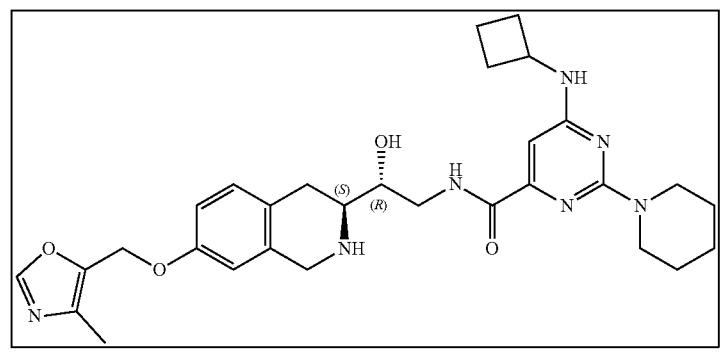

Step 1: Synthesis of tert-butyl (3S)-3-[(1R)-2-[[6-(cyclobutylamino)-2-(1-piperidyl)-pyrimidine-4-carbonyl]amino]-1-hydroxy-ethyl]-7-(methoxymethoxy)-3,4-dihydro-1H-isoquinoline-2-carboxylate 6-(Cyclobutylamino)-2-(1-piperidyl)pyrimidine-4-carboxylic acid (177.51 mg, 567.50 µmol, HCl), tert-butyl (3S)-3-[(1R)-2-amino-1-hydroxy-ethyl]-7-(methoxymethoxy)-3,4-dihydro-1H-isoquinoline-2-carboxylate (200 mg, 567.50 µmol), triethylamine (574.25 mg, 5.67 mmol, 790.98 µL) were mixed in DMF (4 mL) and then HATU (323.67 mg, 851.25 µmol) was added. The resulting mixture were stirred at 25° C. for 12 hr. After the completion of the reaction, the mixture was evaporated under reduce pressure and purified with HPLC 100% R1—123 BAR; 100% H₂O—192 BAR) to obtain tert-butyl (3S)-3-[(1R)-2-[[6-(cyclobutylamino)-2-(1-piperidyl)pyrimidine-4-carbonyl]amino]-1-hydroxy-ethyl]-7-(methoxymethoxy)-3,4-dihydro-1H-isoquinoline-2-carboxylate (199.6 mg, 326.82 µmol, 57.59% yield). $^1$H NMR (DMSO-$d_6$, 400 MHz): δ 1.45 (m, 12H), 1.66 (m, 6H), 1.87 (m, 3H), 2.24 (m, 3H), 2.93 (m, 2H), 3.36 (m, 4H), 3.49 (m, 2H), 3.68 (m, 4H), 4.18 (m, 2H), 4.75 (m, 1H), 5.15 (m, 2H), 6.27 (s, 1H), 6.82 (m, 2H), 7.06 (d, 1H), 7.51 (m, 1H), 8.38 (m, 1H). LCMS (ESI): [M+H]$^+$ m/z: calc'd 610.3; found 611.3; Rt=1.72 min.

Step 2: Synthesis of 6-(cyclobutylamino)-N-[(2R)-2-hydroxy-2-[(3S)-7-hydroxy-1,2,3,4-tetrahydroisoquinolin-3-yl]ethyl]-2-(1-piperidyl)pyrimidine-4-carboxamide The solution of tert-butyl (3S)-3-[(1R)-2-[[6-(cyclobutylamino)-2-(1-piperidyl)pyrimidine-4-carbonyl]amino]-1-hydroxy-ethyl]-7-(methoxymethoxy)-3,4-dihydro-1H-isoquinoline-2-carboxylate (199.6 mg, 326.82 µmol) in dioxane/HCl (2 mL) and Methanol (2 mL) were stirred for 12 hr at 25° C. Then the solution was evaporated to obtain 6-(cyclobutylamino)-N-[(2R)-2-hydroxy-2-[(3S)-7-hydroxy-1,2,3,4-tetrahydroisoquinolin-3-yl]ethyl]-2-(1-piperidyl)pyrimidine-4-carboxamide (182 mg, crude, 3HCl). $^1$H NMR (MeOD, 400 MHz): δ 1.78 (m, 8H), 2.25 (m, 4H), 3.52 (m, 8H), 3.76 (m, 4H), 4.27 (m, 4H), 6.58 (m, 2H), 6.53 (s, 1H), 6.58 (s, 1H), 6.62 (d, 1H), 7.09 (d, 1H). LCMS (ESI): [M+H]$^+$ m/z: calc'd 466.3; found 467.2; Rt=1.03 min.

Step 3: Synthesis of tert-butyl (3S)-3-[(1R)-2-[[6-(cyclobutylamino)-2-(1-piperidyl)-pyrimidine-4-carbonyl]amino]-1-hydroxy-ethyl]-7-hydroxy-3,4-dihydro-1H-isoquinoline-2-carboxylate To a stirred solution of sodium hydrogen carbonate (132.73 mg, 1.58 mmol, 61.45 µL) in water (2 mL), 6-(cyclobutylamino)-N-[(2R)-2-hydroxy-2-[(3S)-7-hydroxy-1,2,3,4-tetrahydroisoquinolin-3-yl]ethyl]-2-(1-piperidyl)pyrimidine-4-carboxamide (182 mg, 316.00 µmol, 3HCl) was added in THF (1.5 mL) followed by di-tert-butyl dicarbonate (72.41 mg, 331.80 µmol, 76.14 µL) in THF (1.5 mL). The resulting mixture was stirred at 25° C. for 12 hr. Then EtOAc (10 mL) was added and organic phase was separated and washed with brine (2*5 mL). Then solvent was dried over sodium sulfate, filtered off and evaporated to obtain tert-butyl (3S)-3-[(1R)-2-[[6-(cyclobutylamino)-2-(1-piperidyl)pyrimidine-4-carbonyl]amino]-1-hydroxy-ethyl]-7-hydroxy-3,4-dihydro-1H-isoquinoline-2-carboxylate (150 mg, crude). $^1$H NMR (CDCl₃, 400 MHz): δ 1.25 (m, 4H), 1.55 (m, 9H), 1.83 (m, 8H), 2.40 (m, 2H), 3.05 (m, 4H), 3.69 (m, 4H), 4.62 (m, 4H), 6.35 (s, 1H), 6.54 (s, 1H), 6.60 (d, 1H), 6.99 (d, 1H), 9.04 (m, 1H). LCMS (ESI): [M+H]+ m/z: calc'd 566.3; found 567.4; Rt=1.45 min.

Step 4: Synthesis of tert-butyl (3S)-3-[(1R)-2-[[6-(cyclobutylamino)-2-(1-piperidyl)-pyrimidine-4-carbonyl]amino]-1-hydroxy-ethyl]-7-[(4-methyloxazol-5-yl)methoxy]-3,4-dihydro-1H-isoquinoline-2-carboxylate To the solution of tert-butyl (3S)-3-[(1R)-2-[[6-(cyclobutylamino)-2-(1-piperidyl)pyrimidine-4-carbonyl]amino]-1-hydroxy-ethyl]-7-hydroxy-3,4-dihydro-1H-isoquinoline-2-carboxylate (150 mg, 264.69 µmol), the suspension of cesium carbonate (258.73 mg, 794.08 µmol) in DMF (3 mL) was added. The resulting mixture was stirred for 5 min at room temperature followed by the addition of 5-(chloromethyl)-4-methyl-oxazole (53.37 mg, 317.63 µmol, HCl). The resulting mixture was heated at 50° C. for 12 hr. After the completion of the reaction, the mixture was filtered off and evaporated to obtain tert-butyl (3S)-3-[(1R)-2-[[6-(cyclobutylamino)-2-(1-piperidyl)pyrimidine-4-carbonyl]amino]-1-hydroxy-ethyl]-7-[(4-methyloxazol-5-yl)methoxy]-3,4-dihydro-1H-isoquinoline-2-carboxylate (170 mg, crude) that was used without further purification. $^1$H NMR (CDCl₃, 500 MHz): δ 1.64 (m, 18H), 2.38 (m, 8H), 3.6 (m, 11H), 4.93 (m, 4H), 6.82 (m, 3H), 7.77 (m, 2H), 9.07 (m, 1H). LCMS (ESI): [M+H]+ m/z: calc'd 661.3; found 662.4; Rt=1.53 min.

Step 5: Synthesis of 6-(cyclobutylamino)-N-[(2R)-2-hydroxy-2-[(3S)-7-[(4-methyloxazol-5-yl)methoxy]-1,2,3,4-tetrahydroisoquinolin-3-yl]ethyl]-2-(1-piperidyl)pyrimidine-4-carboxamide (Compound 49) The solution of tert-butyl (3S)-3-[(1R)-2-[[6-(cyclobutylamino)-2-(1-piperidyl)pyrimidine-4-carbonyl]amino]-1-hydroxy-ethyl]-7-[(4-methyloxazol-5-yl)methoxy]-3,4-dihydro-1H-isoquinoline-2-carboxylate (170 mg, 256.88 µmol) in Dioxane/HCl (2 mL) and methanol (2 mL) was stirred for 3 hr at 25° C. The resulting mixture was stirred with SiliaMetS© DMT (30 mg) in methanol (1 mL) for 12 hr. The suspension was filtered off, evaporated and purified by HPLC (65-90% water-R1+ NH₃) to obtain 6-(cyclobutylamino)-N-[(2R)-2-hydroxy-2-[(3S)-7-[(4-methyloxazol-5-yl)methoxy]-1,2,3,4-tetrahydro-isoquinolin-3-yl]ethyl]-2-(1-piperidyl)pyrimidine-4-carboxamide (7.1 mg, 12.64 µmol, 4.92% yield). $^1$H NMR (400 MHz, CDCl₃) δ 1.57 (m, 4H), 1.64 (m, 2H), 1.77 (m, 3H), 1.88 (m, 3H), 2.22 (s, 3H), 2.39 (m, 2H), 2.74 (m, 1H), 2.83 (m, 1H), 2.99 (m, 1H), 3.58 (m, 1H), 3.72 (m, 5H), 3.84 (m, 1H), 4.01 (m, 2H), 4.27 (m, 1H), 4.97 (s, 2H), 5.02 (m, 1H), 6.38 (s, 1H), 6.61 (d, 1H), 6.77 (m, 1H), 7.05 (d, 1H), 7.80 (s, 1H), 8.39 (t, 1H). LCMS (ESI): [M+2H]$^+$ m/z: calc'd 561.3; found 563.4; Rt=2.83 min.

Example 4A12. Synthesis of 6-[(1-acetyl-4-piperidyl)amino]-N-[(2R)-2-hydroxy-2-[(3S)-7-((4-methyloxazol-5-yl)methoxy]-1,2,3,4-tetrahydroisoquinolin-3-yl]ethyl]-2-(1-piperidyl)pyrimidine-4-carboxamide (Compound 50)

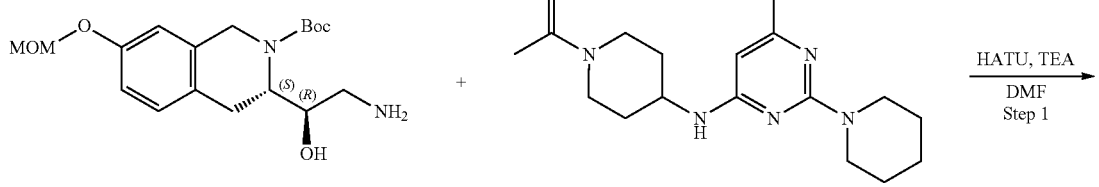

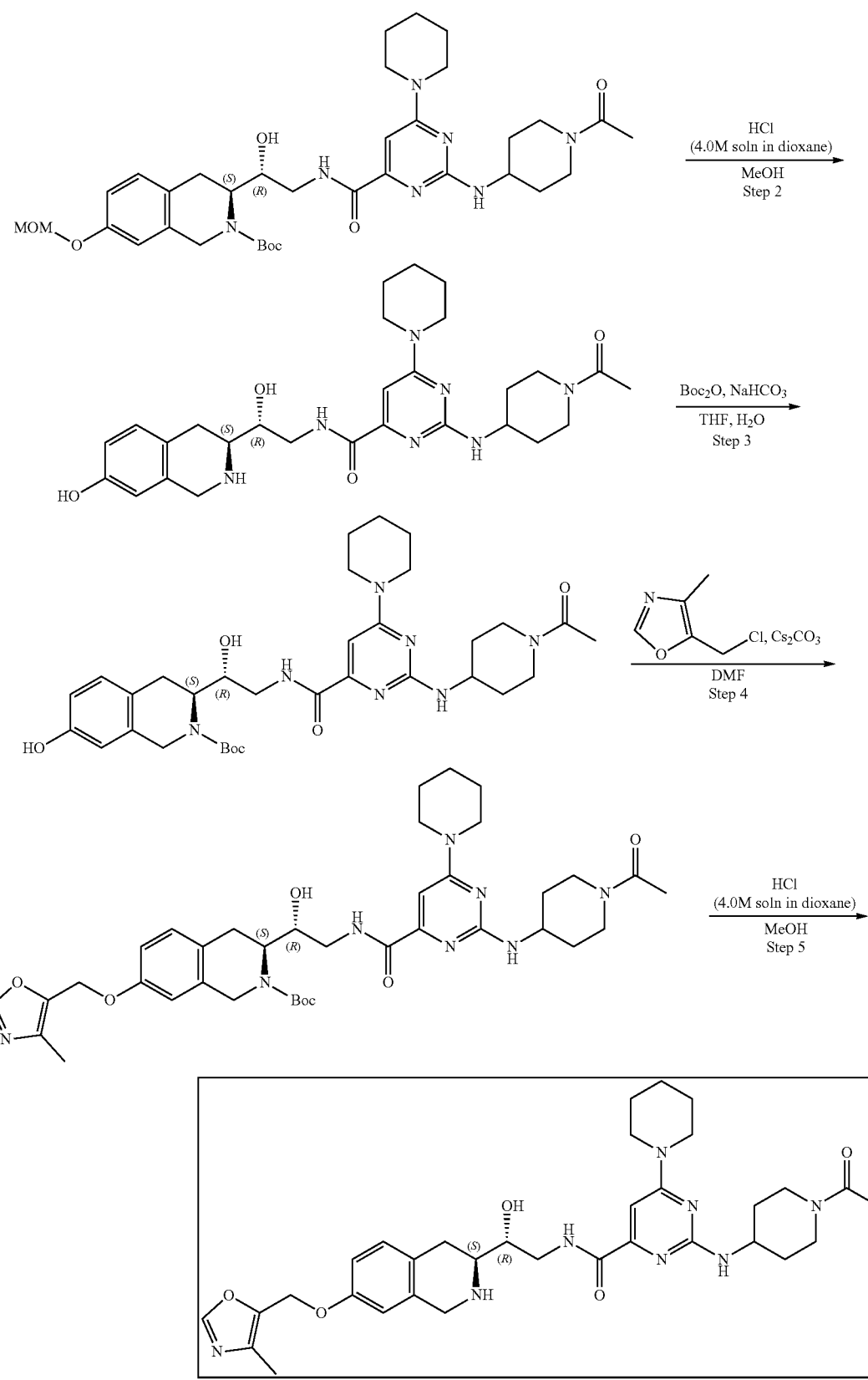

Step 1: Synthesis of tert-butyl (3S)-3-[(1R)-2-[[6-[(1-acetyl-4-piperidyl)amino]-2-(1-piperidyl)pyrimidine-4-carbonyl]amino]-1-hydroxy-ethyl]-7-(methoxymethoxy)-3,4-dihydro-1H-isoquinoline-2-carboxylate 6-((1-Acetylpiperidin-4-yl)amino)-2-(piperidin-1-yl)pyrimidine-4-carboxylic acid (197.16 mg, 567.50 µmol), tert-butyl (3S)-3-[(1R)-2-amino-1-hydroxy-ethyl]-7-(methoxymethoxy)-3,4-dihydro-1H-isoquinoline-2-carboxylate (200 mg, 567.50 µmol), and triethylamine (574.25 mg, 5.67 mmol, 790.98 µL) were mixed in DMF (4 mL). The resulting mixture was stirred for 5 min at room temperature followed by the addition of HATU (323.67 mg, 851.25 µmol). The resulting mixture was stirred at 25° C. for 12 hr. After the completion of the reaction, the mixture was evaporated under reduce pressure and purified with HPLC (70-95% water-acetonitrile, 10 min, flow 30 mL/min) to obtain tert-butyl (3S)-3-[(1R)-2-[[6-[(1-acetyl-4-piperidyl)amino]-2-(1-piperidyl)pyrimidine-4-carbonyl]amino]-1-hydroxy-ethyl]-7-(methoxymethoxy)-3,4-dihydro-TH-isoquinoline-2-carboxylate (217 mg, 318.27 µmol, 56.08% yield). $^1$H NMR (DMSO-d$_6$, 400 MHz): δ 1.39 (m, 18H), 1.92 (m, 5H), 2.94 (m, 5H), 3.45 (m, 4H), 4.00 (m, 9H), 4.71 (m, 1H), 5.14 (m, 3H), 6.36 (s, 1H), 6.83 (s, 2H), 7.06 (d, 1H), 7.27 (m, 1H), 8.47 (m, 1H). LCMS (ESI): [M+H]$^+$ m/z: calc'd 681.3; found 682.2; Rt=1.54 min.

Step 2: Synthesis of 6-[(1-acetyl-4-piperidyl)amino]-N-[(2R)-2-hydroxy-2-[(3S)-7-hydroxy-1,2,3,4-tetrahydroisoquinolin-3-yl]ethyl]-2-(1-piperidyl)pyrimidine-4-carboxamide The solution of tert-butyl (3S)-3-[(1R)-2-[[6-[(1-acetyl-4-piperidyl)amino]-2-(1-piperidyl)-pyrimidine-4-carbonyl]amino]-1-hydroxy-ethyl]-7-(methoxymethoxy)-3,4-dihydro-TH-isoquinoline-2-carboxylate (217 mg, 318.27 µmol) in dioxane/HCl (2 mL) and Methanol (2 mL) was stirred for 12 hr at 25° C. Then the solution was evaporated to obtain 6-[(1-acetyl-4-piperidyl)amino]-N-[(2R)-2-hydroxy-2-[(3S)-7-hydroxy-1,2,3,4-tetrahydroisoquinolin-3-yl]ethyl]-2-(1-piperidyl)pyrimidine-4-carboxamide (201 mg, crude, 3HCl). $^1$H NMR (MeOD, 400 MHz): δ 1.68 (m, 4H), 2.11 (m, 6H), 3.07 (m, 2H), 3.93 (m, 10H), 4.24 (m, 8H), 6.59 (s, 2H), 6.71 (d, 1H), 7.07 (d, 1H). LCMS (ESI): [M+H]$^+$ m/z: calc'd 537.3; found 538.4; Rt=0.88 min.

Step 3: Synthesis of tert-butyl (3S)-3-[(1R)-2-[[6-[(1-acetyl-4-piperidyl)amino]-2-(1-piperidyl)pyrimidine-4-carbonyl]amino]-1-hydroxy-ethyl]-7-hydroxy-3,4-dihydro-1H-isoquinoline-2-carboxylate To a stirred solution of sodium hydrogen carbonate (130.48 mg, 1.55 mmol, 60.41 µL) in water (2 mL) the solution of 6-[(1-acetyl-4-piperidyl)amino]-N-[(2R)-2-hydroxy-2-[(3S)-7-hydroxy-1,2,3,4-tetrahydroisoquinolin-3-yl]ethyl]-2-(1-piperidyl)pyrimidine-4-carboxamide (201 mg, 310.65 µmol, 3HCl) in THF (1.5 mL) was added. The resulting mixture was stirred for 5 min at room temperature followed by the addition of di-tert-butyl dicarbonate (71.19 mg, 326.18 µmol, 74.86 µL) in THF (1.5 mL). The resulting mixture was stirred at 25° C. for 12 hr. After the completion of the reaction, EtOAc (10 mL) was added and the organic phase was separated and washed with brine (2*5 mL). Then the solvent was dried over sodium sulfate, filtered off, and evaporated to obtain tert-butyl (3S)-3-[(1R)-2-[[6-[(1-acetyl-4-piperidyl)amino]-2-(1-piperidyl)pyrimidine-4-carbonyl]amino]-1-hydroxy-ethyl]-7-hydroxy-3,4-dihydro-1H-isoquinoline-2-carboxylate (170 mg, crude). $^1$H NMR (CDCl$_3$, 400 MHz): δ 1.20 (m, 8H), 1.57 (m, 12H), 1.92 (m, 2H), 2.09 (s, 3H), 2.95 (m, 2H), 3.43 (m, 1H), 3.73 (m, 9H), 4.44 (m, 4H), 5.50 (m, 1H), 6.39 (s, 1H), 6.52 (s, 1H), 6.62 (d, 1H), 7.10 (d, 1H), 9.03 (s, 1H). LCMS (ESI): [M+H]$^+$ m/z: calc'd 637.3; found 638.4; Rt=1.35 min.

Step 4: Synthesis of tert-butyl (3S)-3-[(1R)-2-[[6-[(1-acetyl-4-piperidyl)amino]-2-(1-piperidyl)pyrimidine-4-carbonyl]amino]-1-hydroxy-ethyl]-7-[(4-methyloxazol-5-yl)methoxy]-3,4-dihydro-1H-isoquinoline-2-carboxylate To the solution of tert-butyl (3S)-3-[(1R)-2-[[6-[(1-acetyl-4-piperidyl)amino]-2-(1-piperidyl)-pyrimidine-4-carbonyl]amino]-1-hydroxy-ethyl]-7-hydroxy-3,4-dihydro-1H-isoquinoline-2-carboxylate (170 mg, 266.55 µmol), cesium carbonate (260.55 mg, 799.66 µmol) in DMF (3 mL) 5-(chloromethyl)-4-methyl-oxazole (53.74 mg, 319.87 µmol, HCl) was added. The resulting mixture was heated at 50° C. for 12 hr. After the completion of the reaction, the mixture was filtered off and evaporated to obtain tert-butyl (3S)-3-[(1R)-2-[[6-[(1-acetyl-4-piperidyl)amino]-2-(1-piperidyl)pyrimidine-4-carbonyl]amino]-1-hydroxy-ethyl]-7-[(4-methyloxazol-5-yl)methoxy]-3,4-dihydro-1H-isoquinoline-2-carboxylate (200 mg, crude) that was used without further purification. $^1$H NMR (CDCl$_3$, 500 MHz): δ 1.19 (m, 28H), 1.89 (m, 2H), 2.18 (s, 3H), 4.37 (m, 14H), 6.35 (s, 1H), 6.60 (s, 1H), 6.67 (m, 2H), 7.03 (d, 1H), 7.79 (s, 1H), 9.06 (m, 1H). LCMS (ESI): [M+H]$^+$ m/z: calc'd 732.4; found 733.4; Rt=1.40 min.

Step 5: Synthesis of 6-[(1-acetyl-4-piperidyl)amino]-N-[(2R)-2-hydroxy-2-[(3S)-7-[(4-methyloxazol-5-yl)methoxy]-1,2,3,4-tetrahydroisoquinolin-3-yl]ethyl]-2-(1-piperidyl)pyrimidine-4-carboxamide (Compound 50) The solution of tert-butyl (3S)-3-[(1R)-2-[[6-[(1-acetyl-4-piperidyl)amino]-2-(1-piperidyl)-pyrimidine-4-carbonyl]amino]-1-hydroxy-ethyl]-7-[(4-methyloxazol-5-yl)methoxy]-3,4-dihydro-1H-isoquinoline-2-carboxylate (200 mg, 272.90 µmol) in Dioxane/HCl (2 mL) and methanol (2 mL) was stirred for 3 hr at 25° C. After the completion of the reaction, the resulting mixture was stirred with SiliaMetS® DMT (30 mg) in methanol (1 mL) for 12 hr. The obtained suspension was filtered off, evaporated and purified by HPLC (30-40% water+HCl-R1) to obtain 6-[(1-acetyl-4-piperidyl)amino]-N-[(2R)-2-hydroxy-2-[(3S)-7-[(4-methyloxazol-5-yl)methoxy]-1,2,3,4-tetrahydroisoquinolin-3-yl]ethyl]-2-(1-piperidyl)pyrimidine-4-carboxamide (25.9 mg, 34.90 µmol, 12.79% yield, 3HCl). $^1$H NMR (400 MHz, CD$_3$OD) δ 1.50 (m, 1H), 1.60 (m, 1H), 1.71 (m, 7H), 2.04 (m, 2H), 2.13 (s, 3H), 2.21 (s, 3H), 2.94 (m, 1H), 3.17 (m, 2H), 3.52 (m, 1H), 3.66 (m, 2H), 3.78 (m, 4H), 3.95 (m, 1H), 4.32 (m, 3H), 4.41 (m, 1H), 4.47 (m, 1H), 5.11 (s, 2H), 6.64 (s, 1H), 6.87 (s, 1H), 6.96 (m, 1H), 7.23 (d, 1H), 8.30 (m, 1H). LCMS (ESI): [M+H]$^+$ m/z: calc'd 632.3; found 633.4; Rt=1.02 min.

Example 4A13. Synthesis of 6-[(1-acetylazetidin-3-yl)amino]-N-[(2R)-2-hydroxy-2-[(3S)-7-[(4-methyl-oxazol-5-yl)methoxy]-1,2,3,4-tetrahydroisoquinolin-3-yl]ethyl]-2-(4-methyl-1-piperidyl)pyrimidine-4-carboxamide (Compound 62)
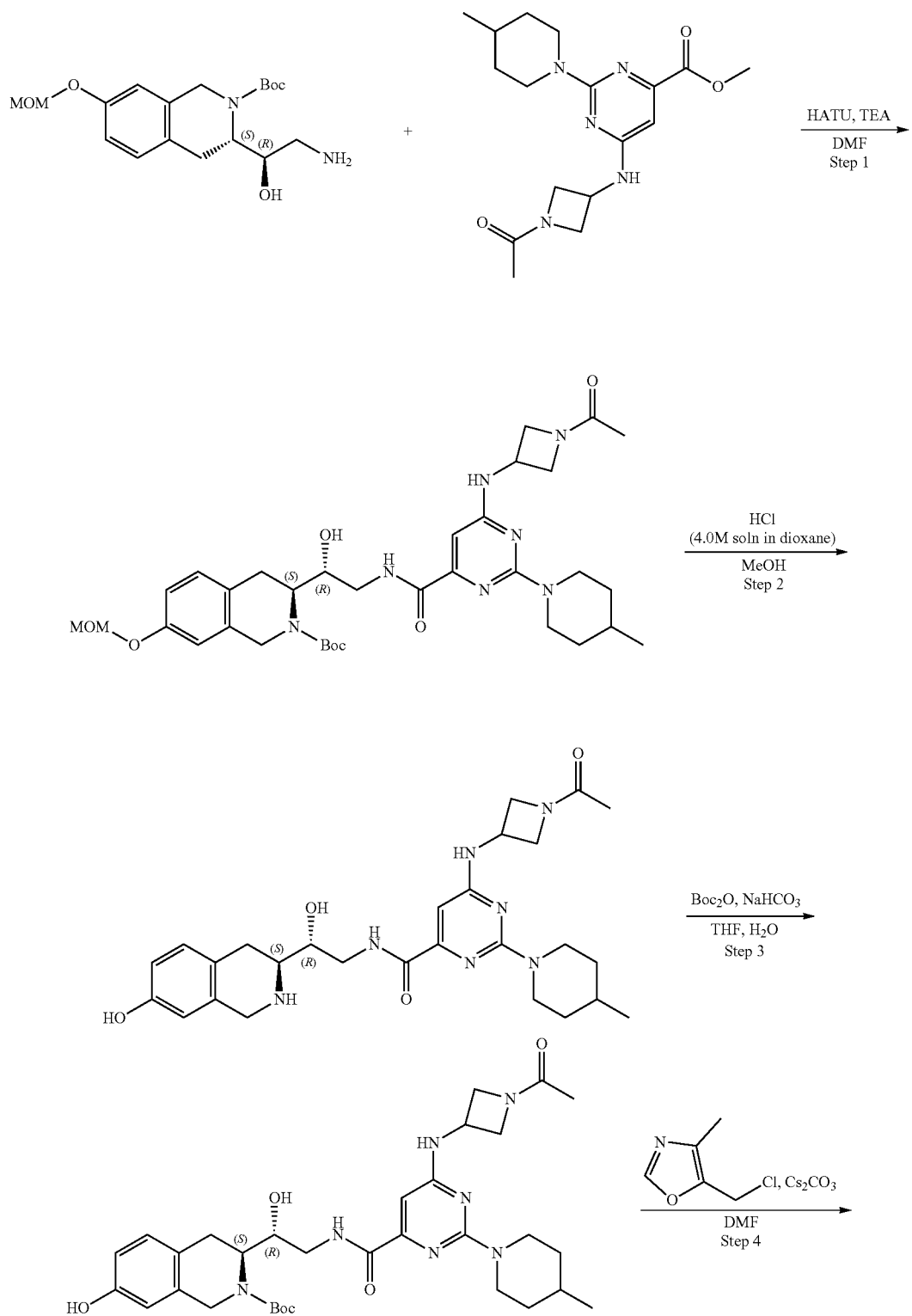

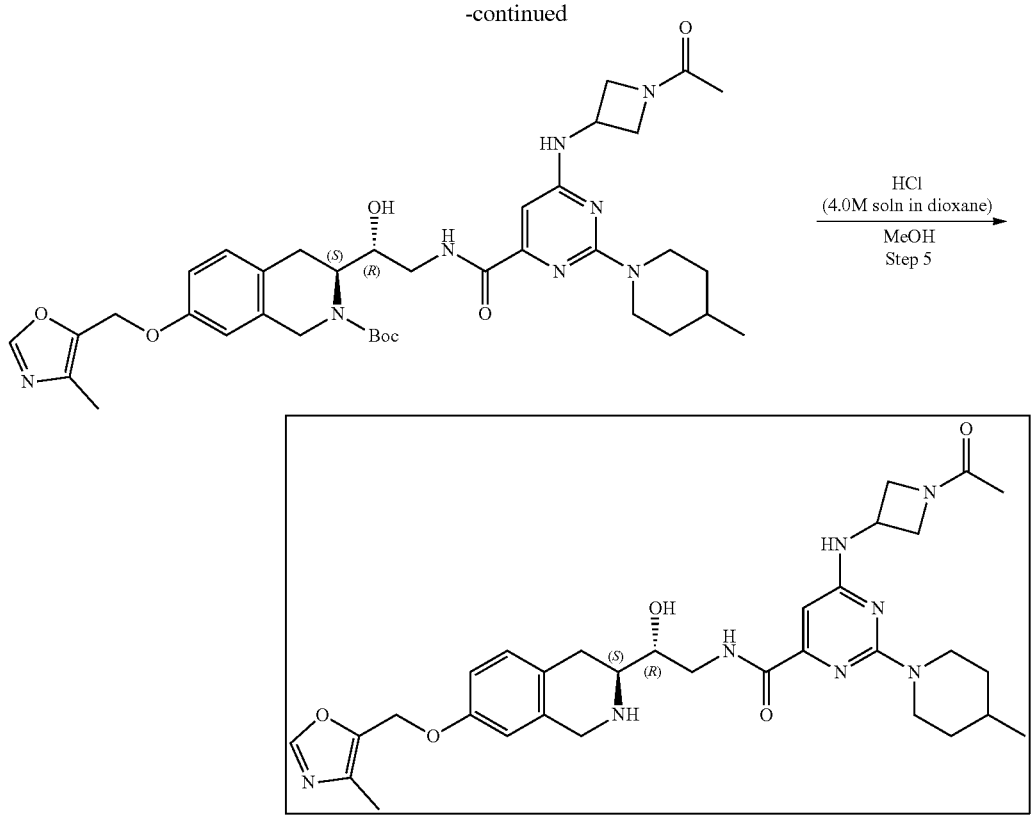

Step 1: Synthesis of tert-butyl (3S)-3-[(1R)-2-[[6-[(1-acetylazetidin-3-yl)amino]-2-(4-methyl-1-piperidyl)pyrimidine-4-carbonyl]amino]-1-hydroxy-ethyl]-7-(methoxymethoxy)-3,4-dihydro-1H-isoquinoline-2-carboxylate Methyl 6-[(1-acetylazetidin-3-yl)amino]-2-(4-methyl-1-piperidyl)pyrimidine-4-carboxylate (197.16 mg, 567.50 μmol) and tert-butyl (3S)-3-[(1R)-2-amino-1-hydroxy-ethyl]-7-(methoxymethoxy)-3,4-dihydro-1H-isoquinoline-2-carboxylate (200 mg, 567.50 μmol) were mixed in methanol (2 mL) and heated at 75° C. for 72 hr. After the completion of the reaction, the solution was evaporated under reduce pressure. The resulting crude product was purified by HPLC (70-95% water-acetonitrile, 2-10 min, Flow: 30 mL/min) to obtain tert-butyl (3S)-3-[(1R)-2-[[6-[(1-acetylazetidin-3-yl)amino]-2-(4-methyl-1-piperidyl)pyrimidine-4-carbonyl]amino]-1-hydroxy-ethyl]-7-(methoxymethoxy)-3,4-dihydro-1H-iso-quinoline-2-carboxylate (107.8 mg, 161.43 μmol, 28.45% yield). $^1$H NMR (CDCl$_3$, 400 MHz): δ 1.40 (m, 2H), 1.53 (m, 9H), 1.61 (m, 4H), 1.88 (s, 3H), 3.00 (m, 5H), 3.48 (m, 5H), 4.33 (m, 12H), 5.15 (s, 2H), 5.78 (m, 1H), 6.47 (s, 1H), 6.79 (s, 1H), 7.08 (d, 1H), 7.12 (d, 1H), 9.15 (m, 1H). LCMS (ESI): [M+H]$^+$ m/z: calc'd 667.3; found 668.4; Rt=1.58 min.

Step 2: Synthesis of 6-[(1-acetylazetidin-3-yl)amino]-N-[(2R)-2-hydroxy-2-[(3S)-7-hydroxy-1,2,3,4-tetrahydroisoquinolin-3-yl]ethyl]-2-(4-methyl-1-piperidyl)pyrimidine-4-carboxamide The solution of tert-butyl (3S)-3-[(1R)-2-[[6-[(1-acetylazetidin-3-yl)amino]-2-(4-methyl-1-piperidyl)pyrimidine-4-carbonyl]amino]-1-hydroxy-ethyl]-7-(methoxymethoxy)-3,4-dihydro-1H-isoquinoline-2-carboxylate (107.8 mg, 161.43 μmol) in dioxane/HCl (2 mL) and methanol (2 mL) was stirred for 12 hr at 25° C. Then the solution was evaporated to obtain 6-[(1-acetylazetidin-3-yl)amino]-N-[(2R)-2-hydroxy-2-[(3S)-7-hydroxy-1,2,3,4-tetrahydroisoquinolin-3-yl]ethyl]-2-(4-methyl-1-piperidyl)-pyrimidine-4-carboxamide (100 mg, crude, 3HCl). $^1$H NMR (MeOD, 400 MHz): δ 1.14 (m, 5H), 1.82 (m, 5H), 3.07 (m, 2H), 3.50 (m, 2H), 4.21 (m, 17H), 6.63 (s, 1H), 6.71 (s, 1H), 6.85 (d, 1H), 7.07 (d, 1H). LCMS (ESI): [M+H]$^+$ m/z: calc'd 523.3; found 524.2; Rt=0.95 min.

Step 3: Synthesis of tert-butyl (3S)-3-[(1R)-2-[[6-[(1-acetylazetidin-3-yl)amino]-2-(4-methyl-1-piperidyl)pyrimidine-4-carbonyl]amino]-1-hydroxy-ethyl]-7-hydroxy-3,4-dihydro-1H-isoquinoline-2-carboxylate To a stirred solution of sodium hydrogen carbonate (66.36 mg, 789.88 μmol, 30.72 μL) in water (2 mL) the solution of 6-[(1-acetylazetidin-3-yl)amino]-N-[(2R)-2-hydroxy-2-[(3S)-7-hydroxy-1,2,3,4-tetrahydroisoquinolin-3-yl]ethyl]-2-(4-methyl-1-piperidyl)pyrimidine-4-carboxamide (100 mg, 157.98 μmol, 3HCl) in THF (1.5 mL) was added. The resulting mixture was stirred for 5 min at room temperature followed by the addition of di-tert-butyl dicarbonate (36.20 mg, 165.87 μmol, 38.07 μL) in THF (1.5 mL). The resulting mixture was stirred at 25° C. for 12 hr. After the completion of the reaction, EtOAc (10 mL) was added and the organic phase was separated and washed with brine (2*5 mL). Then the solvent was dried over sodium sulfate, filtered off and evaporated to obtain tert-butyl (3S)-3-[(1R)-2-[[6-[(1-acetylazetidin-3-yl)amino]-2-(4-methyl-1-piperidyl)pyrimidine-4-carbonyl]amino]-1-hydroxy-ethyl]-7-hydroxy-3,4-dihydro-1H-isoquinoline-2-carboxylate (85 mg, crude). LCMS (ESI): [M+H]$^+$ m/z: calc'd 623.3; found 624.4; Rt=1.42 min.

Step 4: Synthesis of tert-butyl (3S)-3-[(1R)-2-[[6-[(1-acetylazetidin-3-yl)amino]-2-(4-methyl-1-piperidyl)pyrimidine-4-carbonyl]amino]-1-hydroxy-ethyl]-7-[(4-methyloxazol-5-yl)methoxy]-3,4-dihydro-1H-isoquinoline-2-carboxylate To the solution of tert-butyl (3S)-3-[(1R)-2-[[6-[(1-acetylazetidin-3-yl)amino]-2-(4-methyl-1-piperidyl)pyrimidine-4-carbonyl]amino]-1-hydroxy-ethyl]-7-hydroxy-3,4-dihydro-1H-isoquinoline-2-carboxylate (85 mg, 136.27 µmol), cesium carbonate (133.20 mg, 408.82 µmol) in DMF (3 mL) 5-(chloromethyl)-4-methyl-oxazole (27.48 mg, 163.53 µmol, HCl) was added. The resulting mixture was heated at 50° C. for 12 hr. After the completion of the reaction, the mixture was filtered off and evaporated to obtain tert-butyl (3S)-3-[(1R)-2-[[6-[(1-acetylazetidin-3-yl)amino]-2-(4-methyl-1-piperidyl)pyrimidine-4-carbonyl]amino]-1-hydroxy-ethyl]-7-[(4-methyloxazol-5-yl)methoxy]-3,4-dihydro-1H-isoquinoline-2-carboxylate (95 mg, crude) that was used without further purification. LCMS (ESI): [M+H]⁺ m/z: calc'd 718.4; found 719.4; Rt=1.46 min.

Step 5: Synthesis of 6-[(1-acetylazetidin-3-yl)amino]-N-[(2R)-2-hydroxy-2-[(3S)-7-[(4-methyloxazol-5-yl)methoxy]-1,2,3,4-tetrahydroisoquinolin-3-yl]ethyl]-2-(4-methyl-1-piperidyl)-pyrimidine-4-carboxamide (Compound 62) The solution of tert-butyl (3S)-3-[(1R)-2-[[6-[(1-acetylazetidin-3-yl)amino]-2-(4-methyl-1-piperidyl)pyrimidine-4-carbonyl]amino]-1-hydroxy-ethyl]-7-[(4-methyloxazol-5-yl)methoxy]-3,4-dihydro-1H-isoquinoline-2-carboxylate (95 mg, 132.16 µmol) in Dioxane/HCl (2 mL) and methanol (2 mL) was stirred for 3 hr at 25° C. After that the resulting mixture was stirred with SiliaMetS® DMT (30 mg) in methanol (1 mL) for 12 hr. The obtained solution was filtered off, evaporated and purified by HPLC (05_methanol+NH₃) to obtain 6-[(1-acetylazetidin-3-yl)amino]-N-[(2R)-2-hydroxy-2-[(3S)-7-[(4-methyloxazol-5-yl)methoxy]-1,2,3,4-tetrahydroisoquinolin-3-yl]ethyl]-2-(4-methyl-1-piperidyl)pyrimidine-4-carboxamide (10.4 mg, 16.81 µmol, 12.72% yield). ¹H NMR (500 MHz, DMSO-d₆) δ 0.97 (d, 3H), 1.09 (m, 3H), 1.66 (m, 3H), 1.77 (s, 3H), 2.18 (s, 3H), 2.60 (m, 1H), 2.78 (m, 4H), 3.39 (m, 1H), 3.56 (m, 2H), 3.79 (m, 1H), 3.92 (s, 2H), 4.00 (m, 1H), 4.13 (m, 1H), 4.38 (m, 1H), 4.59 (m, 1H), 4.69 (m, 2H), 4.94 (m, 1H), 4.98 (s, 2H), 6.37 (s, 1H), 6.61 (s, 1H), 6.70 (d, 1H), 6.98 (d, 1H), 7.74 (m, 1H), 8.02 (s, 1H), 8.56 (m, 1H). LCMS (ESI): [M+H]⁺ m/z: calc'd 618.3; found 619.4; Rt=1.07 min.

Example 4A14. Synthesis of 6-[(1-acetylazetidin-3-yl)amino]-2-(3-azabicyclo[2.2.1]heptan-3-yl)-N-[(2R)-2-hydroxy-2-[(3S)-7-[(4-methyloxazol-5-yl)methoxy]-1,2,3,4-tetrahydroisoquinolin-3-yl]ethyl]pyrimidine-4-carboxamide (Compound 53)

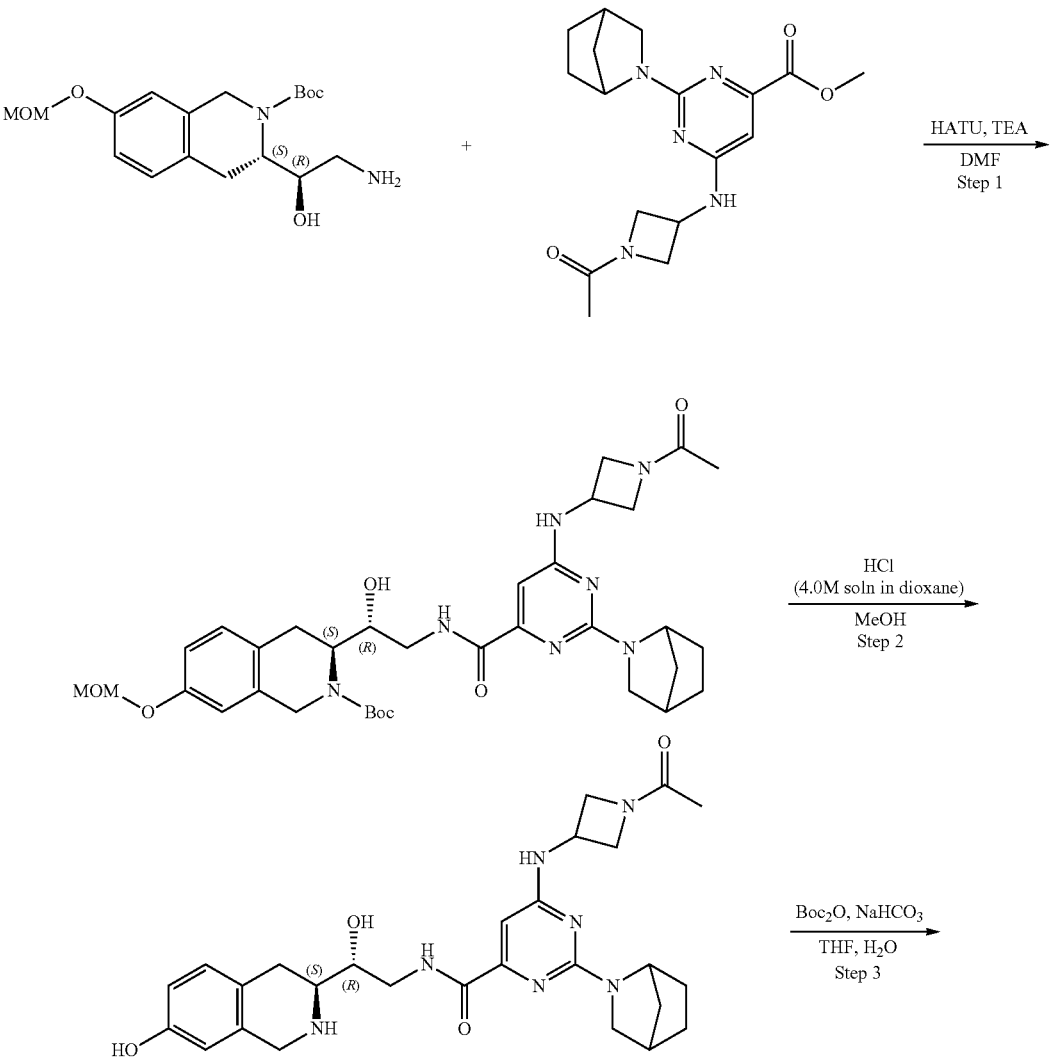

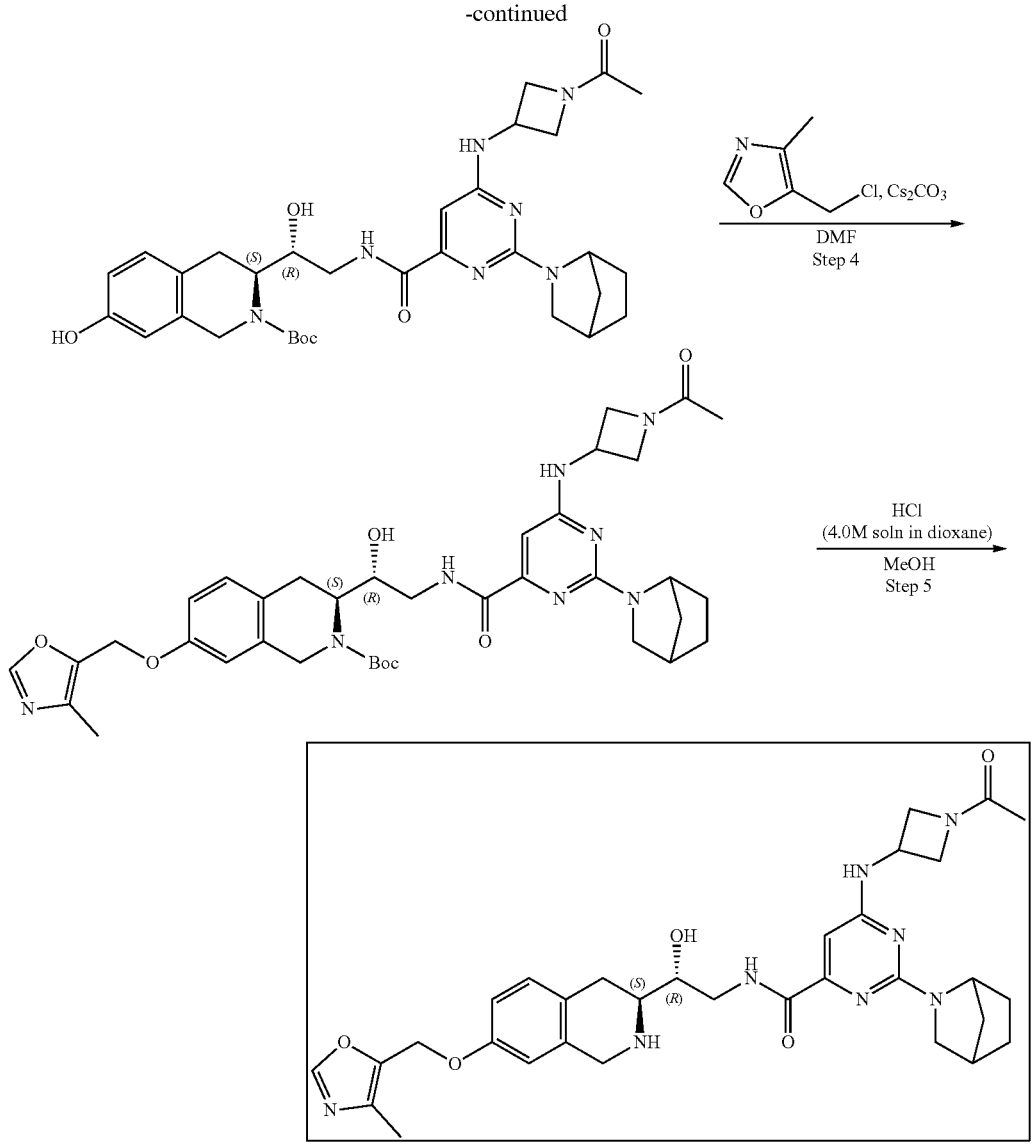

Step 1: Synthesis of tert-butyl (3S)-3-[(1R)-2-[[6-[(1-acetylazetidin-3-yl)amino]-2-(3-azabicyclo[2.2.1]heptan-3-yl)pyrimidine-4-carbonyl]amino]-1-hydroxy-ethyl]-7-(methoxymethoxy)-3,4-dihydro-1H-isoquinoline-2-carboxylate Methyl 6-[(1-acetylazetidin-3-yl)amino]-2-(3-azabicyclo[2.2.1]heptan-3-yl)pyrimidine-4-carboxylate (196.01 mg, 567.50 µmol) and tert-butyl (3S)-3-[(1R)-2-amino-1-hydroxy-ethyl]-7-(methoxymethoxy)-3,4-dihydro-1H-isoquinoline-2-carboxylate (200 mg, 567.50 µmol) were mixed in methanol (2 mL) and heated at 75° C. for 72 hr. After the completion of the reaction, the solution was evaporated under reduce pressure. The resulting crude product was purified by HPLC (70-95% water-acetonitrile, 2-10 min, Flow: 30 mL/min) to obtain tert-butyl (3S)-3-[(1R)-2-[[6-[(1-acetylazetidin-3-yl)amino]-2-(3-azabicyclo[2.2.1]heptan-3-yl)pyrimidine-4-carbonyl]amino]-1-hydroxy-ethyl]-7-(methoxymethoxy)-3,4-dihydro-1H-isoquinoline-2-carboxylate (111 mg, crude). LCMS (ESI): [M+H]+ m/z: calc'd 665.3; found 666.4; Rt=1.38 min.

Step 2: Synthesis of 6-[(1-acetylazetidin-3-yl)amino]-2-(3-azabicyclo[2.2.1]heptan-3-yl)-N-[(2R)-2-hydroxy-2-[(3S)-7-hydroxy-1, 2, 3,4-tetrahydroisoquinolin-3-yl]ethyl]pyrimidine-4-carboxamide The solution of tert-butyl (3S)-3-[(1R)-2-[[6-[(1-acetylazetidin-3-yl)amino]-2-(3-azabicyclo-[2.2.1]heptan-3-yl)pyrimidine-4-carbonyl]amino]-1-hydroxy-ethyl]-7-(methoxymethoxy)-3,4-dihydro-1H-isoquinoline-2-carboxylate (111 mg, 166.72 µmol) in Dioxane/HCl (2 mL) and methanol (2 mL) was stirred for 12 hr at 25° C. Then the solution was evaporated under reduced pressure to obtain 6-[(1-acetylazetidin-3-yl)amino]-2-(3-azabicyclo[2.2.1]heptan-3-yl)-N-[(2R)-2-hydroxy-2-[(3S)-7-hydroxy-1,2,3,4-tetrahydroisoquinolin-3-yl]ethyl]pyrimidine-4-carboxamide (101 mg, crude, 3HCl). LCMS (ESI): [M+H]+ m/z: calc'd 521.3; found 522.2; Rt=0.80 min.

Step 3: Synthesis of tert-butyl (3S)-3-[(1R)-2-[[6-[(1-acetylazetidin-3-yl)amino]-2-(3-azabicyclo[2.2.1]heptan-3-yl)pyrimidine-4-carbonyl]amino]-1-hydroxy-ethyl]-7-hydroxy-3,4-dihydro-1H-isoquinoline-2-carboxylate To a stirred solution of sodium hydrogen carbonate (67.23 mg, 800.33 µmol, 31.13 µL) in water (2 mL) the solution of 6-[(1-acetylazetidin-3-yl)amino]-2-(3-azabicyclo[2.2.1]

heptan-3-yl)-N-[(2R)-2-hydroxy-2-[(3S)-7-hydroxy-1,2,3,4-tetrahydroisoquinolin-3-yl]ethyl]pyrimidine-4-carboxamide (101 mg, 160.07 µmol, 3HCl) in THF (1.5 mL) was added. The resulting mixture was stirred for 5 min at room temperature followed by the solution of di-tert-butyl dicarbonate (36.68 mg, 168.07 µmol, 38.57 µL) in THF (1.5 mL). The resulting mixture was stirred at 25° C. for 12 hr. After the completion of the reaction, EtOAc (10 mL) was added and organic phase was separated and washed with brine (2*5 mL). Then the solvent was dried over sodium sulfate, filtered off and evaporated to obtain tert-butyl (3S)-3-[(1R)-2-[[6-[(1-acetylazetidin-3-yl)amino]-2-(3-azabicyclo[2.2.1]heptan-3-yl)pyrimidine-4-carbonyl]amino]-1-hydroxy-ethyl]-7-hydroxy-3,4-dihydro-1H-isoquinoline-2-carboxylate (83 mg, crude). LCMS (ESI): [M+H]+ m/z: calc'd 621.3; found 622.4; Rt=1.23 min.

Step 4: Synthesis of tert-butyl (3S)-3-[(1R)-2-[[6-[(1-acetylazetidin-3-yl)amino]-2-(3-azabicyclo[2.2.1]heptan-3-yl)pyrimidine-4-carbonyl]amino]-1-hydroxy-ethyl]-7-[(4-methyloxazol-5-yl)methoxy]-3,4-dihydro-1H-isoquinoline-2-carboxylate To the solution of tert-butyl (3S)-3-[(1R)-2-[[6-[(1-acetylazetidin-3-yl)amino]-2-(3-azabicyclo-[2.2.1]heptan-3-yl)pyrimidine-4-carbonyl]amino]-1-hydroxy-ethyl]-7-hydroxy-3,4-dihydro-1H-isoquinoline-2-carboxylate (83 mg, 133.50 µmol), cesium carbonate (130.49 mg, 400.50 µmol) in DMF (3 mL) 5-(chloromethyl)-4-methyl-oxazole (26.92 mg, 160.20 µmol, HCl) was added. The resulting mixture was heated at 50° for 12 hr. After the completion of the reaction, the resulting mixture was filtered off and evaporated in vacuo to obtain tert-butyl (3S)-3-[(1R)-2-[[6-[(1-acetylazetidin-3-yl)amino]-2-(3-azabicyclo[2.2.1]heptan-3-yl)pyrimidine-4-carbonyl]amino]-1-hydroxy-ethyl]-7-[(4-methyloxazol-5-yl)methoxy]-3,4-dihydro-1H-isoquinoline-2-carboxylate (95 mg, crude) that was used without further purification. LCMS (ESI): [M+H]+ m/z: calc'd 716.3; found 717.4; Rt=1.30 min.

Step 5: Synthesis of 6-[(1-acetylazetidin-3-yl)amino]-2-(3-azabicyclo[2.2.1]heptan-3-yl)-N-[(2R)-2-hydroxy-2-[(3S)-7-[(4-methyloxazol-5-yl)methoxy]-1,2,3,4-tetrahydroisoquinolin-3-yl]ethyl]pyrimidine-4-carboxamide (Compound 53) The solution of tert-butyl (3S)-3-[(1R)-2-[[6-[(1-acetylazetidin-3-yl)amino]-2-(3-azabicyclo[2.2.1]heptan-3-yl)pyrimidine-4-carbonyl]amino]-1-hydroxy-ethyl]-7-[(4-methyloxazol-5-yl)methoxy]-3,4-dihydro-1H-isoquinoline-2-carboxylate (95 mg, 132.53 µmol) in dioxane/HCl (2 mL) and methanol (2 mL) was stirred for 3 hr at 25° C. The resulting mixture was stirred with SiliaMetS® DMT (30 mg) in methanol (1 mL) for 12 hr. The suspension was filtered off, evaporated under reduced pressure and purified by HPLC (65-90% water-MeOH+NH3) to obtain 6-[(1-acetylazetidin-3-yl)amino]-2-(3-azabicyclo[2.2.1]heptan-3-yl)-N-[(2R)-2-hydroxy-2-[(3S)-7-[(4-methyloxazol-5-yl)methoxy]-1,2,3,4-tetrahydroisoquinolin-3-yl]ethyl]pyrimidine-4-carboxamide (7.4 mg, 12.00 µmol, 9.05% yield). 1H NMR (400 MHz, CDCl3) δ 1.44 (m, 3H), 1.68 (m, 6H), 1.88 (s, 3H), 2.22 (s, 3H), 2.75 (m, 1H), 2.84 (m, 1H), 3.00 (m, 1H), 3.16 (m, 1H), 3.42 (m, 1H), 3.62 (m, 1H), 3.69 (m, 1H), 3.83 (m, 1H), 4.02 (m, 4H), 4.34 (m, 1H), 4.44 (m, 1H), 4.68 (m, 2H), 4.97 (s, 2H), 6.09 (m, 1H), 6.52 (s, 1H), 6.62 (d, 1H), 6.77 (d, 1H), 7.05 (d, 1H), 7.80 (s, 1H), 8.57 (m, 1H). LCMS (ESI): [M+H]+ m/z: calc'd 616.3; found 617.4; Rt=0.96 min.

Example 4A15. Synthesis of 6-[(1-acetylazetidin-3-yl)amino]-2-(3-azabicyclo(3.1.1]heptan-3-yl)-N-[(2R)-2-hydroxy-2-[(3S)-7-[(4-methyloxazol-5-yl)methoxy]-1,2,3,4-tetrahydroisoquinolin-3-yl]ethyl]pyrimidine-4-carboxamide (Compound 51)

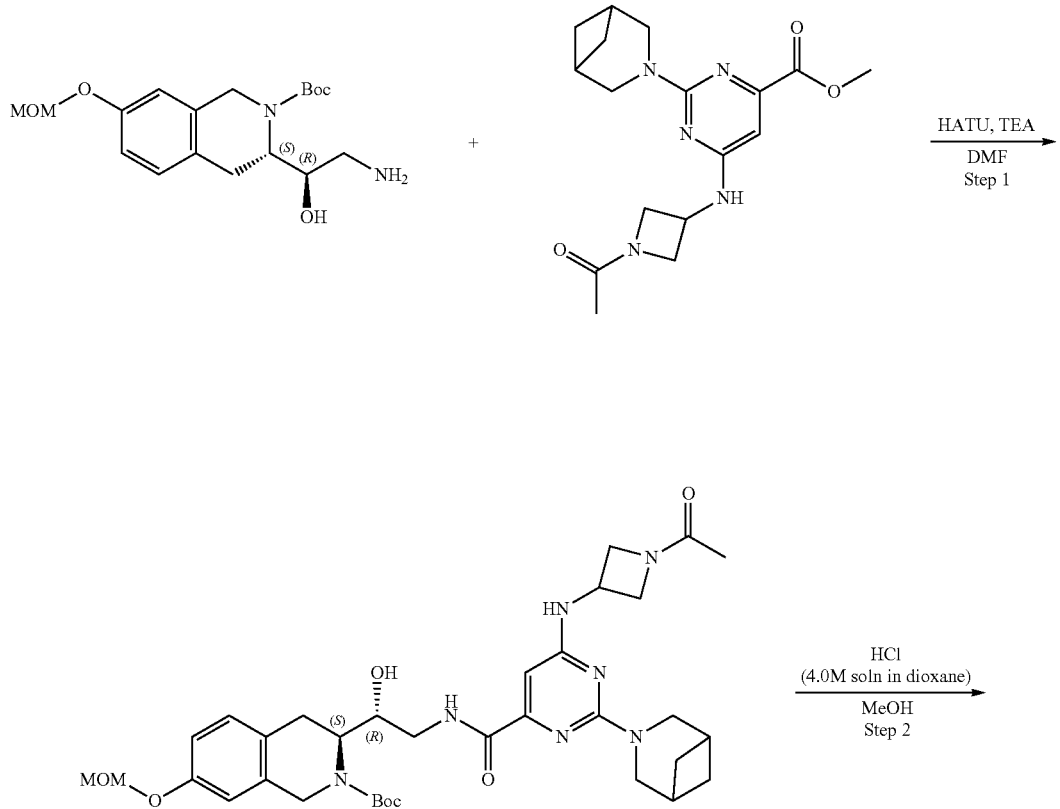

-continued
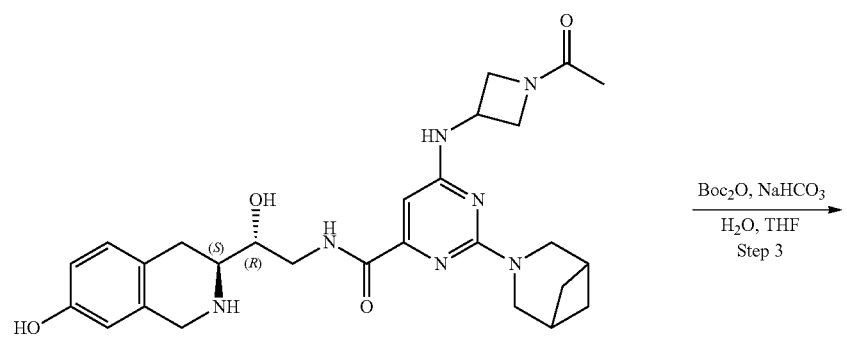
Boc₂O, NaHCO₃
———————→
H₂O, THF
Step 3
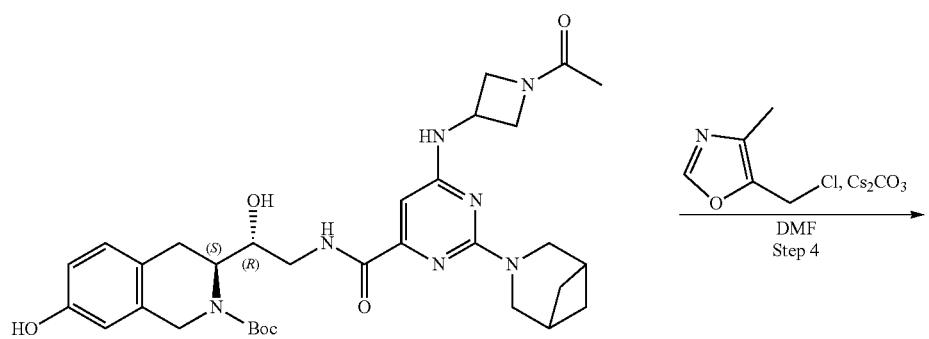
4-methyl-5-(chloromethyl)oxazole, Cs₂CO₃
———————→
DMF
Step 4
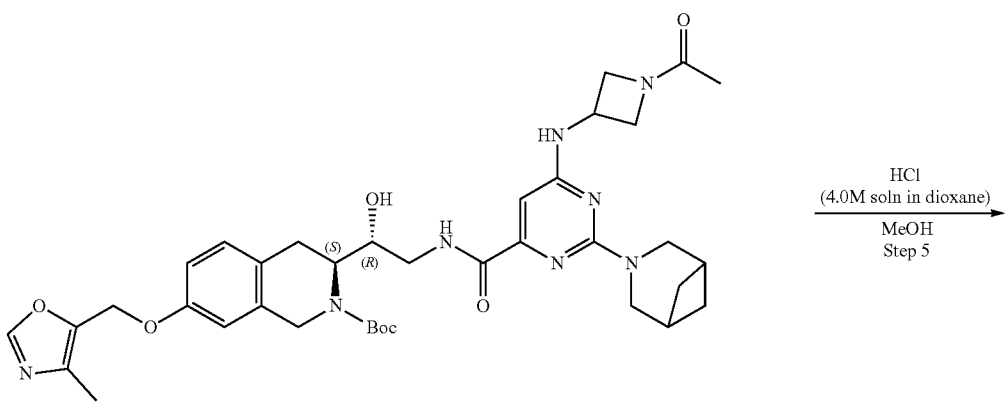
HCl
(4.0M soln in dioxane)
———————→
MeOH
Step 5
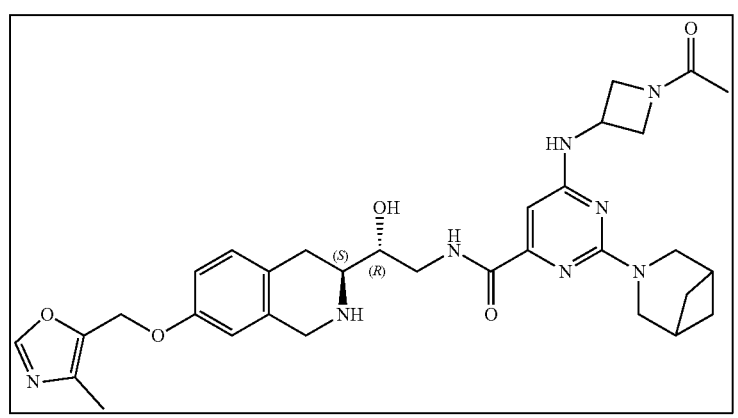

Step 1: Synthesis of tert-butyl (3S)-3-[(1R)-2-[[6-[(1-acetylazetidin-3-yl)amino]-2-(3-azabicyclo[3.1.1]heptan-3-yl)pyrimidine-4-carbonyl]amino]-1-hydroxy-ethyl]-7-(methoxymethoxy)-3,4-dihydro-1H-isoquinoline-2-carboxylate Methyl 6-[(1-acetylazetidin-3-yl)amino]-2-(3-azabicyclo[3.1.1]heptan-3-yl)pyrimidine-4-carboxylate (196.01 mg, 567.50 μmol) and tert-butyl (3S)-3-[(1R)-2-amino-1-hydroxy-ethyl]-7-(methoxymethoxy)-3,4-dihydro-1H-isoquinoline-2-carboxylate (200 mg, 567.50 μmol) were mixed in methanol (2 mL) and stirred at 75° C. for 72 hr. After the completion of the reaction, the solution was evaporated under reduce pressure. The resulting crude product was purified by HPLC (70-95% water-acetonitrile, 2-10 min, Flow: 30 mL/min) to obtain tert-butyl (3S)-3-[(1R)-2-[[6-[(1-acetylazetidin-3-yl)amino]-2-(3-azabicyclo[3.1.1]heptan-3-yl)pyrimidine-4-carbonyl]amino]-1-hydroxy-ethyl]-7-(methoxymethoxy)-3,4-dihydro-1H-isoquinoline-2-carboxylate (100.9 mg, 151.55 μmol, 26.71% yield). $^1$H NMR (CDCl$_3$, 400 MHz): δ 1.52 (m, 11H), 1.88 (s, 3H), 2.32 (m, 3H), 3.03 (m, 3H), 3.48 (s, 4H), 4.18 (m, 14H), 5.14 (s, 2H), 5.85 (m, 1H), 6.56 (s, 1H), 6.79 (s, 1H), 6.83 (d, 1H), 7.07 (d, 1H), 9.23 (m, 1H). LCMS (ESI): [M+H]$^+$ m/z: calc'd 665.3; found 666.4; Rt=3.75 min.

Step 2: Synthesis of 6-[(1-acetylazetidin-3-yl)amino]-2-(3-azabicyclo[3.1.1]heptan-3-yl)-N-[(2R)-2-hydroxy-2-[(3S)-7-hydroxy-1, 2, 3,4-tetrahydroisoquinolin-3-yl]ethyl]pyrimidine-4-carboxamide The solution of tert-butyl (3S)-3-[(1R)-2-[[6-[(1-acetylazetidin-3-yl)amino]-2-(3-azabicyclo-[3.1.1]heptan-3-yl)pyrimidine-4-carbonyl]amino]-1-hydroxy-ethyl]-7-(methoxymethoxy)-3,4-dihydro-1H-isoquinoline-2-carboxylate (100.9 mg, 151.55 μmol) in dioxane/HCl (2 mL) and methanol (2 mL) was stirred for 12 hr at 25° C. Then the solution was evaporated to obtain 6-[(1-acetylazetidin-3-yl)amino]-2-(3-azabicyclo[3.1.1]heptan-3-yl)-N-[(2R)-2-hydroxy-2-[(3S)-7-hydroxy-1,2,3,4-tetrahydroisoquinolin-3-yl]ethyl]pyrimidine-4-carboxamide (90 mg, crude, 3HCl). LCMS (ESI): [M+2H]$^+$ m/z: calc'd 521.3; found 523.2; Rt=0.88 min.

Step 3: Synthesis of tert-butyl (3S)-3-[(1R)-2-[[6-[(1-acetylazetidin-3-yl)amino]-2-(3-azabicyclo[3.1.1]heptan-3-yl)pyrimidine-4-carbonyl]amino]-1-hydroxy-ethyl]-7-hydroxy-3,4-dihydro-1H-isoquinoline-2-carboxylate To a stirred solution of sodium hydrogen carbonate (59.91 mg, 713.16 μmol, 27.74 μL) in water (2 mL) the solution of 6-[(1-acetylazetidin-3-yl)amino]-2-(3-azabicyclo[3.1.1]heptan-3-yl)-N-[(2R)-2-hydroxy-2-[(3S)-7-hydroxy-1,2,3,4-tetrahydroisoquinolin-3-yl]ethyl]pyrimidine-4-carboxamide (90 mg, 142.63 μmol, 3HCl) in THF (1.5 mL) was added. The resulting mixture was stirred for 5 min at room temperature followed by the addition of di-tert-butyl dicarbonate (32.69 mg, 149.76 μmol, 34.37 μL) in THF (1.5 mL). The resulting mixture was stirred at 25° C. for 12 hr. After the completion of the reaction, EtOAc (10 mL) was added and the organic phase was separated and washed with brine (2*5 mL). Then the solvent was dried over sodium sulfate, filtered off and evaporated to obtain tert-butyl (3S)-3-[(1R)-2-[[6-[(1-acetylazetidin-3-yl)amino]-2-(3-azabicyclo[3.1.1]heptan-3-yl)pyrimidine-4-carbonyl]amino]-1-hydroxy-ethyl]-7-hydroxy-3,4-dihydro-1H-isoquinoline-2-carboxylate (75 mg, crude). LCMS (ESI): [M+H]$^+$ m/z: calc'd 621.3; found 622.4; Rt=1.34 min.

Step 4: Synthesis of tert-butyl (3S)-3-[(1R)-2-[[6-[(1-acetylazetidin-3-yl)amino]-2-(3-azabicyclo[3.1.1]heptan-3-yl)pyrimidine-4-carbonyl]amino]-1-hydroxy-ethyl]-7-[(4-methyloxazol-5-yl)methoxy]-3,4-dihydro-1H-isoquinoline-2-carboxylate To the solution of tert-butyl (3S)-3-[(1R)-2-[[6-[(1-acetylazetidin-3-yl)amino]-2-(3-azabicyclo-[3.1.1]heptan-3-yl)pyrimidine-4-carbonyl]amino]-1-hydroxy-ethyl]-7-hydroxy-3,4-dihydro-1H-isoquinoline-2-carboxylate (75 mg, 120.63 μmol), cesium carbonate (117.91 mg, 361.90 μmol) in DMF (3 mL) 5-(chloromethyl)-4-methyl-oxazole (24.32 mg, 144.76 μmol, HCl) was added. The resulting mixture was stirred at 50° C. for 12 hr. After the completion of the reaction, the mixture was filtered off and evaporated under reduced pressure to obtain tert-butyl (3S)-3-[(1R)-2-[[6-[(1-acetylazetidin-3-yl)amino]-2-(3-azabicyclo[3.1.1]heptan-3-yl)pyrimidine-4-carbonyl]amino]-1-hydroxy-ethyl]-7-[(4-methyloxazol-5-yl)methoxy]-3,4-dihydro-1H-isoquinoline-2-carboxylate (80 mg, crude) that was used without further purification. LCMS (ESI): [M+H]$^+$ m/z: calc'd 716.3; found 717.4; Rt=1.40 min.

Step 5: Synthesis of 6-[(1-acetylazetidin-3-yl)amino]-2-(3-azabicyclo[3.1.1]heptan-3-yl)-N-[(2R)-2-hydroxy-2-[(3S)-7-[(4-methyloxazol-5-yl)methoxy]-1,2,3,4-tetrahydroisoquinolin-3-yl]ethyl]pyrimidine-4-carboxamide (Compound 51) The solution of tert-butyl (3S)-3-[(1R)-2-[[6-[(1-acetylazetidin-3-yl)amino]-2-(3-azabicyclo-[3.1.1]heptan-3-yl)pyrimidine-4-carbonyl]amino]-1-hydroxy-ethyl]-7-[(4-methyloxazol-5-yl)methoxy]-3,4-dihydro-1H-isoquinoline-2-carboxylate (80 mg, 111.60 μmol) in Dioxane/HCl (2 mL) and Methanol (2 mL) was stirred for 3 hr at 25° C. The resulting mixture was stirred with SiliaMetS® DMT (30 mg) in methanol (1 mL) for 12 hr. After the completion of the reaction, the solution was filtered off, evaporated in vacuo and purified by HPLC (65-90% water-MeOH+NH$_3$) to obtain 6-[(1-acetylazetidin-3-yl)amino]-2-(3-azabicyclo[3.1.1]heptan-3-yl)-N-[(2R)-2-hydroxy-2-[(3S)-7-[(4-methyloxazol-5-yl)methoxy]-1,2,3,4-tetrahydroisoquinolin-3-yl]ethyl]pyrimidine-4-carboxamide (7.9 mg, 12.81 μmol, 11.48% yield). $^1$H NMR (400 MHz, CDCl$_3$) δ 1.40 (m, 2H), 1.81 (m, 2H), 1.88 (s, 3H), 2.19 (m, 2H), 2.22 (s, 3H), 2.55 (m, 2H), 2.77 (m, 1H), 2.83 (m, 1H), 3.03 (m, 1H), 3.64 (m, 1H), 3.75 (m, 5H), 3.87 (m, 1H), 4.03 (m, 4H), 4.36 (m, 1H), 4.46 (m, 1H), 4.72 (m, 1H), 4.97 (s, 2H), 5.97 (m, 1H), 6.61 (m, 2H), 6.78 (d, 1H), 7.05 (d, 1H), 7.80 (s, 1H), 8.64 (m, 1H). LCMS (ESI): [M+H]$^+$ m/z: calc'd 616.3; found 617.4; Rt=1.02 min.

Example 4A16. Synthesis of 6-[(1-acetylazetidin-3-yl)amino]-2-(3-azabicyclo[3.2.1]octan-3-yl)-N-[(2R)-2-hydroxy-2-[(3S)-7-[(4-methyloxazol-5-yl)methoxy]-1,2,3,4-tetrahydroisoquinolin-3-yl]ethyl]pyrimidine-4-carboxamide (Compound 56)

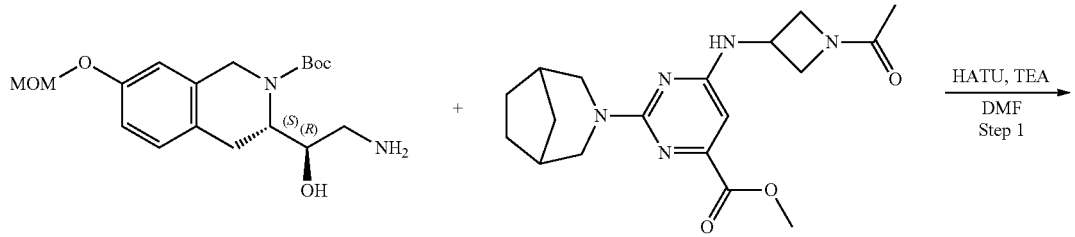

-continued
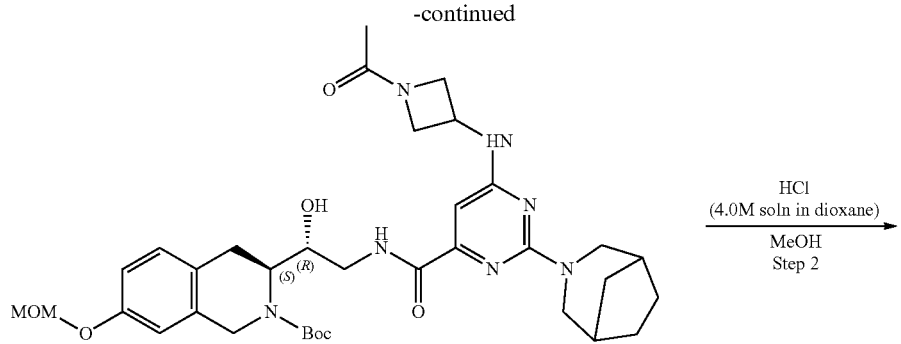
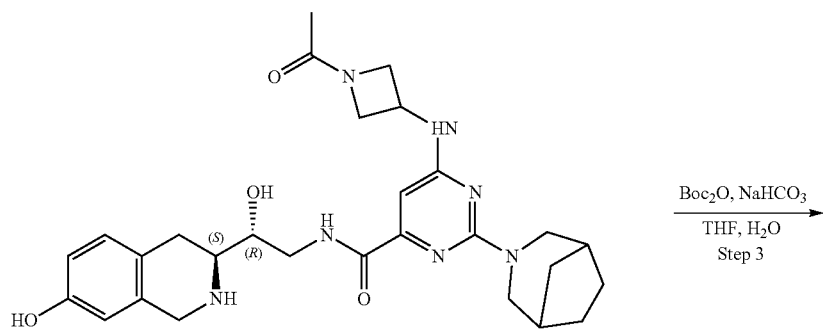
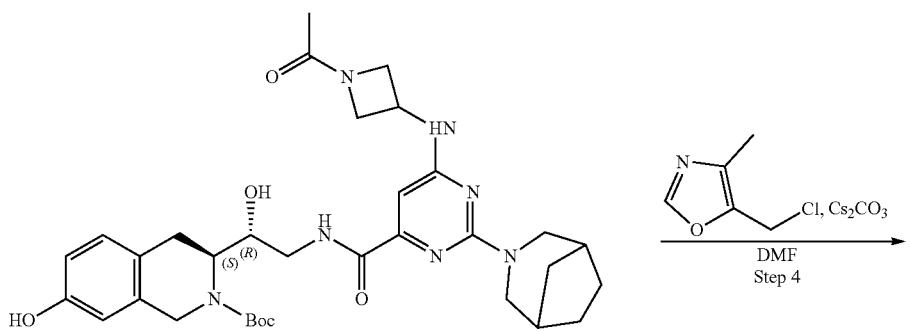
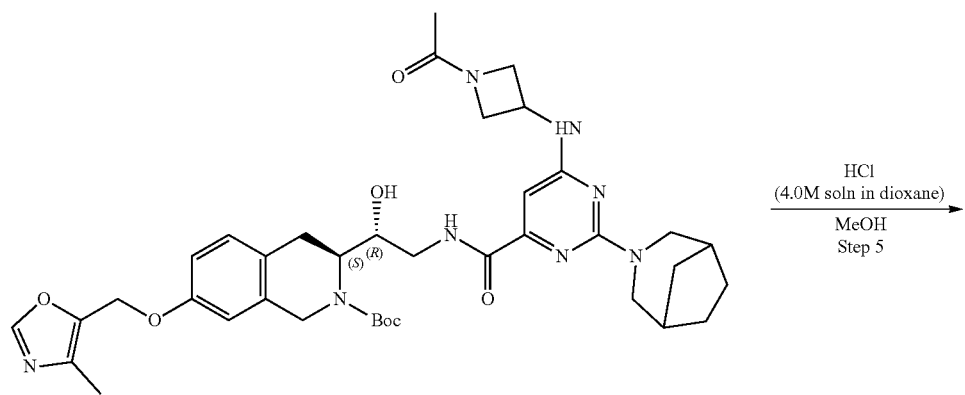

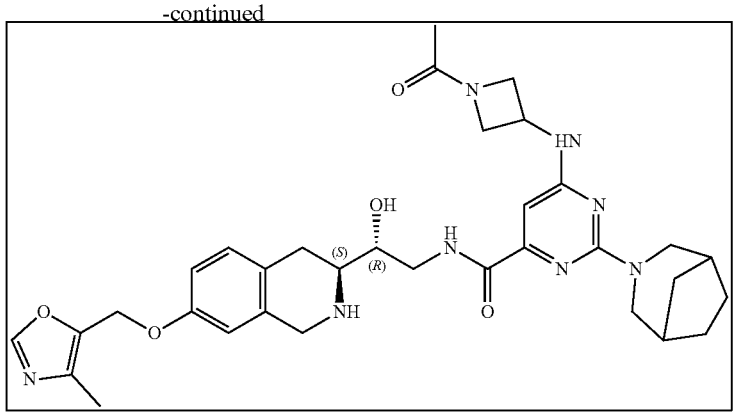

Step 1: Synthesis of tert-butyl (3S)-3-[(1R)-2-[[6-[(1-acetylazetidin-3-yl)amino]-2-(3-azabicyclo[3.2.1]octan-3-yl)pyrimidine-4-carbonyl]amino]-1-hydroxy-ethyl]-7-(methoxymethoxy)-3,4-dihydro-1H-isoquinoline-2-carboxylate Methyl 6-[(1-acetylazetidin-3-yl)amino]-2-(3-azabicyclo[3.2.1]octan-3-yl)pyrimidine-4-carboxylate (203.97 mg, 567.50 μmol) and tert-butyl (3S)-3-[(1R)-2-amino-1-hydroxy-ethyl]-7-(methoxymethoxy)-3,4-dihydro-1H-isoquinoline-2-carboxylate (200 mg, 567.50 μmol) were mixed in methanol (2 mL) and stirred at 75° C. for 72 hr. After the completion of the reaction, the solution was evaporated under reduce pressure. The resulting crude product was purified by HPLC (70-95% water-acetonitrile, 2-10 min, Flow: 30 mL/min) to obtain tert-butyl (3S)-3-[(1R)-2-[[6-[(1-acetylazetidin-3-yl)amino]-2-(3-azabicyclo-[3.2.1]octan-3-yl)pyrimidine-4-carbonyl]amino]-1-hydroxy-ethyl]-7-(methoxymethoxy)-3,4-dihydro-1H-isoquinoline-2-carboxylate (140.6 mg, 206.82 μmol, 36.44% yield). $^1$H NMR (CDCl$_3$, 400 MHz): δ 1.61 (m, 14H), 1.88 (s, 3H), 2.31 (m, 2H), 3.06 (m, 5H), 3.49 (m, 8H), 4.33 (m, 8H), 5.14 (s, 2H), 5.69 (m, 1H), 6.47 (s, 1H), 6.80 (s, 1H), 6.96 (d, 1H), 6.99 (d, 1H), 9.15 (m, 1H). LCMS (ESI): [M+H]$^+$ m/z: calc'd 679.3; found 680.4; Rt=1.57 min.

Step 2: Synthesis of 6-[(1-acetylazetidin-3-yl)amino]-2-(3-azabicyclo[3.2.1]octan-3-yl)-N-[(2R)-2-hydroxy-2-[(3S)-7-hydroxy-1, 2, 3,4-tetrahydroisoquinolin-3-yl]ethyl]pyrimidine-4-carboxamide The solution of tert-butyl (3S)-3-[(1R)-2-[[6-[(1-acetylazetidin-3-yl)amino]-2-(3-azabicyclo-[3.2.1]octan-3-yl)pyrimidine-4-carbonyl]amino]-1-hydroxy-ethyl]-7-(methoxymethoxy)-3,4-dihydro-1H-isoquinoline-2-carboxylate (140.6 mg, 206.82 μmol) in Dioxane/HCl (2 mL) and Methanol (2 mL) was stirred for 12 hr at 25° C. Then the solution was evaporated under reduced to obtain 6-[(1-acetylazetidin-3-yl)amino]-2-(3-azabicyclo[3.2.1]octan-3-yl)-N-[(2R)-2-hydroxy-2-[(3S)-7-hydroxy-1,2,3,4-tetrahydro-isoquinolin-3-yl]ethyl]pyrimidine-4-carboxamide (125 mg, crude, 3HCl). LCMS (ESI): [M+H]$^+$ m/z: calc'd 535.3; found 536.4; Rt=0.95 min.

Step 3: Synthesis of tert-butyl (3S)-3-[(1R)-2-[[6-[(1-acetylazetidin-3-yl)amino]-2-(3-azabicyclo[3.2.1]octan-3-yl)pyrimidine-4-carbonyl]amino]-1-hydroxy-ethyl]-7-hydroxy-3,4-dihydro-1H-isoquinoline-2-carboxylate To a stirred solution of sodium hydrogen carbonate (81.40 mg, 968.96 μmol, 37.68 μL) in water (2 mL) the solution of 6-[(1-acetylazetidin-3-yl)amino]-2-(3-azabicyclo[3.2.1]octan-3-yl)-N-[(2R)-2-hydroxy-2-[(3S)-7-hydroxy-1,2,3,4-tetrahydroisoquinolin-3-yl]ethyl]pyrimidine-4-carboxamide (125 mg, 193.79 μmol, 3HCl) in THF (1.5 mL) was added. The reaction mixture was stirred for 5 min at room temperature followed the addition of the solution of di-tert-butyl dicarbonate (44.41 mg, 203.48 μmol, 46.70 μL) in THF (1.5 mL). The resulting mixture was stirred at 25° C. for 12 hr.

After the completion of the reaction, EtOAc (10 mL) was added and the organic phase was separated and washed with brine (2*5 mL). Then the solvent was dried over sodium sulfate, filtered off and evaporated to obtain tert-butyl (3S)-3-[(1R)-2-[[6-[(1-acetylazetidin-3-yl)amino]-2-(3-azabicyclo[3.2.1]octan-3-yl)pyrimidine-4-carbonyl]amino]-1-hydroxy-ethyl]-7-hydroxy-3,4-dihydro-1H-isoquinoline-2-carboxylate (105 mg, crude). LCMS (ESI): [M+H]$^+$ m/z: calc'd 635.3; found 636.4; Rt=1.42 min.

Step 4: Synthesis of tert-butyl (3S)-3-[(1R)-2-[[6-[(1-acetylazetidin-3-yl)amino]-2-(3-azabicyclo[3.2.1]octan-3-yl)pyrimidine-4-carbonyl]amino]-1-hydroxy-ethyl]-7-[(4-methyloxazol-5-yl)methoxy]-3,4-dihydro-1H-isoquinoline-2-carboxylate) To the solution of tert-butyl (3S)-3-[(1R)-2-[[6-[(1-acetylazetidin-3-yl)amino]-2-(3-azabicyclo-[3.2.1]octan-3-yl)pyrimidine-4-carbonyl]amino]-1-hydroxy-ethyl]-7-hydroxy-3,4-dihydro-1H-isoquinoline-2-carboxylate (105 mg, 165.16 μmol), cesium carbonate (161.44 mg, 495.48 μmol) in DMF (3 mL), 5-(chloromethyl)-4-methyl-oxazole (33.30 mg, 198.19 μmol, HCl) was added. The resulting mixture was stirred at 50° C. for 12 hr. After the completion of the reaction, the mixture was filtered off and evaporated under reduced pressure to obtain tert-butyl (3S)-3-[(1R)-2-[[6-[(1-acetylazetidin-3-yl)amino]-2-(3-azabicyclo[3.2.1]octan-3-yl)pyrimidine-4-carbonyl]amino]-1-hydroxy-ethyl]-7-[(4-methyloxazol-5-yl)methoxy]-3,4-dihydro-1H-isoquinoline-2-carboxylate (125 mg, crude) that was used without further purification. LCMS (ESI): [M+H]$^+$ m/z: calc'd 730.3; found 731.4; Rt=1.47 min.

Step 5: Synthesis of 6-[(1-acetylazetidin-3-yl)amino]-2-(3-azabicyclo[3.2.1]octan-3-yl)-N-[(2R)-2-hydroxy-2-[(3S)-7-[(4-methyloxazol-5-yl)methoxy]-1,2,3,4-tetrahydroisoquinolin-3-yl]ethyl]pyrimidine-4-carboxamide (Compound 56) The solution of tert-butyl (3S)-3-[(1R)-2-[[6-[(1-acetylazetidin-3-yl)amino]-2-(3-azabicyclo-[3.2.1]octan-3-yl)pyrimidine-4-carbonyl]amino]-1-hydroxy-ethyl]-7-[(4-methyloxazol-5-yl)methoxy]-3,4-dihydro-1H-isoquinoline-2-carboxylate (125 mg, 171.03 μmol) in Dioxane/HCl (2 mL) and methanol (2 mL) was stirred for 3 hr at 25° C. The resulting mixture was stirred with SiliaMetS® DMT (30 mg) in methanol (1 mL) for 12 hr. The solution was filtered off, evaporated under reduced pressure and purified by HPLC (30-40% water-methanol+NH$_3$) to obtain 6-[(1-acetylazetidin-3-yl)amino]-2-(3-azabicyclo[3.2.1]octan-3-yl)-N-[(2R)-2-hydroxy-2-[(3S)-7-[(4-methyloxazol-5-yl)methoxy]-1,2,3,4-tetrahydroisoquinolin-3-yl]ethyl]pyrimidine-4-carboxamide (14.5 mg, 22.99 μmol, 13.44% yield). $^1$H NMR (400 MHz, CDCl$_3$) δ 1.50 (m, 2H), 1.59 (m, 2H), 1.65 (m, 2H), 1.87 (s, 3H), 2.22 (s, 3H), 2.28 (m, 2H), 2.73 (m, 1H), 2.86 (m, 3H), 3.00 (m, 1H), 3.66 (m, 2H), 3.83 (m, 1H), 4.01 (m, 4H), 4.32 (m, 3H), 4.45 (m, 1H), 4.71 (m, 1H), 4.96 (s, 2H), 6.43 (m, 1H), 6.58 (m, 1H), 6.61

(d, 1H), 6.77 (dd, 1H), 7.04 (d, 1H), 7.80 (s, 1H), 8.65 (t, 1H). LCMS (ESI): [M+H]⁺ m/z: calc'd 630.3; found 631.4; Rt=1.06 min.
Example 4A17. Synthesis of 6-[(1-acetyl-4-piperidyl)amino]-N-[(2R)-2-hydroxy-2-[(3S)-7-((4-methyloxazol-5-yl)methoxy]-1,2,3,4-tetrahydroisoquinolin-3-yl]ethyl]-2-pyrrolidin-1-yl-pyrimidine-4-carboxamide
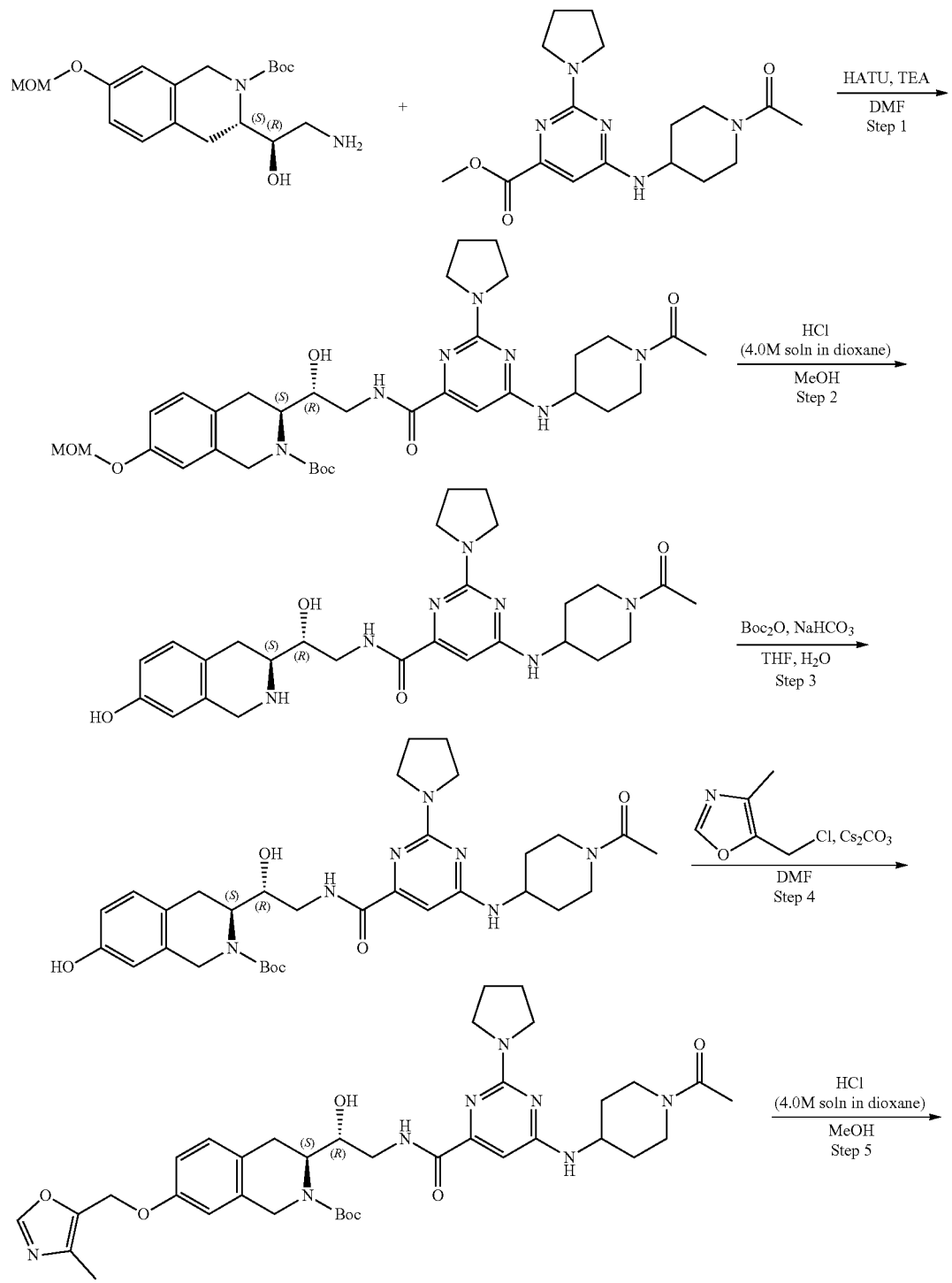

-continued

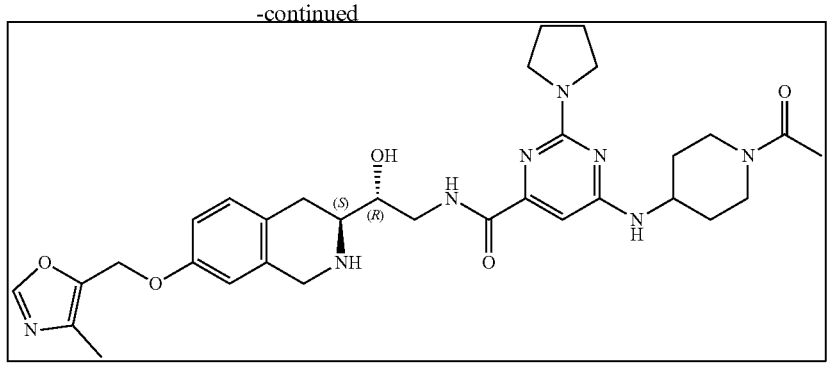

Step 1: Synthesis of tert-butyl (3S)-3-[(1R)-2-[[6-[(1-acetyl-4-piperidyl)amino]-2-pyrrolidin-1-yl-pyrimidine-4-carbonyl]amino]-1-hydroxy-ethyl]-7-(methoxymethoxy)-3,4-dihydro-1H-isoquinoline-2-carboxylate tert-Butyl (3S)-3-[(1R)-2-amino-1-hydroxy-ethyl]-7-(methoxymethoxy)-3,4-dihydro-1H-iso-quinoline-2-carboxylate (0.2 g, 567.50 µmol) and methyl 6-[(1-acetyl-4-piperidyl)amino]-2-pyrrolidin-1-yl-pyrimidine-4-carboxylate (197.16 mg, 567.50 µmol) were dissolved in Methanol (3 mL) and stirred at 75° C. for 72 hr. After the completion of the reaction, the solvent was evaporated in vacuo at 45° C. to give crude product which was purified by HPLC (15-40% water-acetonitrile, 2-10 min, flow 30 mL/min (loading pump 4 mL/min acetonitrile) column: SunFire C18 100*19 mm) to give tert-butyl (3S)-3-[(1R)-2-[[6-[(1-acetyl-4-piperidyl)amino]-2-pyrrolidin-1-yl-pyrimidine-4-carbonyl]amino]-1-hydroxy-ethyl]-7-(methoxymethoxy)-3,4-dihydro-1H-isoquinoline-2-carboxylate (0.14 g, 209.65 µmol, 36.94% yield). $^1$H NMR (DMSO-d$_6$, 400 MHz): δ 1.03 (m, 1H), 1.24 (m, 9H), 1.39 (m, 6H), 1.45 (m, 4H), 1.86 (m, 2H), 1.86 (m, 2H), 2.00 (m, 2H), 2.88 (m, 2H), 3.32 (m, 4H), 3.44 (m, 1H), 3.74 (m, 1H), 4.02 (m, 1H), 4.16 (m, 4H), 4.74 (m, 1H), 5.14 (s, 3H), 6.35 (s, 1H), 6.82 (m, 2H), 7.05 (d, 1H), 7.20 (m, 1H), 8.43 (m, 1H). LCMS (ESI): [M+H]$^+$ m/z: calc'd 667.3; found 668.4; Rt=1.33 min.

Step 2: Synthesis of 6-[(1-acetyl-4-piperidyl)amino]-N-[(2R)-2-hydroxy-2-[(3S)-7-hydroxy-1,2,3,4-tetrahydroiso-quinolin-3-yl]ethyl]-2-pyrrolidin-1-yl-pyrimidine-4-carboxamide tert-Butyl (3S)-3-[(1R)-2-[[6-[(1-acetyl-4-piperidyl)amino]-2-pyrrolidin-1-yl-pyrimidine-4-carbonyl]amino]-1-hydroxy-ethyl]-7-(methoxymethoxy)-3,4-dihydro-1H-isoquinoline-2-carboxylate (0.14 g, 209.65 µmol) was dissolved in MeOH (4 mL). Then hydrogen chloride solution 4.0M in dioxane (573.29 mg, 15.72 mmol, 716.61 µL) was added. The resulting mixture was stirred for 3 hr at 20° C. After the completion of the reaction, the solvent was removed in vacuo at 35° C. to give 6-[(1-acetyl-4-piperidyl)amino]-N-[(2R)-2-hydroxy-2-[(3S)-7-hydroxy-1,2,3,4-tetrahydroisoquinolin-3-yl]ethyl]-2-pyrrolidin-1-yl-pyrimidine-4-carboxamide (0.124 g, 195.89 µmol, 93.44% yield, 3HCl) which was used in the next step without further purification. $^1$H NMR (DMSO-d$_6$, 500 MHz): δ 1.40 (m, 3H), 1.89 (m, 6H), 2.00 (m, 4H), 2.80 (m, 2H), 2.99 (m, 3H), 3.16 (m, 3H), 3.48 (m, 4H), 3.78 (m, 2H), 4.13 (m, 4H), 6.43 (s, 1H), 6.59 (s, 1H), 6.68 (d, 1H), 7.05 (d, 1H), 8.89 (m, 1H), 9.41 (m, 1H). LCMS (ESI): [M+H]$^+$ m/z: calc'd 523.3; found 524.4; Rt=1.85 min.

Step 3: Synthesis of tert-butyl (3S)-3-[(1R)-2-[[6-[(1-acetyl-4-piperidyl)amino]-2-pyrrolidin-1-yl-pyrimidine-4-carbonyl]amino]-1-hydroxy-ethyl]-7-hydroxy-3,4-dihydro-1H-isoquinoline-2-carboxylate 6-[(1-Acetyl-4-piperidyl)amino]-N-[(2R)-2-hydroxy-2-[(3S)-7-hydroxy-1,2,3,4-tetrahydroiso-quinolin-3-yl]ethyl]-2-pyrrolidin-1-yl-pyrimidine-4-carboxamide (0.124 g, 195.89 µmol, 3HCl) was dissolved in a mixture of water (2 mL) and THF (2 mL) then sodium hydrogen carbonate, 99% (82.28 mg, 979.45 µmol, 38.09 µL) was added in one portion. The resulting mixture was stirred for 5 min at room temperature followed by the dropwise addition of the solution of di-tert-butyl dicarbonate (42.75 mg, 195.89 µmol, 44.96 µL) in THF (0.2 mL). The reaction mixture was stirred for 4 hr at room temperature. After all starting material was consumed, as was shown by LCMS, ethyl acetate (15 mL) was added to the reaction mixture. The organic phase was separated, and the aqueous phase was extracted with ethyl acetate (2*15 mL). The organic phase was washed with brine, dried over Na$_2$SO$_4$, filtered off and evaporated in vacuo at 40° C. to give tert-butyl (3S)-3-[(1R)-2-[[6-[(1-acetyl-4-piperidyl)amino]-2-pyrrolidin-1-yl-pyrimidine-4-carbonyl]amino]-1-hydroxy-ethyl]-7-hydroxy-3,4-dihydro-TH-isoquinoline-2-carboxylate (0.121 g, 193.99 µmol, 99.03% yield) which was used in the next step without purification. $^1$H NMR (CDCl$_3$, 400 MHz): δ 1.24 (m, 2H), 1.34 (m, 2H), 1.49 (s, 9H), 1.58 (m, 4H), 1.92 (m, 4H), 2.00 (m, 2H), 2.09 (m, 2H), 2.78 (m, 2H), 2.98 (m, 2H), 3.10 (m, 2H), 3.50 (m, 2H), 3.93 (m, 2H), 4.12 (m, 1H), 4.39 (m, 1H), 4.59 (m, 1H), 4.80 (m, 1H), 6.41 (s, 1H), 6.54 (m, 1H), 6.62 (d, 1H), 6.98 (s, 1H), 9.06 (m, 1H). LCMS (ESI): [M+H]$^+$ m/z: calc'd 623.3; found 624.2; Rt=3.06 min.

Step 4: Synthesis of tert-butyl (3S)-3-[(1R)-2-[[6-[(1-acetyl-4-piperidyl)amino]-2-pyrrolidin-1-yl-pyrimidine-4-carbonyl]amino]-1-hydroxy-ethyl]-7-[(4-methyloxazol-5-yl)methoxy]-3,4-dihydro-1H-isoquinoline-2-carboxylate tert-Butyl (3S)-3-[(1R)-2-[[6-[(1-acetyl-4-piperidyl)amino]-2-pyrrolidin-1-yl-pyrimidine-4-carbonyl]amino]-1-hydroxy-ethyl]-7-hydroxy-3,4-dihydro-1H-isoquinoline-2-carboxylate (0.121 g, 193.99 µmol), 5-(chloromethyl)-4-methyl-oxazole (45.63 mg, 271.59 µmol, HCl) and cesium carbonate (252.82 mg, 775.96 µmol) were dissolved in DMF (3 mL) and stirred at 50° C. overnight. The reaction mixture was filtered off and washed with DMF (2 mL). The obtained filtrate was concentrated in vacuo at 60° C. to give tert-butyl (3S)-3-[(1R)-2-[[6-[(1-acetyl-4-piperidyl)amino]-2-pyrrolidin-1-yl-pyrimidine-4-carbonyl]amino]-1-hydroxy-ethyl]-7-[(4-methyloxazol-5-yl)methoxy]-3,4-dihydro-1H-isoquinoline-2-carboxylate (0.136 g, 189.19 µmol, 97.53% yield) which was used in the next step without further purification. $^1$H NMR (CDCl$_3$, 400 MHz): δ 1.51 (s, 9H), 1.95 (m, 4H), 2.11 (m, 4H), 2.22 (s, 3H), 3.13 (m, 4H), 3.51 (m, 4H), 3.78 (m, 4H), 3.97 (m, 2H), 4.18 (m, 2H), 4.40 (m, 2H), 4.71 (m, 2H), 5.00 (s, 2H), 6.40 (s, 1H), 6.68 (s, 1H), 6.82 (d, 1H), 7.13 (d, 1H), 7.81 (s, 1H). LCMS (ESI): [M+H]+ m/z: calc'd 718.3; found 719.4; Rt=3.81 min.

Step 5: Synthesis of 6-[(1-acetyl-4-piperidyl)amino]-N-[(2R)-2-hydroxy-2-[(3S)-7-[(4-methyloxazol-5-yl)methoxy]-1,2,3,4-tetrahydroisoquinolin-3-yl]ethyl]-2-pyrrolidin-1-yl-pyrimidine-4-carboxamide tert-Butyl (3S)-3-[(1R)-2-[[6-[(1-acetyl-4-piperidyl)amino]-2-pyrrolidin-1-yl-pyrimidine-4-carbonyl]amino]-1-hydroxy-ethyl]-7-[(4-methyloxazol-5-yl)methoxy]-3,4-dihydro-1H-isoquinoline-2-carboxylate (0.136 g, 189.19 μmol) was dissolved in MeOH (2 mL). Then hydrogen chloride solution 4.0M in dioxane (517.36 mg, 14.19 mmol, 646.70 μL) was added. The resulting mixture was stirred for 4 hr at RT. After that the solvent was removed in vacuo at 45° C. The residue was dissolved in 5 mL of methanol and 10 mg of scavenger (SiliaMetS© Dimercaptotriazine(DMT)) was added thereto and the resulting suspension was stirred for 12 h at room temperature. The resulting suspension was filtered off and the filtrate was evaporated under reduced pressure. The residue was purified by HPLC (10-65% water-methanol+NH$_3$, 0-10 min, flow 30 mL/min (loading pump 4 mL/min methanol+NH$_3$), column: YMC-Actus Triart C18 100*20 mm) to give 6-[(1-acetyl-4-piperidyl)amino]-N-[(2R)-2-hydroxy-2-[(3S)-7-[(4-methyloxazol-5-yl)methoxy]-1,2,3,4-tetrahydroisoquinolin-3-yl]ethyl]-2-pyrrolidin-1-yl-pyrimidine-4-carboxamide (0.043 g, 69.50 μmol, 36.73% yield). $^1$H NMR (CDCl$_3$, 400 MHz): δ 1.40 (m, 1H), 1.67 (m, 4H), 1.92 (m, 4H), 2.08 (m, 4H), 2.21 (s, 3H), 2.83 (m, 3H), 2.97 (m, 1H), 3.21 (m, 1H), 3.53 (m, 5H), 3.79 (m, 3H), 3.99 (s, 3H), 4.50 (m, 1H), 4.87 (m, 1H), 4.95 (s, 2H), 6.44 (s, 1H), 6.60 (s, 1H), 6.74 (d, 1H), 7.03 (d, 1H), 7.78 (s, 1H), 8.46 (t, 1H). LCMS (ESI): [M+H]$^+$ m/z: calc'd 618.3; found 619.2; Rt=1.02 min.

Example 5—Synthesis of Compounds of Formula (IIa3i)

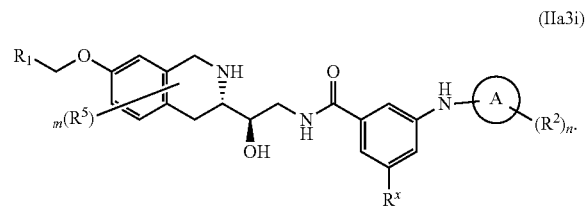

(IIa3i)

wherein $R^1$, $R^2$, $R^5$, $R^x$, m, n and A are as defined herein

Scheme 5A

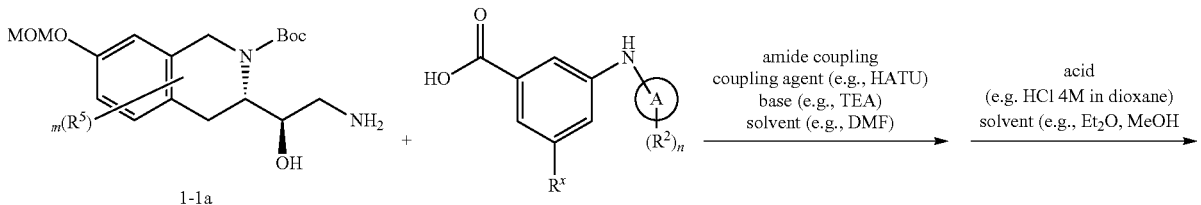

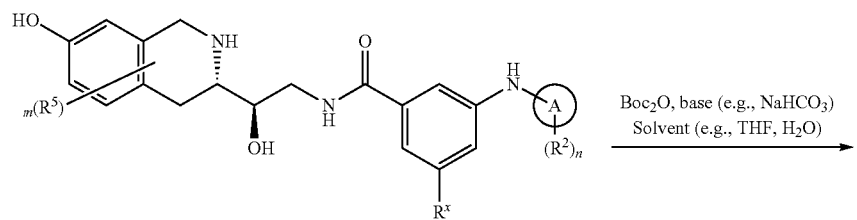

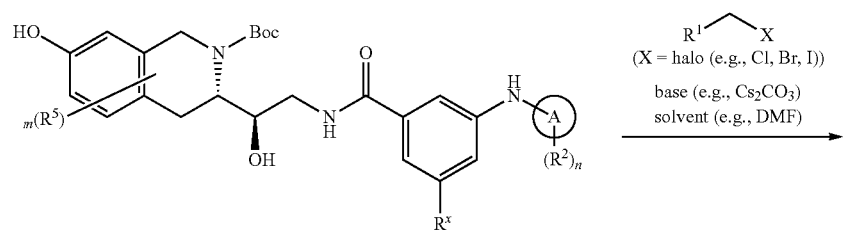

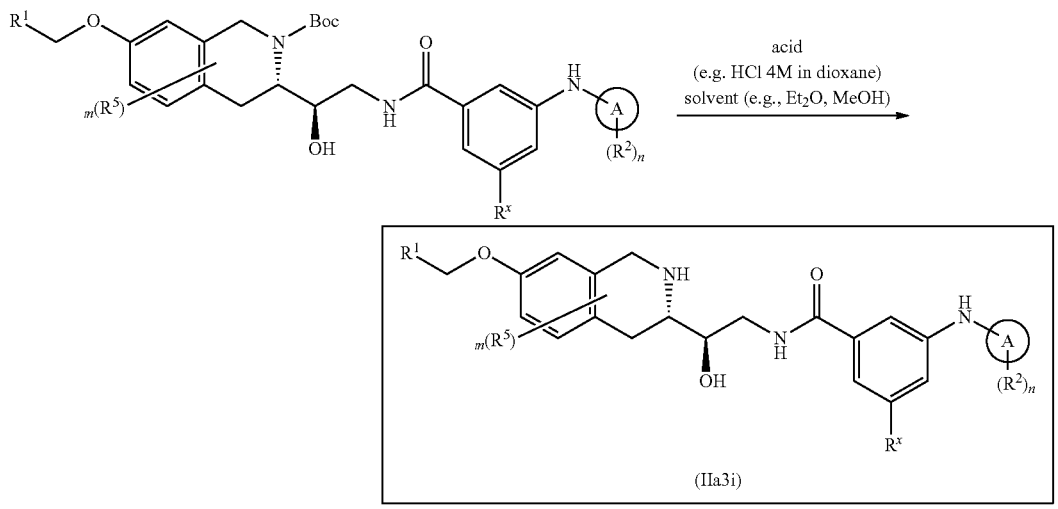
wherein X is a leaving group. In some embodiments, X is selected from Cl, Br, and I. In some embodiments X is Cl or Br.
Example 5A1. Synthesis of 3-(cyclobutylamino)-N—((R)-2-hydroxy-2-((S)-7-((4-methyloxazol-5-yl)methoxy)-1,2,3,4-tetrahydroisoquinolin-3-yl)ethyl)benzamide (Compound 28)
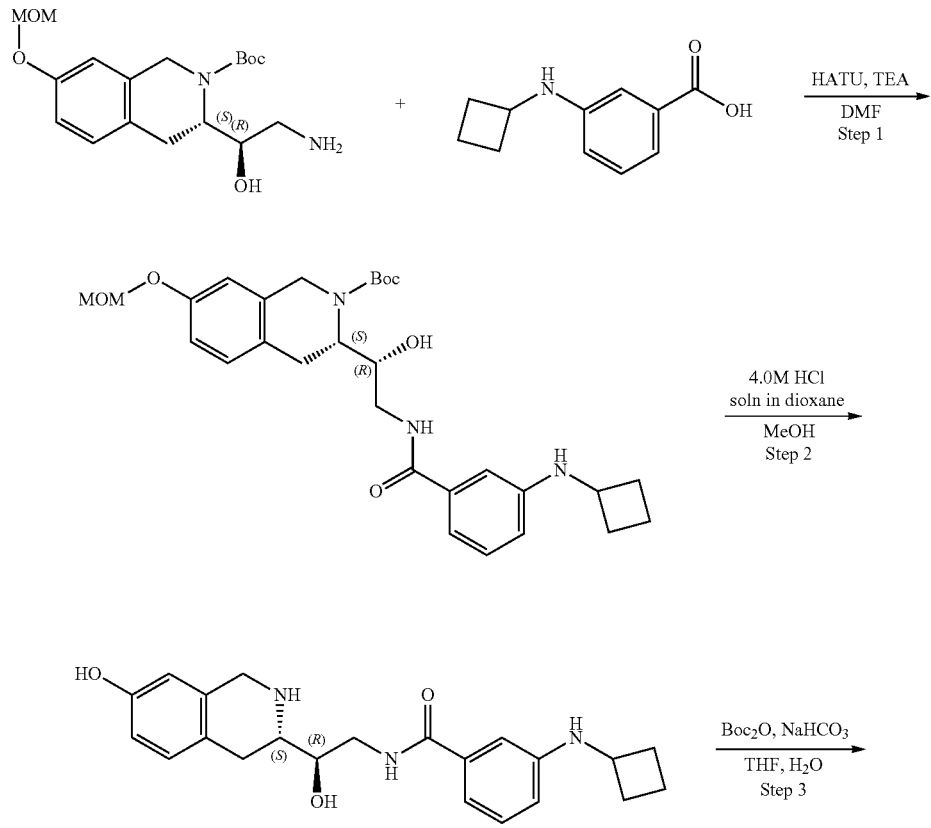

-continued

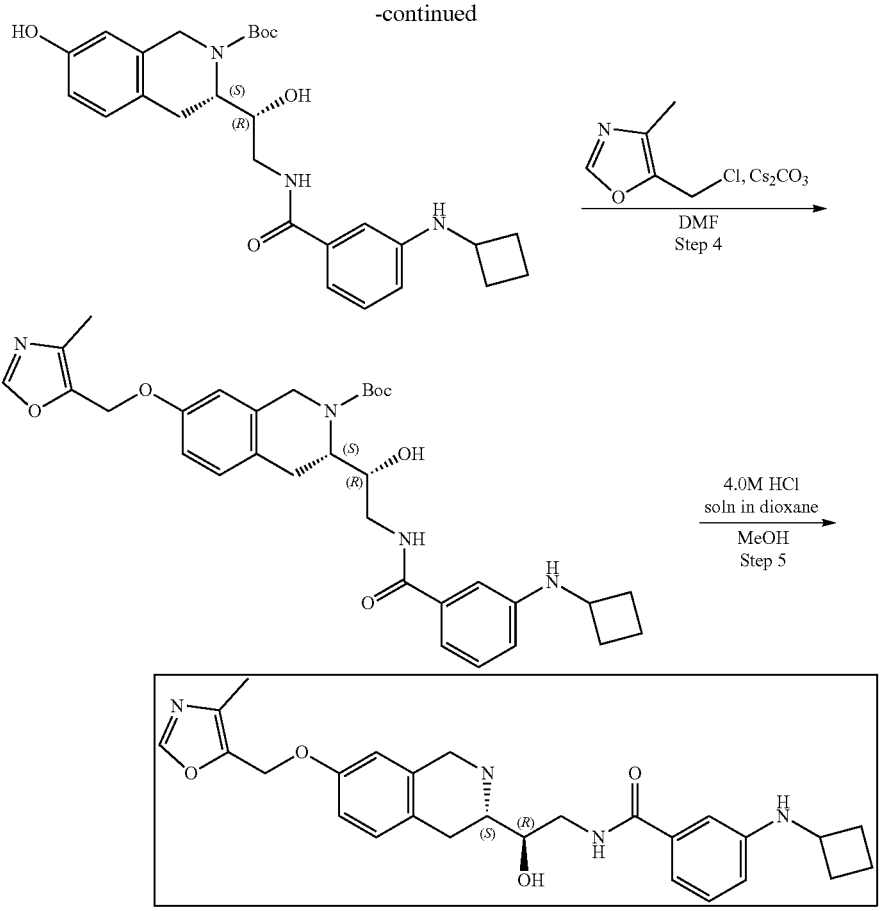

Step 1: Synthesis of (S)-tert-butyl 3-((R)-2-(3-(cyclobutylamino)benzamido)-1-hydroxyethyl)-7-(methoxymethoxy)-3,4-dihydroisoquinoline-2(1H)-carboxylate 3-(Cyclobutylamino)benzoic acid (81.39 mg, 425.62 μmol) and TEA (430.69 mg, 4.26 mmol, 593.23 μL) were dissolved in DMF (3 mL) and cooled to 0° C., HATU (242.75 mg, 638.44 μmol) was added and the mixture was stirred for 15 min at 0° C. tert-Butyl (3S)-3-[(1R)-2-amino-1-hydroxy-ethyl]-7-(methoxymethoxy)-3,4-dihydro-1H-isoquinoline-2-carboxylate (0.15 g, 425.62 μmol) was added and the mixture was warmed to r.t. and stirred overnight. 10 mL of Ethyl acetate was added, and organic phase was washed with brine three times. Organic phase was dried over Na$_2$SO$_4$, filtered off and concentrated in vacuo at 45° C. to give crude product which was purified by HPLC (15-40% water-acetonitrile, 2-10 min, flow: 30 mL/min (loading pump 4 mL/min acetonitrile) column: SunFire C18 100×19 mm) to give tert-butyl (3S)-3-[(1R)-2-[[3-(cyclobutylamino)benzoyl]amino]-1-hydroxy-ethyl]-7-(methoxymethoxy)-3,4-dihydro-1H-isoquinoline-2-carboxylate (0.091 g, 173.12 μmol, 40.68% yield). $^1$H NMR (DMSO-d$_6$, 400 MHz) δ:1.40 (m, 9H), 1.77 (m, 4H), 2.32 (m, 2H), 2.92 (m, 3H), 3.50 (m, 4H), 3.84 (m, 2H), 4.14 (m, 1H), 4.28 (m, 2H), 4.76 (m, 1H), 5.15 (s, 2H), 6.00 (m, 1H), 6.59 (d, 1H), 6.85 (m, 2H), 6.95 (m, 2H), 7.07 (m, 2H), 8.14 (m, 1H). LCMS (ESI): [M+H]$^+$ m/z: calc'd 525.3; found 526.4; Rt=1.54 min.

Step 2: Synthesis of 3-(cyclobutylamino)-N—((R)-2-hydroxy-2-((S)-7-hydroxy-1,2,3,4-tetrahydroisoquinolin-3-yl)ethyl)benzamide tert-Butyl (3S)-3-[(1R)-2-[[3-(cyclobutylamino)benzoyl]amino]-1-hydroxy-ethyl]-7-(methoxymethoxy)-3,4-dihydro-1H-isoquinoline-2-carboxylate (0.091 g, 173.12 μmol) was dissolved in the mixture of MeOH (2 mL). Hydrogen chloride solution 4.0M in dioxane (473.42 mg, 12.98 mmol, 591.77 μL) was added. The mixture was stirred for 12 h at 20° C. Solvent was removed in vacuo at 35° C. to give 3-(cyclobutylamino)-N-[(2R)-2-hydroxy-2-[(3S)-7-hydroxy-1,2,3,4-tetrahydroisoquinolin-3-yl]ethyl]-benzamide (69 mg, 151.85 μmol, 87.71% yield, 2HCl). $^1$H NMR (CD$_3$OD, 400 MHz) δ:1.91 (m, 3H), 2.28 (m, 5H), 3.15 (m, 3H), 3.59 (m, 4H), 4.11 (m, 1H), 4.27 (m, 2H), 4.39 (m, 1H), 6.61 (s, 1H), 6.75 (d, 1H), 7.11 (d, 1H), 7.46 (d, 1H), 7.60 (m, 1H), 7.83 (s, 1H), 7.85 (d, 1H). LCMS (ESI): [M+H]$^+$ m/z: calc'd 381.2; found 382.2; Rt=3.01 min Step 3: Synthesis of (S)-tert-butyl 3-((R)-2-(3-(cyclobutylamino)benzamido)-1-hydroxyethyl)-7-hydroxy-3,4-dihydroisoquinoline-2(1H)-carboxylate 3-(Cyclobutylamino)-N-[(2R)-2-hydroxy-2-[(3S)-7-hydroxy-1,2,3,4-tetrahydroisoquinolin-3-yl]-ethyl]benzamide (69 mg, 151.85 μmol, 2HCl) was dissolved in the mixture of water (1 mL) and THF (1 mL) then sodium hydrogen carbonate, 99% (38.27 mg, 455.56 μmol, 17.72 μL) was added in one portion, after that solution of di-tert-butyl dicarbonate (33.14 mg, 151.85 μmol, 34.85 μL) in THF (0.2 mL) was added dropwise. The reaction mixture was stirred overnight at room temperature. Ethyl acetate (15 mL) was added to the reaction mixture, organic phase was separated, and the aqueous phase was extracted with ethyl acetate (2*15 mL). Organic phase was washed with brine, dried over Na$_2$SO$_4$, filtered and evaporated in vacuo at 40° C. to give tert-butyl (3S)-3-[(1R)-2-[[3-(cyclobutylamino)benzoyl]amino]-1-hydroxy-ethyl]-7-hydroxy-3,4-dihydro-1H-isoquinoline-2-carboxylate (0.071 g, 147.43 μmol, 97.09% yield) which was used in the next step without purification. $^1$H NMR (CD$_3$OD, 500 MHz) δ: 1.49 (m, 9H), 1.80 (m, 4H), 2.41 (m, 2H), 2.85 (m, 1H), 3.09 (m, 1H), 3.61 (m, 1H), 3.73 (m, 1H), 3.84 (m, 2H), 3.95 (m, 1H), 4.25 (m, 2H), 6.57 (s, 1H), 6.63 (d, 1H), 6.71 (d, 1H), 7.00 (m, 2H), 7.06 (d, 1H), 7.14 (d, 1H). LCMS (ESI): [M+H]$^+$ m/z: calc'd 481.2; found 482.2; Rt=3.68 min.

Step 4: Synthesis of (S)-tert-butyl 3-((R)-2-(3-(cyclobutylamino)benzamido)-1-hydroxyethyl)-7-((4-methyloxazol-5-yl)methoxy)-3,4-dihydroisoquinoline-2(1H)-carboxylate tert-Butyl (3S)-3-[(1R)-2-[[3-(cyclobutylamino)benzoyl]amino]-1-hydroxy-ethyl]-7-hydroxy-3,4-di-hydro-1H-isoquinoline-2-carboxylate (0.071 g, 147.43 μmol), 5-(chloromethyl)-4-methyl-oxazole (29.73 mg, 176.92 μmol, HCl) and cesium carbonate (144.11 mg, 442.29 μmol) was dissolved in DMF (2 mL) and heated at 50° C. overnight. Reaction mixture was diluted with water end extracted three times with EA, then EA was extracted three times with brine. Organic phase was dried over Na$_2$SO$_4$, filtered and evaporated at 40° C. to give tert-butyl (3S)-3-[(1R)-2-[[3-(cyclobutylamino)benzoyl]amino]-1-hydroxy-ethyl]-7-[(4-methyloxazol-5-yl)methoxy]-3,4-dihydro-1H-isoquinoline-2-carboxylate (0.083 g, 143.93 μmol, 97.62% yield) which was used in the next step without further purification. $^1$H NMR (CD$_3$OD, 500 MHz) δ: 1.49 (m, 9H), 1.81 (m, 4H), 2.21 (m, 4H), 2.42 (m, 2H), 3.14 (m, 1H), 3.74 (m, 4H), 4.28 (m, 2H), 4.41 (m, 2H), 5.08 (s, 2H), 6.72 (s, 1H), 6.83 (d, 2H), 6.98 (m, 4H), 8.13 (s, 1H). LCMS (ESI): [M+H]$^+$ m/z: calc'd 576.3; found 577.2; Rt=3.75 min.

Step 5: Synthesis of 3-(cyclobutylamino)-N—((R)-2-hydroxy-2-((S)-7-((4-methyloxazol-5-yl)methoxy)-1,2,3,4-tetrahydroisoquinolin-3-yl)ethyl)benzamide (Compound 28) tert-Butyl (3S)-3-[(1R)-2-[[3-(cyclobutylamino)benzoyl]amino]-1-hydroxy-ethyl]-7-[(4-methyl-oxazol-5-yl)methoxy]-3,4-dihydro-1H-isoquinoline-2-carboxylate (0.083 g, 143.93 μmol) was dissolved in the mixture of methanol (1.5 mL). Then, hydrogen chloride solution 4.0M in dioxane (393.57 mg, 10.79 mmol, 491.96 μL) was added. The mixture was stirred for 20° C. at RT. Solvent was removed in vacuo at 45° C. The residue was dissolved in 5 ml of methanol and 10 mg of scavenger (SiliaMetS© Dimercaptotriazine(DMT) was added thereto and the resulting suspension was stirred for 12 h. The suspension was filtered off, the filtrate was evaporated under reduced pressure and the residue was purified by HPLC (15-65% water-methanol, 10 min, flow: 30 mL/min (loading pump 4 mL/min methanol), column: SunFire C18 100*19 mm to give 3-(cyclobutylamino)-N-[(2R)-2-hydroxy-2-[(3S)-7-[(4-methyloxazol-5-yl)methoxy]-1,2,3,4-tetrahydroisoquinolin-3-yl]ethyl]benzamide (0.0258 g, 44.03 μmol, 30.59% yield, 3HCl). $^1$H NMR (CDCl$_3$, 400 MHz) δ 1.74 (m, 2H), 1.84 (m, 2H), 2.18 (s, 3H), 2.36 (m, 2H), 2.93 (m, 3H), 3.16 (m, 1H), 3.40 (m, 1H), 3.47 (m, 1H), 3.86 (q, 1H), 4.01 (m, 1H), 4.11 (AB-system, 2H), 5.01 (m, 2H), 5.46 (m, 1H), 5.75 (d, 1H), 6.55 (d, 1H), 6.75 (s, 1H), 6.81 (dd, 1H), 6.98 (s, 2H), 7.08 (m, 2H), 8.04 (s, 1H), 8.28 (m, 1H). LCMS (ESI): [M+H]$^+$ m/z: calc'd 476.2; found 477.0; Rt=1.09 min.

Example 5A2. Synthesis of 3-[(1-acetyl-4-piperidyl)amino]-N-[(2R)-2-hydroxy-2-[(3S)-7-[(4-methyloxazol-5-yl)methoxy]-1,2,3,4-tetrahydroisoquinolin-3-yl]ethyl]-5-(1-piperidyl)benzamide (Compound 60)

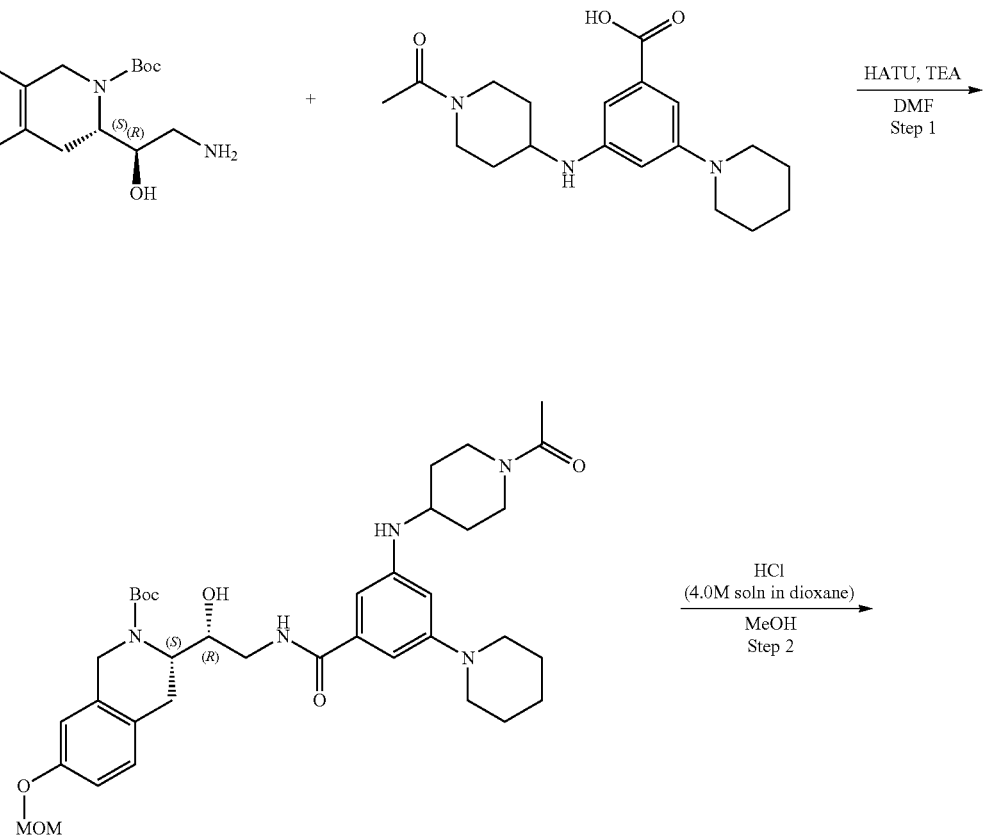

-continued
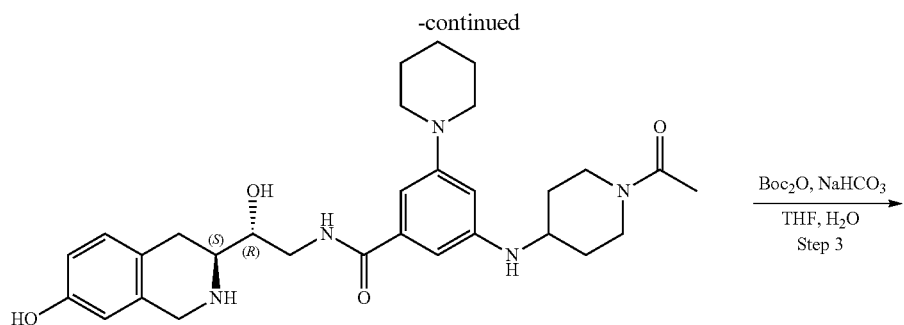
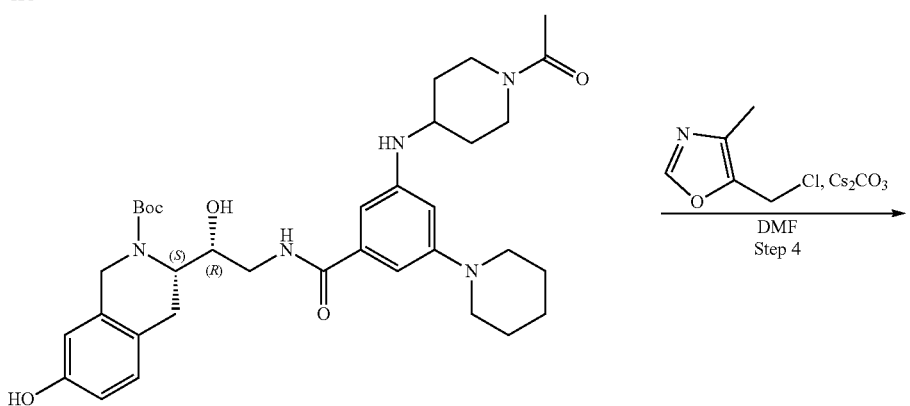
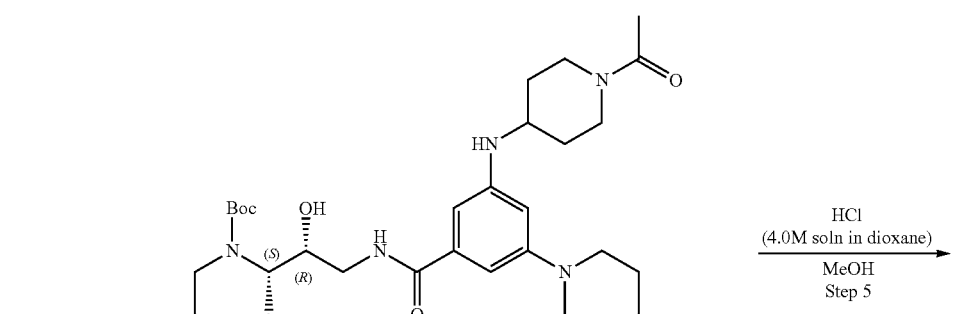
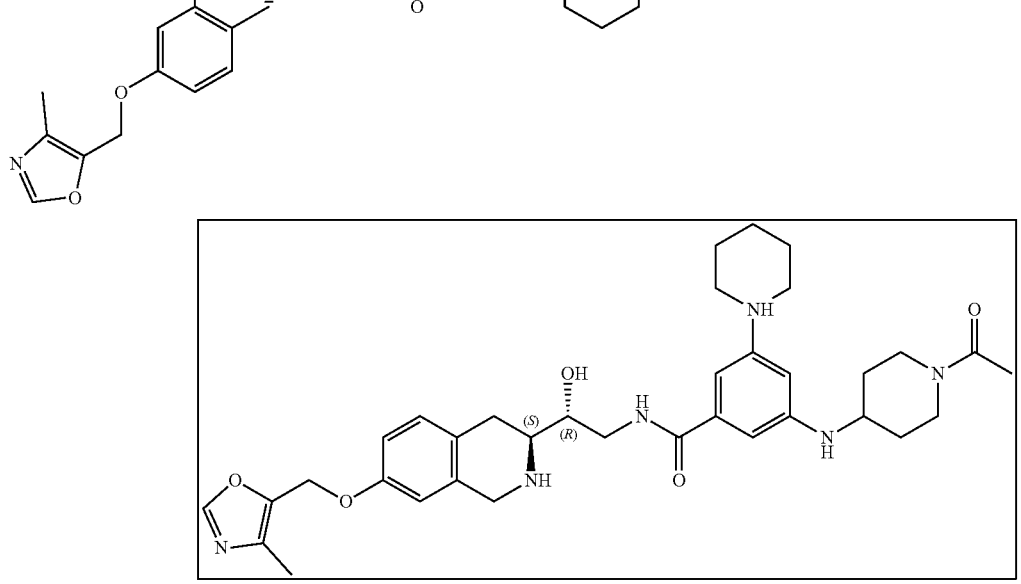

Step 1: Synthesis of tert-butyl (3S)-3-[(1R)-2-[[3-[(1-acetyl-4-piperidyl)amino]-5-(1-piperidyl)benzoyl]amino]-1-hydroxy-ethyl]-7-(methoxymethoxy)-3,4-dihydro-1H-isoquinoline-2-carboxylate HATU (323.67 mg, 851.25 µmol) was added to the cooled to 0° C. mixture of 3-[(1-Acetyl-4-piperidyl)amino]-5-(1-piperidyl)benzoic acid (325.45 mg, 567.50 µmol, 2CF$_3$COOH) and TEA (574.25 mg, 5.67 mmol, 790.98 µL) in DMF (5 mL). The resulting mixture was stirred for 15 min at 0° C. followed by the addition of tert-butyl (3S)-3-[(1R)-2-amino-1-hydroxy-ethyl]-7-(methoxymethoxy)-3,4-dihydro-1H-isoquinoline-2-carboxylate (0.2 g, 567.50 µmol). The reaction mixture was warmed to room temperature and stirred for 3 hr. After the completion of the reaction, monitored by LCMS, 10 mL of ethyl acetate was added, and the organic phase was washed with brine three times. The organic phase was dried over Na$_2$SO$_4$, filtered off and concentrated in vacuo at 45° C. to give crude product which was purified by HPLC (25-40% water-acetonitrile, 10 min, flow 30 mL/min (loading pump 4 mL/min acetonitrile) column: SunFire C18 100*19 mm) to give tert-butyl (3S)-3-[(1R)-2-[[3-[(1-acetyl-4-piperidyl)amino]-5-(1-piperidyl)benzoyl]amino]-1-hydroxy-ethyl]-7-(methoxymethoxy)-3,4-dihydro-1H-isoquinoline-2-carboxylate (0.23 g, 338.31 µmol, 59.61% yield). $^1$H NMR (DMSO-d$_6$, 400 MHz): δ 1.04 (m, 6H), 1.42 (m, 9H), 1.52 (m, 6H), 1.82 (m, 2H), 2.79 (m, 2H), 3.07 (m, 6H), 3.29 (m, 2H), 3.46 (m, 2H), 3.73 (m, 2H), 4.10 (m, 2H), 4.34 (m, 2H), 4.78 (s, 2H), 5.15 (m, 3H), 6.26 (s, 1H), 6.48 (s, 1H), 6.59 (s, 1H), 6.85 (m, 2H), 7.08 (d, 1H), 8.07 (m, 1H). LCMS (ESI): [M+H]$^+$ m/z: calc'd 679.3; found 680.4; Rt=1.27 min.

Step 2: Synthesis of 3-[(1-acetyl-4-piperidyl)amino]-N-[(2R)-2-hydroxy-2-[(3S)-7-hydroxy-1, 2, 3,4-tetrahydroisoquinolin-3-yl]ethyl]-5-(1-piperidyl)benzamide tert-Butyl (3S)-3-[(1R)-2-[[3-[(1-acetyl-4-piperidyl)amino]-5-(1-piperidyl)benzoyl]amino]-1-hydroxy-ethyl]-7-(methoxymethoxy)-3,4-dihydro-1H-isoquinoline-2-carboxylate (0.23 g, 338.31 µmol) was dissolved in MeOH (4 mL) and hydrogen chloride solution 4.0M in dioxane (925.14 mg, 25.37 mmol, 1.16 mL) was added. The resulting mixture was stirred for 3 hr at 20° C. After that the solvent was removed in vacuo at 35° C. to give 3-[(1-acetyl-4-piperidyl)amino]-N-[(2R)-2-hydroxy-2-[(3S)-7-hydroxy-1,2,3,4-tetrahydroisoquinolin-3-yl]ethyl]-5-(1-piperidyl)benzamide (0.215 g, 333.30 µmol, 98.52% yield, 3HCl) which was used in the next step without further purification. $^1$H NMR (DMSO-d$_6$, 500 MHz): δ 1.04 (m, 6H), 1.39 (m, 6H), 1.87 (m, 6H), 2.02 (m, 2H), 2.36 (m, 2H), 2.63 (m, 2H), 2.99 (m, 2H), 3.16 (m, 4H), 3.45 (m, 4H), 6.58 (s, 1H), 6.60 (s, 1H), 6.69 (m, 2H), 7.04 (m, 1H), 7.15 (d, 1H), 8.82 (m, 2H), 9.38 (m, 2H). LCMS (ESI): [M+H]$^+$ m/z: calc'd 535.3; found 536.4; Rt=1.69 min Step 3: Synthesis of tert-butyl (3S)-3-[(1R)-2-[[3-[(1-acetyl-4-piperidyl)amino]-5-(1-piperidyl)benzoyl]amino]-1-hydroxy-ethyl]-7-hydroxy-3,4-dihydro-1H-isoquinoline-2-carboxylate 3-[(1-Acetyl-4-piperidyl)amino]-N-[(2R)-2-hydroxy-2-[(3S)-7-hydroxy-1,2,3,4-tetrahydroiso-quinolin-3-yl]ethyl]-5-(1-piperidyl)benzamide (0.215 g, 333.30 µmol, 3HCl) was dissolved in the mixture of water (2 mL) and THF (2 mL) then sodium hydrogen carbonate, 99% (112.00 mg, 1.33 mmol, 51.85 µL) was added in one portion. The resulting mixture was stirred for 5 min at room temperature followed by the dropwise addition of the solution of di-tert-butyl dicarbonate (72.74 mg, 333.30 µmol, 76.49 µL) in THF (0.2 mL). The reaction mixture was stirred for 4 hr at room temperature. After that ethyl acetate (15 mL) was added to the reaction mixture, the organic phase was separated, and the aqueous phase was extracted with ethyl acetate (2*15 mL). The organic phase was washed with brine, dried over Na$_2$SO$_4$, filtered off, and evaporated in vacuo at 40° C. to give tert-butyl (3S)-3-[(1R)-2-[[3-[(1-acetyl-4-piperidyl)amino]-5-(1-piperidyl)benzoyl]amino]-1-hydroxy-ethyl]-7-hydroxy-3,4-dihydro-1H-isoquinoline-2-carboxylate (0.148 g, 232.78 µmol, 69.84% yield) which was used in the next step without purification. $^1$H NMR (CDCl$_3$, 400 MHz): δ 1.28 (m, 3H), 1.50 (m, 8H), 1.56 (m, 6H), 1.69 (m, 3H), 1.83 (m, 2H), 2.08 (m, 3H), 2.84 (m, 3H), 3.10 (m, 4H), 3.18 (m, 1H), 3.45 (m, 2H), 3.55 (m, 2H), 4.12 (m, 2H), 4.37 (m, 2H), 4.61 (m, 1H), 6.31 (s, 1H), 6.56 (s, 1H), 6.67 (m, 2H), 6.89 (s, 1H) 6.99 (d, 1H), 7.93 (m, 1H). LCMS (ESI): [M+2H]$^+$ m/z: calc'd 635.3; found 637.2; Rt=2.83 min.

Step 4: Synthesis of tert-butyl (3S)-3-[(1R)-2-[[3-[(1-acetyl-4-piperidyl)amino]-5-(1-piperidyl)benzoyl]amino]-1-hydroxy-ethyl]-7-[(4-methyloxazol-5-yl)methoxy]-3,4-dihydro-1H-isoquinoline-2-carboxylate tert-Butyl (3S)-3-[(1R)-2-[[3-[(1-acetyl-4-piperidyl)amino]-5-(1-piperidyl)benzoyl]amino]-1-hydroxy-ethyl]-7-hydroxy-3,4-dihydro-1H-isoquinoline-2-carboxylate (0.148 g, 232.78 µmol), 5-(chloromethyl)-4-methyl-oxazole (54.76 mg, 325.89 µmol, HCl) and cesium carbonate (303.38 mg, 931.12 µmol) were dissolved in DMF (3 mL) and stirred at 50° C. overnight. The reaction mixture was filtered off and washed with DMF (2 mL). The obtained filtrate was concentrated in vacuo at 60° C. to give tert-butyl (3S)-3-[(1R)-2-[[3-[(1-acetyl-4-piperidyl)amino]-5-(1-piperidyl)benzoyl]amino]-1-hydroxy-ethyl]-7-[(4-methyloxazol-5-yl)methoxy]-3,4-dihydro-1H-isoquinoline-2-carboxylate (0.144 g, 197.02 µmol, 84.64% yield) which was used in the next step without further purification. $^1$H NMR (CDCl$_3$, 400 MHz): δ 1.32 (m, 3H), 1.53 (m, 9H), 1.59 (m, 8H), 2.10 (m, 4H), 2.25 (s, 3H), 3.20 (m, 6H), 3.46 (m, 1H), 3.56 (m, 2H), 3.77 (m, 2H), 4.19 (m, 2H), 4.43 (m, 2H), 4.69 (m, 1H), 4.97 (s, 2H), 6.68 (m, 2H), 6.82 (d, 1H), 6.95 (s, 1H), 7.18 (d, 1H), 7.81 (s, 1H), 7.96 (s, 1H). LCMS (ESI): [M+H]+ m/z: calc'd 730.4; found 731.4; Rt=3.53 min.

Step 5: Synthesis of 3-[(1-acetyl-4-piperidyl)amino]-N-[(2R)-2-hydroxy-2-[(3S)-7-[(4-methyloxazol-5-yl)methoxy]-1,2,3,4-tetrahydroisoquinolin-3-yl]ethyl]-5-(1-piperidyl)benzamide (Compound 60) tert-Butyl (3S)-3-[(1R)-2-[[3-[(1-acetyl-4-piperidyl)amino]-5-(1-piperidyl)benzoyl]amino]-1-hydroxy-ethyl]-7-[(4-methyloxazol-5-yl)methoxy]-3,4-dihydro-1H-isoquinoline-2-carboxylate (0.144 g, 197.02 µmol) was dissolved in MeOH (2 mL) and hydrogen chloride solution 4.0M in dioxane (538.76 mg, 14.78 mmol, 673.46 µL) was added. The resulting mixture was stirred for 20° C. at room temperature. After the completion of the reaction, the solvent was removed in vacuo at 45° C. The residue was dissolved in 5 mL of methanol and 10 mg of scavenger (SiliaMetS© Dimercaptotriazine(DMT)) was added. The resulting suspension was stirred for 12 hr at room temperature. The suspension was filtered off, the filtrate was evaporated under reduced pressure and the residue was purified by HPLC (10-50% water-methanol+NH$_3$, 0-10 min, flow 30 mL/min methanol (loading pump 4 mL/min methanol+NH$_3$), column: YMC-Actus Triart C18 100*20 mm) to give 3-[(1-acetyl-4-piperidyl)amino]-N-[(2R)-2-hydroxy-2-[(3S)-7-[(4-methyloxazol-5-yl)methoxy]-1,2,3,4-tetrahydroisoquinolin-3-yl]ethyl]-5-(1-piperidyl)benzamide (0.045 g, 71.34 µmol, 36.21% yield). $^1$H NMR (400 MHz, CDCl$_3$) δ 1.29 (m, 2H), 1.55 (m, 3H), 1.65 (m, 5H), 2.01 (m, 2H), 2.07 (s, 3H), 2.10 (m, 1H), 2.20 (s, 3H), 2.70 (m, 1H), 2.80 (m, 2H), 2.98 (m, 1H), 3.12 (m, 5H), 3.54 (m, 3H), 3.78 (m, 3H), 3.98 (m, 2H), 4.43 (d, 1H), 4.95 (s, 2H), 6.23 (s, 1H), 6.50 (s, 1H), 6.60 (s, 1H), 6.65 (s, 1H), 6.76 (dd, 1H), 6.95 (m, 1H), 7.02 (d, 1H), 7.78 (s, 1H). LCMS (ESI): [M+H]+ m/z: calc'd 630.3; found 631.2; Rt=1.02 min.
Example 5A3. Synthesis of 3-[(1-acetylazetidin-3-yl)amino]-N-[(2R)-2-hydroxy-2-[(3S)-7-1(4-methyl-oxazol-5-yl)methoxy]-1,2,3,4-tetrahydroisoquinolin-3-yl]ethyl]-5-(1-piperidyl)benzamide (Compound 59)
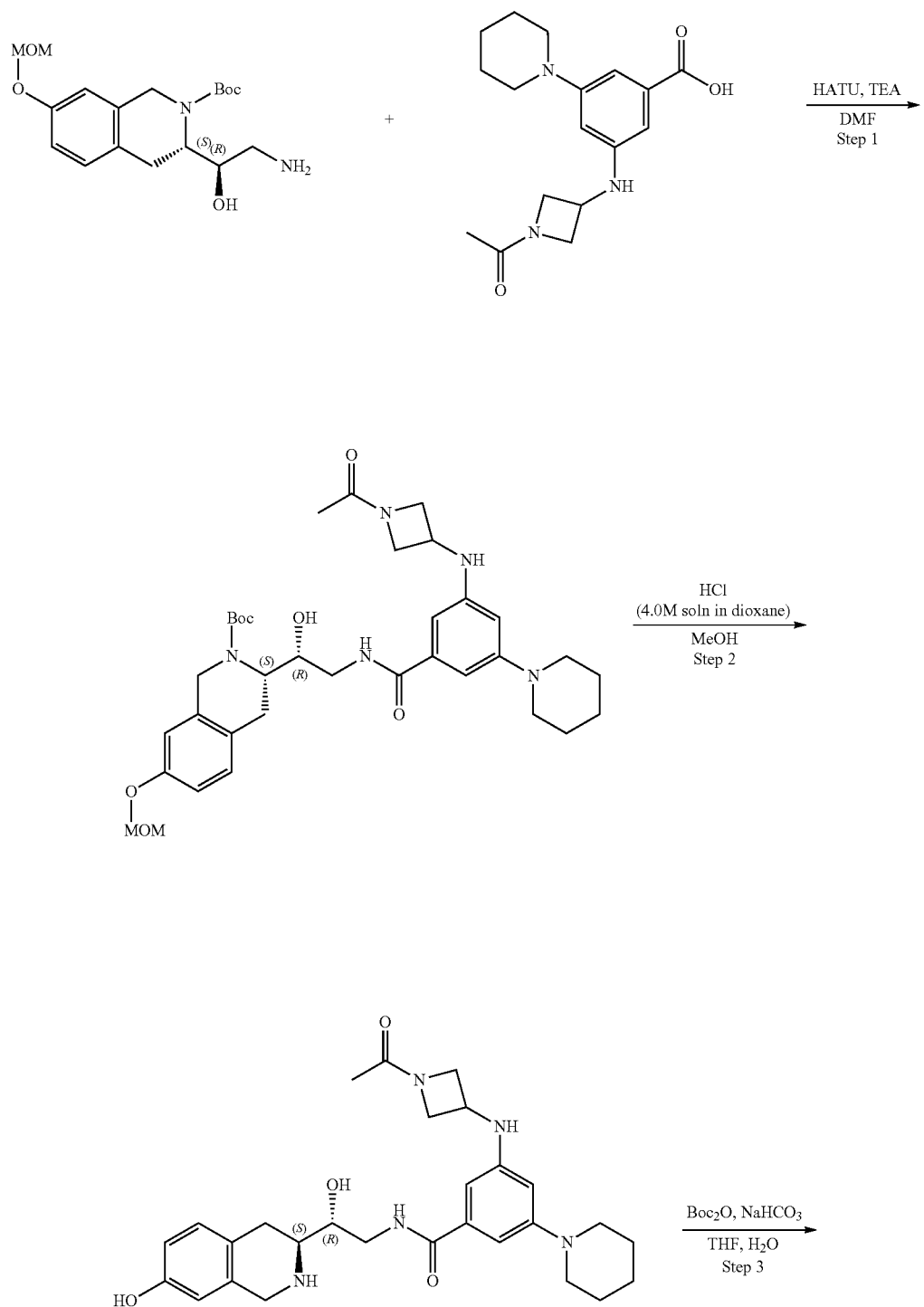

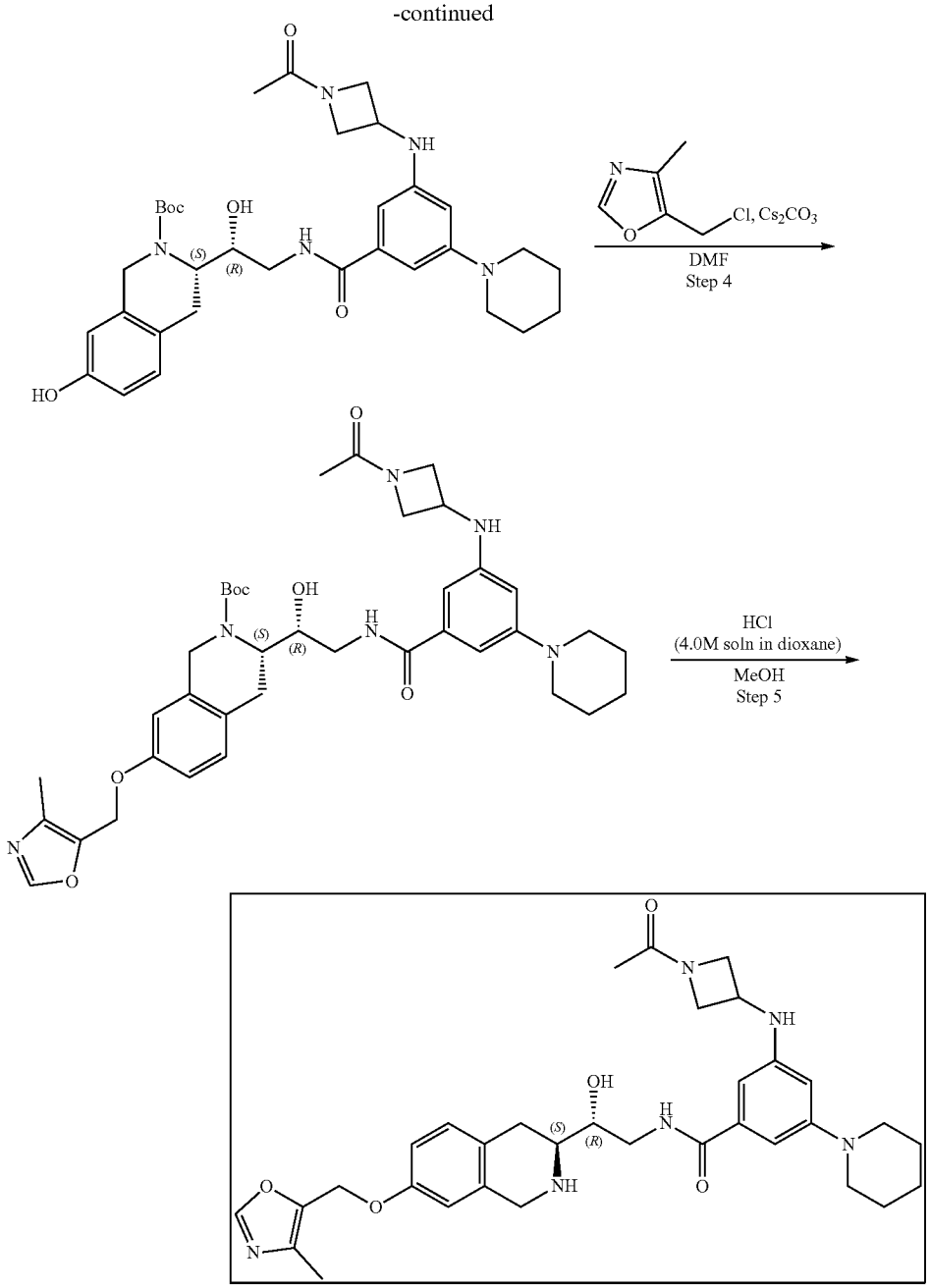

Step 1: Synthesis of tert-butyl (3S)-3-[(1R)-2-[[3-[(1-acetylazetidin-3-yl)amino]-5-(1-piperidyl)benzoyl]amino]-1-hydroxy-ethyl]-7-(methoxymethoxy)-3,4-dihydro-1H-isoquinoline-2-carboxylate HATU (323.67 mg, 851.25 µmol) was added to the cooled to 0° C. solution of 3-[(1-Acetylazetidin-3-yl)amino]-5-(1-piperidyl)benzoic acid (309.53 mg, 567.50 µmol, 2CF$_3$COOH) and TEA (574.25 mg, 5.67 mmol, 790.98 µL) in DMF (7 mL). The resulting mixture was stirred for 15 min at 0° C. followed by the addition of tert-butyl (3S)-3-[(1R)-2-amino-1-hydroxy-ethyl]-7-(methoxymethoxy)-3,4-dihydro-1H-isoquinoline-2-carboxylate (0.2 g, 567.50 µmol). The reaction mixture was warmed to room temperature and stirred for 3 hr. After the completion of the reaction 10 mL of ethyl acetate was added and the organic phase was washed with brine three times. The organic phase was dried over Na$_2$SO$_4$, filtered off and concentrated in vacuo at 45° C. to give tert-butyl (3S)-3-[(1R)-2-[[3-[(1-acetylazetidin-3-yl)amino]-5-(1-piperidyl)-benzoyl]amino]-1-hydroxy-ethyl]-7-(methoxymethoxy)-3,4-dihydro-1H-isoquinoline-2-carboxylate (0.357 g, 547.72 µmol, 96.52% yield). $^1$H NMR (DMSO-d$_6$, 400 MHz): δ 1.53 (s, 9H), 1.60 (m, 2H), 1.72 (m, 4H), 1.88 (m, 3H), 2.81 (m, 5H), 3.14 (m, 4H), 3.60 (m, 4H), 3.76 (m, 2H), 3.85 (m, 2H), 3.96 (m, 2H), 4.35 (m, 2H), 4.53 (m, 2H), 5.15 (s, 2H), 6.35 (s, 1H), 6.50 (d, 1H), 6.58 (m, 3H), 7.09 (d, 1H), 7.98 (m, 1H). LCMS (ESI): [M-Boc]$^+$ m/z: calc'd 551.3; found 552.4; Rt=2.83 min.

Step 2: Synthesis of 3-[(1-acetylazetidin-3-yl)amino]-N-[(2R)-2-hydroxy-2-[(3S)-7-hydroxy-1,2,3,4-tetrahydroisoquinolin-3-yl]ethyl]-5-(1-piperidyl)benzamide tert-Butyl (3S)-3-[(1R)-2-[[3-[(1-acetylazetidin-3-yl)amino]-5-(1-piperidyl)benzoyl]amino]-1-hydroxy-ethyl]-7-(methoxymethoxy)-3,4-dihydro-1H-isoquinoline-2-carboxylate (358.08 mg, 549.38 µmol) was dissolved in MeOH (5 mL) and hydrogen chloride solution 4.0M in dioxane (1.50 g, 41.20 mmol, 1.88 mL) was added. The resulting mixture was stirred for 12 hr at 20° C. After the completion of the reaction, the solvent was removed in vacuo at 35° C. to give 3-[(1-acetylazetidin-3-yl)amino]-N-[(2R)-2-hydroxy-2-[(3S)-7-hydroxy-1,2,3,4-tetrahydroisoquinolin-3-yl]ethyl]-5-(1-piperidyl)benzamide (337 mg, 546.19 µmol, 99.42% yield, 3HCl) which was used in the next step without further purification. $^1$H NMR (CD$_3$OD, 500 MHz): δ 1.91 (s, 3H), 2.07 (m, 4H), 2.73 (m, 2H), 2.83 (m, 4H), 3.17 (m, 2H), 3.67 (m, 4H), 3.77 (m, 4H), 4.05 (m, 1H), 4.30 (m, 2H), 4.38 (m, 4H), 4.66 (m, 1H), 6.62 (s, 1H), 6.74 (d, 1H), 6.97 (s, 1H), 7.11 (d, 1H), 7.17 (s, 1H), 7.46 (s, 1H). LCMS (ESI): [M+H]$^+$ m/z: calc'd 507.3; found 508.2; Rt=1.78 min.

Step 3: Synthesis of tert-butyl (3S)-3-[(1R)-2-[[3-[(1-acetylazetidin-3-yl)amino]-5-(1-piperidyl)benzoyl]amino]-1-hydroxy-ethyl]-7-hydroxy-3,4-dihydro-1H-isoquinoline-2-carboxylate 3-[(1-Acetylazetidin-3-yl)amino]-N-[(2R)-2-hydroxy-2-[(3S)-7-hydroxy-1,2,3,4-tetrahydroiso-quinolin-3-yl]ethyl]-5-(1-piperidyl)benzamide (0.337 g, 546.19 µmol, 3HCl) was dissolved in the mixture of water (2 mL) and THF (2 mL) then sodium hydrogen carbonate, 99% (229.42 mg, 2.73 mmol, 106.21 µL) was added in one portion. The resulting mixture was stirred for 5 min at room temperature followed by the dropwise addition of the solution of di-tert-butyl dicarbonate (119.20 mg, 546.19 µmol, 125.35 µL) in THF (0.2 mL). The reaction mixture was stirred for 4 hr at room temperature. After the completion of the reaction, ethyl acetate (15 mL) was added to the reaction mixture, the organic phase was separated, and the aqueous phase was extracted with ethyl acetate (2*15 mL). The organic phase was washed with brine, dried over Na$_2$SO$_4$, filtered off and evaporated in vacuo at 40° C. to give tert-butyl (3S)-3-[(1R)-2-[[3-[(1-acetylazetidin-3-yl)amino]-5-(1-piperidyl)benzoyl]amino]-1-hydroxy-ethyl]-7-hydroxy-3,4-dihydro-1H-isoquinoline-2-carboxylate (0.247 g, 406.42 µmol, 74.41% yield) which was used in the next step without purification. LCMS (ESI): [M+H]$^+$ m/z: calc'd 607.3; found 608.4; Rt=2.65 min.

Step 4: Synthesis of tert-butyl (3S)-3-[(1R)-2-[[3-[(1-acetylazetidin-3-yl)amino]-5-(1-piperidyl)benzoyl]amino]-1-hydroxy-ethyl]-7-[(4-methyloxazol-5-yl)methoxy]-3,4-dihydro-1H-isoquinoline-2-carboxylate tert-Butyl (3S)-3-[(1R)-2-[[3-[(1-acetylazetidin-3-yl)amino]-5-(1-piperidyl)benzoyl]amino]-1-hydroxy-ethyl]-7-hydroxy-3,4-dihydro-1H-isoquinoline-2-carboxylate (0.247 g, 406.42 µmol), 5-(chloromethyl)-4-methyl-oxazole (95.60 mg, 568.99 µmol, HCl) and cesium carbonate (529.68 mg, 1.63 mmol) were dissolved in DMF (4 mL) and stirred at 50° C. overnight. The reaction mixture was filtered off and washed with DMF (2 mL). The obtained filtrate was concentrated in vacuo at 60° C. to give tert-butyl (3S)-3-[(1R)-2-[[3-[(1-acetylazetidin-3-yl)amino]-5-(1-piperidyl)benzoyl]amino]-1-hydroxy-ethyl]-7-[(4-methyloxazol-5-yl)methoxy]-3,4-dihydro-1H-isoquinoline-2-carboxylate (0.255 g, 362.81 µmol, 89.27% yield) which was used in the next step without further purification. $^1$H NMR (CD$_3$OD, 400 MHz): δ 1.49 (m, 2H), 1.57 (m, 8H), 1.67 (m, 4H), 1.86 (s, 3H), 2.15 (m, 6H), 3.13 (m, 5H), 3.52 (m, 2H), 3.73 (m, 2H), 3.93 (m, 2H), 4.30 (m, 4H), 4.54 (m, 2H), 5.04 (m, 2H), 6.32 (d, 1H), 6.47 (s, 1H), 6.80 (m, 3H), 7.07 (d, 1H), 8.10 (m, 2H). LCMS (ESI): [M+H]$^+$ m/z: calc'd 702.4; found 703.4; Rt=2.94 min.

Step 5: Synthesis of 3-[(1-acetylazetidin-3-yl)amino]-N-[(2R)-2-hydroxy-2-[(3S)-7-[(4-methyloxazol-5-yl)methoxy]-1,2,3,4-tetrahydroisoquinolin-3-yl]ethyl]-5-(1-piperidyl)benzamide (Compound 59) tert-Butyl (3S)-3-[(1R)-2-[[3-[(1-acetylazetidin-3-yl)amino]-5-(1-piperidyl)benzoyl]amino]-1-hydroxy-ethyl]-7-[(4-methyloxazol-5-yl)methoxy]-3,4-dihydro-1H-isoquinoline-2-carboxylate (0.255 g, 362.81 µmol) was dissolved in MeOH (3 mL) and hydrogen chloride solution 4.0M in dioxane (992.14 mg, 27.21 mmol, 1.24 mL) was added. The reaction mixture was stirred for 20° C. at room temperature. After the completion of the reaction, solvent was removed in vacuo at 45° C. The residue was dissolved in 5 mL of methanol and 10 mg of scavenger (SiliaMetS© Dimercaptotriazine(DMT)) was added. The resulting suspension was stirred for 12 h at room temperature. The resulting suspension was filtered off. The filtrate was evaporated under reduced pressure and the residue was purified by HPLC (45-60% water-methanol+NH$_3$, 10 min, flow 30 mL/min (loading pump 4 mL/min methanol+NH$_3$), column: SunFire C18 100*19 mm) to give 3-[(1-acetylazetidin-3-yl)amino]-N-[(2R)-2-hydroxy-2-[(3S)-7-[(4-methyloxazol-5-yl)methoxy]-1,2,3,4-tetrahydroisoquinolin-3-yl]ethyl]-5-(1-piperidyl)benzamide (0.018 g, 29.86 µmol, 8.23% yield). $^1$H NMR (400 MHz, CDCl$_3$) δ 1.56 (m, 2H), 1.65 (m, 4H), 1.83 (s, 3H), 2.21 (s, 3H), 2.76 (m, 2H), 2.98 (m, 1H), 3.12 (m, 4H), 3.53 (m, 1H), 3.75 (m, 2H), 3.82 (m, 2H), 3.98 (m, 2H), 4.20 (m, 1H), 4.29 (m, 1H), 4.39 (m, 2H), 4.96 (s, 2H), 6.14 (s, 1H), 6.42 (s, 1H), 6.60 (s, 1H), 6.76 (m, 2H), 7.03 (d, 1H), 7.30 (m, 1H), 7.80 (s, 1H). LCMS (ESI): [M+H]$^+$ m/z: calc'd 602.3; found 603.4; Rt=0.89 min.

Example 5A4. Synthesis of 3-(cyclobutylamino)-N-[(2R)-2-hydroxy-2-[(3S)-7-[(4-methyloxazol-5-yl)methoxy]-1,2,3,4-tetrahydroisoquinolin-3-yl]ethyl]-5-(1-piperidyl)benzamide (Compound 58)

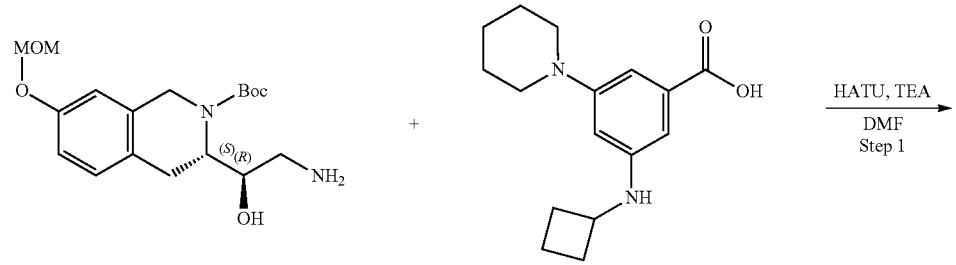

-continued
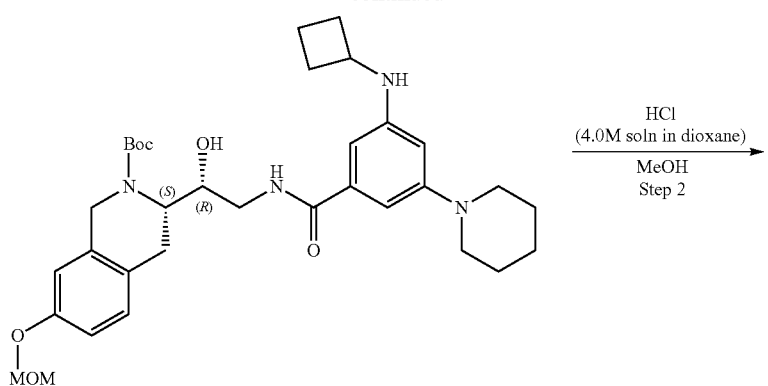
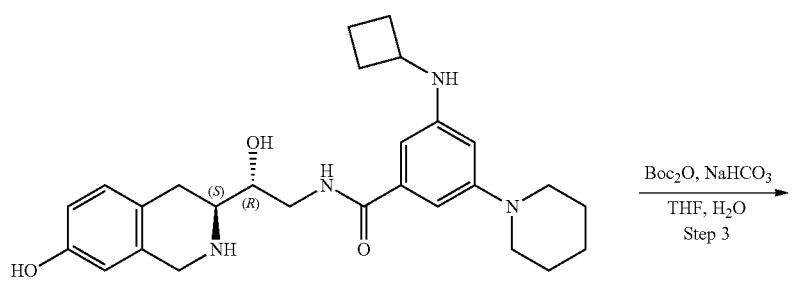
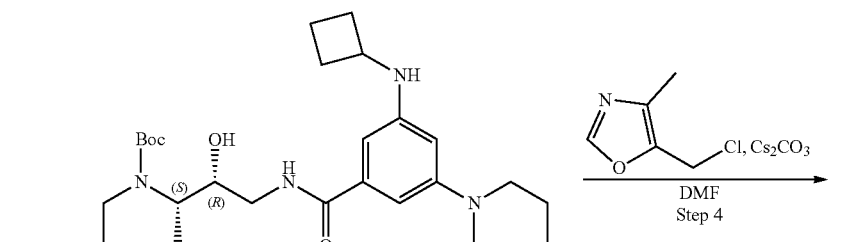
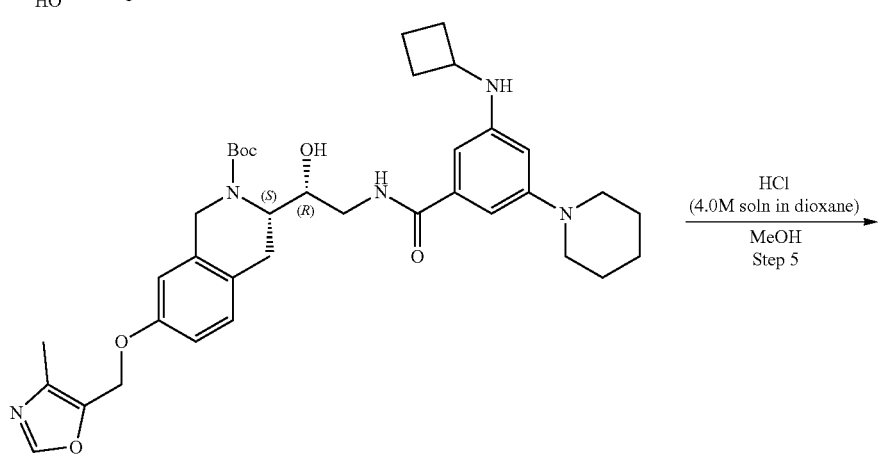

-continued

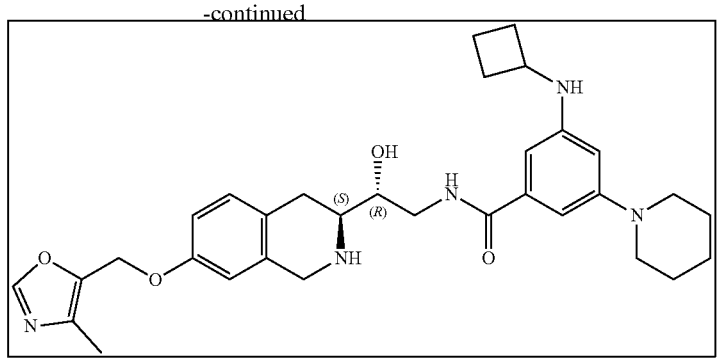

Step 1: Synthesis of tert-butyl (3S)-3-[(1R)-2-[[3-(cyclobutylamino)-5-(1-piperidyl)-benzoyl]amino]-1-hydroxyethyl]-7-(methoxymethoxy)-3,4-dihydro-1H-isoquinoline-2-carboxylate 3-(Cyclobutylamino)-5-(1-piperidyl)benzoic acid (197.08 mg, 567.50 μmol, 2HCl) and TEA (574.25 mg, 5.67 mmol, 790.98 μL) were dissolved in DMF (7 mL) and cooled to 0° C., HATU (323.67 mg, 851.25 μmol) was added. The mixture was stirred for 15 min at 0° C. followed by the addition of tert-butyl (3S)-3-[(1R)-2-amino-1-hydroxy-ethyl]-7-(methoxymethoxy)-3,4-dihydro-1H-isoquinoline-2-carboxylate (0.2 g, 567.50 μmol). The reaction mixture was warmed to r.t. and stirred for 3 hr. After the completion of the reaction, 10 mL of ethyl acetate was added, and the organic phase was washed with brine three times. The organic phase was dried over $Na_2SO_4$, filtered off and concentrated in vacuo at 45° C. to give crude product which was purified by HPLC (30-40% water-ACN, 10 min, flow 30 mL/min (loading pump 4 mL/min ACN) column: SunFire C18 100*19 mm) to give tert-butyl (3S)-3-[(1R)-2-[[3-(cyclobutylamino)-5-(1-piperidyl)benzoyl]amino]-1-hydroxy-ethyl]-7-(methoxymethoxy)-3,4-dihydro-1H-isoquinoline-2-carboxylate (0.135 g, 221.76 μmol, 39.08% yield). $^1$H NMR (DMSO-$d_6$, 400 MHz): δ 1.03 (m, 4H), 1.45 (m, 9H), 1.53 (m, 2H), 1.57 (m, 2H), 1.72 (m, 2H), 2.29 (m, 2H), 2.77 (m, 2H), 3.07 (m, 2H), 3.37 (m, 2H), 3.54 (m, 2H), 3.77 (m, 2H), 4.14 (m, 2H), 4.35 (s, 2H), 4.78 (m, 1H), 5.15 (m, 3H), 5.75 (m, 1H), 6.15 (s, 1H), 6.38 (s, 1H), 6.59 (s, 1H), 6.85 (m, 2H), 7.09 (d, 1H), 8.06 (m, 1H). LCMS (ESI): [M+H]$^+$ m/z: calc'd 608.3; found 609.4; Rt=1.22 min.

Step 2: Synthesis of 3-(cyclobutylamino)-N-[(2R)-2-hydroxy-2-[(3S)-7-hydroxy-1,2,3,4-tetrahydroisoquinolin-3-yl]ethyl]-5-(1-piperidyl)benzamide tert-Butyl (3S)-3-[(1R)-2-[[3-(cyclobutylamino)-5-(1-piperidyl)benzoyl]amino]-1-hydroxy-ethyl]-7-(methoxymethoxy)-3,4-dihydro-1H-isoquinoline-2-carboxylate (0.135 g, 221.76 μmol) was dissolved in the mixture of MeOH (4 mL) and hydrogen chloride solution 4.0M in dioxane (606.42 mg, 16.63 mmol, 758.02 μL) was added. The resulting mixture was stirred for 3 hr at 20° C. Then the solvent was removed in vacuo at 35° C. to give 3-(cyclobutylamino)-N-[(2R)-2-hydroxy-2-[(3S)-7-hydroxy-1,2,3,4-tetrahydroisoquinolin-3-yl]ethyl]-5-(1-piperidyl)benzamide (0.109 g, 189.90 μmol, 85.63% yield, 3HCl) which was used in the next step without further purification. LCMS (ESI): [M+H]$^+$ m/z: calc'd 464.2; found 465.4; Rt=1.92 min.

Step 3: Synthesis of tert-butyl (3S)-3-[(1R)-2-[[3-(cyclobutylamino)-5-(1-piperidyl)benzoyl]-amino]-1-hydroxy-ethyl]-7-hydroxy-3,4-dihydro-1H-isoquinoline-2-carboxylate 3-(Cyclobutylamino)-N-[(2R)-2-hydroxy-2-[(3S)-7-hydroxy-1,2,3,4-tetrahydroisoquinolin-3-yl]ethyl]-5-(1-piperidyl)benzamide (0.109 g, 189.90 μmol, 3HCl) was dissolved in the mixture of water (2 mL) and THF (2 mL) then sodium hydrogen carbonate, 99% (63.81 mg, 759.61 μmol, 29.54 μL) was added in one portion. The resulting mixture was stirred for 5 min at room temperature followed by the dropwise addition of the solution of di-tert-butyl dicarbonate (41.45 mg, 189.90 μmol, 43.58 μL) in THF (0.2 mL). The reaction mixture was stirred for 4 hr at room temperature. After the completion of the reaction, ethyl acetate (15 mL) was added to the reaction mixture, the organic phase was separated, and the aqueous phase was extracted with ethyl acetate (2*15 mL). The organic phase was washed with brine, dried over $Na_2SO_4$, filtered off and evaporated in vacuo at 40° C. to give tert-butyl (3S)-3-[(1R)-2-[[3-(cyclobutylamino)-5-(1-piperidyl)-benzoyl]amino]-1-hydroxy-ethyl]-7-hydroxy-3,4-dihydro-1H-isoquinoline-2-carboxylate (0.085 g, 150.52 μmol, 79.26% yield) which was used in the next step without purification. $^1$H NMR (CDCl$_3$, 400 MHz): δ 1.23 (m, 5H), 1.53 (m, 9H), 1.69 (m, 8H), 2.46 (m, 2H), 2.82 (m, 2H), 3.11 (m, 4H), 3.21 (m, 1H), 3.46 (m, 1H), 3.72 (m, 2H), 3.97 (m, 1H), 4.16 (m, 2H), 4.37 (m, 1H), 6.54 (s, 1H), 6.64 (m, 2H), 6.92 (d, 1H), 7.02 (s, 1H), 7.97 (s, 1H). LCMS (ESI): [M+H]$^+$ m/z: calc'd 564.3; found 565.2; Rt=3.08 min.

Step 4: Synthesis of tert-butyl (3S)-3-[(1R)-2-[[3-(cyclobutylamino)-5-(1-piperidyl)benzoyl]-amino]-1-hydroxy-ethyl]-7-[(4-methyloxazol-5-yl)methoxy]-3,4-dihydro-1H-isoquinoline-2-carboxylate tert-Butyl (3S)-3-[(1R)-2-[[3-(cyclobutylamino)-5-(1-piperidyl)benzoyl]amino]-1-hydroxy-ethyl]-7-hydroxy-3,4-dihydro-1H-isoquinoline-2-carboxylate (0.085 g, 150.52 μmol), 5-(chloromethyl)-4-methyl-oxazole (30.35 mg, 180.62 μmol, HCl) and cesium carbonate (147.13 mg, 451.56 μmol) were dissolved in DMF (3 mL) and heated at 50° C. overnight. After the completion of the reaction, the resulting mixture was filtered off and washed with DMF (2 mL). The obtained filtrate was concentrated in vacuo at 60° C. to give tert-butyl (3S)-3-[(1R)-2-[[3-(cyclobutylamino)-5-(1-piperidyl)benzoyl]amino]-1-hydroxy-ethyl]-7-[(4-methyloxazol-5-yl)methoxy]-3,4-dihydro-1H-isoquinoline-2-carboxylate (0.087 g, 131.86 μmol, 87.60% yield) which was used in the next step without further purification. $^1$H NMR (CDCl$_3$, 400 MHz): δ 1.23 (m, 2H), 1.53 (m, 9H), 1.66 (m, 4H), 1.80 (m, 4H), 2.03 (m, 2H), 2.21 (s, 3H), 2.43 (m, 2H), 2.85 (s, 3H), 3.18 (m, 2H), 3.43 (m, 1H), 3.67 (m, 1H), 3.96 (m, 2H), 4.12 (m, 2H), 4.36 (m, 1H), 4.64 (m, 1H), 4.96 (s, 2H), 6.21 (s, 1H), 6.55 (s, 1H), 6.67 (s, 1H), 6.82 (d, 1H), 6.88 (s, 1H), 7.13 (d, 1H), 7.80 (s, 1H), 7.91 (m, 1H). LCMS (ESI): [M+H]$^+$ m/z: calc'd 659.3; found 660.2; Rt=3.35 min.

Step 5: Synthesis of 3-(cyclobutylamino)-N-[(2R)-2-hydroxy-2-[(3S)-7-[(4-methyloxazol-5-yl)methoxy]-1,2,3,4-tetrahydroisoquinolin-3-yl]ethyl]-5-(1-piperidyl)benzamide (Compound 58) tert-Butyl (3S)-3-[(1R)-2-[[3-(cyclobutylamino)-5-(1-piperidyl)benzoyl]amino]-1-hydroxy-ethyl]-7-[(4-methyloxazol-5-yl)methoxy]-3,4-dihydro-1H-isoquinoline-2-carboxylate (0.087 g, 131.86 μmol) was dissolved in MeOH (2 mL) and hydrogen chloride solution 4.0M in dioxane (360.57 mg, 9.89 mmol, 450.71 μL) was added. The resulting mixture was stirred for 20° C. at room temperature. Then the solvent was removed in vacuo at 45° C. The residue was dissolved in 5 mL of methanol and 10 mg of scavenger (SiliaMetS© Dimercaptotriazine(DMT)) was added and the resulting suspension was stirred for 12 h. The obtained suspension was filtered off, the filtrate was evaporated under reduced pressure and the residue was purified by HPLC (50-95% water+NH$_3$-methanol+NH$_3$, 0-5 min, flow 30 mL/min methanol (loading pump 4 mL/min methanol+NH$_3$), column: YMC-Actus Triart C18 100*19 mm) to give 3-(cyclobutylamino)-N-[(2R)-2-hydroxy-2-[(3S)-7-[(4-methyloxazol-5-yl)methoxy]-1,2,3,4-tetrahydroisoquinolin-3-yl]ethyl]-5-(1-piperidyl)benzamide (0.025 g, 44.67 μmol, 33.88% yield). $^1$H NMR (400 MHz, CDCl$_3$) δ 1.54 (m, 2H), 1.64 (m, 4H), 1.78 (m, 4H), 2.21 (s, 3H), 2.38 (m, 2H), 2.75 (m, 2H), 2.95 (m, 1H), 3.11 (m, 4H), 3.54 (m, 1H), 3.73 (m, 1H), 3.80 (m, 1H), 3.92 (m, 2H), 3.96 (m, 2H), 4.95 (s, 2H), 6.17 (m, 1H), 6.43 (s, 1H), 6.59 (d, 1H), 6.69 (s, 1H), 6.76 (dd, 1H), 7.02 (d, 1H), 7.15 (t, 1H), 7.80 (s, 1H). LCMS (ESI): [M+H]$^+$ m/z: calc'd 559.3; found 560.3; Rt=0.96 min.

Example 6—Synthesis of Compounds of Formula (IIa4i)

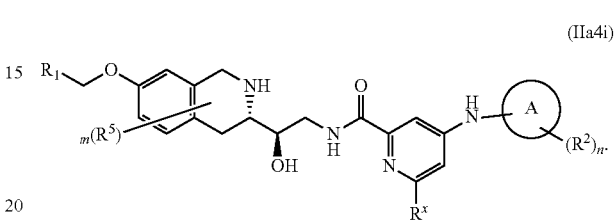

wherein $R^1$, $R^2$, $R^5$, $R^x$, m, n and A are as defined herein

Scheme 6A

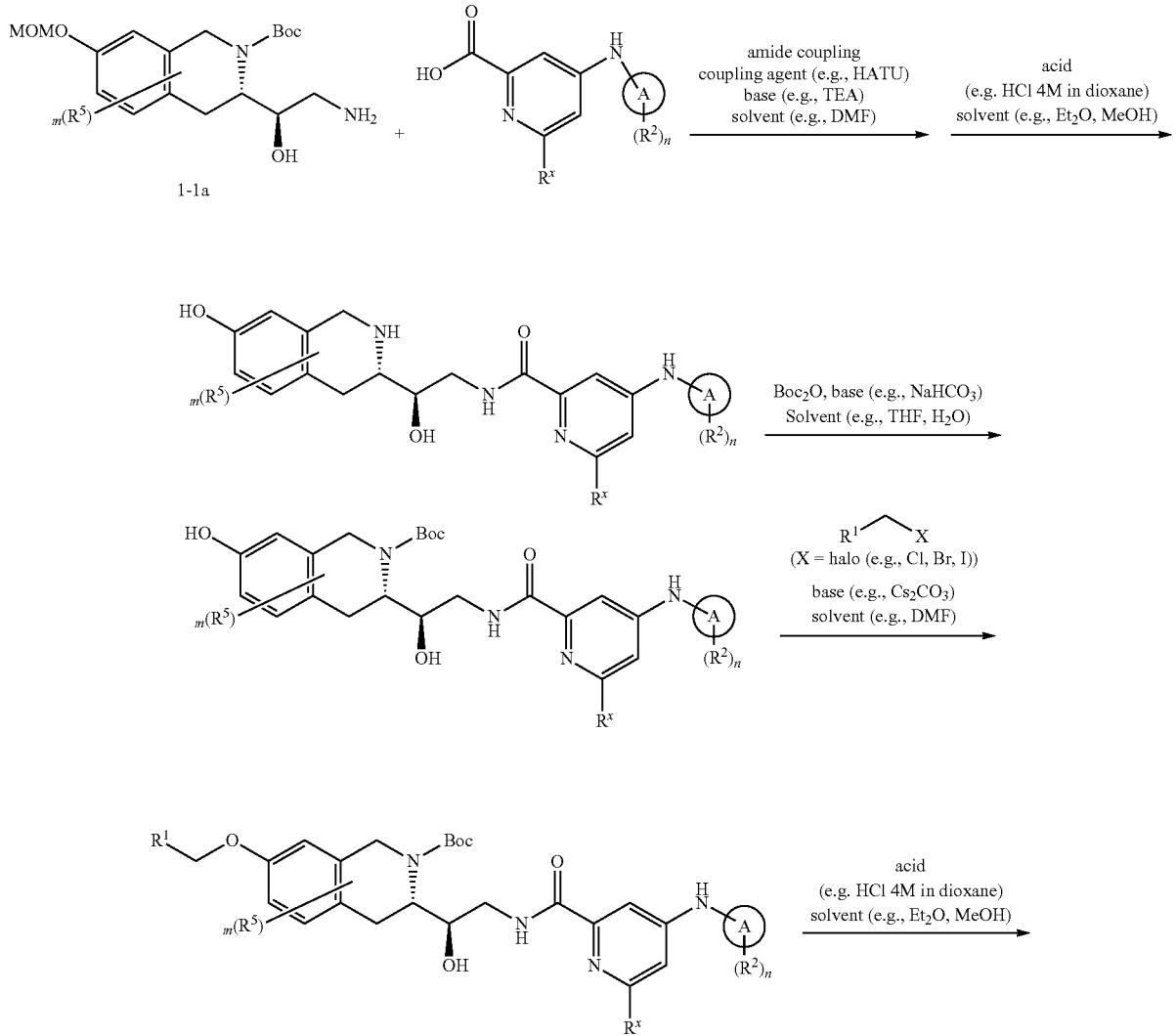

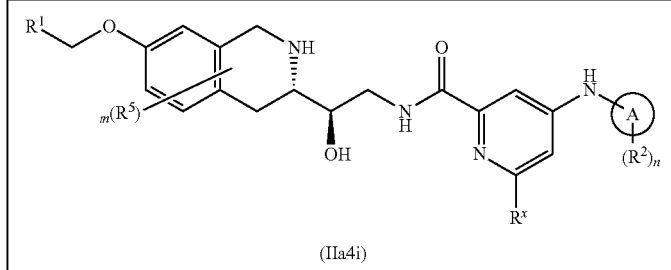
(IIa4i)
wherein X is a leaving group. In some embodiments, X is selected from Cl, Br, and I. In some embodiments X is Cl or Br.
Example 6A1. Synthesis of 4-(cyclobutylamino)-N—((R)-2-hydroxy-2-((S)-7-((4-methyloxazol-5-yl)methoxy)-1,2,3,4-tetrahydroisoquinolin-3-yl)ethyl)picolinamide (Compound 35)
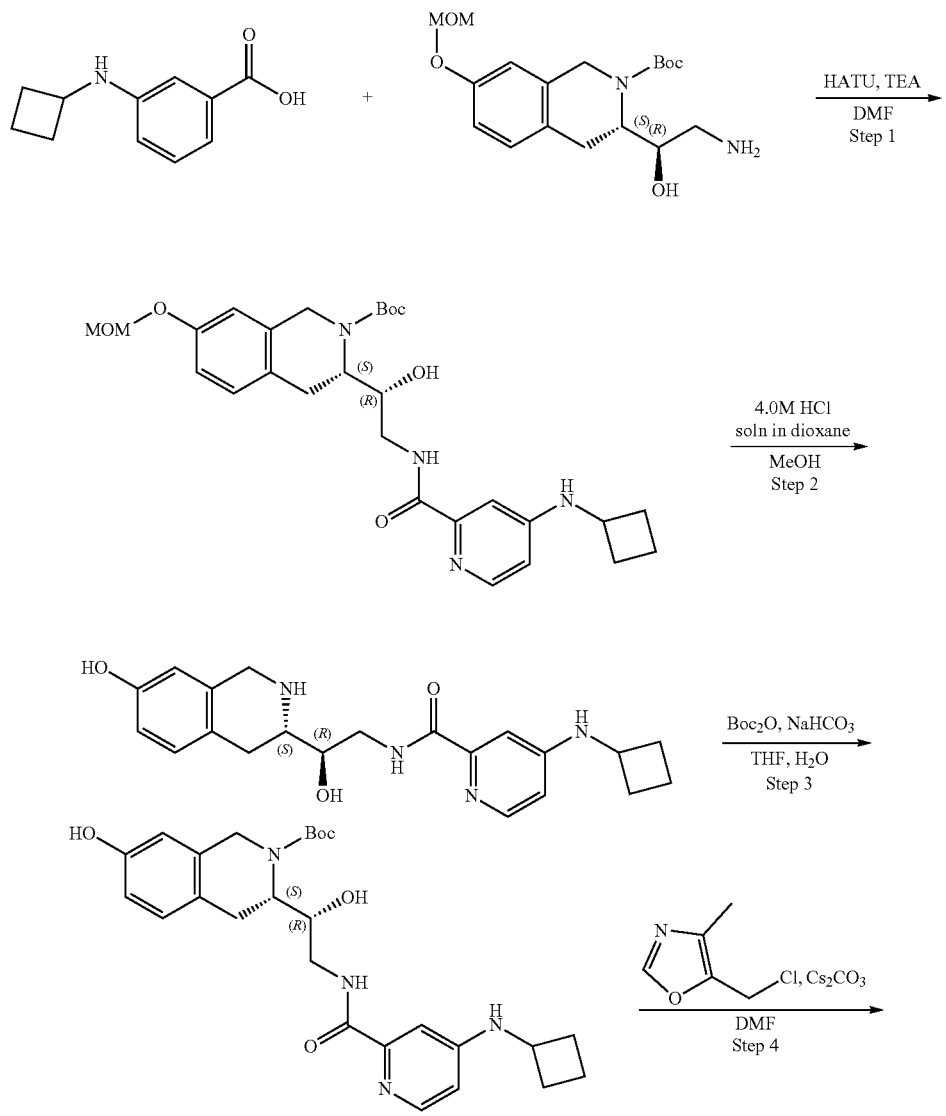

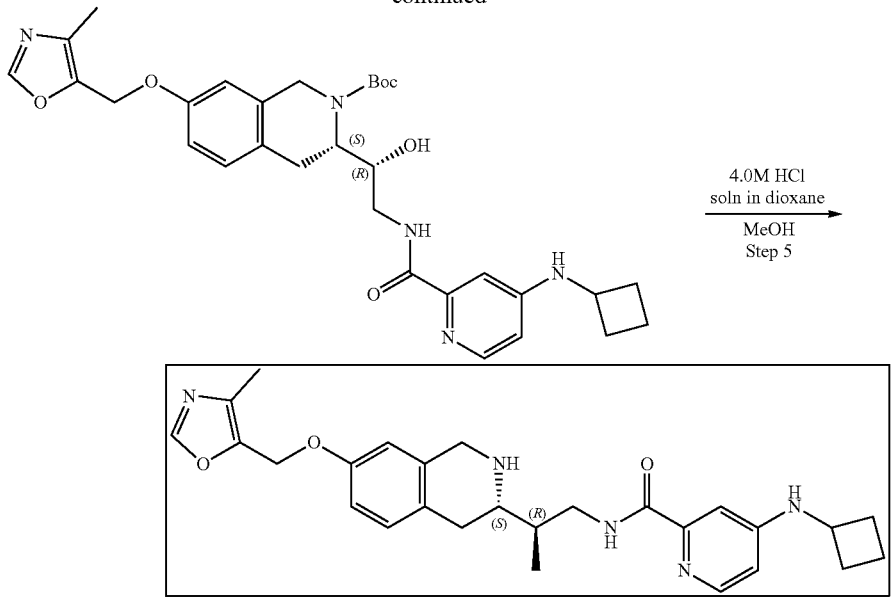

Step 1: Synthesis of (S)-tert-butyl 3-((R)-2-(4-(cyclobutylamino)picolinamido)-1-hydroxyethyl)-7-(methoxymethoxy)-3,4-dihydroisoquinoline-2(1H)-carboxylate 4-(Cyclobutylamino)pyridine-2-carboxylic acid (130.34 mg, 425.62 µmol, CF₃COOH), tert-butyl (3S)-3-[(1R)-2-amino-1-hydroxy-ethyl]-7-(methoxymethoxy)-3,4-dihydro-1H-isoquinoline-2-carboxylate (150.00 mg, 425.62 µmol), triethylamine (430.69 mg, 4.26 mmol, 593.23 µL) were mixed in DMF (3 mL) and then HATU (242.75 mg, 638.44 µmol) was added. The resulting mixture was stirred at 25° C. for 12 h. The mixture was evaporated under reduce pressure and purified with HPLC (50-65% water-acetonitrile, 2-10 min, Flow: 30 mL/min) to obtain tert-butyl (3S)-3-[(1R)-2-[[4-(cyclobutyl-amino)pyridine-2-carbonyl]amino]-1-hydroxy-ethyl]-7-(methoxymethoxy)-3,4-dihydro-1H-isoquinoline-2-carboxylate (42.4 mg, 80.51 µmol, 18.92% yield). ¹H NMR (DMSO-d₆, 400 MHz) δ:1.40 (m, 9H), 1.73 (m, 2H), 1.77 (m, 2H), 2.29 (m, 2H), 2.59 (m, 3H), 3.04 (m, 3H), 3.37 (m, 4H), 4.22 (m, 3H), 4.78 (m, 1H), 5.15 (m, 3H), 6.83 (m, 4H), 7.02 (d, 1H), 7.98 (d, 1H), 8.48 (m, 1H). LCMS (ESI): [M+H]⁺ m/z: calc'd 526.3; found 527.2; Rt=1.20 min.

Step 2: Synthesis of 4-(cyclobutylamino)-N—((R)-2-hydroxy-2-((S)-7-hydroxy-1, 2, 3,4-tetrahydroisoquinolin-3-yl)ethyl)picolinamide A solution of tert-butyl (3S)-3-[(1R)-2-[[4-(cyclobutylamino)pyridine-2-carbonyl]amino]-1-hydroxy-ethyl]-7-(methoxymethoxy)-3,4-dihydro-1H-isoquinoline-2-carboxylate (42.4 mg, 80.51 µmol) in Dioxane/HCl (2 mL) and methanol (2 mL) was stirred for 12 h at 25° C. Then, the solution was evaporated to obtain 4-(cyclobutylamino)-N-[(2R)-2-hydroxy-2-[(3S)-7-hydroxy-1,2,3,4-tetrahydroisoquinolin-3-yl]ethyl]pyridine-2-carboxamide (36 mg, crude, 2HCl). ¹H NMR (CD₃OD, 500 MHz) δ:1.92 (m, 2H), 2.13 (m, 2H), 2.55 (m, 2H), 3.16 (m, 3H), 3.36 (m, 2H), 3.56 (m, 4H), 3.75 (m, 1H), 4.29 (m, 4H), 6.63 (s, 1H), 6.75 (d, 1H), 7.10 (d, 1H), 7.18 (d, 1H), 7.41 (s, 1H), 7.90 (m, 1H). LCMS (ESI): [M+H]⁺ m/z: calc'd 382.2; found 383.2; Rt=0.72 min.

Step 3: Synthesis of (S)-tert-butyl 3-((R)-2-(4-(cyclobutylamino)picolinamido)-1-hydroxyethyl)-7-hydroxy-3,4-dihydroisoquinoline-2(1H)-carboxylate To a stirred solution of sodium hydrogen carbonate (19.92 mg, 237.17 µmol, 9.22 µL) in water (1 mL) 4-(cyclobutylamino)-N-[(2R)-2-hydroxy-2-[(3S)-7-hydroxy-1,2,3,4-tetrahydroisoquinolin-3-yl]ethyl]-pyridine-2-carboxamide (36 mg, 79.06 µmol, 2HCl) was added in THF (1 mL) followed by di-tert-butyl dicarbonate (17.25 mg, 79.06 µmol, 18.14 µL) in THF (1 mL). The resulting mixture was stirred at 25° C. for 12 h. EtOAc (10 mL) was added and organic phase was separated and washed with brine (2×5 mL). Then, the solvent was dried over sodium sulfate, filtered off and evaporated to obtain tert-butyl (3S)-3-[(1R)-2-[[4-(cyclobutylamino)pyridine-2-carbonyl]amino]-1-hydroxy-ethyl]-7-hydroxy-3,4-dihydro-1H-isoquinoline-2-carboxylate (38 mg, crude). ¹H NMR (CD₃OD, 400 MHz) δ:1.51 (m, 9H), 1.80 (m, 5H), 2.39 (m, 2H), 2.81 (m, 1H), 3.11 (m, 2H), 3.71 (m, 4H), 4.24 (m, 2H), 6.56 (s, 1H), 6.58 (d, 1H), 6.76 (m, 2H), 6.96 (m, 2H), 7.96 (m, 1H). LCMS (ESI): [M+H]+ m/z: calc'd 482.2; found 483.2; Rt=1.04 min.

Step 4: Synthesis of (S)-tert-butyl 3-((R)-2-(4-(cyclobutylamino)picolinamido)-1-hydroxyethyl)-7-((4-methyloxazol-5-yl)methoxy)-3,4-dihydroisoquinoline-2(1H)-carboxylate To the solution of tert-butyl (3S)-3-[(1R)-2-[[4-(cyclobutylamino)pyridine-2-carbonyl]amino]-1-hydroxy-ethyl]-7-hydroxy-3,4-dihydro-1H-isoquinoline-2-carboxylate (38 mg, 78.74 µmol), cesium carbonate (76.97 mg, 236.23 µmol) in DMF (2 mL) was added followed by 5-(chloromethyl)-4-methyl-oxazole (15.88 mg, 94.49 µmol, HCl). The resulting mixture was heated at 50° C. for 12 h. The mixture was filtered off and evaporated to obtain tert-butyl (3S)-3-[(1R)-2-[[4-(cyclobutylamino)pyridine-2-carbonyl]amino]-1-hydroxy-ethyl]-7-[(4-methyloxazol-5-yl)methoxy]-3,4-dihydro-1H-isoquinoline-2-carboxylate (50 mg, crude). The obtained crude product was used in the next step without further purification. ¹H NMR (CD₃OD, 500 MHz) δ:1.53 (m, 9H), 1.88 (m, 4H), 2.15 (m, 5H), 2.43 (m, 2H), 2.82 (m, 3H), 3.05 (s, 3H), 4.24 (m, 1H), 4.55 (m, 1H), 5.07 (m, 2H), 6.81 (m, 3H), 7.11 (m, 1H), 8.10 (m, 2H). LCMS (ESI): [M+H]⁺ m/z: calc'd 577.3; found 578.4; Rt=1.11 min.

Step 5: Synthesis of 4-(cyclobutylamino)-N—((R)-2-hydroxy-2-((S)-7-((4-methyloxazol-5-yl)methoxy)-1,2,3,4-tetrahydroisoquinolin-3-yl)ethyl)picolinamide Compound 35) A solution of tert-butyl (3S)-3-[(1R)-2-[[4-(cyclobutylamino)pyridine-2-carbonyl]amino]-1-hydroxy-ethyl]-7-[(4-methyloxazol-5-yl)methoxy]-3,4-dihydro-1H-isoquinoline-2-carboxylate (50 mg, 86.55 μmol) in dioxane/HCl (2 mL) and methanol (2 mL) was stirred for 12 h at 25° C. Then, the solution was evaporated and the resulting crude product was purified by HPLC (water(0.0034% HCl)-methanol, 10 min, flow: 30 mL/min) to obtain 4-(cyclobutylamino)-N-[(2R)-2-hydroxy-2-[(3S)-7-[(4-methyloxazol-5-yl)-methoxy]-1,2,3,4-tetrahydroisoquinolin-3-yl]ethyl]pyridine-2-carboxamide (7.2 mg, 13.08 μmol, 15.11% yield, 2HCl). $^1$H NMR (Methanol-$d_4$, 400 MHz): δ (ppm) 1.90 (m, 2H), 2.10 (m, 2H), 2.23 (s, 3H), 2.52 (m, 2H), 3.14 (m, 1H), 3.21 (m, 1H), 3.53 (m, 1H), 3.65 (m, 2H), 4.22 (m, 1H), 4.32 (m, 2H), 4.47 (d, 1H), 5.12 (s, 2H), 6.88 (s, 1H), 6.96 (d, 1H), 7.19 (d, 1H), 7.24 (d, 1H), 7.44 (s, 1H), 7.90 (d, 1H), 8.44 (s, 1H). LCMS (ESI): [M+H]$^+$ m/z: calc'd 477.2; found 478.2; Rt=0.85 min.

Example 7—Synthesis of Compounds of Formula (IIa3ii)

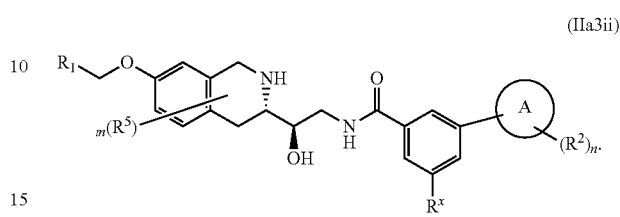

wherein $R^1$, $R^2$, $R^5$, $R^x$, m, n and A are as defined herein

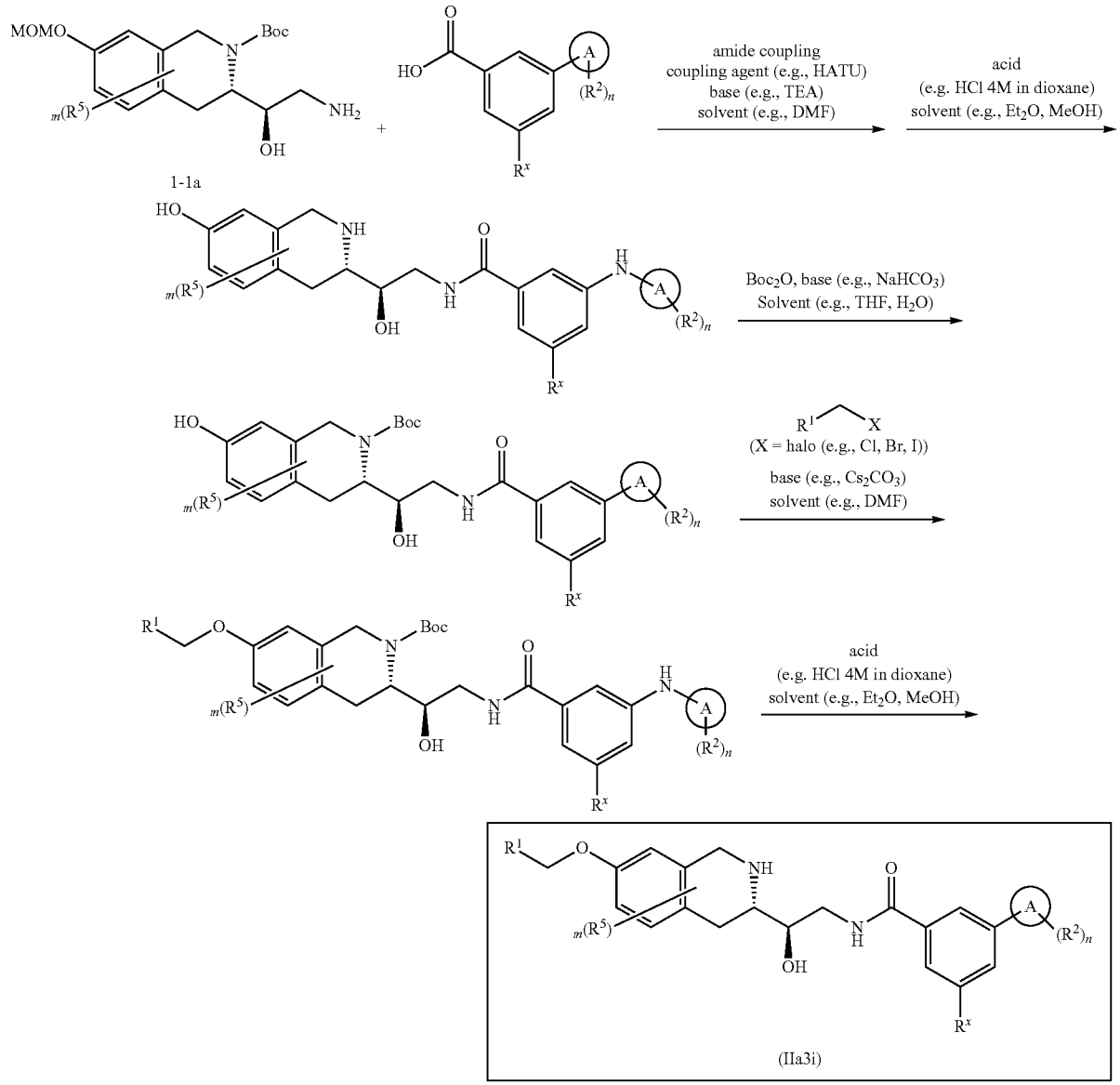

Scheme 7A wherein X is a leaving group. In some embodiments, X is selected from Cl, Br, and I. In some embodiments X is Cl or Br.
Example 7A1. Synthesis of N—((R)-2-hydroxy-2-((S)-7-((4-methyloxazol-5-yl)methoxy)-1,2,3,4-tetrahydroisoquinolin-3-yl)ethyl)-3-(pyridin-2-yl)benzamide (Compound 25)
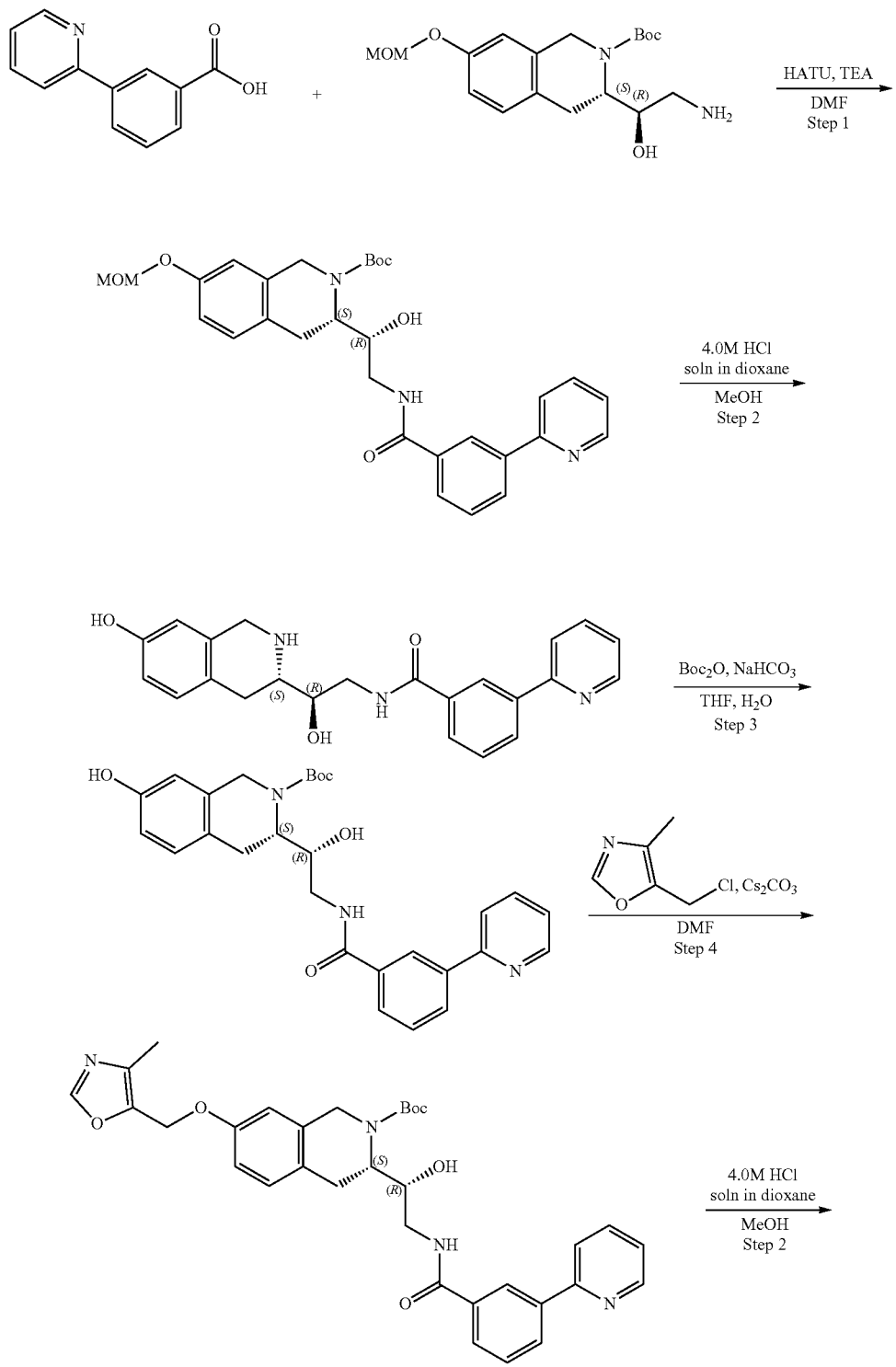

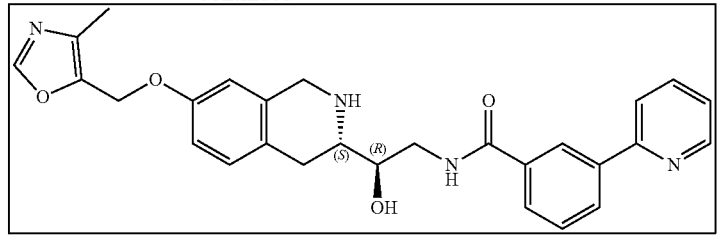

Step 1: Synthesis of (S)-tert-butyl 3-((R)-1-hydroxy-2-(3-(pyridin-2-yl)benzamido)ethyl)-7-(methoxymethoxy)-3,4-dihydroisoquinoline-2(1H)-carboxylate 3-(2-Pyridyl)benzoic acid (100.30 mg, 425.62 µmol, HCl), tert-butyl (3S)-3-[(1R)-2-amino-1-hydroxy-ethyl]-7-(methoxymethoxy)-3,4-dihydro-1H-isoquinoline-2-carboxylate (150 mg, 425.62 µmol), triethylamine (430.69 mg, 4.26 mmol, 593.23 µL) were mixed in DMF (3 mL) and then HATU (242.75 mg, 638.44 µmol) was added. Resulting mixture were stirred at 25° C. for 12 h. The mixture was evaporated under reduce pressure and purified with HPLC (50-65% water-acetonitrile, 2-10 min, Flow: 30 mL/min) to obtain tert-butyl (3S)-3-[(1R)-1-hydroxy-2-[[3-(2-pyridyl)benzoyl]amino]ethyl]-7-(methoxymethoxy)-3,4-dihydro-1H-isoquinoline-2-carboxylate (112.4 mg, 210.64 µmol, 49.49% yield). $^1$H NMR (DMSO-$d_6$, 400 MHz) δ: 1.44 (m, 9H), 2.07 (s, 2H), 2.54 (s, 1H), 2.78 (m, 1H), 3.07 (m, 2H), 3.37 (m, 1H), 3.53 (m, 2H), 4.22 (m, 2H), 4.78 (m, 1H), 5.15 (s, 2H), 6.87 (m, 2H), 7.09 (d, 1H), 7.40 (td, 1H), 7.56 (td, 1H), 7.90 (m, 2H), 8.02 (d, 1H), 8.20 (d, 1H), 8.54 (s, 1H), 8.57 (m, 1H), 8.68 (m, 1H). LCMS (ESI): [M+H]$^+$ m/z: calc'd 533.2; found 534.2; Rt=1.43 min.

Step 2: Synthesis of N—((R)-2-hydroxy-2-((S)-7-hydroxy-1,2,3,4-tetrahydroisoquinolin-3-yl)ethyl)-3-(pyridin-2-yl)benzamide A solution of tert-butyl (3S)-3-[(1R)-1-hydroxy-2-[[3-(2-pyridyl)benzoyl]amino]ethyl]-7-(methoxymethoxy)-3,4-dihydro-1H-isoquinoline-2-carboxylate (112.4 mg, 210.64 µmol) in dioxane/HCl (2 mL) and methanol (2 mL) was stirred for 12 h at 25° C. Then, the solution was evaporated to obtain N-[(2R)-2-hydroxy-2-[(3S)-7-hydroxy-1,2,3,4-tetrahydroisoquinolin-3-yl]ethyl]-3-(2-pyridyl)benzamide (89 mg, crude, HCl). $^1$H NMR (CD$_3$OD, 500 MHz) δ:1.32 (m, 2H), 1.52 (m, 1H), 3.15 (m, 3H), 3.65 (m, 4H), 4.01 (m, 1H), 4.48 (m, 1H), 6.64 (s, 1H), 6.76 (d, 1H), 7.13 (d, 1H), 7.66 (m, 2H), 8.00 (d, 1H), 8.07 (m, 1H), 8.15 (m, 2H), 8.48 (s, 1H), 8.72 (m, 1H). LCMS (ESI): [M+H]$^+$ m/z: calc'd 389.2; found 390.2; Rt=0.83 min.

Step 3: Synthesis of (S)-tert-butyl 7-hydroxy-3-((R)-1-hydroxy-2-(3-(pyridin-2-yl)benzamido)ethyl)-3,4-dihydroisoquinoline-2(1H)-carboxylate To a stirred solution of sodium hydrogen carbonate (52.66 mg, 626.90 µmol, 24.38 µL) in water (1 mL) N-[(2R)-2-hydroxy-2-[(3S)-7-hydroxy-1,2,3,4-tetrahydroisoquinolin-3-yl]ethyl]-3-(2-pyridyl)-benza-mide (89 mg, 208.97 µmol, HCl) was added in THF (1 mL) followed by di-tert-butyl dicarbonate (45.61 mg, 208.97 µmol, 47.96 µL) in THF (1 mL). Resulting mixture was stirred at 25° C. for 12 h. EtOAc (10 mL) was added and organic phase was separated and washed with brine (2×5 mL). Then, the solvent was dried over sodium sulfate, filtered and evaporated to obtain tert-butyl (3S)-7-hydroxy-3-[(1R)-1-hydroxy-2-[[3-(2-pyridyl)benzoyl]amino]ethyl]-3,4-dihydro-1H-isoquinoline-2-carboxylate (100 mg, crude). $^1$H NMR (CD$_3$OD, 500 MHz) δ:1.52 (m, 9H), 2.99 (m, 2H), 3.84 (m, 2H), 4.31 (m, 2H), 5.14 (s, 2H), 6.56 (s, 1H), 6.58 (d, 1H), 6.99 (d, 1H), 7.39 (td, 1H), 7.60 (m, 2H), 8.14 (m, 2H), 8.40 (m, 1H), 8.42 (m, 1H), 8.60 (m, 1H). LCMS (ESI): [M+H]$^+$ m/z: calc'd 489.2; found 490.2; Rt=1.25 min.

Step 4: Synthesis of (S)-tert-butyl 3-((R)-1-hydroxy-2-(3-(pyridin-2-yl)benzamido)ethyl)-7-((4-methyloxazol-5-yl)methoxy)-3,4-dihydroisoquinoline-2(1H)-carboxylate To the solution of tert-butyl (3S)-7-hydroxy-3-[(1R)-1-hydroxy-2-[[3-(2-pyridyl)benzoyl]-amino]ethyl]-3,4-dihydro-1H-isoquinoline-2-carboxylate (100 mg, 204.26 µmol), cesium carbonate (199.66 mg, 612.79 µmol) in DMF (2 mL) was added 5-(chloromethyl)-4-methyl-oxazole (41.18 mg, 245.12 µmol, HCl). Resulting mixture was heated at 50° C. for 12 h. The mixture was filtered and evaporated to obtain tert-butyl (3S)-3-[(1R)-1-hydroxy-2-[[3-(2-pyridyl)benzoyl]amino]ethyl]-7-[(4-methyloxazol-5-yl)-methoxy]-3,4-dihydro-1H-isoquinoline-2-carboxylate (130 mg, crude) that was used in the next step without further purification. $^1$H NMR (CD$_3$OD, 500 MHz) δ:1.51 (m, 9H), 2.18 (m, 4H), 2.65 (s, 3H), 3.84 (m, 1H), 4.56 (m, 2H), 5.07 (m, 3H), 6.65 (d, 1H), 7.10 (s, 1H), 7.93 (m, 1H), 7.62 (m, 1H), 7.93 (m, 3H), 7.96 (s, 1H), 8.13 (m, 2H), 8.63 (m, 1H). LCMS (ESI): [M+H]$^+$ m/z: calc'd 584.3; found 585.3; Rt=1.32 min.

Step 5: Synthesis of N—((R)-2-hydroxy-2-((S)-7-((4-methyloxazol-5-yl)methoxy)-1, 2, 3,4-tetrahydroisoquinolin-3-yl)ethyl)-3-(pyridin-2-yl)benzamide (Compound 25) A solution of tert-butyl (3S)-3-[(1R)-1-hydroxy-2-[[3-(2-pyridyl)benzoyl]amino]ethyl]-7-[(4-methyl-oxazol-5-yl)methoxy]-3,4-dihydro-1H-isoquinoline-2-carboxylate (130 mg, 222.35 µmol) in dioxane/HCl (2 mL) and methanol (2 mL) was stirred for 12 h at 25° C. Then, the solution was evaporated and resulting crude product was purified by HPLC (10-40% water-methanol, 10 min, flow: 30 mL/min) to obtain N-[(2R)-2-hydroxy-2-[(3S)-7-[(4-methyloxazol-5-yl)methoxy]-1,2,3,4-tetrahydroisoquinolin-3-yl]ethyl]-3-(2-pyridyl)benzamide (16.3 mg, 31.29 µmol, 14.07% yield, HCl). $^1$H NMR (CD$_3$OD, 400 MHz) δ: 2.27 (s, 3H), 2.67 (s, 2H), 3.25 (m, 4H), 3.68 (m, 3H), 4.41 (m, 3H), 5.14 (s, 2H), 6.90 (s, 1H), 6.95 (d, 1H), 7.25 (d, 1H), 7.78 (dd, 1H), 8.12 (m, 3H), 8.57 (m, 2H), 8.74 (m, 2H), 8.88 (d, 1H). LCMS (ESI): [M+H]$^+$ m/z: calc'd 484.2; found 485.2; Rt=0.96 min.

Example 8—Synthesis of Compounds of Formula (IIa2i)

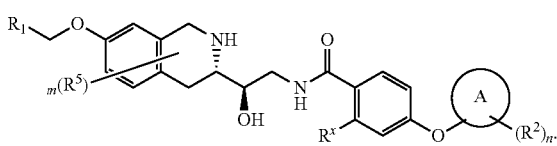

wherein $R^1$, $R^2$, $R^5$, $R^x$, m, n and A are as defined herein
Scheme 8A
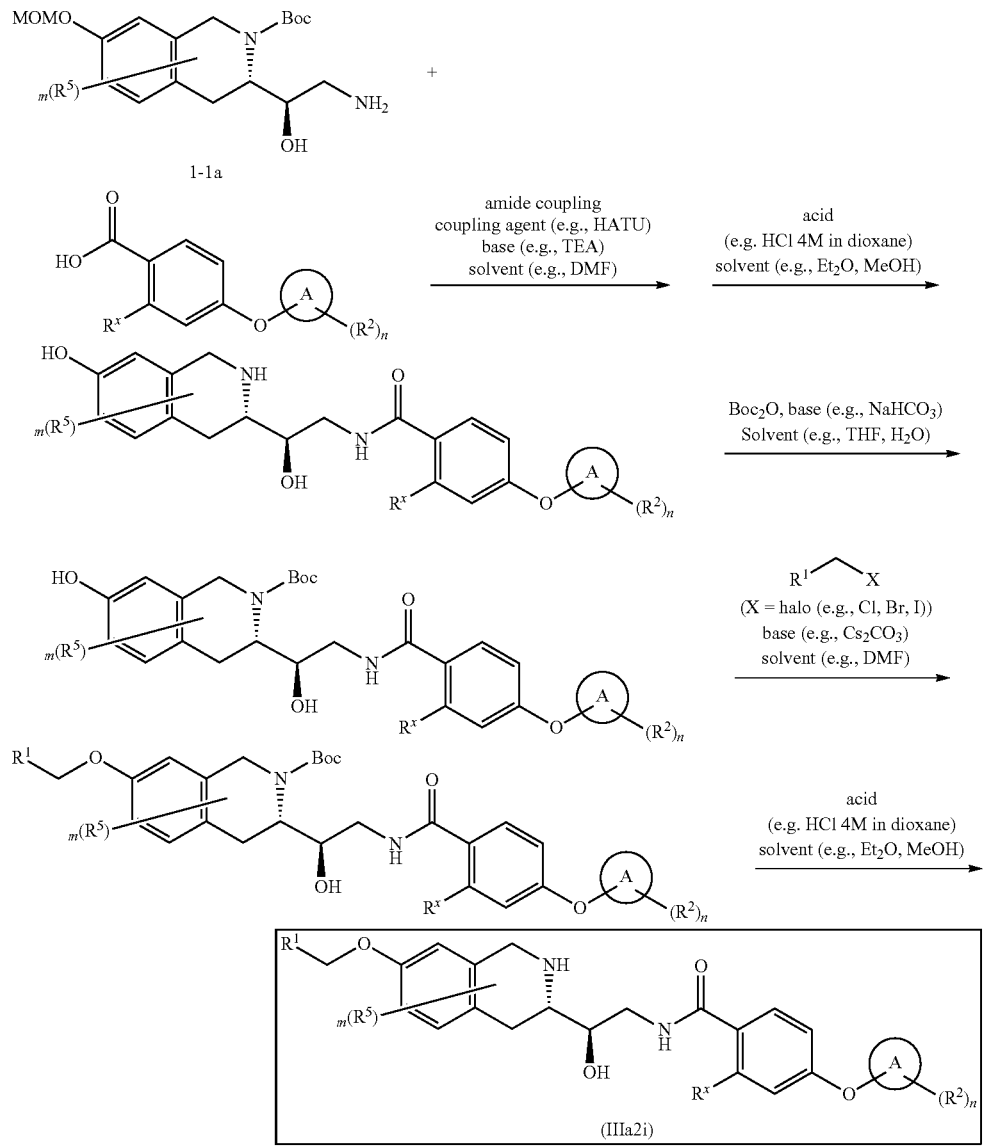
wherein X is a leaving group. In some embodiments, X is selected from Cl, Br, and I. In some embodiments X is Cl or Br.
Example 8A1. Synthesis of N—((R)-2-hydroxy-2-((S)-7-((4-methyloxazol-5-yl)methoxy)-1,2,3,4-tetrahydroisoquinolin-3-yl)ethyl)-4-((1-(pyridin-4-ylmethyl)piperidin-4-yl)oxy)benzamide (Compound 23)
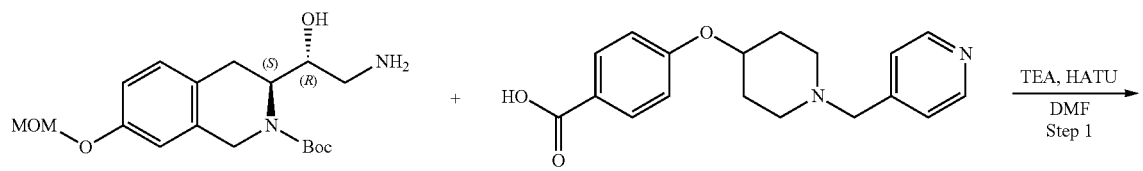

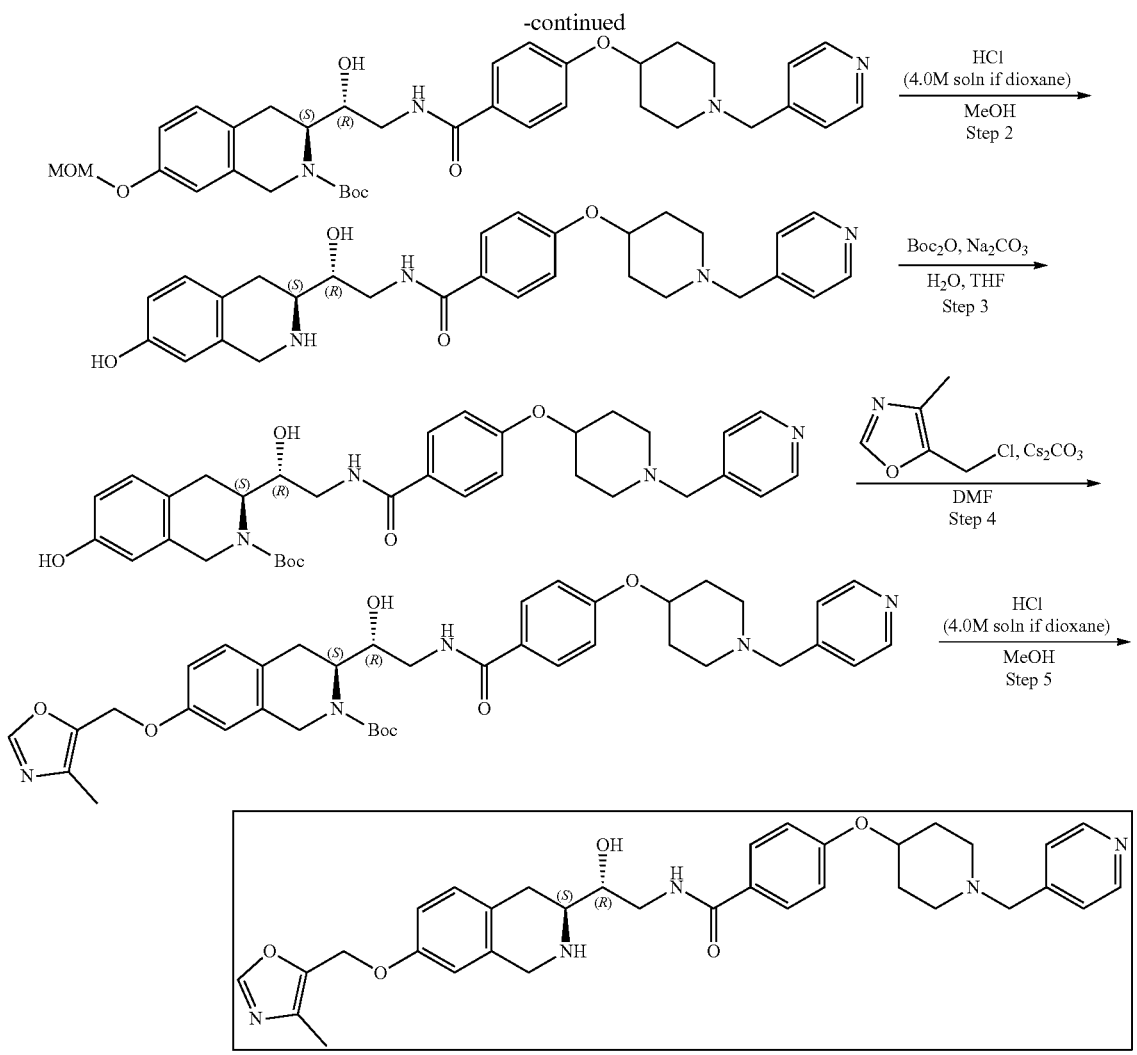

Step 1: Synthesis of (S)-tert-butyl 3-((R)-1-hydroxy-2-(4-((1-(pyridin-4-ylmethyl)piperidin-4-yl)oxy)benzamido)ethyl)-7-(methoxymethoxy)-3,4-dihydroisoquinoline-2(1H)-carboxylate. 4-[[1-(4-Pyridylmethyl)-4-piperidyl]oxy]benzoic acid (163.99 mg, 425.62 μmol, 2HCl) was dissolved in DMF (2 mL) and triethylamine (430.69 mg, 4.26 mmol, 593.23 μL) followed by HATU (242.75 mg, 638.44 μmol) were added. The resulting mixture was stirred for 15 min and the solution of tert-butyl (3S)-3-[(1R)-2-amino-1-hydroxyethyl]-7-(methoxymethoxy)-3,4-dihydro-1H-isoquinoline-2-carboxylate (0.15 g, 425.62 μmol) in DMF (1 mL) was added thereto. The reaction mixture was stirred for 12 h. After the completion of the reaction, the resulting mixture was diluted with EtOAc (50 mL) and the solution was washed with brine three times, dried over Na₂SO₄, filtered and evaporated. The crude product was purified by HPLC (50-60% water-acetonitrile, 10 min, flow: 30 mL/min, (loading pump 4 ml/min acetonitrile), column: SunFire C18 100*19 mm) to obtain tert-butyl (3S)-3-[(1R)-1-hydroxy-2-[[4-[[1-(4-pyridylmethyl)-4-piperidyl]oxy]benzoyl]amino]ethyl]-7-(methoxymethoxy)-3,4-dihydro-1H-isoquinoline-2-carboxylate (0.0737 g, 113.95 μmol, 26.77% yield). ¹H NMR (CDCl₃, 400 MHz) δ:1.52 (s, 9H), 1.84 (m, 2H), 2.33 (m, 2H), 2.69 (m, 3H), 2.85 (m, 2H), 3.13 (m, 1H), 3.45 (s, 3H), 3.51 (s, 2H), 3.55 (m, 1H), 4.16 (m, 2H), 4.40 (m, 2H), 4.63 (m, 1H), 5.13 (s, 2H), 6.76 (s, 1H), 6.85 (d, 1H), 6.92 (m, 2H), 7.07 (d, 1H), 7.29 (m, 2H), 7.83 (m, 3H), 8.53 (m, 2H), NH and OH aren't observed. LCMS (ESI): [M+H]⁺ m/z: calc'd 646.3; found 647.2; Rt=1.15 min.

Step 2: Synthesis of N—((R)-2-hydroxy-2-((S)-7-hydroxy-1,2,3,4-tetrahydroisoquinolin-3-yl)ethyl)-4-((1-(pyridin-4-ylmethyl)piperidin-4-yl)oxy)benzamide tert-Butyl (3S)-3-[(1R)-1-hydroxy-2-[[4-[[1-(4-pyridylmethyl)-4-piperidyl]oxy]benzoyl]amino]-ethyl]-7-(methoxymethoxy)-3,4-dihydro-1H-isoquinoline-2-carboxylate (0.0737 g, 113.95 μmol) was dissolved in MeOH (2.0 mL) and hydrogen chloride solution 4.0M in dioxane (49.86 mg, 1.37 mmol, 62.32 μL) was added thereto. The reaction mixture was stirred for 15 h. Then, the resulting mixture was evaporated to dryness to obtain N-[(2R)-2-hydroxy-2-[(3S)-7-hydroxy-1,2,3,4-tetrahydroisoquinolin-3-yl]ethyl]-4-[[1-(4-pyridylmethyl)-4-piperidyl]oxy]benzamide (0.0737 g, crude, 3HCl). ¹H NMR (CD₃OD, 400 MHz) δ: 2.30 (m, 4H), 3.15 (m, 4H), 3.45 (m, 2H), 3.58 (m, 5H), 4.28 (m, 3H), 4.75 (s, 2H), 6.62 (s, 1H), 6.75 (d, 1H), 7.12 (m, 3H), 7.87 (m, 2H), 8.39 (m, 2H), 9.02 (m, 2H), OH and NH aren't observed. LCMS (ESI): [M+2H]⁺ m/z: calc'd 502.2; found 504.4; Rt=0.71 min.

Step 3: Synthesis of (S)-tert-butyl 7-hydroxy-3-((R)-1-hydroxy-2-(4-((1-(pyridin-4-ylmethyl)piperidin-4-yl)oxy)

benzamido)ethyl)-3,4-dihydroisoquinoline-2(1H)-carboxylate. N-[(2R)-2-Hydroxy-2-[(3S)-7-hydroxy-1,2,3,4-tetrahydroisoquinolin-3-yl]ethyl]-4-[[1-(4-pyridyl-methyl)-4-piperidyl]oxy]benzamide (0.068 g, 111.11 μmol, 3HCl) was dissolved in water (3.0 mL) and sodium bicarbonate (65.34 mg, 777.80 μmol, 30.25 μL) was added. The resulting mixture was diluted with THF (2 mL) and a solution of di-tert-butyl dicarbonate (24.25 mg, 111.11 μmol, 25.50 μL) in THF (1.0 mL) was added dropwise. The reaction mixture was stirred for 5 h. The observed mixture was transferred to a separating funnel and an organic layer was separated. An aqueous layer was extracted with EtOAc (2*20 mL) and combined organic layers were washed with brine, dried over Na$_2$SO$_4$, filtered off and evaporated to obtain tert-butyl (3S)-7-hydroxy-3-[(1R)-1-hydroxy-2-[[4-[[1-(4-pyridylmethyl)-4-piperidyl]oxy]benzoyl]-amino]ethyl]-3,4-dihydro-1H-isoquinoline-2-carboxylate (0.067 g, crude). $^1$H NMR (CDCl$_3$, 500 MHz) δ: 1.48 (s, 9H), 1.90 (m, 3H) 2.01 (m, 2H), 2.34 (m, 2H), 2.73 (m, 2H), 3.49 (m, 6H), 3.72 (m, 4H), 4.17 (m, 2H), 4.44 (m, 3H), 6.71 (s, 1H), 6.96 (m, 3H), 7.07 (m, 1H), 7.82 (m, 2H), 8.57 (m, 2H). LCMS (ESI): [M+H]$^+$ m/z: calc'd 602.3; found 603.2; Rt=0.96 min.

Step 4: Synthesis of (S)-tert-butyl 3-((R)-1-hydroxy-2-(4-((1-(pyridin-4-ylmethyl)piperidin-4-yl)oxy)benzamido) ethyl)-7-((4-methyloxazol-5-yl)methoxy)-3,4-dihydroisoquinoline-2(1H)-carboxylate tert-Butyl (3S)-7-hydroxy-3-[(1R)-1-hydroxy-2-[[4-[[1-(4-pyridylmethyl)-4-piperidyl]oxy]benzoyl]-amino]ethyl]-3,4-dihydro-1H-isoquinoline-2-carboxylate (0.067 g, 111.16 μmol) was dissolved in DMF (2.0 mL) and cesium carbonate (108.66 mg, 333.49 μmol) followed by 5-(chloromethyl)-4-methyl-oxazole (22.41 mg, 133.40 μmol, HCl) were added. The reaction mixture was heated at 60° C. for 12 h. The obtained mixture was cooled and poured into water (20 mL). The resulting mixture was extracted with EtOAc (2*25 mL) and combined organic layers were washed three times with brine, dried over Na$_2$SO$_4$, filtered off and evaporated to obtain tert-butyl (3S)-3-[(1R)-1-hydroxy-2-[[4-[[1-(4-pyridylmethyl)-4-piperidyl]oxy]-benzoyl]amino]ethyl]-7-[(4-methyloxazol-5-yl)methoxy]-3,4-dihydro-1H-isoquinoline-2-carboxylate (0.0638 g, 91.43 μmol, 82.25% yield). $^1$H NMR (CDCl$_3$, 500 MHz) δ: 1.50 (s, 9H), 1.87 (m, 2H), 2.02 (m, 2H), 2.24 (s, 3H), 2.37 (m, 2H), 2.74 (m, 2H), 3.47 (m, 2H), 3.54 (m, 2H), 3.71 (m, 2H), 4.20 (m, 2H), 4.40 (m, 2H), 5.00 (s, 2H), 5.37 (s, 2H), 6.71 (s, 1H), 6.83 (m, 1H), 6.95 (m, 2H), 7.15 (m, 1H), 7.76 (m, 1H), 7.85 (m, 3H), 8.56 (m, 2H), OH isn't observed. LCMS (ESI): [M+2H]$^+$ m/z: calc'd 697.3; found 699.4; Rt=1.14 min.

Step 5: Synthesis of N—((R)-2-hydroxy-2-((S)-7-((4-methyloxazol-5-yl)methoxy)-1,2,3,4-tetrahydroisoquinolin-3-yl)ethyl)-4-((1-(pyridin-4-ylmethyl)piperidin-4-yl)oxy) benzamide (Compound 23) tert-Butyl (3S)-3-[(1R)-1-hydroxy-2-[[4-[[1-(4-pyridylmethyl)-4-piperidyl]oxy] benzoyl]amino]-ethyl]-7-[(4-methyloxazol-5-yl)methoxy]-3,4-dihydro-1H-isoquinoline-2-carboxylate (0.0638 g, 91.43 μmol) was dissolved in MeOH (2.0 mL) and hydrogen chloride solution 4.0M in dioxane (33.34 mg, 914.28 μmol, 41.67 μL) was added. The reaction mixture was stirred for 12 h. The obtained mixture was evaporated to dryness. The residue was purified by HPLC (Column: SunFire C18 100*19 mm, 5 μm, 0-55% water-acetonitrile, 2-10 min, Flow: 30 mL/min (Loading pump 4 mL/min Acetonitrile)) to obtain N-[(2R)-2-hydroxy-2-[(3S)-7-[(4-methyloxazol-5-yl)methoxy]-1,2,3,4-tetrahydroisoquinolin-3-yl]-ethyl]-4-[[1-(4-pyridylmethyl)-4-piperidyl]oxy]benzamide (0.0176 g, 23.67 μmol, 25.89% yield, 4HCl). $^1$H NMR (Methanol-d$_4$, 400 MHz): δ (ppm) 2.23 (s, 5H), 2.36 (m, 2H), 2.66 (s, 3H), 3.20 (m, 2H), 3.55 (m, 8H), 4.25 (m, 1H), 4.33 (d, 1H), 4.45 (d, 1H), 4.78 (s, 2H), 5.12 (s, 2H), 6.88 (s, 1H), 6.96 (d, 1H), 7.11 (m, 2H), 7.23 (d, 1H), 7.86 (m, 2H), 8.42 (s, 1H), 8.47 (d, 2H), 9.02 (d, 2H). LCMS (ESI): [M+H]$^+$ m/z: calc'd 597.3; found 598.4; Rt=0.81 min.

Example 9—Synthesis of Compounds of Formula (IVa)

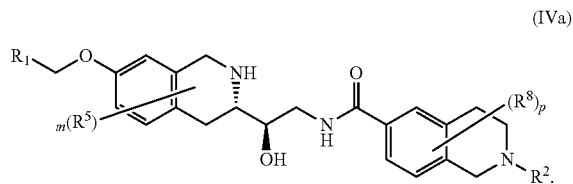

wherein $R^1$, $R^2$, $R^5$, $R^8$, m and p are as defined herein

Scheme 9A

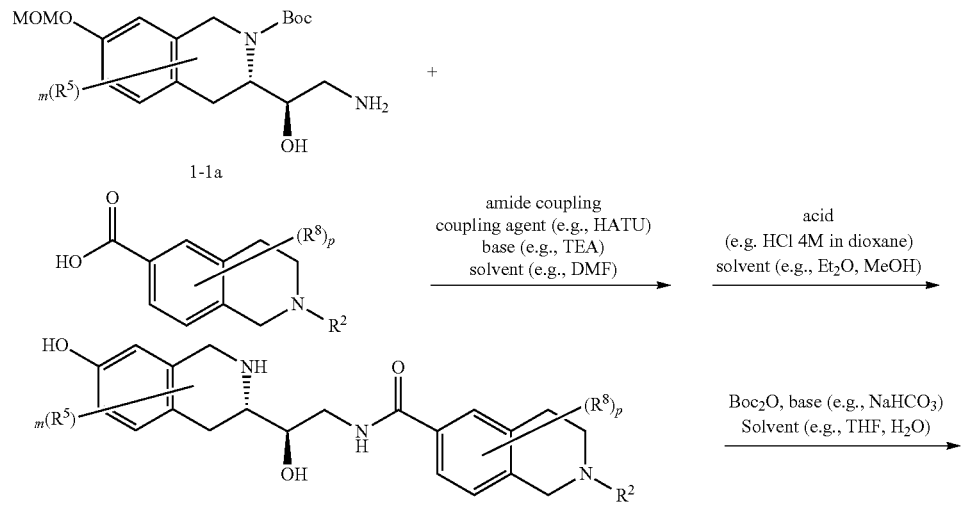

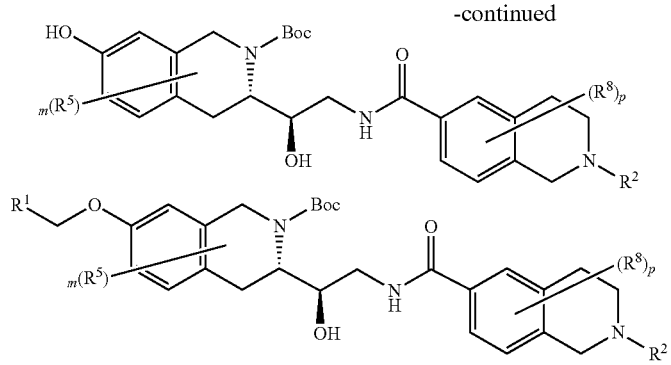
-continued
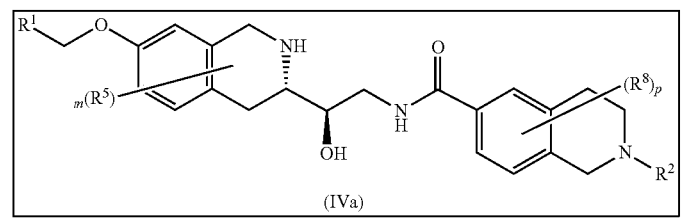
wherein X is a leaving group. In some embodiments, X is selected from Cl, Br, and I. In some embodiments X is Cl or Br.
Example 9A1. Synthesis of 2-(4-bromobenzoyl)-N—((R)-2-hydroxy-2-((S)-7-((4-methyloxazol-5-yl)methoxy)-1,2,3,4-tetrahydroisoquinolin-3-yl)ethyl)-1,2,3,4-tetrahydroisoquinoline-6-carboxamide (Compound 20)
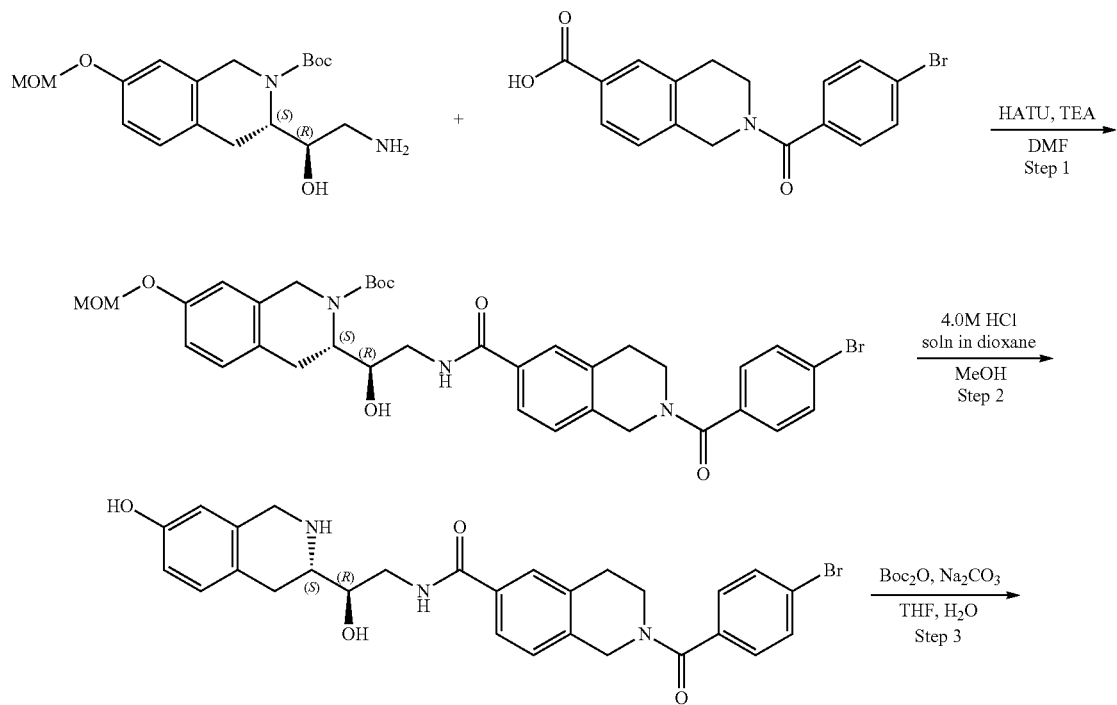

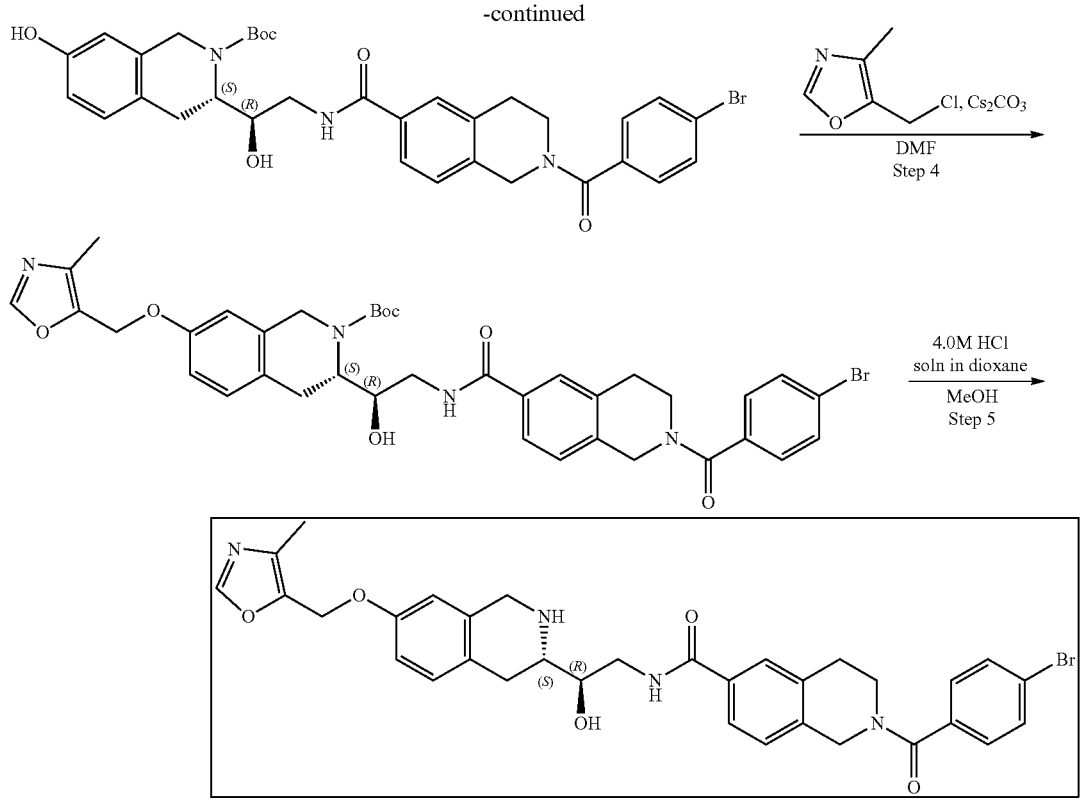

Step 1: Synthesis of (S)-tert-butyl 3-((R)-2-(2-(4-bromobenzoyl)-1,2,3,4-tetrahydroisoquinoline-6-carboxamido)-1-hydroxyethyl)-7-(methoxymethoxy)-3,4-dihydroisoquinoline-2(1H)-carboxylate 2-(4-Bromobenzoyl)-3,4-dihydro-1H-isoquinoline-6-carboxylic acid (153.31 mg, 425.62 µmol) and TEA (430.69 mg, 4.26 mmol, 593.23 µL) were dissolved in DMF (3 mL) and cooled to 0° C., HATU (242.75 mg, 638.44 µmol) was added and the mixture was stirred for 15 min at 0° C. tert-Butyl (3S)-3-[(1R)-2-amino-1-hydroxy-ethyl]-7-(methoxymethoxy)-3,4-dihydro-1H-isoquinoline-2-carboxylate (0.15 g, 425.62 µmol) was added and the mixture was warmed to r.t. and stirred overnight. 10 mL of Ethyl acetate was added, and organic phase was washed with brine three times. The organic phase was dried over Na₂SO₄, filtered and concentrated in vacuo at 45° C. to give crude product which was purified by HPLC (55-60% water-acetonitrile, 2-10 min, flow: 30 mL/min (loading pump 4 mL/min acetonitrile) column: SunFire C18 100*19 mm) to give tert-butyl (3S)-3-[(1R)-2-[[2-(4-bromobenzoyl)-3,4-dihydro-1H-isoquinoline-6-carbonyl]amino]-1-hydroxy-ethyl]-7-(methoxymethoxy)-3,4-dihydro-1H-isoquinoline-2-carboxylate (0.1435 g, 206.59 µmol, 48.54% yield)¹H NMR (CDCl₃, 400 MHz) δ:1.52 (m, 10H), 1.98 (s, 2H), 2.88 (m, 4H), 3.13 (m, 1H), 3.46 (m, 2H), 3.94 (m, 1H), 4.17 (m, 2H), 4.35 (m, 1H), 4.63 (m, 3H), 5.13 (s, 2H), 6.77 (s, 1H), 6.85 (d, 1H), 7.08 (d, 1H), 7.33 (m, 2H), 5.57 (m, 2H), 7.72 (m, 2H), 7.94 (m, 1H). LCMS (ESI): [M-Boc]⁺ m/z: calc'd 593.2; found 594.2; Rt=1.53 min.

Step 2: Synthesis of 2-(4-bromobenzoyl)-N—((R)-2-hydroxy-2-((S)-7-hydroxy-1,2,3,4-tetrahydroisoquinolin-3-yl)ethyl)-]1,2,3,4-tetrahydroisoquinoline-6-carboxamide tert-Butyl (3S)-3-[(1R)-2-[[2-(4-bromobenzoyl)-3,4-dihydro-1H-isoquinoline-6-carbonyl]amino]-1-hydroxy-ethyl]-7-(methoxymethoxy)-3,4-dihydro-1H-isoquinoline-2-carboxylate (0.1435 g, 206.59 µmol) was dissolved in the mixture of MeOH (3 mL). Hydrogen chloride solution 4.0M in dioxane (564.94 mg, 15.49 mmol, 706.17 µL) was added. The mixture was stirred for 12 h at 20° C. The solvent was removed in vacuo at 35° C. to give 2-(4-bromobenzoyl)-N-[(2R)-2-hydroxy-2-[(3S)-7-hydroxy-1,2,3,4-tetrahydroisoquinolin-3-yl]ethyl]-3,4-dihydro-1H-isoquinoline-6-carboxamide (0.075 g, 127.79 µmol, 61.86% yield, HCl) which was used in the next step without further purification. ¹H NMR (DMSO-d₆, 400 MHz) δ: 3.01 (m, 4H), 4.13 (m, 4H), 4.33 (m, 2H), 4.80 (m, 2H), 5.90 (m, 1H), 6.59 (s, 1H), 6.71 (d, 1H), 7.07 (d, 1H), 7.42 (m, 2H), 7.69 (m, 2H), 8.64 (m, 1H), 8.69 (m, 1H), 9.23 (m, 1H), 9.45 (m, 1H). LCMS (ESI): [M+3H]⁺ m/z: calc'd 549.1; found 552.2; Rt=2.74 min.

Step 3: Synthesis of (S)-tert-butyl 3-((R)-2-(2-(4-bromobenzoyl)-1,2,3,4-tetrahydroisoquinoline-6-carboxamido)-1-hydroxyethyl)-7-hydroxy-3,4-dihydroisoquinoline-2(1H)-carboxylate 2-(4-Bromobenzoyl)-N-[(2R)-2-hydroxy-2-[(3S)-7-hydroxy-1,2,3,4-tetrahydroisoquinolin-3-yl]-ethyl]-3,4-dihydro-1H-isoquinoline-6-carboxamide (0.075 g, 127.79 µmol, HCl) was dissolved in the mixture of water (1 mL) and THF (1 mL) then sodium hydrogen carbonate, 99% (32.21 mg, 383.37 µmol, 14.91 µL) was added in one portion, after that solution of di-tert-butyl dicarbonate (27.89 mg, 127.79 µmol, 29.33 µL) in THF (0.2 mL) was added dropwise. The reaction mixture was stirred overnight at room temperature. Ethyl acetate (15 mL) was added to the reaction mixture, organic phase was separated, and the aqueous phase was extracted with ethyl acetate (2*15 mL). The organic phase was washed with brine, dried over Na₂SO₄, filtered off and evaporated in vacuo at 40° C. to give tert-butyl (3S)-3-[(1R)-2-[[2-(4-bromobenzoyl)-3,4-dihydro-1H-isoquinoline-6-carbonyl]amino]-1-hydroxy-ethyl]-7-hydroxy-3,4-dihydro-1H-isoquinoline-2-carboxylate (0.081 g, 124.51 μmol, 97.43% yield) which was used in the next step without purification. ¹H NMR (CD₃OD, 500 MHz) δ: 1.50 (m, 9H), 2.86 (m, 2H), 3.00 (m, 4H), 3.67 (m, 4H), 3.98 (m, 2H), 4.28 (m, 2H), 4.64 (m, 1H), 6.57 (s, 1H), 6.63 (d, 1H), 7.00 (m, 2H), 7.41 (m, 2H), 7.66 (m, 4H). LCMS (ESI): [M+H]⁺ m/z: calc'd 649.2; found 651.2; Rt=1.43 min.

Step 4: Synthesis of (S)-tert-butyl 3-((R)-2-(2-(4-bromobenzoyl)-1,2,3,4-tetrahydroisoquinoline-6-carboxamido)-1-hydroxyethyl)-7-((4-methyloxazol-5-yl)methoxy)-3,4-dihydroisoquinoline-2(1H)-carboxylate tert-Butyl (3S)-3-[(1R)-2-[[2-(4-bromobenzoyl)-3,4-dihydro-1H-isoquinoline-6-carbonyl]amino]-1-hydroxy-ethyl]-7-hydroxy-3,4-dihydro-1H-isoquinoline-2-carboxylate (0.081 g, 124.51 μmol), 5-(chloromethyl)-4-methyl-oxazole (25.10 mg, 149.41 μmol, HCl) and cesium carbonate (121.70 mg, 373.53 μmol) was dissolved in DMF (2 mL) and heated at 50° C. overnight. The reaction mixture was diluted with water end extracted three times with EA, then EA was extracted three times with brine. The combined organic phase was dried over Na₂SO₄, filtered off and evaporated at 40° C. to give tert-butyl (3S)-3-[(1R)-2-[[2-(4-bromobenzoyl)-3,4-dihydro-1H-isoquinoline-6-carbonyl]amino]-1-hydroxy-ethyl]-7-[(4-methyl-oxazol-5-yl)methoxy]-3,4-dihydro-1H-isoquinoline-2-carboxylate (0.09 g, 120.70 μmol, 96.94% yield) which was used in the next step without further purification. ¹H NMR (CDCl₃, 400 MHz) δ:1.59 (m, 9H), 2.21 (m, 3H), 3.50 (m, 6H), 3.63 (m, 2H), 4.00 (m, 2H), 4.89 (m, 6H), 6.68 (s, 1H), 6.83 (d, 1H), 7.1 (d, 1H), 7.56 (m, 2H), 7.73 (m, 2H), 7.80 (m, 2H), 7.99 (m, 2H). LCMS (ESI): [M-Boc]⁺ m/z: calc'd 644.2; found 645.2; Rt=4.41 min.

Step 5: Synthesis of 2-(4-bromobenzoyl)-N—((R)-2-hydroxy-2-((S)-7-((4-methyloxazol-5-yl)methoxy)-1,2,3,4-tetrahydroisoquinolin-3-yl)ethyl)-1,2,3,4-tetrahydroisoquinoline-6-carboxamide (Compound 20) tert-Butyl (3S)-3-[(1R)-2-[[2-(4-bromobenzoyl)-3,4-dihydro-1H-isoquinoline-6-carbonyl]amino]-1-hydroxy-ethyl]-7-[(4-methyloxazol-5-yl)methoxy]-3,4-dihydro-1H-isoquinoline-2-carboxylate (0.09 g, 120.70 μmol) was dissolved in the mixture of Et₂O (1 mL) and MeOH (0.2 mL). Hydrogen chloride solution 4.0M in dioxane (330.06 mg, 9.05 mmol, 412.57 μL) was added. The mixture was stirred for 2 h at 20° C. The solvent was removed in vacuo at 45° C. The residue was dissolved in 5 mL of methanol and 15 mg of scavenger (SiliaMetS© Dimercaptotriazine(DMT) was added thereto and the resulting suspension was stirred for 12 h. The suspension was filtered off, the filtrate was evaporated under reduced pressure and the residue was purified by HPLC (25-60% water-methanol, 10 min, flow 30 mL/min (loading pump 4 mL/min methanol), column: SunFire C18 100*19 mm to give 2-(4-bromobenzoyl)-N-[(2R)-2-hydroxy-2-[(3S)-7-[(4-methyloxazol-5-yl)methoxy]-1,2,3,4-tetrahydroisoquinolin-3-yl]ethyl]-3,4-dihydro-1H-isoquinoline-6-carboxamide (0.026 g, 36.19 μmol, 29.98% yield, 2HCl). ¹H NMR (Methanol-d₄, 400 MHz): δ (ppm) 2.24 (s, 3H), 2.97 (m, 2H), 3.17 (m, 2H), 3.60 (m, 4H), 3.95 (m, 1H), 4.27 (m, 1H), 4.34 (m, 1H), 4.45 (m, 1H), 4.65 (m, 1H), 4.82 (m, 1H), 5.12 (s, 2H), 6.88 (s, 1H), 6.96 (d, 1H), 7.06 (s, 1H), 7.22 (d, 1H), 7.38 (m, 3H), 7.64 (d, 2H), 7.71 (s, 2H), 8.49 (s, 1H). LCMS (ESI): [M+H]+ m/z: calc'd 644.2; found 645.2; Rt=1.08 min.

Example 9A2. Synthesis of N—((R)-2-hydroxy-2-((S)-7-((4-methyloxazol-5-yl)methoxy)-1,2,3,4-tetrahydroisoquinolin-3-yl)ethyl)-2-(4-methoxybenzoyl)-1,2,3,4-tetrahydroisoquinoline-6-carboxamide (Compound 21)

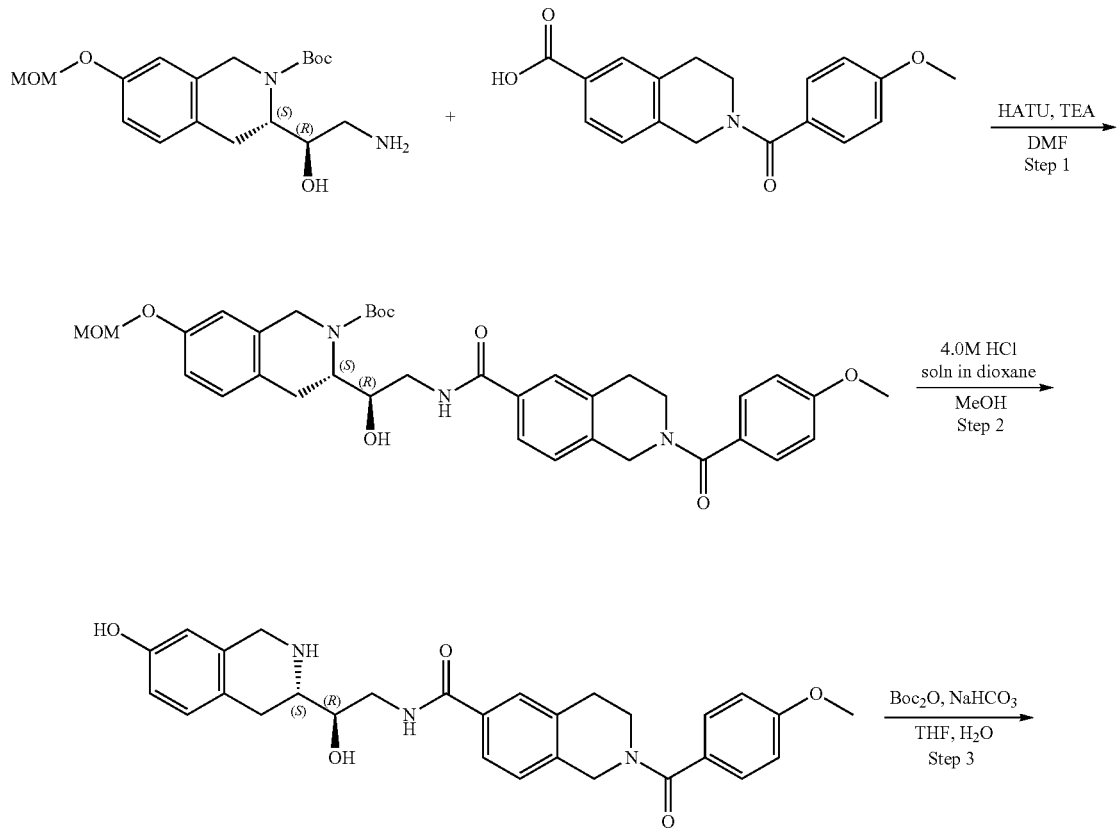

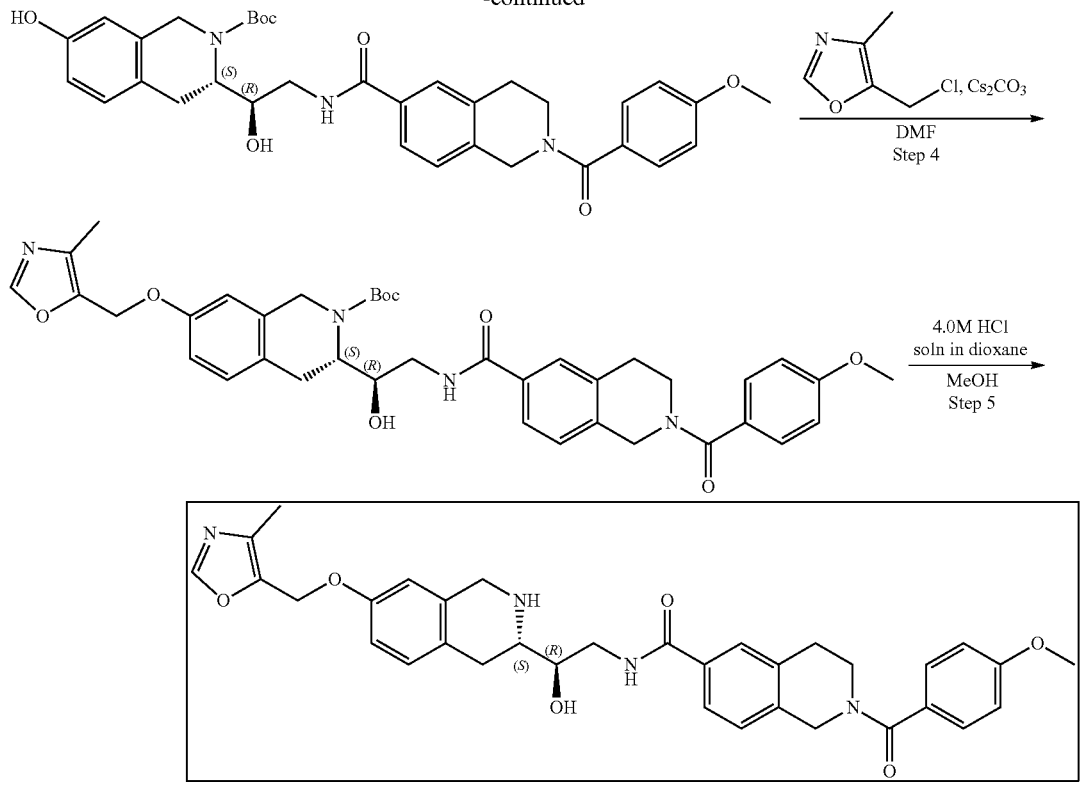

Step 1: Synthesis of (S)-tert-butyl 3-((R)-1-hydroxy-2-(2-(4-methoxybenzoyl)-1,2,3,4-tetrahydroisoquinoline-6-carboxamido)ethyl)-7-(methoxymethoxy)-3,4-dihydroisoquinoline-2(1H)-carboxylate 2-(4-Methoxybenzoyl)-3,4-dihydro-1H-isoquinoline-6-carboxylic acid (132.51 mg, 425.62 μmol) and triethylamine (430.69 mg, 4.26 mmol, 593.23 μL) were dissolved in DMF (3 mL) and cooled to 0° C. HATU (242.75 mg, 638.44 μmol) was added and the mixture was stirred for 15 min at 0° C. After that, tert-butyl (3S)-3-[(1R)-2-amino-1-hydroxy-ethyl]-7-(methoxymethoxy)-3,4-dihydro-1H-isoquinoline-2-carboxylate (150 mg, 425.62 μmol) was added and resulting mixture was allowed to warm to rt and stirred overnight. 50 mL of EtOAc was added and organic phase was washed with brine three times. The combined organic phase was dried over Na$_2$SO$_4$ and concentrated in vacuo at 45° C. The obtained crude material was purified by HPLC (35-45% water-methanol, 2-10 min, flow: 30 mL/min) to afford tert-butyl (3S)-3-[(1R)-1-hydroxy-2-[[2-(4-methoxybenzoyl)-3,4-dihydro-1H-isoquinoline-6-carbonyl]amino]ethyl]-7-(methoxy-methoxy)-3,4-dihydro-TH-isoquinoline-2-carboxylate (154 mg, 238.49 μmol, 56.03% yield). $^1$H NMR (CDCl$_3$, 400 MHz) δ:1.48 (s, 9H), 2.86 (m, 4H), 3.10 (m, 1H), 3.52 (m, 5H), 3.82 (m, 5H), 4.08 (m, 2H), 4.41 (m, 1H), 4.63 (m, 1H), 4.79 (m, 2H), 5.15 (s, 2H), 6.46 (s, 1H), 6.63 (m, 3H), 7.08 (m, 1H), 7.52 (m, 2H), 7.86 (m, 2H), 7.99 (m, 1H). LCMS (ESI): [M-Boc]$^+$ m/z: calc'd 545.3; found 546.2; Rt=1.44 min.

Step 2: Synthesis of N—((R)-2-hydroxy-2-((S)-7-hydroxy-1,2,3,4-tetrahydroisoquinolin-3-yl)ethyl)-2-(4-methoxybenzoyl)-1,2,3,4-tetrahydroisoquinoline-6-carboxamide A solution of tert-butyl (3S)-3-[(1R)-1-hydroxy-2-[[2-(4-methoxybenzoyl)-3,4-dihydro-TH-iso-quinoline-6-carbonyl]amino]ethyl]-7-(methoxymethoxy)-3,4-dihydro-1H-isoquinoline-2-carboxylate (154 mg, 238.49 μmol) in methanol (2 mL) and dioxane/HCl (2 mL) was stirred for 10 h at 25° C. Then, the solution was evaporated to obtain N-[(2R)-2-hydroxy-2-[(3S)-7-hydroxy-1,2,3,4-tetrahydroisoquinolin-3-yl]ethyl]-2-(4-methoxybenzoyl)-3,4-dihydro-1H-isoquinoline-6-carboxamide (52 mg, 96.65 μmol, 40.53% yield, HCl). $^1$H NMR (DMSO-d$_6$, 500 MHz) δ:1.17 (m, 4H), 4.10 (m, 4H), 4.32 (m, 2H), 4.72 (m, 4H), 5.64 (m, 3H), 5.87 (m, 1H), 6.57 (m, 2H), 6.69 (m, 1H), 6.99 (m, 1H), 7.34 (m, 1H), 7.41 (m, 1H), 7.67 (m, 1H), 8.58 (m, 1H), 8.84 (m, 1H), 9.13 (m, 1H), 9.39 (m, 1H). LCMS (ESI): [M+H]$^+$ m/z: calc'd 501.2; found 502.3; Rt=0.97 min.

Step 3: Synthesis of (S)-tert-butyl 7-hydroxy-3-((R)-1-hydroxy-2-(2-(4-methoxybenzoyl)-1,2,3,4-tetrahydroisoquinoline-6-carboxamido)ethyl)-3,4-dihydroisoquinoline-2(1H)-carboxylate. To a stirred solution of Sodium hydrogen carbonate, 99% (24.36 mg, 289.94 μmol, 11.28 μL) in water (1 mL), N-[(2R)-2-hydroxy-2-[(3S)-7-hydroxy-1,2,3,4-tetrahydroisoquinolin-3-yl]ethyl]-2-(4-methoxybenzoyl)-3,4-dihydro-1H-isoquinoline-6-carboxamide (52 mg, 96.65 μmol, HCl) was added in THF (1 mL) followed by di-tert-butyl dicarbonate (21.09 mg, 96.65 μmol, 22.18 μL) in THF (1 mL). The resulting mixture was stirred at 25° C. for 12 h. EtOAc (10 mL) was added and organic phase was separated and washed with brine (2*5 mL). Then, the solvent was dried over sodium sulfate, filtered off and evaporated to obtain tert-butyl (3S)-7-hydroxy-3-[(1R)-1-hydroxy-2-[[2-(4-methoxybenzoyl)-3,4-dihydro-1H-isoquinoline-6-carbonyl]amino]ethyl]-3,4-dihydro-1H-isoquinoline-2-carboxylate (42 mg, 69.80 μmol, 72.22% yield). $^1$H NMR (CDCl$_3$, 500 MHz) δ: 1.56 (m, 12H), 2.93 (m, 3H), 3.16 (m, 1H), 3.52 (m, 2H), 3.73 (m, 2H), 3.86 (s, 3H), 4.17 (m, 2H), 4.34 (m, 2H), 4.84 (m, 2H), 6.00 (s, 1H), 6.68 (d, 1H), 6.96 (d, 1H), 7.08 (d, 1H), 7.45 (m, 2H), 7.70 (s, 1H), 7.76 (s, 1H), 7.96 (m, 1H). LCMS (ESI): [M-Boc]+ m/z: calc'd 501.3; found 502.4; Rt=1.33 min.

Step 4: Synthesis of (S)-tert-butyl 3-((R)-1-hydroxy-2-(2-(4-methoxybenzoyl)-1,2,3,4-tetrahydroisoquinoline-6-carboxamido)ethyl)-7-((4-methyloxazol-5-yl)methoxy)-3,4-dihydroisoquinoline-2(1H)-carboxylate To the solution of tert-butyl (3S)-7-hydroxy-3-[(1R)-1-hydroxy-2-[[2-(4-methoxybenzoyl)-3,4-di-hydro-1H-isoquinoline-6-carbonyl]amino]ethyl]-3,4-dihydro-1H-isoquinoline-2-carboxylate (42 mg, 69.80 μmol), cesium carbonate (68.23 mg, 209.41 μmol) in DMF (2 mL) was added 5-(chloromethyl)-4-methyl-oxazole (14.07 mg, 83.76 μmol, HCl). The resulting mixture was heated at 50° C. for 12 h. The mixture was filtered off and evaporated to obtain tert-butyl (3S)-3-[(1R)-1-hydroxy-2-[[2-(4-methoxybenzoyl)-3,4-dihydro-1H-isoquinoline-6-carbonyl]amino]ethyl]-7-[(4-methyloxazol-5-yl)methoxy]-3,4-dihydro-1H-iso-quinoline-2-carboxylate (46 mg, crude) that was used in the next step without further purification. ¹H NMR (CDCl₃, 500 MHz) δ:1.23 (m, 4H), 1.56 (m, 4H), 1.65 (m, 9H), 2.24 (m, 4H), 3.14 (m, 3H), 3.53 (m, 3H), 3.76 (m, 2H), 3.86 (m, 4H), 4.19 (m, 2H), 4.39 (m, 1H), 4.68 (m, 2H), 4.85 (m, 2H), 5.00 (s, 2H), 6.71 (s, 1H), 6.84 (d, 1H), 6.95 (d, 2H), 7.15 (d, 1H), 7.43 (m, 2H), 7.72 (d, 1H), 7.75 (s, 1H), 7.83 (s, 1H), 8.03 (m, 2H). LCMS (ESI): [M-Boc]+ m/z: calc'd 596.3; found 597.2; Rt=1.44 min.

Step 5: Synthesis of N—((R)-2-hydroxy-2-((S)-7-((4-methyloxazol-5-yl)methoxy)-1,2,3,4-tetrahydroisoquinolin-3-yl)ethyl)-2-(4-methoxybenzoyl)-1,2,3,4-tetrahydroisoquinoline-6-carboxamide (Compound 21) A solution of tert-butyl (3S)-3-[(1R)-1-hydroxy-2-[[2-(4-methoxybenzoyl)-3,4-dihydro-1H-iso-quinoline-6-carbonyl]amino]ethyl]-7-[(4-methyloxazol-5-yl)methoxy]-3,4-dihydro-1H-isoquinoline-2-carboxylate (46 mg, 66.02 μmol) in dioxane/HCl (1 mL) and methanol (1 mL) was stirred for 3 h at 25° C. Then, the solution was evaporated and the resulting crude product was purified by HPLC (25-60% water-methanol, 10 min, flow: 30 mL/min) to obtain N-[(2R)-2-hydroxy-2-[(3S)-7-[(4-methyloxazol-5-yl)methoxy]-1,2,3,4-tetrahydroisoquinolin-3-yl]ethyl]-2-(4-methoxybenzoyl)-3,4-dihydro-1H-isoquinoline-6-carboxamide (17.9 mg, 28.27 μmol, 42.83% yield, HCl). ¹H NMR (Methanol-d₄, 400 MHz): δ (ppm) 2.23 (s, 3H), 2.66 (m, 2H), 2.97 (m, 2H), 3.19 (m, 2H), 3.61 (m, 3H), 3.74 (m, 1H), 3.84 (s, 3H), 3.97 (m, 1H), 4.25 (m, 1H), 4.33 (m, 1H), 4.44 (m, 1H), 4.80 (m, 1H), 5.11 (s, 2H), 6.87 (s, 1H), 6.96 (d, 1H), 7.01 (d, 2H), 7.22 (m, 2H), 7.43 (d, 2H), 7.71 (s, 2H), 8.41 (s, 1H). LCMS (ESI): [M+H]+ m/z: calc'd 596.2; found 597.2; Rt=1.01 min.

Example 9A3. Synthesis of N-[(2R)-2-hydroxy-2-[(3S)-7-(oxazol-5-ylmethoxy)-1,2,3,4-tetrahydroisoquinolin-3-yl]ethyl]-2-(4-methoxybenzoyl)-3,4-dihydro-1H-isoquinoline-6-carboxamide (Compound 74)

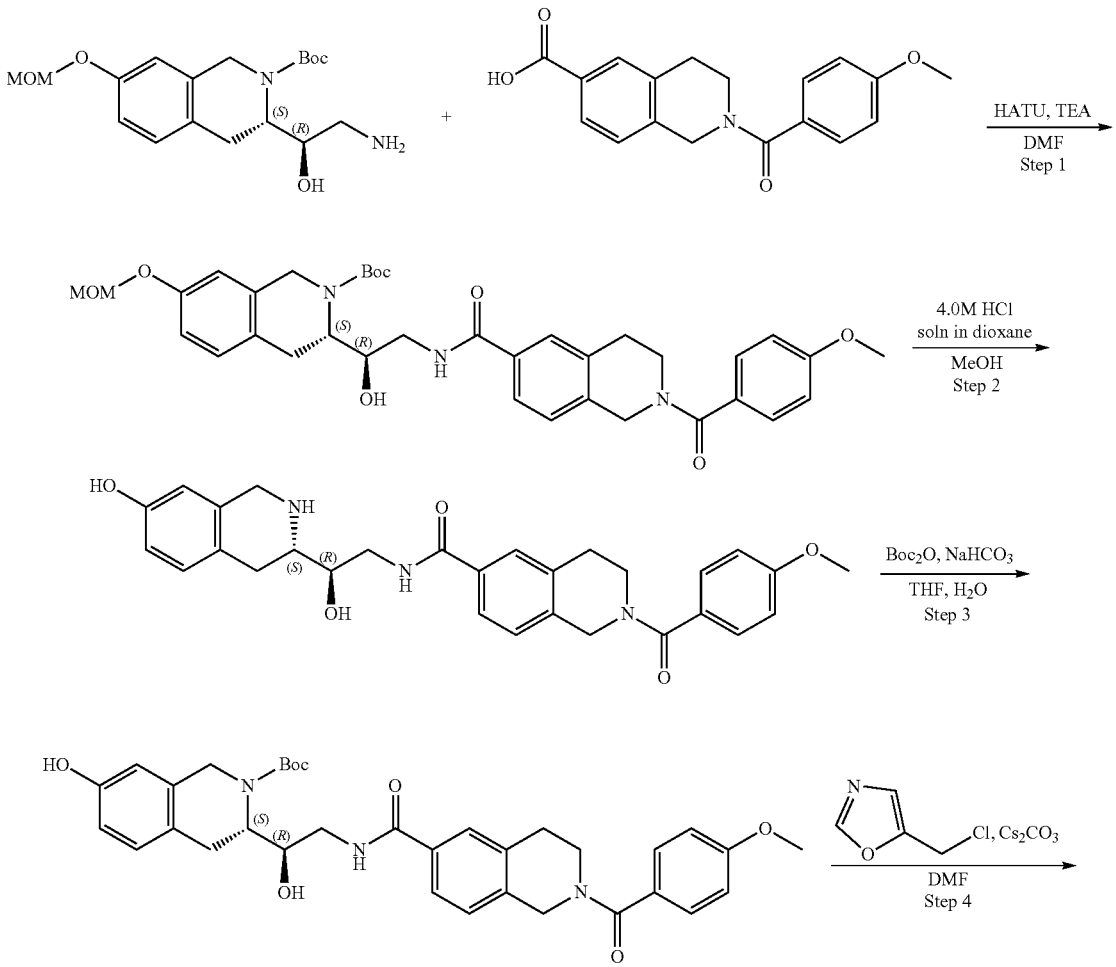

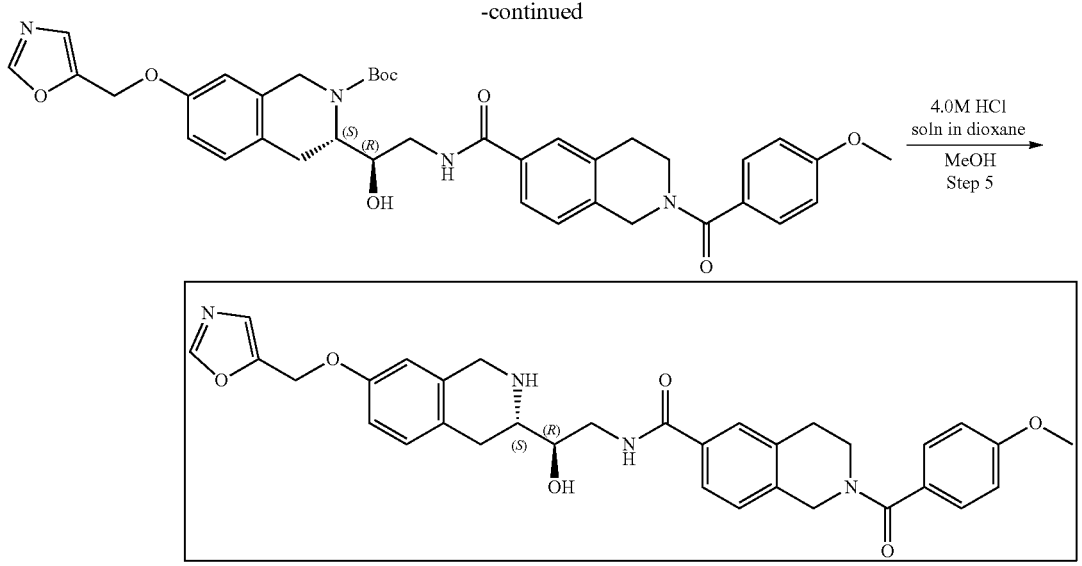

Step 1: Synthesis of tert-butyl (3S)-3-[(1R)-1-hydroxy-2-[[2-(4-methoxybenzoyl)-3,4-dihydro-1H-isoquinoline-6-carbonyl]amino]ethyl]-7-(methoxymethoxy)-3,4-dihydro-]H-isoquinoline-2-carboxylate tert-Butyl (3S)-3-[(1R)-2-amino-1-hydroxy-ethyl]-7-(methoxymethoxy)-3,4-dihydro-1H-iso-quinoline-2-carboxylate (0.23 g, 652.62 μmol), 2-(4-methoxybenzoyl)-3,4-dihydro-1H-isoquinoline-6-carboxylic acid (203.18 mg, 652.62 μmol) and HATU (372.22 mg, 978.93 μmol) was dissolved in DMF (5 mL) and stirred at 20° C. for 3 hr. The reaction mixture was diluted with water end extracted three times with EtOAc, then EtOAc was extracted three times with brine. The organic phase was dried over Na₂SO₄, filtered off and evaporated at 40° C. to give crude product which was purified by HPLC (30-40% water-acetonitrile, 10 min, flow 30 mL/min (loading pump 4 mL/min acetonitrile) column: SunFire C18 100*19 mm) to give tert-butyl (3S)-3-[(1R)-1-hydroxy-2-[[2-(4-methoxybenzoyl)-3,4-dihydro-1H-iso-quinoline-6-carbonyl]-amino]ethyl]-7-(methoxymethoxy)-3,4-dihydro-1H-isoquinoline-2-carboxylate (0.206 g, 319.01 μmol, 48.88% yield). LCMS (ESI): [M-Boc]⁺ m/z: calc'd 545.3; found 546.2; Rt=1.48 min.

Step 2: Synthesis of N-[(2R)-2-hydroxy-2-[(3S)-7-hydroxy-1, 2, 3,4-tetrahydroisoquinolin-3-yl]ethyl]-2-(4-methoxybenzoyl)-3,4-dihydro-1H-isoquinoline-6-carboxamide tert-Butyl (3S)-3-[(1R)-1-hydroxy-2-[[2-(4-methoxybenzoyl)-3,4-dihydro-1H-isoquinoline-6-carbonyl]amino]ethyl]-7-(methoxymethoxy)-3,4-dihydro-1H-isoquinoline-2-carboxylate (0.206 g, 319.01 μmol) was dissolved in MeOH (3 mL) and hydrogen chloride solution 4.0M in dioxane (872.36 mg, 23.93 mmol, 1.09 mL) was added. The reaction mixture was stirred for 3 hr at 25° C. After the completion of the reaction, the solvent was removed in vacuo at 35° C. to give N-[(2R)-2-hydroxy-2-[(3S)-7-hydroxy-1,2,3,4-tetrahydroisoquinolin-3-yl]ethyl]-2-(4-methoxybenzoyl)-3,4-dihydro-1H-isoquinoline-6-carboxamide (0.166 g, 308.53 μmol, 96.71% yield, HCl) which was used in the next step without further purification. LCMS (ESI): [M+H]⁺ m/z: calc'd 501.2; found 502.2; Rt=2.73 min.

Step 3: Synthesis of (S)-tert-butyl 7-hydroxy-3-((R)-1-hydroxy-2-(2-(4-methoxybenzoyl)-1,2,3,4-tetrahydroiso-quinoline-6-carboxamido)ethyl)-3,4-dihydroisoquinoline-2 (1H)-carboxylate N-[(2R)-2-Hydroxy-2-[(3S)-7-hydroxy-1, 2,3,4-tetrahydroisoquinolin-3-yl]ethyl]-2-(4-methoxybenzoyl)-3,4-dihydro-1H-isoquinoline-6-carboxamide (0.166 g, 308.53 μmol, HCl) was dissolved in the mixture of water (2 mL) and THF (2 mL) then sodium hydrogen carbonate, 99% (77.76 mg, 925.59 μmol, 36.00 μL) was added in one portion. The resulting mixture was stirred for 5 min at room temperature followed by the dropwise addition of the solution of di-tert-butyl dicarbonate (67.34 mg, 308.53 μmol, 70.81 μL) in THF (0.2 mL). The reaction mixture was stirred for 4 hr at room temperature. After the completion of the reaction, Ethyl acetate (15 mL) was added to the reaction mixture, the organic phase was separated, and the aqueous phase was extracted with ethyl acetate (2*15 mL). The organic phase was washed with brine, dried over Na₂SO₄, filtered off and evaporated in vacuo at 40° C. to give product (0.17 g, 282.54 μmol, 91.58% yield) which was used in the next step without purification. LCMS (ESI): [M-Boc]⁺ m/z: calc'd 501.2; found 502.2; Rt=3.55 min.

Step 4: Synthesis of tert-butyl (3S)-3-[(1R)-1-hydroxy-2-[[2-(4-methoxybenzoyl)-3,4-dihydro-1H-isoquinoline-6-carbonyl]amino]ethyl]-7-(oxazol-5-ylmethoxy)-3,4-dihydro-1H-isoquinoline-2-carboxylate tert-Butyl (3S)-7-hydroxy-3-[(1R)-1-hydroxy-2-[[2-(4-methoxybenzoyl)-3,4-dihydro-1H-isoquinoline-6-carbonyl]amino]ethyl]-3,4-dihydro-1H-isoquinoline-2-carboxylate (0.085 g, 141.27 μmol), 5-(chloromethyl)oxazole (30.46 mg, 197.78 μmol, HCl) and cesium carbonate (184.11 mg, 565.08 μmol) were dissolved in DMF (2 mL) and stirred at 50° C. overnight. The reaction mixture was filtered off and washed with DMF (2 mL). The filtrate was concentrated in vacuo at 60° C. to give tert-butyl (3S)-3-[(1R)-1-hydroxy-2-[[2-(4-methoxybenzoyl)-3,4-dihydro-1H-isoquinoline-6-carbonyl]amino]ethyl]-7-(oxazol-5-ylmethoxy)-3,4-dihydro-1H-isoquinoline-2-carboxylate (0.091 g, 133.28 μmol, 94.35% yield) which was used in the next step without further purification. LCMS (ESI): [M-Boc]⁺ m/z: calc'd 582.3; found 583.2; Rt=3.84 min.

Step 5: Synthesis of N-[(2R)-2-hydroxy-2-[(3S)-7-(oxazol-5-ylmethoxy)-1,2,3,4-tetrahydro-isoquinolin-3-yl] ethyl]-2-(4-methoxybenzoyl)-3,4-dihydro-1H-isoquinoline-6-carboxamide (Compound 74) tert-Butyl (3S)-3-[(1R)-1-hydroxy-2-[[2-(4-methoxybenzoyl)-3,4-dihydro-1H- isoquinoline-6-carbonyl]amino]ethyl]-7-(oxazol-5-ylmethoxy)-3,4-dihydro-1H-isoquinoline-2-carboxylate (0.091 g, 133.28 µmol) was dissolved in MeOH (3 mL) and hydrogen chloride solution 4.0M in dioxane (364.47 mg, 10.00 mmol, 455.59 µL) was added. The resulting mixture was stirred for 4 hr at 20° C. After the completion of the reaction, the solvent was removed in vacuo at 45° C. The residue was dissolved in 5 mL of methanol and 12 mg of scavenger (SiliaMetS© Dimercaptotriazine(DMT)) was added. The resulting suspension was stirred for 12 h. The resulting suspension was filtered off, the filtrate was evaporated under reduced pressure and the residue was purified by HPLC (60-100% water+NH$_3$-methanol+NH$_3$, 2-7 min, flow 30 mL/min (loading pump 4 mL/min methanol+NH$_3$), column: YMC-Actus Triart C18 100*20 mm) to give N-[(2R)-2-hydroxy-2-[(3S)-7-(oxazol-5-ylmethoxy)-1,2,3,4-tetrahydroisoquinolin-3-yl]ethyl]-2-(4-methoxybenzoyl)-3,4-dihydro-1H-isoquinoline-6-carboxamide (0.0128 g, 21.97 µmol, 16.48% yield). $^1$H NMR (400 MHz, CDCl$_3$) δ 2.70 (m, 1H), 2.80 (m, 1H), 2.93 (m, 2H), 3.01 (m, 1H), 3.56 (m, 1H), 3.77 (m, 2H), 3.83 (m, 5H), 3.93 (m, 1H), 4.00 (s, 2H), 4.80 (m, 2H), 5.02 (s, 2H), 6.61 (m, 1H), 6.77 (m, 1H), 6.92 (d, 2H), 6.98 (m, 1H), 7.04 (d, 1H), 7.12 (s, 1H), 7.41 (d, 2H), 7.56 (d, 1H), 7.62 (s, 1H), 7.88 (s, 1H). LCMS (ESI): [M+H]$^+$ m/z: calc'd 582.2; found 583.2; Rt=1.00 min.

Example 9A4. Synthesis of N-[(2R)-2-hydroxy-2-[(3S)-7-[(2-methylpyrazol-3-yl)methoxy]-1,2,3,4-tetrahydroisoquinolin-3-yl]ethyl]-2-(4-methoxybenzoyl)-3,4-dihydro-1H-isoquinoline-6-carboxamide (Compound 77)

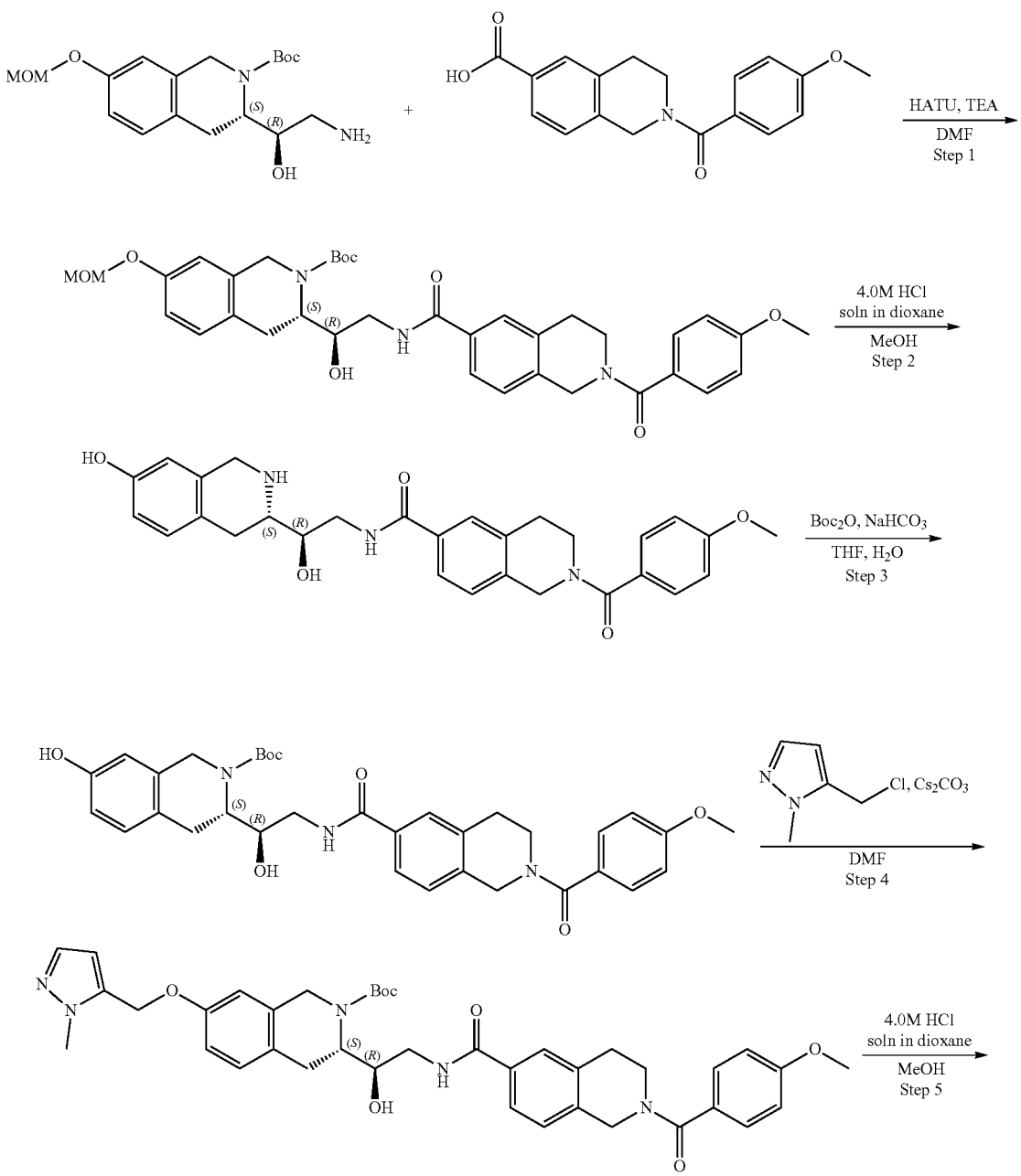

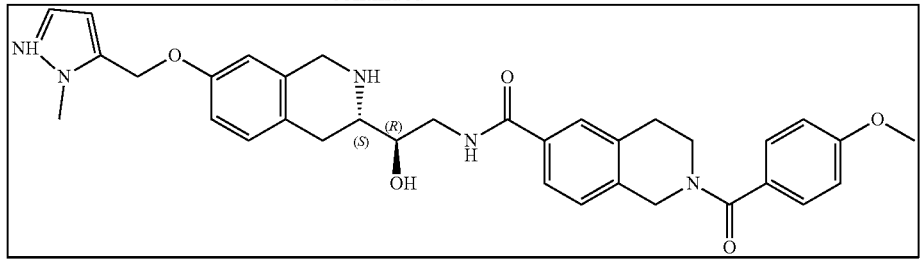

Step 1: Synthesis of tert-butyl (3S)-3-[(1R)-1-hydroxy-2-[[2-(4-methoxybenzoyl)-3,4-dihydro-1H-isoquinoline-6-carbonyl]amino]ethyl]-7-(methoxymethoxy)-3,4-dihydro-1H-isoquinoline-2-carboxylate tert-Butyl (3S)-3-[(1R)-2-amino-1-hydroxy-ethyl]-7-(methoxymethoxy)-3,4-dihydro-1H-isoquinoline-2-carboxylate (0.23 g, 652.62 µmol), 2-(4-methoxybenzoyl)-3,4-dihydro-1H-isoquinoline-6-carboxylic acid (203.18 mg, 652.62 µmol) and HATU (372.22 mg, 978.93 µmol) was dissolved in DMF (5 mL) and stirred at 20° C. for 3 hr. The reaction mixture was diluted with water end extracted three times with EtOAc, then EtOAc was extracted three times with brine. The organic phase was dried over Na$_2$SO$_4$, filtered off and evaporated at 40° C. to give crude product which was purified by HPLC (30-40% water-acetonitrile, 10 min, flow 30 mL/min (loading pump 4 mL/min acetonitrile) column: SunFire C18 100*19 mm) to give tert-butyl (3S)-3-[(1R)-1-hydroxy-2-[[2-(4-methoxybenzoyl)-3,4-dihydro-1H-isoquinoline-6-carbonyl]-amino]ethyl]-7-(methoxymethoxy)-3,4-dihydro-1H-isoquinoline-2-carboxylate (0.206 g, 319.01 µmol, 48.88% yield). LCMS (ESI): [M-Boc]$^+$ m/z: calc'd 545.3; found 546.2; Rt=1.48 min.

Step 2: Synthesis of N-[(2R)-2-hydroxy-2-[(3S)-7-hydroxy-1, 2, 3,4-tetrahydroisoquinolin-3-yl]ethyl]-2-(4-methoxybenzoyl)-3,4-dihydro-1H-isoquinoline-6-carboxamide tert-Butyl (3S)-3-[(1R)-1-hydroxy-2-[[2-(4-methoxybenzoyl)-3,4-dihydro-1H-isoquinoline-6-carbonyl]amino]ethyl]-7-(methoxymethoxy)-3,4-dihydro-1H-isoquinoline-2-carboxylate (0.206 g, 319.01 µmol) was dissolved in MeOH (3 mL) and hydrogen chloride solution 4.0M in dioxane (872.36 mg, 23.93 mmol, 1.09 mL) was added. The resulting mixture was stirred for 3 hr at 25° C. After the completion of the reaction, the solvent was removed in vacuo at 35° C. to give N-[(2R)-2-hydroxy-2-[(3S)-7-hydroxy-1,2,3,4-tetrahydroisoquinolin-3-yl]ethyl]-2-(4-methoxybenzoyl)-3,4-dihydro-1H-isoquinoline-6-carboxamide (0.166 g, 308.53 µmol, 96.71% yield, HCl) which was used in the next step without further purification. LCMS (ESI): [M+H]$^+$ m/z: calc'd 501.2; found 502.2; Rt=2.73 min.

Step 3: Synthesis of (S)-tert-butyl 7-hydroxy-3-((R)-1-hydroxy-2-(2-(4-methoxybenzoyl)-1,2,3,4-tetrahydroisoquinoline-6-carboxamido)ethyl)-3,4-dihydroisoquinoline-2(1H)-carboxylate N-[(2R)-2-Hydroxy-2-[(3S)-7-hydroxy-1,2,3,4-tetrahydroisoquinolin-3-yl]ethyl]-2-(4-methoxybenzoyl)-3,4-dihydro-1H-isoquinoline-6-carboxamide (0.166 g, 308.53 µmol, HCl) was dissolved in the mixture of water (2 mL) and THF (2 mL) then sodium hydrogen carbonate, 99% (77.76 mg, 925.59 µmol, 36.00 µL) was added in one portion. The resulting mixture was stirred for 5 min at room temperature followed by the dropwise addition of the solution of di-tert-butyl dicarbonate (67.34 mg, 308.53 µmol, 70.81 µL) in THF (0.2 mL). The reaction mixture was stirred for 4 hr at room temperature. After the completion of the reaction, ethyl acetate (15 mL) was added to the reaction mixture, the organic phase was separated, and the aqueous phase was extracted with ethyl acetate (2*15 mL). The organic phase was washed with brine, dried over Na$_2$SO$_4$, filtered off and evaporated in vacuo at 40° C. to give product (0.17 g, 282.54 µmol, 91.58% yield) which was used in the next step without purification. LCMS (ESI): [M-Boc]$^+$ m/z: calc'd 501.2; found 502.2; Rt=3.55 min.

Step 4: Synthesis of tert-butyl (3S)-3-[(1R)-1-hydroxy-2-[[2-(4-methoxybenzoyl)-3,4-dihydro-1H-isoquinoline-6-carbonyl]amino]ethyl]-7-[(2-methylpyrazol-3-yl)methoxy]-3,4-dihydro-1H-isoquinoline-2-carboxylate tert-Butyl (3S)-7-hydroxy-3-[(1R)-1-hydroxy-2-[[2-(4-methoxybenzoyl)-3,4-dihydro-1H-isoquinoline-6-carbonyl]amino]ethyl]-3,4-dihydro-1H-isoquinoline-2-carboxylate (0.085 g, 141.27 µmol), 5-(chloromethyl)-1-methyl-pyrazole (33.04 mg, 197.78 µmol, HCl) and cesium carbonate (184.11 mg, 565.08 µmol) were dissolved in DMF (2 mL) and stirred at 50° C. overnight. The reaction mixture was filtered off and washed with DMF (2 mL). The obtained filtrate was concentrated in vacuo at 60° C. to give tert-butyl (3S)-3-[(1R)-1-hydroxy-2-[[2-(4-methoxybenzoyl)-3,4-dihydro-1H-isoquinoline-6-carbonyl]amino]ethyl]-7-[(2-methylpyrazol-3-yl)methoxy]-3,4-dihydro-1H-isoquinoline-2-carboxylate (0.096 g, 137.97 µmol, 97.66% yield) which was used in the next step without further purification. LCMS (ESI): [M+H]$^+$ m/z: calc'd 595.3; found 596.3; Rt=1.02 min.

Step 5: Synthesis of N-[(2R)-2-hydroxy-2-[(3S)-7-[(2-methylpyrazol-3-yl)methoxy]-1,2,3,4-tetrahydroisoquinolin-3-yl]ethyl]-2-(4-methoxybenzoyl)-3,4-dihydro-1H-isoquinoline-6-carboxamide (Compound 77) tert-Butyl (3S)-3-[(1R)-1-hydroxy-2-[[2-(4-methoxybenzoyl)-3,4-dihydro-1H-isoquinoline-6-carbonyl]amino]ethyl]-7-[(2-methylpyrazol-3-yl)methoxy]-3,4-dihydro-1H-isoquinoline-2-carboxylate (0.096 g, 137.97 µmol) was dissolved in the mixture of MeOH (3 mL) and hydrogen chloride solution 4.0M in dioxane (377.29 mg, 10.35 mmol, 471.61 µL) was added. The resulting mixture was stirred for 4 hr at 20° C. After the completion of the reaction, the solvent was removed in vacuo at 45° C. The residue was dissolved in 5 mL of methanol and 12 mg of scavenger (SiliaMetS© Dimercaptotriazine(DMT)) was added. The resulting suspension was stirred for 12 h. The suspension was filtered off, the filtrate was evaporated under reduced pressure and the residue was purified by HPLC (60-100% water+NH$_3$-methanol+NH$_3$, 2-7 min, flow 30 mL/min (loading pump 4 mL/min methanol+NH$_3$), column: YMC-Actus Triart C18 100*20 mm) to give N-[(2R)-2-hydroxy-2-[(3S)-7-[(2-methylpyrazol-3-yl)methoxy]-1,2,3,4-tetrahydroisoquinolin-3-yl]ethyl]-2-(4-methoxybenzoyl)-3,4-dihydro-1H-isoquinoline-6-carboxamide (0.0074 g, 12.42 µmol, 9.00% yield). $^1$H NMR (400 MHz, CDCl$_3$) δ 2.70 (m, 1H), 2.81 (m, 1H), 2.92 (m, 2H), 2.99 (m, 1H), 3.56 (m, 1H), 3.67 (m, 2H), 3.83 (m, 6H), 3.88 (s, 3H), 3.94 (m, 1H), 3.99 (s, 2H), 4.79 (m, 2H), 4.98 (s, 2H), 6.27 (m, 1H), 6.61 (m, 1H), 6.76 (m, 1H), 6.91 (d, 2H), 7.03 (m, 1H), 7.07 (m, 1H), 7.13 (m, 1H), 7.41 (m, 3H), 7.56 (d, 1H), 7.61 (s, 1H). LCMS (ESI): [M+H]$^+$ m/z: calc'd 595.3; found 596.3; Rt=1.02 min.

Example 10. PRMT5 Cooperativity Assay

PRMT5 inhibitor potency and cooperativity in the absence and presence of cofactors SAM or MTA was assessed at equilibrium by measuring the dose dependent displacement of a fixed concentration of C-terminal 5'-TAMRA labeled peptide from Prmt5, utilizing fluorescent anisotropy as a signal. Two peptides were utilized for these studies:

```
                                              (SEQ ID NO: 1)
Me0:
Ac-SGRGKGGKGLGKGGAKRHRKV-K(5-TAMRA)-NH2; and (SEQ ID NO: 2)
Me2:
Ac-SGR(Sym Me2)GKGGKGLGKGGAKRHRKV-K(5-TAMRA)-NH2.
```

Peptide Me0 was used to determine the affinity of compounds in the absence of cofactor and in the presence of MTA as cofactor. Peptide Me2 was used to determine the affinity of compounds in the presence of SAM as cofactor.
Study Compounds and Reference Compounds:
  Study compounds are dissolved in DMSO starting with a stock concentration of 10 mM
  Reference compound 1: EPZ015666 (GSK3235025) (SelleckChem, cat #57748-5 mgs, 10 mM in DMSO)
  Reference compound 2: (S)-2-(cyclobutylamino)-N-(3-(8,9-dihydro-[1,3]dioxolo[4,5-f]isoquinolin-7(6H)-yl)-2-hydroxypropyl)isonicotinamide (Tango, 10 mM in DMSO)
Assay Conditions:
  Study compound and reference compound concentration: 3-fold serial dilution from 125 µM
  Each assay plate contains the above two reference compounds
  DMSO concentration in each well: 1.25% DMSO
  Compound IC$_{50}$ was determined in 3 assay conditions:
    1. 50 µM Cofactor SAM+25 nM Me2+100 nM PRMT5
    2. 50 µM Cofactor MTA+25 nM Me0+25 nM PRMT5
    3. No cofactor+25 nM Me0+100 nM PRMT5

Materials

| Reagents | Vendor |
| --- | --- |
| Bicine pH 8.0, 0.5M | Alfa Aesar, Cat# A14957 |
| Sodium Chloride, 5M | Sigma-Aldrich, Cat# S5150 |
| Tween-20, 10% | Sigma-Aldrich, Cat# 11332465001 |
| DL-Dithiothreitol or DTT, 0.5M in water | Sigma-Aldrich, Cat# 43816 |
| PRMT5: MEP50, 51 µM; Storage Buffer 50 mM Tris, 250 mM NaCl, 1 mM TCEP, pH 8.0 | Viva custom protein |
| Me0-PEP21, Unmethylated Peptide, 1.9 mM in water | Anaspec custom order |
| Me2-PEP21-sDMA, Dimethylated Peptide, 1.9 mM in water | Anaspec custom order |
| Dimethyl Sulfoxide | Sigma-Aldrich, Cat# D8418-1L |
| S-adenosyl methionine (SAM), 32 mM | CAYMAN CHEMICAL, Cat# 0461501-31 |
| methylthioadenosine (MTA), 25 mM | EMD Millipore, Cat# 260585 |

Preparation of Cofactor Solutions
  SAM was dissolved in distilled deionized water to make a 32 mM solution, which was stored at −20° C. and discarded after one freeze-thaw cycle
  MTA—was dissolved in distilled deionized water to make 2.5 mM stock solution. Gentle heating 37° C. for 1 minute was used as necessary to fully solubilize. The solution was stored at −20° C. and used over multiple freeze-thaw cycles Plates:

| Plate | Vendor | Application |
| --- | --- | --- |
| Greiner 384-well flat-bottom clear, polypropylene plates | Greiner, Cat#781201 or Cat#781280 | Compound dilution |
| ECHO LDV 384-well plate | Labcyte, Cat# LP-0200 | Compound dilution |
| Greiner 384-well Black, polypropylene plates | Greiner, Cat# 781076 | Assay plate |

Instrumentation:

| Instrument | Application |
| --- | --- |
| Echo (Labcyte # 555) | Compound dilution |
| Perkin Elmer Envision, Cat# 2104 | Plate reader, FP TAMRA, Ex540/Em590 |

Reagent Preparation:
Prepare Compound Dilution in Assay Plate:
  9 µL of 10 mM compound in DMSO was prepared
  A 10-point, 3-fold dilution, top working concentration at 125 µM was prepared as detailed in Table 2.
  4 copies of compound plate were generated for the four assay conditions

TABLE 2

| Point | Plate type | Source (mM) | Transfer (nL) | Backfill DMSO (nL) | Final Concentration (µM) |
| --- | --- | --- | --- | --- | --- |
| 1 | Source plate 1 | 10 | 187.5 | 0 | 1.250 |
| 2 | Source plate 1 | 10 | 62.5 | 125 | 416.7 |
| 3 | Inter plate 1 | 1.534 | 135 | 52.5 | 138.9 |
| 4 | Inter plate 1 | 1.534 | 45 | 142.5 | 46.3 |
| 5 | Inter plate 1 | 1.534 | 15 | 172.5 | 15.43 |
| 6 | Inter plate 1 | 1.534 | 5 | 182.5 | 5.144 |
| 7 | Inter plate 2 | 0.01905 | 135 | 52.5 | 1.715 |
| 8 | Inter plate 2 | 0.01905 | 45 | 142.5 | 0.5716 |
| 9 | Inter plate 2 | 0.01905 | 15 | 172.5 | 0.01905 |
| 10 | Inter plate 2 | 0.01905 | 5 | 182.5 | 0.006351 |

The compound concentration of source plate 1 is 10 mM
The compound concentration of Inter plate 1 is 1.534 mM, which is prepared by transferring 1.2 µL of 10 mM compound to 6.576 µL DMSO
The compound concentration of Inter plate 2 is 0.01905 mM, which is prepared by transferring 15 nL of 0.1 mM compound to 7.858 µL DMSO
187.5 nL of DMSO was dispensed in columns 1, 12, 13 & 24 for the control reaction, 187.5 nL of compound dilutions in columns 3 to 22 in the assay plate shown in table 3

TABLE 3

| | 1 | 2 | 3 | 4 | 5 | 6 | 7 | 8 | 9 | 10 | 11 | 12 |
|---|---|---|---|---|---|---|---|---|---|---|---|---|
| A | min control (100% Inh) | | | | cpd 1, 10 dose, 3-fold, top 125 uM | | | | | | | max control (100% Inh) |
| B | min control (100% Inh) | | | | cpd 2, 10 dose, 3-fold, top 125 uM | | | | | | | max control (100% Inh) |
| C | min control (100% Inh) | | | | cpd 3, 10 dose, 3-fold, top 125 uM | | | | | | | max control (100% Inh) |
| D | | | | | cpd 4, 10 dose, 3-fold, top 125 uM | | | | | | | |
| E | | | | | cpd 5, 10 dose, 3-fold, top 125 uM | | | | | | | |
| F | | | | | cpd 6, 10 dose, 3-fold, top 125 uM | | | | | | | |
| G | | | | | cpd 7, 10 dose, 3-fold, top 125 uM | | | | | | | |
| H | | | | | cpd 8, 10 dose, 3-fold, top 125 uM | | | | | | | |
| I | | | | | cpd 9, 10 dose, 3-fold, top 125 uM | | | | | | | |
| J | | | | | cpd 10, 10 dose, 3-fold, top 125 uM | | | | | | | |
| K | | | | | cpd 11, 10 dose, 3-fold, top 125 uM | | | | | | | |
| L | | | | | cpd 12, 10 dose, 3-fold, top 125 uM | | | | | | | |
| M | | | | | cpd 13, 10 dose, 3-fold, top 125 uM | | | | | | | |
| N | | | | | cpd 14, 10 dose, 3-fold, top 125 uM | | | | | | | |
| O | | | | | cpd 15, 10 dose, 3-fold, top 125 uM | | | | | | | |
| P | | | | | cpd 16, 10 dose, 3-fold, top 125 uM | | | | | | | |

| | 13 | 14 | 15 | 16 | 17 | 18 | 19 | 20 | 21 | 22 | 23 | 24 |
|---|---|---|---|---|---|---|---|---|---|---|---|---|
| A | min control (100% Inh) | | | | cpd 17, 10 dose, 3-fold, top 125 uM | | | | | | | max control (100% Inh) |
| B | min control (100% Inh) | | | | cpd 18, 10 dose, 3-fold, top 125 uM | | | | | | | max control (100% Inh) |
| C | min control (100% Inh) | | | | cpd 19, 10 dose, 3-fold, top 125 uM | | | | | | | max control (100% Inh) |
| D | | | | | cpd 20, 10 dose, 3-fold, top 125 uM | | | | | | | |
| E | | | | | cpd 21, 10 dose, 3-fold, top 125 uM | | | | | | | |
| F | | | | | cpd 22, 10 dose, 3-fold, top 125 uM | | | | | | | |
| G | | | | | cpd 23, 10 dose, 3-fold, top 125 uM | | | | | | | |
| H | | | | | cpd 24, 10 dose, 3-fold, top 125 uM | | | | | | | |
| I | | | | | cpd 25, 10 dose, 3-fold, top 125 uM | | | | | | | |
| J | | | | | cpd 26, 10 dose, 3-fold, top 125 uM | | | | | | | |
| K | | | | | cpd 27, 10 dose, 3-fold, top 125 uM | | | | | | | |
| L | | | | | cpd 28, 10 dose, 3-fold, top 125 uM | | | | | | | |
| M | | | | | cpd 29, 10 dose, 3-fold, top 125 uM | | | | | | | |
| N | | | | | cpd 30, 10 dose, 3-fold, top 125 uM | | | | | | | |
| O | | | | | cpd 31, 10 dose, 3-fold, top 125 uM | | | | | | | |
| P | | | | | cpd 32, 10 dose, 3-fold, top 125 uM | | | | | | | |

The assay buffer was freshly prepared: 30 mM Bicine pH 8, 0.003% Tween 20, 1.5 mM DTT, and 150 mM NaCl Preparation of the four assay samples:
  PRMT5 was thawed on ice; Me2, Me0, SAM and MTA were thawed at room temperature. The peptide stock was diluted to 7 µM in ddH$_2$O.
  SAM Me2 assay samples:
    3×SAM (cofactor): 150 µM SAM (Cayman) in assay buffer was prepared.
    1.5×PRMT5/Me2 (Max control): 150 nM PRMT5, and 37.5 nM Me2 in assay buffer was prepared.
    1.5×Me2 (Min control): 37.5 nM Me2 in assay buffer was prepared.
  Apo-Me0 assay samples:
    3×No Cofactor: assay buffer only was prepared
    1.5×PRMT5/Me0 (Max control): 150 nM PRMT5, and 37.5 nM Me2 in assay buffer was prepared.
    1.5×Me0 (Min control): 37.5 nM Me2 in assay buffer was prepared
  MTA-Me0 assay samples:
    3×MTA (cofactor): 150 µM MTA in assay buffer was prepared.
    1.5×PRMT5/Me0 (Max control): 37.5 nM PRMT5, and 37.5 nM Me0 in assay buffer was prepared.
    1.5×Me0 (Min control): 37.5 nM Me0 in assay buffer was prepared.

Assay Procedure:
  Above reagents were prepared
  5 µL 3× cofactor solution was dispensed to wells in all columns by 16-channel electronic pipettes
  Assay plate containing compound was spinned 60 sec at 1000 rpm
  10 µL Min control (peptide) solution was dispensed to the wells (columns 1&13) by 16-channel electronic pipettes
  10 µL enzyme (1.5×enzyme/peptide) solution was dispensed to the wells (columns 2-12&14-24) by 16-channel electronic pipettes
  Assay plate containing compound was spinned 60 sec at 1000 rpm, and incubated at 23° C. for 30 min
  Procedure was repeated for other three assay conditions and all plates were incubated for 30 min
  Assay plate was read on Envision instrument Data Analysis
  Fluorescence polarization is normalized to calculate % inhibition.

$$\% \text{ inhibition} - i = \left(1 - \frac{i - P}{Prmt5\_P - P}\right) * 100 \qquad \text{Equation 1}$$

Where:
  % inhibition is the percentage inhibition at a given concentration of inhibitor
  i is the Fluorescent anisotropy at a given inhibitor concentration
  P is the anisotropy signal given by the peptide alone and represents the minimum signal
  Prmt5_P is the anisotropy signal given by the Prmt5 and peptide complex in the presence of DMSO, representing the maximum fluorescent anisotropy signal
  % inhibition data were fit with a 4-parameter logistic model. Bottom and Top were fixed to 0% and 100%, respectively. IC$_{50}$ values are reported.

The Ki can be calculated from the $IC_{50}$ using the Cheng-Prussof equation:

$$IC_{50} = Ki \times \left(1 + \frac{[\text{Peptide}]}{Kd, \text{Peptide}}\right)$$

For the assay performed in the presence of SAM, the Me2 peptide binding affinity to PRMT5 in the presence of SAM was determined to be 50 nM, and the peptide concentration is 25 nM, therefore $IC_{50}=Ki \times 1.5$ For the assay performed in the presence of MTA, the Me0 peptide binding affinity to PRMT5 in the presence of MTA was determined to be 2 nM, and the peptide concentration is 25 nM, therefore $IC_{50}=Ki \times 13.5$ Envision® Set Up:
Mirror (Barcode 682)
Filter (Barcode 245)
Filter (Barcode 246)
Filter (Barcode 132)

The data for this example is shown in Table 1, Columns 3-6.

Example 11—Cellular Assay—SDMA In-Cell Western Protocol

A HAP1 MTAP-isogenic cell line pair was acquired from Horizon Discovery (HZGHC004894c005) and maintained in DMEM (ThermoFisher 11965)+10% FBS (Gemini 100-500) in a humidified, 10% $CO_2$ tissue culture incubator. The SAM-cooperative PRMT5 inhibitor, GSK3326595, was sourced from SelleckChem and maintained as a 10 mM DMSO stock. All test compounds are maintained as 10 mM DMSO stocks.

On Day 0, MTAP-intact or MTAP-deleted cells are seeded in a 384-well plate, and incubated in a humidified, 10% $CO_2$ tissue culture incubator for 16-24 hours. On Day 1, the test compounds are dispensed to wells at defined concentrations using a Tecan D300e digital dispenser (n=4), and the volume of DMSO is normalized to highest class volume. Each plate includes wells dosed with defined concentrations of GSK33226595 as a plate control. The compounds are incubated with cells for 24 hours in a humidified, 10% $CO_2$ tissue culture incubator.

On Day 2, the compound-treated cells are fixed with a final concentration of 4% formaldehyde. The cells are then washed/permeabilized with 1×PBS+0.1% Triton X-100, and then blocked with 5% goat serum/1×TBS. The fixed cells are then incubated overnight at 4° C. with a primary SDMA antibody cocktail (Cell Signaling 13222).

On Day 3, the cells are washed with 1×PBS+0.1% Triton X-100, and then incubated at room temperature for 1 hour with a NIR fluorescent secondary antibody cocktail that also contains DRAQ5 (LiCor 926-32211 and VWR 10761-508). The cells are washed with 1×PBS+0.1% Triton X-100, and then washed again with $ddH_2O$. The plates are then imaged using a NIR fluorescent imager (LiCor Odyssey).

For data analysis, the SDMA signal is normalized to the DRAQ5 signal. Assay background is determined by the signal from wells treated with 10 μM GSK3326595 and subtracted from every well. The data are plotted as % of the DMSO control wells for the MTAP-intact and the MTAP-deleted cell lines independently, with a 4-parameter fit non-linear regression model constrained to 0 (GraphPad Prism).

The data obtained in this experiment is presented in Table 1, columns 7-9.

OTHER EMBODIMENTS

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I)

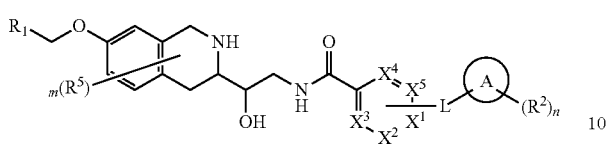

(I)

or a pharmaceutically acceptable salt thereof;
wherein:
$X^1$, $X^2$, $X^3$, $X^4$ and $X^5$ are each independently N or $CR^x$;
L is a bond, —C(=O)—, —NH— or —O—;
Ring A is a carbocycle, heterocycle or a 5-6 membered monocyclic heteroaryl;
$R^1$ is a 5-6 membered heteroaryl substituted with 0-3 instances of $R^4$;
each $R^2$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, heteroarylalkyl, arylalkyl, cycloalkylalkyl, —$OR^3$, —$N(R^3)_2$, —C(=O)$R^3$, —C(=O)$OR^3$, —$NR^3$C(=O)$R^3$, —$NR^3$C(=O)$OR^3$, —C(=O)$N(R^3)_2$, —OC(=O)$N(R^3)_2$, —S(=O)$R^3$, —S(=O)$_2R^3$, —$SR^3$, —S(=O)(=$NR^3$)$R^3$, —$NR^3$S(=O)$_2R^3$ and —S(=O)$_2N(R^3)_2$;
each $R^3$ is independently selected from H, $C_1$-$C_6$ alkyl, —$C_1$-$C_6$ heteroalkyl, $C_3$-$C_9$ carbocyclyl, 3-7 membered heterocyclyl, cycloalkylalkyl, heterocyclylalkyl, aryl, 5-6 membered heteroaryl, arylalkyl and heteroarylalkyl wherein each alkyl, carbocyclyl, heterocyclyl, cycloalkylalkyl, heterocyclylalkyl, aryl, heteroaryl, arylalkyl and heteroarylalkyl is optionally substituted;
each $R^4$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, cycloalkylalkyl, —$OR^3$, —$N(R^3)_2$, —C(=O)$R^3$, —C(=O)$OR^3$, —$NR^3$C(=O)$R^3$, —$NR^3$C(=O)$OR^3$, —C(=O)$N(R^3)_2$, —OC(=O)$N(R^3)_2$, —S(=O)$R^3$, —S(=O)$_2R^3$, —$SR^3$, —S(=O)(=$NR^3$)$R^3$, —$NR^3$S(=O)$_2R^3$ and —S(=O)$_2N(R^3)_2$;
each $R^x$ is independently selected from hydrogen, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, cycloalkylalkyl, —$OR^3$, —$N(R^3)_2$, —C(=O)$R^3$, —C(=O)$OR^3$, —$NR^3$C(=O)$R^3$, —$NR^3$C(=O)$OR^3$, —C(=O)$N(R^3)_2$, —OC(=O)$N(R^3)_2$, —S(=O)$R^3$, —S(=O)$_2R^3$, —$SR^3$, —S(=O)(=$NR^3$)$R^3$, —$NR^3$S(=O)$_2R^3$ and —S(=O)$_2N(R^3)_2$ wherein each alkyl, carbocyclyl, heterocyclyl, heterocyclylalkyl, cycloalkylalkyl is optionally substituted;
each $R^5$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, $C_6$-$C_{10}$ aryl, 5-10 membered heteroaryl, cycloalkylalkyl, heterocyclylalkyl, arylalkyl, heteroarylalkyl, —$OR^3$, —$N(R^3)_2$, —C(=O)$R^3$, —C(=O)$OR^3$, —$NR^3$C(=O)$R^3$, —$NR^3$C(=O)$OR^3$, —C(=O)$N(R^3)_2$, —OC(=O)$N(R^3)_2$, —S(=O)$R^3$, —S(=O)$_2R^3$, —$SR^3$, —S(=O)(=$NR^3$)$R^3$, —$NR^3$S(=O)$_2R^3$, —S(=O)$_2N(R^3)_2$, or two $R^5$ can be taken together with the atoms to which they are attached to form a —$C_3$-$C_9$ carbocyclyl or a 3-10 membered heterocyclyl;
m is 0, 1, 2 or 3; and
n is 0, 1, 2 or 3.

2. The compound of claim 1 wherein the compound is of Formula (Ia):

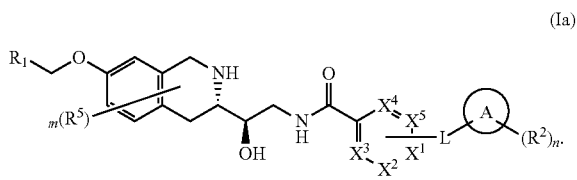

(Ia)

3. A compound of Formula (VI)

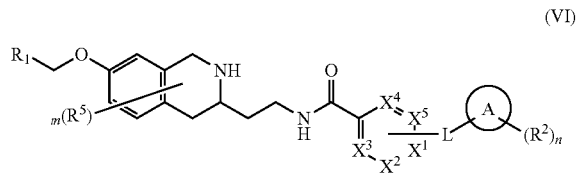

(VI)

or a pharmaceutically acceptable salt thereof;
wherein:
$X^1$, $X^2$, $X^3$, $X^4$ and $X^5$ are each independently N or $CR^x$;
L is a bond, —C(=O)—, —NH— or —O—;
Ring A is a carbocycle, heterocycle or a 5-6 membered monocyclic heteroaryl;
$R^1$ is a 5-6 membered heteroaryl substituted with 0-3 instances of $R^4$;
each $R^2$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, heteroarylalkyl, arylalkyl, cycloalkylalkyl, —$OR^3$, —$N(R^3)_2$, —C(=O)$R^3$, —C(=O)$OR^3$, —$NR^3$C(=O)$R^3$, —$NR^3$C(=O)$OR^3$, —C(=O)$N(R^3)_2$, —OC(=O)$N(R^3)_2$, —S(=O)$R^3$, —S(=O)$_2R^3$, —$SR^3$, —S(=O)(=$NR^3$)$R^3$, —$NR^3$S(=O)$_2R^3$ and —S(=O)$_2N(R^3)_2$;
each $R^3$ is independently selected from H, $C_1$-$C_6$ alkyl, —$C_1$-$C_6$ heteroalkyl, $C_3$-$C_9$ carbocyclyl, 3-7 membered heterocyclyl, cycloalkylalkyl, heterocyclylalkyl, aryl, 5-6 membered heteroaryl, arylalkyl and heteroarylalkyl wherein each alkyl, carbocyclyl, heterocyclyl, cycloalkylalkyl, heterocyclylalkyl, aryl, heteroaryl, arylalkyl and heteroarylalkyl is optionally substituted;
each $R^4$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, cycloalkylalkyl, —$OR^3$, —$N(R^3)_2$, —C(=O)$R^3$, —C(=O)$OR^3$, —$NR^3$C(=O)$R^3$, —$NR^3$C(=O)$OR^3$, —C(=O)$N(R^3)_2$, —OC(=O)$N(R^3)_2$, —S(=O)$R^3$, —S(=O)$_2R^3$, —$SR^3$, —S(=O)(=$NR^3$)$R^3$, —$NR^3$S(=O)$_2R^3$ and —S(=O)$_2N(R^3)_2$;
each $R^x$ is independently selected from hydrogen, halo, CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, cycloalkylalkyl, —$OR^3$, —$N(R^3)_2$, —C(=O)$R^3$, —C(=O)$OR^3$, —$NR^3$C(=O)

$R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$ and —$S(=O)_2N(R^3)_2$ wherein each alkyl, carbocyclyl, heterocyclyl, heterocyclylalkyl, cycloalkylalkyl is optionally substituted;

each $R^5$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, $C_6$-$C_{10}$ aryl, 5-10 membered heteroaryl, cycloalkylalkyl, heterocyclylalkyl, arylalkyl, heteroarylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$, —$S(=O)_2N(R^3)_2$, or two $R^5$ can be taken together with the atoms to which they are attached to form a —$C_3$-$C_9$ carbocyclyl or a 3-10 membered heterocyclyl;

m is 0, 1, 2 or 3; and n is 0, 1, 2 or 3.

4. The compound of claim 1 wherein L is a bond.

5. The compound of claim 1, wherein L is —O—.

6. The compound of claim 1 wherein L is —C(=O)—.

7. The compound of claim 1, wherein $R^x$ is —$C_3$-$C_9$ carbocyclyl or 3-10 membered heterocyclyl substituted with 0-1 instances of $R^7$, wherein $R^7$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, $C_6$-$C_{10}$ aryl, 5-10 membered heteroaryl, cycloalkylalkyl, heterocyclylalkyl, arylalkyl, heteroarylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$ or —$S(=O)_2N(R^3)_2$.

8. The compound of claim 7, wherein $R^7$ is —$C_1$-$C_6$ alkyl or —$C(=O)R^3$.

9. The compound of claim 1, wherein $R^x$ is selected from piperidinyl, piperazinyl, morpholinyl, 2-azabicyclo[2.2.1]heptanyl, 3-azabicyclo[3.1.1]heptanyl, and 3-azabicyclo[3.2.1]octanyl.

10. The compound of claim 1 wherein $R^x$ is H.

11. The compound of claim 1, wherein ring A is piperidinyl, piperazinyl, pyrrolidinyl, oxetanyl, tetrahydrofuranyl, azetidinyl, tetrahydropyranyl, 1,4-dioxan-2-yl or morpholinyl.

12. The compound of claim 1 wherein ring A is selected from:

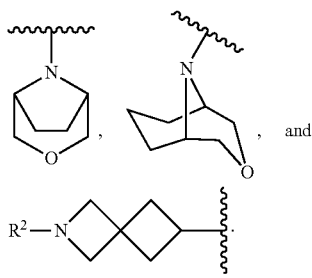

13. The compound of claim 1 wherein ring A is pyridinyl.

14. The compound of claim 1 wherein ring A is cyclopropyl, cyclobutyl, cyclopentyl, cyclohexyl, cycloheptyl, spiro[2.3]hexyl or spiro[3.3]heptyl.

15. A compound of Formula (IV) or a pharmaceutically acceptable salt thereof, wherein:

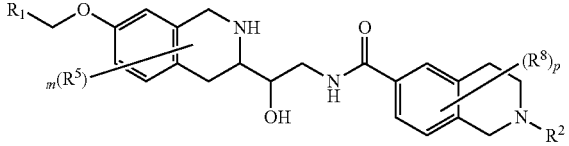

(IV)

$R^1$ is a 5-6 membered heteroaryl substituted with 0-3 instances of $R^4$;

each $R^2$ is independently selected from =O, halo, —CN, —$C_1$-$C_6$ alkyl, $C_1$-$C_6$ heteroalkyl, —$C_1$-$C_6$ haloalkyl, —$C_3$-$C_9$ carbocyclyl, 3-10 membered heterocyclyl, heterocyclylalkyl, cycloalkylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$ and —$S(=O)_2N(R^3)_2$;

each $R^3$ is independently selected from H, $C_1$-$C_6$ alkyl, $C_3$-$C_9$ carbocyclyl, 3-10 membered heterocyclyl, cycloalkylalkyl, heterocyclylalkyl, aryl, 5-6 membered heteroaryl, arylalkyl and heteroarylalkyl wherein each alkyl, carbocyclyl, heterocyclyl, cycloalkylalkyl, heterocyclylalkyl, aryl, heteroaryl, arylalkyl and heteroarylalkyl is optionally substituted;

each $R^4$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, heterocyclylalkyl, cycloalkylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$ and —$S(=O)_2N(R^3)_2$;

each $R^5$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, $C_6$-$C_{10}$ aryl, 5-10 membered heteroaryl, cycloalkylalkyl, heterocyclylalkyl, arylalkyl, heteroarylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$, —$S(=O)_2N(R^3)_2$, or two $R^5$ can be taken together with the atoms to which they are attached to form a —$C_3$-$C_9$ carbocyclyl or a 3-10 membered heterocyclyl;

each $R^8$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ carbocyclyl, 3-10 membered heterocyclyl, $C_6$-$C_{10}$ aryl, 5-10 membered heteroaryl, cycloalkylalkyl, heterocyclylalkyl, arylalkyl, heteroarylalkyl, —$OR^3$, —$N(R^3)_2$, —$C(=O)R^3$, —$C(=O)OR^3$, —$NR^3C(=O)R^3$, —$NR^3C(=O)OR^3$, —$C(=O)N(R^3)_2$, —$OC(=O)N(R^3)_2$, —$S(=O)R^3$, —$S(=O)_2R^3$, —$SR^3$, —$S(=O)(=NR^3)R^3$, —$NR^3S(=O)_2R^3$, —$S(=O)_2N(R^3)_2$, or two $R^8$ can be taken together with the atoms to which they are attached to form a —$C_3$-$C_9$ carbocyclyl or a 3-10 membered heterocyclyl;

m is 0, 1, 2 or 3; and p is 0, 1, 2 or 3.

16. The compound of claim 1, wherein $R^1$ is selected from:

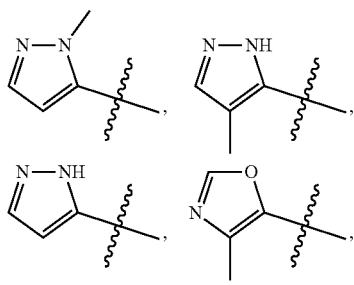

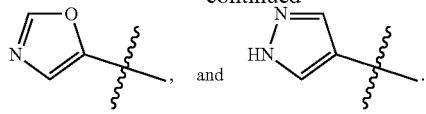

, and .

17. The compound of claim 1, wherein $R^4$ is methyl.
18. The compound of claim 1, wherein $R^2$ is benzyl or pyridinylmethyl.
19. The compound of claim 1, wherein $R^2$ is —C(=O)CH$_3$, —C(O)cyclopropyl, —C(O)cyclobutyl, —C(O)$^t$Bu, —C(O)$^i$Pr, —C(O)Pr, —C(O)$^i$Bu, or —C(=O)OMe.
20. The compound of claim 1 wherein m is 0.
21. The compound of claim 1 wherein the compound is selected from the group consisting of

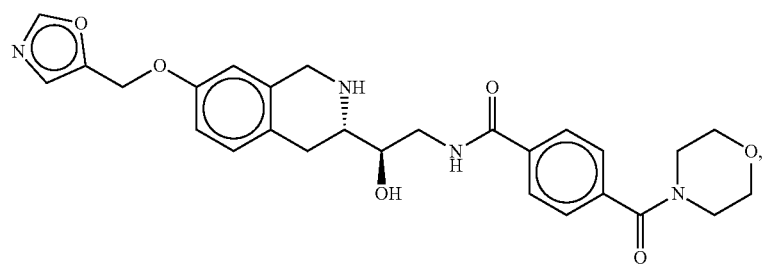

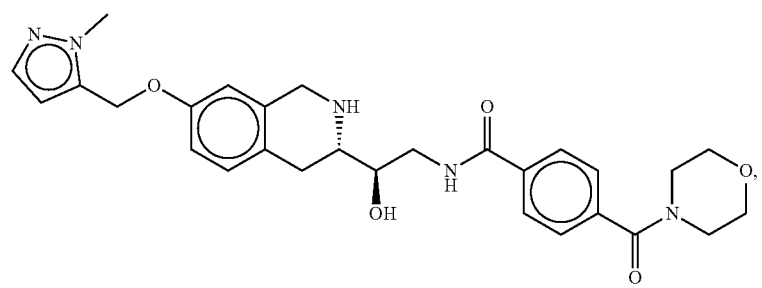

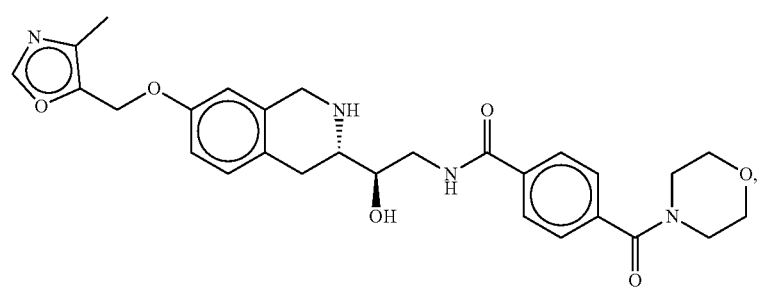

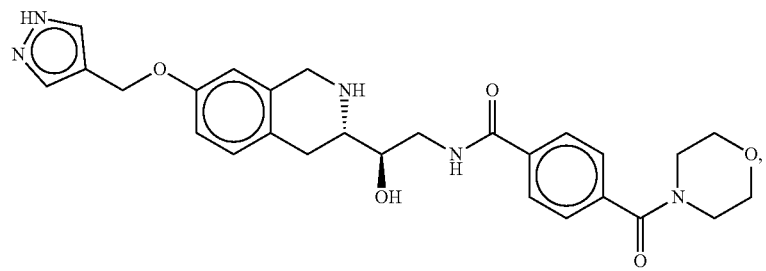

-continued
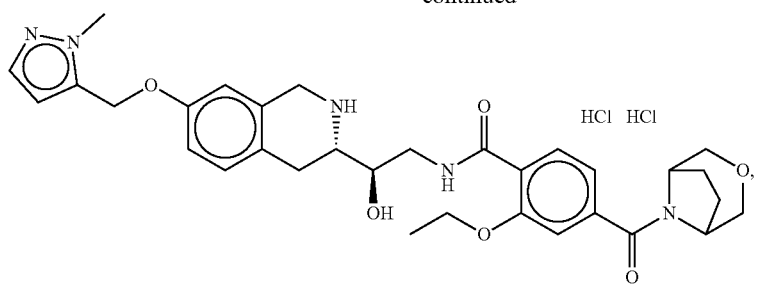
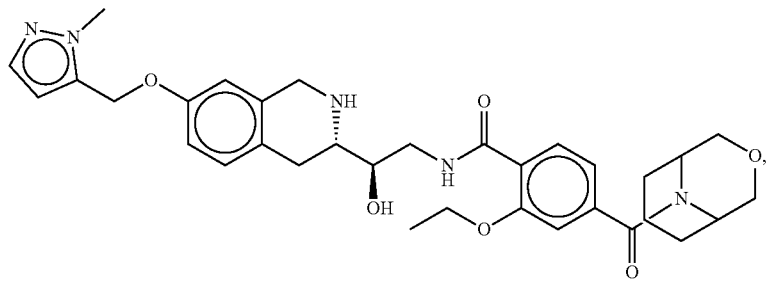
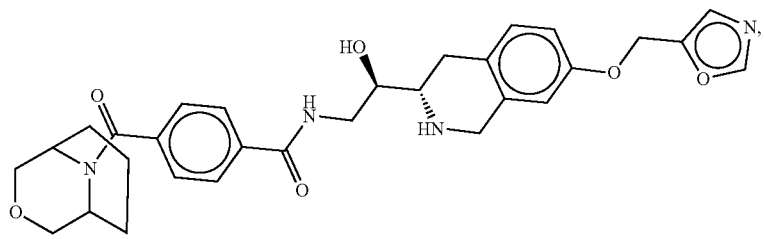
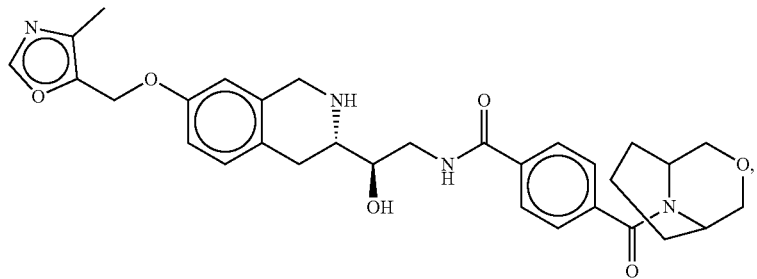
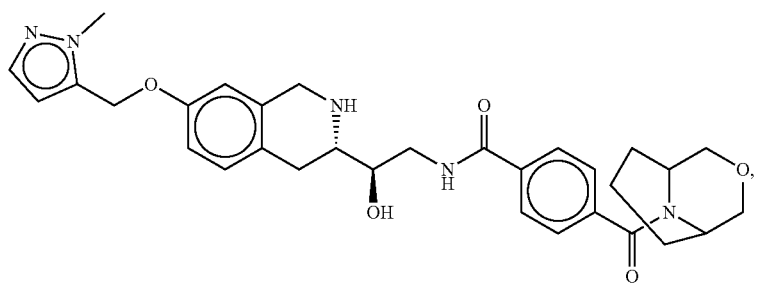
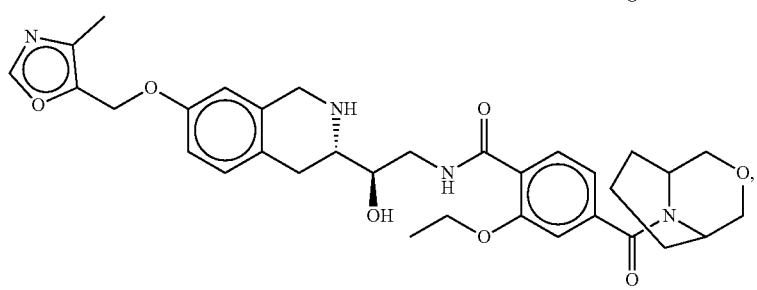

-continued
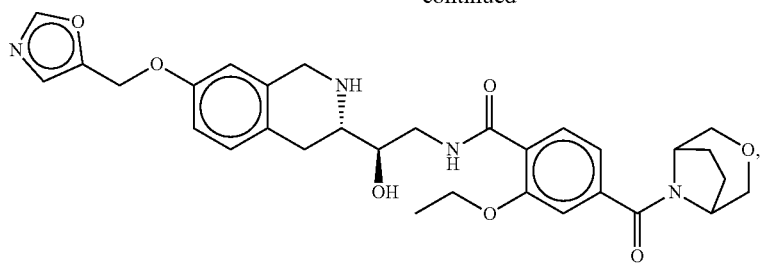
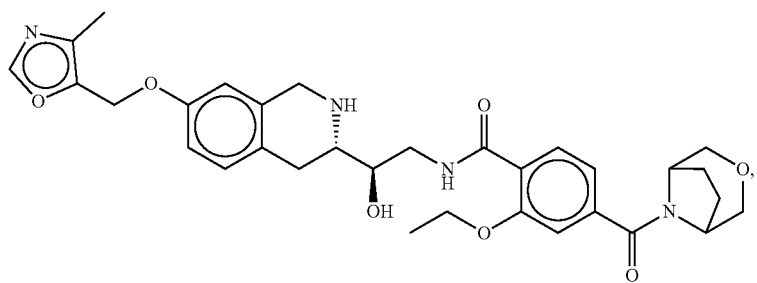
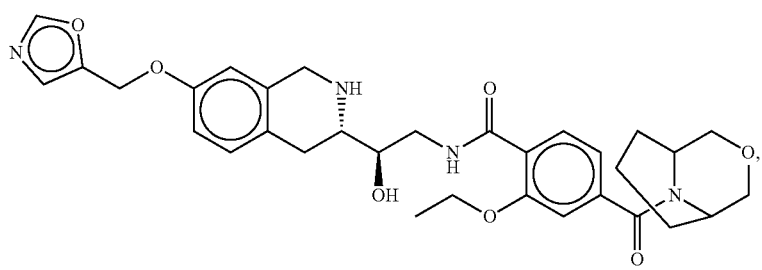
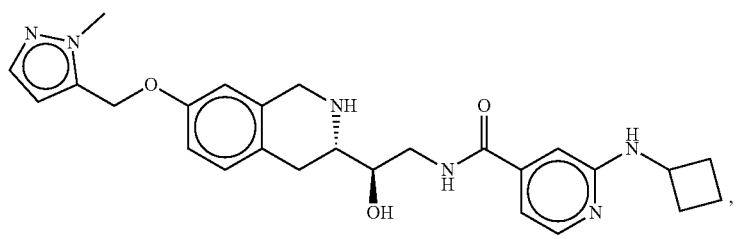
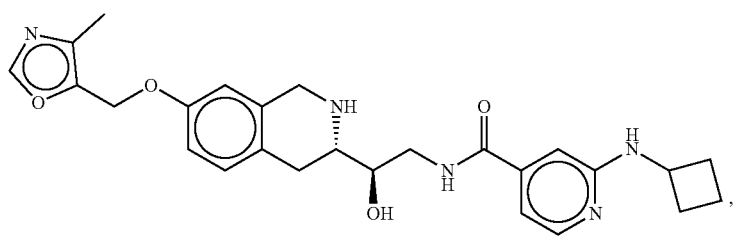
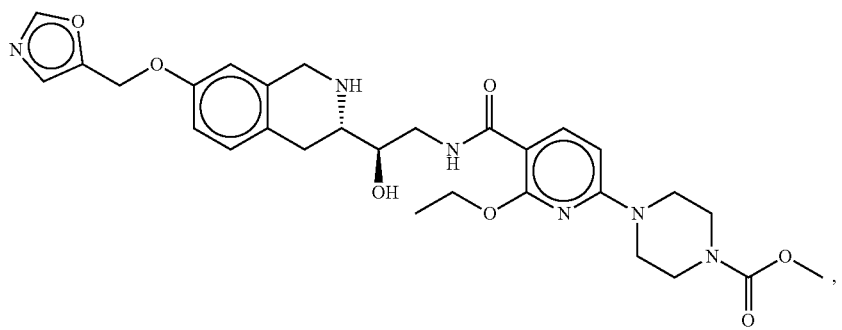

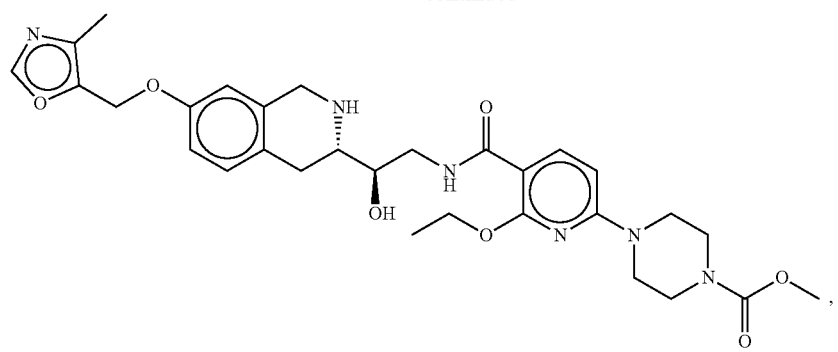
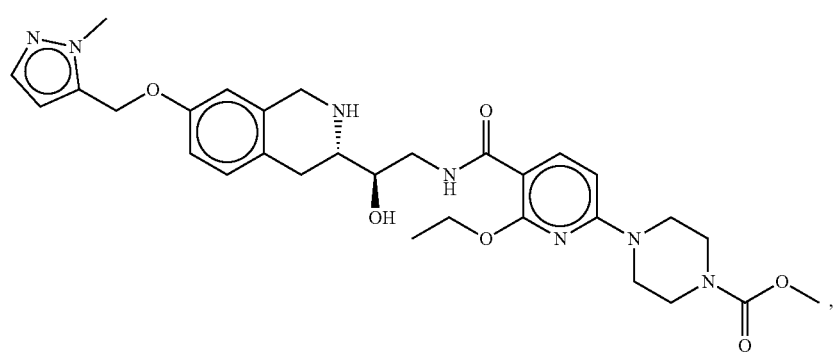
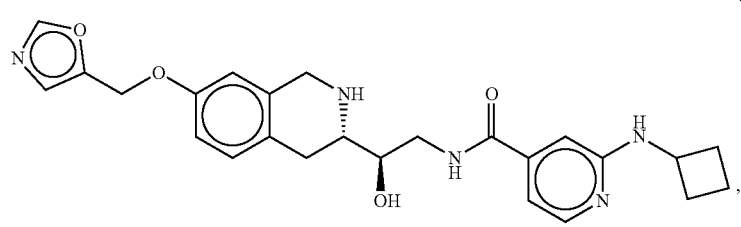
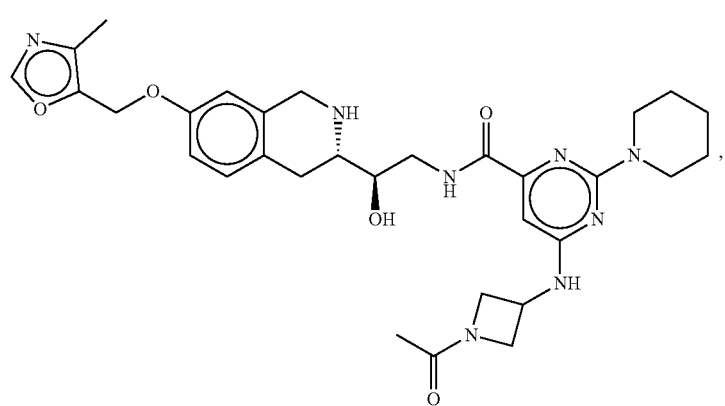
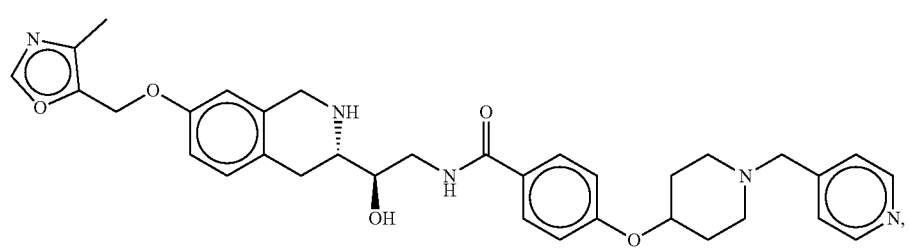

-continued
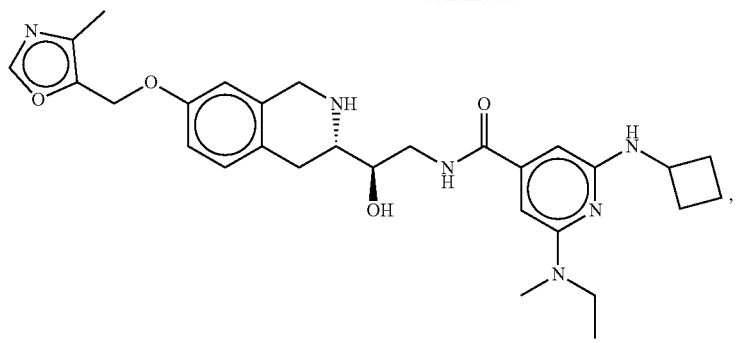
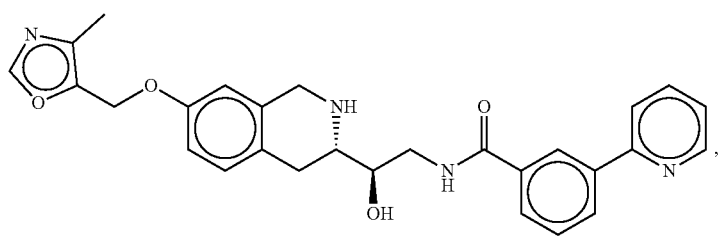
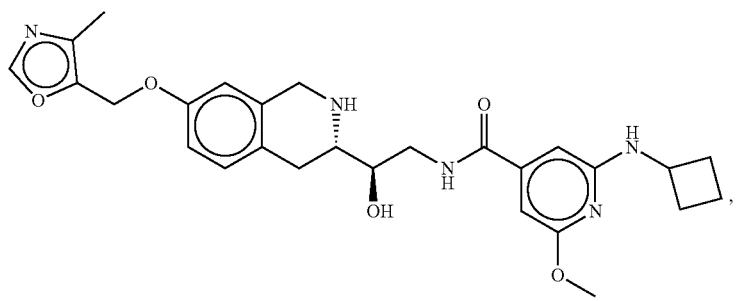
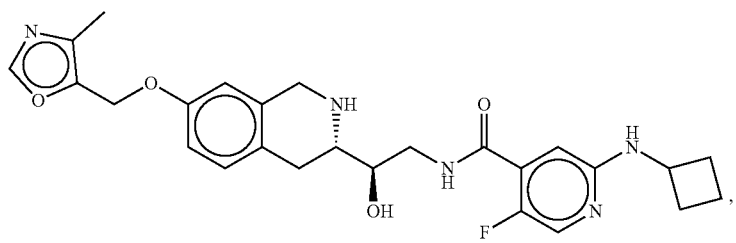
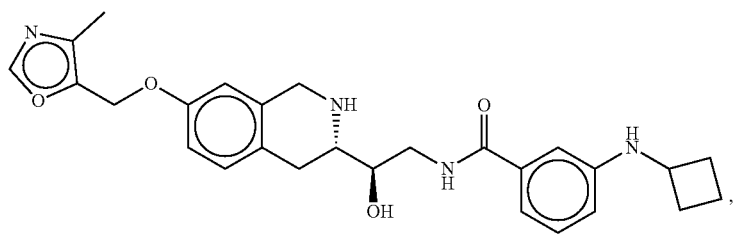
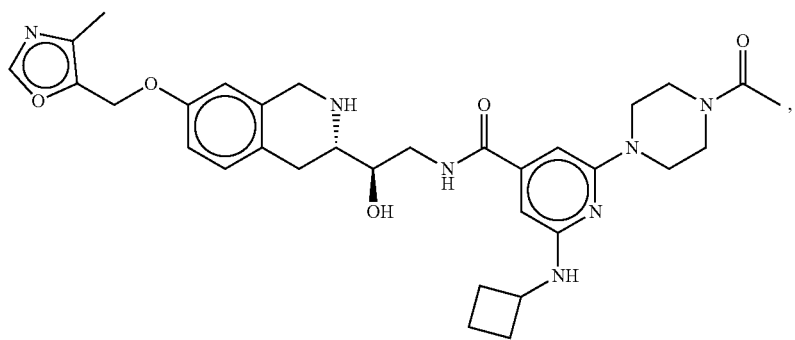

-continued
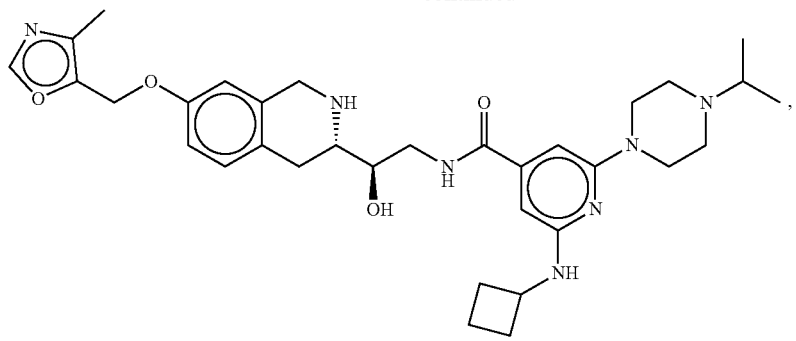
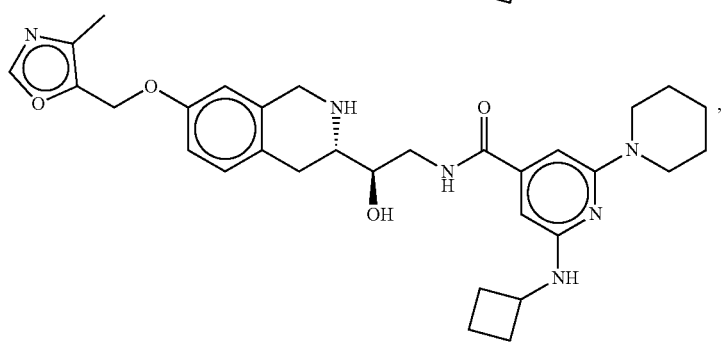
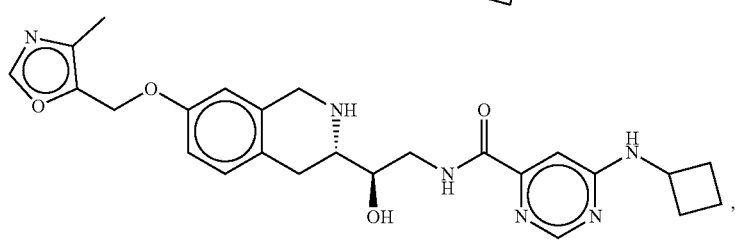
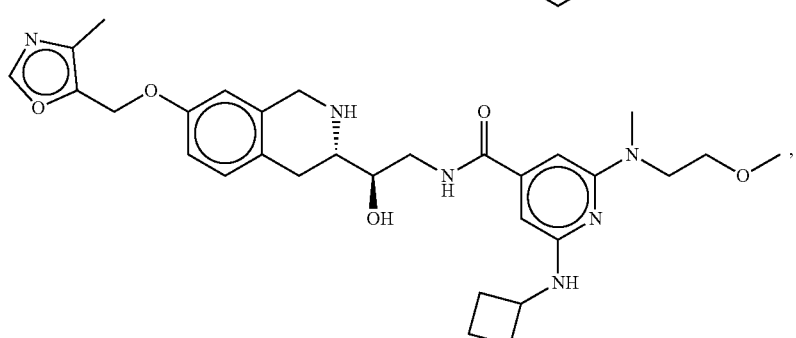
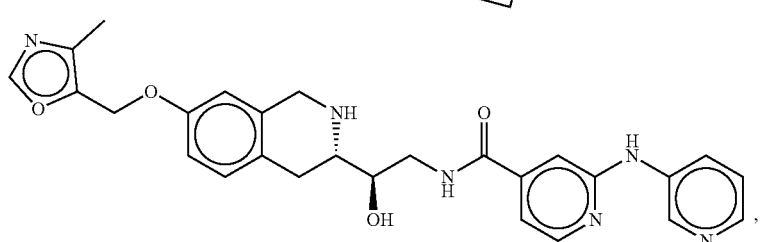
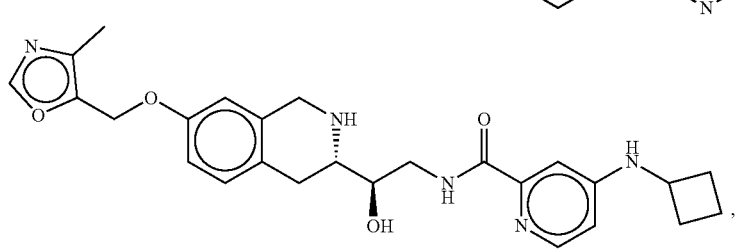

-continued
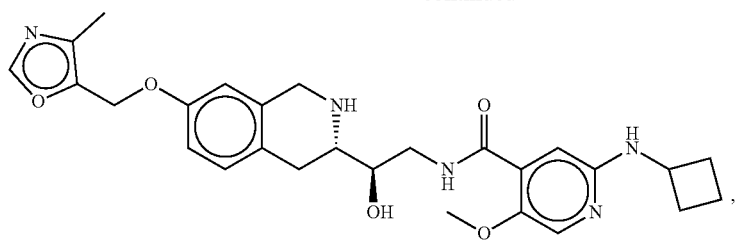
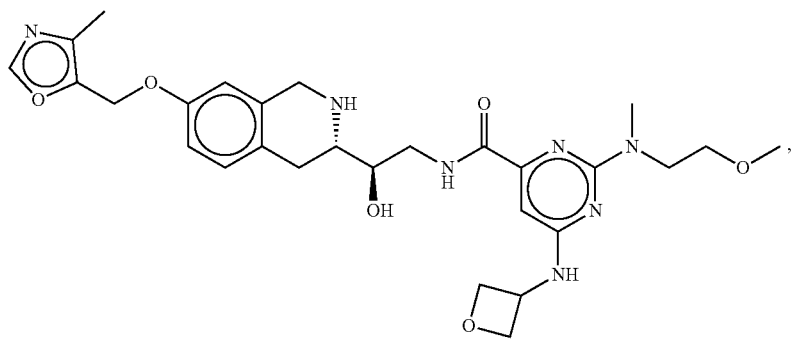
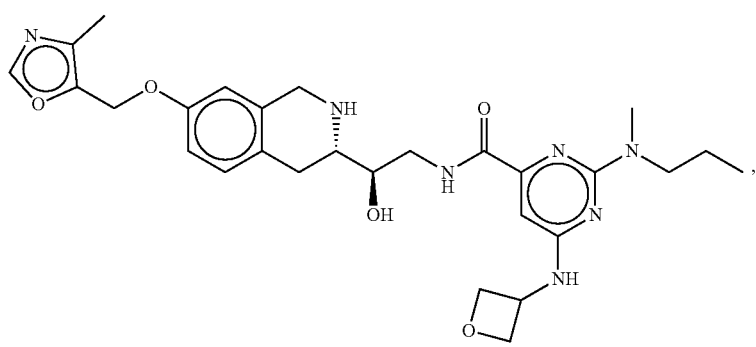
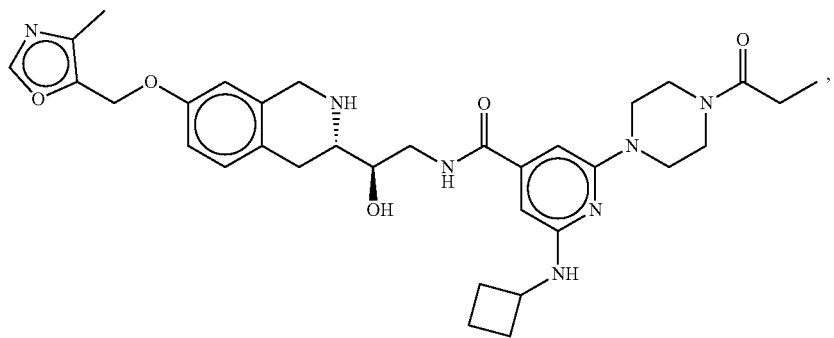
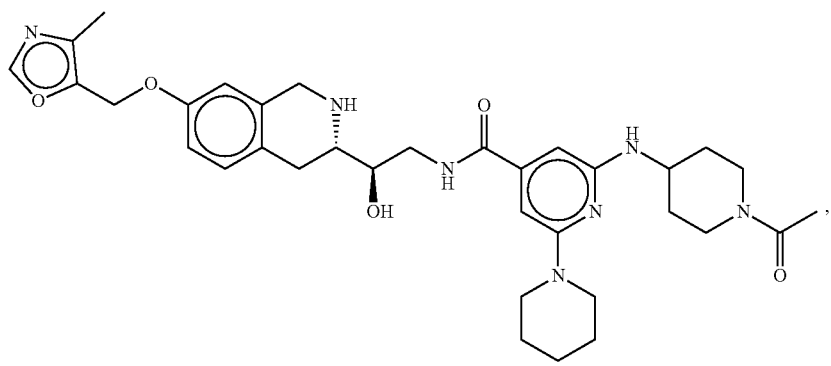

-continued
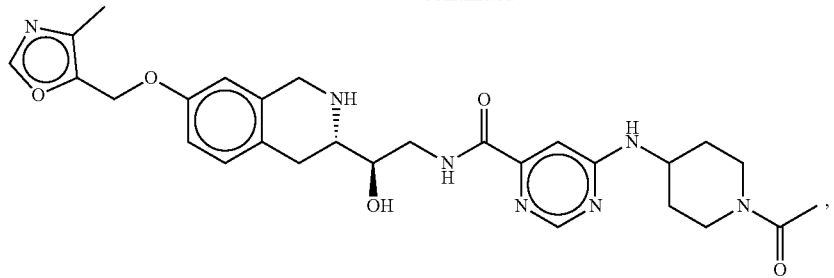
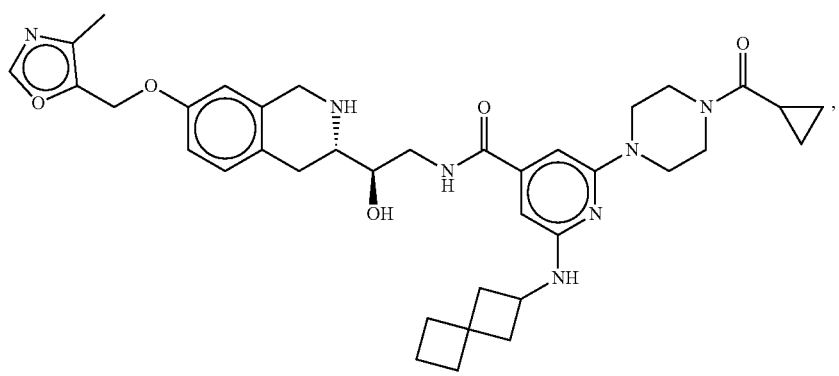
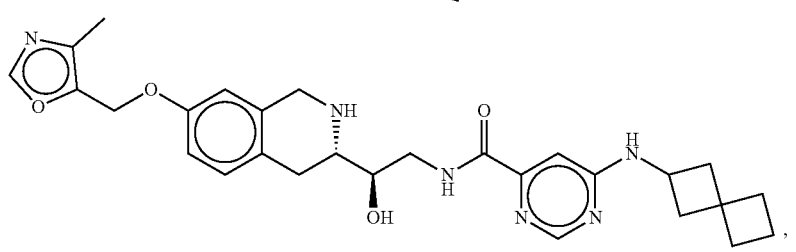
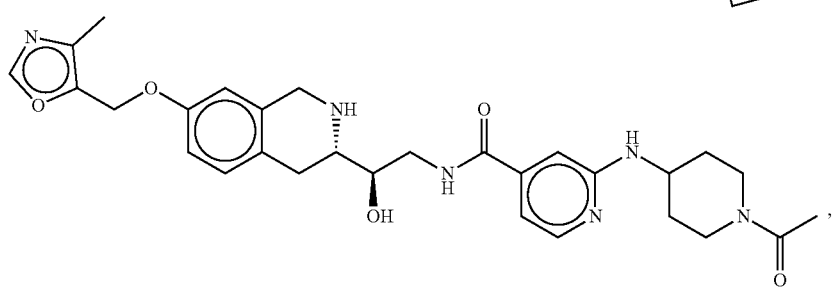
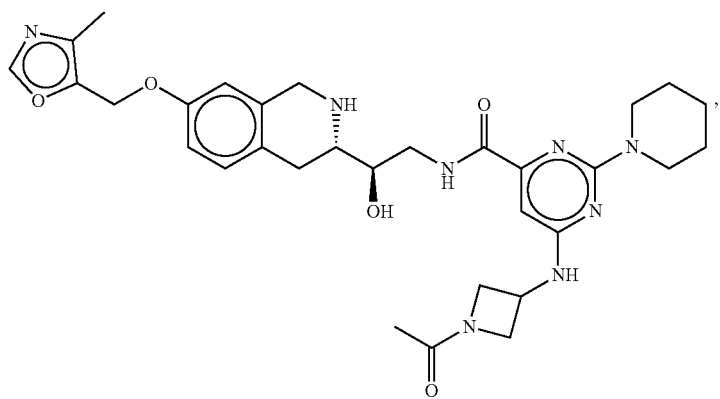

-continued
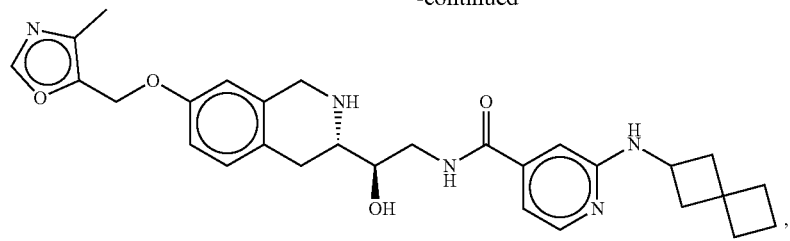
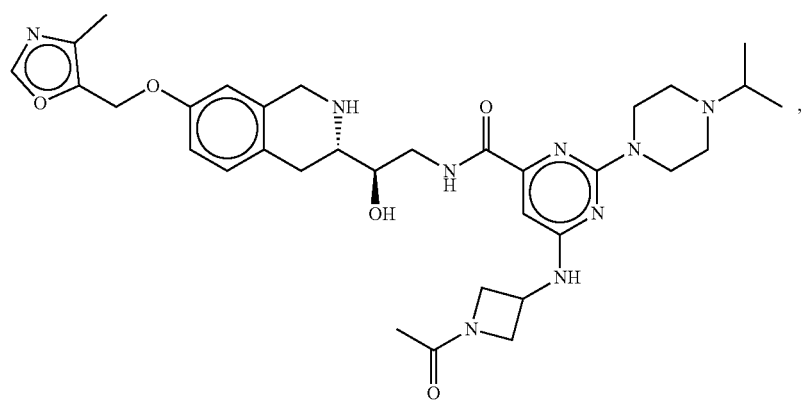
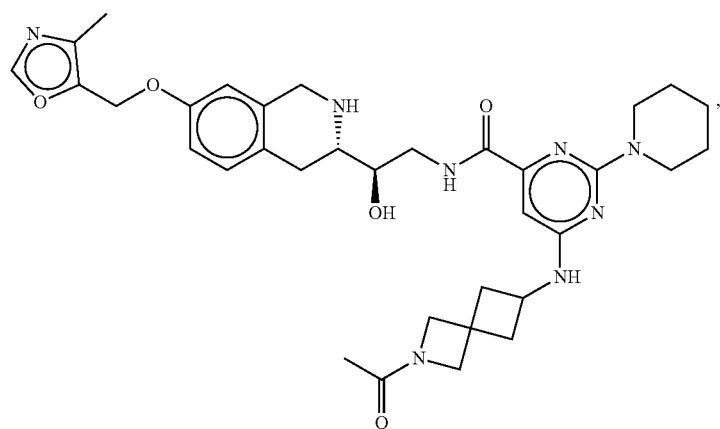
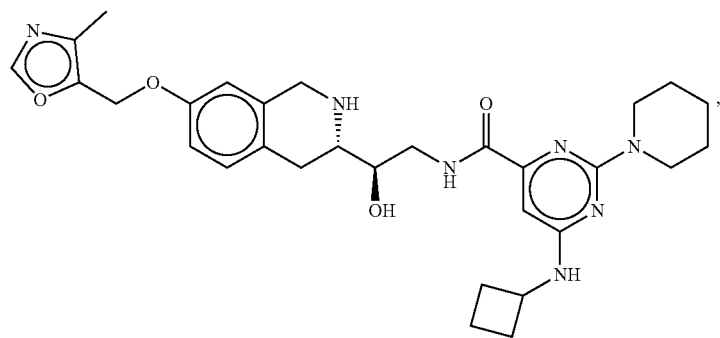

-continued
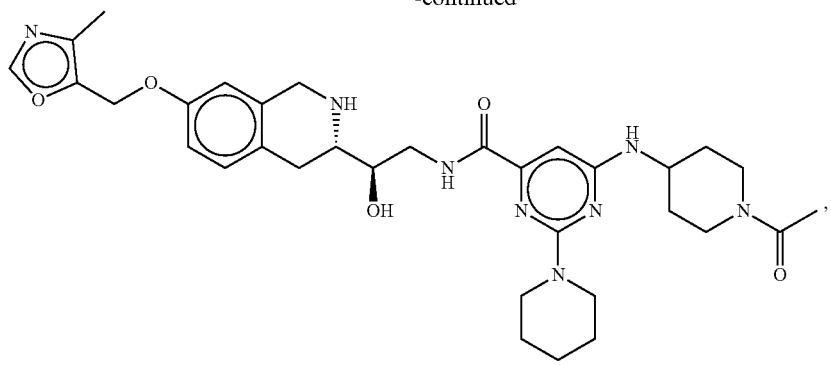
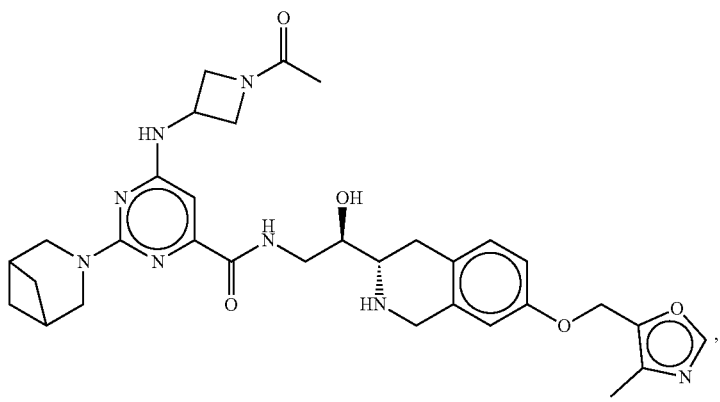
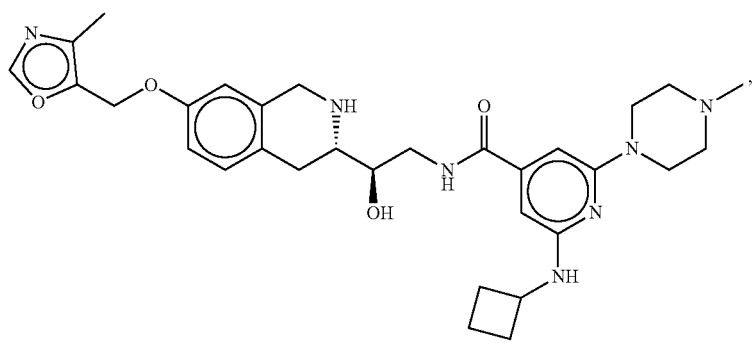
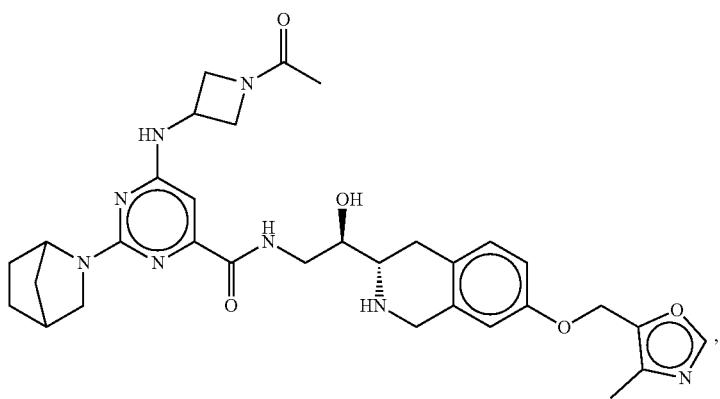

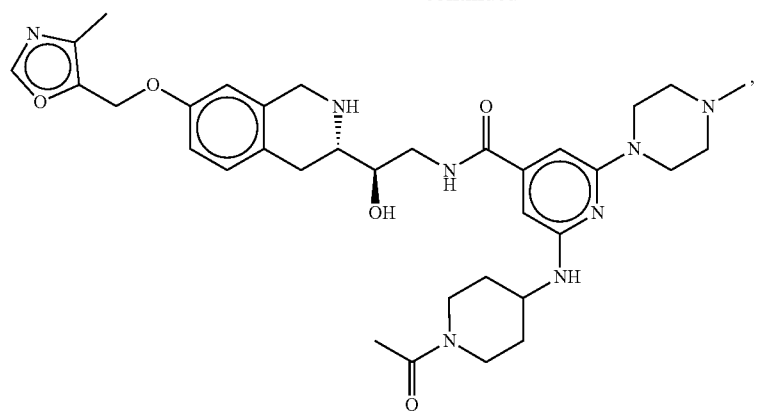
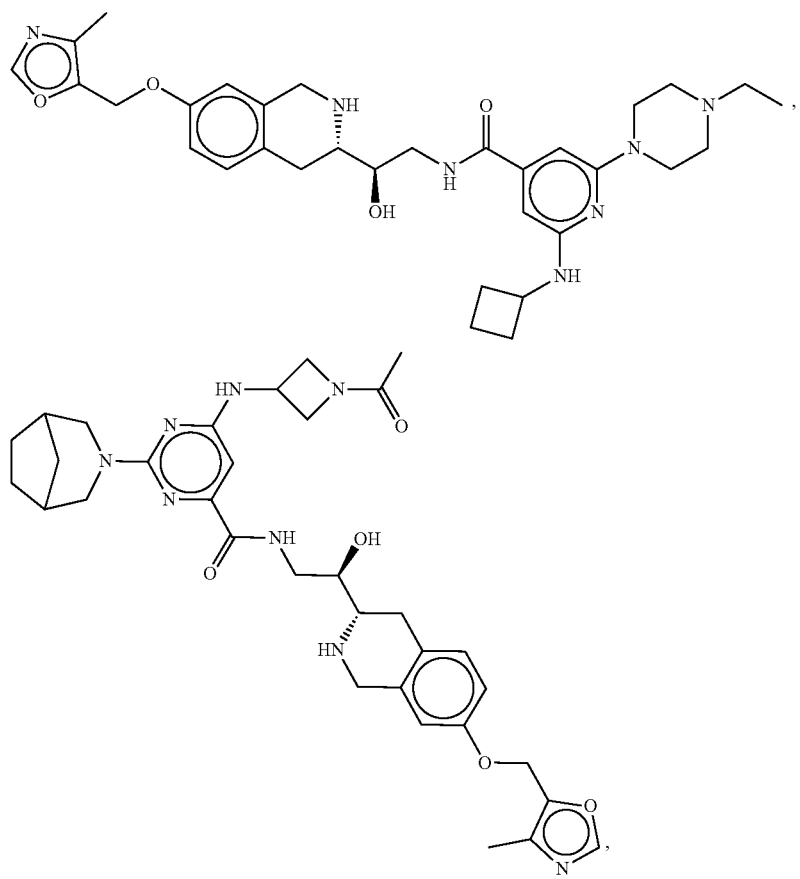
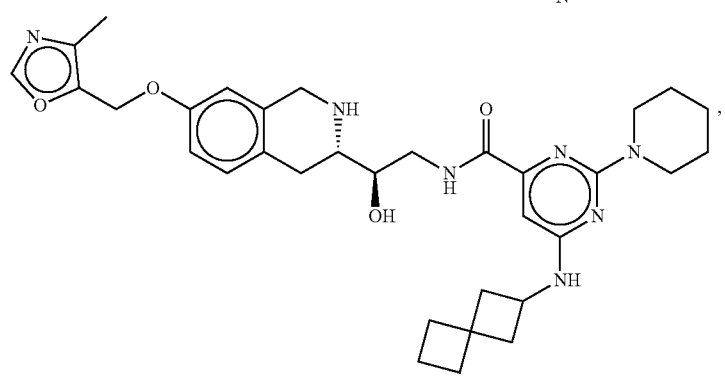

-continued
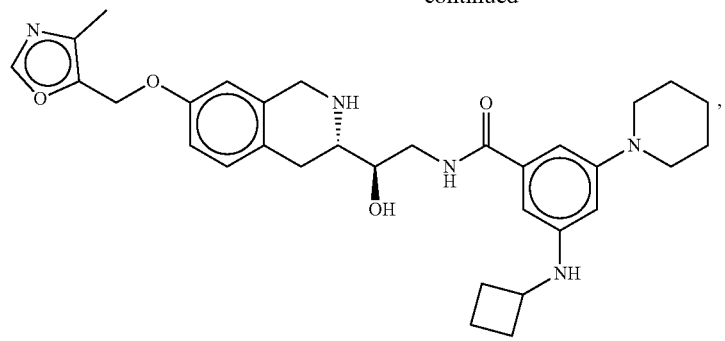
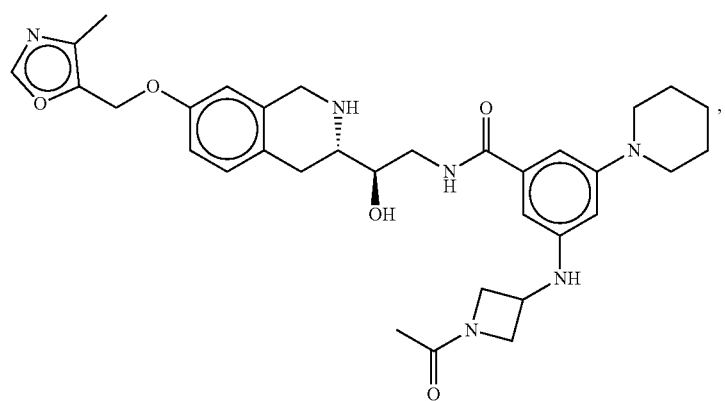
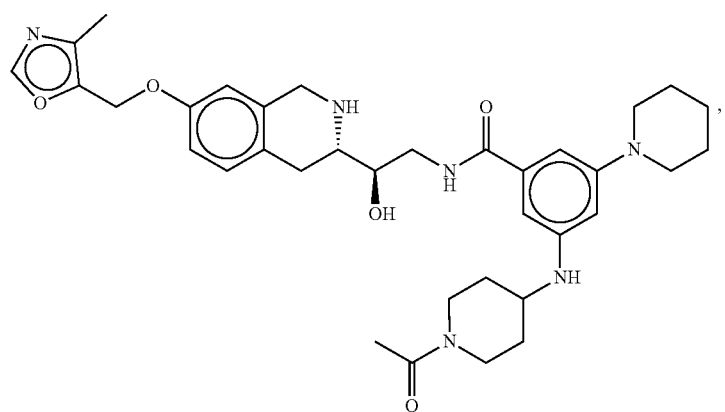
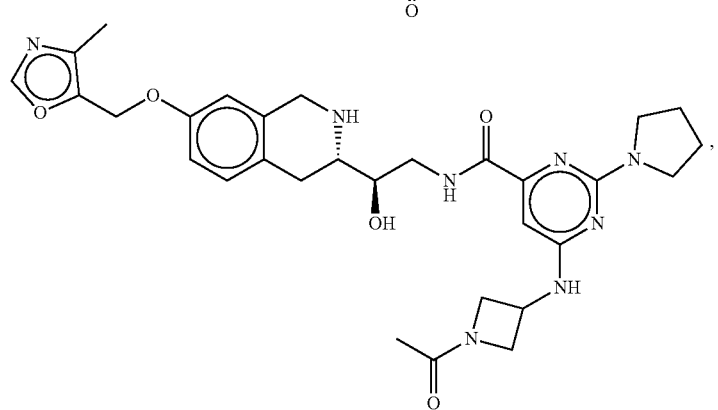

-continued
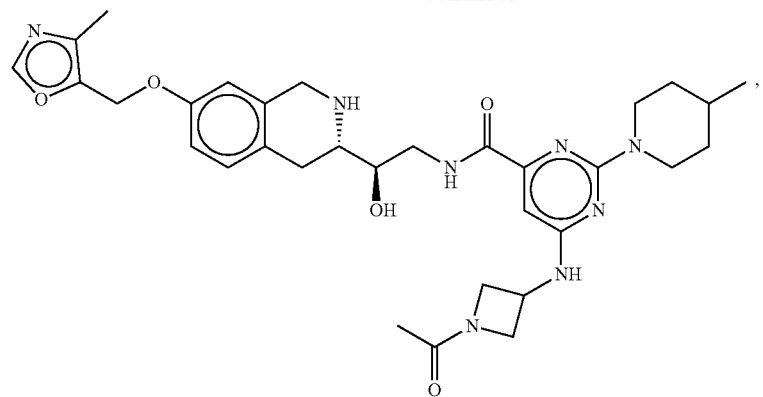
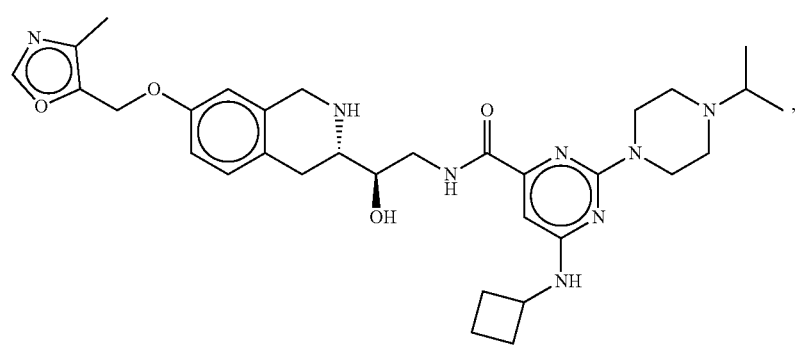
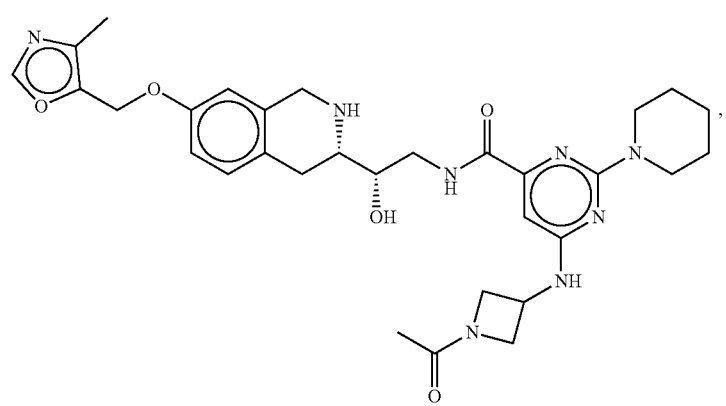
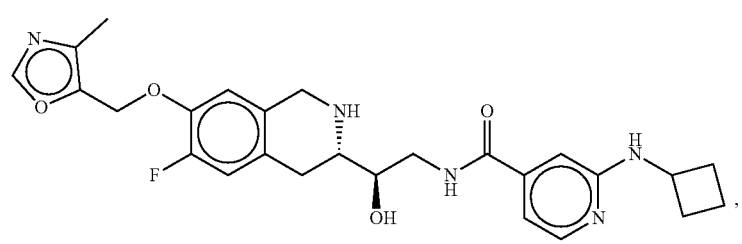

-continued
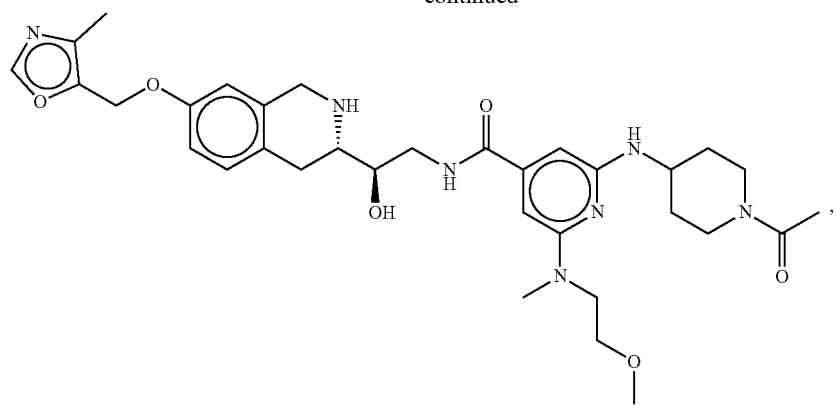
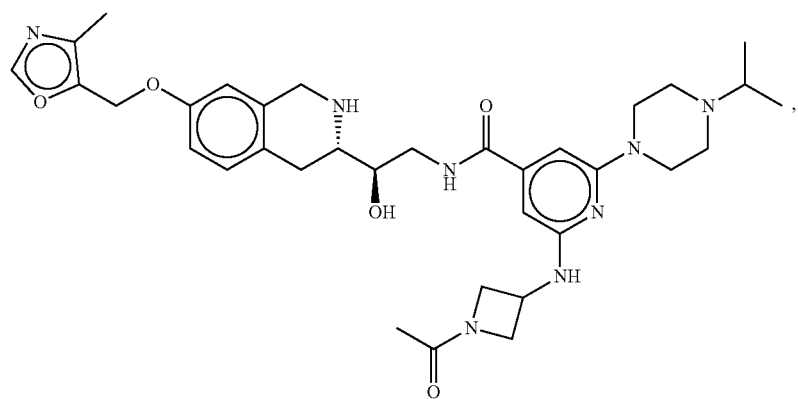
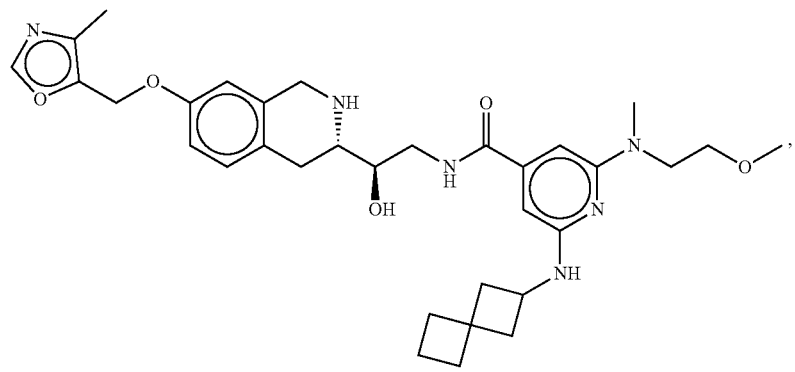
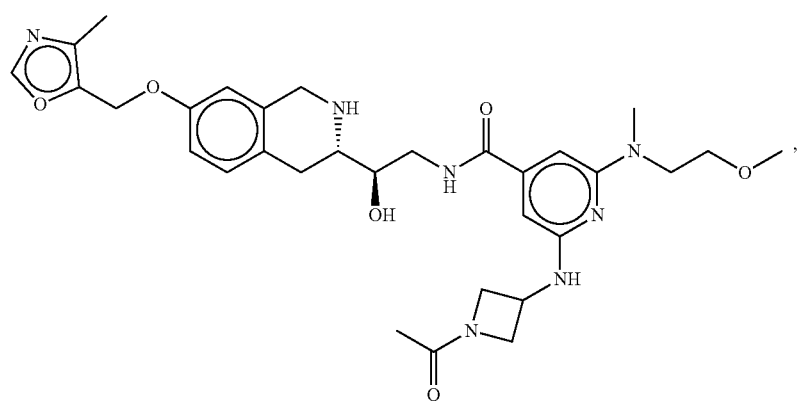

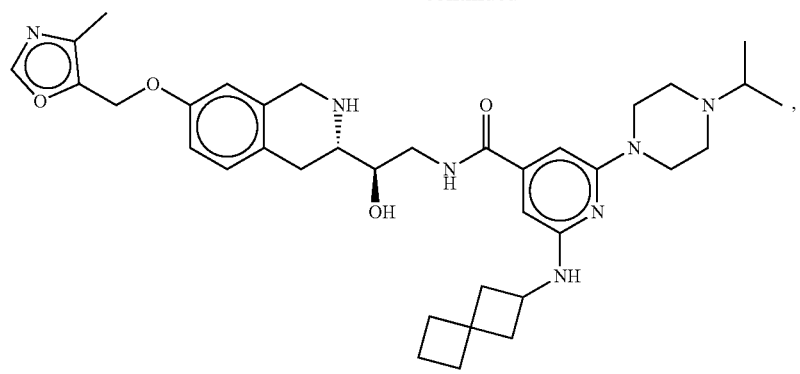
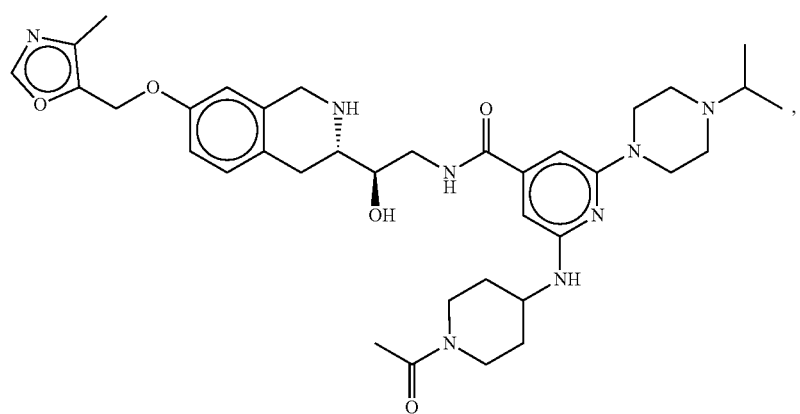
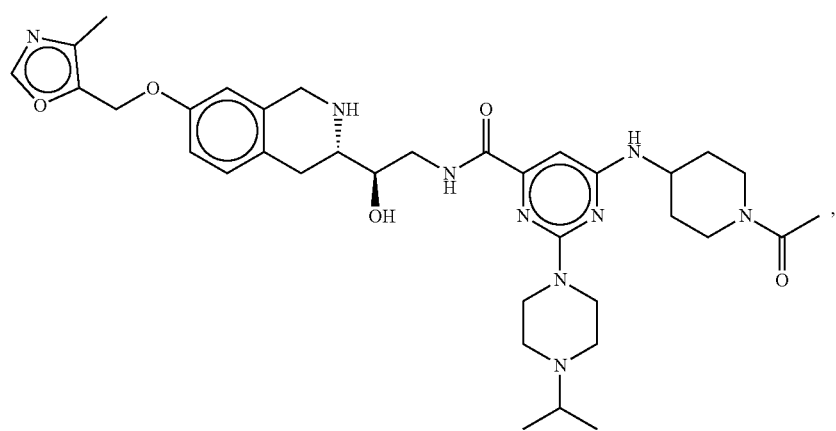
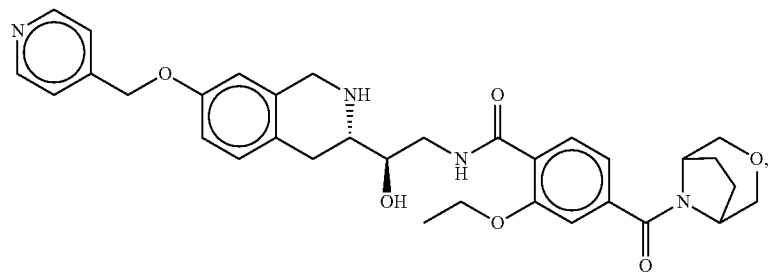

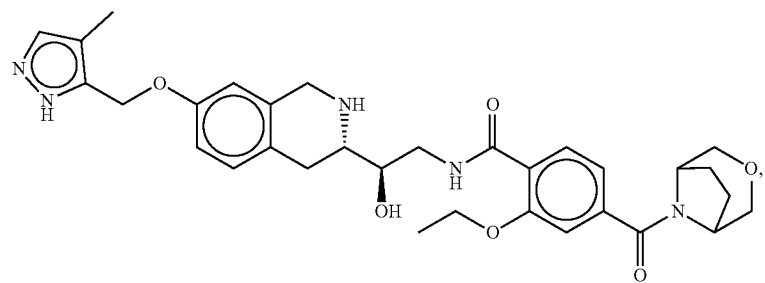
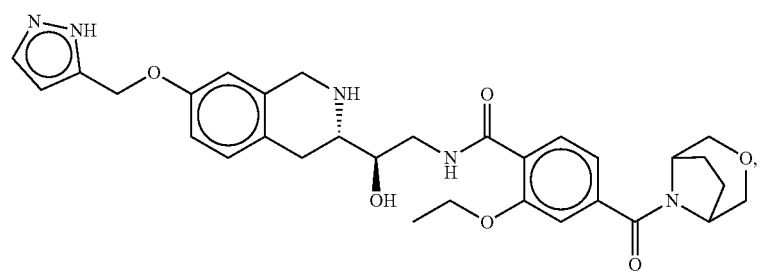
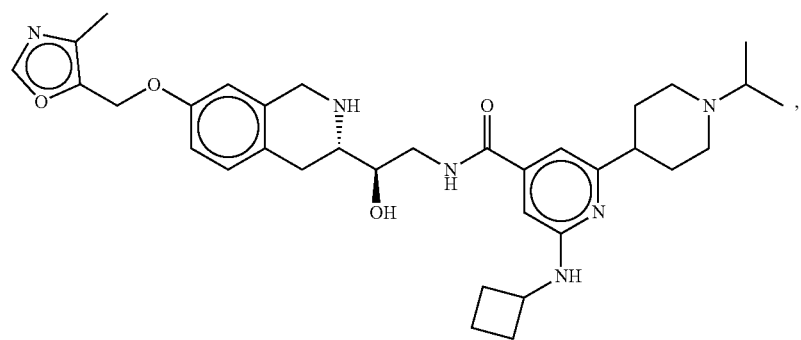

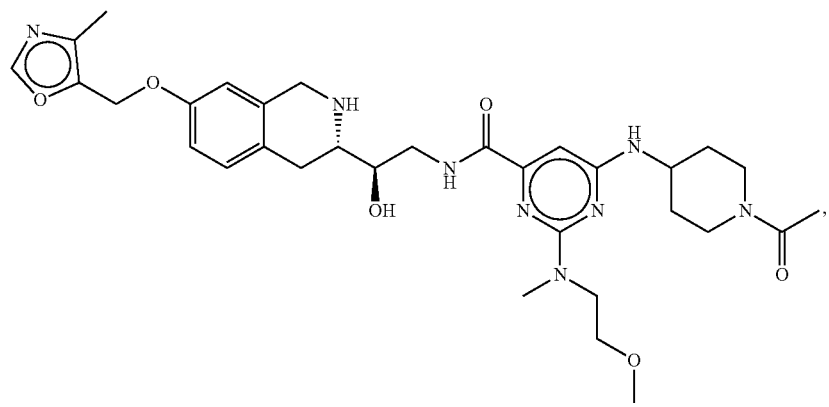
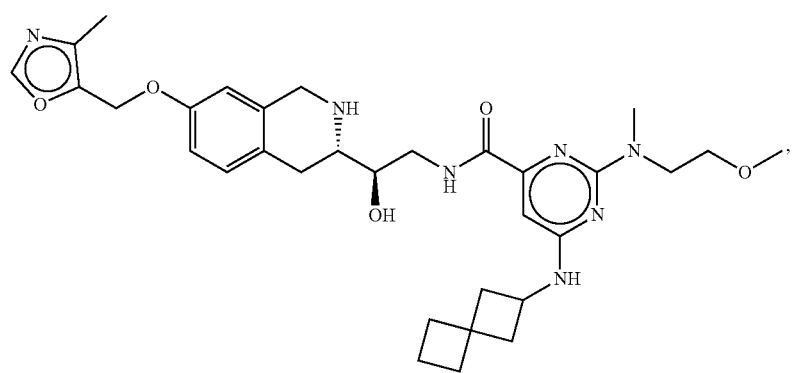
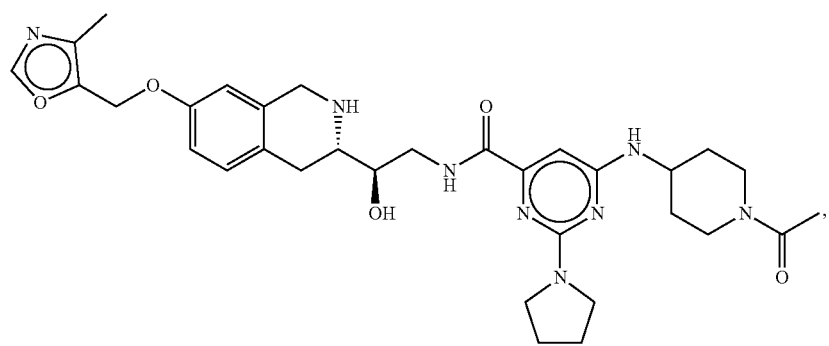

-continued
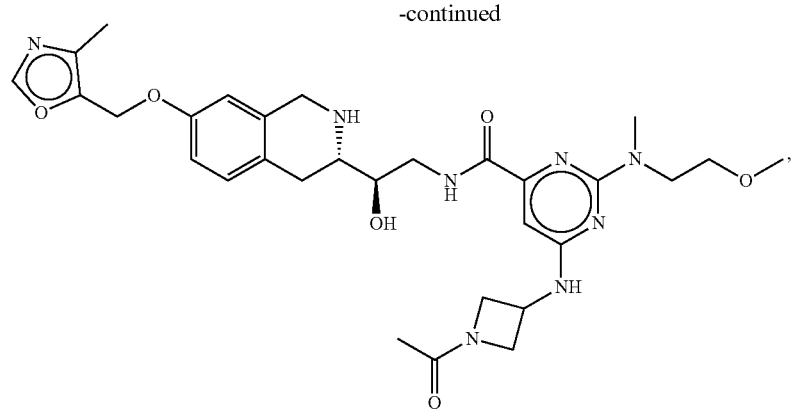
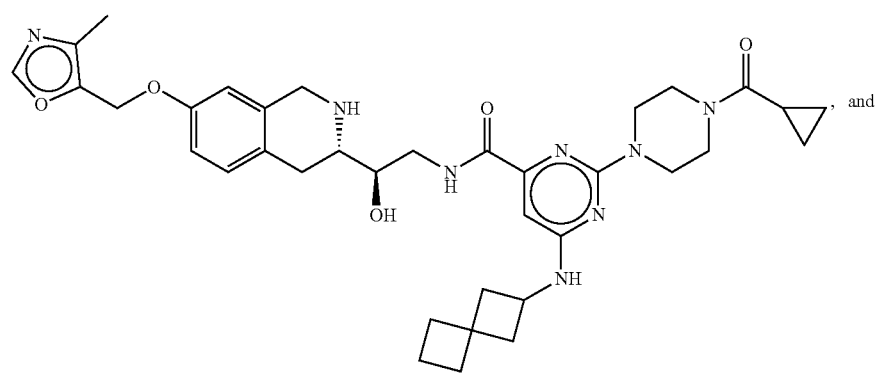
, and
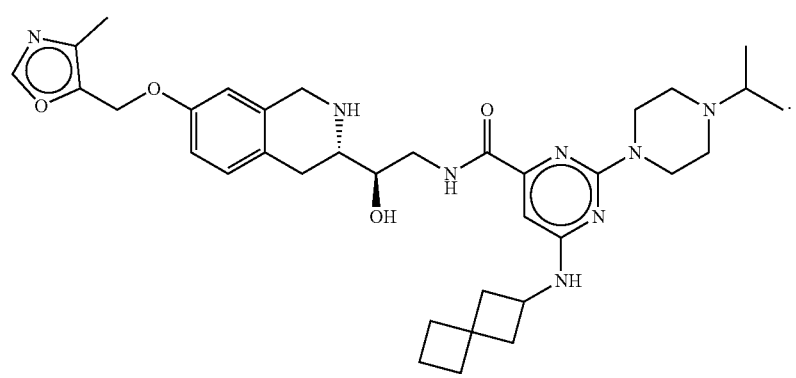
.

22. A pharmaceutical composition comprising a compound of claim 1 and a pharmaceutically acceptable carrier.

23. A method of treating an MTAP-deficient and/or an MTA-accumulating disease in a subject in need thereof by administering to the subject a therapeutically effective amount of a compound of claim 1.

24. The method of claim 23 wherein the disease is an MTAP-deficient and/or MTA-accumulating cancer.

* * * * *